(12) United States Patent
Chackalamannil et al.

(10) Patent No.: US 8,987,242 B2
(45) Date of Patent: *Mar. 24, 2015

(54) MORPHOLINONE COMPOUNDS AS FACTOR IXA INHIBITORS

(75) Inventors: Samuel Chackalamannil, Califon, NJ (US); Tin-Yau Chan, Edison, NJ (US); Mariappan V. Chelliah, Edison, NJ (US); Martin C. Clasby, Plainsboro, NJ (US); Michael Dwyer, Scotch Plains, NJ (US); William J. Greenlee, Teaneck, NJ (US); Tomokazu Hirabayashi, Shinjuku-ku (JP); Santhosh Neelamkavil, Scotch Plains, NJ (US); Hidemitsu Nishida, Shinjuku-ku (JP); Fumihiko Saitoh, Shinjuku-ku (JP); Unmesh Shah, Green Brook, NJ (US); Yan Xia, Edison, NJ (US)

(73) Assignees: Merck Sharp & Dohme Corp., Rahway, NJ (US); Mochida Pharmaceuticals Co., Ltd., Tokyo (JP)

( * ) Notice: Subject to any disclaimer, the term of this patent is extended or adjusted under 35 U.S.C. 154(b) by 520 days.

This patent is subject to a terminal disclaimer.

(21) Appl. No.: 12/791,464

(22) Filed: Jun. 1, 2010

(65) Prior Publication Data

US 2011/0135650 A1 Jun. 9, 2011

Related U.S. Application Data

(63) Continuation-in-part of application No. 12/744,736, filed as application No. PCT/US2009/066548 on Dec. 3, 2009, now Pat. No. 8,642,582.

(60) Provisional application No. 61/120,328, filed on Dec. 5, 2008, provisional application No. 61/150,955, filed on Feb. 9, 2009, provisional application No. 61/165,214, filed on Mar. 31, 2009, provisional application No. 61/238,455, filed on Aug. 31, 2009.

(51) Int. Cl.
| | | |
|---|---|---|
| A61K 31/535 | (2006.01) |
| A01N 43/00 | (2006.01) |
| A61K 31/33 | (2006.01) |
| C07D 413/12 | (2006.01) |
| A61K 31/397 | (2006.01) |
| A61K 31/496 | (2006.01) |
| A61K 31/5375 | (2006.01) |
| A61K 31/5377 | (2006.01) |
| A61K 31/54 | (2006.01) |
| A61K 31/7088 | (2006.01) |
| A61K 39/395 | (2006.01) |
| A61K 45/06 | (2006.01) |
| C07D 265/32 | (2006.01) |
| C07D 413/10 | (2006.01) |
| C07D 413/14 | (2006.01) |
| C07D 417/10 | (2006.01) |

(52) U.S. Cl.
CPC ............ *C07D 413/12* (2013.01); *A61K 31/397* (2013.01); *A61K 31/496* (2013.01); *A61K 31/5375* (2013.01); *A61K 31/5377* (2013.01); *A61K 31/54* (2013.01); *A61K 31/7088* (2013.01); *A61K 39/395* (2013.01); *A61K 45/06* (2013.01); *C07D 265/32* (2013.01); *C07D 413/10* (2013.01); *C07D 413/14* (2013.01); *C07D 417/10* (2013.01)
USPC ........................................ 514/183; 514/228.8

(58) Field of Classification Search
None
See application file for complete search history.

(56) References Cited

U.S. PATENT DOCUMENTS 6,958,402 B2 * 10/2005 Allerton et al. ............ 548/340.1
2003/0171218 A1 * 9/2003 Bojack et al. ................. 504/221

FOREIGN PATENT DOCUMENTS

| DE | 103 15 377 A1 | 10/2004 |
|---|---|---|
| EP | 1 182 202 A1 | 2/2002 |
| EP | 1 447 401 A1 | 8/2004 |
| EP | 1864971 A1 | 12/2007 |
| WO | WO03005824 A2 | 1/2003 |
| WO | WO 03/061652 | 7/2003 |
| WO | WO 2005/026165 | 3/2005 |
| WO | 2005/073201 | 8/2005 |

(Continued)

OTHER PUBLICATIONS

Anderson, "The Process of Structure-Based Drug Design," Chemistry and Biology, vol. 10, 787-797, Sep. 2003.*

(Continued)

*Primary Examiner* — Craig Ricci
*Assistant Examiner* — Jared D Barsky
(74) *Attorney, Agent, or Firm* — Nichole M. Beeler; Catherine D. Fitch

(57) ABSTRACT

The present invention provides a compound of Formula (I)

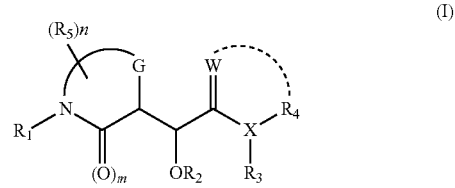

as described herein, or a pharmaceutically acceptable salt or a solvate thereof. The present invention also provides pharmaceutical compositions comprising one or more said compounds, and methods for using said compounds for treating or preventing a thromboses, embolisms, hypercoagulability or fibrotic changes.

9 Claims, No Drawings

(56) References Cited

FOREIGN PATENT DOCUMENTS

| WO | 2005121130 A2 | 12/2005 |
| WO | WO2008/031508 A1 | 3/2008 |
| WO | 2010/065717 A1 | 6/2010 |

OTHER PUBLICATIONS

Wiedemann et al., "Sc3+-Catalyzed Aldol-Type Additions of N-Benzoylcyclopropanecarboxamides via Iodide-Mediated Ring-Opening: Stereoselective Synthesis of y-Lactams" Organic Letters 2008, vol. 10, No. 8, pp. 1661-1664.

Matsunaga S, Shibasaki M et al. : "Sc3+-Catalyzed Aldol-Type Additions of N-Benzolycyclopropanecarboxamides via Iodide-Mediated Ring-Opening: Stereoselective Synthesis of gamma-Lactams", Organic Letters, vol. 10, No. 8, Mar. 18, 2008, pp. 1661-1664, XP002573322, the general formula of the products in the abstract; entry 5 in table 2.

Tsukada, Hidetaka et al: "Synthesis and lateral root-inducting activity of N-benzyl-3-substituted-2-piperidones" Journal of the Faculty of Agriculture Kyushu Univerisity, Kyushu Daigaku Nogakubu, Fukuoka, JP, vol. 44, No. 1-2, Jan. 1, 1999, pp. 119-126, XP009131017, ISSN: 0023-6152, compounds 25-30 in table 1.

Bellesia, Franco et al. "Rearrangement of N-allyl-.alpha.,.alpha.-dichloroamides,.beta.- or .gamma.-functionalized, to substituted analogues of the .gamma.-aminobutyric acid (GABA) " Synthetic Communications, Taylor & Francis Group, Philadelphia, PA, vol. 29, No. 21, Mar. 19, 1999, pp. 3739-3748, XP009131002, ISSN: 0039-7911, compound G5 on p. 3746; scheme 2; table.

Lee, Jin Soo et al.: "Synthesis and structure-activity relationships of 1 .beta.-Methyl-2-( .alpha.-functionalized lactamyl) Carbapenems" Korean Journal of Medicinal Chemistry, Korean Chemical Society, Seoul, KR, vol. 8, No. 2, Jan. 1, 1998, pp. 102-116, XP009131001 ISSN: 1225-0058 , Compounds 7f, 7g in scheme 1, table 1 and on pp. 114-115.

J.M. Smallheer et al: "SAR and factor IXa crystal structure of a dual inhibitor of factors IXa and Xa" Bioorganic & Medicinal Chemistry Letters, Pergamon, Elsevier Science, GB LNKD-DOI:10.1016/J/BMCL. 2004.08.034, vol. 14, No. 21, Nov. 1, 2004 5263-5267-XP004580511 ISSN: 0960-894X. The Whole Document.

International Search Report for PCT/US2009/066548; Performed by the European Patent Office; Completed Mar. 23, 2010; by authorized Officer Inken Hanisch.

International Search Report for PCT/US2010/036853; Performed by the European Patent Office; Completed Jul. 8, 2010; By authorized Officer Ambrogio Usuelli.

EPO Search Report for PCT/US2009/066548; Performed by Authorized Officer Inken Hanisch; Completed on Mar. 23, 2010.

* cited by examiner

MORPHOLINONE COMPOUNDS AS FACTOR IXA INHIBITORS

CROSS-REFERENCE TO RELATED APPLICATIONS

This application is a continuation-in-part which claims the benefit, under 35 U.S.C. 120, of U.S. patent application Ser. No. 12/744,736, filed on May 26, 2010, which is a U.S. National Phase application under 35 U.S.C. Section 371 of PCT/US2009/066548, filed Dec. 3, 2009, which claims priority under 35 U.S.C. 119(e) of U.S. provisional applications 61/238,455 filed Aug. 31, 2009, 61/165,214, filed Mar. 31, 2009, 61/150,955, filed Feb. 9, 2009, and 61/120,328, filed Dec. 5, 2008.

FIELD OF THE INVENTION

The invention relates to novel compounds of the Formula (I) having antithrombotic activity which, in particular, inhibit blood clotting factor IXa, to processes for their preparation and to use thereof as medicaments.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, as shown in the Patent Document 1, and the subsequent dissolution of the clot after wound healing has taken place commences after vascular damage and can be divided into four phases:
1. The phase of vasoconstriction or vasocontraction: By means of this the blood loss in the damaged area is decreased.
2. The next phase is platelet activation by thrombin. The platelets attach to the site of the vessel wall damage and form a platelet aggregate. The protein fibrinogen is responsible here for the crosslinkage of the platelets by means of appropriate surface receptors. Platelets also bind to exposed collagen of the extracellular matrix of the damaged vessel wall and are activated by this means. After activation of the platelets, a number of messenger substances are secreted, which induce the activation of further platelets. At the same time, a membrane lipid, phosphatidylserine, is transported from the inside of the membrane of the platelets to the outside, on which complexes of clotting factors can accumulate. The platelets accelerate blood clotting by means of this mechanism.
3. The formation of these clotting complexes leads to the massive formation of thrombin, which converts soluble fibrinogen to fibrin by cleavage of two small peptides. Fibrin monomers spontaneously form threadlike strands, from which, after crosslinkage by clotting factor XIII, a stable protein network forms. The initially even looser platelet aggregate is stabilized by this fibrin network; platelet aggregates and fibrin network are the two essential constituents of a thrombus.
4. After wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors.

The intrinsic pathway requires the clotting factors V, VIII, IX, X, XI and XII and also prekallikrein, high molecular weight kininogen, calcium ions and phospholipids from platelets.

The intrinsic pathway is initiated when prekallikrein, high molecular weight kininogen factor XI and XII bind to a negatively charged surface. This point in time is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, such that activation is the result. With increasing activation of factor XII, activation of factor XI occurs, which leads to a release of bradykinin, a vasodilator. As a result, the ending of the initial phase of vasoconstriction occurs. Bradykinin is formed from high molecular weight kininogen. In the presence of $Ca^{2+}$ ions, factor XIa activates factor IX. Factor IX is a proenzyme, which contains vitamin K-dependent, γ-carboxyglutamic acid (GLA) residues. The serine protease activity becomes noticeable after binding of $Ca^{2+}$ to these GLA residues. A number of the serine proteases of the blood clotting cascade (factors II, VII, IX and X) contain such vitamin K-dependent GLA residues. Factor IXa cleaves factor X and leads to activation to factor Xa. The prerequisite for the formation of factor IXa is the formation of a tenase complex from $Ca^{2+}$ and the factors VIIIa, IXa and X on the surface of activated platelets. One of the reactions of activated platelets is the presentation of phosphatidylserine and phosphatidylinositol along the surfaces. The exposure of these phospholipids first makes the formation of the tenase complex possible. Factor VIII in this process has the function of a receptor for the factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further and inactivated by thrombin. This dual activity of thrombin in relation to factor VIII leads to a self-restriction of tenase complex formation and thus to a limitation of blood clotting.

The extrinsic pathway requires a tissue factor (TF) and clotting factors V, VII, VIII, IX and X. In the case of a vessel injury, the tissue factor (TF) accumulates with the clotting factor VII and the latter is activated. The complex of TF and clotting factor VII has two substrates, clotting factors X and IX.

Clotting factor IX can be activated by means of the intrinsic pathway and the extrinsic pathway. The activation of factor IXa is thus a central point of intersection between the two pathways of activation of clotting.

Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445).

Recently, compounds having a Factor IXa antagonism are being studied. Known compounds each having an amide bond are disclosed in, for example, PCT Publication No. 08/031,508 pamphlet (Patent Document 1), PCT Publication No. 08/031,509 pamphlet (Patent Document 2). However, these patent documents do not disclose cyclic morpholinone derivatives.

In the development of pharmaceuticals, it is required to satisfy strict criteria for not only target pharmacological activity but also absorption, distribution, metabolism, excretion, and the like. With respect to drug interactions, desensitization or tolerance, digestive absorption in oral administration, the rate of transfer to a small intestine, the rate of absorption and first-pass effect, an organ barrier, protein binding, induction of a drug-metabolizing enzyme, an excretion pathway and body clearance, a method of administration (an application site, a method, and purpose), and the like, various agenda are required. However, a drug that satisfies these requirements is seldom discovered.

These comprehensive problems in drug development might also exist for Factor IXa antagonists, and Factor IXa antagonists have not yet been released onto the market. More specifically, known compounds having a Factor IXa antagonism may also include problems in terms of usefulness and safety. For example, these compounds may have low absorption, and oral administration of these compounds may be difficult; these compounds also may exhibit inhibitory activity of the human ether-a-go-go related gene (hERG) channel, which may cause arrhythmia, and pharmacokinetics of these compounds might not satisfactory.

Accordingly, a compound in which these problems are solved and which has high activity has been desired.

SUMMARY OF THE INVENTION

In its many embodiments, the present invention provides a novel class of cyclic morpholine compounds or its analogue, pharmaceutical compositions comprising one or more said compounds, and methods for using said compounds for treating or preventing a thromboses, embolisms, hypercoagulability or fibrotic changes.

The compounds of the Formula (I) according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound of Formula (I)

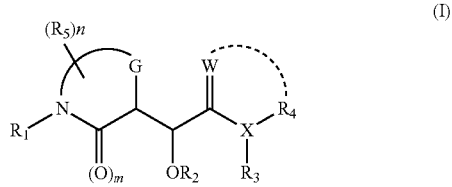

(I)

or a pharmaceutically acceptable salt or a solvate thereof;

wherein:
R1 is selected from the group consisting of:
1) —($C_6$-$C_{14}$)-aryl, which is unsubstituted or substituted independently with one to four Y;
2) -(three- to fifteen-membered heterocyclic ring), which is unsubstituted or substituted independently with one to four Y;
3) —($C_6$-$C_{14}$)-aryl-U—($C_6$-$C_{14}$)-aryl, wherein each of said —($C_6$-$C_{14}$)-aryl- independently is unsubstituted or substituted independently with one to four Y;
4) —($C_6$-$C_{14}$)-aryl-U—($C_3$-$C_{12}$)-cycloalkyl, wherein said —($C_6$-$C_{14}$)-aryl and —($C_3$-$C_{12}$)-cycloalkyl independently are unsubstituted or substituted independently with one to four Y;
5) —($C_6$-$C_{14}$)-aryl-U-(three- to fifteen-membered heterocyclic ring), wherein said —($C_6$-$C_{14}$)-aryl and said (three- to fifteen-membered heterocyclic ring) are independently unsubstituted or substituted independently with one to four Y;
6) -(three- to fifteen-membered heterocyclic ring)-U—($C_6$-$C_{14}$)-aryl, wherein said —($C_6$-$C_{14}$)-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) -(three- to fifteen-membered heterocyclic ring)-U—($C_3$-$C_{12}$)-cycloalkyl, wherein said —($C_3$-$C_{12}$)-cycloalkyl, and said -(three- to fifteen-membered heterocyclic ring)- are independently unsubstituted or substituted independently with one to four Y;
9) —V—($C_6$-$C_{14}$)-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —($C_1$-$C_6$)-alkyl, wherein each R6 independently is selected from the group consisting of hydrogen atom, —($C_1$-$C_6$)-alkyl, —($C_3$-$C_8$)-cycloalkyl, —($C_6$-$C_{14}$)-aryl and a three- to fifteen-membered heterocyclic ring;

R3 is absent, or selected from the group consisting of hydrogen atom and —($C_1$-$C_4$)-alkyl, R4 is selected from the group consisting of:
1) —($C_6$-$C_{14}$)-aryl-Z, wherein said Z is a basic nitrogen-containing group and wherein said —($C_6$-$C_{14}$)-aryl is unsubstituted or substituted independently with one to four Y;
2) —($C_3$-$C_{12}$)-cycloalkyl-Z, wherein said Z is a basic nitrogen-containing group and wherein said —($C_3$-$C_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —($C_6$-$C_{14}$)-aryl, which is unsubstituted or substituted independently with one to four Y;
6) —($C_3$-$C_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;

each R5 independently is selected from the group consisting of:
1) halogen;
2) —($C_1$-$C_6$)-alkyl, which is unsubstituted or substituted independently with one to four —($C_1$-$C_3$)-haloalkyl, —N—C(O)—OH, —N—C(O)—($C_1$-$C_4$)-alkyl, or —C(O)OR7;
3) —($C_1$-$C_3$)-haloalkyl;
4) —($C_3$-$C_8$)-cycloalkyl;
5) —OH;
6) —O—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) =O (oxo);
20) —C(O)OR7; and
21) C(O)R7
wherein each of R7 and R8 is independently selected from the group consisting of hydrogen atom, —($C_6$-$C_{14}$)-aryl, —($C_3$-$C_8$)-cycloalkyl, and —($C_1$-$C_6$)-alkyl, wherein said —($C_1$-$C_6$)-alkyl is unsubstituted or substituted with at least one substituent selected from the group consisting of OH, —O—($C_1$-$C_4$)-alkyl, —($C_1$-$C_3$)-fluoroalky, —O—($C_1$-$C_3$)-haloalkyl, C(O)OH, and C(O)O—($C_1$-$C_6$)-alkyl;

each U independently is selected from the group consisting of a covalent bond, —($C_1$-$C_4$)-alkylene, —NH—, —N(($C_1$-$C_4$)-alkyl)-, —O—, —$SO_2$— or —S—,
wherein said —($C_1$-$C_4$)-alkylene or —($C_1$-$C_4$)-alkyl is unsubstituted or substituted independently with one to four T,
or wherein geminal hydrogens in said —($C_1$-$C_4$)-alkylene or —($C_1$-$C_4$)-alkyl can be replaced by a ($C_3$-$C_8$)-cycloalkyl to form a spiro cyclic ring;

each V independently is selected from the group consisting of —($C_1$-$C_4$)-alkylene, —$SO_2$—, —C(O)—, —C(O)—NH— and —$SO_2$—NH—,
wherein the carbon atom of said —C(O)—NH— or the sulfur atom of said —$SO_2$—NH— is connected to a nitrogen atom of the morpholinone ring,
and wherein said —($C_1$-$C_4$)-alkylene is unsubstituted or substituted independently with one to four T,
or wherein geminal hydrogens in said —($C_1$-$C_4$)-alkylene can be replaced by a ($C_3$-$C_8$)-cycloalkyl to form a spiro cyclic ring;

each T independently is selected from the group consisting of:
1) halogen;
2) —($C_1$-$C_6$)-alkyl, which is unsubstituted or substituted independently with one to four substituents selected from the group consisting of OH, —O—($C_1$-$C_4$)-alkyl, —($C_1$-$C_3$)-haloalkyl, —O—($C_1$-$C_3$)-haloalkyl, —N—C(O)—OH and —N—C(O)—($C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo); and
22) —C(O)OR7;
23) —C(O)OR7;
24) —N—C(O)—OR7
wherein each of R7 and R8 independently is selected from the group consisting of a hydrogen atom, —($C_3$-$C_8$)-cycloalkyl, halogen and —($C_1$-$C_6$)-alkyl, wherein said —($C_1$-$C_6$)-alkyl is optionally substituted with at least one substituent selected from the group consisting of OH, —O—($C_1$-$C_4$)-alkyl, —($C_1$-$C_3$)-fluoroalky, and —O—($C_1$-$C_3$)-haloalkyl;

G is selected from the group consisting of oxygen atom, imino, sulfur atom, sulfoxide, sulfone and methylene;
W is selected from the group consisting of oxygen atom, nitrogen atom and carbon atom;
X is selected from the group consisting of nitrogen atm, carbon atom and oxygen atom;
Y is selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_6$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7; 14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);

20) —N(R8)—C(O)—N(R7)(R8);
21) =O (oxo);
22) —SF$_5$;
23) —C(O)OR7;
24) —N—C(O)—OR7
25) —N(R8)—C(O)—(C$_1$-C$_4$)-alkyl-O—(C$_1$-C$_4$)-alkyl-(C$_6$-C$_{14}$)-aryl, wherein said —(C$_6$-C$_{14}$)-aryl is unsubstituted or substituted independently with one to four Y selected from (1) to (24) as set forth above;
26) —N(R8)—C(O)—(C$_1$-C$_4$)-alkyl-O—(C$_1$-C$_4$)-alkyl-(three- to fifteen-membered heterocyclic ring), wherein said -(three- to fifteen-membered heterocyclic ring) is unsubstituted or substituted independently with one to four Y selected from (1) to (24) as set forth above;
wherein said —(C$_1$-C$_4$)-alkyl part or —(C$_1$-C$_6$)-alkyl part of 2), 6), 14), 17), 19), 25) or 26) of said Y is unsubstituted or substituted independently with one to four T;
wherein each of R7 and R8 of 10), 11), 12), 13), 15), 19), 20), 23), 24), 25) or 26) of said Y independently is selected from the group consisting of hydrogen atom, —(C$_3$-C$_8$)-cycloalkyl, and —(C$_1$-C$_6$)-alkyl, wherein said —(C$_1$-C$_6$)-alkyl is optionally substituted with OH, —O—(C$_1$-C$_4$)-alkyl, —(C$_1$-C$_3$)-fluoroalky, —O—(C$_1$-C$_3$)-haloalkyl, —C(O)OH, or C(O)O—(C$_1$-C$_6$)-alkyl;
m is 0 or 1,
n is 0, 1, 2, 3 or 4,
the linkage between G atom and Nitrogen atom of the substructure (II)

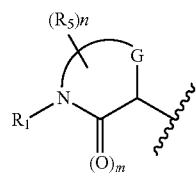

(II)

in Formula (I) comprises one to four carbon atoms to form alkylene chain, wherein said alkylene chain or G (imino or methylene) is unsubstituted or substituted independently with one to four R5;
the dotted linkage between W and R4 of the substructure (III)

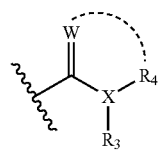

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

In another aspect, the present invention relates to a compound of Formula (I)-(A)

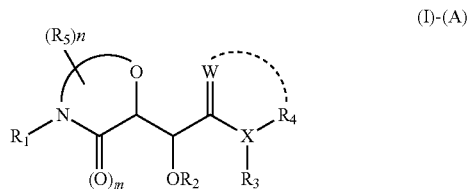

(I)-(A)

or a pharmaceutically acceptable salt or a solvate thereof;
wherein:
R1 is selected from the group consisting of:
1) —(C$_6$-C$_{14}$)-aryl, which is unsubstituted or substituted independently with one to four Y;
2) -(three- to fifteen-membered heterocyclic ring), which is unsubstituted or substituted independently with one to four Y;
3) —(C$_6$-C$_{14}$)-aryl-U—(C$_6$-C$_{14}$)-aryl, wherein each of said —(C$_6$-C$_{14}$)-aryl- independently is unsubstituted or substituted independently with one to four Y;
4) —(C$_6$-C$_{14}$)-aryl-U—(C$_3$-C$_{12}$)-cycloalkyl, wherein said —(C$_6$-C$_{14}$)-aryl and —(C$_3$-C$_{12}$)-cycloalkyl independently are unsubstituted or substituted independently with one to four Y;
5) —(C$_6$-C$_{14}$)-aryl-U-(three- to fifteen-membered heterocyclic ring), wherein said —(C$_6$-C$_{14}$)-aryl and said (three- to fifteen-membered heterocyclic ring) are independently unsubstituted or substituted independently with one to four Y;
6) -(three- to fifteen-membered heterocyclic ring)-U—(C$_6$-C$_{14}$)-aryl, wherein said —(C$_6$-C$_{14}$)-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) -(three- to fifteen-membered heterocyclic ring)-U—(C$_3$-C$_{12}$)-cycloalkyl, wherein said —(C$_3$-C$_{12}$)-cycloalkyl, and said -(three- to fifteen-membered heterocyclic ring)- are independently unsubstituted or substituted independently with one to four Y;
9) —V—(C$_6$-C$_{14}$)-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —(C$_1$-C$_6$)-alkyl, wherein
each R6 independently is selected from the group consisting of hydrogen atom, —(C$_1$-C$_6$)-alkyl, —(C$_3$-C$_8$)-cycloalkyl, —(C$_6$-C$_{14}$)-aryl and a three- to fifteen-membered heterocyclic ring;
R3 is absent, or selected from the group consisting of hydrogen atom and —(C$_1$-C$_4$)-alkyl,
R4 is selected from the group consisting of:
1) —(C$_6$-C$_{14}$)-aryl-Z, wherein said Z is a basic nitrogen-containing group and wherein said —(C$_6$-C$_{14}$)-aryl is unsubstituted or substituted independently with one to four Y;
2) —(C$_3$-C$_{12}$)-cycloalkyl-Z, wherein said Z is a basic nitrogen-containing group and wherein said —(C$_3$-C$_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —(C$_6$-C$_{14}$)-aryl, which is unsubstituted or substituted independently with one to four Y;
6) —(C$_3$-C$_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;
each R5 independently is selected from the group consisting of:
1) halogen;
2) —(C$_1$-C$_6$)-alkyl, which is unsubstituted or substituted independently with one to four —(C$_1$-C$_3$)-haloalkyl, —N—C(O)—OH or —N—C(O)—(C$_1$-C$_4$)-alkyl;
3) —(C$_1$-C$_3$)-haloalkyl;
4) —(C$_3$-C$_8$)-cycloalkyl;
5) —OH;
6) —O—(C$_1$-C$_4$)-alkyl;
7) —O—(C$_1$-C$_3$)-haloalkyl;
8) —NO$_2$;
9) —CN;
10) —N(R7)(R8);
11) —C(O)—NH—R7;
12) —NH—C(O)—R7;
13) —NH—SO$_2$—R7;
14) —SO$_2$—(C$_1$-C$_4$)-alkyl;
15) —SO$_2$—NH—R7;
16) —SO$_2$—(C$_1$-C$_3$)-haloalkyl;
17) —S—(C$_1$-C$_4$)-alkyl;
18) —S—(C$_1$-C$_3$)-haloalkyl; and
19) =O (oxo);
wherein each of R7 and R8 is independently selected from the group consisting of hydrogen atom, —(C$_3$-C$_8$)-cycloalkyl, halogen and —(C$_1$-C$_6$)-alkyl, wherein said —(C$_1$-C$_6$)-alkyl is unsubstituted or substituted with at least one substituent selected from the group consisting of OH, —O—(C$_1$-C$_4$)-alkyl, —(C$_1$-C$_3$)-fluoroalky, and —O—(C$_1$-C$_3$)-haloalkyl;
each U independently is selected from the group consisting of a covalent bond, —(C$_1$-C$_4$)-alkylene, —NH—, —N((C$_1$-C$_4$)-alkyl)-, —O—, —SO$_2$— or —S—,
wherein said —(C$_1$-C$_4$)-alkylene or —(C$_1$-C$_4$)-alkyl is unsubstituted or substituted independently with one to four T,
or wherein geminal hydrogens in said —(C$_1$-C$_4$)-alkylene or —(C$_1$-C$_4$)-alkyl can be replaced by a (C$_3$-C$_8$)-cycloalkyl to form a spiro cyclic ring;
each V independently is selected from the group consisting of —(C$_1$-C$_4$)-alkylene, —SO$_2$—, —C(O)—, —C(O)—NH— and —SO$_2$—NH—,
wherein the carbon atom of said —C(O)—NH— or the sulfur atom of said —SO$_2$—NH— is connected to a nitrogen atom of the morpholinone ring,
and wherein said —(C$_1$-C$_4$)-alkylene is unsubstituted or substituted independently with one to four T,
or wherein geminal hydrogens in said —(C$_1$-C$_4$)-alkylene can be replaced by a (C$_3$-C$_8$)-cycloalkyl to form a spiro cyclic ring;
each T independently is selected from the group consisting of:
1) halogen;
2) —(C$_1$-C$_6$)-alkyl, which is unsubstituted or substituted independently with one to four substituents selected from the group consisting of OH, —O—(C$_1$-C$_4$)-alkyl, —(C$_1$-C$_3$)-haloalkyl, —O—(C$_1$-C$_3$)-haloalkyl, —N—C(O)—OH and —N—C(O)—(C$_1$-C$_4$)-alkyl;
3) —(C$_1$-C$_3$)-haloalkyl;
4) —(C$_3$-C$_8$)-cycloalkyl;
5) —OH;
6) —O—(C$_1$-C$_4$)-alkyl, which is unsubstituted or mono substituted with OH, —O—(C$_1$-C$_4$)-alkyl, —(C$_1$-C$_3$)-haloalkyl, —O—(C$_1$-C$_3$)-haloalkyl, —N—C(O)—OH or —N—C(O)—(C$_1$-C$_4$)-alkyl;
7) —O—(C$_1$-C$_3$)-haloalkyl;
8) —NO$_2$;
9) —CN;
10) —N(R7)(R8);
11) —C(O)—NH—R7;
12) —NH—C(O)—R7;
13) —NH—SO$_2$—R7;
14) —SO$_2$—(C$_1$-C$_4$)-alkyl;
15) —SO$_2$—NH—R7;
16) —SO$_2$—(C$_1$-C$_3$)-haloalkyl;
17) —S—(C$_1$-C$_4$)-alkyl;
18) —S—(C$_1$-C$_3$)-haloalkyl;
19) —(C$_1$-C$_6$)-alkyl-N(R7)(R8);
20) —NH—C(O)—N(R7)(R8);
21) =O (oxo); and
22) —C(O)OR7;
wherein each of R7 and R8 independently is selected from the group consisting of a hydrogen atom, —(C$_3$-C$_8$)-cycloalkyl, halogen and —(C$_1$-C$_6$)-alkyl, wherein said —(C$_1$-C$_6$)-alkyl is optionally substituted with at least one substituent selected from the group consisting of OH, —O—(C$_1$-C$_4$)-alkyl, —(C$_1$-C$_3$)-fluoroalky, and —O—(C$_1$-C$_3$)-haloalkyl;
W is selected from the group consisting of oxygen atom, nitrogen atom and carbon atom;
X is selected from the group consisting of nitrogen atom, carbon atom and oxygen atom;

Y is selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—NH—R7;
12) —NH—C(O)—R7;
13) —NH—$SO_2$—R7;
14) —$SO_2$—($C_1$-$C_4$)-alkyl;
15) —$SO_2$—NH—R7;
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo);
22) —NH—C(O)—($C_1$-$C_4$)-alkyl-O—($C_1$-$C_4$)-alkyl-($C_6$-$C_{14}$)-aryl, wherein said —($C_6$-$C_{14}$)-aryl is unsubstituted or substituted independently with one to four Y selected from (1) to (21) as set forth above;
23) —NH—C(O)—($C_1$-$C_4$)-alkyl-O—($C_1$-$C_4$)-alkyl-(three- to fifteen-membered heterocyclic ring), wherein said -(three- to fifteen-membered heterocyclic ring) is unsubstituted or substituted independently with one to four Y selected from (1) to (21) as set forth above;
wherein said —($C_1$-$C_4$)-alkyl or —($C_1$-$C_6$)-alkyl of said 2), 6), 10), 14), 17), 19), 22) or 23) of said Y is unsubstituted or substituted independently with one to four T;
wherein each of R7 and R8 independently is selected from the group consisting of hydrogen atom, —($C_3$-$C_8$)-cycloalkyl, halogen and —($C_1$-$C_6$)-alkyl, wherein said —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl;

m is 0 or 1,
n is 0, 1, 2, 3 or 4,
the linkage between Oxygen atom and Nitrogen atom of the substructure (II)

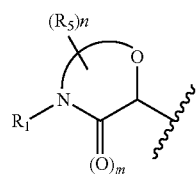

(II)

in Formula (I) comprises one to four carbon atoms, wherein said linkage is unsubstituted or substituted independently with one to four R5;

the dotted linkage between W and R4 of the substructure (III)

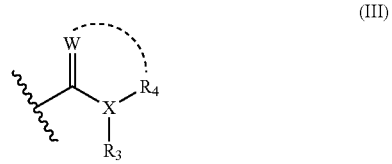

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

In another aspect, the present invention relates to a compound of Formula (I)-(B)

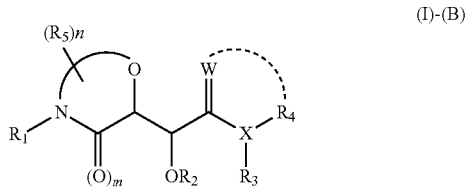

(I)-(B)

or a pharmaceutically acceptable salt or a solvate thereof;
wherein:
R1 is
1) —($C_6$-$C_{14}$)-aryl, in which aryl is unsubstituted or substituted independently with one to four Y,
2) -(three- to fifteen-membered heterocyclic ring), in which ring is unsubstituted or substituted independently with one to four Y,
3) —($C_6$-$C_{14}$)-aryl-U—($C_6$-$C_{14}$)-aryl, in which the two aryls in each case independently of one another are unsubstituted or substituted independently with one to four Y,
4) —($C_6$-$C_{14}$)-aryl-U—($C_3$-$C_{12}$)-cycloalkyl, in which aryl and cycloalkyl in each case independently of one another are unsubstituted or substituted independently with one to four Y,
5) —($C_6$-$C_{14}$)-aryl-U-(three- to fifteen-membered heterocyclic ring), in which aryl and (three- to fifteen-membered heterocyclic ring) in each case independently of one another are unsubstituted or substituted independently with one to four Y, 6) -(three- to fifteen-membered heterocyclic ring)-U—($C_6$-$C_{14}$)-aryl, in which aryl and (three- to fifteen-membered heterocyclic ring) in each case independently of one another are unsubstituted or substituted independently with one to four Y,
7) -(three- to fifteen-membered heterocyclic ring)-U-(three- to fifteen-membered heterocyclic ring), in which the two heterocyclic ring radicals in each case independently of one another are unsubstituted or substituted independently with one to four Y,
8) -(three- to fifteen-membered heterocyclic ring)-U—($C_3$-$C_{12}$)-cycloalkyl, in which ($C_3$-$C_{12}$)-cycloalkyl, and (three- to fifteen-membered heterocyclic ring) in each case independently of one another are unsubstituted or substituted independently with one to four Y,
9) —V—($C_6$-$C_{14}$)-aryl, in which aryl is unsubstituted or substituted independently with one to four Y,
10) —V-(three- to fifteen-membered heterocyclic ring), in which (three- to fifteen-membered heterocyclic ring) is unsubstituted or substituted independently with one to four Y, R2 is independently selected from hydrogen atom, —C(O)—R6, —C(O)—O—R6, —C(O)—NH—R6, —C(O)—N(R6)$_2$, —P(O)(OR6)$_2$ or —($C_1$-$C_6$)-alkyl, in which R6 is independently selected from hydrogen atom, —($C_1$-$C_6$)-alkyl, —($C_3$-$C_8$)-cycloalkyl, —($C_6$-$C_{14}$)-aryl or three- to fifteen-membered heterocyclic ring, R3 is independently selected from absent, hydrogen atom or —($C_1$-$C_4$)-alkyl, R4 is
1) —($C_6$-$C_{14}$)-aryl-Z, in which Z is a basic nitrogen-containing group and in which aryl is unsubstituted or substituted independently with one to four Y,
2) —($C_3$-$C_{12}$)-cycloalkyl-Z, in which Z is a basic nitrogen-containing group and in which cycloalkyl is unsubstituted or substituted independently with one to four Y,
3) -(three- to fifteen-membered heterocyclic ring)-Z, in which Z is a basic nitrogen-containing group and in which (three- to fifteen-membered heterocyclic ring) is unsubstituted or additionally substituted independently with one to four Y,
4) -(three- to fifteen-membered heterocyclic ring)-U-(three- to fifteen-membered heterocyclic ring)-Z, in which Z is a basic nitrogen-containing group and in which the two (three- to fifteen-membered heterocyclic ring) radicals in each case independently of one another are unsubstituted or additionally substituted independently with one to four Y,
5) —($C_6$-$C_{14}$)-aryl, in which aryl is unsubstituted or substituted independently with one to four Y,
6) —($C_3$-$C_{12}$)-cycloalkyl, in which cycloalkyl is unsubstituted or substituted independently with one to four Y,
7) -(three- to fifteen-membered heterocyclic ring), in which heterocyclic ring is unsubstituted or substituted independently with one to four Y,
8) -(three- to fifteen-membered heterocyclic ring)-U-(three- to fifteen-membered heterocyclic ring), in which the two (three- to fifteen-membered heterocyclic ring) radicals in each case independently of one another are unsubstituted or substituted independently with one to four Y, R5 is
1) halogen,
2) —($C_1$-$C_6$)-alkyl, in which alkyl is unsubstituted or substituted independently with one to four —($C_1$-$C_3$)-haloalkyl, —N—C(O)—OH or —N—C(O)—($C_1$-$C_4$)-alkyl,
3) —($C_1$-$C_3$)-haloalkyl,
4) —($C_3$-$C_8$)-cycloalkyl,
5) —OH,
6) —O—($C_1$-$C_4$)-alkyl,
7) —O—($C_1$-$C_3$)-haloalkyl,
8) —NO$_2$,
9) —CN,
10) —N(R7)(R8),
11) —C(O)—NH—R7,
12) —NH—C(O)—R7,
13) —NH—SO$_2$—R7,
14) —SO$_2$—($C_1$-$C_4$)-alkyl,
15) —SO$_2$—NH—R7,
16) —SO$_2$—($C_1$-$C_3$)-haloalkyl,
17) —S—($C_1$-$C_4$)-alkyl or
18) —S—($C_1$-$C_3$)-haloalkyl,
19) =O
in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl, U is independently selected from a covalent bond, —($C_1$-$C_4$)-alkylene, —NH—, —N((($C_1$-$C_4$)-alkyl)-, —O—, —SO$_2$— or —S—,
in which —($C_1$-$C_4$)-alkylene or —($C_1$-$C_4$)-alkyl is unsubstituted or substituted independently with one to four T, or substituted geminal hydrogens by ($C_3$-$C_8$)-cycloalkyl to form a spiro cyclic ring, V is independently selected from —($C_1$-$C_4$)-alkylene, —SO$_2$—, —C(O)—, —C(O)—NH— and —SO$_2$—NH—,
in which carbon atom or sulfur atom of —C(O)—NH— and —SO$_2$—NH— is connected to a nitrogen atom of the morpholinone ring,
in which —($C_1$-$C_4$)-alkylene is unsubstituted or substituted independently with one to four T,
or substituted geminal hydrogens by ($C_3$-$C_8$)-cycloalkyl to form a spiro cyclic ring, T is
1) halogen,
2) —($C_1$-$C_6$)-alkyl, in which alkyl is unsubstituted or substituted independently with one to four substituents selected from OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
3) —($C_1$-$C_3$)-haloalkyl,
4) —($C_3$-$C_8$)-cycloalkyl,
5) —OH,
6) —O—($C_1$-$C_4$)-alkyl, in which alkyl is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
7) —O—($C_1$-$C_3$)-haloalkyl,
8) —NO$_2$,
9) —CN,
10) —N(R7)(R8),
11) —C(O)—NH—R7,
12) —NH—C(O)—R7,
13) —NH—SO$_2$—R7,
14) —SO$_2$—($C_1$-$C_4$)-alkyl,
15) —SO$_2$—NH—R7,
16) —SO$_2$—($C_1$-$C_3$)-haloalkyl,
17) —S—($C_1$-$C_4$)-alkyl,
18) —S—($C_1$-$C_3$)-haloalkyl,
19) —($C_1$-$C_6$)-alkyl-N(R7)(R8),
20) —NH—C(O)—N(R7)(R8), 21) =O
22) —C(O)OR7
in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl,
W is independently selected from oxygen atom, nitrogen atom or carbon atom,
X is independently selected from nitrogen atom, carbon atom or oxygen atom,
Y is
1) halogen,
2) —($C_1$-$C_6$)-alkyl,
3) —($C_1$-$C_3$)-haloalkyl,
4) —($C_3$-$C_8$)-cycloalkyl,
5) —OH,
6) —O—($C_1$-$C_4$)-alkyl, in which alkyl is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
7) —O—($C_1$-$C_3$)-haloalkyl,
8) —$NO_2$,
9) —CN,
10) —N(R7)(R8),
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-haloalkyl,
17) —S—($C_1$-$C_4$)-alkyl,
18) —S—($C_1$-$C_3$)-haloalkyl,
19) —($C_1$-$C_6$)-alkyl-N(R7)(R8),
20) —NH—C(O)—N(R7)(R8),
21) =O
22) —NH—C(O)—($C_1$-$C_4$)-alkyl-O—($C_1$-$C_4$)-alkyl-($C_6$-$C_{14}$)-aryl, in which aryl is unsubstituted or substituted independently with one to four Y (selected from (1) to (21)),
23) —NH—C(O)—($C_1$-$C_4$)-alkyl-O—($C_1$-$C_4$)-alkyl-(three- to fifteen-membered heterocyclic ring), in which -(three- to fifteen-membered heterocyclic ring) is unsubstituted or substituted independently with one to four Y (selected from (1) to (21)),
in which —($C_1$-$C_4$)-alkyl or —($C_1$-$C_6$)-alkyl of 2), 6), 10), 14), 17), 19), 22) or 23) is unsubstituted or substituted independently with one to four T, in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl,
T is
1) halogen,
2) —($C_1$-$C_6$)-alkyl, in which alkyl is unsubstituted or substituted independently with one to four substituents selected from OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
3) —($C_1$-$C_3$)-haloalkyl,
4) —($C_3$-$C_8$)-cycloalkyl,
5) —OH,
6) —O—($C_1$-$C_4$)-alkyl, in which alkyl is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
7) —O—($C_1$-$C_3$)-haloalkyl,
8) —$NO_2$,
9) —CN,
10) —N(R7)(R8),
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-haloalkyl,
17) —S—($C_1$-$C_4$)-alkyl,
18) —S—($C_1$-$C_3$)-haloalkyl,
19) —($C_1$-$C_6$)-alkyl-N(R7)(R8),
20) —NH—C(O)—N(R7)(R8),
21) =O
22) —C(O)OR7
in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl,
m is 0 or 1,
n is 0, 1, 2, 3 or 4,
the linkage between Oxygen atom and Nitrogen atom of the substructure (II)

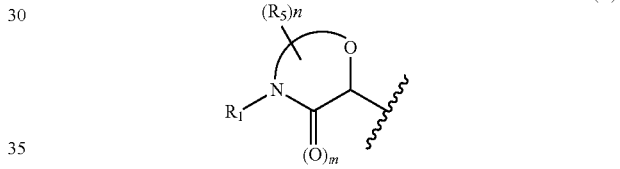

in Formula (I) describes one to four carbon atoms, which is unsubstituted or substituted independently with one to four R5,
the dotted linkage between W and R4 of the substructure (III)

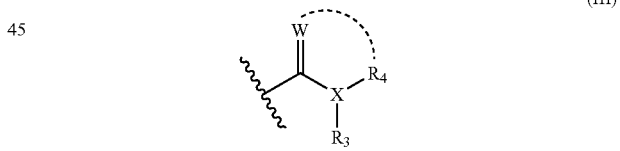

in Formula (I) is
1) absent,
2) attached to form (three- to fifteen-membered heterocyclic ring)-Z as a whole of the substructure (III), in which Z is a basic nitrogen-containing group and in which (three- to fifteen-membered heterocyclic ring) is unsubstituted or additionally substituted independently with one to four Y,
3) attached to form (three- to fifteen-membered heterocyclic ring)-U-(three- to fifteen-membered heterocyclic ring)-Z as a whole of the substructure (III), in which Z is a basic nitrogen-containing group and in which the two (three- to fifteen-membered heterocyclic ring) radicals in each case independently of one another are unsubstituted or additionally substituted independently with one to four Y, 4) attached to form (three- to fifteen-membered heterocyclic ring) as a whole of the substructure (III), in which (three- to fifteen-membered heterocyclic ring) is unsubstituted or substituted independently with one to four Y,
5) attached to form (three- to fifteen-membered heterocyclic ring)-U-(three- to fifteen-membered heterocyclic ring), as a whole of the substructure (III), in which the two (three- to fifteen-membered heterocyclic ring) radicals in each case independently of one another are unsubstituted or substituted independently with one to four Y.

In another aspect, the present invention relates to a compound of Formula (I)-(C)

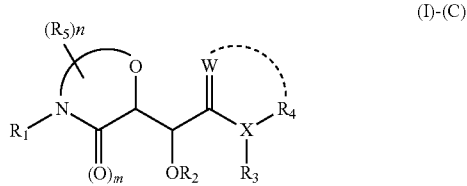

or a pharmaceutically acceptable salt or solvate thereof;
wherein:
R1 is
1) $(C_6-C_{14})$-aryl, in which aryl is unsubstituted or substituted independently with one to four Y,
2) four- to fifteen-membered heterocyclic ring, in which ring is unsubstituted or substituted independently with one to four Y,
3) $(C_6-C_{14})$-aryl-U—$(C_6-C_{14})$-aryl, in which the two aryls in each case independently of one another are unsubstituted or substituted independently with one to four Y,
4) $(C_6-C_{14})$-aryl-U—$(C_3-C_{12})$-cycloalkyl, in which aryl and cycloalkyl in each case independently of one another are unsubstituted or substituted independently with one to four Y,
5) $(C_6-C_{14})$-aryl-U-(four- to fifteen-membered heterocyclic ring), in which aryl and (four- to fifteen-membered heterocyclic ring) in each case independently of one another are unsubstituted or substituted independently with one to four Y,
6) (four- to fifteen-membered heterocyclic ring)-U—$(C_6-C_{14})$-aryl, in which aryl and (four- to fifteen-membered heterocyclic ring) in each case independently of one another are unsubstituted or substituted independently with one to four Y,
7) (four- to fifteen-membered heterocyclic ring)-U-(four- to fifteen-membered heterocyclic ring), in which the two heterocyclic ring radicals in each case independently of one another are unsubstituted or substituted independently with one to four Y,
8) —V—$(C_6-C_{14})$-aryl, in which aryl is unsubstituted or substituted independently with one to four Y,
9) —V-(four- to fifteen-membered heterocyclic ring), in which (four- to fifteen-membered heterocyclic ring) is unsubstituted or substituted independently with one to four Y,
R2 is hydrogen atom, —C(O)—R6, —C(O)—O—R6, —C(O)—NH—R6, —P(O)(OR6)$_2$ or —$(C_1-C_4)$-alkyl, in which
R6 is —$(C_1-C_6)$-alkyl, —$(C_3-C_8)$-cycloalkyl, —$(C_6-C_{14})$-aryl or four- to fifteen-membered heterocyclic ring,
R3 is hydrogen atom or —$(C_1-C_4)$-alkyl,
R4 is
1) —$(C_6-C_{14})$-aryl-Z, in which Z is a basic nitrogen-containing group and in which aryl is unsubstituted or substituted independently with one to four Y,
2) —$(C_3-C_{12})$-cycloalkyl-Z, in which Z is a basic nitrogen-containing group and in which cycloalkyl is unsubstituted or substituted independently with one to four Y,
3) (four- to fifteen-membered heterocyclic ring)-Z, in which Z is a basic nitrogen-containing group and in which (four- to fifteen-membered heterocyclic ring) is unsubstituted or additionally substituted independently with one to four Y,
4) (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
5) —$(C_6-C_{14})$-aryl, in which aryl is unsubstituted or substituted independently with one to four Y,
6) —$(C_3-C_{12})$-cycloalkyl, in which cycloalkyl is unsubstituted or substituted independently with one to four Y,
7) A four- to fifteen-membered heterocyclic ring, in which heterocyclic ring is unsubstituted or substituted independently with one to four Y,
8) (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y,
R5 is
1) halogen,
2) —$(C_1-C_6)$-alkyl, in which alkyl is unsubstituted or substituted independently with one to four —$(C_1-C_3)$-fluoroalkyl, —N—C(O)—OH or —N—C(O)—$(C_1-C_4)$-alkyl,
3) —$(C_1-C_3)$-fluoroalkyl,
4) —$(C_3-C_8)$-cycloalkyl,
5) —OH,
6) —O—$(C_1-C_4)$-alkyl,
7) —O—$(C_1-C_3)$-fluoroalkyl,
8) —NO$_2$,
9) —CN,
10) —N(R7)(R8), in which R7 and R8 independently of one another are a hydrogen atom, —$(C_3-C_8)$-cycloalkyl, halogen or —$(C_1-C_6)$-alkyl, in which —$(C_1-C_6)$-alkyl is optionally substituted with OH,
11) —C(O)—NH—R7,
12) —NH—C(O)—R7,
13) —NH—SO$_2$—R7,
14) —SO$_2$—$(C_1-C_4)$-alkyl,
15) —SO$_2$—NH—R7,
16) —SO$_2$—$(C_1-C_3)$-fluoroalkyl,
17) —S—$(C_1-C_4)$-alkyl or
18) —S—$(C_1-C_3)$-fluoroalkyl,
U is a covalent bond, —$(C_1-C_4)$-alkylene, —NH—, —N(($C_1-C_4$)-alkyl)-, —O—, —SO$_2$— or —S—,
V is —$(C_1-C_4)$-alkylene, —SO$_2$—, —C(O)—NH— and —SO$_2$—NH—,
W is oxygen atom, nitrogen atom or carbon atom,
X is nitrogen atom, carbon atom or oxygen atom,
Y is
1) halogen,
2) —$(C_1-C_6)$-alkyl, in which alkyl is unsubstituted or substituted independently with one to four —$(C_1-C_3)$-fluoroalkyl, —N—C(O)—OH or —N—C(O)—$(C_1-C_4)$-alkyl, 3) —(C$_1$-C$_3$)-fluoroalkyl,
4) —(C$_3$-C$_8$)-cycloalkyl,
5) —OH,
6) —O—(C$_1$-C$_4$)-alkyl, in which alkyl is unsubstituted or mono substituted with OH,
7) —O—(C$_1$-C$_3$)-fluoroalkyl,
8) —NO$_2$,
9) —CN,
10) —N(R7)(R8), in which R7 and R8 independently of one another are a hydrogen atom, —(C$_3$-C$_8$)-cycloalkyl, halogen or —(C$_1$-C$_6$)-alkyl,
11) —C(O)—NH—R7,
12) —NH—C(O)—R7,
13) —NH—SO$_2$—R7,
14) —SO$_2$—(C$_1$-C$_4$)-alkyl,
15) —SO$_2$—NH—R7,
16) —SO$_2$—(C$_1$-C$_3$)-fluoroalkyl,
17) —S—(C$_1$-C$_4$)-alkyl or
18) —S—(C$_1$-C$_3$)-fluoroalkyl,
19) —(C$_1$-C$_6$)-alkyl-N(R7)(R8),
m is 0 or 1,
n is 0 to 4,

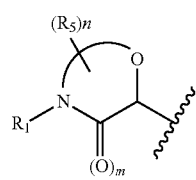

(II)

the linkage between Oxygen atom and Nitrogen atom of the substructure (II) describes one to four carbon atoms, which is unsubstituted or substituted independently with one to four R5,

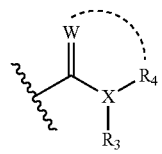

(III)

the linkage between W and R4 of the substructure (III) is
1) absent,
2) attached to form (four- to fifteen-membered heterocyclic ring)-Z, in which Z is a basic nitrogen-containing group and in which (four- to fifteen-membered heterocyclic ring) is unsubstituted or additionally substituted independently with one to four Y,
3) attached to form (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
4) attached to form (four- to fifteen-membered heterocyclic ring) in which (four- to fifteen-membered heterocyclic ring) is unsubstituted or substituted independently with one to four Y,
5) attached to form (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y,
wherein,
each nitrogen atom of Z in Formula (I) is unsubstituted or substituted independently with —OH, —O—(C$_1$-C$_4$)-alkyl group, —(CO)—(C$_1$-C$_4$)-alkyl, or —O(CO)—(C$_1$-C$_4$)-alkyl group.

In another aspect, the present invention relates to a compound of Formula (I)-(D)

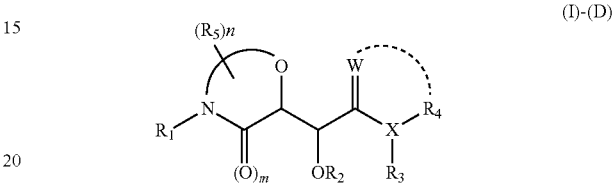

(I)-(D)

or a pharmaceutically acceptable salt or solvate thereof;
wherein:
R1 is
1) (C$_6$-C$_{14}$)-aryl, in which aryl is unsubstituted or substituted independently with one to four Y,
2) four- to fifteen-membered heterocyclic ring, in which ring is unsubstituted or substituted independently with one to four Y,
3) (C$_6$-C$_{14}$)-aryl-U—(C$_6$-C$_{14}$)-aryl, in which the two aryls in each case independently of one another are unsubstituted or substituted independently with one to four Y,
4) (C$_6$-C$_{14}$)-aryl-U—(C$_3$-C$_{12}$)-cycloalkyl, in which aryl and cycloalkyl in each case independently of one another are unsubstituted or substituted independently with one to four Y,
5) (C$_6$-C$_{14}$)-aryl-U-(four- to fifteen-membered heterocyclic ring), in which aryl and (four- to fifteen-membered heterocyclic ring) in each case independently of one another are unsubstituted or substituted independently with one to four Y,
6) (four- to fifteen-membered heterocyclic ring)-U—(C$_6$-C$_{14}$)-aryl, in which aryl and (four- to fifteen-membered heterocyclic ring) in each case independently of one another are unsubstituted or substituted independently with one to four Y,
7) (four- to fifteen-membered heterocyclic ring)-U-(four- to fifteen-membered heterocyclic ring), in which the two heterocyclic ring radicals in each case independently of one another are unsubstituted or substituted independently with one to four Y,
8) —V—(C$_6$-C$_{14}$)-aryl, in which aryl is unsubstituted or substituted independently with one to four Y,
9) —V-(four- to fifteen-membered heterocyclic ring), in which (four- to fifteen-membered heterocyclic ring) is unsubstituted or substituted independently with one to four Y,
R2 is hydrogen atom, —C(O)—R6, —C(O)—O—R6, —C(O)—NH—R6, —P(O)(OR6)$_2$ or —(C$_1$-C$_4$)-alkyl, in which
R6 is —(C$_1$-C$_6$)-alkyl, —(C$_3$-C$_8$)-cycloalkyl, —(C$_6$-C$_{14}$)-aryl or four- to fifteen-membered heterocyclic ring,
R3 is hydrogen atom or —(C$_1$-C$_4$)-alkyl, R4 is
1) —($C_6$-$C_{14}$)-aryl-Z, in which Z is a basic nitrogen-containing group and in which aryl is unsubstituted or substituted independently with one to four Y,
2) —($C_3$-$C_{12}$)-cycloalkyl-Z, in which Z is a basic nitrogen-containing group and in which cycloalkyl is unsubstituted or substituted independently with one to four Y,
3) (four- to fifteen-membered heterocyclic ring)-Z, in which Z is a basic nitrogen-containing group and in which (four- to fifteen-membered heterocyclic ring) is unsubstituted or additionally substituted independently with one to four Y,
4) (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
5) —($C_6$-$C_{14}$)-aryl, in which aryl is unsubstituted or substituted independently with one to four Y,
6) —($C_3$-$C_{12}$)-cycloalkyl, in which cycloalkyl is unsubstituted or substituted independently with one to four Y,
7) A four- to fifteen-membered heterocyclic ring, in which heterocyclic ring is unsubstituted or substituted independently with one to four Y,
8) (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y, R5 is
1) halogen,
2) —($C_1$-$C_6$)-alkyl, in which alkyl is unsubstituted or substituted independently with one to four —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_8$)-cycloalkyl,
5) —OH,
6) —O—($C_1$-$C_4$)-alkyl,
7) —O—($C_1$-$C_3$)-fluoroalkyl,
8) —$NO_2$,
9) —CN,
10) —N(R7)(R8), in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH,
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-fluoroalkyl,
17) —S—($C_1$-$C_4$)-alkyl or
18) —S—($C_1$-$C_3$)-fluoroalkyl, U is a covalent bond, —($C_1$-$C_4$)-alkylene, —NH—, —N(($C_1$-$C_4$)-alkyl)-, —O—, —$SO_2$— or —S—,
V is —($C_1$-$C_4$)-alkylene, —$SO_2$—, —C(O)—NH— and —$SO_2$—NH—,
W is nitrogen atom or carbon atom,
X is nitrogen atom, carbon atom or oxygen atom,
Y is
1) halogen,
2) —($C_1$-$C_6$)-alkyl, in which alkyl is unsubstituted or substituted independently with one to four —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_8$)-cycloalkyl,
5) —OH,
6) —O—($C_1$-$C_4$)-alkyl, in which alkyl is unsubstituted or mono substituted with OH,
7) —O—($C_1$-$C_3$)-fluoroalkyl,
8) —$NO_2$,
9) —CN,
10) —N(R7)(R8), in which R7 and R8 independently of one another are a hydrogen atom, —($C_3$-$C_8$)-cycloalkyl, halogen or —($C_1$-$C_6$)-alkyl,
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-fluoroalkyl,
17) —S—($C_1$-$C_4$)-alkyl or
18) —S—($C_1$-$C_3$)-fluoroalkyl,
19) —($C_1$-$C_6$)-alkyl-N(R7)(R8), M is 0 or 1,
n is 0 to 4,

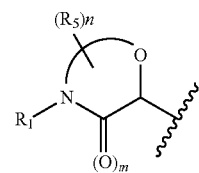

(II)

the linkage between Oxygen atom and Nitrogen atom of the substructure (II) describes one to four carbon atoms, which is unsubstituted or substituted independently with one to four R5,

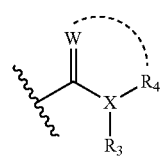

(III)

the linkage between W and R4 of the substructure (III) is
1) absent,
2) attached to form (four- to fifteen-membered heterocyclic ring)-Z, in which Z is a basic nitrogen-containing group and in which (four- to fifteen-membered heterocyclic ring) is unsubstituted or additionally substituted independently with one to four Y,
3) attached to form (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
4) attached to form (four- to fifteen-membered heterocyclic ring) in which (four- to fifteen-membered heterocyclic ring) is unsubstituted or substituted independently with one to four Y,
5) attached to form (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y, wherein, each nitrogen atom of Z in Formula (I) is unsubstituted or substituted independently with —OH, —O—($C_1$-$C_4$)-alkyl group, —(CO)—($C_1$-$C_4$)-alkyl, or —O(CO)—($C_1$-$C_4$)-alkyl group.

In another aspect, compounds of the Formula (I), or (I)(A)-(I)(D) or a pharmaceutical acceptable salt or a solvate thereof can be useful for treating or preventing a disorder or disease mediated by factor IXa, or a thromboembolic disorder (each disorder being a "Condition").

In another aspect, the present invention provides pharmaceutical compositions comprising at least one compound of the Formula (I) or (I)(A)-(I)(D) or a pharmaceutically acceptable carrier. The composition can be useful for treating or preventing a Condition.

In another aspect, the present invention provides a method for treating a Condition, the method comprising administering to a patient an effective amount of at least one compound of Formula (I) or (I)(A)-(I)(D) or a pharmaceutically acceptable salt or a solvate thereof.

DETAILED DESCRIPTION OF THE INVENTION

In an embodiment, the present invention provides compounds of Formula (I) or (I)(A)-(I)(D) and/or pharmaceutically acceptable salts, solvates and prodrugs thereof. The compounds of Formula (I) or (I)(A)-(I)(D) can be useful for treating or preventing a Condition in a patient.

As used above, and throughout this disclosure, the following terms, unless otherwise indicated, shall be understood to have the following meanings: the linkage between G atom and Nitrogen atom of the substructure (II)

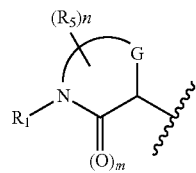

(II)

in Formula (I) comprises one to four carbon atoms to form alkylene chain, wherein said alkylene chain or G (imino or methylene) is unsubstituted or substituted independently with one to four R5, the dotted linkage between W and R4 of the substructure (III)

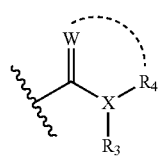

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

When the substructure (III) denotes the oxazole-Z as a whole, for example, W represents nitrogen atom, X represents oxygen atom and R3 represents absent and R4 and the dotted line represents ethylene carbon atoms, one of which is substituted with —Z, to form oxazole as a whole.

The term "($C_a$-$C_b$)-alkyl", in which a and b is each independently integers representing 1 to 6, is understood as meaning hydrocarbon radicals whose carbon chain are each straight-chain or branched and contains a to b carbon atoms, for example methyl, ethyl, propyl, isopropyl, butyl, isobutyl, tertiary-butyl, pentyl, isopentyl, neopentyl, hexyl, 2,3-dimethylbutyl or neohexyl.

The term "—($C_0$-$C_4$)-alkylene" is understood as meaning a bond or hydrocarbon radicals whose carbon chain is straight-chain or branched and contains 1 to 4 carbon atoms, for example methylene, ethylene, propylene, isopropylene, isobutylene, butylene or tertiary-butylene. "—$C_0$-alkylene" is a covalent bond. The term "—($C_1$-$C_4$)-alkylene" is understood as meaning hydrocarbon radicals whose carbon chain is straight-chain or branched and contains 1 to 4 carbon atoms, for example methylene (—$CH_2$—), ethylene (—$CH_2$—$CH_2$—), (—$CH_2(CH_3)$—), propylene (—$CH_2$—$CH_2$—$CH_2$—), isopropylene, isobutylene, butylene or tertiary-butylene.

The term "—($C_3$-$C_{12}$)-cycloalkyl" is understood as meaning rings of 3 to 12 carbon atoms such as compounds which partially have monocycles having 3 to 8 carbon atoms in the ring such as cyclopropane, cyclobutane, cyclopentane, cyclohexane, cycloheptane or cyclooctane, which are derived from the bicycles bicyclo[4.2.0]octane, octahydroindene, decahydronaphthalene, decahydroazulene, decahydrobenzocycloheptene or dodecahydroheptalene or from the bridged cycles such as spiro[2.5]octane, spiro[3.4]octane, spiro[3.5]nonane, bicyclo[3.1.1]heptane, bicyclo[2.2.1]heptane or bicyclo[2.2.2]octane.

The term "—($C_3$-$C_8$)-cycloalkyl" is understood as meaning radicals which are derived from monocycles having 3 to 8 carbon atoms in the ring such as cyclopropane, cyclobutane, cyclopentane, cyclohexane, cyclo-heptane or cyclooctane.

The term "—($C_6$-$C_{14}$)-aryl" is understood as meaning aromatic hydrocarbon radicals having 6 to 14 carbon atoms in the ring. —($C_6$-$C_{14}$)-aryl radicals are, for example, phenyl, 1-naphthyl, 2-naphthyl, anthryl or fluorenyl. Naphthyl radicals and in particular phenyl radicals are preferred aryl radicals.

The term "three- to fifteen-membered heterocyclic ring" is understood as meaning ring systems having 3 to 15 carbon atoms, which are present in one, two or three ring systems connected to one another and in which one, two, three or four identical or different heteroatoms from the group consisting of oxygen, nitrogen or sulfur can replace the respective carbon atoms.

One of the examples of "three- to fifteen-membered heterocyclic ring" is a bicyclic ring system represented by Formula (a):
In the bicyclic ring system represented by Formula (a);

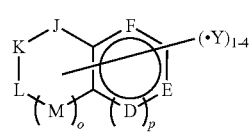

Formula (a)

wherein Formula (a) is unsubstituted or substituted independently with one to four Y;
and wherein:
o and p are independently selected from 0 or 1;
J, K, L and M are independently selected from the group consisting of CH2, C(O), NH, O and S(O)$_q$, wherein q is 0, 1 or 2;
D, E and F are independently selected from the group consisting of carbon atom, nitrogen atom, oxygen atom and sulfur atom.

Examples of three- to fifteen-membered heterocyclic ring are the radicals acridinyl, azepinyl, azetidinyl, aziridinyl, benzimidazolinyl, benzimidazolyl, benzisoxazole, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4H-carbazolyl, carbolinyl, beta-carbolinyl, chromanyl, chromenyl, cinnolinyl, deca-hydroquinolinyl, dibenzofuranyl, dibenzothiophenyl, dihydrofuran [2,3-b]-tetrahydrofuranyl, dihydrofuranyl, 1,1-dioxido-2H-1,2,4-benzothiadiazinyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxiranyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, pyrrolyl, 2H-pyrrolyl, quinazolinyl, quinolinyl, quinolizinyl, 4H-quinolizinyl, quinoxalinyl, quinuclidinyl, tetrahydrofuranyl, tetrahydroisoquinolinyl, tetrahydroquinolinyl, tetrahydropyridinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl, xanthenyl, oxindolyl, benzimidazolinyl, benzoxalonyl, 1,3-dihydro-benzisothiazolyl, 3,4-dihydro-2,3-benzothiazinyl, 2,3-dihydro-isoindolyl, 1,4-dihydro-isoquinolinonyl, 3,4-dihydro-quinolinonyl or 3,4-dihydro-benzothiadiazinyl.

The term "—($C_1$-$C_3$)-haloalkyl" is understood as meaning a partially or completely fluorinated or chlorinated alkyl radical which is selected, for example, from the following radical —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, $CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "halogen" is understood as meaning fluorine, chlorine, bromine or iodine; fluorine, chlorine or bromine is preferred, in particular fluorine or chlorine is preferred.

The term "a basic nitrogen-containing group" is understood as meaning radicals where the conjugated acid of this group has a pKa of approximately 5 to 15, and preferably 7 to 12, of which nitrogen group can be optionally substituted by one or two the same or different ($C_1$-$C_6$) alkyl group.

Examples of this basic nitrogen-containing group are amino, imino, aminomethyl, amidino (carbamidoyl), guanidino, azetidinyl, pyrrolidinyl, piperidinyl, pyridinyl or aminopyridinyl, and any of the nitrogen atom of these basic nitrogen-containing group can be substituted independently with one or two ($C_1$-$C_3$)-alkyl group.

Examples of —($C_6$-$C_{14}$)-aryl-Z, wherein Z is a basic nitrogen-containing group and wherein —($C_6$-$C_{14}$)-aryl is unsubstituted or substituted independently with one to four Y, are amidino phenyl (preferably 4-amidino phenyl), amidino chloro phenyl (preferably 4-amidino-2-chloro phenyl), amidino fluoro phenyl (preferably 4-amidino-2-fluoro-phenyl or 4-amidino-3-fluoro-phenyl), amidino methyl phenyl (preferably 4-amidino-2-methyl-phenyl), and aminomethyl phenyl (preferably 4-aminomethyl phenyl).

Examples of (three- to fifteen-membered heterocyclic ring)-Z, wherein Z is a basic nitrogen-containing group and wherein (three- to fifteen-membered heterocyclic ring) is unsubstituted or additionally substituted independently with one to four Y, are 1-aminoisoquinolinyl (preferably 1-aminoisoquinolin-6-yl), 1-imino-2,3-dihydroisoindolyl (preferably 1-imino-2,3-dihydroisoindol-5-yl), 2-amino-3H-benzimidazolyl (preferably 2-amino-3H-benzimidazol-5-yl), 3-amino-benzoisoxazolyl (preferably 3-amino-benzoisoxazole-6-yl), 3-amino-indazolyl (preferably 3-amino-indazole-6-yl), 4-amino-quinazolinyl (preferably 4-amino-quinazoline-7-yl).

Examples of the substructure (III) in Formula (I),

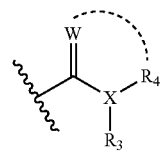

(III)

wherein the dotted linkage between W and R4 is present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y, are 6-amidino-benzimidazole-2-yl, 7-amidino-1,1-dioxo-2H-1,2,4-benzothiadiazin-3-yl.

Functional groups of the intermediates used, for example amino or carboxyl groups, can be masked here by suitable protective groups. Suitable protective groups for amino functions are, for example, para methoxy benzyl, benzyl, t-butoxycarbonyl, benzyloxycarbonyl, phthalolyl, trityl or tosyl protective group. Suitable protective groups for the carboxyl function are, for example, alkyl, aryl or arylalkyl esters. Protective groups can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme). The term protective group can also include polymer-bound protective groups. Such masked compounds according to Formula (I) or (I)(A)-(I)(D), in which, for example, the functional groups of the radicals R1, R2, R3 or R4 can optionally also be masked, can, although optionally themselves not pharmacologically active, optionally be converted after administration to mammals by metabolization to the pharmacologically active compounds according to the invention.

When any variable (e.g., aryl, R1, etc.) occurs more than one time in any constituent or in Formula (I) or (I)(A)-(I)(D), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

In the embodiments described below in [1-1] to [8-1] of the present invention, unless otherwise noted, R1, R2, R3, R4, R5, G, W, X, m, n or other definitions, for example, R6, R7, R8, V, Y, Z, T, U, etc in the substituents as well as D, E, F, J, K, L, M, o or p etc in the sub-Formulae, shown in the each descriptions are the same as defined above for the Formula (I) or (I)(A)-(I)(D). In the embodiments, compounds having Factor IXa antagonistic activity (determined by, for example, pharmacological examples described below: a measurement of fluorescence value using microtiter plate reader, ARVO 1420 Multilabel Counter) of 30 µM or less, preferably 1 µM or less, more preferably 100 nM or less, and the most preferably 50 nM or less in terms of an IC50 value are preferably used.

In the embodiments described in this description, "agent" or "drug" means a material which is used for improvement of disease or symptom, not only for treatment of disease or symptom.

In all the above embodiments, when the term "compound" is used, the term also refers to pharmaceutically acceptable salts thereof. The compounds of the present invention have asymmetric carbon atoms. Accordingly, the compounds of the present invention include mixtures of various stereoisomers, such as geometrical isomers, tautomers, such as keto- and enol-tautomers, or amidino- and imidino-tautomers, and optical isomers, and isolated isomers, for example, (R,R), (S,S), (R,S) and (S,R) isomers. (R,R) isomer is preferred. Specific example of (R,R) isomer compound is, for example, (2R)—N-(4-amidinophenyl)-2-hydroxy-2-[(2R)-3-oxo-4-p-tolylmorpholin-2-yl]acetamide hydrochloride (EXAMPLE 7). The isolation and the purification of such stereoisomers can be performed by those skilled in the art with a known technique such as optical resolution using preferential crystallization or column chromatography, or asymmetric synthesis.

The compounds represented by Formula (I) or (I)(A)-(I)(D) of the present invention may form acid addition salts. Alternatively, these compounds may form salts with a base according to the type of substituent. These salts are not particularly limited as long as the salts are pharmaceutically acceptable salts. Specific examples of the salts include acid addition salts with a mineral acid such as hydrochloric acid, hydrobromic acid, hydroiodic acid, sulfuric acid, nitric acid, or phosphoric acid; an organic carboxylic acid such as an aliphatic monocarboxylic acid, e.g., formic acid, acetic acid, trifluoroacetic acid (TFA), propionic acid, butyric acid, valeric acid, enanthic acid, capric acid, myristic acid, palmitic acid, stearic acid, lactic acid, sorbic acid, or mandelic acid, an aromatic monocarboxylic acid, e.g., benzoic acid or salicylic acid, an aliphatic dicarboxylic acid, e.g., oxalic acid, malonic acid, succinic acid, fumaric acid, maleic acid, malic acid, or tartaric acid, and an aliphatic tricarboxylic acid e.g., citric acid; an organic sulfonic acid such as an aliphatic sulfonic acid, e.g., methanesulfonic acid, ethanesulfonic acid, trifluoromethanesulfonic acid, or 2-hydroxyethanesulfonic acid, or an aromatic sulfonic acid, e.g., benzenesulfonic acid or p-toluenesulfonic acid; or an acidic amino acid, e.g., aspartic acid or glutamic acid; salts with a metal such as an alkali metal, e.g., sodium or potassium, or an alkaline earth metal, e.g., magnesium or calcium; salts with an organic base such as methylamine, ethylamine, ethanolamine, pyridine, lysine, arginine, or ornithine; and ammonium salts.

These salts can be obtained by a known method, for example, by mixing a compound of the present invention with an equivalent amount and a solution containing a desired acid, base, or the like, and then collecting the desired salt by filtering the salt or distilling off the solvent.

The compounds of the present invention and salts thereof can form solvates with a solvent such as water, ethanol, or glycerol.

The salts of a compound of the present invention include monosalts and di-salts. The compounds of the present invention can form an acid addition salt and a salt with a base at the same time according to the type of substituent of the side chain.

Furthermore, the present invention includes hydrates, pharmaceutically acceptable various solvates, and crystal polymorphism of the compounds represented by Formula (I) or (I)(A)-(I)(D) of the present invention. The present invention is not limited to the compounds described in examples below and includes all compounds represented by Formula (I) or (I)(A)-(I)(D) of the present invention and pharmaceutically acceptable salts thereof.

Prodrugs and solvates of the compounds of the invention are also contemplated herein. A discussion of prodrugs is provided in T. Higuchi and V. Stella, Pro-drugs as Novel Delivery Systems, 14, 1987, of the A.C.S. Symposium Series, and in Bioreversible Carriers in Drug Design, 1987, Edward B. Roche, ed., American Pharmaceutical Association and Pergamon Press. The term "prodrug" means a compound (e.g, a drug precursor) that is transformed in vivo to yield a compound of Formula (I) or (I)(A)-(I)(D) or a pharmaceutically acceptable salt, hydrate or a solvate of the compound. The transformation may occur by various mechanisms (e.g., by metabolic or chemical processes), such as, for example, through hydrolysis in blood. A discussion of the use of pro-drugs is provided by T. Higuchi and W. Stella, "Pro-drugs as Nobel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or (I)(A)-(I)(D) or a pharmaceutically acceptable salt, hydrate or a solvate of the compound contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, ($C_1-C_6$)alkoxycarbonyloxymethyl, N—($C_1-C_6$)alkoxycarbonylaminomethyl, succinoyl, ($C_1-C_6$)alkanoyl, α-amino($C_1-C_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal from of a carbohydrate), and the like.

If a compound of Formula (I) or (I)(A)-(I)(D) incorporates an amine functional group or imine functional group, for example, such as a part of amidino group, a prodrug can be formed by the replacement of a hydrogen atom of the amine group or imine group with a group such as, for example, hydroxyl group, RO—, R-carbonyl, RO-carbonyl, NRR'-carbonyl where R and R' are each independently hydrogen atom, ($C_1-C_{10}$)alkyl, ($C_3-C_7$)cycloalkyl, benzyl, or R-carbonyl is a natural α-aminoacyl or natural β-aminoacyl, —CH(OY2)Y3 wherein Y2 is ($C_1-C_4$) alkyl and Y3 is ($C_1-C_6$)alkyl, carboxy ($C_1-C_6$)alkyl, amino($C_1-C_4$)alkyl or mono-N- or di-N,N-($C_1-C_6$)alkylaminoalkyl, —CH(Y4)Y5 wherein Y4 is H or methyl and Y5 is mono-N- or di-N,N—($C_1-C_6$)alkylamino morpholino, piperidin-1-yl or pyrrolidin-1-yl and the like.

Morpholinone Compounds of the Invention

[1-1] The invention therefore relates to a compound of Formula (I)

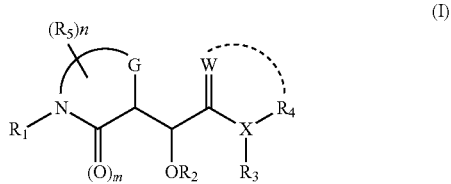

or a pharmaceutically acceptable salt or a solvate thereof;
wherein:
R1 is selected from the group consisting of:
1) —($C_6-C_{14}$)-aryl, which is unsubstituted or substituted independently with one to four Y;
2) -(three- to fifteen-membered heterocyclic ring), which is unsubstituted or substituted independently with one to four Y;
3) —($C_6-C_{14}$)-aryl-U—($C_6-C_{14}$)-aryl, wherein each of said —($C_6-C_{14}$)-aryl- independently is unsubstituted or substituted independently with one to four Y;
4) —($C_6-C_{14}$)-aryl-U—($C_3-C_{12}$)-cycloalkyl, wherein said —($C_6-C_{14}$)-aryl and —($C_3-C_{12}$)-cycloalkyl independently are unsubstituted or substituted independently with one to four Y;
5) —($C_6-C_{14}$)-aryl-U-(three- to fifteen-membered heterocyclic ring), wherein said —($C_6-C_{14}$)-aryl and said (three- to fifteen-membered heterocyclic ring) are independently unsubstituted or substituted independently with one to four Y;
6) -(three- to fifteen-membered heterocyclic ring)-U—($C_6-C_{14}$)-aryl, wherein said —($C_6-C_{14}$)-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) -(three- to fifteen-membered heterocyclic ring)-U—($C_3-C_{12}$)-cycloalkyl, wherein said —($C_3-C_{12}$)-cycloalkyl, and said -(three- to fifteen-membered heterocyclic ring)- are independently unsubstituted or substituted independently with one to four Y;
9) —V—($C_6-C_{14}$)-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —($C_1-C_6$)-alkyl, wherein
each R6 independently is selected from the group consisting of hydrogen atom, —($C_1-C_6$)-alkyl, —($C_3-C_8$)-cycloalkyl, —($C_6-C_{14}$)-aryl and a three- to fifteen-membered heterocyclic ring;

R3 is absent, or selected from the group consisting of hydrogen atom and —($C_1-C_4$)-alkyl, R4 is selected from the group consisting of:
1) —($C_6-C_{14}$)-aryl-Z, wherein said Z is a basic nitrogen-containing group and wherein said —($C_6-C_{14}$)-aryl is unsubstituted or substituted independently with one to four Y;
2) —($C_3-C_{12}$)-cycloalkyl-Z, wherein said Z is a basic nitrogen-containing group and wherein said —($C_3-C_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —($C_6-C_{14}$)-aryl, which is unsubstituted or substituted independently with one to four Y;
6) —($C_3-C_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;

each R5 independently is selected from the group consisting of:
1) halogen;
2) —($C_1-C_6$)-alkyl, which is unsubstituted or substituted independently with one to four —($C_1-C_3$)-haloalkyl, —N—C(O)—OH, —N—C(O)—($C_1-C_4$)-alkyl, or —C(O)OR7;

3) —($C_1$-$C_3$)-haloalkyl;
4) —($C_3$-$C_8$)-cycloalkyl;
5) —OH;
6) —O—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) =O (oxo);
20) —C(O)OR7; and
21) C(O)R7
  wherein each of R7 and R8 is independently selected from the group consisting of hydrogen atom, —($C_6$-$C_{14}$)-aryl, —($C_3$-$C_8$)-cycloalkyl, and —($C_1$-$C_6$)-alkyl, wherein said —($C_1$-$C_6$)-alkyl is unsubstituted or substituted with at least one substituent selected from the group consisting of OH, —O—($C_1$-$C_4$)-alkyl, —($C_1$-$C_3$)-fluoroalky, —O—($C_1$-$C_3$)-haloalkyl, C(O)OH, and C(O)O—($C_1$-$C_6$)-alkyl;
each U independently is selected from the group consisting of a covalent bond, —($C_1$-$C_4$)-alkylene, —NH—, —N(($C_1$-$C_4$)-alkyl)-, —O—, —$SO_2$— or —S—,
  wherein said —($C_1$-$C_4$)-alkylene or —($C_1$-$C_4$)-alkyl is unsubstituted or substituted independently with one to four T,
  or wherein geminal hydrogens in said —($C_1$-$C_4$)-alkylene or —($C_1$-$C_4$)-alkyl can be replaced by a ($C_3$-$C_8$)-cycloalkyl to form a spiro cyclic ring;
each V independently is selected from the group consisting of —($C_1$-$C_4$)-alkylene, —$SO_2$—, —C(O)—, —C(O)—NH— and —$SO_2$—NH—,
  wherein the carbon atom of said —C(O)—NH— or the sulfur atom of said —$SO_2$—NH— is connected to a nitrogen atom of the morpholinone ring,
  and wherein said —($C_1$-$C_4$)-alkylene is unsubstituted or substituted independently with one to four T,
  or wherein geminal hydrogens in said —($C_1$-$C_4$)-alkylene can be replaced by a ($C_3$-$C_8$)-cycloalkyl to form a spiro cyclic ring;
each T independently is selected from the group consisting of:
1) halogen;
2) —($C_1$-$C_6$)-alkyl, which is unsubstituted or substituted independently with one to four substituents selected from the group consisting of OH, —O—($C_1$-$C_4$)-alkyl, —($C_1$-$C_3$)-haloalkyl, —O—($C_1$-$C_3$)-haloalkyl, —N—C(O)—OH and —N—C(O)—($C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo); and
22) —C(O)OR7;
23) —C(O)OR7;
24) —N—C(O)—OR7
  wherein each of R7 and R8 independently is selected from the group consisting of a hydrogen atom, —($C_3$-$C_8$)-cycloalkyl, halogen and —($C_1$-$C_6$)-alkyl, wherein said —($C_1$-$C_6$)-alkyl is optionally substituted with at least one substituent selected from the group consisting of OH, —O—($C_1$-$C_4$)-alkyl, —($C_1$-$C_3$)-fluoroalky, and —O—($C_1$-$C_3$)-haloalkyl;
G is selected from the group consisting of oxygen atom, imino, sulfur atom, sulfoxide, sulfone and methylene;
W is selected from the group consisting of oxygen atom, nitrogen atom and carbon atom;
X is selected from the group consisting of nitrogen atm, carbon atom and oxygen atom;
Y is selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_6$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —N(R8)—C(O)—N(R7)(R8);
21) =O (oxo);
22) —$SF_5$;
23) —C(O)OR7;
24) —N—C(O)—OR7
25) —N(R8)—C(O)—($C_1$-$C_4$)-alkyl-O—($C_1$-$C_4$)-alkyl-($C_6$-$C_{14}$)-aryl, wherein said —($C_6$-$C_{14}$)-aryl is unsubstituted or substituted independently with one to four Y selected from (1) to (24) as set forth above;
26) —N(R8)—C(O)—($C_1$-$C_4$)-alkyl-O—($C_1$-$C_4$)-alkyl-(three- to fifteen-membered heterocyclic ring), wherein said -(three- to fifteen-membered heterocyclic ring) is unsubstituted or substituted independently with one to four Y selected from (1) to (24) as set forth above;
wherein said —($C_1$-$C_4$)-alkyl part or —($C_1$-$C_6$)-alkyl part of 2), 6), 14), 17), 19), 25) or 26) of said Y is unsubstituted or substituted independently with one to four T;
wherein each of R7 and R8 of 10), 11), 12), 13), 15), 19), 20), 23), 24), 25) or 26) of said Y independently is selected from the group consisting of hydrogen atom, —($C_3$-$C_8$)-cycloalkyl, and —($C_1$-$C_6$)-alkyl, wherein said —($C_1$-$C_6$)-alkyl is optionally substituted with OH, —O—($C_1$-$C_4$)-alkyl, —($C_1$-$C_3$)-fluoroalky, —O—($C_1$-$C_3$)-haloalkyl, —C(O)OH, or C(O)O—($C_1$-$C_6$)-alkyl;

m is 0 or 1, n is 0, 1, 2, 3 or 4, the linkage between G atom and Nitrogen atom of the substructure (II)

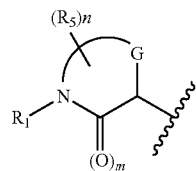
(II)

in Formula (I) comprises one to four carbon atoms to form alkylene chain, wherein said alkylene chain or G (imino or methylene) is unsubstituted or substituted independently with one to four R5;

the dotted linkage between W and R4 of the substructure (III)

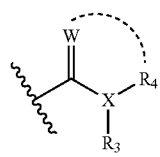
(III)

in Formula (I) is 1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

[1-2] In another aspect, the present invention provides compounds of the Formula (I), wherein m is 1 and n is 0.

[1-3] In another aspect, the present invention provides compounds of the Formula (I), wherein m is 1 and n is 1.

[1-4] In another aspect, the present invention provides compounds of the Formula (I), wherein m is 0 and n is 0.

[1-5] In another aspect, the present invention provides compounds of the Formula (I), wherein m is 0 and n is 1.

[2-1] In another aspect, the present invention provides compounds of the Formula (I), wherein Formula (II),

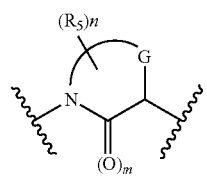
(II)

in Formula (I) is

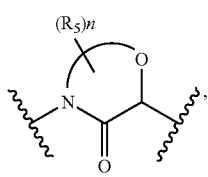
(IIa)

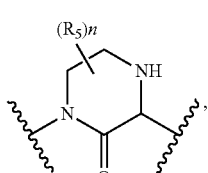
(IIb)

(IIc)
, or

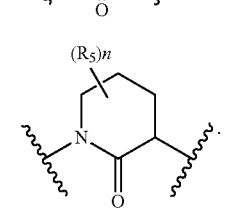
(IId)

[2-2] In another aspect, the present invention provides compounds of the Formula (I), wherein Formula (II),

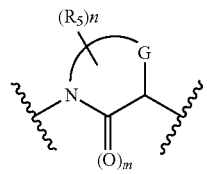
(II)

in Formula (I) is,

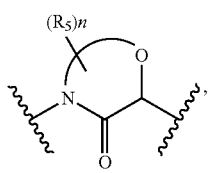
(IIa)

and preferably,

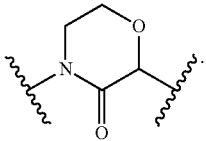

(IIa1)

[2-3] In another aspect, the present invention provides compounds of the Formula (I), wherein Formula (III),

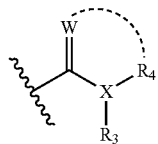

(III)

in Formula (I) is

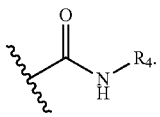

[2-4] In another aspect, the present invention provides compounds of the Formula (I'),

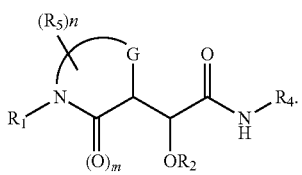

(I')

[2-5] In another aspect, the present invention provides compounds of the Formula (I"),

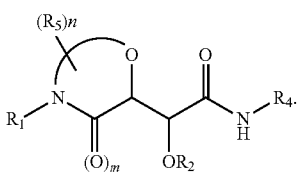

(I")

[2-6] In another aspect, the present invention provides compounds of the Formula (I'''),

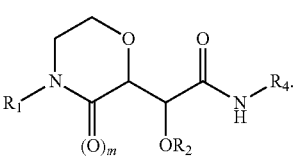

(I''')

[3-1] In another aspect, the present invention provides compounds of the Formula (I), wherein:

R1 is selected from the group consisting of:

1) —$(C_6$-$C_{14})$-aryl, which is unsubstituted or substituted independently with one to four Y;

2) -(three- to fifteen-membered heterocyclic ring), which is unsubstituted or substituted independently with one to four Y;

3) —$(C_6$-$C_{14})$-aryl-U—$(C_6$-$C_{14})$-aryl, wherein each of said —$(C_6$-$C_{14})$-aryl independently is unsubstituted or substituted independently with one to four Y;

5) —$(C_6$-$C_{14})$-aryl-U-(three- to fifteen-membered heterocyclic ring), in which said —$(C_6$-$C_{14})$-aryl and said (three- to fifteen-membered heterocyclic ring) are independently unsubstituted or substituted independently with one to four Y; and 9) —V—$(C_6$-$C_{14})$-aryl, wherein said —V—$(C_6$-$C_{14})$-aryl is unsubstituted or substituted independently with one to four Y.

[3-2] In another aspect, the present invention provides compounds of the Formula (I), wherein:

R1 is

1) —$(C_6$-$C_{14})$-aryl, which is unsubstituted or substituted independently with one to four Y

[3-3] In another aspect, the present invention provides compounds of the Formula (I), wherein:

R1 is

2) -(three- to fifteen-membered heterocyclic ring), which is unsubstituted or substituted independently with one to four Y

[3-4] In another aspect, the present invention provides compounds of the Formula (I), wherein:

R1 is

3) —$(C_6$-$C_{14})$-aryl-U—$(C_6$-$C_{14})$-aryl, wherein each of said —$(C_6$-$C_{14})$aryl independently is unsubstituted or substituted independently with one to four Y

[3-5] In another aspect, the present invention provides compounds of the Formula (I), wherein:

R1 is

5) —$(C_6$-$C_{14})$-aryl-U-(three- to fifteen-membered heterocyclic ring), in which said —$(C_6$-$C_{14})$-aryl and said (three- to fifteen-membered heterocyclic ring) are independently unsubstituted or substituted independently with one to four Y

[3-5-1] In another aspect, the present invention provides compounds of the Formula (I), wherein:

R1 is

5) —$(C_6$-$C_{14})$-aryl-U-(three- to fifteen-membered heterocyclic ring), in which said —$(C_6$-$C_{14})$-aryl and said (three- to fifteen-membered heterocyclic ring) are independently unsubstituted or substituted independently with one to four Y wherein U is a covalent bond.

[3-5-2] In another aspect, the present invention provides compounds of the Formula (I), wherein:

R1 is

5) —$(C_6$-$C_{14})$-aryl-U-(three- to fifteen-membered heterocyclic ring), in which said —$(C_6$-$C_{14})$-aryl and said (three- to fifteen-membered heterocyclic ring) are independently unsubstituted or substituted independently with one to four Y;
wherein U is methylene which is substituted with oxo to form carbonyl group (—C(O)—).

[3-6] In another aspect, the present invention provides compounds of the Formula (I), wherein:
R1 is
9) —V—($C_6$-$C_{14}$)-aryl, wherein said —V—($C_6$-$C_{14}$)-aryl is unsubstituted or substituted independently with one to four Y.

[3-7] In another aspect, the present invention provides compounds of the Formula (I), wherein R1 is a phenyl group, which is unsubstituted or substituted independently with one to four Y.

[3-8] In another aspect, the present invention provides compounds of the Formula (I), wherein said three- to fifteen-membered heterocyclic ring of R1 is represented by the Formula (a)

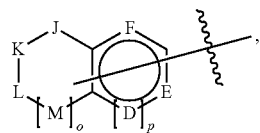

Formula (a)

wherein Formula (a) is unsubstituted or substituted independently with one to four Y; and wherein:
o and p are independently selected from 0 or 1;
J, K, L and M are independently selected from the group consisting of $CH_2$, C(O), NH, O and $S(O)_q$, wherein q is 0, 1 or 2;
D, E and F are independently selected from the group consisting of carbon atom, nitrogen atom, oxygen atom and sulfur atom.

[4-1] In another aspect, the present invention provides compounds of the Formula (I), wherein Z represents a radical whose conjugate acid has a pKa of 5 to 15.

[4-2] In another aspect, the present invention provides compounds of the Formula (I), wherein Z represents a radical whose conjugate acid has a pKa of 7 to 12.

[4-3] In another aspect, the present invention provides compounds of the Formula (I), wherein Z represents a radical selected from the group consisting of amino, imino, aminomethyl, amidino (carbamimidoyl), guanidino, azetidinyl, pyrrolidinyl, piperidinyl, pyridinyl and aminopyridinyl, and wherein any nitrogen atom of each of said aforementioned Z radicals is unsubstituted or substituted independently with one or two ($C_{1-3}$) alkyl.

[5-1] In another aspect, the present invention provides compounds of the Formula (I), wherein the substructure Formula (III)

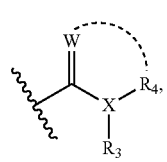

(III)

W is oxygen atom, X(R3) is NH, the dotted linkage is absent, and R4 is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y.

[5-2] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is —($C_6$-$C_{14}$)-aryl-Z, wherein Z is a basic nitrogen-containing group and wherein said —($C_6$-$C_{14}$)-aryl is unsubstituted or additionally substituted independently with one to four Y.

[5-3] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -benzimidazole-Z, wherein Z is a basic nitrogen-containing group and wherein said benzimidazole is unsubstituted or additionally substituted independently with one to four Y.

[5-4] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted independently with one to four Y.

[5-5] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_6$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)—$SO_2$—R7;

[5-6] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl; and
7) —O—($C_1$-$C_3$)-haloalkyl

[5-7] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
1) halogen;
2) —($C_1$-$C_6$)-alkyl;
3) —($C_1$-$C_3$)-haloalkyl;
4) —($C_3$-$C_8$)-cycloalkyl.

[5-8] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is 1-imino-2,3-dihydroisoindol-5-yl.

[6] In another aspect, the present invention provides compounds of combination at least two embodiments selected from aforementioned [1-1] to [5-7] as a preferable sub embodiment. For example, the compounds drawn from the combination embodiment [2-3] and [3-8] is shown with the formula:

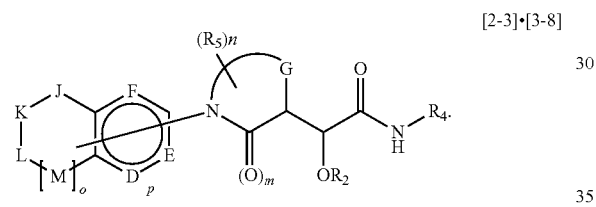

[2-3]•[3-8]

[7-1] In another aspect, the present invention provides compounds of the Formula (IV):

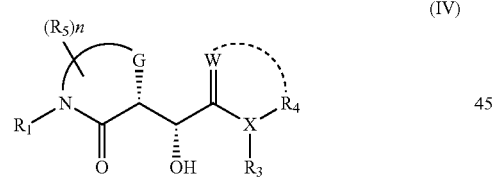

(IV)

((R,R) isomer) or a pharmaceutically acceptable salt or solvate thereof, wherein $R_1$ is a group selected from the group consisting of:

a1 a2

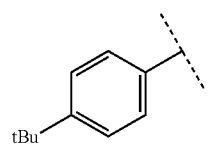

a3

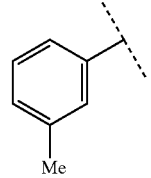

a4

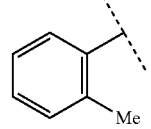

a5

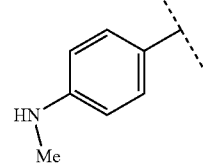

a6

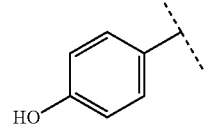

a7

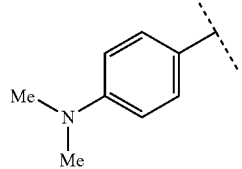

a8

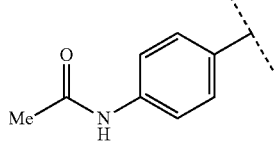

a9

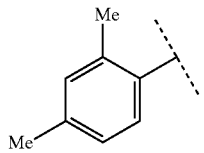

a10

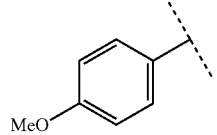

a11

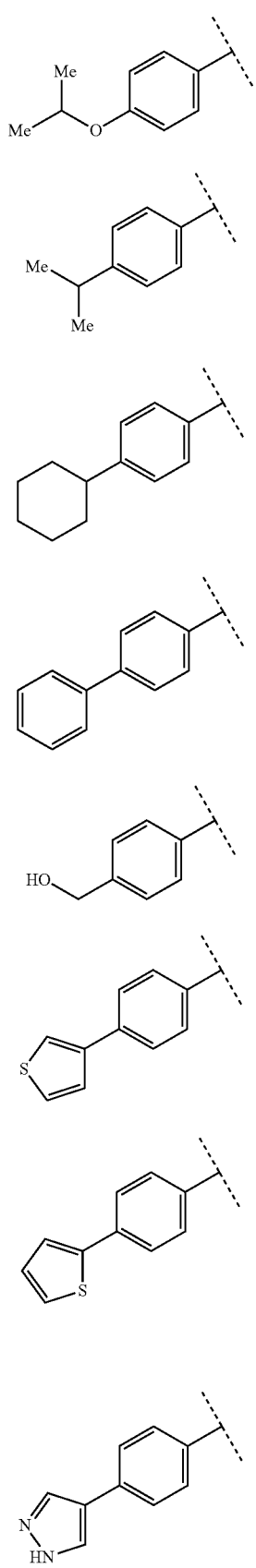
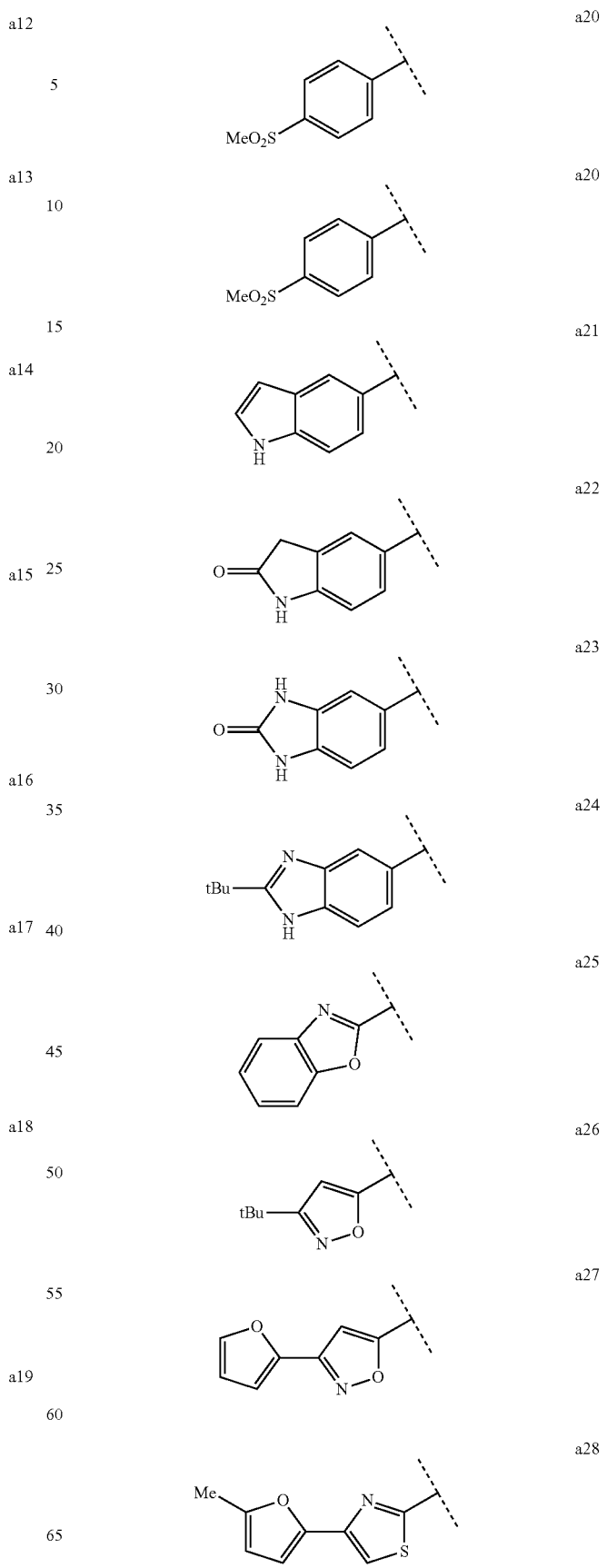

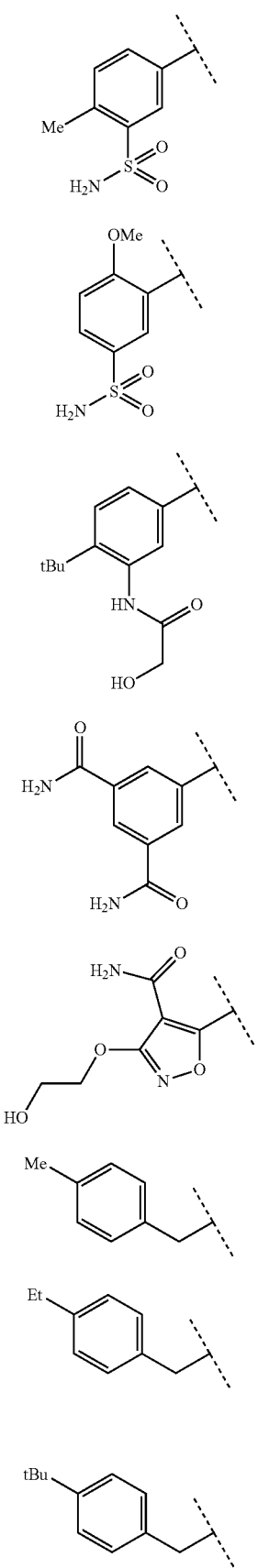
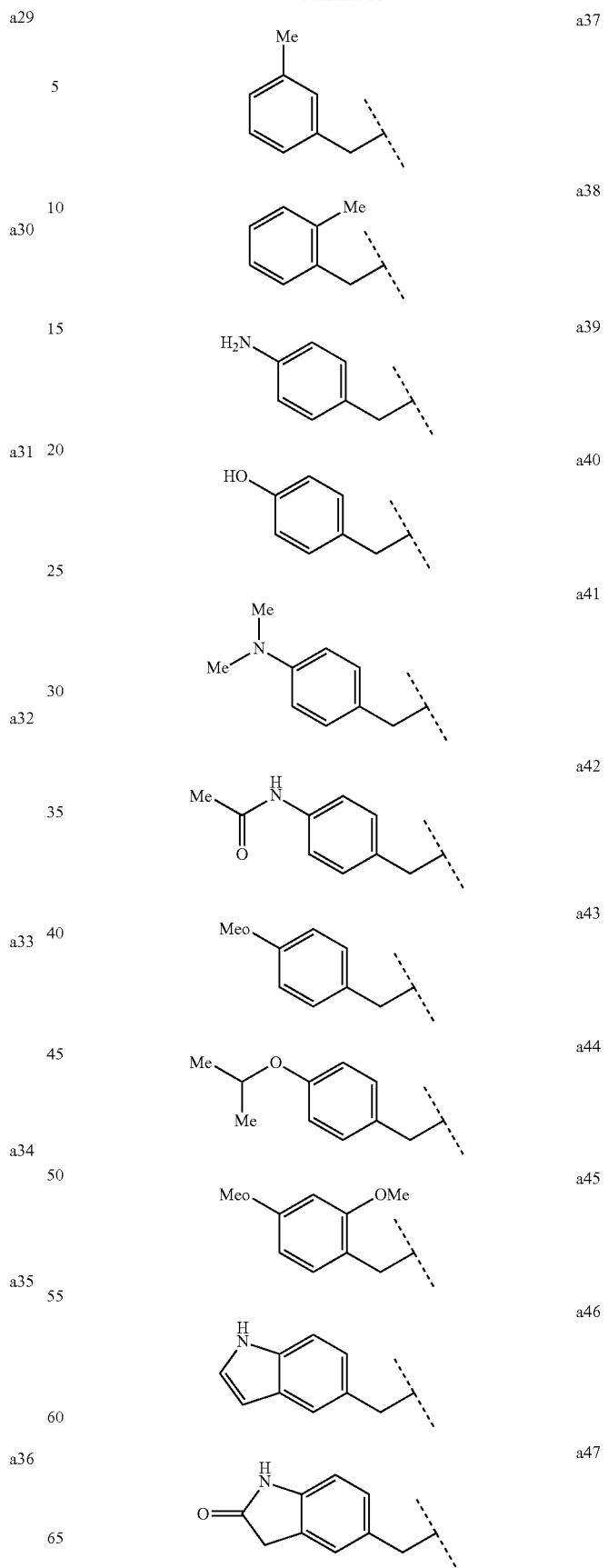

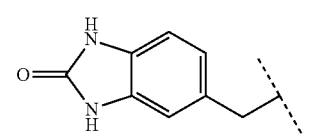 a48
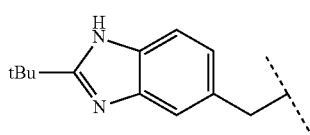 a49
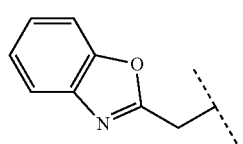 a50
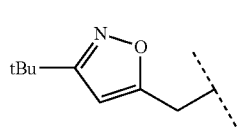 a51
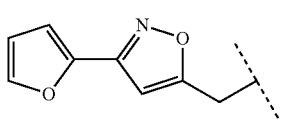 a52
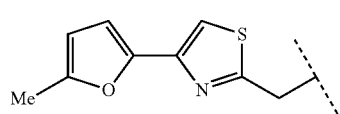 a53
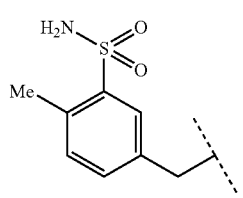 a54
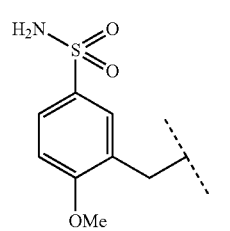 a55
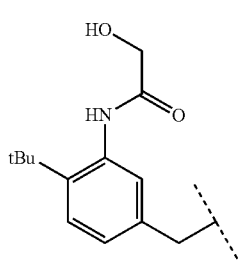 a56
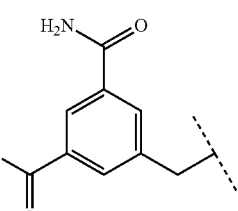 a57
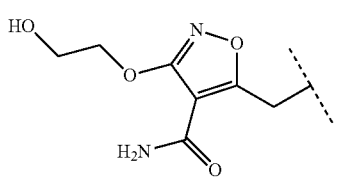 a58
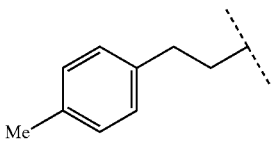 a59
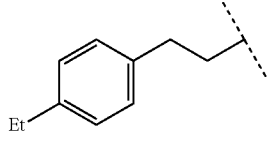 a60
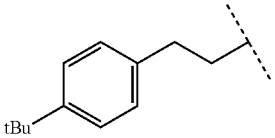 a61
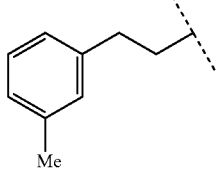 a62
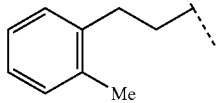 a63
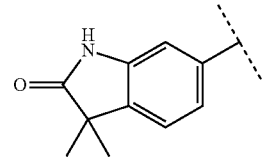 a64
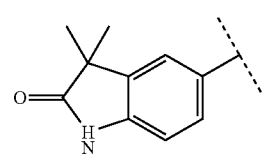 a65

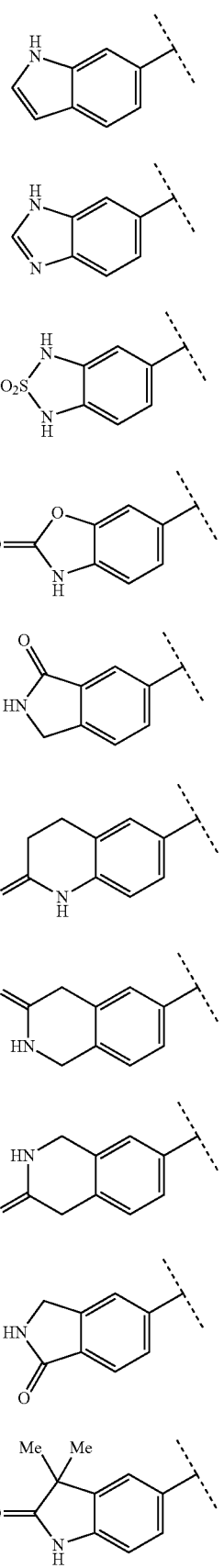
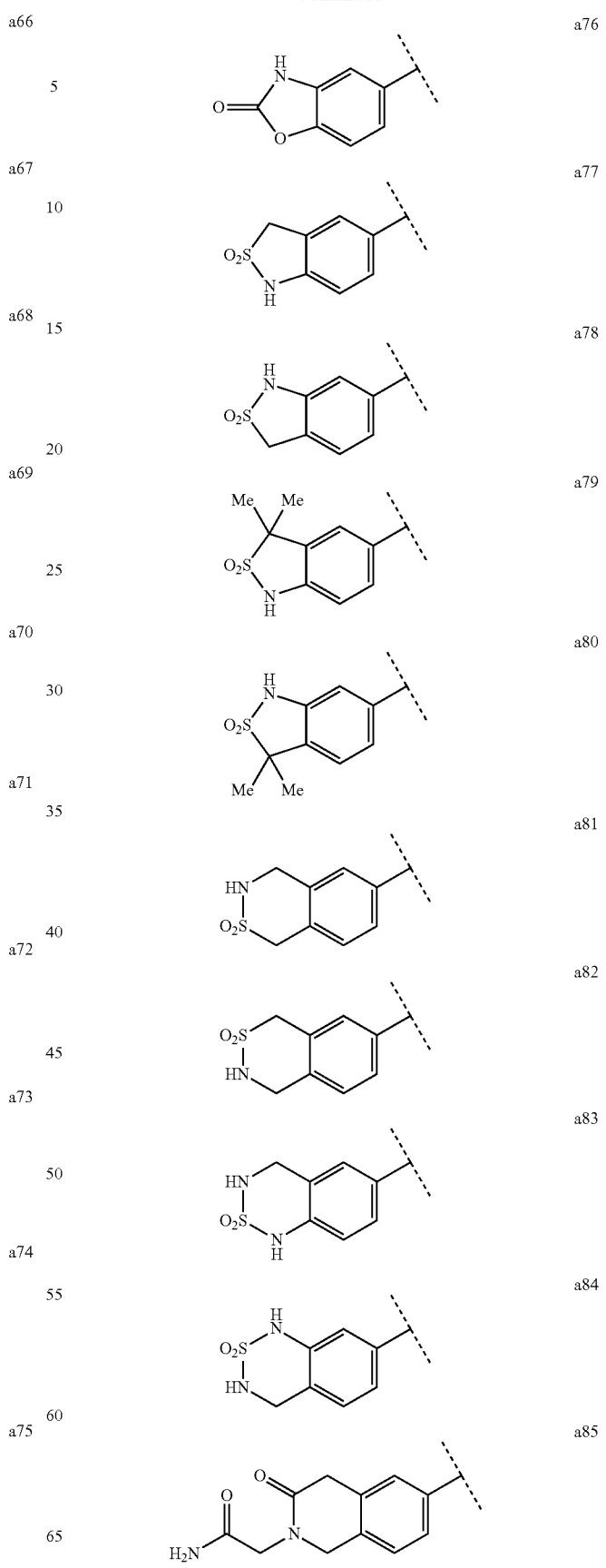

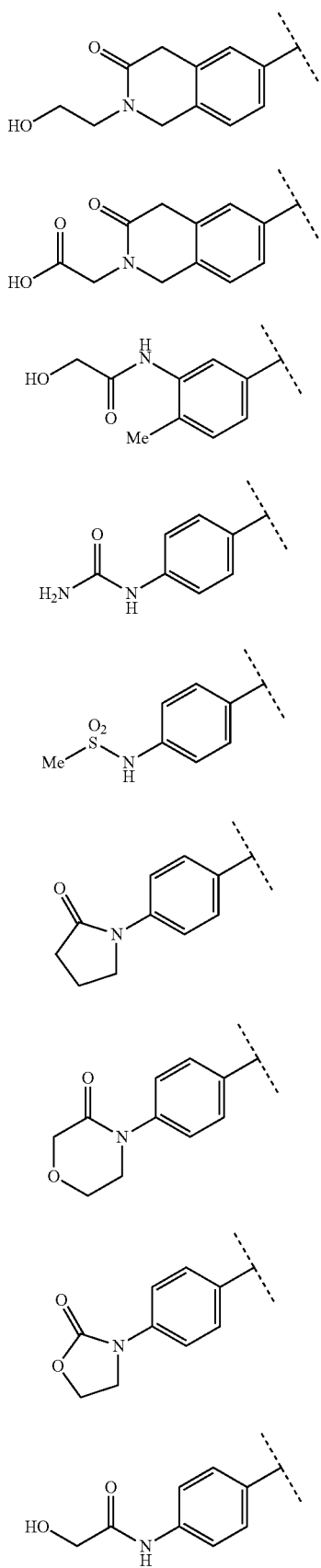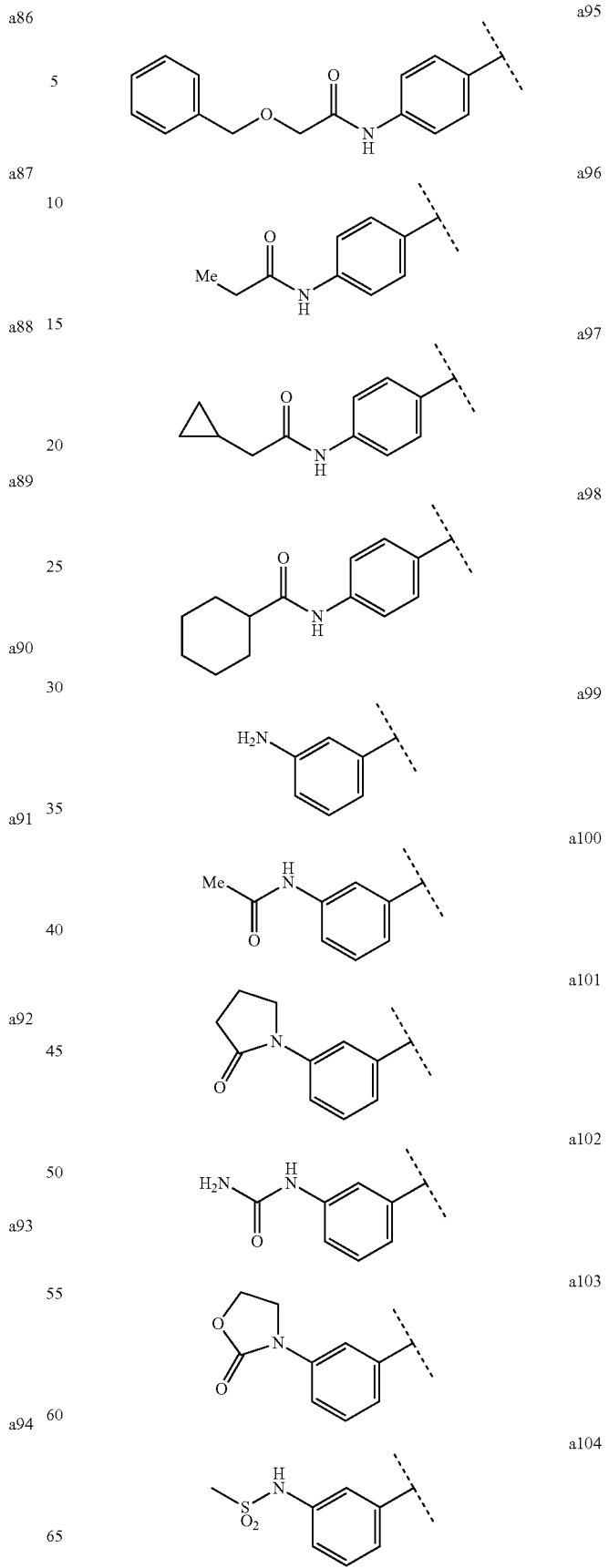

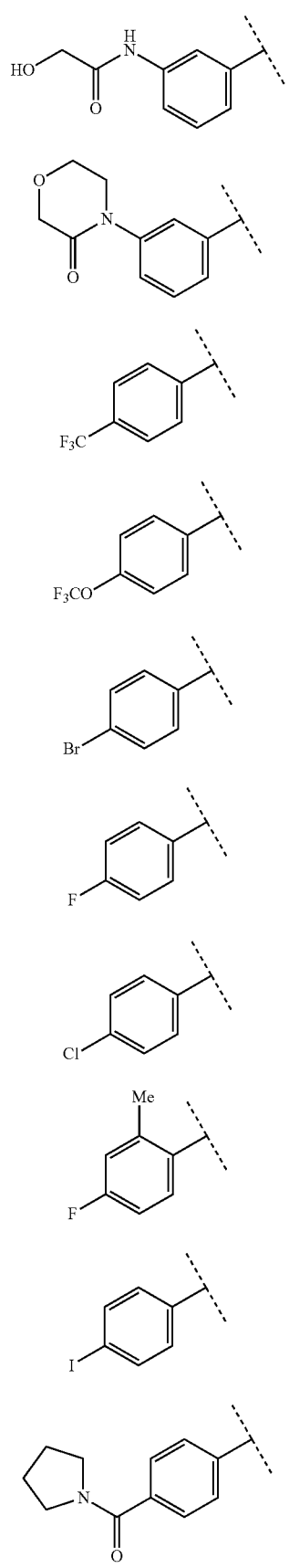
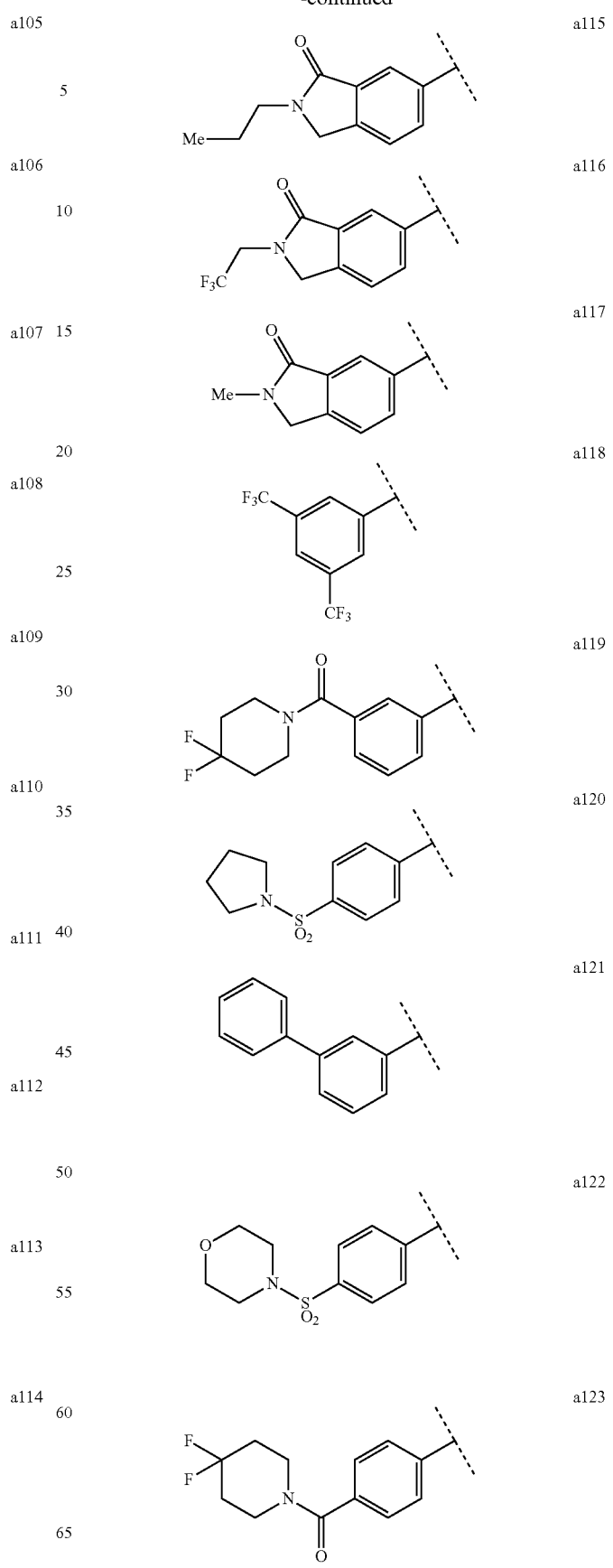

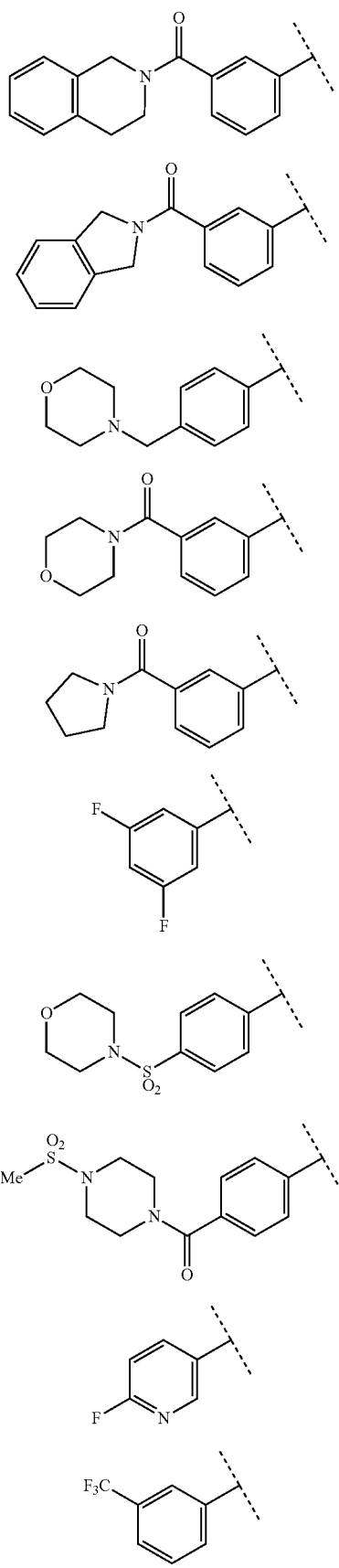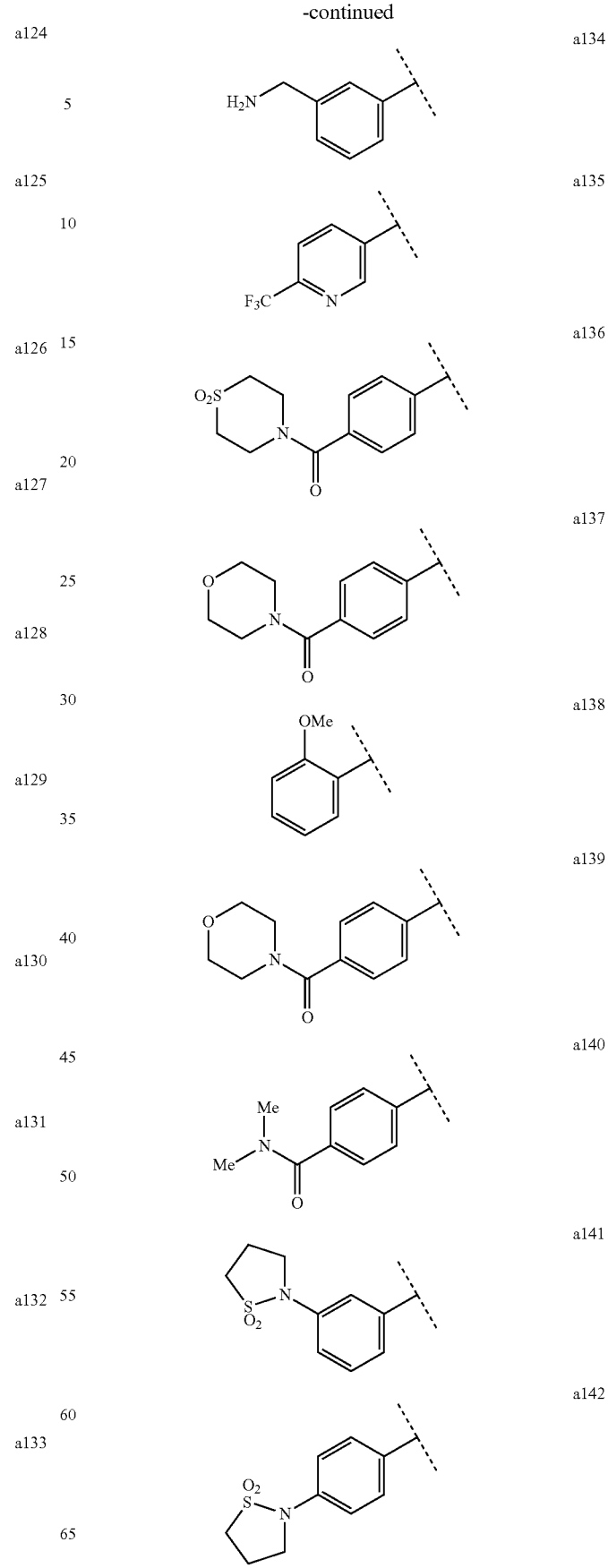

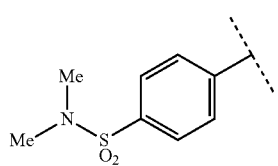 a143
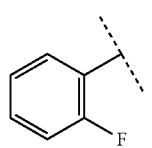 a144
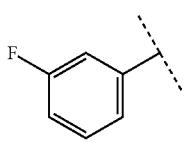 a145
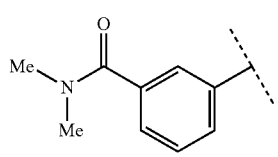 a146
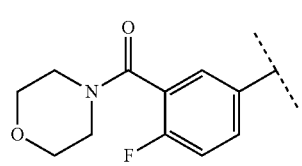 a147
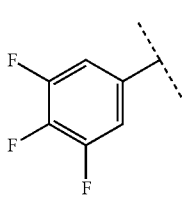 a148
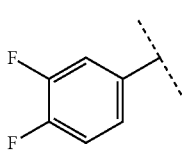 a149
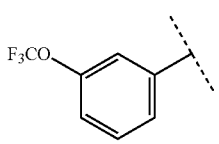 a150
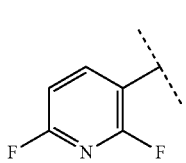 a151
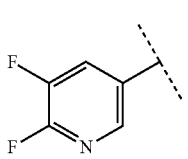 a152
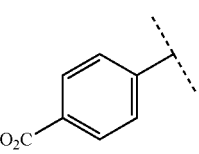 a153
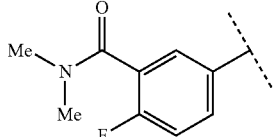 a154
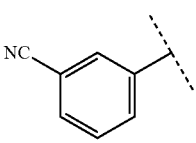 a155
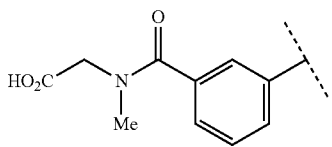 a156
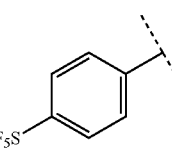 a157
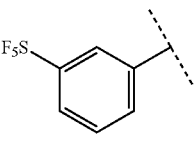 a158
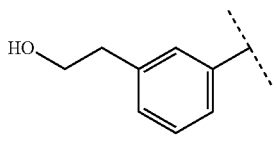 a159
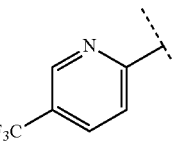 a160
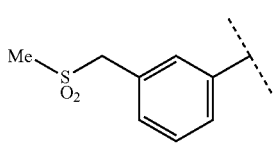 a161
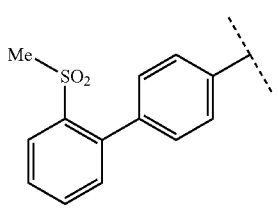 a162

| | |
|---|---|
| a163 | 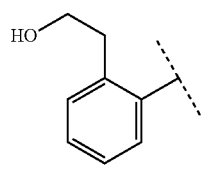 |
| a164 | 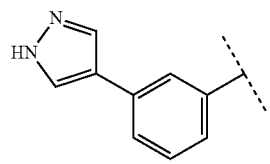 |
| a165 | 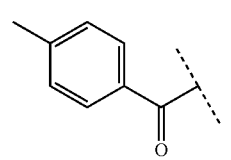 |
| a166 | 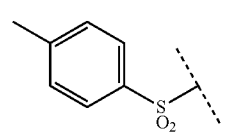 |
| a167 | 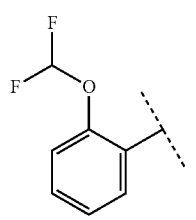 |
| a168 | 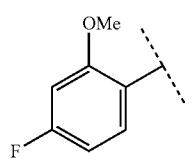 |
| a169 | 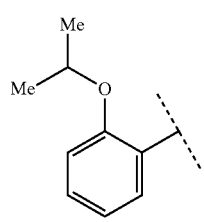 |
| a170 | 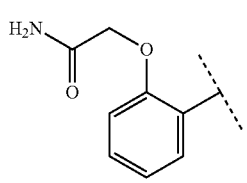 |
| a171 | 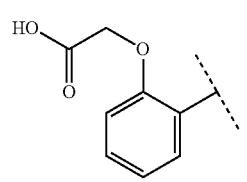 |
| a172 | 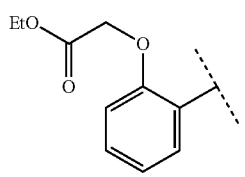 |
| a173 | 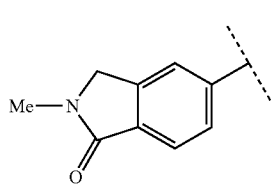 |
| a174 | 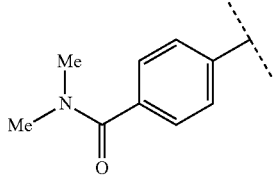 |
| a175 | 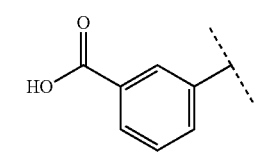 |
| a176 | 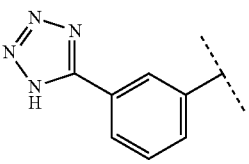 |
| a177 | 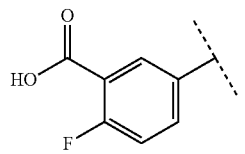 |
| a178 | 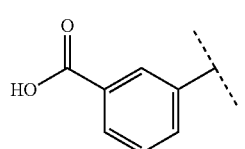 |
| a179 | 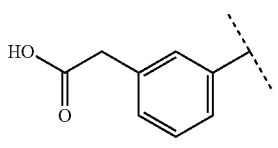 |
| a180 | |

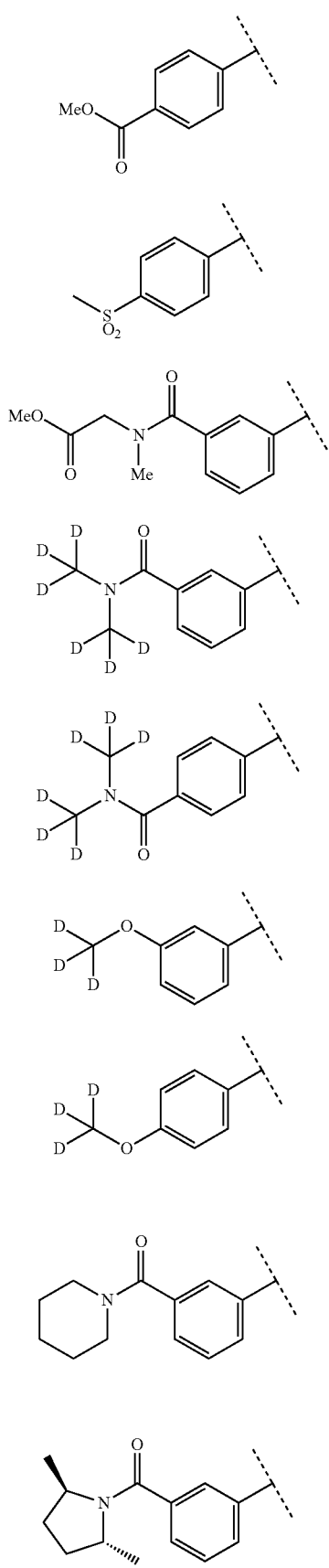
a181
a182
a183
a184
a185
a186
a187
a188
a189
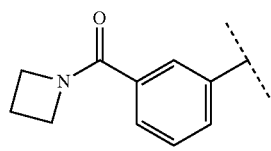
a190
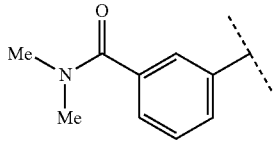
a191
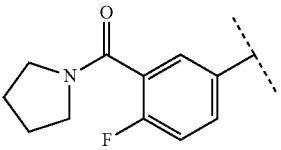
a192
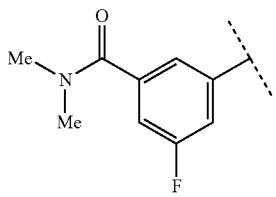
a193
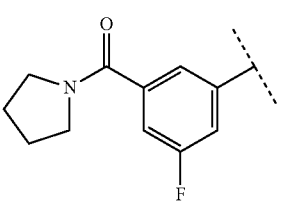
a194
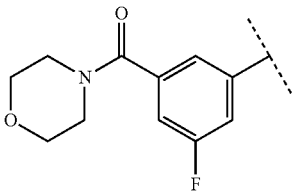
a195
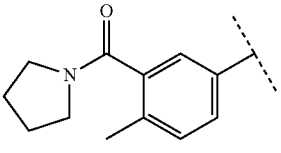
a196
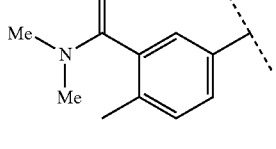
a197
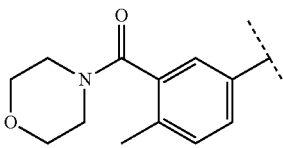
a198

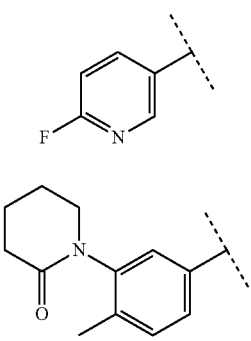
a199
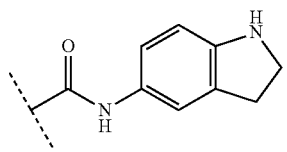
b6
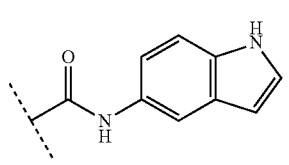
b7
and wherein
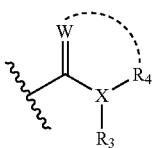
is selected from the group consisting of
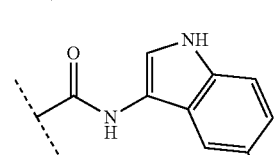
b8
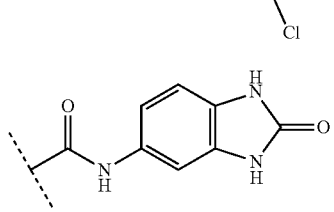
b9
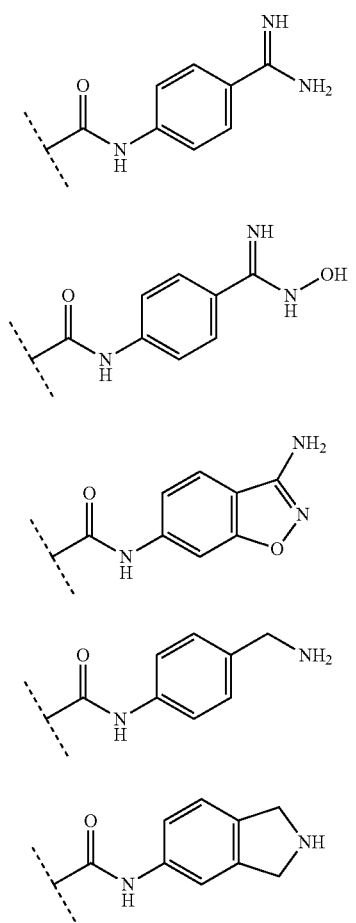
b1
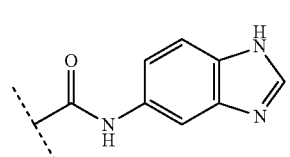
b10
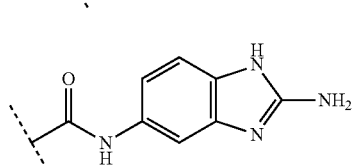
b11
b2
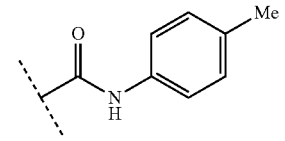
b12
b3
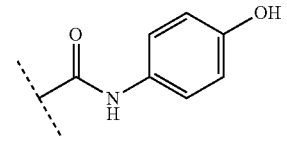
b13
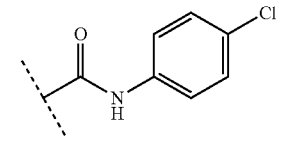
b14
b4
b5
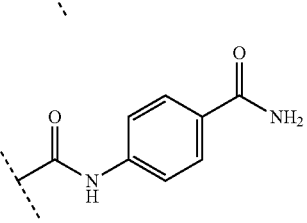
b15

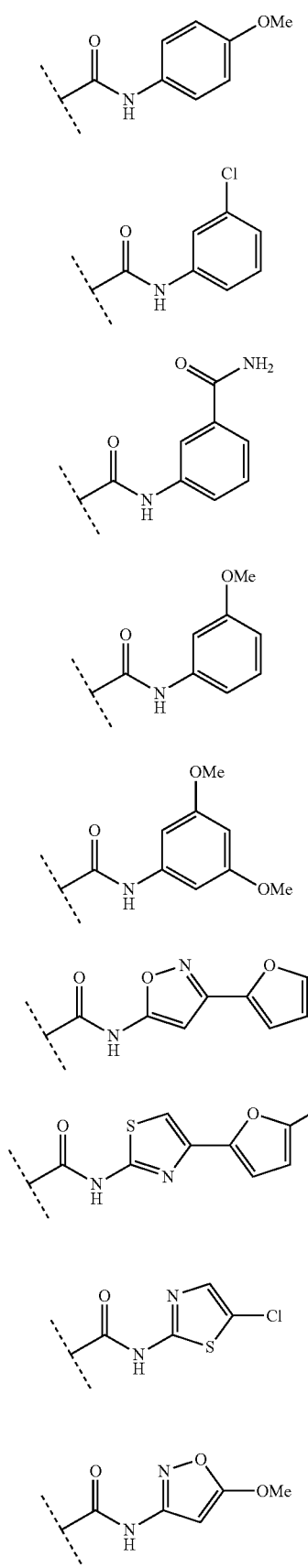
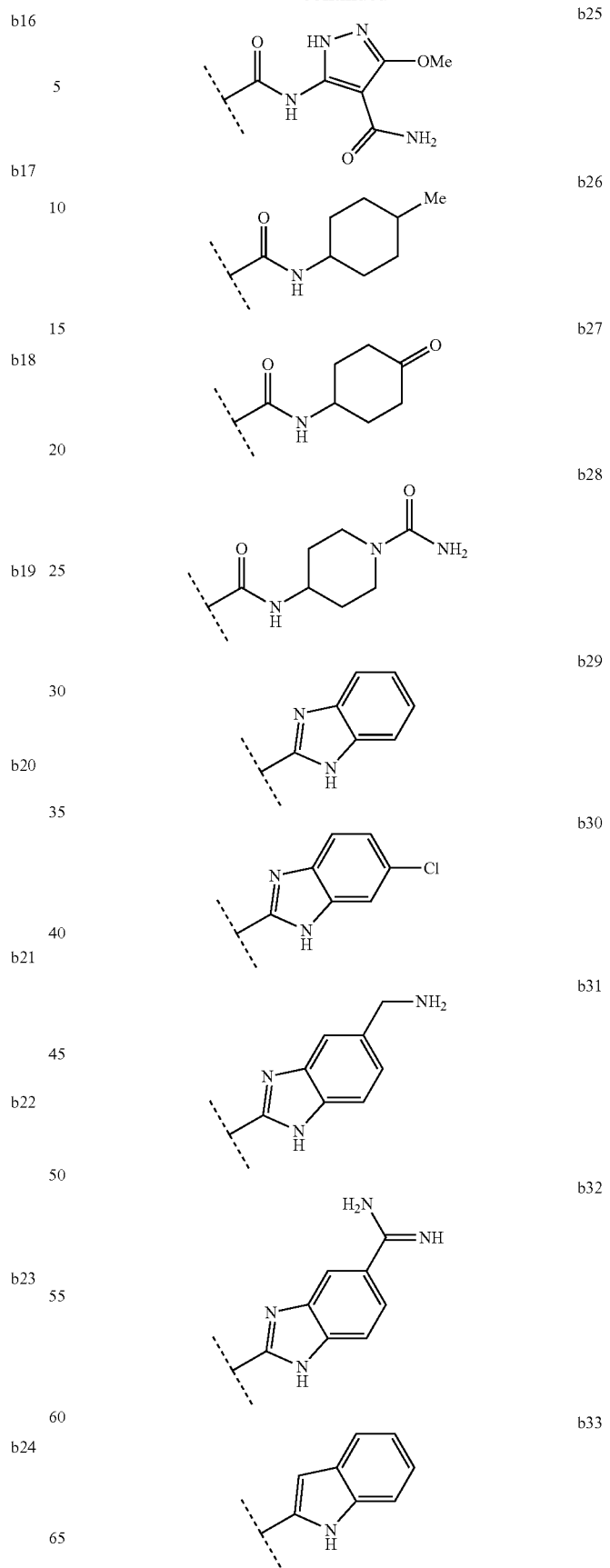

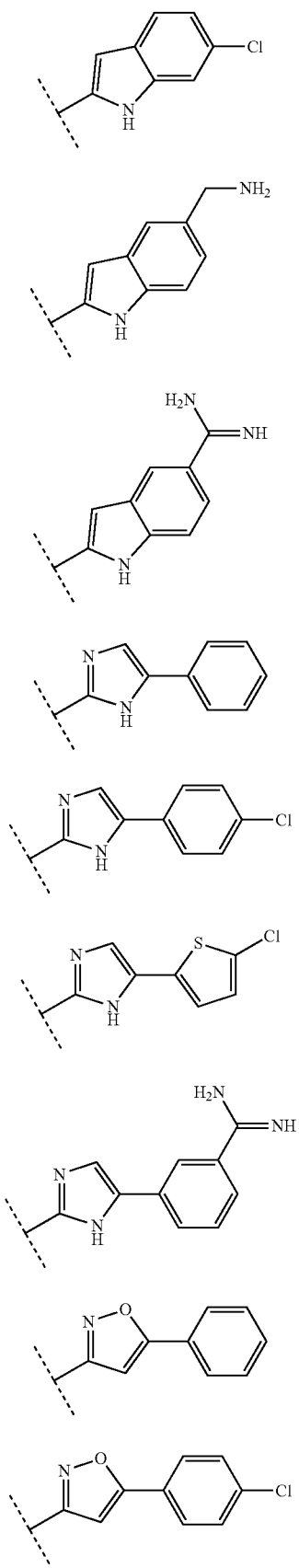
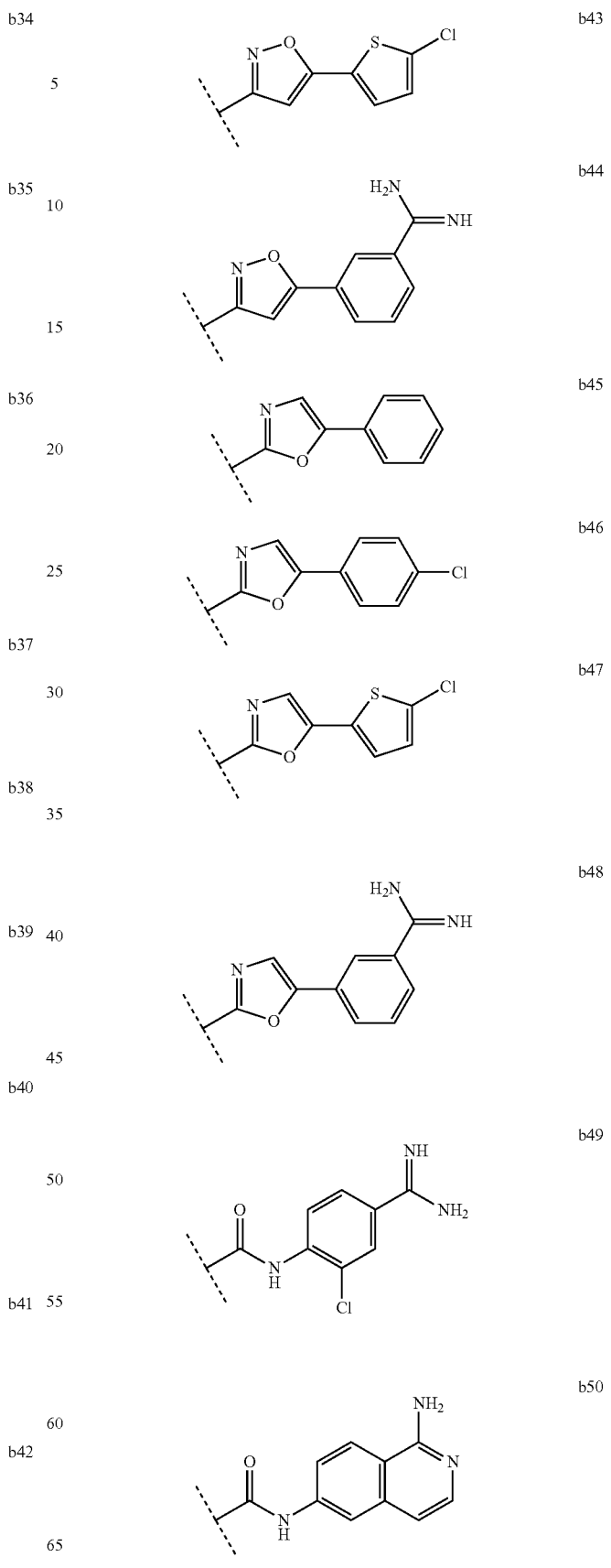

b51 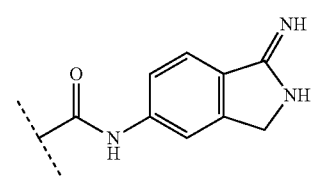
b52 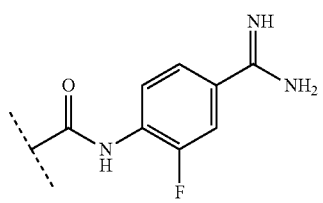
b53 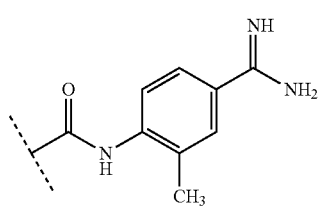
b54 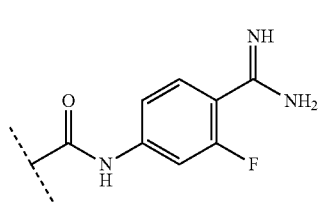
b55 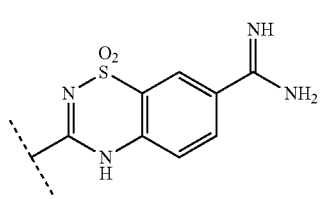
b56 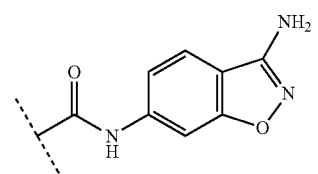
b57 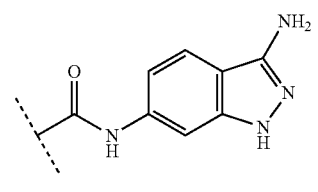
b58 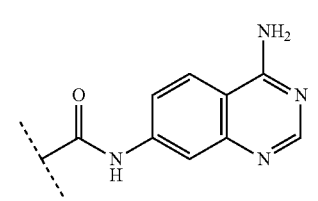
b59 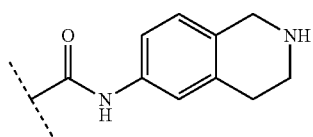
b60 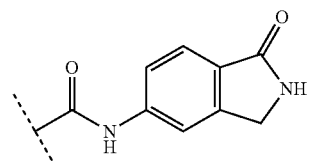
b61 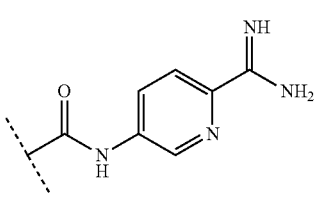
b62 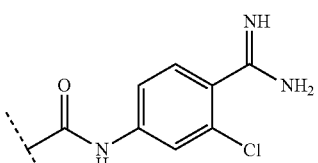
b63 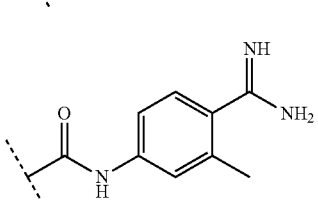
b64 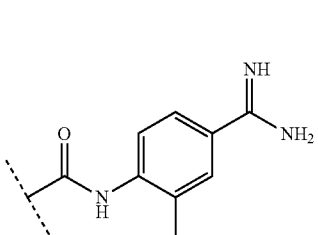
b65 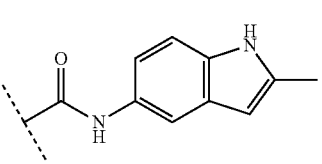
b66 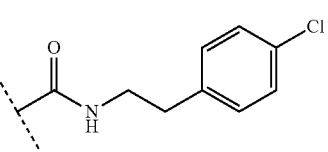

-continued
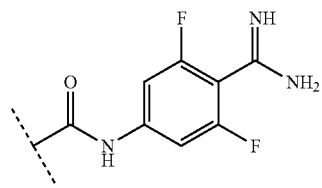
b67
[7-1-1] In another aspect, the present invention provides compounds of [7-1] wherein R$_1$ is a group selected from the group consisting of:
a1 to a33, a64 to a164,
and wherein the substructure of the Formula (IV)
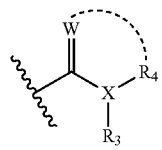
is selected from the group consisting of:
b1, b4, b49 to b61.
[7-2] In another aspect, the present invention provides compounds selected from the group consisting of:
1
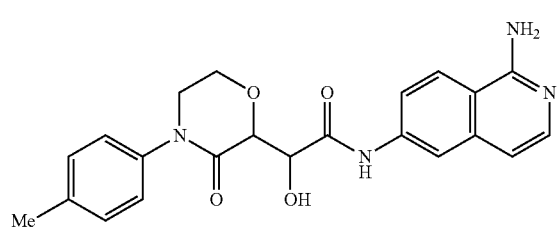
2
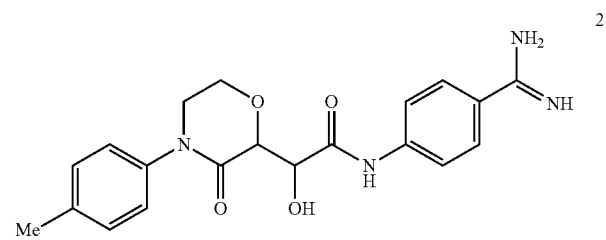
3
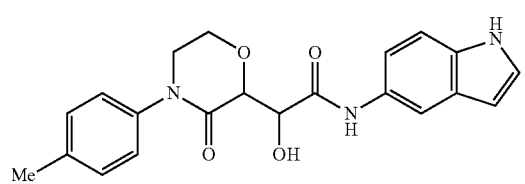
4
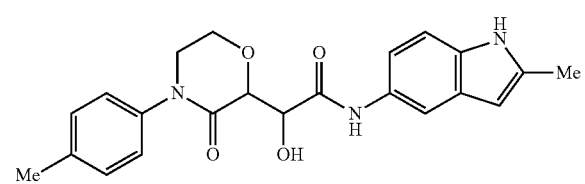
5
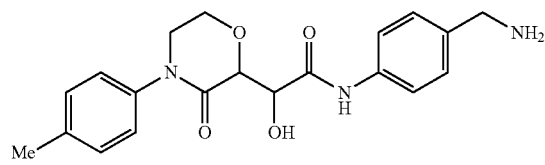
6
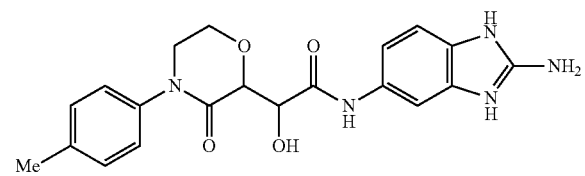
7
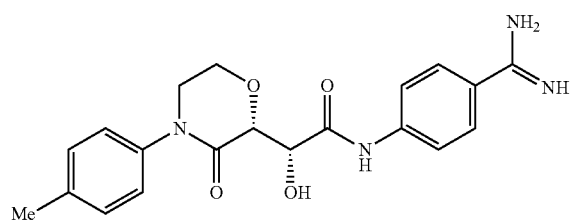
8
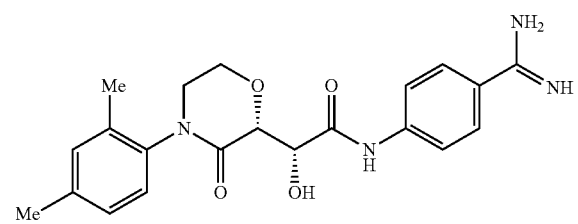
9
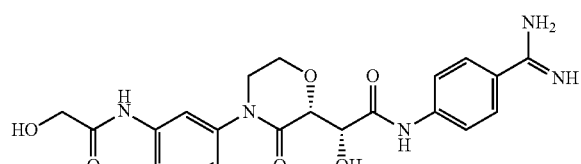
10
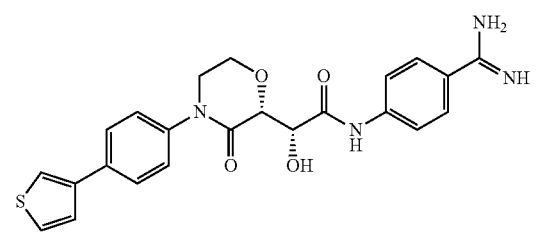

-continued
11
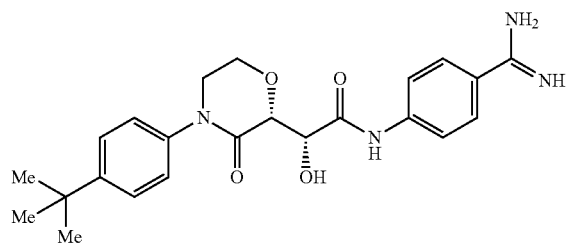
12
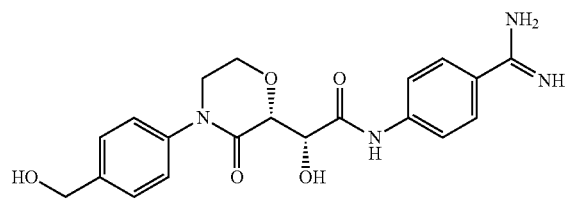
13
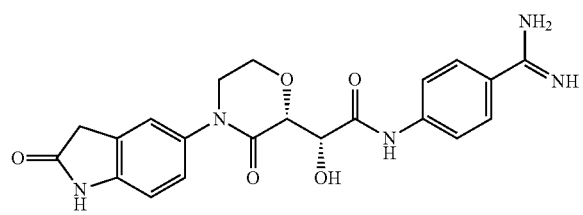
14
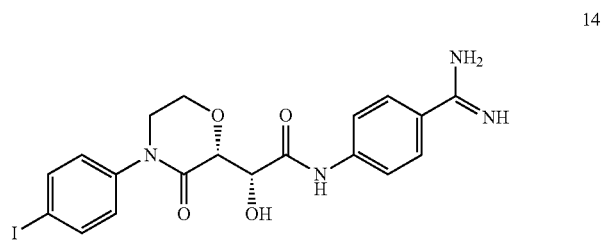
15
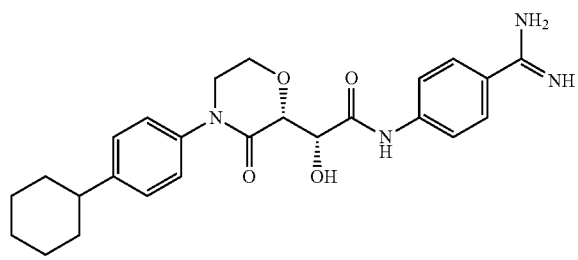
16
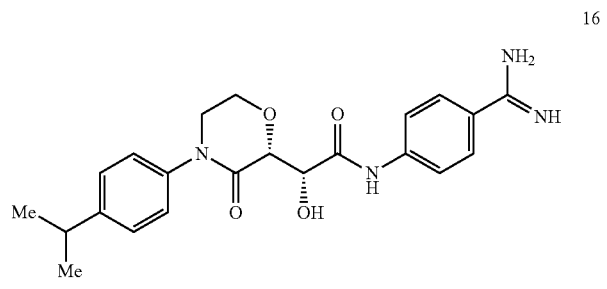
17
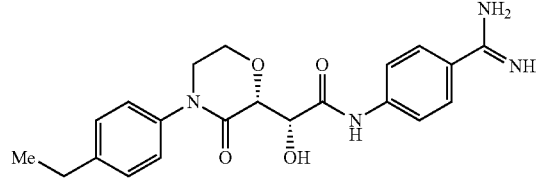
18
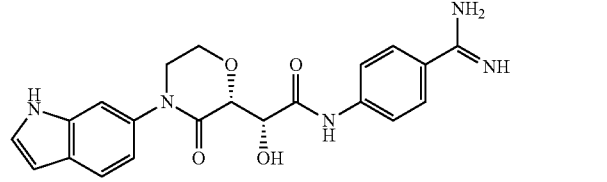
19
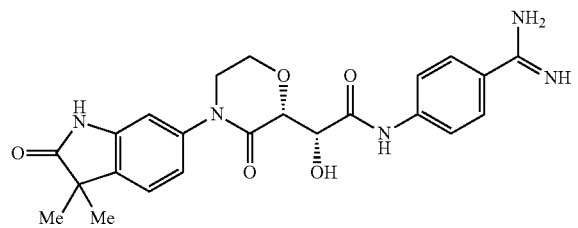
20
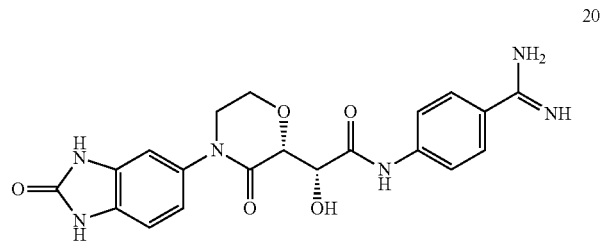
21
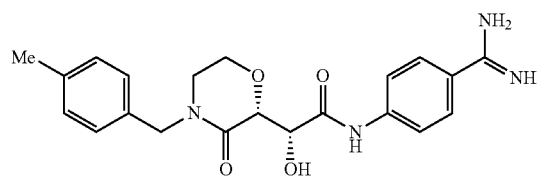
22
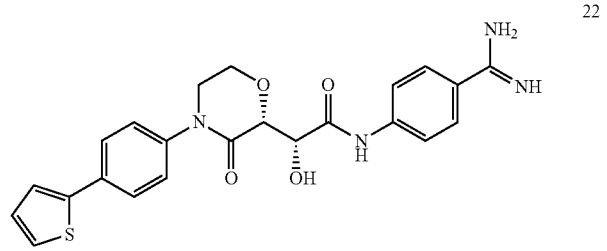

-continued
23 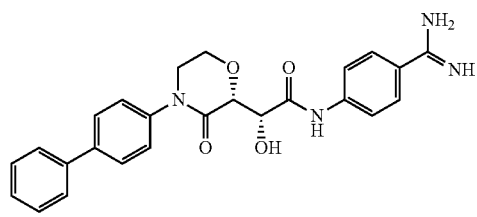
24 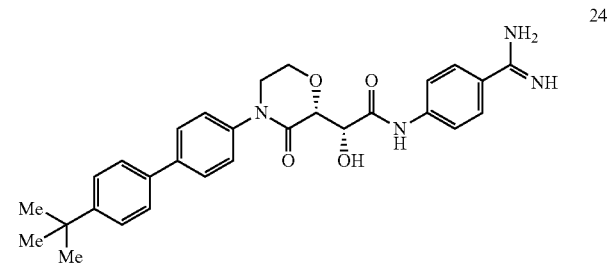
25 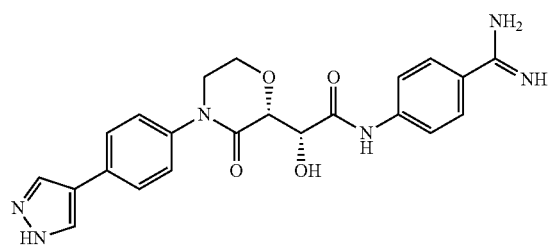
26 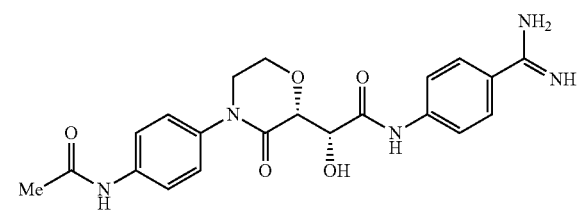
27 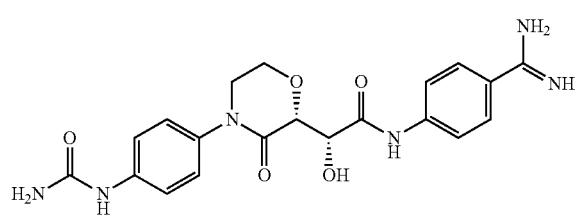
28 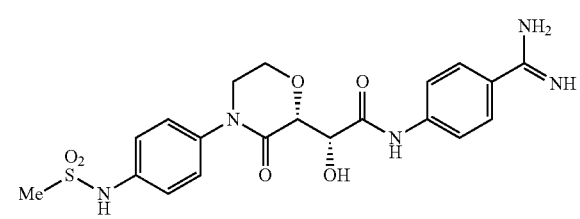
29 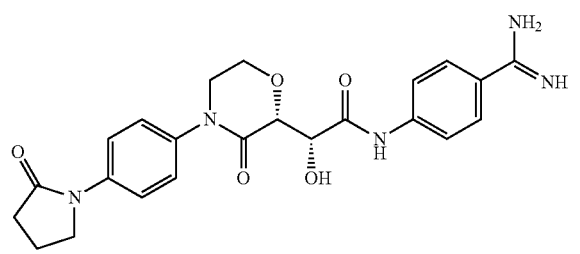
30 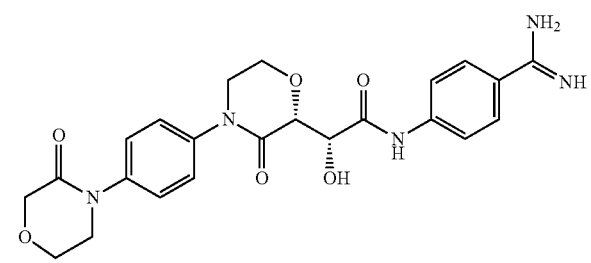
31 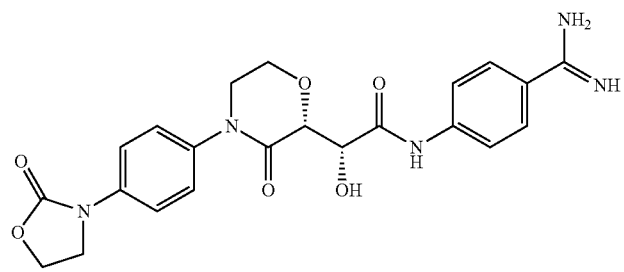
32 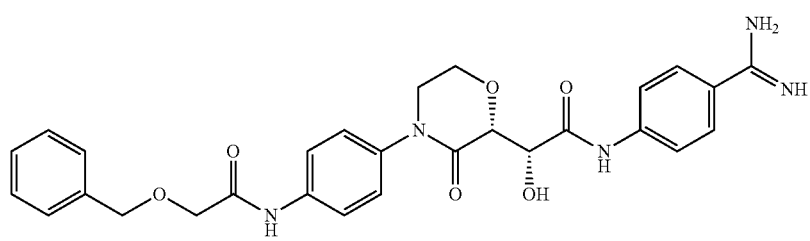

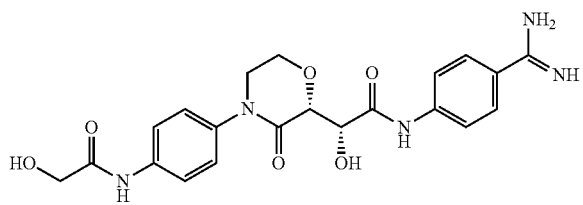

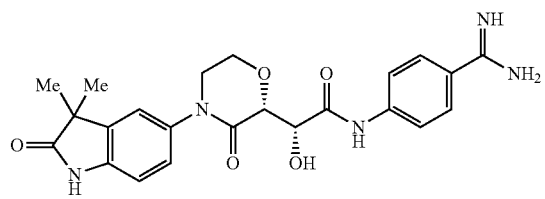

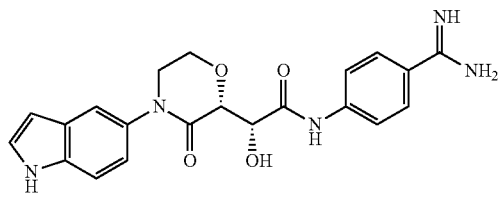

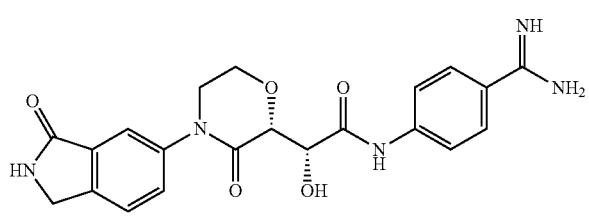

or its pharmaceutically acceptable salt or a solvate thereof.
Each compound name from example 1 to example 37 is, 1: N-(1-aminoisoquinolin-6-yl)-2-hydroxy-2-(3-oxo-4-p-tolylmorpholin-2-yl)acetamide;
2: N-(4-amidinophenyl)-2-hydroxy-2-(3-oxo-4-p-tolylmorpholin-2-yl)acetamide;
3: 2-hydroxy-N-(1H-indol-5-yl)-2-(3-oxo-4-p-tolylmorpholin-2-yl)acetamide;
4: 2-hydroxy-N-(2-methyl-1H-indol-5-yl)-2-(3-oxo-4-p-tolylmorpholin-2-yl)acetamide;
5: N-[4-(aminomethyl)phenyl]-2-hydroxy-2-(3-oxo-4-p-tolylmorpholin-2-yl)acetamide;
6: N-(2-amino-3H-benzimidazol-5-yl)-2-hydroxy-2-(3-oxo-4-p-tolylmorpholin-2-yl)-acetamide;
7: (2R)—N-(4-amidinophenyl)-2-hydroxy-2-[(2R)-3-oxo-4-p-tolylmorpholin-2-yl]acetamide;
8: (2R)—N-(4-amidinophenyl)-2-[(2R)-4-(2,4-dimethylphenyl)-3-oxomorpholin-2-yl]-2-hydroxyacetamide;
9: (2R)—N-(4-amidinophenyl)-2-hydroxy-2-[(2R)-4-[3-[(2-hydroxyacetyl)amino]-4-methylphenyl]-3-oxomorpholin-2-yl]acetamide;
10: (2R)—N-(4-amidinophenyl)-2-hydroxy-2-[(2R)-3-oxo-4-(4-thiophen-3-ylphenyl)-morpholin-2-yl]acetamide;
11: (2R)—N-(4-amidinophenyl)-2-[(2R)-4-(4-tert-butylphenyl)-3-oxomorpholin-2-yl]-2-hydroxyacetamide;
12: (2R)—N-(4-amidinophenyl)-2-hydroxy-2-[(2R)-4-[4-(hydroxymethyl)phenyl]-3-oxo morpholin-2-yl]acetamide;
13: (2R)—N-(4-amidinophenyl)-2-hydroxy-2-[(2R)-3-oxo-4-(2-oxo-1,3-dihydroindol-5-yl)-morpholin-2-yl]acetamide;
14: (2R)—N-(4-amidinophenyl)-2-hydroxy-2-[(2R)-4-(4-iodophenyl)-3-oxomorpholin-2-yl]-acetamide;
15: (2R)—N-(4-amidinophenyl)-2-[(2R)-4-(4-cyclohexylphenyl)-3-oxomorpholin-2-yl]-2-hydroxyacetamide;
16: (2R)—N-(4-amidinophenyl)-2-hydroxy-2-[(2R)-3-oxo-4-(4-propan-2-ylphenyl)-morpholin-2-yl]acetamide;
17: (2R)—N-(4-amidinophenyl)-2-[(2R)-4-(4-ethylphenyl)-3-oxomorpholin-2-yl]-2-hydr oxyacetamide;
18: (2R)—N-(4-amidinophenyl)-2-hydroxy-2-[(2R)-4-(1H-indol-6-yl)-3-oxomorpholin-2-yl]-acetamide;
19: (2R)—N-(4-amidinophenyl)-2-[(2R)-4-(3,3-dimethyl-2-oxo-1H-indol-6-yl)-3-oxomorpholin-2-yl]-2-hydroxyacetamide;
20: (2R)—N-(4-amidinophenyl)-2-hydroxy-2-[(2R)-3-oxo-4-(2-oxo-1,3-dihydrobenzimidazol-5-yl)morpholin-2-yl]acetamide;
21: (2R)—N-(4-amidinophenyl)-2-hydroxy-2-[(2R)-3-oxo-4-p-tolylmethylmorpholin-2-yl]-acetamide;
22: (2R)—N-(4-amidinophenyl)-2-hydroxy-2-[(2R)-3-oxo-4-(4-thiophen-2-ylphenyl)-morpholin-2-yl]acetamide;
23: (2R)—N-(4-amidinophenyl)-2-[(2R)-4-biphenyl-3-oxomorpholin-2-yl]-2-hydroxy-acetamide;
24: (2R)—N-(4-amidinophenyl)-2-[(2R)-4-(4'-tert-butylbiphenyl)-3-oxomorpholin-2-yl]-2-hydroxyacetamide;
25: (2R)—N-(4-amidinophenyl)-2-hydroxy-2-[(2R)-3-oxo-4-[4-(1H-pyrazol-4-yl)phenyl]-morpholin-2-yl]acetamide;
26: (2R)-2-[(2R)-4-(4-acetamidophenyl)-3-oxomorpholin-2-yl]-N-(4-amidinophenyl)-2-hydroxyacetamide;
27: (2R)—N-(4-amidinophenyl)-2-[(2R)-4-[4-(carbamoylamino)phenyl]-3-oxomorpholin-2-yl]-2-hydroxyacetamide;
28: (2R)—N-(4-amidinophenyl)-2-hydroxy-2-[(2R)-4-[4-(methanesulfonamido)phenyl]-3-oxomorpholin-2-yl]acetamide;
29: (2R)—N-(4-amidinophenyl)-2-hydroxy-2-[(2R)-3-oxo-4-[4-(2-oxopyrrolidin-1-yl)phenyl]morpholin-2-yl]acetamide;
30: (2R)—N-(4-amidinophenyl)-2-hydroxy-2-[(2R)-3-oxo-4-[4-(3-oxomorpholin-4-yl)phenyl]morpholin-2-yl]acetamide;
31: (2R)—N-(4-amidinophenyl)-2-hydroxy-2-[(2R)-3-oxo-4-[4-(2-oxo-1,3-oxazolidin-3-yl)-phenyl]morpholin-2-yl]acetamide;

32: (2R)—N-(4-amidinophenyl)-2-hydroxy-2-[(2R)-3-oxo-4-[4-[(2-phenylmethoxyacetyl)-amino]phenyl]morpholin-2-yl]acetamide;

33: (2R)—N-(4-amidinophenyl)-2-hydroxy-2-[(2R)-4-[4-[(2-hydroxyacetyl)amino]phenyl]-3-oxomorpholin-2-yl]acetamide;

34: (2R)—N-(4-amidinophenyl)-2-[(2R)-4-(3,3-dimethyl-2-oxo-1H-indol-5-yl)-3-oxomorpholin-2-yl]-2-hydroxyacetamide;

35: (2R)—N-(4-amidinophenyl)-2-hydroxy-2-[(2R)-4-(1H-indol-5-yl)-3-oxomorpholin-2-yl]-acetamide;

36: (2R)—N-(4-amidinophenyl)-2-hydroxy-2-[(2R)-3-oxo-4-(2-oxo-3H-1,3-benzoxazol-6-yl)morpholin-2-yl]acetamide;

and

37: (2R)—N-(4-amidinophenyl)-2-hydroxy-2-[(2R)-3-oxo-4-(3-oxo-1,2-dihydroisoindol-5-yl)morpholin-2-yl]acetamide.

[7-3] In another aspect, the present invention also provides a compound selected from the group consisting of:

1p
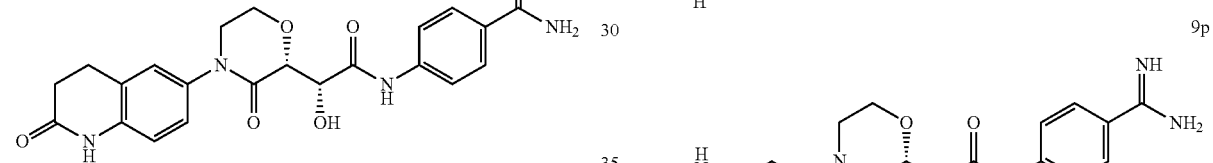

2p

3p

4p

5p

6p
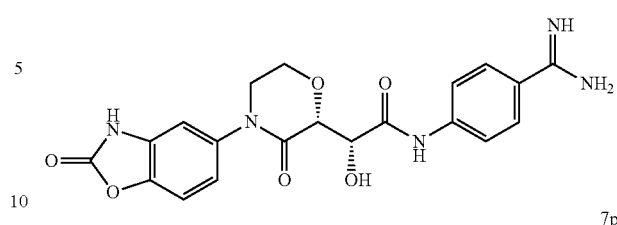

7p

8p
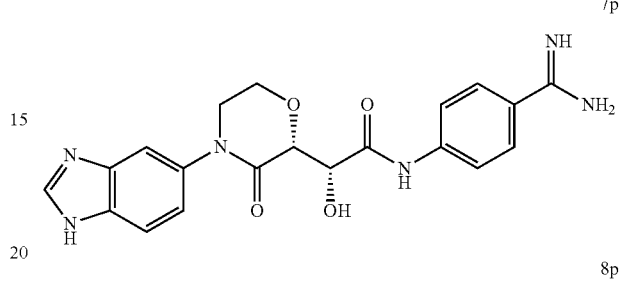

9p

10p
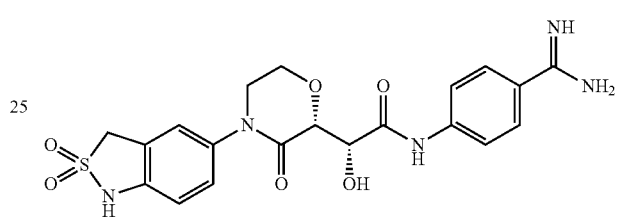

11p

12p
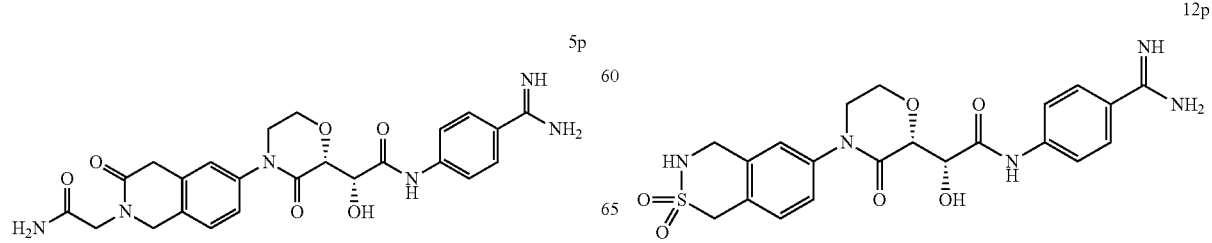

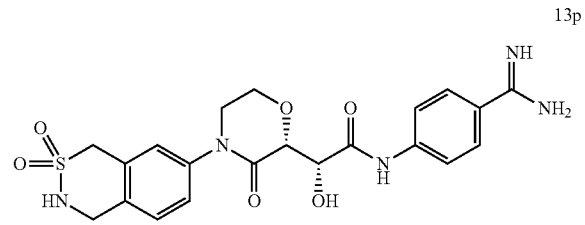

13p

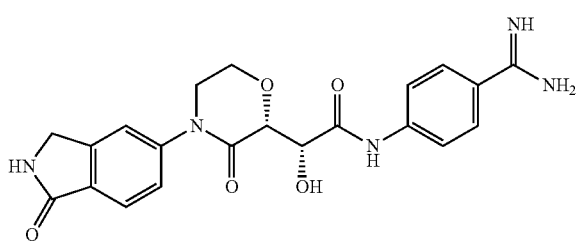

14p

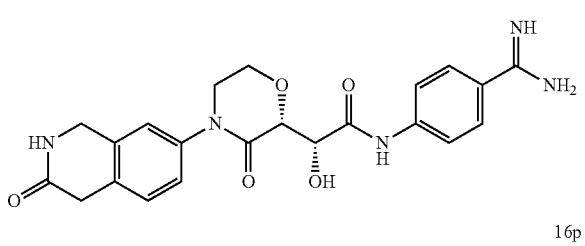

15p

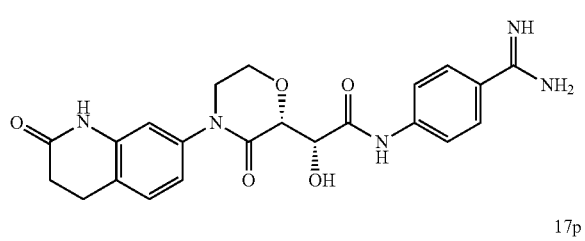

16p


17p

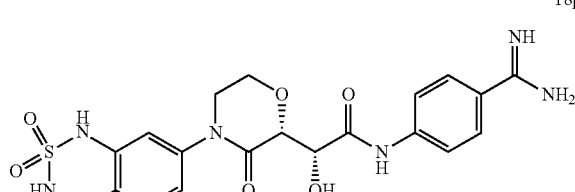

18p

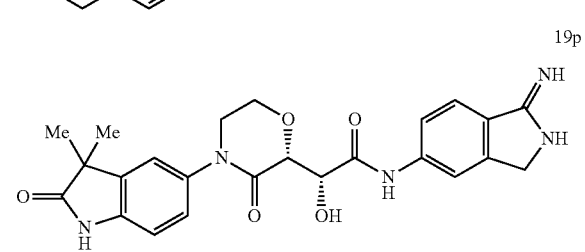

19p

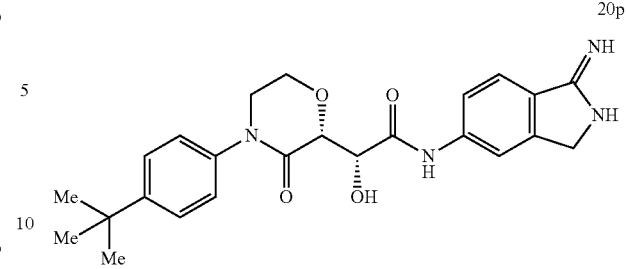

20p

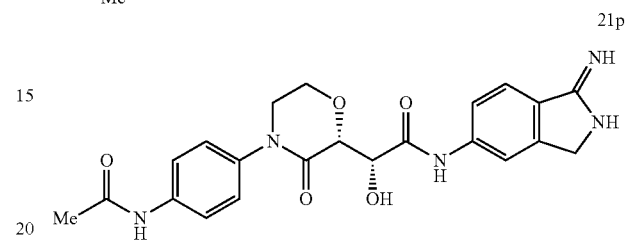

21p

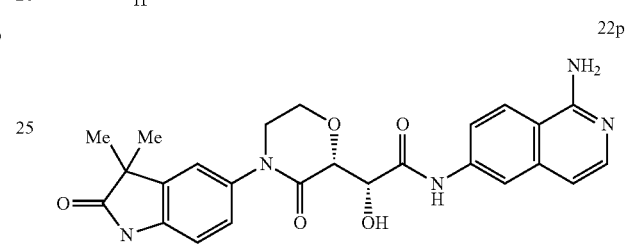

22p

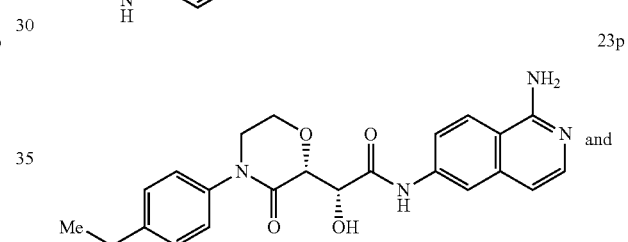

23p

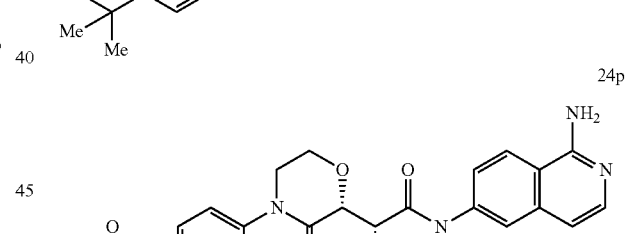

and

24p

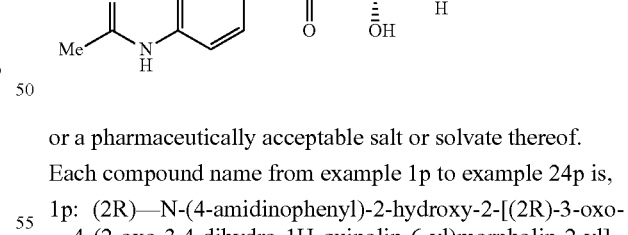

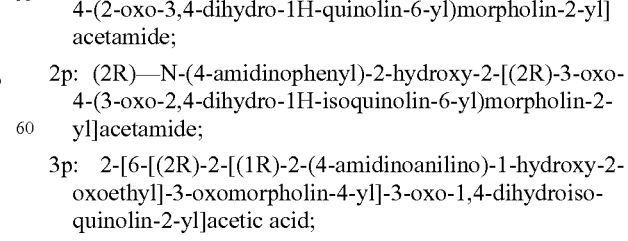

or a pharmaceutically acceptable salt or solvate thereof.

Each compound name from example 1p to example 24p is,

1p: (2R)—N-(4-amidinophenyl)-2-hydroxy-2-[(2R)-3-oxo-4-(2-oxo-3,4-dihydro-1H-quinolin-6-yl)morpholin-2-yl]acetamide;

2p: (2R)—N-(4-amidinophenyl)-2-hydroxy-2-[(2R)-3-oxo-4-(3-oxo-2,4-dihydro-1H-isoquinolin-6-yl)morpholin-2-yl]acetamide;

3p: 2-[6-[(2R)-2-[(1R)-2-(4-amidinoanilino)-1-hydroxy-2-oxoethyl]-3-oxomorpholin-4-yl]-3-oxo-1,4-dihydroisoquinolin-2-yl]acetic acid;

4p: (2R)—N-(4-amidinophenyl)-2-hydroxy-2-[(2R)-4-[2-(2-hydroxyethyl)-3-oxo-1,4-dihydroisoquinolin-6-yl]-3-oxomorpholin-2-yl]acetamide;

5p: (2R)—N-(4-amidinophenyl)-2-[(2R)-4-[2-(2-amino-2-oxoethyl)-3-oxo-1,4-dihydroisoquinolin-6-yl]-3-oxomorpholin-2-yl]-2-hydroxyacetamide;

6p: (2R)—N-(4-amidinophenyl)-2-hydroxy-2-[(2R)-3-oxo-4-(2-oxo-3H-1,3-benzoxazol-5-yl)morpholin-2-yl]acetamide;

7p: (2R)—N-(4-amidinophenyl)-2-[(2R)-4-(1H-benzimidazol-5-yl)-3-oxomorpholin-2-yl]-2-hydroxyacetamide;

8p: (2R)—N-(4-amidinophenyl)-2-[(2R)-4-(2,2-dioxo-1,3-dihydro-2,1-benzothiazol-5-yl)-3-oxomorpholin-2-yl]-2-hydroxyacetamide;

9p: (2R)—N-(4-amidinophenyl)-2-[(2R)-4-(2,2-dioxo-1,3-dihydro-2,1-benzothiazol-6-yl)-3-oxomorpholin-2-yl]-2-hydroxyacetamide;

10p: (2R)—N-(4-amidinophenyl)-2-[(2R)-4-(3,3-dimethyl-2,2-dioxo-1H-2,1-benzothiazol-5-yl)-3-oxomorpholin-2-yl]-2-hydroxyacetamide;

11p: (2R)—N-(4-amidinophenyl)-2-[(2R)-4-(3,3-dimethyl-2,2-dioxo-1H-2,1-benzothiazol-6-yl)-3-oxomorpholin-2-yl]-2-hydroxyacetamide;

12p: (2R)—N-(4-amidinophenyl)-2-[(2R)-4-(2,2-dioxo-3,4-dihydro-1H-benzo[d]thiazin-6-yl)-3-oxomorpholin-2-yl]-2-hydroxyacetamide;

13p: (2R)—N-(4-amidinophenyl)-2-[(2R)-4-(2,2-dioxo-3,4-dihydro-1H-benzo[d]thiazin-7-yl)-3-oxomorpholin-2-yl]-2-hydroxyacetamide;

14p: (2R)—N-(4-amidinophenyl)-2-hydroxy-2-[(2R)-3-oxo-4-(1-oxo-2,3-dihydroisoindol-5-yl)morpholin-2-yl]acetamide;

15p: (2R)—N-(4-amidinophenyl)-2-hydroxy-2-[(2R)-3-oxo-4-(3-oxo-2,4-dihydro-1H-isoquinolin-7-yl)morpholin-2-yl]acetamide;

16p: (2R)—N-(4-amidinophenyl)-2-hydroxy-2-[(2R)-3-oxo-4-(2-oxo-3,4-dihydro-1H-quinolin-7-yl)morpholin-2-yl]acetamide;

17p: (2R)—N-(4-amidinophenyl)-2-[(2R)-4-(2,2-dioxo-3,4-dihydro-1H-benzo[c][1,2,6]thia-diazin-6-yl)-3-oxomorpholin-2-yl]-2-hydroxyacetamide;

18p: (2R)—N-(4-amidinophenyl)-2-[(2R)-4-(2,2-dioxo-3,4-dihydro-1H-benzo[c][1,2,6]thia-diazin-7-yl)-3-oxomorpholin-2-yl]-2-hydroxyacetamide;

19p: (2R)-2-[(2R)-4-(3,3-dimethyl-2-oxo-1H-indol-5-yl)-3-oxomorpholin-2-yl]-2-hydroxy-N-(1-imino-2,3-dihydroisoindol-5-yl)acetamide;

20p: (2R)-2-[(2R)-4-(4-tert-butylphenyl)-3-oxomorpholin-2-yl]-2-hydroxy-N-(1-imino-2,3-dihydroisoindol-5-yl)acetamide;

21p: (2R)-2-[(2R)-4-(4-acetamidophenyl)-3-oxomorpholin-2-yl]-2-hydroxy-N-(1-imino-2,3-dihydroisoindol-5-yl)acetamide;

22p: (2R)—N-(1-aminoisoquinolin-6-yl)-2-[(2R)-4-(3,3-dimethyl-2-oxo-1H-indol-5-yl)-3-oxomorpholin-2-yl]-2-hydroxyacetamide;

23p: (2R)—N-(1-aminoisoquinolin-6-yl)-2-[(2R)-4-(4-tert-butylphenyl)-3-oxomorpholin-2-yl]-2-hydroxyacetamide;

and

24p: (2R)-2-[(2R)-4-(4-acetamidophenyl)-3-oxomorpholin-2-yl]-N-(1-aminoisoquinolin-6-yl)-2-hydroxyacetamide.

[7-4] In another aspect, the present invention provides a compound selected from the group consisting of:

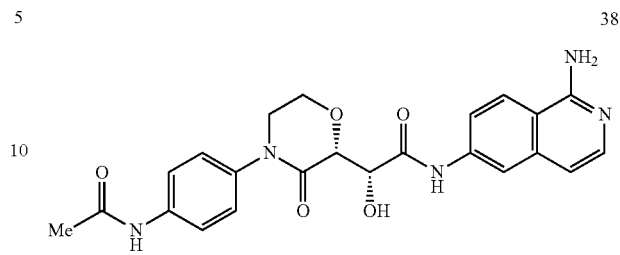

38

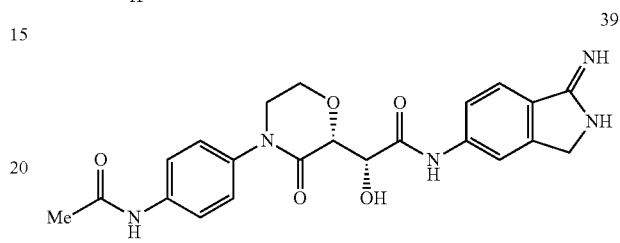

39

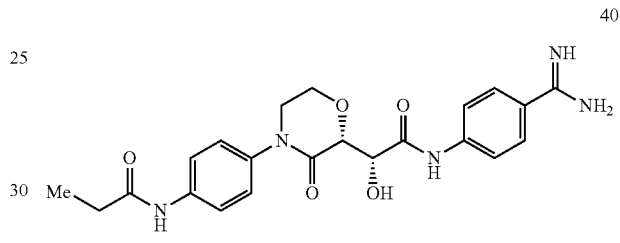

40

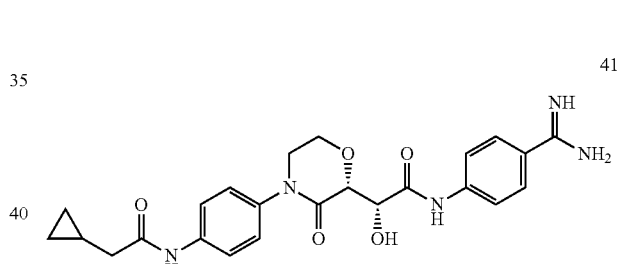

41

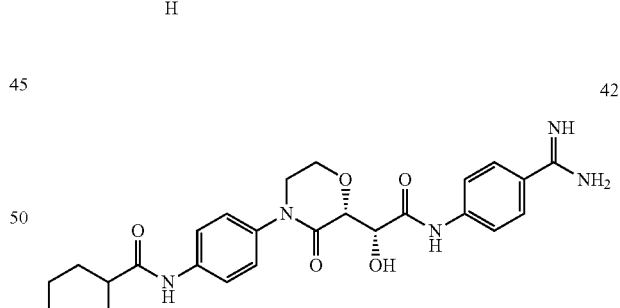

42

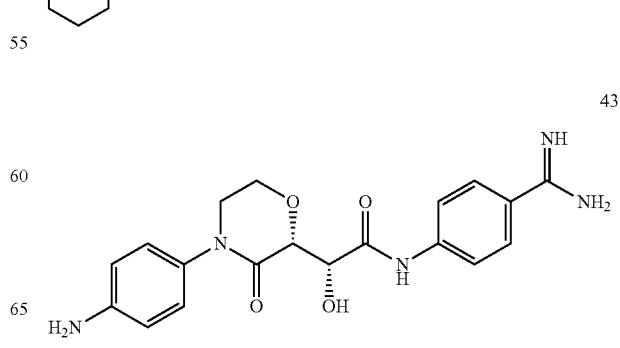

43

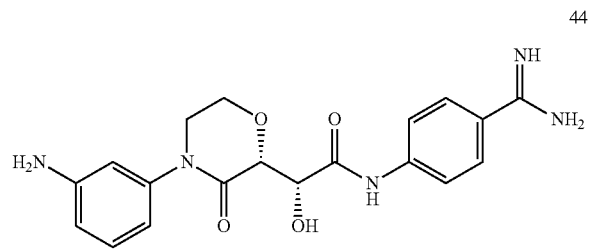
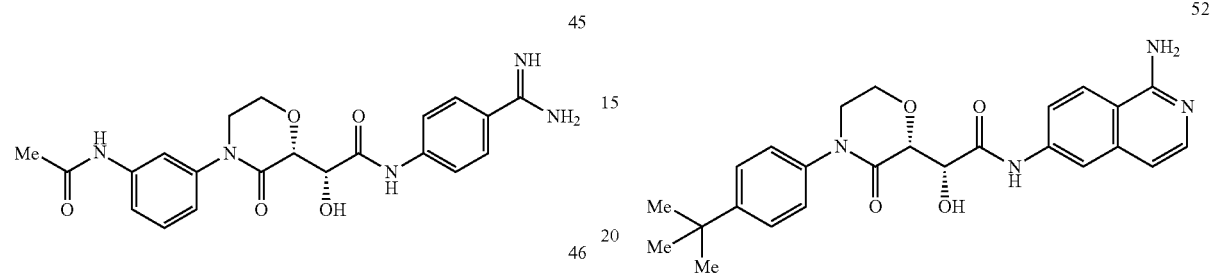
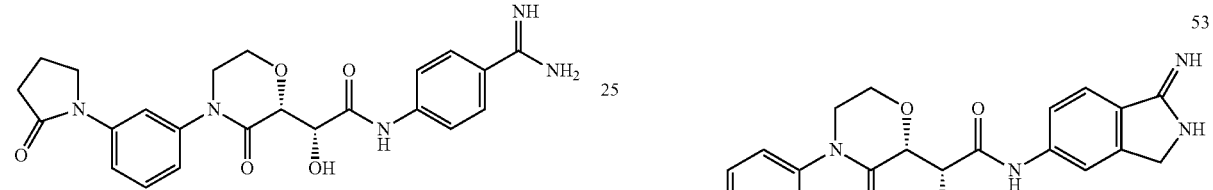
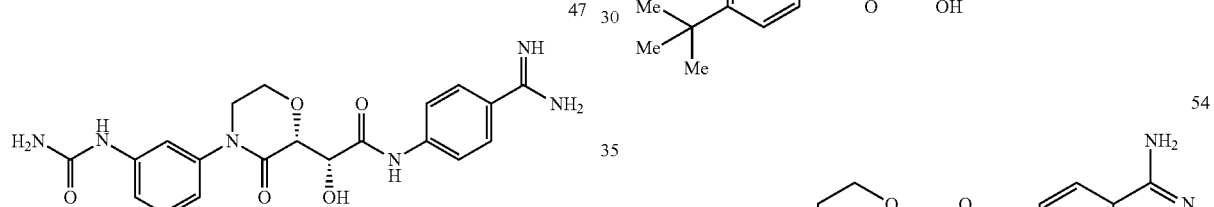
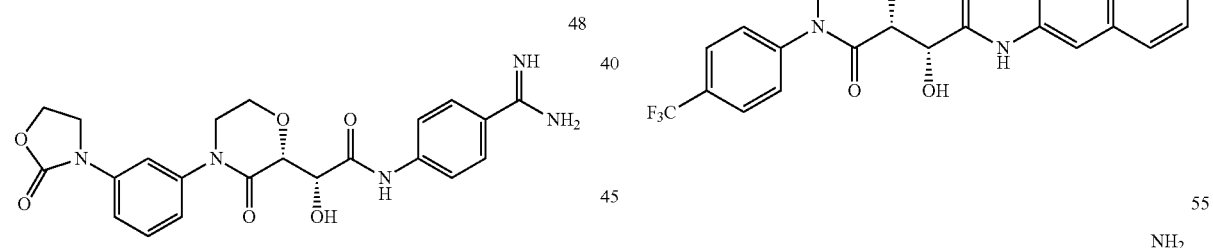
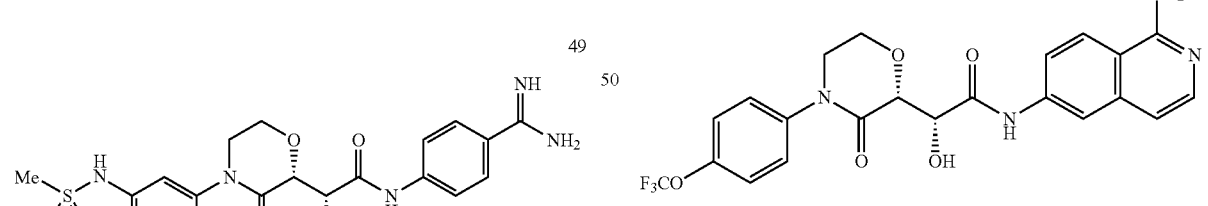
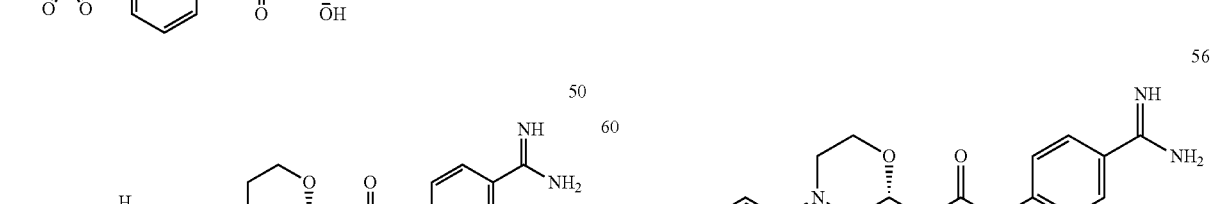
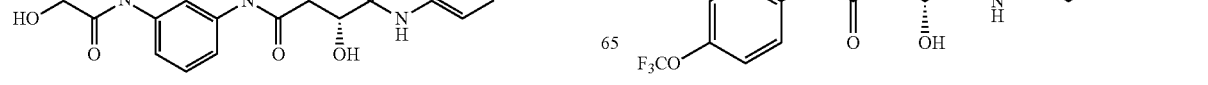

57

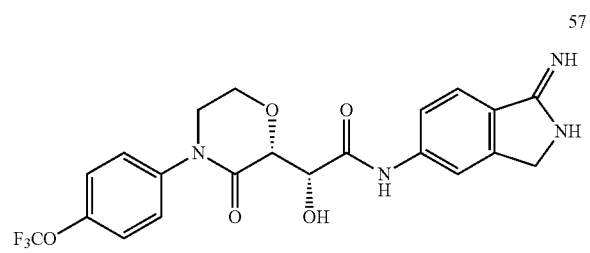

58

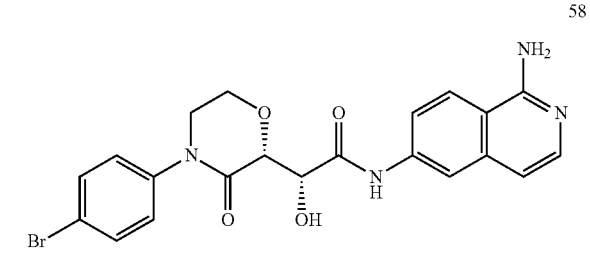

59

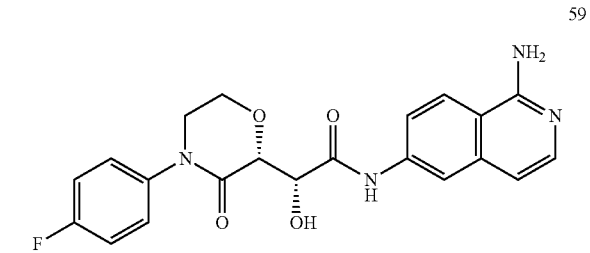

60

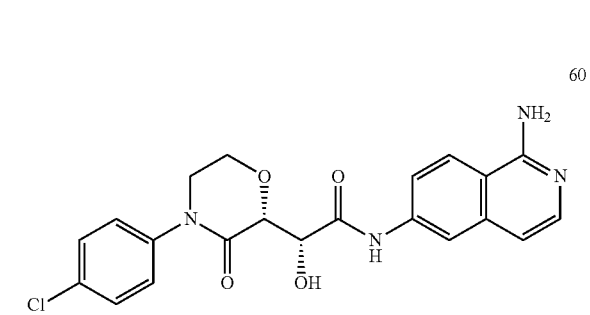

61

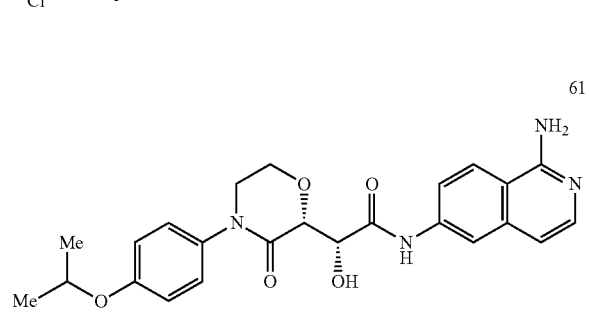

62

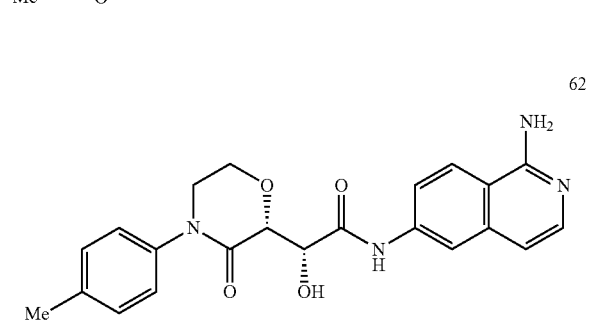

63

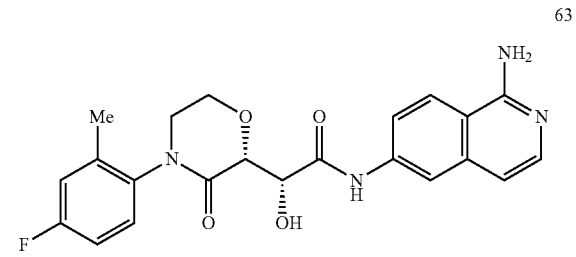

64

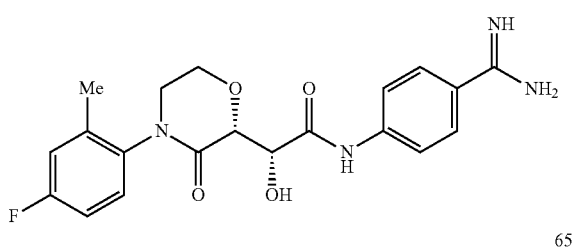

65

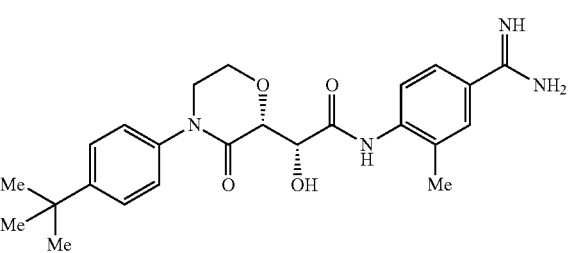

66

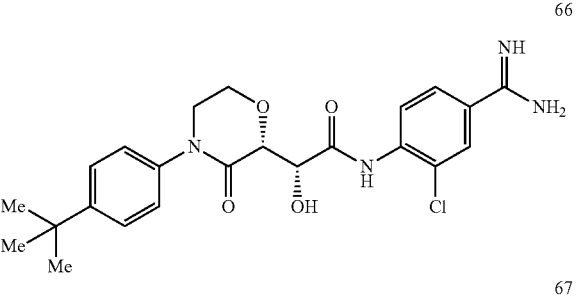

67

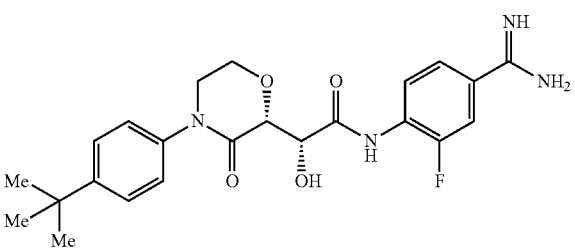

or a pharmaceutically acceptable salt or solvate thereof.

Each compound name from example 38 to example 67 is,

38: (2R)-2-[(2R)-4-(4-Acetamidophenyl)-3-oxomorpholin-2-yl]-N-(1-aminoisoquinolin-6-yl)-2-hydroxyacetamide;

39: (2R)-2-[(2R)-4-(4-Acetamidophenyl)-3-oxomorpholin-2-yl]-2-hydroxy-N-(1-imino-2,3-dihydroisoindol-5-yl)acetamide;

40: N-[4-[(2R)-2-[(1R)-2-(4-amidinoanilino)-1-hydroxy-2-oxoethyl]-3-oxomorpholin-4-yl]phenyl]propanamide;

41: (2R)—N-(4-Amidinophenyl)-2-[(2R)-4-[4-[(2-cyclopropylacetyl)amino]phenyl]-3-oxomorpholin-2-yl]-2-hydroxyacetamide;

42: N-[4-[(2R)-2-[(1R)-2-(4-Amidinoanilino)-1-hydroxy-2-oxoethyl]-3-oxomorpholin-4-yl]phenyl]cyclohexanecarboxamide;
43: (2R)—N-(4-Amidinophenyl)-2-[(2R)-4-(4-aminophenyl)-3-oxomorpholin-2-yl]-2-hydroxyacetamide;
44: (2R)—N-(4-Amidinophenyl)-2-[(2R)-4-(3-aminophenyl)-3-oxomorpholin-2-yl]-2-hydroxyacetamide;
45: (2R)-2-[(2R)-4-(3-Acetamidophenyl)-3-oxomorpholin-2-yl]-N-(4-amidinophenyl)-2-hydroxyacetamide;
46: (2R)—N-(4-Amidinophenyl)-2-hydroxy-2-[(2R)-3-oxo-4-[3-(2-oxopyrrolidin-1-yl)phenyl]morpholin-2-yl]acetamide;
47: (2R)—N-(4-Amidinophenyl)-2-[(2R)-4-[3-(carbamoylamino)phenyl]-3-oxomorpholin-2-yl]-2-hydroxyacetamide;
48: (2R)—N-(4-Amidinophenyl)-2-hydroxy-2-[(2R)-3-oxo-4-[3-(2-oxo-1,3-oxazolidin-3-yl)phenyl]morpholin-2-yl]acetamide;
49: (2R)—N-(4-Amidinophenyl)-2-hydroxy-2-[(2R)-4-[3-(methanesulfonamido)phenyl]-3-oxomorpholin-2-yl]acetamide;
50: (2R)—N-(4-Amidinophenyl)-2-hydroxy-2-[(2R)-4-[3-[(2-hydroxyacetyl)amino]phenyl]-3-oxomorpholin-2-yl]acetamide;
51: (2R)—N-(4-Amidinophenyl)-2-hydroxy-2-[(2R)-3-oxo-4-[3-(3-oxomorpholin-4-yl)phenyl]morpholin-2-yl]acetamide;
52: (2R)—N-(1-Aminoisoquinolin-6-yl)-2-[(2R)-4-(4-tert-butylphenyl)-3-oxomorpholin-2-yl]-2-hydroxyacetamide;
53: (2R)-2-[(2R)-4-(4-tert-Butylphenyl)-3-oxomorpholin-2-yl]-2-hydroxy-N-(1-imino-2,3-dihydroisoindol-5-yl)acetamide;
54: (2R)—N-(1-Amino isoquinolin-6-yl)-2-hydroxy-2-[(2R)-3-oxo-4-[4-(trifluoromethyl)phenyl]morpholin-2-yl]acetamide;
55: (2R)—N-(1-Aminoisoquinolin-6-yl)-2-hydroxy-2-[(2R)-3-oxo-4-[4-(trifluoromethoxy)phenyl]morpholin-2-yl]acetamide;
56: (2R)—N-(4-Amidinophenyl)-2-hydroxy-2-[(2R)-3-oxo-4-[4-(trifluoromethoxy)phenyl]morpholin-2-yl]acetamide;
57: (2R)-2-Hydroxy-N-(1-imino-2,3-dihydroisoindol-5-yl)-2-[(2R)-3-oxo-4-[4-(trifluoromethoxy)phenyl]morpholin-2-yl]acetamide;
58: (2R)—N-(1-Aminoisoquinolin-6-yl)-2-[(2R)-4-(4-bromophenyl)-3-oxomorpholin-2-yl]-2-hydroxyacetamide;
59: (2R)—N-(1-Aminoisoquinolin-6-yl)-2-[(2R)-4-(4-fluorophenyl)-3-oxomorpholin-2-yl]-2-hydroxyacetamide;
60: (2R)—N-(1-Aminoisoquinolin-6-yl)-2-[(2R)-4-(4-chlorophenyl)-3-oxomorpholin-2-yl]-2-hydroxyacetamide;
61: (2R)—N-(1-Aminoisoquinolin-6-yl)-2-hydroxy-2-[(2R)-4-(4-isopropyloxyphenyl)-3-oxomorpholin-2-yl]acetamide;
62: (2R)—N-(1-Aminoisoquinolin-6-yl)-2-hydroxy-2-[(2R)-3-oxo-4-p-tolylmorpholin-2-yl]acetamide;
63: (2R)—N-(1-Aminoisoquinolin-6-yl)-2-[(2R)-4-(4-fluoro-o-tolyl)-3-oxomorpholin-2-yl]-2-hydroxyacetamide;
64: (2R)—N-(4-Amidinophenyl)-2-[(2R)-4-(4-fluoro-o-tolyl)-3-oxomorpholin-2-yl]-2-hydroxyacetamide;
65: (2R)—N-(4-Amidino-o-tolyl)-2-[(2R)-4-(4-tert-butylphenyl)-3-oxomorpholin-2-yl]-2-hydroxyacetamide;
66: (2R)—N-(4-Amidino-2-chlorophenyl)-2-[(2R)-4-(4-tert-butylphenyl)-3-oxomorpholin-2-yl]-2-hydroxyacetamide;

and

67: (2R)—N-(4-Amidino-2-fluorophenyl)-2-[(2R)-4-(4-tert-butylphenyl)-3-oxomorpholin-2-yl]-2-hydroxyacetamide;

[7-5] In another aspect, the present invention provides a compound selected from the group consisting of:

68

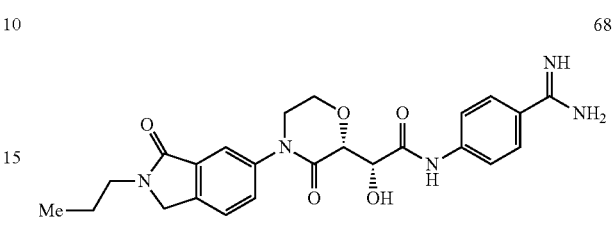

69

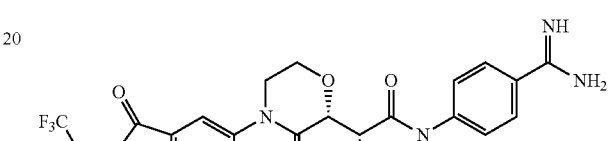

70

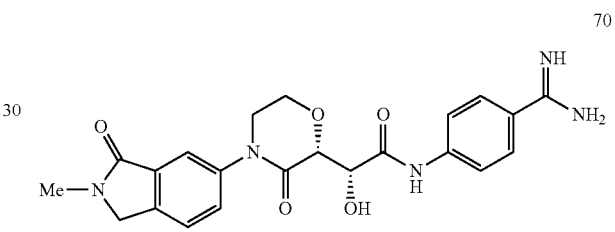

71

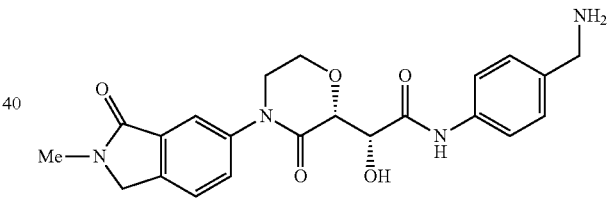

72

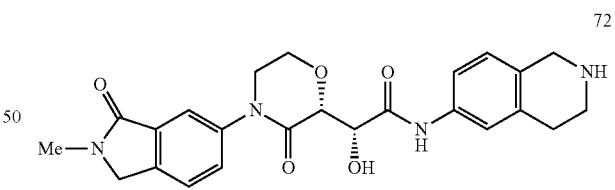

73

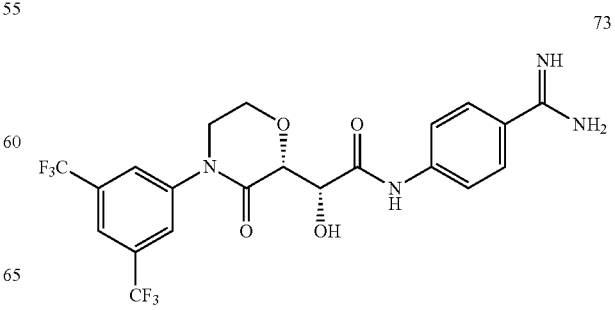

74
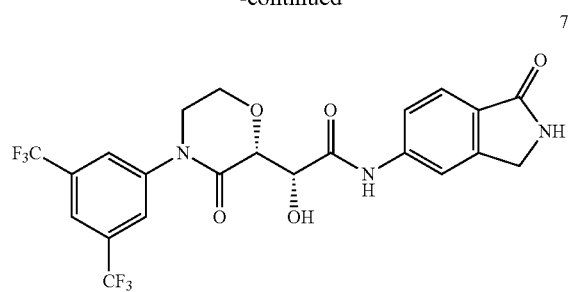
75
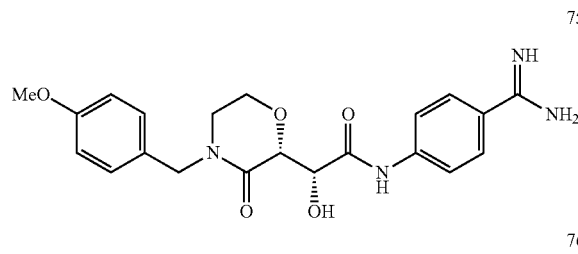
76
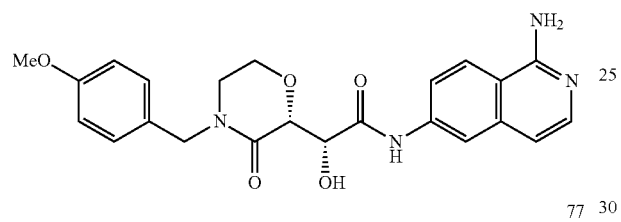
77
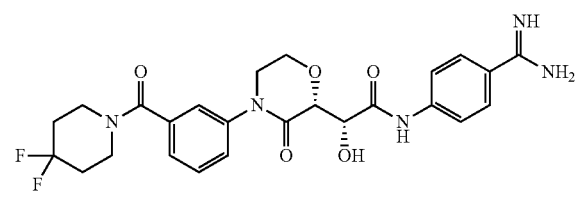
78
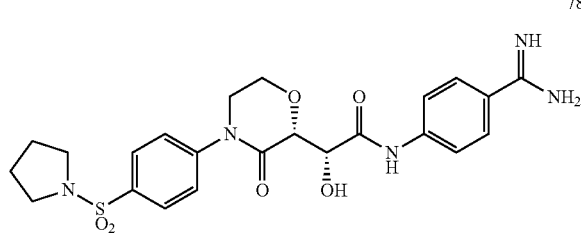
79
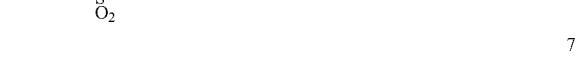
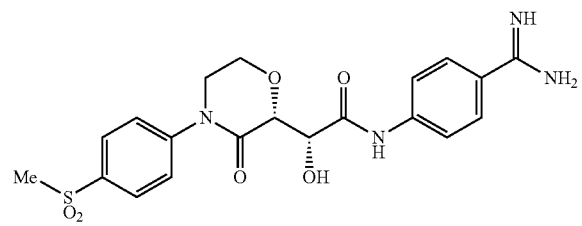
80

81
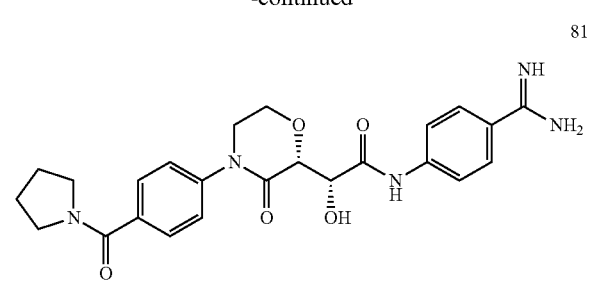
82
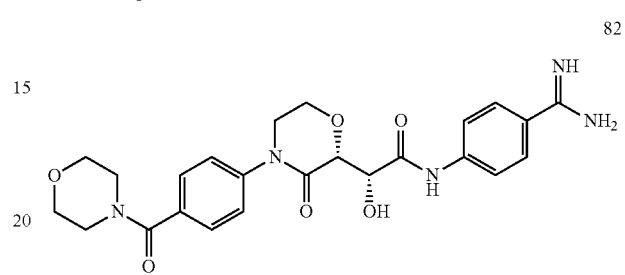
83
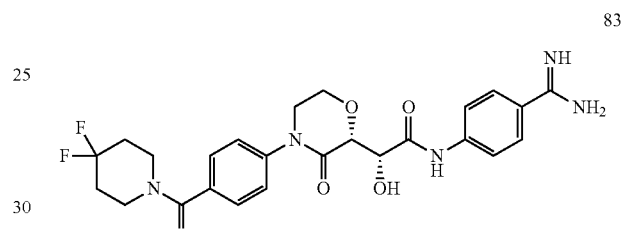
84
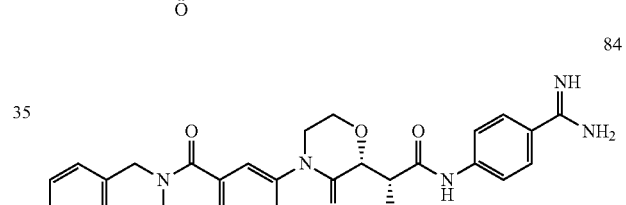
85

86
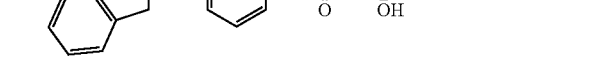
87

88
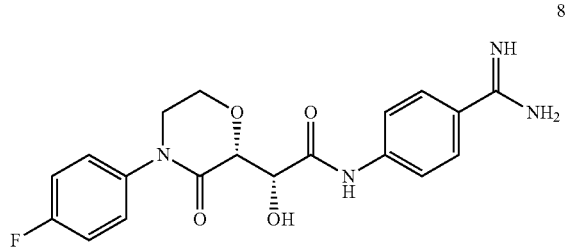
89
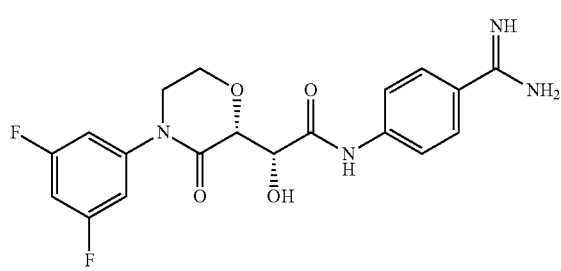
90
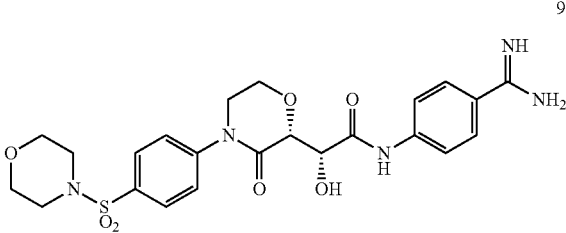
91
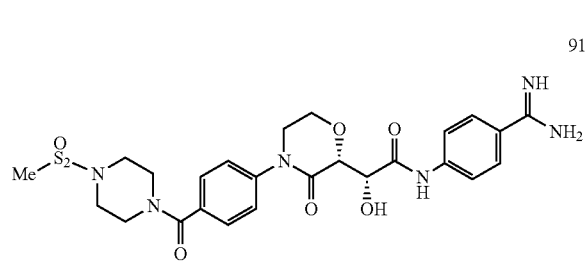
92
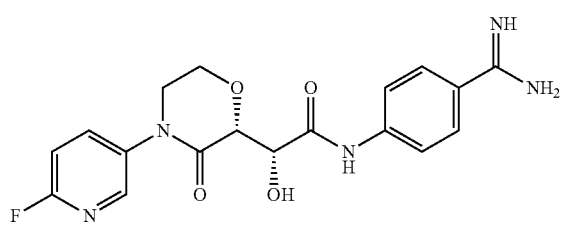
93
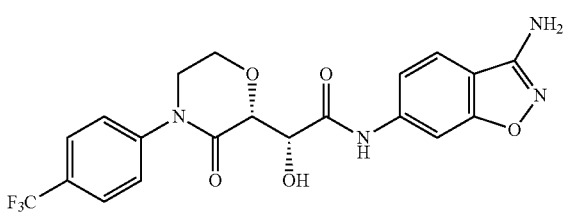
94
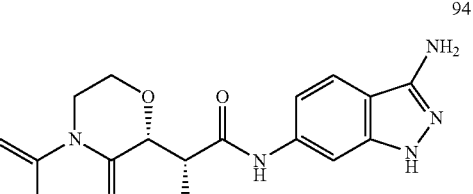
95
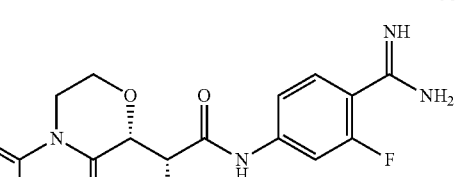
96
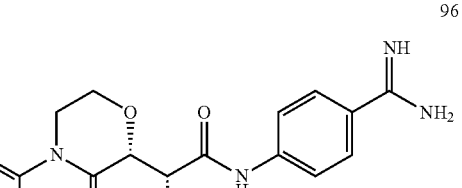
97
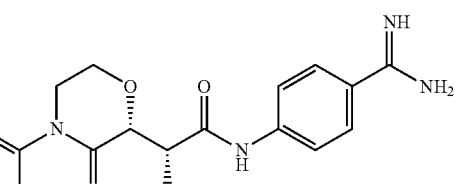
98
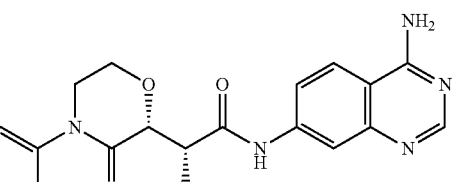
99
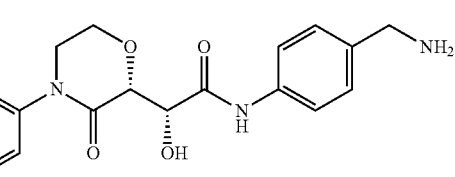
100
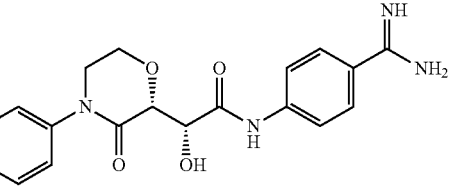

-continued
101
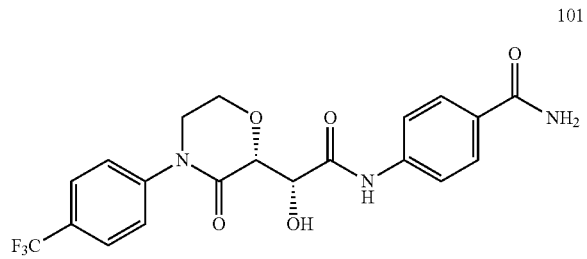
102
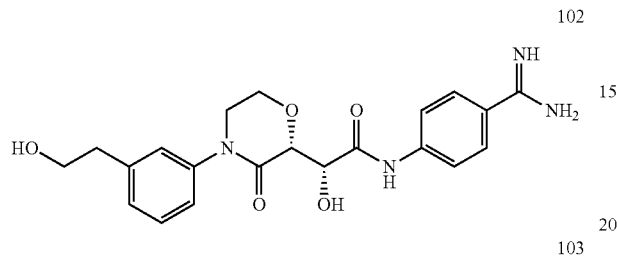
103
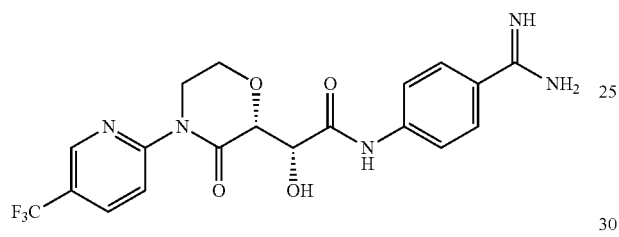
104
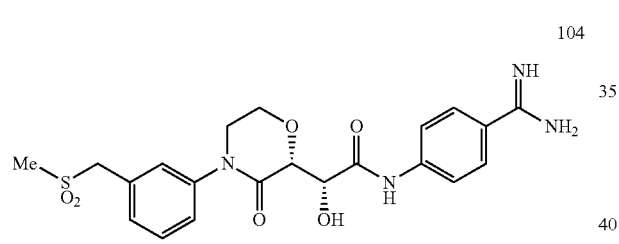
105
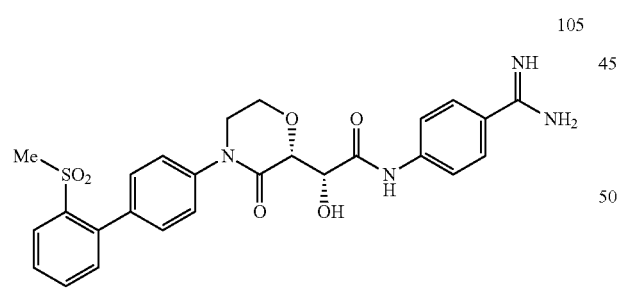
106
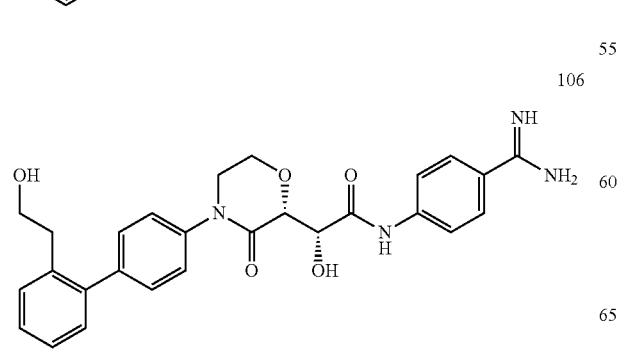
-continued
107
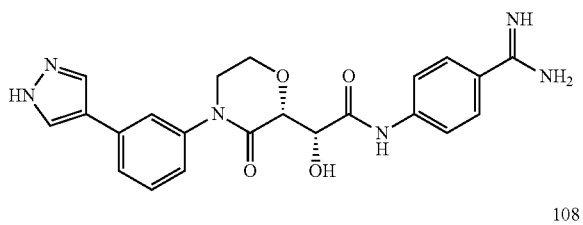
108
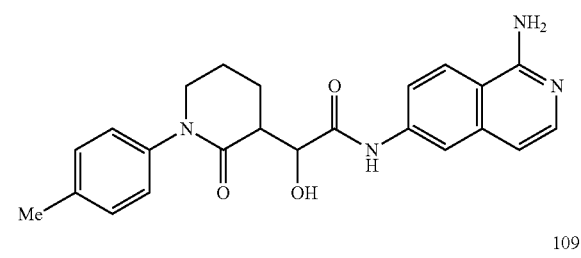
109
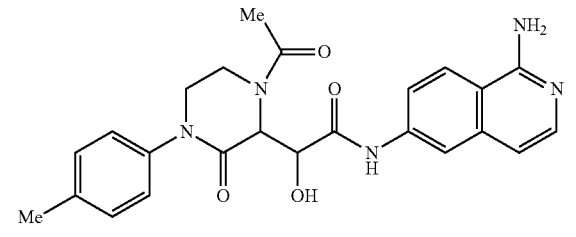
110
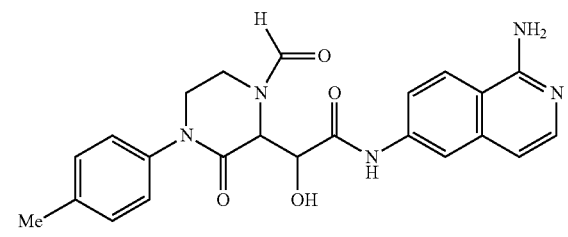
111
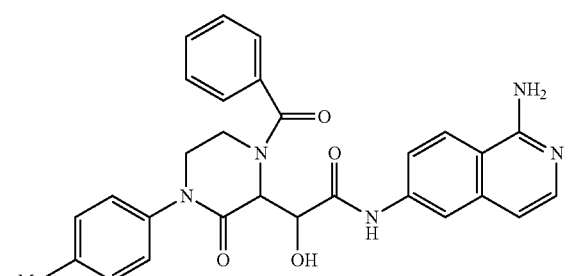
112
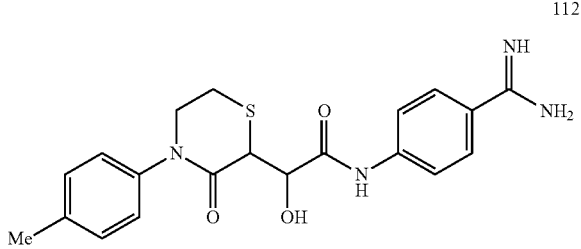

113
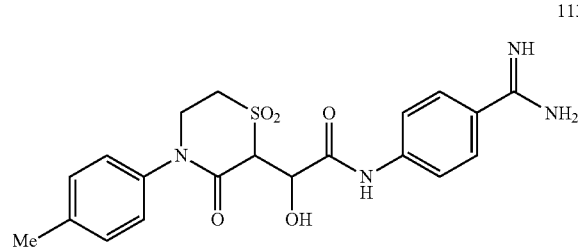
120
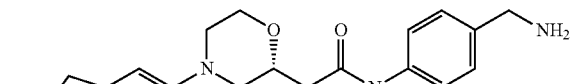
114
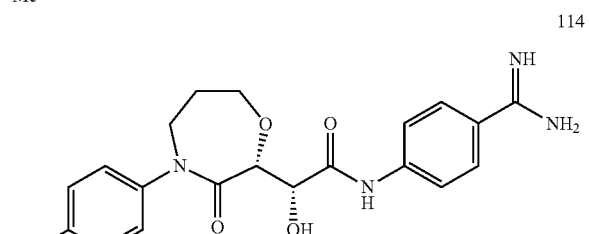
121
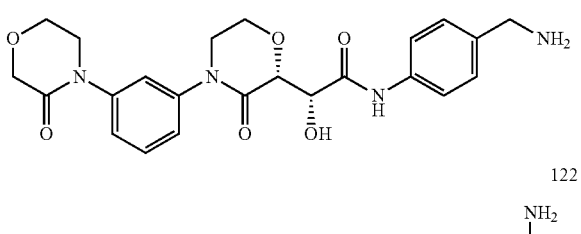
115
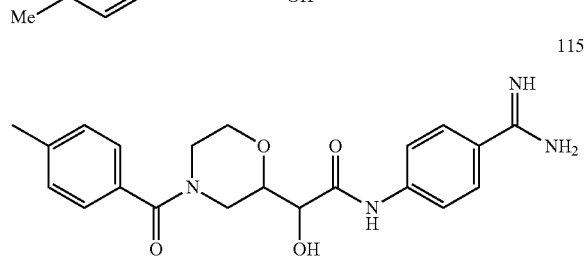
122
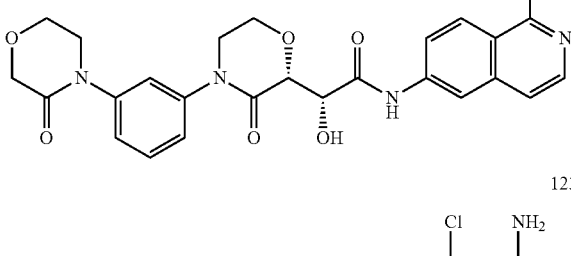
116
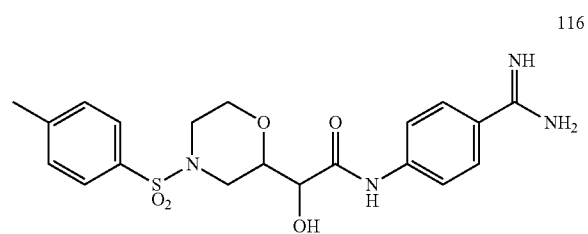
123
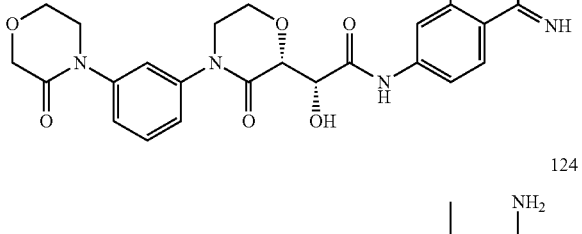
117
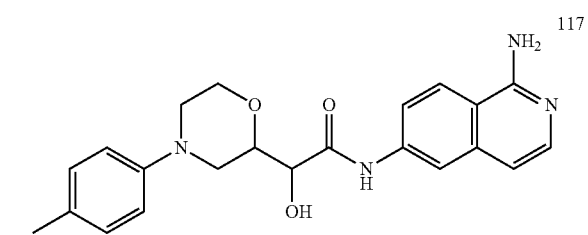
124
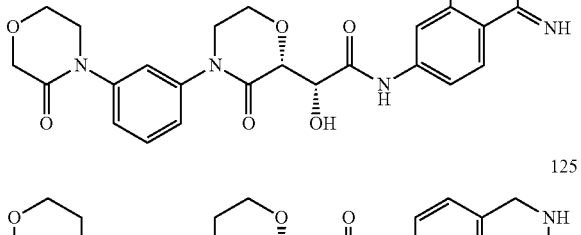
118
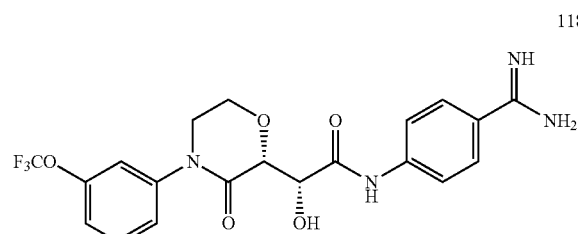
125
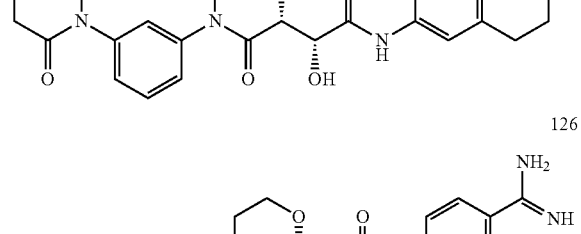
119
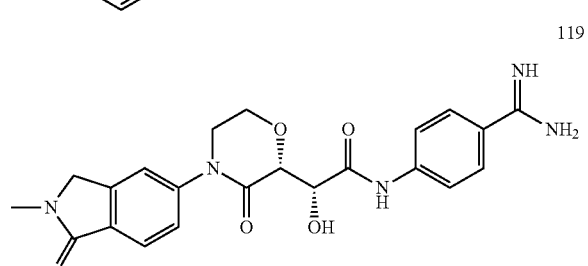
126
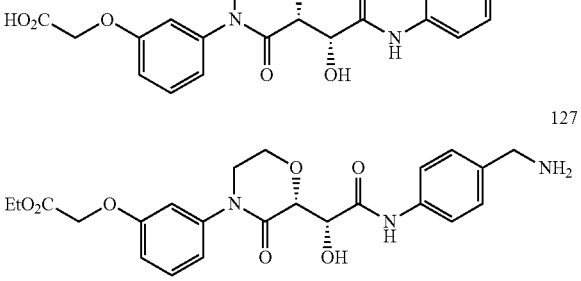
127

128
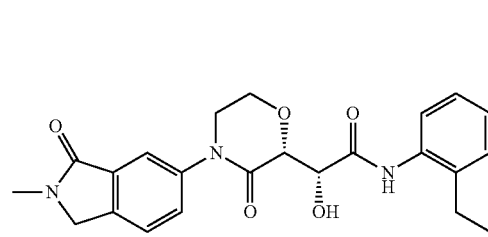
129
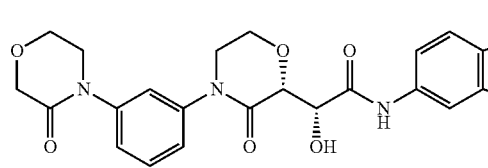
130
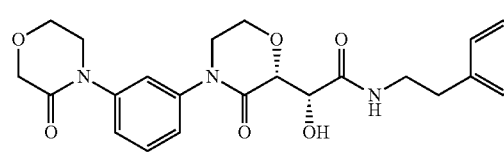
131
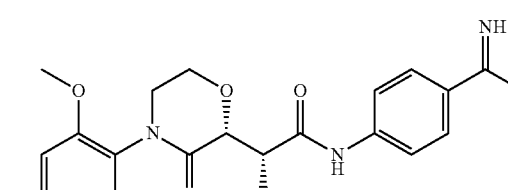
132
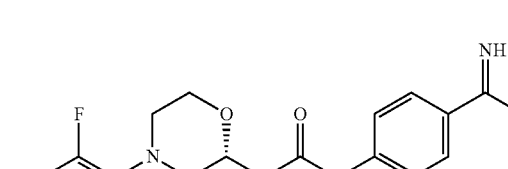
133
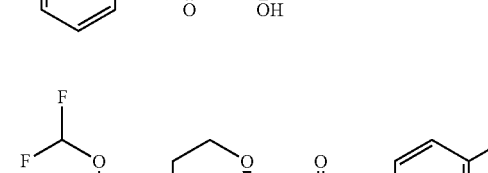
134
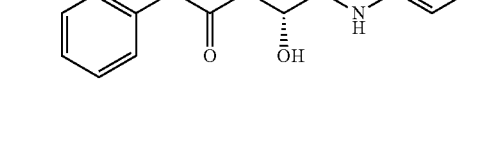
135
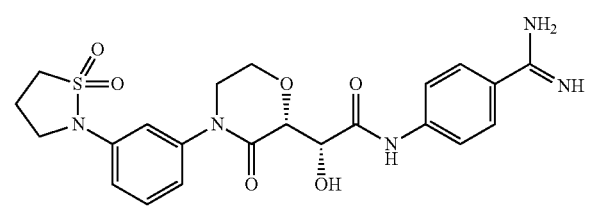
136
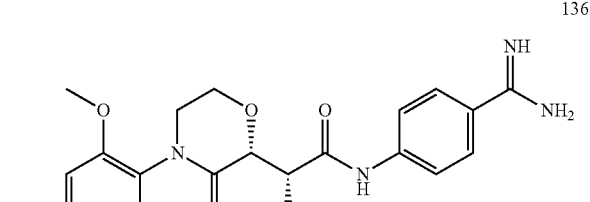
137
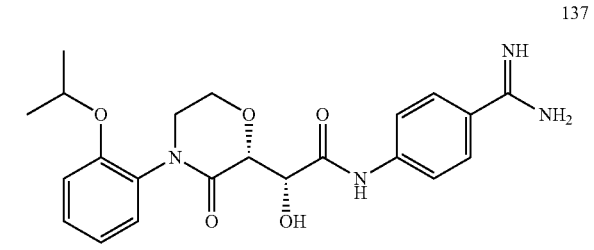
138

139
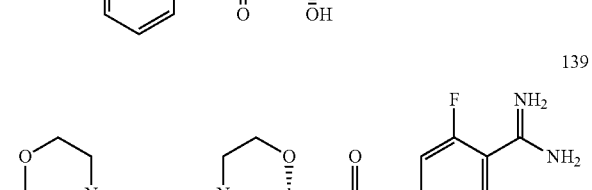
140
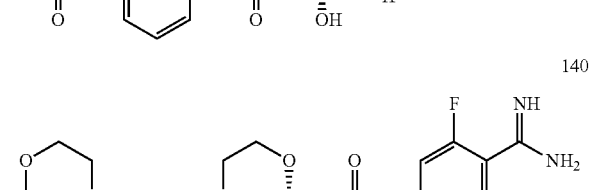
141
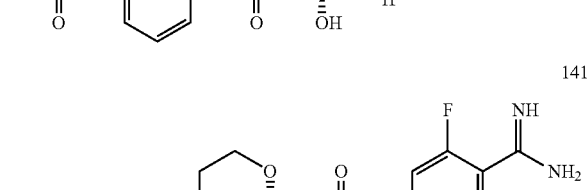

-continued
142
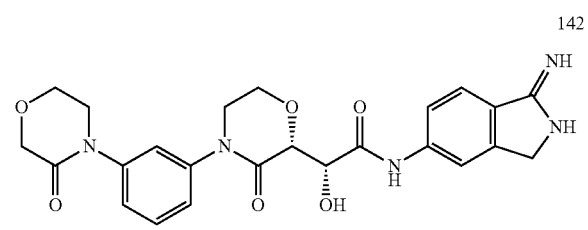
143
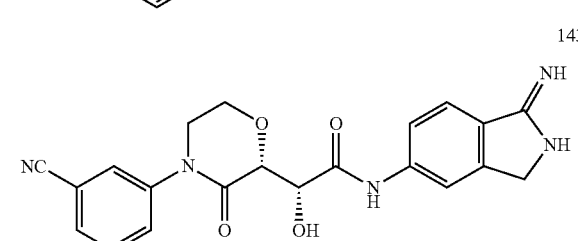
144
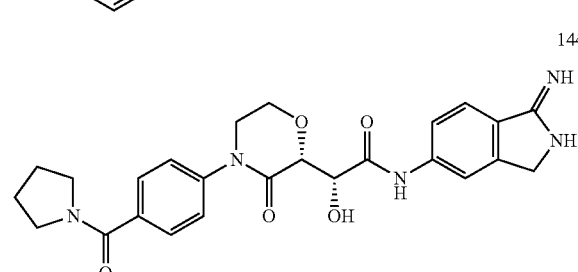
145
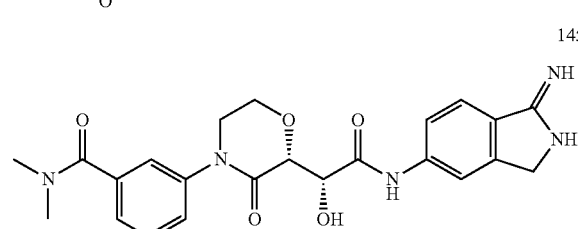
146
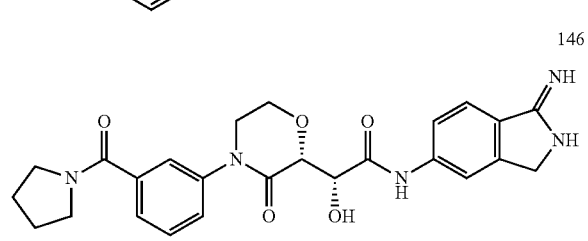
147
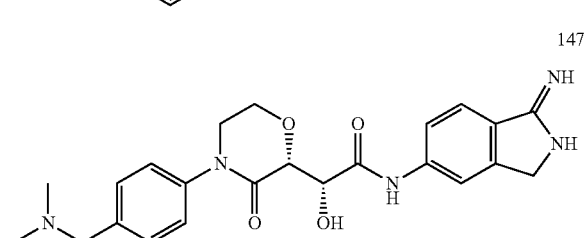
148
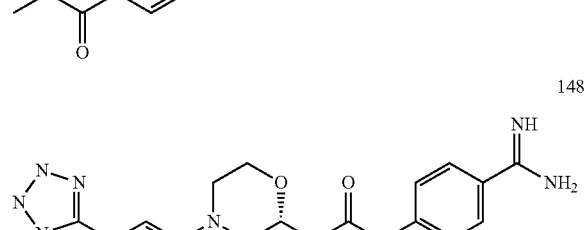
-continued
149
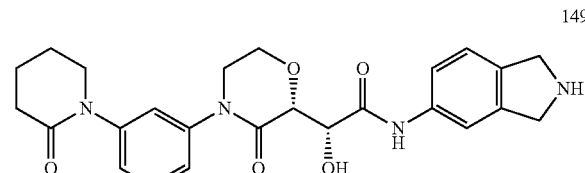
150
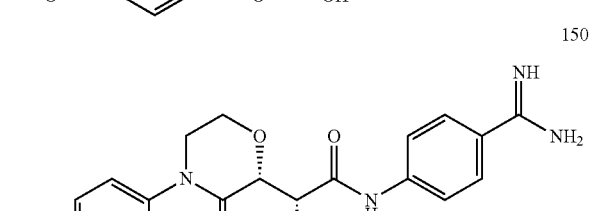
151
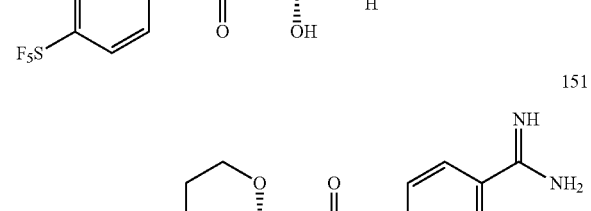
152
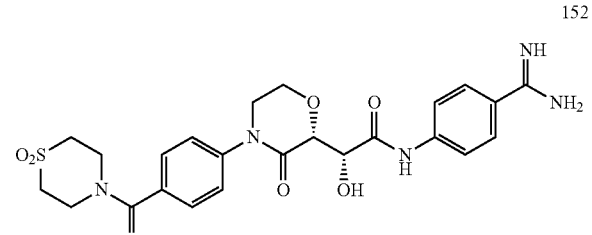
153
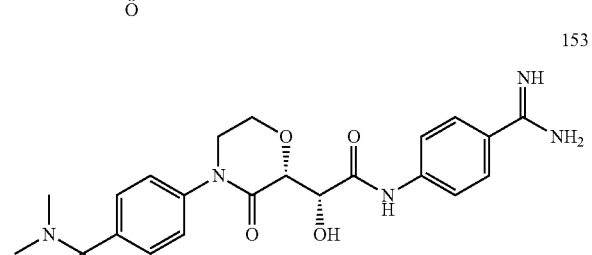
154
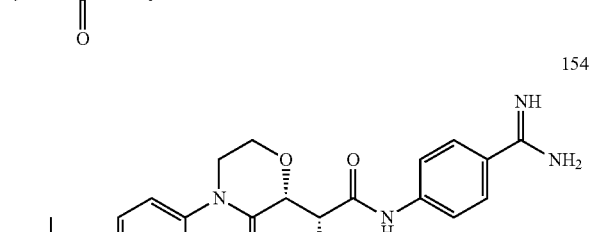
155
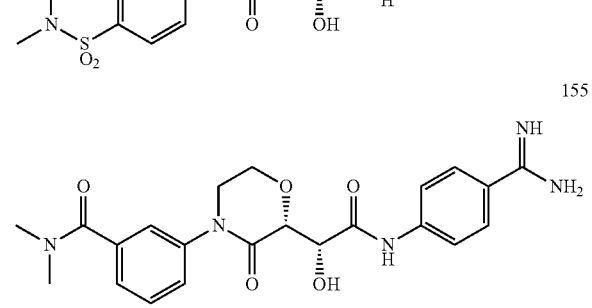

156
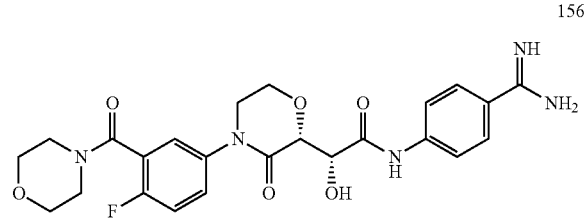
157
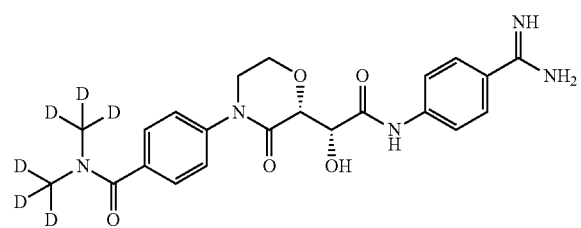
158
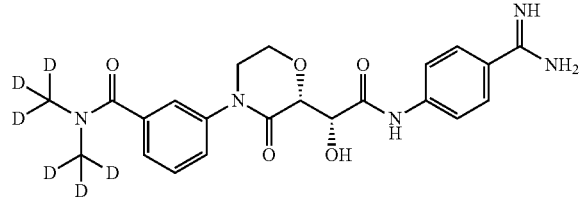
159
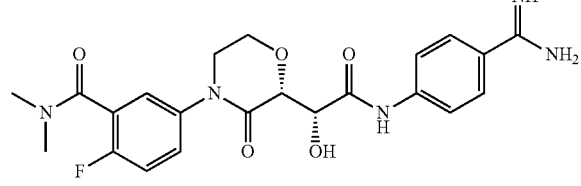
160
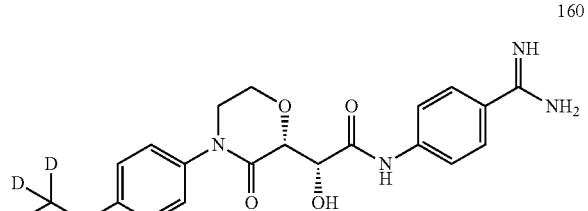
161
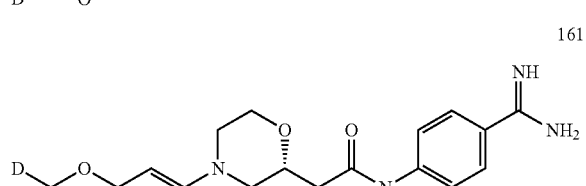
162
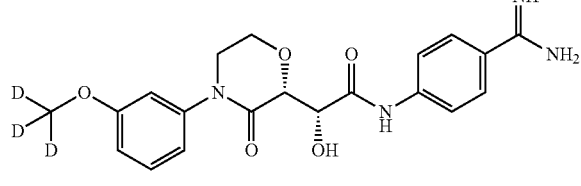
163
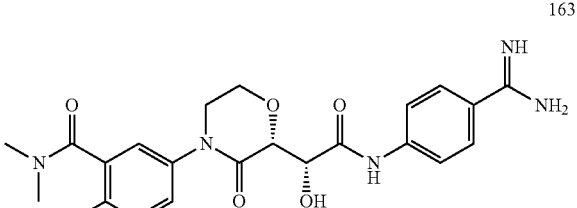
164
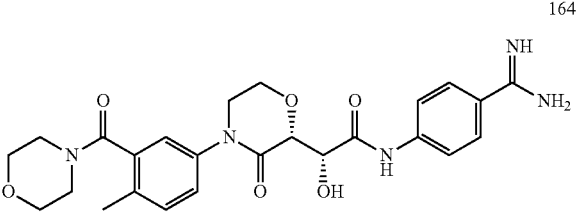
165
166
167
168
169

170
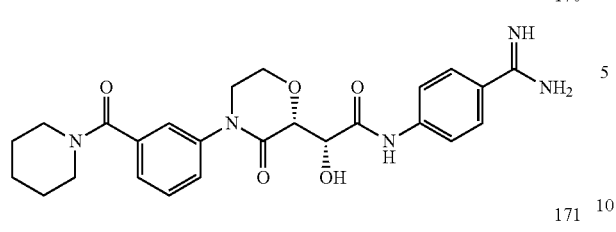
171
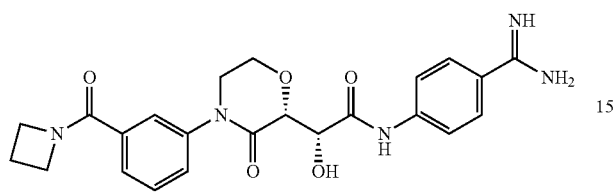
172
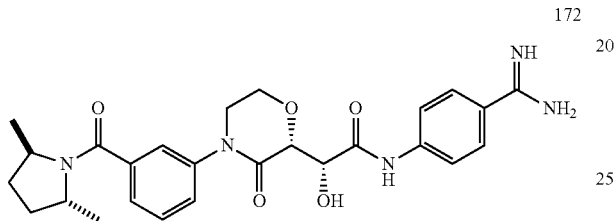
173

174
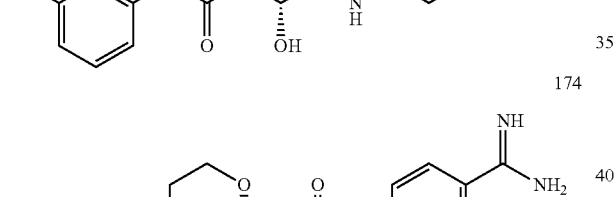
175

176
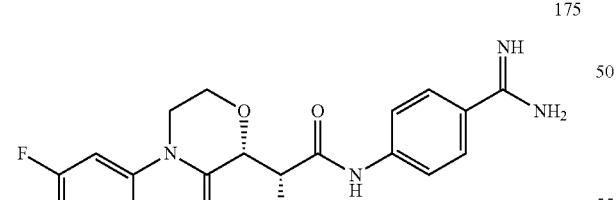
177
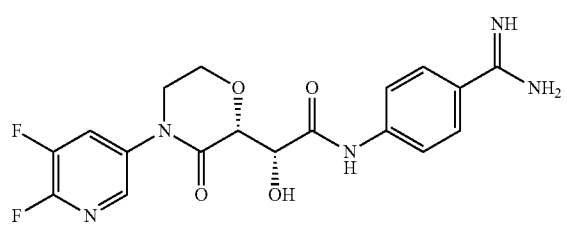
178
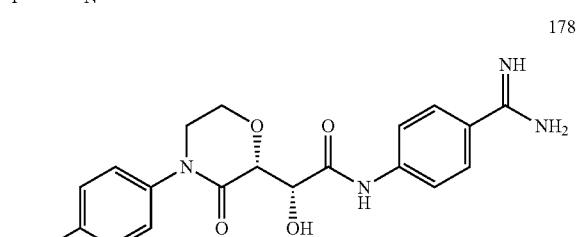
179
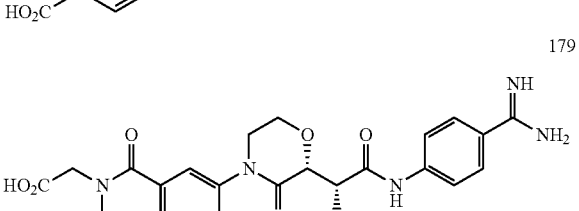
180
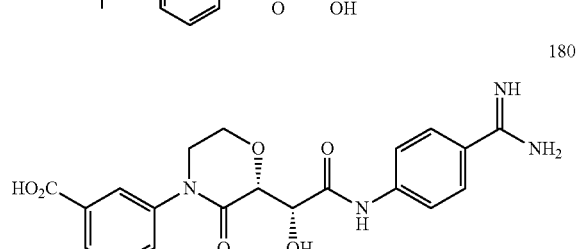
181
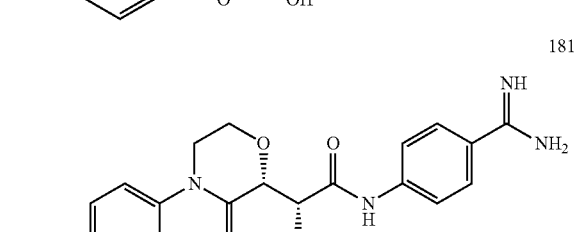
182
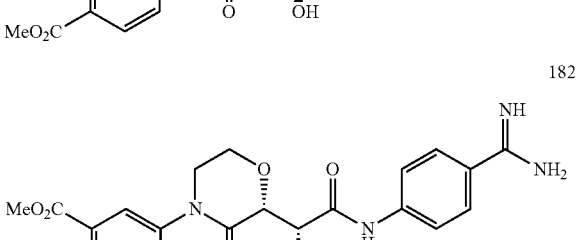
183
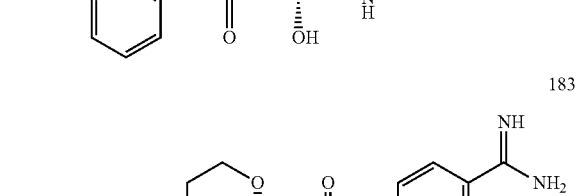

-continued

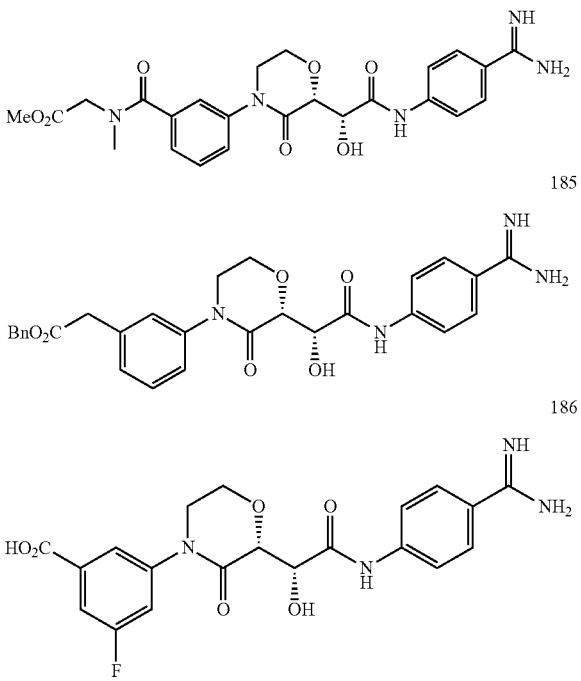

or a pharmaceutically acceptable salt or solvate thereof.

Each compound name from example 68 to example 217 is,

68: (R)—N-(4-carbamimidoylphenyl)-2-hydroxy-2-((R)-3-oxo-4-(3-oxo-2-propylisoindolin-5-yl)morpholin-2-yl)acetamide;
69: (R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide;
70: (R)—N-(4-carbamimidoylphenyl)-2-hydroxy-2-((R)-4-(2-methyl-3-oxoisoindolin-5-yl)-3-oxomorpholin-2-yl)acetamide;
71: (R)—N-(4-(aminomethyl)phenyl)-2-hydroxy-2-((R)-4-(2-methyl-3-oxoisoindolin-5-yl)-3-oxomorpholin-2-yl)acetamide;
72: (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide;
73: (R)-2-((R)-4-(3,5-bis(trifluoromethyl)phenyl)-3-oxomorpholin-2-yl)-N-(4-carbamimidoylphenyl)-2-hydroxyacetamide;
74: (R)-2-((R)-4-(3,5-bis(trifluoromethyl)phenyl)-3-oxomorpholin-2-yl)-2-hydroxy-N-(1-oxoisoindolin-5-yl)acetamide;
75: (R)—N-(4-carbamimidoylphenyl)-2-hydroxy-2-((R)-4-(4-methoxybenzyl)-3-oxomorpholin-2-yl)acetamide;
76: (R)—N-(1-aminoisoquinolin-6-yl)-2-hydroxy-2-((R)-4-(4-methoxybenzyl)-3-oxomorpholin-2-yl)acetamide;
77: (2R)—N-(4-amidinophenyl)-2-hydroxy-2-[(2R)-3-oxo-4-(3-(4,4-difluoropiperidin-1-ylcarbonyl)phenyl)morpholin-2-yl]acetamide;
78: (2R)—N-(4-amidinophenyl)-2-hydroxy-2-[(2R)-3-oxo-4-(4-(pyrrolidin-1-ylsulfonyl)phenyl)morpholin-2-yl]acetamide;
79: (2R)—N-(4-amidinophenyl)-2-hydroxy-2-[(2R)-3-oxo-4-(4-(methylsulfonyl)phenyl)morpholin-2-yl]acetamide;
80: (2R)—N-(4-amidinophenyl)-2-hydroxy-2-[(2R)-3-oxo-4-(3-phenylphenyl)morpholin-2-yl]acetamide;
81: (2R)—N-(4-amidinophenyl)-2-hydroxy-2-[(2R)-3-oxo-4-(4-(pyrrolidin-1-ylcarbonyl)phenyl)morpholin-2-yl]acetamide;
82: (2R)—N-(4-amidinophenyl)-2-hydroxy-2-[(2R)-3-oxo-4-(4-(morpholin-4-ylcarbonyl)phenyl)morpholin-2-yl]acetamide;
83: (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide;
84: (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide;
85: (2R)—N-(4-amidinophenyl)-2-hydroxy-2-[(2R)-3-oxo-4-(3-(isoindolin-2-ylcarbonyl)phenyl)morpholin-2-yl]acetamide;
86: (2R)—N-(4-amidinophenyl)-2-hydroxy-2-[(2R)-3-oxo-4-(3-(morpholin-4-ylcarbonyl)phenyl)morpholin-2-yl]acetamide;
87: (2R)—N-(4-amidinophenyl)-2-hydroxy-2-[(2R)-3-oxo-4-(3-(pyrrolidin-1-ylcarbonyl)phenyl)morpholin-2-yl]acetamide;
88: (2R)—N-(4-amidinophenyl)-2-hydroxy-2-[(2R)-3-oxo-4-(4-fluorophenyl)morpholin-2-yl]acetamide;
89: (2R)—N-(4-amidinophenyl)-2-hydroxy-2-[(2R)-3-oxo-4-(3,5-difluorophenyl)morpholin-2-yl]acetamide;
90: (2R)—N-(4-amidinophenyl)-2-hydroxy-2-[(2R)-3-oxo-4-(4-(morpholin-1-ylsulfonyl)phenyl)morpholin-2-yl]acetamide;
91: (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide;
92: (2R)—N-(4-amidinophenyl)-2-hydroxy-2-[(2R)-3-oxo-4-(2-fluoropyridin-5-yl)morpholin-2-yl]acetamide;
93: (R)—N-(3-aminobenzo[d]isoxazol-6-yl)-2-hydroxy-2-((R)-3-oxo-4-(4-(trifluoromethyl)phenyl)morpholin-2-yl)acetamide;
94: (R)—N-(3-amino-1H-indazol-6-yl)-2-hydroxy-2-((R)-3-oxo-4-(4-(trifluoromethyl)phenyl)morpholin-2-yl)acetamide;
95: (R)—N-(4-carbamimidoyl-3-fluorophenyl)-2-hydroxy-2-((R)-3-oxo-4-(4-(trifluoro methyl)phenyl)morpholin-2-yl)acetamide;
96: (R)—N-(4-carbamimidoylphenyl)-2-hydroxy-2-{(R)-3-oxo-4-[4-(trifluoromethyl)phenyl]morpholin-2-yl}acetamide;
97: (R)—N-(4-carbamimidoylphenyl)-2-hydroxy-2-((R)-3-oxo-4-(3-(trifluoromethyl)phenyl)morpholin-2-yl)acetamide;
98: N-(4-amino-7-quinazolinyl)-alpha(R)-hydroxy-3-oxo-4-[4-(trifluoromethyl)phenyl]-2(R)-morpholineacetamide;
99: N-[4-(aminomethyl)phenyl]-alpha(R)-hydroxy-3-oxo-4-[4-(trifluoromethyl)phenyl]-2(R)-morpholineacetamide;
100: N-[4-(aminoiminomethyl)phenyl]-4-[3-(aminomethyl)phenyl]-alpha(R)-hydroxy-3-oxo-2(R)-morpholineacetamide; and
101: N-[4-(aminocarbonyl)phenyl]-alpha(R)-hydroxy-3-oxo-4-[4-(trifluoromethyl)phenyl]-2(R)-morpholineacetamide;
102: (2R)—N-(4-amidinophenyl)-2-hydroxy-2-[(2R)-4-[3-(2-hydroxyethyl)phenyl]-3-oxomorpholin-2-yl]acetamide;
103: (2R)—N-(4-amidinophenyl)-2-hydroxy-2-[(2R)-3-oxo-4-[5-(trifluoromethyl)-2-pyridyl]morpholin-2-yl]acetamide;
104: (2R)—N-[4-amidinophenyl]-2-hydroxy-2-[(2R)-4-[3-(methylsulfonylmethyl)phenyl]-3-oxomorpholin-2-yl]acetamide;

105: (2R)—N-(4-amidinophenyl)-2-hydroxy-2-[(2R)-4-[4-(2-methylsulfonylphenyl)phenyl]-3-oxomorpholin-2-yl]acetamide;

106: (2R)—N-(4-amidinophenyl)-2-hydroxy-2-[(2R)-4-[4-[2-(2-hydroxyethyl)phenyl]phenyl]-3-oxomorpholin-2-yl]acetamide;

107: (2R)—N-(4-amidinophenyl)-2-hydroxy-2-[(2R)-3-oxo-4-[3-(1H-pyrazol-4-yl)phenyl]morpholin-2-yl]acetamide;

108: N-(1-amino-6-isoquinolyl)-2-hydroxy-2-[2-oxo-1-(p-tolyl)-3-piperidyl]acetamide 109: 2-[1-acetyl-3-oxo-4-(p-tolyl)piperazin-2-yl]-N-(1-amino-6-isoquinolyl)-2-hydroxy-acetamide;

110: N-(1-amino-6-isoquinolyl)-2-[1-formyl-3-oxo-4-(p-tolyl)piperazin-2-yl]-2-hydroxyacetamide;

111: N-(1-amino-6-isoquinolyl)-2-[1-benzoyl-3-oxo-4-(p-tolyl)piperazin-2-yl]-2-hydroxyacetamide;

112: N-(4-amidinophenyl)-2-hydroxy-2-[3-oxo-4-(p-tolyl)thiomorpholin-2-yl]acetamide;

113: N-(4-amidinophenyl)-2-hydroxy-2-[1,1,3-trioxo-4-(p-tolyl)-1,4-thiazinan-2-yl]acetamide;

114: (2R)—N-(4-amidinophenyl)-2-hydroxy-2-[(2R)-3-oxo-4-(p-tolyl)-1,4-oxazepan-2-yl]acetamide;

115: N-(4-amidinophenyl)-2-hydroxy-2-[4-(4-methylbenzoyl)morpholin-2-yl]acetamide;

116: N-(4-amidinophenyl)-2-hydroxy-2-[4-(p-tolylsulfonyl)morpholin-2-yl]acetamide;

117: N-(1-amino-6-isoquinolyl)-2-hydroxy-2-[4-(p-tolyl)morpholin-2-yl]acetamide ditrifluoroacetate;

118: (R)—N-(4-Carbamimidoylphenyl)-2-hydroxy-2-((R)-3-oxo-4-(3-(trifluoromethoxy)phenyl)morpholin-2-yl)acetamide;

119: (R)—N-(4-Carbamimidoylphenyl)-2-hydroxy-2-((R)-4-(2-methyl-3-oxoisoindolin-5-yl)-3-oxomorpholin-2-yl)acetamide;

120: (R)—N-(4-(Aminomethyl)phenyl)-2-hydroxy-2-((R)-4-(2-methyl-1-oxoisoindolin-5-yl)-3-oxomorpholin-2-yl)acetamide;

121: (R)—N-(4-(Aminomethyl)phenyl)-2-hydroxy-2-((R)-3-oxo-4-(3-(3-oxomorpholino)phenyl)morpholin-2-yl)acetamide;

122: (R)—N-(1-Aminoisoquinolin-6-yl)-2-hydroxy-2-((R)-3-oxo-4-(3-(3-oxomorpholino)phenyl)morpholin-2-yl)acetamide;

123: (R)—N-(4-Carbamimidoyl-3-chlorophenyl)-2-hydroxy-2-((R)-3-oxo-4-(3-(3-oxomorpholino)phenyl)morpholin-2-yl)acetamide;

124: (R)—N-(4-Carbamimidoyl-3-methylphenyl)-2-hydroxy-2-((R)-3-oxo-4-(3-(3-oxomorpholino)phenyl)morpholin-2-yl)acetamide;

125: (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide;

126: 2-(3-((R)-2-((R)-2-(4-Carbamimidoylphenylamino)-1-hydroxy-2-oxoethyl)-3-oxo morpholino)phenoxy)acetic acid;

127: Ethyl 2-(3-((R)-2-((R)-2-(4-(aminomethyl)phenylamino)-1-hydroxy-2-oxo ethyl)-3-oxomorpholino)phenoxy)acetate;

128: (R)—N-(4-carbamimidoyl-2-ethylphenyl)-2-hydroxy-2-((R)-4-(2-methyl-3-oxoisoindolin-5-yl)-3-oxomorpholin-2-yl)acetamide;

129: (R)-2-Hydroxy-N-(2-methyl-1H-indol-5-yl)-2-((R)-3-oxo-4-(3-(3-oxomorpholino)phenyl)morpholin-2-yl)acetamide;

130: (R)—N-(4-Chlorophenethyl)-2-hydroxy-2-((R)-3-oxo-4-(3-(3-oxomorpholino)phenyl)morpholin-2-yl)acetamide;

131: (R)—N-(4-carbamimidoylphenyl)-2-hydroxy-2-((R)-4-(2-methoxyphenyl)-3-oxomorpholin-2-yl)acetamide;

132: (R)—N-(4-carbamimidoylphenyl)-2-hydroxy-2-((R)-4-(2-fluorophenyl)-3-oxomorpholin-2-yl)acetamide;

133: (R)—N-(4-carbamimidoylphenyl)-2-hydroxy-2-((R)-4-(2-(difluoromethoxy)phenyl)-3-oxomorpholin-2-yl)acetamide;

134: (R)—N-(6-carbamimidoylpyridin-3-yl)-2-hydroxy-2-((R)-3-oxo-4-(3-(3-oxomorpholino)phenyl)morpholin-2-yl)acetamide;

135: N-[4-(aminoiminomethyl)phenyl]-4-[3-(1,1-dioxido-2-isothiazolidinyl)phenyl]-alpha(R)-hydroxy-3-oxo-2(R)-morpholineacetamide;

136: (R)—N-(4-carbamimidoylphenyl)-2-((R)-4-(4-fluoro-2-methoxyphenyl)-3-oxomorpholin-2-yl)-2-hydroxyacetamide;

137: (R)—N-(4-carbamimidoylphenyl)-2-hydroxy-2-((R)-4-(2-isopropoxyphenyl)-3-oxo morpholin-2-yl)acetamide;

138: (R)-2-((R)-4-(2-(2-amino-2-oxo ethoxy)phenyl)-3-oxomorpholin-2-yl)-N-(4-carbamimidoylphenyl)-2-hydroxyacetamide;

139: (R)—N-(4-carbamimidoyl-3-fluorophenyl)-2-hydroxy-2-((R)-3-oxo-4-(3-(3-oxomorpholino)phenyl)morpholin-2-yl)acetamide;

140: (R)—N-(4-carbamimidoyl-3,5-difluorophenyl)-2-hydroxy-2-((R)-3-oxo-4-(3-(3-oxomorpholino)phenyl)morpholin-2-yl)acetamide;

141: 3-((R)-2-((R)-2-(4-carbamimidoyl-3-fluorophenylamino)-1-hydroxy-2-oxoethyl)-3-oxomorpholino)benzoic acid;

142: N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide;

143: 4-(3-Cyanophenyl)-N-(2,3-dihydro-1-imino-1H-isoindol-5-yl)-alpha(R)-hydroxy-3-oxo-2(R)-morpholineacetamide;

144: N-(2,3-Dihydro-1-imino-1H-isoindol-5-yl)-alpha(R)-hydroxy-3-oxo-4-[4-(1-pyrrolidinylcarbonyl)phenyl]-2(R)-morpholineacetamide;

145: N-(2,3-Dihydro-1-imino-1H-isoindol-5-yl)-4-[3-[(dimethylamino)carbonyl]phenyl]-alpha(R)-hydroxy-3-oxo-2(R)-morpholineacetamide;

146: n-(2,3-Dihydro-1-imino-1H-isoindol-5-yl)-alpha(R)-hydroxy-3-oxo-4-[3-(1-pyrrolidinylcarbonyl)phenyl]-2(R)-morpholineacetamide;

147: N-(2,3-Dihydro-1-imino-1H-isoindol-5-yl)-4-[4-[(dimethylamino)carbonyl]phenyl]-alpha(R)-hydroxy-3-oxo-2(R)-morpholineacetamide;

148: N-[4-(Aminoiminomethyl)phenyl]-alpha(R)-hydroxy-3-oxo-4-[3-(1h-tetrazol-5-yl)phenyl]-2(R)-morpholineacetamide;

149: N-(2,3-dihydro-1H-isoindol-5-yl)-alpha(R)-hydroxy-3-oxo-4-[3-(3-oxo-4-morpholinyl)phenyl]-2(R)-morpholineacetamide;

150: [4-[2(R)-[2-[[4-(Aminoiminomethyl)phenyl]amino]-1(R)-hydroxy-2-oxoethyl]-3-oxo-4-morpholinyl]phenyl]pentafluorosulfur;

151: [3-[2(R)-[2-[[4-(Aminoiminomethyl)phenyl]amino]-1(R)-hydroxy-2-oxoethyl]-3-oxo-4-morpholinyl]phenyl]pentafluorosulfur;

152: (2R)—N-(4-amidinophenyl)-2-hydroxy-2-[(2R)-3-oxo-4-(4-(1,1-dioxothiomorpholin-4-ylcarbonyl)phenyl)morpholin-2-yl]acetamide;

153: (2R)—N-(4-amidinophenyl)-2-hydroxy-2-[(2R)-3-oxo-4-(4-(dimethylaminocarbonyl)phenyl)morpholin-2-yl]acetamide;
154: (2R)—N-(4-amidinophenyl)-2-hydroxy-2-[(2R)-3-oxo-4-(4-(dimethylaminolsulfonyl)phenyl)morpholin-2-yl]acetamide;
155: (2R)—N-(4-amidinophenyl)-2-hydroxy-2-[(2R)-3-oxo-4-(3-(dimethylaminocarbonyl)phenyl)morpholin-2-yl]acetamide;
156: (2R)—N-(4-amidinophenyl)-2-hydroxy-2-[(2R)-3-oxo-4-(4-fluoro-3-(morpholin-4-ylcarbonyl)phenyl)morpholin-2-yl]acetamide;
157: (2R)—N-(4-amidinophenyl)-2-hydroxy-2-[(2R)-3-oxo-4-(4-(dimethyl-$D_6$-aminocarbonyl)phenyl)morpholin-2-yl]acetamide;
158: (2R)—N-(4-amidinophenyl)-2-hydroxy-2-[(2R)-3-oxo-4-(3-(dimethyl-$D_6$-aminocarbonyl)phenyl)morpholin-2-yl]acetamide;
159: (2R)—N-(4-amidinophenyl)-2-hydroxy-2-[(2R)-3-oxo-4-(3-(dimethylaminocarbonyl)-4-fluorophenyl)morpholin-2-yl]acetamide;
160: (2R)—N-(4-amidinophenyl)-2-hydroxy-2-[(2R)-3-oxo-4-(4-methoxy-$D_3$-phenyl)morpholin-2-yl]acetamide;
161: (2R)—N-(4-amidinophenyl)-2-hydroxy-2-[(2R)-3-oxo-4-(3-methoxy-$D_3$-phenyl)morpholin-2-yl]acetamide;
162: (2R)—N-(4-amidinophenyl)-2-hydroxy-2-[(2R)-3-oxo-4-(4-fluoro-3-(pyrrolidin-1-ylcarbonyl)phenyl)morpholin-2-yl]acetamide;
163: (2R)—N-(4-amidinophenyl)-2-hydroxy-2-[(2R)-3-oxo-4-(3-(dimethylaminocarbonyl)-4-methylphenyl)morpholin-2-yl]acetamide;
164: (2R)—N-(4-amidinophenyl)-2-hydroxy-2-[(2R)-3-oxo-4-(4-methyl-3-(morpholin-4-ylcarbonyl)phenyl)morpholin-2-yl]acetamide;
165: (2R)—N-(4-amidinophenyl)-2-hydroxy-2-[(2R)-3-oxo-4-(4-methyl-3-(pyrrolidin-1-ylcarbonyl)phenyl)morpholin-2-yl]acetamide;
166: (2R)—N-(4-amidinophenyl)-2-hydroxy-2-[(2R)-3-oxo-4-(3-fluoro-5-(pyrrolidin-1-ylcarbonyl)phenyl)morpholin-2-yl]acetamide;
167: (2R)—N-(4-amidinophenyl)-2-hydroxy-2-[(2R)-3-oxo-4-(3-fluoro-5-(morpholin-4-ylcarbonyl)phenyl)morpholin-2-yl]acetamide;
168: (2R)—N-(4-amidinophenyl)-2-hydroxy-2-[(2R)-3-oxo-4-(3-(dimethylaminocarbonyl)-5-fluorophenyl)morpholin-2-yl]acetamide;
169: (2R)—N-(4-amidinophenyl)-2-hydroxy-2-[(2R)-3-oxo-4-(3-(dimethylaminocarbonyl)-2-methylphenyl)morpholin-2-yl]acetamide;
170: (2R)—N-(4-amidinophenyl)-2-hydroxy-2-[(2R)-3-oxo-4-(3-(piperidin-1-ylcarbonyl)phenyl)morpholin-2-yl]acetamide;
171: (2R)—N-(4-amidinophenyl)-2-hydroxy-2-[(2R)-3-oxo-4-(3-(azetidin-1-ylcarbonyl)phenyl)morpholin-2-yl]acetamide;
172: (2R)—N-(4-amidinophenyl)-2-hydroxy-2-[(2R)-3-oxo-4-(3-((2R,5R)-(−)-trans-dim ethylpyrrolidin-1-ylcarbonyl)phenyl)morpholin-2-yl]acetamide;
173: (2R)—N-(4-amidinophenyl)-2-hydroxy-2-[(2R)-3-oxo-4-(3-fluorophenyl)morpholin-2-yl]acetamide;
174: (2R)—N-(4-amidinophenyl)-2-hydroxy-2-[(2R)-3-oxo-4-(3,4,5-trifluorophenyl)morpholin-2-yl]acetamide;
175: (2R)—N-(4-amidinophenyl)-2-hydroxy-2-[(2R)-3-oxo-4-(3,4-difluorophenyl)morpholin-2-yl]acetamide;
176: (2R)—N-(4-amidinophenyl)-2-hydroxy-2-[(2R)-3-oxo-4-(2,4-difluoropyridin-3-yl)morpholin-2-yl]acetamide;
177: (2R)—N-(4-amidinophenyl)-2-hydroxy-2-[(2R)-3-oxo-4-(4,5-difluoropyridin-3-yl)morpholin-2-yl]acetamide;
178: (2R)—N-(4-amidinophenyl)-2-hydroxy-2-[(2R)-3-oxo-4-(4-carboxyphenyl)morpholin-2-yl]acetamide;
179: (2R)—N-(4-amidinophenyl)-2-hydroxy-2-[(2R)-3-oxo-4-(3-(carboxymethyl)(methyl)carbamoylphenyl)morpholin-2-yl]acetamide;
180: (2R)—N-(4-amidinophenyl)-2-hydroxy-2-[(2R)-3-oxo-4-(3-carboxyphenyl)morpholin-2-yl]acetamide;
181: (2R)—N-(4-amidinophenyl)-2-hydroxy-2-[(2R)-3-oxo-4-(4-methoxycarbonylphenyl)morpholin-2-yl]acetamide;
182: (2R)—N-(4-amidinophenyl)-2-hydroxy-2-[(2R)-3-oxo-4-(3-methoxycarbonylphenyl)morpholin-2-yl]acetamide;
183: (2R)—N-(4-amidinophenyl)-2-hydroxy-2-[(2R)-3-oxo-4-(3-carboxy-4-fluorophenyl)morpholin-2-yl]acetamide;
184: (2R)—N-(4-amidinophenyl)-2-hydroxy-2-[(2R)-3-oxo-4-(3-(methoxycarbonylmethyl)(methyl)carbamoylphenyl)morpholin-2-yl]acetamide;
185: (2R)—N-(4-amidinophenyl)-2-hydroxy-2-[(2R)-3-oxo-4-(3-carboxymethylphenyl)morpholin-2-yl]acetamide; and
186: (2R)—N-(4-amidinophenyl)-2-hydroxy-2-[(2R)-3-oxo-4-(3-carboxy-5-fluorophenyl)morpholin-2-yl]acetamide.

[7-6] In another aspect, the present invention provides a compound of the Formula

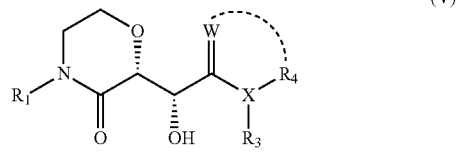

((R,R) isomer) or a pharmaceutically acceptable salt or solvate thereof, wherein $R_1$ is a group selected from the group consisting of a1 to a166 described in [7-1],
and wherein formula (III) in the formula (V)

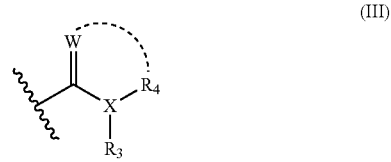

is selected from the group consisting of b1 to b61 described in [7-1].

[7-6-1] In another aspect, the present invention provides compounds of [7-6] wherein $R_1$ is a group selected from the group consisting of:
a1 to a33, a64 to a199,
and wherein the substructure of the Formula (V)

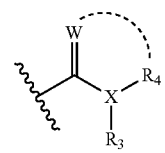

is selected from the group consisting of:
b1, b4, b49 to b67.

[8-1] In another aspect, the present invention provides (R,R) optically active isomers of compounds selected from the group consisting of compounds represented by Formula (I), Example compounds 1 to 208, Example compounds 1p to 24p, combination compounds represented by Formula (IV), or a pharmaceutically acceptable salt or a solvate thereof.

Combination compounds represented by Formula (IV) are expressed as general Compound (a1, b1) (IV) to Compound (a200, b67) (IV) as total 13400 subformula. For example, Compound (a1, b1) (IV) corresponds to the structure of:

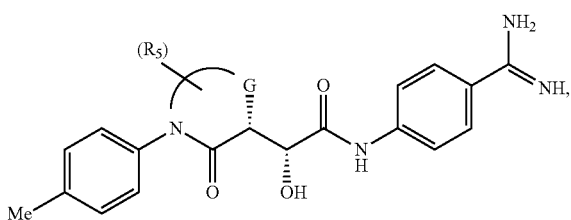

wherein n, G and R5 is the same definition as Formula (I).

Combination compounds represented by Formula (V) are expressed as Compound (a1, b1) to Compound (a200, b67) as total 13400 compounds. For example, Compound (a1, b1) corresponds to the structure of:

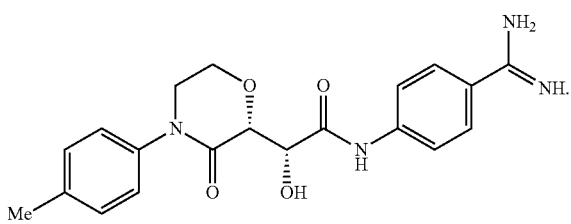 [SMILES: Cc1ccc(N2CCO[C@H]([C@@H](O)C(=O)Nc3ccc(C(=N)N)cc3)C2=O)cc1]

The invention also provides compounds of Formula (aI)

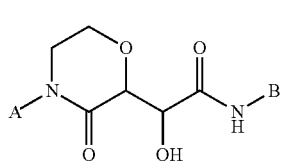
(aI)

or a pharmaceutically acceptable salt or a solvate thereof, wherein
A is

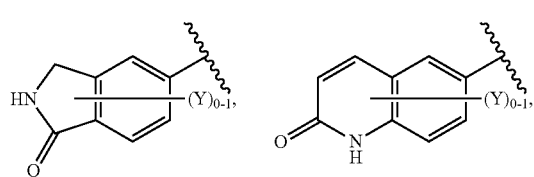

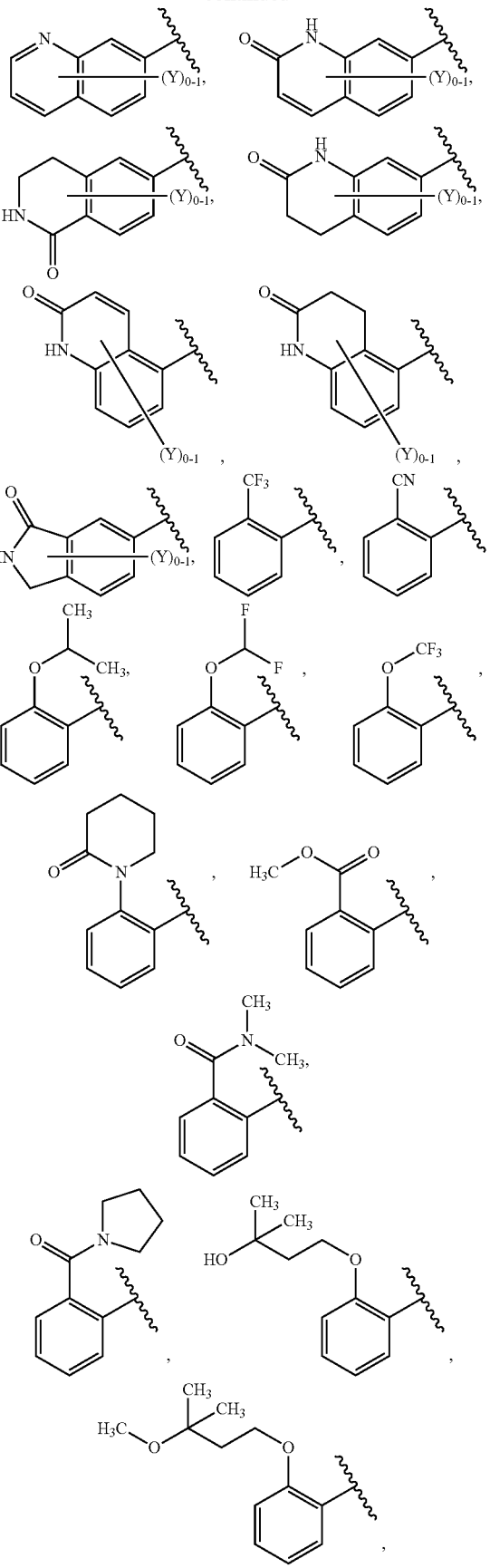

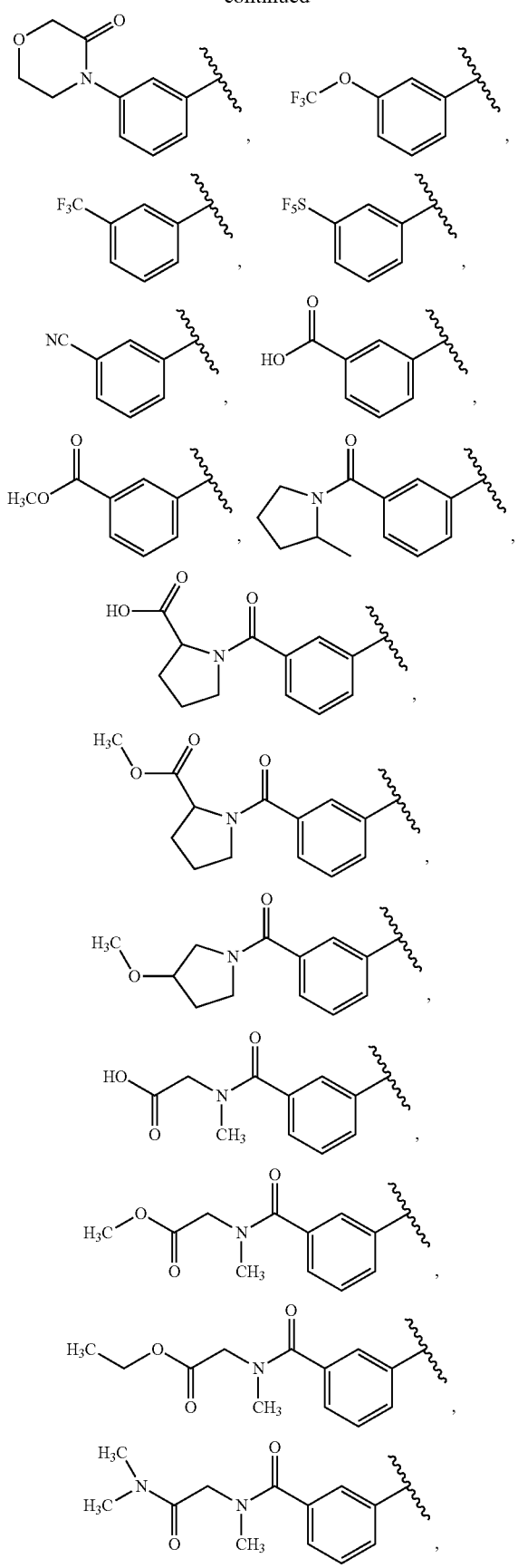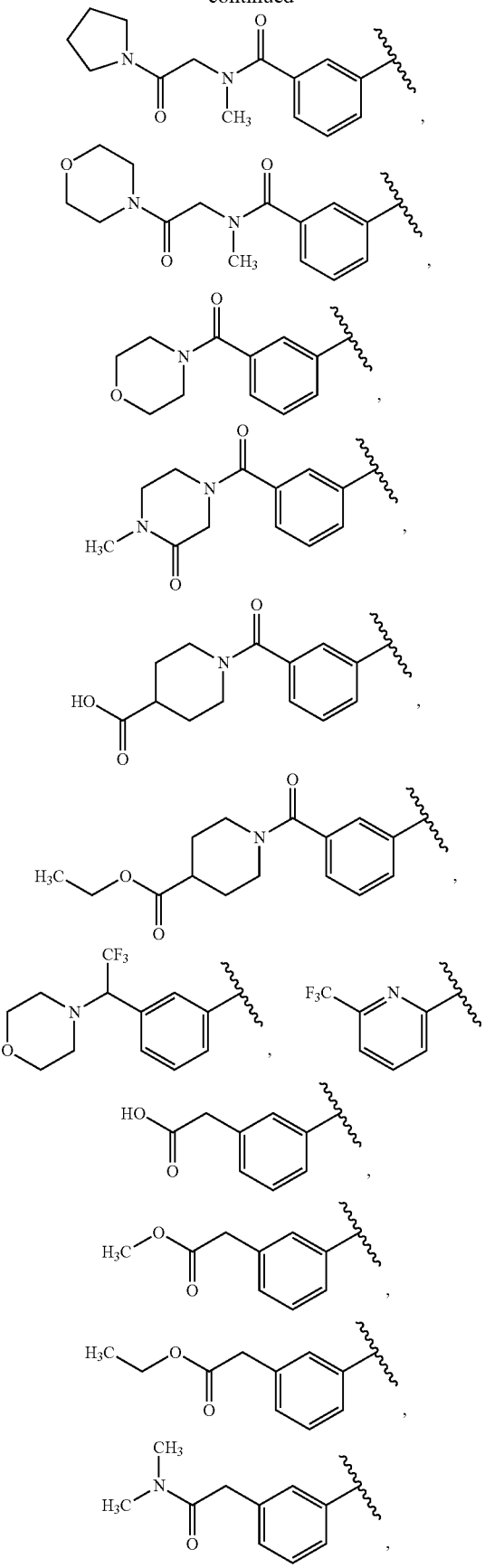

115
-continued
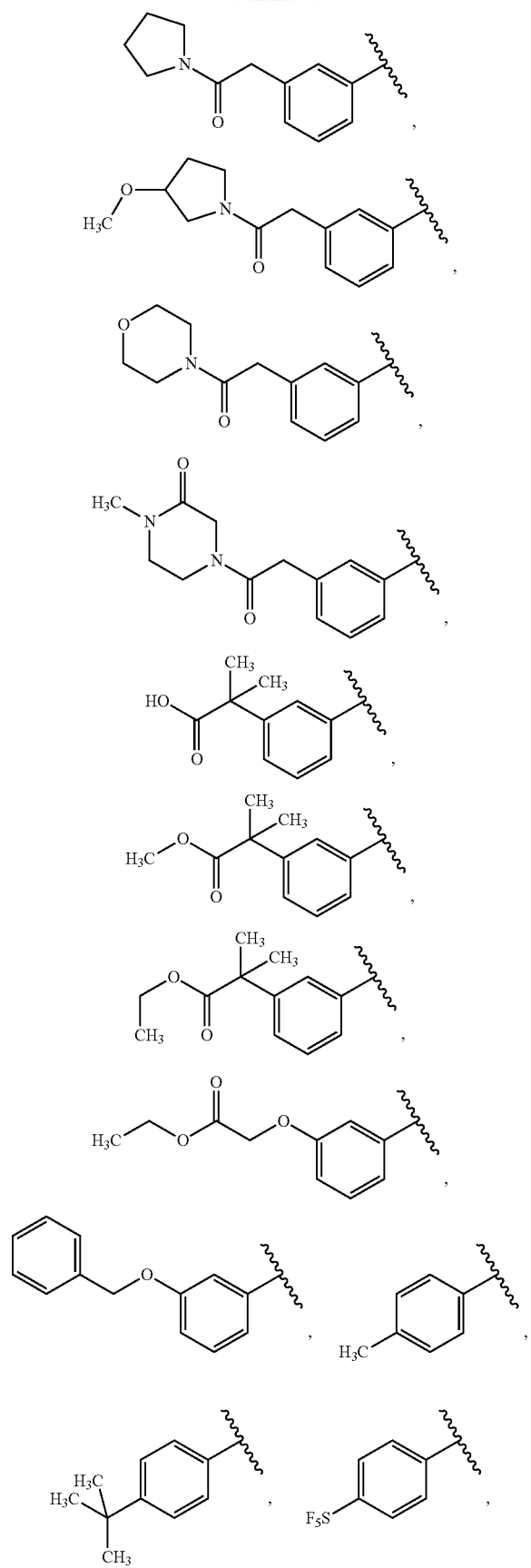
116
-continued
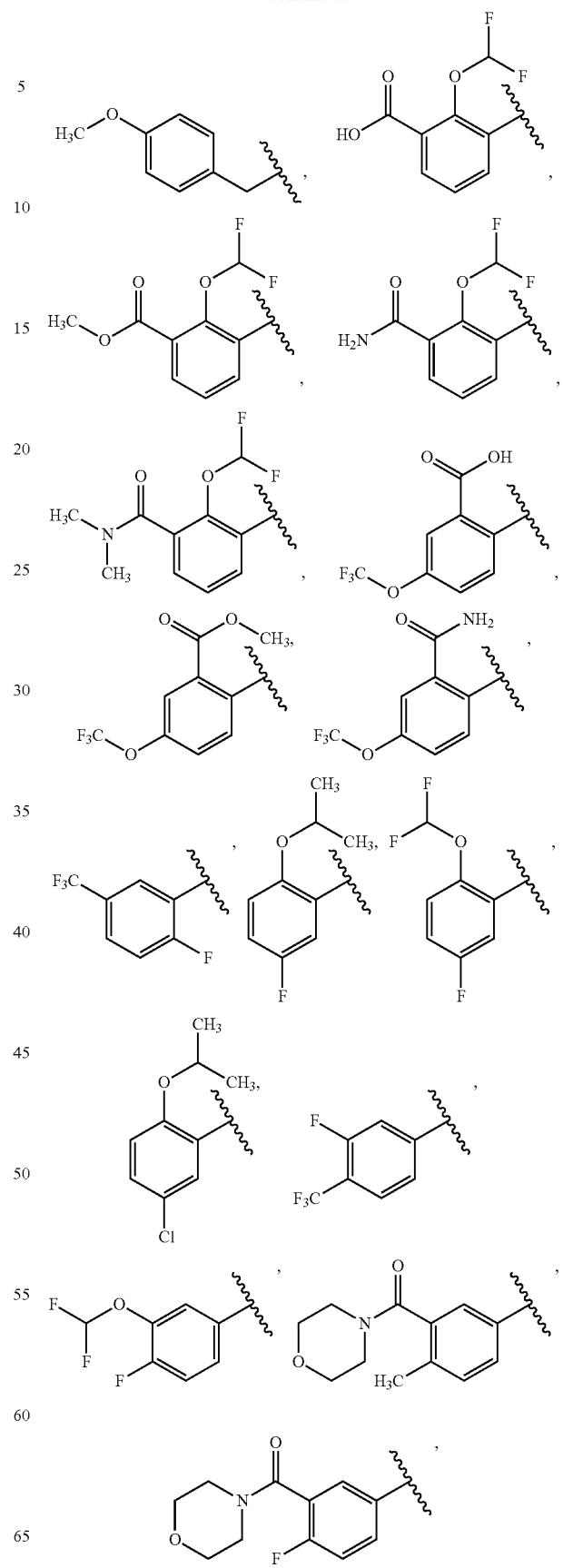

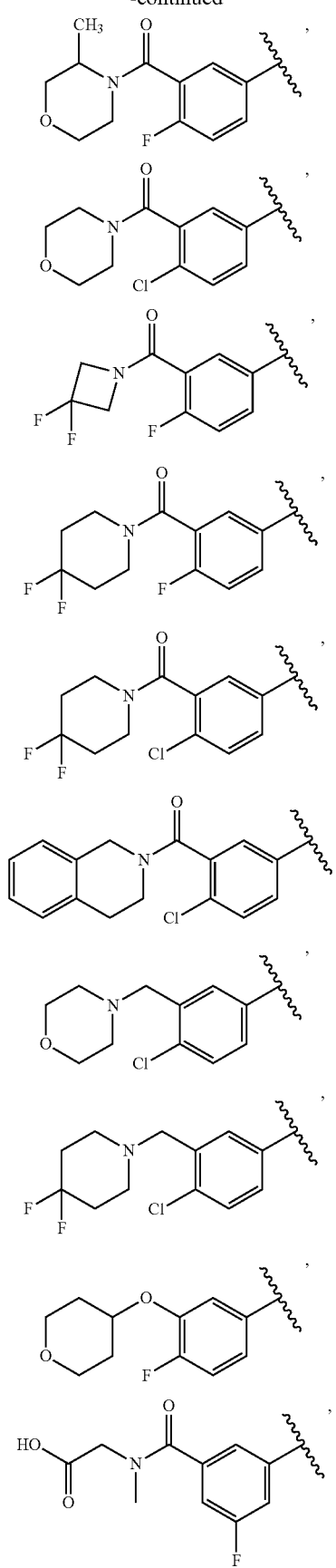
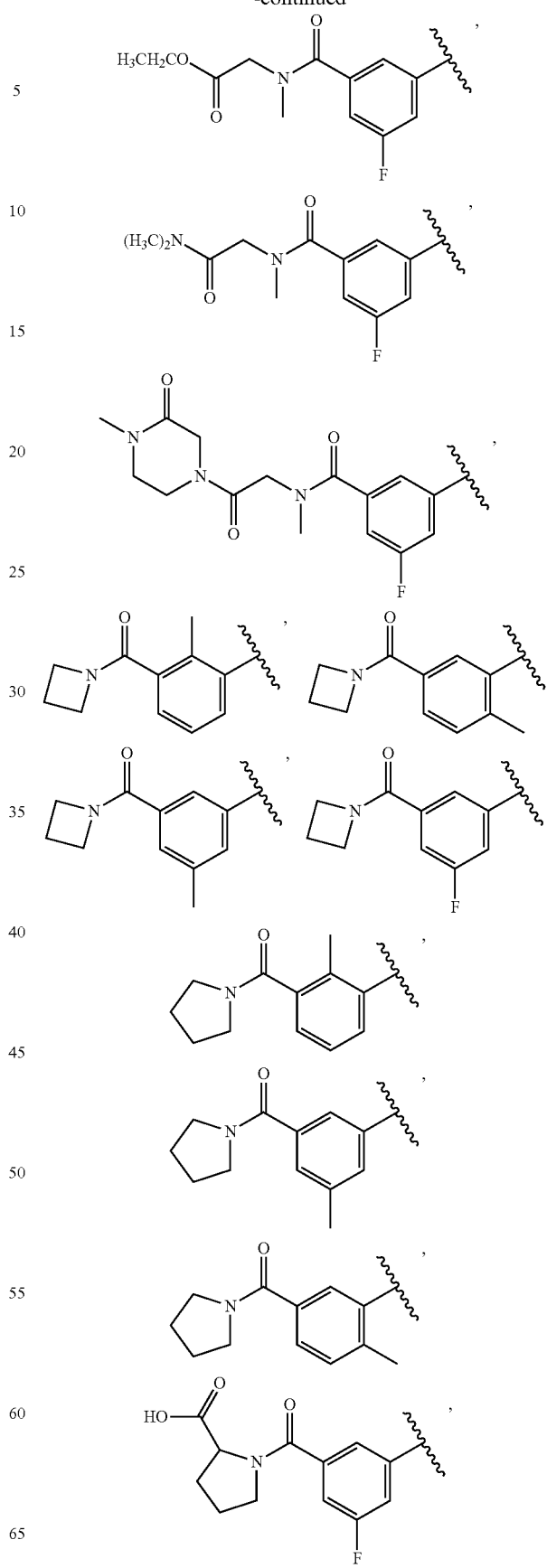

119

-continued

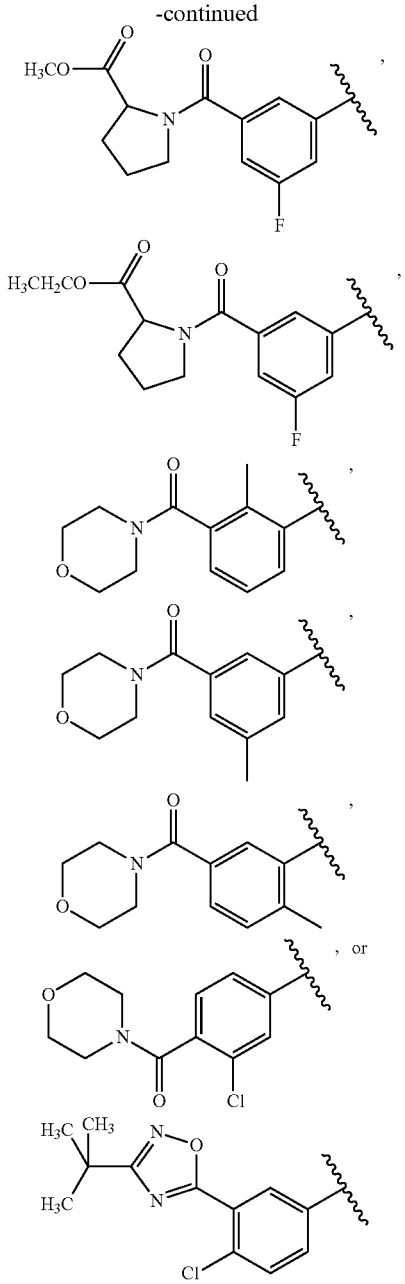

Y, attached to a carbon or nitrogen ring atom, is
1) halogen,
2) —($C_1$-$C_6$)-alkyl,
3) —($C_1$-$C_3$)-haloalkyl,
4) —($C_3$-$C_8$)-cycloalkyl,
5) —OH,
6) —O—($C_1$-$C_6$)-alkyl,
7) —O—($C_1$-$C_3$)-haloalkyl,
8) =O (oxo),
wherein said —($C_1$-$C_6$)-alkyl part of 2) and 6) of said Y is unsubstituted or substituted independently with the substituents selected from the group consisting of —($C_3$-$C_8$)-cycloalkyl, —C(O)OH, and —C(O)—($C_1$-$C_6$)-alkyl,

120

B is

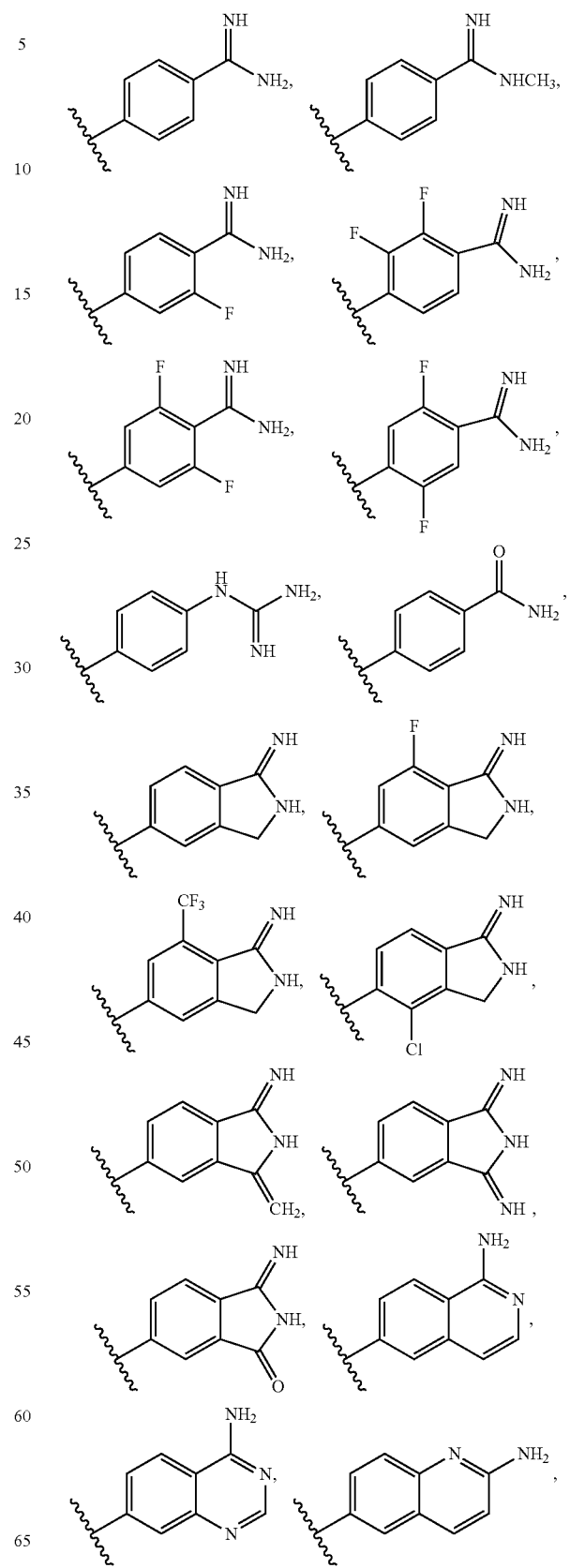

-continued
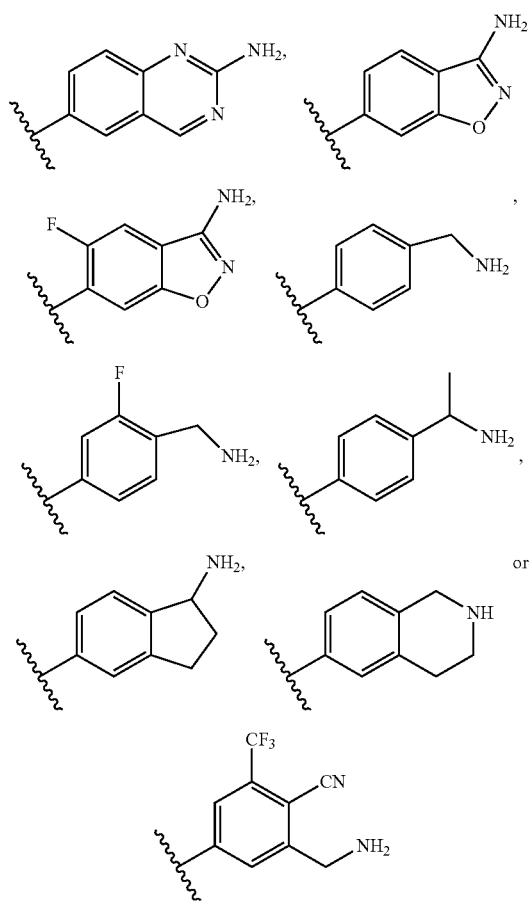
provided that
when A is
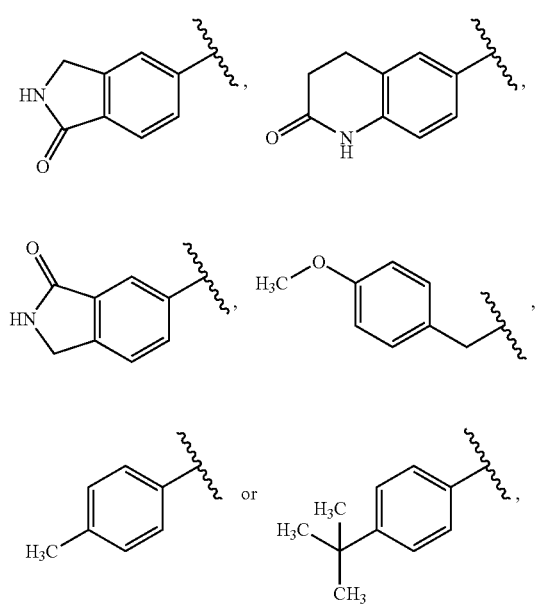
B is not
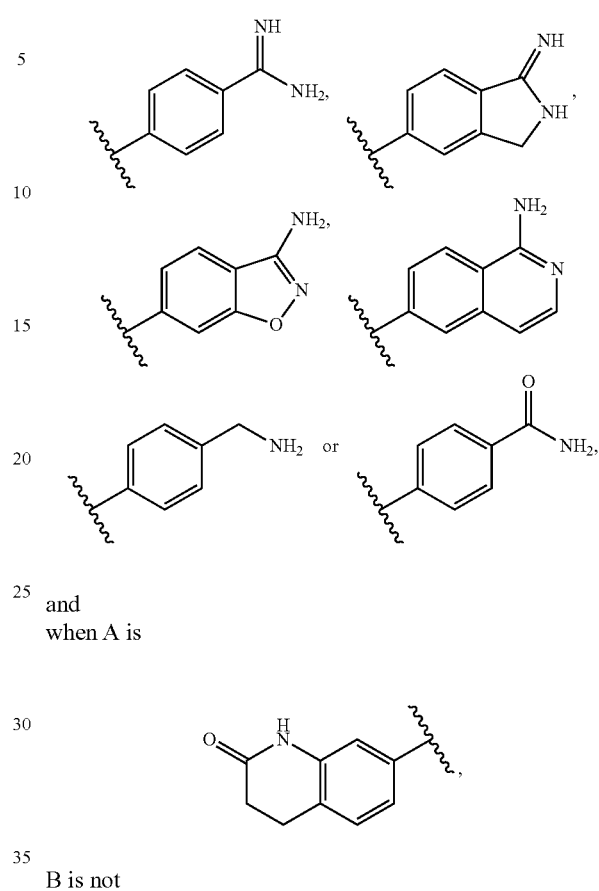
and
when A is
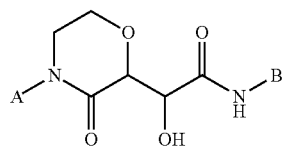
B is not
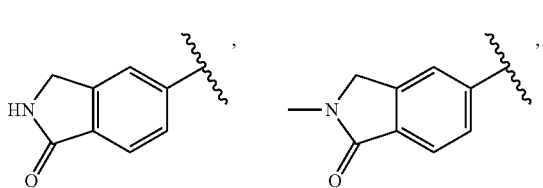
In one aspect of the invention, the compounds are of the formula
(aI)
or a pharmaceutically acceptable salt or a solvate thereof, wherein
A is

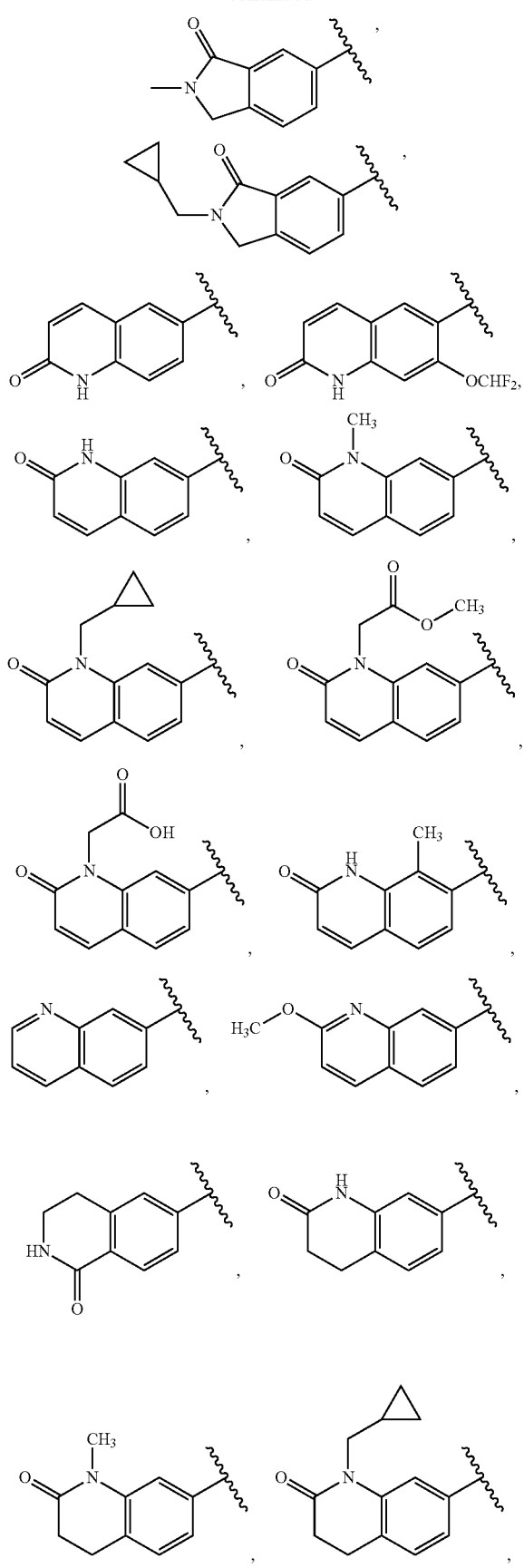
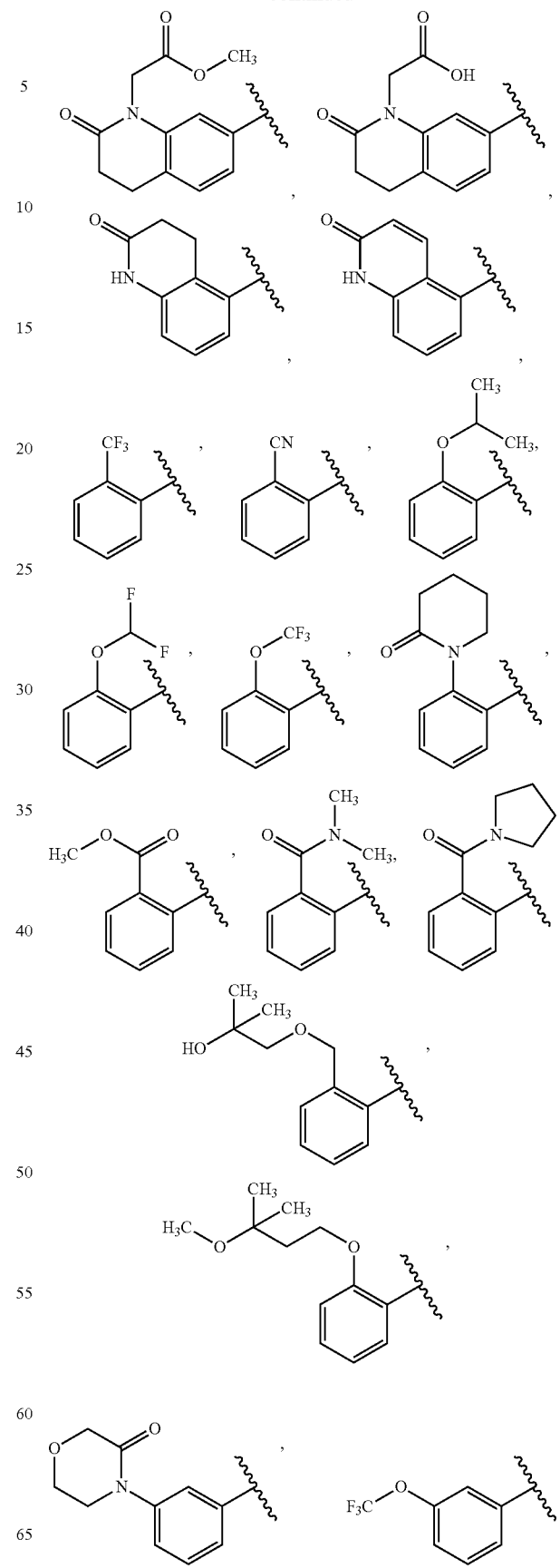

125
-continued
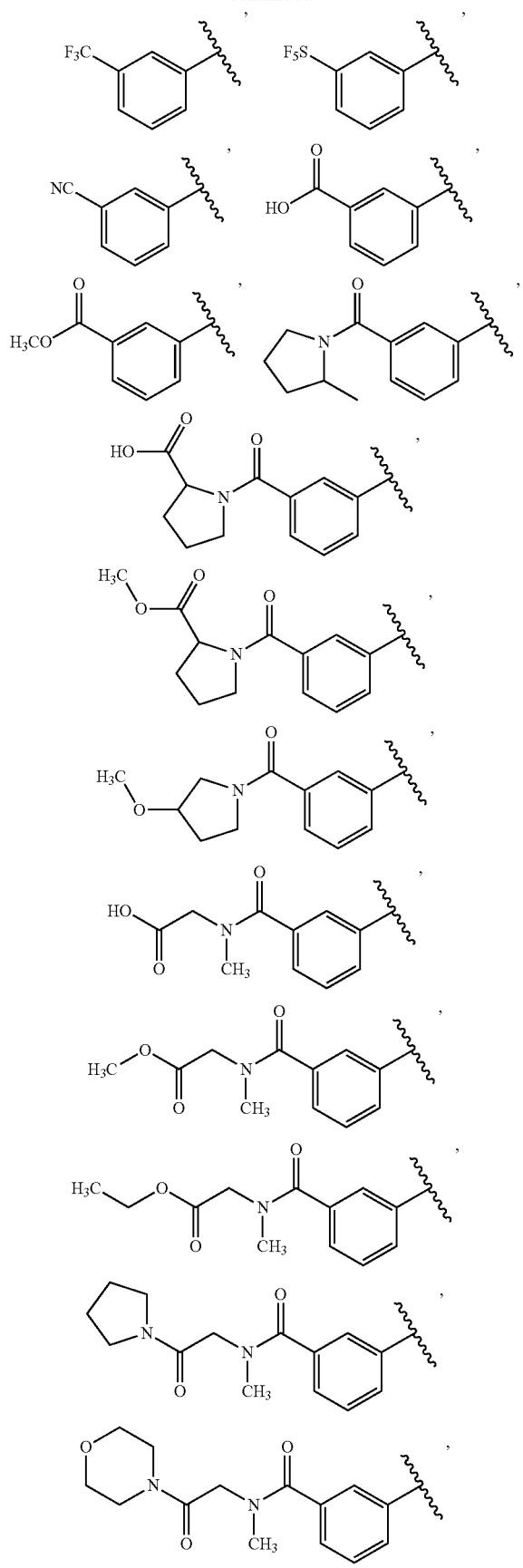
126
-continued
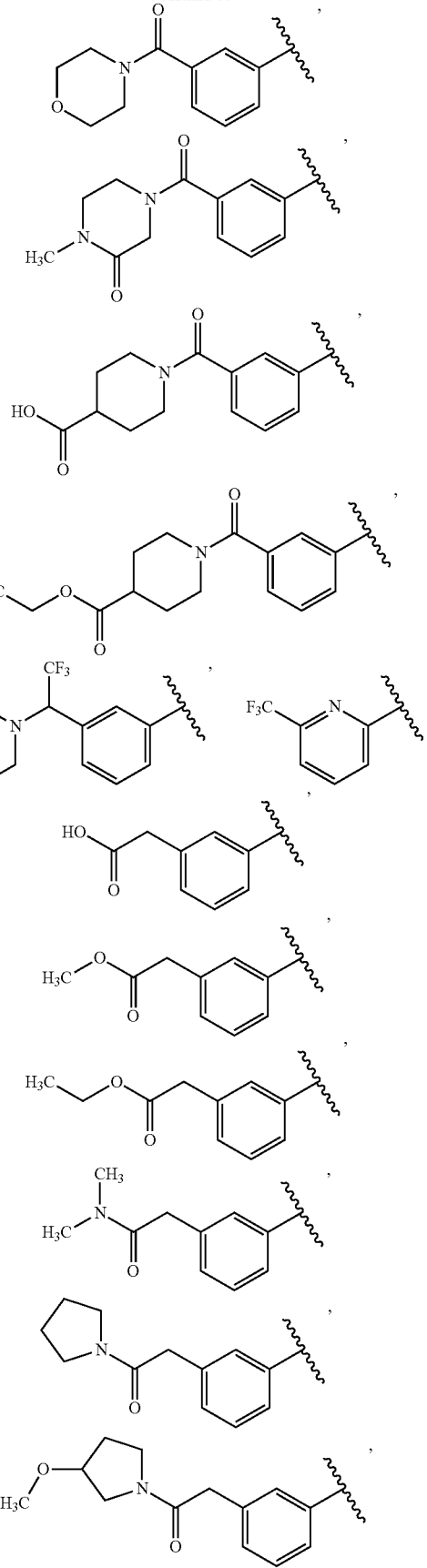

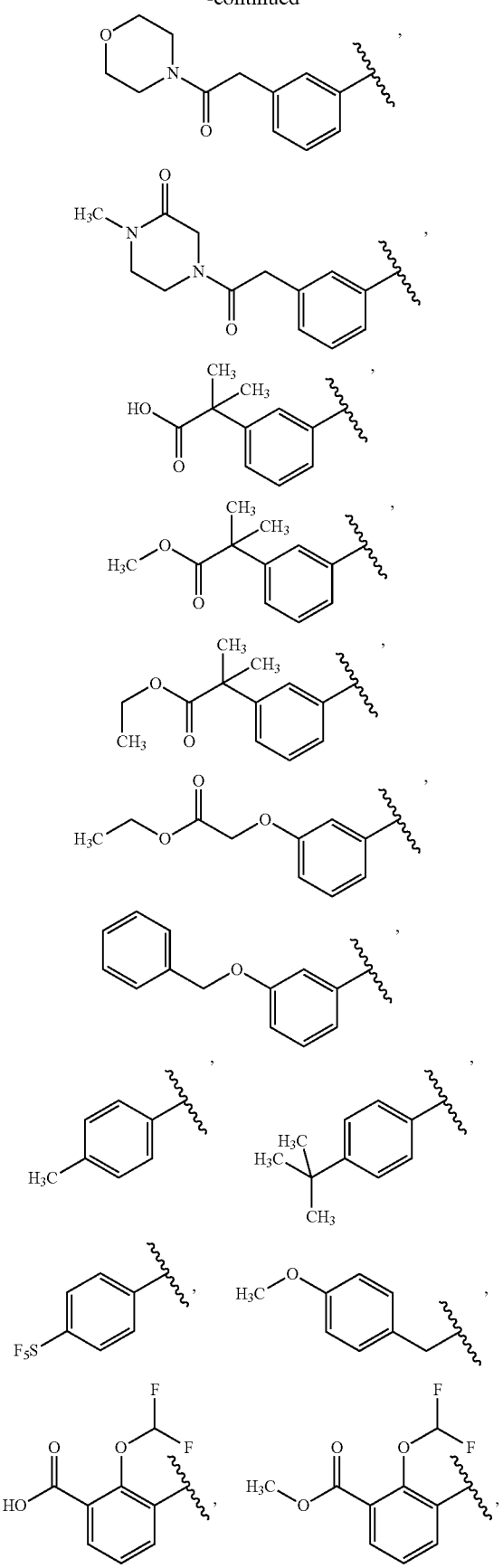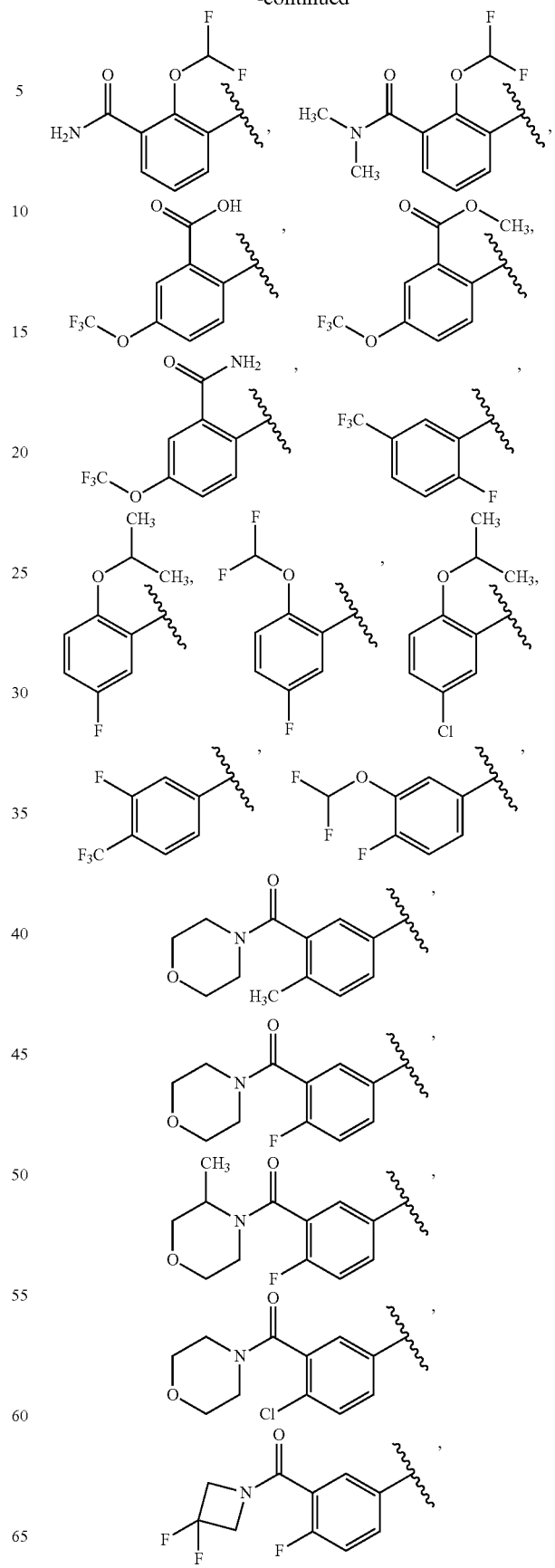

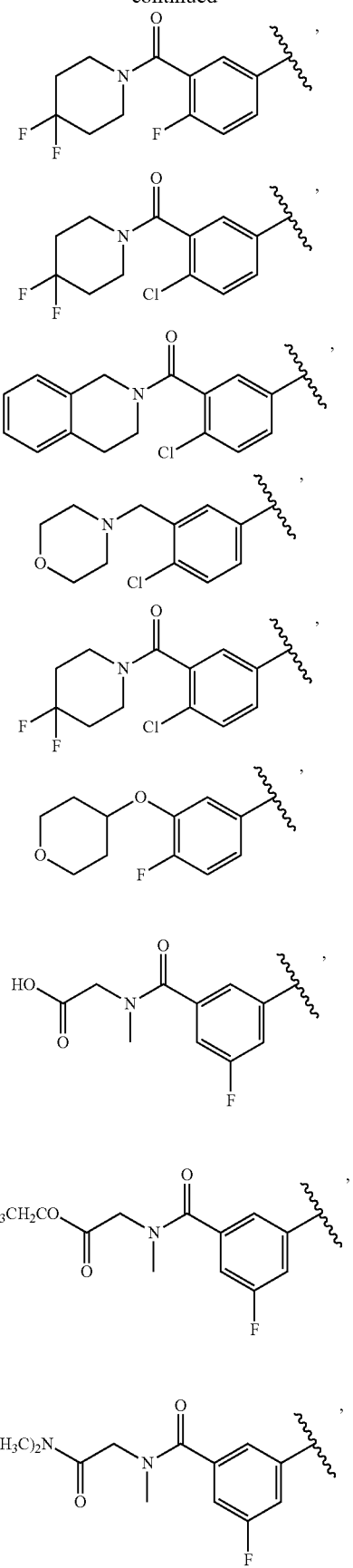
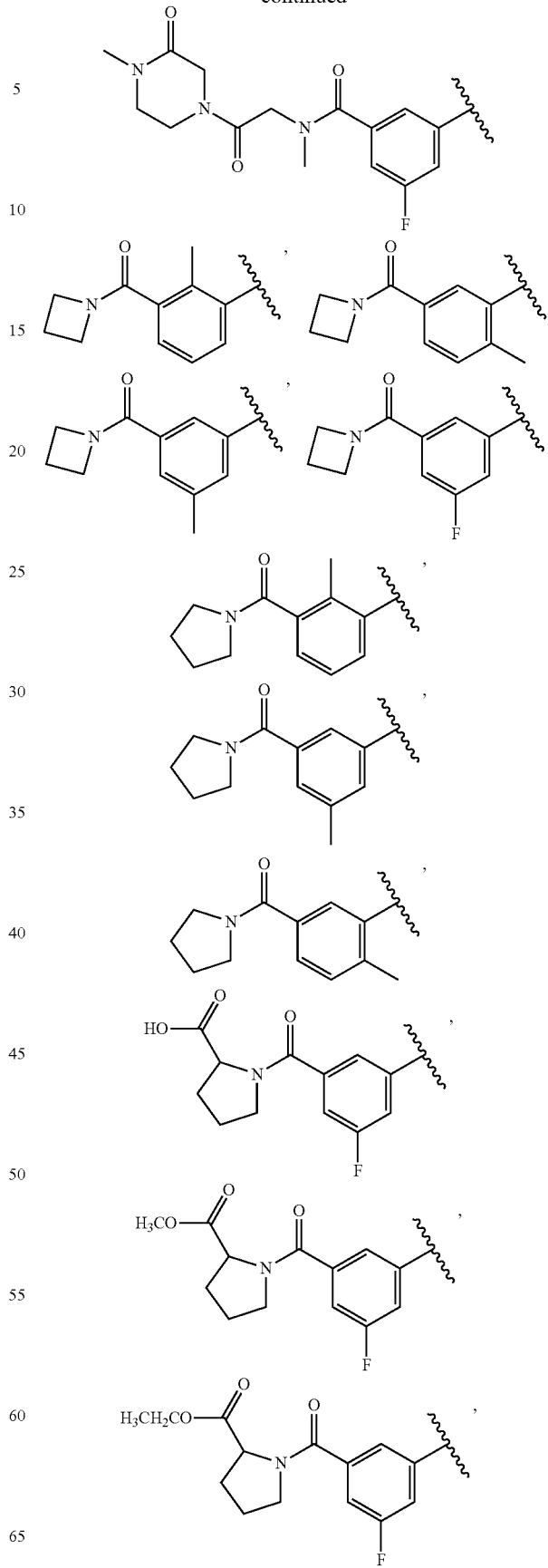

131
-continued
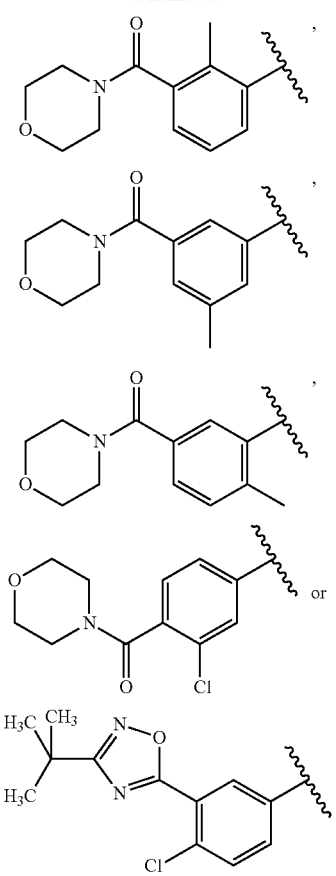
B is
132
-continued
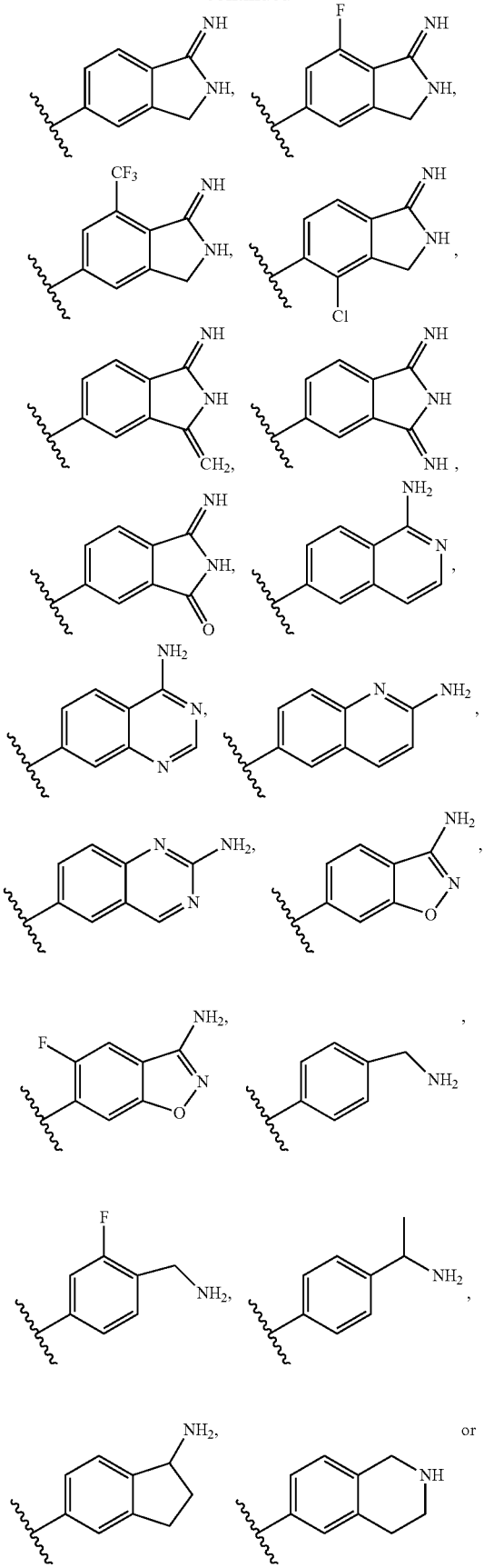

-continued

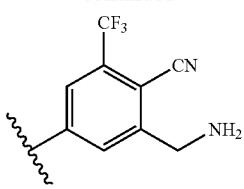

provided that
when A is

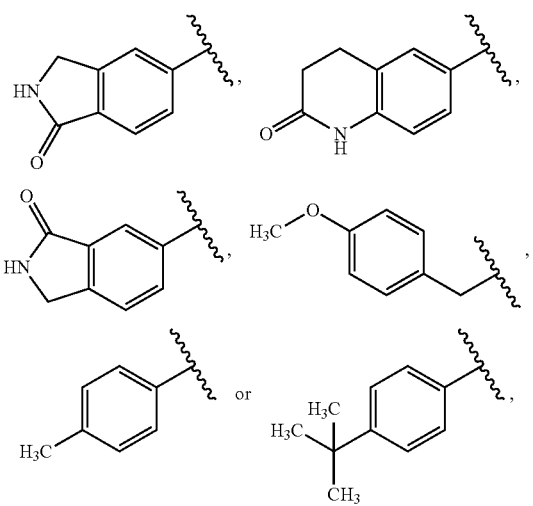

B is not

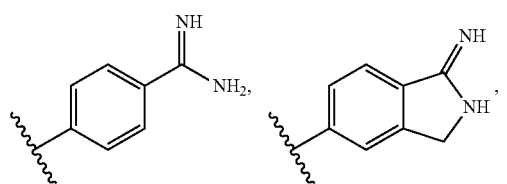

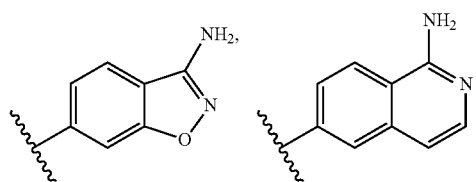

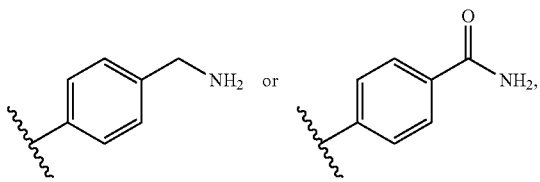

and
when A is

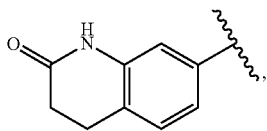 [SMILES: *c1ccc2c(c1)NC(=O)CC2]

B is not

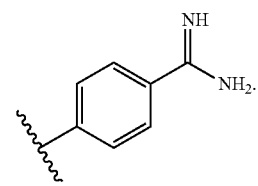 [SMILES: *c1ccc(C(=N)N)cc1]

In another aspect of the invention, the compounds are of the absolute configuration of Formula (aIa) is (aIa)

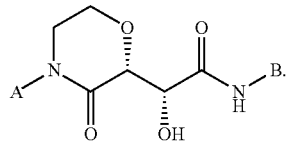

In another aspect of the invention, the compound is
(2R)-2-[(2R)-4-(4-tert-butylphenyl)-3-oxomorpholin-2-yl]-2-hydroxy-N-[4-(N-methylcarbamimidoyl)phenyl]acetamide,
(2R)-2-hydroxy-N-(1-imino-2,3-dihydroisoindol-5-yl)-2-[(2R)-3-oxo-4-(1-oxo-2,3-dihydroisoindol-5-yl)morpholin-2-yl]acetamide,
(2R)-2-hydroxy-N-(1-imino-2,3-dihydroisoindol-5-yl)-2-[(2R)-3-oxo-4-(2-oxo-1H-quinolin-6-yl)morpholin-2-yl]acetamide,
(2R)-2-[(2R)-4-[7-(difluoromethoxy)-2-oxo-1H-quinolin-6-yl]-3-oxomorpholin-2-yl]-2-hydroxy-N-(1-imino-2,3-dihydroisoindol-5-yl)acetamide,
(2R)—N-(4-carbamimidoylphenyl)-2-hydroxy-2-[(2R)-3-oxo-4-(2-oxo-1H-quinolin-6-yl)morpholin-2-yl]acetamide,
(2R)—N-(4-carbamimidoyl-3-fluorophenyl)-2-hydroxy-2-[(2R)-3-oxo-4-(2-oxo-1H-quinolin-6-yl)morpholin-2-yl]acetamide,
(2R)-2-hydroxy-N-(1-imino-2,3-dihydroisoindol-5-yl)-2-[(2R)-3-oxo-4-(2-oxo-1H-quinolin-7-yl)morpholin-2-yl]acetamide,
(2R)-2-hydroxy-N-(1-imino-2,3-dihydroisoindol-5-yl)-2-[(2R)-4-(1-methyl-2-oxoquinolin-7-yl)-3-oxomorpholin-2-yl]acetamide,
(2R)-2-[(2R)-4-[1-(cyclopropylmethyl)-2-oxoquinolin-7-yl]-3-oxomorpholin-2-yl]-2-hydroxy-N-(1-imino-2,3-dihydroisoindol-5-yl)acetamide,
2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetate,
2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetic acid,
(2R)-2-hydroxy-N-(1-imino-2,3-dihydroisoindol-5-yl)-2-[(2R)-4-(8-methyl-2-oxo-1H-quinolin-7-yl)-3-oxomorpholin-2-yl]acetamide, (2R)-2-hydroxy-N-(1-imino-2,3-dihydroisoindol-5-yl)-2-[(2R)-4-(2-methoxyquinolin-7-yl)-3-oxomorpholin-2-yl]acetamide,
(2R)-2-hydroxy-N-(1-imino-2,3-dihydroisoindol-5-yl)-2-[(2R)-3-oxo-4-quinolin-7-ylmorpholin-2-yl]acetamide,
(2R)—N-(3-amino-1,2-benzisoxazol-6-yl)-2-hydroxy-2-[(2R)-3-oxo-4-quinolin-7-ylmorpholin-2-yl]acetamide,
(2R)-2-hydroxy-N-(1-imino-2,3-dihydroisoindol-5-yl)-2-[(2R)-3-oxo-4-(2-oxo-1H-quinolin-5-yl)morpholin-2-yl]acetamide,
(2R)-2-hydroxy-N-(1-imino-2,3-dihydroisoindol-5-yl)-2-[(2R)-3-oxo-4-(1-oxo-3,4-dihydro-2H-isoquinolin-6-yl)morpholin-2-yl]acetamide,
(2R)-2-hydroxy-N-(1-imino-2,3-dihydroisoindol-5-yl)-2-[(2R)-3-oxo-4-(2-oxo-3,4-dihydro-1H-quinolin-7-yl)morpholin-2-yl]acetamide,
(2R)-2-hydroxy-N-(1-imino-2,3-dihydroisoindol-5-yl)-2-[(2R)-4-(1-methyl-2-oxo-3,4-dihydroquinolin-7-yl)-3-oxomorpholin-2-yl]acetamide,
(2R)-2-[(2R)-4-[1-(cyclopropylmethyl)-2-oxo-3,4-dihydroquinolin-7-yl]-3-oxomorpholin-2-yl]-2-hydroxy-N-(1-imino-2,3-dihydroisoindol-5-yl)acetamide,
methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetate,
2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetic acid,
(2R)—N-(4-carbamimidoyl-3-fluorophenyl)-2-hydroxy-2-[(2R)-3-oxo-4-(2-oxo-3,4-dihydro-1H-quinolin-7-yl)morpholin-2-yl]acetamide,
(2R)—N-(3-amino-1,2-benzisoxazol-6-yl)-2-hydroxy-2-[(2R)-3-oxo-4-(2-oxo-3,4-dihydro-1H-quinolin-7-yl)morpholin-2-yl]acetamide
(2R)—N-(1-aminoisoquinolin-6-yl)-2-hydroxy-2-[(2R)-3-oxo-4-(2-oxo-3,4-dihydro-1H-quinolin-7-yl)morpholin-2-yl]acetamide,
(2R)—N-(4-aminoquinazolin-7-yl)-2-hydroxy-2-[(2R)-3-oxo-4-(2-oxo-3,4-dihydro-1H-quinolin-7-yl)morpholin-2-yl]acetamide,
(2R)-2-hydroxy-N-(1-imino-2,3-dihydroisoindol-5-yl)-2-[(2R)-3-oxo-4-(2-oxo-3,4-dihydro-1H-quinolin-5-yl)morpholin-2-yl]acetamide,
(2R)-2-hydroxy-2-[(2R)-4-[2-(3-hydroxy-3-methylbutoxy)phenyl]-3-oxomorpholin-2-yl]-N-(1-imino-2,3-dihydroisoindol-5-yl)acetamide,
(2R)-2-hydroxy-N-(1-imino-2,3-dihydroisoindol-5-yl)-2-[(2R)-4-[2-(3-methoxy-3-methylbutoxy)phenyl]-3-oxomorpholin-2-yl]acetamide,
(2R)-2-hydroxy-N-(1-imino-2,3-dihydroisoindol-5-yl)-2-[(2R)-3-oxo-4-[2-(2-oxopiperidin-1-yl)phenyl]morpholin-2-yl]acetamide,
(2R)-2-[(2R)-4-[2-(difluoromethoxy)-5-fluorophenyl]-3-oxomorpholin-2-yl]-2-hydroxy-N-(1-imino-2,3-dihydroisoindol-5-yl)acetamide,
methyl 2-(difluoromethoxy)-3-[(2R)-2-[(1R)-1-hydroxy-2-[(1-imino-2,3-dihydro-isoindol-5-yl)amino]-2-oxoethyl]-3-oxomorpholin-4-yl]benzoate,
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoic acid,
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]-N,N-dimethylbenzamide,
2-(difluoromethoxy)-3-[2-[(1-hydroxy-2-[(1-imino-2,3-dihydroisoindol-5-yl)amino]-2-oxoethyl]-3-oxomorpholin-4-yl]benzamide,
methyl 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoate,
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoic acid,
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzamide,
(2R)—N-(3-amino-1,2-benzisoxazol-6-yl)-2-hydroxy-2-[(2R)-3-oxo-4-(2-oxo-1H-quinolin-6-yl)morpholin-2-yl]acetamide,
(2R)—N-(3-amino-1,2-benzisoxazol-6-yl)-2-hydroxy-2-[(2R)-3-oxo-4-(2-oxo-1H-quinolin-7-yl)morpholin-2-yl]acetamide, or
(2R)—N-(3-amino-1,2-benzisoxazol-6-yl)-2-hydroxy-2-[(2R)-3-oxo-4-(2-oxo-1H-quinolin-5-yl)morpholin-2-yl]acetamide,
or a pharmaceutically acceptable salt or a solvate thereof.
In another embodiment, the compound is
(2R)-2-[(2R)-4-(4-tert-butylphenyl)-3-oxomorpholin-2-yl]-2-hydroxy-N-[4-(N-methylcarbamimidoyl)phenyl]acetamide hydrochloride (Example aa1),
(2R)-2-hydroxy-N-(1-imino-2,3-dihydroisoindol-5-yl)-2-[(2R)-3-oxo-4-(1-oxo-2,3-dihydroisoindol-5-yl)morpholin-2-yl]acetamide hydrochloride (Example aa2),
(2R)-2-hydroxy-N-(1-imino-2,3-dihydroisoindol-5-yl)-2-[(2R)-3-oxo-4-(2-oxo-1H-quinolin-6-yl)morpholin-2-yl]acetamide hydrochloride (Example aa3),
(2R)-2-[(2R)-4-[7-(difluoromethoxy)-2-oxo-1H-quinolin-6-yl]-3-oxomorpholin-2-yl]-2-hydroxy-N-(1-imino-2,3-dihydroisoindol-5-yl)acetamide hydrochloride (Example aa4),
(2R)—N-(4-carbamimidoylphenyl)-2-hydroxy-2-[(2R)-3-oxo-4-(2-oxo-1H-quinolin-6-yl)morpholin-2-yl]acetamide hydrochloride (Example aa5),
(2R)—N-(4-carbamimidoyl-3-fluorophenyl)-2-hydroxy-2-[(2R)-3-oxo-4-(2-oxo-1H-quinolin-6-yl)morpholin-2-yl]acetamide hydrochloride (Example aa6),
(2R)-2-hydroxy-N-(1-imino-2,3-dihydroisoindol-5-yl)-2-[(2R)-3-oxo-4-(2-oxo-1H-quinolin-7-yl)morpholin-2-yl]acetamide hydrochloride (Example aa7),
(2R)-2-hydroxy-N-(1-imino-2,3-dihydroisoindol-5-yl)-2-[(2R)-4-(1-methyl-2-oxoquinolin-7-yl)-3-oxomorpholin-2-yl]acetamide hydrochloride (Example aa8),
(2R)-2-[(2R)-4-[1-(cyclopropylmethyl)-2-oxoquinolin-7-yl]-3-oxomorpholin-2-yl]-2-hydroxy-N-(1-imino-2,3-dihydroisoindol-5-yl)acetamide hydrochloride (Example aa9),
2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetate hydrochloride (Example aa10),
2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetic acid hydrochloride (Example aa11),
(2R)-2-hydroxy-N-(1-imino-2,3-dihydroisoindol-5-yl)-2-[(2R)-4-(8-methyl-2-oxo-1H-quinolin-7-yl)-3-oxomorpholin-2-yl]acetamide hydrochloride (Example aa12),
(2R)-2-hydroxy-N-(1-imino-2,3-dihydroisoindol-5-yl)-2-[(2R)-4-(2-methoxyquinolin-7-yl)-3-oxomorpholin-2-yl]acetamide hydrochloride (Example aa13),
(2R)-2-hydroxy-N-(1-imino-2,3-dihydroisoindol-5-yl)-2-[(2R)-3-oxo-4-quinolin-7-ylmorpholin-2-yl]acetamide dihydrochloride (Example aa14), (2R)—N-(3-amino-1,2-benzisoxazol-6-yl)-2-hydroxy-2-[(2R)-3-oxo-4-quinolin-7-ylmorpholin-2-yl]acetamide hydrochloride (Example aa15),
(2R)-2-hydroxy-N-(1-imino-2,3-dihydroisoindol-5-yl)-2-[(2R)-3-oxo-4-(2-oxo-1H-quinolin-5-yl)morpholin-2-yl]acetamide hydrochloride (Example aa16),
(2R)-2-hydroxy-N-(1-imino-2,3-dihydroisoindol-5-yl)-2-[(2R)-3-oxo-4-(1-oxo-3,4-dihydro-2H-isoquinolin-6-yl)morpholin-2-yl]acetamide hydrochloride (Example aa17),
(2R)-2-hydroxy-N-(1-imino-2,3-dihydroisoindol-5-yl)-2-[(2R)-3-oxo-4-(2-oxo-3,4-dihydro-1H-quinolin-7-yl)morpholin-2-yl]acetamide hydrochloride (Example aa18),
(2R)-2-hydroxy-N-(1-imino-2,3-dihydroisoindol-5-yl)-2-[(2R)-4-(1-methyl-2-oxo-3,4-dihydroquinolin-7-yl)-3-oxomorpholin-2-yl]acetamide hydrochloride (Example aa19),
(2R)-2-[(2R)-4-[1-(cyclopropylmethyl)-2-oxo-3,4-dihydroquinolin-7-yl]-3-oxomorpholin-2-yl]-2-hydroxy-N-(1-imino-2,3-dihydroisoindol-5-yl)acetamide hydrochloride (Example aa20),
methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetate hydrochloride (Example aa21),
2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetic acid hydrochloride (Example aa22),
(2R)—N-(4-carbamimidoyl-3-fluorophenyl)-2-hydroxy-2-[(2R)-3-oxo-4-(2-oxo-3,4-dihydro-1H-quinolin-7-yl)morpholin-2-yl]acetamide hydrochloride (Example aa23),
(2R)—N-(3-amino-1,2-benzoxazol-6-yl)-2-hydroxy-2-[(2R)-3-oxo-4-(2-oxo-3,4-dihydro-1H-quinolin-7-yl)morpholin-2-yl]acetamide (Example aa24),
(2R)—N-(1-aminoisoquinolin-6-yl)-2-hydroxy-2-[(2R)-3-oxo-4-(2-oxo-3,4-dihydro-1H-quinolin-7-yl)morpholin-2-yl]acetamide hydrochloride (Example aa25),
(2R)—N-(4-aminoquinazolin-7-yl)-2-hydroxy-2-[(2R)-3-oxo-4-(2-oxo-3,4-dihydro-1H-quinolin-7-yl)morpholin-2-yl]acetamide (Example aa26),
(2R)-2-hydroxy-N-(1-imino-2,3-dihydroisoindol-5-yl)-2-[(2R)-3-oxo-4-(2-oxo-3,4-dihydro-1H-quinolin-5-yl)morpholin-2-yl]acetamide hydrochloride (Example aa27),
(2R)-2-hydroxy-2-[(2R)-4-[2-(3-hydroxy-3-methylbutoxy)phenyl]-3-oxomorpholin-2-yl]-N-(1-imino-2,3-dihydroisoindol-5-yl)acetamide hydrochloride (Example aa28),
(2R)-2-hydroxy-N-(1-imino-2,3-dihydroisoindol-5-yl)-2-[(2R)-4-[2-(3-methoxy-3-methylbutoxy)phenyl]-3-oxomorpholin-2-yl]acetamide hydrochloride (Example aa29),
(2R)-2-hydroxy-N-(1-imino-2,3-dihydroisoindol-5-yl)-2-[(2R)-3-oxo-4-[2-(2-oxopiperidin-1-yl)phenyl]morpholin-2-yl]acetamide hydrochloride (Example aa30),
(2R)-2-[(2R)-4-[2-(difluoromethoxy)-5-fluorophenyl]-3-oxomorpholin-2-yl]-2-hydroxy-N-(1-imino-2,3-dihydroisoindol-5-yl)acetamide hydrochloride (Example aa31),
methyl 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoate hydrochloride (Example aa32),
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoic acid hydrochloride (Example aa33),
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]-N,N-dimethylbenzamide hydrochloride (Example aa34),
2-(difluoromethoxy)-3-[2-[(1-hydroxy-2-[(1-imino-2,3-dihydroisoindol-5-yl)amino]-2-oxoethyl]-3-oxomorpholin-4-yl]benzamide hydrochloride (Example aa35),
methyl 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoate hydrochloride (Example aa36),
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoic acid hydrochloride (Example aa37),
or
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzamide hydrochloride (Example aa38),
or a solvate thereof.

In another embodiment, the compound is
2-(3-((R)-2-((R)-2-(4-carbamimidoylphenylamino)-1-hydroxy-2-oxoethyl)-3-oxomorpholino)phenyl)acetate (Example aa40),
(R)—N-(4-carbamimidoylphenyl)-2-hydroxy-2-((R)-4-(3-methyl-5-(pyrrolidine-1-carbonyl)phenyl)-3-oxomorpholin-2-yl)acetamide (Example aa53),
(R)-2-hydroxy-N-(1-iminoisoindolin-5-yl)-2-((R)-4-(3-methyl-5-(pyrrolidine-1-carbonyl)phenyl)-3-oxomorpholin-2-yl)acetamide (Example aa54),
2-(3-((R)-2-((R)-1-hydroxy-2-(1-iminoisoindolin-5-ylamino)-2-oxoethyl)-3-oxomorpholino)-N-methylbenzamido)acetic acid (Example aa50),
2-(3-((R)-2-((R)-1-hydroxy-2-(1-iminoisoindolin-5-ylamino)-2-oxoethyl)-3-oxomorpholino)-N-methylbenzamido)acetate (Example aa51),
(S)-1-(3-((R)-2-((R)-2-(4-carbamimidoylphenylamino)-1-hydroxy-2-oxoethyl)-3-oxomorpholino)benzoyl)pyrrolidine-2-carboxylic acid (Example aa58),
1-(3-((R)-2-((R)-2-(4-carbamimidoylphenylamino)-1-hydroxy-2-oxoethyl)-3-oxomorpholino)benzoyl)pyrrolidine-2-carboxylate (Example aa52),
3-((R)-2-((R)-2-(4-carbamimidoylphenylamino)-1-hydroxy-2-oxoethyl)-3-oxomorpholino)-N-methyl-N-(2-oxo-2-(pyrrolidin-1-yl)ethyl)benzamide (Example aa56),
3-((R)-2-((R)-1-hydroxy-2-(1-iminoisoindolin-5-ylamino)-2-oxoethyl)-3-oxomorpholino)-N-methyl-N-(2-oxo-2-(pyrrolidin-1-yl)ethyl)benzamide (Example aa59),
(R)—N-(4-carbamimidoylphenyl)-2-hydroxy-2-((R)-4-(3-methyl-5-(morpholine-4-carbonyl)phenyl)-3-oxomorpholin-2-yl)acetamide (Example aa60),
(R)-2-hydroxy-N-(1-iminoisoindolin-5-yl)-2-((R)-4-(3-methyl-5-(morpholine-4-carbonyl)phenyl)-3-oxomorpholin-2-yl)acetamide (Example aa61),
(R)-2-hydroxy-N-(1-iminoisoindolin-5-yl)-2-((R)-4-(3-((R)-3-methoxypyrrolidine-1-carbonyl)phenyl)-3-oxomorpholin-2-yl)acetamide (Example aa63),
(R)-2-hydroxy-N-(1-iminoisoindolin-5-yl)-2-((R)-4-(3-((S)-3-methoxypyrrolidine-1-carbonyl)phenyl)-3-oxomorpholin-2-yl)acetamide (Example aa64),
(R)-2-((R)-4-(3-chloro-4-(morpholine-4-carbonyl)phenyl)-3-oxomorpholin-2-yl)-2-hydroxy-N-(1-iminoisoindolin-5-yl)acetamide (Example aa66),
(R)-2-hydroxy-N-(1-iminoisoindolin-5-yl)-2-((R)-4-(3-(2-morpholino-2-oxoethyl)phenyl)-3-oxomorpholin-2-yl)acetamide (Example aa68), (S)-1-(3-((R)-2-((R)-1-hydroxy-2-(1-iminoisoindolin-5-ylamino)-2-oxoethyl)-3-oxomorpholino)benzoyl)pyrrolidine-2-carboxylic acid (Example aa55), 1-(3-((R)-2-((R)-1-hydroxy-2-(1-iminoisoindolin-5-ylamino)-2-oxoethyl)-3-oxomorpholino)benzoyl)pyrrolidine-2-carboxylate (Example aa57), 2-(3-((R)-2-((R)-1-hydroxy-2-(1-iminoisoindolin-5-ylamino)-2-oxoethyl)-3-oxomorpholino)phenyl)acetate (Example aa65), 2-(3-((R)-2-((R)-1-hydroxy-2-(1-iminoisoindolin-5-ylamino)-2-oxoethyl)-3-oxomorpholino)phenyl)acetic acid (Example aa67), 2-(3-((R)-2-((R)-1-hydroxy-2-(1-iminoisoindolin-5-ylamino)-2-oxoethyl)-3-oxomorpholino)-N-methylbenzamido)acetate (Example aa62), 2-(3-((R)-2-((R)-1-hydroxy-2-(1-iminoisoindolin-5-ylamino)-2-oxoethyl)-3-oxomorpholino)phenyl)-2-methylpropanoate (Example aa70), (R)-2-hydroxy-N-(1-iminoisoindolin-5-yl)-2-((R)-4-(3-(morpholine-4-carbonyl)phenyl)-3-oxomorpholin-2-yl)acetamide (Example aa69), 3-((R)-2-((R)-1-hydroxy-2-(1-iminoisoindolin-5-ylamino)-2-oxoethyl)-3-oxomorpholino)-N-methyl-N-(2-morpholino-2-oxoethyl)benzamide (Example aa71), (R)-2-hydroxy-N-(1-iminoisoindolin-5-yl)-2-((R)-4-(3-(2-((R)-3-methoxypyrrolidin-1-yl)-2-oxoethyl)phenyl)-3-oxomorpholin-2-yl)acetamide (Example aa72), (R)-2-hydroxy-N-(1-iminoisoindolin-5-yl)-2-((R)-4-(3-(2-((S)-3-methoxypyrrolidin-1-yl)-2-oxoethyl)phenyl)-3-oxomorpholin-2-yl)acetamide (Example aa73), 2-(3-((R)-2-((R)-1-hydroxy-2-(1-iminoisoindolin-5-ylamino)-2-oxoethyl)-3-oxomorpholino)phenyl)-2-methylpropanoate (Example aa74), 2-(3-((R)-2-((R)-1-hydroxy-2-(1-iminoisoindolin-5-ylamino)-2-oxoethyl)-3-oxomorpholino)phenyl)acetate (Example aa75), (R)-2-hydroxy-N-(1-iminoisoindolin-5-yl)-2-((R)-4-(3-(4-methyl-3-oxopiperazine-1-carbonyl)phenyl)-3-oxomorpholin-2-yl)acetamide (Example aa76), 2-(3-((R)-2-((R)-1-hydroxy-2-(1-iminoisoindolin-5-ylamino)-2-oxoethyl)-3-oxomorpholino)phenyl)-2-methylpropanoate (Example aa77), (R)-2-hydroxy-N-(1-iminoisoindolin-5-yl)-2-((R)-4-(3-(2-(4-methyl-3-oxopiperazin-1-yl)-2-oxoethyl)phenyl)-3-oxomorpholin-2-yl)acetamide (Example aa79), (R)-2-((R)-4-(3-(2-(dimethylamino)-2-oxoethyl)phenyl)-3-oxomorpholin-2-yl)-2-hydroxy-N-(1-iminoisoindolin-5-yl)acetamide (Example aa82), 1-(3-((R)-2-((R)-1-hydroxy-2-(1-iminoisoindolin-5-ylamino)-2-oxoethyl)-3-oxomorpholino)benzoyl)piperidine-4-carboxylic acid (Example aa83), 1-(3-((R)-2-((R)-1-hydroxy-2-(1-iminoisoindolin-5-ylamino)-2-oxoethyl)-3-oxomorpholino)benzoyl)piperidine-4-carboxylate (Example aa84), 2-(3-((R)-2-((R)-1-acetoxy-2-(1-imino-3-oxoisoindolin-5-ylamino)-2-oxoethyl)-3-oxo morpholino)-N-methylbenzamido)acetic acid (Example aa85), (R)—N-(1,3-diiminoisoindolin-5-yl)-2-((R)-4-(3-(2-(dimethylamino)-2-oxoethyl)phenyl)-3-oxomorpholin-2-yl)-2-hydroxyacetamide (Example aa86), (R)-2-(1-imino-3-oxoisoindolin-5-ylamino)-1-((R)-4-(3-(methyl(2-oxo-2-(pyrrolidin-1-yl)ethyl)carbamoyl)phenyl)-3-oxomorpholin-2-yl)-2-oxoethyl acetate (Example aa87), (R)—N-(3-aminobenzo[d]isoxazol-6-yl)-2-((R)-4-(4-fluoro-3-(morpholine-4-carbonyl)phenyl)-3-oxomorpholin-2-yl)-2-hydroxyacetamide ((Example aa95), (R)—N-(3-aminobenzo[d]isoxazol-6-yl)-2-((R)-4-(4-chloro-3-((4,4-difluoropiperidin-1-yl)methyl)phenyl)-3-oxomorpholin-2-yl)-2-hydroxyacetamide (Example aa97), (R)—N-(3-aminobenzo[d]isoxazol-6-yl)-2-hydroxy-2-((R)-3-oxo-4-(3-(3-oxomorpholino)phenyl)morpholin-2-yl)acetamide (Example aa98), (R)—N-(3-aminobenzo[d]isoxazol-6-yl)-2-((R)-4-(2-(difluoromethoxy)phenyl)-3-oxomorpholin-2-yl)-2-hydroxyacetamide (Example aa99), (R)—N-(3-aminobenzo[d]isoxazol-6-yl)-2-hydroxy-2-((R)-4-(2-isopropoxyphenyl)-3-oxomorpholin-2-yl)acetamide (Example aa100), (R)—N-(3-aminobenzo[d]isoxazol-6-yl)-2-((R)-4-(3-cyanophenyl)-3-oxomorpholin-2-yl)-2-hydroxyacetamide (Example aa101), (R)—N-(3-aminobenzo[d]isoxazol-6-yl)-2-((R)-4-(4-chloro-3-(morpholine-4-carbonyl)phenyl)-3-oxomorpholin-2-yl)-2-hydroxyacetamide (Example aa103), (R)—N-(3-aminobenzo[d]isoxazol-6-yl)-2-hydroxy-2-((R)-4-(4-methyl-3-(morpholine-4-carbonyl)phenyl)-3-oxomorpholin-2-yl)acetamide (Example aa104), (R)—N-(3-aminobenzo[d]isoxazol-6-yl)-2-hydroxy-2-((R)-3-oxo-4-(3-(trifluoromethoxy)phenyl)morpholin-2-yl)acetamide (Example aa105), (R)—N-(3-aminobenzo[d]isoxazol-6-yl)-2-hydroxy-2-((R)-3-oxo-4-(3-(trifluoromethyl)phenyl)morpholin-2-yl)acetamide (Example aa106), (R)—N-(3-aminobenzo[d]isoxazol-6-yl)-2-((R)-4-(4-chloro-3-(1,2,3,4-tetrahydroisoquinoline-2-carbonyl)phenyl)-3-oxomorpholin-2-yl)-2-hydroxyacetamide (Example aa107), (R)—N-(3-aminobenzo[d]isoxazol-6-yl)-2-((R)-4-(4-chloro-3-(4,4-difluoropiperidine-1-carbonyl)phenyl)-3-oxomorpholin-2-yl)-2-hydroxyacetamide (Example aa108), (R)—N-(3-aminobenzo[d]isoxazol-6-yl)-2-((R)-4-(3-fluoro-4-(trifluoromethyl)phenyl)-3-oxomorpholin-2-yl)-2-hydroxyacetamide (Example aa109), (R)—N-(4-carbamimidoyl-3-fluorophenyl)-2-hydroxy-2-((R)-3-oxo-4-(3-(3-oxomorpholino)phenyl)morpholin-2-yl)acetamide (Example aa114), (R)-2-hydroxy-N-(1-imino-7-(trifluoromethyl)isoindolin-5-yl)-2-((R)-3-oxo-4-(3-(3-oxomorpholino)phenyl)morpholin-2-yl)acetamide (Example aa116), (R)-2-Hydroxy-N-(1-iminoisoindolin-5-yl)-2-((R)-3-oxo-4-(3-(trifluoromethoxy)phenyl)morpholin-2-yl)acetamide (Example aa117), Ethyl 2-(3-((R)-2-((R)-1-hydroxy-2-(1-iminoisoindolin-5-ylamino)-2-oxoethyl)-3-oxomorpholino)phenoxy)acetate (Example aa120), (R)-2-Hydroxy-N-(1-iminoisoindolin-5-yl)-2-((R)-4-(4-methoxybenzyl)-3-oxomorpholin-2-yl)acetamide (Example aa121), (R)-2-((R)-4-(3-(Benzyloxy)phenyl)-3-oxomorpholin-2-yl)-2-hydroxy-N-(1-iminoisoindolin-5-yl)acetamide (Example aa123), (R)—N-(1-Aminoisoquinolin-6-yl)-2-((R)-4-(4-fluoro-3-(morpholine-4-carbonyl)phenyl)-3-oxomorpholin-2-yl)-2-hydroxyacetamide (Example aa132), N-(2,3-Dihydro-1-imino-1h-isoindol-5-yl)-4-[2-[(dimethylamino)carbonyl]phenyl]-alpha(R)-hydroxy-3-oxo-2(R)-morpholineacetamide ((Example aa140), N-(2,3-Dihydro-1-imino-1H-isoindol-5-yl)-alpha(R)-hydroxy-3-oxo-4-[2-(1-pyrrolidin ylcarbonyl)phenyl]-2(R)-morpholineacetamide ((Example aa141), 4-(2-Cyanophenyl)-N-(2,3-dihydro-1-imino-1h-isoindol-5-yl)-alpha(R)-hydroxy-3-oxo-2(R)-morpholineacetamide ((Example aa142), N-(2,3-Dihydro-1-imino-1h-isoindol-5-yl)-4-[4-fluoro-3-(4-morpholinylcarbonyl)phenyl]-alpha(R)-hydroxy-3-oxo-2(R)-morpholineacetamide (Example aa144), N-(2,3-Dihydro-1-imino-1h-isoindol-5-yl)-4-[4-fluoro-3-[(3(R)-methyl-4-morpholinyl) carbonyl]phenyl]-alpha(R)-hydroxy-3-oxo-2(R)-morpholineacetamide (Example aa145), N-(2,3-Dihydro-1-imino-1h-isoindol-5-yl)-4-[4-fluoro-3-[(3(S)-methyl-4-morpholinyl) carbonyl]phenyl]-alpha(R)-hydroxy-3-oxo-2(R)-morpholineacetamide (Example aa146), N-[4-(Aminoiminomethyl)phenyl]-4-(2-cyanophenyl)-alpha(R)-hydroxy-3-oxo-2(R)-morpholineacetamide (Example aa147), N-(4-Amino-7-quinazolinyl)-4-[4-fluoro-3-(4-morpholinylcarbonyl)phenyl]-alpha(R)-hydroxy-3-oxo-2(R)-morpholineacetamide (Example aa148),

[3-[2(R)-[2-[(3-Amino-1,2-benzisoxazol-6-yl)amino]-1(R)-hydroxy-2-oxoethyl]-3-oxo-4-morpholinyl]phenyl]pentafluorosulfur (Example aa150),

[4-[2(R)-[2-[(3-Amino-1,2-benzisoxazol-6-yl)amino]-1(R)-hydroxy-2-oxoethyl]-3-oxo-4-morpholinyl]phenyl]pentafluorosulfur (Example aa151), N-(3-Amino-5-fluoro-1,2-benzisoxazol-6-yl)-4-[4-fluoro-3-(4-morpholinylcarbonyl)phenyl]-alpha(R)-hydroxy-3-oxo-2(R)-morpholineacetamide (Example aa152), N-(2-Amino-6-quinazolinyl)-4-[4-fluoro-3-(4-morpholinylcarbonyl)phenyl]-alpha(R)-hydroxy-3-oxo-2(R)-morpholineacetamide ((Example aa153), (R)-2-((R)-4-(5-fluoro-2-isopropoxyphenyl)-3-oxomorpholin-2-yl)-2-hydroxy-N-(1-iminoisoindolin-5-yl)acetamide (Example aa154), (R)-2-hydroxy-N-(1-iminoisoindolin-5-yl)-2-((R)-3-oxo-4-(2-(trifluoromethyl)phenyl)morpholin-2-yl)acetamide (Example aa155), (R)-2-((R)-4-(2-(difluoromethoxy)phenyl)-3-oxomorpholin-2-yl)-2-hydroxy-N-(1-iminoisoindolin-5-yl)acetamide (Example aa156), (R)-2-hydroxy-N-(1-iminoisoindolin-5-yl)-2-((R)-4-(2-isopropoxyphenyl)-3-oxomorpholin-2-yl)acetamide (Example aa157), (R)-2-hydroxy-N-(1-iminoisoindolin-5-yl)-2-((R)-3-oxo-4-(2-(trifluoromethoxy)phenyl)morpholin-2-yl)acetamide ((Example aa159), N-(3-Amino-1,2-benzisoxazol-6-yl)-4-[4-fluoro-3-[(tetrahydro-2H-pyran-4-yl)oxy]phenyl]-alpha(R)-hydroxy-3-oxo-2(R)-morpholineacetamide ((Example aa160), N-(3-Amino-1,2-benzisoxazol-6-yl)-4-[3-[(3,3-difluoro-1-azetidinyl)carbonyl]-4-fluoro phenyl]-alpha(R)-hydroxy-3-oxo-2(R)-morpholineacetamide ((Example aa162), N-(3-Amino-1,2-benzisoxazol-6-yl)-4-[3-[(4,4-difluoro-1-piperidinyl)carbonyl]-4-fluorophenyl]-alpha(R)-hydroxy-3-oxo-2(R)-morpholineacetamide (Example aa163), N-(3-amino-1,2-benzisoxazol-6-yl)-4-[4-chloro-3-[3-(1,1-dimethylethyl)-1,2,4-oxadiazol-5-yl]phenyl]-alpha(R)-hydroxy-3-oxo-2(R)-morpholineacetamide (Example aa164), N-(3-amino-1,2-benzisoxazol-6-yl)-4-[2-fluoro-5-(trifluoromethyl)phenyl]-alpha(R)-hydroxy-3-oxo-2(R)-morpholineacetamide ((Example aa165), or a solvate thereof.

In another embodiment, the compound is (R)—N-(4-carbamimidoylphenyl)-2-hydroxy-2-((R)-4-(3-((S)-2-methylpyrrolidine-1-carbonyl)phenyl)-3-oxomorpholin-2-yl)acetamide (Example aa39), (R)—N-(4-carbamimidoylphenyl)-2-hydroxy-2-((R)-4-(2-methyl-3-(morpholine-4-carbonyl)phenyl)-3-oxomorpholin-2-yl)acetamide (Example aa41), (R)—N-(4-carbamimidoylphenyl)-2-hydroxy-2-((R)-4-(2-methyl-3-(pyrrolidine-1-carbonyl)phenyl)-3-oxomorpholin-2-yl)acetamide (Example aa42), (R)-2-((R)-4-(3-(azetidine-1-carbonyl)-5-fluorophenyl)-3-oxomorpholin-2-yl)-N-(4-carbamimidoylphenyl)-2-hydroxyacetamide (Example aa43), (R)-2-((R)-4-(3-(azetidine-1-carbonyl)-2-methylphenyl)-3-oxomorpholin-2-yl)-N-(4-carbamimidoylphenyl)-2-hydroxyacetamide (Example aa44), (R)-2-((R)-4-(5-(azetidine-1-carbonyl)-2-methylphenyl)-3-oxomorpholin-2-yl)-N-(4-carbamimidoylphenyl)-2-hydroxyacetamide (Example a45), (R)—N-(4-carbamimidoylphenyl)-2-hydroxy-2-((R)-3-oxo-4-(6-(trifluoromethyl)pyridin-2-yl)morpholin-2-yl)acetamide (Example aa46), (R)—N-(4-carbamimidoylphenyl)-2-hydroxy-2-((R)-4-(2-methyl-5-(pyrrolidine-1-carbonyl)phenyl)-3-oxomorpholin-2-yl)acetamide (Example aa47), (R)-2-((R)-4-(3-(azetidine-1-carbonyl)-5-methylphenyl)-3-oxomorpholin-2-yl)-N-(4-carbamimidoylphenyl)-2-hydroxyacetamide (Example aa48), (R)—N-(4-carbamimidoylphenyl)-2-hydroxy-2-((R)-4-(2-methyl-5-(morpholine-4-carbonyl)phenyl)-3-oxomorpholin-2-yl)acetamide (Example aa49), (S)-1-(3-((R)-2-((R)-2-(4-carbamimidoylphenylamino)-1-hydroxy-2-oxoethyl)-3-oxomorpholino)-5-fluorobenzoyl)pyrrolidine-2-carboxylic acid (Example aa78), 1-(3-((R)-2-((R)-2-(4-carbamimidoylphenylamino)-1-hydroxy-2-oxoethyl)-3-oxomorpholino)-5-fluorobenzoyl) pyrrolidine-2-carboxylate (Example aa80), 1-(3-((R)-2-((R)-2-(4-carbamimidoylphenylamino)-1-hydroxy-2-oxoethyl)-3-oxomorpholino)-5-fluorobenzoyl) pyrrolidine-2-carboxylate (Example aa81), 2-(3-((R)-2-((R)-2-(4-carbamimidoylphenylamino)-1-hydroxy-2-oxoethyl)-3-oxomorpholino)-5-fluoro-N-methylbenzamido)acetic acid (Example aa88), 2-(3-((R)-2-((R)-2-(4-carbamimidoylphenylamino)-1-hydroxy-2-oxoethyl)-3-oxomorpholino)-5-fluoro-N-methylbenzamido)acetate (Example aa89), 3-((R)-2-((R)-2-(4-carbamimidoylphenylamino)-1-hydroxy-2-oxoethyl)-3-oxomorpholino)-N-(2-(dimethylamino)-2-oxoethyl)-5-fluoro-N-methylbenzamide (Example aa90), (R)—N-(1,3-diiminoisoindolin-5-yl)-2-hydroxy-2-((R)-4-(3-(2-(4-methyl-3-oxopiperazin-1-yl)-2-oxoethyl)phenyl)-3-oxomorpholin-2-yl)acetamide (Example aa91), N-(2-(dimethylamino)-2-oxoethyl)-3-((R)-2-((R)-1-hydroxy-2-(1-iminoisoindolin-5-ylamino)-2-oxoethyl)-3-oxomorpholino)-N-methylbenzamide (Example aa92), 2-((S)-hydroxy((R)-3-oxo-4-p-tolylmorpholin-2-yl)methyl)-4-oxo-1,4-dihydroquinazoline-6-carboximidamide (Example aa93), 1,1-dioxo-3-((S)-hydroxy((R)-3-oxo-4-p-tolylmorpholin-2-yl)methyl)-4H-benzo[e][1,2,4]thiadiazine-7-carboximidamide (Example aa94), (R)—N-(3-aminobenzo[d]isoxazol-6-yl)-2-((R)-4-(4-chloro-3-(morpholinomethyl)phenyl)-3-oxomorpholin-2-yl)-2-hydroxyacetamide (Example aa96), (R)—N-(3-aminobenzo[d]isoxazol-6-yl)-2-hydroxy-2-((R)-4-(3-(morpholine-4-carbonyl)phenyl)-3-oxomorpholin-2-yl)acetamide (Example aa102), 3-((R)-2-((R)-2-(4-carbamimidoyl-3-fluorophenylamino)-1-hydroxy-2-oxoethyl)-3-oxo morpholino)benzoic acid (Example aa110),
(R)—N-(4-carbamimidoyl-3,5-difluorophenyl)-2-hydroxy-2-((R)-3-oxo-4-(3-(3-oxomorpholino)phenyl)morpholin-2-yl)acetamide (Example aa111),
(R)—N-(4-carbamimidoyl-2,3-difluorophenyl)-2-hydroxy-2-((R)-3-oxo-4-(3-(3-oxomorpholino)phenyl)morpholin-2-yl)acetamide (Example aa112),
(R)—N-(4-carbamimidoyl-2,5-difluorophenyl)-2-hydroxy-2-((R)-3-oxo-4-(3-(3-oxomorpholino)phenyl)morpholin-2-yl)acetamide (Example aa113),
(R)—N-(3-(aminomethyl)-4-cyano-5-(trifluoromethyl)phenyl)-2-hydroxy-2-((R)-3-oxo-4-(3-(3-oxomorpholino)phenyl)morpholin-2-yl)acetamide (Example aa115),
(R)-2-Hydroxy-N-(1-iminoisoindolin-5-yl)-2-((R)-4-(2-methyl-1-oxoisoindolin-5-yl)-3-oxomorpholin-2-yl)acetamide (Example aa118),
(R)-2-Hydroxy-N-(1-iminoisoindolin-5-yl)-2-((R)-4-(2-methyl-3-oxoisoindolin-5-yl)-3-oxomorpholin-2-yl)acetamide hydrochloride (Example aa119),
(R)-2-((R)-4-(2-(Cyclopropylmethyl)-3-oxoisoindolin-5-yl)-3-oxomorpholin-2-yl)-2-hydroxy-N-(1-iminoisoindolin-5-yl)acetamide (Example aa124),
(R)—N-(4-(Aminomethyl)-3-fluorophenyl)-2-hydroxy-2-((R)-3-oxo-4-(3-(3-oxomorpholino)phenyl)morpholin-2-yl)acetamide (Example aa125),
(R)—N-(4-Guanidinophenyl)-2-hydroxy-2-((R)-3-oxo-4-(3-(3-oxomorpholino)phenyl)morpholin-2-yl)acetamide (Example aa126),
(R)—N-(4-(Aminomethyl)phenyl)-2-((R)-4-(4-fluoro-3-(morpholine-4-carbonyl)phenyl)-3-oxomorpholin-2-yl)-2-hydroxyacetamide (Example aa127),
(R)-2-(4-Carbamoylphenylamino)-1-((R)-4-(4-fluoro-3-(morpholine-4-carbonyl)phenyl)-3-oxomorpholin-2-yl)-2-oxoethyl acetate (Example aa128),
(R)-2-((R)-4-(4-Fluoro-3-(morpholine-4-carbonyl)phenyl)-3-oxomorpholin-2-yl)-2-hydroxy-N-(1,2,3,4-tetrahydroisoquinolin-6-yl)acetamide (Example aa129),
(R)—N-(4-(Aminomethyl)-3-fluorophenyl)-2-((R)-4-(4-fluoro-3-(morpholine-4-carbonyl)phenyl)-3-oxomorpholin-2-yl)-2-hydroxyacetamide (Example aa130),
(R)—N-(4-((R)-1-Aminoethyl)phenyl)-2-((R)-4-(4-fluoro-3-(morpholine-4-carbonyl)phenyl)-3-oxomorpholin-2-yl)-2-hydroxyacetamide (Example aa131),
(R)—N—((R)-1-amino-2,3-dihydro-1H-inden-5-yl)-2-((R)-4-(4-fluoro-3-(morpholine-4-carbonyl)phenyl)-3-oxomorpholin-2-yl)-2-hydroxyacetamide (Example aa133),
(R)—N—((S)-1-Amino-2,3-dihydro-1H-inden-5-yl)-2-((R)-4-(4-fluoro-3-(morpholine-4-carbonyl)phenyl)-3-oxomorpholin-2-yl)-2-hydroxyacetamide (Example aa134),
(R)—N-(2-Aminoquinolin-6-yl)-2-((R)-4-(4-fluoro-3-(morpholine-4-carbonyl)phenyl)-3-oxomorpholin-2-yl)-2-hydroxyacetamide (Example aa135),
fluoro-2,3-dihydro-1-imino-1H-isoindol-5-yl)-alpha(R)-hydroxy-3-oxo-4-[3-(3-oxo-4-morpholinyl)phenyl]-2(R)-morpholineacetamide (Example aa136),
N-(4-chloro-2,3-dihydro-1-imino-1H-isoindol-5-yl)-alpha(R)-hydroxy-3-oxo-4-[3-(3-oxo-4-morpholinyl)phenyl]-2(R)-morpholineacetamide (Example aa137),
3-[2(R)-[2-[(2,3-Dihydro-1-imino-1h-isoindol-5-yl)amino]-1(R)-hydroxy-2-oxoethyl]-3-oxo-4-morpholinyl]benzoic acid (Example aa138),
Methyl 3-[2(R)-[2-[(2,3-dihydro-1-imino-1H-isoindol-5-yl)amino]-1(R)-hydroxy-2-oxoethyl]-3-oxo-4-morpholinyl]benzoate (Example aa139),
Methyl 2-[2(R)-[2-[(2,3-dihydro-1-imino-1h-isoindol-5-yl)amino]-1(R)-hydroxy-2-oxoethyl]-3-oxo-4-morpholinyl]benzoate (Example aa143),
N-(3-Amino-1,2-benzisoxazol-6-yl)-4-[4-fluoro-3-[2,2,2-trifluoro-1-(4-morpholinyl)ethyl]phenyl]-alpha(R)-hydroxy-3-oxo-2(R)-morpholineacetamide (Example aa149),
(R)-2-((R)-4-(5-chloro-2-isopropoxyphenyl)-3-oxomorpholin-2-yl)-2-hydroxy-N-(1-iminoisoindolin-5-yl)acetamide (Example aa158),
N-(3-Amino-1,2-benzisoxazol-6-yl)-4-[3-(difluoromethoxy)-4-fluorophenyl]-alpha(R)-hydroxy-3-oxo-2(R)-morpholineacetamide (Example aa161),
(2R)—N-(3-amino-1,2-benzoxazol-6-yl)-2-hydroxy-2-[(2R)-3-oxo-4-(2-oxo-1H-quinolin-6-yl)morpholin-2-yl]acetamide,
(2R)—N-(3-amino-1,2-benzoxazol-6-yl)-2-hydroxy-2-[(2R)-3-oxo-4-(2-oxo-1H-quinolin-7-yl)morpholin-2-yl]acetamide,
(2R)—N-(3-amino-1,2-benzoxazol-6-yl)-2-hydroxy-2-[(2R)-3-oxo-4-(2-oxo-1H-quinolin-5-yl)morpholin-2-yl]acetamide,
2-((S)-hydroxy((R)-3-oxo-4-p-tolylmorpholin-2-yl)methyl)-4-oxo-1,4-dihydroquinazoline-6-carboximidamide
1,1-dioxo-3-((S)-hydroxy((R)-3-oxo-4-p-tolylmorpholin-2-yl)methyl)-4H-benzo[e][1,2,4]thiadiazine-7-carboximidamide
or a solvate thereof.

Methods for Making the Compounds of Present Invention

General Methods

The compounds represented by Formula (I) and salts thereof, which are the compounds of the present invention can be readily produced from known compounds or commercially available compounds by, for example, known processes described in published documents, and produced by production processes described below. The present invention is not limited to the production processes described below.

Unless otherwise noted, R1, R2, R3, R4, R5, G, W, X, m, and n in the formulae shown in the description of the production method are as defined above for the Formula (I). The alkylene group in the side chain or ring of the compound may be substituted with the substituents defined for the Formula (I). R4' and R in the formulae shown in the description of the production method are defined in the corresponding part.

Unless otherwise noted, each of $P^1$, $P^2$, $P^3$, $P^4$ or $P^5$ in the production method independently designate protecting group, and exemplary appropriate protecting groups include typical an arylmethyl group such as benzyl group, para methoxy benzyl group or triphenylmethyl group; acyl protecting groups, namely, an alkanoyl group such as acetyl group; an alkoxycarbonyl group such as methoxycarbonyl group, ethoxycarbonyl group, or t-butoxycarbonyl group; an arylmethoxycarbonyl group such as benzyloxycarbonyl group, paramethoxybenzyloxycarbonyl group, or para(ortho)nitrobenzyloxycarbonyl group; or an aroyl group such as benzoyl group. The method used for deprotecting such protecting group differs depending on the chemical nature of the protecting group employed, and in the case of an arylmethyl group such as para methoxy benzyl group or benzyl group, the deprotection can be accomplished by hydrogenation using a palladium-carbon catalyst for conversion into nitrogen-hydrogen bond, or alternatively, by Birch reduction using metal sodium in liquid ammonia, or by oxidative condition using such as CAN (ceric ammonium nitrate) or DDQ (2,3-dichloro-5,6-dicyano-p-benzoquinone). The triphenylmethyl group can be removed by using an appropriate acid such as acetic acid, hydrochloric acid, hydrobromic acid, sulfuric acid, phosphoric acid, trifluoroacetic acid, trifluoromethanesulfonic acid, or a combination thereof, or alternatively, or by Birch reduction using metal sodium in liquid ammonia.

In the case of an acyl protecting group such as an alkanoyl group, an alkoxycarbonyl group, or aroyl group, the deprotection can be accomplished by the hydrolysis using an appropriate base such as an alkaline metal hydroxide such as lithium hydroxide, sodium hydroxide, or potassium hydroxide.

The substituted methoxycarbonyl protecting group such as t-butoxycarbonyl group or paramethoxybenzyloxycarbonyl group can be removed by an appropriate acid such as acetic acid, hydrochloric acid, hydrobromic acid, sulfuric acid, phosphoric acid, trifluoroacetic acid, trifluoromethanesulfonic acid, or a combination thereof.

The arylmethoxycarbonyl group such as benzyloxycarbonyl group, paramethoxybenzyloxycarbonyl group, or para(ortho)nitrobenzyloxycarbonyl group can be removed by the hydrolysis using a palladium-carbon catalyst. The protecting groups $P^1$, $P^2$, $P^3$, $P^4$ or $P^5$ of the imino group (—NH—) can be independently or simultaneously deprotected by adequately selecting the type of the protecting group and deprotection conditions, and if desired, the protecting group can be re-introduced.

Unless otherwise noted, each of $L_1$, $L_2$, $L_3$, $L_4$, $L_5$, $L_6$, $L_7$ or $L_8$ in the production method designates a leaving group such as a halogen atom (for example, fluorine, chlorine, bromine, or iodine), methanesulfonyloxy group, or p-toluenesulfonyloxy group, or a replaceable substituent such as hydroxy group or an alkoxy group.

It should be noted that, when the derivative of the Formula (I) of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme. The required starting materials, such as (i-a), (i-b), (i-c), (i-d), (i-e), (i-f), (i-g), (ii-a), (iii-a), (iii-b), (v-b), (viii-a), (viii-b), (viii-c), (viii-d), (viii-e), (ix-a), (xvi-a), or (xvii-a) are either commercially available, or capable of being readily synthesized by the method commonly used in the organic chemistry from commercially available products. Unless otherwise noted, the reaction conditions employed in the production method are as described below:

Reaction temperature is in the range of −78° C. to the solvent-reflux temperature, and reaction time is the time sufficient for required progress of the reaction. Solvent which is not involved in the reaction may be any of the aromatic hydrocarbon solvents such as toluene and benzene; polar solvents such as water, methanol, DMF, and DMSO; basic solvents such as triethylamine and pyridine; halogen solvents such as chloroform, methylene chloride, and 1,2-dichloroethane; ethereal solvent such as diethylether, tetrahydrofuran, and dioxane; and mixed solvents thereof; and the solvent used may be adequately selected depending on the reaction conditions. Base may be any of inorganic bases such as potassium carbonate, cesium carbonate, sodium hydroxide, potassium hydroxide, and sodium hydride; and organic bases such as triethylamine, pyridine, N,N-dialkylaniline, lithium diisopropylamide and lithium hexamethyldisilazide; and acid may be any of mineral acids such as hydrochloric acid, and sulfuric acid; and organic acids such as methanesulfonic acid, trifluoroacetic acid and p-toluenesulfonic acid. The base and the acid are not necessarily limited to those mentioned above. The production processes will now be described in detail.

Scheme 1 Synthetic route of the key intermediate (iii-a)

(Reaction scheme 1)

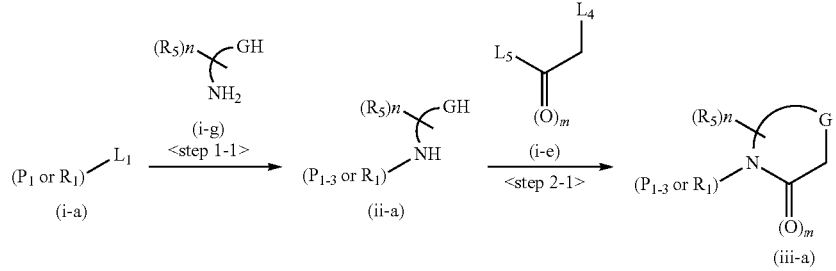

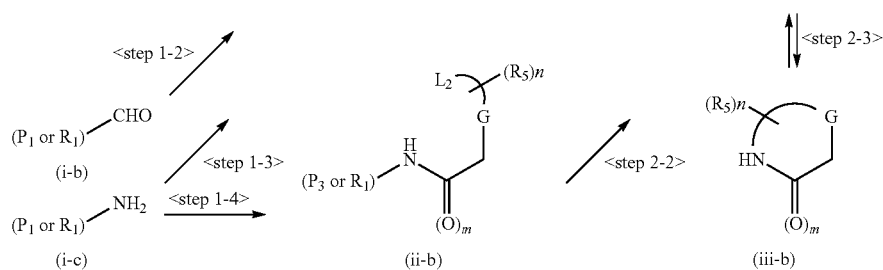

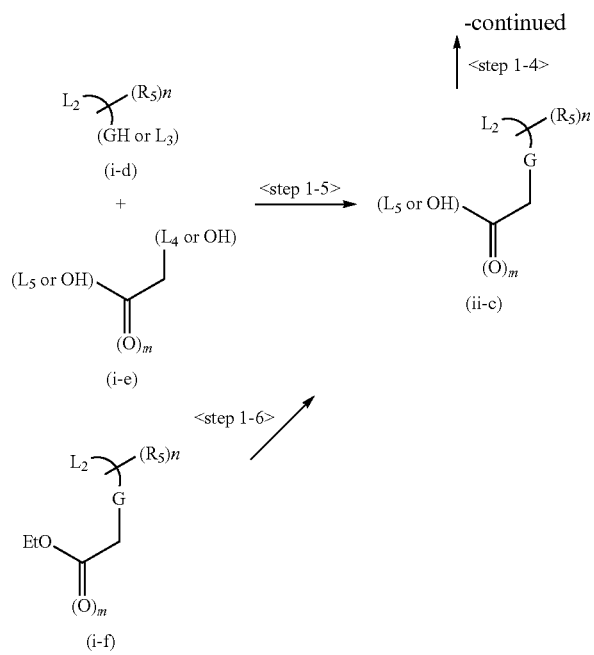

G represents O or S in the Scheme 1

Step 1-1

A compound represented by formula (ii-a) can be produced by allowing a compound represented by formula (i-a) to react with a commercially available aminoalcohol or aminothiol (i-g), readily prepared aminoalcohol or aminothiol from known compounds by a process similar to that described in published documents, for example, *Organic Synthesis, Collective Vol.* 5, pp. 88 1973, in the presence of a base such as potassium tert-buthoxide, sodium hydride, lithium hydroxide, sodium hydroxide, potassium hydroxide, lithium carbonate, sodium carbonate, or potassium carbonate using a solvent which is inactive to the reaction, such as methanol, ethanol, acetone, N,N-dimethylformamide, dioxane or tetrahydrofuran, or a mixed solvent thereof at a temperature in the range of room temperature to the solvent-reflux temperature.

Step 1-2

Alternatively, a compound represented by formula (ii-a) can be produced by conducting a reaction using a compound represented by formula (i-b) by a process of reductive amination. After a compound represented by formula (i-b) is converted to an imine with a suitable aminoalcohol (i-g), an aminothiol (i-g) using a solvent which is inactive to the reaction, such as a halogenated solvent, e.g., dichloromethane or chloroform, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature, a compound represented by formula (ii-a) can be produced by a process similar to that described in published documents, for example, Journal of Medical Chemistry, 23(12), pp. 1405-1410, 1980 in the presence of a reductive reagent such as sodium borohydride using a solvent which is inactive to the reaction, such as an alcoholic solvent, e.g., methanol, ethanol, 2-propanol, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature.

Alternatively, hydrogen gas can be used to an imine with a suitable process similar to that described in published documents, for example, Jikken Kagaku Koza (Experimental Chemistry Series), 4th edition, 26, Organic synthesis VIII, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide (PtO$_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid at a temperature in the range of room temperature to the solvent-reflux temperature, thereby producing a compound represented by formula (ii-a).

Step 1-3

Alternatively, a compound represented by formula (ii-a) can be produced by conducting a reaction using a compound represented by formula (i-c) by a process similar to that of <step 1-1> with a suitable alcohol or thiol in the presence of copper iodide and cesium carbonate using a solvent which is inactive to the reaction, such as acetonitrile.

Step 1-4

A compound represented by formula (II-b) can be produced by conducting a reaction using a compound represented by formula (II-c) and a compound represented by formula (i-c) (for example, a known amine) as follows. When a compound represented by formula (II-c) is a carboxylic acid, a compound represented by formula (II-b) can be produced by allowing a compound represented by formula (II-c) to react with a compound represented by formula (i-c) by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl) carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (II-c) is an acid halide, a compound represented by formula (II-b) can be similarly produced by conducting a reaction with a compound represented by formula (i-c) by a process similar to that described in, for example, Jikken Kagaku Koza (Experimental Chemistry Series), 4th edition, 22, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

Step 1-5

A compound represented by formula (II-c) can be produced by the same process as that used in <Step 1-1> of (Reaction Scheme 1) using a compound represented by formula (i-d) and compound represented by formula (i-e).

Step 1-6

A compound represented by formula (II-c) can be produced from a compound represented by formula (i-f) by a process similar to that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of a base such as lithium hydroxide, sodium hydroxide, potassium hydroxide, lithium carbonate, sodium carbonate, or potassium carbonate using water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

Step 2-1

A compound represented by formula (iii-a) can be produced by a process similar to that described in published documents, for example, *Zhurnal Organicheskoi Khimii*, (6), 1305-8, 1970, or by a similar process as that used in <Step 1-4> and <step 1-5> of (Reaction Scheme 1) using a compound represented by formula (i-e) as an acid halide, and compound represented by formula (ii-a) as a suitable aminoalcohol or aminothiol. When aminothiol (ii-a) was used, cyclization process of producing a compound represented by formula (iii-a) can be also conducted step by step process using different base or different solvent system.

Step 2-2

Alternatively, a compound represented by formula (iii-a) can be produced by the same process as that used in <Step 2-1> of (Reaction Scheme 1) using a compound represented by formula (II-b).

Step 2-3

Protective groups of a compound represented by formula (iii-a) can be introduced and removed between (iii-a) and (iii-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Scheme 2 Synthetic route of Example compounds and combination compounds.

(Reaction scheme 2)

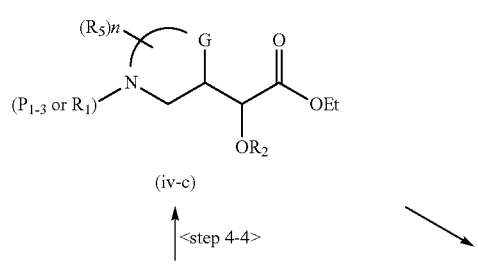

(iv-c)

<step 4-4>

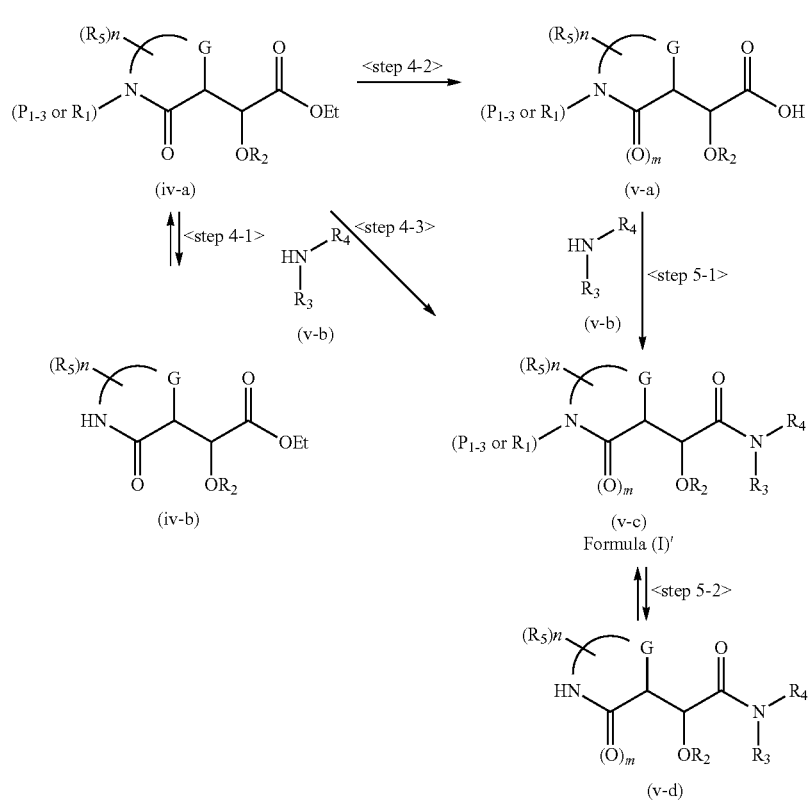

G represents O, S, NH, or CH₂ in the Scheme 2

Step 3-1

A compound represented by formula (iv-a) can be produced by allowing a compound represented by formula (iii-a) or (iii-b), which was produced in the Reaction scheme 1 or commercially available, to react with alkyl glyoxylate, such as ethyl glyoxylate by a process similar to that described in published documents, for example, *Journal of Medicinal Chemistry*, 31(1), pp. 230-243, 1988, in the presence of a base such as lithium hexamethyldisiladide, sodium hydride, lithium hydroxide, sodium hydroxide, potassium hydroxide, lithium carbonate, sodium carbonate, or potassium carbonate using a solvent which is inactive to the reaction, such as tetrahydrofuran, N,N-dimethylformamide, dioxane, or a mixed solvent thereof at a temperature in the range of room temperature to the solvent-reflux temperature. The resulting alcoholic compound (iv-a) wherein R2 represents hydrogen can be protected in any step described hereafter by techniques which are well-known or described here (see Greene, T. W., et. al., *Protective Groups in Organic Synthesis* (2007), 4th Ed., Wiley, New York, or Kocienski, P., *Protecting Groups* (1994), Thieme), to be, for example, alcoxy groups or ester groups.

Step 4-1

Protective groups of a compound represented by formula (iv-a) can be introduced and removed between (iv-a) and (iv-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 4-2

A compound represented by formula (v-a) can be produced by the same process as that used in <Step 1-6> of (Reaction Scheme 1) using a compound represented by formula (iv-a) or (iv-c).

Step 4-3

A compound represented by formula (v-c) can be produced by allowing a compound represented by formula (iv-a) to react with a compound represented by formula (v-b) by a process similar to that described in published documents, for example, Organic synthesis IV, Acids, amino acids, and peptides, pp. 191-309, 1992, Maruzen Co., Ltd., in the presence of a condensing agent, in a solvent which is inactive to the reaction, such as an alcoholic solvent, e.g., methanol, ethanol, or 2-propanol, in the presence or absence of a base such as triethylamine or pyridine at a temperature in the range of 0° C. to the solvent-reflux temperature.

Step 4-4

A compound represented by formula (iv-c) can be produced by a process similar to that described in published documents, for example, Organic synthesis, Collective Vol. 7, pp. 221, 1990, Organic synthesis, Collective Vol. 7, pp. 530, 1990, *Jikken Kagaku Koza* (*Experimental Chemistry Series*), 4*th edition*, 26, Reduction by borane, hydrazine or diimide pp 237-248, using a compound represented by formula (iv-a) in the presence of borane-THF complex, borane-diethyl ether complex, borane-dimethyl sulfide complex, hydradine or hydroxylamine using a solvent such as an ethereal solvent, e.g., diethyl ether or tetrahydrofuran at a temperature in the range of −78° C. to the solvent-reflux temperature.

Step 5-1

A compound represented by formula (v-c) can be produced by allowing a compound represented by formula (v-a) to react with a compound represented by formula (v-b) by a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (v-a) is converted to an acid halide, a compound represented by formula (v-c) can be similarly produced by conducting a reaction by a process similar to that described in, for example, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

Alternatively, a compound represented by formula (v-c) can be produced by using triphosgene by a process similar to that described in published documents, for example, *Letters in Organic Chemistry*, 4, 20-22, 2007, in the presence of a base such as triethyl amine using a solvent which is inactive to the reaction, such as tetrahydrofuran, N,N-dimethylformamide, dioxane, $CH_2Cl_2$ or a mixed solvent thereof at a temperature in the range of room temperature to the solvent-reflux temperature.

Step 5-2

Protective groups of a compound represented by formula (v-c) can be introduced and removed between (v-c) and (v-d) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

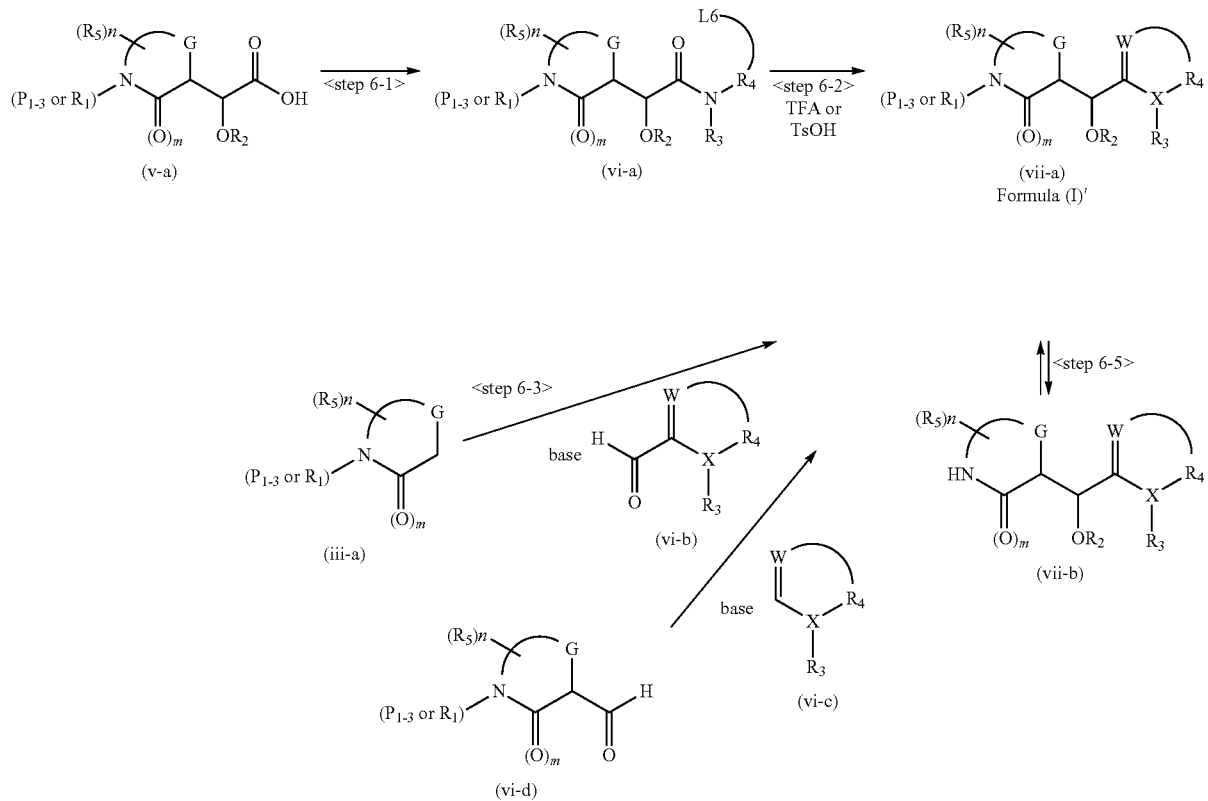

Scheme 3 Synthetic route of Example compounds and combination compounds.

(Reaction scheme 3)

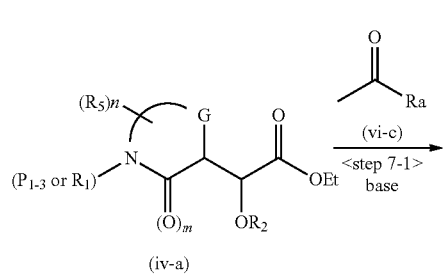

(iv-a)

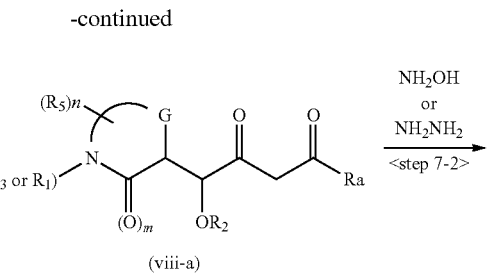

(viii-a)

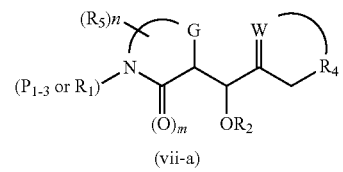

(vii-a)

G represents O, S, NH, or CH₂ in the Scheme 3

Step 6-1

A compound represented by formula (vi-d) can be produced by the similar process as that used in <Step 5-1> of (Reaction Scheme 2) using a compound represented by formula (v-a).

Step 6-2

A compound represented by formula (vii-a) can be produced by allowing a compound represented by formula (vi-a) to react with by a process similar to that described in published documents, for example, *Synthetic Communications*, 37(24), 2007, in the presence of an acid such as acetic acid, trifluoroacetic acid or p-toluenesulfonic acid using a solvent such as acetic acid, trifluoroacetic acid, or a mixed solvent thereof at a temperature in the range of room temperature to the solvent-reflux temperature.

Step 6-3

Alternately, a compound represented by formula (vii-a) can be produced by the similar process as that used in <Step 3-1> of (Reaction Scheme 2) using a compound represented by formula (iii-a) and a compound represented by formula (vi-b).

Step 6-4

Alternatively, a compound represented by formula (vii-a) can be produced by a process similar to that described in published documents, for example, *Bioorganic & Medicinal Chemistry Letters*, 17(14), 2007, 3860 using a compound represented by formula (vi-d) and a compound represented by formula (vi-c), wherein Ra represents a suitable substituent.

Step 6-5

Protective groups of a compound represented by formula (vi-a) can be introduced and removed between (vii-a) and (vii-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 7-1

A compound represented by formula (viii-a) can be produced by allowing a compound represented by formula (iv-a) to react with by a process similar to that described in published documents, for example, Organic synthesis, Collective Vol 1, pp. 238, 1941, Maruzen Co., Ltd, in the presence of a base such as sodium ethoxide using a solvent such as ethanol at a temperature in the range of room temperature to the solvent-reflux temperature.

Ra of the formula (vi-c) represents a suitable substituent or leaving group of L1 to L4 described above.

Step 7-2

A compound represented by formula (vii-a) can be produced by a process similar to that described in published documents, for example, *Journal of Medicinal Chemistry*, 48, 14, pp 4541, 2005, using a compound represented by formula (viii-a) in the presence of hydradine or hydroxylamine using a solvent such as ethanol at a temperature in the range of room temperature to the solvent-reflux temperature.

Furthermore, in the case of some of the compounds according to the invention the possibility arises of employing diastereomerically or enantiomerically pure starting products for the preparation of the ring structures. By this means, other or simplified processes can be employed for the purification of the final products. These starting products were prepared beforehand in enantiomerically or diastereomerically pure form according to processes known from the literature. This can mean, in particular, that in the synthesis of the scaffold structures either enantioselective processes are used, or else an enantiomeric (or diastereomeric) separation is carried out at an earlier stage of the synthesis and not only at the stage of the final products. Likewise, a simplification of the separations can be achieved by proceeding in two or more stages.

Scheme 4 Synthetic route of intermediate compounds (viii-d)

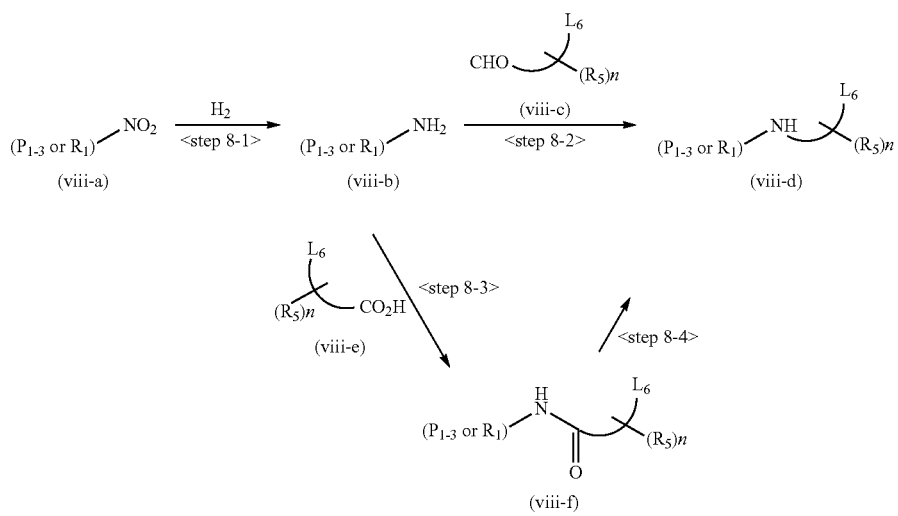

(Reaction scheme 4)

Step 8-1

A compound represented by formula (viii-b) can be produced from (viii-a) by conducting a reaction using the compound represented by formula (viii-a) by a process similar to that described in published documents, for example, *Jikken Kagaku Koza* (*Experimental Chemistry Series*), 4th edition, 26, *Organic synthesis VIII*, Asymmetric synthesis, reduction, sugar, and labeled compound, pp. 159-266, 1992, Maruzen Co., Ltd., in the presence of a catalyst such as palladium-carbon (Pd—C), Raney-Ni, platinum oxide (PtO2), or dichloro triphenyl phosphine ruthenium, under hydrogen atmosphere, using a solvent which is inactive to the reaction, such as an alcoholic solvent, e.g., methanol, ethanol, or 2-propanol, an ethereal solvent, e.g., diethyl ether or tetrahydrofuran, 1,2-dimethoxyethane, or 1,4-dioxane, a polar solvent, e.g., ethyl acetate or methyl acetate, or a mixed solvent thereof at a temperature in the range of room temperature to the solvent-reflux temperature.

Alternatively, a compound represented by formula (viii-b) can be produced from (viii-a) by using Fe, or Sn, in hydrochloric acid or acetic acid, at a temperature in the range of 0° C. to the solvent-reflux temperature. Furthermore, a compound represented by formula (viii-b) can also be produced from (viii-a) by using sodium borohydride in the presence of Lewis Acid, e.g., Nickel(II) chloride ($NiCl_2$), Tin(II) chloride ($SnCl_2$) using a solvent which is inactive to the reaction, such as an alcoholic solvent, e.g., methanol, ethanol, or 2-propanol, an ethereal solvent, e.g., diethyl ether or tetrahydrofuran, 1,2-dimethoxyethane, or 1,4-dioxane, or a mixed solvent thereof at a temperature in the range of 0° C. to the solvent-reflux temperature.

Step 8-2

A compound represented by formula (viii-d) can be produced by conducting a reaction using a compound represented by formula (viii-b) by a process of reductive amination. After a compound represented by formula (viii-c) is converted to an imine with a suitable amine (viii-b) using a solvent which is inactive to the reaction, such as an alcoholic solvent, e.g., methanol, ethanol, or 2-propanol, such as a halogenated solvent, e.g., dichloromethane or chloroform, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature, a compound represented by formula (viii-d) can be produced by a process similar to that described in published documents, for example, *Journal of Medical Chemistry*, 23(12), pp. 1405-1410, 1980 in the presence of a reductive reagent such as sodium borohydride or sodium triacetoxy borohydride in the presence of acid such as acetyl alcohol, using a solvent which is inactive to the reaction, such as an alcoholic solvent, e.g., methanol, ethanol, 2-propanol, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature.

Alternatively, hydrogen gas can be used to hydrogenate an imine with a suitable process similar to that described in published documents, for example, *Jikken Kagaku Koza* (*Experimental Chemistry Series*), 4th edition, 26, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide ($PtO_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid at a temperature in the range of room temperature to the solvent-reflux temperature, thereby producing a compound represented by formula (viii-d).

Step 8-3

A compound represented by formula (viii-f) can be produced by the similar process as that used in <Step 5-1> of (Reaction Scheme 2) using a compound represented by formula (viii-e).

Step 8-4

A compound represented by formula (viii-d) can be produced by a process similar to that described in published documents, for example, *Jikken Kagaku Koza* (*Experimental Chemistry Series*), 4th edition, 26, Reduction by borane, hydrazine or diimide pp 237-248, using a compound represented by formula (viii-f) in the presence of hydradine or hydroxylamine using a solvent such as ethanol at a temperature in the range of room temperature to the solvent-reflux temperature.

mamide, dioxane, $CH_2Cl_2$ or a mixed solvent thereof at a temperature in the range of room temperature to the solvent-reflux temperature.

Step 9-2

A compound represented by formula (x-a) can be produced by allowing a compound represented by formula (ix-b) to react with a compound represented by formula (viii-d) by a process similar to that described in published documents, for example, *Jikken Kagaku Koza* (*Experimental Chemistry*

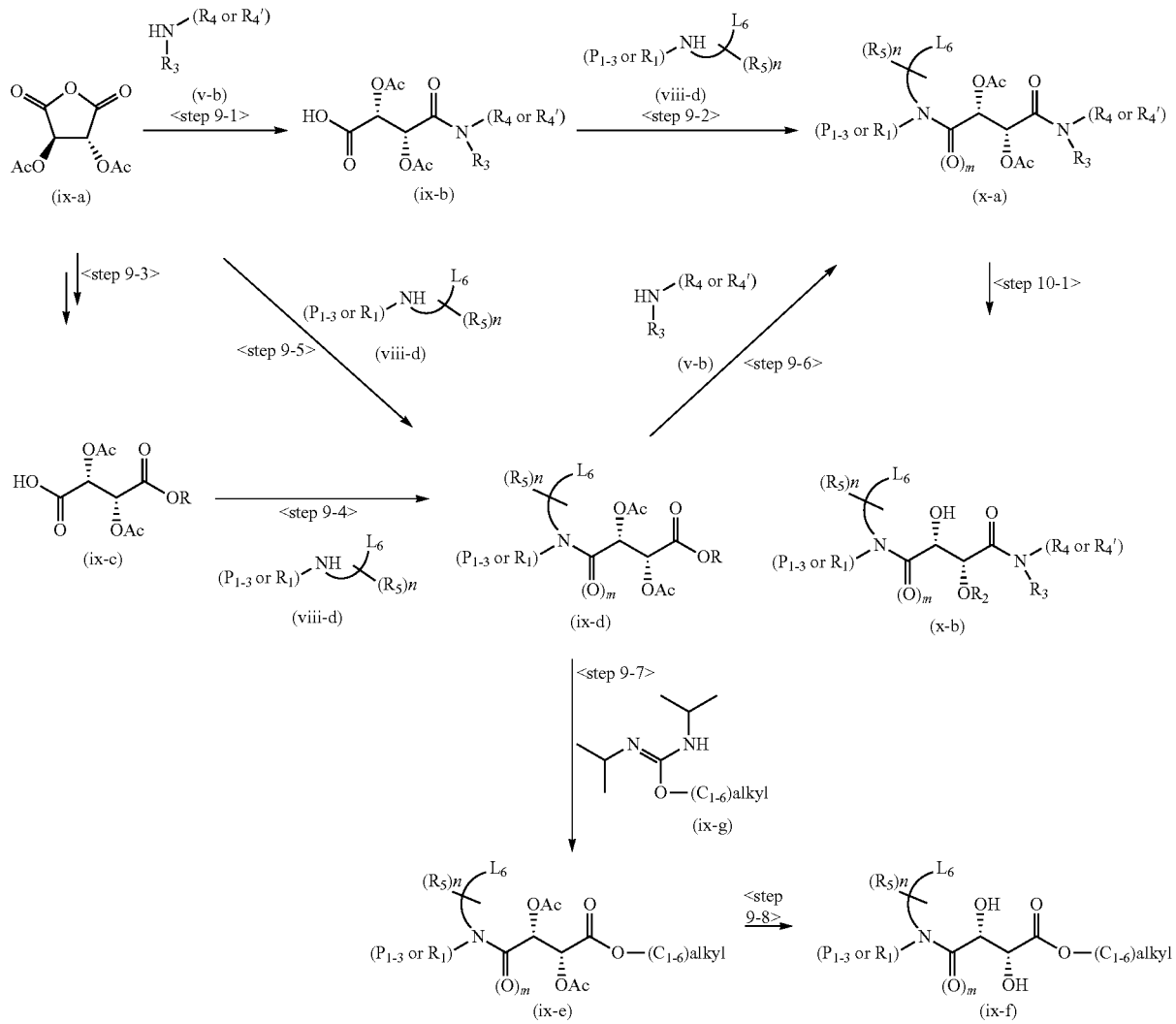

Scheme 5
Synthetic route of optically active compounds (x-b)

(Reaction scheme 5)

Step 9-1

A compound represented by formula (ix-b) can be produced by conducting a reaction using (2R,3R)-2,3-diacetoxysuccinic anhydride represented by formula (ix-a) in the presence of amine (v-b) by a process similar to that described in published documents, for example, *Organic Synthesis, Collective Vol.* 3, pp. 169 1955, using a solvent which is inactive to the reaction, such as tetrahydrofuran, N, N-dimethylfor-

*Series*), 4th edition, 26, Acids, amino acids, and peptides, pp. 193-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of −78° C. to the solvent-reflux temperature. When a compound represented by formula (ix-b) is converted to an acid halide, a compound represented by formula (x-a) can be similarly produced by conducting a reaction by a process similar to that described in, for example, *Jikken Kagaku Koza* (*Experimental Chemistry Series*), 4*th edition*, 26, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of −78° C. to the solvent-reflux temperature.

Alternatively, a compound represented by formula (x-a) can be produced by using triphosgene with (ix-b) by a process similar to that described in published documents, for example, *Letters in Organic Chemistry*, 4, 20-22, 2007, in the presence of a base such as triethyl amine using a solvent which is inactive to the reaction, such as tetrahydrofuran, N,N-dimethylformamide, dioxane, $CH_2Cl_2$ or a mixed solvent thereof at a temperature in the range of room temperature to the solvent-reflux temperature.

Step 9-3

A compound represented by formula (ix-c), wherein R represents hydrogen or C1-6 alkyl group, can be produced by conducting a reaction using (2R,3R)-2,3-diacetoxysuccinic anhydride represented by formula (ix-a) in the presence of suitable alcoholic solvent by a process similar to that described in published documents, for example, *Organic Synthesis, Collective Vol.* 3, pp. 169 1955, using a solvent, such as an alcoholic solvent, e.g., benzyl alcohol, tert-buthyl alcohol, methanol, ethanol, 2-propanol, or tetrahydrofuran, N,N-dimethylformamide, dioxane, $CH_2Cl_2$ or a mixed solvent thereof in the presence of DMAP at a temperature in the range of 0° C. to the solvent-reflux temperature.

Step 9-4

A compound represented by formula (ix-d) can be produced by the same process as that used in <Step 9-2> of (Reaction Scheme 5) using a compound represented by formula (ix-c).

Step 9-5

A compound represented by formula (ix-d) wherein R represents hydrogen atom can be produced by allowing (2R, 3R)-2,3-diacetoxysuccinic anhydride represented by formula (ix-a) to react with a compound represented by formula (viii-d) by a process similar to that described in published documents, for example, *Organic Synthesis, Collective Vol.* 3, pp. 169 1955, *Organic Synthesis, Collective Vol.* 5, pp. 944, 1973, *Vol.* 41, 93, 1961, or *Jikken Kagaku Koza* (*Experimental Chemistry Series*), 4*th edition*, 26, Acids, amino acids, and peptides, pp. 146-148, 1992, Maruzen Co., Ltd., using a solvent, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., DMF, ethyl acetate or acetonitrile, an aromatic hydrocarbon solvent, e.g., toluene or benzene, or an acid solvent, e.g., acetic acid or a mixed solvent thereof in the presence of DMAP, Pyridine or sulfuric acid as a catalyst if needed at a temperature in the range of 0° C. to the solvent-reflux temperature.

Step 9-6

A compound represented by formula (x-a) can also be produced by the same process as that used in <Step 4-3> of (Reaction Scheme 2) using a compound represented by formula (ix-d) wherein R represents C1-6 alkyl group in the presence of amine (v-b), and also be produced by the same process as that used in <step 5-1> of (Reaction scheme 2) or <step 13-3> and <step 13-4> of (Reaction scheme 11) using a compound represented by formula (ix-d) wherein R represents hydrogen atom, in the presence of amine (v-b).

Protective groups of a compound in the process of producing a compound represented by formula (x-a) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 9-7

A compound represented by formula (ix-e) can be produced by allowing a compound represented by formula (ix-d) to react with a compound represented by formula (ix-g) by a process similar to that described in published documents, for example, Jikken Kagaku Koza (Experimental Chemistry Series), 4th edition, 22, Organic synthesis IV, Acids, amino acids, and peptides, pp. 1-82, 1992, Maruzen Co., Ltd., in the presence of an acidic reagent such as hydrochloric acid, sulfuric acid, thionyl chloride, or acetyl chloride, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

Step 9-8

A compound represented by formula (ix-d) can be produced by conducting a reaction using a compound represented by formula (ix-e) by a process similar to that described in published documents, for example, *Can. J. Chem.*, 49, 493 (1971) or Greene, T. W., et. al., *Protective Groups in Organic Synthesis* (2007), 4th Ed., in the presence of ammonia, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

Step 10-1

A compound represented by formula (x-b) can be produced by the similar process as that used in <Step 9-8> of (Reaction Scheme 6) using a compound represented by formula (x-a).

Protective groups of a compound in the process of producing a compound represented by formula (x-b) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Scheme 6
Synthetic route of optically active compounds (x-c) and (x-e)

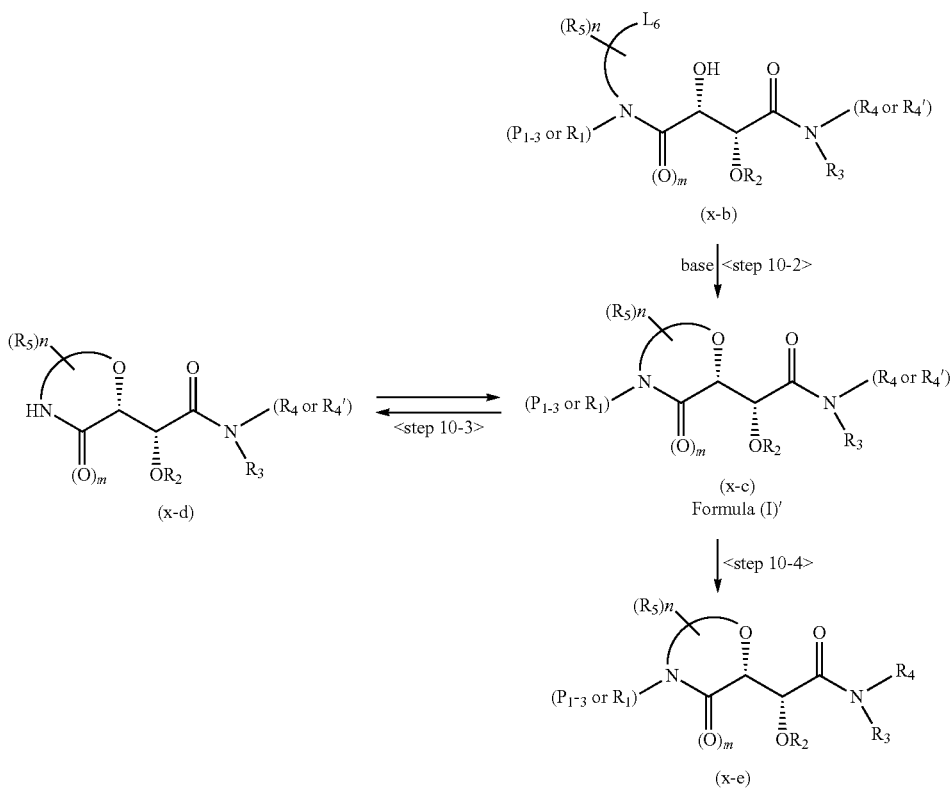

(Reaction scheme 6)

Step 10-2

A compound represented by formula (x-c) can be produced by allowing a compound represented by formula (x-b) by a process similar to that described in published documents, for example, *Organic Synthesis, Collective Vol.* 6, pp. 301, 395, 1988, or *Jikken Kagaku Koza* (*Experimental Chemistry Series*), 4th edition, 20, alcohol and amine, pp. 187-194, 1992, Maruzen Co., Ltd., in the presence of a base such as potassium tert-buthoxide, sodium hydride, lithium hydroxide, sodium hydroxide, potassium hydroxide, lithium carbonate, sodium carbonate, or potassium carbonate using a solvent which is inactive to the reaction, such as an alcoholic solvent, e.g., methanol, ethanol, or 2-propanol, tert-buthanol, or a polar solvent, e.g., DMF, DMSO, ethyl acetate, or acetonitril, or an aromatic hydrocarbon solvent, e.g., toluene or benzene, or acetone, dioxane or tetrahydrofuran, or a mixed solvent thereof at a temperature in the range of 0° C. to the solvent-reflux temperature.

Step 10-3

Protective groups of a compound represented by formula (x-c) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 10-4

When R4' is used as a precursor for R4 representing 4-amidino-phenyl group or its analogue, R4' represents 4-cyano-phenyl group or 1,2,4-oxadiazol-5-one-3-yl phenyl group or their analogues, which can be converted to 4-amidino-phenyl group R4 or its analogue by techniques which are well-known or described:

Scheme 7

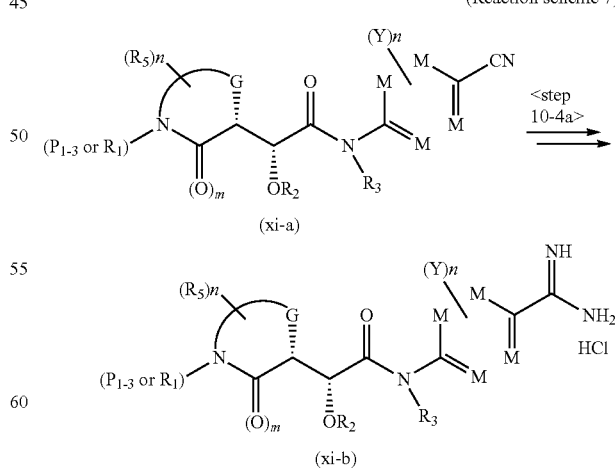

(Reaction scheme 7)

G represents O, S, NH, or $CH_2$, and
M represents independently CH or N, and n represents 1 to 4 in the Scheme 7

Step 10-4a

When R4' of a compound represented by formula (x-c) of Scheme 6 represents 4-cyano-(aryl or heteroaryl) group or its analogue wherein 4-cyano-(aryl or heteroaryl) ring is optionally substituted with one to four Y, a compound represented by formula (xi-a) which corresponds to a compound (x-c) can be converted to a compound represented by formula (xi-b) via its imidate compound.

4-cyano-(aryl or heteroaryl) group or, R4' of a compound represented by formula (xi-a), can be converted to its imidate by allowing a compound represented by formula (xi-a) to acidic condition such as HCl gas solution of, such as an alcoholic solvent, e.g., methanol, ethanol, or 2-propanol, a halogenated solvent, e.g., dichloromethane or chloroform, or a mixed solvent thereof at a temperature in the range of 0° C. to the room temperature.

Resulting imidate compound is converted to 4-amidino-(aryl or heteroaryl) compound (xi-b) or its analogue by conducting an imidate compound to ammonium or ammonium carbonate alcoholic solvent, e.g. methanol, ethanol, tert-buthanol or in a mixed solvent thereof at a temperature in the range of 0° C. to the solvent-reflux temperature in a sealed tube.

Alternatively, when R4' represents 4-cyano-(aryl or heteroaryl) group or its analogue wherein 4-cyano-(aryl or heteroaryl) is optionally substituted with one to four Y, a compound represented by formula (xi-a) can be converted to 4-amidino-(aryl or heteroaryl) group R4 via its N-hydroxy amidino compound.

4-cyano group, R4' of a compound represented by formula (xi-a), can be converted to its N-hydroxy amidino group by allowing a compound (xi-a) in the presence of a base such as triethyl amine, hunig base, potassium tert-buthoxide, sodium hydride, lithium hydroxide, sodium hydroxide, potassium hydroxide, lithium carbonate, sodium carbonate, or potassium carbonate using a solvent which is inactive to the reaction, such as water, methanol, ethanol, acetone, N,N-dimethylformamide, dioxane or tetrahydrofuran, or a mixed solvent thereof at a temperature in the range of 0° C. to the solvent-reflux temperature in a sealed tube.

Resulting N-hydroxy amidino group can be converted to its amidine compound represented by formula (xi-b) by a suitable process similar to that described in published documents, for example, Jikken Kagaku Koza (Experimental Chemistry Series), 4th edition, 26, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide (PtO$_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid or a mixed solvent thereof at a temperature in the range of room temperature to the solvent-reflux temperature.

Scheme 8

(Reaction scheme 8)

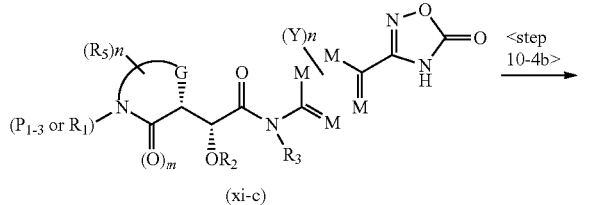

(xi-c)

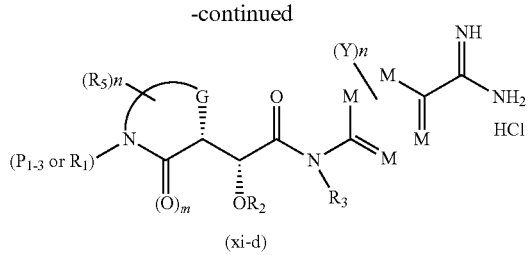

(xi-d)

G represents O, S, NH, or CH$_2$, and
M represents independently CH or N, and n represents 1 to 4 in the Scheme 8

Step 10-4b

When R4' is used as a precursor for R4 representing 4-amidino-(aryl or heteroaryl) group or its analogue wherein 4-amidino-(aryl or heteroaryl) group is optionally substituted with one to four Y, R4' also represents 1,2,4-oxadiazol-5-one-3-yl (aryl or heteroaryl) group or its analogues wherein phenyl group is optionally substituted with one to four Y, which can be converted to 4-amidino-(aryl or heteroaryl) group R4 by techniques which are well-known or described here.

A compound represented by formula (xi-d) can be produced by the same process as that used in <Step 8-1> of (Reaction Scheme 4) using a compound represented by formula (xi-c).

When G in the formula (xi-c) represents sulfur atom, sulfur can be oxidized to its sulfone or sulfoxide with Oxone® by a process similar to that described in published documents, for example, *Shin-Jikken Kagaku Kouza, Vol. 14-III, p* 1759, R. J. Kennedy, *J. Org. Chem.*, 25, 1901 (1960), B. M. Trost, *Tetrahedron Lett.*, 22, 1287 (1981), in the presence of Oxone® using a solvent which is inactive to the reaction, such as water, or an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of 0° C. to the solvent-reflux temperature.

Scheme 9

(Reaction scheme 9)

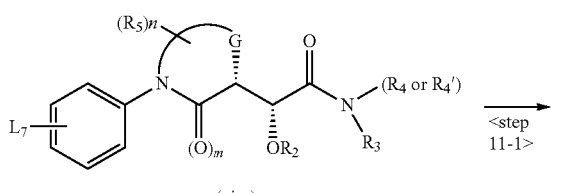

(xi-e)

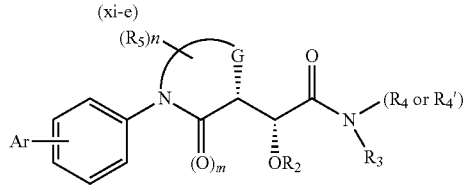

(xi-f)

G represents O, S, NH, or CH$_2$ in the Scheme 9

Step 11-1

When R1 in the Formula (I) represents biaryl groups optionally substituted with one to four Y, such as, for example, 4-thienyl phenyl group or 4-phenyl phenyl group, a compound represented by formula (xi-f) can be produced by conducting a reaction using a compound represented by formula (xi-e) by a process of Suzuki-Miyaura coupling similar to that described in published documents, for example, Miyaura, N, et. al., *Tetrahedron Lett.*, 1979, 3437, *J. Chem. Soc. Chem. Commun.*, 1979, 866, *Chem. Rev.* 1995, 95, 2457, in the presence of catalyst such as palladium-carbon (Pd—C), Raney-Ni, or platinum oxide ($PtO_2$), and in the presence of a base such as potassium tert-buthoxide, sodium hydride, lithium hydroxide, sodium hydroxide, potassium hydroxide, lithium carbonate, sodium carbonate, or potassium carbonate with a corresponding arylboronic acid using a solvent which is inactive to the reaction, such as water, acetone, toluene, dioxane or tetrahydrofuran, or a mixed solvent thereof at a temperature in the range of room temperature to the solvent-reflux temperature.

Scheme 10

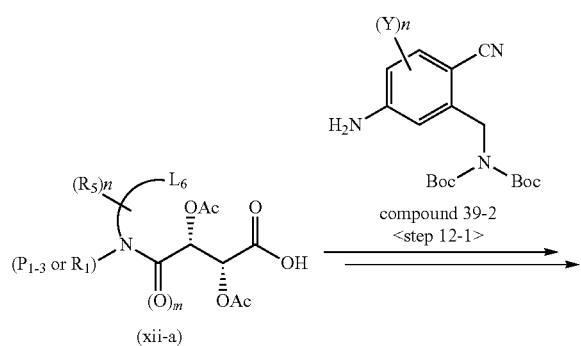

(Reaction scheme 10)

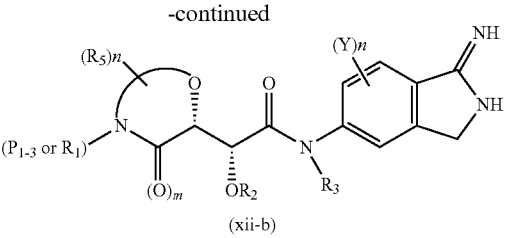

(xii-b)

Step 12-1

When R4 represents 1-imino-2,3-dihydroisoindol-5-yl group, or its heteroaryl analogue wherein M represents nitrogen atom, are optionally substituted with one to four Y, which is shown as a partial structure of a compound represented by formula (xii-b) in Scheme 10 or its analogue, a compound represented by formula (xii-b) can be produced from a compound represented by formula (xii-a) which is identical to the compound represented by formula (ix-d) in the Scheme 5, wherein its R is hydrogen atom, and from a compound 39-2 (N-[(5-Amino-2-cyanophenyl)-methyl]-N-[(2-methylpropan-2-yl)oxycarbonyl]carbamate) which is described in Experimental section 39. A compound represented by formula (ix-d) is converted to its analogous compound of 39-3 in the Example 39 procedure similar to that used in <Step 5-1> of (Reaction Scheme 2), which is followed by the conversion to compounds analogous to compounds 39-4, 39-5 and 39-6 by a process similar to that used in <Step 10-1> of (Reaction Scheme 5), <Step 10-2> of (Reaction Scheme 6) and deprotection of Boc group by a process similar to that used in the Experimental section Example 38-6 or by techniques which are well-known or described here (see Greene, T. W., et. al., *Protective Groups in Organic Synthesis* (2007), 4th Ed., Wiley, New York, or Kocienski, P., *Protecting Groups* (1994), Thieme). A compound represented by formula (xii-b) can be produced with resulting amine compound analogous to the compound 39-6 by a process similar to that described in the Experimental section 39 [ step 39-7] using alcoholic solvent, other solvent or a mixed solvent thereof at a temperature in the range of room temperature to the solvent-reflux temperature.

Scheme 11
Alternative synthetic route of optically active compounds (xiii-f) subset of compounds (x-e)

(Reaction Scheme 11)

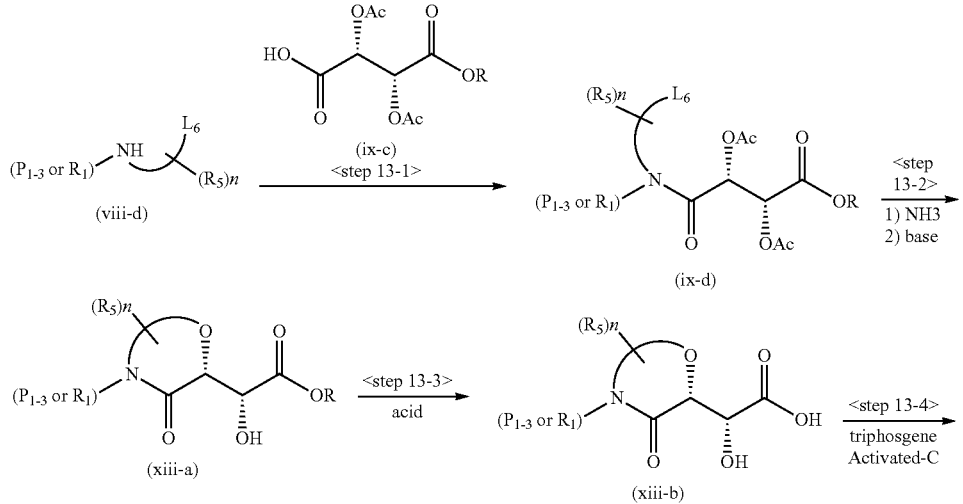

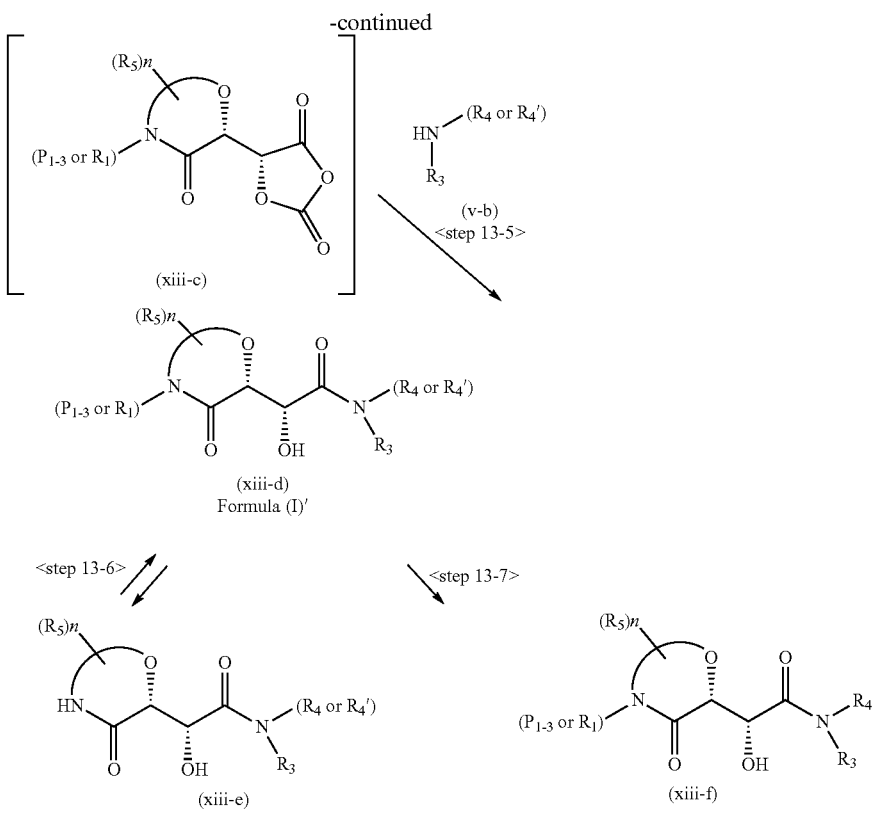

Step 13-1

A compound represented by formula (ix-d) can be produced by the similar process as that used in <Step 5-1> of (Reaction Scheme 2) using compounds represented by formula (viii-d) and represented by formula (ix-c). When R represents tert-butyl group, a compound represented by formula (ix-c) could be prepared by a similar process that described in published document, for example, *Tetrahedron*, 45, 3071-3080, 1989.

Step 13-2

A compound represented by formula (xiii-a) can be produced by the similar process as that used in <Step 10-1> of (Reaction Scheme 5) using a compound represented by formula (ix-d), and followed by the similar process as that used in <step 10-2> of (Reaction Scheme 6) using the resulting alcoholic compound from a compound represented by formula (ix-d).

Step 13-3

A compound represented by formula (xiii-b) can be produced from a compound represented by formula (xiii-a) by a well-known or similar process that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of inorganic or organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid using water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

Step 13-4 and Step 13-5

A compound represented by formula (xiii-d) can be produced by the similar process as that used in <Step 5-1> of (Reaction Scheme 2) using a compound represented by formula (xiii-b) via its intermediate represented by formula (xiii-c), with a compound represented by formula (v-b).

Step 13-6

Protective groups of a compound represented by formula (xiii-d) can be introduced and removed between (xiii-d) and (xiii-e) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 13-7

A compound represented by formula (xiii-f), which is identical to the compound represented by formula (x-e) in Scheme 6 wherein m is 1 and R is hydrogen atom, can be produced by a similar process as that used in <Step 10-4> of (Reaction Scheme 6) using a compound represented by formula (xiii-d).

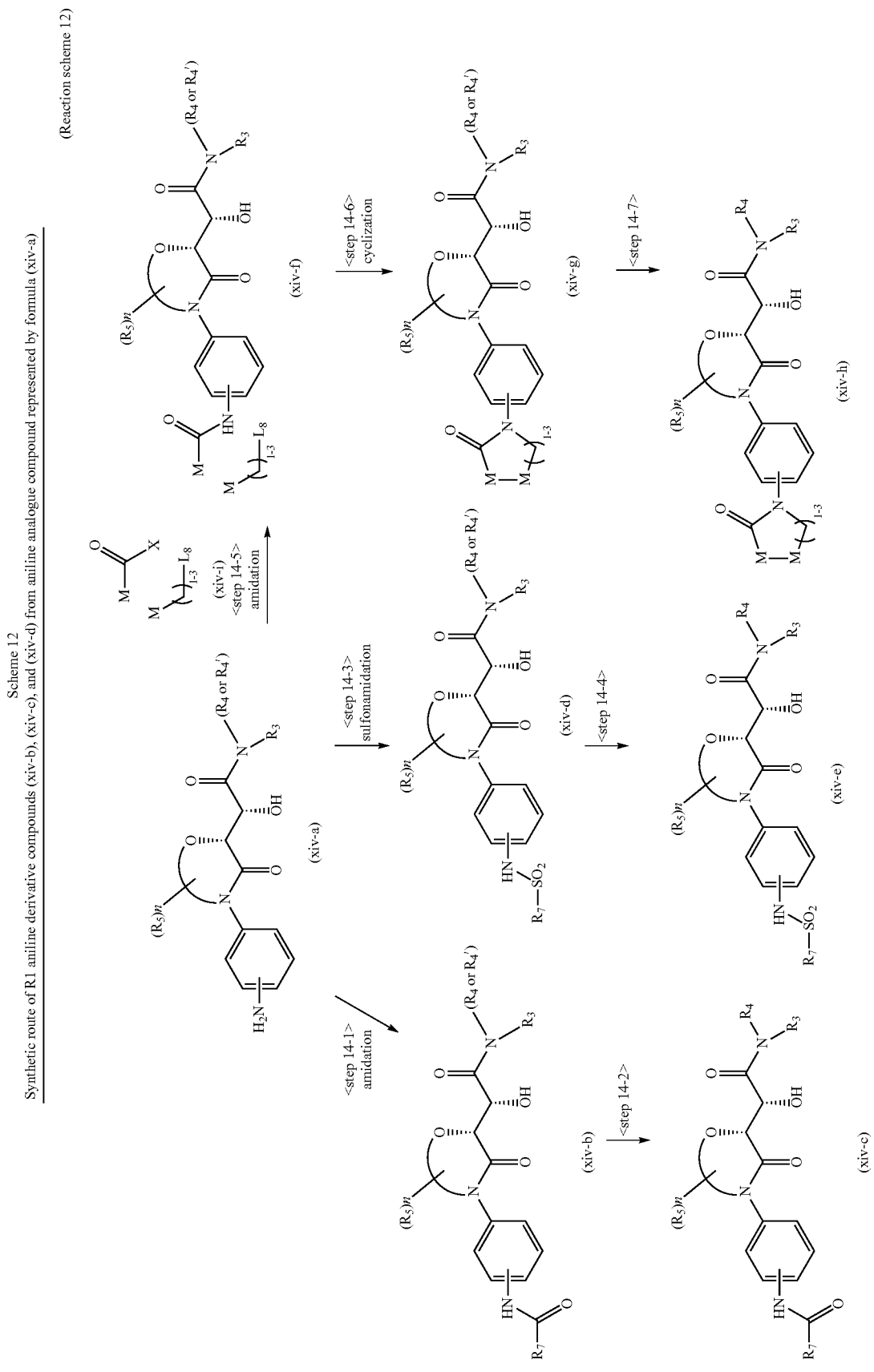

Step 14-1

A compound represented by formula (xiv-b) can be produced by the similar process as that used in <Step 5-1> of (Reaction Scheme 2) using a compound represented by formula (xiv-a).

Step 14-2

A compound represented by formula (xiv-c) can be produced by the similar process as that used in <Step 10-4> of (Reaction Scheme 6) using a compound represented by formula (xiv-b).

Step 14-3

A compound represented by formula (xiv-d) can be produced by the similar process as that used in <Step 5-1> of (Reaction Scheme 2) using a compound represented by formula (xiv-a) and corresponding sulfonyl halide such as sulfonyl chloride reagent.

Step 14-4

A compound represented by formula (xiv-e) can be produced by the similar process as that used in <Step 10-4> of (Reaction Scheme 6) using a compound represented by formula (xiv-d).

Step 14-5

A compound represented by formula (xiv-f) wherein each M represents independently oxygen atom, nitrogen atom or carbon atom, can be produced with step by step cyclization process as that used in <Step 5-1> of (Reaction Scheme 2) using a compound represented by formula (xiv-a) and a compound represented by formula (xiv-i) denoting acid halide or acid reagent wherein X represents halogen or hydroxyl group, such as 2-chloroethoxy acetic acid.

Step 14-6

The resulting compound represented by formula (xiv-f) can be cyclized to produce a compound represented by formula (xiv-g) by the same process as that used in <Step 10-2> of (Reaction Scheme 6).

Step 14-7

A compound represented by formula (xiv-g) can be produced by the similar process as that used in <Step 10-4> of (Reaction Scheme 6) using a compound represented by formula (xiv-f).

Scheme 13
Alternative synthetic route of optically active compounds represented by a formula (xv-f) which is a subset of compounds represented by a formula (x-e) via key intermediate compound represented by formula (xv-b).

(Reaction scheme 13)

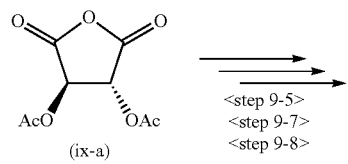

(ix-a)

<step 9-5>
<step 9-7>
<step 9-8>

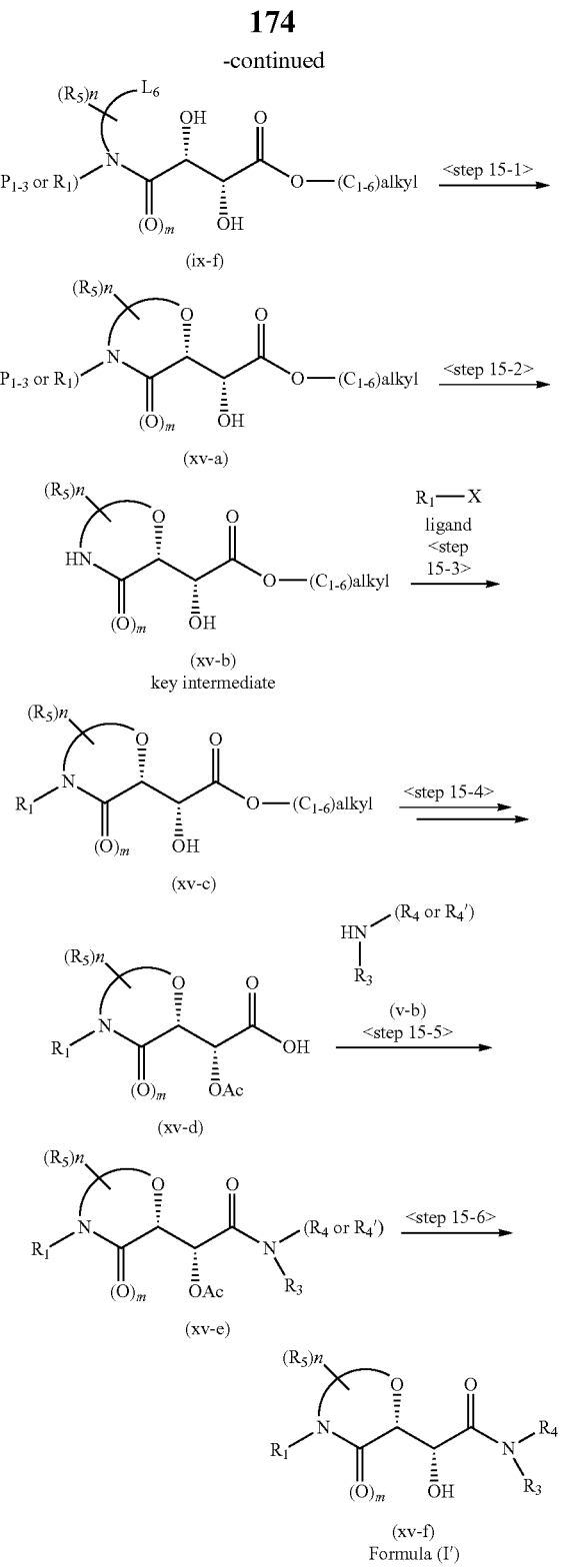

Step 15-1

A compound represented by formula (xv-a) can be produced by the similar process as that used in <Step 10-2> of (Reaction Scheme 6) using a compound represented by formula (ix-f) in the Scheme 5.

Step 15-2

A compound represented by formula (xv-b), a key intermediate to produce compounds represented by formula (xv-f) which corresponds to the compounds represented by Formula (I), can be produced by deprotection of the compound represented by formula (xv-a) using CAN (ceric ammonium nitrate) using a solvent which is inactive to the reaction, such as a polar solvent, e.g., DMF, DMSO, ethyl acetate, water, or acetonitril, or an ethereal solvent, e.g., diethyl ether, tetrahydrofuran, 1,2-dimethoxyethane, 1,4-dioxane, or a mixed solvent thereof at a temperature in the range of 0° C. to the solvent-reflux temperature, or by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step 15-3

A compound represented by formula (xv-c) can be produced by allowing a key intermediate compound represented by formula (xv-b) to react with a compound represented by R1-X (aryl halide or heteroaryl halide, wherein X represents halogen atom) by a process known as Goldberg reaction which are similar to that described in published documents, for example, *JACS*, 2002, 124, 7421 in the presence of a base such as potassium phosphate, cesium carbonate, potassium tert-buthoxide, sodium hydride, lithium hydroxide, sodium hydroxide, potassium hydroxide, lithium carbonate, sodium carbonate, or potassium carbonate in the presence of 1,2-diamine ligand such as trans-1,2-cyclohexanediamine, trans-N,N'-dimethylcyclohexane-1,2-diamine, or ethylene diamine, and in the presence of catalytic amount of cupper iodide using a solvent which is inactive to the reaction, such as an ethereal solvent, e.g., diethyl ether, tetrahydrofuran, 1,2-dimethoxyethane, 1,4-dioxane, polar solvents such as DMF, and DMSO; or an aromatic hydrocarbon solvent, e.g., toluene or benzene or a mixed solvent thereof at a temperature in the range of room temperature to the solvent-reflux temperature.

Step 15-4

A compound represented by formula (xv-c) can be produced by allowing a compound represented by formula (xv-b) to react with acetic anhydride by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd., and resulting acetylated alcohol compound can be hydrolyzed by the similar process as that used in <Step 4-2> of (Reaction Scheme 2).

Step 15-5

A compound represented by formula (xv-e) can be produced by the similar process as that used in <Step 5-1> of (Reaction Scheme 2) using a compound represented by formula (xv-d) in the Scheme 13 and a compound represented by formula (v-b).

Step 15-6

A compound represented by formula (xv-f) can be produced by a similar process as that used in <Step 10-4> of (Reaction Scheme 6) using a compound represented by formula (xv-e).

Scheme 14
Alternative synthetic route of compounds (xvi-h) identical to the compound represented Formula (I) wherein G represents nitrogen group.

(Reaction Scheme 14)

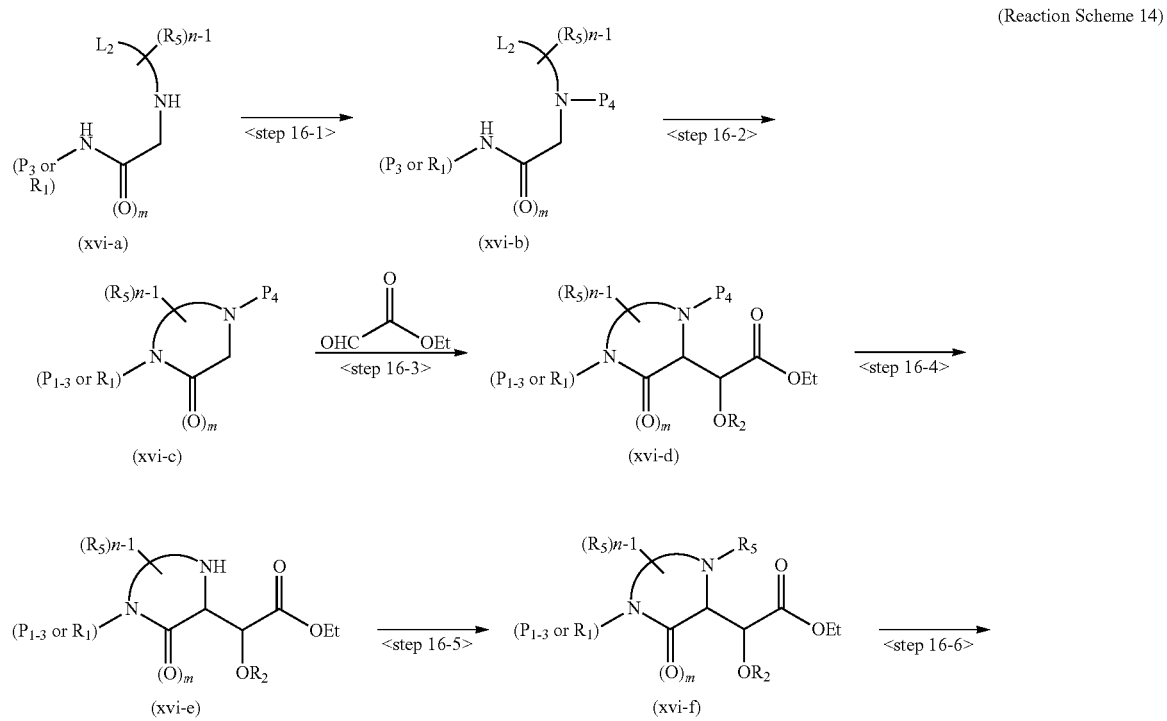

-continued

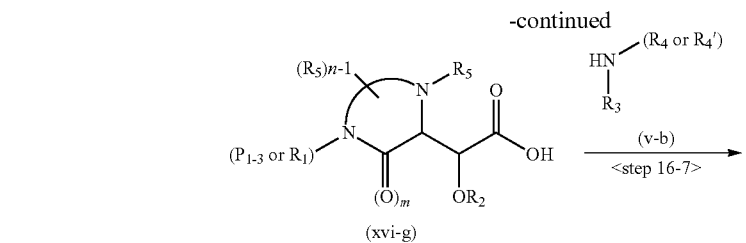

(xvi-g)

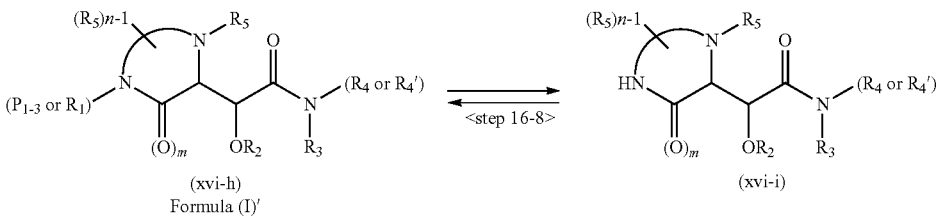

(xvi-h)
Formula (I)′

(xvi-i)

Step 16-1

A compound represented by formula (xvi-a) are commercially available, or capable of being readily synthesized by the method as identical to the route described in Scheme 1 to synthesize a compound represented by formula (II-b), or commonly used in the organic chemistry from commercially available products.

A compound represented by formula (xvi-b) can be produced by the similar process as that used in <Step 2-3> of (Reaction Scheme 1) using a compound represented by formula (xvi-a) in the Scheme 14.

Step 16-2

A compound represented by formula (xvi-c) can be produced by a similar process as that used in <Step 2-2> of (Reaction Scheme 1) using a compound represented by formula (xvi-b) in the Scheme 14.

Step 16-3

A compound represented by formula (xvi-d) can be produced by the similar process as that used in <Step 3-1> of (Reaction Scheme 2) using a compound represented by formula (xvi-c) in the Scheme 14.

Step 16-4

A compound represented by formula (xvi-e) can be produced by a similar process as that used in <Step 2-2> of (Reaction Scheme 1) using a compound represented by formula (xvi-d) in the Scheme 14.

Step 16-5

A compound represented by formula (xvi-f) can be produced by the similar process as that used in <Step 5-1> of (Reaction Scheme 2) using a compound represented by formula (xvi-e) in the Scheme 14 when R5 represents acyl group such as, for example, acetyl group or benzyl group.

Step 16-6

A compound represented by formula (xvi-g) can be produced by a similar process as that used in <Step 1-6> of (Reaction Scheme 1) using a compound represented by formula (xvi-f) in the Scheme 14.

Step 16-7

A compound represented by formula (xvi-h) can be produced by a similar process as that used in <Step 5-1> of (Reaction Scheme 2) using a compound represented by formula (xvi-g) in the Scheme 14.

Step 16-8

A compound represented by formula (xvi-i) can be produced by a similar process as that used in <Step 5-2> of (Reaction Scheme 2) using a compound represented by formula (xvi-h) in the Scheme 14.

Scheme 15
Alternative synthetic route of morpholine compounds.

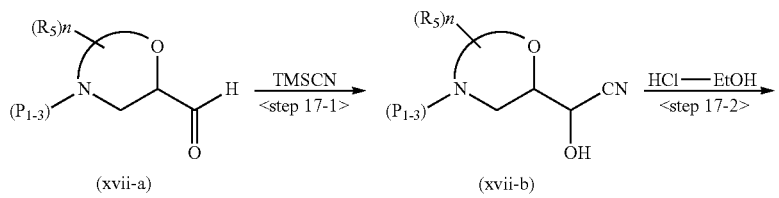

(xvii-a)    (xvii-b)

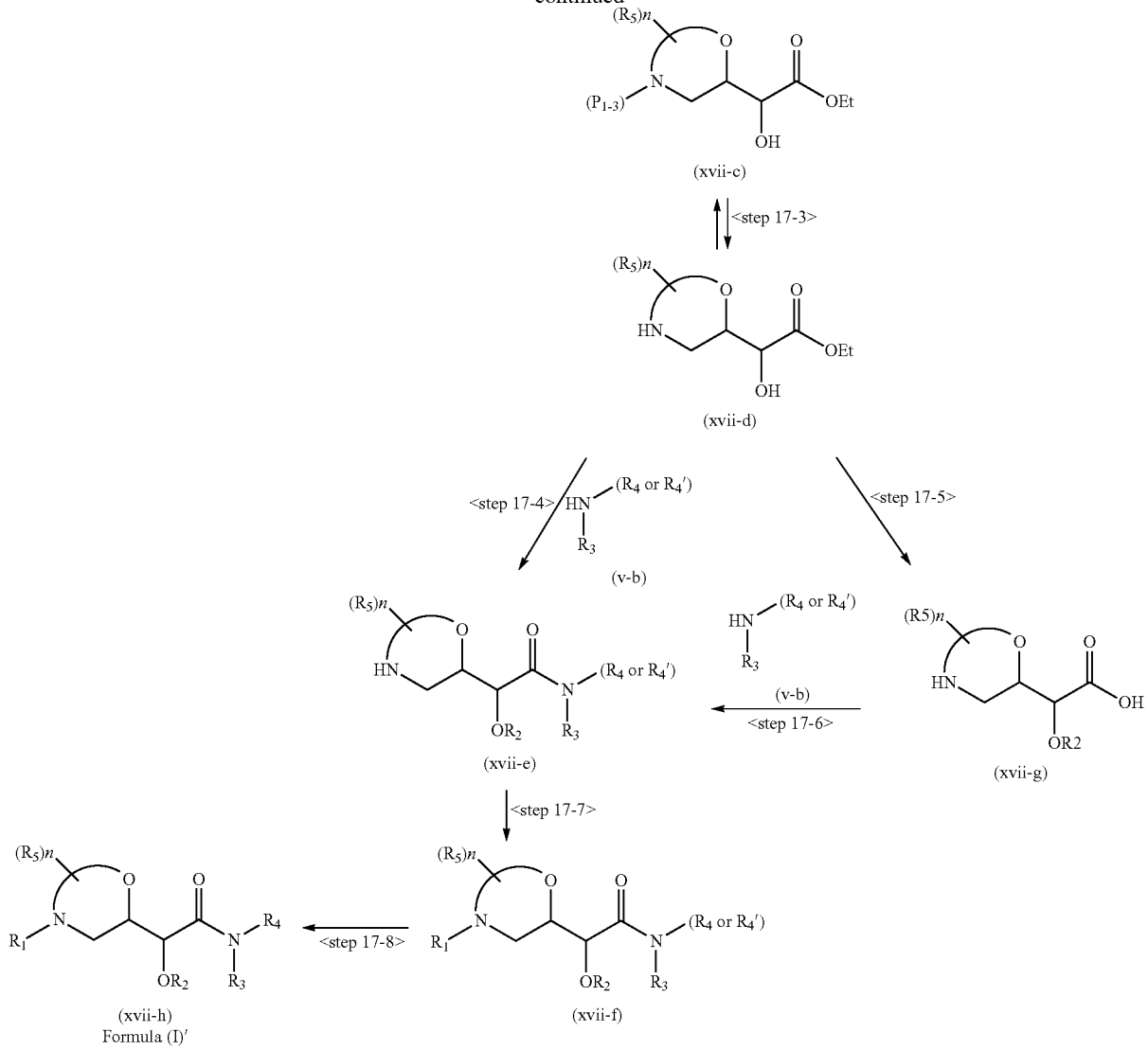

Step 17-1

A compound represented by formula (xvii-b) can be produced by allowing a compound represented by formula (xvii-a) to react with TMSCN(trimethylsilyl cyanide) by a process similar to that described in published documents, for example, Organic synthesis Collective Vol. 1, pp. 336 (1941), Collective Vol. 2, pp. 7 (1943), Collective Vol. 7, pp. 521 (1990) using a solvent which is inactive to the reaction, such as an alcoholic solvent, e.g., methanol, ethanol, 2-propanol, or a mixed solvent thereof at a temperature in the range of −78° C. to the solvent-reflux temperature. $P_{1-3}$ represents typically a benzyl group and deprotection of benzyl group can be reductive deprotection by a similar process of <step 8-1>.

Step 17-2

A compound represented by formula (xvii-c) can be produced by allowing a compound represented by formula (xvii-b) by a process similar to that described in published documents, for example, Organic synthesis Collective Vol. 1, pp. 270 (1941), Collective Vol. 2, pp. 310 (1943) in the presence of concentrated HCl using a solvent such as an alcoholic solvent containing hydrogen chloride, e.g., methanol-HCl, ethanol-HCl, or a mixed solvent thereof at a temperature in the range of 0° C. to the solvent-reflux temperature.

Step 17-3

Protective groups of a compound represented by formula (xvii-c) can be introduced and removed by techniques which are well-known or described here (see Greene, T. W., et. al., Protective Groups in Organic Synthesis (2007), 4th Ed., Wiley, New York, or Kocienski, P., Protecting Groups (1994), Thieme).

Step 17-4

A compound represented by formula (xvii-e) can be produced by the same process as that used in <Step 4-3> of (Reaction Scheme 2) using a compound represented by formula (xvii-c) and a compound represented by formula (v-b).

Step 17-5

A compound represented by formula (xvii-g) can be produced by a similar process as that used in <Step 1-6> of (Reaction Scheme 1) using a compound represented by formula (xvii-c) in the Scheme 15.

Step 17-6

A compound represented by formula (xvii-e) can be produced by the same process as that used in <Step 5-1> of (Reaction Scheme 2) using a compound represented by formula (xvii-g) and a compound represented by formula (v-b).

Step 17-7

A compound represented by formula (xvii-f) can be produced by the same process as that used in <step 14-1> or <step 14-3> of (Reaction Scheme 12), or <step 15-3> of (Reaction Scheme 13) using a compound represented by formula (xvii-f).

Step 17-8

A compound represented by formula (xvii-h) can be produced by a similar process as that used in <Step 10-4> of (Reaction Scheme 6) using a compound represented by formula (xvii-g).

(S,S), (R,S) and (S,R) forms of compounds represented by Formula (I) can also be made from corresponding starting materials. The required starting materials for the synthesis of (S,S), (R,S) and (S,R) isoforms of compound (ix-a) are either commercially available, or capable of being readily synthesized by the method commonly used in the organic chemistry from commercially available products.

Acidic or basic products of the compound of the Formula (I) can be present in the form of their salts or in free form. Pharmacologically acceptable salts are preferred, for example alkali metal or alkaline earth metal salts such as hydrochlorides, hydrobromides, sulfates, hemisulfates, all possible phosphates, and salts of the amino acids, natural bases or carboxylic acids.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

EXAMPLES

The present invention will now be described in more detail using examples, but the present invention is not limited to the examples.

The measurement of nuclear magnetic resonance (NMR) spectrum (Table 3) was performed using a JEOL JNM-ECX300 FT-NMR (manufactured by JEOL Ltd.) or a JEOL JNM-ECX400 FT-NMR (manufactured by JEOL Ltd.).

Liquid chromatography-mass spectrometry (LC-MS, Table 4) was performed using a Waters FractionLynx MS system (manufactured by Waters Corporation) from the Example 1 to Example 67. A SunFire Column™ (4.6 mm×5 cm, 5 microm) (manufactured by Waters Corporation) was used as an analytical column. A SunFire Column™ (19 mm×5 cm, 5 microm) (manufactured by Waters Corporation) was used as a preparative column. Acetonitrile and a 0.05% aqueous acetic acid solution or 0.05% aqueous trifluoroacetic acid solution were used as the mobile phase. Methanol and 0.05% aqueous acetic acid solution or 0.05% aqueous trifluoroacetic acid solution were also used as the mobile phase. The analysis was performed under the following gradient conditions: acetonitrile: 0.05% aqueous acetic acid solution or 0.05% aqueous trifluoroacetic acid solution=1:9 (0 minutes), 9:1 (5 minutes), and 9:1 (7 minutes). Methanol: 0.05% aqueous acetic acid solution or 0.05% aqueous trifluoroacetic acid solution=1:9 (0 minutes), 10:0 (5 minutes), and 10:0 (7 minutes). The solvent systems are described as the followings: A indicates MeCN—AcOH, B indicates MeCN-TFA, C indicates MeOH—AcOH, and D indicates MeOH-TFA.

Method E:
Electro Spray Ionization Liquid Chromatography-Mass Spectrometry (ESI-LC/MS)
Column: Phenomenex Gemini C18, 50×4.6 mm, 5 micron
Mobile Phase:
   A: 0.05% Trifluoroacetic acid in water
   B: 0.05% Trifluoroacetic acid in acetonitrile
Gradient: 90% A and 10% B to 5% A and 95% B over 5 minutes
Flow rate: 1.0 ml/min
UV detection: 254 nM
Spectrometer: PE SCIEX API-150EX, single quadrupole mass spectrometer
Method F:
Column: Zorbax SB-C-18; 1.8 micron
Mobile Phase:
   A: 0.1% Trifluoroacetic acid in water
   B: 0.1% Trifluoroacetic acid in acetonitrile
Gradient:
   0 min=10% B
   1.3 min=55% B
   2.7 min=95% B
   2.8 min=10% B
Flow rate: 1.0 ml/min
UV detection: 254 nM
Spectrometer: Agilent 6140 Quadrapole LC-MS, single quadrupole mass spectrometer
Solvent G: Column: Agilent SBC (3.0×50 mm, 1.8 u); Flow: 1.0 ml/min; solvent A: H2O-0.1% TFA: Solvent B: ACN-0.1% TFA; Gradient Table: 0.1 min: 5% B, 2.3 min: 99% B, 2.90 min: 99% B, 3.0 min: 5% B stop time 3.50 min.
Solvent H: Column: Agilent SBC (3.0×50 mm, 1.8 u); Flow: 1.0 ml/min; solvent A: H2O-0.1% TFA: Solvent B: ACN-0.1% TFA; Gradient Table: 0 min: 10% B, 1.5 min: 95% B, 2.76 min: 10% B, stop time 3.60 min, Post Time 0.70 min.
I: Instrument: Agilent Technologies 6140; Column: Agilent SBC (3.0×50 mm, 1.8 u); Flow: 1.0 ml/min; solvent A: H2O-0.1% TFA: Solvent B: ACN-0.1% TFA; Gradient Table: 0.1 min: 5% B, 2.3 min: 99% B, 2.90 min: 99% B, 3.0 min: 5% B stop time 3.50 min.
J: Agilent Technologies 6140; Column: Agilent SBC (3.0×50 mm, 1.8 u); Flow: 1.0 ml/min; solvent A: H2O-0.1% TFA:

Solvent B: ACN-0.1% TFA; Gradient Table: 0 min: 10% B, 1.5 min: 95% B, 2.76 min: 10% B, stop time 3.60 min, Post Time 0.70 min.
K: Instrument: PE-Sciex API 150 EX; Column. Alltech Platinum C18, 33×7 mm, 3 micron; Solvent A: Water w/0.05% TFA; Solvent B: Acetonitrile w/0.05% TFA; Flow rate: 1 mL/min; Gradient: 0 min: 10% B, 5 min: 95% B, 7 min: 95% B, 7.5 min: 10, 9 min: stop.
Method A for EX118 to EX131
Electro Spray Ionization Liquid Chromatography-Mass Spectrometry (ESI-LC/MS)
Column: Phenomenex Gemini C18, 50×4.6 mm, 5 micron
Mobile Phase:
  A: 0.05% Trifluoroacetic acid in water
  B: 0.05% Trifluoroacetic acid in acetonitrile
Gradient: 90% A and 10% B to 5% A and 95% B over 5 minutes
Flow rate: 1.0 ml/min
UV detection: 254 nM
Spectrometer: PE SCIEX API-150EX, single quadrupole mass spectrometer Method B for EX118 to EX131
Column: Zorbax SB-C-18; 1.8 micron
Mobile Phase:
  A: 0.1% Trifluoroacetic acid in water
  B: 0.1% Trifluoroacetic acid in acetonitrile
Gradient:
  0 min=10% B
  1.3 min=55% B
  2.7 min=95% B
  2.8 min=10% B
Flow rate: 1.0 ml/min
UV detection: 254 nM
Spectrometer: Agilent 6140 Quadrapole LC-MS, single quadrupole mass spectrometer
Solvent A for Ex 139-141
Column: Agilent SBC (3.0×50 mm, 1.8 u); Flow: 1.0 ml/min; solvent A: H2O-0.1%
TFA: Solvent B: ACN-0.1% TFA; Gradient Table: 0.1 min: 5% B, 2.3 min: 99% B, 2.90 min: 99% B, 3.0 min: 5% B stop time 3.50 min.

Deuterated starting materials are capable of being used in certain Examples.

Example 1

Synthesis of N-(1-aminoisoquinolin-6-yl)-2-hydroxy-2-(3-oxo-4-p-tolylmorpholin-2-yl)acetamide trifluoroacetate

Step 1-1

Synthesis of ethyl 2-hydroxy-2-(3-oxo-4-p-tolylmorpholin-2-yl)acetate (compound 1-1 (LP) and compound 1-1 (MP))

To a solution of 4-(4-Methylphenyl)-3-morpholinone (Zhurnal Organicheskoi Khimii, 6(6), 1305-8, 1970) (1.08 g) in THF (21.6 ml), was added 1 M lithium hexamethyldisilazide solution (7.34 ml) in THF at −78° C. The mixture was stirred at −78° C. for 15 minutes then 0° C. for 1 hour. Then the reaction mixture was cooled down at −78° C. and ethyl glyoxylate solution (1.84 ml) in toluene was added into the reaction mixture. The reaction mixture was stirred at 0° C. overnight. At the end of the reaction, saturated NH4Cl aqueous solution was added into the reaction mixture. The mixture was concentrated in vacuo and the resulting mixture was extracted with AcOEt. The organic layer was washed with brine and dried with anhydrous Na2SO4. The solvent was removed under reduced pressure and the resulting residue was purified by silica gel flash column chromatography (eluent: n-Hex/AcOEt=50/50-0/100) to obtain two diastereomers, compound 1-1 (LP) (405 mg; Rf value=0.36 on TLC (n-Hex/AcOEt=1/2)) as a pale yellow amorphous solid and 1-1 (MP) (287 mg; Rf value=0.27 on TLC (n-Hex/AcOEt=1/2)) as yellow oil. LP indicates a less polar spot on TLC, MP indicates a more polar spot on TLC.

Step 1-2

Synthesis of 2-hydroxy-2-(3-oxo-4-p-tolylmorpholin-2-yl)acetic acid (compound 1-2)

To a solution of compound 1-1 (LP) (100 mg) in EtOH (1 mL), was added 1 N NaOH aqueous solution (1 mL) at 0° C. The reaction mixture was stirred at room temperature for 1 hour. Then DowEx®-50Wx8-200 was added into the reaction mixture, then the mixture was filtered to remove DowEx®-50Wx8-200. The filtrate was concentrated in vacuo to obtain compound 1-2 (90 mg) as a colorless amorphous solid. Compound 1-2 was used in the next step without further purification.

Step 1-3

Synthesis of N—[N,N-bis(tert-butoxylcarbonyl)-1-aminoisoquinolin-6-yl]-2-hydroxy-2-(3-oxo-4-p-tolylmorpholin-2-yl)acetamide (compound 1-3)

To a solution of compound 1-2 (90 mg) in THF (2 ml), were added activated-charcoal (4.5 mg) and triphosgene (403 mg) at 0° C. The reaction mixture was stirred at room temperature for 15 hours. Then activated-charcoal was removed by filtration and the filtrate was concentrated in vacuo. The resulting residue was resolved in $CH_2Cl_2$ (2 ml). 6-Amino-1-bis(tert-butoxyl carbonyl)aminoisoquinoline (146 mg) was added into the $CH_2Cl_2$ solution at 0° C. The reaction mixture was stirred at room temperature for 4 hours. The reaction mixture was concentrated in vacuo and a half volume of the resulting residue was purified by LC/MS to obtain compound 1-3 (30.6 mg) as a colorless amorphous solid.

Step 1-4

Synthesis of N-(1-aminoisoquinolin-6-yl)-2-hydroxy-2-(3-oxo-4-p-tolylmorpholin-2-yl)acetamide trifluoroacetate (EXAMPLE 1)

To a solution of compound 1-3 (30.6 mg) in $CH_2Cl_2$ (1.5 ml), was added trifluoroacetic acid (0.5 ml) at 0° C. The reaction mixture was stirred at room temperature for 1 hour and the mixture was concentrated in vacuo. To the resulting residue, $Et_2O$ was added and the residue was triturated. Then the precipitate was collected by filtration to obtain EXAMPLE 1 (19.3 mg) as a colorless amorphous solid.

Example 2

Synthesis of N-(4-amidinophenyl)-2-hydroxy-2-(3-oxo-4-p-tolylmorpholin-2-yl)acetamide trifluoroacetate Step 2-1

Synthesis of N-(4-cyanophenyl)-2-hydroxy-2-(3-oxo-4-p-tolylmorpholin-2-yl)acetamide (compound 2-1)

According to the Step 1-3 in synthetic method for Example 1, 4-aminobenzonitrile (17.8 mg) was used instead of 6-amino-1-bis(tert-butyl carbonyl)aminoisoquinoline to obtain compound 2-1 (24 mg) as a colorless amorphous solid.

Step 2-2

Synthesis of N-(4-amidinophenyl)-2-hydroxy-2-(3-oxo-4-p-tolylmorpholin-2-yl)acetamide trifluoroacetate (EXAMPLE 2)

HCl gas was bubbled into a solution of compound 2-1 (15 mg) in MeOH—$CH_2Cl_2$ (10-6 ml) at 0° C. for 30 minutes. The reaction mixture was stirred at 0° C. overnight to form the methyl imidate. Then the mixture was concentrated in vacuo and the resulting residue was solved in MeOH (8 mL). Ammonium carbonate (39 mg) was added into the above MeOH solution at 0° C. The reaction mixture was stirred at room temperature for 24 hours. Then 8N $NH_3$-MeOH (2 ml) was added into the reaction mixture and the mixture was stirred at 60° C. for 6 hours until the methyl imidate intermediate disappeared. The reaction mixture was concentrated in vacuo and the resulting residue was purified by LC/MS to obtain EXAMPLE 2 (14.5 mg) as a colorless amorphous solid.

Example 3 to Example 6

The following compounds were synthesized from compound 1-2 in a similar manner to compound 1-3 using an appropriate amine instead of 6-amino-1-bis(tert-butoxycarbonyl)aminoisoquinoline, and using DMF instead of $CH_2Cl_2$.

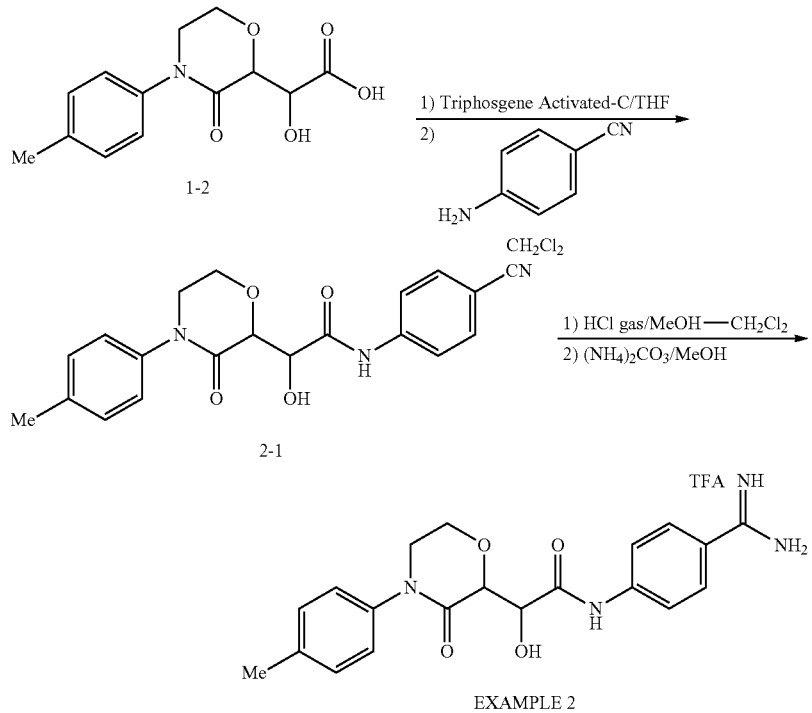

EXAMPLE 2

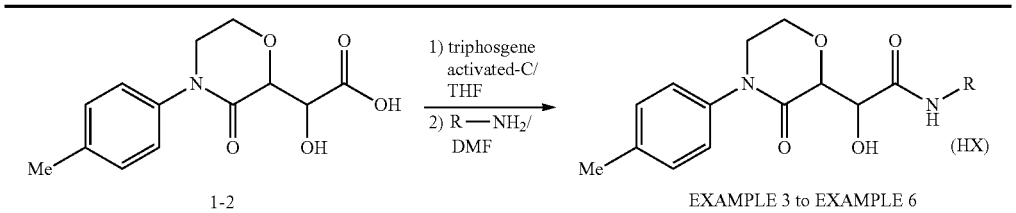

| EXAMPLE | STRUCTURE | NAME |
|---|---|---|
| 3 | 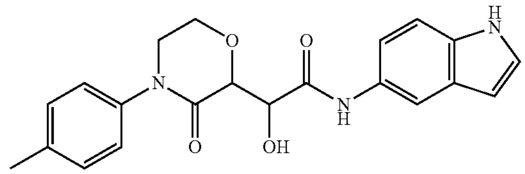 [SMILES: Cc1ccc(N2CCOC(C(O)C(=O)Nc3ccc4[nH]ccc4c3)C2=O)cc1] | 2-Hydroxy-N-(1H-indol-5-yl)-2-(3-oxo-4-p-tolylmorpholin-2-yl)acetamide |
| 4 | 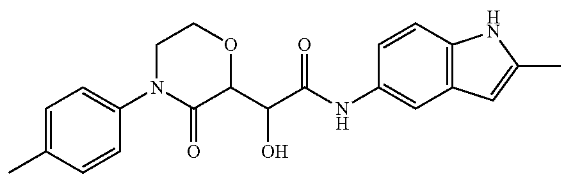 | 2-Hydroxy-N-(2-methyl-1H-indol-5-yl)-2-(3-oxo-4-p-tolylmorpholin-2-yl)acetamide |
| 5 | TFA | N-[4-(Aminomethyl)phenyl]-2-hydroxy-2-(3-oxo-4-p-tolylmorpholin-2-yl)acetamide trifluoroacetate |
| 6 | TFA | N-(2-Amino-3H-benzimidazol-5-yl)-2-hydroxy-2-(3-oxo-4-p-tolylmorpholin-2-yl)acetamide trifluoroacetate |

Example 7

Synthesis of (2R)—N-(4-amidinophenyl)-2-hydroxy-2-[(2R)-3-oxo-4-p-tolylmorpholin-2-yl]acetamide hydrochloride (EXAMPLE 7)

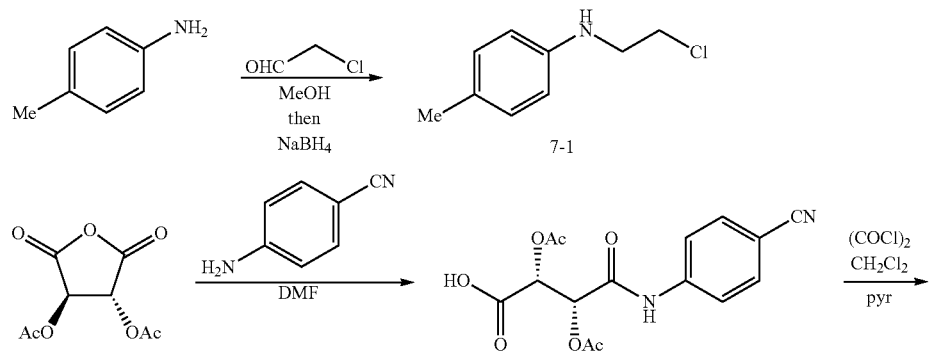

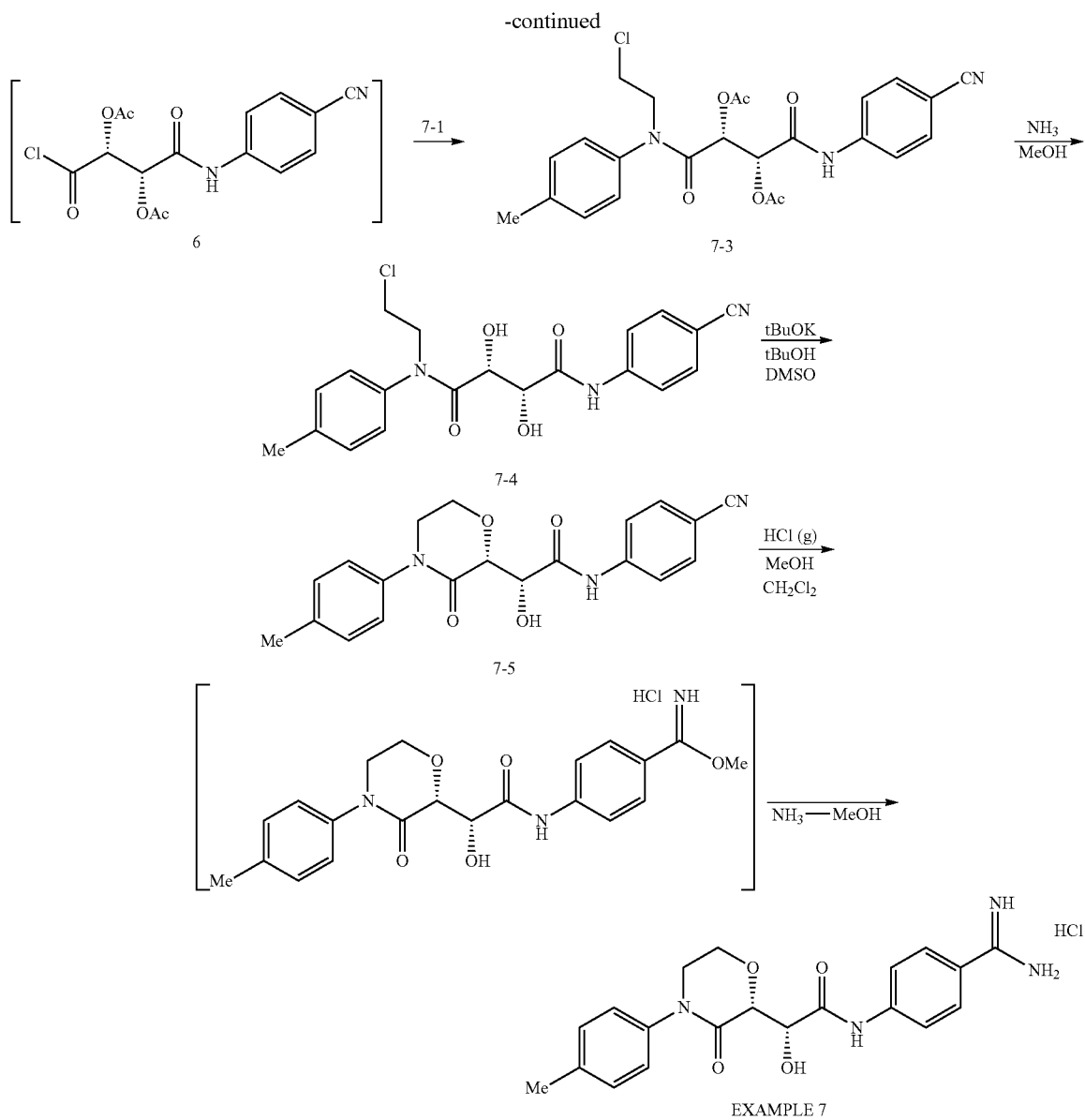

EXAMPLE 7

Step 7-1

Synthesis of N-(2-chloroethyl)-4-methylaniline (compound 7-1)

To a solution of 4-methylaniline (100 mg) in MeOH (2.0 mL) was added 40% chroloacetaldehyde solution in water (0.17 mL) at 0° C. The mixture was stirred for 45 minutes at the same temperature, sodium borohydride (NaBH$_4$; 70.6 mg) was added into the reaction mixture at one portion and the mixture was stirred for 1 hour.

The reaction mixture was diluted with water and was extracted with EtOAc. The extract was washed with water, sat.NaHCO$_3$ and brine. The organic layer was dried with anhyd. Na$_2$SO$_4$. It was filtrated to remove insoluble matters and it was concentrated in vacuo. The residue was purified by silica gel flush chromatography (eluent:Hexane:EtOAc=95: 5~75:25) to obtain 7-1 (27 mg) as brown oil.

Step 7-2

Synthesis of (2R,3R)-2,3-diacetyloxy-4-(4-cyanoanilino)-4-oxobutanoic acid (compound 7-2)

To a solution of (+)-Diacetyl-L-tartaric anhydride (9.15 g) in dry DMF (100 mL), was added 4-aminobenzonitrile (5 g,) under ice cooling and the reaction mixture was stirred to obtain compound 7-2 at room temperature overnight. The solution of compound 7-2 was used in the next step without any treatment.

Step 7-3

Synthesis of [(2R,3R)-3-acetyloxy-1-[N-(2-chloroethyl)-4-methylanilino]-4-(4-cyanoanilino)-1,4-dioxobutan-2-yl]acetate (compound 7-3)

The above DMF solution of 7-2 (13.8 mL) was diluted with CH$_2$Cl$_2$ (13.8 mL). The internal temperature of the mixture was kept below −60° C. over all additions with dry ice bath.

Oxalyl chloride (0.55 mL) in CH$_2$Cl$_2$ (1.7 mL) was added dropwise into the reaction mixture. After stirring for 1 hour, pyridine (1.99 mL) was added dropwise thereto and stirred for 15 min. Then 7-1 (0.99 g) in CH$_2$Cl$_2$ (6 mL) was added dropwise into the reaction mixture. The mixture was stirred below −60° C. for 20 min, then it was stirred at −30° C. for 15 hours.

The reaction mixture was quenched with water and was extracted with EtOAc. The extract was washed with water, 1N HCl, sat.NaHCO$_3$ and brine. The organic layer was dried with anhyd. Na$_2$SO$_4$. It was filtrated and was concentrated in vacuo. The residue was purified by silica gel flush chromatography (eluent:Hexane:EtOAc=75:25~25:75) to obtain 7-3 (1.70 g) as a light brown solid.

Step 7-4

Synthesis of (2R,3R)—N-(2-chloroethyl)-N'-(4-cyanophenyl)-2,3-dihydroxy-N-p-tolylbutanediamide (compound 7-4)

To a solution of 7-3 (0.20 g) in MeOH (4 mL), was added 8N NH$_3$/MeOH (0.26 mL) at 0° C. and the mixture was stirred for 10 minutes in the same temperature. The mixture was concentrated and was dried in vacuo to obtain crude 7-4. The crude 7-4 was used in the next step without further purification.

Step 7-5

Synthesis of (2R)—N-(4-cyanophenyl)-2-hydroxy-2-[(2R)-3-oxo-4-p-tolylmorpholin-2-yl]acetamide (compound 7-5)

The crude 7-4 was dissolved in t-BuOH (12 mL)-DMSO (8 mL), and t-BuOK (554 mg) was added portionwise into the reaction mixture at 0° C. The mixture was stirred for 10 minutes in the same temperature.

To the reaction mixture was added 1N HCl and Et$_2$O to obtain precipitate. Then the precipitate was collected by filtration, was rinsed with water, was washed with Et$_2$O and was dried in vacuo to obtain 7-5 (603 mg) as a white solid.

Step 7-6

Synthesis of (2R)—N-(4-amidinophenyl)-2-hydroxy-2-[(2R)-3-oxo-4-p-tolylmorpholin-2-yl]acetamide hydrochloride (EXAMPLE 7)

Compound 7-5 (27 mg) was suspended in MeOH (15 mL)-CH$_2$Cl$_2$ (7 mL). The suspension was saturated with HCl gas by bubbling at 0° C. for 0.5 hours. Then the mixture was stood to form the imidate at the same temperature overnight. The reaction mixture was concentrated and was dried in vacuo to obtain crude imidate. The crude imidate was dissolved in MeOH (10 mL), then 8N NH$_3$-MeOH (2 mL) was added into the above MeOH solution. The reaction mixture was stirred in sealed tube at 80° C. for 3 hours to convert EXAMPLE 7. The reaction mixture was stirred for 1 day at room temperature then it was concentrated in vacuo. The resulting residue was dissolved in 1N HCl-MeOH, then the mixture was purified by preparative LC/MS to obtain EXAMPLE 7 (7 mg) as a colorless amorphous solid.

Example 8

Synthesis of (2R)—N-(4-amidinophenyl)-2-[(2R)-4-(2,4-dimethylphenyl)-3-oxomorpholin-2-yl]-2-hydroxyacetamide hydrochloride (EXAMPLE 8)

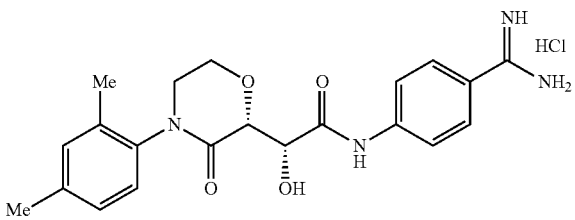

EXAMPLE 8

Step 8-1

Synthesis of N-(2-chloroethyl)-2,4-dimethylaniline (compound 8-1)

According to the Step 7-1 in synthetic method for EXAMPLE 7, 2,4-dimethylaniline (7 g) was used instead of 4-methylaniline to obtain compound 8-1 (2.8 g) as pale brown oil.

Step 8-2

Synthesis of [(2R,3R)-3-acetyloxy-1-[N-(2-chloroethyl)-2,4-dimethylanilino]-4-(4-cyanoanilino)-1,4-dioxobutan-2-yl]acetate (compound 8-2)

According to the Step 7-3 in synthetic method for EXAMPLE 7, compound 8-1 (1.65 g) was used instead of compound 7-1 to obtain compound 8-2 (480 mg) as a colorless amorphous solid.

Step 8-3

Synthesis of (2R,3R)—N-(2-chloroethyl)-N'-(4-cyanophenyl)-2,3-dihydroxy-N-(2,4-dimethylphenyl)-butanediamide (compound 8-3)

According to the Step 7-4 in synthetic method for EXAMPLE 7, compound 8-2 (0.15 g) was used instead of compound 7-3 to obtain crude 8-3. The crude 8-3 was used in the next step without further purification.

Step 8-4

Synthesis of (2R)—N-(4-cyanophenyl)-2-[(2R)-4-(2,4-dimethylphenyl)-3-oxomorpholin-2-yl]-2-hydroxyacetamide (compound 8-4)

According to the Step 7-5 in synthetic method for EXAMPLE 7, crude 8-3 was used instead of compound 7-4 to obtain compound 8-4 (70 mg) as a colorless amorphous solid.

Step 8-5

Synthesis of (2R)—N-(4-amidinophenyl)-2-[(2R)-4-(2,4-dimethylphenyl)-3-oxomorpholin-2-yl]-2-hydroxyacetamide hydrochloride (EXAMPLE 8)

According to the Step 7-6 in synthetic method for EXAMPLE 7, compound 8-4 (50 mg) was used instead of compound 7-5 to obtain EXAMPLE 8 (11.7 mg) as a colorless amorphous solid.

Example 9

Synthesis of (2R)—N-(4-amidinophenyl)-2-hydroxy-2-[(2R)-4-[3-[(2-hydroxyacetyl)amino]-4-methylphenyl]-3-oxomorpholin-2-yl]acetamide hydrochloride (EXAMPLE 9)

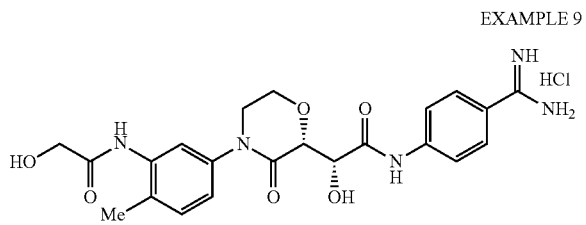 [SMILES: Cc1ccc(N2CCO[C@H]([C@@H](O)C(=O)Nc3ccc(C(=N)N)cc3)C2=O)cc1NC(=O)CO ; Cl]

EXAMPLE 9

Step 9-1

Synthesis of N-(2-chloroethyl)-4-methyl-3-nitroaniline (compound 9-1)

According to the Step 7-1 in synthetic method for EXAMPLE 7, 4-methyl-3-nitroaniline (7 g) was used instead of 4-methylaniline to obtain compound 9-1 (1.63 g) as pale yellow oil.

Step 9-2

Synthesis of [(2R,3R)-3-acetyloxy-1-[N-(2-chloroethyl)-4-methyl-3-nitroanilino]-4-(4-cyanoanilino)-1,4-dioxobutan-2-yl]acetate (compound 9-2)

According to the Step 7-3 in synthetic method for EXAMPLE 7, compound 9-1 (1.61 g) was used instead of compound 7-1 to obtain compound 9-2 (2.88 g) as a colorless amorphous solid.

Step 9-3

Synthesis of (2R,3R)—N-(2-chloroethyl)-N'-(4-cyanophenyl)-2,3-dihydroxy-N-(4-methyl-3-nitrophenyl)butanediamide (compound 9-3)

According to the Step 7-4 in synthetic method for EXAMPLE 7, compound 9-2 (0.9 g) was used instead of compound 7-3 to obtain crude 9-3. The crude 9-3 was used in the next step without further purification.

Step 9-4

Synthesis of (2R)—N-(4-cyanophenyl)-2-hydroxy-2-[(2R)-4-(4-methyl-3-nitrophenyl)-3-oxomorpholin-2-yl]acetamide (compound 9-4)

According to the Step 7-5 in synthetic method for EXAMPLE 7, crude 9-3 was used instead of compound 7-4 to obtain compound 9-4 (70 mg) as a colorless amorphous solid.

Step 9-5

Synthesis of (2R)-2-[(2R)-4-(3-amino-4-methylphenyl)-3-oxomorpholin-2-yl]-N-(4-cyanophenyl)-2-hydroxyacetamide (compound 9-5)

To a solution of compound 9-4 (70 mg) in AcOH—H$_2$O (2 mL-0.1 mL), was added electrolytic iron powder (95.3 mg). The reaction mixture was stirred at room temperature for 1 hour then at 40° C. for 2 hours to complete the reaction. The reaction mixture was filtered with Celite® pad to remove iron powder. The filtrate was concentrated in vacuo. The resulting residue was purified by amino-silica gel flash column chromatography (eluent: CH$_2$Cl$_2$/MeOH=98/2-95/5) to obtain compound 9-5 (30 mg) as a colorless amorphous solid.

Step 9-6

Synthesis of [2-[5-[(2R)-2-[(1R)-2-(4-cyanoanilino)-1-hydroxy-2-oxoethyl]-3-oxomorpholin-4-yl]-2-methylanilino]-2-oxoethyl]acetate (compound 9-6)

To a solution of compound 9-5 (16.5 mg) in CH$_2$Cl$_2$ (1 mL), were added triethylamine (6.7 microL) and acetoxyacetyl chloride (5.1 microL) at 0° C. The reaction mixture was stirred at room temperature for 30 minutes. Then EtOAc and water were added into the mixture and it was extracted with EtOAc. The organic layer was washed with H$_2$O, 1N HCl, sat. NaHCO$_3$ aq. and brine, respectively and dried with anhydr. Na$_2$SO$_4$. The solvent was removed under reduced pressure to obtain compound 9-6 (20 mg) as a pale yellow amorphous solid.

Step 9-7

Synthesis of (2R)—N-(4-amidinophenyl)-2-hydroxy-2-[(2R)-4-[3-[(2-hydroxyacetyl)amino]-4-methylphenyl]-3-oxomorpholin-2-yl]acetamide hydrochloride (EXAMPLE 9)

According to the Step 7-6 in synthetic method for EXAMPLE 7, compound 9-6 (20 mg) was used instead of compound 7-5 to obtain EXAMPLE 9 (0.8 mg) as a colorless amorophous solid.

Example 10

Synthesis of (2R)—N-(4-amidinophenyl)-2-hydroxy-2-[(2R)-3-oxo-4-(4-thiophen-3-ylphenyl)morpholin-2-yl]acetamide hydrochloride (EXAMPLE 10)

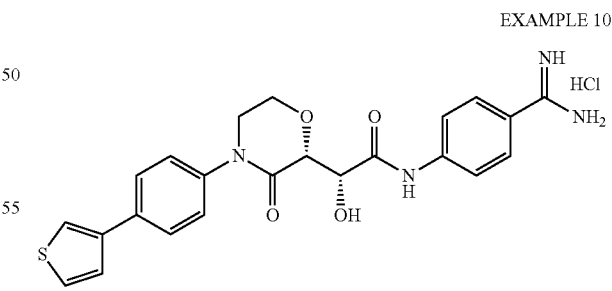

EXAMPLE 10

Step 10-1

Synthesis of N-(2-chloroethyl)-4-thiophen-3-ylaniline (compound 10-1)

According to the Step 7-1 in synthetic method for EXAMPLE 7, 4-(thiophen-3-yl)aniline (50 mg) was used instead of 4-methylaniline to obtain compound 10-1 (15 mg) a pale yellow amorphous solid.

Step 10-2

Synthesis of [(2R,3R)-3-acetyloxy-1-[N-(2-chloroethyl)-4-thiophen-3-ylanilino]-4-(4-cyanoanilino)-1,4-dioxobutan-2-yl]acetate (compound 10-2)

According to the Step 7-3 in synthetic method for EXAMPLE 7, compound 10-1 (160 mg) was used instead of compound 7-1 to obtain compound 10-2 (122 mg) as a colorless amorphous solid.

Step 10-3

Synthesis of (2R,3R)—N-(2-chloroethyl)-N'-(4-cyanophenyl)-2,3-dihydroxy-N-(4-thiophen-3-ylphenyl)butanediamide (compound 10-3)

According to the Step 7-4 in synthetic method for EXAMPLE 7, compound 10-2 (115 mg) was used instead of compound 7-3 to obtain crude 10-3. The crude 10-3 was used in the next step without further purification.

Step 10-4

Synthesis of (2R)—N-(4-cyanophenyl)-2-hydroxy-2-[(2R)-3-oxo-4-(4-thiophen-3-ylphenyl)morpholin-2-yl]acetamide (compound 10-4)

According to the Step 7-5 in synthetic method for EXAMPLE 7, crude 10-3 was used instead of compound 7-4 to obtain compound 10-4 (46 mg) as a pale brown amorphous solid.

Step 10-5

Synthesis of (2R)—N-(4-amidinophenyl)-2-hydroxy-2-[(2R)-3-oxo-4-(4-thiophen-3-ylphenyl)morpholin-2-yl]acetamide hydrochloride (EXAMPLE 10)

According to the Step 7-6 in synthetic method for EXAMPLE 7, compound 10-4 (45 mg) was used instead of compound 7-5 to obtain EXAMPLE 10 (8.2 mg) as a colorless amorphous solid.

Example 11

Synthesis of (2R)—N-(4-amidinophenyl)-2-[(2R)-4-(4-tert-butylphenyl)-3-oxomorpholin-2-yl]-2-hydroxyacetamide hydrochloride (EXAMPLE 11)

Step 11-1

Synthesis of 4-tert-butyl-N-(2-chloroethyl)aniline (compound 11-1)

According to the Step 7-1 in synthetic method for EXAMPLE 7, 4-tert-butylaniline (5 g) was used instead of 4-methylaniline to obtain compound 11-1 (4.8 g) as pale brown oil.

Step 11-2

Synthesis of [(2R,3R)-3-acetyloxy-1-[4-tert-butyl-N-(2-chloroethyl)anilino]-4-(4-cyanoanilino)-1,4-dioxobutan-2-yl]acetate (compound 11-2)

According to the Step 7-3 in synthetic method for EXAMPLE 7, compound 11-1 (2.28 g) was used instead of compound 7-1 to obtain compound 11-2 (1.19 g) as a colorless amorphous solid.

Step 11-3

Synthesis of (2R,3R)—N-(4-tert-Butylphenyl)-N-(2-chloroethyl)-N'-(4-cyanophenyl)-2,3-dihydroxybutanediamide (compound 11-3)

According to the Step 7-4 in synthetic method for EXAMPLE 7, compound 11-2 (0.3 g) was used instead of compound 7-3 to obtain crude 11-3. The crude 11-3 was used in the next step without further purification.

Step 11-4

Synthesis of (2R)-2-[(2R)-4-(4-tert-butylphenyl)-3-oxomorpholin-2-yl]-N-(4-cyanophenyl)-2-hydroxyacetamide (compound 11-4)

According to the Step 7-5 in synthetic method for EXAMPLE 7, crude 11-3 was used instead of compound 7-4 to obtain compound 11-4 (115 mg) as a colorless amorphous solid.

Step 11-5

Synthesis of (2R)—N-(4-amidinophenyl)-2-[(2R)-4-(4-tert-butylphenyl)-3-oxomorpholin-2-yl]-2-hydroxyacetamide hydrochloride (EXAMPLE 11)

According to the Step 7-6 in synthetic method for EXAMPLE 7, compound 11-4 (0.11 g) was used instead of compound 7-5 to obtain EXAMPLE 11 (30.9 mg) as a colorless amorphous solid.

Example 12

Synthesis of (2R)—N-(4-amidinophenyl)-2-hydroxy-2-[(2R)-4-[4-(hydroxymethyl)phenyl]-3-oxomorpholin-2-yl]acetamide hydrochloride (EXAMPLE 12)

Step 12-1

Synthesis of [4-(2-chloroethylamino)phenyl]methanol (compound 12-1)

According to the Step 7-1 in synthetic method for EXAMPLE 7, 4-hydroxymethylaniline (1 g) was used instead of 4-methylaniline to obtain compound 12-1 (690 mg) as pale yellow oil.

Step 12-2

Synthesis of [(2R,3R)-3-acetyloxy-1-[N-(2-chloroethyl)-4-(hydroxymethyl)anilino]-4-(4-cyanoanilino)-1,4-dioxobutan-2-yl]acetate (compound 12-2)

According to the Step 7-3 in synthetic method for EXAMPLE 7, compound 12-1 (2 g) was used instead of compound 7-1 to obtain compound 12-2 (1.91 g) as a colorless amorphous solid.

Step 12-3

Synthesis of (2R,3R)—N-(2-chloroethyl)-N'-(4-cyanophenyl)-2,3-dihydroxy-N-[4-(hydroxymethyl)phenyl]butanediamide (compound 12-3)

According to the Step 7-4 in synthetic method for EXAMPLE 7, compound 12-2 (0.2 g) was used instead of compound 7-3 to obtain crude 12-3. The crude 12-3 was used in the next step without further purification.

Step 12-4

Synthesis of (2R)—N-(4-cyanophenyl)-2-hydroxy-2-[(2R)-4-[4-(hydroxymethyl)phenyl]-3-oxomorpholin-2-yl]acetamide (compound 12-4)

According to the Step 7-5 in synthetic method for EXAMPLE 7, crude 12-3 was used instead of compound 7-4 to obtain compound 12-4 (80 mg) as a pale brown amorphous solid.

Step 12-5
Synthesis of (2R)—N-(4-amidinophenyl)-2-hydroxy-2-[(2R)-4-[4-(hydroxymethyl)phenyl]-3-oxomorpholin-2-yl]acetamide hydrochloride (EXAMPLE 12)

According to the Step 7-6 in synthetic method for EXAMPLE 7, compound 12-4 (73 mg) was used instead of compound 7-5 to obtain EXAMPLE 12 (16.6 mg) a colorless amorphous solid.

Example 13

Synthesis of (2R)—N-(4-amidinophenyl)-2-hydroxy-2-[(2R)-3-oxo-4-(2-oxo-1,3-dihydroindol-5-yl)morpholin-2-yl]acetamide hydrochloride (EXAMPLE 13)

EXAMPLE 13

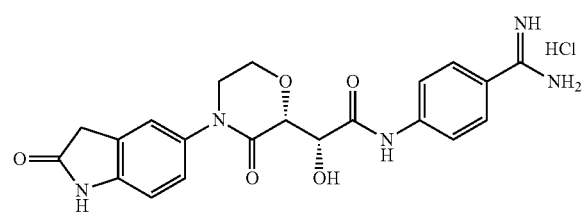

Step 13-1

5-(2-Chloroethylamino)-1,3-dihydroindol-2-one (compound 13-1)

According to the Step 7-1 in synthetic method for EXAMPLE 7, 5-amino-2-indolinone (0.46 g) was used instead of 4-methylaniline to obtain compound 13-1 (470 mg) as a brown amorphous solid.

Step 13-2

Synthesis of [(2R,3R)-3-acetyloxy-1-[2-chloroethyl-(2-oxo-1,3-dihydroindol-5-yl)amino]-5-(4-cyanophenyl)-1,4-dioxopentan-2-yl]acetate (compound 13-2)

According to the Step 7-3 in synthetic method for EXAMPLE 7, compound 13-1 (0.47 g) was used instead of compound 7-1 to obtain compound 13-2 (330 mg) as a brown amorphous solid.

Step 13-3

Synthesis of (2R,3R)—N-(2-chloroethyl)-N'-(4-cyanophenyl)-2,3-dihydroxy-N-(2-oxo-1,3-dihydroindol-5-yl)butanediamide (compound 13-3)

According to the Step 7-4 in synthetic method for EXAMPLE 7, compound 13-2 (100 mg) was used instead of compound 7-3 to obtain crude 13-3. The crude 13-3 was used in the next step without further purification.

Step 13-4

Synthesis of (2R)—N-(4-cyanophenyl)-2-hydroxy-2-[(2R)-3-oxo-4-(2-oxo-1,3-dihydroindol-5-yl)morpholin-2-yl]acetamide (compound 13-4)

According to the Step 7-5 in synthetic method for EXAMPLE 7 crude 13-3 was used instead of compound 7-4 to obtain compound 13-4 (40 mg) as a brown amorphous solid.

Step 13-5
Synthesis of (2R)—N-(4-amidinophenyl)-2-hydroxy-2-[(2R)-3-oxo-4-(2-oxo-1,3-dihydroindol-5-yl)morpholin-2-yl]acetamide hydrochloride (EXAMPLE 13)

According to the Step 7-6 in synthetic method for EXAMPLE 7, compound 13-4 (0.76 g) was used instead of compound 7-5, to obtain EXAMPLE 13 (8 mg) as a pale yellow amorphous solid.

Example 14

Synthesis of (2R)—N-(4-amidinophenyl)-2-hydroxy-2-[(2R)-4-(4-iodophenyl)-3-oxomorpholin-2-yl]acetamide hydrochloride (EXAMPLE 14)

EXAMPLE 14

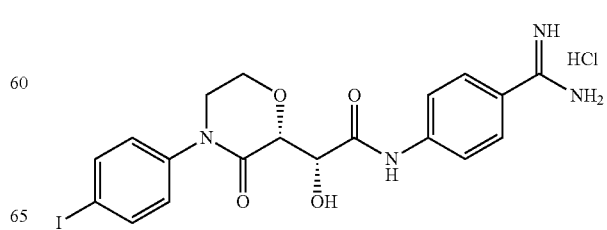

Step 14-1

Synthesis of N-(2-chloroethyl)-4-iodoaniline (compound 14-1)

According to the Step 7-1 in synthetic method for EXAMPLE 7, 4-iodoaniline (10 g) was used instead of 4-methylaniline to obtain compound 14-1 (2.5 g) as colorless oil.

Step 14-2

Synthesis of [R2R,3R)-3-acetyloxy-1-[N-(2-chloroethyl)-4-iodoanilino]-4-(4-cyanoanilino)-1,4-dioxobutan-2-yl]acetate (compound 14-2)

According to the Step 7-3 in synthetic method for EXAMPLE 7, compound 14-1 (2.39 g) was used instead of compound 7-1 to obtain compound 14-2 (2.4 g) as a colorless amorphous solid.

Step 14-3

Synthesis of (2R,3R)—N-(2-chloroethyl)-N'-(4-cyanophenyl)-2,3-dihydroxy-N-(4-iodophenyl)butane diamide (compound 14-3)

According to the Step 7-4 in synthetic method for EXAMPLE 7, compound 14-2 (0.3 g) was used instead of compound 7-3 to obtain crude 14-3. The crude 14-3 was used in the next step without further purification.

Step 14-4

Synthesis of (2R)—N-(4-cyanophenyl)-2-hydroxy-2-[(2R)-4-(4-iodophenyl)-3-oxomorpholin-2-yl]acetamide (compound 14-4)

According to the Step 7-5 in synthetic method for EXAMPLE 7, crude 14-3 was used instead of compound 7-4 to obtain compound 14-4 (160 mg) as a colorless amorphous solid.

Step 14-5

Synthesis of (2R)—N-(4-amidinophenyl)-2-hydroxy-2-[(2R)-4-(4-iodophenyl)-3-oxomorpholin-2-yl]acetamide hydrochloride (EXAMPLE 14)

According to the Step 7-6 in synthetic method for EXAMPLE 7, compound 14-4 (80 mg) was used instead of compound 7-5 to obtain EXAMPLE 14 (11 mg) as a pale yellow amorphous solid.

Example 15

Synthesis of (2R)—N-(4-amidinophenyl)-2-[(2R)-4-(4-cyclohexylphenyl)-3-oxomorpholin-2-yl]-2-hydroxyacetamide hydrochloride (EXAMPLE 15)

EXAMPLE 15

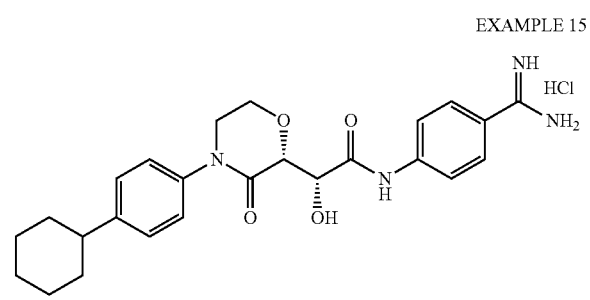 [SMILES: N=C(N)c1ccc(NC(=O)[C@H](O)[C@H]2OCCN(c3ccc(C4CCCCC4)cc3)C2=O)cc1 ; Cl]

Step 15-1

Synthesis of N-(2-chloroethyl)-4-cyclohexylaniline (compound 15-1)

According to the Step 7-1 in synthetic method for EXAMPLE 7, 4-cyclohexylaniline (0.9 g) was used instead of 4-methylaniline to obtain compound 15-1 (1.04 g) as brown oil.

Step 15-2

Synthesis of [(2R,3R)-3-acetyloxy-4-[N-(2-chloroethyl)-4-cyclohexylanilino]-1-(4-cyanoanilino)-1,4-dioxobutan-2-yl]acetate (compound 15-2)

According to the Step 7-3 in synthetic method for EXAMPLE 7, compound 15-1 (1 g) was used instead of compound 7-1 to obtain compound 15-2 (1.05 g) as a colorless amorphous solid.

Step 15-3

Synthesis of (2R)—N-(4-cyanophenyl)-2-[(2R)-4-(4-cyclohexylphenyl)-3-oxomorpholin-2-yl]-2-hydroxyacetamide (compound 15-3)

According to the Step 7-4 and 7-5 in synthetic method for EXAMPLE 7, compound 15-2 (1 g) was used instead of compound 7-3 to obtain compound 15-3 (610 mg) as a colorless amorphous solid.

Step 15-4

Synthesis of (2R)—N-(4-amidinophenyl)-2-[(2R)-4-(4-cyclohexylphenyl)-3-oxomorpholin-2-yl]-2-hydroxyacetamide hydrochloride (EXAMPLE 15)

According to the Step 7-6 in synthetic method for EXAMPLE 7, compound 15-3 (30 mg) was used instead of compound 7-5 to obtain EXAMPLE 15 (1.8 mg) as a colorless amorphous solid.

Example 16

Synthesis of (2R)—N-(4-amidinophenyl)-2-hydroxy-2-[(2R)-3-oxo-4-(4-propan-2-ylphenyl)morpholin-2-yl]acetamide hydrochloride (EXAMPLE 16)

EXAMPLE 16

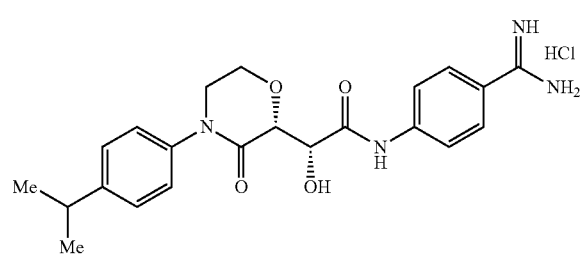

Step 16-1

Synthesis of N-(2-chloroethyl)-4-propan-2-ylaniline (compound 16-1)

According to the Step 7-1 in synthetic method for EXAMPLE 7, 4-isopropylaniline (1 g) was used instead of 4-methylaniline to obtain compound 16-1 (1.35 g) as brown oil.

Step 16-2

Synthesis of [(2R,3R)-3-acetyloxy-4-[N-(2-chloroethyl)-4-propan-2-ylanilino]-1-(4-cyanoanilino)-1,4-dioxobutan-2-yl]acetate (compound 16-2)

According to the Step 7-3 in synthetic method for EXAMPLE 7, compound 16-1 (1.3 g) was used instead of compound 7-1 to obtain compound 16-2 (1.27 g) as a brown amorphous solid.

Step 16-3

Synthesis of (2R)—N-(4-cyanophenyl)-2-hydroxy-2-[(2R)-3-oxo-4-(4-propan-2-ylphenyl)morpholin-2-yl]acetamide (compound 16-3)

According to the Step 7-4 and 7-5 in synthetic method for EXAMPLE 7, compound 16-2 (1.2 g) was used instead of compound 7-3 to obtain compound 16-3 (570 mg) as a colorless amorphous solid.

Step 16-4

Synthesis of (2R)—N-(4-amidinophenyl)-2-hydroxy-2-[(2R)-3-oxo-4-(4-(propan-2-yl)phenyl)morpholin-2-yl]acetamide hydrochloride (EXAMPLE 16)

According to the Step 7-6 in synthetic method for EXAMPLE 7, compound 16-3 (30 mg) was used instead of compound 7-5 to obtain EXAMPLE 16 (1.8 mg) as a colorless amorphous solid.

Example 17

Synthesis of (2R)—N-(4-amidinophenyl)-2-[(2R)-4-(4-ethylphenyl)-3-oxomorpholin-2-yl]-2-hydroxy acetamide hydrochloride (EXAMPLE 17)

EXAMPLE 17

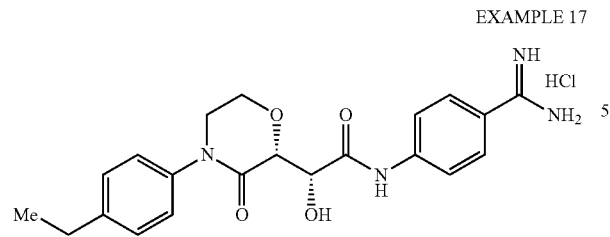

Step 17-1

Synthesis of N-(2-chloroethyl)-4-ethylaniline (compound 17-1)

According to the Step 7-1 in synthetic method for EXAMPLE 7, 4-ethylaniline (5.15 mL) was used instead of 4-methylaniline to obtain crude 17-1. The crude 17-1 was used in the next step without further purification.

Step 17-2

Synthesis of [(2R,3R)-3-acetyloxy-4-[N-(2-chloroethyl)-4-ethylanilino]-1-(4-cyanoanilino)-1,4-dioxobutan-2-yl]acetate (compound 17-2)

According to the Step 7-3 in synthetic method for EXAMPLE 7, crude 17-1 (2.31 g) was used instead of compound 7-1 to obtain compound 17-2 (1.57 g) as a colorless amorphous solid.

Step 17-3

Synthesis of (2R,3R)—N-(2-chloroethyl)-N'-(4-cyanophenyl)-N-(4-ethylphenyl)-2,3-dihydroxybutane diamide (compound 17-3)

According to the Step 7-4 in synthetic method for EXAMPLE 7, compound 17-2 (1.5 g) was used instead of compound 7-3 to obtain crude 17-3. The crude 17-3 was used in the next step without further purification.

Step 17-4

Synthesis of (2R)—N-(4-cyanophenyl)-2-[(2R)-4-(4-ethylphenyl)-3-oxomorpholin-2-yl]-2-hydroxyacetamide (compound 17-4)

According to the Step 7-5 in synthetic method for EXAMPLE 7, crude 17-3 was used instead of compound 7-4 to obtain compound 17-4 (0.76 g) as a colorless amorphous solid.

Step 17-5

Synthesis of (2R)—N-(4-amidinophenyl)-2-[(2R)-4-(4-ethylphenyl)-3-oxomorpholin-2-yl]-2-hydroxy acetamide hydrochloride (EXAMPLE 17)

According to the Step 7-6 in synthetic method for EXAMPLE 7, compound 17-4 (0.1 g) was used instead of compound 7-5 to obtain EXAMPLE 17 (5 mg) as a colorless amorphous solid.

Example 18

Synthesis of Synthesis of (2R)—N-(4-amidinophenyl)-2-hydroxy-2-[(2R)-4-(1H-indol-6-yl)-3-oxomorpholin-2-yl]acetamide trifluoroacetate (EXAMPLE 18)

EXAMPLE 18

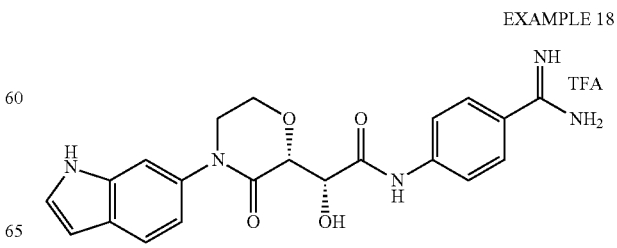

Step 18-1

Synthesis of [(2R,3R)-3-acetyloxy-4-(4-cyanoanilino)-1-[2-hydroxyethyl(1H-indol-6-yl)amino]-1,4-dioxobutan-2-yl]acetate (compound 18-1)

According to the Step 7-3 in synthetic method for EXAMPLE 7, 6-(2-hydroxyethyl)aminoindole (1.99 g; EP424261A1) was used instead of compound 7-1 to obtain compound 18-1 (620 mg) as a colorless amorphous solid.

Step 18-2

Synthesis of [(2R,3R)-3-acetyloxy-4-(4-cyanoanilino)-1-[1H-indol-6-yl(2-methylsulfonyloxyethyl)amino]-1,4-dioxobutan-2-yl]acetate (compound 18-2)

To a solution of compound 18-1 (0.3 g) in $CH_2Cl_2$ (9 mL), were added triethylamine (127 microL) and mesylchloride (51.9 microL) at 0° C. The reaction mixture was stirred at 0° C. for 20 minutes. Then EtOAc and water were added into the mixture and it was extracted with EtOAc. The organic layer was washed with $H_2O$, 1N HCl, sat. $NaHCO_3$ aq, and brine. Then it was dried with anhyd. $Na_2SO_4$. The solvent was removed under reduced pressure to obtain compound 18-2 (350 mg) as a pale yellow amorphous solid. Compound 18-2 was used in the next step without further purification.

Step 18-3

Synthesis of (2R)—N-(4-cyanophenyl)-2-hydroxy-2-[(2R)-4-(1H-indol-6-yl)-3-oxomorpholin-2-yl]acetamide (compound 18-3)

To a solution of compound 18-2 (0.34 g) in MeOH (10.2 mL), was added $K_2CO_3$ (272 mg) at 0° C. The reaction mixture was stirred at 0° C. overnight. Then 1N HCl (2 mL), $H_2O$ (5 mL) and $Et_2O$ (15 mL) were added into the reaction mixture. The precipitate was collected by filtration and was rinsed with $H_2O$ and $Et_2O$ to obtain compound 18-3 (40 mg) as a colorless amorphous solid.

Step 18-4

Synthesis of (2R)—N-(4-amidinophenyl)-2-hydroxy-2-[(2R)-4-(1H-indol-6-yl)-3-oxomorpholin-2-yl]acetamide trifluoroacetate (EXAMPLE 18)

To a solution of compound 18-3 (50 mg) in EtOH—$H_2O$ (10 mL-2.5 mL), were added triethylamine (143 microL) and hydroxyl-amine hydrochloride salt (71.2 mg). The reaction mixture was stirred at 80° C. in a sealed tube for 20 hours. Then the reaction mixture was concentrated in vacuo. The resulting residue which include hydroxyamidine compound (54 mg) was solved in AcOH-MeOH (1 mL-9 mL) and 10% palladium-charcoal (54 mg) was added into the above mixture. The reaction mixture was stirred under hydrogen gas atmosphere at room temperature overnight. After confirming the completion of the reaction by LC/MS, Pd—C was removed by filtration with Celite® pad. The filtrate was concentrated in vacuo and the resulting residue was purified by prep LC/MS to obtain EXAMPLE 18 (4.2 mg) as a pale yellow amorphous solid.

Example 19

Synthesis of (2R)—N-(4-amidinophenyl)-2-[(2R)-4-(3,3-dimethyl-2-oxo-1H-indol-6-yl)-3-oxomorpholin-2-yl]-2-hydroxyacetamide hydrochloride (EXAMPLE 19)

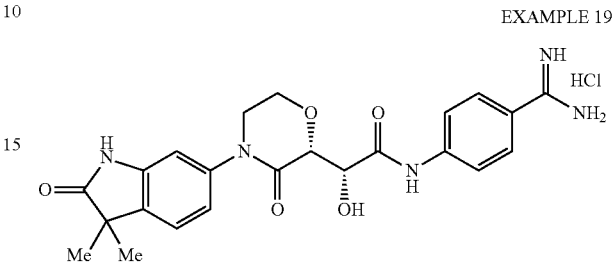

EXAMPLE 19

Step 19-1

Synthesis of 6-(2-chloroethylamino)-3,3-dimethyl-1H-indol-2-one 19-1

According to the Step 7-1 in synthetic method for EXAMPLE 7, 6-amino-1,3-dihydro-3,3-dimethyl-2H-indol-2-one (1 g) was used instead of 4-methylaniline to obtain compound 19-1 (1.05 g) as a brown amorphous solid.

Step 19-2

Synthesis of [(2R,3R)-3-acetyloxy-1-[2-chloroethyl-(3,3-dimethyl-2-oxo-1H-indol-6-yl)amino]-4-(4-cyanoanilino)-1,4-dioxobutan-2-yl]acetate (compound 19-2)

According to the Step 7-3 in synthetic method for EXAMPLE 7, compound 19-1 (1 g) was used instead of compound 7-1 to obtain compound 19-2 (0.39 g) as a yellow amorphous solid.

Step 19-3

Synthesis of (2R,3R)—N-(2-chloroethyl)-N'-(4-cyanophenyl)-N-(3,3-dimethyl-2-oxo-1H-indol-6-yl)-2,3-dihydroxybutanediamide (compound 19-3)

According to the Step 7-4 in synthetic method for EXAMPLE 7, compound 19-2 (0.38 g) was used instead of compound 7-3 to obtain crude 19-3. The crude 19-3 was used in the next step without further purification.

Step 19-4

Synthesis of (2R)—N-(4-cyanophenyl)-2-[(2R)-4-(3,3-dimethyl-2-oxo-1H-indol-6-yl)-3-oxomorpholin-2-yl]-2-hydroxyacetamide (compound 19-4)

According to the Step 7-5 in synthetic method for EXAMPLE 7, crude 19-3 was used instead of compound 7-4 to obtain compound 19-4 (190 mg) as a colorless amorphous solid.

Step 19-5

Synthesis of (2R)—N-(4-amidinophenyl)-2-[(2R)-4-(3,3-dimethyl-2-oxo-1H-indol-6-yl)-3-oxomorpholin-2-yl]-2-hydroxyacetamide hydrochloride (EXAMPLE 19)

According to the Step 7-6 in synthetic method for EXAMPLE 7, compound 19-4 (50 mg) was used instead of compound 7-5 to obtain EXAMPLE 19 (18 mg) as a pale yellow amorphous solid.

2R)—N-(4-Amidinophenyl)-2-hydroxy-2-[(2R)-3-oxo-4-(2-oxo-1,3-dihydrobenzimidazol-5-yl)morpholin-2-yl]acetamide hydrochloride (EXAMPLE 20

EXAMPLE 20

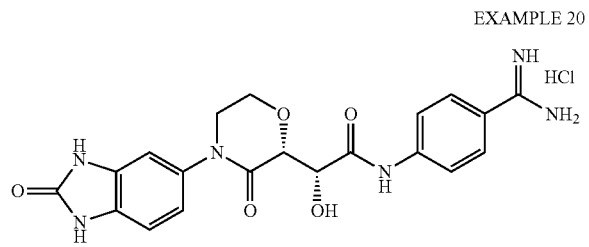 [SMILES: N=C(N)c1ccc(NC(=O)[C@H](O)[C@H]2OCCN(c3ccc4[nH]c(=O)[nH]c4c3)C2=O)cc1 ; Cl]

Step 20-1

Synthesis of 2-chloro-N-(2-oxo-1,3-dihydrobenzimidazol-5-yl)acetamide 20-1

To a suspension of 5-amino-1,3-dihydro-2H-benzimidazol-2-one (1 g) and $K_2CO_3$ (1.02 g) in DMF (20 mL), was added dropwise a solution of chloroacetylchloride (0.59 mL) in DMF (10 mL) at 0° C. The reaction mixture was stirred at room temperature for 3 hours. Then the mixture was diluted with water to precipitate. The precipitate was collected by filtration, rinsed with $H_2O$ to obtain compound 20-1 (1.2 g) as a colorless amorphous solid.

Step 20-2

Synthesis of 5-(2-chloroethylamino)-1,3-dihydrobenzimidazol-2-one (compound 20-2)

To a suspension of compound 20-1 (1 g) in THF (10 mL), was added dropwise 1M $BH_3$-THF complex at 0° C. The reaction mixture was stirred at room temperature for 3 hours to complete the reaction. Then MeOH was carefully added to decompose an excess of $BH_3$ and then conc. HCl was added at 0° C. After stirring under reflux condition for 20 minutes, the mixture was diluted with water. It was extracted with EtOAc and the organic layer was washed with brine and dried with anhyd. $Na_2SO_4$. The solvent was removed under reduced pressure to obtain compound 20-2 (0.85 g) as a colorless amorphous solid.

Step 20-3

Synthesis of [(2R,3R)-3-acetyloxy-4-[2-chloroethyl-(2-oxo-1,3-dihydrobenzimidazol-5-yl)amino]-1-(4-cyanoanilino)-1,4-dioxobutan-2-yl]acetate (compound 20-3)

According to the Step 7-3 in synthetic method for EXAMPLE 7, compound 20-2 (0.8 g) was used instead of compound 7-2 to obtain compound 20-3 (1.6 g) as a colorless amorphous solid.

Step 20-4

Synthesis of (2R,3R)—N-(2-chloroethyl)-N'-(4-cyanophenyl)-2,3-dihydroxy-N-(2-oxo-1,3-dihydrobenzimidazol-5-yl)butanediamide (compound 20-4)

According to the Step 7-4 in synthetic method for EXAMPLE 7, compound 20-3 (1.6 g) was used instead of compound 7-3 to obtain crude 20-4. The crude 20-4 was used in the next step without further purification.

Step 20-5

Synthesis of (2R)—N-(4-cyanophenyl)-2-hydroxy-2-[(2R)-3-oxo-4-(2-oxo-1,3-dihydrobenzimidazol-5-yl)morpholin-2-yl]acetamide (compound 20-5)

According to the Step 7-5 in synthetic method for EXAMPLE 7, crude 20-4 was used instead of compound 7-4 to obtain compound 20-5 (100 mg) as a brown amorphous solid.

Step 20-6

Synthesis of (2R)—N-(4-amidinophenyl)-2-hydroxy-2-[(2R)-3-oxo-4-(2-oxo-1,3-dihydrobenzimidazo 1-5-yl)morpholin-2-yl]acetamide hydrochloride (EXAMPLE 20)

According to the Step 7-6 in synthetic method for EXAMPLE 7, compound 20-5 (50 mg) was used instead of compound 7-5 to obtain EXAMPLE 20 (8 mg) as a pale yellow amorphous solid.

Example 21

Synthesis of (2R)—N-(4-amidinophenyl)-2-hydroxy-2-[(2R)-3-oxo-4-methylphenylmethylmorpholin-2-yl]acetamide hydrochloride (EXAMPLE 21)

EXAMPLE 21

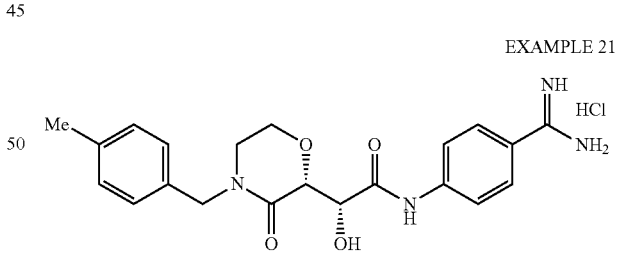

Step 21-1

Synthesis of [(2R,3R)-3-acetyloxy-1-(2-chloroethylmethylphenylmethylamino)-4-(4-cyanoanilino)-1,4-dioxobutan-2-yl]acetate (compound 21-1)

According to the Step 7-1 and 7-3 in synthetic method for EXAMPLE 7, 4-methylbenzylamine (1.04 mL) was used instead of 4-methylaniline to obtain compound 21-1 (62 mg) as a colorless amorphous solid.

Step 21-2

Synthesis of (2R,3R)—N-(2-chloroethyl)-N'-(4-cyanophenyl)-2,3-dihydroxy-N-methylphenylmethylbutanediamide (compound 21-2)

According to the Step 7-4 in synthetic method for EXAMPLE 7, compound 21-1 (60 mg) was used instead of compound 7-3 to obtain crude 21-2. The crude 21-2 was used in the next step without further purification.

Step 21-3

Synthesis of (2R)—N-(4-cyanophenyl)-2-hydroxy-2-[(2R)-3-oxo-4-methylphenylmethylmorpholin-2-yl]acetamide (compound 21-3)

According to the Step 7-5 in synthetic method for EXAMPLE 7, crude 21-2 was used instead of compound 7-4 to obtain compound 21-3 (13 mg) as a colorless amorphous solid.

Step 21-4

Synthesis of (2R)—N-(4-amidinophenyl)-2-hydroxy-2-[(2R)-3-oxo-4-methylphenylmethylmorpholin-2-yl]acetamide hydrochloride (EXAMPLE 21)

According to the Step 7-6 in synthetic method for EXAMPLE 7, compound 21-3 (12 mg) was used instead of compound 7-5 to obtain EXAMPLE 21 (2 mg) as a pale yellow amorphous solid.

Example 22

Synthesis of (2R)—N-(4-amidinophenyl)-2-hydroxy-2-[(2R)-3-oxo-4-(4-(thiophen-2-yl)phenyl)morpholin-2-yl]acetamide hydrochloride (EXAMPLE 22)

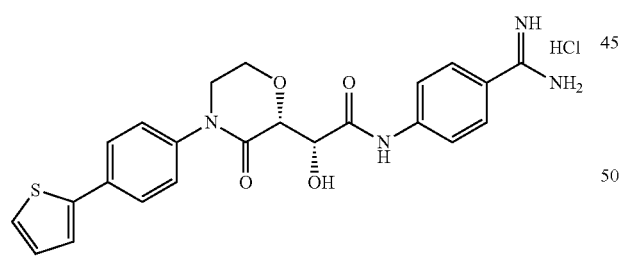

EXAMPLE 22

Step 22-1

Synthesis of (2R)—N-(4-cyanophenyl)-2-hydroxy-2-[(2R)-3-oxo-4-(4-(thiophen-2-yl)phenyl)morpholin-2-yl]acetamide (compound 22-1)

To a suspension of compound 14-4 (80 mg) in THF—H$_2$O (2 mL-0.67 mL), were added 2-thiopheneboronic acid (43 mg), Cs$_2$CO$_3$ (0.44 g), and Pd(Ph$_3$P)$_4$ (19.4 mg). The mixture was stirred at 80° C. for 15 hours. The reaction mixture was filtered with Celite® pad and rinsed with the mixed solvent (EtOAc-MeOH=1-1). The filtrate was concentrated in vacuo and the resulting residue was washed with H$_2$O and Et$_2$O. The precipitate was collected by filtration to obtain compound 22-1 (35 mg) as a pale brown amorphous solid.

Step 22-2

Synthesis of (2R)—N-(4-amidinophenyl)-2-hydroxy-2-[(2R)-3-oxo-4-(4-thiophen-2-ylphenyl)morpholin-2-yl]acetamide hydrochloride (EXAMPLE 22)

According to the Step 7-6 in synthetic method for EXAMPLE 7, compound 22-1 (25 mg) was used instead of compound 7-5 to obtain EXAMPLE 22 (1.4 mg) a brown amorphous solid.

Example 23

Synthesis of (2R)—N-(4-amidinophenyl)-2-[(2R)-4-biphenyl-3-oxomorpholin-2-yl]-2-hydroxyacetamide hydrochloride (EXAMPLE 23)

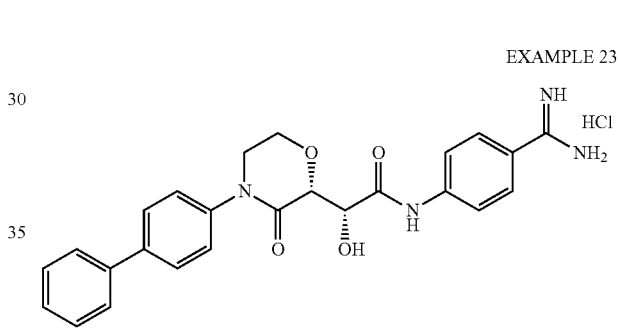

EXAMPLE 23

Step 23-1

Synthesis of (2R)-2-[(2R)-4-biphenyl-3-oxomorpholin-2-yl]-N-(4-cyanophenyl)-2-hydroxyacetamide (compound 23-1)

According to the Step 22-1 in synthetic method for EXAMPLE 22, phenyl boronic acid (41 mg) was used instead of 2-thiopheneboronic acid to obtain compound 23-1 (42 mg) as a pale brown amorphous solid.

Step 23-2

Synthesis of (2R)—N-(4-amidinophenyl)-2-[(2R)-4-biphenyl-3-oxomorpholin-2-yl]-2-hydroxyacetamide hydrochloride (EXAMPLE 23)

According to the Step 7-6 in synthetic method for EXAMPLE 7, compound 23-1 (25 mg) was used instead of compound 7-5 to obtain EXAMPLE 23 (4.2 mg) as a colorless amorphous solid.

Example 24

Synthesis of (2R)—N-(4-amidinophenyl)-2-[(2R)-4-(4'-tert-butylbiphenyl)-3-oxomorpholin-2-yl]-2-hydroxyacetamide hydrochloride (EXAMPLE 24)

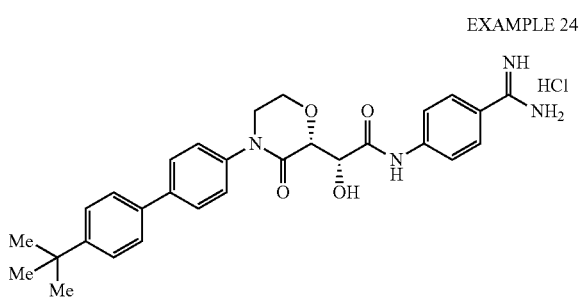 [SMILES: CC(C)(C)c1ccc(-c2ccc(N3CCO[C@H]([C@@H](O)C(=O)Nc4ccc(C(=N)N)cc4)C3=O)cc2)cc1 ; Cl]

EXAMPLE 24

Step 24-1

Synthesis of (2R)-2-[(2R)-4-(4'-tert-butylbiphenyl)-3-oxomorpholin-2-yl]-N-(4-cyanophenyl)-2-hydroxyacetamide (compound 24-1)

According to the Step 22-1 in synthetic method for EXAMPLE 22, 4-tert-butylphenyl boronic acid (60 mg) was used instead of 2-thiopheneboronic acid to obtain compound 24-1 (65 mg) as a pale brown amorphous solid.

Step 24-2

Synthesis of (2R)—N-(4-amidinophenyl)-2-[(2R)-4-(4'-tert-butylbiphenyl)-3-oxomorpholin-2-yl]-2-hydroxyacetamide hydrochloride (EXAMPLE 24)

According to the Step 7-6 in synthetic method for EXAMPLE 7, compound 24-1 (35 mg) was used instead of compound 7-5 to obtain EXAMPLE 24 (8 mg) as a colorless amorphous solid.

Example 25

Synthesis of (2R)—N-(4-amidinophenyl)-2-hydroxy-2-[(2R)-3-oxo-4-[4-(1H-pyrazol-4-yl)phenyl]morpholin-2-yl]acetamide dihydrochloride (EXAMPLE 25)

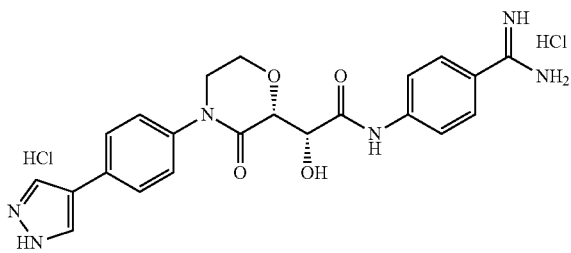

EXAMPLE 25

Step 25-1

Synthesis of (2R)—N-(4-cyanophenyl)-2-hydroxy-2-[(2R)-3-oxo-4-[4-(1H-pyrazol-4-yl)phenyl]morpholin-2-yl]acetamide (compound 25-1)

According to the Step 22-1 in synthetic method for EXAMPLE 22, 1-Boc-4-(4,4,5,5-tetramethyl-1,3,2-dioxaborolan-2-yl)pyrazole (98 mg) was used instead of 2-thiopheneboronic acid to obtain compound 25-1 (36 mg) as a pale brown amorphous solid.

Step 25-2

Synthesis of (2R)—N-(4-amidinophenyl)-2-hydroxy-2-[(2R)-3-oxo-4-[4-(1H-pyrazol-4-yl)phenyl]morpholin-2-yl]acetamide dihydrochloride (EXAMPLE 25)

According to the Step 7-6 in synthetic method for EXAMPLE 7, compound 25-1 (32 mg) was used instead of compound 7-5 to obtain EXAMPLE 25 (6.4 mg) as a colorless amorphous solid.

Example 26

Synthesis of (2R)-2-[(2R)-4-(4-acetamidophenyl)-3-oxomorpholin-2-yl]-N-(4-amidinophenyl)-2-hydroxyacetamide hydrochloride (EXAMPLE 26)

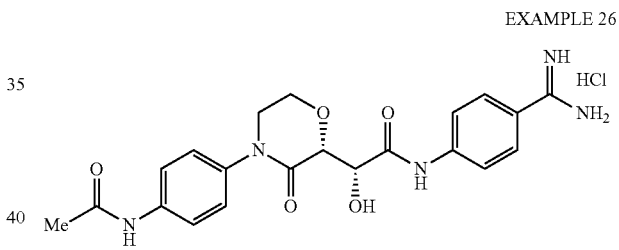

EXAMPLE 26

Method A

Step 26-1

Synthesis of tert-butyl N-[4-(2-chloroethylamino)phenyl]carbamate (compound 26-1)

According to the Step 7-1 in synthetic method for EXAMPLE 7, 4-(tert-butoxycarbonylamino)aniline (11.6 g) was used instead of 4-methylaniline to obtain compound 26-1 (3.2 g) as a yellow brown amorphous solid.

Step 26-2

Synthesis of [(2R,3R)-3-acetyloxy-1-[N-(2-chloroethyl)-4-[(2-methylpropan-2-yl)oxycarbonylamino]anilino]-4-(4-cyanoanilino)-1,4-dioxobutan-2-yl] acetate (compound 26-2)

According to the Step 7-3 in synthetic method for EXAMPLE 7, compound 26-1 (3.2 g) was used instead of compound 7-1 to obtain compound 26-2 (3.2 g) as colorless amorphous solid.

Step 26-3

Synthesis of tert-butyl N-[4-[2-chloroethyl-[(2R,3R)-4-(4-cyanoanilino)-2,3-dihydroxy-4-oxobutanoyl]amino]phenyl]carbamate (compound 26-3)

According to the Step 7-4 in synthetic method for EXAMPLE 7, compound 26-2 (3.2 g) was used instead of compound 7-3 to obtain crude 26-3. The crude 26-3 was used in the next step without further purification.

Step 26-4

Synthesis of tert-butyl N-[4-[(2R)-2-[(1R)-2-(4-cyanoanilino)-1-hydroxy-2-oxoethyl]-3-oxomorpholin-4-yl]phenyl]carbamate (compound 26-4)

According to the Step 7-5 in synthetic method for EXAMPLE 7, crude 26-3 was used instead of compound 7-4 to obtain compound 26-4 (1.68 g) as a colorless amorphous solid.

Step 26-5

Synthesis of (2R)-2-[(2R)-4-(4-aminophenyl)-3-oxomorpholin-2-yl]-N-(4-cyanophenyl)-2-hydroxyacetamide (compound 26-5)

To compound 26-4 (1.65 g), was added trifluoroacetic acid (10 mL) with anisole (0.2 mL) at 0° C. The reaction mixture was stirred at 0° C. for 1 hour then $Et_2O$ was added into the mixture to precipitate. The precipitate was collected by filtration and washed with $Et_2O$. Then the precipitate was solved in water and the solution was basified with sat. $NaHCO_3$ aq. The precipitate was collected by filtration and washed with $H_2O$ to obtain compound 26-5 (1.2 g) as a pale brown amorphous solid.

Step 26-6

Synthesis of [(1R)-1-[(2R)-4-(4-acetamidophenyl)-3-oxomorpholin-2-yl]-2-(4-cyanoanilino)-2-oxoethyl]acetate (compound 26-6)

To a suspension of compound 26-5 (70 mg) in pyridine (1 mL), was added $Ac_2O$ (43.4 microL). The mixture was stirred at room temperature overnight. The reaction mixture was diluted with water to precipitate. The precipitate was collected by filtration and rinsed with water to obtain compound 26-6 (85 mg) as a colorless amorphous solid.

Step 26-A

Synthesis of (2R)-2-[(2R)-4-(4-acetamidophenyl)-3-oxomorpholin-2-yl]-N-(4-amidinophenyl)-2-hydroxyacetamide hydrochloride (EXAMPLE 26)

According to the Step 7-6 in synthetic method for EXAMPLE 7, compound 26-6 (50 mg) was used instead of compound 7-5 to obtain EXAMPLE 26 (2 mg) as a colorless amorphous solid.

Method B

Step 26-7

Synthesis of tert-butyl N-[4-[(2-chloroacetyl)amino]phenyl]carbamate (compound 26-7)

According to the Step 20-1 in synthetic method for EXAMPLE 20, 4-(tert-butoxycarbonylamino)aniline (15 g) was used instead of 5-amino-1,3-dihydro-2H-benzimidazol-2-one to obtain compound 26-7 (19.5 g) as a gray amorphous solid.

Step 26-8

Synthesis of tert-butyl N-[4-(2-chloroethylamino)phenyl]carbamate (compound 26-1)

According to the Step 20-2 in synthetic method for EXAMPLE 20, compound 26-7 (4 g) was used instead of compound 20-1 to obtain compound 26-1 (3.84 g).

Step 26-9

Synthesis of (2R,3R)-2,3-diacetyloxy-4-[N-(2-chloroethyl)-4-[(2-methylpropan-2-yl)oxycarbonylamino]anilino]-4-oxobutanoic acid (compound 26-9)

To a solution of (+)-diacetyl-L-tartaric anhydride (3.01 g) in $CH_2Cl_2$ (40 mL), was added compound 26-1 (3.77 g) at 0° C. The mixture was stirred at room temperature for 1 hour. The solvent was removed under reduced pressure to obtain compound 26-9 (7.41 g) as a gray amorphous solid.

Step 26-10

Synthesis of [(2R,3R)-3-acetyloxy-4-[N-(2-chloroethyl)-4-[(2-methylpropan-2-yl)oxycarbonylamino]anilino]-1,4-dioxo-1-[4-(5-oxo-4H-1,2,4-oxadiazol-3-yl)anilino]butan-2-yl]acetate (compound 26-10)

To a solution of compound 26-9 (4 g) in $CH_2Cl_2$ (40 mL), were added 3-(4-aminophenyl)-1,2,4-oxadiazol-5(2H)-one (1.46 g; EP1574516 A1), 1-hydroxybenzotriazole hydrate (HOBt-$H_2O$; 0.13 g), and WSC—HCl (1.73 g). The reaction mixture was stirred at room temperature for 1.5 hours and it was concentrated in vacuo. The resulting residue was solved in EtOAc, the organic layer was washed with brine and dried with anhyd. $Na_2SO_4$. The solvent was removed under reduced pressure and the resulting residue was suspended in Hex-$Et_2O$=1-1. The precipitate was collected by filtration and rinsed with the above solvent to obtain compound 26-10 (4.45 g) as a pale brown amorphous solid.

Step 26-11

Synthesis of tert-butyl N-[4-[2-chloroethyl-[(2R,3R)-2,3-dihydroxy-4-oxo-4-[4-(5-oxo-4H-1,2,4-oxadiazol-3-yl)anilino]butanoyl]amino]phenyl]carbamate ammonium salt (compound 26-11)

According to the Step 7-4 in synthetic method for EXAMPLE 7, compound 26-10 (3.5 g) was used instead of compound 7-3 to obtain compound 26-11 (3.04 g) as a pale brown amorphous solid.

Step 26-12

Synthesis of tert-butyl N-[4-[(2R)-2-[(1R)-1-Hydroxy-2-oxo-2-[4-(5-oxo-4H-1,2,4-oxadiazol-3-yl)anilino]ethyl]-3-oxomorpholin-4-yl]phenyl]carbamate (compound 26-12)

According to the Step 7-5 in synthetic method for EXAMPLE 7, compound 26-11 (2.8 g) was used instead of compound 7-4 to obtain compound 26-12 (1.24 g) as an ivory weight amorphous solid.

Step 26-13

Synthesis of (2R)-2-[(2R)-4-(4-aminophenyl)-3-oxomorpholin-2-yl]-2-hydroxy-N-[4-(5-oxo-4H-1,2,4-oxadiazol-3-yl)phenyl]acetamide hydrochloride (compound 26-13)

According to the Step 26-5 in synthetic method for EXAMPLE 26, compound 26-12 (1 g) was used instead of compound 26-4 to obtain compound 26-13 (830 mg) as a pale brown amorphous solid.

Step 26-14

Synthesis of (2R)-2-[(2R)-4-(4-acetamidophenyl)-3-oxomorpholin-2-yl]-2-hydroxy-N-[4-(5-oxo-4H-1,2,4-oxadiazol-3-yl)phenyl]acetamide (compound 26-14)

According to the Step 26-6 in synthetic method for EXAMPLE 26, compound 26-13 (0.1 g) was used instead of compound 26-5 to obtain compound 26-14 (83 mg) as a colorless amorphous solid.

Step 26-B

Synthesis of (2R)-2-[(2R)-4-(4-acetamidophenyl)-3-oxomorpholin-2-yl]-N-(4-amidinophenyl)-2-hydroxyacetamide hydrochloride (EXAMPLE 26)

To a suspension of compound 26-14 (80 mg) in MeOH-1N HCl (8 mL-8 mL), was added 10% Pd—C (80 mg) at room temperature. The reaction mixture was stirred under $H_2$ gas atmosphere at room temperature overnight. The reaction mixture was filtered with Celite® pad. The Celite® pad was washed with DMF and the filtrate was concentrated in vacuo. The resulting residue was suspended in MeOH and the precipitate was collected by filtration to obtain EXAMPLE 26 (38 mg) as a colorless amorphous solid.

Example 27

Synthesis of (2R)—N-(4-amidinophenyl)-2-[(2R)-4-[4-(carbamoylamino)phenyl]-3-oxomorpholin-2-yl]-2-hydroxyacetamide hydrochloride (EXAMPLE 27)

EXAMPLE 27

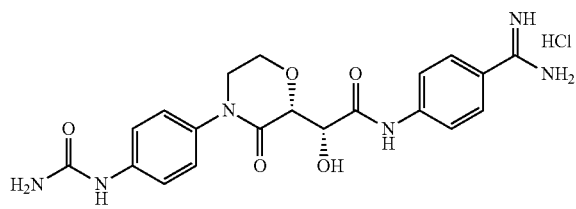

Step 27-1

Synthesis of (2R)-2-[(2R)-4-[4-(carbamoylamino)phenyl]-3-oxomorpholin-2-yl]-N-(4-cyanophenyl)-2-hydroxyacetamide (compound 27-1)

To a solution of compound 26-5 (70 mg) in AcOH—$H_2O$ (6 mL-2 mL), was added a solution of potassium cyanate (KOCN; 31 mg) in water (2 mL). The reaction mixture was stirred at 40-50° C. for 3 hours and at room temperature overnight to precipitate. The resulting precipitate was collected by filtration, rinsed with waster and dried in vacuo to obtain compound 27-1 (70 mg) as a colorless amorphous solid.

Step 27-2

Synthesis of (2R)—N-(4-amidinophenyl)-2-[(2R)-4-[4-(carbamoylamino)phenyl]-3-oxomorpholin-2-yl]-2-hydroxyacetamide hydrochloride (EXAMPLE 27)

According to the Step 7-6 in synthetic method for EXAMPLE 7, compound 27-1 (50 mg) was used instead of compound 7-5 to obtain EXAMPLE 27 (3 mg) as a colorless amorphous solid.

Example 28

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

EXAMPLE 28

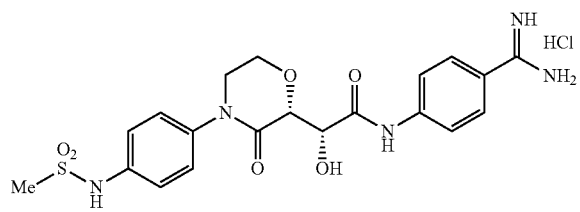

Method A

Step 28-1

Synthesis of (2R)—N-(4-cyanophenyl)-2-hydroxy-2-[(2R)-4-[4-(methanesulfonamido)phenyl]-3-oxomorpholin-2-yl]acetamide (compound 28-1)

To a solution of compound 26-5 (70 mg) in DMF-pyridine (2 mL-2 mL), was added mesyl chloride (16.3 microL). The reaction mixture was stirred at room temperature overnight. The mixture was diluted with water then it was extracted with EtOAc. The extract was washed with water, 1N HCl and brine. The organic layer was dried with anhyd. $Na_2SO_4$ and the solvent was removed under reduced pressure to obtain compound 28-1 (30 mg) as a pale yellow amorphous solid.

Step 28-A

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

According to the Step 7-6 in synthetic method for EXAMPLE 7, compound 28-1 (28 mg) was used instead of compound 7-5 to obtain EXAMPLE 28 (4.9 mg) as a pale yellow amorphous solid.

Method B

Step 28-2

Synthesis of (2R)-2-hydroxy-2-[(2R)-4-[4-(methanesulfonamido)phenyl]-3-oxomorpholin-2-yl]-N-[4-(5-oxo-4H-1,2,4-oxadiazol-3-yl)phenyl]acetamide (compound 28-2)

According to the Step 28-1 in synthetic method for EXAMPLE 28, compound 26-13 (0.1 g) was used instead of compound 26-5 to obtain compound 28-2 (50 mg) as a pale pink amorphous solid.

Step 28-B

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

According to the Step 26-B in synthetic method for EXAMPLE 26, compound 28-2 (50 mg) was used instead of compound 26-14 to obtain EXAMPLE 28 (32 mg) as a pale yellow amorphous solid.

Example 29

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

EXAMPLE 29

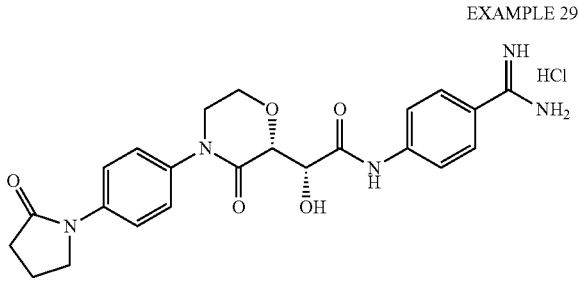 [SMILES: N=C(N)c1ccc(NC(=O)[C@H](O)[C@H]2OCCN(c3ccc(N4CCCC4=O)cc3)C2=O)cc1 ; Cl]

Method A

Step 29-1

Synthesis of (2R)—N-(4-cyanophenyl)-2-hydroxy-2-[(2R)-3-oxo-4-[4-(2-oxopyrrolidin-1-yl)phenyl]morpholin-2-yl]acetamide (compound 29-1)

According to the Step 26-6 in synthetic method for EXAMPLE 26, chlorobutyryl chloride (33.6 microL) was used instead of acetyl chloride to obtain an acylated intermediate. After confirming the formation of it by LC/MS, tBuOK (91.9 mg) was added to the above solution. The reaction mixture was stirred at room temperature and for 2 hours. Then the mixture was diluted with water and it was extracted with EtOAc. The organic layer was washed with $H_2O$, 1N HCl, and brine. The organic layer was dried with anhyd. $Na_2SO_4$. The solvent was removed under reduced pressure to obtain compound 29-1 (73 mg) as a pale yellow amorphous solid.

Step 29-A

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

According to the Step 7-6 in synthetic method for EXAMPLE 7, compound 29-1 (67 mg) was used instead of compound 7-5 to obtain EXAMPLE 29 (6.6 mg) as a colorless amorphous solid.

Method B

Step 29-2

Synthesis of (2R)-2-hydroxy-N-[4-(5-oxo-4H-1,2,4-oxadiazol-3-yl)phenyl]-2-[(2R)-3-oxo-4-[4-(2-oxopyrrolidin-1-yl)phenyl]morpholin-2-yl]acetamide (compound 29-2)

According to the Step 29-1 in synthetic method for EXAMPLE 29, compound 26-13 (0.1 g) was used instead of compound 26-5 to obtain compound 29-2 (68 mg) as a pale brown amorphous solid.

Step 29-B

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

According to the Step 26-B in synthetic method for EXAMPLE 26, compound 29-2 (65 mg) was used instead of compound 26-14 to obtain EXAMPLE 29 (23 mg) as a colorless amorphous solid.

Example 30

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

EXAMPLE 30

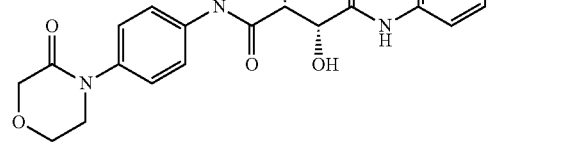

217

Method A

Step 30-1

Synthesis of (2R)—N-(4-cyanophenyl)-2-hydroxy-2-[(2R)-3-oxo-4-[4-(3-oxomorpholin-4-yl)phenyl]morpholin-2-yl]acetamide (compound 30-1)

To a suspension of compound 26-5 (0.1 g) and 2-chloroethoxy acetic acid (45.4 mg) in DMF (2 mL), was added 4-(4,6-dimethoxy-1,3,5-triazin-2-yl)-4-methylmorpholinium chloride (DMT-MM; 87.7 mg). The reaction mixture was stirred at room temperature overnight. Then, according to the Step 29-1 in synthetic method for EXAMPLE 29, cyclization reaction was pursued to obtain compound 30-1 (90 mg) as a colorless amorphous solid.

Step 30-A

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

According to the Step 7-6 in synthetic method for EXAMPLE 7, compound 30-1 (85 mg) was used instead of compound 7-5 to obtain EXAMPLE 30 (15.7 mg) as a colorless amorphous solid.

Method B

Step 30-2

Synthesis of (2R)-2-hydroxy-N-[4-(5-oxo-4H-1,2,4-oxadiazol-3-yl)phenyl]-2-[(2R)-3-oxo-4-[4-(3-oxomorpholin-4-yl)phenyl]morpholin-2-yl]acetamide (compound 30-2)

According to the Step 30-1 in synthetic method for EXAMPLE 30, compound 26-13 (0.1 g) was used instead of compound 26-5 to obtain compound 30-2 (42 mg) as a colorless amorphous solid.

Step 30-B

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

According to the Step 26-B in synthetic method for EXAMPLE 26, compound 30-2 (40 mg) was used instead of compound 26-14 to obtain EXAMPLE 30 (26.7 mg) as a colorless amorphous solid.

218

Example 31

Synthesis of (2R)—N-(4-amidinophenyl)-2-hydroxy-2-[(2R)-3-oxo-4-[4-(2-oxo-1,3-oxazolidin-3-yl)phenyl]morpholin-2-yl]acetamide hydrochloride (EXAMPLE 31)

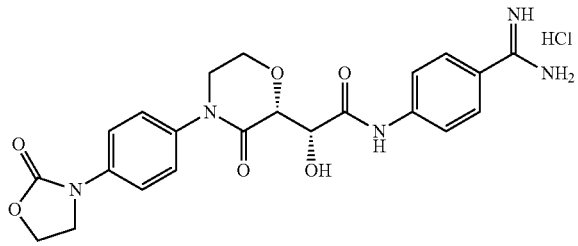

EXAMPLE 31

Step 31-1

Synthesis of (2R)—N-(4-cyanophenyl)-2-hydroxy-2-[(2R)-3-oxo-4-[4-(2-oxo-1,3-oxazolidin-3-yl)phenyl]morpholin-2-yl]acetamide (compound 31-1)

According to the Step 29-1 in synthetic method for EXAMPLE 29, 2-chloroethyl chloroformate (31 microL) was used instead of chlorobutyryl chloride to obtain compound 31-1 (76 mg) as a colorless amorphous solid.

Step 31-2

Synthesis of (2R)—N-(4-amidinophenyl)-2-hydroxy-2-[(2R)-3-oxo-4-[4-(2-oxo-1,3-oxazolidin-3-yl)phenyl]morpholin-2-yl]acetamide hydrochloride (EXAMPLE 31)

According to the Step 7-6 in synthetic method for EXAMPLE 7, compound 31-1 (70 mg) was used instead of compound 7-5 to obtain EXAMPLE 31 (10.1 mg) as a colorless amorphous solid.

Example 32

Synthesis of (2R)—N-(4-amidinophenyl)-2-hydroxy-2-[(2R)-3-oxo-4-[4-[(2-phenylmethoxyacetyl)amino]phenyl]morpholin-2-yl]acetamide hydrochloride (EXAMPLE 32)

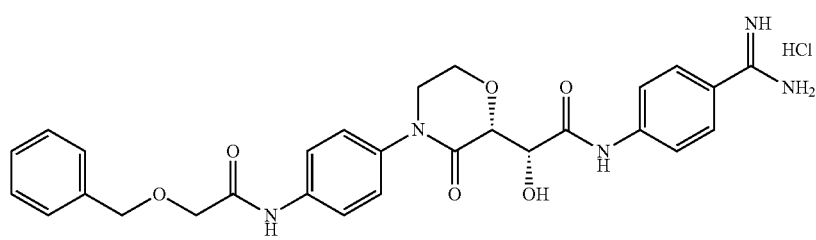

EXAMPLE 32

Step 32-1

Synthesis of (2R)—N-(4-cyanophenyl)-2-hydroxy-2-[(2R)-3-oxo-4-[4-[(2-phenylmethoxyacetyl)amino]phenyl]morpholin-2-yl]acetamide (compound 32-1)

According to the Step 28-1 in synthetic method for EXAMPLE 28, (benzyloxy)acetyl chloride (94.8 microL) was used instead of mesyl chloride to obtain compound 32-1 (160 mg) as a colorless amorphous solid.

Step 32-2

Synthesis of (2R)—N-(4-amidinophenyl)-2-hydroxy-2-[(2R)-3-oxo-4-[4-[(2-phenylmethoxyacetyl)amino]phenyl]morpholin-2-yl]acetamide hydrochloride (EXAMPLE 32)

According to the Step 7-6 in synthetic method for EXAMPLE 7, compound 32-1 (150 mg) was used instead of compound 7-5 to obtain EXAMPLE 32 (150 mg) as a colorless amorphous solid.

Example 33

Synthesis of (2R)—N-(4-amidinophenyl)-2-hydroxy-2-[(2R)-4-[4-[(2-hydroxyacetyl)amino]phenyl]-3-oxomorpholin-2-yl]acetamide hydrochloride (EXAMPLE 33)

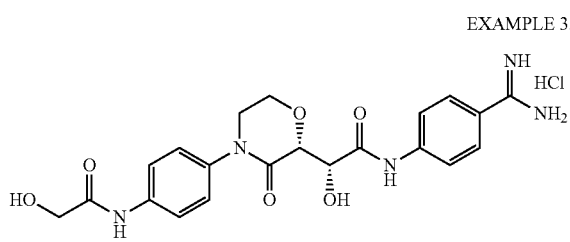

EXAMPLE 33

Step 33-1

Synthesis of (2R)—N-(4-amidinophenyl)-2-hydroxy-2-[(2R)-4-[4-[(2-hydroxyacetyl)amino]phenyl]-3-oxomorpholin-2-yl]acetamide hydrochloride (EXAMPLE 33)

To a solution of EXAMPLE 32 (0.12 g) in MeOH—AcOH (20 mL-1 mL), was added 10% Pd—C (20 mg). The reaction mixture was stirred under $H_2$ gas atmosphere at room temperature overnight. The reaction mixture was filtered to remove Pd—C and the filtrate was purified by prep. LC/MS. Before collecting the fractions, conc. HCl was added into each fraction to obtain EXAMPLE 33 (2 mg) as a colorless amorphous solid.

Example 34

Synthesis of (2R)—N-(4-amidinophenyl)-2-[(2R)-4-(3,3-dimethyl-2-oxo-1H-indol-5-yl)-3-oxomorpholin-2-yl]-2-hydroxyacetamide hydrochloride (EXAMPLE 34)

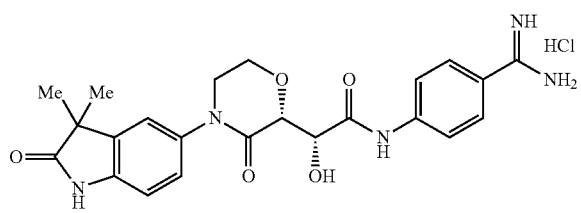

EXAMPLE 34

Step 34-1

5-(2-Chloroethylamino)-3,3-dimethyl-1H-indol-2-one (compound 34-1)

According to the Step 7-1 in synthetic method for EXAMPLE 7, 3,3-dimethyl-1H-indol-2-one (0.5 g; J. Med. Chem., 51, 4465-4475, 2008) was used instead of 4-methylaniline to obtain compound 34-1 (0.68 g) as a pale brown amorphous solid.

Step 34-2

Synthesis of (2R,3R)-2,3-diacetyloxy-4-[2-chloroethyl-(3,3-dimethyl-2-oxo-1H-indol-5-yl)amino]-4-oxobutanoic acid (compound 34-2)

According to the Step 26-9 in synthetic method for EXAMPLE 26, compound 34-1 (680 mg) was used instead of compound 26-1 to obtain crude 34-2. The crude 34-2 was used in the next step without further purification.

Step 34-3

Synthesis of [(2R,3R)-3-acetyloxy-1-[2-chloroethyl-(3,3-dimethyl-2-oxo-1H-indol-5-yl)amino]-1,4-dioxo-4-[4-(5-oxo-4H-1,2,4-oxadiazol-3-yl)anilino]butan-2-yl]acetate (compound 34-3)

According to the Step 26-10 in synthetic method for EXAMPLE 26, crude 34-2 was used instead of compound 26-9 to obtain compound 34-3 (1.26 g) as a pale brown amorphous solid.

Step 34-4

Synthesis of (2R,3R)—N-(2-chloroethyl)-N-(3,3-dimethyl-2-oxo-1H-indol-5-yl)-2,3-dihydroxy-N'-[4-(5-oxo-4H-1,2,4-oxadiazol-3-yl)phenyl]butanediamide ammonium salt (compound 34-4)

According to the Step 7-4 in synthetic method for EXAMPLE 7, compound 34-3 (0.4 g) was used instead of compound 7-3 to obtain compound 34-4 (356 mg) as a colorless amorphous solid.

221

Step 34-5

Synthesis of (2R)-2-[(2R)-4-(3,3-dimethyl-2-oxo-1H-indol-5-yl)-3-oxomorpholin-2-yl]-2-hydroxy-N-[4-(5-oxo-4H-1,2,4-oxadiazol-3-yl)phenyl]acetamide (compound 34-5)

According to the Step 7-5 in synthetic method for EXAMPLE 7, compound 34-4 (0.12 g) was used instead of compound 7-4 to obtain compound 34-5 (20.1 mg) as a pale yellow amorphous solid.

Step 34-6

Synthesis of (2R)—N-(4-amidinophenyl)-2-[(2R)-4-(3,3-dimethyl-2-oxo-1H-indol-5-yl)-3-oxomorpholin-2-yl]-2-hydroxyacetamide hydrochloride (EXAMPLE 34)

According to the Step 26-B in synthetic method for EXAMPLE 26, compound 34-5 (19 mg) was used instead of compound 26-14 to obtain EXAMPLE 34 (16.4 mg) as a pale yellow amorphous solid.

Example 35

Synthesis of (2R)—N-(4-amidinophenyl)-2-hydroxy-2-[(2R)-4-(1H-indol-5-yl)-3-oxomorpholin-2-yl]acetamide acetate (EXAMPLE 35)

EXAMPLE 35

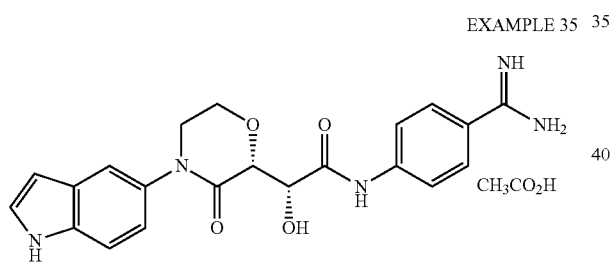

Step 35-1

Synthesis of 2-chloro-N-(1H-indol-5-yl)acetamide (compound 35-1)

According to the Step 20-1 in synthetic method for EXAMPLE 20, 5-aminoindole (5.31 g) was used instead of 5-amino-1,3-dihydro-2H-benzimidazol-2-one to obtain compound 35-1 (8.38 g) as a brown amorphous solid.

Step 35-2

Synthesis of N-(2-chloroethyl)-1H-indol-5-amine (compound 35-2)

According to the Step 20-2 in synthetic method for EXAMPLE 20, compound 35-1 (1 g) was used instead of compound 20-1 to obtain compound 35-2 (930 mg) as brown oil.

222

Step 35-3

Synthesis of (2R,3R)-2,3-diacetyloxy-4-[2-chloroethyl(1H-indol-5-yl)amino]-4-oxobutanoic acid (compound 35-3)

According to the Step 26-9 in synthetic method for EXAMPLE 26, compound 35-2 (327 mg) was used instead of compound 26-8 to obtain crude 35-3. The crude 35-3 was used in the next step without further purification.

Step 35-4

Synthesis of [(2R,3R)-3-acetyloxy-1-[2-chloroethyl(1H-indol-5-yl)amino]-1,4-dioxo-4-[4-(5-oxo-4H-1,2,4-oxadiazol-3-yl)anilino]butan-2-yl]acetate (compound 35-4)

According to the Step 26-10 in synthetic method for EXAMPLE 26, crude 35-3 was used instead of compound 26-9 to obtain compound 35-4 (0.47 g) as a pale brown amorphous solid.

Step 35-5

Synthesis of (2R,3R)—N-(2-chloroethyl)-2,3-dihydroxy-N-(1H-indol-5-yl)-N'-[4-(5-oxo-4H-1,2,4-oxadiazol-3-yl)phenyl]butanediamide ammonium salt (compound 35-5)

According to the Step 7-4 in synthetic method for EXAMPLE 7, compound 35-4 (0.2 g) was used instead of compound 7-3 to obtain crude 35-5. The crude 35-5 was used in the next step without further purification.

Step 35-6

Synthesis of (2R)-2-hydroxy-2-[(2R)-4-(1H-indol-5-yl)-3-oxomorpholin-2-yl]-N-[4-(5-oxo-4H-1,2,4-oxadiazol-3-yl)phenyl]acetamide (compound 35-6)

According to the Step 7-5 in synthetic method for EXAMPLE 7, crude 35-5 was used instead of compound 7-4 to obtain 35-6 (65 mg) as a pale brown amorphous solid.

Step 35-7

Synthesis of (2R)—N-(4-amidinophenyl)-2-hydroxy-2-[(2R)-4-(1H-indol-5-yl)-3-oxomorpholin-2-yl]acetamide acetate (EXAMPLE 35)

According to the Step 26-B in synthetic method for EXAMPLE 26, compound 35-6 (20 mg) was used instead of compound 26-14 to obtain EXAMPLE 35 (13.6 mg) as pale brown amorphous solid.

Example 36

Synthesis of (2R)—N-(4-amidinophenyl)-2-hydroxy-2-[(2R)-3-oxo-4-(2-oxo-3H-1,3-benzoxazol-6-yl)morpholin-2-yl]acetamide hydrochloride (EXAMPLE 36)

EXAMPLE 36

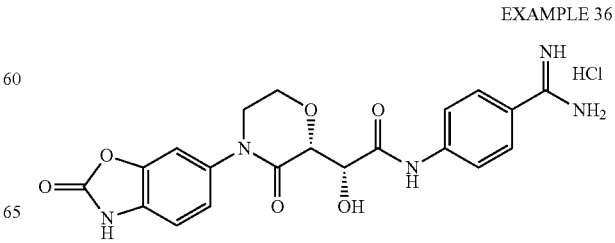

Step 36-1

Synthesis of 6-(2-chloroethylamino)-3H-1,3-benzoxazol-2-one (compound 36-1)

According to the Step 7-1 in synthetic method for EXAMPLE 7, 6-amino-2-benzoxazolinone (0.5 g) was used instead of 4-methylaniline to obtain compound 36-1 (0.68 g) as brown oil.

Step 36-2

Synthesis of (2R,3R)-2,3-diacetyloxy-4-[2-chloroethyl-(2-oxo-3H-1,3-benzoxazol-6-yl)amino]-4-oxobutanoic acid (compound 36-2)

According to the Step 26-9 in synthetic method for EXAMPLE 26, compound 36-1 (0.67 g) was used instead of compound 26-8 to obtain crude 36-2. The crude 36-2 was used in the next step without further purification.

Step 36-3

Synthesis of [(2R,3R)-3-acetyloxy-1-[2-chloroethyl-(2-oxo-3H-1,3-benzoxazol-6-yl)amino]-1,4-dioxo-4-[4-(5-oxo-4H-1,2,4-oxadiazol-3-yl)anilino]butan-2-yl]acetate (compound 36-3)

According to the Step 26-10 in synthetic method for EXAMPLE 26, crude 36-2 was used instead of compound 26-9 to obtain compound 36-3 (0.1 g) as a pale brown amorphous solid.

Step 36-4

Synthesis of (2R,3R)—N-(2-chloroethyl)-2,3-dihydroxy-N-(2-oxo-3H-1,3-benzoxazol-6-yl)-N'-[4-(5-oxo-4H-1,2,4-oxadiazol-3-yl)phenyl]butanediamide ammonium salt (compound 36-4)

According to the Step 7-4 in synthetic method for EXAMPLE 7, compound 36-3 (98 mg) was used instead of compound 7-3 to obtain crude 36-4. The crude 36-4 was used in the next step without further purification.

Step 36-5

Synthesis of (2R)-2-hydroxy-N-[4-(5-oxo-4H-1,2,4-oxadiazol-3-yl)phenyl]-2-[(2R)-3-oxo-4-(2-oxo-3H-1,3-benzoxazol-6-yl)morpholin-2-yl]acetamide (compound 36-5)

According to the Step 7-5 in synthetic method for EXAMPLE 7, crude 36-4 was used instead of compound 7-4 to obtain 36-5 (23 mg) as a pale brown amorphous solid.

Step 36-6

Synthesis of (2R)—N-(4-amidinophenyl)-2-hydroxy-2-[(2R)-3-oxo-4-(2-oxo-3H-1,3-benzoxazol-6-yl)morpholin-2-yl]acetamide hydrochloride (EXAMPLE 36)

According to the Step 26-B in synthetic method for EXAMPLE 26, compound 36-5 (21 mg) was used instead of compound 26-14 to obtain EXAMPLE 36 (15.5 mg) as a yellow-green amorphous solid.

Example 37

Synthesis of (2R)—N-(4-amidinophenyl)-2-hydroxy-2-[(2R)-3-oxo-4-(3-oxo-1,2-dihydroisoindol-5-yl)morpholin-2-yl]acetamide hydrochloride (EXAMPLE 37)

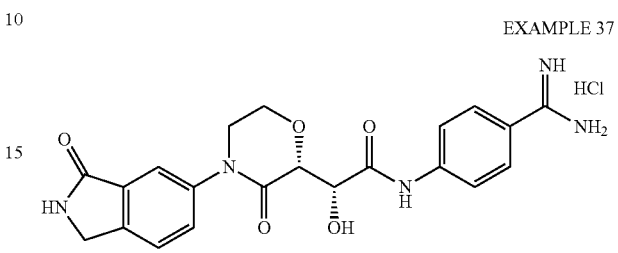

EXAMPLE 37

Step 37-1

Synthesis of 6-(2-chloroethylamino)-2,3-dihydroisoindol-1-one (compound 37-1)

According to the Step 7-1 in synthetic method for EXAMPLE 7, 6-amino-2,3-dihydro-1H-isoindol-1-one, (0.8 g) was used instead of 4-methylaniline to obtain compound 37-1 (0.36 g) as a orange amorphous solid.

Step 37-2

Synthesis of (2R,3R)-2,3-diacetyloxy-4-[2-chloroethyl-(3-oxo-1,2-dihydroisoindol-5-yl)amino]-4-oxobutanoic acid (compound 37-2)

According to the Step 26-9 in synthetic method for EXAMPLE 26, compound 37-1 (353 mg) was used instead of compound 26-8 to obtain crude 37-2. The crude 37-2 was used in the next step without further purification.

Step 37-3

Synthesis of [(2R,3R)-3-acetyloxy-1-[2-chloroethyl-(3-oxo-1,2-dihydroisoindol-5-yl)amino]-1,4-dioxo-4-[4-(5-oxo-4H-1,2,4-oxadiazol-3-yl)anilino]butan-2-yl]acetate (compound 37-3)

According to the Step 26-10 in synthetic method for EXAMPLE 26, crude 37-2 was used instead of compound 26-9 to obtain compound 37-3 (419 mg) as a brown solid.

Step 37-4

Synthesis of (2R,3R)—N-(2-chloroethyl)-2,3-dihydroxy-N-(3-oxo-1,2-dihydroisoindol-5-yl)-N'-[4-(5-oxo-4H-1,2,4-oxadiazol-3-yl)phenyl]butanediamide ammonium salt (compound 37-4)

According to the Step 7-4 in synthetic method for EXAMPLE 7, compound 37-3 (0.3 g) was used instead of compound 7-3 to obtain crude 37-4. The crude 37-4 was used in the next step without further purification.

Step 37-5

Synthesis of (2R)-2-hydroxy-N-[4-(5-oxo-4H-1,2,4-oxadiazol-3-yl)phenyl]-2-[(2R)-3-oxo-4-(3-oxo-1,2-dihydroisoindol-5-yl)morpholin-2-yl]acetamide (compound 37-5)

According to the Step 7-5 in synthetic method for EXAMPLE 7, crude 37-4 was used instead of compound 7-4 to obtain compound 37-5 (38 mg) as a pale brown amorphous solid.

Step 37-6

Synthesis of (2R)—N-(4-amidinophenyl)-2-hydroxy-2-[(2R)-3-oxo-4-(3-oxo-1,2-dihydroisoindol-5-yl)morpholin-2-yl]acetamide hydrochloride (EXAMPLE 37)

According to the Step 26-B in synthetic method for EXAMPLE 26, compound 37-5 (32.9 mg) was used instead of compound 26-14 to obtain EXAMPLE 37 (21.4 mg) as a colorless amorphous solid.

Example 38

Synthesis of (2R)-2-[(2R)-4-(4-acetamidophenyl)-3-oxomorpholin-2-yl]-N-(1-aminoisoquinolin-6-yl)-2-hydroxyacetamide hydrochloride (EXAMPLE 38)

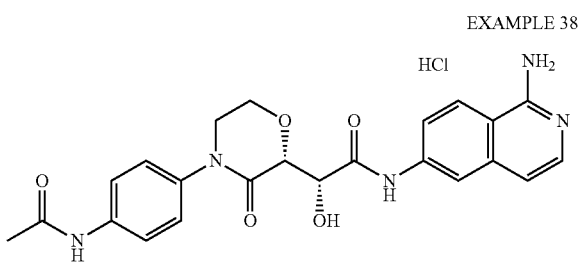 [SMILES: CC(=O)Nc1ccc(N2CCO[C@H]([C@@H](O)C(=O)Nc3ccc4c(N)nccc4c3)C2=O)cc1 ; Cl]

EXAMPLE 38

Step 38-1

Synthesis of N-[4-(2-chloroethylamino)phenyl]acetamide (compound 38-1)

According to the Step 7-1 in synthetic method for EXAMPLE 7, N-(4-aminophenyl)acetamide (10 g) was used instead of 4-methylaniline to obtain compound 38-1 (7.9 g) as a pale yellow amorphous solid.

Step 38-2

Synthesis of (2R,3R)-4-[4-acetamido-N-(2-chloroethyl)anilino]-2,3-diacetyloxy-4-oxobutanoic acid (compound 38-2)

According to the Step 26-9 in synthetic method for EXAMPLE 26, compound 38-1 (7.5 g) was used instead of compound 26-1 to obtain compound 38-2 (15.1 g) as a beige amorphous solid.

Step 38-3

Synthesis of [(2R,3R)-1-[4-acetamido-N-(2-chloroethyl)anilino]-3-acetyloxy-4-[[1-[bis[(2-methylpropan-2-yl)oxycarbonyl]amino]isoquinolin-6-yl]amino]-1,4-dioxobutan-2-yl]acetate (compound 38-3)

To a solution of compound 38-2 (0.7 g) in CH$_2$Cl$_2$-DMF (30-2 mL), was added oxalyl chloride (0.25 mL) at 0° C. The reaction mixture was stirred for 1 hour in the same temperature. Then the mixture was concentrated in vacuo to remove excess oxalyl chloride. The resulting residue was resolved in CH$_2$Cl$_2$ (20 mL) and pyridine (0.19 mL) was added to the above solution at 0° C. The mixture was stirred for 10 minutes at the same temperature and then a solution of 6-amino-1-bis(tert-butoxycarbonyl)aminoisoquinoline (0.52 g) in CH$_2$Cl$_2$ (10 mL) was added to the mixture at 0° C. The reaction mixture was stirred for 1 hour at 0° C., then for 2 days at room temperature. MeOH was added to the reaction mixture and the mixture was concentrated in vacuo. Then sat. NaHCO$_3$ aq. was added to residue and the mixture was extracted with EtOAc. The organic layer was washed with water, brine and dried with anhyd. Na$_2$SO$_4$. The solvent was removed under reduced pressure and the resulting residue was purified by silica gel flash chromatography (eluent:Hexane/EtOAc=1/4) to obtain compound 38-3 (0.52 g) as a pale yellow amorphous solid.

Step 38-4

Synthesis of tert-butyl N-[6-[[(2R,3R)-4-[4-acetamido-N-(2-chloroethyl)anilino]-2,3-dihydroxy-4-oxobutanoyl]amino]isoquinolin-1-yl]-N-[(2-methylpropan-2-yl)oxycarbonyl]carbamate (compound 38-4)

According to the Step 7-4 in synthetic method for EXAMPLE 7, compound 38-3 (0.5 g) was used instead of 7-3 to obtain compound 38-4 (0.42 g) as a yellow amorphous solid.

Step 38-5

Synthesis of (2R)-2-[(2R)-4-(4-acetamidophenyl)-3-oxomorpholin-2-yl]-N—[N,N-bis(tert-butoxycarbonyl)-1-aminoisoquinolin-6-yl]-2-hydroxyacetamide (compound 38-5)

According to the Step 7-5 in synthetic method for EXAMPLE 7, compound 38-4 (0.4 g) and DMF were used instead of 7-4 and t-BuOH-DMSO to obtain compound 38-5 (0.13 g) as a yellow amorphous solid.

Step 38-6

Synthesis of (2R)-2-[(2R)-4-(4-acetamidophenyl)-3-oxomorpholin-2-yl]-N-(1-aminoisoquinolin-6-yl)-2-hydroxyacetamide hydrochloride (EXAMPLE 38)

To a solution of compound 38-5 (40 mg) in MeOH (0.4 mL), was added 4N—HCl/EtOAc (1 mL) at 0° C. The reaction mixture was stirred for 21 hours at room temperature. After the reaction, the precipitate was collected by filtration to obtain EXAMPLE 38 (22 mg) as a pale yellow amorphous solid.

Example 39

Synthesis of (2R)-2-[(2R)-4-(4-acetamidophenyl)-3-oxomorpholin-2-yl]-2-hydroxy-N-(1-imino-2,3-dihydroisoindol-5-yl)acetamide hydrochloride (EXAMPLE 39)

EXAMPLE 39

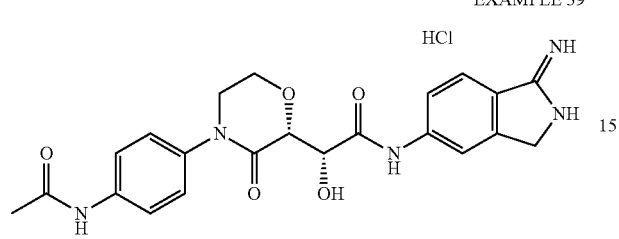

Step 39-1

Synthesis of tert-butyl N-[(2-cyano-5-nitrophenyl)methyl]-N-[(2-methylpropan-2-yl)oxycarbonyl]carbamate (compound 39-1)

To a suspension of 2-(bromomethyl)-4-nitro-benzonitrile (1.0 g: WO 2005082368 A1) and $K_2CO_3$ (1.1 g) in DMF (15 mL), were added di-tert-butyl imidodicarboxylate (1.17 g) and tetrabutylammonium iodide (0.15 g) at room temperature. The reaction mixture was stirred at room temperature overnight. Water was added into the mixture and it was extracted with EtOAc. The organic layer was washed with brine and dried with anhyd. $Na_2SO_4$. The solvent was removed under reduced pressure and the resulting residue was purified by silica gel flash chromatography (eluent: Hexane/EtOAc=100/0-3/1) to obtain compound 39-1 (1.29 g) as a colorless amorphous solid.

Step 39-2

Synthesis of tert-butyl N-[(5-Amino-2-cyanophenyl)methyl]-N-[(2-methylpropan-2-yl)oxycarbonyl]carbamate (compound 39-2)

To a solution of compound 39-1 (0.3 g) in MeOH-THF (3 mL-3 mL), was added 10% Pd/C (30 mg). The reaction mixture was stirred under hydrogen atmosphere for 3 hours at room temperature. Then the reaction mixture was filtered with Celite® pad to remove catalyst. The filtrate was concentrated in vacuo to obtain compound 39-2 (0.27 g) as pale brown oil.

Step 39-3

Synthesis of [(2R,3R)-1-[4-acetamido-N-(2-chloroethyl)anilino]-3-acetyloxy-4-[3-[[bis[(2-methylpropan-2-yl)oxycarbonyl]amino]methyl]-4-cyanoanilino]-1,4-dioxobutan-2-yl]acetate (compound 39-3)

According to the Step 26-10 in synthetic method for EXAMPLE 26, compound 38-2 (3.0 g) and 39-2 (2.43 g) were used instead of 26-9 and 3-(4-Aminophenyl)-1,2,4-oxadiazol-5(2H)-one to obtain compound 39-3 (5.25 g) as a beige amorphous solid.

Step 39-4

Synthesis of tert-butyl N-[[5-[[(2R,3R)-4-[4-acetamido-N-(2-chloroethyl)anilino]-2,3-dihydroxy-4-oxobutanoyl]amino]-2-cyanophenyl]methyl]-N-[(2-methylpropan-2-yl)oxycarbonyl]carbamate (compound 39-4)

According to the Step 7-4 in synthetic method for EXAMPLE 7, compound 39-3 (5.2 g) was used instead of 7-3 to obtain compound 39-4 (4.3 g) as a beige amorphous solid.

Step 39-5

Synthesis of tert-butyl N-[[5-[[(2R)-2-[(2R)-4-(4-acetamidophenyl)-3-oxomorpholin-2-yl]-2-hydroxyacetyl]amino]-2-cyanophenyl]methyl]-N-[(2-methylpropan-2-yl)oxycarbonyl]carbamate (compound 39-5)

According to the Step 7-5 in synthetic method for EXAMPLE 7, compound 39-4 (4.3 g) and DMF were used instead of 7-4 and t-BuOH-DMSO to obtain compound 39-5 (1.46 g) as a colorless amorphous solid.

Step 39-6

Synthesis of (2R)-2-[(2R)-4-(4-acetamidophenyl)-3-oxomorpholin-2-yl]-N-[3-(aminomethyl)-4-cyanophenyl]-2-hydroxyacetamide hydrochloride (compound 39-6)

According to the Step 38-6 in synthetic method for EXAMPLE 38, compound 39-5 (1.45 g) was used instead of 38-5 to obtain compound 39-6 (1.2 g) as a colorless amorphous solid.

Step 39-7

Synthesis of (2R)-2-[(2R)-4-(4-acetamidophenyl)-3-oxomorpholin-2-yl]-2-hydroxy-N-(1-imino-2,3-dihydroisoindol-5-yl)acetamide hydrochloride (EXAMPLE 39)

Compound 39-6 (1.2 g) was suspended in EtOH (30 mL) and the mixture was refluxed for 6 hours. After cooling, the precipitate was collected by filtration to obtain EXAMPLE 39 (0.95 g) as a colorless amorphous solid.

Example 40

Synthesis of N-[4-[(2R)-2-[(1R)-2-(4-amidinoanilino)-1-hydroxy-2-oxoethyl]-3-oxomorpholin-4-yl]phenyl]propanamide hydrochloride (EXAMPLE 40)

EXAMPLE 40

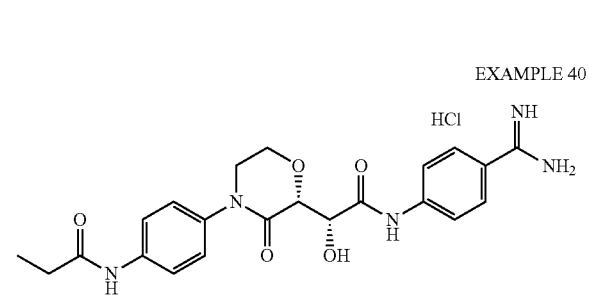 [SMILES: CCC(=O)Nc1ccc(N2CCO[C@H]([C@@H](O)C(=O)Nc3ccc(C(=N)N)cc3)C2=O)cc1 ; Cl]

Step 40-1

Synthesis of N-[4-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]propanamide (compound 40-1)

According to the Step 28-1 in synthetic method for EXAMPLE 28, propionyl chloride (15.1 microL) was used instead of mesyl chloride to obtain compound 40-1 (80.3 mg) as a colorless amorphous solid.

Step 40-2

Synthesis of N-[4-[(2R)-2-[(1R)-2-(4-amidinoanilino)-1-hydroxy-2-oxoethyl]-3-oxomorpholin-4-yl]phenyl]propanamide hydrochloride (EXAMPLE 40)

According to the Step 26-B in synthetic method for EXAMPLE 26, compound 40-1 (70 mg) was used instead of 26-14 to obtain EXAMPLE 40 (53.5 mg) as a pale beige amorphous solid.

Example 41

Synthesis of (2R)—N-(4-amidinophenyl)-2-[(2R)-4-[4-[(2-cyclopropylacetyl)amino]phenyl]-3-oxomorpholin-2-yl]-2-hydroxyacetamide hydrochloride (EXAMPLE 41)

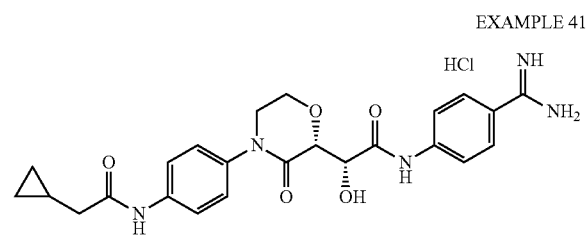 [SMILES: N=C(N)c1ccc(NC(=O)[C@H](O)[C@H]2OCCN(c3ccc(NC(=O)CC4CC4)cc3)C2=O)cc1 ; Cl]

EXAMPLE 41

Step 41-1

Synthesis of (2R)-2-[(2R)-4-[4-[(2-cyclopropylacetyl)amino]phenyl]-3-oxomorpholin-2-yl]-2-hydroxy-N-[4-(5-oxo-4H-1,2,4-oxadiazol-3-yl)phenyl]acetamide (compound 41-1)

According to the Step 28-1 in synthetic method for EXAMPLE 28, an acid chloride derived from cyclopropylacetic acid (15.2 mg) was used instead of mesyl chloride to obtain compound 41-1 (53.5 mg) as a pale beige amorphous solid.

Step 41-2

Synthesis of (2R)—N-(4-amidinophenyl)-2-[(2R)-4-[4-[(2-cyclopropylacetyl)amino]phenyl]-3-oxomorpholin-2-yl]-2-hydroxyacetamide hydrochloride (EXAMPLE 41)

According to the Step 26-B in synthetic method for EXAMPLE 26, 41-1 (50 mg) was used instead of 26-14 to obtain EXAMPLE 41 (45.5 mg) as a colorless amorphous solid.

Example 42

Synthesis of N-[4-[(2R)-2-[(1R)-2-(4-amidinoanilino)-1-hydroxy-2-oxoethyl]-3-oxomorpholin-4-yl]phenyl]cyclohexanecarboxamide hydrochloride (EXAMPLE 42)

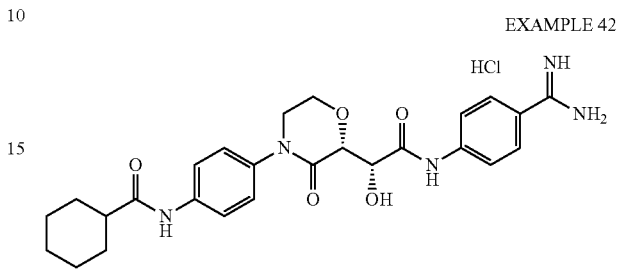

EXAMPLE 42

Step 42-1

Synthesis of N-[4-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]cyclohexanecarboxamide (compound 42-1)

According to the Step 28-1 in synthetic method for EXAMPLE 28, cyclohexanecarbonyl chloride (20.6 microL) was used instead of mesyl chloride to obtain compound 42-1 (57.7 mg) as a pale beige amorphous solid.

Step 42-2

Synthesis of N-[4-[(2R)-2-[(1R)-2-(4-amidinoanilino)-1-hydroxy-2-oxoethyl]-3-oxomorpholin-4-yl]phenyl]cyclohexanecarboxamide hydrochloride (EXAMPLE 42)

According to the Step 26-B in synthetic method for EXAMPLE 26, 42-1 (50 mg) was used instead of 26-14 to obtain EXAMPLE 42 (35 mg) as a colorless amorphous solid.

Example 43

Synthesis of (2R)—N-(4-amidinophenyl)-2-[(2R)-4-(4-aminophenyl)-3-oxomorpholin-2-yl]-2-hydroxyacetamide dihydrochloride (EXAMPLE 43)

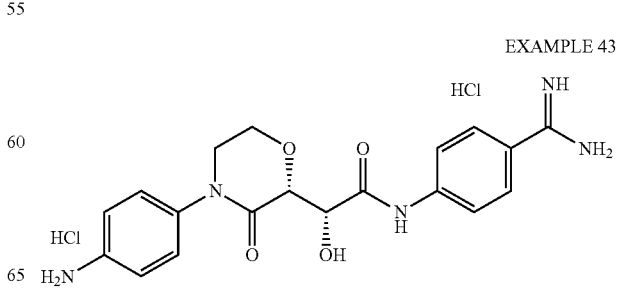

EXAMPLE 43

Step 43-1

Synthesis of (2R)—N-(4-amidinophenyl)-2-[(2R)-4-(4-aminophenyl)-3-oxomorpholin-2-yl]-2-hydroxyacetamide dihydrochloride (EXAMPLE 43)

According to the Step 26-B in synthetic method for EXAMPLE 26, 26-13 (49.7 mg) was used instead of 26-14 to obtain EXAMPLE 43 (37.9 mg) as a pale yellow amorphous solid.

Example 44

Synthesis of (2R)—N-(4-amidinophenyl)-2-[(2R)-4-(3-aminophenyl)-3-oxomorpholin-2-yl]-2-hydroxyacetamide dihydrochloride (EXAMPLE 44)

EXAMPLE 44

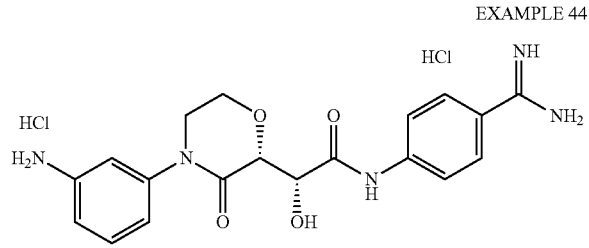 [SMILES: Cl ; N=C(N)c1ccc(NC(=O)[C@H](O)[C@H]2OCCN(c3cccc(N)c3)C2=O)cc1 ; Cl]

Step 44-1

Synthesis of tert-butyl N-[3-[(2-chloroacetyl)amino]phenyl]carbamate (compound 44-1)

According to the Step 20-1 in synthetic method for EXAMPLE 20, N-Boc-m-phenylenediamine (2 g) was used instead of 5-amino-1,3-dihydro-2H-benzimidazol-2-one to obtain compound 44-1 (2.35 g) as a gray amorphous solid.

Step 44-2

Synthesis of tert-butyl N-[3-(2-chloroethylamino)phenyl]carbamate (compound 44-2)

According to the Step 20-2 in synthetic method for EXAMPLE 20, compound 44-1 (11.4 g) was used instead of 20-1 to obtain compound 44-2 (10.9 g) as a colorless amorphous solid.

Step 44-3

Synthesis of (2R,3R)-2,3-diacetyloxy-4-[N-(2-chloroethyl)-3-[(2-methylpropan-2-yl)oxycarbonylamino]anilino]-4-oxobutanoic acid (compound 44-3)

According to the Step 26-9 in synthetic method for EXAMPLE 26, 44-2 (10.8 g) was used instead of 26-1 to obtain compound 44-3 (20.7 g) as a colorless amorphous solid.

Step 44-4

Synthesis of [(2R,3R)-3-acetyloxy-4-[N-(2-chloroethyl)-3-[(2-methylpropan-2-yl)oxycarbonylamino]anilino]-1,4-dioxo-1-[4-(5-oxo-4H-1,2,4-oxadiazol-3-yl)anilino]butan-2-yl]acetate (compound 44-4)

According to the Step 26-10 in synthetic method for EXAMPLE 26, compound 44-3 (10 g) was used instead of 26-9 to obtain compound 44-4 (13.5 g) as a beige amorphous solid.

Step 44-5

Synthesis of tert-butyl N-[3-[2-chloroethyl-[(2R,3R)-2,3-dihydroxy-4-oxo-4-[4-(5-oxo-4H-1,2,4-oxadiazol-3-yl)anilino]butanoyl]amino]phenyl]carbamate (compound 44-5)

According to the Step 7-4 in synthetic method for EXAMPLE 7, 44-4 (13.4 g) was used instead of 7-3 to obtain compound 44-5 (12.9 g) as a beige amorphous solid.

Step 44-6

Synthesis of tert-butyl N-[3-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]carbamate (compound 44-6)

According to the Step 7-5 in synthetic method for EXAMPLE 7, 44-5 (1 g) and DMF were used instead of 7-4 and t-BuOH-DMSO to obtain compound 44-6 (0.66 g) as a beige amorphous solid.

Step 44-7

Synthesis of (2R)-2-[(2R)-4-(3-aminophenyl)-3-oxomorpholin-2-yl]-2-hydroxy-N-[4-(5-oxo-4H-1,2,4-oxadiazol-3-yl)phenyl]acetamide hydrochloride (compound 44-7)

According to the Step 38-6 in synthetic method for EXAMPLE 38, 44-6 (6.0 g) was used instead of 38-5 to obtain compound 44-7 (6.3 g) as a beige amorphous solid.

Step 44-8

Synthesis of (2R)—N-(4-amidinophenyl)-2-[(2R)-4-(3-aminophenyl)-3-oxomorpholin-2-yl]-2-hydroxyacetamide dihydrochloride (EXAMPLE 44)

According to the Step 26-B in synthetic method for EXAMPLE 26, compound 44-7 (75 mg) was used instead of 26-14 to obtain EXAMPLE 44 (32.3 mg) as a colorless amorphous solid.

Example 45

Synthesis of (2R)-2-[(2R)-4-(3-acetamidophenyl)-3-oxomorpholin-2-yl]-N-(4-amidinophenyl)-2-hydroxyacetamide hydrochloride (EXAMPLE 45)

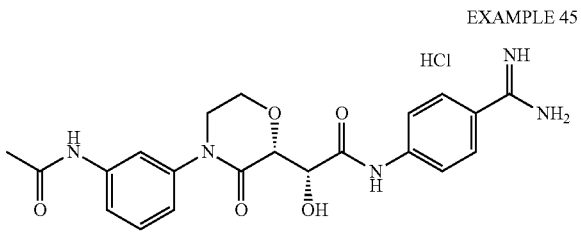 [SMILES: CC(=O)Nc1cccc(N2CCO[C@H]([C@@H](O)C(=O)Nc3ccc(C(=N)N)cc3)C2=O)c1 ; Cl]

Step 45-1

2R)-2-[(2R)-4-(3-acetamidophenyl)-3-oxomorpholin-2-yl]-2-hydroxy-N-[4-(5-oxo-4H-1,2,4-oxadiazol-3-yl)phenyl]acetamide (compound 45-1)

According to the Step 26-6 in synthetic method for EXAMPLE 26, 44-7 (150 mg) was used instead of 26-5 to obtain compound 45-1 (80.8 mg) as a beige amorphous solid.

Step 45-2

Synthesis of (2R)-2-[(2R)-4-(3-acetamidophenyl)-3-oxomorpholin-2-yl]-N-(4-amidinophenyl)-2-hydroxyacetamide hydrochloride (EXAMPLE 45)

According to the Step 26-B in synthetic method for EXAMPLE 26, compound 45-1 (65 mg) was used instead of 26-14 to obtain EXAMPLE 45 (34.9 mg) as a colorless amorphous solid.

Example 46

Synthesis of (2R)—N-(4-amidinophenyl)-2-hydroxy-2-[(2R)-3-oxo-4-[3-(2-oxopyrrolidin-1-yl)phenyl]morpholin-2-yl]acetamide hydrochloride (EXAMPLE 46)

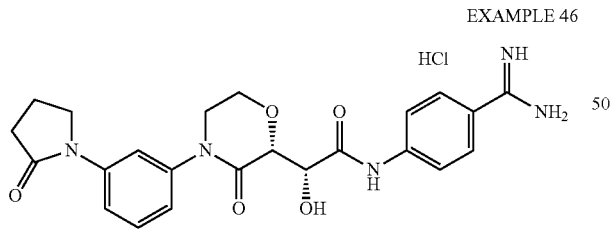

Step 46-1

Synthesis of (2R)-2-hydroxy-N-[4-(5-oxo-4H-1,2,4-oxadiazol-3-yl)phenyl]-2-[(2R)-3-oxo-4-[3-(2-oxopyrrolidin-1-yl)phenyl]morpholin-2-yl]acetamide (compound 46-1)

According to the Step 29-1 in synthetic method for EXAMPLE 29, compound 44-7 (150 mg) was used instead of 26-5 to obtain compound 46-1 (74.7 mg) as a beige amorphous solid.

Step 46-2

Synthesis of (2R)—N-(4-amidinophenyl)-2-hydroxy-2-[(2R)-3-oxo-4-[3-(2-oxopyrrolidin-1-yl)phenyl]morpholin-2-yl]acetamide hydrochloride (EXAMPLE 46)

According to the Step 26-B in synthetic method for EXAMPLE 26, compound 46-1 (65 mg) was used instead of 26-14 to obtain EXAMPLE 46 (20.9 mg) as a colorless amorphous solid.

Example 47

Synthesis of (2R)—N-(4-amidinophenyl)-2-[(2R)-4-[3-(carbamoylamino)phenyl]-3-oxomorpholin-2-yl]-2-hydroxyacetamide hydrochloride (EXAMPLE 47)

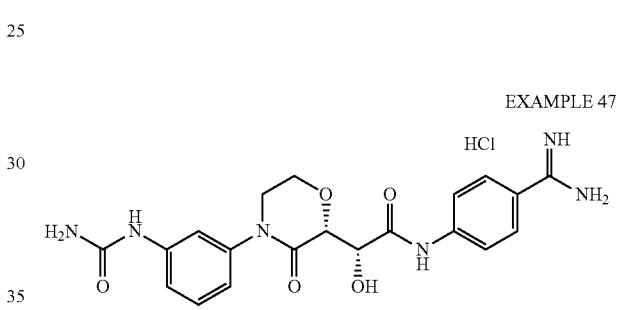

Step 47-1

Synthesis of (2R)-2-[(2R)-4-[3-(carbamoylamino)phenyl]-3-oxomorpholin-2-yl]-2-hydroxy-N-[4-(5-oxo-4H-1,2,4-oxadiazol-3-yl)phenyl]acetamide (compound 47-1)

According to the Step 27-1 in synthetic method for EXAMPLE 27, compound 44-7 (150 mg) was used instead of 26-5 to obtain compound 47-1 (51.3 mg) as a colorless amorphous solid.

Step 47-2

Synthesis of (2R)—N-(4-amidinophenyl)-2-[(2R)-4-[3-(carbamoylamino)phenyl]-3-oxomorpholin-2-yl]-2-hydroxyacetamide hydrochloride (EXAMPLE 47)

According to the Step 26-B in synthetic method for EXAMPLE 26, compound 47-1 (45 mg) was used instead of 26-14 to obtain EXAMPLE 47 (23 mg) as a colorless amorphous solid.

Example 48

Synthesis of (2R)—N-(4-amidinophenyl)-2-hydroxy-2-[(2R)-3-oxo-4-[3-(2-oxo-1,3-oxazolidin-3-yl)phenyl]morpholin-2-yl]acetamide hydrochloride (EXAMPLE 48)

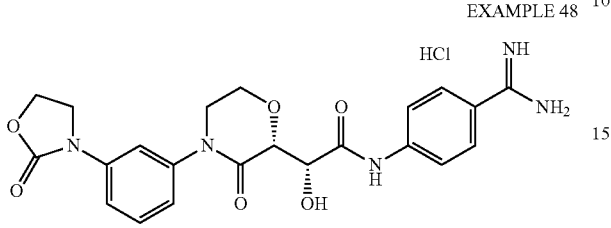

EXAMPLE 48

Step 48-1

Synthesis of (2R)-2-hydroxy-N-[4-(5-oxo-4H-1,2,4-oxadiazol-3-yl)phenyl]-2-[(2R)-3-oxo-4-[3-(2-oxo-1,3-oxazolidin-3-yl)phenyl]morpholin-2-yl]acetamide (compound 48-1)

According to the Step 29-1 in synthetic method for EXAMPLE 29, compound 44-7 (150 mg) was used instead of 26-5 to obtain compound 48-1 (79.4 mg) as a beige amorphous solid.

Step 48-2

Synthesis of (2R)—N-(4-amidinophenyl)-2-hydroxy-2-[(2R)-3-oxo-4-[3-(2-oxo-1,3-oxazolidin-3-yl)phenyl]morpholin-2-yl]acetamide hydrochloride (EXAMPLE 48)

According to the Step 26-B in synthetic method for EXAMPLE 26, compound 48-1 (65 mg) was used instead of 26-14 to obtain EXAMPLE 48 (37.2 mg) as a colorless amorphous solid.

Example 49

Synthesis of (2R)—N-(4-amidinophenyl)-2-hydroxy-2-[(2R)-4-[3-(methanesulfonamido)phenyl]-3-oxomorpholin-2-yl]acetamide hydrochloride (EXAMPLE 49)

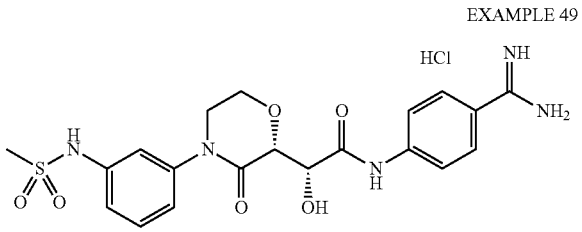 [SMILES: CS(=O)(=O)Nc1cccc(N2CCO[C@H]([C@@H](O)C(=O)Nc3ccc(C(=N)N)cc3)C2=O)c1 ; Cl]

EXAMPLE 49

Step 49-1

Synthesis of (2R)-2-hydroxy-2-[(2R)-4-[3-(methanesulfonamido)phenyl]-3-oxomorpholin-2-yl]-N-[4-(5-oxo-4H-1,2,4-oxadiazol-3-yl)phenyl]acetamide (compound 49-1)

According to the Step 28-1 in synthetic method for EXAMPLE 28, compound 44-7 (150 mg) was used instead of 26-5 to obtain compound 49-1 (28.6 mg) as a pale pink amorphous solid.

Step 49-2

Synthesis of (2R)—N-(4-amidinophenyl)-2-hydroxy-2-[(2R)-4-[3-(methanesulfonamido)phenyl]-3-oxomorpholin-2-yl]acetamide hydrochloride (EXAMPLE 49)

According to the Step 26-B in synthetic method for EXAMPLE 26, compound 49-1 (25 mg) was used instead of 26-14 to obtain EXAMPLE 49 (10.1 mg) as a colorless amorphous solid.

Example 50

Synthesis of (2R)—N-(4-amidinophenyl)-2-hydroxy-2-[(2R)-4-[3-[(2-hydroxyacetyl)amino]phenyl]-3-oxomorpholin-2-yl]acetamide hydrochloride (EXAMPLE 50)

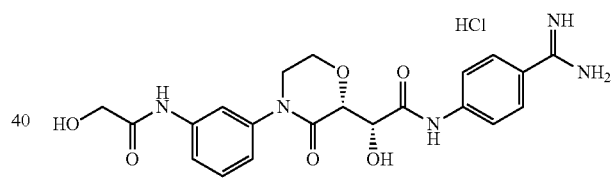

EXAMPLE 50

Step 50-1

Synthesis of (2R)-2-hydroxy-N-[4-(5-oxo-4H-1,2,4-oxadiazol-3-yl)phenyl]-2-[(2R)-3-oxo-4-[3-[(2-phenylmethoxyacetyl)amino]phenyl]morpholin-2-yl]acetamide (compound 50-1)

According to the Step 28-1 in synthetic method for EXAMPLE 28, compound 44-7 (150 mg) was used instead of 26-5 to obtain compound 50-1 (41.4 mg) as a pale pink amorphous solid.

Step 50-2

Synthesis of (2R)—N-(4-amidinophenyl)-2-hydroxy-2-[(2R)-4-[3-[(2-hydroxyacetyl)amino]phenyl]-3-oxomorpholin-2-yl]acetamide hydrochloride (EXAMPLE 50)

According to the Step 26-B in synthetic method for EXAMPLE 26, compound 50-1 (38 mg) was used instead of 26-14 to obtain EXAMPLE 50 (15 mg) as a colorless amorphous solid.

Example 51

Synthesis of (2R)—N-(4-amidinophenyl)-2-hydroxy-2-[(2R)-3-oxo-4-[3-(3-oxomorpholin-4-yl)phenyl]morpholin-2-yl]acetamide hydrochloride (EXAMPLE 51)

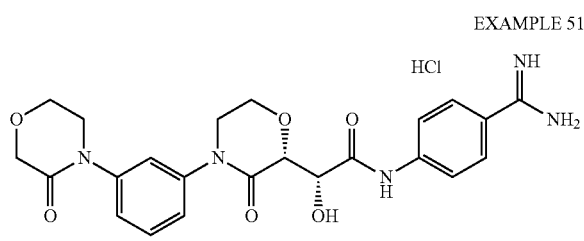 [SMILES: N=C(N)c1ccc(NC(=O)[C@H](O)[C@H]2OCCN(c3cccc(N4CCOCC4=O)c3)C2=O)cc1 ; Cl]

EXAMPLE 51

Step 51-1

Synthesis of (2R)-2-hydroxy-N-[4-(5-oxo-4H-1,2,4-oxadiazol-3-yl)phenyl]-2-[(2R)-3-oxo-4-[3-(3-oxomorpholin-4-yl)phenyl]morpholin-2-yl]acetamide (compound 51-1)

According to the Step 30-1 in synthetic method for EXAMPLE 30, 44-7 (150 mg) was used instead of 26-5 to obtain compound 51-1 (46.8 mg) as a beige amorphous solid.

Step 51-2

Synthesis of (2R)—N-(4-amidinophenyl)-2-hydroxy-2-[(2R)-3-oxo-4-[3-(3-oxomorpholin-4-yl)phenyl]morpholin-2-yl]acetamide hydrochloride (EXAMPLE 51)

According to the Step 26-B in synthetic method for EXAMPLE 26, compound 51-1 (43 mg) was used instead of 26-14 to obtain EXAMPLE 51 (9.8 mg) as a pale beige amorphous solid.

Example 52

Synthesis of (2R)—N-(1-aminoisoquinolin-6-yl)-2-[(2R)-4-(4-tert-butylphenyl)-3-oxomorpholin-2-yl]-2-hydroxyacetamide hydrochloride (EXAMPLE 52)

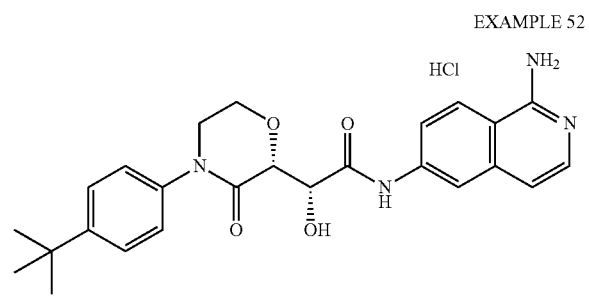 [SMILES: CC(C)(C)c1ccc(N2CCO[C@H]([C@@H](O)C(=O)Nc3ccc4c(N)nccc4c3)C2=O)cc1 ; Cl]

EXAMPLE 52

Step 52-1

Synthesis of tert-butyl (2R,3R)-2,3-diacetyloxy-4-[4-tert-butyl-N-(2-chloroethyl)anilino]-4-oxobutanoate (compound 52-1)

To a solution of (R,R)-2,3-bis(acetyloxy)-butanedioic acid mono tert-butyl ester (9 g: Tetrahedron, 45, 3071-3080, 1989) in $CH_2Cl_2$ (90 mL), were added compound 11-1 (6.6 g) and 1-ethyl-3-(3'-dimethylaminopropyl)carbodiimide hydrochloride at 0° C. The reaction mixture was stirred for 5 hours at room temperature. Then water was added into the mixture and it was extracted with $CH_2Cl_2$. The organic layer was washed with brine, dried with anhyd. $Na_2SO_4$. The solvent was removed under reduced pressure to obtain compound 52-1 (15.8 g) as a brown amorphous solid.

Step 52-2

Synthesis of tert-butyl (2R,3R)-4-[4-tert-butyl-N-(2-chloroethyl)anilino]-2,3-dihydroxy-4-oxobutanoate (compound 52-2)

According to the Step 7-4 in synthetic method for EXAMPLE 7, compound 52-1 (15.5 g) was used instead of 7-3 to obtain compound 52-2 (13 g) as a brown oil.

Step 52-3

Synthesis of tert-butyl (2R)-2-[(2R)-4-(4-tert-butylphenyl)-3-oxomorpholin-2-yl]-2-hydroxyacetate (compound 52-3)

According to the Step 7-5 in synthetic method for EXAMPLE 7, compound 52-2 (12.8 g) was used instead of 7-4 to obtain compound 52-3 (4.85 g) as a pale yellow amorphous solid.

Step 52-4

Synthesis of (2R)-2-[(2R)-4-(4-tert-butylphenyl)-3-oxomorpholin-2-yl]-2-hydroxyacetic acid (compound 52-4)

Compound 52-3 (1.5 g) was resolved in 4N HCl-dioxane (30 mL). The reaction mixture was stirred at room temperature overnight. The mixture was concentrated in vacuo to obtain compound 52-4 (1.44 g) as a beige amorphous hygroscopic solid.

Step 52-5

Synthesis of (2R)—N—[N,N-bis(tert-butoxycarbonyl)-1-aminoisoquinolin-6-yl]-2-[(2R)-4-(4-tert-butyl phenyl)-3-oxomorpholin-2-yl]-2-hydroxyacetamide (compound 52-5)

According to the Step 1-3 in synthetic method for EXAMPLE 1, 52-4 (0.38 g) was used instead of 1-2 to obtain compound 52-5 (92 mg) as a colorless amorphous solid.

Step 52-6

Synthesis of (2R)—N-(1-aminoisoquinolin-6-yl)-2-[(2R)-4-(4-tert-butylphenyl)-3-oxomorpholin-2-yl]-2-hydroxyacetamide hydrochloride (EXAMPLE 52)

According to the Step 38-6 in synthetic method for EXAMPLE 38, 52-5 (91 mg) was used instead of 38-5 to obtain EXAMPLE 52 (60 mg) as a colorless amorphous solid.

Example 53

Synthesis of (2R)-2-[(2R)-4-(4-tert-butylphenyl)-3-oxomorpholin-2-yl]-2-hydroxy-N-(1-imino-2,3-dihydroisoindol-5-yl)acetamide hydrochloride (EXAMPLE 53)

EXAMPLE 53

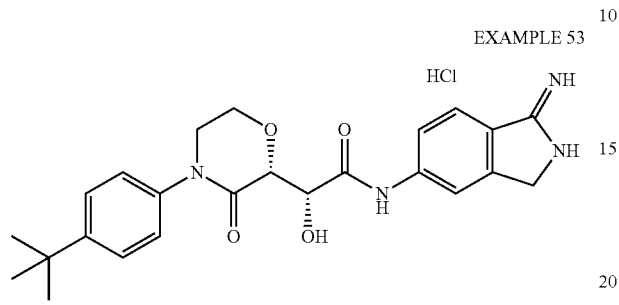

Step 53-1

Synthesis of tert-butyl N—[[5-[[(2R)-2-[(2R)-4-(4-tert-butylphenyl)-3-oxomorpholin-2-yl]-2-hydroxyacetyl]amino]-2-cyanophenyl]methyl]-N-[(2-methylpropan-2-yl)oxycarbonyl]carbamate (compound 53-1)

According to the Step 1-3 in synthetic method for EXAMPLE 1, 52-4 (0.38 g) and compound 39-2 (0.1 g) were used instead of 1-2 and 6-amino-1-bis(tert-butoxy carbonyl)aminoisoquinoline to obtain compound 53-1 (96 mg) as a colorless amorphous solid.

Step 53-2

Synthesis of (2R)—N-[3-(aminomethyl)-4-cyanophenyl]-2-[(2R)-4-(4-tert-butylphenyl)-3-oxomorpholin-2-yl]-2-hydroxyacetamide hydrochloride (compound 53-2)

According to the Step 38-6 in synthetic method for EXAMPLE 38, compound 53-1 (95 mg) was used instead of 38-5 to obtain compound 53-2 (63 mg) as a colorless amorphous solid.

Step 53-3

Synthesis of (2R)-2-[(2R)-4-(4-tert-butylphenyl)-3-oxomorpholin-2-yl]-2-hydroxy-N-(1-imino-2,3-dihydroisoindol-5-yl)acetamide hydrochloride (EXAMPLE 53)

According to the Step 39-7 in synthetic method for EXAMPLE 39, compound 53-2 (63 mg) was used instead of 39-6 to obtain EXAMPLE 53 (52 mg) as a colorless amorphous solid.

Example 54

Synthesis of (2R)—N-(1-aminoisoquinolin-6-yl)-2-hydroxy-2-[(2R)-3-oxo-4-[4-(trifluoromethyl)phenyl]morpholin-2-yl]acetamide hydrochloride (EXAMPLE 54)

EXAMPLE 54

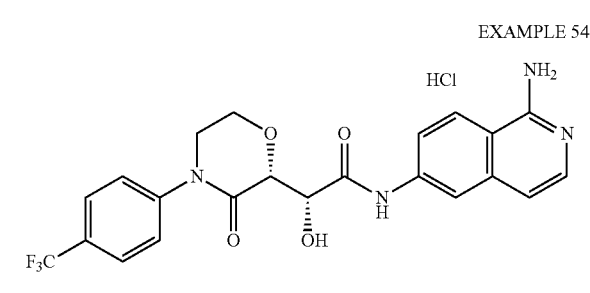 [SMILES: Nc1nccc2cc(NC(=O)[C@H](O)[C@H]3OCCN(c4ccc(C(F)(F)F)cc4)C3=O)ccc12 ; Cl]

Step 54-1

Synthesis of N-(2-chloro-N-[4-(trifluoromethyl)phenyl]acetamide (compound 54-1)

According to the Step 20-1 in synthetic method for EXAMPLE 20, 4-trifluoromethyl aniline (5 g) was used instead of 5-amino-1,3-dihydro-2H-benzimidazol-2-one to obtain compound 54-1 (6.94 g) as a brown amorphous solid.

Step 54-2

Synthesis of N-(2-chloroethyl)-4-(trifluoromethyl)aniline (compound 54-2)

According to the Step 20-2 in synthetic method for EXAMPLE 20, compound 54-1 (3.5 g) was used instead of 20-1 to obtain compound 54-2 (3.36 g) as brown oil.

Step 54-3

Synthesis of tert-butyl (2R,3R)-2,3-diacetyloxy-4-[N-(2-chloroethyl)-4-(trifluoromethyl)anilino]-4-oxobutanoate (compound 54-3)

To a solution of (R,R)-2,3-bis(acetyloxy)-butanedioic acid mono tert-butyl ester (3.25 g: Tetrahedron, 45, 3071-3080, 1989) in CH$_2$Cl$_2$ (65 mL), were added oxalyl chloride (1.06 mL) and DMF (50 microL) at 0° C. The reaction mixture was stirred at 0° C. for 30 minutes then pyridine (3.82 mL) was added into the mixture at the same temperature. The reaction mixture was stirred at the same temperature for 5 minutes. To the mixture, was added a solution of compound 54-2 (2.5 g) in CH$_2$Cl$_2$ (12.5 mL) at 0° C. The mixture was stirred for 1 hour at the same temperature. Then the mixture was concentrated in vacuo and the resulting residue was suspended in water. The mixture was extracted with EtOAc and the organic layer was washed with 1N HCl aq., sat. NaHCO$_3$ aq., brine, and it was dried with anhyd. Na$_2$SO$_4$. The solvent was removed under reduced pressure to obtain compound 54-3 (5.7 g) as brown oil.

Step 54-4

Synthesis of tert-butyl (2R,3R)-4-[N-(2-chloroethyl)-4-(trifluoromethyl)anilino]-2,3-dihydroxy-4-oxobutanoate (compound 54-4)

According to the Step 7-4 in synthetic method for EXAMPLE 7, compound 54-3 (5.5 g) was used instead of 7-3 to obtain compound 54-4 (4.57 g) as a brown amorphous solid.

Step 54-5

Synthesis of tert-butyl (2R)-2-hydroxy-2-[(2R)-3-oxo-4-[4-(trifluoromethyl)phenyl]morpholin-2-yl]acetate (compound 54-5)

According to the Step 7-5 in synthetic method for EXAMPLE 7, compound 54-4 (3 g) was used instead of 7-4 to obtain compound 54-5 (220 mg) as a pale yellow amorphous solid.

Step 54-6

Synthesis of (2R)-2-hydroxy-2-[(2R)-3-oxo-4-[4-(trifluoromethyl)phenyl]morpholin-2-yl]acetic acid (compound 54-6)

According to the Step 52-4 in synthetic method for EXAMPLE 52, compound 54-5 (0.2 g) was used instead of 52-3 to obtain compound 54-6 (128 mg) as a colorless amorphous solid.

Step 54-7

Synthesis of (2R)—N—[N,N-bis(tert-butoxycarbonyl)-1-aminoisoquinolin-6-yl]-2-hydroxy-2-[(2R)-3-oxo-4-[4-(trifluoromethyl)phenyl]morpholin-2-yl]acetamide (compound 54-7)

According to the Step 1-3 in synthetic method for EXAMPLE 1, compound 54-6 (128 mg) was used instead of 1-2 to obtain compound 54-7 (107 mg) as a beige amorphous solid.

Step 54-8

Synthesis of (2R)—N-(1-aminoisoquinolin-6-yl)-2-hydroxy-2-[(2R)-3-oxo-4-[4-(trifluoromethyl)phenyl]morpholin-2-yl]acetamide hydrochloride (EXAMPLE 54)

According to the Step 38-6 in synthetic method for EXAMPLE 38, 54-7 (50 mg) was used instead of 38-5 to obtain EXAMPLE 54 (28.3 mg) as a leaf green amorphous solid.

Example 55

Synthesis of (2R)—N-(1-aminoisoquinolin-6-yl)-2-hydroxy-2-[(2R)-3-oxo-4-[4-(trifluoromethoxy)phenyl]morpholin-2-yl]acetamide hydrochloride (EXAMPLE 55)

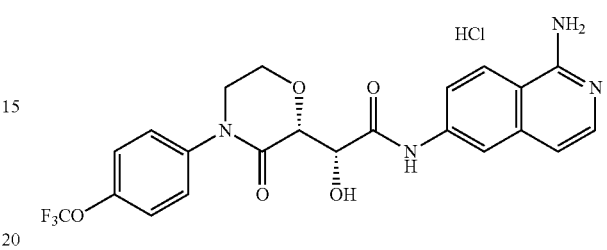

EXAMPLE 55

Step 55-1

Synthesis of 2-chloro-N-[4-(trifluoromethoxy)phenyl]acetamide (compound 55-1)

According to the Step 20-1 in synthetic method for EXAMPLE 20, 4-trifluoromethoxyaniline (5 g) was used instead of 5-amino-1,3-dihydro-2H-benzimidazol-2-one to obtain compound 55-1 (6.67 g) as a khaki amorphous solid.

Step 55-2

Synthesis of N-(2-chloroethyl)-4-(trifluoromethoxy)aniline (compound 55-2)

According to the Step 20-2 in synthetic method for EXAMPLE 20, compound 55-1 (3.3 g) was used instead of 20-1 to obtain compound 55-2 (3.21 g) as brown oil.

Step 55-3

Synthesis of tert-butyl (2R,3R)-2,3-diacetyloxy-4-[N-(2-chloroethyl)-4-(trifluoromethoxy)anilino]-4-oxobutan oate (compound 55-3)

According to the Step 54-3 in synthetic method for EXAMPLE 54, compound 55-2 (3.05 g) was used instead of 54-2 to obtain compound 55-3 (6.51 g) as brown oil.

Step 55-4

Synthesis of tert-butyl (2R,3R)-4-[N-(2-chloroethyl)-4-(trifluoromethoxy)anilino]-2,3-dihydroxy-4-oxobutanoate (compound 55-4)

According to the Step 7-4 in synthetic method for EXAMPLE 7, compound 55-3 (6.45 g) was used instead of 7-3 to obtain compound 55-4 (5.39 g) as brown amorphous solid.

Step 55-5

Synthesis of tert-butyl (2R)-2-hydroxy-2-[(2R)-3-oxo-4-[4-(trifluoromethoxy)phenyl]morpholin-2-yl]acetate (compound 55-5)

According to the Step 7-5 in synthetic method for EXAMPLE 7, compound 55-4 (3 g) was used instead of 7-4 to obtain compound 55-5 (0.81 g) as a brown amorphous solid.

Step 55-6

Synthesis of (2R)-2-hydroxy-2-[(2R)-3-oxo-4-[4-(trifluoromethoxy)phenyl]morpholin-2-yl]acetic acid (compound 55-6)

According to the Step 52-4 in synthetic method for EXAMPLE 52, compound 55-5 (0.6 g) was used instead of 52-3 to obtain compound 55-6 (0.7 g) as brown oil.

Step 55-7

Synthesis of (2R)—N—[N,N-bis(tert-butoxycarbonyl)-1-aminoisoquinolin-6-yl]-2-hydroxy-2-[(2R)-3-oxo-4-[4-(trifluoromethoxy)phenyl]morpholin-2-yl]acetamide (compound 55-7)

According to the Step 1-3 in synthetic method for EXAMPLE 1, compound 55-6 (0.3 g) was used instead of 1-2 to obtain compound 55-7 (157 mg) as a beige powder.

Step 55-8

Synthesis of (2R)—N-(1-aminoisoquinolin-6-yl)-2-hydroxy-2-[(2R)-3-oxo-4-[4-(trifluoromethoxy)phenyl]morpholin-2-yl]acetamide hydrochloride (EXAMPLE 55)

According to the Step 38-6 in synthetic method for EXAMPLE 38, compound 55-7 (50 mg) was used instead of 38-5 to obtain EXAMPLE 55 (28.5 mg) as a leaf green amorphous solid.

Example 56

Synthesis of (2R)—N-(4-amidinophenyl)-2-hydroxy-2-[(2R)-3-oxo-4-[4-(trifluoromethoxy)phenyl]morpholin-2-yl]acetamide hydrochloride (EXAMPLE 56)

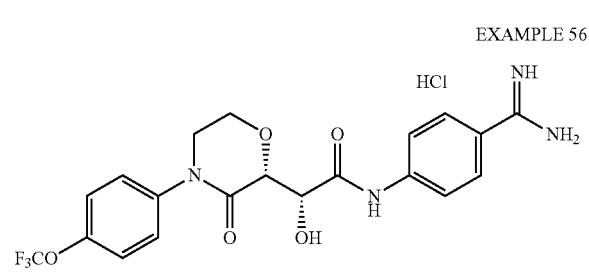 [SMILES: N=C(N)c1ccc(NC(=O)[C@H](O)[C@H]2OCCN(c3ccc(OC(F)(F)F)cc3)C2=O)cc1 ; Cl]

EXAMPLE 56

Step 56-1

Synthesis of (2R)-2-hydroxy-N-[4-(5-oxo-4H-1,2,4-oxadiazol-3-yl)phenyl]-2-[(2R)-3-oxo-4-[4-(trifluoromethoxy)phenyl]morpholin-2-yl]acetamide (compound 56-1)

According to the Step 1-3 in synthetic method for EXAMPLE 1, compound 55-6 (0.3 g) and 3-(4-aminophenyl)-1,2,4-oxadiazol-5(2H)-one with DMF were used instead of 1-2 and 6-amino-1-bis(tert-butoxycarbonyl)aminoisoquinoline to obtain compound 56-1 (26 mg) as a colorless amorphous solid.

Step 56-2

Synthesis of (2R)—N-(4-amidinophenyl)-2-hydroxy-2-[(2R)-3-oxo-4-[4-(trifluoromethoxy)phenyl]morpholin-2-yl]acetamide hydrochloride (EXAMPLE 56)

According to the Step 26-B in synthetic method for EXAMPLE 26, compound 56-1 (23 mg) was used instead of 26-14 to obtain EXAMPLE 56 (13.5 mg) as a pale yellow amorphous solid.

Example 57

Synthesis of (2R)-2-hydroxy-N-(1-imino-2,3-dihydroisoindol-5-yl)-2-[(2R)-3-oxo-4-[4-(trifluoromethoxy)phenyl]morpholin-2-yl]acetamide hydrochloride (EXAMPLE 57)

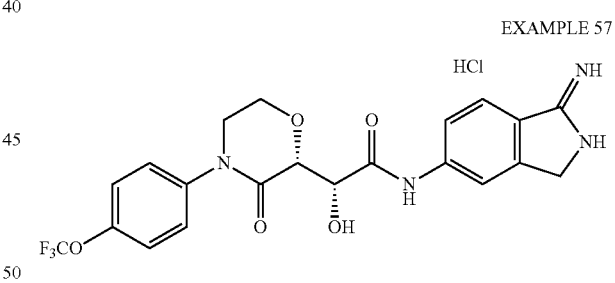

EXAMPLE 57

Step 57-1

Synthesis of N—[[2-cyano-5-[[(2R)-2-hydroxy-2-[(2R)-3-oxo-4-[4-(trifluoromethoxy)phenyl]morpholin-2-yl]acetyl]amino]phenyl]methyl]-N-[(2-methylpropan-2-yl)oxycarbonyl]carbamate (compound 56-1)

According to the Step 1-3 in synthetic method for EXAMPLE 1, a cyclic carbonate analogue (0.15 g) derived from compound 55-6 and 39-2 (0.14 g) were used instead of 1-2 and 6-amino-1-bis(tert-butoxycarbonyl)aminoisoquinoline to obtain compound 57-1 (147 mg) as a pale yellow amorphous solid.

Step 57-2

Synthesis of (2R)—N-[3-(aminomethyl)-4-cyanophenyl]-2-hydroxy-2-[(2R)-3-oxo-4-[4-(trifluoromethoxy)phenyl]morpholin-2-yl]acetamide hydrochloride (compound 57-2)

According to the Step 38-6 in synthetic method for EXAMPLE 38, 57-1 (0.14 g) was used instead of 38-5 to obtain compound 57-2 (93 mg) as a pale yellow amorphous solid.

Step 57-3

Synthesis of (2R)-2-hydroxy-N-(1-imino-2,3-dihydroisoindol-5-yl)-2-[(2R)-3-oxo-4-[4-(trifluoromethoxy)phenyl]morpholin-2-yl]acetamide hydrochloride (EXAMPLE 57)

According to the Step 39-7 in synthetic method for EXAMPLE 39, 57-3 (89 mg) was used instead of 39-6 to obtain EXAMPLE 57 (66.4 mg) as a pale yellow amorphous solid.

Example 58

Synthesis of (2R)—N-(1-aminoisoquinolin-6-yl)-2-[(2R)-4-(4-bromophenyl)-3-oxomorpholin-2-yl]-2-hydroxyacetamide hydrochloride (EXAMPLE 58)

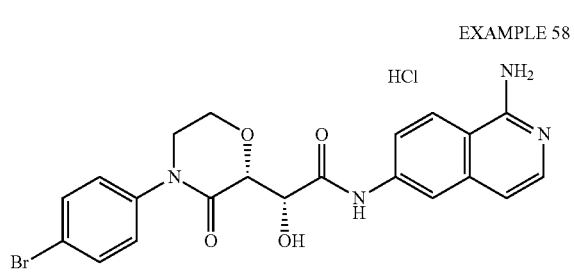 [SMILES: Nc1nccc2cc(NC(=O)[C@H](O)[C@H]3OCCN(c4ccc(Cl)cc4)C3=O)ccc12 ; Cl]

EXAMPLE 58

Step 58-1

Synthesis of N-(4-bromophenyl)-2-chloroacetamide (compound 58-1)

According to the Step 20-1 in synthetic method for EXAMPLE 20, 4-bromoaniline (5 g) was used instead of 5-amino-1,3-dihydro-2H-benzimidazol-2-one to obtain compound 58-1 (7.28 g) as a gray amorphous solid.

Step 58-2

Synthesis of 4-bromo-N-(2-chloroethyl)aniline (compound 58-2)

According to the Step 20-2 in synthetic method for EXAMPLE 20, compound 58-1 (7 g) was used instead of 20-1 to obtain compound 58-2 (6.81 g) as brown oil.

Step 58-3

Synthesis of tert-butyl (2R,3R)-2,3-diacetyloxy-4-[4-bromo-N-(2-chloroethyl)anilino]-4-oxobutanoate (compound 58-3)

According to the Step 54-3 in synthetic method for EXAMPLE 54, compound 58-2 (6.06 g) was used instead of 54-2 to obtain compound 58-3 (13.2 g) as brown oil.

Step 58-4

Synthesis of tert-butyl (2R,3R)-4-[4-bromo-N-(2-chloroethyl)anilino]-2,3-dihydroxy-4-oxobutanoate (compound 58-4)

According to the Step 7-4 in synthetic method for EXAMPLE 7, compound 58-3 (12.5 g) was used instead of 7-3 to obtain compound 58-4 (10.7 g) as brown oil.

Step 58-5

Synthesis of tert-butyl (2R)-2-[(2R)-4-(4-bromophenyl)-3-oxomorpholin-2-yl]-2-hydroxyacetate (compound 58-5)

According to the Step 7-5 in synthetic method for EXAMPLE 7, compound 58-4 (4 g) was used instead of 7-4 to obtain compound 58-5 (242 mg) as a colorless amorphous solid.

Step 58-6

Synthesis of (2R)-2-[(2R)-4-(4-bromophenyl)-3-oxomorpholin-2-yl]-2-hydroxyacetic acid (compound 58-6)

According to the Step 52-4 in synthetic method for EXAMPLE 52, compound 58-5 (0.22 g) was used instead of 52-3 to obtain compound 58-6 (188 mg) as a colorless amorphous solid.

Step 58-7

Synthesis of (2R)—N—[N,N-bis(tert-butoxycarbonyl)-1-aminoisoquinolin-6-yl]-2-[(2R)-4-(4-bromophenyl)-3-oxomorpholin-2-yl]-2-hydroxyacetamide (compound 58-7)

According to the Step 1-3 in synthetic method for EXAMPLE 1, compound 58-6 (150 mg) was used instead of 1-2 to obtain compound 58-7 (110 mg) as a colorless amorphous solid.

Step 58-8

Synthesis of (2R)—N-(1-aminoisoquinolin-6-yl)-2-[(2R)-4-(4-bromophenyl)-3-oxomorpholin-2-yl]-2-hydroxyacetamide hydrochloride (EXAMPLE 58)

According to the Step 38-6 in synthetic method for EXAMPLE 38, compound 58-7 (50 mg) was used instead of 38-5 to obtain EXAMPLE 58 (29.3 mg) as a pale yellow amorphous solid.

Example 59

Synthesis of (2R)—N-(1-aminoisoquinolin-6-yl)-2-[(2R)-4-(4-fluorophenyl)-3-oxomorpholin-2-yl]-2-hydroxyacetamide hydrochloride (EXAMPLE 59)

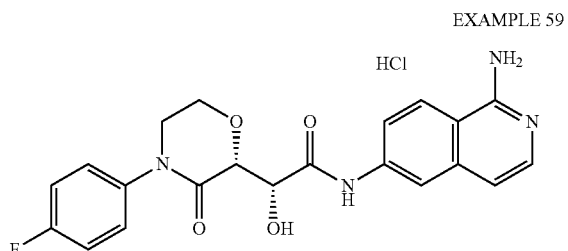

EXAMPLE 59

Step 59-1

Synthesis of 2-chloro-N-(4-fluorophenyl)acetamide (compound 59-1)

According to the Step 20-1 in synthetic method for EXAMPLE 20, 4-fluoroaniline (2.65 g) was used instead of 5-amino-1,3-dihydro-2H-benzimidazol-2-one to obtain compound 59-1 (3.4 g) as a colorless amorphous solid.

Step 59-2

Synthesis of N-(2-chloroethyl)-4-fluoroaniline (compound 59-2)

According to the Step 20-2 in synthetic method for EXAMPLE 20, compound 59-1 (2 g) was used instead of 20-1 to obtain compound 59-2 (1.95 g) as colorless oil.

Step 59-3

Synthesis of tert-butyl (2R,3R)-2,3-diacetyloxy-4-[N-(2-chloroethyl)-4-fluoroanilino]-4-oxobutanoate (compound 59-3)

According to the Step 54-3 in synthetic method for EXAMPLE 54, compound 59-2 (1.57 g) was used instead of 54-2 to obtain compound 59-3 (2.1 g) as a colorless amorphous solid.

Step 59-4

Synthesis of tert-butyl (2R,3R)-4-[N-(2-chloroethyl)-4-fluoroanilino]-2,3-dihydroxy-4-oxobutanoate (compound 59-4)

According to the Step 7-4 in synthetic method for EXAMPLE 7, compound 59-3 (2.1 g) was used instead of 7-3 to obtain compound 59-4 (1.62 g) as a colorless amorphous solid.

Step 59-5

Synthesis of tert-butyl (2R)-2-[(2R)-4-(4-fluorophenyl)-3-oxomorpholin-2-yl]-2-hydroxyacetate (compound 59-5)

According to the Step 7-5 in synthetic method for EXAMPLE 7, compound 59-4 (1.62 g) and DMF were used instead of 7-4 and t-BuOH-DMSO to obtain compound 59-5 (400 mg) as a colorless amorphous solid.

Step 59-6

Synthesis of (2R)-2-[(2R)-4-(4-fluorophenyl)-3-oxomorpholin-2-yl]-2-hydroxyacetic acid (compound 59-6)

According to the Step 52-4 in synthetic method for EXAMPLE 52, compound 59-5 (0.39 g) was used instead of 52-3 to obtain compound 59-6 (330 mg) as a colorless amorphous solid.

Step 59-7

Synthesis of (2R)—N—[N,N-bis(tert-butoxycarbonyl)-1-aminoisoquinolin-6-yl]-2-[(2R)-4-(4-fluorophenyl)-3-oxomorpholin-2-yl]-2-hydroxyacetamide (compound 59-7)

According to the Step 1-3 in synthetic method for EXAMPLE 1, compound 59-6 (0.1 g) was used instead of 1-2 to obtain compound 59-7 (85 mg) as a beige amorphous solid.

Step 59-8

Synthesis of (2R)—N-(1-aminoisoquinolin-6-yl)-2-[(2R)-4-(4-fluorophenyl)-3-oxomorpholin-2-yl]-2-hydroxyacetamide hydrochloride (EXAMPLE 59)

According to the Step 38-6 in synthetic method for EXAMPLE 38, compound 59-7 (75 mg) was used instead of 38-5 to obtain EXAMPLE 59 (43 mg) as a beige amorphous solid.

Example 60

Synthesis of (2R)—N-(1-aminoisoquinolin-6-yl)-2-[(2R)-4-(4-chlorophenyl)-3-oxomorpholin-2-yl]-2-hydroxyacetamide hydrochloride (EXAMPLE 60)

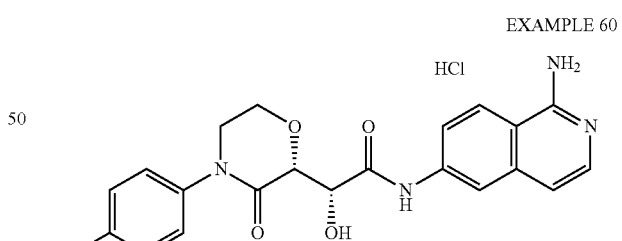

EXAMPLE 60

Step 60-1

Synthesis of 2-chloro-N-(4-chlorophenyl)acetamide (compound 60-1)

According to the Step 20-1 in synthetic method for EXAMPLE 20, 4-chloroaniline (3.04 g) was used instead of 5-amino-1,3-dihydro-2H-benzimidazol-2-one to obtain compound 60-1 (4 g) as a colorless amorphous solid.

Step 60-2

Synthesis of 4-chloro-N-(2-chloroethyl)aniline (compound 60-2)

According to the Step 20-2 in synthetic method for EXAMPLE 20, compound 60-1 (2 g) was used instead of 20-1 to obtain compound 60-2 (1.95 g) as colorless oil.

Step 60-3

Synthesis of tert-butyl (2R,3R)-2,3-diacetyloxy-4-[4-chloro-N-(2-chloroethyl)anilino]-4-oxobutanoate (compound 60-3)

According to the Step 54-3 in synthetic method for EXAMPLE 54, compound 60-2 (1.87 g) was used instead of 54-2 to obtain compound 60-3 (2.2 g) as a light pink amorphous solid.

Step 60-4

Synthesis of tert-butyl (2R,3R)-4-[4-chloro-N-(2-chloroethyl)anilino]-2,3-dihydroxy-4-oxobutanoate (compound 60-4)

According to the Step 7-4 in synthetic method for EXAMPLE 7, compound 60-3 (2.2 g) was used instead of 7-3 to obtain compound 60-4 (1.78 g) as a light yellow amorphous solid.

Step 60-5

Synthesis of tert-butyl (2R)-2-[(2R)-4-(4-chlorophenyl)-3-oxomorpholin-2-yl]-2-hydroxyacetate (compound 60-5)

According to the Step 7-5 in synthetic method for EXAMPLE 7, compound 60-4 (1.78 g) and DMF were used instead of 7-4 and t-BuOH-DMSO to obtain compound 60-5 (400 mg) as a pale yellow amorphous solid.

Step 60-6

Synthesis of (2R)-2-[(2R)-4-(4-chlorophenyl)-3-oxomorpholin-2-yl]-2-hydroxyacetic acid (compound 60-6)

According to the Step 52-4 in synthetic method for EXAMPLE 52, compound 60-5 (0.39 g) was used instead of 52-3 to obtain compound 60-6 (310 mg) as a pale yellow amorphous solid.

Step 60-7

Synthesis of (2R)—N—[N,N-bis(tert-butoxycarbonyl)-1-aminoisoquinolin-6-yl]-2-[(2R)-4-(4-chlorophenyl)-3-oxomorpholin-2-yl]-2-hydroxyacetamide (compound 60-7)

According to the Step 1-3 in synthetic method for EXAMPLE 1, compound 60-6 (0.1 g) was used instead of 1-2 to obtain compound 60-7 (75 mg) as a beige amorphous solid.

Step 60-8

Synthesis of (2R)—N-(1-aminoisoquinolin-6-yl)-2-[(2R)-4-(4-chlorophenyl)-3-oxomorpholin-2-yl]-2-hydroxyacetamide hydrochloride (EXAMPLE 60)

According to the Step 38-6 in synthetic method for EXAMPLE 38, compound 60-7 (65 mg) was used instead of 38-5 to obtain EXAMPLE 60 (40 mg) as a beige amorphous solid.

Example 61

Synthesis of (2R)—N-(1-aminoisoquinolin-6-yl)-2-hydroxy-2-[(2R)-4-(4-isopropyloxyphenyl)-3-oxo morpholin-2-yl]acetamide hydrochloride (EXAMPLE 61)

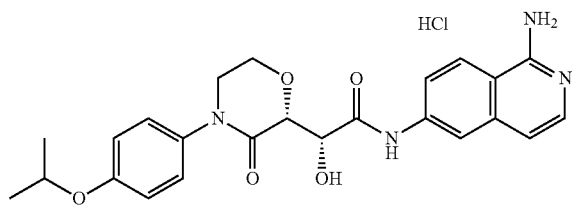

EXAMPLE 61

Step 61-1

Synthesis of 2-chloro-N-(4-isopropyloxyphenyl)acetamide (compound 61-1)

According to the Step 20-1 in synthetic method for EXAMPLE 20, 4-isopropoxyaniline (3.61 g) was used instead of 5-amino-1,3-dihydro-2H-benzimidazol-2-one to obtain compound 61-1 (3.6 g) as a beige amorphous solid.

Step 61-2

Synthesis of -(2-chloroethyl)-4-isopropyloxyaniline (compound 61-2)

According to the Step 20-2 in synthetic method for EXAMPLE 20, compound 61-1 (1.8 g) was used instead of 20-1 to obtain compound 61-2 (1.7 g) as colorless oil.

Step 61-3

Synthesis of tert-butyl (2R,3R)-2,3-diacetyloxy-4-[N-(2-chloroethyl)-4-isopropyloxyanilino]-4-oxobutanoate (compound 61-3)

According to the Step 54-3 in synthetic method for EXAMPLE 54, compound 61-2 (1.69 g) was used instead of 54-2 to obtain compound 61-3 (2.86 g) as colorless oil.

Step 61-4

Synthesis of tert-butyl (2R,3R)-4-[N-(2-chloroethyl)-4-isopropyloxyanilino]-2,3-dihydroxy-4-oxobutanoate (compound 61-4)

According to the Step 7-4 in synthetic method for EXAMPLE 7, compound 61-3 (2.8 g) was used instead of 7-3 to obtain compound 61-4 (2.13 g) as pale yellow oil.

Step 61-5

Synthesis of tert-butyl (2R)-2-hydroxy-2-[(2R)-4-(4-isopropyloxyphenyl)-3-oxomorpholin-2-yl]acetate (compound 61-5)

According to the Step 7-5 in synthetic method for EXAMPLE 7, compound 61-4 (0.8 g) was used instead of 7-4 to obtain compound 61-5 (220 mg) as a colorless amorphous solid.

Step 61-6

Synthesis of (2R)-2-hydroxy-2-[(2R)-4-(4-isopropyloxyphenyl)-3-oxomorpholin-2-yl]acetic acid (compound 61-6)

According to the Step 52-4 in synthetic method for EXAMPLE 52, compound 61-5 (0.21 g) was used instead of 52-3 to obtain compound 61-6 (112 mg) as a colorless amorphous solid.

Step 61-7

Synthesis of (2R)—N—[N,N-bis(tert-butoxycarbonyl)-1-aminoisoquinolin-6-yl]-2-hydroxy-2-[(2R)-4-(4-isopropyloxlphenyl)-3-oxomorpholin-2-yl]acetamide (compound 61-7)

According to the Step 1-3 in synthetic method for EXAMPLE 1, compound 61-6 (0.1 g) was used instead of 1-2 to obtain compound 61-7 (71 mg) as a pale brown amorphous solid.

Step 61-8

Synthesis of (2R)—N-(1-aminoisoquinolin-6-yl)-2-hydroxy-2-[(2R)-4-(4-isopropyloxyphenyl)-3-oxomorpholin-2-yl]acetamide hydrochloride (EXAMPLE 61)

According to the Step 38-6 in synthetic method for EXAMPLE 38, compound 61-7 (59 mg) was used instead of 38-5 to obtain EXAMPLE 61 (19 mg) as a pale brown amorphous solid.

Example 62

Synthesis of (2R)—N-(1-aminoisoquinolin-6-yl)-2-hydroxy-2-[(2R)-3-oxo-4-p-tolylmorpholin-2-yl]acetamide hydrochloride (EXAMPLE 62)

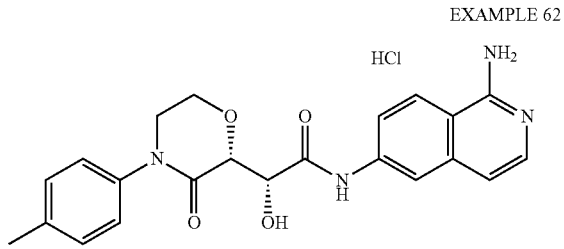 [SMILES: Cc1ccc(N2CCO[C@H]([C@@H](O)C(=O)Nc3ccc4c(N)nccc4c3)C2=O)cc1 ; Cl]

EXAMPLE 62

Step 62-1

Synthesis of tert-butyl (2R,3R)-2,3-diacetyloxy-4-[N-(2-chloroethyl)-4-methylanilino]-4-oxobutanoate (compound 62-1)

According to the Step 52-1 in synthetic method for EXAMPLE 52, compound 7-1 (3 g) was used instead of 11-1 to obtain compound 62-1 (5.81 g) as pale yellow oil.

Step 62-2

Synthesis of tert-butyl (2R,3R)-4-[N-(2-chloroethyl)-4-methylanilino]-2,3-dihydroxy-4-oxobutanoate (compound 62-2)

According to the Step 7-4 in synthetic method for EXAMPLE 7, compound 62-1 (5.45 g) was used instead of 7-3 to obtain compound 62-2 (4.7 g) as pale yellow oil.

Step 62-3

Synthesis of tert-butyl (2R)-2-hydroxy-2-[(2R)-3-oxo-4-p-tolylmorpholin-2-yl]acetate (compound 62-3)

According to the Step 7-5 in synthetic method for EXAMPLE 7, compound 62-2 (2.5 g) was used instead of 7-4 to obtain compound 62-3 (1.02 g) as a pale brown amorphous solid.

Step 62-4

Synthesis of (2R)-2-hydroxy-2-[(2R)-3-oxo-4-p-tolylmorpholin-2-yl]acetic acid (compound 62-4)

According to the Step 52-4 in synthetic method for EXAMPLE 52, compound 62-3 (1 g) was used instead of 52-3 to obtain compound 62-4 (777 mg) as a pale purple amorphous solid.

Step 62-5

Synthesis of (2R)—N—[N,N-bis(tert-butoxycarbonyl)-1-aminoisoquinolin-6-yl]-2-hydroxy-2-[(2R)-3-oxo-4-p-tolylmorpholin-2-yl]acetamide (compound 62-5)

According to the Step 1-3 in synthetic method for EXAMPLE 1, compound 62-4 (0.2 g) was used instead of 1-2 to obtain compound 62-5 (0.11 g) as a pale brown solid.

Step 62-6

Synthesis of (2R)—N-(1-aminoisoquinolin-6-yl)-2-hydroxy-2-[(2R)-3-oxo-4-p-tolylmorpholin-2-yl]acetamide hydrochloride (EXAMPLE 62)

According to the Step 38-6 in synthetic method for EXAMPLE 38, compound 62-5 (0.1 g) was used instead of 38-5 to obtain EXAMPLE 62 (51.5 mg) as a pale yellow amorphous solid.

Example 63

Synthesis of (2R)—N-(1-aminoisoquinolin-6-yl)-2-[(2R)-4-(4-fluoro-o-tolyl)-3-oxomorpholin-2-yl]-2-hydroxyacetamide hydrochloride (EXAMPLE 63)

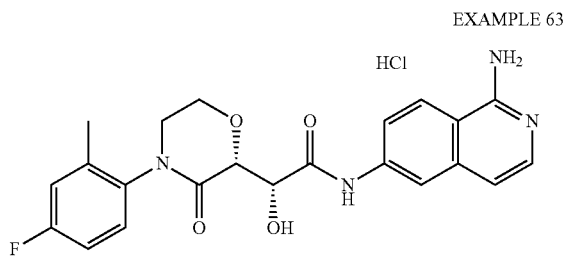

EXAMPLE 63

Step 63-1

Synthesis of 2-chloro-N-(4-fluoro-o-tolyl)acetamide (compound 63-1)

According to the Step 20-1 in synthetic method for EXAMPLE 20, 4-fluoro-2-methylaniline (5 g) was used instead of 5-amino-1,3-dihydro-2H-benzimidazol-2-one to obtain compound 63-1 (8 g) as a gray amorphous solid.

Step 63-2

Synthesis of N-(2-chloroethyl)-4-fluoro-2-methylaniline (compound 63-2)

According to the Step 20-2 in synthetic method for EXAMPLE 20, compound 63-1 (8 g) was used instead of 20-1 to obtain compound 63-2 (7.87 g) as brown oil.

Step 63-3

Synthesis of tert-butyl (2R,3R)-2,3-diacetyloxy-4-[N-(2-chloroethyl)-4-fluoro-2-methylanilino]-4-oxobutanoate (compound 63-3)

According to the Step 54-3 in synthetic method for EXAMPLE 54, compound 63-2 (7.37 g) was used instead of 54-2 to obtain compound 63-3 (10.4 g) as pale yellow oil.

Step 63-4

Synthesis of tert-butyl (2R,3R)-4-[N-(2-chloroethyl)-4-fluoro-2-methylanilino]-2,3-dihydroxy-4-oxobutanoate (compound 63-4)

According to the Step 7-4 in synthetic method for EXAMPLE 7, compound 63-3 (10.4 g) was used instead of 7-3 to obtain compound 63-4 (8 g) as a pale yellow amorphous solid.

Step 63-5

Synthesis of tert-butyl (2R)-2-[(2R)-4-(4-fluoro-o-tolyl)-3-oxomorpholin-2-yl]-2-hydroxyacetate (compound 63-5)

According to the Step 7-5 in synthetic method for EXAMPLE 7, compound 63-4 (3 g) was used instead of 7-4 to obtain compound 63-5 (710 mg) as a colorless amorphous solid.

Step 63-6

Synthesis of (2R)-2-[(2R)-4-(4-fluoro-o-tolyl)-3-oxomorpholin-2-yl]-2-hydroxyacetic acid (compound 63-6)

According to the Step 52-4 in synthetic method for EXAMPLE 52, compound 63-5 (0.7 g) was used instead of 52-3 to obtain compound 63-6 (0.72 g) as a colorless amorphous solid.

Step 63-7

Synthesis of (2R)—N—[N,N-bis(tert-butoxycarbonyl)-1-aminoisoquinolin-6-yl]-2-[(2R)-4-(4-fluoro-o-tolyl)-3-oxomorpholin-2-yl]-2-hydroxyacetamide (compound 63-7)

According to the Step 1-3 in synthetic method for EXAMPLE 1, compound 63-6 (0.3 g) was used instead of 1-2 to obtain compound 63-7 (198 mg) as a pale yellow amorphous solid.

Step 63-8

Synthesis of (2R)—N-(1-aminoisoquinolin-6-yl)-2-[(2R)-4-(4-fluoro-o-tolyl)-3-oxomorpholin-2-yl]-2-hydroxyacetamide hydrochloride (EXAMPLE 63)

According to the Step 38-6 in synthetic method for EXAMPLE 38, compound 63-7 (57.2 mg) was used instead of 38-5 to obtain EXAMPLE 63 (28.8 mg) as a pale yellow amorphous solid.

Example 64

Synthesis of (2R)—N-(4-amidinophenyl)-2-[(2R)-4-(4-fluoro-o-tolyl)-3-oxomorpholin-2-yl]-2-hydroxyacetamide hydrochloride (EXAMPLE 64)

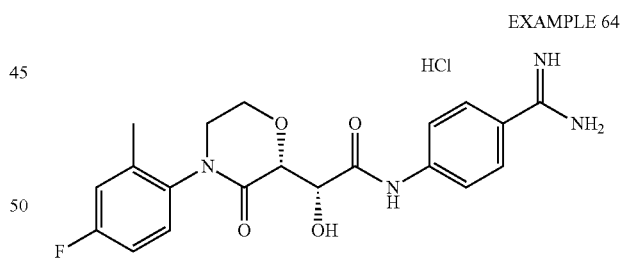

EXAMPLE 64

Step 64-1

Synthesis of (2R)-2-[(2R)-4-(4-fluoro-o-tolyl)-3-oxomorpholin-2-yl]-2-hydroxy-N-[4-(5-oxo-4H-1,2,4-oxadiazol-3-yl)phenyl]acetamide (compound 64-1)

According to the Step 1-3 in synthetic method for EXAMPLE 1, a cyclic carbonate analogue (0.11 g) derived from compound 63-6 and 3-(4-aminophenyl)-1,2,4-oxadiazol-5(2H)-one with DMF were used instead of 1-2 and 6-amino-1-bis(tert-butoxycarbonyl)aminoisoquinoline to obtain compound 64-1 (43.2 mg) as a pale pink amorphous solid.

Step 64-2

Synthesis of (2R)—N-(4-amidinophenyl)-2-[(2R)-4-(4-fluoro-o-tolyl)-3-oxomorpholin-2-yl]-2-hydroxyacetamide hydrochloride (EXAMPLE 64)

According to the Step 26-B in synthetic method for EXAMPLE 26, compound 64-1 (28.2 mg) was used instead of 26-14 to obtain EXAMPLE 64 (15.7 mg) as a pale yellow amorphous solid.

Example 65

Synthesis of (2R)—N-(4-amidino-o-tolyl)-2-[(2R)-4-(4-tert-butylphenyl)-3-oxomorpholin-2-yl]-2-hydroxyacetamide (EXAMPLE 65)

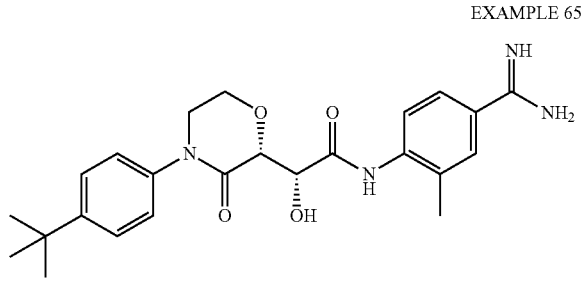 [SMILES: Cc1cc(C(=N)N)ccc1NC(=O)[C@H](O)[C@H]1OCCN(c2ccc(C(C)(C)C)cc2)C1=O]

EXAMPLE 65

Step 65-1

Synthesis of (2R)-2-[(2R)-4-(4-tert-butylphenyl)-3-oxomorpholin-2-yl]-N-(4-cyano-o-tolyl)-2-hydroxyacetamide (compound 65-1)

According to the Step 1-3 in synthetic method for EXAMPLE 1, a cyclic carbonate analogue (0.2 g) derived from compound 52-4 and 4-amino-3-methylbenzonitrile (79.3 mg) were used instead of 1-2 and 6-amino-1-bis(tert-butoxy carbonyl)aminoisoquinoline, under high concentration condition (1M), to obtain compound 65-1 (129 mg) as a colorless amorphous solid.

Step 65-2

Synthesis of (2R)—N-(4-amidino-o-tolyl)-2-[(2R)-4-(4-tert-butylphenyl)-3-oxomorpholin-2-yl]-2-hydroxyacetamide (EXAMPLE 65)

According to the Step 7-6 in synthetic method for EXAMPLE 7, compound 65-1 (60 mg) was used instead of 7-5 to obtain EXAMPLE 65 (8.3 mg) as a pale yellow amorphous solid.

Example 66

Synthesis of (2R)—N-(4-amidino-2-chlorophenyl)-2-[(2R)-4-(4-tert-butylphenyl)-3-oxomorpholin-2-yl]-2-hydroxyacetamide acetate (EXAMPLE 66)

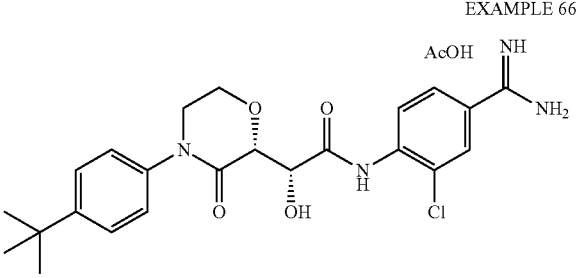 [SMILES: "AcOH" ; CC(C)(C)c1ccc(N2CCO[C@H]([C@@H](O)C(=O)Nc3ccc(C(=N)N)cc3F)C2=O)cc1]

EXAMPLE 66

Step 66-1

Synthesis of (2R)-2-[(2R)-4-(4-tert-butylphenyl)-3-oxomorpholin-2-yl]-N-(2-chloro-4-cyanophenyl)-2-hydroxyacetamide (compound 66-1)

According to the Step 1-3 in synthetic method for EXAMPLE 1, a cyclic carbonate analogue (0.2 g) derived from compound 52-4 and 4-amino-3-chlorobenzonitrile (91.6 mg) were used instead of 1-2 and 6-amino-1-bis(tert-butoxy carbonyl)aminoisoquinoline, under high concentration condition (1M), to obtain compound 66-1 (93.1 mg) as a colorless amorphous solid.

Step 66-2

Synthesis of (2R)-2-[(2R)-4-(4-tert-butylphenyl)-3-oxomorpholin-2-yl]-N-[2-chloro-4-(N'-hydroxyamidino)phenyl]-2-hydroxyacetamide (compound 66-2)

To a suspension of compound 66-1 (60 mg) in EtOH (2 mL), was added 50% $NH_2OH$ aq. (22.4 microL). The reaction mixture was stirred at room temperature overnight. Then the mixture was concentrated in vacuo to obtain compound 66-2 (67 mg) as a colorless amorphous solid.

Step 66-3

Synthesis of (2R)—N-(4-amidino-2-chlorophenyl)-2-[(2R)-4-(4-tert-butylphenyl)-3-oxomorpholin-2-yl]-2-hydroxyacetamide acetate (EXAMPLE 66)

To a solution of compound 66-2 (19 mg) in EtOH (3 mL), were added cat. Raney-Ni and AcOH (0.1 mL). The mixture was stirred under hydrogen atmosphere for 3 hours at room temperature. The mixture was filtered with Celite® pad to remove catalyst. The filtrate was concentrated with toluene in vacuo. The residue was dried by vacuum pump to obtain EXAMPLE 66 (15 mg) as a colorless amorphous solid.

Example 67

Synthesis of (2R)—N-(4-amidino-2-fluorophenyl)-2-[(2R)-4-(4-tert-butylphenyl)-3-oxomorpholin-2-yl]-2-hydroxyacetamide acetate (EXAMPLE 67)

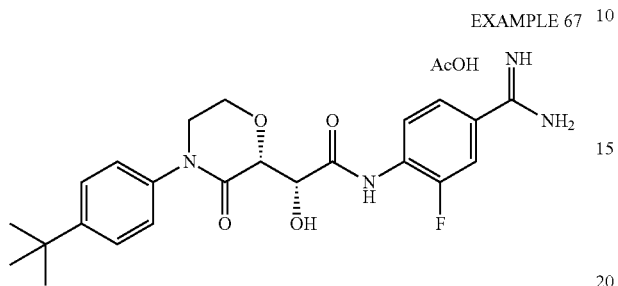

Step 67-1

Synthesis of (2R)-2-[(2R)-4-(4-tert-butylphenyl)-3-oxomorpholin-2-yl]-N-(4-cyano-2-fluorophenyl)-2-hydroxyacetamide (compound 67-1)

According to the Step 1-3 in synthetic method for EXAMPLE 1, a cyclic carbonate analogue (0.2 g) derived from compound 52-4 and 4-amino-3-fluorobenzonitrile (81.7 mg) were used instead of 1-2 and 6-amino-1-bis(tert-butoxy carbonyl)aminoisoquinoline, under high concentration condition (1M), to obtain compound 67-1 (130 mg) as a colorless amorphous solid.

Step 67-2

Synthesis of (2R)-2-[(2R)-4-(4-tert-butylphenyl)-3-oxomorpholin-2-yl]-N-[2-fluoro-4-(N'-hydroxyamidino)phenyl]-2-hydroxyacetamide (compound 67-2)

According to the Step 66-2 in synthetic method for EXAMPLE 66, compound 67-1 (67.1 mg) was used instead of 66-1 to obtain compound 67-2 (71.9 mg) as a colorless amorphous solid.

Step 67-3

Synthesis of (2R)—N-(4-amidino-2-fluorophenyl)-2-[(2R)-4-(4-tert-butylphenyl)-3-oxomorpholin-2-yl]-2-hydroxyacetamide acetate (EXAMPLE 67)

According to the Step 66-3 in synthetic method for EXAMPLE 66, compound 67-2 (62 mg) was used instead of 66-2 to obtain EXAMPLE 67 (46.7 mg) as a colorless amorphous solid.

Example 68

Synthesis of (R)—N-(4-carbamimidoylphenyl)-2-hydroxy-2-((R)-3-oxo-4-(3-oxo-2-propylisoindolin-5-yl)morpholin-2-yl)acetamide hydrochloride (EXAMPLE 68)

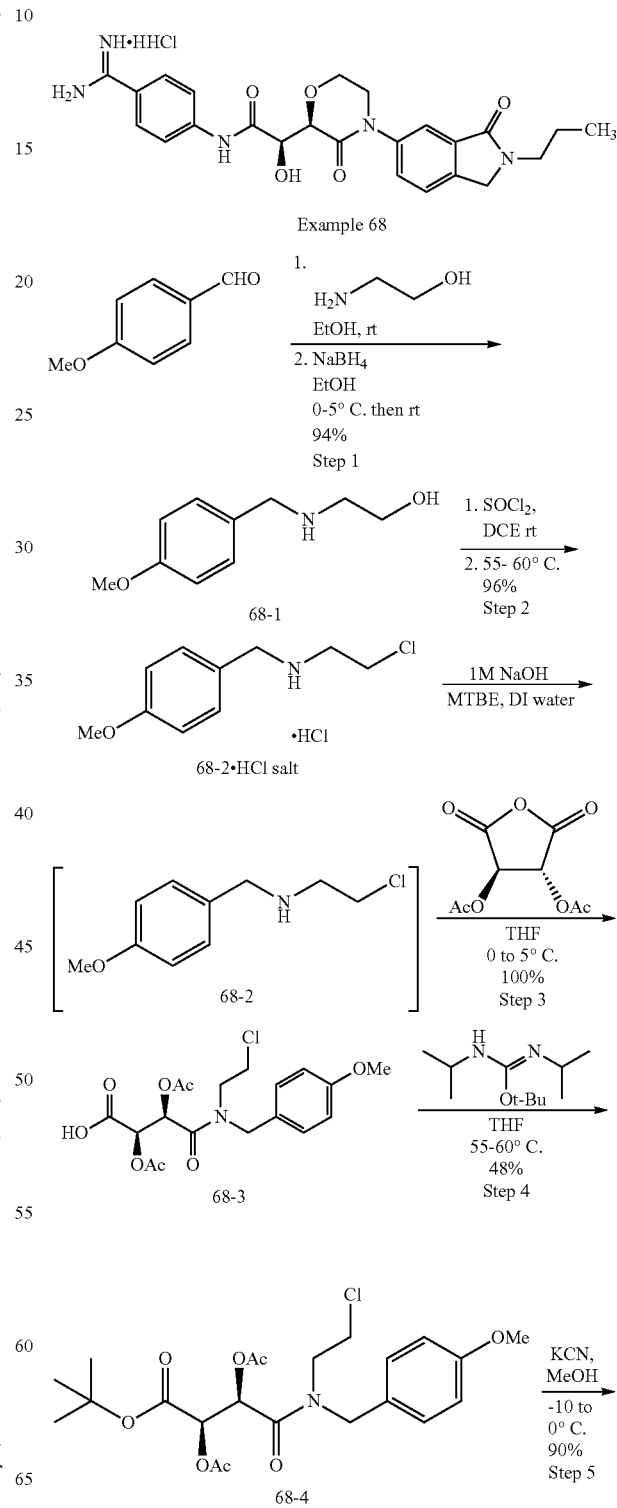

-continued

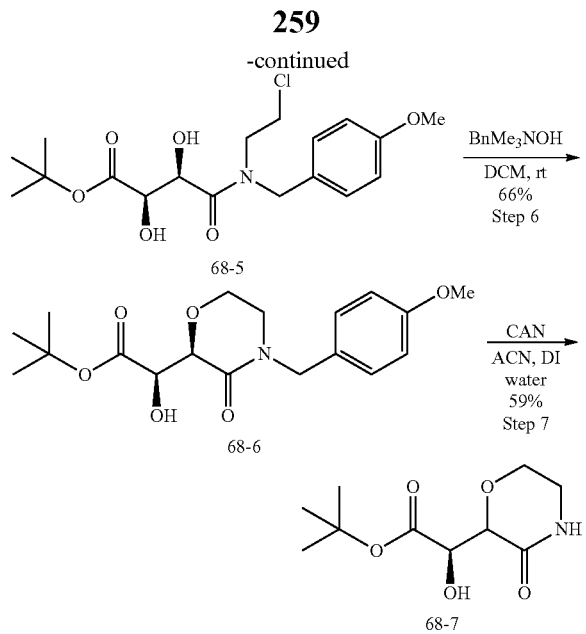

Step 68-1

Synthesis of Compound 68-1

A 100-L glass jacketed reactor was charged with 4-methoxybenzaldehyde (3440 g, 25.3 mol, Aldrich lot #05826 MH and 20098PJ) and absolute ethanol (34.4 L). 2-Aminoethanol (1840 mL, 30.0 mol, Aldrich lot #06201PE) was added over 30 minutes while maintaining the temperature of the batch between 20 and 30° C. After the addition was complete, the batch was held at 20-25° C. for 2 hours until formation of the imine intermediate was deemed complete by $^1$H NMR analysis (DMSO-$d_6$, aldehyde peak at 9.8 ppm not observed). The batch was cooled to 0-5° C. and sodium borohydride (1050 g, 27.8 mol, Aldrich lot #10106TC) was added portionwise over 2.8 hours while maintaining the temperature of the batch between 0 and 10° C. Once the addition was complete, the batch was allowed to gradually warm to 20-25° C. (20° C./hour) and was held at this temperature for 16 hours until the reduction of the imine intermediate was deemed complete by HPLC analysis [<1.0% (AUC) of imine by HPLC]. The reaction mixture was quenched by carefully adding 1 M aqueous sodium hydroxide (25.0 L) to the batch. This process led to the formation of insoluble masses of solid. These solids were dissolved by adding DI water (25.0 L) and the quenched was resumed. The batch was extracted with dichloromethane (CH$_2$Cl$_2$, 3×17.2 L). The combined organic extracts were concentrated on a rotary evaporator at 40-45° C. until distillation ceased and then the concentrate was slurried in DI water (17.2 L). The batch was cooled to 10-15° C. and the pH was adjusted to 1-2 using concentrated hydrochloric acid (2.2 L). The batch was washed with tert-butyl methyl ether (MTBE, 3×10.3 L), cooled to 10-15° C. and the pH was adjusted to 13-14 using 6 M aqueous sodium hydroxide (6.0 L). The batch was extracted with CH$_2$Cl$_2$ (2×10.3 L). The combined organic extracts were dried over anhydrous sodium sulfate, filtered and the filter cake was washed with CH$_2$Cl$_2$ (6.0 L). The filtrate was concentrated on a rotary evaporator at 30-35° C. until distillation ceased to afford compound 68-1 (4325 g, 94%).

Step 68-2

Synthesis of Compound 68-2

A 100-L glass jacketed reactor was charged with compound 68-1 (4325 g, 23.9 mol) and 1,2-dichloroethane (86.5 L). Thionyl chloride (1900 mL, 26.1 mol, Aldrich lot #05497DJ) was added over 50 minutes while maintaining the temperature of the batch between 20 and 30° C. Once the addition was complete, the batch was heated to 55-60° C. and held at this temperature for 5.5 hours until the reaction was deemed complete by $^1$H NMR analysis (DMSO-$d_6$, doublets at 7.3 ppm and 6.9 ppm shifted to 7.5 ppm and 7.0 ppm respectively, and doublets at 9.2 min and multiplet at 4.4 ppm disappeared). The batch was cooled to 20-25° C. and concentrated using a rotavap at 40-45° C. until distillation ceased. The concentrate was swapped once with MTBE (22.0 L), slurried in MTBE (21.7 L) and filtered to afford 68-2.HCl (5420 g, 96%) as white solids after drying in a vacuum oven at 20-30° C. for 17 hours.

Step 68-3

Synthesis of Compound 68-3

A 50-L glass jacketed reactor was charged with compound 68-2.HCl (1940 g, 8.2 mol), DI water (19.4 L) and MTBE (19.4 L). The pH of the aqueous layer was adjusted to 11-12 using 1 M aqueous sodium hydroxide (10.5 L) and maintaining the temperature of the batch between 15 and 30° C. The phases were separated and the aqueous layer was extracted with MTBE (2×9.7 L). The combined organic extracts were dried over anhydrous sodium sulfate, filtered, washed with MTBE (8.0 L) and the filtrate was concentrated on a rotary evaporator at 20-25° C. until distillation ceased, affording free amine 68-2 (1720 g, containing 6.8 wt % of MTBE by $^1$H NMR (DMSO-$d_6$), corrected weight: 1604 g, 98%)

A 50-L glass jacketed reactor was charged with di-O-acetyl-L-tartaric anhydride (1775 g, 8.2 mol, Alfa Aesar lot # E13U033) and tetrahydrofuran (17.5 L, THF). The batch was cooled to 0-5° C. and a solution of compound 68-2 (1720 g) in THF (2.0 L) was added over 1.3 hours while maintaining the temperature of the batch between 0 and 10° C. The batch was held at 0-5° C. for 18 hours until the reaction was deemed complete by HPLC analysis [2.8% (AUC) of compound 68-2 remaining] and then it was concentrated on a rotary evaporator at 20-25° C. until distillation ceased to afford compound 68-3 [4485 g, containing 22.7 wt % of THF by $^1$H NMR (DMSO-$d_6$), corrected weight: 3467 g, 102%, 86.9% (AUC) by HPLC].

Step 68-4

Synthesis of Compound 68-4

A 50-L glass jacketed reactor was charged with compound 68-3 (3520 g, assuming theoretical yield for step 3, 8.5 mol) and THF (35.0 L), and the batch was heated to 50-60° C. Two portions of O-tert-butyl-N,N-diisopropylurea (2115 g, 10.6 mol, and 1700 g, 8.9 mol) were each added dropwise over 30 minutes while maintaining the temperature of the batch between 50 and 60° C. In-process assay by HPLC analysis after these additions were complete indicated that 19.5% (AUC) of compound 68-3 remained and that 70.9% (AUC) of compound 68-4 had formed. Additional O-tert-butyl-N,N-diisopropylurea (2×425 g, 4.2 mol) was added to the batch until the reaction was deemed complete by HPLC analysis

[4.4% (AUC) of compound 68-3 remaining]. The batch was cooled to 15-25° C. and MTBE (19.4 L) was added. The batch was filtered over Celite® and washed with MTBE (15.0 L). The combined filtrate and washes were concentrated on a rotary evaporator at 40-45° C. until distillation ceased to afford crude compound 68-4 [4675 g, containing 10.6 wt % of THF by $^1$H NMR (DMSO-$d_6$), corrected weight 4180 g, 105%, 55.7% (AUC) by HPLC]. This material was purified by silica-gel column chromatography (Four 1.1 to 1.3-kg batches using 5.5 kg of silica gel each, 20 to 60% EtOAc in heptane) to afford compound 68-4 [1915 g, 48%, 96.7-97.1% (AUC) by HPLC] as well as mixed fractions that were combined with other lots for further purification.

Step 68-5

Synthesis of Compound 68-5

A 50-L glass jacketed reactor was charged with compound 68-4 (1100 g, 2.3 mol) and methanol (10.2 L), and the batch was cooled to −10 to 0° C. A slurry of potassium cyanide (80 g, 1.2 mol, Aldrich lot #14614KA) in methanol (800 mL) was added over 5 minutes while maintaining the temperature of the batch between −10 and 0° C. The batch was held at −10 to 0° C. for 3.3 hours until the reaction was deemed complete by HPLC analysis [5.3% (AUC) of compound 68-4 remaining]. Solid sodium bicarbonate (200 g, 2.4 mol, Natrium Products lot #01096A) was added and the batch was concentrated on a rotary evaporator at 20-25° C. until distillation ceased. MTBE (11.0 L) and DI water (11.0 L) were added to the concentrate, and the layers were separated. The organic layer was washed with saturated aqueous sodium bicarbonate (6.0 L), dried over anhydrous sodium sulfate, filtered, washed with MTBE (7.0 L) and concentrated on a rotary evaporator at 20-25° C. until distillation ceased to yield compound 68-5 [910 g, containing 10.2 wt % of MTBE by $^1$H NMR (CDCl$_3$), corrected weight 817 g, 90%, 82.4% (AUC) by HPLC]. This material was stored in the freezer.

Step 68-6

Synthesis of Compound 68-6

A 50-L glass jacketed reactor was charged with compound 68-5 (817 g, 2.1 mol), CH$_2$Cl$_2$ (8.2 L) and deionized water (1.9 L). Benzyltrimethylammonium hydroxide (1912 mL, 40 wt % in methanol, 4.2 mol, Aldrich lot #10896HJ) was added to the batch over 10 minutes while maintaining the temperature between 20 and 25° C. The batch was held at 20-25° C. for 1.5 hours until the reaction was deemed complete by HPLC analysis [<1.0% (AUC) of compound 68-5 remaining]. At completion of the reaction, DI water (6.5 L) was added and the layers were separated. The aqueous layer was extracted with CH$_2$Cl$_2$ (8.2 L). The combined organic extracts were washed with brine (8.2 L), dried over anhydrous sodium sulfate, filtered and washed with CH$_2$Cl$_2$ (2.5 L). The combined filtrate and washes were concentrated on a rotary evaporator at 30-35° C. until distillation ceased to afford crude compound 68-6 [625 g, 84%, 82.5% (AUC) by HPLC]. This material was purified by silica-gel column chromatography [5 kg of silica gel, 20 to 60% EtOAc in heptane] and the pure fractions were slurried in 1:4 MTBE/heptane to yield compound 68-6 [Two lots: 155 g, 21%, >99% (AUC) by HPLC, and 335 g, 45%, >99% (AUC) by HPLC] as white solids.

Step 68-7

Synthesis of Compound 68-7

A 50-L glass jacketed reactor was charged with compound 68-6 (490 g, 1.4 mol), acetonitrile (10.1 L) and DI water (2.0 L). The batch was cooled to 0-5° C. and a slurry of cerium (IV) ammonium nitrate (3060 g, 5.6 mol, Alfa Aesar lot # H22T016) in acetonitrile (8.0 L) was added while maintaining the temperature of the batch between 0 and 5° C. The batch was held at 0-5° C. for 30 minutes, warmed to 20-25° C. and held at this temperature for 3.5 hours until the reaction was deemed complete by HPLC analysis. Saturated aqueous sodium bicarbonate (17.0 L) was added until the pH of the reaction mixture reached 4.5 to 5. The resulting suspension was filtered over Celite® and the filter cake was washed with CH$_2$Cl$_2$ (2×10.0 L) followed by 5% methanol in CH$_2$Cl$_2$ (10.0 L). The combined filtrate and washes were transferred to a 50-L, glass jacketed reactor and the phases were separated. The aqueous layer was extracted with CH$_2$Cl$_2$ (15.0 L). The combined organic extracts were washed with brine, dried over anhydrous sodium sulfate, filtered and the filter cake was washed with CH$_2$Cl$_2$ (10.0 L). The combined filtrate and washes were concentrated on a rotary evaporator at 30-35° C. until distillation ceased to give crude compound 68-7 [700 g, >100%]. This material was purified by silica-gel column chromatography [4 kg of silica gel, 1 to 5% methanol in dichloromethane]. The pure fractions were slurried in 1:4 CH$_2$Cl$_2$/MTBE to yield compound 68-7 [Two lots: 189 g, 59%] as white to off-white solids.

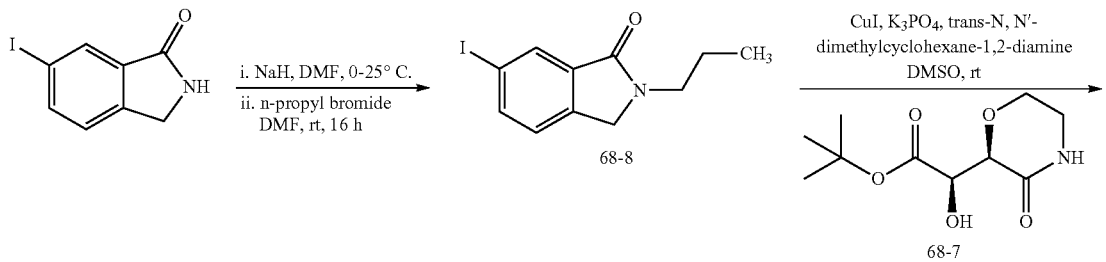

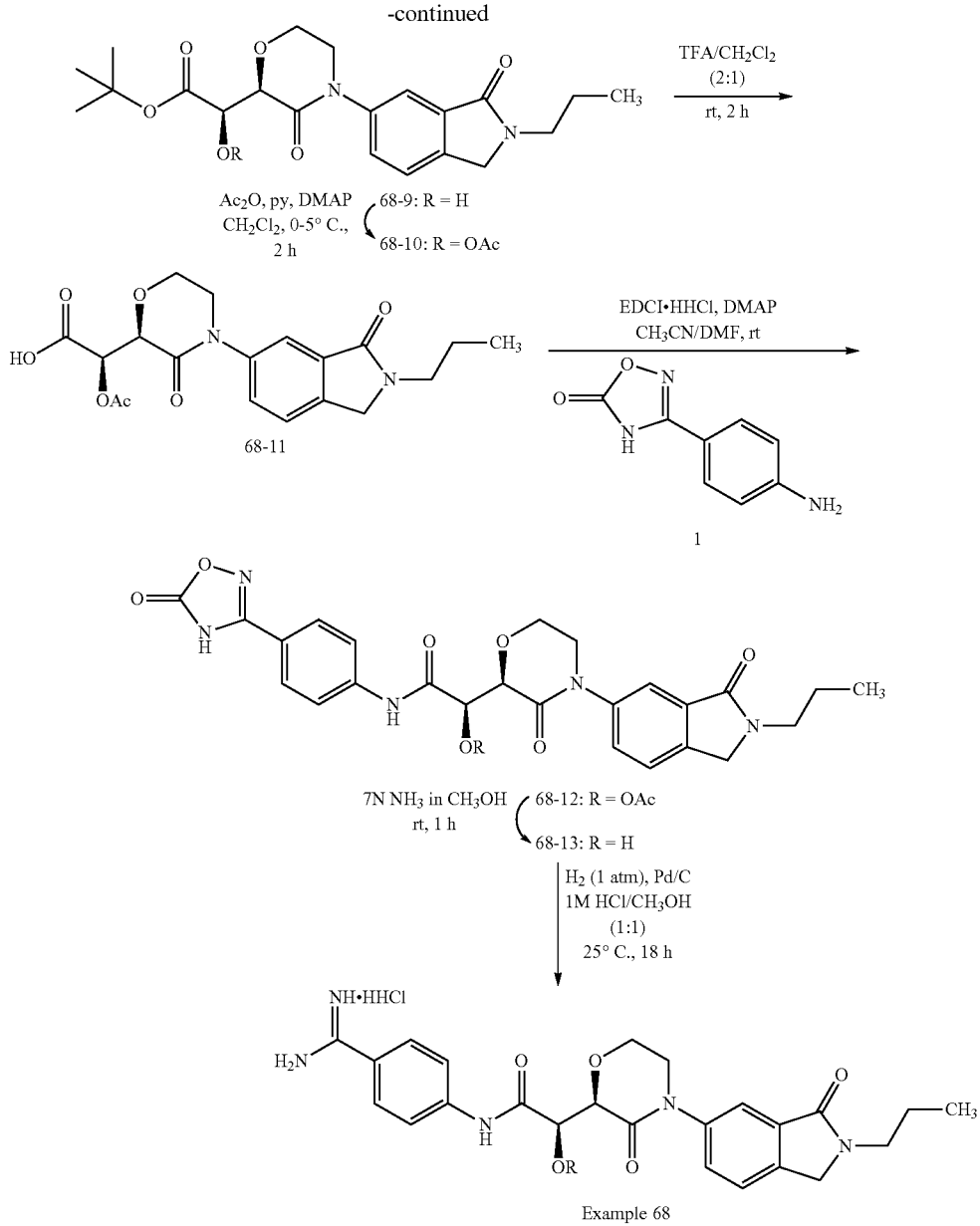

Example 68

Step 68-8

Synthesis of Compound 68-8

To a 50 mL round bottom flask was added 5-iodo-3-oxo-isoindolin (1.00 g, 3.86 mmol) in DMF (10.0 mL) and the reaction mixture was stirred at 0-5° C. NaH (60% in oil, 186 mg, 4.65 mmol) was added, and the reaction mixture was allowed to warm to room temperature. After 20 min, the reaction obtained a green color, and a solution of n-propyl bromide (706 mg, 5.78 mmol) in DMF (2.00 mL) was added dropwise over a period of 15 min. The reaction mixture was stirred overnight at room temperature, then diluted with EtOAc (100 mL), washed with saturated aqueous NH$_4$Cl (2×25 mL), saturated aqueous LiCl (25 mL), brine (25 mL), dried over Na$_2$SO$_4$, filtered and concentrated under reduced pressure. The resulting residue was purified by CombiFlash (80 g, Hex/EtOAc, 100:0 to 30:70 over 30 min) to provide compound 68-8 (700 mg, 60%) as a white solid.[1]

Step 68-9

Synthesis of Compound 68-9

A mixture of compound 68-7 (100 mg, 0.432 mmol), aryl iodide compound 68-8 (156 mg, 0.518 mmol), CuI (8.1 mg, 43 µmol), K$_3$PO$_4$ (183 mg, 0.861 mmol), DMSO (1.5 mL), and trans-N,N'-dimethylcyclohexane-1,2-diamine (13.6 µL, 86.1 µmol) were stirred at room temperature under nitrogen in the dark. After 14 h, additional CuI (8.1 mg, 43 µmol) and trans-N,N'-dimethylcyclohexane-1,2-diamine (13.6 µL, 86.1 µmol) were added and the mixture was stirred for an additional 2.5 h. The mixture was diluted with EtOAc (100 mL), washed with water (3×25 mL), brine (25 mL), dried over Na$_2$SO$_4$, filtered, and concentrated under reduced pressure.

Step 68-10

Synthesis of Compound 68-10

To a 50 mL round bottom flask was added compound 68-9 (114 mg, 0.281 mmol), DMAP (3.4 mg, 28 μmol), pyridine (45 μL, 0.56 mmol) and $CH_2Cl_2$ (5.00 mL). The reaction mixture was cooled to 0-5° C., $Ac_2O$ (53 μL, 0.56 mmol) was added, stirred at 0-5° C. for 2 h, and then diluted with EtOAc (40 mL), washed with saturated aqueous $CuSO_4$ (2×25 mL), brine (25 mL), dried over $Na_2SO_4$, filtered and concentrated under reduced pressure to provide crude compound 68-10 (125 mg, quant) as a yellow solid. The product was used in the next reaction without any further purification.

Step 68-11

Synthesis of Compound 68-11

In a 50 mL round bottom flask containing compound 68-10 (125 mg, 0.281 mmol) was added $CH_2Cl_2$ (1.00 mL) and TFA (2.00 mL). The reaction mixture was stirred at room temperature for 2 h, then TFA and $CH_2Cl_2$ were removed under reduced pressure. The crude product was triturated with ether to provide pure 68-11 (110 mg, quant.) as a yellow solid.

Step 68-12

Synthesis of Compound 68-12

To a 100 mL round bottom flask was added compound 68-11 (110 mg, 0.281 mmol), DMAP (3.4 mg, 28 μmol), and 3-(4-aminophenyl)-1,2,4-oxadiazol-5(2H)-one 1 (53.1 mg, 0.299 mmol) in $CH_3CN$ (3.00 mL). The reaction mixture was cooled to 0-5° C., then EDCI.HCl (57.5 mg, 0.299 mmol) was added and the reaction mixture was warmed to room temperature. After 30 min DMF (1.00 mL) was added to dissolve the precipitate and stirring was continued for an additional 3 h. The solvents were removed under reduced pressure and the residue was triturated with ether (20.0 mL) then decanted. The undissolved material was washed with water (2×5 mL) and acetonitrile (2×5 mL) then dried on under vacuum to provide pure product 68-12 (95 mg, 62%) as off-white solid.

Step 68-13

Synthesis of Compound 68-13

To a 50 mL round bottom flask was added compound 68-12 (95 mg, 0.17 mmol), $CH_3OH$ (2.00 mL) and 7 N $NH_3$ in $CH_3OH$ (6.00 mL). The reaction mixture was stirred at room temperature for 1 h then the volatiles were removed under reduced pressure. Additional $CH_3OH$ (2×50 mL) was used to strip off excess $NH_3$. The crude product was redissolved in $CH_3OH$ (50 mL) and the solvent degassed with $N_2$ to remove trace ammonia then concentrated under reduced pressure to provide compound 68-13 (85 mg, 99%) as off-white solid.

Step 68-14

Synthesis of (R)—N-(4-carbamimidoylphenyl)-2-hydroxy-2-((R)-3-oxo-4-(3-oxo-2-propylisoindolin-5-yl)morpholin-2-yl)acetamide hydrochloride (EXAMPLE 68)

To a 250 mL round bottom flask was added compound 68-13 (84 mg, 0.17 mmol) in $CH_3OH$ (6.00 mL) and 1 M HCl (6.00 mL). The solvent was degassed for 10 min with $N_2$, then 10% Pd/C (84 mg, 39 mmol) was added and the reaction mixture was hydrogenated at 1 atm overnight. The mixture was diluted with hot $CH_3OH$ (250 mL), filtered and the filtrate was concentrated under reduced pressure. The residue was triturated with $CH_3OH$ (5.00 mL) and filtered to provide pure product compound 68 (51 mg, 64%) as off-white solid.

Example 69

Synthesis of (R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide hydrochloride (EXAMPLE 69)

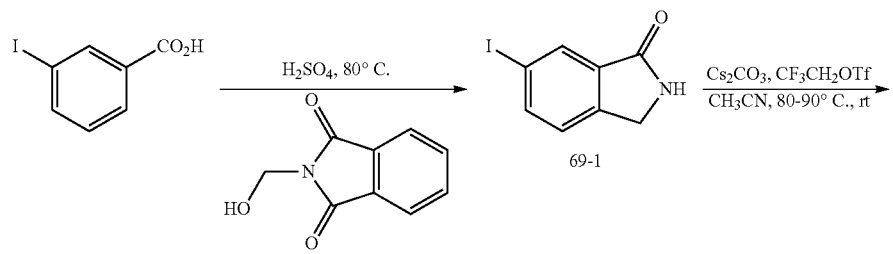

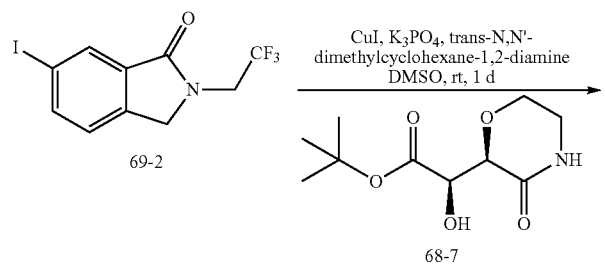

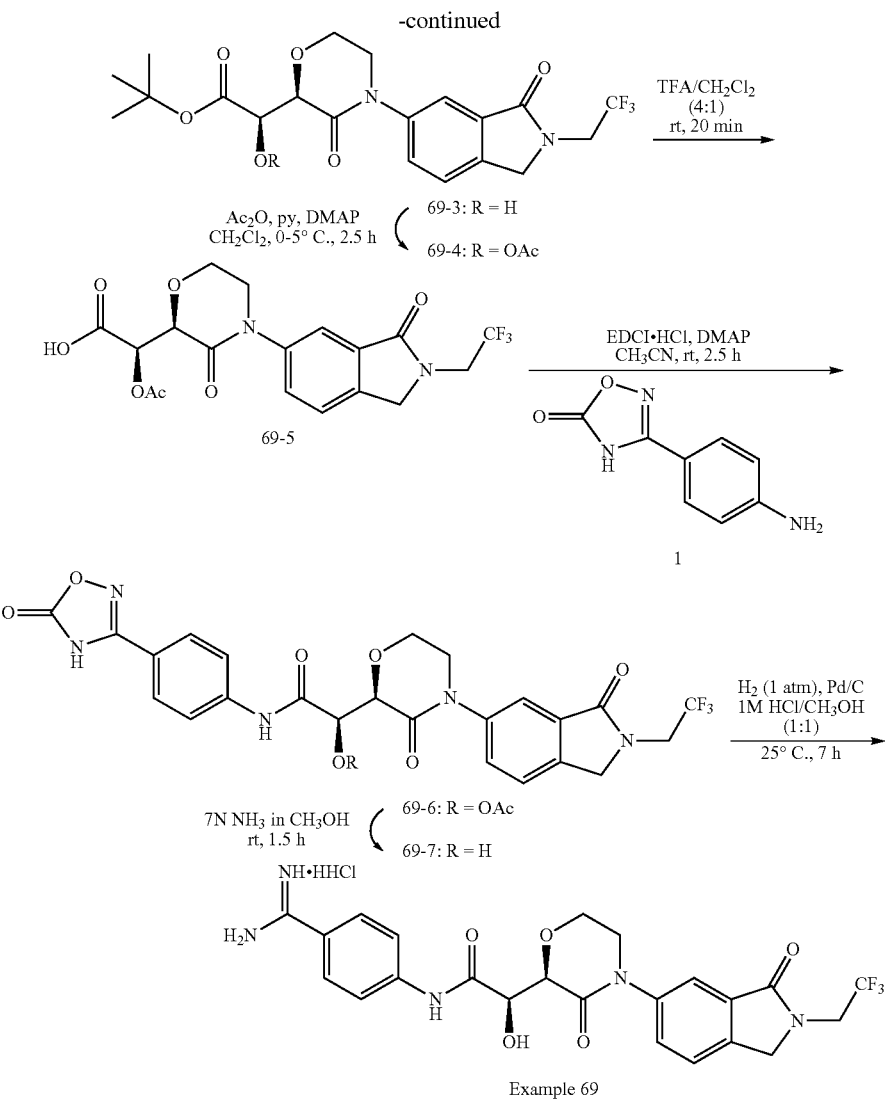

Example 69

Step 69-1

Synthesis of Compound 69-1

A mixture of 2-(hydroxymethyl)isoindoline-1,3-dione (50.0 g, 202 mmol), 3-iodobenzoic acid (35.7 g, 202 mmol) and H$_2$SO$_4$ was heated at 80° C. for 3.5 h. The mixture was cooled to room temperature and then poured into ice. The precipitate was filtered off, washed with H$_2$O (1.0 L), dilute NH$_4$OH (500 mL) and recrystallized from EtOH (300 mL) to provide compound 69-1 (25.2 g, 48%) as an off-white solid.

Step 69-2

Synthesis of Compound 69-2

A mixture of compound 69-1 (3.00 g, 11.6 mmol), Cs$_2$CO$_3$ (15.1 g, 46.3 mmol), 2,2,2-trifluoroethyl trifluoromethanesulfonate (2.50 mL, 17.4 mmol) and CH$_3$CN (120 mL) was heated at 80-90° C. for 1.5 h. Additional Cs$_2$CO$_3$ (7.52 g, 23.1 mmol) and 2,2,2-trifluoroethyl trifluoromethanesulfonate (1.0 mL, 6.93 mmol) were added and the mixture was heated for an additional 0.5 h. The resulting mixture was cooled to room temperature, diluted with EtOAc (250 mL), washed with saturated aqueous NH$_4$Cl (2×20 mL), brine (3×20 mL), dried over Na$_2$SO$_4$, filtered and concentrated under reduced pressure. The resulting residue was purified by CombiFlash (120 g, Hex/EtOAc, 100:0 to 85:15 over 35 min) to provide compound 69-2 (1.78 g, 45%) as a brown solid.

Step 69-3

Synthesis of Compound 69-3

A mixture of compound 68-7 (215 mg, 0.929 mmol), aryl iodide 69-2 (348 mg, 1.02 mmol), CuI (8.8 mg, 46 µmol), K$_3$PO$_4$ (394 mg, 1.86 mmol), DMSO (3.1 mL), and trans-N,N'-dimethylcyclohexane-1,2-diamine (15 µL, 92 µmol) were stirred at room temperature under nitrogen in the dark for 4 h. Additional CuI (8.8 mg, 46 µmol) and trans-N,N'-dimethylcyclohexane-1,2-diamine (15 µL, 92 µmol) were added three times over the course of 20 h. After stirring for total 24 h the mixture was diluted with EtOAc (150 mL), washed with water (3×20 mL), dried over Na$_2$SO$_4$, filtered, and concentrated under reduced pressure. The crude product was purified on CombiFlash (40 g, Hex/EtOAc, 100:0 to 50:50 over 35 min) to provide pure product compound 69-3 (185 mg, 45%) as a yellow solid.

Step 69-4

Synthesis of Compound 69-4

To a solution of compound 69-3 (180 mg, 0.405 mmol), DMAP (4.9 mg, 40 μmol) and $CH_2Cl_2$ (4.00 mL) were added pyridine (66 μL, 0.81 mmol) and $Ac_2O$ (77 μL, 0.81 mmol) at 0-5° C. The resulting mixture was stirred for 2.5 h at 0-5° C., and then diluted with EtOAc (200 mL), washed with saturated aqueous $CuSO_4$ (2×10 mL), $H_2O$ (10 mL), brine (10 mL), dried over $Na_2SO_4$, filtered and concentrated under reduced pressure to provide crude compound 69-4 (197 mg, quant.) as a yellow solid. The product was used in the next reaction without further purification.

Step 69-5

Synthesis of Compound 69-5

In a 50 mL round bottom flask containing compound 69-4 (192 mg, 0.394 mmol) was added $CH_2Cl_2$ (1.00 mL) and TFA (4.00 mL). The reaction mixture was stirred at room temperature for 20 min, then TFA and $CH_2Cl_2$ were removed under reduced pressure. The crude product was triturated with ether and filtered to provide pure compound 69-5 (174 mg, quant.) as a yellow solid.

Step 69-6

Synthesis of Compound 69-6

A solution of compound 69-6 (165 mg, 0.383 mmol), DMAP (4.6 mg, 38 mmol), 3-(4-aminophenyl)-1,2,4-oxadiazol-5(2H)-one (74.6 mg, 0.421 mmol), EDCI.HCl (80.7 mg, 0.421 mmol) and $CH_3CN$ (3 mL) was stirred at room temperature for 2.5 h. The solvent was removed under reduced pressure and the residue purified by semi-preparative HPLC to provide pure product compound 69-6 (51 mg, 23%) as an off-white solid.

Step 69-7

Synthesis of Compound 69-7

To a 50 mL round bottom flask was added compound 69-6 (51 mg, 86 mmol), and 7 N $NH_3$ in $CH_3OH$ (5.00 mL). The reaction mixture was stirred at room temperature for 1.5 h then the volatiles were removed under reduced pressure. Residual ammonia was removed by evaporating with $CH_3OH$ (2×15 mL) and $CH_2Cl_2$ (2×15 mL) to provide compound 69-7 (47 mg, quant.) as an off-white solid.

Step 69-8

Synthesis of (R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide hydrochloride (EXAMPLE 69)

To a 100 mL round bottom flask was added compound 69-7 (45 mg, 82 μmol) in $CH_3OH$ (4.00 mL) and 1 M HCl (4.00 mL). The solvent was degassed for 10 min with $N_2$, then 10% Pd/C (45 mg, 21 μmol) was added and the reaction mixture was hydrogenated at 1 atm for 7 h. The mixture was filtered, washed with hot $CH_3OH$ (200 mL), and the filtrate was concentrated under reduced pressure. The residue was purified by semi-preparative HPLC. The isolated product was dissolved in MeOH (5 mL) and then added 1 N HCl in $Et_2O$ (5 mL) and stirred for 5 min. The volatiles were removed under reduced pressure to provide pure product EXAMPLE 69 (22 mg, 50%) as an off-white solid.

Example 70

Synthesis of (R)—N-(4-Carbamimidoylphenyl)-2-hydroxy-2-((R)-4-(2-methyl-3-oxoisoindolin-5-yl)-3-oxomorpholin-2-yl)acetamide hydrochloride (EXAMPLE 70)

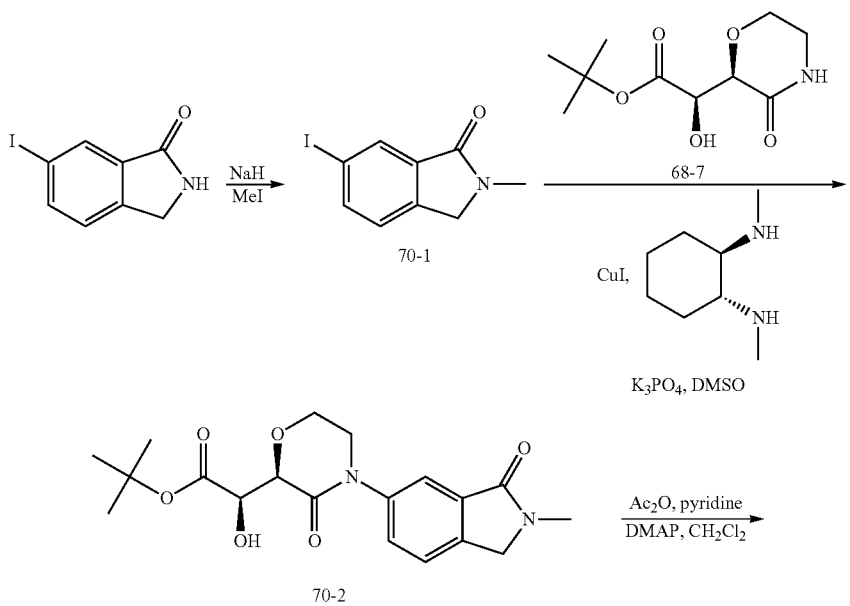

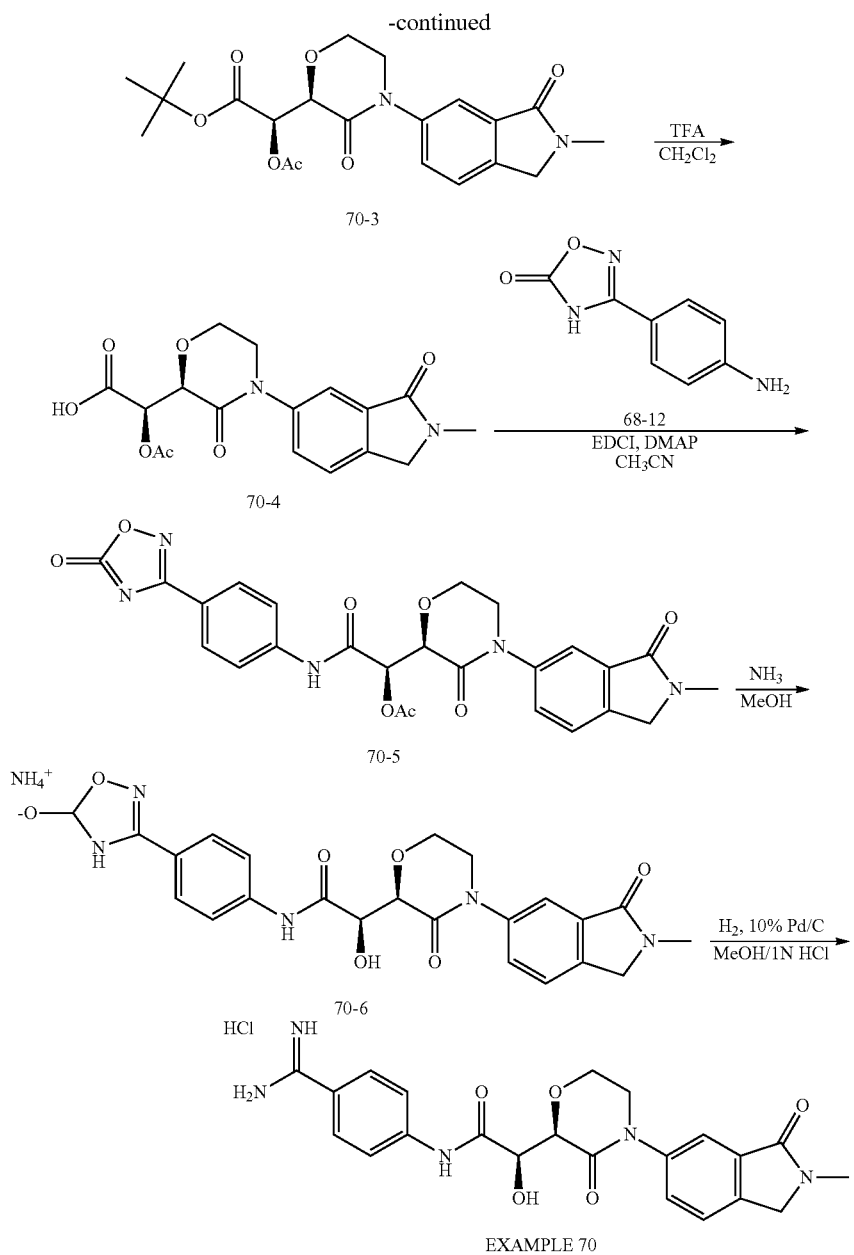

Step 70-1

Synthesis of Compound 70-1

To a mixture of 2,3-dihydro-6-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. $NH_4Cl$ (~3 mL) and was diluted with EtOAc (10 mL). The layers were separated and the aqueous layer was extracted with EtOAc. The organic layers were combined and washed sequentially with water and brine. The organic layer was dried ($Na_2SO_4$), filtered, and concentrated under reduced pressure. The crude material was purified The crude product was purified by flash chromatography (ISCO, 120 g) using a gradient of 100% hexanes to 80:20 hexanes/EtOAc to afford compound 70-1 (0.84 g) as a yellow solid. LC-MS: M+H=274.

Step 70-2

Synthesis of (R)-tert-butyl 2-hydroxy-2-((R)-4-(2-methyl-3-oxoisoindolin-5-yl)-3-oxomorpholin-2-yl) acetate (compound 70-2)

To a round bottom flask charged with a stir bar was added morpholinone compound 68-7 (0.28 g) and compound 70-1 (0.40 g) in DMSO (8 mL) at rt was added $K_3PO_4$ (0.51 g), and CuI (23 mg) under $N_2$. trans-N,N'-Dimethylcyclohexane-1,2-diamine (37 µL) was added dropwise and the mixture was affixed with a condenser. The mixture was degassed under vacuum (~20 mm), filled with $N_2$, and heated to 80° C. The mixture stirred for 2.5 h at 80° C., cooled to rt, and was diluted with EtOAc. The mixture was then sequentially washed with conc NH₄OH, water, and brine. The organic layer was dried (Na₂SO₄), filtered, and concentrated under reduced pressure to afford a yellow oil. The crude product was purified by flash chromatography using a gradient of 100% CH₂Cl₂ to 60% CH₂Cl₂/40% MeOH to afford compound 70-2 (0.23 g) of a yellow solid. LC-MS: M+H=377.

Step 70-3

Synthesis of (R)-tert-butyl 2-acetoxy-2-((R)-4-(2-methyl-3-oxoisoindolin-5-yl)-3-oxomorpholin-2-yl)acetate (compound 70-3)

To a solution of compound 70-2 (80 mg) in CH₂Cl₂ (2 ml) at 0° C. was added pyridine (26 µL), Ac₂O (30 µl), and DMAP (4 mg). The mixture was stirred for 1 hour at 0° C., warmed to rt, and stirred for an additional 12 h. The mixture was diluted with EtOAc and the organic layer was washed sequentially with sat. aq. CuSO₄ solution, water, and brine. The organic layer was dried (Na₂SO₄), filtered, and concentrated under reduced pressure to afford compound 70-3 (85 mg) as a light yellow semisolid. LC-MS: M+H=419. This material was used without further purification.

Step 70-4

Synthesis of (R)-2-acetoxy-2-((R)-4-(2-methyl-3-oxoisoindolin-5-yl)-3-oxomorpholin-2-yl)acetic acid (compound 70-4)

To a solution of compound 70-3 (85 mg) in CH₂Cl₂ (2.5 mL) at 0° C. was added TFA (0.5 mL) dropwise. The mixture was stirred for 1 h at 0° C. and at rt for 30 min whereupon an additional portion of TFA (0.5 mL) was added. After an additional 1 h at rt, the mixture was diluted with CH₂Cl₂ and concentrated to dryness under reduced pressure. The crude mixture was redissolved in CH₂Cl₂ and concentrated and this protocol was repeated 5 times with to afford compound 70-4 (65 mg) as a light semisolid. LC-MS: M+H=363. This material was used without further purification.

Step 70-5

Synthesis of (R)-1-((R)-4-(2-methyl-3-oxoisoindolin-5-yl)-3-oxomorpholin-2-yl)-2-oxo-2-(4-(5-oxo-4,5-dihydro-1,2,4-oxadiazol-3-yl)phenylamino)ethyl acetate (compound 70-5)

To a solution of compound 70-4 (40 mg) in CH₃CN (1 mL) at 0° C. was added 4-(5-oxo-4,5-dihydro-[1,2,4]oxadiazol-3-yl)-phenyl amide (21 mg) followed by EDCI (25 mg). The reaction mixture was warmed to rt and stirred for 72 h. The mixture was concentrated under reduced pressure and placed under high vacuum. The crude material was purified by reverse phase HPLC using a C18 column and a gradient of (89.95:9.95:0.1 H₂O:MeCN:HCO₂H to 9.95:89.95:0.1 H₂O:MeCN:HCO₂H) to afford compound 70-5 (30 mg) as a white solid. LC-MS: M+H=522.

Step 70-6

Synthesis of ammonium 3-(4-((R)-2-hydroxy-2-((R)-4-(2-methyl-3-oxoisoindolin-5-yl)-3-oxomorpholin-2-yl)acetamido)phenyl)-1,2,4-oxadiazol-5-olate (compound 70-6)

To a solution of the compound 70-5 (30 mg) in MeOH (2 mL) at 0° C. was added 7M NH₃/MeOH (0.3 mL) dropwise. The mixture was stirred for 1 h at 0° C. and an additional hour at rt. The mixture was concentrated under reduced pressure and placed under high vacuum to afford compound 70-6 (27 mg) as a clear glass. LC-MS: M+H=480 (free base).

Step 70-7

Synthesis of (R)—N-(4-carbamimidoylphenyl)-2-hydroxy-2-((R)-4-(2-methyl-3-oxoisoindolin-5-yl)-3-oxomorpholin-2-yl)acetamide hydrochloride (EXAMPLE 70)

To a solution of the compound 70-6 (27 mg) in MeOH (2 mL) was added 1N HCl (2 mL) followed by 10% Pd/C (50 mg). The mixture was stirred under a H₂ balloon for 3 h and was filtered through a pad of Celite®. The Celite® pad was washed with MeOH and the resultant filtrate was concentrated under reduced pressure. The crude residue was treated with MeOH followed by dilution with Et₂O and the resultant solid was collected by filtration and dried under vacuum to afford 17 mg of Example 70 as a maize solid. LC-MS: M+H=438 (free base).

Example 71

Synthesis of (R)—N-(4-(aminomethyl)phenyl)-2-hydroxy-2-((R)-4-(2-methyl-3-oxoisoindolin-5-yl)-3-oxomorpholin-2-yl)acetamide (EXAMPLE 71)

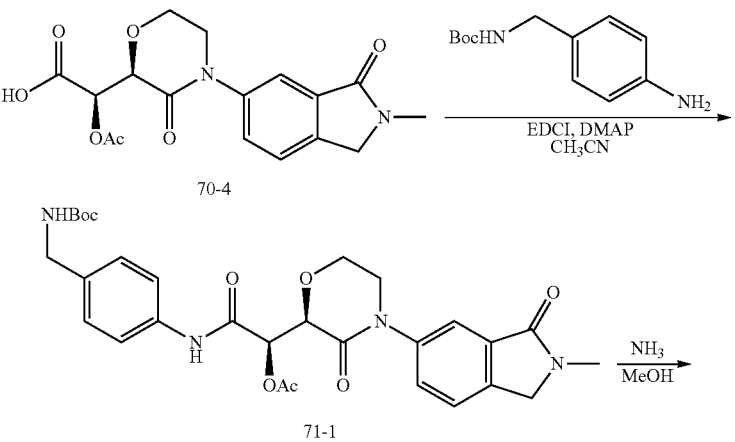

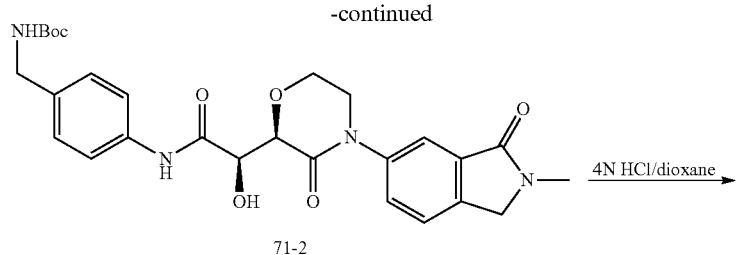

71-2

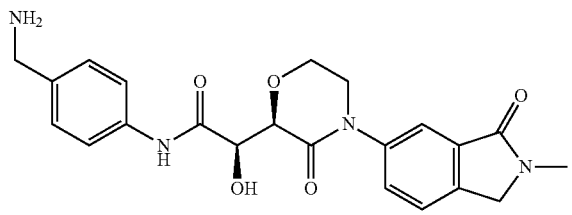

EXAMPLE 71

Step 71-1

Synthesis of (R)-2-(4-((tert-butoxycarbonylamino)methyl)phenylamino)-1-((R)-4-(2-methyl-3-oxoisoindolin-5-yl)-3-oxomorpholin-2-yl)-2-oxoethyl acetate (compound 71-1)

According to the Step 70-5 in the synthetic method for EXAMPLE 70, compound 70-4 (50 mg) was treated with tert-butyl 4-aminobenzylcarbamate (37 mg) to afford compound 71-1 (58 mg) as white solid after preparative LC purification.

Step 71-2

Synthesis of tert-butyl 4-((R)-2-hydroxy-2-((R)-4-(2-methyl-3-oxoisoindolin-5-yl)-3-oxomorpholin-2-yl)acetamido)benzylcarbamate (compound 71-2)

According to the Step 70-6 in the synthetic method for EXAMPLE 70, compound 71-1 (50 mg) was used instead of compound 70-5 to obtain compound 71-2 (50 mg) as a white solid. Crude compound 71-2 was used without further purification in the next step.

Step 71-3

Synthesis of (R)—N-(4-(aminomethyl)phenyl)-2-hydroxy-2-((R)-4-(2-methyl-3-oxoisoindolin-5-yl)-3-oxomorpholin-2-yl)acetamide (EXAMPLE 71)

To round bottom flask charged with the compound 71-2 (50 mg) at rt was added 4 N HCl/dioxane (3 mL). The resulting solution was stirred for 3 h, concentrated under reduced pressure, and placed under high vacuum. The crude product was dissolved in MeOH and Et$_2$O and the resultant solid was collected and dried to afford EXAMPLE 71 (36 mg) as an off-white solid. LC-MS: M+H=425 (free base).

Example 72

Synthesis of (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide (EXAMPLE 72)

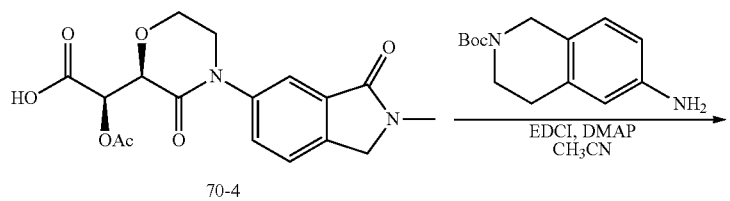

70-4

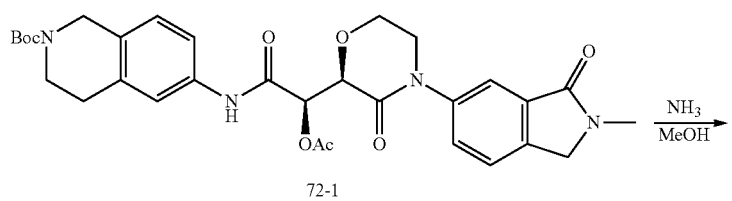

72-1

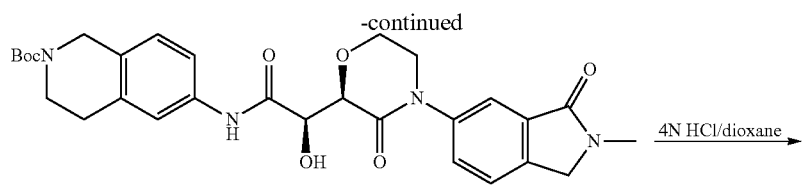

72-2

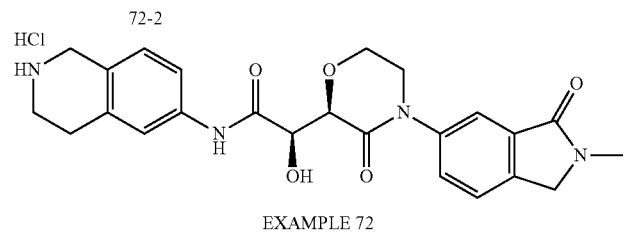

EXAMPLE 72

Step 72-1

Synthesis of tert-butyl 6-((R)-2-acetoxy-2-((R)-4-(2-methyl-3-oxoisoindolin-5-yl)-3-oxomorpholin-2-yl)acetamido)-3,4-dihydroisoquinoline-2(1H)-carboxylate (compound 72-1)

According to the Step 70-5 in the synthetic method for EXAMPLE 70, compound 70-4 (50 mg) was treated with tert-butyl 6-amino-3,4-dihydroisoquinoline-2(1H)-carboxylate (30 mg) to afford compound 72-1 (52 mg) as a light yellow solid after preparative LC purification.

Step 72-2

Synthesis of tert-butyl 6-((R)-2-hydroxy-2-((R)-4-(2-methyl-3-oxoisoindolin-5-yl)-3-oxomorpholin-2-yl)acetamido)-3,4-dihydroisoquinoline-2(1H)-carboxylate (compound 72-2)

According to the Step 70-6 in the synthetic method for EXAMPLE 70, compound 72-1 (50 mg) was used instead of compound 70-5 to obtain compound 72-2 (39 mg) as an off-white solid. Crude compound 72-2 was used without further purification in the next step.

Step 72-3

Synthesis of (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide (EXAMPLE 72)

According to the Step 71-3 in the synthetic method for EXAMPLE 71, 72-2 (39 mg) was used instead of compound 71-2 to obtain EXAMPLE 72 (26 mg) as a maize solid.

Example 73

Synthesis of (R)-2-((R)-4-(3,5-bis(trifluoromethyl)phenyl)-3-oxomorpholin-2-yl)-N-(4-carbamimidoylphenyl)-2-hydroxyacetamide hydrochloride (EXAMPLE 73)

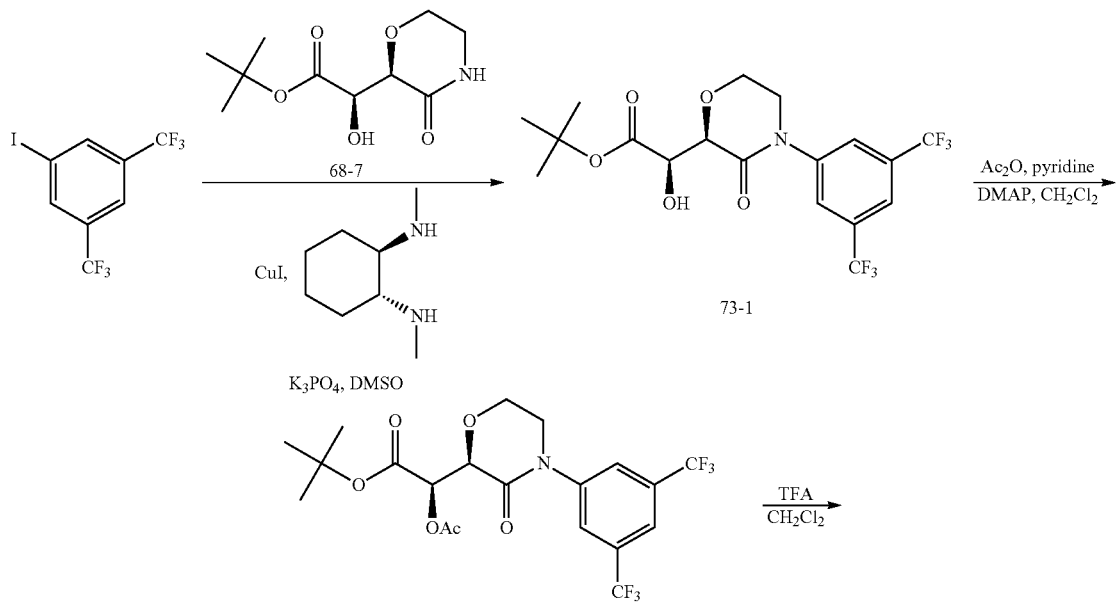

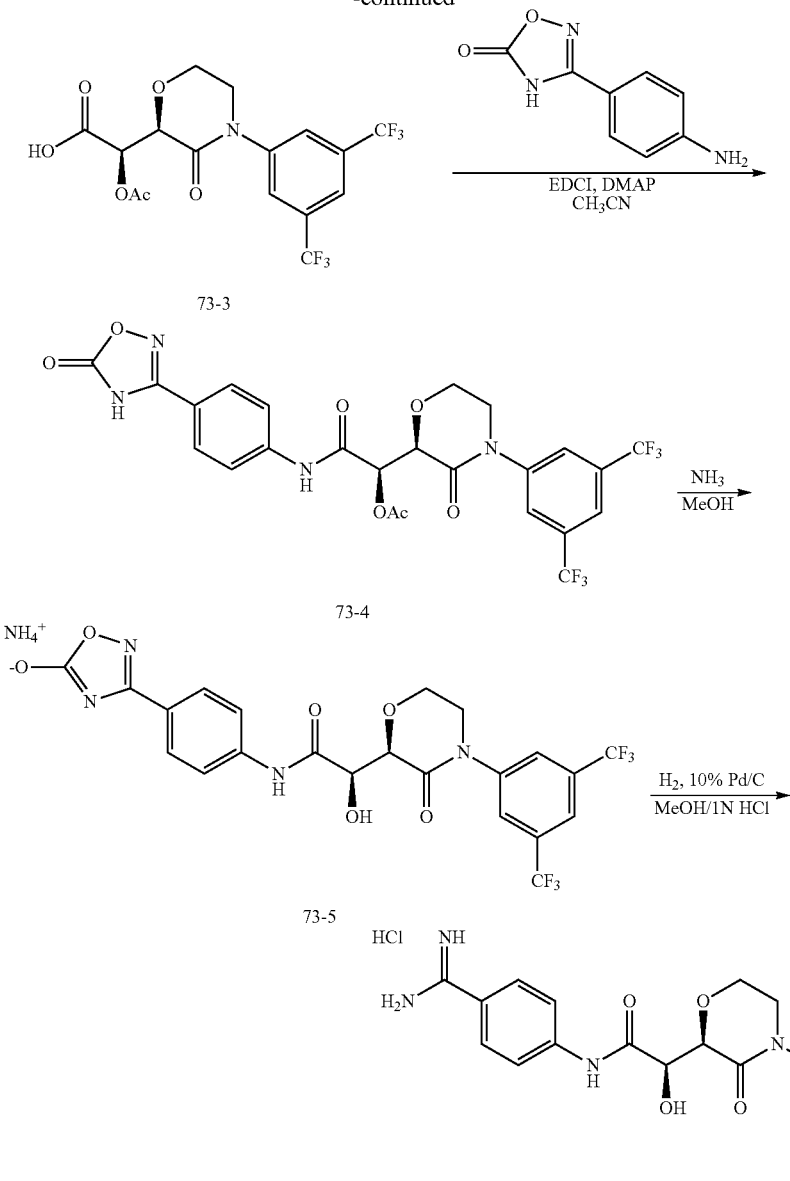

EXAMPLE 73

Step 73-1

Synthesis of (R)-tert-butyl 2-((R)-4-(3,5-bis(trifluoromethyl)phenyl)-3-oxomorpholin-2-yl)-2-hydroxyacetate (compound 73-1)

According to the Step 70-2 in the synthetic method for Example 70, 3,5-(bistrifluoromethyl)iodobenzene (0.11 mL) was used instead of compound 70-1 to obtain compound 73-1 (0.13 g) as a white solid after reverse-phase (C18) purification.

Step 73-2

Synthesis of (R)-tert-butyl 2-acetoxy-2-((R)-4-(3,5-bis(trifluoromethyl)phenyl)-3-oxomorpholin-2-yl) acetate (compound 73-2)

According to the Step 70-3 in the synthetic method for EXAMPLE 70, 73-1 (0.13 g) was used instead of compound 70-2 to obtain compound 73-2 (0.14 g) as a yellow semisolid that was used without further purification.

Step 73-3

Synthesis of (R)-2-acetoxy-2-((R)-4-(3,5-bis(trifluoromethyl)phenyl)-3-oxomorpholin-2-yl)acetic acid (compound 73-3)

According to the Step 70-4 in the synthetic method for EXAMPLE 70, compound 73-2 (0.14 g) was used instead of compound 70-3 to afford compound 73-3 (0.12 g) as a light yellow solid that was used without further purification.

Step 73-4

Synthesis of (R)-1-((R)-4-(3,5-bis(trifluoromethyl)phenyl)-3-oxomorpholin-2-yl)-2-oxo-2-(4-(5-oxo-4,5-dihydro-1,2,4-oxadiazol-3-yl)phenylamino)ethyl acetate (compound 73-4)

According to the Step 70-5 in the synthetic method for EXAMPLE 70, compound 73-3 (65 mg) was used instead of compound 70-4 to obtain compound 73-4 (69 mg) as a white solid after reverse-phase (C18) HPLC purification.

Step 73-5

Synthesis of ammonium 3-(4-((R)-2-((R)-4-(3,5-bis(trifluoromethyl)phenyl)-3-oxomorpholin-2-yl)-2-hydroxyacetamido)phenyl)-1,2,4-oxadiazol-5-olate (compound 73-5)

According to the Step 70-6 in the synthetic method for EXAMPLE 70, compound 73-4 (69 mg) was used instead of compound 70-5 to obtain compound 73-5 (58 mg) as a white solid that was used without further purification.

Step 73-6

Synthesis of (R)-2-((R)-4-(3,5-bis(trifluoromethyl)phenyl)-3-oxomorpholin-2-yl)-N-(4-carbamimidoylphenyl)-2-hydroxyacetamide hydrochloride (EXAMPLE 73)

According to the Step 70-7 in the synthetic method for EXAMPLE 70, compound 73-5 (53 mg) was used instead of compound 70-6 to obtain EXAMPLE 73 (37 mg) as a maize solid.

Example 74

Synthesis of (R)-2-((R)-4-(3,5-bis(trifluoromethyl)phenyl)-3-oxomorpholin-2-yl)-2-hydroxy-N-(1-oxoisoindolin-5-yl)acetamide (EXAMPLE 74)

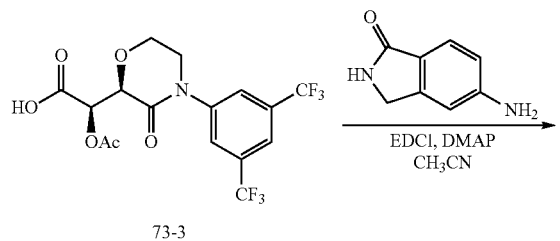

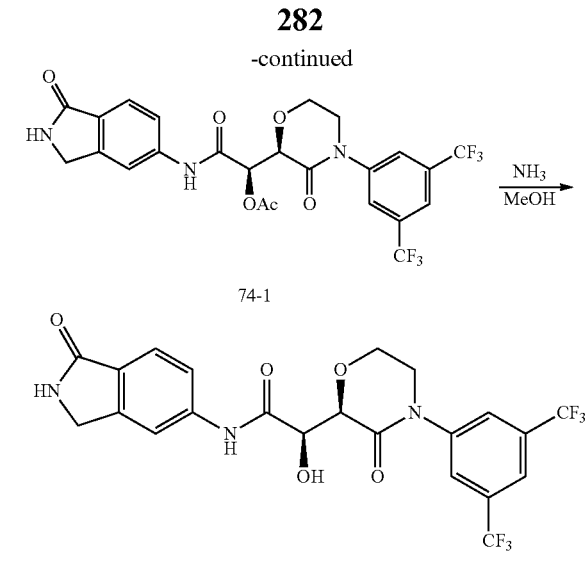

EXAMPLE 74

Step 74-1

Synthesis of (R)-1-((R)-4-(3,5-bis(trifluoromethyl)phenyl)-3-oxomorpholin-2-yl)-2-oxo-2-(1-oxoisoindolin-5-ylamino)ethyl acetate (compound 74-1)

According to the Step 70-5 in the synthetic method for EXAMPLE 70, compound 73-3 (65 mg) was used instead of compound 70-4 to couple to 5-aminoisoindolin-1-one (25 mg) to obtain compound 74-1 (69 mg) as a white solid after reverse-phase (C18) purification.

Step 74-2

Synthesis of (3,5-bis(trifluoromethyl)phenyl)-3-oxomorpholin-2-yl)-2-hydroxy-N-(1-oxoisoindolin-5-yl)acetamide (EXAMPLE 74)

According to the Step 70-6 in the synthetic method for EXAMPLE 70, compound 74-1 (50 mg) was used instead of compound 70-5 to obtain EXAMPLE 74 (48 mg) as white solid.

Example 75

Synthesis of (R)—N-(4-carbamimidoylphenyl)-2-hydroxy-2-((R)-4-(4-methoxybenzyl)-3-oxomorpholin-2-yl)acetamide hydrochloride (EXAMPLE 75)

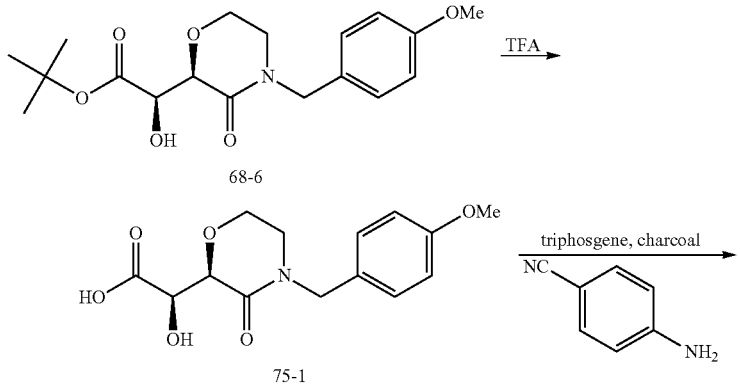

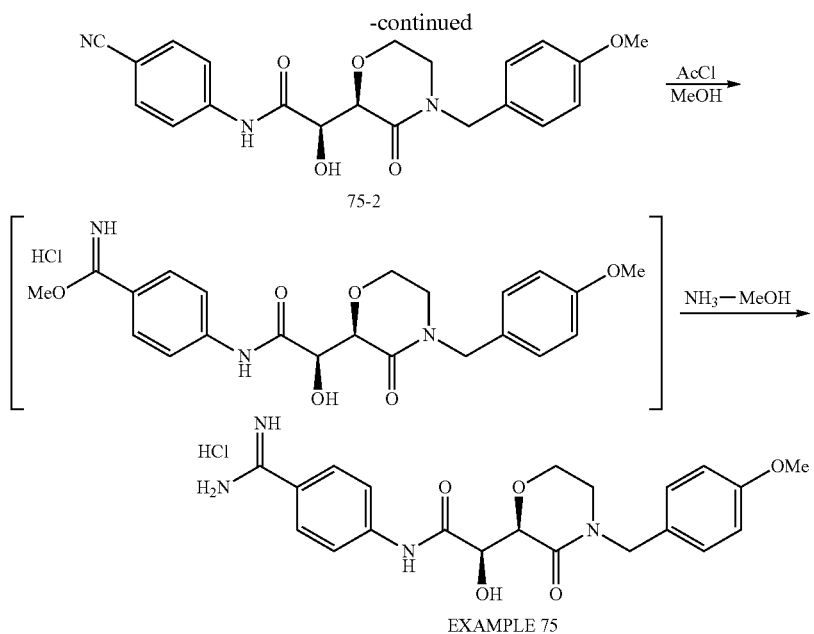

Step 75-1

Synthesis of (R)-2-hydroxy-2-((R)-4-(4-methoxybenzyl)-3-oxomorpholin-2-yl)acetic acid (compound 75-1)

To a solution of compound 68-6 (0.10 g, 0.28 mmol) in CH₂Cl₂ (2 mL) at 0° C. was added TFA (0.6 mL) dropwise. The mixture was stirred for 1 h at 0° C., warmed to rt, and stirred for an additional 3 h. The mixture was diluted with CH₂Cl₂ and concentrated to dryness under reduced pressure. The crude mixture was redissolved in CH₂Cl₂ and concentrated and this protocol was repeated 5 times with to afford compound 75-1 (78 mg) as a light yellow oil that was used without further purification.

Step 75-2

Synthesis of (R)—N-(4-cyanophenyl)-2-hydroxy-2-((R)-4-(4-methoxybenzyl)-3-oxomorpholin-2-yl) acetamide (compound 75-2)

To a solution of compound 75-1 (0.11 g) in THF (2.5 mL) at 0° C. was added activated charcoal (15 mg) followed by triphosgene (0.44 g). The mixture was allowed to warm to rt, stirred for 12 h, and was filtered through a pad of Celite®. The Celite® pad was washed with THF and the resultant filtrated was concentrated under reduced pressure. The crude product was dissolved in DMF (2 mL), 4-aminobenzonitrile (65 mg) was added, and the mixture was stirred for 12 h at rt. The crude mixture was purified directly by reverse phase HPLC using a C18 column and a gradient of (89.95:9.95:0.1 H₂O:MeCN:HCO₂H to 9.95:89.95:0.1 H₂O:MeCN:HCO₂H) to afford compound 75-2 (28%) as a white solid.

Step 75-3

Synthesis of (R)—N-(4-carbamimidoylphenyl)-2-hydroxy-2-((R)-4-(4-methoxybenzyl)-3-oxomorpholin-2-yl)acetamide hydrochloride (EXAMPLE 75)

To a pressure tube charged with compound 75-2 (35 mg) in MeOH (1.2 mL) at 0° C. was added AcCl (1.2 ml) dropwise. The tube was capped, warmed to rt, and stirred for 12 h. The mixture was concentrated to dryness and the pressure tube was charged with the crude mixture in 7M NH₃/MeOH (4 mL). The mixture was stirred for 3 days and was concentrated under reduced pressure. The crude mixture was purified by reverse phase HPLC using a C18 column and a gradient of (89.95:9.95:0.1 H₂O:MeCN:HCO₂H to 9.95:89.95:0.1 H₂O:MeCN:HCO₂H) to afford EXAMPLE 75 (20 mg) as a white solid as the hydrochloride salt after HCl treatment.

Example 76

Synthesis of (R)—N-(1-Aminoisoquinolin-6-yl)-2-hydroxy-2-((R)-4-(4-methoxybenzyl)-3-oxomorpholin-2-yl)acetamide (EXAMPLE 76)

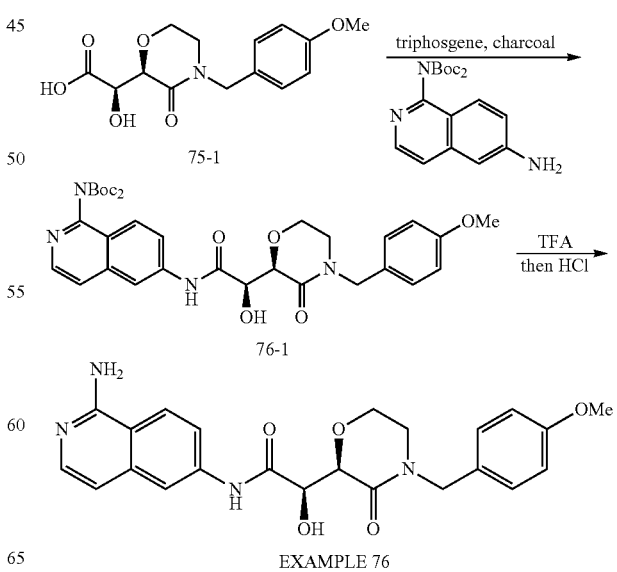

Step 76-1

Synthesis of (R)—N-(1-bis-tertbutoxycarbonyl aminoisoquinolin-6-yl)-2-hydroxy-2-((R)-4-(4-methoxybenzyl)-3-oxomorpholin-2-yl)acetamide (compound 76-1)

According to the Step 75-2 in the synthetic method for EXAMPLE 75, compound 75-1 (0.28 g) was treated with di-tert-butyl(6-aminoisoquinolin-1-yl)imidocarbonate (0.51 g) from WO 2006/062972 to obtain compound 76-1 (0.23 g) as a white solid after reverse-phase purification.

Step 76-2

Synthesis of (R)—N-(1-aminoisoquinolin-6-yl)-2-hydroxy-2-((R)-4-(4-methoxybenzyl)-3-oxomorpholin-2-yl)acetamide (EXAMPLE 76)

To a solution of compound 76-1 (0.23 g) in $CH_2Cl_2$ (2 mL) at 0° C. was added TFA (0.6 mL) dropwise. The mixture was stirred for 1 h at 0° C., warmed to rt, and stirred for an additional 12 h. The mixture was diluted with $CH_2Cl_2$ and concentrated to dryness and this protocol was repeated 5 times. The crude mixture was purified by reverse phase HPLC using a C18 column and a gradient of (89.95:9.95:0.1 $H_2O$:MeCN:$HCO_2H$ to 9.95:89.95:0.1 $H_2O$:MeCN:$HCO_2H$) to afford EXAMPLE 76 (0.10 g) as a white solid as the hydrochloride salt upon HCl treatment.

Example 77

Synthesis of (2R)—N-(4-amidinophenyl)-2-hydroxy-2-[(2R)-3-oxo-4-(3-(4,4-difluoropiperidin-1-ylcarbonyl)phenyl)morpholin-2-yl]acetamide (EXAMPLE 77)

Step 77-1

Synthesis of 4,4-difluoro-1-[(3-iodophenyl)carbonyl]piperidine (compound 77-1)

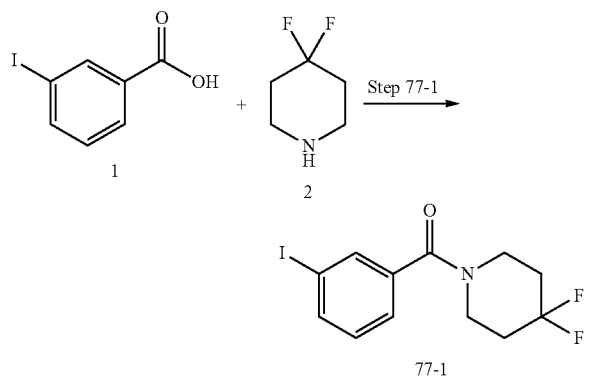

To a solution of 3-iodobenzoic acid 1 (482 mg, 1.94 mmol) in DMF (6 mL) was added 4,4-difluoropiperidine 2 (259 mg, 2.14 mmol), HATU (886 mg, 2.33 mmol) and diisopropylethylamine (750 mg, 5.81 mmol). The reaction mixture was stirred at room temperature for 1.5 hours. Ethyl acetate (100 mL) was added and the organic layer was washed with 1 N sodium hydroxide solution, 1 N hydrochloric acid, water and brine. The organic layer was dried over anhydrous sodium sulfate. The organic solvent was evaporated under reduced pressure. The crude product was purified by flash column chromatography to afford the desired 4,4-difluoro-1-[(3-iodophenyl)carbonyl]piperidine compound 77-1 (362 mg, 1.03 mmol).

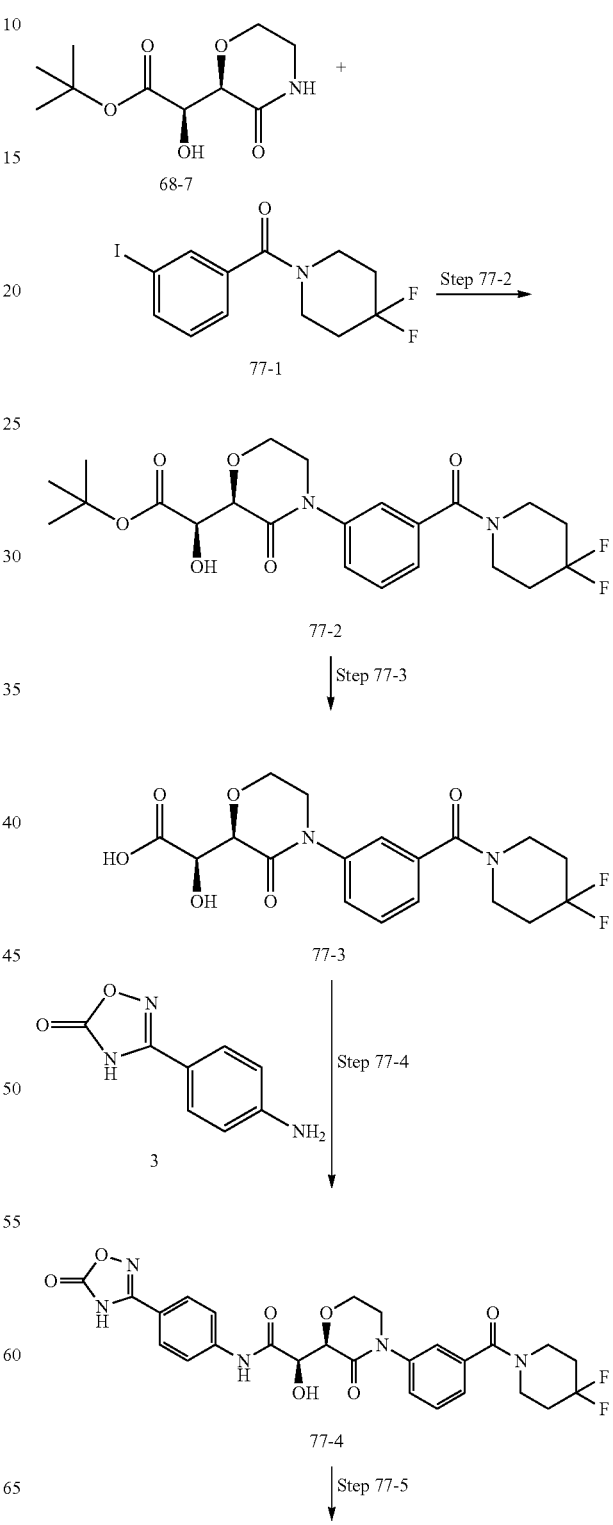

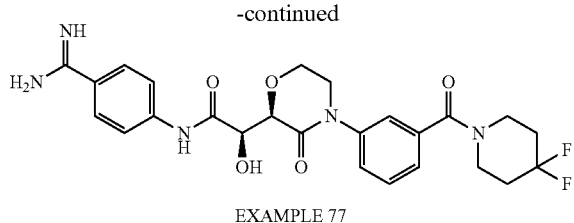

EXAMPLE 77

Step 77-2

Synthesis of Compound 77-2

To a solution of compound 68-7 (200 mg, 0.87 mmol) in anhydrous DMSO (8 mL) under a nitrogen atmosphere was added compound 77-1 (362 mg, 1.03 mmol), potassium phosphate (367 mg, 1.73 mmol), copper (I) iodide (16 mg, 0.084 mmol) and trans-N,N'-dimethylcyclohexane-1,2-diamine (24 mg, 0.17 mmol). The reaction mixture was heated at 80° C. for 2 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 77-2 (251 mg, 0.63 mmol).

Step 77-3

Synthesis of Compound 77-3

To compound 77-2 (251 mg, 0.63 mmol) was added a 50% solution of trifluoroacetic acid in dichloromethane (6 mL). The reaction mixture was stirred at room temperature for 3 hours. The organic solvent was evaporated under reduced pressure to afford the desired compound 77-3 (0.63 mmol) which was used in the next step without further purification.

Step 77-4

Synthesis of Compound 77-4

To a solution of compound 77-3 (0.63 mmol) in acetonitrile (8 mL) was added 3-(4-aminophenyl)-1,2,4-oxadiazol-5 (2H)-one 1 (166 mg, 0.94 mmol), EDCI (156 mg, 0.81 mmol) and DMAP (8 mg, 0.066 mmol). The reaction mixture was stirred at room temperature for 1 hour. The organic solvent was evaporated under reduced pressure. The crude product was purified by flash column chromatography to afford the desired compound 77-4 (226 mg, 0.41 mmol).

Step 77-5

Synthesis of (2R)—N-(4-amidinophenyl)-2-hydroxy-2-[(2R)-3-oxo-4-(3-(4,4-difluoropiperidin-1-ylcarbonyl)phenyl)morpholin-2-yl]acetamide (EXAMPLE 77)

To a solution of compound 77-4 (226 mg, 0.41 mmol) in a 50% solution of 1 N hydrochloric acid in methanol (12 mL) was added palladium-charcoal (10%, 230 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 77 (204 mg, 0.37 mmol) as a white amorphous solid.

Example 78

Synthesis of (2R)—N-(4-amidinophenyl)-2-hydroxy-2-[(2R)-3-oxo-4-(4-(pyrrolidin-1-ylsulfonyl)phenyl)morpholin-2-yl]acetamide (EXAMPLE 78)

Step 78-1

Synthesis of 1-[(4-iodobenzene)sulfonyl]pyrrolidine (compound 78-1)

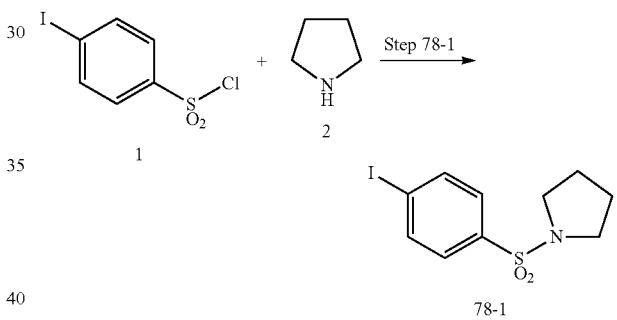

To a solution of 4-iodobenzenesulfonyl chloride 1 (500 mg, 1.66 mmol) in anhydrous acetonitrile (8 mL) under a nitrogen atmosphere was added pyrrolidine 2 (140 mg, 1.97 mmol) and pyridine (261 mg, 3.3 mmol). The reaction mixture was stirred at room temperature for 3 hours. Ethyl acetate (100 mL) was added and the organic layer was washed with 1 N hydrochloric acid, water and brine. The organic layer was dried over anhydrous sodium sulfate. The organic solvent was evaporated under reduced pressure. The crude product was purified by flash column chromatography to afford the desired 1-[(4-iodobenzene)sulfonyl]pyrrolidine compound 78-1 (487 mg, 1.45 mmol).

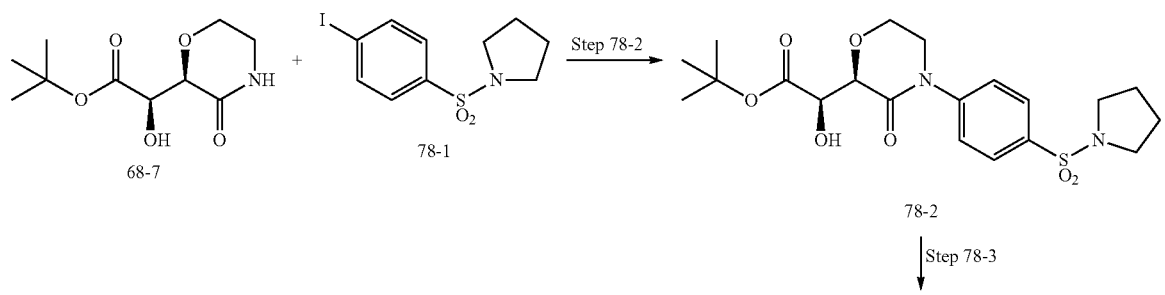

Step 78-3

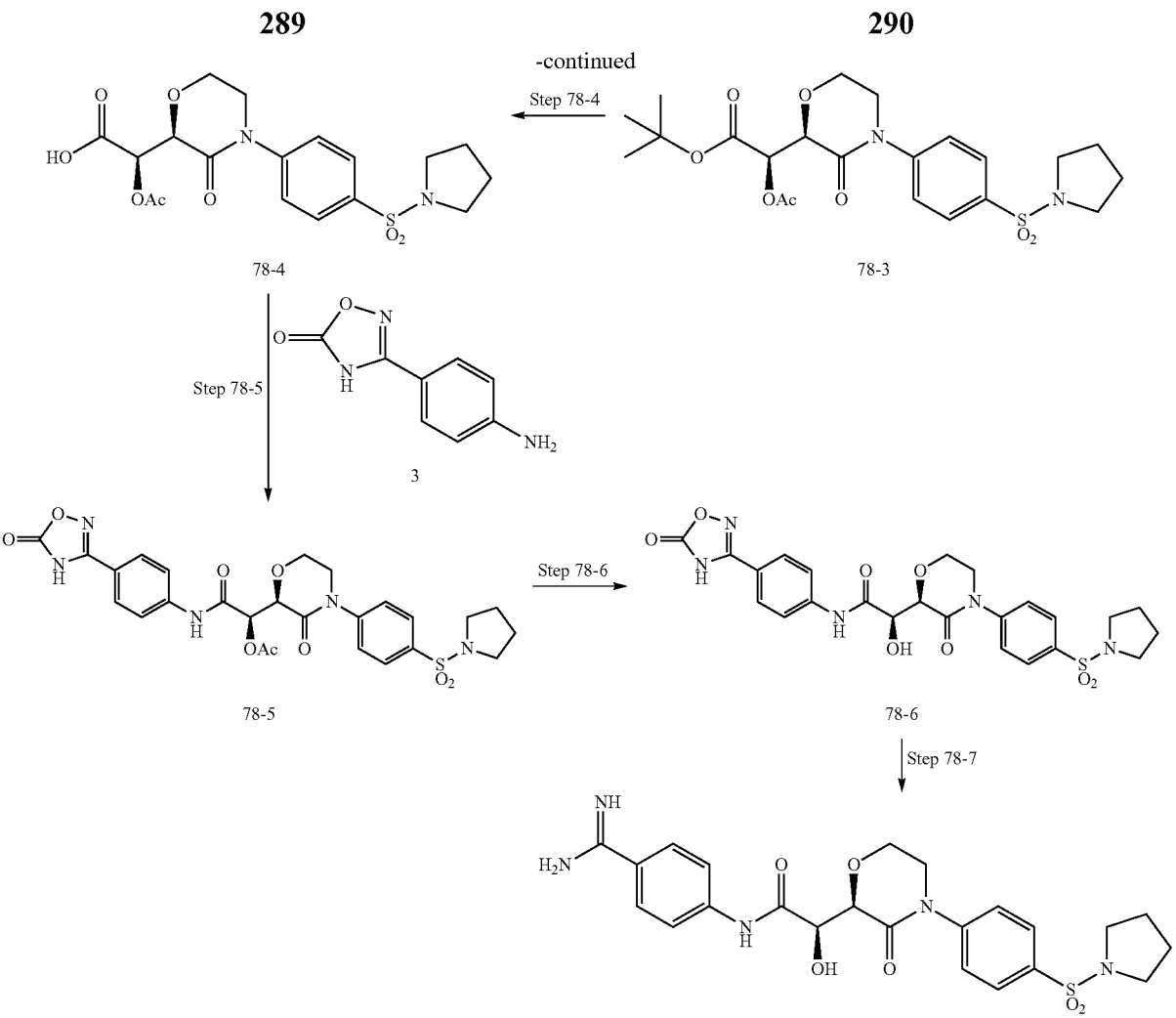

EXAMPLE 78

Step 78-2

Synthesis of Compound 78-2

To a solution of compound 68-7 (200 mg, 0.87 mmol) in anhydrous DMSO (8 mL) under a nitrogen atmosphere was added compound 78-1 (321 mg, 0.95 mmol), potassium phosphate (367 mg, 1.73 mmol), copper (I) iodide (16 mg, 0.084 mmol) and trans-N,N'-dimethylcyclohexane-1,2-diamine (24 mg, 0.17 mmol). The reaction mixture was heated at 80° C. for 3 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 78-2 (335 mg, 0.76 mmol).

Step 78-3

Synthesis of Compound 78-3

To a solution of compound 78-2 (335 mg, 0.76 mmol) in anhydrous dichloromethane (8 mL) under a nitrogen atmosphere was added acetic anhydride (154 mg, 1.51 mmol) and triethylamine (231 mg, 2.29 mmol). The reaction mixture was stirred at room temperature for 16 hours. DMAP (9.3 mg, 0.076 mmol) was added. The reaction mixture was stirred at room temperature for 2 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 78-3 (355 mg, 0.74 mmol).

Step 78-4

Synthesis of Compound 78-4

To compound 78-3 (355 mg, 0.74 mmol) was added a 50% solution of trifluoroacetic acid in dichloromethane (6 mL). The reaction mixture was stirred at room temperature for 1.5 hours. The organic solvent was evaporated under reduced pressure to afford the desired compound 78-4 (0.74 mmol) which was used in the next step without further purification.

Step 78-5

Synthesis of Compound 78-5

To a solution of compound 78-4 (0.74 mmol) in acetonitrile (8 mL) was added 3-(4-aminophenyl)-1,2,4-oxadiazol-5

(2H)-one 1 (191 mg, 1.08 mmol), EDCI (179 mg, 0.93 mmol) and DMAP (9 mg, 0.073 mmol). The reaction mixture was stirred at room temperature for 1 hour. The organic solvent was evaporated under reduced pressure. The crude product was purified by flash column chromatography to afford the desired compound 78-5 (245 mg, 0.42 mmol).

Step 78-6

Synthesis of Compound 78-6

To compound 78-5 (245 mg, 0.42 mmol) was added a solution of 7 N ammonia in methanol (8 mL). The reaction mixture was stirred at room temperature for 40 minutes. The organic solvent was evaporated under reduced pressure to afford the desired compound 78-6 (0.42 mmol) which was used in the next step without further purification.

Step 78-7

Synthesis of (2R)—N-(4-amidinophenyl)-2-hydroxy-2-[(2R)-3-oxo-4-(4-(pyrrolidin-1-ylsulfonyl)phenyl)morpholin-2-yl]acetamide (EXAMPLE 78)

To a solution of compound 78-6 (0.42 mmol) in a 50% solution of 1 N hydrochloric acid in methanol (12 mL) was added palladium-charcoal (10%, 245 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 78 (173 mg, 0.35 mmol) as a white amorphous solid.

Example 79

Synthesis of (2R)—N-(4-amidinophenyl)-2-hydroxy-2-[(2R)-3-oxo-4-(4-(methylsulfonyl)phenyl)morpholin-2-yl]acetamide (EXAMPLE 79)

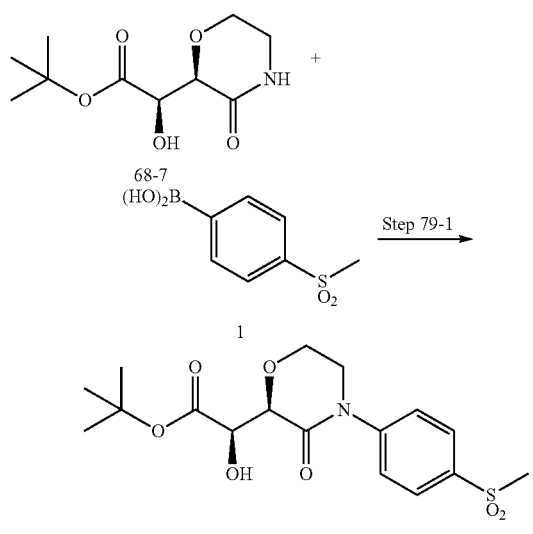

Step 79-1

Synthesis of Compound 79-1

To a solution of 68-7 (200 mg, 0.87 mmol) in anhydrous acetonitrile (4 mL) under a nitrogen atmosphere was added 4-(methylsulfonyl)phenylboronic acid 1 (346 mg, 1.73 mmol), copper (II) acetate (158 mg, 0.89 mmol), trimethylamine N-oxide (65 mg, 0.87 mmol) and triethylamine (175 mg, 1.73 mmol). The reaction mixture was stirred at room temperature for 16 hours. Ethyl acetate (100 mL) was added and the organic layer was washed with ammonium hydroxide, water and brine. The organic layer was dried over anhydrous sodium sulfate. The organic solvent was evaporated under reduced pressure. The crude product was purified by flash column chromatography to afford the desired compound 79-1 (156 mg, 0.41 mmol).

Step 79-2

Synthesis of Compound 79-2

To compound 79-1 (156 mg, 0.41 mmol) was added a 4 N solution of hydrogen chloride in dioxane (8 mL). The reaction mixture was stirred at room temperature for 16 hours. The

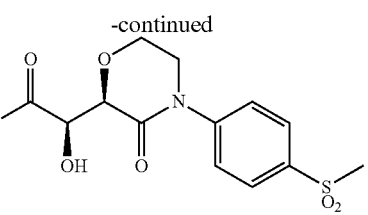

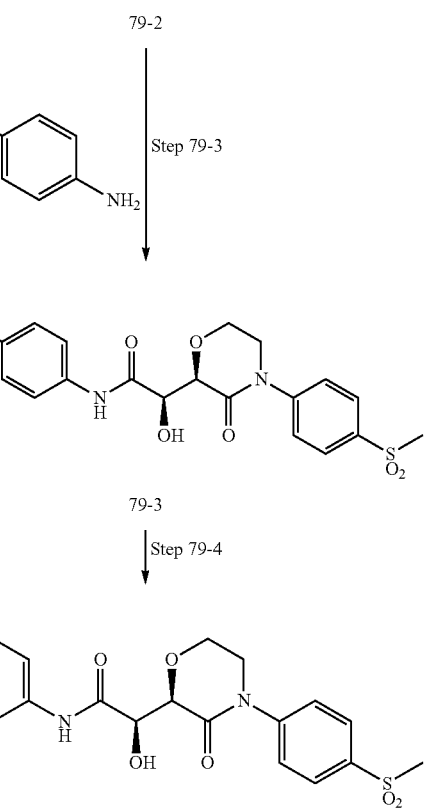

EXAMPLE 79 organic solvent was evaporated under reduced pressure to afford the desired compound 79-2 (0.41 mmol) which was used in the next step without further purification.

Step 79-3

Synthesis of Compound 79-3

To a solution of compound 79-2 (0.41 mmol) in acetonitrile (4 mL) was added 3-(4-aminophenyl)-1,2,4-oxadiazol-5 (2H)-one 2 (191 mg, 1.08 mmol) and EDCI (98 mg, 0.51 mmol). The reaction mixture was stirred at room temperature for 16 hour. The organic solvent was evaporated under reduced pressure. The crude product was purified by flash column chromatography to afford the desired compound 79-3 (28 mg, 0.057 mmol).

Step 79-4

Synthesis of (2R)—N-(4-amidinophenyl)-2-hydroxy-2-[(2R)-3-oxo-4-(4-(methylsulfonyl)phenyl) morpholin-2-yl]acetamide (EXAMPLE 79)

To a solution of compound 79-3 (28 mg, 0.057 mmol) in a 50% solution of 1 N hydrochloric acid in methanol (4 mL) was added palladium-charcoal (10%, 28 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 79 (5 mg, 0.011 mmol) as a white amorphous solid.

Example 80

Synthesis of (2R)—N-(4-amidinophenyl)-2-hydroxy-2-[(2R)-3-oxo-4-(3-phenylphenyl)morpholin-2-yl]acetamide (EXAMPLE 80)

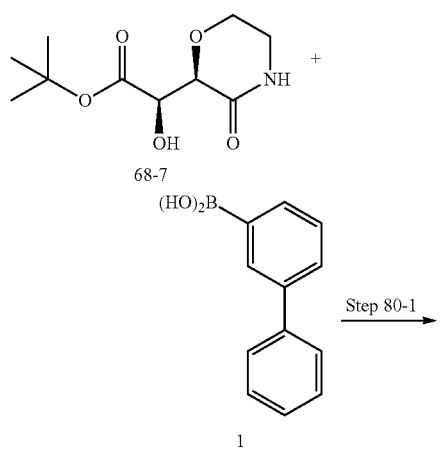

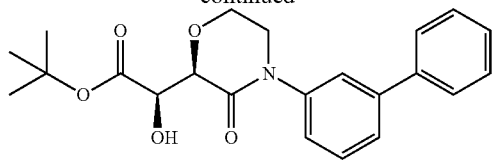

80-1

Step 80-2

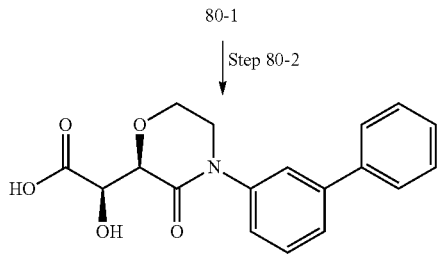

80-2

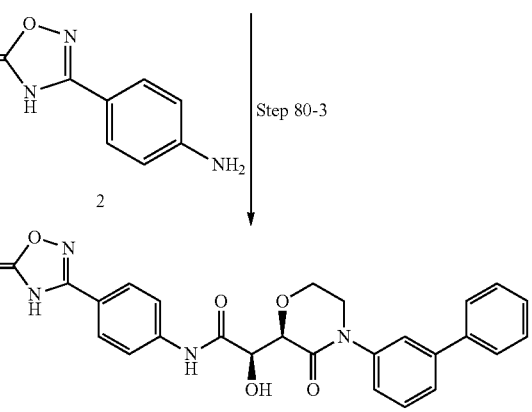

Step 80-3

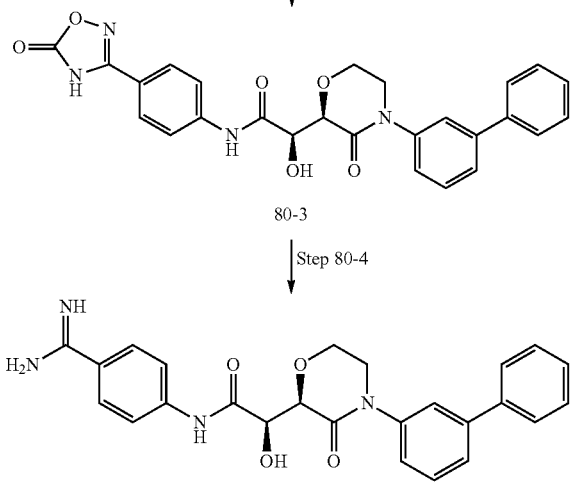

EXAMPLE 80

Step 80-1

Synthesis of Compound 80-1

According to Step 79-1 in the synthetic method for EXAMPLE 79, 3-biphenylboronic acid 1 (342 mg, 1.73 mmol) was used instead of 4-(methylsulfonyl)phenylboronic acid to obtain compound 80-1 (47 mg, 0.12 mmol).

Step 80-2

Synthesis of Compound 80-2

According to Step 79-2 in the synthetic method for EXAMPLE 79, compound 80-1 (47 mg, 0.12 mmol) was used instead of compound 79-1 to obtain compound 80-2 (0.12 mmol) which was used in the next step without further purification.

Step 80-3

Synthesis of Compound 80-3

According to Step 79-3 in the synthetic method for EXAMPLE 79, compound 80-2 (0.12 mmol) was used instead of compound 79-2 to obtain compound 80-3 (17 mg, 0.035 mmol).

Step 80-4

Synthesis of (2R)—N-(4-amidinophenyl)-2-hydroxy-2-[(2R)-3-oxo-4-(3-phenylphenyl)morpholin-2-yl]acetamide (EXAMPLE 80)

According to Step 79-4 in the synthetic method for EXAMPLE 79, compound 80-3 (17 mg, 0.035 mmol) was used instead of compound 79-3 to obtain EXAMPLE 80 (13 mg, 0.029 mmol) as a white amorphous solid.

Example 81

Synthesis of (2R)—N-(4-amidinophenyl)-2-hydroxy-2-[(2R)-3-oxo-4-(4-(pyrrolidin-1-ylcarbonyl)phenyl)morpholin-2-yl]acetamide (EXAMPLE 81)

Step 81-1

Synthesis of 1-[(4-iodophenyl)carbonyl]pyrrolidine compound 81-1

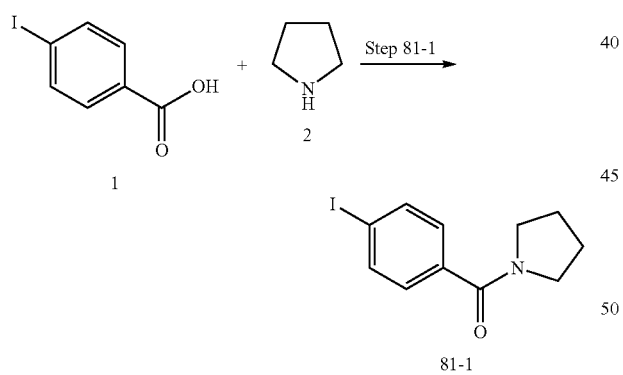

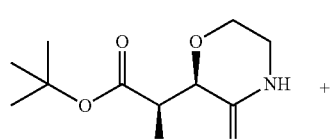

According to Step 77-2 in the synthetic method for EXAMPLE 77, 4-iodobenzoic acid 1 and pyrrolidine 2 were used to obtain compound 81-1.

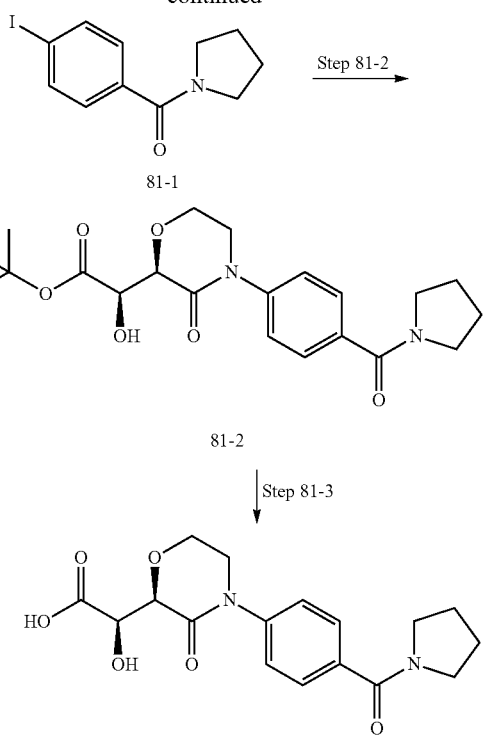

Step 81-2

Synthesis of Compound 81-2

According to Step 77-2 in the synthetic method for EXAMPLE 77, compound 81-1 (187 mg, 0.62 mmol) was used instead of compound 77-1 to obtain compound 81-2 (153 mg, 0.38 mmol).

Step 81-3

Synthesis of Compound 81-3

According to Step 77-3 in the synthetic method for EXAMPLE 77, compound 81-2 (153 mg, 0.38 mmol) was used instead of compound 77-2 to obtain compound 81-3 (0.38 mmol) which was used in the next step without further purification.

Step 81-4

Synthesis of Compound 81-4

According to Step 77-4 in the synthetic method for EXAMPLE 77, compound 81-3 (0.38 mmol) was used instead of compound 77-3 to obtain compound 81-4 (79 mg, 0.16 mmol).

Step 81-5

Synthesis of (2R)—N-(4-amidinophenyl)-2-hydroxy-2-[(2R)-3-oxo-4-(4-(pyrrolidin-1-ylcarbonyl)phenyl)morpholin-2-yl]acetamide (EXAMPLE 81)

According to Step 77-5 in the synthetic method for EXAMPLE 77, compound 81-4 (79 mg, 0.16 mmol) was used instead of compound 77-4 to obtain compound EXAMPLE 81 (72 mg, 0.15 mmol) as a white amorphous solid.

Example 82

Synthesis of (2R)—N-(4-amidinophenyl)-2-hydroxy-2-[(2R)-3-oxo-4-(4-(morpholin-4-ylcarbonyl)phenyl)morpholin-2-yl]acetamide (EXAMPLE 82)

Step 82-1

Synthesis of 1-[(4-iodophenyl)carbonyl]morpholine (compound 82-1)

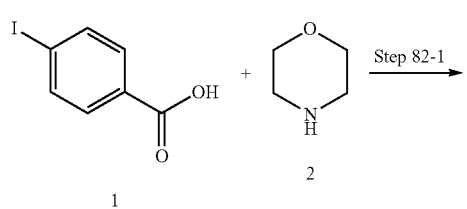

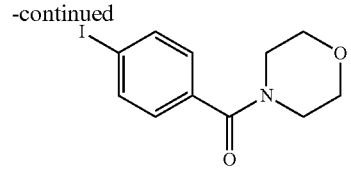

According to Step 77-1 in the synthetic method for EXAMPLE 77, 4-iodobenzoic acid 1 and morpholine 2 were used to obtain compound 82-1.

Step 82-1

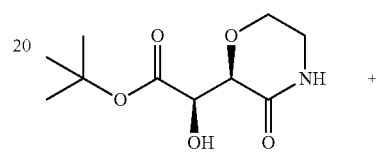

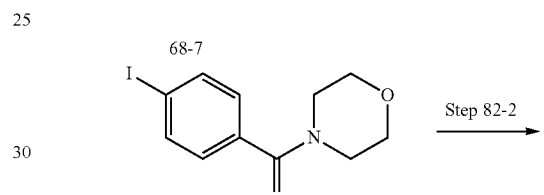

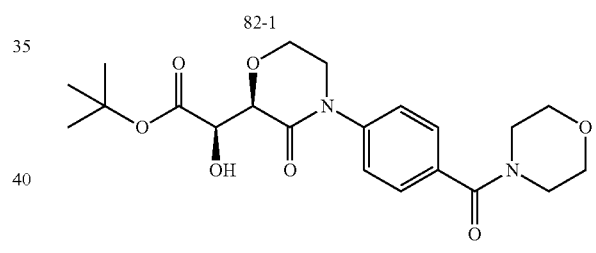

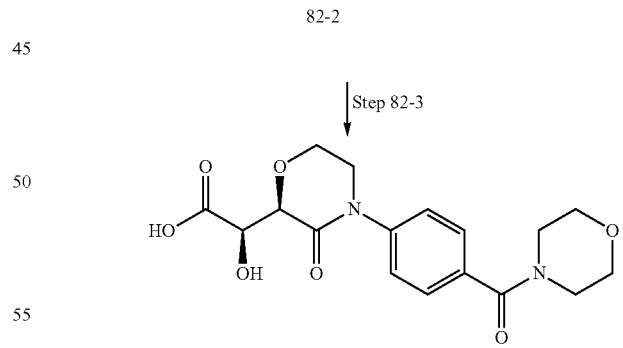

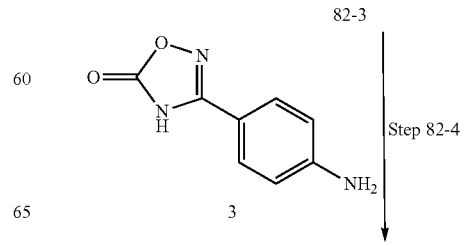

299

-continued

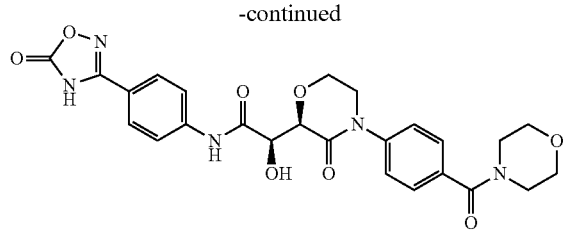

82-4

↓ Step 82-5

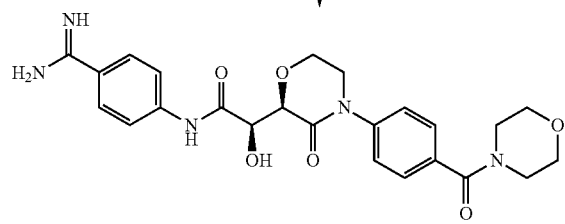

EXAMPLE 82

Step 82-2

Synthesis of Compound 82-2

According to Step 77-2 in the synthetic method for EXAMPLE 77, compound 82-1 (218 mg, 0.69 mmol) was used instead of compound 77-1 to obtain compound 82-2 (221 mg, 0.53 mmol).

Step 82-3

Synthesis of Compound 82-3

According to Step 77-3 in the synthetic method for EXAMPLE 77, compound 82-2 (221 mg, 0.53 mmol) was used instead of compound 77-2 to obtain compound 82-3 (141 mg, 0.39 mmol) which was used in the next step without further purification.

Step 82-4

Synthesis of Compound 82-4

According to Step 77-4 in the synthetic method for EXAMPLE 77, compound 82-3 (40 mg, 0.11 mmol) was used instead of compound 77-3 to obtain compound 82-4 (42 mg, 0.08 mmol).

Step 82-5

Synthesis of (2R)—N-(4-amidinophenyl)-2-hydroxy-2-[(2R)-3-oxo-4-(4-(morpholin-4-ylcarbonyl)phenyl)morpholin-2-yl]acetamide (EXAMPLE 82)

According to Step 77-5 in the synthetic method for EXAMPLE 77, compound 82-4 (42 mg, 0.08 mmol) was used instead of compound 77-4 to obtain EXAMPLE 82 (23 mg, 0.05 mmol) as a white amorphous solid.

300

Example 83

Synthesis of (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide (EXAMPLE 83)

Step 83-1

Synthesis of 4,4-difluoro-1-[(4-iodophenyl)carbonyl]piperidine (compound 83-1)

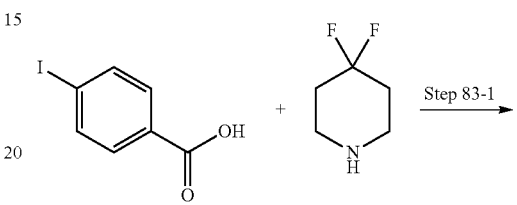

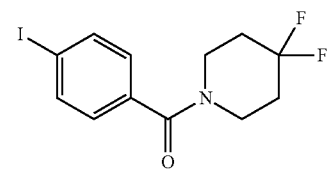

83-1

According to Step 77-1 in the synthetic method for compound 77-1, 4-iodobenzoic acid 1 and 4,4-difluoropiperidine 2 were used to obtain compound 83-1.

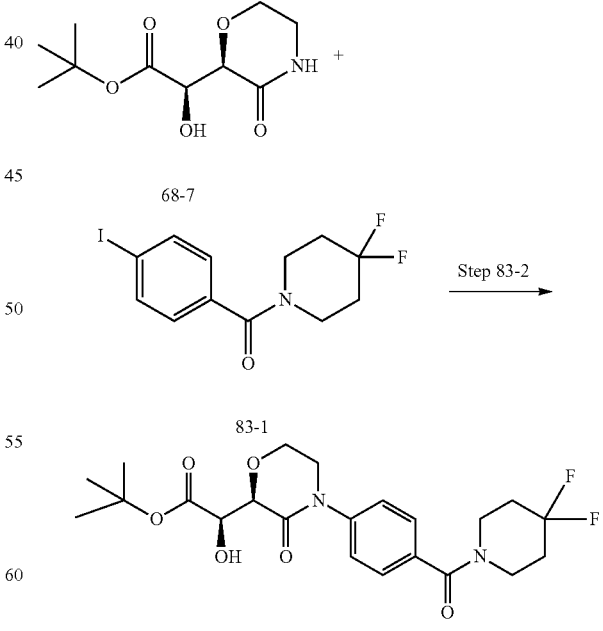

↓ Step 83-3

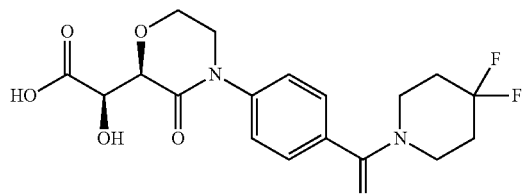

83-3

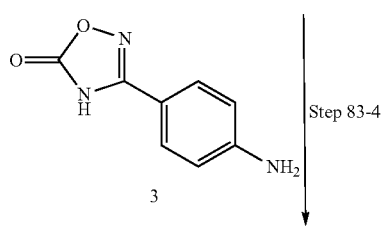

3

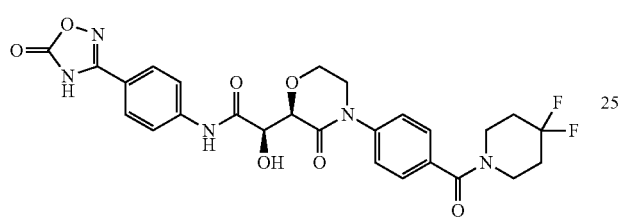

83-4

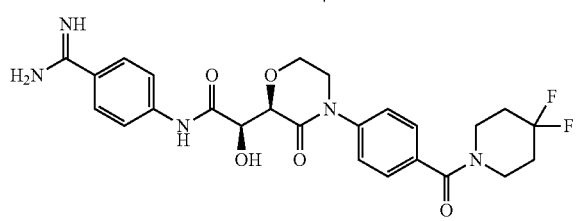

EXAMPLE 83

Step 83-2

Synthesis of Compound 83-2

According to Step 77-2 in the synthetic method for EXAMPLE 77, compound 83-1 (593 mg, 1.69 mmol) was used instead of compound 77-1 to obtain compound 83-2 (256 mg, 0.56 mmol).

Step 83-3

Synthesis of Compound 83-3

According to Step 77-3 in the synthetic method for EXAMPLE 77, compound 83-2 (256 mg, 0.56 mmol) was used instead of compound 77-2 to obtain compound 83-3 (0.56 mmol) which was used in the next step without further purification.

Step 83-4

Synthesis of Compound 83-4

According to Step 77-4 in the synthetic method for EXAMPLE 77, compound 83-3 (0.56 mmol) was used instead of compound 77-3 to obtain compound 83-4 (186 mg, 0.33 mmol).

Step 83-5

Synthesis of (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide (EXAMPLE 83)

According to Step 77-5 in the synthetic method for EXAMPLE 77, compound 83-4 (186 mg, 0.33 mmol) was used instead of compound 77-4 to obtain EXAMPLE 83 (91 mg, 0.18 mmol) as a white amorphous solid.

Example 84

Synthesis of (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide EXAMPLE 84

Step 84-1

Synthesis of 2-[(3-iodophenyl)carbonyl]-1,2,3,4-tetrahydroisoquinoline 84-1

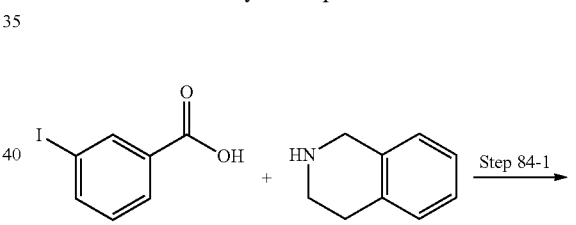

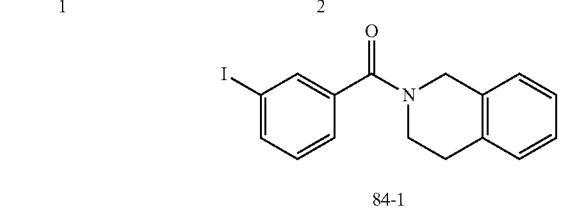

84-1

According to Step 77-1 in the synthetic method for compound 77-1, 3-iodobenzoic acid 1 and 1,2,3,4-tetrahydroisoquinoline 2 were used to obtain compound 84-1.

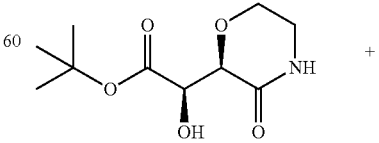

68-7

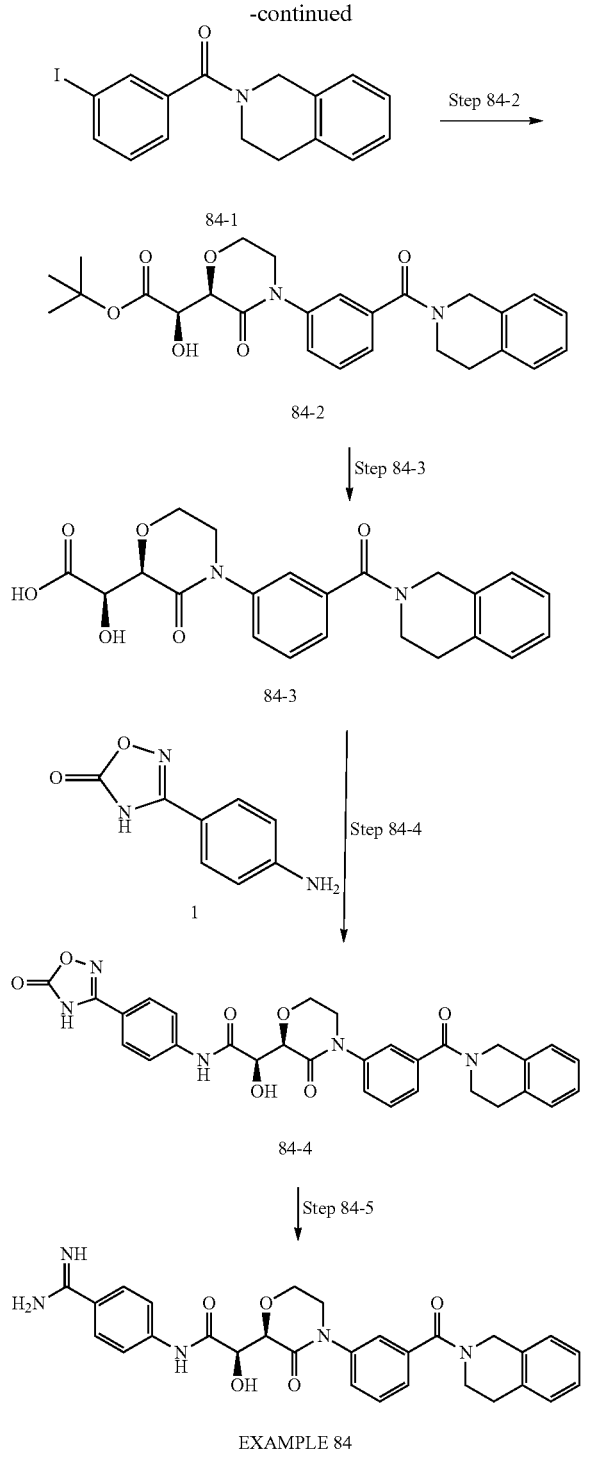

Step 84-2

Synthesis of Compound 84-2

According to Step 77-2 in the synthetic method for EXAMPLE 77, compound 84-1 (518 mg, 1.43 mmol) was used instead of compound 77-1 to obtain compound 84-2 (300 mg, 0.64 mmol).

Step 84-3

Synthesis of Compound 84-3

According to Step 77-3 in the synthetic method for EXAMPLE 77, compound 84-2 (300 mg, 0.64 mmol) was used instead of compound 77-2 to obtain compound 84-3 (0.64 mmol) which was used in the next step without further purification.

Step 84-4

Synthesis of Compound 84-4

According to Step 77-4 in the synthetic method for EXAMPLE 77, compound 84-3 (0.64 mmol) was used instead of compound 77-3 to obtain compound 84-4 (279 mg, 0.49 mmol).

Step 84-5

Synthesis of (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide EXAMPLE 84

According to Step 77-5 in the synthetic method for EXAMPLE 77, compound 84-4 (279 mg, 0.49 mmol) was used instead of compound 77-4 to obtain EXAMPLE 84 (190 mg, 0.36 mmol) as a white amorphous solid.

Example 85

Synthesis of (2R)—N-(4-amidinophenyl)-2-hydroxy-2-[(2R)-3-oxo-4-(3-(isoindolin-2-ylcarbonyl)phenyl)morpholin-2-yl]acetamide EXAMPLE 85

Step 85-1

Synthesis of N-[(3-iodophenyl)carbonyl]isoindoline (compound 85-1)

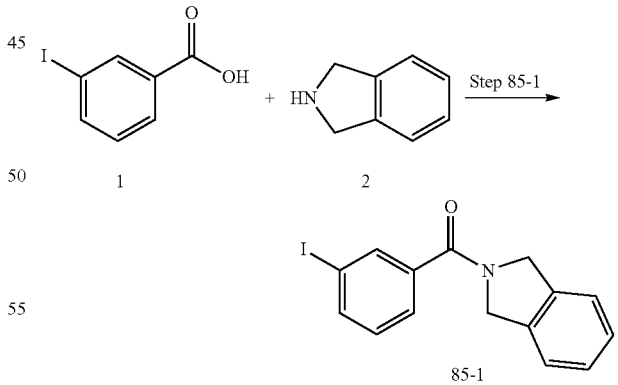

Step 85-1

Synthesis of Compound 85-1

According to Step 77-1 in the synthetic method for compound 77-1, 3-iodobenzoic acid 1 and isoindoline 2 were used to obtain compound 85-1.

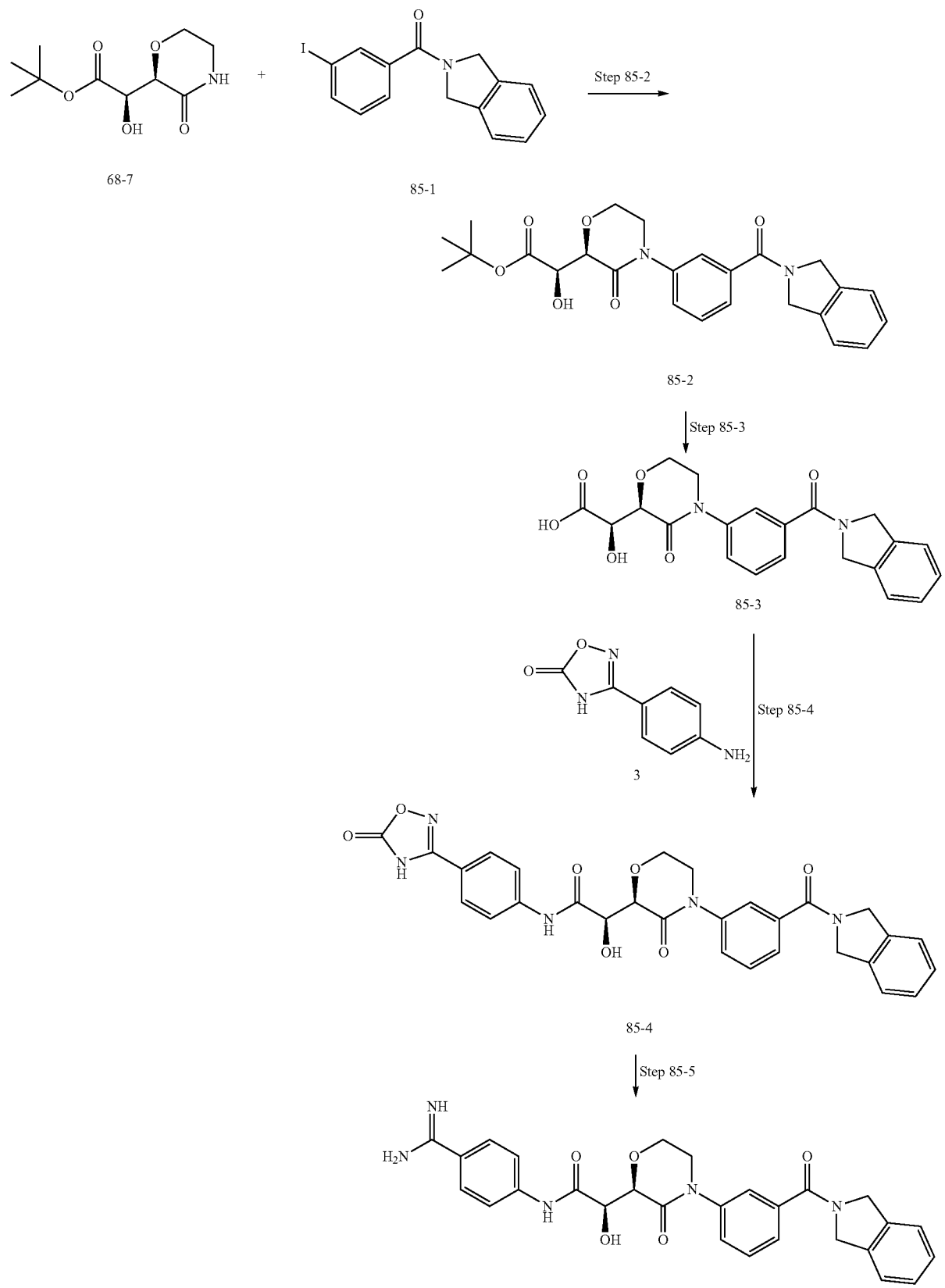

Step 85-2

Synthesis of Compound 85-2

According to Step 77-2 in the synthetic method for EXAMPLE 77, compound 85-1 (499 mg, 1.43 mmol) was used instead of compound 77-1 to obtain compound 85-2 (152 mg, 0.34 mmol).

Step 85-3

Synthesis of Compound 85-3

According to Step 77-3 in the synthetic method for EXAMPLE 77, compound 85-2 (152 mg, 0.34 mmol) was used instead of compound 77-2 to obtain compound 85-3 (0.34 mmol) which was used in the next step without further purification.

Step 85-4

Synthesis of Compound 85-4

According to Step 77-4 in the synthetic method for EXAMPLE 77, compound 85-3 (0.34 mmol) was used instead of compound 77-3 to obtain compound 85-4 (160 mg, 0.29 mmol).

Step 85-5

Synthesis of (2R)—N-(4-amidinophenyl)-2-hydroxy-2-[(2R)-3-oxo-4-(3-(isoindolin-2-ylcarbonyl)phenyl)morpholin-2-yl]acetamide (EXAMPLE 85)

According to Step 77-5 in the synthetic method for EXAMPLE 77, compound 85-4 (160 mg, 0.29 mmol) was used instead of compound 77-4 to obtain EXAMPLE 85 (103 mg, 0.20 mmol) as a white amorphous solid.

Example 86

Synthesis of (2R)—N-(4-amidinophenyl)-2-hydroxy-2-[(2R)-3-oxo-4-(3-(morpholin-4-ylcarbonyl)phenyl)morpholin-2-yl]acetamide EXAMPLE 86

Step 86-1

Synthesis of 1-[(3-iodophenyl)carbonyl]morpholine (compound 86-1)

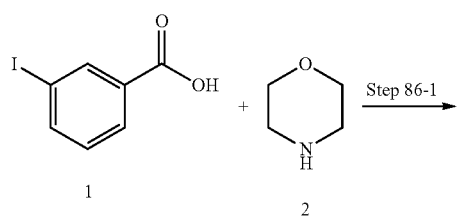

Step 86-1

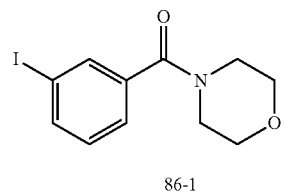

86-1

According to Step 77-1 in the synthetic method for compound 77-1, 3-iodobenzoic acid 1 and morpholine 2 were used to obtain compound 85-1.

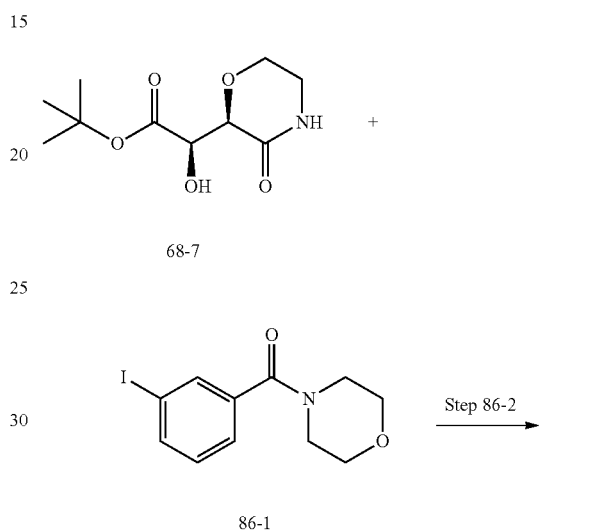

68-7

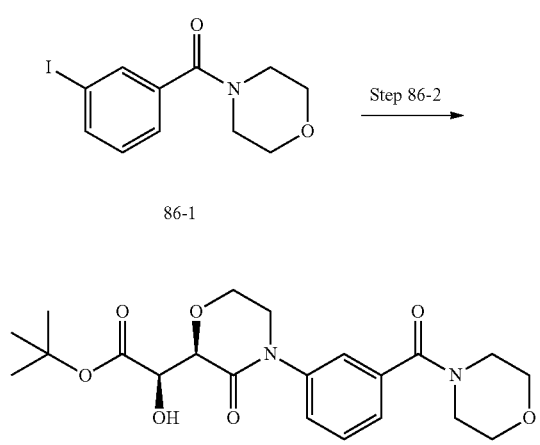

86-1

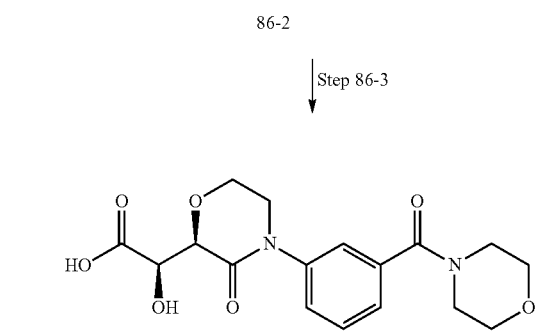

86-2

Step 86-3

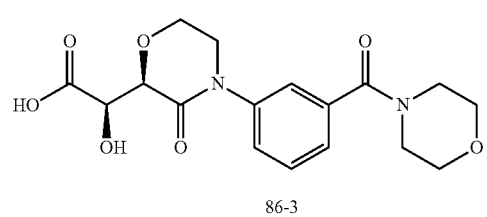

86-3

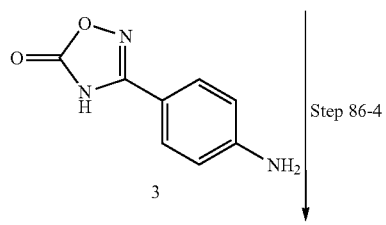

3

Step 86-4

309

-continued

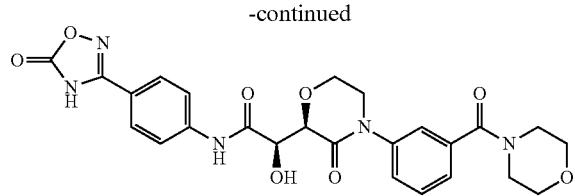

86-4

↓ Step 86-5

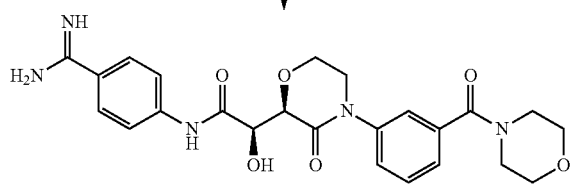

EXAMPLE 86

Step 86-2

Synthesis of Compound 86-2

According to Step 77-2 in the synthetic method for EXAMPLE 77, compound 86-1 (302 mg, 0.95 mmol) was used instead of compound 77-1 to obtain compound 86-2 (250 mg, 0.60 mmol).

Step 86-3

Synthesis of Compound 86-3

According to Step 77-3 in the synthetic method for EXAMPLE 77, compound 86-2 (250 mg, 0.60 mmol) was used instead of compound 77-2 to obtain compound 86-3 (0.60 mmol) which was used in the next step without further purification.

Step 86-4

Synthesis of Compound 86-4

According to Step 77-4 in the synthetic method for EXAMPLE 77, compound 86-3 (0.60 mmol) was used instead of compound 77-3 to obtain compound 86-4 (170 mg, 0.33 mmol).

Step 86-5

Synthesis of (2R)—N-(4-amidinophenyl)-2-hydroxy-2-[(2R)-3-oxo-4-(3-(morpholin-4-ylcarbonyl)phenyl)morpholin-2-yl]acetamide (EXAMPLE 86)

According to Step 77-5 in the synthetic method for EXAMPLE 77, compound 86-4 (170 mg, 0.33 mmol) was used instead of compound 77-4 to obtain EXAMPLE 86 (145 mg, 0.30 mmol) as a white amorphous solid.

310

Example 87

Synthesis of (2R)—N-(4-amidinophenyl)-2-hydroxy-2-[(2R)-3-oxo-4-(3-(pyrrolidin-1-ylcarbonyl)phenyl)morpholin-2-yl]acetamide (EXAMPLE 87)

Step 87-1

Synthesis of 1-[(3-iodophenyl)carbonyl]pyrrolidine (compound 87-1)

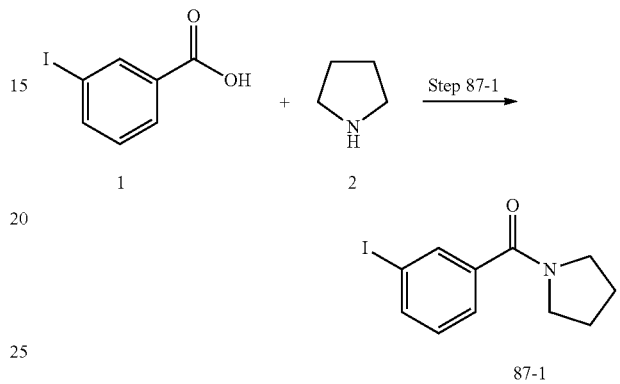

According to Step 77-1 in the synthetic method for compound 77-1, 3-iodobenzoic acid 1 and pyrrolidine 2 were used to obtain compound 87-1.

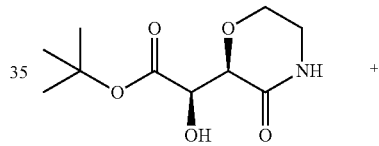

68-7

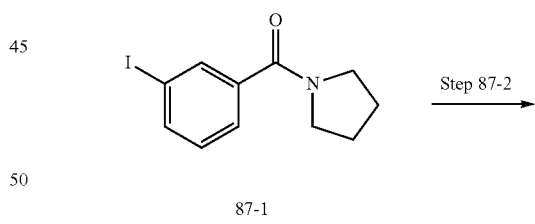

87-1

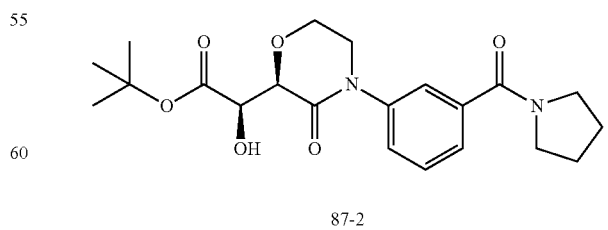

87-2

↓ Step 87-3

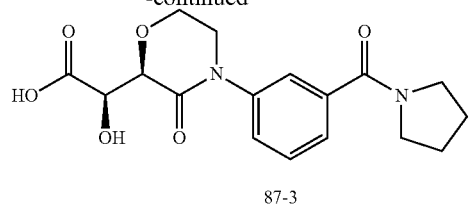

Step 87-2

Synthesis of Compound 87-2

According to Step 77-2 in the synthetic method for EXAMPLE 77, compound 87-1 (286 mg, 0.95 mmol) was used instead of compound 77-1 to obtain compound 87-2 (218 mg, 0.54 mmol).

Step 87-3

Synthesis of Compound 87-3

According to Step 77-3 in the synthetic method for EXAMPLE 77, compound 87-2 (218 mg, 0.54 mmol) was used instead of compound 77-2 to obtain compound 87-3 (0.54 mmol) which was used in the next step without further purification.

Step 87-4

Synthesis of Compound 87-4

According to Step 77-4 in the synthetic method for EXAMPLE 77, compound 87-3 (0.54 mmol) was used instead of compound 77-3 to obtain compound 87-4 (146 mg, 0.29 mmol).

Step 87-5

Synthesis of (2R)—N-(4-amidinophenyl)-2-hydroxy-2-[(2R)-3-oxo-4-(3-(pyrrolidin-1-ylcarbonyl)phenyl)morpholin-2-yl]acetamide (EXAMPLE 87)

According to Step 77-5 in the synthetic method for EXAMPLE 77, compound 87-4 (146 mg, 0.29 mmol) was used instead of compound 77-4 to obtain EXAMPLE 87 (133 mg, 0.29 mmol) as a white amorphous solid.

Example 88

Synthesis of (2R)—N-(4-amidinophenyl)-2-hydroxy-2-[(2R)-3-oxo-4-(4-fluorophenyl)morpholin-2-yl]acetamide (EXAMPLE 88)

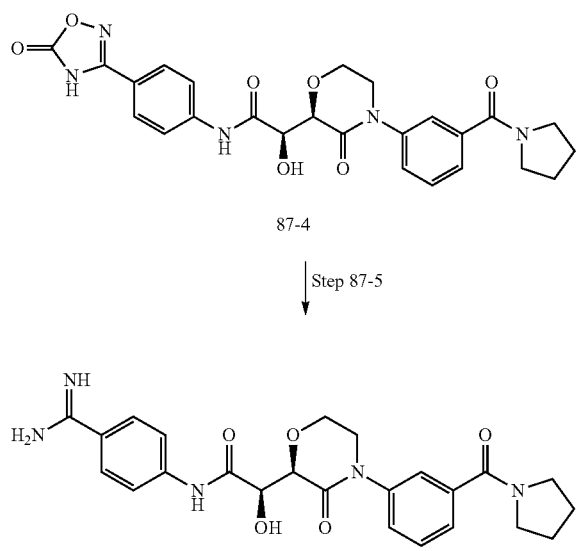

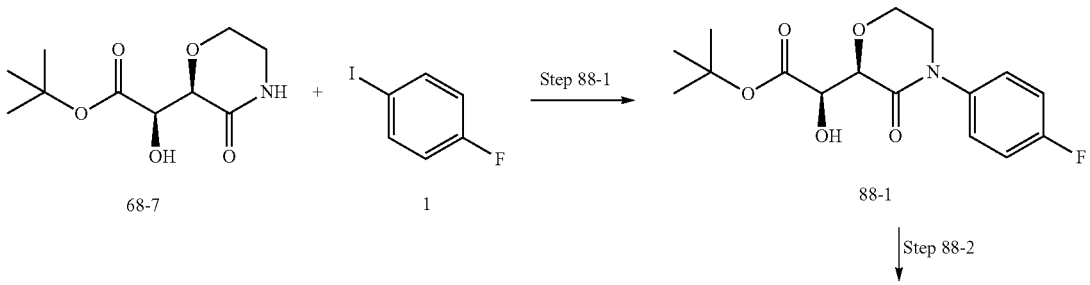

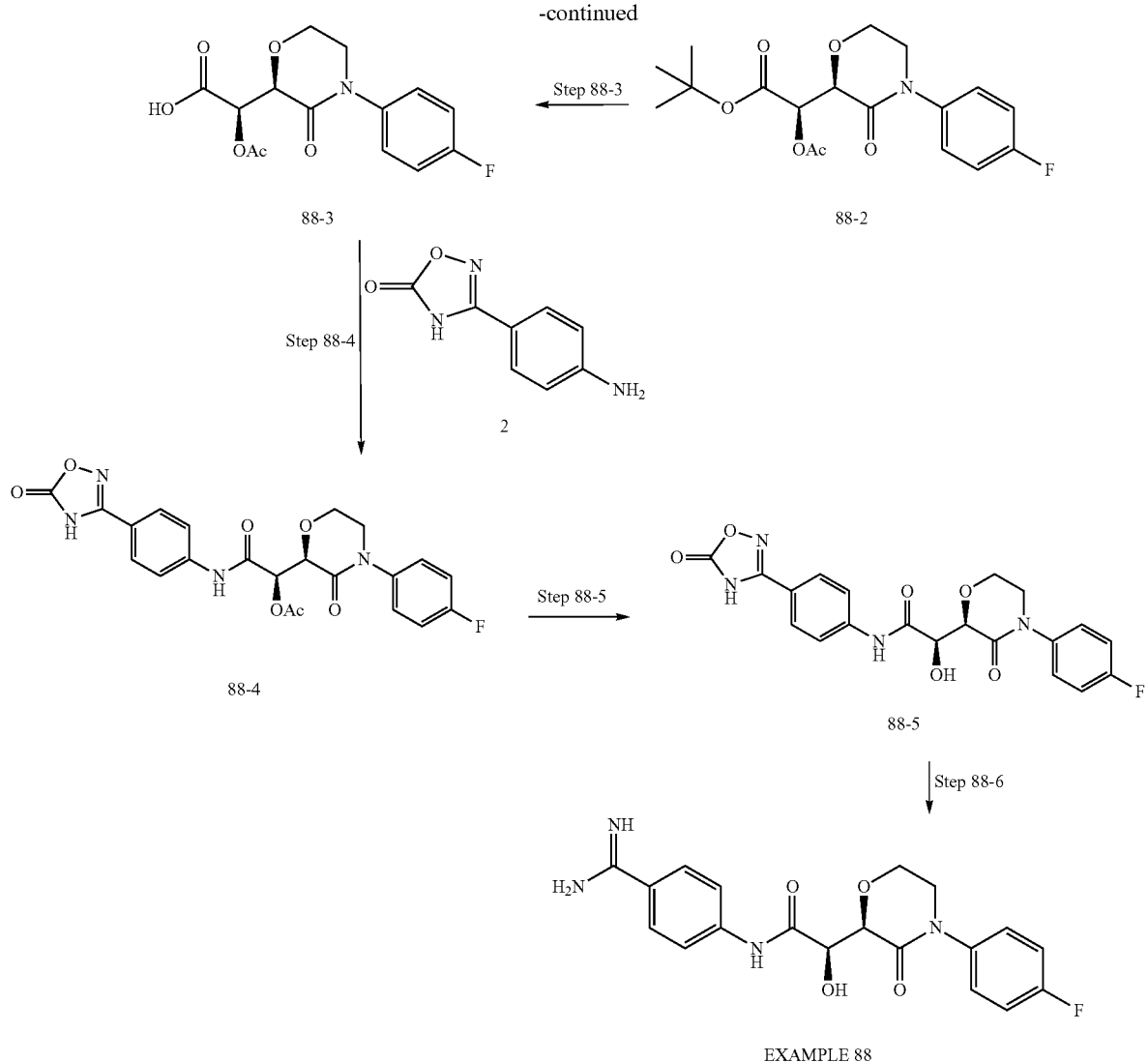

Step 88-1

Synthesis of Compound 88-1

According to Step 78-2 in the synthetic method for EXAMPLE 78, 1-fluoro-4-iodobenzene 1 (67 mg, 0.30 mmol) was used instead of compound 78-2 to obtain compound 88-1 (67 mg, 0.21 mmol).

Step 88-2

Synthesis of Compound 88-2

According to Step 78-3 in the synthetic method for EXAMPLE 78, compound 88-1 (67 mg, 0.21 mmol) was used instead of compound 78-2 to obtain compound 88-2 (77 mg, 0.21 mmol).

Step 88-3

Synthesis of Compound 88-3

According to Step 78-4 in the synthetic method for EXAMPLE 78, compound 88-2 (77 mg, 0.21 mmol) was used instead of compound 78-3 to obtain compound 88-3 (0.21 mmol) which was used in the next step without further purification.

Step 88-4

Synthesis of Compound 88-4

According to Step 78-5 in the synthetic method for EXAMPLE 78, compound 88-3 (0.21 mmol) was used instead of compound 78-4 to obtain compound 88-4 (0.21 mmol) which was used in the next step without further purification.

Step 88-5

Synthesis of Compound 88-5

According to Step 78-6 in the synthetic method for EXAMPLE 78, compound 88-4 (0.21 mmol) was used instead of compound 78-5 to obtain compound 88-5 (0.21 mmol) which was used in the next step without further purification.

Step 88-6
Synthesis of (2R)—N-(4-amidinophenyl)-2-hydroxy-2-[(2R)-3-oxo-4-(4-fluorophenyl)morpholin-2-yl]acetamide (EXAMPLE 88)
According to Step 78-7 in the synthetic method for EXAMPLE 78, compound 88-5 (0.21 mmol) was used instead of compound 78-6 to obtain EXAMPLE 88 (45 mg, 0.12 mmol) as a white amorphous solid.
Example 89
Synthesis of (2R)—N-(4-amidinophenyl)-2-hydroxy-2-[(2R)-3-oxo-4-(3,5-difluorophenyl)morpholin-2-yl]acetamide (EXAMPLE 89)
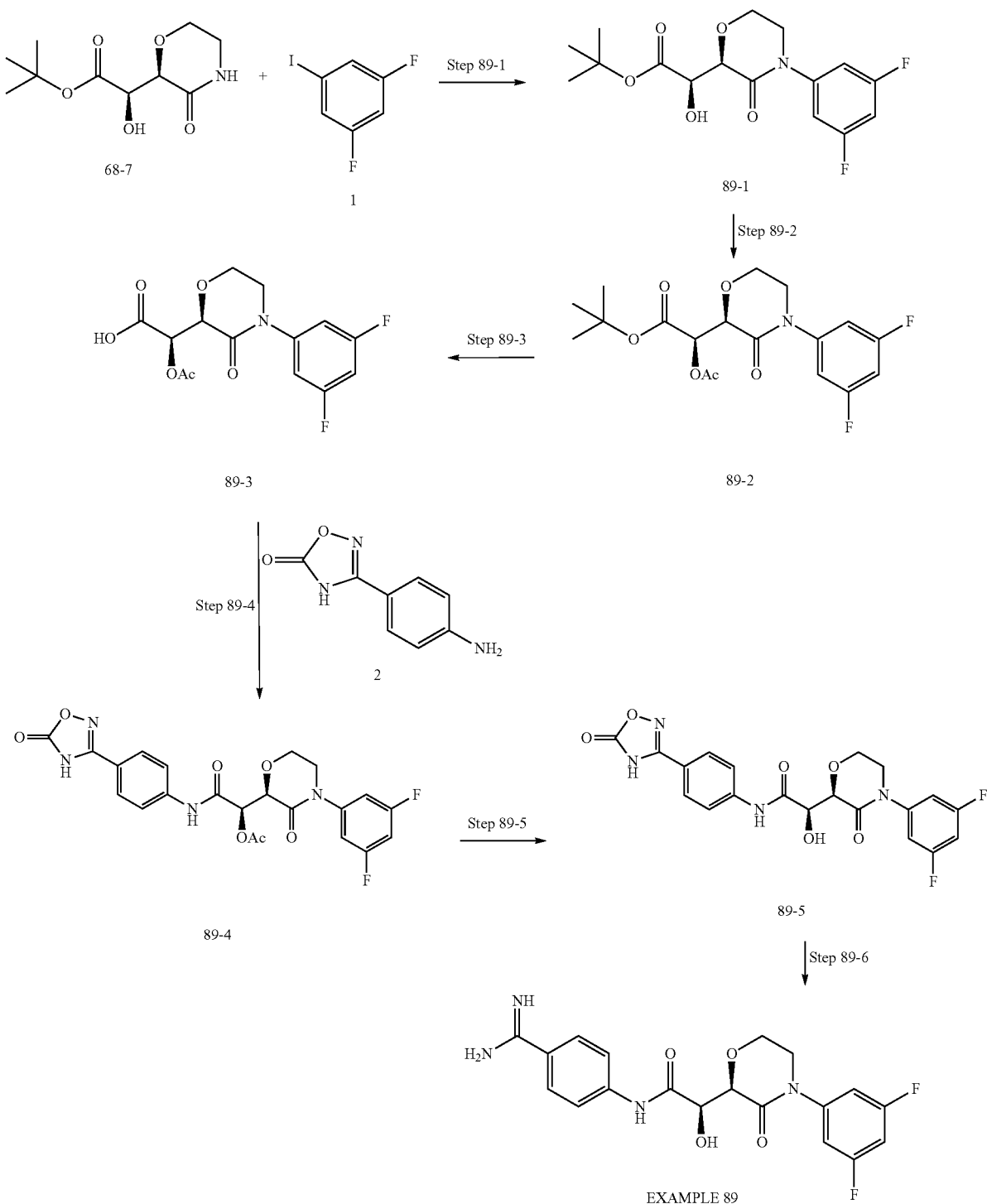

Step 89-1

Synthesis of Compound 89-1

According to Step 78-2 in the synthetic method for EXAMPLE 78, 1,3-difluoro-5-iodobenzene 1 (87 mg, 0.37 mmol) was used instead of compound 78-1 to obtain compound 89-1 (98 mg, 0.29 mmol).

Step 89-2

Synthesis of Compound 89-2

According to Step 78-3 in the synthetic method for EXAMPLE 78, compound 89-1 (98 mg, 0.29 mmol) was used instead of compound 78-2 to obtain compound 89-2 (104 mg, 0.27 mmol).

Step 89-3

Synthesis of Compound 89-3

According to Step 78-4 in the synthetic method for EXAMPLE 78, compound 89-2 (104 mg, 0.27 mmol) was used instead of compound 78-3 to obtain compound 89-3 (0.27 mmol) which was used in the next step without further purification.

Step 89-4

Synthesis of Compound 89-4

According to Step 78-5 in the synthetic method for EXAMPLE 78, compound 89-3 (0.27 mmol) was used instead of compound 78-4 to obtain compound 89-4 (0.27 mmol) which was used in the next step without further purification.

Step 89-5

Synthesis of Compound 89-5

According to Step 78-6 in the synthetic method for EXAMPLE 78, compound 89-4 (0.27 mmol) was used instead of compound 78-5 to obtain compound 89-5 (0.27 mmol) which was used in the next step without further purification.

Step 89-6

Synthesis of (2R)—N-(4-amidinophenyl)-2-hydroxy-2-[(2R)-3-oxo-4-(3,5-difluorophenyl)morpholin-2-yl]acetamide (EXAMPLE 89)

According to Step 78-7 in the synthetic method for EXAMPLE 78, compound 89-5 (0.27 mmol) was used instead of compound 78-6 to obtain EXAMPLE 89 (38 mg, 0.094 mmol) as a white amorphous solid.

Example 90

Synthesis of (2R)—N-(4-amidinophenyl)-2-hydroxy-2-[(2R)-3-oxo-4-(4-(morpholin-1-ylsulfonyl)phenyl)morpholin-2-yl]acetamide (EXAMPLE 90)

Step 90-1

Synthesis of 1-[(4-iodobenzene)sulfonyl]morpholine (compound 90-1)

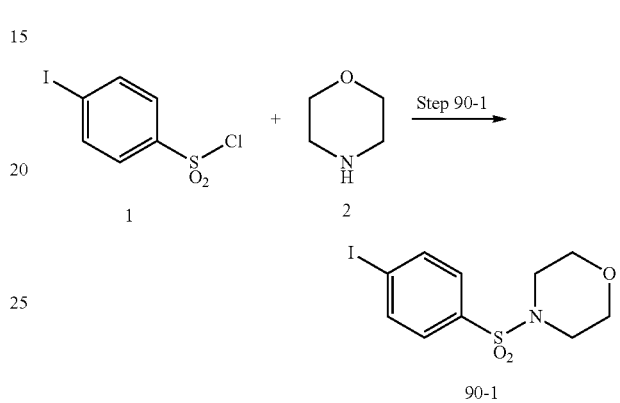

According to Step 77-2 in the synthetic method for EXAMPLE 77, 4-iodobenzenesulfonyl chloride 1 and morpholine 2 were used to obtain compound 90-1.

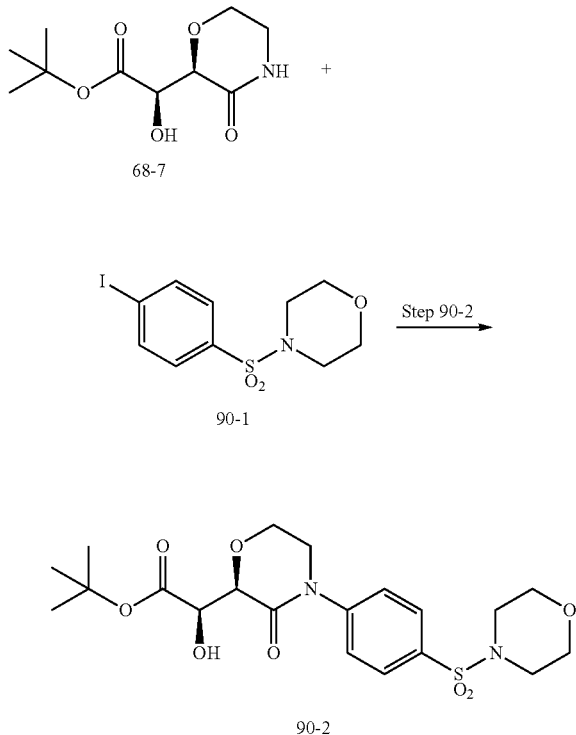

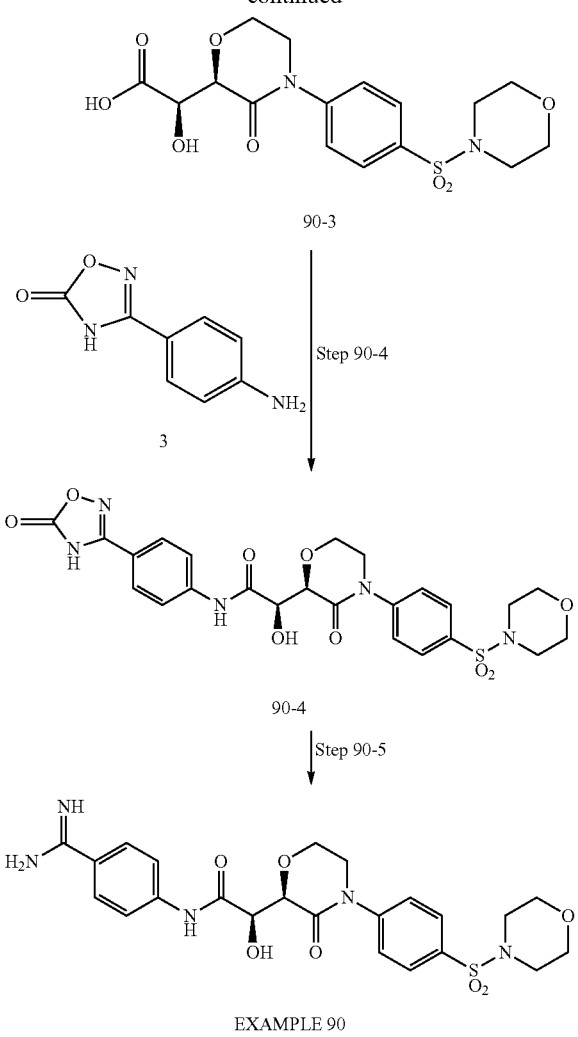

Step 90-2

Synthesis of Compound 90-2

According to Step 77-2 in the synthetic method for EXAMPLE 77, compound 90-1 (336 mg, 0.95 mmol) was used instead of compound 77-1 to obtain compound 90-2 (239 mg, 0.52 mmol).

Step 90-3

Synthesis of Compound 90-3

According to Step 77-3 in the synthetic method for EXAMPLE 77, compound 90-2 (239 mg, 0.52 mmol) was used instead of compound 77-2 to obtain compound 90-3 (208 mg, 0.52 mmol) which was used in the next step without further purification.

Step 90-4

Synthesis of Compound 90-4

According to Step 77-4 in the synthetic method for EXAMPLE 77, compound 90-3 (208 mg, 0.52 mmol) was used instead of compound 77-3 to obtain compound 90-4 (18 mg, 0.032 mmol).

Step 90-5

Synthesis of (2R)—N-(4-amidinophenyl)-2-hydroxy-2-[(2R)-3-oxo-4-(4-(morpholin-1-ylsulfonyl)phenyl)morpholin-2-yl]acetamide (EXAMPLE 90)

According to Step 77-5 in the synthetic method for EXAMPLE 77, compound 90-4 (18 mg, 0.032 mmol) was used instead of compound 77-4 to obtain EXAMPLE 90 (13 mg, 0.025 mmol).

Example 91

Synthesis of (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide (EXAMPLE 91)

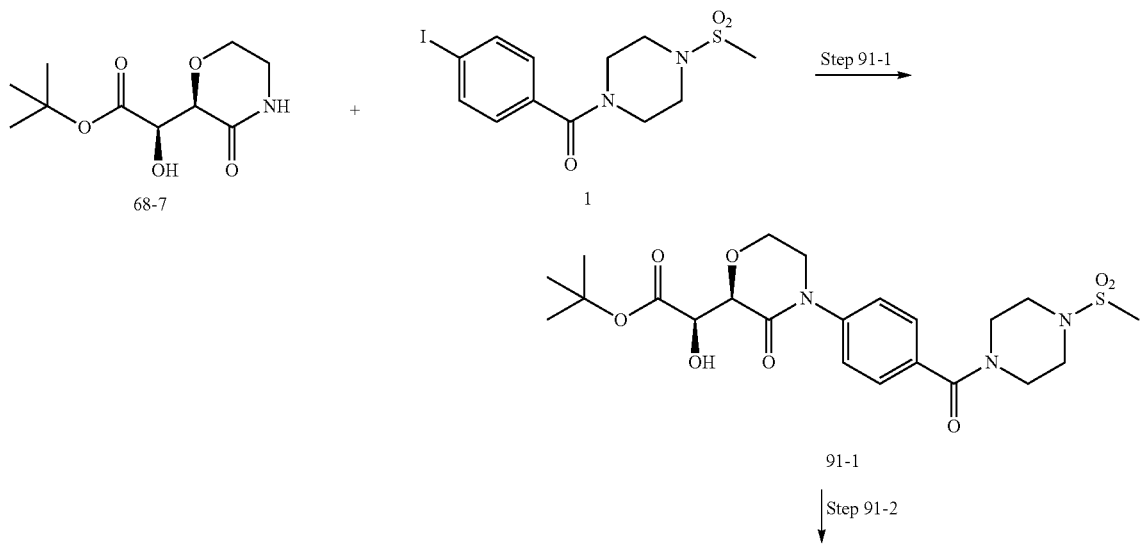

-continued
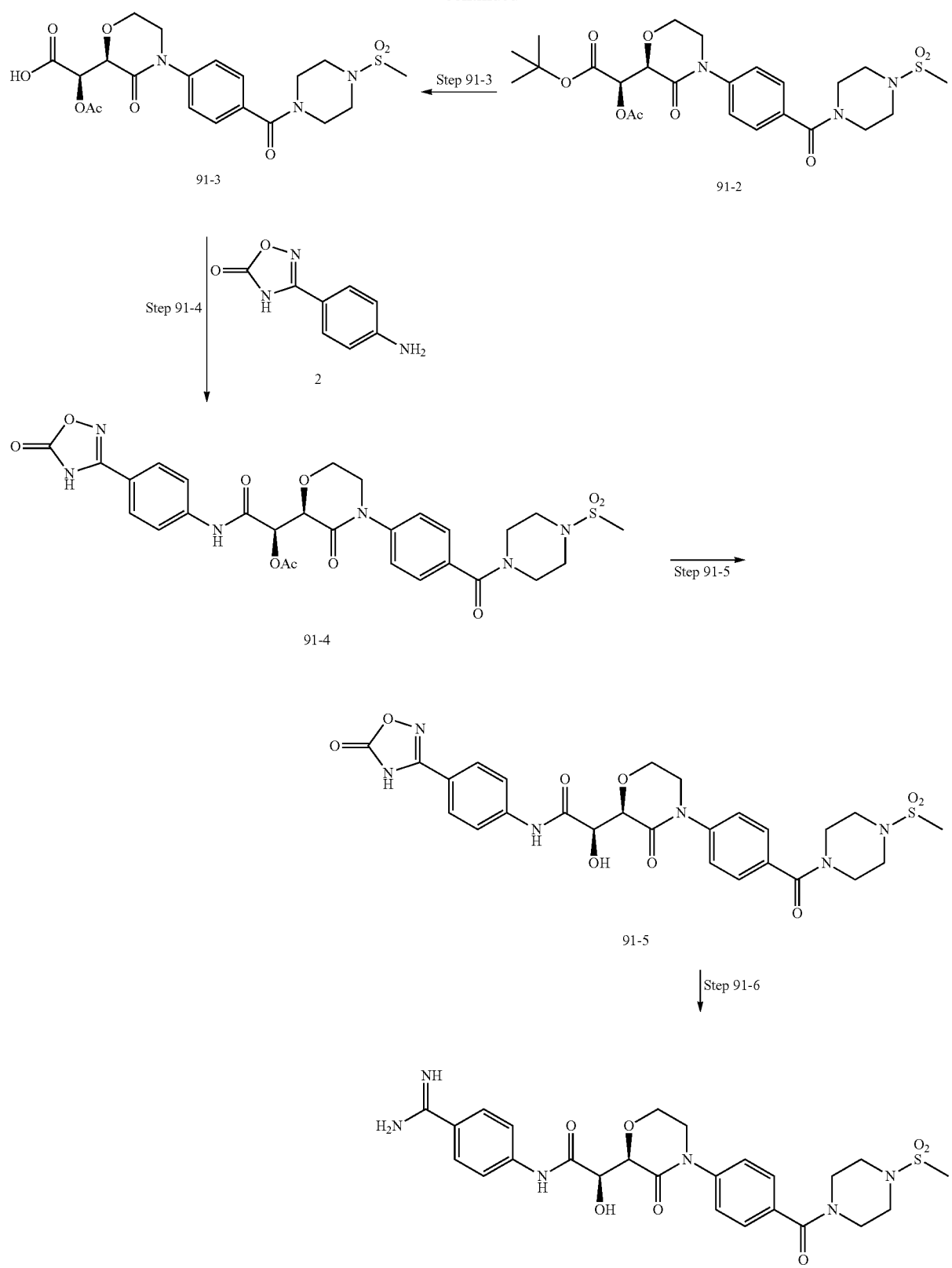

Step 91-1

Synthesis of Compound 91-1

According to Step 78-2 in the synthetic method for EXAMPLE 78, 1-[(4-iodophenyl)carbonyl]-4-methanesulfonylpiperazine 1 (375 mg, 0.95 mmol) was used instead of compound 78-1 to obtain compound 91-1 (264 mg, 0.53 mmol).

Step 91-2

Synthesis of Compound 91-2

According to Step 78-3 in the synthetic method for EXAMPLE 78, compound 91-1 (264 mg, 0.53 mmol) was used instead of compound 78-1 to obtain compound 91-2 (158 mg, 0.29 mmol).

Step 91-3

Synthesis of Compound 91-3

According to Step 78-4 in the synthetic method for EXAMPLE 78, compound 91-2 (158 mg, 0.29 mmol) was used instead of compound 78-2 to obtain compound 91-3 (141 mg, 0.29 mmol) which was used in the next step without further purification.

Step 91-4

Synthesis of Compound 91-4

According to Step 78-5 in the synthetic method for EXAMPLE 78, compound 91-3 (141 mg, 0.29 mmol) was used instead of compound 78-3 to obtain compound 91-4 (151 mg, 0.24 mmol).

Step 91-5

Synthesis of Compound 91-5

According to Step 78-6 in the synthetic method for EXAMPLE 78, compound 91-4 (151 mg, 0.24 mmol) was used instead of compound 78-4 to obtain compound 91-5 (0.24 mmol) which was used in the next step without further purification.

Step 91-6

Synthesis of (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide (EXAMPLE 91)

According to Step 78-7 in the synthetic method for EXAMPLE 78, compound 91-5 (0.24 mmol) was used instead of compound 78-6 to obtain EXAMPLE 91 (115 mg, 0.21 mmol) as a white amorphous solid.

Example 92

Synthesis of (2R)—N-(4-amidinophenyl)-2-hydroxy-2-[(2R)-3-oxo-4-(2-fluoropyridin-5-yl)morpholin-2-yl]acetamide (EXAMPLE 92)

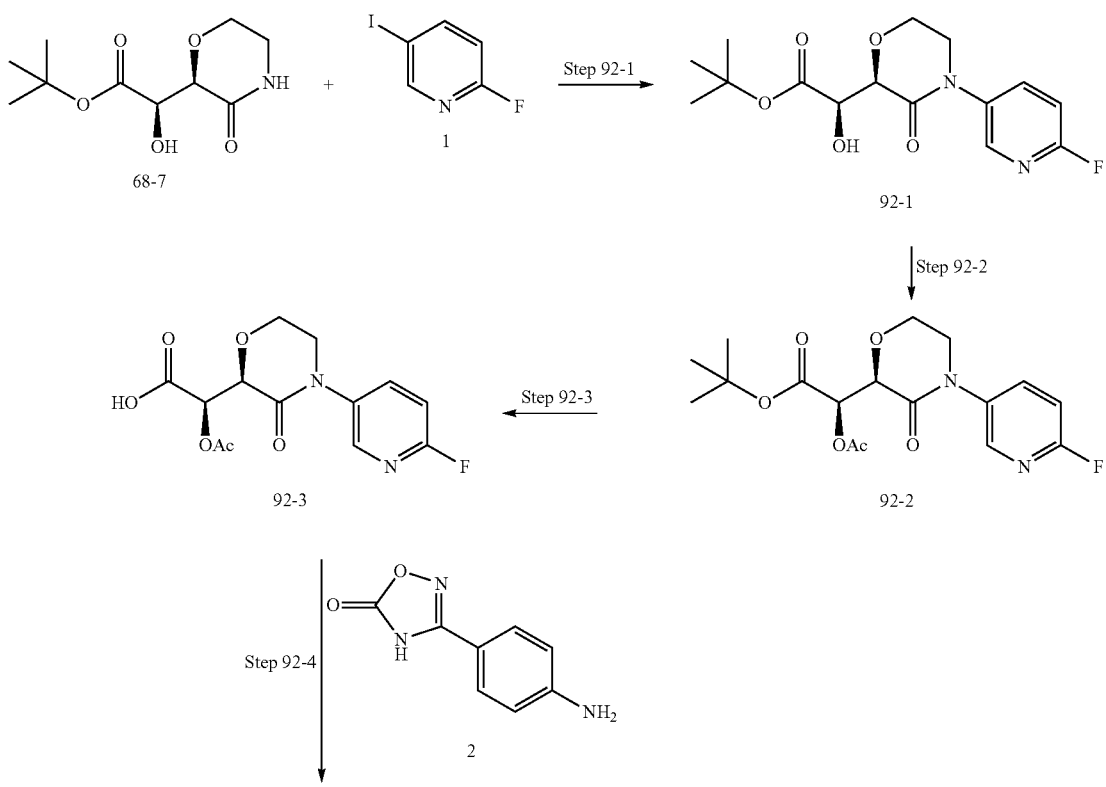

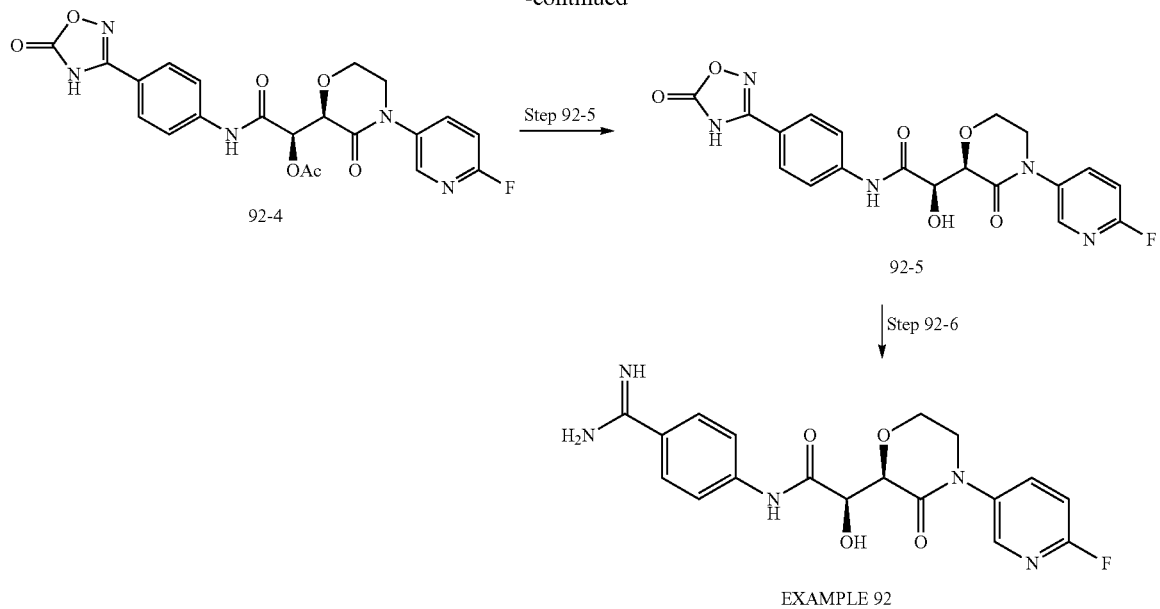

EXAMPLE 92

Step 92-1

Synthesis of Compound 92-1

According to Step 78-2 in the synthetic method for EXAMPLE 78, 2-fluoro-5-iodopyridine 1 (80 mg, 0.36 mmol) was used instead of compound 78-1 to obtain compound 92-1 (94 mg, 0.29 mmol).

Step 92-2

Synthesis of Compound 92-2

According to Step 78-3 in the synthetic method for EXAMPLE 78, compound 92-1 (94 mg, 0.29 mmol) was used instead of compound 78-2 to obtain compound 92-2 (80 mg, 0.22 mmol).

Step 92-3

Synthesis of Compound 92-3

According to Step 78-4 in the synthetic method for EXAMPLE 78, compound 92-2 (80 mg, 0.22 mmol) was used instead of compound 78-3 to obtain compound 92-3 (0.22 mmol) which was used in the next step without further purification.

Step 92-4

Synthesis of Compound 92-4

According to Step 78-5 in the synthetic method for EXAMPLE 78, compound 92-3 (0.22 mmol) was used instead of compound 78-4 to obtain compound 92-4 (0.22 mmol) which was used in the next step without further purification.

Step 92-5

Synthesis of Compound 92-5

According to Step 78-6 in the synthetic method for EXAMPLE 78, compound 92-4 (0.22 mmol) was used instead of compound 78-5 to obtain compound 92-5 (0.22 mmol) which was used in the next step without further purification.

Step 92-6

Synthesis of (2R)—N-(4-amidinophenyl)-2-hydroxy-2-[(2R)-3-oxo-4-(2-fluoropyridin-5-yl)morpholin-2-yl]acetamide (EXAMPLE 92)

According to Step 78-7 in the synthetic method for EXAMPLE 78, compound 92-5 (0.22 mmol) was used instead of compound 78-6 to obtain EXAMPLE 92 (67 mg, 0.17 mmol) as a white amorphous solid.

Example 93

Synthesis of (R)—N-(3-aminobenzo[d]isoxazol-6-yl)-2-hydroxy-2-((R)-3-oxo-4-(4-(trifluoromethyl)phenyl)morpholin-2-yl)acetamide (EXAMPLE 93)

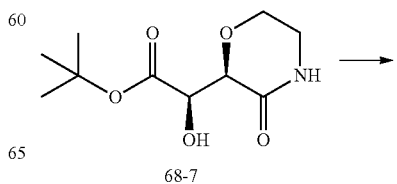

68-7

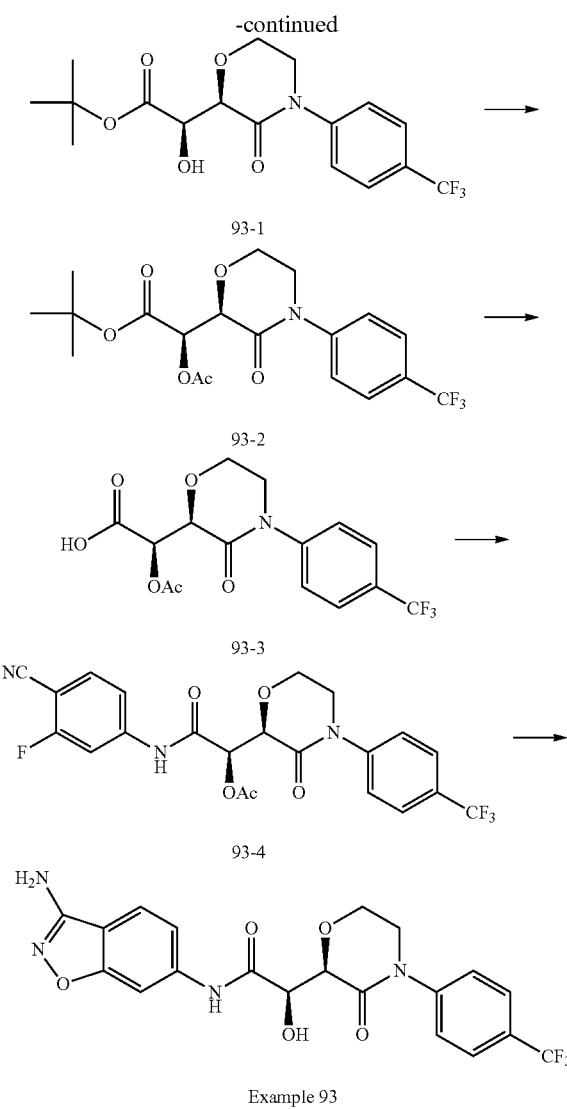

Example 93

Step 93-1

Synthesis of (R)-tert-butyl 2-hydroxy-2-((R)-3-oxo-4-(4-(trifluoromethyl)phenyl)morpholin-2-yl)acetate (compound 93-1)

(R)-tert-butyl 2-hydroxy-2-((R)-3-oxomorpholin-2-yl)acetate (0.5 g, 0.002162 mol) and 4-trifluoromethylphenyl iodide (0.882 g, 1.5 eq) were dissolved in 1,2-dioxane (14 ml), to this mixture were added CuI (82 mg, 0.2 eq), K₂CO₃ (598 mg, 2 eq), and trans-N,N-dimethylcyclohexane-1,2-diamine (0.1 ml, 0.3 eq). The resulting solution was degassed and heated at 115° C. for 5 hours. The mixture was cooled to rt, the solid removed by filtration, solution washed with water, dried (MgSO4), and concentrated. The resulting residue was then purified by silica gel chromatography (0-20% EtOAc in hexane) to give 477 mg of compound 93-1.

Step 93-2

Synthesis of (R)-tert-butyl 2-acetoxy-2-((R)-3-oxo-4-(4-(trifluoromethyl)phenyl)morpholin-2-yl)acetate (compound 93-2)

Compound 93-1 (350 mg, 0.932 mmol) was dissolved in CH₂Cl₂ (4.66 ml) and cooled to 0° C., Ac₂O (0.176 ml, 2 eq), pyridine (0.151 ml, 2 eq), and DMAP (11 mg, 0.1 eq) was added. The mixture was stirred for 2 hours, diluted with EtOAc, washed with CuSO₄ solution, water, dried and concentrated to give 370 mg of compound 93-2.

Step 93-3

Synthesis of (R)-2-acetoxy-2-((R)-3-oxo-4-(4-(trifluoromethyl)phenyl)morpholin-2-yl)acetic acid (compound 93-3)

Compound 93-2 (370 mg, 0.884 mmol) was dissolved in 1:1 CH₂Cl₂/TFA (8.8 ml) and stirred for 30 minutes. The mixture was concentrated to give 310 mg of compound 93-3.

Step 93-4

Synthesis of (R)-2-(4-cyano-3-fluorophenylamino)-2-oxo-1-((R)-3-oxo-4-(4-(trifluoromethyl)phenyl)morpholin-2-yl)ethyl acetate (compound 93-4)

Compound 93-3 (371 mg, 1.03 mmol) was dissolved in CH₂Cl₂ (5.13 ml), (COCl)₂ (0.176 ml, 2 eq), then 1 drop of DMF was added. The mixture was stirred for 1 hour, concentrated to dryness, taken up in DMF and 4-cyano-3-fluoroaniline (0.559 g, 4 eq) added. The mixture was stirred for 2 hours, NH₄Cl(sat) added, the mixture extracted with EtOAc, dried (MgSO₄), concentrated, silica gel chromatography to give 260 mg of compound 93-4.

Step 93-5

Synthesis of (R)—N-(3-aminobenzo[d]isoxazol-6-yl)-2-hydroxy-2-((R)-3-oxo-4-(4-(trifluoromethyl)phenyl)morpholin-2-yl)acetamide (EXAMPLE 93)

Compound 93-4 (160 mg, 0.334 mmol) was dissolved in 10:1 DMF/water (3.34 ml), K₂CO₃ (554 mg, 12 eq) and acetohydroxamic acid (150 mg, 6 eq) were added and the mixture heated at 55° C. for 4 hours. After cooling to room temperature the mixture was diluted with EtOAc, washed with water, dried (MgSO₄) and concentrated. The residue was purified by C18 HPLC (89.95:9.95:0.1 H₂O:MeCN:HCO₂H-9.95:89.95:0.1 H₂O:MeCN:HCO₂H) to give 9 mg of EXAMPLE 93.

Example 94

Synthesis of (R)—N-(3-amino-1H-indazol-6-yl)-2-hydroxy-2-((R)-3-oxo-4-(4-(trifluoromethyl)phenyl)morpholin-2-yl)acetamide (EXAMPLE 94)

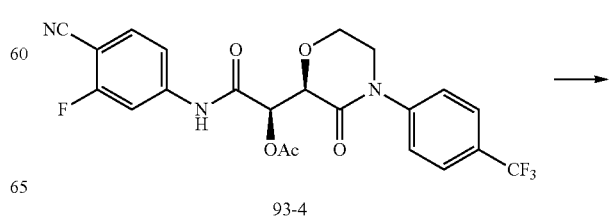

93-4

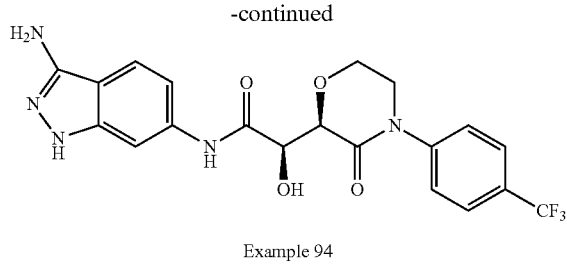

Example 94

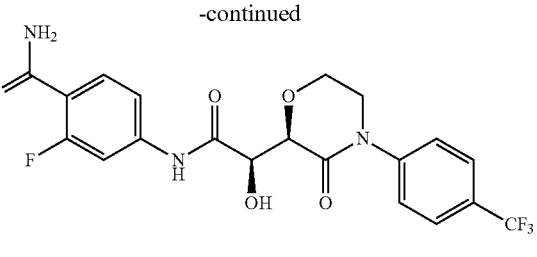

Example 95

Compound 93-4 (20 mg, 0.042 mmol) was dissolved in n-BuOH (0.42 ml) and $NH_2NH_2$ (0.13 ml, 100 eq) was added, heated at 55° C. for 2 hours. The mixture was concentrated and purified by C18 HPLC (89.95:9.95:0.1 $H_2O$:MeCN:$HCO_2H$-9.95:89.95:0.1 $H_2O$:MeCN:$HCO_2H$) to give 2.6 mg EXAMPLE 94.

Example 95

Synthesis of (R)—N-(4-carbamimidoyl-3-fluorophenyl)-2-hydroxy-2-((R)-3-oxo-4-(4-(trifluoromethyl)phenyl)morpholin-2-yl)acetamide (EXAMPLE 95)

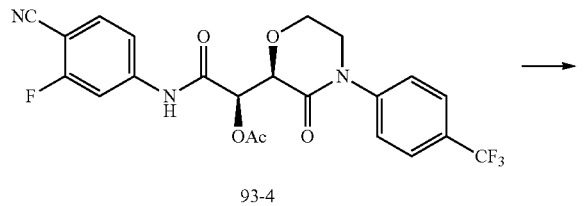

93-4

Compound 93-4 (30 mg, 0.063 mmol) dissolved in EtOH (7.82 ml), cooled to −78° C., HCl(g) was bubbled through for five minutes. The reaction was sealed and allowed to warm to rt with periodic venting and stirred overnight. The mixture was degassed, concentrated and taken up in 7N $NH_3$ in MeOH and stirred overnight. The mixture was concentrated and purified by C18 HPLC (89.95:9.95:0.1 $H_2O$:MeCN:$HCO_2H$-9.95:89.95:0.1 $H_2O$:MeCN:$HCO_2H$) to give 9 mg of EXAMPLE 95.

Example 96

Synthesis of (R)—N-(4-Carbamimidoylphenyl)-2-hydroxy-2-{(R)-3-oxo-4-[4-(trifluoromethyl)phenyl]morpholin-2-yl}acetamide (EXAMPLE 96)

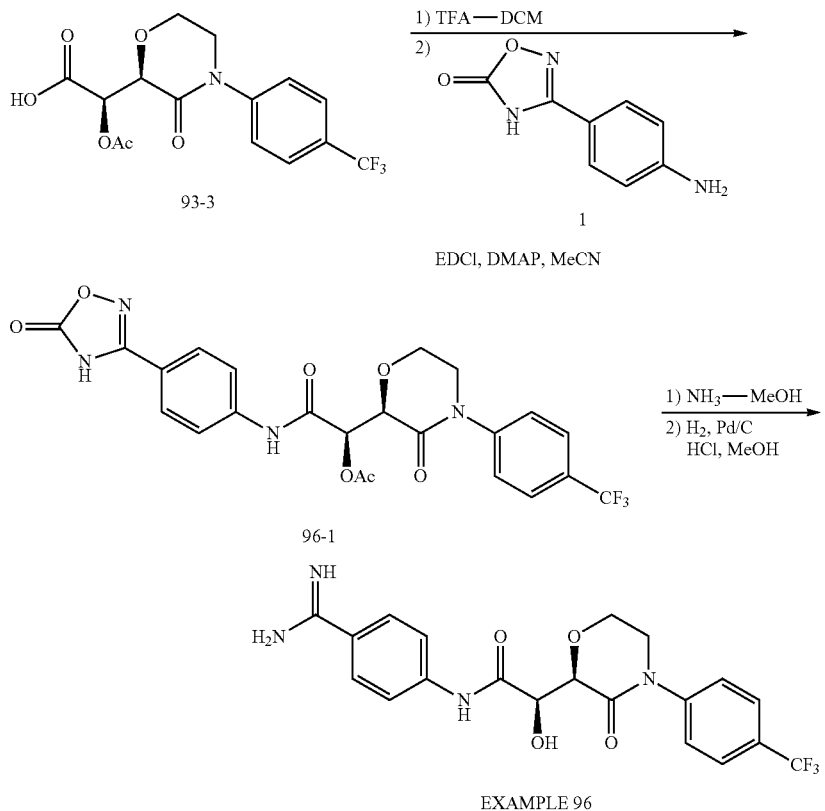

Step 96-1

Synthesis of (R)-2-oxo-2-(4-(5-oxo-4,5-dihydro-1,2,4-oxadiazol-3-yl)phenylamino)-1-((R)-3-oxo-4-(4-(trifluoromethyl)phenyl)morpholin-2-yl)ethyl acetate (compound 96-1)

To a stirred mixture of compound 93-3 (175 mg, 0.50 mmol), DMAP (12 mg, 20 mmol %), and 3-(4-aminophenyl)-1,2,4-oxadiazol-5(2H)-one 1 (177 mg, 2 eq) in MeCN (2.5 ml) at 0° C., EDCI (191 mg, 2 eq) was added. The resulting mixture was stirred at RT for 2 h. The volatile materials were removed on the rotavap. The residue was purified by silica gel chromatography (MeOH/DCM 0 to 10%) to give compound 96-1 (110 mg).

Step 96-2

Synthesis of (R)—N-(4-Carbamimidoylphenyl)-2-hydroxy-2-{(R)-3-oxo-4-[4-(trifluoromethyl)phenyl]morpholin-2-yl}acetamide (EXAMPLE 96)

The compound 96-1 (110 mg) was treated with 7 M NH$_3$/MeOH (1 mL) and the mixture was stirred at RT for 1 h. After removal of the volatile materials on the rotavap, the residue was dissolved in MeOH (1 mL) and 3M HCl (0.25 ml). The resulting suspension was treated with a balloon of H$_2$ over 10% Pd/C (30 mg) and stirred at RT for 2 h. The resulting mixture was filtered through Celite® and concentrated. The residue was purified by reverse phase HPLC to give EXAMPLE 96 which was converted to the HCl salt (88 mg) by treating with one equivalent HCl in ether and concentration on a rotavap.

Example 97

Synthesis of (R)—N-(4-carbamimidoylphenyl)-2-hydroxy-2-((R)-3-oxo-4-(3-(trifluoromethyl)phenyl)morpholin-2-yl)acetamide (EXAMPLE 97)

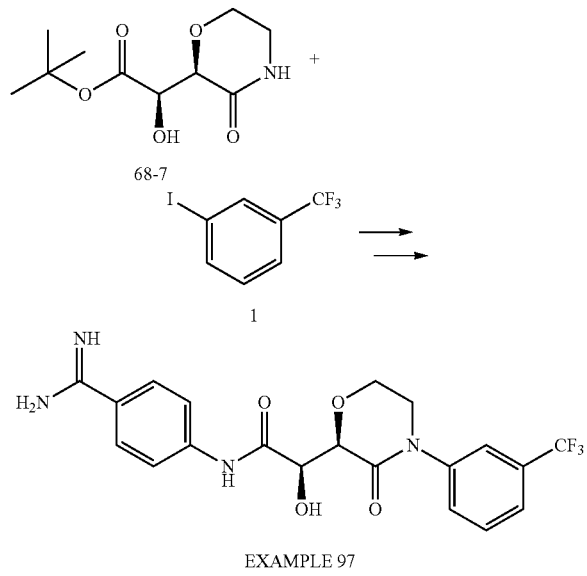

EXAMPLE 97 was synthesized similarly as for the synthesis of EXAMPLE 93 and EXAMPLE 96 using 1-iodo-3-(trifluoromethyl)benzene 1.

Example 98

Synthesis of N-(4-Amino-7-quinazolinyl)-alpha(R)-hydroxy-3-oxo-4-[4-(trifluoromethyl)phenyl]-2(R)-morpholineacetamide (Example 98)

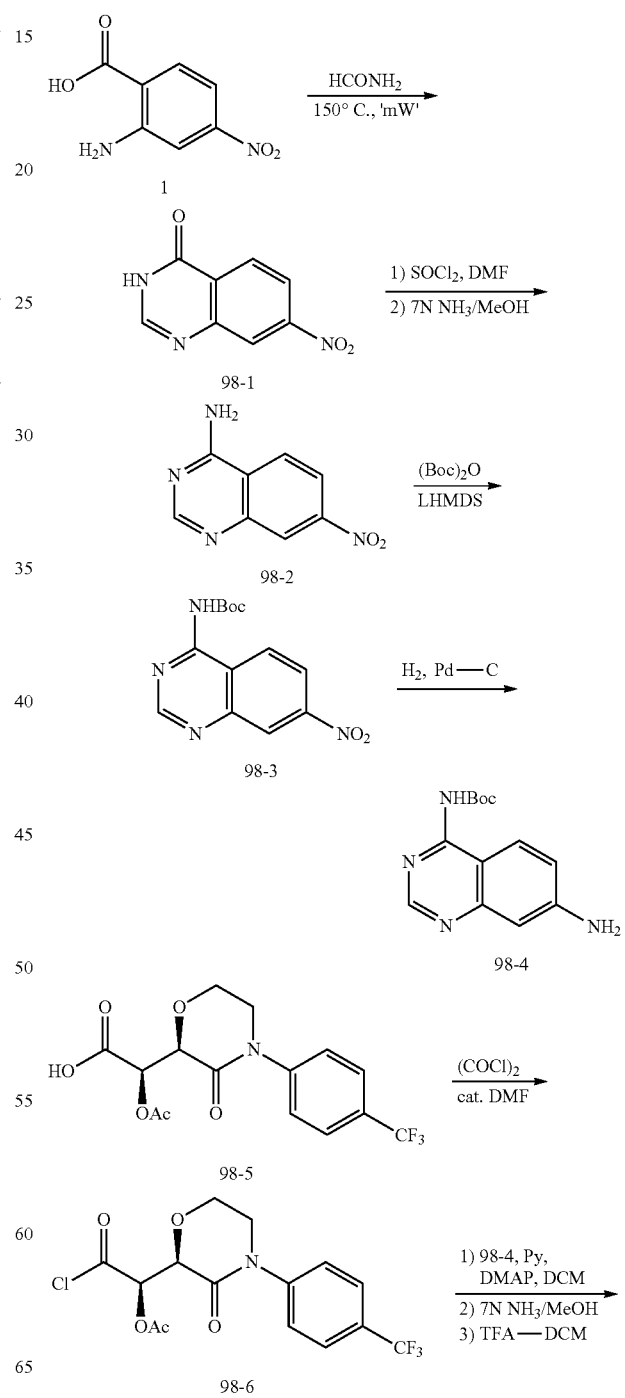

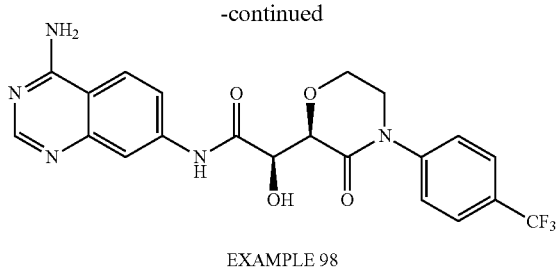

EXAMPLE 98

Step 98-1

Synthesis of 7-Nitroquinazolin-4(3H)-one (compound 98-1)

A mixture of 2-amino-4-nitrobenzoic acid (5.0 g, 27.5 mmol) and formamide (8.0 ml, 201.5 mmol) in a microwave reaction vessel was heated in a microwave reactor at 150° C. for 1 hr. The slurry was cooled to rt, stirred with aq. NaHCO₃, filtered, washed with water followed by ether and dried in vacuum oven to provide 3.7 g of 7-nitroquinazolin-4(3H)-one (compound 98-1).

Step 98-2

Synthesis of 7-Nitroquinazolin-4-amine (compound 98-2)

To a solution of 7-nitroquinazolin-4(3H)-one (2.0 g, 10.5 mmol) in 40 ml thionyl chloride was added 0.8 ml of DMF and the mixture was heated at reflux overnight then evaporated to dryness to provide crude 4-chloro-7-nitroquinazoline.
A mixture of 1.6 g of 4-chloro-7-nitroquinazoline in 50 ml 7N ammonia in methanol was stirred overnight at rt and concentrated to dryness. The solid was suspended in water, filtered, rinsed with water followed by ether and dried overnight in vacuum oven to provide 0.98 g of 7-nitroquinazolin-4-amine (compound 98-2).

Step 98-3

Synthesis of tert-Butyl 7-nitroquinazolin-4-ylcarbamate (compound 98-3)

To a suspension of 7-nitroquinazolin-4-amine (0.98 g, 5.2 mmol) in 20 ml THF at rt was added a 1M solution of di-tert-butyldicarbonate in THF (10.3 ml, 10.3 mmol, 2 eq.) followed by a 1M solution of LHMDS in THF (8.8 mmol, 1.7 eq.). The resultant clear solution was stirred for 10 min. quenched with aq. NH₄Cl, extracted 3× with ethyl acetate, the combined organic layers washed with brine, dried over MgSO₄, filtered, concentrated and purified by chromatography eluting with 30% ethyl acetate in hexanes to provide 713 mg of tert-butyl 7-nitroquinazolin-4-ylcarbamate (compound 98-3).

Step 98-4

Synthesis of tert-butyl 7-aminoquinazolin-4-ylcarbamate (compound 98-4)

A mixture of 600 mg of tert-butyl 7-nitroquinazolin-4-ylcarbamate and 150 mg of 10% Pd—C in 15 ml each of THF and MeOH was stirred overnight under a hydrogen balloon, filtered through a Celite® pad, concentrated and purified by chromatography eluting with 5% methanol in dichloromethane to provide 385 mg of tert-butyl 7-aminoquinazolin-4-ylcarbamate (compound 98-4). MS m/e=261.1 (MH⁺)

Step 98-5

Synthesis of Compound 98-5

Compound 98-5 was prepared using a procedure similar to the preparation of compound 93-3.

Step 98-6

Synthesis of (R)-2-chloro-2-oxo-1-((R)-3-oxo-4-(4-(trifluoromethyl)phenyl)morpholin-2-yl)ethyl acetate (compound 98-6)

To a solution of compound 98-5 (0.30 mmol) in 4 ml of dichloromethane was added oxalylchloride (75 µl, 0.886 mmol, 3 eq.) followed by 1 drop of DMF. Stirred at rt for 1 hr, added toluene and evaporated to dryness to provide crude compound 98-6 which was used as such for the next step.

Step 98-7

Synthesis of N-(4-Amino-7-quinazolinyl)-alpha(R)-hydroxy-3-oxo-4-[4-(trifluoromethyl)phenyl]-2(R)-morpholineacetamide (EXAMPLE 98)

To a solution of compound 98-6 (~0.15 mmol) in 2 ml dichloromethane at 0° C. was added tert-butyl 7-aminoquinazolin-4-ylcarbamate (compound 98-4) (77 mg, 0.30 mmol, 2 eq.) followed by pyridine (24 µA, 0.30 mmol, 2 eq.) and DMAP (2 mg, 0.016 mmol, 0.1 eq.). To the mixture was added 1 ml of acetonitrile and stirred overnight while warming to rt. It was diluted with ethyl acetate, washed with aq. NaHCO₃, water and brine, dried over MgSO₄, filtered, concentrated to dryness. The residue was stirred overnight with 5 ml of 7N ammonia in methanol. The methanol was evaporated and the residue was stirred with 2 ml each of dichloromethane and trifluoroacetic acid for about 75 min. The mixture was evaporated to dryness and the residue was purified by RPHPLC to provide 14 mg of EXAMPLE 98.

Example 99

Synthesis of N-[4-(aminomethyl)phenyl]-alpha(R)-hydroxy-3-oxo-4-[4-(trifluoromethyl)phenyl]-2(R)-morpholineacetamide Example (EXAMPLE 99)

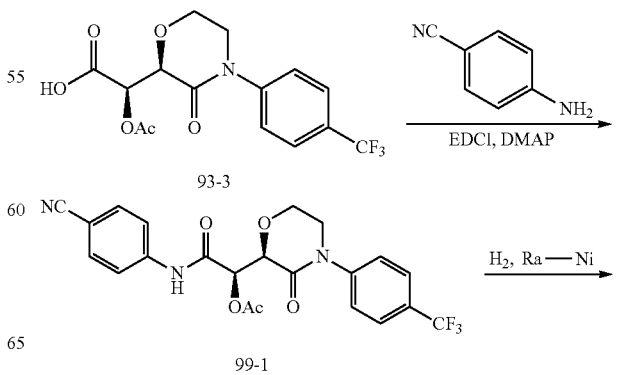

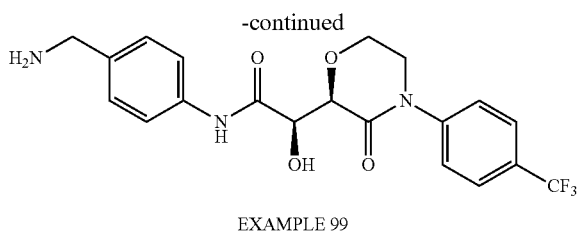

EXAMPLE 99

Step 99-1

Synthesis of (R)-2-acetoxy-2-((R)-3-oxo-4-(4-(trifluoromethyl)phenyl)morpholin-2-yl)acetic acid (compound 99-1)

To 150 mg of compound 93-3 in 4 ml of dry acetonitrile at 0° C. was added 74 mg of 4-amino benzonitrile, 5 mg of DMAP and 103 mg of EDCI and the mixture stirred under argon for two hours. The reaction mixture was poured onto water and extracted three times with ethyl acetate. The combined extracts were washed with brine, dried with $MgSO_4$, filtered and evaporated to dryness. Purification by flash chromatography yielded 151 mg of compound 99-1.

Step 99-2

Synthesis of N-[4-(aminomethyl)phenyl]-alpha(R)-hydroxy-3-oxo-4-[4-(trifluoromethyl)phenyl]-2(R)-morpholineacetamide (EXAMPLE 99)

To Compound 99-1 in 15 mL of 7M $NH_3$ in MeOH was added excess Raney Ni (an aq. suspension) and the mixture stirred under a balloon of hydrogen for two hours. The mixture was filtered and evaporated to dryness yielding a white solid. Purification by RP-HPLC yielded 34 mg of EXAMPLE 99 as a white solid after conversion to the HCl salt by the addition of 1N HCl in diethyl ether and evaporation to dryness.

Example 100

Synthesis of N-[4-(Aminoiminomethyl)phenyl]-4-[3-(aminomethyl)phenyl]-alpha(R)-hydroxy-3-oxo-2(R)-morpholineacetamide (EXAMPLE 100)

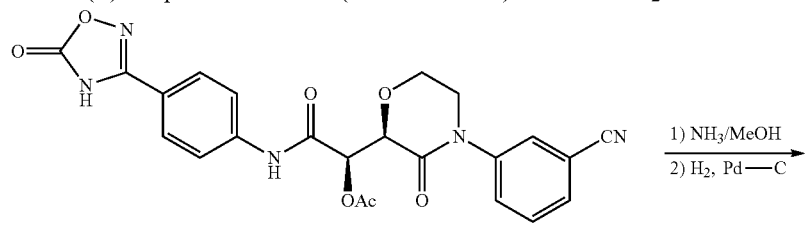

compound 100-1

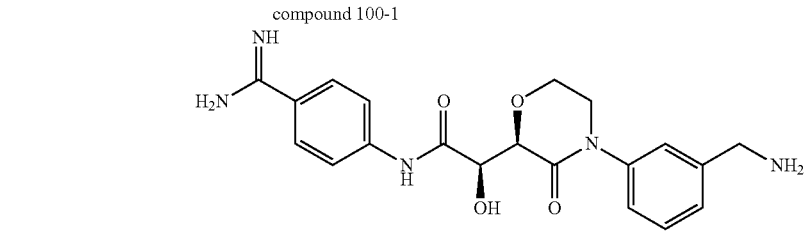

EXAMPLE 100

Compound 100-1 was prepared from compound 68-7 using a procedure similar to the preparation of compound 96-1.

To about 30 mL of 7N $NH_3$/MeOH was added 465 mg of compound 100-1 and the mixture was stirred in a flask sealed with a rubber stopper for 1.5 hrs. The mixture was then evaporated to dryness. To the residue in 3 mL of MeOH was added 45 mg of 10% Pd/C and 2 mL of 1N aq. HCl and the suspension stirred under a balloon of $H_2$. After about 3 hours an additional 60 mg of Pd/C was added and after a further 1 hr, the mixture was filtered and evaporated to dryness. Purification by RP-HPLC yielded 118 mg of EXAMPLE 100 as a white solid after conversion to the di-HCl salt by the addition of 1N HCl in diethyl ether and evaporation to dryness.

Example 101

Synthesis of N-[4-(Aminocarbonyl)phenyl]-alpha (R)-hydroxy-3-oxo-4-[4-(trifluoromethyl)phenyl]-2 (R)-morpholineacetamide (EXAMPLE 101)

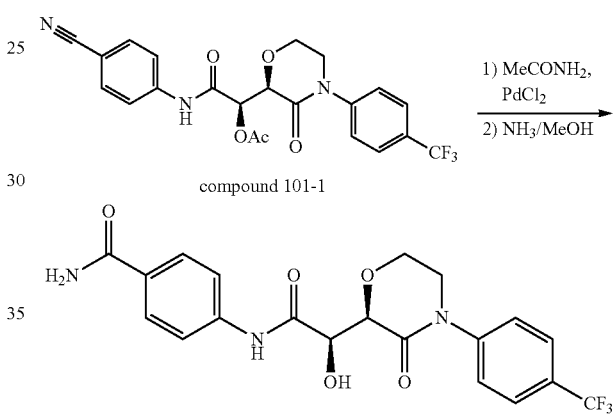

EXAMPLE 101

Compound 101-1 was prepared from compound 68-7 using a procedure similar to the preparation of compound 96-1.

To 25 mg of compound 101-1 in 4 ml of THF and 1 ml of $H_2O$ was added 13 mg of acetamide and 1 mg of $PdCl_2$ and the mixture stirred under argon. After 16 hrs, an additional 1 mg of PdCl$_2$ was added and after an additional 16 hrs. the reaction mixture was filtered and evaporated to dryness. To the residue was added 3 ml of 7N NH$_3$/MeOH and the flask sealed with a septa and stirred for 3 hrs. The resulting mixture was partitioned between ethyl acetate and a mixture of DMSO/water/acetonitrile. The combined ethyl acetate phases were evaporated to dryness yielding about 8 mg of EXAMPLE 101.

Example 102

Synthesis of (2R)—N-(4-amidinophenyl)-2-hydroxy-2-[(2R)-4-[3-(2-hydroxyethyl)phenyl]-3-oxomorpholin-2-yl]acetamide hydrochloride (EXAMPLE 102)

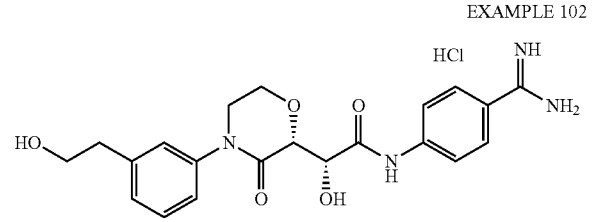 [SMILES: N=C(N)c1ccc(NC(=O)[C@H](O)[C@H]2OCCN(c3cccc(CCO)c3)C2=O)cc1 ; Cl]

EXAMPLE 102

Step 102-1

Synthesis of tert-butyl (2R)-2-[(2R)-4-[3-(2-benzyloxyethyl)phenyl]-3-oxomorpholin-2-yl]-2-hydroxyacetate (compound 102-1)

According to the Step 68-9 in synthetic method for EXAMPLE 68, 1-bromo-3-[2-(benzyloxyethyl)]benzene (0.3 g) was used instead of compound 68-8 to obtain compound 102-1 (234 mg) as colorless oil.

Step 102-2

Synthesis of (2R)-2-[(2R)-4-[3-(2-benzyloxyethyl)phenyl]-3-oxomorpholin-2-yl]-2-hydroxyacetic acid (compound 102-2)

According to the Step 52-4 in synthetic method for EXAMPLE 52, compound 102-1 (0.13 g) was used instead of 52-3 to obtain compound 102-2 (0.11 g) as colorless oil.

Step 102-3

Synthesis of (2R)-2-[(2R)-4-[3-(2-benzyloxyethyl)phenyl]-3-oxomorpholin-2-yl]-2-hydroxy-N-[4-(5-oxo-4H-1,2,4-oxadiazol-3-yl)phenyl]acetamide (compound 102-3)

According to the Step 1-3 in synthetic method for EXAMPLE 1, 102-2 (0.11 g) and 3-(4-aminophenyl)-1,2,4-oxadiazol-5(2H)-one (47 mg) with DMF were used instead of 1-2 and 6-Amino-1-bis(tert-butoxyl carbonyl)aminoisoquinoline to obtain compound 102-3 (38 mg) as a yellow amorphous solid.

Step 102-4

Synthesis of (2R)—N-(4-amidinophenyl)-2-hydroxy-2-[(2R)-4-[3-(2-hydroxyethyl)phenyl]-3-oxomorpholin-2-yl]acetamide hydrochloride (EXAMPLE 102)

According to the Step 26-B in synthetic method for EXAMPLE 26, compound 102-3 (30 mg) was used instead of 26-14 to obtain EXAMPLE 102 (26 mg) as a beige amorphous solid.

Example 103

Synthesis of (2R)—N-(4-amidinophenyl)-2-hydroxy-2-[(2R)-3-oxo-4-[5-(trifluoromethyl)-2-pyridyl]morpholin-2-yl]acetamide hydrochloride (EXAMPLE 103)

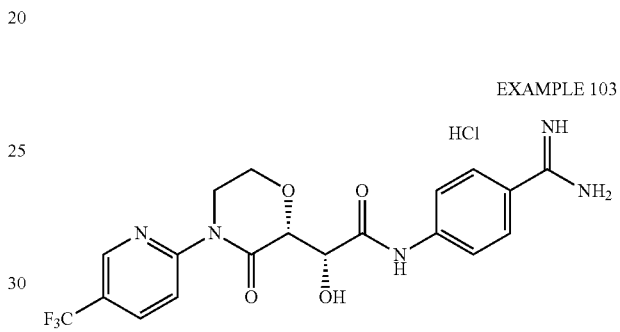

EXAMPLE 103

Step 103-1

Synthesis of tert-butyl (2R)-2-hydroxy-2-[(2R)-3-oxo-4-[5-(trifluoromethyl)-2-pyridyl]morpholin-2-yl]acetate (compound 103-1)

According to the Step 68-9 in synthetic method for EXAMPLE 68, 2-iodo-5-trifluoromethylpyridine (0.28 g) was used instead of compound 68-8 to obtain compound 103-1 (105 mg) as a pale yellow amorphous solid.

Step 103-2

Synthesis of (2R)-2-hydroxy-2-[(2R)-3-oxo-4-[5-(trifluoromethyl)-2-pyridyl]morpholin-2-yl]acetic acid (compound 103-2)

According to the Step 52-4 in synthetic method for EXAMPLE 52, compound 103-1 (98 mg) was used instead of 52-3 to obtain compound 103-2 (76 mg) as colorless oil.

Step 103-3

Synthesis of (2R)-2-hydroxy-N-[4-(5-oxo-4H-1,2,4-oxadiazol-3-yl)phenyl]-2-[(2R)-3-oxo-4-[5-(trifluoromethyl)-2-pyridyl]morpholin-2-yl]acetamide (compound 103-3)

According to the Step 1-3 in synthetic method for EXAMPLE 1, 103-2 (75 mg) and 3-(4-aminophenyl)-1,2,4-oxadiazol-5(2H)-one (41 mg) were used instead of 1-2 and 6-Amino-1-bis(tert-butoxyl carbonyl)aminoisoquinoline to obtain compound 103-3 (7 mg) as pale red amorphous solid.

339

Step 103-4

Synthesis of (2R)—N-(4-amidinophenyl)-2-hydroxy-2-[(2R)-3-oxo-4-[5-(trifluoromethyl)-2-pyridyl]morpholin-2-yl]acetamide hydrochloride (EXAMPLE 103)

According to the Step 26-B in synthetic method for EXAMPLE 26, compound 103-3 (6 mg) was used instead of 26-14 to obtain EXAMPLE 103 (6 mg) as a pale yellow amorphous solid.

Example 104

Synthesis of (2R)—N-[4-amidinophenyl]-2-hydroxy-2-[(2R)-4-[3-(methylsulfonylmethyl)phenyl]-3-oxomorpholin-2-yl]acetamide hydrochloride (EXAMPLE 104)

EXAMPLE 104

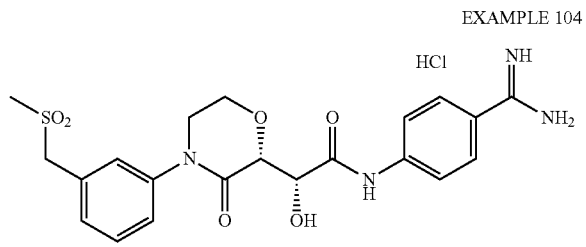 [SMILES: CS(=O)(=O)Cc1cccc(N2CCO[C@H]([C@@H](O)C(=O)Nc3ccc(C(=N)N)cc3)C2=O)c1 ; Cl]

Step 104-1

Synthesis of tert-butyl (2R)-2-hydroxy-2-[(2R)-4-[3-(methylsulfonylmethyl)phenyl]-3-oxomorpholin-2-yl]acetate (compound 104-1)

According to the Step 68-9 in synthetic method for EXAMPLE 68, 1-bromo-3-[(methylsulfonyl)methyl]benzene (0.39 g) was used instead of compound 68-8 to obtain compound 104-1 (0.22 g) as a colorless amorphous solid.

Step 104-2

Synthesis of (2R)-2-hydroxy-2-[(2R)-4-[3-(methylsulfonylmethyl)phenyl]-3-oxomorpholin-2-yl]acetic acid (compound 104-2)

According to the Step 52-4 in synthetic method for EXAMPLE 52, compound 104-1 (0.2 g) was used instead of 52-3 to obtain compound 104-2 (170 mg) as colorless oil.

Step 104-3

Synthesis of (2R)-2-hydroxy-2-[(2R)-4-[3-(methylsulfonylmethyl)phenyl]-3-oxomorpholin-2-yl]-N-[4-(5-oxo-4H-1,2,4-oxadiazol-3-yl)phenyl]acetamide (compound 104-3)

According to the Step 1-3 in synthetic method for EXAMPLE 1, 104-2 (170 mg) and 3-(4-aminophenyl)-1,2,4-oxadiazol-5(2H)-one (82 mg) with DMF were used instead of 1-2 and 6-Amino-1-bis(tert-butoxyl carbonyl)aminoisoquinoline to obtain compound 104-3 (54 mg) as a pale red amorphous solid.

340

Step 104-4

Synthesis of (2R)—N-[4-amidinophenyl]-2-hydroxy-2-[(2R)-4-[3-(methylsulfonylmethyl)phenyl]-3-oxomorpholin-2-yl]acetamide hydrochloride (EXAMPLE 104)

According to the Step 26-B in synthetic method for EXAMPLE 26, compound 104-3 (30 mg) was used instead of 26-14 to obtain EXAMPLE 104 (16 mg) as a colorless amorphous solid.

Example 105

Synthesis of (2R)—N-(4-amidinophenyl)-2-hydroxy-2-[(2R)-4-[4-(2-methylsulfonylphenyl)phenyl]-3-oxomorpholin-2-yl]acetamide hydrochloride (EXAMPLE 105)

EXAMPLE 105

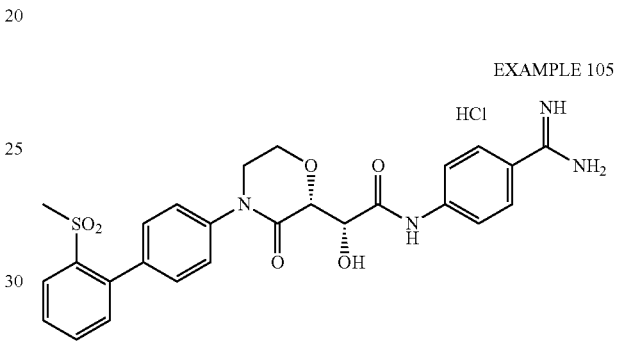

Step 105-1

Synthesis of tert-butyl (2R)-2-hydroxy-2-[(2R)-4-(4-iodophenyl)-3-oxomorpholin-2-yl]acetate (compound 105-1)

According to the Step 68-9 in synthetic method for EXAMPLE 68, 1,4-diiodobenzene (74.9 mg) was used instead of compound 68-8 to obtain compound 105-1 (23.1 mg) as a colorless amorphous solid.

Step 105-2

Synthesis of tert-butyl (2R)-2-hydroxy-2-[(2R)-4-[4-(2-methylsulfonylphenyl)phenyl]-3-oxomorpholin-2-yl]acetate (compound 105-2)

According to the Step 22-1 in synthetic method for EXAMPLE 22, compound 105-1 (0.12 g) and 2-methylsulfonylphenylboronic acid (0.11 g) were used instead of 14-4 and 2-thiopheneboronic acid to obtain compound 105-2 (102 mg) as yellow oil.

Step 105-3

Synthesis of (2R)-2-hydroxy-2-[(2R)-4-[4-(2-methylsulfonylphenyl)phenyl]-3-oxomorpholin-2-yl]acetic acid (compound 105-3)

According to the Step 52-4 in synthetic method for EXAMPLE 52, compound 105-2 (98 mg) was used instead of 52-3 to obtain compound 105-2 (87.1 mg) as a pale yellow amorphous solid.

Step 105-4

Synthesis of (2R)-2-hydroxy-2-[(2R)-4-[4-(2-methylsulfonylphenyl)phenyl]-3-oxomorpholin-2-yl]-N-[4-(5-oxo-4H-1,2,4-oxadiazol-3-yl)phenyl]acetamide (compound 105-4)

According to the Step 1-3 in synthetic method for EXAMPLE 1, 105-3 (0.1 g) and 3-(4-aminophenyl)-1,2,4-oxadiazol-5(2H)-one (41 mg) with DMF were used instead of 1-2 and 6-Amino-1-bis(tert-butoxyl carbonyl)aminoisoquinoline to obtain compound 105-4 (52 mg) as a pale yellow amorphous solid.

Step 105-5

Synthesis of (2R)—N-(4-amidinophenyl)-2-hydroxy-2-[(2R)-4-[4-(2-methylsulfonylphenyl)phenyl]-3-oxomorpholin-2-yl]acetamide hydrochloride (EXAMPLE 105)

According to the Step 26-B in synthetic method for EXAMPLE 26, compound 105-4 (20 mg) was used instead of 26-14 to obtain EXAMPLE 105 (15 mg) as a colorless amorphous solid.

Example 106

Synthesis of (2R)—N-(4-amidinophenyl)-2-hydroxy-2-[(2R)-4-[4-[2-(2-hydroxyethyl)phenyl]phenyl]-3-oxomorpholin-2-yl]acetamide hydrochloride (EXAMPLE 106)

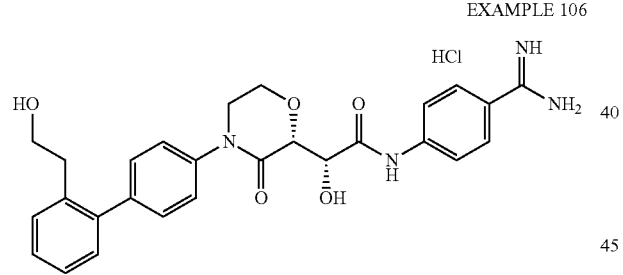

EXAMPLE 106

Step 106-1

Synthesis of (2R)-2-hydroxy-2-[(2R)-4-(4-iodophenyl)-3-oxomorpholin-2-yl]acetic acid (compound 106-1)

According to the Step 52-4 in synthetic method for EXAMPLE 52, compound 105-1 (0.12 g) was used instead of 52-3 to obtain compound 106-1 (102 mg) as a pale yellow amorphous solid.

Step 106-2

Synthesis of (2R)-2-hydroxy-2-[(2R)-4-(4-iodophenyl)-3-oxomorpholin-2-yl]-N-[4-(5-oxo-4H-1,2,4-oxadiazol-3-yl)phenyl]acetamide (compound 106-2)

According to the Step 1-3 in synthetic method for EXAMPLE 1, 106-1 (86 mg) and 3-(4-aminophenyl)-1,2,4-oxadiazol-5(2H)-one (38 mg) with DMF were used instead of 1-2 and 6-Amino-1-bis(tert-butoxyl carbonyl)aminoisoquinoline to obtain compound 106-2 (42 mg) as a gray amorphous solid.

Step 106-3

Synthesis of (2R)-2-hydroxy-2-[(2R)-4-[4-[2-(2-hydroxyethyl)phenyl]phenyl]-3-oxomorpholin-2-yl]-N-[4-(5-oxo-4H-1,2,4-oxadiazol-3-yl)phenyl]acetamide (compound 106-3)

According to the Step 22-1 in synthetic method for EXAMPLE 22, compound 106-2 (30 mg) and [2-[2-[[(1,1-dimethylethyl)dimethylsilyl]oxy]ethyl]phenyl]boronic acid (31.4 mg) were used instead of 14-4 and 2-thiopheneboronic acid to obtain compound 106-3 (10 mg) as a colorless amorphous solid.

Step 106-4

Synthesis of (2R)—N-(4-amidinophenyl)-2-hydroxy-2-[(2R)-4-[4-[2-(2-hydroxyethyl)phenyl]phenyl]-3-oxomorpholin-2-yl]acetamide hydrochloride (EXAMPLE 106)

According to the Step 26-B in synthetic method for EXAMPLE 26, compound 106-3 (28 mg) was used instead of 26-14 to obtain EXAMPLE 106 (1.2 mg) as a colorless amorphous solid.

Example 107

Synthesis of (2R)—N-(4-amidinophenyl)-2-hydroxy-2-[(2R)-3-oxo-4-[3-(1H-pyrazol-4-yl)phenyl]morpholin-2-yl]acetamide dihydrochloride (EXAMPLE 107)

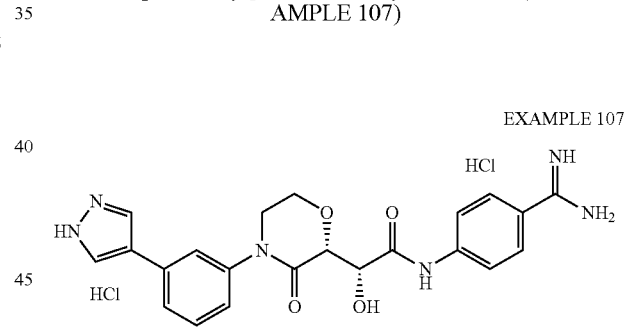

EXAMPLE 107

Step 107-1

Synthesis of tert-butyl (2R)-2-hydroxy-2-[(2R)-4-(3-iodophenyl)-3-oxomorpholin-2-yl]acetate (compound 107-1)

According to the Step 68-9 in synthetic method for EXAMPLE 68, 1,3-diiodobenzene (1.5 g) was used instead of compound 68-8 to obtain compound 107-1 (425 mg) as a pale yellow amorphous solid.

Step 107-2

Synthesis of tert-butyl 4-[3-[(2R)-2-[(1R)-2-tert-butoxy-1-hydroxy-2-oxoethyl]-3-oxomorpholin-4-yl]phenyl]pyrazole-1-carboxylate (compound 107-2)

According to the Step 22-1 in synthetic method for EXAMPLE 22, compound 107-1 (0.2 g) and 3-(4,4,5,5-tetramethyl-1,3,2-dioxaborolan-2-yl)-1H-pyrazole-1-carboxylic acid 1,1-dimethylethyl ester (0.27 g) were used instead of 14-4 and 2-thiopheneboronic acid to obtain compound 107-2 (137 mg) as a pale yellow amorphous solid.

Step 107-3

Synthesis of (2R)-2-hydroxy-2-[(2R)-3-oxo-4-[3-(1H-pyrazol-4-yl)phenyl]morpholin-2-yl]acetic acid hydrochloride (compound 107-3)

According to the Step 52-4 in synthetic method for EXAMPLE 52, compound 107-2 (0.12 g) was used instead of 52-3 to obtain compound 107-3 (89 mg) as a colorless amorphous solid.

Step 107-4

Synthesis of (2R)-2-hydroxy-N-[4-(5-oxo-4H-1,2,4-oxadiazol-3-yl)phenyl]-2-[(2R)-3-oxo-4-[3-(1H-pyrazol-4-yl)phenyl]morpholin-2-yl]acetamide (compound 107-4)

According to the Step 77-1 in synthetic method for EXAMPLE 77, compound 107-3 (35 mg) and 5-amino-1,3-dihydro-2H-benzimidazol-2-one (17.5 mg) were used instead of 3-iodobenzoic acid and 4,4-difluoropiperidine to obtain compound 107-4 (7 mg) as a colorless amorphous solid.

Step 107-5

Synthesis of (2R)—N-(4-amidinophenyl)-2-hydroxy-2-[(2R)-3-oxo-4-[3-(1H-pyrazol-4-yl)phenyl]morpholin-2-yl]acetamide dihydrochloride (EXAMPLE 107)

According to the Step 26-B in synthetic method for EXAMPLE 26, compound 107-4 (7 mg) was used instead of 26-14 to obtain EXAMPLE 107 (7 mg) as a pale yellow amorphous solid.

Example 108

Synthesis of N-(1-amino-6-isoquinolyl)-2-hydroxy-2-[2-oxo-1-(p-tolyl)-3-piperidyl]acetamide trifluoroacetate (EXAMPLE 108)

EXAMPLE 108

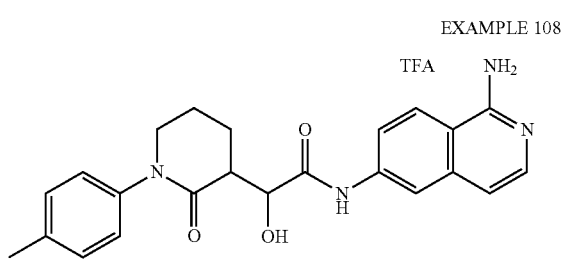 [SMILES: Cc1ccc(N2CCCC(C(O)C(=O)Nc3ccc4c(N)nccc4c3)C2=O)cc1 ; "TFA"]

Step 108-1

Synthesis of ethyl 2-hydroxy-2-[2-oxo-1-(p-tolyl)-3-piperidyl]acetate (compound 108-1)

According to the Step 1-1 in synthetic method for EXAMPLE 1, 1-(4-methylphenyl)-2-piperidinone (4 g) was used instead of 4-(4-methylphenyl)-3-morpholinone to obtain compound 108-1 (0.5 g) as a colorless amorphous solid.

Step 108-2

Synthesis of 2-hydroxy-2-[2-oxo-1-(p-tolyl)-3-piperidyl]acetic acid (compound 108-2)

According to the Step 1-2 in synthetic method for EXAMPLE 1, compound 108-1 (0.5 g) was used instead of 1-1 (LP) to obtain compound 108-2 (0.1 g) as a colorless amorphous solid.

Step 108-3

Synthesis of tert-butyl N-tert-butoxycarbonyl-N-[6-[[2-hydroxy-2-[2-oxo-1-(p-tolyl)-3-piperidyl]acetyl]amino]-1-isoquinolyl]carbamate (compound 108-3)

To a solution of 108-2 (0.1 g), Diisopropylethylamine (0.2 mL), HOAt (77.5 mg), 2-Chloro-1,3-dimethylimidazolidinium hexafluorophosphate (158 mg), was added 6-Amino-1-bis(tert-butoxyl carbonyl)aminoisoquinoline (164 mg) at room temperature. The reaction mixture was stirred at room temperature for 6 hours. To the mixture, was added sat.NaHCO3 aq. and the mixture was extracted with EtOAc. The organic layer was washed with water and brine, dried with anhydr.Na2SO4. The solvent was removed under reduced pressure and the resulting residue was purified by silica gel flash column chromatography (eluent: Hex-EtOAc=1-1~1-2~1-4) to obtain compound 108-3 (53.4 mg) as a colorless amorphous solid.

Step 108-4

Synthesis of N-(1-amino-6-isoquinolyl)-2-hydroxy-2-[2-oxo-1-(p-tolyl)-3-piperidyl]acetamide trifluoroacetate (EXAMPLE 108)

According to the Step 1-4 in synthetic method for EXAMPLE 1, compound 108-3 (34.8 mg) was used instead of 1-3 to obtain EXAMPLE 108 (17.8 mg) as a colorless amorphous solid.

Example 109

Synthesis of 2-[1-acetyl-3-oxo-4-(p-tolyl)piperazin-2-yl]-N-(1-amino-6-isoquinolyl)-2-hydroxy-acetamide trifluoroacetate (EXAMPLE 109)

EXAMPLE 109

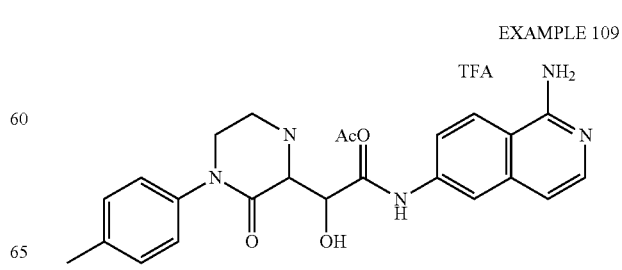

Step 109-1

Synthesis of benzyl 2-(2-ethoxy-1-hydroxy-2-oxo-ethyl)-3-oxo-4-(p-tolyl)piperazine-1-carboxylate (compound 109-1)

According to the Step 1-1 in synthetic method for EXAMPLE 1, 4-(4-methylphenyl)-3-oxopiperazine-1-carboxylic acid benzyl ester (2.3 g) was used instead of 4-(4-methylphenyl)-3-morpholinone to obtain compound 109-1 (2.2 g) as diastereomeric mixture.

Step 109-2

Synthesis of ethyl 2-hydroxy-2-[3-oxo-4-(p-tolyl)piperazin-2-yl]acetate (compound 109-2)

According to the Step 33-1 in synthetic method for EXAMPLE 33, compound 109-1 (0.3 g) with EtOH was used instead of EXAMPLE 32 to obtain compound 109-2 (0.2 g) as a pale yellow amorphous solid.

Step 109-3

Synthesis of ethyl 2-[1-acetyl-3-oxo-4-(p-tolyl)piperazin-2-yl]-2-hydroxyacetate (compound 109-3)

According to the Step 26-6 in synthetic method for EXAMPLE 26, compound 109-2 (0.2 g) was used instead of 26-5 to obtain compound 109-3 (0.11 g) as a colorless amorphous solid.

Step 109-4

Synthesis of 2-[1-acetyl-3-oxo-4-(p-tolyl)piperazin-2-yl]-2-hydroxyacetic acid lithium salt (compound 109-4)

According to the Step 1-2 in synthetic method for EXAMPLE 1, compound 109-3 (0.11 g) and LiOH—H$_2$O (13.8 mg) were used instead of 1-1 (LP) and NaOH to obtain compound 109-4 (90 mg) as a beige amorphous solid.

Step 109-5

Synthesis of tert-butyl N-[6-[[2-[1-acetyl-3-oxo-4-(p-tolyl)piperazin-2-yl]-2-hydroxyacetyl]amino]-1-isoquinolyl]-N-tert-butoxycarbonylcarbamate (compound 109-5)

According to the Step 108-3 in synthetic method for EXAMPLE 108, compound 109-4 (90 mg) was used instead of 108-2 to obtain compound 109-5 (14.9 mg) as a pale yellow amorphous solid.

Step 109-6

Synthesis of 2-[1-acetyl-3-oxo-4-(p-tolyl)piperazin-2-yl]-N-(1-amino-6-isoquinolyl)-2-hydroxy-acetamide trifluoroacetate (EXAMPLE 109)

According to the Step 1-4 in synthetic method for EXAMPLE 1, compound 109-5 (14.9 mg) was used instead of 1-3 to obtain EXAMPLE 109 (12.9 mg) as a beige amorphous solid.

Example 110

Synthesis of N-(1-amino-6-isoquinolyl)-2-[1-formyl-3-oxo-4-(p-tolyl)piperazin-2-yl]-2-hydroxyacetamide trifluoroacetate (EXAMPLE 110)

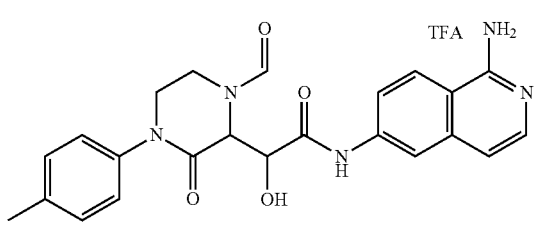

EXAMPLE 110

Step 110-1

Synthesis of ethyl 2-[1-formyl-3-oxo-4-(p-tolyl)piperazin-2-yl]-2-hydroxyacetate (compound 110-1)

To a solution of 109-2 (0.3 g) in EtOH (10 mL), were added 4-(4,6-dimethoxy-1,3,5-triazin-2-yl)-4-methylmorpholinium chloride (426 mg) and formic acid (0.05 mL) at room temperature. The reaction mixture was stirred at room temperature for 3 hours. After the reaction, water was added into the reaction mixture. Then the mixture was extracted with EtOAc. The organic layer was washed with water, sat. NaHCO3 aq., and brine, then dried with anhydr. Na2SO4. The solvent was removed under reduced pressure to obtain 110-1 (0.14 g) as diastereomeric mixture. 110-1 was used in the next step without further purification.

Step 110-2

Synthesis of 2-[1-formyl-3-oxo-4-(p-tolyl)piperazin-2-yl]-2-hydroxyacetic acid lithium salt (compound 110-2)

According to the Step 1-2 in synthetic method for EXAMPLE 1, compound 110-1 (0.14 g) and LiOH—H2O (18 mg) were used instead of 1-1 (LP) and NaOH to obtain compound 110-2 (0.12 g) as a colorless amorphous solid.

Step 110-3

Synthesis of tert-butyl N-tert-butoxycarbonyl-N-[6-[[2-[1-formyl-3-oxo-4-(p-tolyl)piperazin-2-yl]-2-hydroxyacetyl]amino]-1-isoquinolyl]carbamate (compound 110-3)

According to the Step 108-3 in synthetic method for EXAMPLE 108, compound 110-2 (0.12 g) was used instead of 108-2 to obtain compound 110-3 (6.2 mg) as a colorless amorphous solid.

Step 110-4

Synthesis of N-(1-amino-6-isoquinolyl)-2-[1-formyl-3-oxo-4-(p-tolyl)piperazin-2-yl]-2-hydroxyacetamide trifluoroacetate (EXAMPLE 110)

According to the Step 1-4 in synthetic method for EXAMPLE 1, compound 110-3 (6.2 mg) was used instead of 1-3 to obtain EXAMPLE 110 (3.8 mg) as a pale brown amorphous solid.

Example 111

Synthesis of N-(1-amino-6-isoquinolyl)-2-[1-benzoyl-3-oxo-4-(p-tolyl)piperazin-2-yl]-2-hydroxyacetamide trifluoroacetate (EXAMPLE 111)

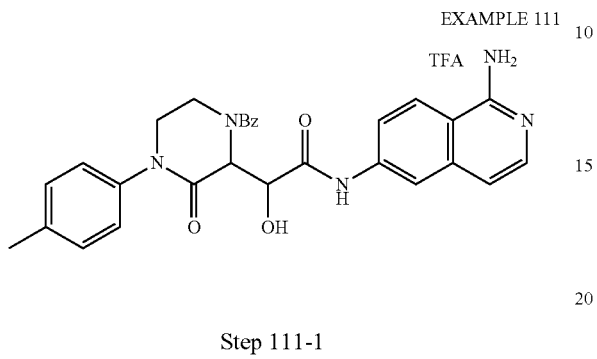

EXAMPLE 111

Step 111-1

Synthesis of ethyl 2-[1-benzoyl-3-oxo-4-(p-tolyl)piperazin-2-yl]-2-hydroxyacetate (compound 111-1)

According to the Step 110-1 in synthetic method for EXAMPLE 110, benzoic acid (87 mg) was used instead of formic acid to obtain compound 111-1 (128 mg) as a beige amorphous solid.

Step 111-2

Synthesis of 2-[1-benzoyl-3-oxo-4-(p-tolyl)piperazin-2-yl]-2-hydroxyacetic acid (compound 111-2)

According to the Step 1-2 in synthetic method for EXAMPLE 1, compound 111-1 (128 mg) and LiOH—H2O (14.5 mg) were used instead of 1-1 (LP) and NaOH to obtain compound 111-2 (100 mg) as a beige amorphous solid.

Step 111-3

Synthesis of tert-butyl N-[6-[[2-[1-benzoyl-3-oxo-4-(p-tolyl)piperazin-2-yl]-2-hydroxyacetyl]amino]-1-isoquinolyl]-N-tert-butoxycarbonylcarbamate (compound 111-3)

According to the Step 1-3 in synthetic method for EXAMPLE 1, compound 111-2 (80 mg) was used instead of 1-2 to obtain compound 111-3 (7 mg) as a pale yellow amorphous solid.

Step 111-4

Synthesis of N-(1-amino-6-isoquinolyl)-2-[1-benzoyl-3-oxo-4-(p-tolyl)piperazin-2-yl]-2-hydroxyacetamide trifluoroacetate (EXAMPLE 111)

According to the Step 1-4 in synthetic method for EXAMPLE 1, compound 111-3 (7 mg) was used instead of 1-3 to obtain EXAMPLE 111 (1.7 mg) as a beige amorphous solid.

Example 112

Synthesis of N-(4-amidinophenyl)-2-hydroxy-2-[3-oxo-4-(p-tolyl)thiomorpholin-2-yl]acetamide acetate (EXAMPLE 112)

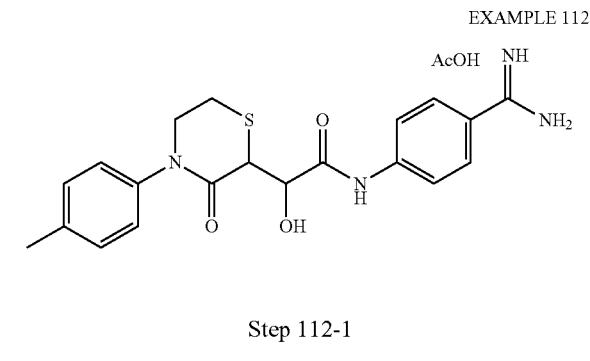

EXAMPLE 112

Step 112-1

Synthesis of ethyl 2-hydroxy-2-[3-oxo-4-(p-tolyl)thiomorpholin-2-yl]acetate (compound 112-1)

According to the Step 1-1 in synthetic method for EXAMPLE 1, 4-(4-Methylphenyl)-thiomorpholin-3-one (3 g) was used instead of 4-(4-Methylphenyl)-3-morpholinone to obtain compound 112-1 (2 g) as a pale yellow amorphous solid.

Step 112-2

Synthesis of 2-hydroxy-2-[3-oxo-4-(p-tolyl)thiomorpholin-2-yl]acetic acid (compound 112-2)

According to the Step 1-2 in synthetic method for EXAMPLE 1, compound 112-1 (0.88 g) was used instead of 1-1 (LP) to obtain compound 112-2 (0.59 g) as a pale yellow amorphous solid.

Step 112-3

Synthesis of 2-hydroxy-N-[4-(5-oxo-4H-1,2,4-oxadiazol-3-yl)phenyl]-2-[3-oxo-4-(p-tolyl)thiomorpholin-2-yl]acetamide (compound 112-3)

According to the Step 77-1 in synthetic method for EXAMPLE 77, compound 112-2 (0.55 g) and 3-(4-aminophenyl)-1,2,4-oxadiazol-5(2H)-one (0.52 g) were used instead of 3-iodobenzoic acid and 4,4-difluoropiperidine to obtain compound 112-3 (0.52 g) as a pale yellow amorphous solid.

Step 112-4

Synthesis of N-(4-amidinophenyl)-2-hydroxy-2-[3-oxo-4-(p-tolyl)thiomorpholin-2-yl]acetamide acetate (EXAMPLE 112)

To a solution of 112-3 (30 mg) in AcOH (1.5 mL), was added zinc powder (0.22 g) at room temperature. The reaction mixture was stirred at 80° C. for 3 hours. After the reaction, the mixture was filtered through Celite® pad to remove zinc powder. The filtrate was concentrated in vacuo to obtain EXAMPLE 112 (4.2 mg) as a pale brawn amorphous solid.

Example 113

Synthesis of N-(4-amidinophenyl)-2-hydroxy-2-[1,1,3-trioxo-4-(p-tolyl)-1,4-thiazinan-2-yl]acetamide hydrochloride (EXAMPLE 113)

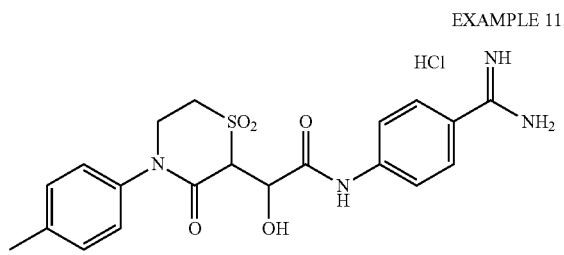

EXAMPLE 113

Step 113-1

Synthesis of 2-hydroxy-N-[4-(5-oxo-4H-1,2,4-oxadiazol-3-yl)phenyl]-2-[1,1,3-trioxo-4-(p-tolyl)-1,4-thiazinan-2-yl]acetamide (compound 113-1)

To a solution of 112-3 (5 mg) in MeOH—$H_2O$ (1-0.5 mL), was added oxone (27.9 mg) at 0° C. The reaction mixture was stirred at room temperature overnight. Then water was added into the reaction to precipitate. The precipitate was collected by filtration and was dried to obtain 113-1 (4 mg) as a pale amorphous solid.

Step 113-2

Synthesis of N-(4-amidinophenyl)-2-hydroxy-2-[1,1,3-trioxo-4-(p-tolyl)-1,4-thiazinan-2-yl]acetamide hydrochloride (EXAMPLE 113)

According to the Step 26-B in synthetic method for EXAMPLE 26, compound 113-1 (25 mg) was used instead of 26-14 to obtain EXAMPLE 113 (15.8 mg) as a pale green amorphous solid.

Example 114

Synthesis of (2R)—N-(4-amidinophenyl)-2-hydroxy-2-[(2R)-3-oxo-4-(p-tolyl)-1,4-oxazepan-2-yl]acetamide hydrochloride (EXAMPLE 114)

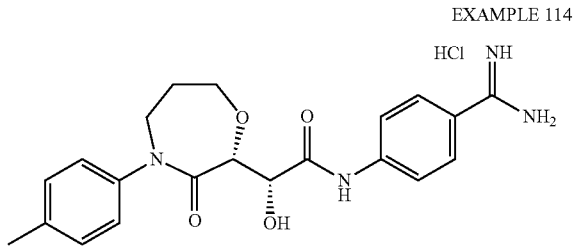 [SMILES: Cl ; Cc1ccc(N2CCCO[C@H]([C@@H](O)C(=O)Nc3ccc(C(=N)N)cc3)C2=O)cc1]

EXAMPLE 114

Step 114-1

Synthesis of (2R,3R)-2,3-diacetoxy-4-[N-(3-chloropropyl)-4-methylanilino]-4-oxobutanoic acid (compound 114-1)

According to the Step 26-9 in synthetic method for EXAMPLE 26, N-(3-chloropropyl)-4-methylaniline (1.85 g) was used instead of 26-1 to obtain compound 114-1 (4.46 g) as a colorless amorphous solid.

Step 114-2

Synthesis of [(2R,3R)-3-acetyloxy-4-[N-(3-chloropropyl)-4-methylanilino]-1,4-dioxo-1-[4-(5-oxo-4H-1,2,4-oxadiazol-3-yl)anilino]butan-2-yl]acetate (compound 114-1)

According to the Step 26-10 in synthetic method for EXAMPLE 26, 114-1 (3 g) was used instead of 26-9 to obtain compound 114-2 (1.17 g) as a pale pink amorphous solid.

Step 114-3

Synthesis of (2R,3R)—N-(3-chloropropyl)-2,3-dihydroxy-N'-[4-(5-oxo-4H-1,2,4-oxadiazol-3-yl)phenyl]-N-(p-tolyl)butanediamide ammonium salt (compound 114-3)

According to the Step 7-4 in synthetic method for EXAMPLE 7, 114-2 (0.6 g) was used instead of 7-3 to obtain compound 114-3 (0.54 g) as a yellow amorphous solid.

Step 114-4

Synthesis of (2R)-2-hydroxy-N-[4-(5-oxo-4H-1,2,4-oxadiazol-3-yl)phenyl]-2-[(2R)-3-oxo-4-(p-tolyl)-1,4-oxazepan-2-yl]acetamide (compound 114-4)

According to the Step 7-5 in synthetic method for EXAMPLE 7, 114-3 (0.2 g) was used instead of 7-4 to obtain compound 114-4 (40 mg) as a pale red amorphous solid.

Step 114-5

Synthesis of (2R)—N-(4-amidinophenyl)-2-hydroxy-2-[(2R)-3-oxo-4-(p-tolyl)-1,4-oxazepan-2-yl]acetamide hydrochloride (EXAMPLE 114)

According to the Step 26-B in synthetic method for EXAMPLE 26, compound 114-4 (20 mg) was used instead of 26-14 to obtain EXAMPLE 114 (20 mg) as a yellow amorphous solid.

Example 115

Synthesis of N-(4-amidinophenyl)-2-hydroxy-2-[4-(4-methylbenzoyl)morpholin-2-yl]acetamide hydrochloride (EXAMPLE 115)

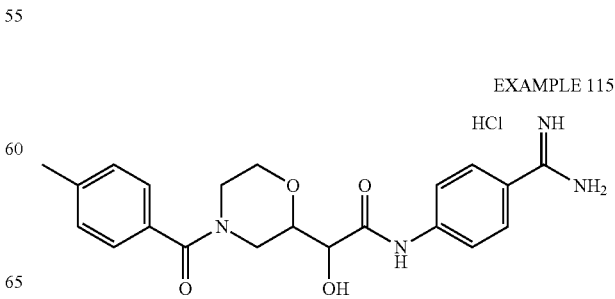

EXAMPLE 115

351

Step 115-1

Synthesis of 2-(4-benzylmorpholin-2-yl)-2-hydroxy-acetonitrile (compound 115-1)

To a solution of 4-(phenylmethyl)-2-morpholinecarboxaldehyde (78 mg) in MeOH (1.4 mL), was added TMSCN (0.073 mL) at room temperature. The reaction mixture was stirred at room temperature overnight. The mixture was concentrated in vacuo to obtain 115-1 (83 mg) as diastereomeric mixture.

Step 115-2

Synthesis of ethyl 2-(4-benzylmorpholin-2-yl)-2-hydroxyacetate hydrochloride (compound 115-2)

To a solution of 115-1 (0.68 g) in HCl-EtOH (20 mL), was added conc. HCl (10 mL) at room temperature. The reaction mixture was refluxed for 2.5 hours. Then the mixture was concentrated in vacuo to obtain 115-2 (0.94 g) as a pale yellow amorphous solid.

Step 115-3

Synthesis of ethyl 2-hydroxy-2-morpholin-2-ylacetate hydrochloride (compound 115-3)

According to the Step 33-1 in synthetic method for EXAMPLE 33, compound 115-2 (0.9 g) with EtOH was used instead of EXAMPLE 32 to obtain compound 115-3 (0.65 g) as pale yellow amorphous solid.

Step 115-4 ethyl 2-hydroxy-2-[4-(4-methylbenzoyl)morpholin-2-yl]acetate (compound 115-4)

According to the Step 28-1 in synthetic method for EXAMPLE 28, compound 115-3 (0.2 g) and 4-methylbenzoyl chloride (164 mg) were used instead of 26-5 and mesyl chloride to obtain compound 115-4 (85 mg) as a pale yellow amorphous solid.

Step 115-5

2-hydroxy-2-[4-(4-methylbenzoyl)morpholin-2-yl] acetic acid (compound 115-5)

According to the Step 1-2 in synthetic method for EXAMPLE 1, compound 115-4 (82.7 mg) was used instead of 1-1 (LP) to obtain compound 115-5 (87.5 mg) as a colorless amorphous solid.

Step 115-6

Synthesis of 2-hydroxy-2-[4-(4-methylbenzoyl)morpholin-2-yl]-N-[4-(5-oxo-4H-1,2,4-oxadiazol-3-yl) phenyl]acetamide (compound 115-6)

According to the Step 77-1 in synthetic method for EXAMPLE 77, compound 115-5 (74 mg) and 3-(4-aminophenyl)-1,2,4-oxadiazol-5(2H)-one (70.4 mg) were used instead of 3-iodobenzoic acid and 4,4-difluoropiperidine to obtain compound 115-6 (75.1 mg) as a pale yellow amorphous solid.

352

Step 115-7

Synthesis of N-(4-amidinophenyl)-2-hydroxy-2-[4-(4-methylbenzoyl)morpholin-2-yl]acetamide hydrochloride (EXAMPLE 115)

According to the Step 26-B in synthetic method for EXAMPLE 26, compound 115-6 (20 mg) was used instead of 26-14 to obtain EXAMPLE 115 (11.2 mg) as a brown amorphous solid.

Example 116

Synthesis of N-(4-amidinophenyl)-2-hydroxy-2-[4-(p-tolylsulfonyl)morpholin-2-yl]acetamide hydrochloride (EXAMPLE 116)

EXAMPLE 116

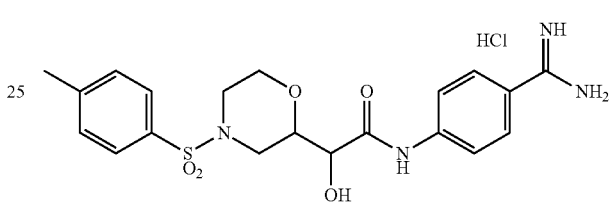

Step 116-1 ethyl 2-hydroxy-2-[4-(p-tolylsulfonyl)morpholin-2-yl]acetate (compound 116-1)

According to the Step 28-1 in synthetic method for EXAMPLE 28, compound 115-3 (0.2 g) and tosylchloride (203 mg) were used instead of 26-5 and mesyl chloride to obtain compound 116-1 (108 mg) as a pale yellow amorphous solid.

Step 116-2

Synthesis of 2-hydroxy-2-[4-(p-tolylsulfonyl)morpholin-2-yl]acetic acid (compound 116-2)

According to the Step 1-2 in synthetic method for EXAMPLE 1, compound 116-1 (108 mg) was used instead of 1-1 (LP) to obtain compound 116-2 (101 mg) as a colorless amorphous solid.

Step 116-3

Synthesis of 2-hydroxy-N-[4-(5-oxo-4H-1,2,4-oxadiazol-3-yl)phenyl]-2-[4-(p-tolylsulfonyl)morpholin-2-yl]acetamide (compound 116-3)

According to the Step 77-1 in synthetic method for EXAMPLE 77, compound 116-2 (94 mg) and 3-(4-aminophenyl)-1,2,4-oxadiazol-5(2H)-one (79.2 mg) were used instead of 3-iodobenzoic acid and 4,4-difluoropiperidine to obtain compound 116-3 (83 mg) as a pale yellow amorphous solid.

Step 116-4

Synthesis of N-(4-amidinophenyl)-2-hydroxy-2-[4-(p-tolylsulfonyl)morpholin-2-yl]acetamide hydrochloride (EXAMPLE 116)

According to the Step 26-B in synthetic method for EXAMPLE 26, compound 116-3 (20 mg) was used instead of 26-14 to obtain EXAMPLE 116 (16.7 mg) as a pale yellow amorphous solid.

Example 117

Synthesis of N-(1-amino-6-isoquinolyl)-2-hydroxy-2-[4-(p-tolyl)morpholin-2-yl]acetamide ditrifluoroacetate (EXAMPLE 117)

EXAMPLE 117

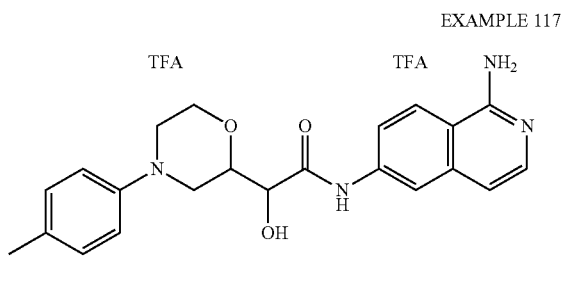 [SMILES: Cc1ccc(N2CCOC(C(O)C(=O)Nc3ccc4c(N)nccc4c3)C2)cc1]

Step 117-1

Synthesis of ethyl 2-hydroxy-2-[4-(p-tolyl)morpholin-2-yl]acetate (compound 117-1)

According to the Step 20-2 in synthetic method for EXAMPLE 20, compound 1-1(LP) (0.2 g) was used instead of 20-1 to obtain compound 117-1 (0.2 g) as a pale yellow amorphous solid.

Step 117-2

Synthesis of 2-hydroxy-2-[4-(p-tolyl)morpholin-2-yl]acetic acid lithium salt (compound 117-2)

According to the Step 1-2 in synthetic method for EXAMPLE 1, compound 117-1 (45 mg) and LiOH—H2O (6.8 mg) were used instead of 1-1 (LP) and NaOH to obtain compound 117-2 (41 mg) as a pale yellow amorphous solid.

Step 117-3

Synthesis of tert-butyl N-tert-butoxycarbonyl-N-[6-[[2-hydroxy-2-[4-(p-tolyl)morpholin-2-yl]acetyl]amino]-1-isoquinolyl]carbamate (compound 117-3)

According to the Step 1-3 in synthetic method for EXAMPLE 1, compound 117-2 (30 mg) was used instead of 1-2 to obtain compound 117-3 (4 mg) as a pale yellow amorphous solid.

Step 117-4

Synthesis of N-(1-amino-6-isoquinolyl)-2-hydroxy-2-[4-(p-tolyl)morpholin-2-yl]acetamide ditrifluoroacetate (EXAMPLE 117)

According to the Step 1-4 in synthetic method for EXAMPLE 1, compound 117-3 (3.1 mg) was used instead of 1-3 to obtain EXAMPLE 117 (3.7 mg) as a colorless amorphous solid.

Example 118

Synthesis of (R)—N-(4-Carbamimidoylphenyl)-2-hydroxy-2-((R)-3-oxo-4-(3-(trifluoromethoxy)phenyl)morpholin-2-yl)acetamide hydrochloride (EXAMPLE 118)

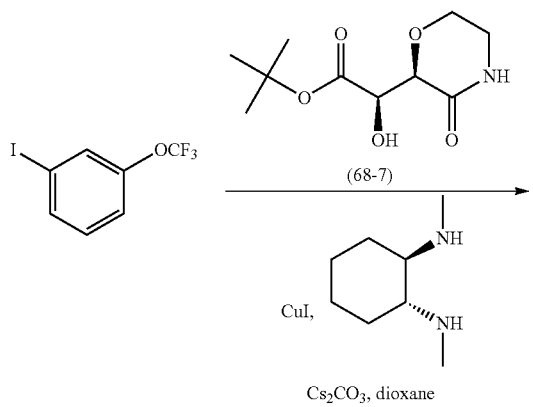

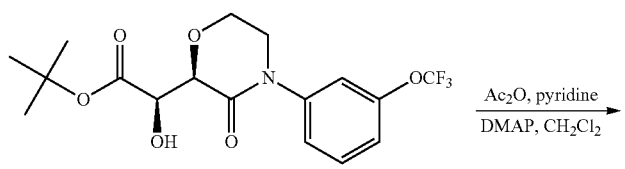

118-1

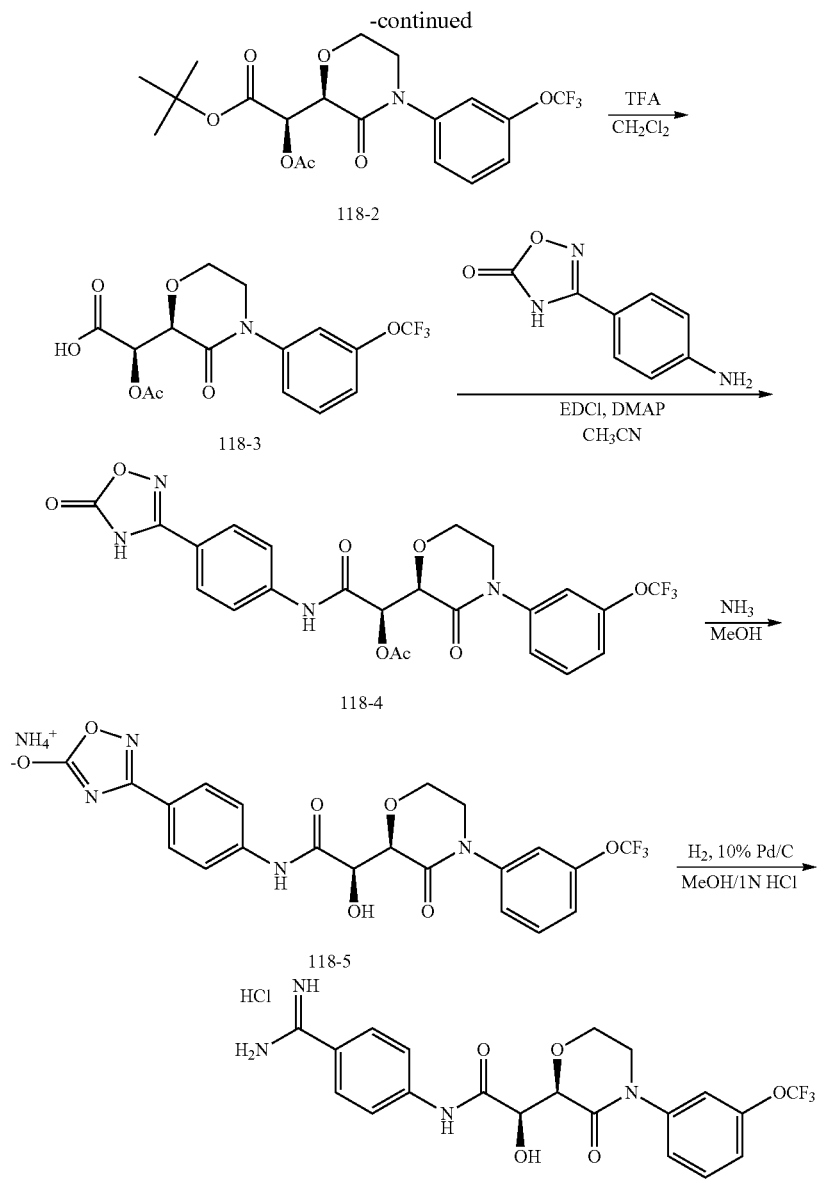

EXAMPLE 118

Step 118-1

(R)-tert-Butyl 2-hydroxy-2-((R)-3-oxo-4-(3-(trifluoromethoxy)phenyl)morpholin-2-yl)acetate (compound 118-1)

To a round bottom flask charged with a stir bar was added morpholinone (0.15 g) (68-7) and 3-trifluoromethoxyiodobenzene (0.12 mL) in dioxane (4 mL) at rt was added $Cs_2CO_3$ (0.42 g), and CuI (37 mg) under $N_2$. trans-N,N'-Dimethylcyclohexane-1,2-diamine (31 microL) was added dropwise and the mixture was affixed with a condenser. The mixture was degassed under vacuum (~20 mm), filled with $N_2$, and heated to 90° C. The mixture stirred for 3 h at 90° C., cooled to rt, and was diluted with conc $NH_4OH$ and water, EtOAc. The mixture was extracted with EtOAc three times and the organic layers were combined. The organic layer was washed with brine, dried ($Na_2SO_4$), filtered, and concentrated under reduced pressure to afford a yellow oil. The crude product was purified by flash chromatography using a 95% $CH_2Cl_2$/5% MeOH mixture to afford 118-1 (0.21 g) as a white solid.

Step 118-2

Synthesis of (R)-tert-butyl 2-acetoxy-2-((R)-3-oxo-4-(3-(trifluoromethoxy)phenyl)morpholin-2-yl)acetate (compound 118-2)

To a solution of 118-1 (0.21 g) in $CH_2Cl_2$ (2.5 ml) at 0° C. was added pyridine (63 microL), $Ac_2O$ (74 microl), and DMAP (5 mg). The mixture was stirred for 1 hour at 0° C., warmed to rt, and stirred for an additional 12 h. The mixture was diluted with EtOAc and the organic layer was washed sequentially with sat. aq. $CuSO_4$ solution, water, and brine. The organic layer was dried ($Na_2SO_4$), filtered, and concentrated under reduced pressure to afford 118-2 (0.22 g) as a light yellow semisolid. This material was used without further purification.

Step 118-3

Synthesis of (R)-2-acetoxy-2-((R)-3-oxo-4-(3-(trifluoromethoxy)phenyl)morpholin-2-yl)acetic acid (compound 118-3)

To a solution of 118-2 (0.22 g) in $CH_2Cl_2$ (2 mL) at 0° C. was added TFA (0.6 mL) dropwise. The mixture was stirred for 1 h at 0° C. and at rt for 30 min whereupon an additional portion of TFA (0.4 mL) was added. After an additional 1 h at rt, the mixture was diluted with $CH_2Cl_2$ and concentrated to dryness under reduced pressure. The crude mixture was redissolved in a 10:1 mixture of toluene/$CH_2Cl_2$ and concentrated and this protocol was repeated 5 times with to afford 118-3 (0.18 g) as a light yellow solid. This material was used without further purification.

Step 118-4

Synthesis of (R)-2-oxo-2-(4-(5-oxo-4,5-dihydro-1,2,4-oxadiazol-3-yl)phenylamino)-1-((R)-3-oxo-4-(3-(trifluoromethoxy)phenyl)morpholin-2-yl)ethyl acetate (compound 118-4)

To a solution of 118-3 (80 mg) n $CH_3CN$ (1.5 mL) at 0° C. was added 4-(5-oxo-4,5-dihydro-[1,2,4]oxadiazol-3-yl)-phenyl amide (50 mg) followed by EDCI (53 mg) and DMAP (3 mg). The reaction mixture was warmed to rt and stirred for 2.5 h. The mixture was concentrated under reduced pressure and placed under high vacuum. The crude material was purified by reverse phase HPLC using a C18 column and a gradient of (89.95:9.95:0.1 $H_2O$:MeCN:$HCO_2H$ to 9.95:89.95:0.1 $H_2O$:MeCN:$HCO_2H$) to afford 118-4 (37 mg) as a white solid.

Step 118-5

Ammonium 3-(4-((R)-2-hydroxy-2-((R)-3-oxo-4-(3-(trifluoromethoxy)phenyl)morpholin-2-yl)acetamido)phenyl)-1,2,4-oxadiazol-5-olate (compound 118-5)

To a solution of the 118-4 (27 mg) in MeOH (1.5 mL) at 0° C. was added 7M $NH_3$/MeOH (0.5 mL) dropwise. The mixture was stirred for 1 h at 0° C. and an additional hour at rt. The mixture was concentrated under reduced pressure and placed under high vacuum to afford 118-5 (25 mg) as a white solid. This material was used without further purification.

Step 118-6

Synthesis of (R)—N-(4-Carbamimidoylphenyl)-2-hydroxy-2-((R)-3-oxo-4-(3-(trifluoromethoxy)phenyl)morpholin-2-yl)acetamide hydrochloride (EXAMPLE 118)

To a solution of the 118-5 (25 mg) in a mixture of MeOH/1N HCl (1.5 mL/1.5 mL) was added 10% Pd/C (15 mg). The mixture was stirred under a $H_2$ balloon for 3 h and was filtered thru a pad of Celite. The Celite pad was washed with MeOH and the resultant filtrate was concentrated under reduced pressure. The crude residue was treated with MeOH followed by dilution with $Et_2O$ and the resultant solid was collected by filtration and dried under vacuum to afford Example 118 (24 mg) as a maize crystalline solid.

Example 119

Synthesis of (R)—N-(4-Carbamimidoylphenyl)-2-hydroxy-2-((R)-4-(2-methyl-1-oxoisoindolin-5-yl)-3-oxomorpholin-2-yl)acetamide hydrochloride (EXAMPLE 119)

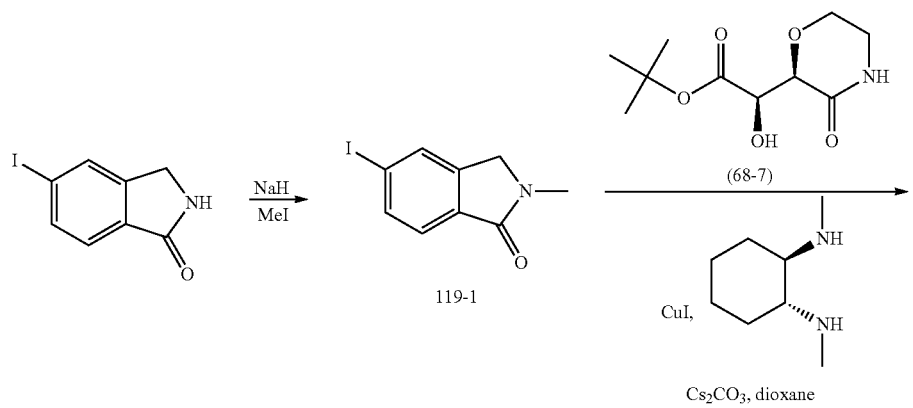

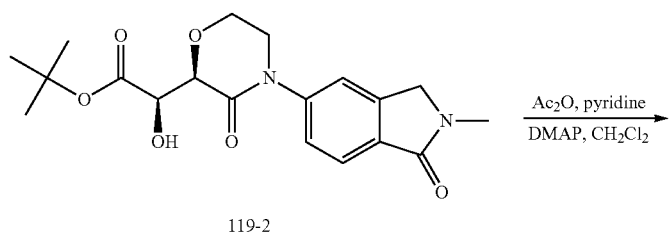

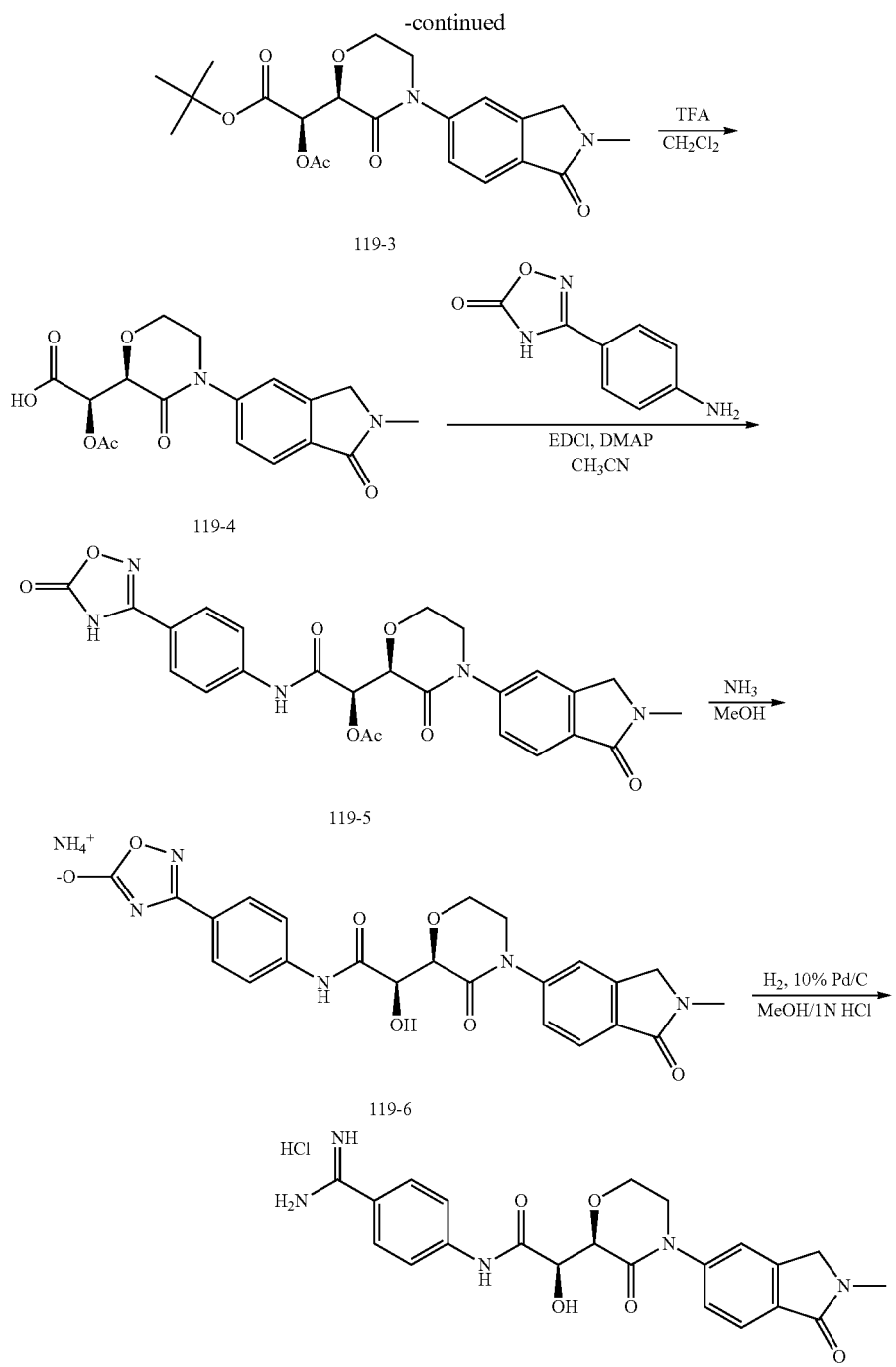

EXAMPLE 119

Step 119-1

Synthesis of 5-Iodo-2-methylisoindolin-1-one (compound 119-1)

To a mixture of 2,3-dihydro-5-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. NH$_4$Cl (~3 mL) and was diluted with EtOAc (10 mL). The layers were separated and the aqueous layer was extracted with EtOAc. The organic layers were combined and washed sequentially with water and brine. The organic layer was dried (Na$_2$SO$_4$), filtered, and concentrated under reduced pressure. The crude material was purified The crude product was purified by flash chromatography (ISCO, 120 g) using a gradient of 100% hexanes to 80:20 hexanes/EtOAc to afford 119-1 (0.78 g) as a light yellow solid.

Step 119-2

Synthesis of (R)-tert-Butyl 2-hydroxy-2-((R)-4-(2-methyl-1-oxoisoindolin-5-yl)-3-oxomorpholin-2-yl)acetate (compound 119-2)

According to the Step 118-1 in the synthetic method for EXAMPLE 118, compound 119-1 (0.20 g) was used instead of 3-trifluoromethoxy iodobenzene 118-1 to obtain 119-2 (0.29 g) as an off-white solid.

Step 119-3

Synthesis of (R)-tert-butyl 2-acetoxy-2-((R)-4-(2-methyl-1-oxoisoindolin-5-yl)-3-oxomorpholin-2-yl)acetate (compound 119-3)

According to the Step 118-2 in the synthetic method for EXAMPLE 118, compound 119-2 (0.29 g) was used instead of 118-1 to obtain 119-3 (0.31 g) as an off-white solid which was used without further purification.

Step 119-4

Synthesis of (R)-2-acetoxy-2-((R)-4-(2-methyl-1-oxoisoindolin-5-yl)-3-oxomorpholin-2-yl)acetic acid (compound 119-4)

According to the Step 118-3 in the synthetic method for EXAMPLE 118, compound 119-3 (0.31 g) was used instead of 118-2 to obtain 119-4 (0.27 g) as a white solid which was used without further purification.

Step 119-5

Synthesis of (R)-1-((R)-4-(2-Methyl-1-oxoisoindolin-5-yl)-3-oxomorpholin-2-yl)-2-oxo-2-(4-(5-oxo-4,5-dihydro-1,2,4-oxadiazol-3-yl)phenylamino)ethyl acetate (compound 119-5)

According to the Step 118-4 in the synthetic method for EXAMPLE 118, compound 119-4 (0.10 g) was used instead of 118-3 to obtain 119-5 (0.11 g) as an off-white solid which was purified by flash chromatography using 15:1 $CH_2Cl_2$/MeOH as eluent.

Step 119-6

Synthesis of Ammonium 3-(4-((R)-2-hydroxy-2-((R)-4-(2-methyl-1-oxoisoindolin-5-yl)-3-oxomorpholin-2-yl)acetamido)phenyl)-1,2,4-oxadiazol-5-olate (compound 119-6)

According to the Step 118-5 in the synthetic method for EXAMPLE 118, compound 119-5 (0.11 g) was used instead of 118-4 to obtain 119-6 (95 mg) as a white solid which was used without further purification.

Step 119-7

Synthesis of (R)—N-(4-Carbamimidoylphenyl)-2-hydroxy-2-((R)-4-(2-methyl-1-oxoisoindolin-5-yl)-3-oxomorpholin-2-yl)acetamide hydrochloride (EXAMPLE 119)

According to the Step 118-6 in the synthetic method for EXAMPLE 118, compound 119-5 (0.11 g) was used instead of 118-5 to obtain EXAMPLE 119 (95 mg) as a white solid which was used without further purification.

Example 120

Synthesis of (R)—N-(4-(Aminomethyl)phenyl)-2-hydroxy-2-((R)-4-(2-methyl-1-oxoisoindolin-5-yl)-3-oxomorpholin-2-yl)acetamide hydrochloride (EXAMPLE 120)

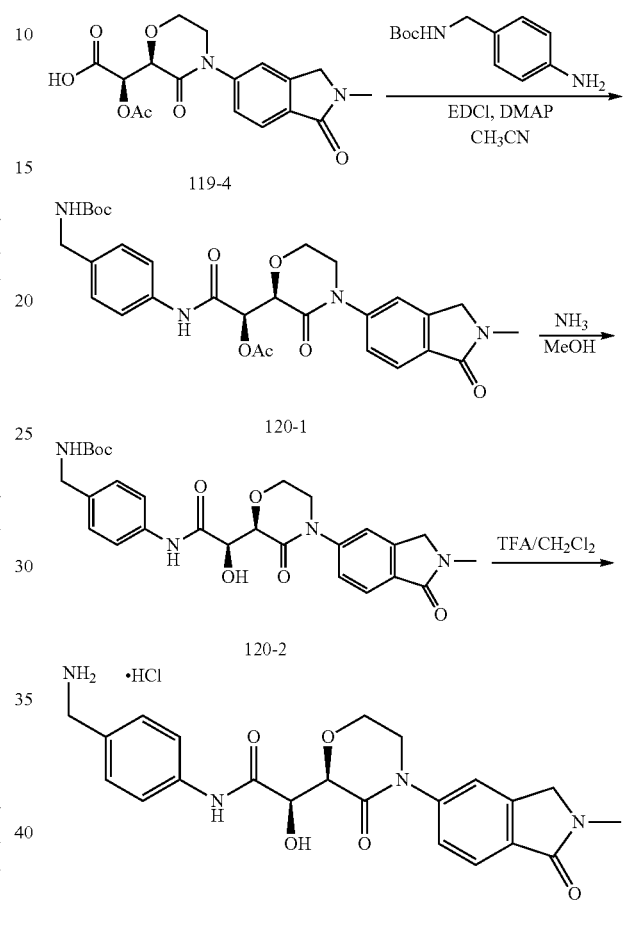

EXAMPLE 120

Step 120-1

Synthesis of (R)-2-(4-((tert-Butoxycarbonylamino)methyl)phenylamino)-1-((R)-4-(2-methyl-1-oxoisoindolin-5-yl)-3-oxomorpholin-2-yl)-2-oxoethyl acetate (compound 120-1)

According to the Step 118-4 in the synthetic method for EXAMPLE 118, 119-4 (0.10 g) was treated with tert-butyl 4-aminobenzylcarbamate (80 mg) to afford 120-1 (0.10 g) as yellow semisolid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step 120-2

Synthesis of tert-Butyl 4-((R)-2-hydroxy-2-((R)-4-(2-methyl-1-oxoisoindolin-5-yl)-3-oxomorpholin-2-yl)acetamido)benzylcarbamate (compound 120-2)

According to the Step 118-5 in the synthetic method for EXAMPLE 118, 120-1 (0.10 g) was used instead of compound 118-4 to obtain 120-2 (90 mg) as a white solid. Crude 120-2 was used without further purification in the next step.

Step 120-3

Synthesis of (R)—N-(4-(Aminomethyl)phenyl)-2-hydroxy-2-((R)-4-(2-methyl-1-oxoisoindolin-5-yl)-3-oxomorpholin-2-yl)acetamide hydrochloride (EXAMPLE 120)

To round bottom flask charged with the 120-2 (90 mg) at rt in CH$_2$Cl$_2$ (1.5 mL) was added TFA (0.5 mL). The resulting solution was stirred for 3 h, concentrated under reduced pressure, and placed under high vacuum. The crude product was dissolved in MeOH and diluted with 1M HCl in Et$_2$O and the resultant solid was collected and dried to afford EXAMPLE 120 (66 mg) at the hydrochloride salt as an off-white solid.

Example 121

Synthesis of (R)—N-(4-(Aminomethyl)phenyl)-2-hydroxy-2-((R)-3-oxo-4-(3-(3-oxomorpholino)phenyl)morpholin-2-yl)acetamide hydrochloride (EXAMPLE 121)

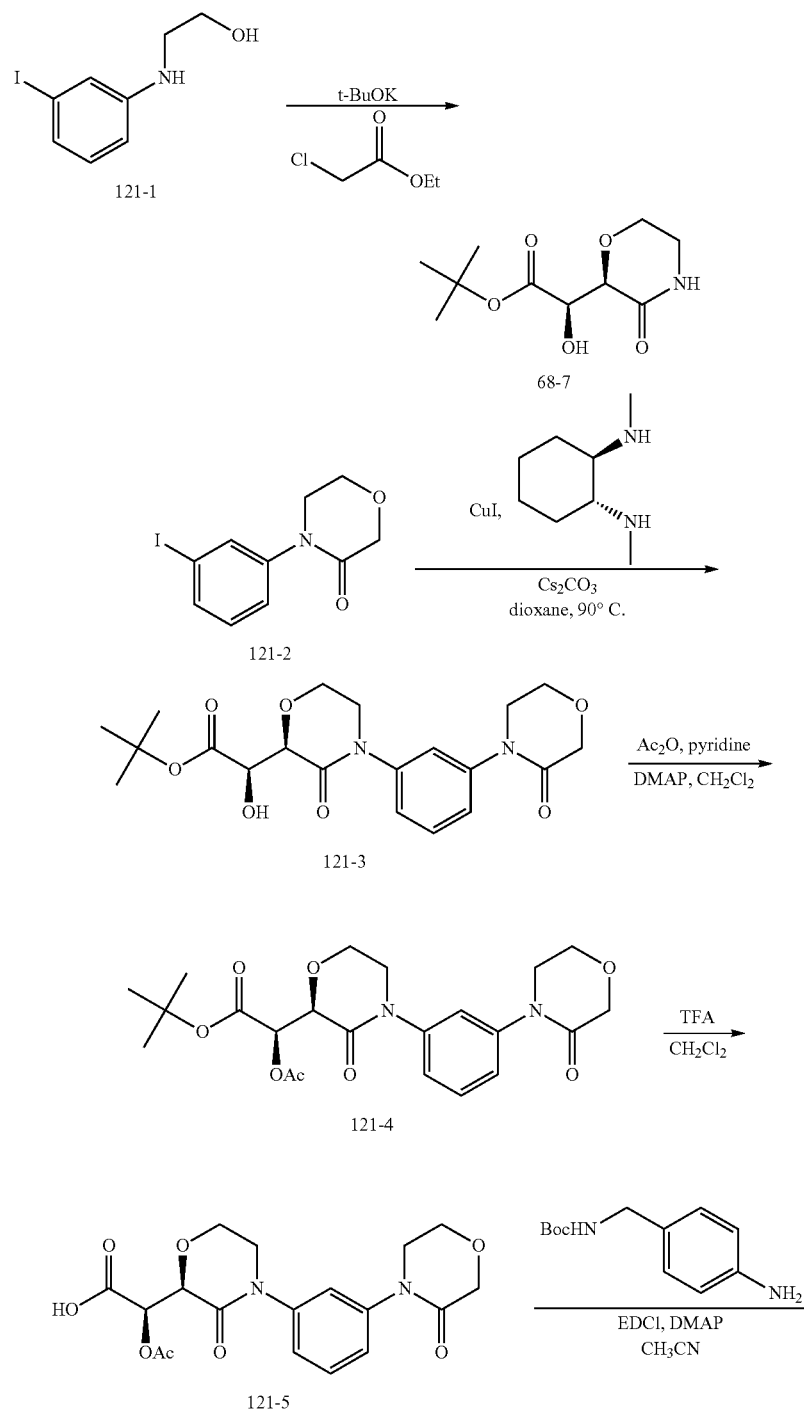

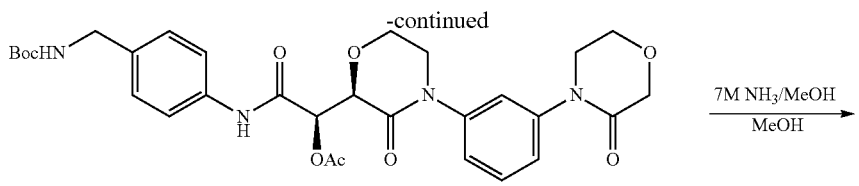

121-6

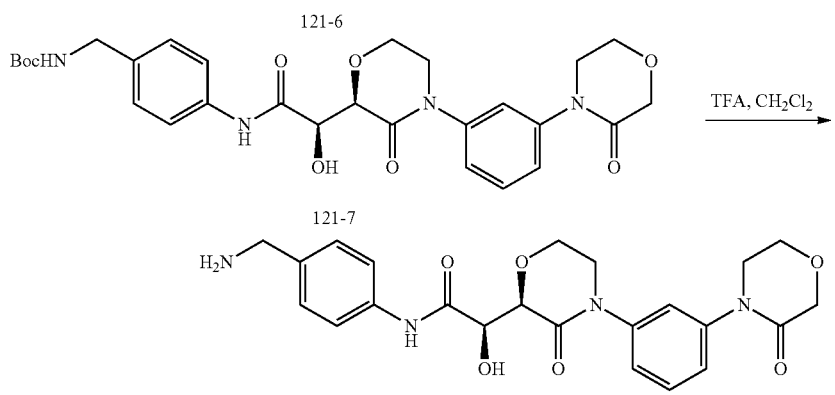

121-7

EXAMPLE 121

Step 121-2

Synthesis of 4-(3-Iodophenyl)morpholin-3-one (compound 121-2)

To a solution of t-BuOK (1.3 g) in THF (15 mL) at rt was added 2-(3-iodophenylamino) ethanol 121-1 (3.0 g) prepared from US 2004/0167188 followed by ethyl chloroacetate (1.1 mL). The resulting mixture was stirred for 12 h at rt whereupon an additional portion of t-BuOK (0.6 g) and ethyl chloroacetate (0.5 mL) was added. The mixture was heated to 55° C., stirred for 12 h, and was cooled to rt. The mixture was treated with sat. aq NaHCO$_3$ and water and was extracted with EtOAc. The organic layers were combined, dried (Na$_2$SO$_4$), filtered, and concentrated under reduced pressure. The crude material was purified by flash chromatography using a gradient of 100% hexanes to 20% hexanes/80% EtOAc to afford 121-2 (1.5 g) of the title compound as a light yellow solid.

Step 121-3

Synthesis of (R)-tert-butyl 2-hydroxy-2-((R)-3-oxo-4-(3-(3-oxomorpholino)phenyl)morpholin-2-yl)acetate (compound 121-3)

According to the Step 118-1 in the synthetic method for EXAMPLE 118, compound 121-2 (0.72 g) was used in the presence of 68-7 (0.50 g) to obtain 121-3 (0.65 g) as yellow crystalline solid after flash chromatography using a 20:1 mixture of CH$_2$Cl$_2$/MeOH.

Step 121-4

Synthesis of (R)-tert-butyl 2-acetoxy-2-((R)-3-oxo-4-(3-(3-oxomorpholino)phenyl)morpholin-2-yl)acetate (compound 121-4)

According to the Step 118-2 in the synthetic method for EXAMPLE 118, compound 121-3 (0.65 g) was used instead of 118-1 to obtain 121-4 (0.72 g) as an off-white solid which was used without further purification.

Step 121-5

Synthesis of (R)-2-acetoxy-2-((R)-3-oxo-4-(3-(3-oxomorpholino)phenyl)morpholin-2-yl)acetic acid (compound 121-5)

According to the Step 118-3 in the synthetic method for EXAMPLE 118, compound 121-4 (0.72 g) was used instead of 118-2 to obtain 121-5 (0.60 g) as a light yellow solid which was used without further purification.

Step 121-6

Synthesis of (R)-2-(4-((tert-butoxycarbonylamino)methyl)phenylamino)-2-oxo-1-((R)-3-oxo-4-(3-(3-oxomorpholino)phenyl)morpholin-2-yl)ethyl acetate (compound 121-6)

According to the Step 118-4 in the synthetic method for EXAMPLE 118, 121-5 (70 mg) was treated with tert-butyl 4-aminobenzylcarbamate (60 mg) to afford 121-6 (45 mg) as an off-white solid after flash chromatography using a 20:1 mixture of CH$_2$Cl$_2$/MeOH as eluent.

Step 121-7

Synthesis of tert-Butyl 4-((R)-2-hydroxy-2-((R)-3-oxo-4-(3-(3-oxomorpholino)phenyl)morpholin-2-yl)acetamido)benzylcarbamate (compound 121-7)

According to the Step 118-5 in the synthetic method for EXAMPLE 118, 121-6 (45 mg) was used instead of compound 118-4 to obtain 121-7 (43 mg) as a white solid. Crude 121-7 was used without further purification in the next step.

Step 121-8

Synthesis of (R)—N-(4-(Aminomethyl)phenyl)-2-hydroxy-2-((R)-3-oxo-4-(3-(3-oxomorpholino)phenyl)morpholin-2-yl)acetamide hydrochloride (EXAMPLE 121)

According to the Step 120-3 in the synthetic method for EXAMPLE 120, 121-7 (45 mg) was used instead of compound 120-2 to obtain EXAMPLE 121 (35 mg) as a pale yellow solid after treatment with HCl.

Example 122

Synthesis of (R)—N-(1-Aminoisoquinolin-6-yl)-2-hydroxy-2-((R)-3-oxo-4-(3-(3-oxomorpholino)phenyl)morpholin-2-yl)acetamide hydrochloride (EXAMPLE 122)

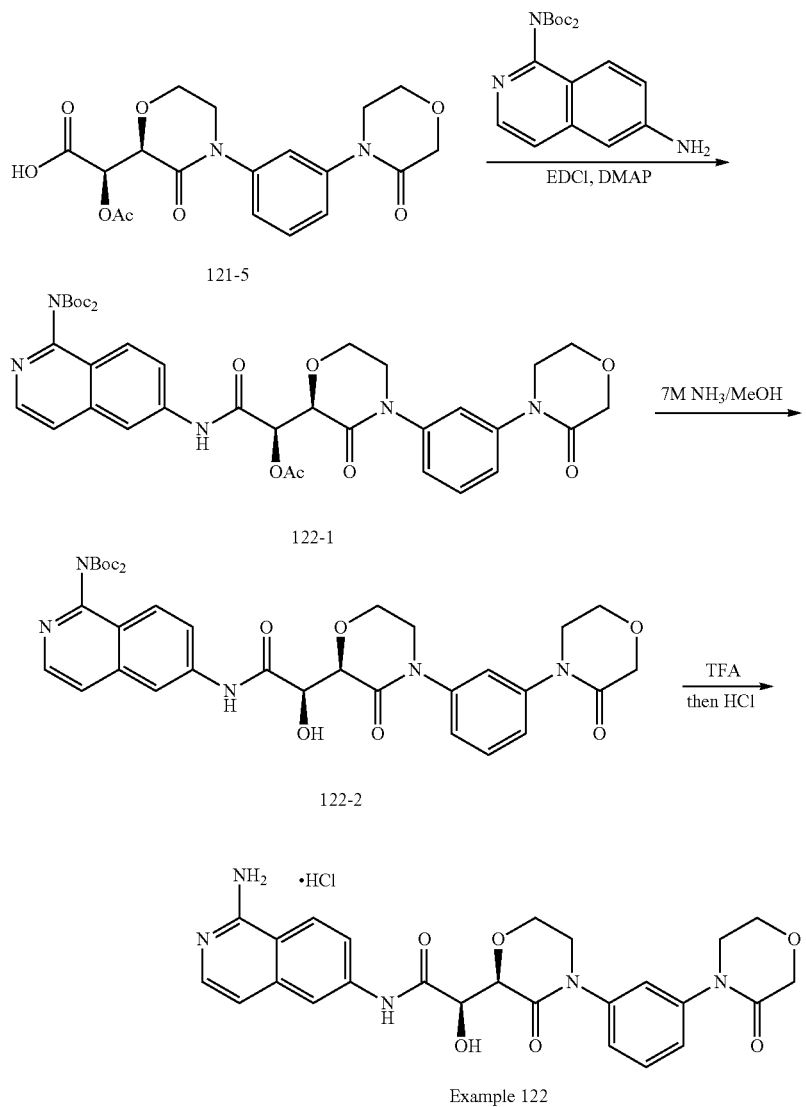

Step 122-1

Synthesis of (R)-2-(1-(Bis(tert-butoxycarbonyl)amino)isoquinolin-6-ylamino)-2-oxo-1-((R)-3-oxo-4-(3-(3-oxomorpholino)phenyl)morpholin-2-yl)ethyl acetate (compound 122-1)

According to the Step 118-4 in the synthetic method for EXAMPLE 118, compound 121-5 (0.25 g) was treated with di-tert-butyl (6-aminoisoquinolin-1-yl)imidocarbonate (0.30 g) from WO 2006/062972 to obtain 122-1 (0.17 g) as a yellow semisolid after reverse-phase purification using a C18 column and a gradient of 89.95:9.95:0.1 $H_2O$:MeCN:$HCO_2H$ to 9.95:89.95:0.1 $H_2O$:MeCN:$HCO_2H$.

Step 122-2

Synthesis of (R)—N-(1-(Bis(tert-butoxycarbonyl)aminoisoquinolin-6-yl)-2-hydroxy-2-((R)-3-oxo-4-(3-(3-oxomorpholino)phenyl)morpholin-2-yl)acetamide (compound 122-2)

According to the Step 118-5 in the synthetic method for EXAMPLE 118, 122-1 (0.17 g) was used instead of compound 118-4 to obtain 122-2 (0.10 g) as an off-white semisolid after reverse-phase purification using a C18 column and a gradient of 89.95:9.95:0.1 $H_2O$:MeCN:$HCO_2H$ to 9.95:89.95:0.1 $H_2O$:MeCN:$HCO_2H$.

Step 122-3

Synthesis of (R)—N-(1-Aminoisoquinolin-6-yl)-2-hydroxy-2-((R)-3-oxo-4-(3-(3-oxomorpholino)phenyl)morpholin-2-yl)acetamide hydrochloride (EXAMPLE 122)

To a solution of 122-2 (0.10 g) in CH₂Cl₂ (2 mL) at 0° C. was added TFA (0.5 mL) dropwise. The mixture was stirred for 1 h at 0° C., warmed to rt, and stirred for an additional 12 h. The mixture was diluted with CH₂Cl₂ and concentrated to dryness and this protocol was repeated 5 times. The crude mixture was purified by reverse phase HPLC using a C18 column and a gradient of 89.95:9.95:0.1 H₂O:MeCN:HCO₂H to 9.95:89.95:0.1 H₂O:MeCN:HCO₂H to afford EXAMPLE 122 (50 mg) as a white solid as the hydrochloride salt upon treatment with HCl.

Example 123

Synthesis of (R)—N-(4-Carbamimidoyl-3-chlorophenyl)-2-hydroxy-2-((R)-3-oxo-4-(3-(3-oxomorpholino)phenyl)morpholin-2-yl)acetamide hydrochloride (EXAMPLE 123)

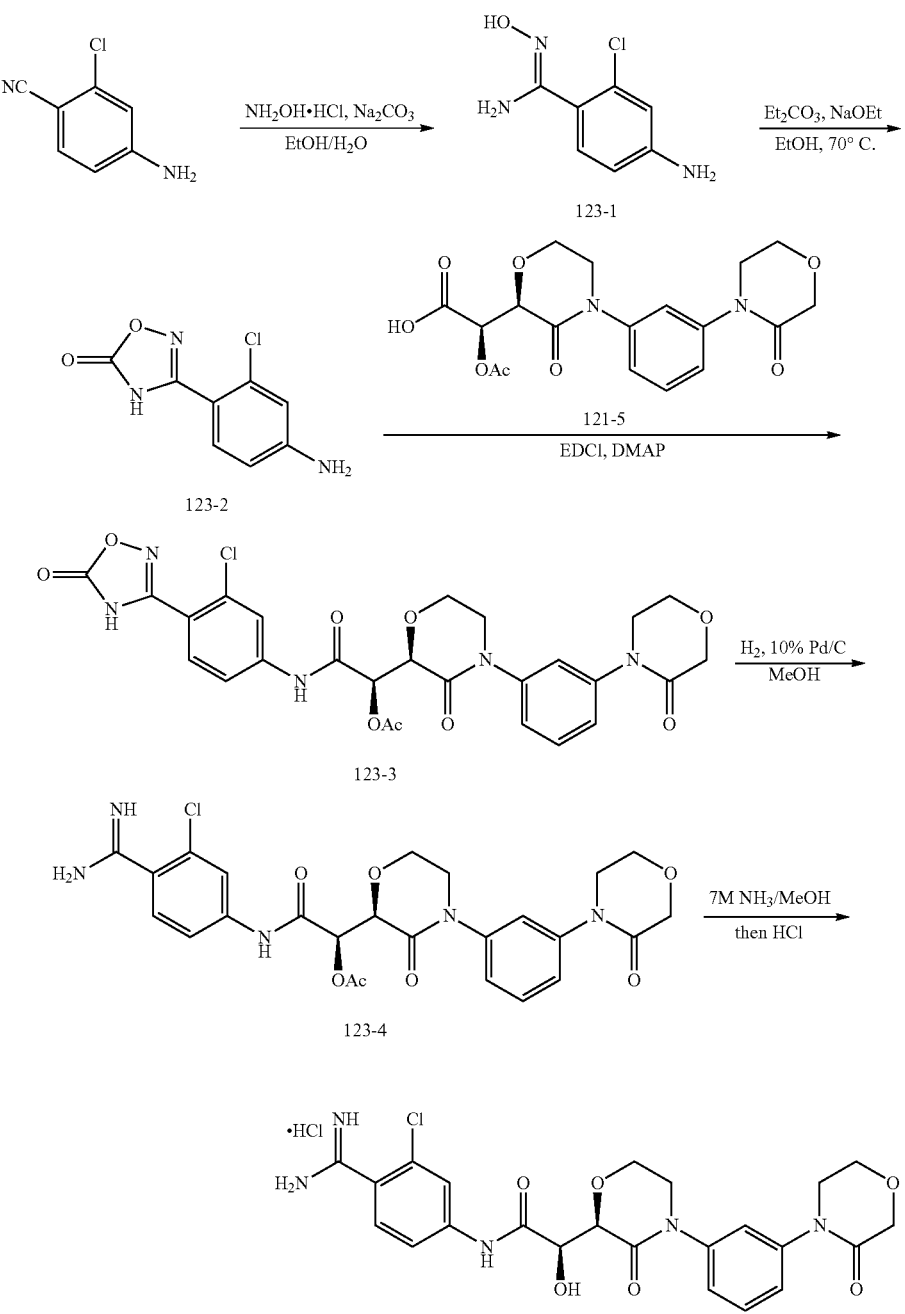

Example 123

Step 123-1

Synthesis of 4-Amino-2-chloro-N'-hydroxybenzimidamide (compound 123-1)

To a solution of 2-chloro-4-aminobenzonitrile (5 g) in EtOH/H$_2$O (22 mL/4 mL) was added Na$_2$CO$_3$ (2.3 g) and NH$_2$OH.HCl (2.5 g). The mixture was stirred for 8 h at 60° C. where upon an additional portion of both Na$_2$CO$_3$ (2.3 g) and NH$_2$OH.HCl (2.5 g) were added and continued heating at 60° C. for 72 h. The mixture was cooled to rt, filtered, and the resultant precipitate was washed with water, EtOH, and Et$_2$O. The crude precipitate was dried under vacuum to afford 123-1 (4.3 g) as a pale white solid which was used without further purification.

Step 123-2

Synthesis of 3-(4-Amino-2-chlorophenyl)-1,2,4-oxadiazol-5(4H)-one (compound 123-2)

To a solution of 123-1 (2.0 g) in EtOH (10 mL) at rt was added diethyl carbonate (1.3 mL) and the mixture was heated to 65° C. A 21% wt NaOEt soln (7.31 mL) was added dropwise to the solution which was then heated to 70° C. and stirred for 2 h. The mixture was cooled to rt, concentrated to dryness, and dissolved in a minimum amount of water. Concentrated HCl was added dropwise until pH ~2 and the resultant precipitate was filtered. The precipitate was washed sequentially with water, EtOH, and Et$_2$O to afford 123-2 (1.7 g) as a brown solid. This material was used without further purification.

Step 123-3

Synthesis of (R)-2-(3-Chloro-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl)ethyl acetate (compound 123-3)

According to the Step 118-4 in the synthetic method for EXAMPLE 118, compound 121-5 (0.20 g) was used instead of 118-3 to couple with 123-2 (0.13 g) to obtain 123-3 (60 mg) as an off-white solid which was purified by flash chromatography using a CH$_2$Cl$_2$/MeOH mixture.

Step 123-4

Synthesis of (R)-2-(4-Carbamimidoyl-3-chlorophenylamino)-2-oxo-1-((R)-3-oxo-4-(3-(3-oxomorpholino)phenyl)morpholin-2-yl)ethyl acetate (compound 123-4)

To a solution of 123-3 (25 mg) in MeOH (2.5 mL) at rt was added 10% Pd/C (6 mg). The mixture was stirred under a H$_2$ balloon for 4.5 h whereupon the mixture was filtered thru a pad of Celite and the filtrate was concentrated under reduced pressure. The crude material was purified by reverse phase HPLC using a C18 column and a gradient of 89.95:9.95:0.1 H$_2$O:MeCN:HCO$_2$H to 9.95:89.95:0.1 H$_2$O:MeCN:HCO$_2$H to afford 123-4 (8 mg) as an off-white solid.

Step 123-5

Synthesis of (R)—N-(4-carbamimidoyl-3-chlorophenyl)-2-hydroxy-2-((R)-3-oxo-4-(3-(3-oxomorpholino)phenyl)morpholin-2-yl)acetamide hydrochloride (EXAMPLE 123)

To a solution of 123-4 (8 mg) in MeOH (1 mL) at rt was added 7M NH$_3$ in MeOH (0.3 mL). The mixture was stirred for 3 h at rt and was concentrated under reduced pressure. The crude material was taken up in MeOH and diluted with 1 M HCl/Et$_2$O to afford EXAMPLE 123 (1.3 mg) as a pale yellow solid.

Example 124

Synthesis of (R)—N-(4-Carbamimidoyl-3-methylphenyl)-2-hydroxy-2-((R)-3-oxo-4-(3-(3-oxomorpholino)phenyl)morpholin-2-yl)acetamide hydrochloride (EXAMPLE 124)

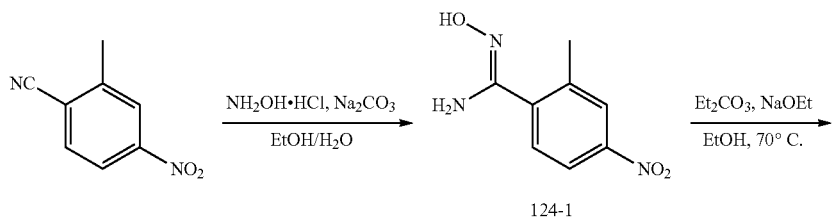

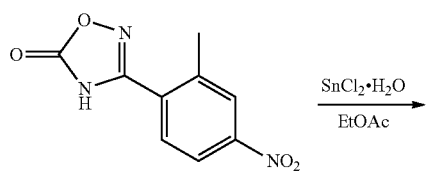

124-2

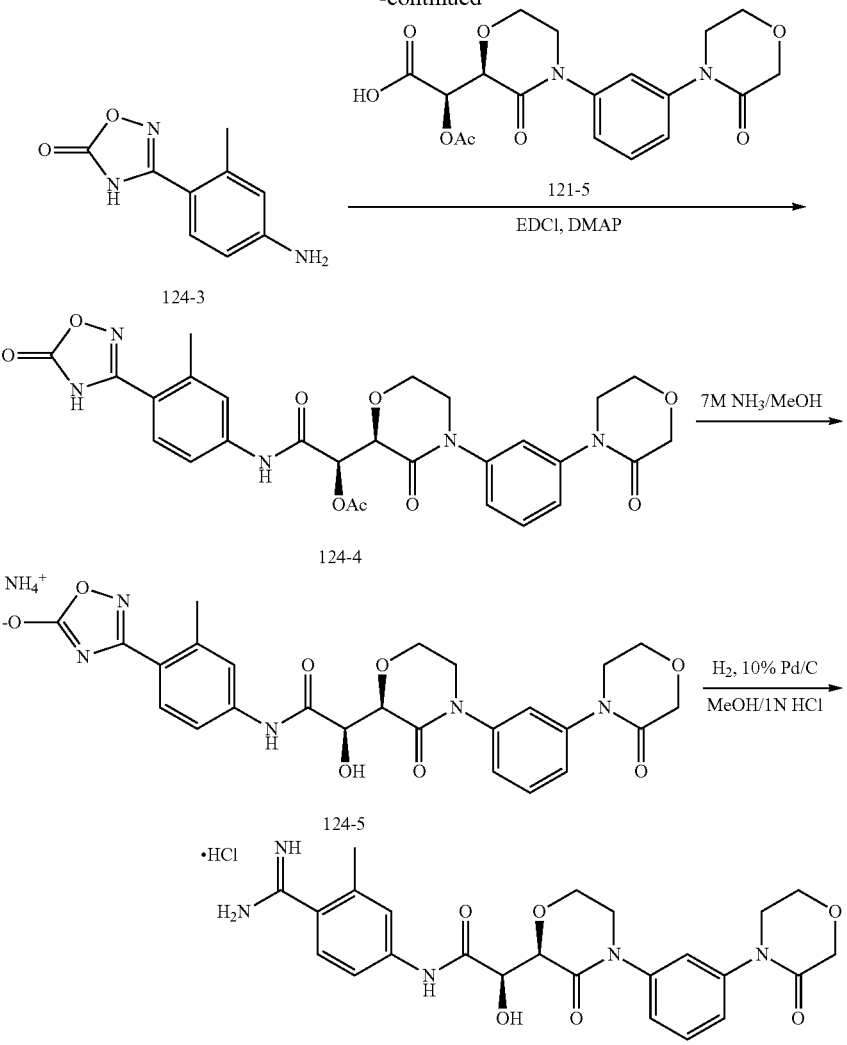

Example 124

Step 124-1

Synthesis of N-Hydroxy-2-methyl-4-nitrobenzimidamide (compound 124-1)

To a solution of 2-methyl-4-nitrobenzonitrile (5 g) in EtOH/H$_2$O (30 mL/6 mL) was added Na$_2$CO$_3$ (3.6 g) and NH$_2$OH.HCl (4.3 g). The mixture was stirred for 8 h at 60° C. where upon an additional portion of both Na$_2$CO$_3$ (3.6 g) and NH$_2$OH.HCl (4.3 g) were added and continued heating at 60° C. for 72 h. The mixture was cooled to rt, filtered, and the resultant precipitate was washed with water, EtOH, and Et$_2$O. The crude precipitate was dried under vacuum to afford 124-1 (3.4 g) as a pale yellow solid which was used without further purification.

Step 124-2

Synthesis of 3-(2-Methyl-4-nitrophenyl)-1,2,4-oxadiazol-5(4H)-one (compound 124-2)

To a solution of 124-1 (2.0 g) in EtOH (10 mL) at rt was added diethyl carbonate (1.3 mL) and the mixture was heated to 65° C. A 21% wt NaOEt soln (7.31 mL) was added dropwise to the solution which was then heated to 70° C. and stirred for 2 h. The mixture was cooled to rt, concentrated to dryness, and dissolved in a minimum amount of water. Concentrated HCl was added dropwise until pH and the resultant precipitate was filtered. The precipitate was washed sequentially with water, EtOH, and Et$_2$O to afford a dark brown solid. The crude product was purified by flash chromatography using a mixture of CH$_2$Cl$_2$/MeOH to afford 124-2 (0.9 g) as a brown solid.

Step 124-3

Synthesis of 3-(4-Amino-2-methylphenyl)-1,2,4-oxadiazol-5(4H)-one (compound 124-3)

To a solution of 124-2 (0.44 g) in EtOAc (25 mL) at rt was added SnCl$_2$.H$_2$O (1.7 g) in one portion. The mixture was heated at 80° C. for 12 h, cooled to rt, and quenched with sat. aq NaHCO$_3$. The mixture was filtered thru a pad of Celite and the aqueous layer was extracted with EtOAc. The combined organic layers were dried over Na$_2$SO$_4$, filtered, and concentrated under reduced pressure to afford 124-3 (0.16 g) as a brown solid. This material was used without further purification.

Step 124-4

Synthesis of (R)-2-(3-Methyl-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl)ethyl acetate (compound 124-4)

According to the Step 118-4 in the synthetic method for EXAMPLE 118, compound 121-5 (0.28 g) was used instead of 118-3 to couple with 124-3 (0.16 g) to obtain 124-4 (0.16 g) as an a pale yellow solid after reverse-phase HPLC purification using a C18 column and a gradient of 89.95:9.95:0.1 H₂O:MeCN:HCO₂H to 9.95:89.95:0.1 H₂O:MeCN:HCO₂H.

Step 124-5

Synthesis of Ammonium 3-(4-((R)-2-hydroxy-2-((R)-3-oxo-4-(3-(3-oxomorpholino)phenyl)morpholin-2-yl)acetamido)-2-methylphenyl)-1,2,4-oxadiazol-5-olate (compound 124-5)

According to the Step 118-5 in the synthetic method for EXAMPLE 118, compound 124-4 (0.16 g) was used instead of 118-4 to obtain 124-5 (0.15 g) as a white solid which was used without further purification.

Step 124-6

Synthesis of (R)—N-(4-Carbamimidoyl-3-methylphenyl)-2-hydroxy-2-((R)-3-oxo-4-(3-(3-oxomorpholino)phenyl)morpholin-2-yl)acetamide hydrochloride (EXAMPLE 124)

According to the Step 118-6 in the synthetic method for EXAMPLE 118, compound 124-5 (0.15 g) was used instead of 118-5 to obtain EXAMPLE 124 (90 mg) of the hydrochloride salt as a white solid which was used without further purification.

Example 125

Synthesis of (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide hydrochloride (EXAMPLE 125)

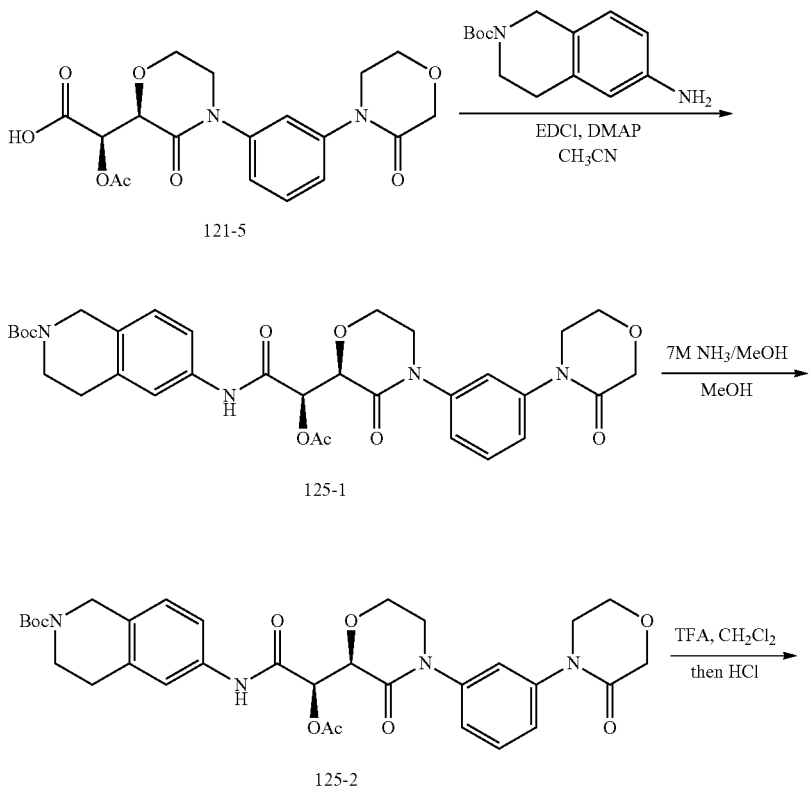

Step 125-1

Synthesis of tert-Butyl 6-((R)-2-acetoxy-2-((R)-3-oxo-4-(3-(3-oxomorpholino)phenyl)morpholin-2-yl)acetamido)-3,4-dihydroisoquinoline-2(1H)-carboxylate (compound 125-1)

According to the Step 118-4 in the synthetic method for EXAMPLE 118, compound 121-5 (70 mg) was treated with tert-butyl 6-amino-3,4-dihydroisoquinoline-2(1H)-carboxylate (67 mg) to obtain 125-1 (58 mg) as a yellow solid after flash chromatography purification using a 20:1 mixture of $CH_2Cl_2$/MeOH as eluent.

Step 125-2

Synthesis of tert-Butyl 6-((R)-2-acetoxy-2-((R)-3-oxo-4-(3-(3-oxomorpholino)phenyl)morpholin-2-yl)acetamido)-3,4-dihydroisoquinoline-2(1H)-carboxylate (compound 125-2)

According to the Step 118-5 in the synthetic method for EXAMPLE 118, 125-1 (58 mg) was used instead of compound 118-4 to obtain 125-2 (50 mg) as a white solid which was taken on without further purification.

Step 125-3

Synthesis of (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide hydrochloride (EXAMPLE 125)

According to the Step 120-3 in the synthetic method for EXAMPLE 120, 125-2 (50 mg) was used instead of compound 120-2 to obtain EXAMPLE 125 (35 mg) as a pale yellow hydrochloride salt upon treatment with HCl.

Example 126

Synthesis of 2-(3-((R)-2-((R)-2-(4-Carbamimidoylphenylamino)-1-hydroxy-2-oxoethyl)-3-oxomorpholino)phenoxy)acetic acid hydrochloride (EXAMPLE 126)

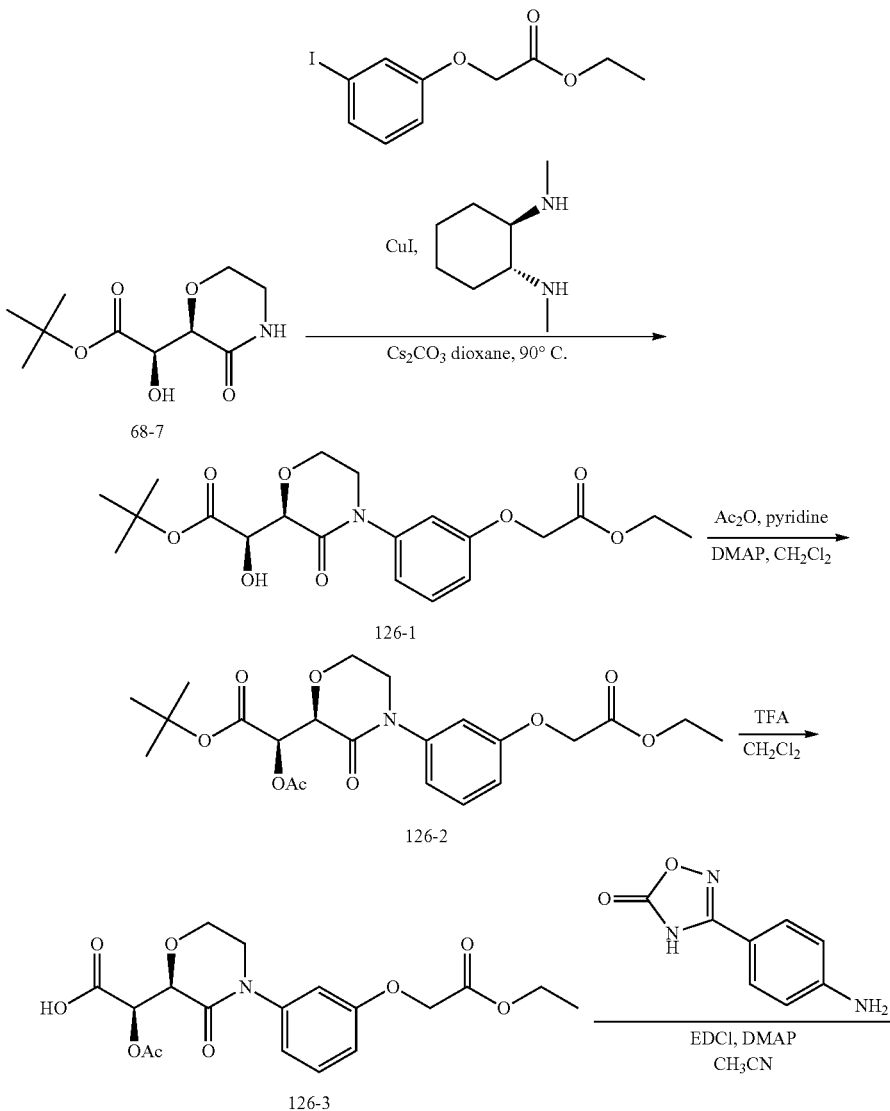

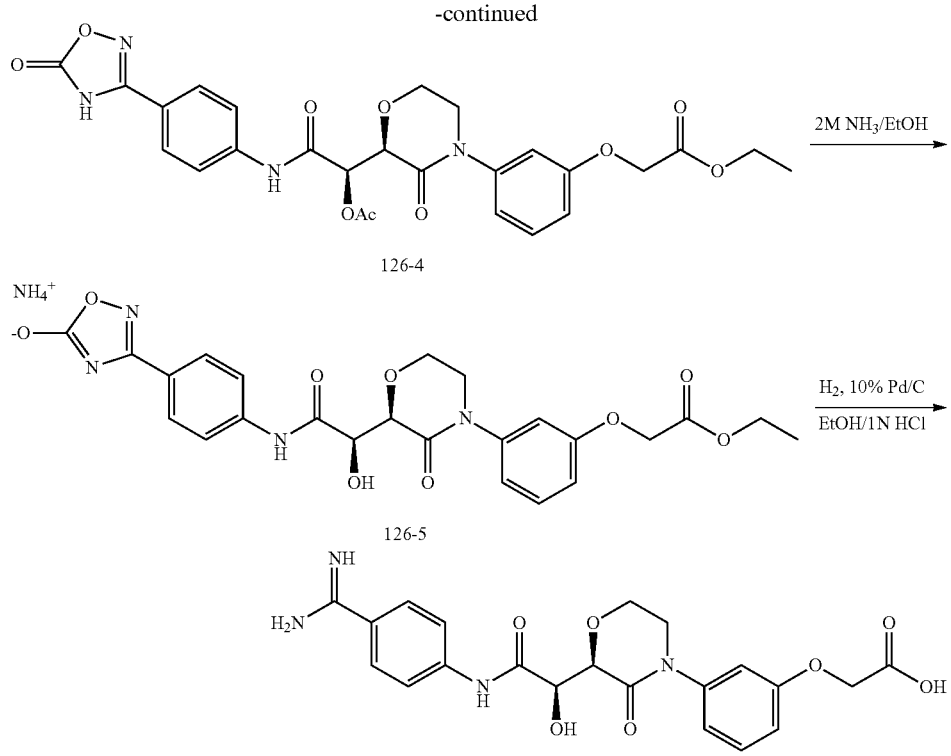

EXAMPLE 126

Step 126-1

Synthesis of (R)-tert-Butyl 2-((R)-4-(3-(2-ethoxy-2-oxo ethoxy)phenyl)-3-oxomorpholin-2-yl)-2-hydroxyacetate (compound 126-1)

According to the Step 118-1 in the synthetic method for EXAMPLE 118, 68-7 (0.35 g) was treated with ethyl 2-(3-iodophenoxy)acetate (0.56 g) from *Eur. J. Org. Chem.* 2008, 337 to obtain 126-1 (0.54 g) as an yellow solid after flash chromatography with 40:1 CH$_2$Cl$_2$/MeOH as eluent.

Step 126-2

Synthesis of (R)-tert-Butyl 2-acetoxy-2-((R)-4-(3-(2-ethoxy-2-oxo ethoxy)phenyl)-3-oxomorpholin-2-yl)acetate (compound 126-2)

According to the Step 118-2 in the synthetic method for EXAMPLE 118, compound 126-1 (0.54 g) was used instead of 118-1 to obtain 126-2 (0.56 g) as a yellow oil which was used without further purification.

Step 126-3

Synthesis of (R)-2-Acetoxy-2-((R)-4-(3-(2-ethoxy-2-oxo ethoxy)phenyl)-3-oxomorpholin-2-yl)acetic acid (compound 126-3)

According to the Step 118-3 in the synthetic method for EXAMPLE 118, compound 126-2 (0.55 g) was used instead of 118-2 to obtain 126-3 (0.45 g) as a yellow solid which was used without further purification.

Step 126-4

Synthesis of Ethyl 2-(3-((R)-2-((R)-1-acetoxy-2-oxo-2-(4-(5-oxo-4,5-dihydro-1,2,4-oxadiazol-3-yl) phenyl amino)ethyl)-3-oxomorpholino)phenoxy) acetate (compound 126-4)

According to the Step 118-4 in the synthetic method for EXAMPLE 118, compound 126-3 (0.18 g) was used instead of 118-3 to obtain 126-4 (90 mg) as an off-white solid after purification by reverse-phase HPLC using a C18 column and a gradient of 89.95:9.95:0.1 H$_2$O:MeCN:HCO$_2$H to 9.95:89.95:0.1 H$_2$O:MeCN:HCO$_2$H.

Step 126-5

Synthesis of Ammonium 3-(4-((R)-2-((R)-4-(3-(2-ethoxy-2-oxoethoxy)phenyl)-3-oxomorpholin-2-yl)-2-hydroxy acetamido)phenyl)-1,2,4-oxadiazol-5-olate (compound 126-5)

According to the Step 118-5 in the synthetic method for EXAMPLE 118 except using 2M NH$_3$ in EtOH, compound 126-4 (85 mg) was used instead of 118-4 to obtain 126-5 (60 mg) as a yellow solid which was used without further purification.

Step 126-6

Synthesis of 2-(3-((R)-2-((R)-2-(4-Carbamimidoylphenylamino)-1-hydroxy-2-oxoethyl)-3-oxomorpholino)phenoxy)acetic acid hydrochloride (EXAMPLE 126)

According to the Step 118-6 in the synthetic method for EXAMPLE 118 except substituting EtOH for MeOH as solvent, compound 126-5 (58 mg) was used instead of 118-5 to obtain EXAMPLE 126 (36 mg) as a maize solid.

Example 127

Synthesis of Ethyl 2-(3-((R)-2-((R)-2-(4-(aminomethyl)phenylamino)-1-hydroxy-2-oxoethyl)-3-oxomorpholino)phenoxy)acetate trifluoroacetate (EXAMPLE 127)

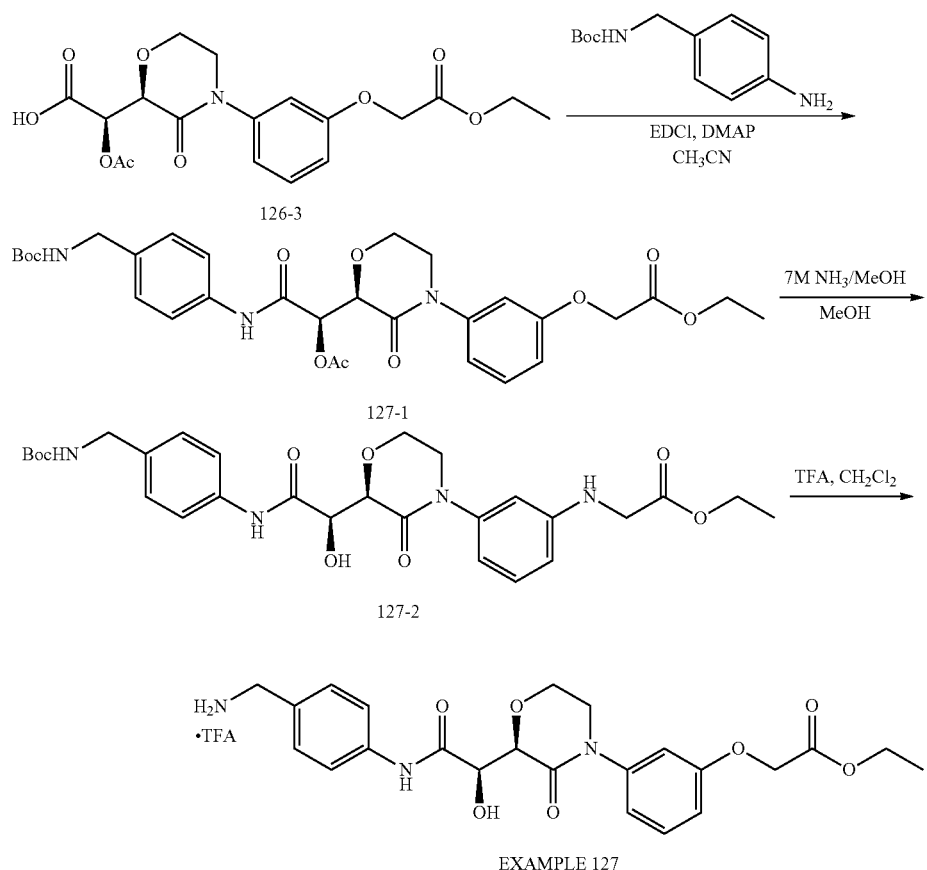

EXAMPLE 127

Step 127-1

Synthesis of Ethyl 2-(3-((R)-2-((R)-1-acetoxy-2-(4-((tert-butoxycarbonylamino)methyl)phenylamino)-2-oxoethyl)-3-oxomorpholino)phenoxy)acetate (compound 127-1)

According to the Step 118-4 in the synthetic method for EXAMPLE 118, 126-3 (0.18 g) was treated with tert-butyl 4-aminobenzylcarbamate (0.13 g) to afford 127-1 (100 mg) as an yellow semisolid after purification by reverse-phase HPLC using a C18 column and a gradient of 89.95:9.95:0.1 $H_2O$:MeCN:$HCO_2H$ to 9.95:89.95:0.1 $H_2O$:MeCN:$HCO_2H$.

Step 127-2

Synthesis of Ethyl 2-(3-((R)-2-((R)-2-(4-((tert-butoxycarbonylamino)methyl)phenylamino)-1-hydroxy-2-oxoethyl)-3-oxomorpholino)phenylamino)acetate (compound 127-2)

According to the Step 118-5 in the synthetic method for EXAMPLE 118 except using 2M $NH_3$ in EtOH, 127-1 (0.10 g) was used instead of compound 118-4 to obtain 127-2 (90 mg) as a white solid. Crude 127-2 was used without further purification in the next step.

Step 127-3

Synthesis of Ethyl 2-(3-((R)-2-((R)-2-(4-(aminomethyl)phenylamino)-1-hydroxy-2-oxoethyl)-3-oxomorpholino)phenoxy)acetate trifluoroacetate (EXAMPLE 127)

According to the Step 120-3 in the synthetic method for EXAMPLE 120, 127-2 (90 mg) was used instead of compound 120-2 to obtain EXAMPLE 127 (55 mg) as the trifluoroacetate salt as a white solid after purification by reverse-phase HPLC using a C18 column and a gradient of 89.95:9.95:0.1 $H_2O$:MeCN:TFA to 9.95:89.95:0.1 $H_2O$:MeCN:TFA.

Example 128
Synthesis of (R)—N-(4-carbamimidoyl-2-ethylphenyl)-2-hydroxy-2-((R)-4-(2-methyl-3-oxoisoindolin-5-yl)-3-oxomorpholin-2-yl)acetamide hydrochloride (EXAMPLE 128)
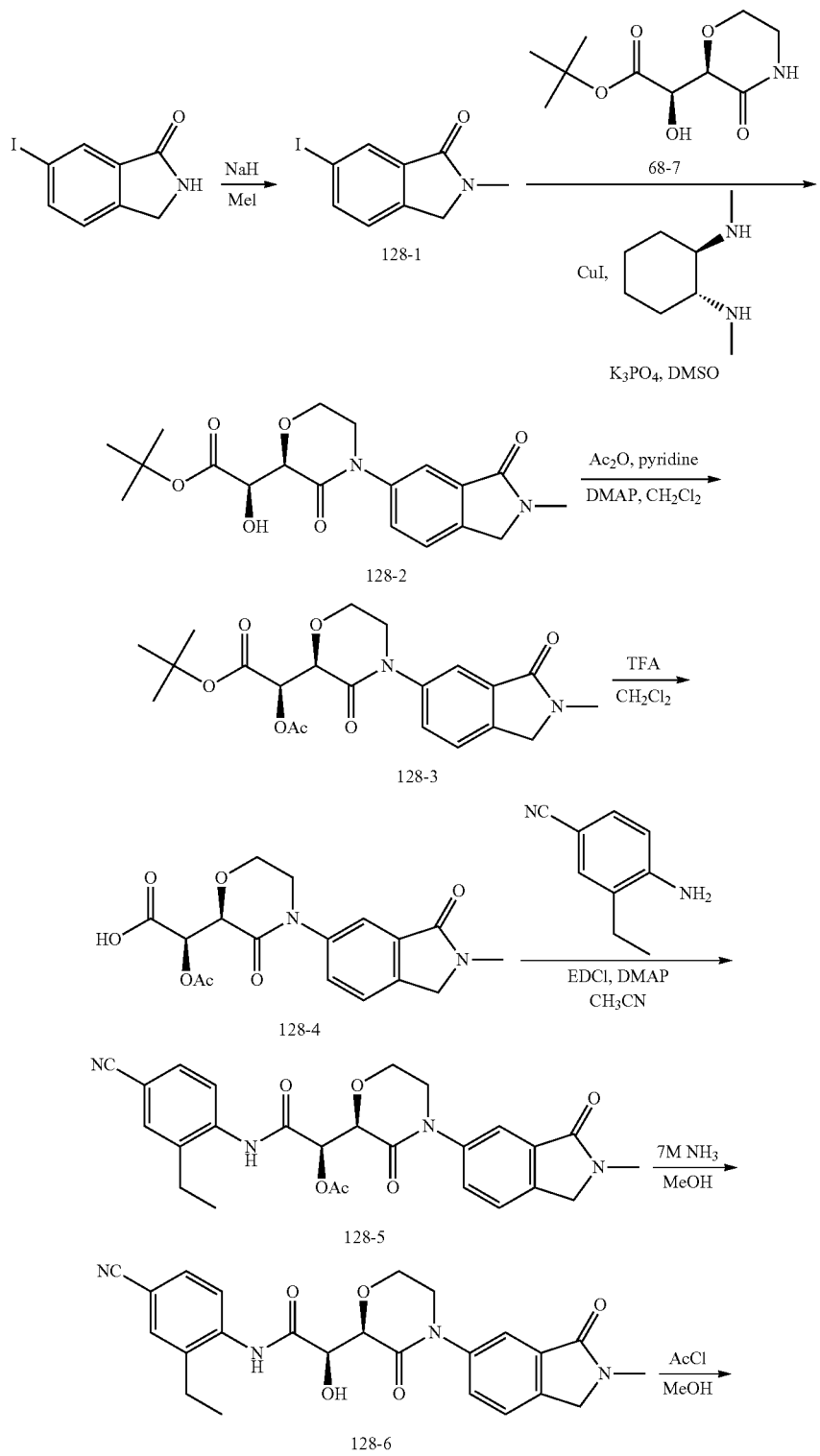

-continued

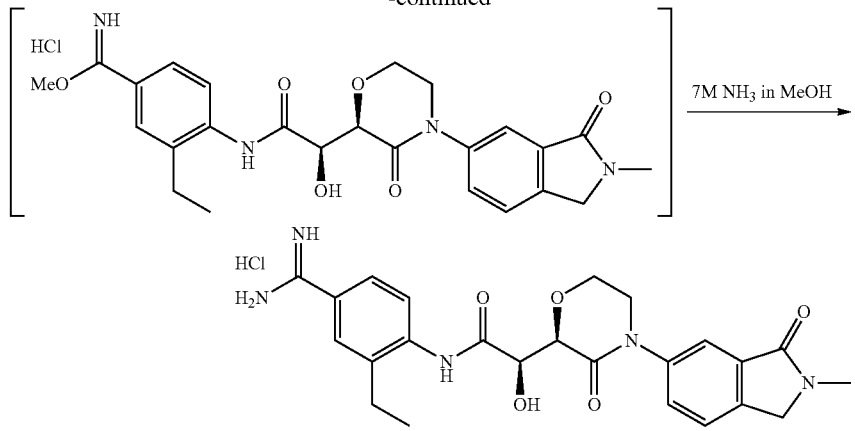

EXAMPLE 128

Step 128-1

Synthesis of 6-Iodo-2-methylisoindolin-1-one (compound 128-1)

To a mixture of 2,3-dihydro-6-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. $NH_4Cl$ (~3 mL) and was diluted with EtOAc (10 mL). The layers were separated and the aqueous layer was extracted with EtOAc. The organic layers were combined and washed sequentially with water and brine. The organic layer was dried ($Na_2SO_4$), filtered, and concentrated under reduced pressure. The crude material was purified The crude product was purified by flash chromatography (ISCO, 120 g) using a gradient of 100% hexanes to 80:20 hexanes/EtOAc to afford 128-1 (0.84 g) as a yellow solid.

Step 128-2

Synthesis of (R)-tert-Butyl 2-hydroxy-2-((R)-4-(2-methyl-3-oxoisoindolin-5-yl)-3-oxomorpholin-2-yl)acetate (compound 128-2)

To a round bottom flask charged with a stir bar was added 68-7 (0.28 g) and 128-1 (0.40 g) in DMSO (8 mL) at rt was added $K_3PO_4$ (0.51 g), and CuI (23 mg) under $N_2$. trans-N,N'-Dimethylcyclohexane-1,2-diamine (37 microL) was added dropwise and the mixture was affixed with a condenser. The mixture was degassed under vacuum (~20 mm), filled with $N_2$, and heated to 80° C. The mixture stirred for 2.5 h at 80° C., cooled to rt, and was diluted with EtOAc. The mixture was then sequentially washed with conc $NH_4OH$, water, and brine. The organic layer was dried ($Na_2SO_4$), filtered, and concentrated under reduced pressure to afford a yellow oil. The crude product was purified by flash chromatography using a gradient of 100% $CH_2Cl_2$ to 60% $CH_2Cl_2$/40% MeOH to afford 128-2 (0.23 g) as a yellow solid.

Step 128-3

Synthesis of (R)-tert-Butyl 2-acetoxy-2-((R)-4-(2-methyl-3-oxoisoindolin-5-yl)-3-oxomorpholin-2-yl)acetate (compound 128-3)

According to the Step 118-2 in the synthetic method for EXAMPLE 118, compound 128-2 (80 mg) was used instead of 118-1 to obtain 128-3 (85 mg) as an off-white solid which was used without further purification.

Step 128-4

Synthesis of (R)-2-Acetoxy-2-((R)-4-(2-methyl-3-oxoisoindolin-5-yl)-3-oxomorpholin-2-yl)acetic acid (compound 128-4)

According to the Step 118-3 in the synthetic method for EXAMPLE 118, compound 128-3 (85 mg) was used instead of 118-2 to obtain 128-4 (65 mg) as a light yellow semisolid solid which was used without further purification.

Step 128-5

Synthesis of (R)-2-(4-Cyano-2-ethylphenylamino)-1-((R)-4-(2-methyl-3-oxoisoindolin-5-yl)-3-oxo morpholin-2-yl)-2-oxoethyl acetate (compound 128-5)

According to the Step 118-4 in the synthetic method for EXAMPLE 118, compound 128-4 (75 mg) was used instead of 118-3 to in the presence of 4-amino-3-ethylbenzonitrile (46 mg) to obtain 128-5 (50 mg) as an off-white solid which was purified by flash chromatography using 20:1 $CH_2Cl_2$/MeOH as eluent.

Step 128-6

Synthesis of (R)—N-(4-Cyano-2-ethylphenyl)-2-hydroxy-2-((R)-4-(2-methyl-3-oxoisoindolin-5-yl)-3-oxomorpholin-2-yl)acetamide (compound 128-6)

According to the Step 118-5 in the synthetic method for EXAMPLE 118, compound 128-5 (50 mg) was used instead of 118-4 to obtain 128-6 (49 mg) as a white solid which was used without further purification.

Step 128-7

Synthesis of (R)—N-(4-Carbamimidoyl-2-ethylphenyl)-2-hydroxy-2-((R)-4-(2-methyl-3-oxoisoindolin-5-yl)-3-oxomorpholin-2-yl)acetamide hydrochloride (EXAMPLE 128)

To a pressure tube charged with 128-6 (45 mg) in MeOH (3 mL) at 0° C. was added AcCl (3 ml) dropwise. The tube was capped, warmed to rt, and stirred for 12 h. The mixture was concentrated to dryness and the pressure tube was charged with the crude mixture in 7M $NH_3$/MeOH (4 mL). The mixture was stirred for 3 days and was concentrated under reduced pressure. The crude mixture was purified by reverse phase HPLC using a C18 column and a gradient of 89.95: 9.95:0.1 $H_2O$:MeCN:$HCO_2H$ to 9.95:89.95:0.1 $H_2O$:MeCN: $HCO_2H$ to afford EXAMPLE 128 (6 mg) as a white solid as the hydrochloride salt after HCl treatment.

Example 129

Synthesis of (R)-2-Hydroxy-N-(2-methyl-1H-indol-5-yl)-2-((R)-3-oxo-4-(3-(3-oxomorpholino)phenyl) morpholin-2-yl)acetamide (EXAMPLE 129)

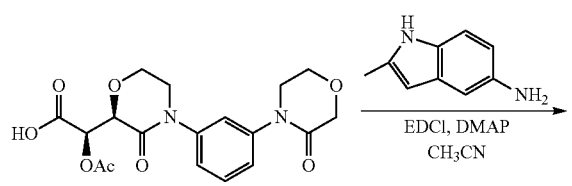

121-5

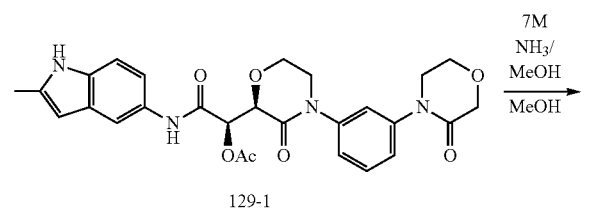

129-1

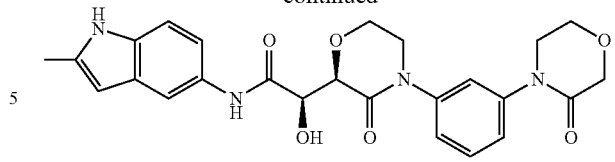

EXAMPLE 129

Step 129-1

Synthesis of (R)-2-(2-Methyl-1H-indol-5-ylamino)-2-oxo-1-((R)-3-oxo-4-(3-(3-oxomorpholino)phenyl) morpholin-2-yl)ethyl acetate (compound 129-1)

According to the Step 118-4 in the synthetic method for EXAMPLE 118, compound 121-5 (70 mg) was treated with 2-methyl-1H-indol-5-amine (34 mg) to obtain 129-1 (73 mg) as a brown solid after flash chromatography purification using a 20:1 mixture of $CH_2Cl_2$/MeOH as eluent.

Step 129-2

Synthesis of (R)-2-Hydroxy-N-(2-methyl-1H-indol-5-yl)-2-((R)-3-oxo-4-(3-(3-oxomorpholino)phenyl) morpholin-2-yl)acetamide (EXAMPLE 129)

According to the Step 118-5 in the synthetic method for EXAMPLE 118, 129-1 (73 mg) was used instead of compound 118-4 to obtain EXAMPLE 129 (62 mg) as a brown solid.

Example 130

Synthesis of (R)—N-(4-Chlorophenethyl)-2-hydroxy-2-((R)-3-oxo-4-(3-(3-oxomorpholino)phenyl) morpholin-2-yl)acetamide (EXAMPLE 130)

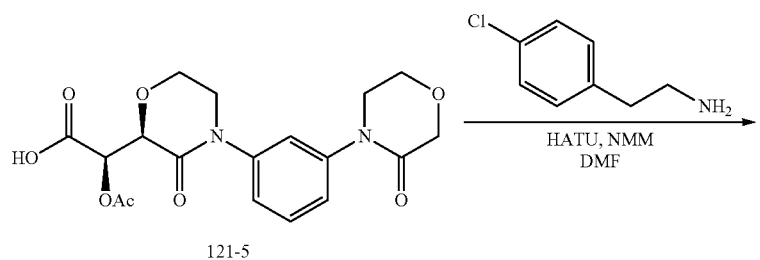

121-5

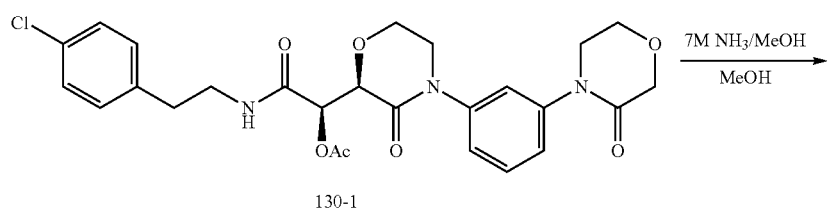

130-1

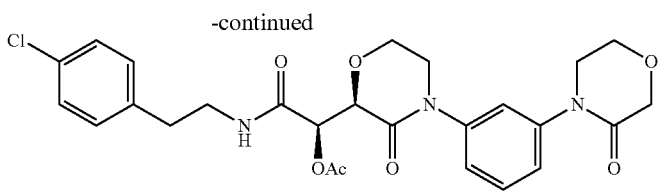

EXAMPLE 130

Step 130-1

Synthesis of (R)-2-(4-Chlorophenethylamino)-2-oxo-1-((R)-3-oxo-4-(3-(3-oxomorpholino)phenyl)morpholin-2-yl)ethyl acetate (compound 130-1)

To a solution of compound 121-5 (70 mg) in DMF (1.5 mL) was added 2-(4-chlorophenyl)ethanamine (32 mg) followed by HATU (88 mg) and NMM (32 mg). The mixture was stirred at rt for 12 h and was loaded directly onto a reverse-phase HPLC using a C18 column and gradient of 89.95:9.95:0.1 H$_2$O:MeCN:HCO$_2$H to 9.95:89.95:0.1 H$_2$O:MeCN:HCO$_2$H to afford 130-1 (50 mg) as a yellow semisolid.

Step 130-2

Synthesis of (R)—N-(4-Chlorophenethyl)-2-hydroxy-2-((R)-3-oxo-4-(3-(3-oxomorpholino)phenyl)morpholin-2-yl)acetamide (EXAMPLE 130)

According to the Step 118-5 in the synthetic method for EXAMPLE 118, 130-1 (73 mg) was used instead of compound 118-4 to obtain EXAMPLE 130 (42 mg) as a pale white solid.

Example 131

Synthesis of (R)—N-(4-carbamimidoylphenyl)-2-hydroxy-2-((R)-4-(2-methoxyphenyl)-3-oxomorpholin-2-yl)acetamide (EXAMPLE 131)

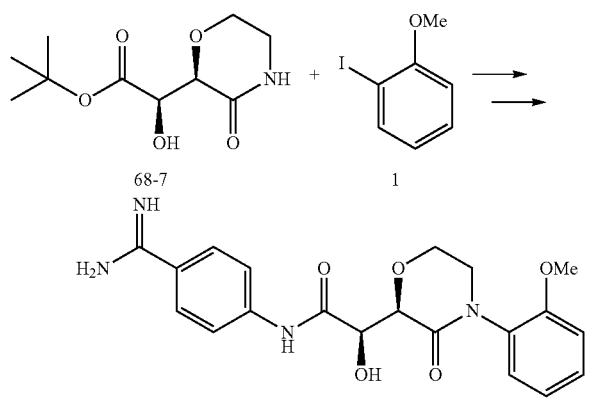

EXAMPLE 131

EXAMPLE 131 was synthesized similarly as for the synthesis of EXAMPLE 96 using 1-iodo-2-methoxybenzene 1.

Example 132

Synthesis of (R)—N-(4-carbamimidoylphenyl)-2-hydroxy-2-((R)-4-(2-fluorophenyl)-3-oxomorpholin-2-yl)acetamide (EXAMPLE 132)

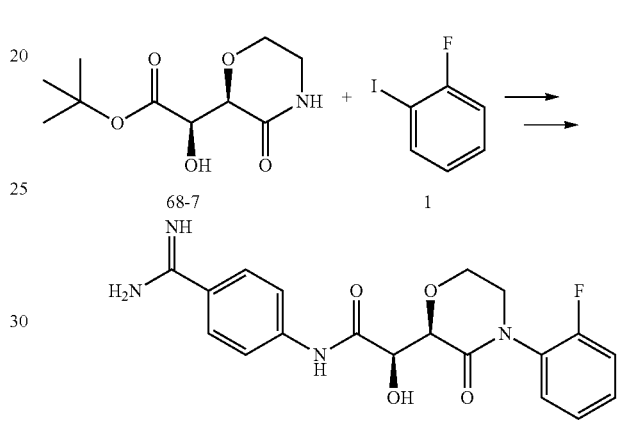

EXAMPLE 132

EXAMPLE 132 was synthesized similarly as for the synthesis of EXAMPLE 96 using 1-iodo-2-fluorobenzene 1.

Synthesis of (R)—N-(4-carbamimidoylphenyl)-2-hydroxy-2-((R)-4-(2-(difluoromethoxy)phenyl)-3-oxomorpholin-2-yl)acetamide (EXAMPLE 133)

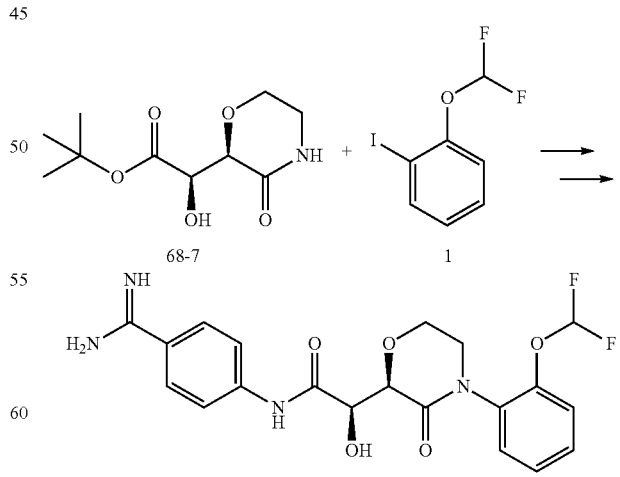

EXAMPLE 133

EXAMPLE 133 was synthesized similarly as for the synthesis of EXAMPLE 96 using 1-iodo-2-(difluoromethoxy)benzene 1.

Synthesis of (R)—N-(6-carbamimidoylpyridin-3-yl)-2-hydroxy-2-((R)-3-oxo-4-(3-(3-oxomorpholino)phenyl)morpholin-2-yl)acetamide (EXAMPLE 134)

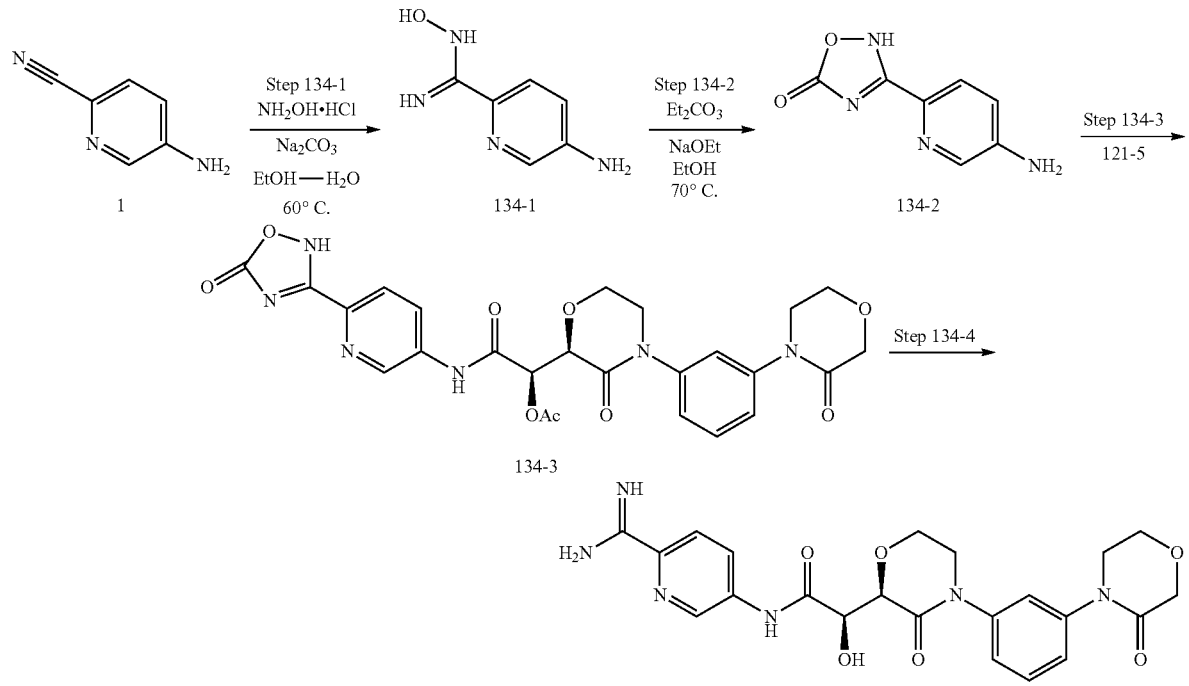

EXAMPLE 134

Step 134-1

Synthesis of 5-amino-N-hydroxypicolinimidamide (Compound 134-1)

To a stirred mixture of 5-aminopicolinonitrile (2.44 g, 20.5 mmol) and $Na_2CO_3$ (2.67 g, 25.2 mmol) in EtOH (10 mL) and $H_2O$ (2 mL) at 60° C. was added a mixture of hydroxylamine hydrochloride (1.85 g, 26.6 mmol) in $H_2O$ (2 mL). The resulting mixture was stirred at 60° C. for 16 h. The mixture was cooled down to room temperature. The solids were filtered, washed with water (5 mL), EtOH (5 mL), and ether (5 mL). The solids were dried in vacuo to give 2.41 g of compound 134-1 which was used in the following step without further purification.

Step 134-2

Synthesis of 3-(5-aminopyridin-2-yl)-1,2,4-oxadiazol-5(2H)-one (Compound 134-2)

To a stirred mixture of compound 134-1 (1.20 g, 7.89 mmol) and $Et_2CO_3$ (1.1 mL, 9.5 mmol) in EtOH (8 mL) at ca 65° C. was added a solution of NaOEt (3.3 mL, 8.8 mmol, 20% in EtOH). The resulting mixture was stirred at 70° C. for 1 h. The mixture was cooled down to room temperature and concentrated. The residue was dissolved in water (5 mL) at 70° C. HCl (concentrated) was added until pH 4. The solids were filtered, washed with water (5 mL), EtOH (5 mL), and ether (5 mL). The solids were dried in vacuo to give 253 mg of Compound 134-2 which was used in the following step without further purification.

Step 134-3

Synthesis of (R)-2-oxo-2-(6-(5-oxo-2,5-dihydro-1,2,4-oxadiazol-3-yl)pyridin-3-ylamino)-1-((R)-3-oxo-4-(3-(3-oxomorpholino)phenyl)morpholin-2-yl)ethyl acetate (Compound 134-3)

Compound 134-3 was synthesized similarly as for the synthesis of Compound 91-4 using Compound 121-5 and Compound 134-2.

Step 134-4

Synthesis of (R)—N-(6-carbamimidoylpyridin-3-yl)-2-hydroxy-2-((R)-3-oxo-4-(3-(3-oxomorpholino)phenyl)morpholin-2-yl)acetamide (EXAMPLE 134)

EXAMPLE 134 was synthesized similarly as for the synthesis of Compound 96, Step 96-2, using Compound 134-3.

Synthesis of N-[4-(aminoiminomethyl)phenyl]-4-[3-(1,1-dioxido-2-isothiazolidinyl)phenyl]-alpha(R)-hydroxy-3-oxo-2(R)-morpholineacetamide (EXAMPLE 135)

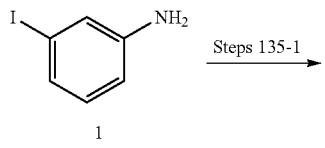

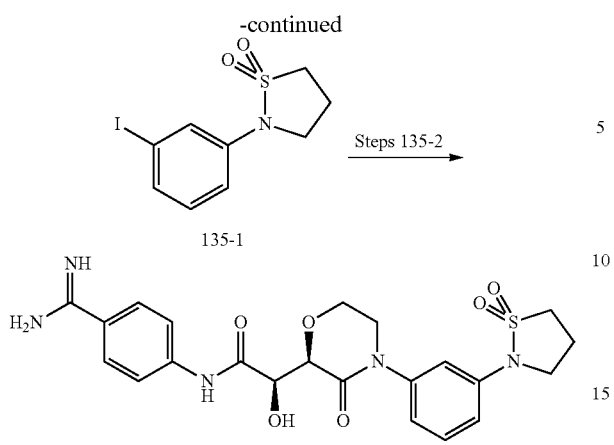

EXAMPLE 135

Step 135-1

Synthesis of Compound 135-1

To a solution of 3-iodoaniline (2 g, 11 mmol) and Et$_3$N (3 mL, 21 mmol) in DCM (20 mL), 3-chloropropane-1-sulfonyl chloride (1.8 mL, 14.8 mmol) was added. The mixture was stirred for 60 h at room temperature, washed with 3M HCl, and evaporated to dryness. The resulting crude mixture was dissolved in DMF (16 mL) and DBU (2 mL, 13.4 mmol) was added. After being stirred for 3 h at room temperature, the reaction mixture was poured into 400 mL of hexane/AcOEt (1/1) and washed with 3M HCl. The organic layer was dried over Na$_2$SO$_4$ and evaporated to dryness. The crude material was purified by silica gel chromatography (Acetone/Hex 0 to 25%) to give Compound 135-1 (2.4 g, 67%).

Step 135-2

N-[4-(aminoiminomethyl)phenyl]-4-[3-(1,1-dioxido-2-isothiazolidinyl)phenyl]-alpha(R)-hydroxy-3-oxo-2(R)-morpholineacetamide (EXAMPLE 135) EXAMPLE 135 was synthesized similarly as for the synthesis of Compound 91, Steps 91-1 to 91-6, using Compound 135-2.

Example 136

Synthesis of (R)—N-(4-carbamimidoylphenyl)-2-((R)-4-(4-fluoro-2-methoxyphenyl)-3-oxomorpholin-2-yl)-2-hydroxyacetamide (EXAMPLE 136)

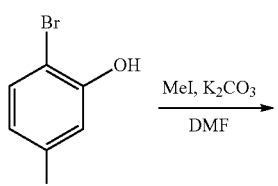

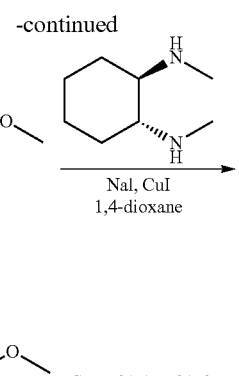

EXAMPLE 136

Step 136-1

Synthesis of Compound 136-1

To a mixture of 2-bromo-5-fluorophenol (2 g, 10.5 mmol) and potassium carbonate (2.9 g, 21 mmol) in DMF (10 mL), iodomethane (2.27 g, 16 mmol) was added. The mixture was heated to 55° C. and stirred for 16 h. The reaction mixture was cooled to room temperature and diluted with diethyl ether. The organics were washed with saturated aqueous ammonium chloride, water, dried with Na$_2$SO$_4$, and evaporated to dryness. The crude material was purified by silica gel chromatography (diethyl ether/Hex 0 to 2%) to give Compound 136-1 (1.2 g, 55%).

Step 136-2

Synthesis of Compound 136-2

To a nitrogen purged vessel, a solution of compound 136-1 (0.5 g, 2.4 mmol) in 1,4-dioxane (3 mL), sodium iodide (0.72 g, 4.8 mmol), copper iodide (0.023 g, 0.12 mmol), and trans-N,N'-dimethylcyclohexane-1,2-diamine (0.034 g, 0.24 mmol) were added. The vessel was sealed and heated to 115° C. for 65 hours. The reaction mixture was cooled to room temperature, washed with aqueous saturated ammonia chloride, and extracted with ethyl acetate. The organics were dried with Na$_2$SO$_4$ and evaporated to dryness to give Compound 136-2 (0.55 g, 91%) which was used without further purification in the next step.

Step 136-3

Synthesis of EXAMPLE 136

EXAMPLE 136 was synthesized similarly as for the synthesis of Compound 91, Steps 91-1 to 91-6, using Compound 136-2.

Example 137

Synthesis of (R)—N-(4-carbamimidoylphenyl)-2-hydroxy-2-((R)-4-(2-isopropoxyphenyl)-3-oxomorpholin-2-yl)acetamide (EXAMPLE 137)

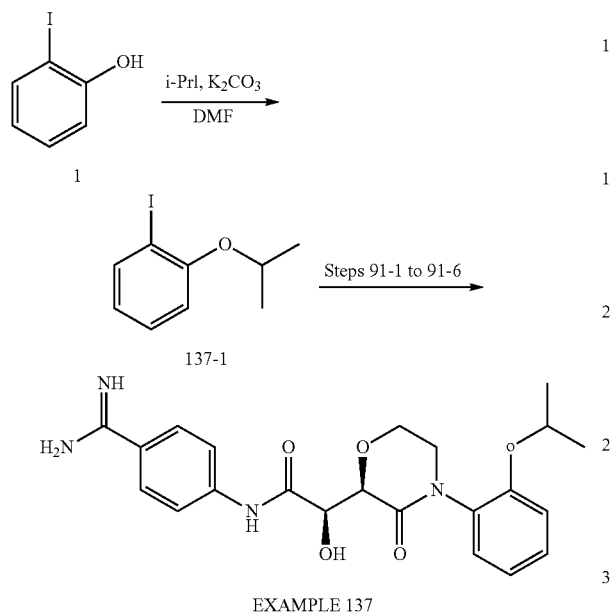

Step 137-1

Synthesis of Compound 137-1

Compound 137-1 was synthesized similarly as for the synthesis of EXAMPLE 136, Step 136-1, using 2-iodophenol and 2-iodopropane.

Step 137-2

Synthesis of EXAMPLE 137

EXAMPLE 137 was synthesized similarly as for the synthesis of Compound 91, Steps 91-1 to 91-6, using Compound 137-1.

Example 138

Synthesis of (R)-2-((R)-4-(2-(2-amino-2-oxoethoxy)phenyl)-3-oxomorpholin-2-yl)-N-(4-carbamimidoylphenyl)-2-hydroxyacetamide (EXAMPLE 138)

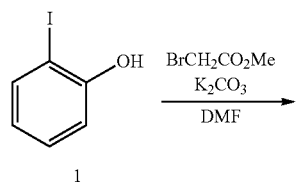

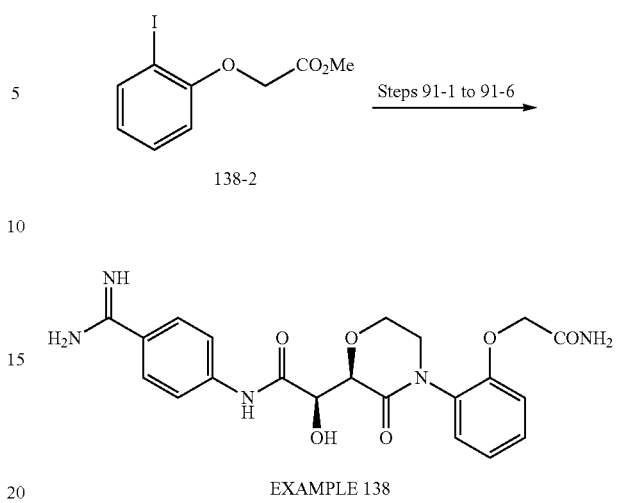

Step 138-1

Synthesis of Compound 138-2

Compound 138-2 was synthesized similarly as for the synthesis of EXAMPLE 136, Step 136-1, using 2-iodophenol and methyl 2-bromoacetate.

Step 138-2

Synthesis of EXAMPLE 138

EXAMPLE 138 was synthesized similarly as for the synthesis of Compound 91, Steps 91-1 to 91-6, using Compound 138-2.

Example 139

Synthesis of (R)—N-(4-carbamimidoyl-3-fluorophenyl)-2-hydroxy-2-((R)-3-oxo-4-(3-(3-oxomorpholino)phenyl)morpholin-2-yl)acetamide (EXAMPLE 139)

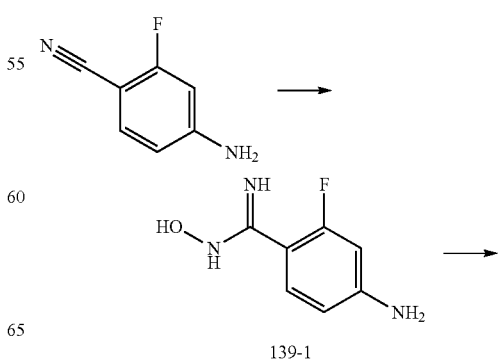

-continued

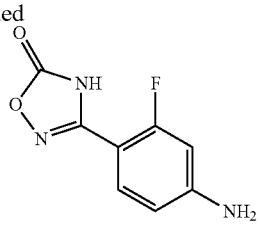
139-2

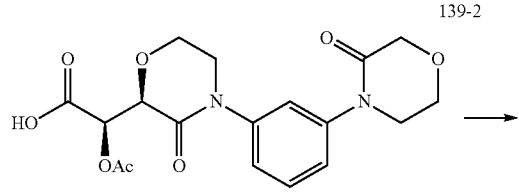
121-5

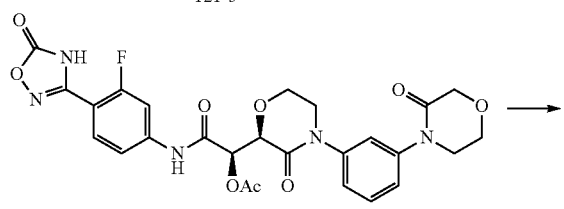
139-3

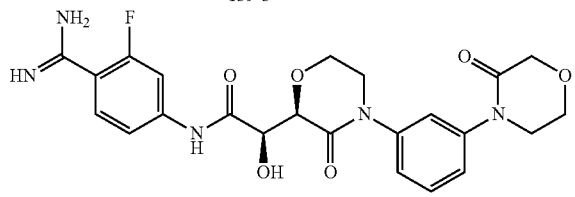
Example 139

Step 139-1

4-amino-2-fluoro-N-hydroxybenzimidamide (compound 139-1)

4-cyano-3-fluoroaniline (10 g, 0.0735 mol) was dissolved in EtOH (36.7 ml) and water (7.3 ml), Na$_2$CO$_3$ (5.06 g, 0.65 eq) was added. The mixture was heated at 60° C. and a solution of NH$_2$OH.HCl (5.615 g, 1.1 eq) in water (7.3 ml) was added slowly, the mixture was heated at 60° C. overnight. The mixture was cooled to 0° C., and the solid collected by filtration. Washed with water (7 ml), EtOH (7 ml), Et$_2$O (20 ml) and dried to give 7.5 g of compound 139-1.

Step 139-2

3-(4-amino-2-fluorophenyl)-1,2,4-oxadiazol-5(4H)-one (compound 139-2)

Compound 139-1 was suspended in EtOH (26 ml), diethyl carbonate (5.344 ml, 1 eq) was added and the mixture heated at 65° C. NaOEt (16.5 g of a 21% solution in EtOH, 1.15 eq) added slowly and the mixture heated at 70° C. for 2 hours. Cooled, concentrated and taken up in water (25 ml) at 70° C., HCl(conc) was added to PH2, and the mixture cooled to 0° C. The solid was collected by filtration and washed with water (20 ml), EtOH (7 ml), and ether (20 ml) to give 6.4 g of compound 139-2.

Step 139-3

R)-2-(3-fluoro-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl)ethyl acetate (compound 139-3

121-5 (1.17 g, 0.00298 mol) and 139-2 (0.698 g, 1.2 eq) dissolved in MeCN (3.98 ml), and cooled to 0° C., EDCI.HCl (0.686 g, 1.2 eq) and DMAP (36 mg, 10%) were added and the mixture stirred overnight. The mixture was diluted with EtOAc, washed with NH$_4$Cl$_{(sat)}$, dried, concentrated, silica gel chromatography (0-5% MeOH in CH$_2$Cl$_2$) gave 1.1 g of 139-3

Step 139-4

R)—N-(4-carbamimidoyl-3-fluorophenyl)-2-hydroxy-2-((R)-3-oxo-4-(3-(3-oxomorpholino)phenyl)morpholin-2-yl)acetamide (EXAMPLE 139

139-3 (0.1 g, 0.000176 mol) dissolved in 5.85 ml MeOH/1 N HCl in ether (4:1), Pd(C) (35 mg) added, placed under H$_2$ 1 atm. Stirred for 4 hours, the catalyst was removed by filtration, and the filtrate concentrated. The resulting solid was dissolved in MeOH (5 ml), 7 N NH$_3$ in MeOH (0.176, 7 eq) was added and the mixture stirred for 1 hour. After cooling to rt the mixture was concentrated and then taken up in MeOH (5 ml), 1N HCl added, then the solution concentrated. Trituration with MeOH/Ether followed by filtration gave 76 mg of EXAMPLE 139 as an HCl salt.

Example 140

R)—N-(4-carbamimidoyl-3,5-difluorophenyl)-2-hydroxy-2-((R)-3-oxo-4-(3-(3-oxomorpholino)phenyl)morpholin-2-yl)acetamide (EXAMPLE 140

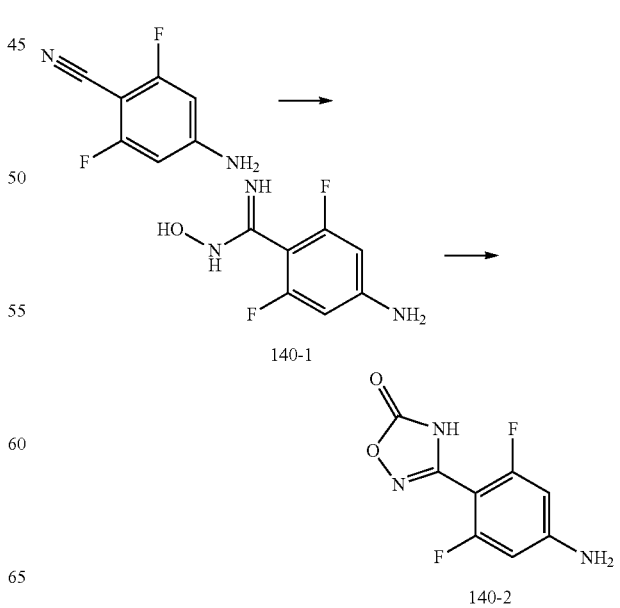
140-1

140-2

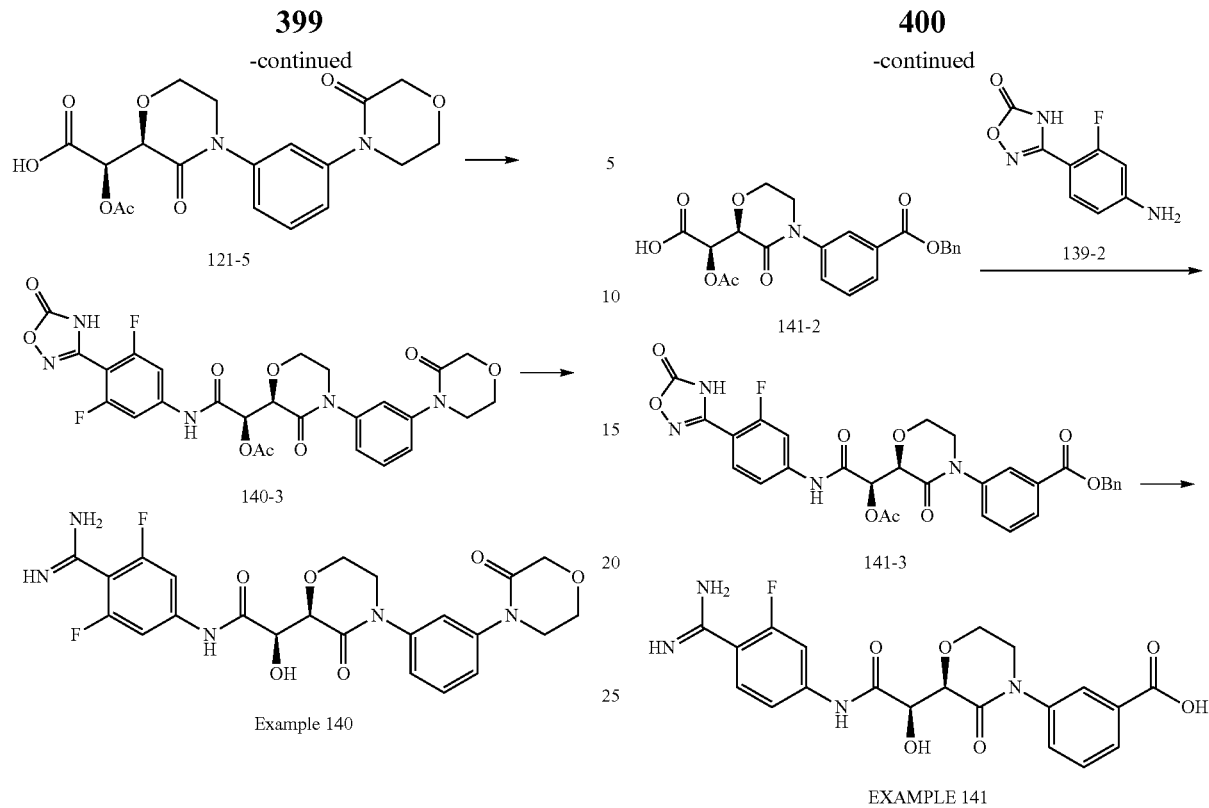

Step 140-1, Step 140-2

3-(4-amino-2,6-difluorophenyl)-1,2,4-oxadiazol-5(4H)-one (140-2)

Compound 140-2 was synthesized in the manner described for 139-2 as shown in the scheme above from 4-amino-2,6-difluorobenzonitrile (*J. Chem. Res.* 1998, p 144-145)

Step 140-3, Step 140-4

R)—N-(4-carbamimidoyl-3,5-difluorophenyl)-2-hydroxy-2-((R)-3-oxo-4-(3-(3-oxomorpholino)phenyl)morpholin-2-yl)acetamide (EXAMPLE 140

Example 140 was synthesized in the manner described for Example 139 as shown in the scheme above from 140-2 and 121-5.

Example 141

3-((R)-2-((R)-2-(4-carbamimidoyl-3-fluorophenylamino)-1-hydroxy-2-oxoethyl)-3-oxo morpholino)benzoic acid (EXAMPLE 141)

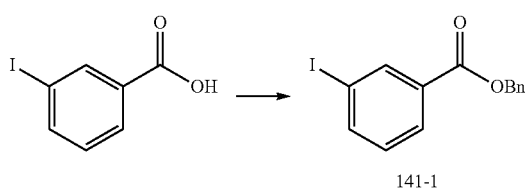

Step 141-1 benzyl 3-iodobenzoate (compound 141-1)

3-iodobenzoic acid (1 g, 0.004032 mol) was dissolved in acetonitrile (20 ml), $Cs_2CO_3$ (2.63 g, 2 eq) and benzyl bromide (0.528 ml, 1.1 eq) were added. The mixture was heated at reflux overnight. Cooled to rt and concentrated. The residue was taken up in EtOAc, washed with water, dried ($MgSO_4$) and concentrated. Silica gel chromatography (0-20% EtOAc in hexane) gave 1 g of 141-1.

Step 141-2

R)-2-acetoxy-2-((R)-4-(3-(benzyloxycarbonyl)phenyl)-3-oxomorpholin-2-yl)acetic acid (compound 141-2

141-2 was synthesized in a similar manner to 121-5 starting with 141-1

Step 141-3 benzyl 3-((R)-2-((R)-1-acetoxy-2-(3-fluoro-4-(5-oxo-4,5-dihydro-1,2,4-oxadiazol-3-yl)phenyl amino)-2-oxoethyl)-3-oxomorpholino)benzoate (compound 141-3)

141-2 (1.15 g, 0.0027 mol) and 139-2 (0.63 g, 1.2 eq) dissolved in MeCN (3.6 ml), and cooled to 0° C., EDCI.HCl (0.619 g, 1.2 eq) and DMAP (33 mg, 10%) were added and the mixture stirred overnight. The mixture was diluted with EtOAc, washed with $NH_4Cl_{(sat)}$, dried, concentrated, silica gel chromatography (0-100% EtOAc in hexane) gave 1.2 g of 141-3.

Step 141-4

3-((R)-2-((R)-2-(4-carbamimidoyl-3-fluorophenylamino)-1-hydroxy-2-oxoethyl)-3-oxo morpholino)benzoic acid (EXAMPLE 141)

141-3 (0.2 g, 0.00033 mol) was dissolved in MeOH (5.5 ml), 7N NH3 in MeOH (0.284, 6 eq) was added, stirred for 1 hour. The mixture was concentrated and taken up in MeOH (5 ml). 1 M HCl in ether (0.662, 2 eq) was then added. Pd(C) (100 mg) was added and the mixture put under H2 (1 atm) for 1 hour. The catalyst was removed by filtration and the solution concentrated. Trituration with ether/MeOH followed by filtration gave 143 mg of Example 141 as an HCl salt.

Example 142

Synthesis of N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide hydrochloride (EXAMPLE 142)

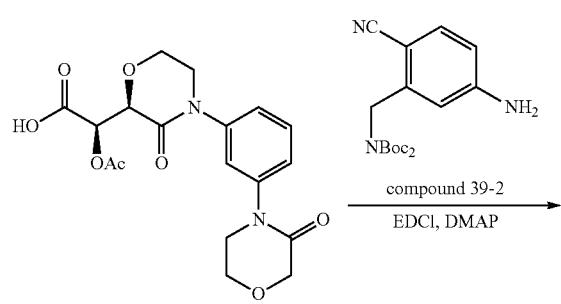

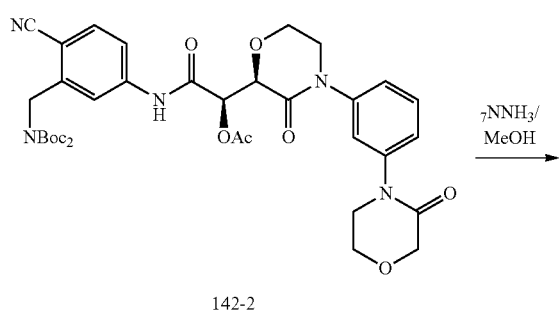

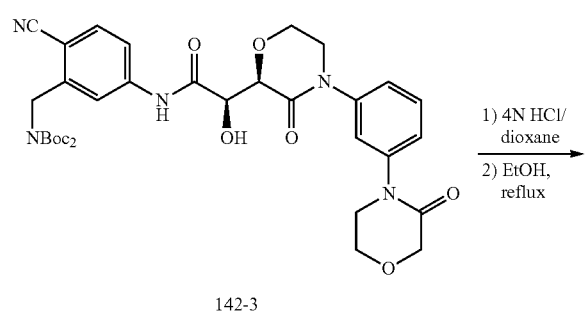

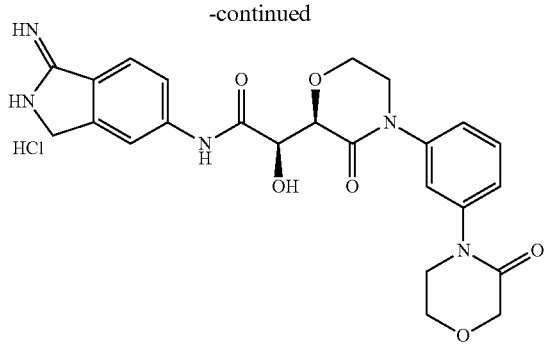

142

Step 142-1

Synthesis of (R)-2-(3-((bis(tert-butoxycarbonyl)amino)methyl)-4-cyanophenylamino)-2-oxo-1-((R)-3-oxo-4-(3-(3-oxomorpholino)phenyl)morpholin-2-yl)ethyl acetate (compound 142-2)

To a solution of 121-5 (3.0 g, 7.65 mmol), compound 39-2 (2.7 g, 7.78 mmol, 1 eq.) and DMAP (95 mg, 0.78 mmol, 0.1 eq) in 30 ml of dichloromethane at 0° C. was added EDCI (1.9 g, 9.91 mmol, 1.3 eq) and the mixture was stirred at 0° C. for 2 hr. It was diluted with ethyl acetate, washed twice with 1N HCl then with brine. The solution was dried over anhydrous MgSO4, filtered and concentrated. The resultant residue was purified by chromatography eluting with 5% methanol in dichloromethane to provide 3.5 g of 142-2.

Step 142-2

Synthesis of (compound 142-3)

A solution of 142-2 (5.2 g, 7.20 mmol) in 50 ml of a solution of 7N NH3 in methanol was stirred at rt for 30 min. and evaporated to dryness. The residue was purified by column chromatography eluting with 5% methanol in dichloromethane to provide 4.87 g of 142-3. (>theoretical weight due to the presence of solvent).

Step 142-3

Synthesis of N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide hydrochloride (EXAMPLE 142)

To a flask containing 142-3 (4.7 g, 6.92 mmol) was added 50 ml of a 4 N solution of HCl in dioxane and the resultant slurry was stirred at rt for 1 hr. It was concentrated to dryness and co-evaporated twice with anhydrous toluene. The above solid was taken in 100 ml of ethanol to give a clear solution which was heated at reflux for 10 hr to give a thick slurry. The solvent was evaporated to dryness and the solid was taken in minimum methanol to give a thick paste. To this was added anhydrous ether while being stirred vigorously. The solid was filtered off, washed with ether and dried in a vacuum oven to provide 3.05 of Example 142 as the HCl salt.

Example 143

4-(3-Cyanophenyl)-N-(2,3-dihydro-1-imino-1H-isoindol-5-yl)-alpha(R)-hydroxy-3-oxo-2(R)-morpholineacetamide (EXAMPLE 143)

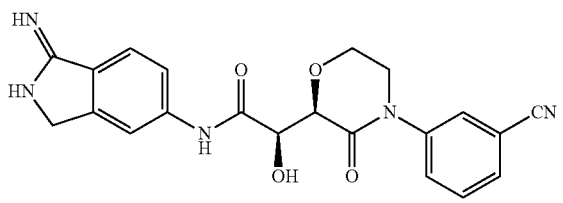 [SMILES: N#Cc1cccc(N2CCO[C@H]([C@@H](O)C(=O)Nc3ccc4c(c3)CNC4=N)C2=O)c1]

Example 143 was prepared using a procedure similar the preparation of EXAMPLE 142.

Example 144

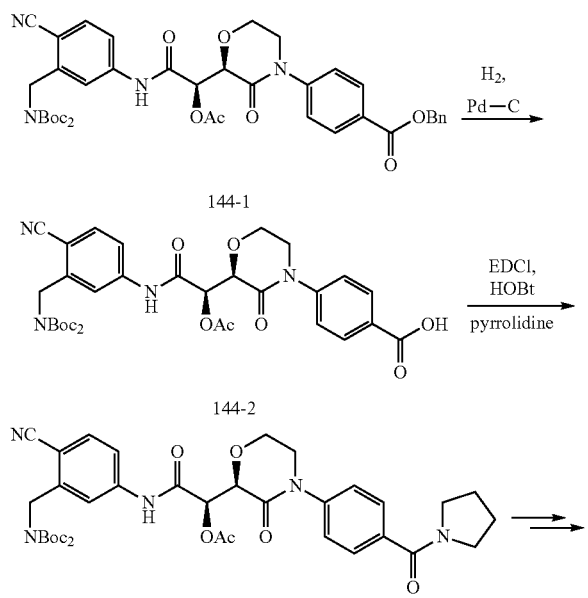

Step 144-1

Synthesis of Benzyl 3-((R)-2-((R)-1-acetoxy-2-(3-((bis(tert-butoxycarbonyl)amino)methyl)-4-cyanophenylamino)-2-oxoethyl)-3-oxomorpholino)benzoate (compound 144-1)

Compound 144-1 was prepared using a procedure similar to the preparation of compound 142-2.

Step 144-2

Synthesis of 3-((R)-2-((R)-1-Acetoxy-2-(3-((bis(tert-butoxycarbonyl)amino)methyl)-4-cyanophenyl amino)-2-oxoethyl)-3-oxomorpholino)benzoic acid (compound 144-2)

To a solution of 144-1 (440 mg, 0.872 mmol) in 10 ml ethyl acetate was added 10% Pd—C (80 mg) and the suspension stirred under hydrogen balloon for 2.5 hr, filtered through a CELITE pad to remove the catalyst and the solvent evaporated to dryness to provide 370 mg of 144-2.

Step 144-3

Synthesis of (R)-2-(3-((Bis(tert-butoxycarbonyl)amino)methyl)-4-cyanophenylamino)-2-oxo-1-((R)-3-oxo-4-(3-(pyrrolidine-1-carbonyl)phenyl)morpholin-2-yl)ethyl acetate (compound 144-3)

To a solution of 144-2 (180 mg, 0.27 mmol), pyrrolidine (45 ul, 0.54 mmol, 2 eq.) and hydroxybenzotriazole hydrate (62 mg, 0.41 mmol, 1.5 q) in 3 ml acetonitrile at rt was added EDCI (78 mg, 0.41 mmol, 1.5 eq.) and the mixture stirred overnight at rt. It was diluted with ethyl acetate and washed twice with 1N HCl and brine. The solution was dried over $MgSO_4$, filtered, concentrated and purified by chromatography eluting with 5% methanol in dichloromethane to provide 160 mg of 144-3.

Step 144-4

Synthesis of N-(2,3-Dihydro-1-imino-1H-isoindol-5-yl)-alpha(R)-hydroxy-3-oxo-4-[4-(1-pyrrolidin ylcarbonyl)phenyl]-2(R)-morpholineacetamide (EXAMPLE 144)

Compound 144-3 was converted to EXAMPLE 144 using a procedure similar to the conversion of compound 142-2 to EXAMPLE 142 Using procedures similar to the preparation of EXAMPLE 144, the following examples were prepared:

| Example | Structure | Name |
|---|---|---|
| 145 | 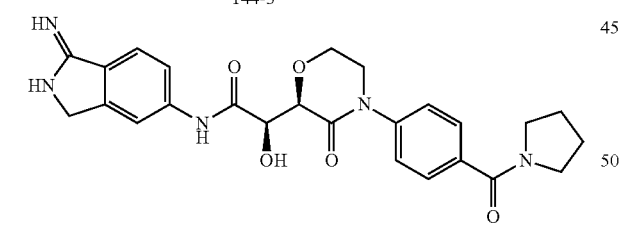 | N-(2,3-Dihydro-1-imino-1H-isoindol-5-yl)-4-[3-[(dimethylamino)carbonyl]phenyl]-alpha(R)-hydroxy-3-oxo-2(R)-morpholineacetamide |

| Example | Structure | Name |
|---|---|---|
| 146 | 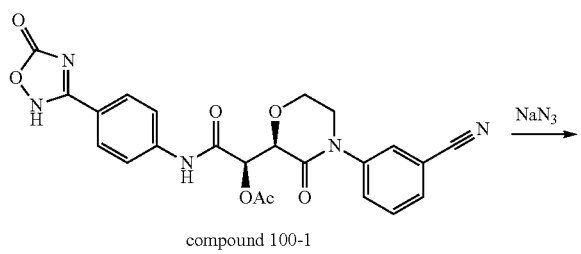 | n-(2,3-Dihydro-1-imino-1H-isoindol-5-yl)-alpha(R)-hydroxy-3-oxo-4-[3-(1-pyrrolidinylcarbonyl)phenyl]-2(R)-morpholineacetamide |
| 147 | 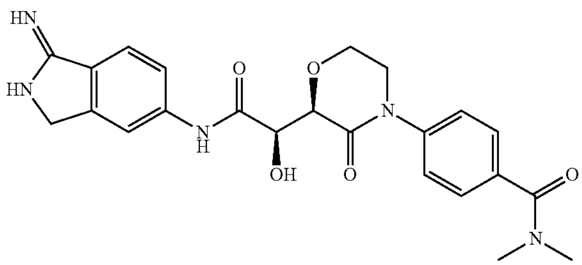 [SMILES: CN(C)C(=O)c1ccc(N2CCO[C@H]([C@@H](O)C(=O)Nc3ccc4c(c3)CNC4=N)C2=O)cc1] | N-(2,3-Dihydro-1-imino-1H-isoindol-5-yl)-4-[4-[(dimethylamino)carbonyl]phenyl]-alpha(R)-hydroxy-3-oxo-2(R)-morpholineacetamide |

Example 148

Synthesis of N-[4-(Aminoiminomethyl)phenyl]-alpha(R)-hydroxy-3-oxo-4-[3-(1h-tetrazol-5-yl)phenyl]-2(R)-morpholineacetamide (EXAMPLE 148)

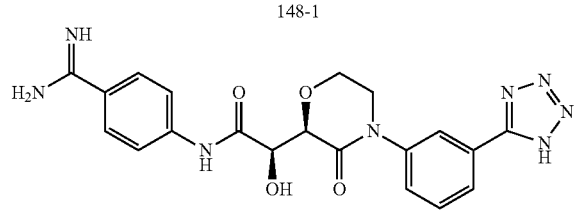

Step 148-1

Synthesis of (R)-2-((R)-4-(3-(1H-Tetrazol-5-yl)phenyl)-3-oxomorpholin-2-yl)-2-hydroxy-N-(4-(5-oxo-2,5-dihydro-1,2,4-oxadiazol-3-yl)phenyl)acetamide (compound 148-1)

To 50 mg of compound 100-1 in 2 mL of dry DMF was added 68 mg (10 eq.) of sodium azide and 56 mg (10 eq.) of ammonium chloride and the mixture heated to 115° C. in a pressure tube for about 16 hours. The reaction mixture was poured onto 1N aq. HCl and extracted three times with ethyl acetate. The combined extracts were washed with brine, dried with magnesium sulfate, filtered and evaporated to dryness yielding about 20 mg of 148-1.

Step 148-2

Synthesis of N-[4-(Aminoiminomethyl)phenyl]-alpha(R)-hydroxy-3-oxo-4-[3-(1h-tetrazol-5-yl)phenyl]-2(R)-morpholineacetamide (example 148)

To about 50 mg of 148-1 in 5 mL of methanol and 3 mL of 1N aq. HCl was added 20 mg of 10% palladium on carbon and the mixture stirred under a balloon of hydrogen gas for two hours. The mixture was filtered and evaporated to dryness. Purification by reversed phase HPLC yielded 18 mg of Example 148.

Example 149

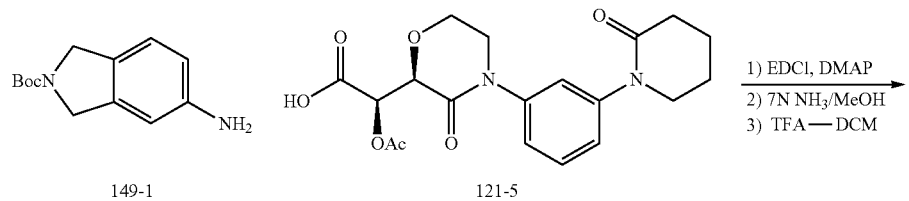

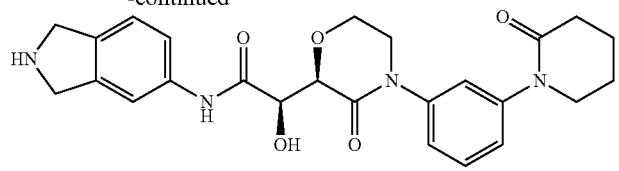

149

Step 149-1

Synthesis of N-(2,3-dihydro-1H-isoindol-5-yl)-alpha (R)-hydroxy-3-oxo-4-[3-(3-oxo-4-morpholinyl)phenyl]-2(R)-morpholineacetamide (EXAMPLE 149)

To 100 mg of 121-5 in about 5 mL of acetonitrile at 0° C. was added 66 mg (1.5 eq.) of 149-1 (WO2005059107(A2, A3)), 64 mg (1.3 eq.) of EDCI and 3 mg (10% mole) of DMAP and the mixture stirred under a balloon of argon for two hours. The reaction mixture was poured onto water and extracted three times with ethyl acetate. The combined extracts were washed with brine, dried with magnesium sulfate, filtered and evaporated to dryness. Purification by flash chromatography yielded 121 mg of amide.

To this was added about 5 mL of 7M ammonia in methanol and the mixture stirred in a flask sealed with a septa for two hours. The reaction mixture was evaporated to dryness and the residue was dissolved in 5 mL of dry DCM. The solution was cooled to 0° C. then 5 mL of trifluoroacetic acid was added and the mixture stirred under a balloon of argon for two hours. The reaction mixture was evaporated to dryness and the residue dissolved in DCM and precipitated from 1N HCl in diethyl ether yielding 71 mg of Example 149 after drying in a vacuum oven.

Example 150

Synthesis of [4-[2(R)-[2-[[4-(Aminoiminomethyl)phenyl]amino]-1(R)-hydroxy-2-oxoethyl]-3-oxo-4-morpholinyl]phenyl]pentafluorosulfur (EXAMPLE 150)

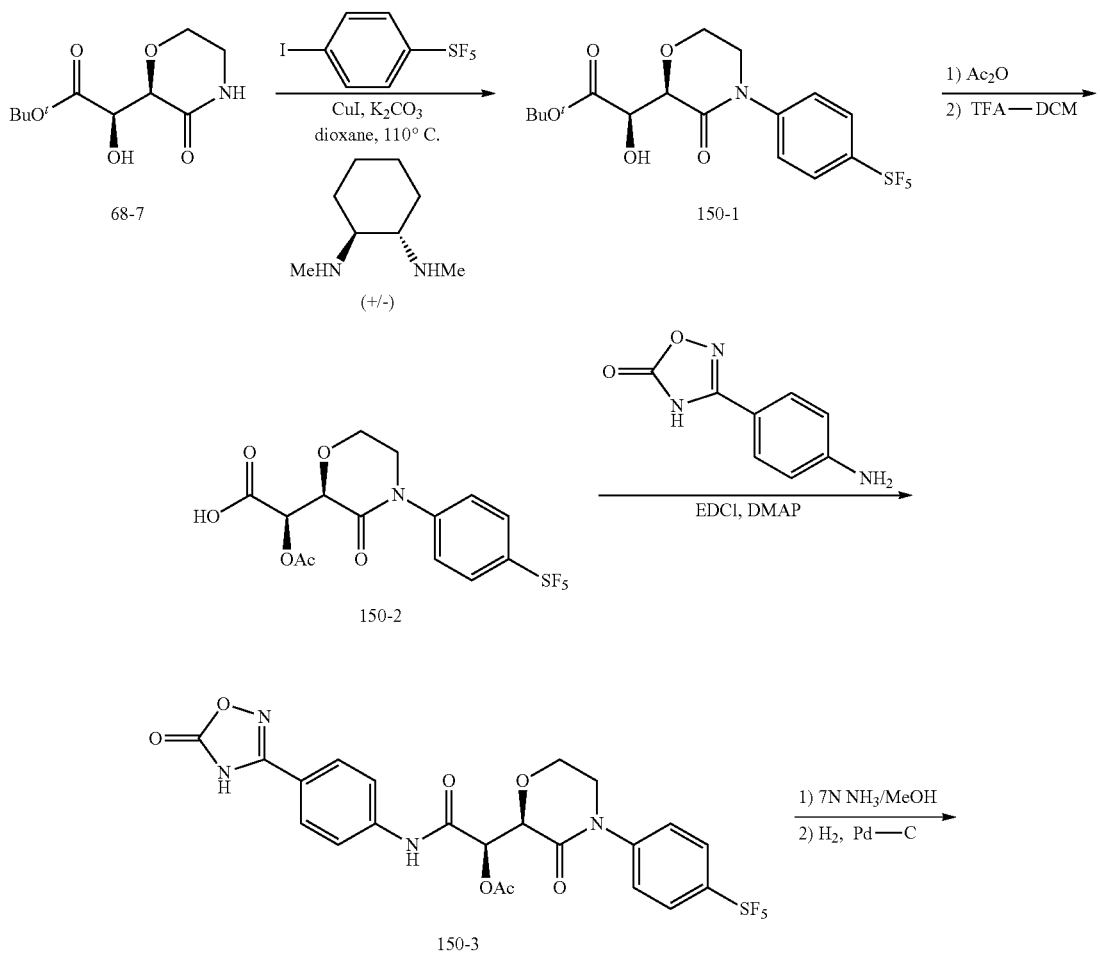

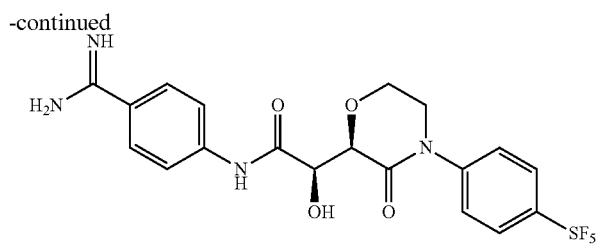

Example 150

Step 150-1

(R)-tert-Butyl 2-((R)-4-((4-pentafluorosulfur)phenyl)-3-oxomorpholin-2-yl)-2-hydroxyacetate (compound 150-1)

To a mixture of (R)-tert-butyl 2-hydroxy-2-((R)-3-oxomorpholin-2-yl)acetate (1.0 g, 4.32 mmol), pentafluoro-(4-iodophenyl)-sulfur (6.36 mmol, 1.5 eq.), powdered potassium carbonate (1.2 g, 8.68 mmol, 2 eq.) in 30 ml dioxane was added copper(I) iodide (83 mg, 0.436 mmol, 0.1 eq.) followed by trans-N,N'-dimethylcyclohexane-1,2-diamine (140 microl, 0.886 mmol, 0.2 eq.). The mixture was degassed by bubbling with argon and heated in a sealed tube 110° C. for about 10 hr. It was filtered through a CELITE pad, rinsed with ethyl acetate, concentrated and purified by chromatography eluting with a mixture of ethyl acetate-dichloromethane-hexane (1:1:3 v/v/v) to provide 1.20 g of 150-1

Step 150-2

Synthesis of (R)-2-Acetoxy-2-((R)-4-((4-pentafluorosulfur)phenyl)-3-oxomorpholin-2-yl)acetic acid (compound 150-2)

To a solution of 150-1 (420 mg, 0.97 mmol), DMAP (12 mg, 0.098 mmol, 0.1 eq.) and pyridine (160 microl, 1.98 mmol, 2 eq.) in 10 ml dichloromethane at 0° C. was added acetic anhydride (185 microl, 1.96 mmol, 2 eq.). The mixture was stirred for 2.5 hr, diluted with ethyl acetate, washed with aqueous copper sulfate, water and brine, dried over MgSO$_4$, filtered and concentrated to provide 480 mg of the acylated product. The above product was stirred with 5 ml each of dichloromethane and trifluoroacetic acid at rt for 1 hr, added toluene and concentrated to dryness. It was evaporated once more time from toluene then twice from ether to provide 460 mg (>theoretical yield due to the presence of some solvent) of 150-2.

Step 150-3

Synthesis of (R)-1-((R)-4-((4-pentafluorosulfur)phenyl)-3-oxomorpholin-2-yl)-2-oxo-2-(4-(5-oxo-4,5-dihydro-1,2,4-oxadiazol-3-yl)phenylamino)ethyl acetate (compound 150-3)

To solution of 150-2 (250 mg, 0.596 mmol), 3-(4-aminophenyl)-1,2,4-oxadiazol-5(4H)-one (160 mg, 0.903 mmol, 1.5 eq.), DMAP (7.3 mg, 0.050 mmol, 0.1 eq.) in 5 ml acetonitrile at 0° C. was added EDCI (150 mg 0.782 mmol, 1.3 eq.) and stirred for 2.5 hr. It was diluted with ethyl acetate, washed with aq. NaHCO$_3$, water, and brine, dried over MgSO$_4$, filtered, concentrated and purified by chromatography eluting with 5% methanol in dichloromethane to provide 225 mg of 150-3.

Step 150-4

Synthesis of [4-[2(R)-[2-[[4-(Aminoiminomethyl)phenyl]amino]-1(R)-hydroxy-2-oxoethyl]-3-oxo-4-morpholinyl]phenyl]pentafluorosulfur (EXAMPLE 150)

A solution of 150-3 (225 mg) in 10 ml of a 7N ammonia in methanol was stirred at rt for 1 hr and concentrated to dryness. To this was added 210 mg of 10% Pd—C, 6 ml each of methanol and 1N hydrochloric acid. The suspension was stirred under a hydrogen balloon for 2 hr, filtered through a CELITE pad, concentrated and purified by RPHPLC to provide 130 mg of EXAMPLE 150 as the hydrochloride salt.

Example 151

Synthesis of [3-[2(R)-[2-[[4-(Aminoiminomethyl)phenyl]amino]-1(R)-hydroxy-2-oxoethyl]-3-oxo-4-morpholinyl]phenyl]pentafluorosulfur (EXAMPLE 151)

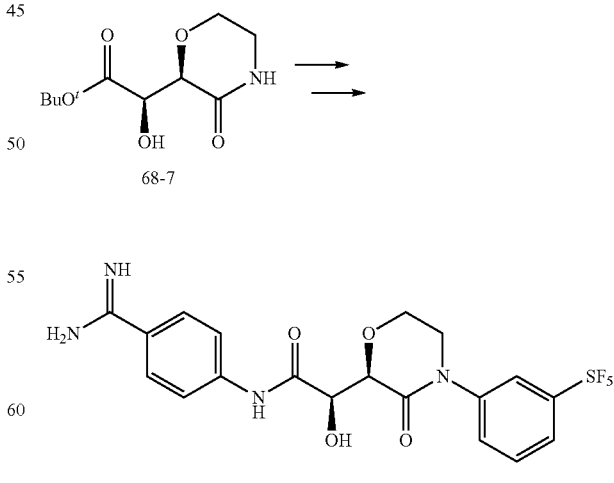

151

EXAMPLE 151 was prepared using a procedure similar to the preparation of EXAMPLE 150.

Example 152
Synthesis of (2R)—N-(4-amidinophenyl)-2-hydroxy-2-[(2R)-3-oxo-4-(4-(1,1-dioxothiomorpholin-4-ylcarbonyl)phenyl)morpholin-2-yl]acetamide (EXAMPLE 152)
Synthesis of 4-[(4-iodophenyl)carbonyl]thiomorpholine-1,1-dione 152-1
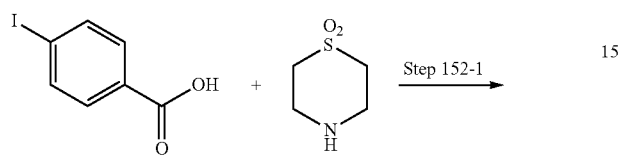
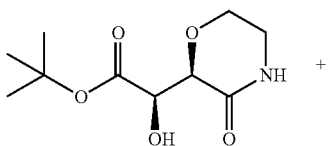
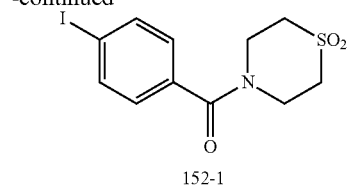
Step 152-1
According to Step 77-1 in the synthetic method for compound 77, 4-iodobenzoic acid and thiomorpholine-1,1-dione were used to obtain compound 152-1.
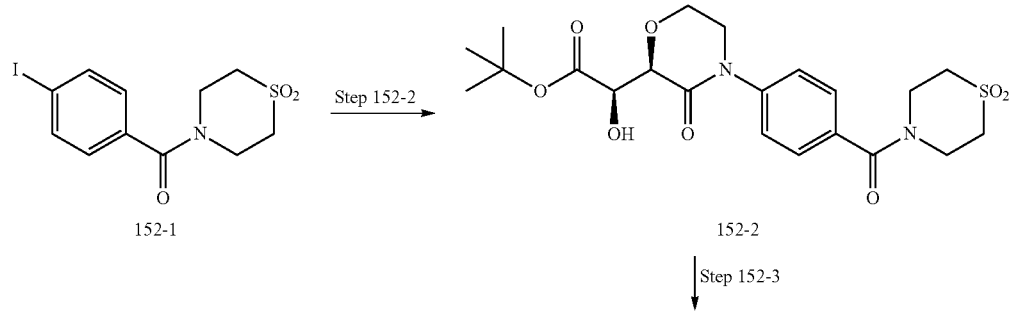
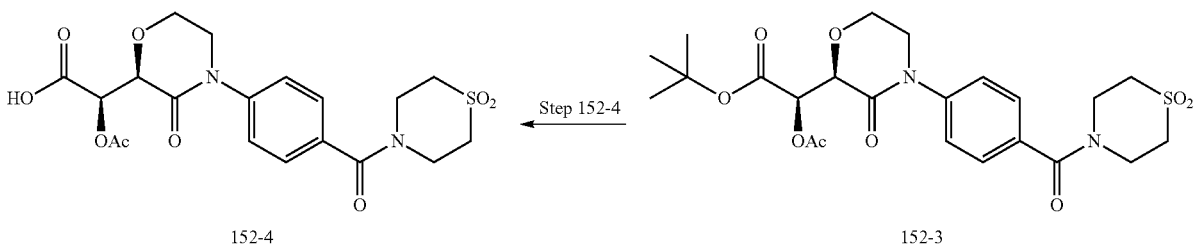
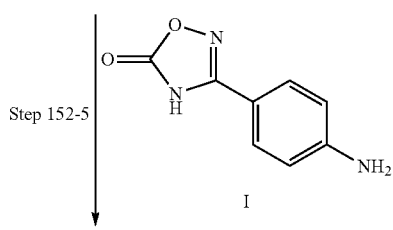

-continued

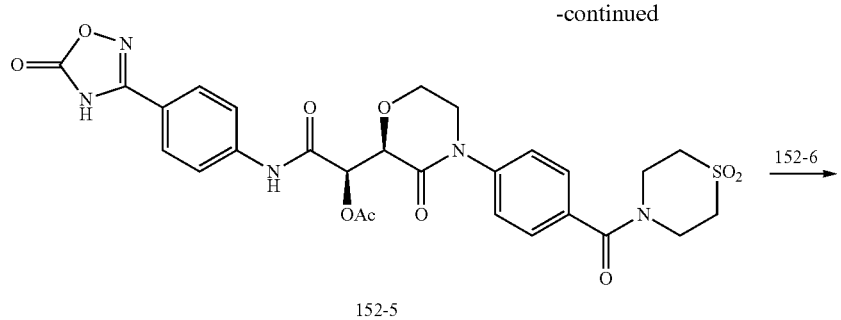

152-5

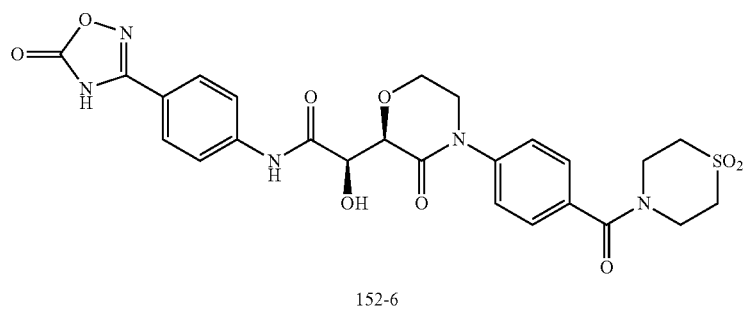

152-6

Step 152-7

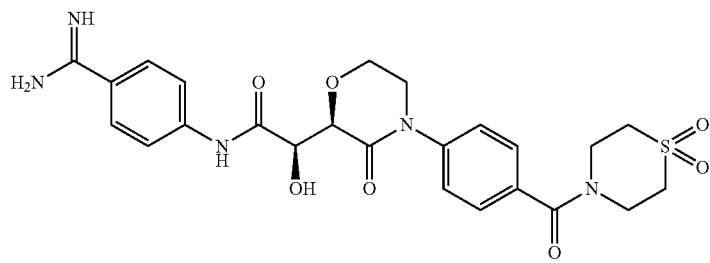

EXAMPLE 152

Step 152-2

According to Step 78-2 in the synthetic method for EXAMPLE 78, compound 152-1 (348 mg, 0.95 mmol) was used instead of compound 78-1 to obtain compound 152-2 (232 mg, 0.50 mmol).

Step 152-3

According to Step 78-3 in the synthetic method for EXAMPLE 78, compound 152-2 (232 mg, 0.50 mmol) was used instead of compound 78-2 to obtain compound 152-3 (242 mg, 0.47 mmol).

Step 152-4

According to Step 78-3 in the synthetic method for EXAMPLE 78, compound 152-2 (242 mg, 0.47 mmol) was used instead of compound 78-2 to obtain compound 152-3 (0.47 mmol) which was used in the next step without further purification.

Step 152-4

According to Step 78-4 in the synthetic method for EXAMPLE 78, compound 152-3 (0.47 mmol) was used instead of compound 78-3 to obtain compound 152-4 (0.47 mmol).

Step 152-5

According to Step 78-5 in the synthetic method for EXAMPLE 78, compound 152-4 (0.47 mmol) was used instead of compound 78-4 to obtain compound 152-5 (0.47 mmol) which was used in the next step without further purification.

Step 152-6

According to Step 78-6 in the synthetic method for EXAMPLE 78, compound 152-5 (0.47 mmol) was used instead of compound 78-5 to obtain EXAMPLE 152 (206 mg, 0.39 mmol) as a white amorphous solid.

Example 153
Synthesis of (2R)—N-(4-amidinophenyl)-2-hydroxy-2-[(2R)-3-oxo-4-(4-(dimethylaminocarbonyl)phenyl)morpholin-2-yl]acetamide (EXAMPLE 153)
Synthesis of 4-iodo-N,N-dimethylbenzamide 153-1
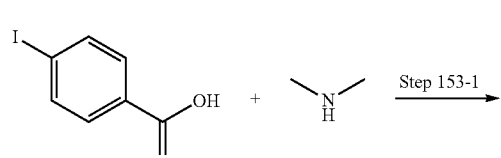
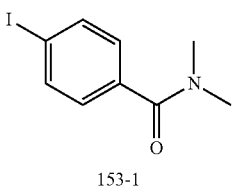
Step 153-1
According to Step 77-1 in the synthetic method for compound 77, 4-iodobenzoic acid and dimethylamine were used to obtain compound 153-1.
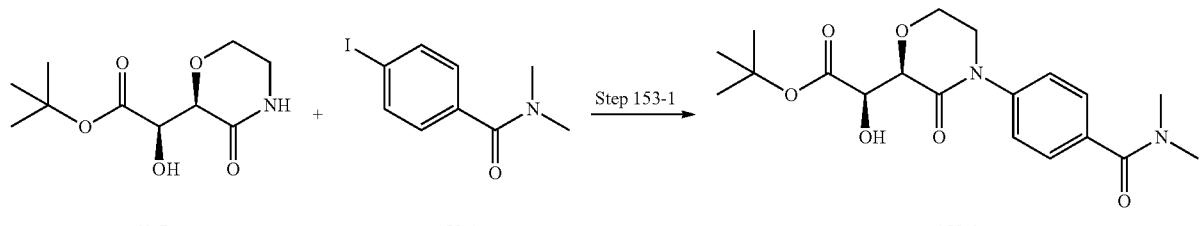
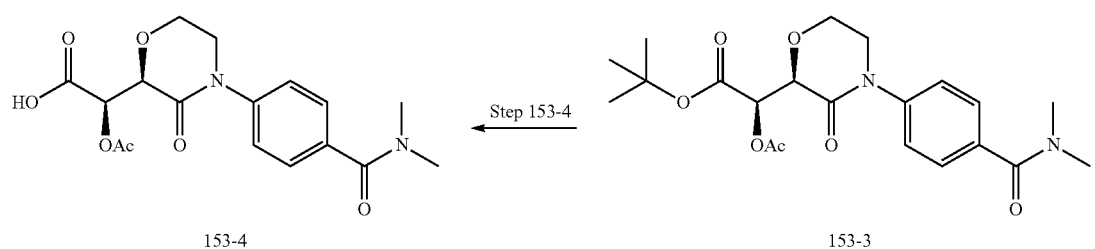
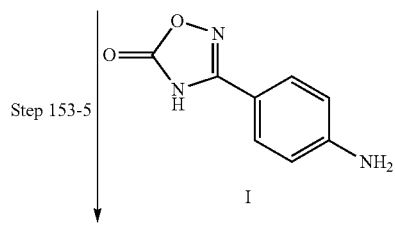
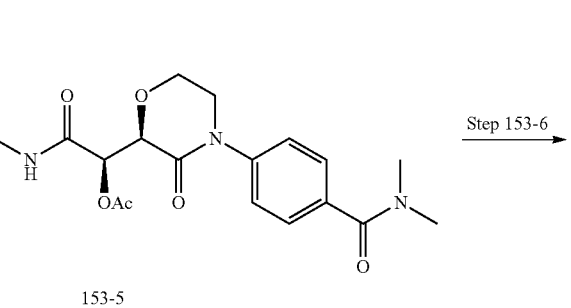

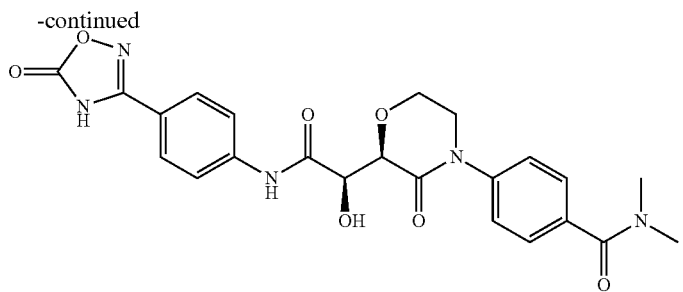

153-6

↓ Step 153-7

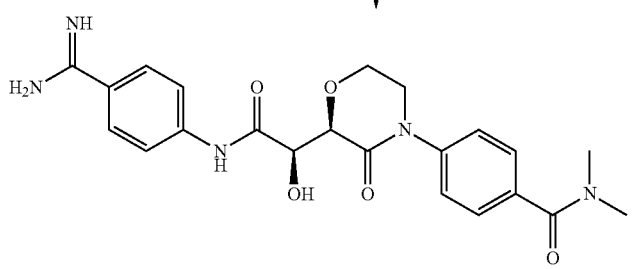

EXAMPLE 153

Step 153-2

According to Step 78-2 in the synthetic method for EXAMPLE 78, compound 153-1 (244 mg, 0.89 mmol) was used instead of compound 78-1 to obtain compound 153-2 (181 mg, 0.48 mmol).

Step 153-3

According to Step 78-3 in the synthetic method for EXAMPLE 78, compound 153-2 (181 mg, 0.48 mmol) was used instead of compound 78-2 to obtain compound 153-3 (80 mg, 0.19 mmol).

Step 153-4

According to Step 78-4 in the synthetic method for EXAMPLE 78, compound 153-3 (80 mg, 0.19 mmol) was used instead of compound 78-3 to obtain compound 153-4 (0.19 mmol) which was used in the next step without further purification.

Step 153-5

According to Step 78-5 in the synthetic method for EXAMPLE 78, compound 153-4 (0.19 mmol) was used instead of compound 78-4 to obtain compound 153-5 (77 mg, 0.15 mmol).

Step 153-6

According to Step 78-6 in the synthetic method for EXAMPLE 78, compound 153-5 (77 mg, 0.15 mmol) was used instead of compound 78-5 to obtain compound 153-6 (0.15 mmol) which was used in the next step without further purification.

Step 153-7

According to Step 78-7 in the synthetic method for EXAMPLE 78, compound 153-6 (0.15 mmol) was used instead of compound 78-6 to obtain EXAMPLE 153 (62 mg, 0.14 mmol) as a white amorphous solid.

Example 154

Synthesis of (2R)—N-(4-amidinophenyl)-2-hydroxy-2-[(2R)-3-oxo-4-(4-(dimethylaminolsulfonyl)phenyl)morpholin-2-yl]acetamide (EXAMPLE 154)

Synthesis of 4-iodo-N,N-dimethylbenzenesulfonamide 154-1

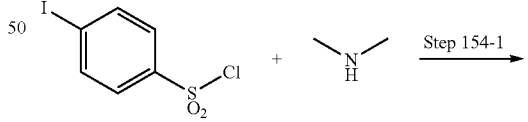

154-1

Step 154-1

According to Step 78-1 in the synthetic method for compound 78-1, 4-iodobenzenesulfonyl chloride and dimethylamine were used to obtain compound 154-1.

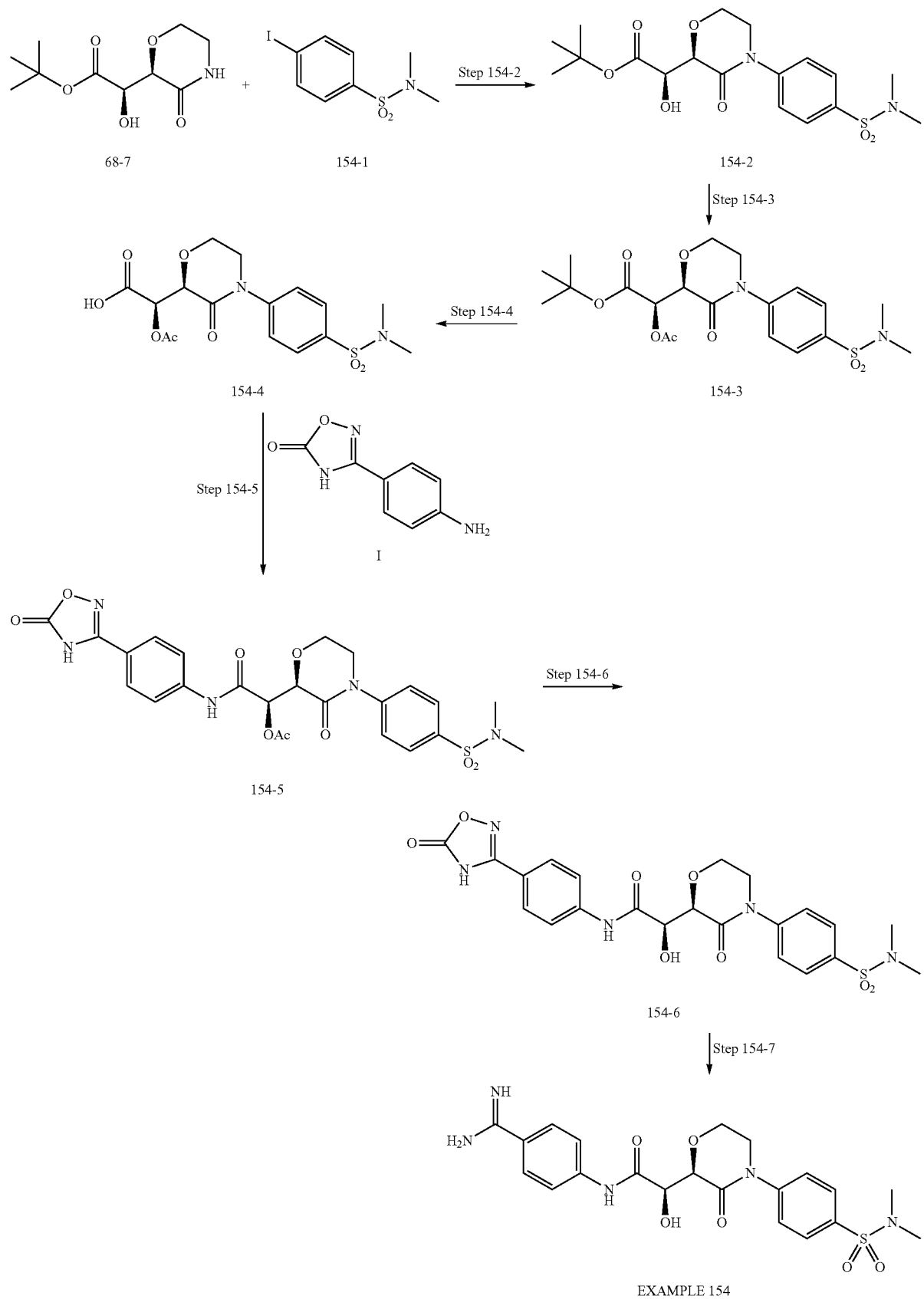

Step 154-2

According to Step 78-2 in the synthetic method for EXAMPLE 78, compound 154-1 (222 mg, 0.71 mmol) was used instead of compound 78-1 to obtain compound 154-2 (147 mg, 0.36 mmol).

Step 154-3

According to Step 78-3 in the synthetic method for EXAMPLE 78, compound 154-2 (147 mg, 0.36 mmol) was used instead of compound 78-2 to obtain compound 154-3 (131 mg, 0.29 mmol).

Step 154-4

According to Step 78-4 in the synthetic method for EXAMPLE 78, compound 154-3 (131 mg, 0.29 mmol) was used instead of compound 78-3 to obtain compound 154-4 (0.29 mmol) which was used in the next step without further purification.

Step 154-5

According to Step 78-5 in the synthetic method for EXAMPLE 78, compound 154-4 (0.29 mmol) was used instead of compound 78-4 to obtain compound 154-5 (120 mg, 0.21 mmol).

Step 154-6

According to Step 78-6 in the synthetic method for EXAMPLE 78, compound 154-5 (120 mg, 0.21 mmol) was used instead of compound 78-5 to obtain compound 154-6 (0.21 mmol) which was used in the next step without further purification.

Step 154-7

According to Step 78-7 in the synthetic method for EXAMPLE 78, compound 154-6 (0.21 mmol) was used instead of compound 78-6 to obtain EXAMPLE 154 (41 mg, 0.086 mmol) as a white amorphous solid.

Example 155

Synthesis of (2R)—N-(4-amidinophenyl)-2-hydroxy-2-[(2R)-3-oxo-4-(3-(dimethylaminocarbonyl)phenyl)morpholin-2-yl]acetamide (EXAMPLE 155)

Synthesis of 3-iodo-N,N-dimethylbenzamide 155-1

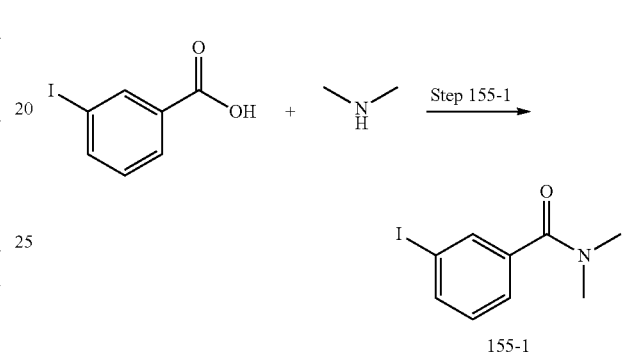

Step 155-1

According to Step 77-1 in the synthetic method for compound 77, 3-iodobenzoic acid and dimethylamine were used to obtain compound 155-1.

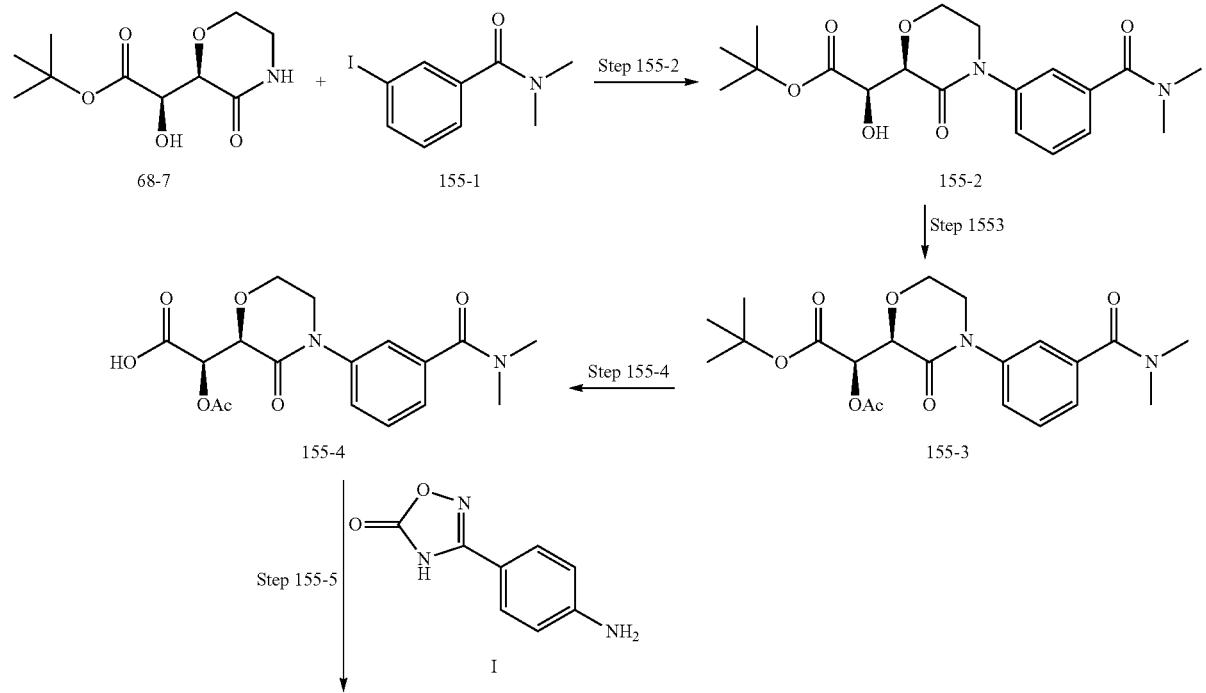

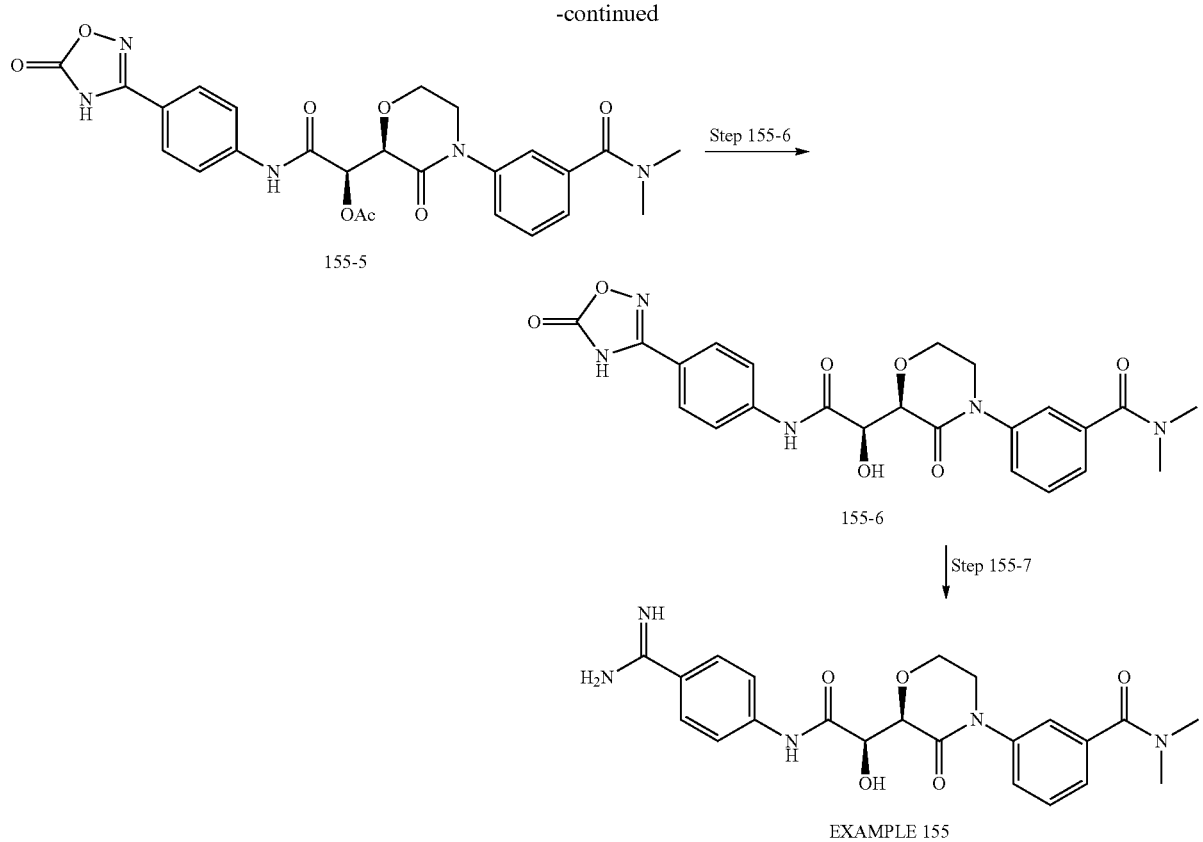

155-5

155-6

EXAMPLE 155

Step 155-2

According to Step 78-2 in the synthetic method for EXAMPLE 78, compound 155-1 (196 mg, 0.71 mmol) was used instead of compound 78-1 to obtain compound 155-2 (156 mg, 0.41 mmol).

Step 155-3

According to Step 78-3 in the synthetic method for EXAMPLE 78, compound 155-2 (156 mg, 0.41 mmol) was used instead of compound 78-2 to obtain compound 155-3 (0.41 mmol).

Step 155-4

According to Step 78-4 in the synthetic method for EXAMPLE 78, compound 155-3 (0.41 mmol) was used instead of compound 78-3 to obtain compound 155-4 (0.41 mmol) which was used in the next step without further purification.

Step 155-5

According to Step 78-5 in the synthetic method for EXAMPLE 78, compound 155-4 (0.41 mmol) was used instead of compound 78-4 to obtain compound 155-5 (171 mg, 0.33 mmol).

Step 155-6

According to Step 78-6 in the synthetic method for EXAMPLE 78, compound 155-5 (171 mg, 0.33 mmol) was used instead of compound 78-5 to obtain compound 155-6 (0.33 mmol) which was used in the next step without further purification.

Step 155-7

According to Step 78-7 in the synthetic method for EXAMPLE 78, compound 155-6 (0.33 mmol) was used instead of compound 78-6 to obtain EXAMPLE 155 (143 mg, 0.33 mmol) as a white amorphous solid. Synthesis of 4-[(2-fluoro-5-iodophenyl)carbonyl]morpholine 173-1

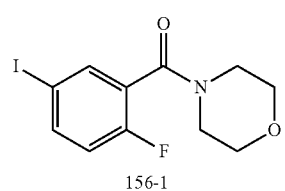

156-1

Example 156
Synthesis of (2R)—N-(4-amidinophenyl)-2-hydroxy-2-[(2R)-3-oxo-4-(4-fluoro-3-(morpholin-4-ylcarbonyl)phenyl)morpholin-2-yl]acetamide (EXAMPLE 156)
Step 156-1
According to Step 77-1 in the synthetic method for compound 77, 2-fluoro-5-iodobenzoic acid and morpholine were used to obtain compound 156-1.
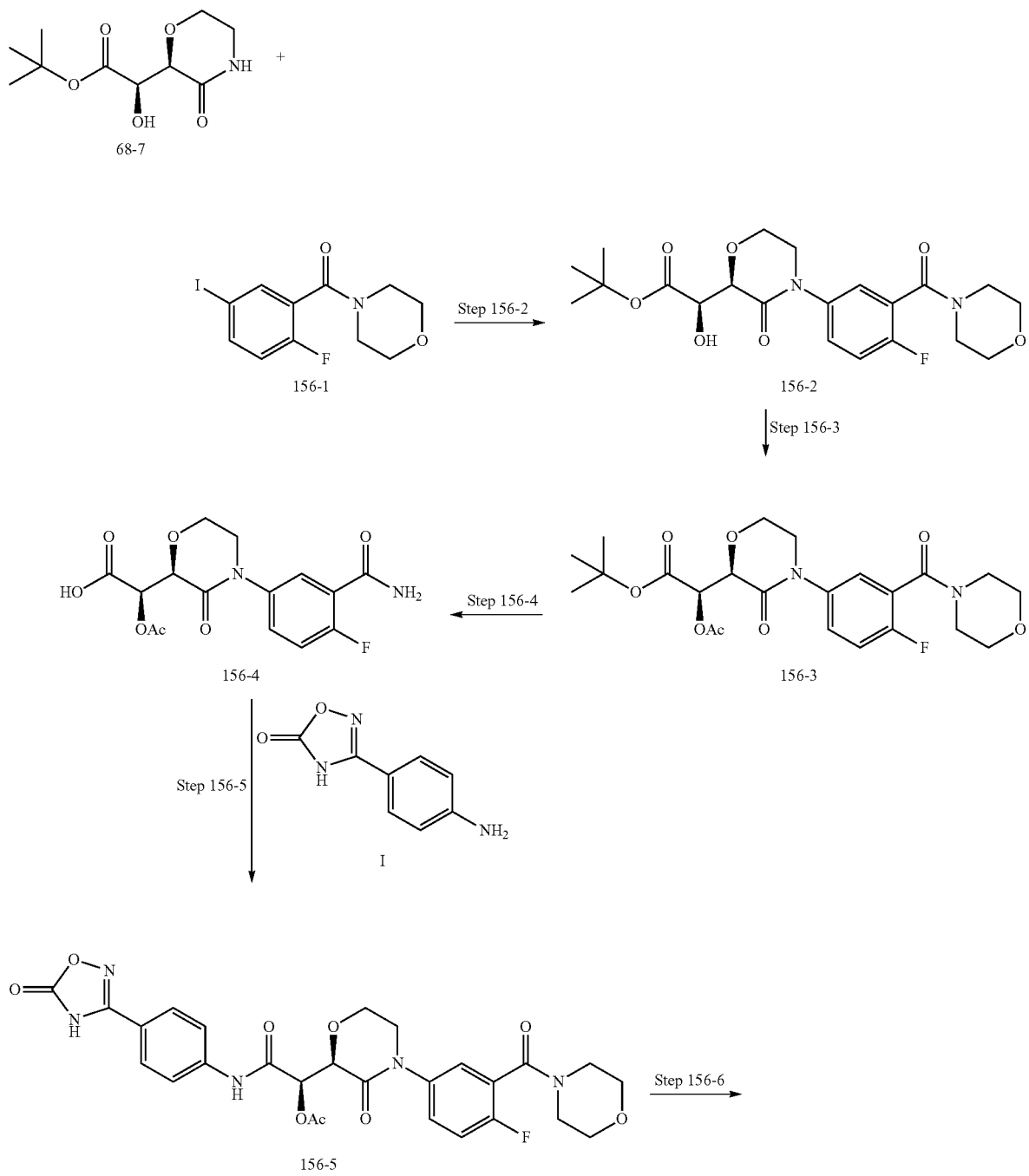

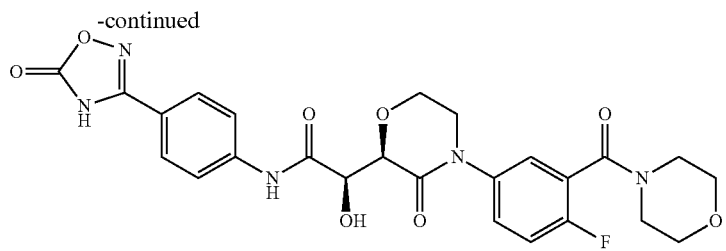

156-6

↓ Step 156-7

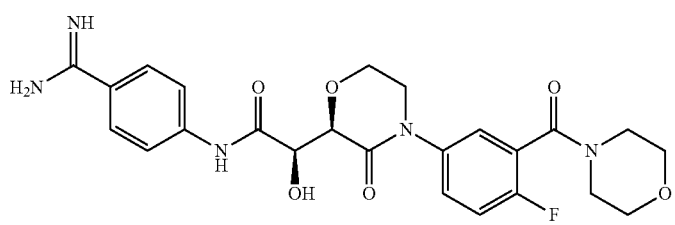

EXAMPLE 156

Step 156-2

According to Step 78-2 in the synthetic method for EXAMPLE 78, compound 156-1 (287 mg, 0.86 mmol) was used instead of compound 78-1 to obtain compound 156-2 (251 mg, 0.57 mmol).

Step 156-3

According to Step 78-3 in the synthetic method for EXAMPLE 78, compound 156-2 (287 mg, 0.57 mmol) was used instead of compound 78-2 to obtain compound 156-3 (0.57 mmol).

Step 156-4

According to Step 78-4 in the synthetic method for EXAMPLE 78, compound 156-3 (0.57 mmol) was used instead of compound 78-3 to obtain compound 156-4 (0.57 mmol) which was used in the next step without further purification.

Step 156-5

According to Step 78-5 in the synthetic method for EXAMPLE 78, compound 156-4 (0.57 mmol) was used instead of compound 78-4 to obtain compound 156-5 (289 mg, 0.50 mmol).

Step 156-6

According to Step 78-6 in the synthetic method for EXAMPLE 78, compound 156-5 (289 mg, 0.50 mmol) was used instead of compound 78-5 to obtain compound 156-6 (0.50 mmol) which was used in the next step without further purification.

Step 156-7

According to Step 78-7 in the synthetic method for EXAMPLE 78, compound 156-6 (0.50 mmol) was used instead of compound 78-6 to obtain EXAMPLE 156 (242 mg, 0.48 mmol) as a white amorphous solid.

Example 157

Synthesis of (2R)—N-(4-amidinophenyl)-2-hydroxy-2-[(2R)-3-oxo-4-(4-(dimethyl-$D_6$-aminocarbonyl)phenyl)morpholin-2-yl]acetamide (EXAMPLE 157)

Step 157-1

Synthesis of 4-iodo-N,N-dimethyl-$D_6$-benzmide 157-1

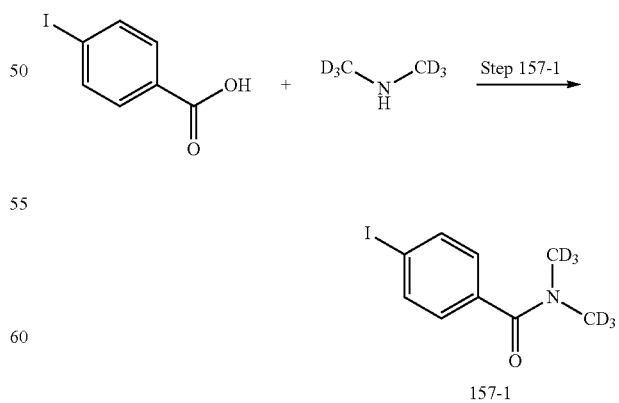

According to Step 77-1 in the synthetic method for compound 77, 4-iodobenzoic acid and dimethyl-$D_6$-amine were used to obtain compound 157-1.

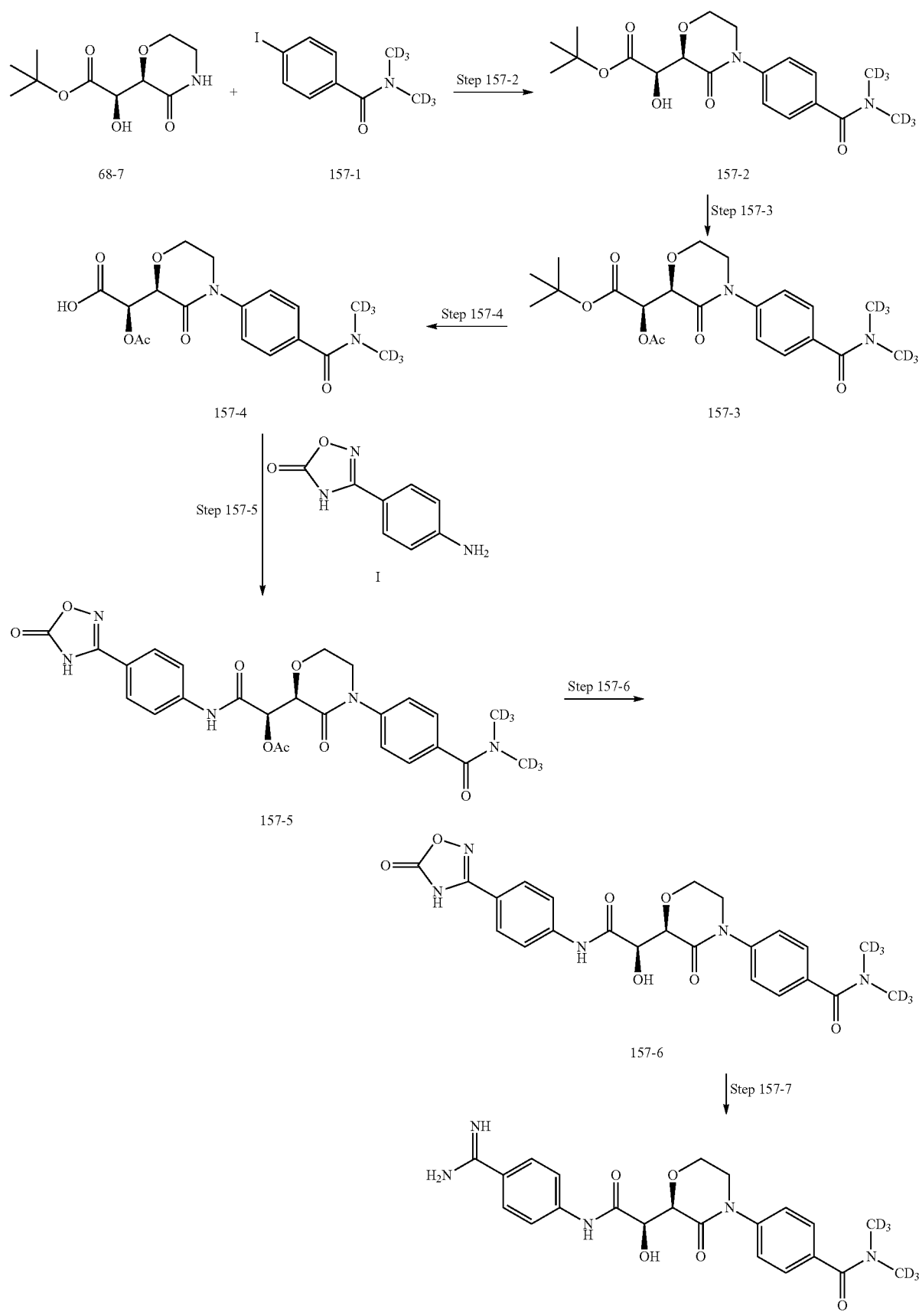

Step 157-2

According to Step 78-2 in the synthetic method for EXAMPLE 78, compound 157-1 (134 mg, 0.48 mmol) was used instead of compound 78-1 to obtain compound 157-2 (100 mg, 0.26 mmol).

Step 157-3

According to Step 78-3 in the synthetic method for EXAMPLE 78, compound 157-2 (100 mg, 0.26 mmol) was used instead of compound 78-2 to obtain compound 157-3 (106 mg, 0.25 mmol).

Step 157-4

According to Step 78-4 in the synthetic method for EXAMPLE 78, compound 157-3 (106 mg, 0.25 mmol) was used instead of compound 78-3 to obtain compound 157-4 (0.25 mmol) which was used in the next step without further purification.

Step 157-5

According to Step 78-5 in the synthetic method for EXAMPLE 78, compound 157-4 (0.25 mmol) was used instead of compound 78-4 to obtain compound 157-5 (0.25 mmol).

Step 157-6

According to Step 78-6 in the synthetic method for EXAMPLE 78, compound 157-5 (0.25 mmol) was used instead of compound 78-5 to obtain compound 157-6 (0.25 mmol) which was used in the next step without further purification.

Step 157-7

According to Step 78-7 in the synthetic method for EXAMPLE 78, compound 157-6 (0.25 mmol) was used instead of compound 78-6 to obtain EXAMPLE 157 (89 mg, 0.20 mmol) as a white amorphous solid.

Example 158

Synthesis of (2R)—N-(4-amidinophenyl)-2-hydroxy-2-[(2R)-3-oxo-4-(3-(dimethyl-$D_6$-aminocarbonyl)phenyl)morpholin-2-yl]acetamide (EXAMPLE 158)

Synthesis of 3-iodo-N,N-dimethyl-$D_6$-benzmide 158-1

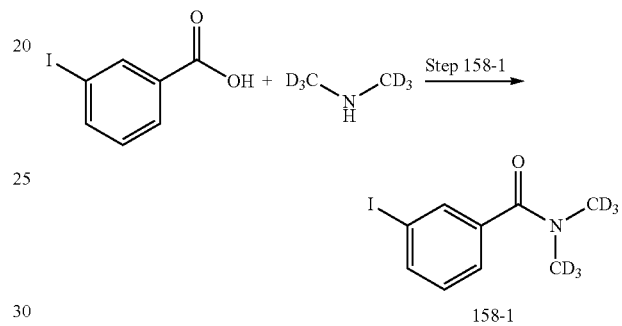

Step 158-1

According to Step 77-1 in the synthetic method for compound 77, 3-iodobenzoic acid and dimethyl-$D_6$-amine were used to obtain compound 158-1.

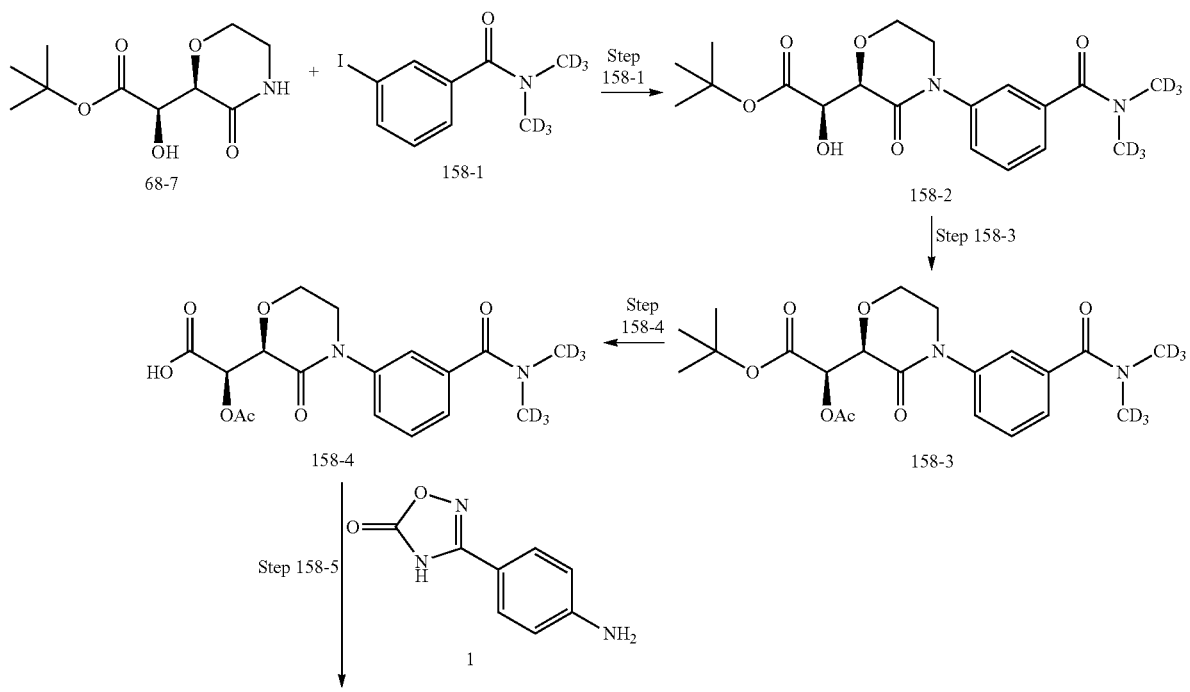

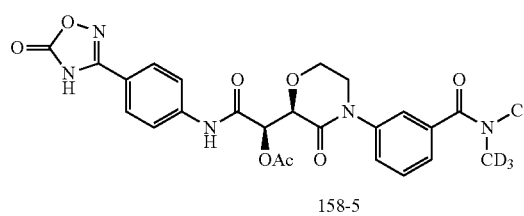

158-5

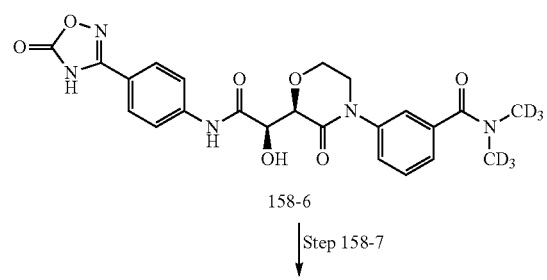

158-6

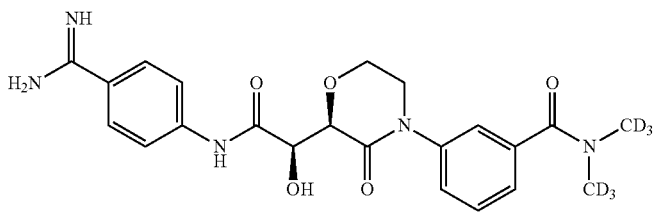

EXAMPLE 158

Step 158-2

According to Step 78-2 in the synthetic method for EXAMPLE 78, compound 158-1 (134 mg, 0.48 mmol) was used instead of compound 78-1 to obtain compound 158-2 (122 mg, 0.32 mmol).

Step 158-3

According to Step 78-3 in the synthetic method for EXAMPLE 78, compound 158-2 (122 mg, 0.32 mmol) was used instead of compound 78-2 to obtain compound 158-3 (130 mg, 0.31 mmol).

Step 158-4

According to Step 78-4 in the synthetic method for EXAMPLE 78, compound 158-3 (130 mg, 0.31 mmol) was used instead of compound 78-3 to obtain compound 158-4 (0.31 mmol) which was used in the next step without further purification.

Step 158-5

According to Step 78-5 in the synthetic method for EXAMPLE 78, compound 158-4 (0.31 mmol) was used instead of compound 78-4 to obtain compound 158-5 (72 mg, 0.14 mmol).

Step 158-6

According to Step 78-6 in the synthetic method for EXAMPLE 78, compound 158-5 (72 mg, 0.14 mmol) was used instead of compound 78-5 to obtain compound 158-6 (0.14 mmol) which was used in the next step without further purification.

Step 158-7

According to Step 78-7 in the synthetic method for EXAMPLE 78, compound 158-6 (0.14 mmol) was used instead of compound 78-6 to obtain EXAMPLE 158 (56 mg, 0.13 mmol) as a white amorphous solid.

Example 159

Synthesis of (2R)—N-(4-amidinophenyl)-2-hydroxy-2-[(2R)-3-oxo-4-(3-(dimethylaminocarbonyl)-4-fluorophenyl)morpholin-2-yl]acetamide (EXAMPLE 159)

Synthesis of 2-fluoro-5-iodo-N,N-dimethylbenzamide 159-1

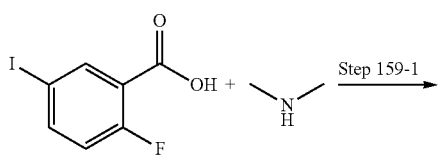

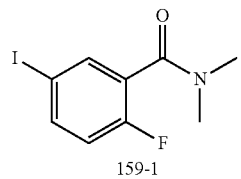

159-1

Step 159-1

According to Step 77-1 in the synthetic method for compound 77, 2-fluoro-5-iodobenzoic acid and dimethylamine were used to obtain compound 159-1.

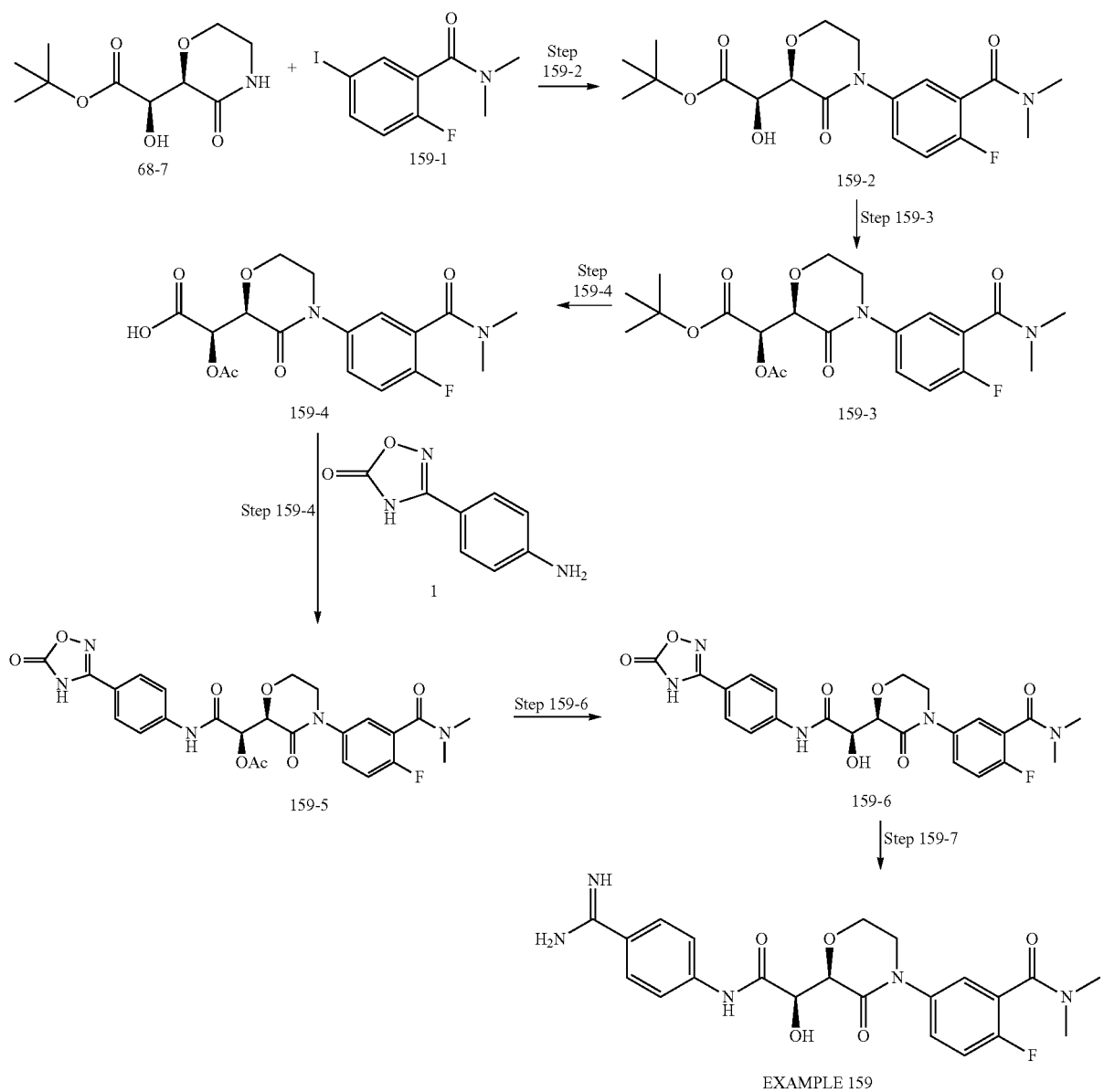

Step 159-2

According to Step 78-2 in the synthetic method for EXAMPLE 78, compound 159-1 (209 mg, 0.71 mmol) was used instead of compound 78-1 to obtain compound 159-2 (171 mg, 0.43 mmol).

Step 159-3

According to Step 78-3 in the synthetic method for EXAMPLE 78, compound 159-2 (171 mg, 0.43 mmol) was used instead of compound 78-2 to obtain compound 159-3 (0.43 mmol).

Step 159-4

According to Step 78-4 in the synthetic method for EXAMPLE 78, compound 159-3 (0.43 mmol) was used instead of compound 78-3 to obtain compound 159-4 (0.43 mmol) which was used in the next step without further purification.

Step 159-5

According to Step 78-5 in the synthetic method for EXAMPLE 78, compound 159-4 (0.43 mmol) was used instead of compound 78-4 to obtain compound 159-5 (170 mg, 0.31 mmol).

Step 159-6

According to Step 78-6 in the synthetic method for EXAMPLE 78, compound 159-5 (170 mg, 0.31 mmol) was used instead of compound 78-5 to obtain compound 159-6 (0.31 mmol) which was used in the next step without further purification.

Step 159-7

According to Step 78-7 in the synthetic method for EXAMPLE 78, compound 159-6 (0.31 mmol) was used instead of compound 78-6 to obtain EXAMPLE 159 (131 mg, 0.29 mmol) as a white amorphous solid.

Example 160

Synthesis of (2R)—N-(4-amidinophenyl)-2-hydroxy-2-[(2R)-3-oxo-4-(4-methoxy-D$_3$-phenyl)morpholin-2-yl]acetamide (EXAMPLE 160)

Step 160-2

According to Step 78-3 in the synthetic method for EXAMPLE 78, compound 160-1 (103 mg, 0.30 mmol) was used instead of compound 78-2 to obtain compound 160-2 (112 mg, 0.29 mmol).

Step 160-3

According to Step 78-4 in the synthetic method for EXAMPLE 78, compound 160-2 (112 mg, 0.29 mmol) was used instead of compound 78-3 to obtain compound 160-3 (0.29 mmol) which was used in the next step without further purification.

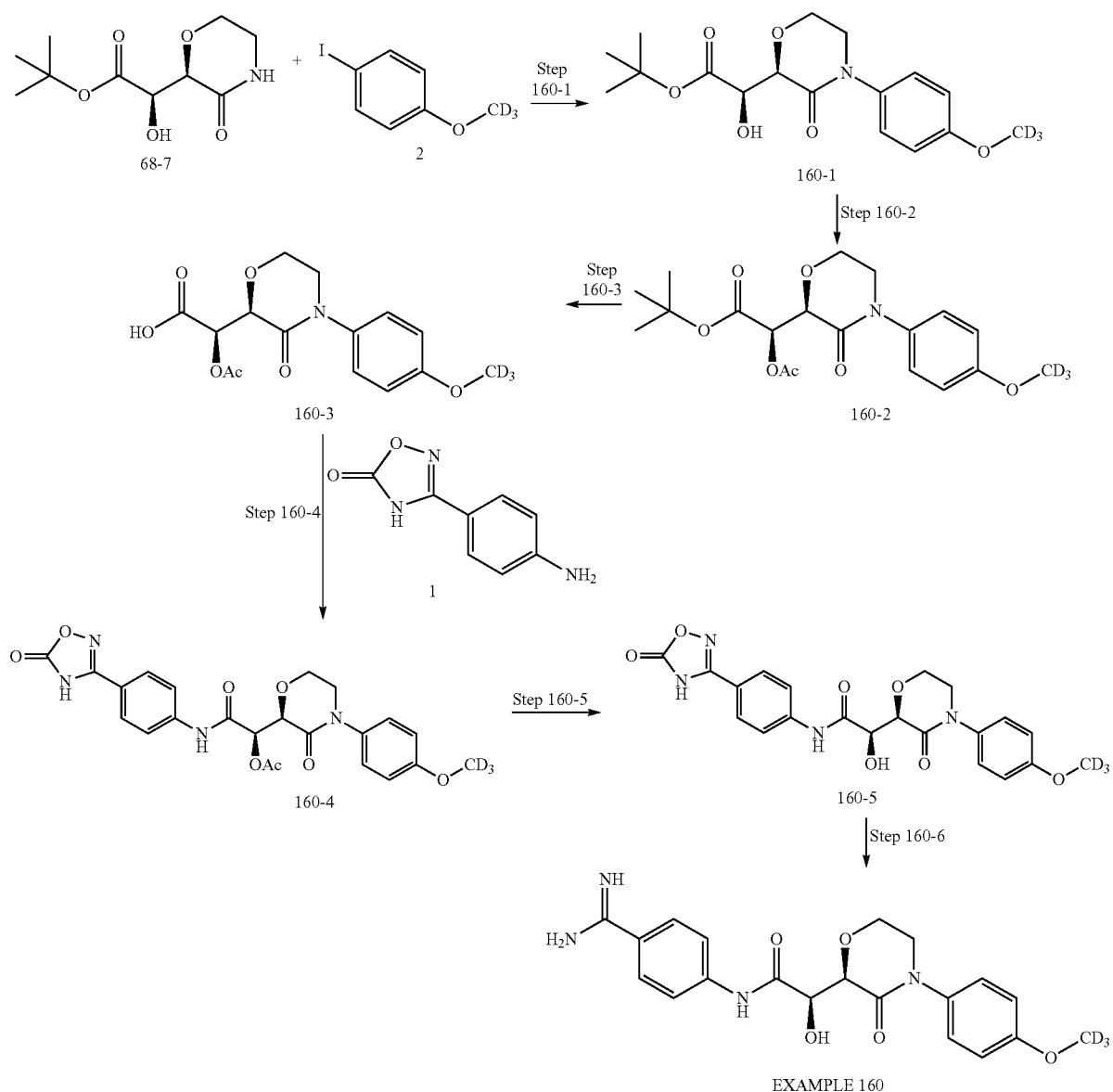

Step 160-1

According to Step 78-2 in the synthetic method for EXAMPLE 78, compound 2 (169 mg, 0.71 mmol) was used instead of compound 78-1 to obtain compound 160-1 (103 mg, 0.30 mmol).

Step 160-4

According to Step 78-5 in the synthetic method for EXAMPLE 78, compound 160-3 (0.29 mmol) was used instead of compound 78-3 to obtain compound 160-4 (44 mg, 0.091 mmol).

Step 160-5

According to Step 78-6 in the synthetic method for EXAMPLE 78, compound 160-4 (44 mg, 0.091 mmol) was used instead of compound 78-5 to obtain compound 160-5 (0.091 mmol) which was used in the next step without further purification.

Step 160-6

According to Step 78-7 in the synthetic method for EXAMPLE 78, compound 160-5 (0.091 mmol) was used instead of compound 78-6 to obtain EXAMPLE 160 (30 mg, 0.075 mmol) as a white amorphous solid.

Example 161

Synthesis of (2R)—N-(4-amidinophenyl)-2-hydroxy-2-[(2R)-3-oxo-4-(3-methoxy-$D_3$-phenyl)morpholin-2-yl]acetamide (EXAMPLE 161)

Step 161-1

According to Step 78-2 in the synthetic method for EXAMPLE 78, compound 2 (169 mg, 0.71 mmol) was used instead of compound 78-1 to obtain compound 161-1 (95 mg, 0.25 mmol).

Step 161-2

According to Step 78-3 in the synthetic method for EXAMPLE 78, compound 161-1 (95 mg, 0.25 mmol) was used instead of compound 78-2 to obtain compound 161-2 (0.25 mmol).

Step 161-3

According to Step 78-4 in the synthetic method for EXAMPLE 78, compound 161-2 (0.25 mmol) was used instead of compound 78-3 to obtain compound 161-3 (0.25 mmol) which was used in the next step without further purification.

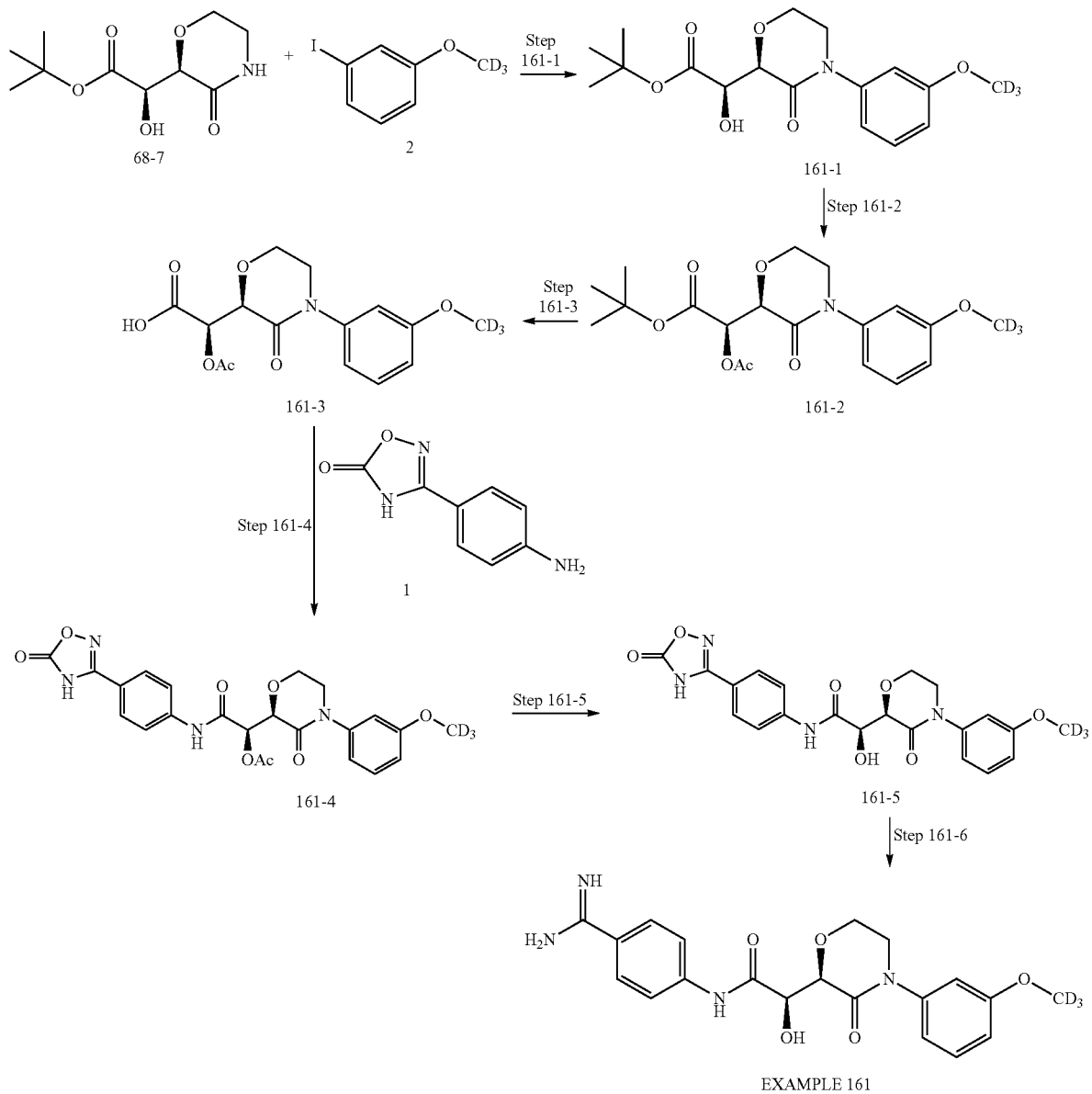

Step 161-4

According to Step 78-5 in the synthetic method for EXAMPLE 78, compound 161-3 (0.25 mmol) was used instead of compound 78-4 to obtain compound 161-4 (64 mg, 0.13 mmol).

Step 161-5

According to Step 78-6 in the synthetic method for EXAMPLE 78, compound 161-4 (64 mg, 0.13 mmol) was used instead of compound 78-5 to obtain compound 161-5 (0.13 mmol) which was used in the next step without further purification.

Step 161-6

According to Step 78-7 in the synthetic method for EXAMPLE 78, compound 161-5 (0.13 mmol) was used instead of compound 78-6 to obtain EXAMPLE 161 (39 mg, 0.097 mmol) as a white amorphous solid.

Example 162

Synthesis of (2R)—N-(4-amidinophenyl)-2-hydroxy-2-[(2R)-3-oxo-4-(4-fluoro-3-(pyrrolidin-1-ylcarbonyl)phenyl)morpholin-2-yl]acetamide (EXAMPLE 162)

Step 162-1

Synthesis of 1-[(2-fluoro-5-iodophenyl)carbonyl]pyrrolidine 162

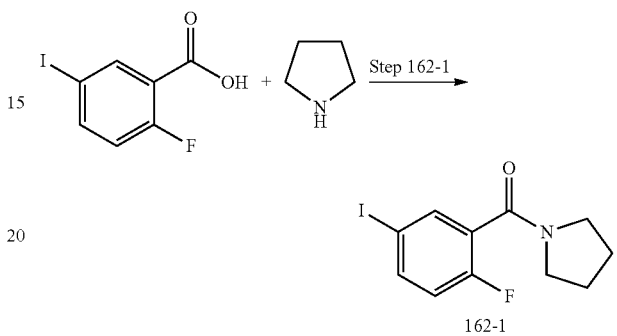

According to Step 77-1 in the synthetic method for compound 77, 2-fluoro-5-iodobenzoic acid and pyrrolidine were used to obtain compound 162-1.

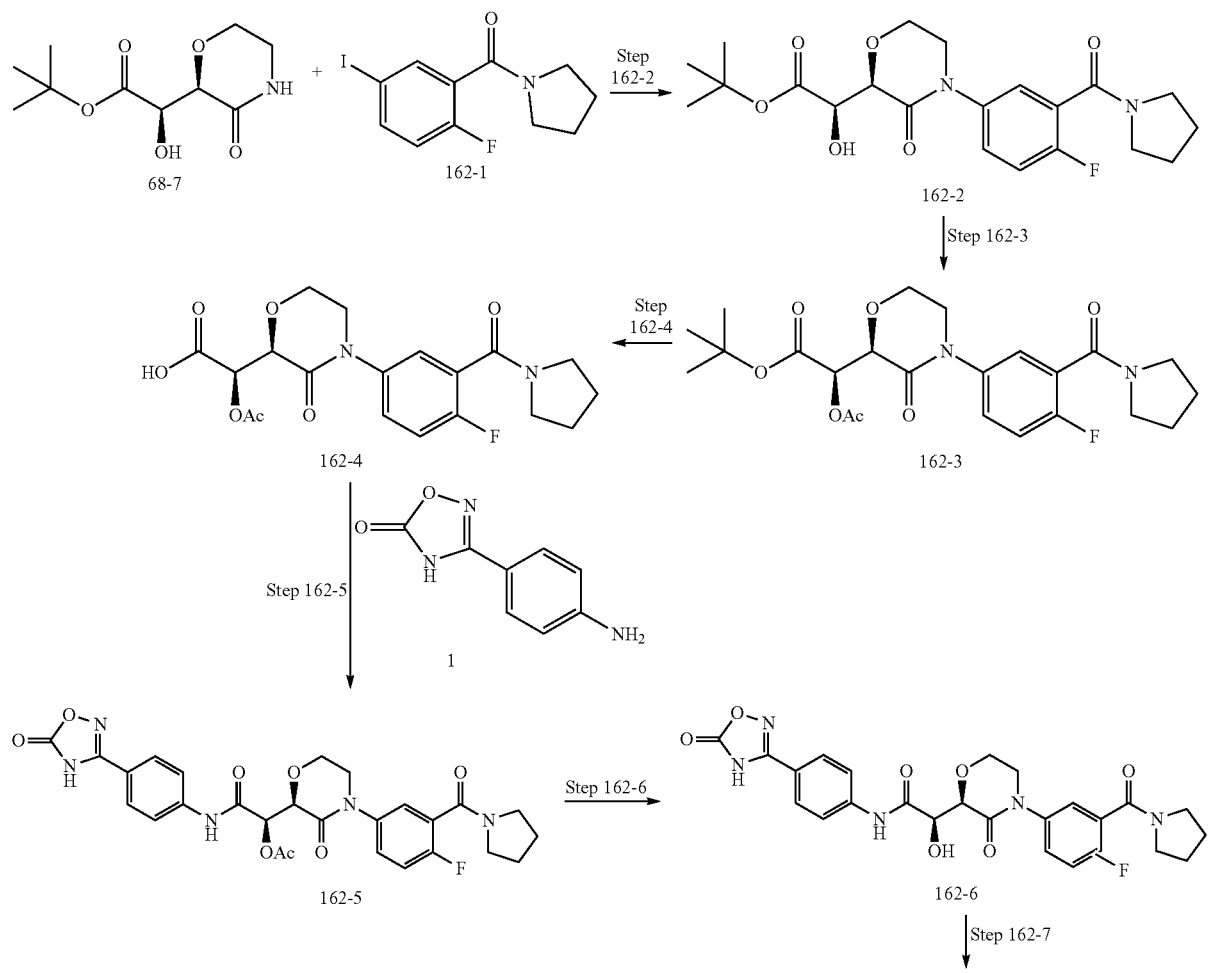

-continued

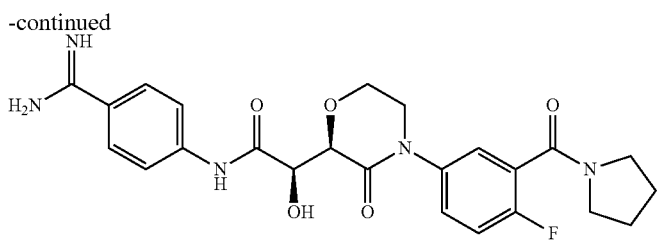

EXAMPLE 162

Step 162-2

According to Step 78-2 in the synthetic method for EXAMPLE 78, compound 162-1 (228 mg, 0.71 mmol) was used instead of compound 78-1 to obtain compound 162-2 (226 mg, 0.54 mmol).

Step 162-3

According to Step 78-3 in the synthetic method for EXAMPLE 78, compound 162-2 (226 mg, 0.54 mmol) was used instead of compound 78-2 to obtain compound 162-3 (244 mg, 0.53 mmol).

Step 162-4

According to Step 78-4 in the synthetic method for EXAMPLE 78, compound 162-3 (244 mg, 0.53 mmol) was used instead of compound 78-3 to obtain compound 162-4 (0.53 mmol) which was used in the next step without further purification.

Step 162-5

According to Step 78-5 in the synthetic method for EXAMPLE 78, compound 162-4 (0.53 mmol) was used instead of compound 78-4 to obtain compound 162-5 (281 mg, 0.50 mmol).

Step 162-6

According to Step 78-6 in the synthetic method for EXAMPLE 78, compound 162-5 (281 mg, 0.50 mmol) was used instead of compound 78-5 to obtain compound 162-6 (0.50 mmol) which was used in the next step without further purification.

Step 162-7

According to Step 78-7 in the synthetic method for EXAMPLE 78, compound 162-6 (0.50 mmol) was used instead of compound 78-6 to obtain EXAMPLE 162 (220 mg, 0.46 mmol) as a white amorphous solid.

Example 163

Synthesis of (2R)—N-(4-amidinophenyl)-2-hydroxy-2-[(2R)-3-oxo-4-(3-(dimethylaminocarbonyl)-4-methylphenyl)morpholin-2-yl]acetamide (EXAMPLE 163)

Step 163-1

Synthesis of 5-iodo-2-methyl-N,N-dimethylbenzamide 163-1

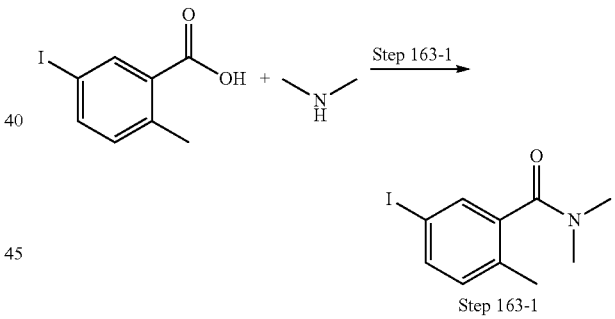

Step 163-1

According to Step 77-1 in the synthetic method for compound 77, 5-iodo-2-methylbenzoic acid and dimethylamine were used to obtain compound 163-1.

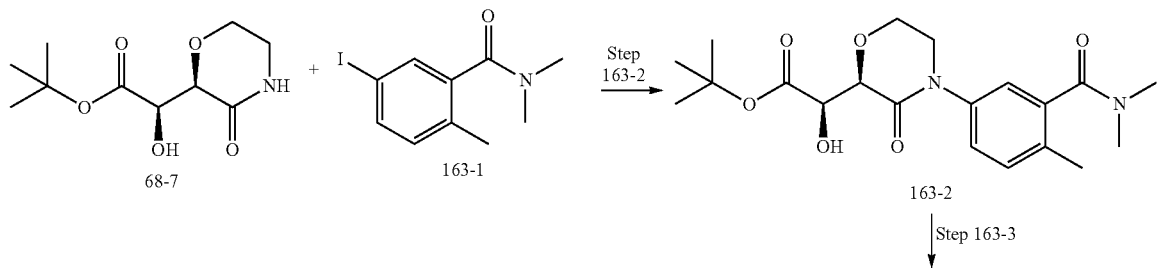

Step 163-3

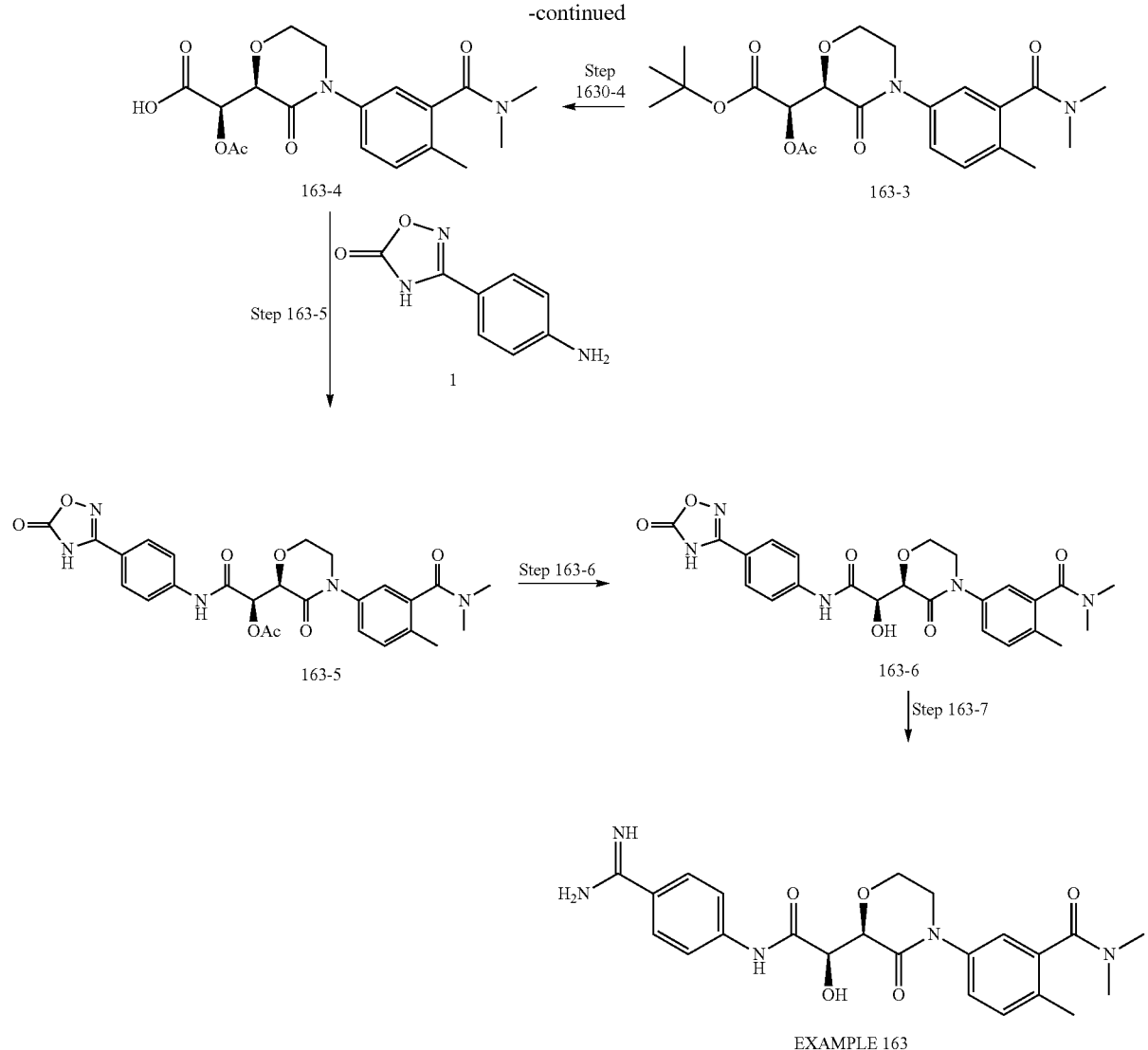

Step 163-2

According to Step 78-2 in the synthetic method for EXAMPLE 78, compound 163-1 (206 mg, 0.71 mmol) was used instead of compound 78-1 to obtain compound 163-2 (208 mg, 0.53 mmol).

Step 163-3

According to Step 78-3 in the synthetic method for EXAMPLE 78, compound 163-2 (208 mg, 0.53 mmol) was used instead of compound 78-2 to obtain compound 163-3 (232 mg, 0.53 mmol).

Step 163-4

According to Step 78-4 in the synthetic method for EXAMPLE 78, compound 163-3 (232 mg, 0.53 mmol) was used instead of compound 78-3 to obtain compound 163-4 (0.53 mmol) which was used in the next step without further purification.

Step 163-5

According to Step 78-5 in the synthetic method for EXAMPLE 78, compound 163-4 (0.53 mmol) was used instead of compound 78-4 to obtain compound 163-5 (260 mg, 0.48 mmol).

Step 163-6

According to Step 78-6 in the synthetic method for EXAMPLE 78, compound 163-5 (260 mg, 0.48 mmol) was used instead of compound 78-5 to obtain compound 163-6 (0.48 mmol) which was used in the next step without further purification.

Step 163-7

According to Step 78-7 in the synthetic method for EXAMPLE 78, compound 163-6 (0.48 mmol) was used instead of compound 78-6 to obtain EXAMPLE 163 (197 mg, 0.43 mmol) as a white amorphous solid.

Example 164
Synthesis of (2R)—N-(4-amidinophenyl)-2-hydroxy-2-[(2R)-3-oxo-4-(4-methyl-3-(morpholin-4-ylcarbonyl)phenyl)morpholin-2-yl]acetamide (EXAMPLE 164)
Step 164-1
Synthesis of 4-[(5-iodo-2-methylphenyl)carbonyl]morpholine 164-1
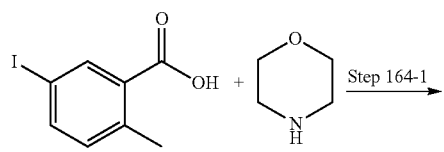
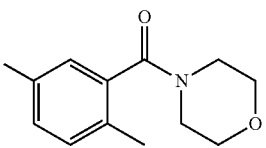
According to Step 77-1 in the synthetic method for compound 77, 5-iodo-2-methylbenzoic acid and morpholine were used to obtain compound 164-1.
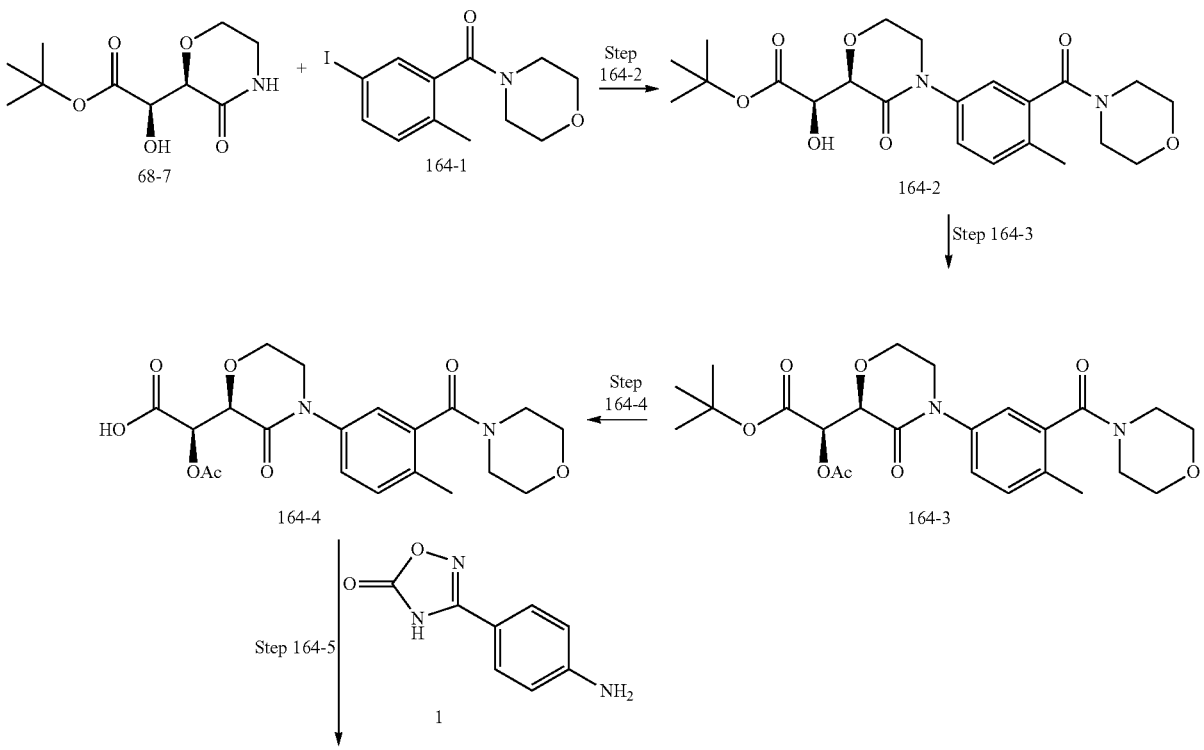
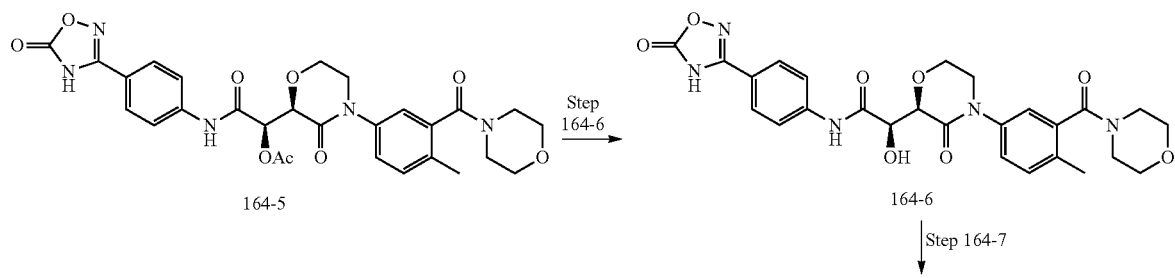

-continued

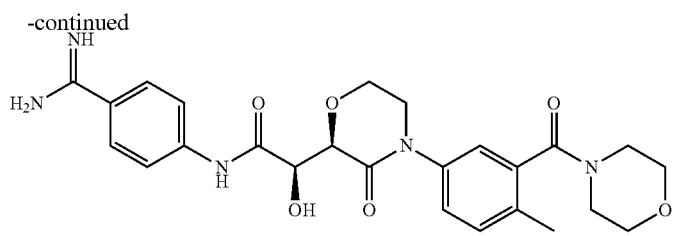

EXAMPLE 164

Step 164-2

According to Step 78-2 in the synthetic method for EXAMPLE 78, compound 164-1 (236 mg, 0.71 mmol) was used instead of compound 78-1 to obtain compound 164-2 (250 mg, 0.58 mmol).

Step 164-3

According to Step 78-3 in the synthetic method for EXAMPLE 78, compound 164-2 (250 mg, 0.58 mmol) was used instead of compound 78-2 to obtain compound 164-3 (219 mg, 0.46 mmol).

Step 164-4

According to Step 78-4 in the synthetic method for EXAMPLE 78, compound 164-3 (219 mg, 0.46 mmol) was used instead of compound 78-3 to obtain compound 164-4 (0.46 mmol) which was used in the next step without further purification.

Step 164-5

According to Step 78-5 in the synthetic method for EXAMPLE 78, compound 164-4 (0.46 mmol) was used instead of compound 78-4 to obtain compound 164-5 (240 mg, 0.41 mmol).

Step 164-6

According to Step 78-6 in the synthetic method for EXAMPLE 78, compound 164-5 (240 mg, 0.41 mmol) was used instead of compound 78-5 to obtain compound 164-6 (0.41 mmol) which was used in the next step without further purification.

Step 164-7

According to Step 78-7 in the synthetic method for EXAMPLE 78, compound 164-6 (0.41 mmol) was used instead of compound 78-6 to obtain EXAMPLE 164 (186 mg, 0.38 mmol) as a white amorphous solid.

Example 165

Synthesis of (2R)—N-(4-amidinophenyl)-2-hydroxy-2-[(2R)-3-oxo-4-(4-methyl-3-(pyrrolidin-1-ylcarbonyl)phenyl)morpholin-2-yl]acetamide (EXAMPLE 165)

Synthesis of 1-[(5-iodo-2-methylphenyl)carbonyl]pyrrolidine 165-1

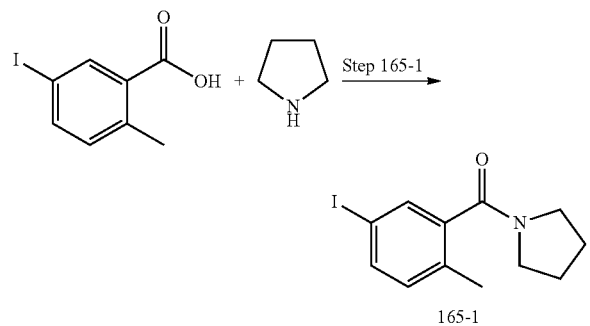

Step 165-1

According to Step 77-1 in the synthetic method for compound 77, 5-iodo-2-methylbenzoic acid and pyrrolidine were used to obtain compound 165-1.

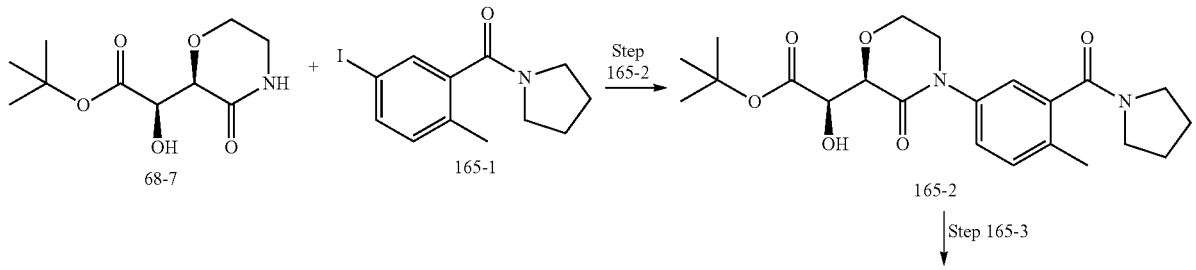

Step 165-3

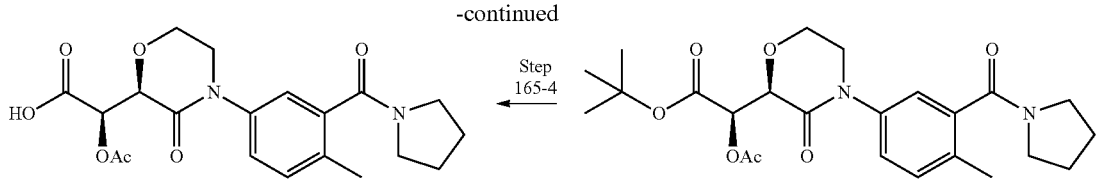

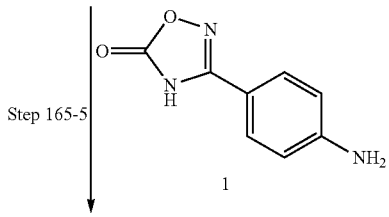

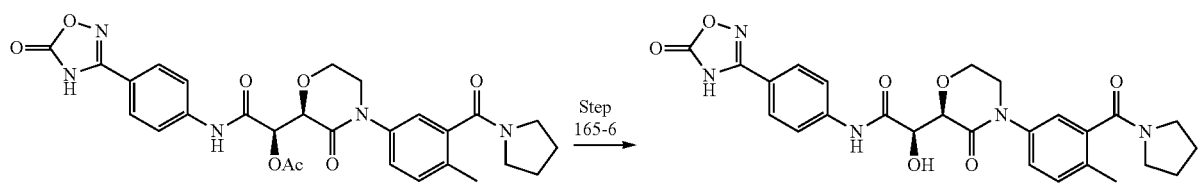

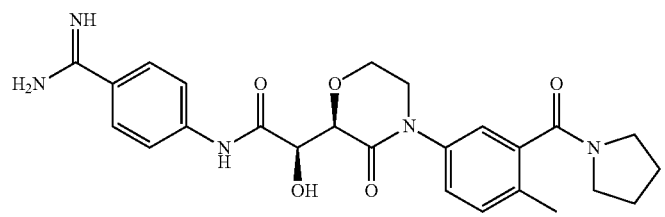

EXAMPLE 165

Step 165-2

According to Step 78-2 in the synthetic method for EXAMPLE 78, compound 165-1 (225 mg, 0.71 mmol) was used instead of compound 78-1 to obtain compound 165-2 (241 mg, 0.58 mmol).

Step 165-3

According to Step 78-3 in the synthetic method for EXAMPLE 78, compound 165-2 (241 mg, 0.58 mmol) was used instead of compound 78-2 to obtain compound 165-3 (264 mg, 0.57 mmol).

Step 165-4

According to Step 78-4 in the synthetic method for EXAMPLE 78, compound 165-3 (264 mg, 0.57 mmol) was used instead of compound 78-3 to obtain compound 165-4 (0.57 mmol) which was used in the next step without further purification.

Step 165-5

According to Step 78-5 in the synthetic method for EXAMPLE 78, compound 165-4 (0.57 mmol) was used instead of compound 78-4 to obtain compound 165-5 (247 mg, 0.44 mmol).

Step 165-6

According to Step 78-6 in the synthetic method for EXAMPLE 78, compound 165-5 (247 mg, 0.44 mmol) was used instead of compound 78-5 to obtain compound 165-6 (0.44 mmol) which was used in the next step without further purification.

Step 165-7

According to Step 78-7 in the synthetic method for EXAMPLE 78, compound 165-6 (0.44 mmol) was used instead of compound 78-6 to obtain EXAMPLE 165 (197 mg, 0.41 mmol) as a white amorphous solid.

Example 166
Synthesis of (2R)—N-(4-amidinophenyl)-2-hydroxy-2-[(2R)-3-oxo-4-(3-fluoro-5-(pyrrolidin-1-ylcarbonyl)phenyl)morpholin-2-yl]acetamide (EXAMPLE 166)
Synthesis of 1-[(3-fluoro-5-iodophenyl)carbonyl]pyrrolidine 166-1
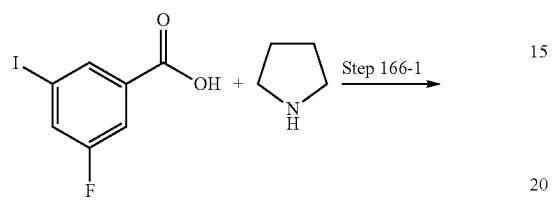
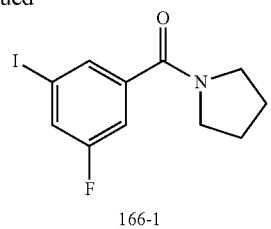
Step 166-1
According to Step 77-1 in the synthetic method for compound 77, 3-fluoro-5-iodobenzoic acid and pyrrolidine were used to obtain compound 166-1.
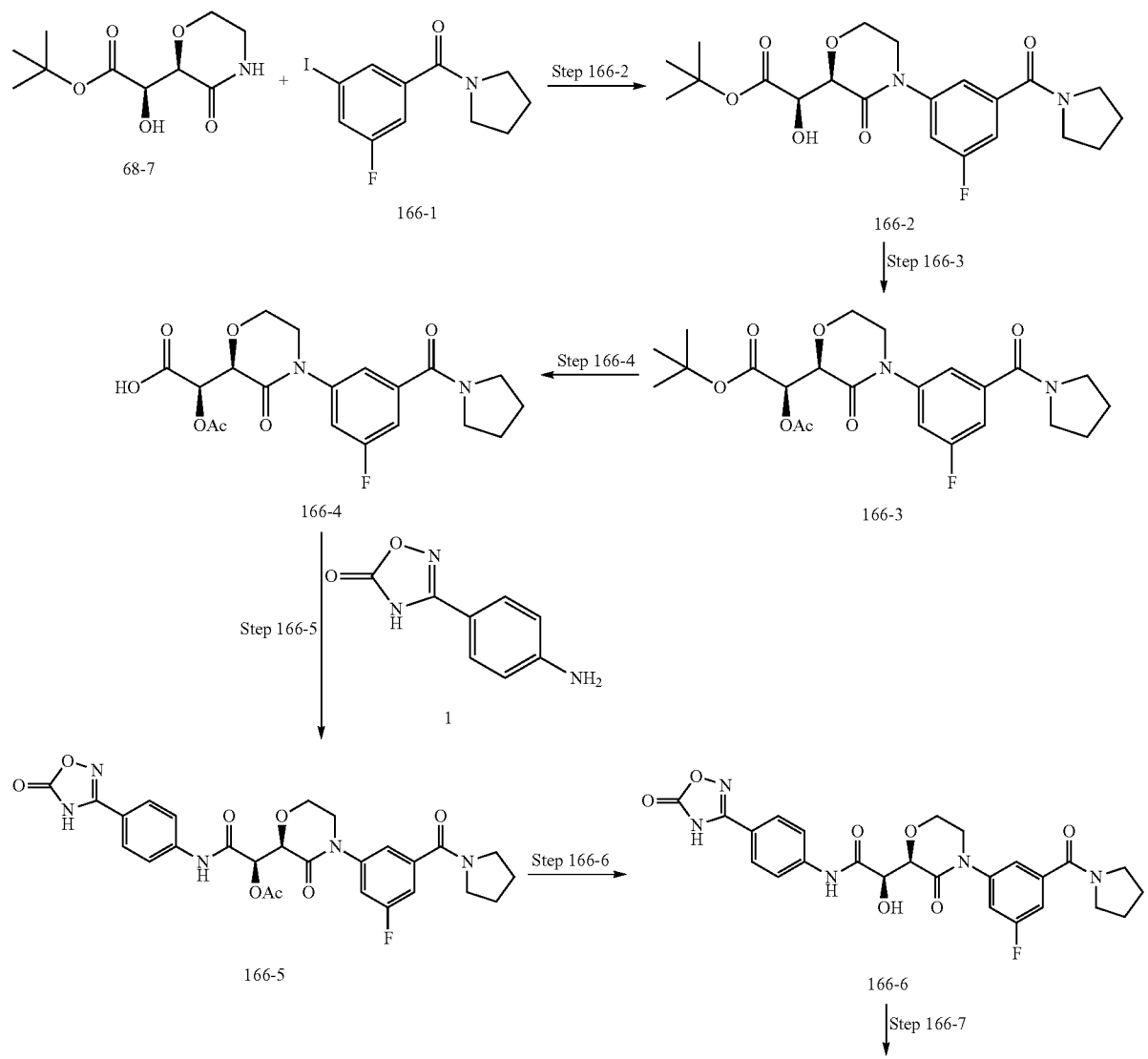

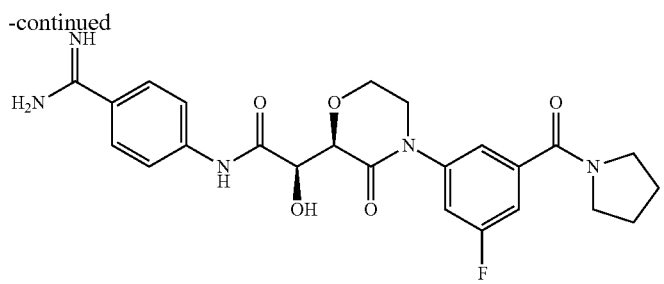

EXAMPLE 166

Step 166-2

According to Step 78-2 in the synthetic method for EXAMPLE 78, compound 166-1 (262 mg, 0.82 mmol) was used instead of compound 78-1 to obtain compound 166-2 (213 mg, 0.50 mmol).

Step 166-3

According to Step 78-3 in the synthetic method for EXAMPLE 78, compound 166-2 (213 mg, 0.50 mmol) was used instead of compound 78-2 to obtain compound 166-3 (0.50 mmol).

Step 166-4

According to Step 78-4 in the synthetic method for EXAMPLE 78, compound 166-3 (0.50 mmol) was used instead of compound 78-3 to obtain compound 166-4 (0.50 mmol) which was used in the next step without further purification.

Step 166-5

According to Step 78-5 in the synthetic method for EXAMPLE 78, compound 166-4 (0.50 mmol) was used instead of compound 78-4 to obtain compound 166-5 (275 mg, 0.49 mmol).

Step 166-6

According to Step 78-6 in the synthetic method for EXAMPLE 78, compound 169-5 (275 mg, 0.49 mmol) was used instead of compound 78-5 to obtain compound 166-6 (0.49 mmol) which was used in the next step without further purification.

Step 166-7

According to Step 78-7 in the synthetic method for EXAMPLE 78, compound 166-6 (0.49 mmol) was used instead of compound 78-6 to obtain EXAMPLE 166 (225 mg, 0.37 mmol) as a white amorphous solid.

Example 167

Synthesis of (2R)—N-(4-amidinophenyl)-2-hydroxy-2-[(2R)-3-oxo-4-(3-fluoro-5-(morpholin-4-ylcarbonyl)phenyl)morpholin-2-yl]acetamide (EXAMPLE 167)

Synthesis of 4-[(3-fluoro-5-iodophenyl)carbonyl]morpholine 167-1

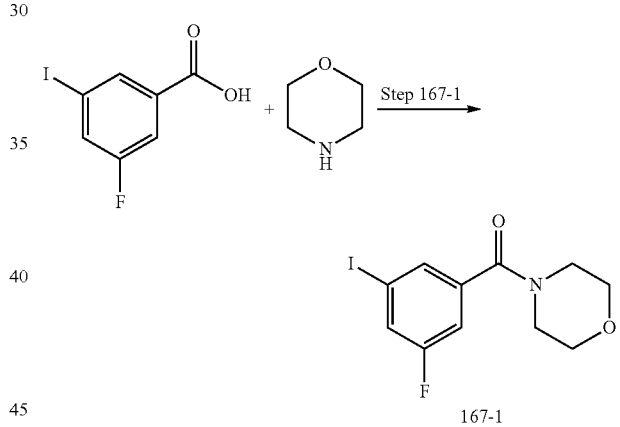

Step 167-1

According to Step 77-1 in the synthetic method for compound 77, 3-fluoro-5-iodobenzoic acid and morpholine were used to obtain compound 167-1.

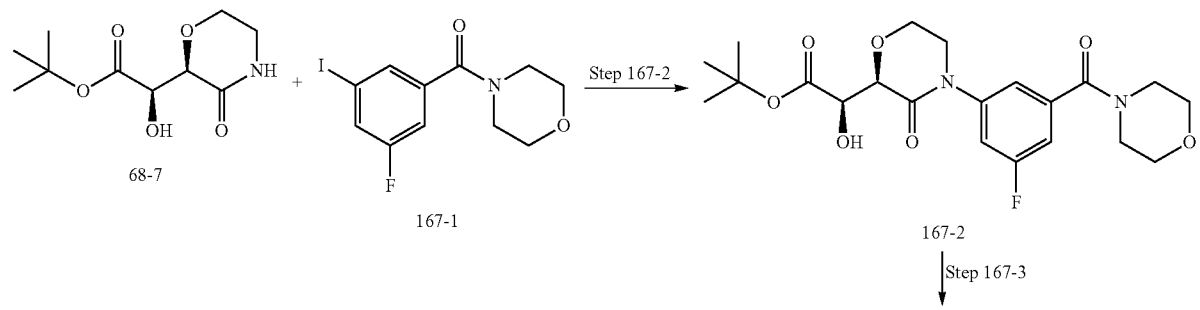

-continued

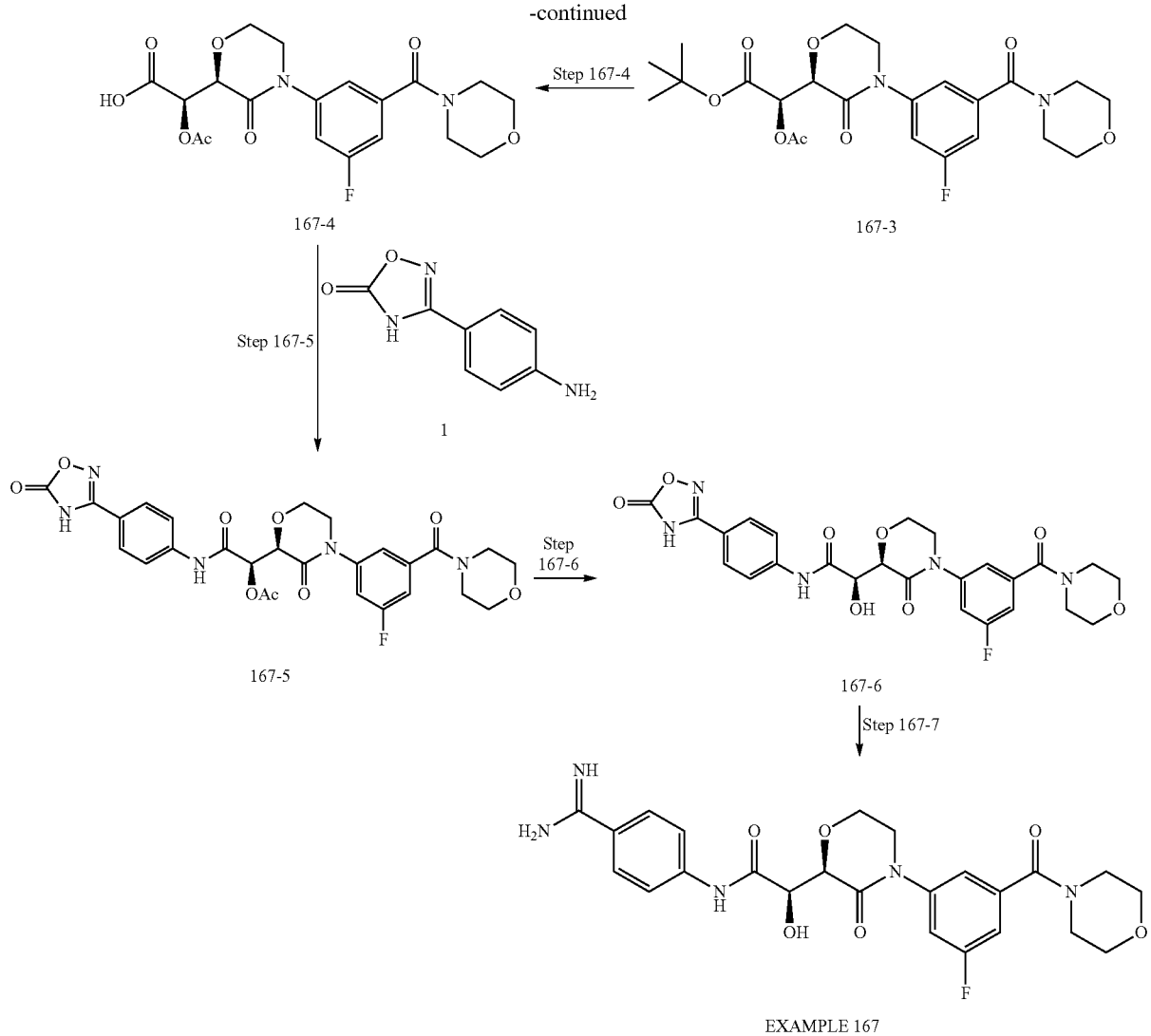

EXAMPLE 167

Step 167-2

According to Step 78-2 in the synthetic method for EXAMPLE 78, compound 167-1 (298 mg, 0.89 mmol) was used instead of compound 78-1 to obtain compound 167-2 (208 mg, 0.47 mmol).

Step 167-3

According to Step 78-3 in the synthetic method for EXAMPLE 78, compound 167-2 (208 mg, 0.47 mmol) was used instead of compound 78-2 to obtain compound 167-3 (197 mg, 0.41 mmol).

Step 167-4

According to Step 78-4 in the synthetic method for EXAMPLE 78, compound 167-3 (197 mg, 0.41 mmol) was used instead of compound 78-3 to obtain compound 167-4 (0.41 mmol) which was used in the next step without further purification.

Step 167-5

According to Step 78-5 in the synthetic method for EXAMPLE 78, compound 167-4 (0.41 mmol) was used instead of compound 78-4 to obtain compound 167-5 (221 mg, 0.38 mmol).

Step 167-6

According to Step 78-6 in the synthetic method for EXAMPLE 78, compound 167-5 (221 mg, 0.38 mmol) was used instead of compound 78-5 to obtain compound 167-6 (0.38 mmol) which was used in the next step without further purification.

Step 167-7

According to Step 78-7 in the synthetic method for EXAMPLE 78, compound 167-6 (0.38 mmol) was used instead of compound 78-6 to obtain EXAMPLE 167 (184 mg, 0.37 mmol) as a white amorphous solid.

Example 168

Synthesis of (2R)—N-(4-amidinophenyl)-2-hydroxy-2-[(2R)-3-oxo-4-(3-(dimethylaminocarbonyl)-5-fluorophenyl)morpholin-2-yl]acetamide (EXAMPLE 168)

Step 168-1

Synthesis of 3-fluoro-5-iodo-N,N-dimethylbenzamide 168-1

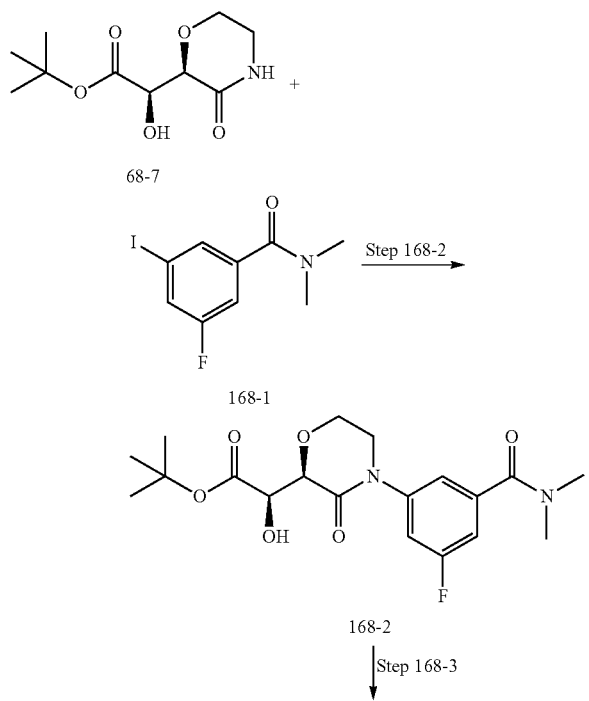

According to Step 77-1 in the synthetic method for compound 77, 3-fluoro-5-iodobenzoic acid and dimethylamine were used to obtain compound 168-1.

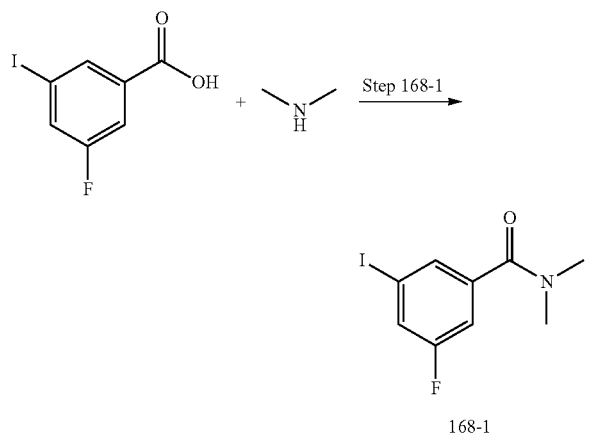

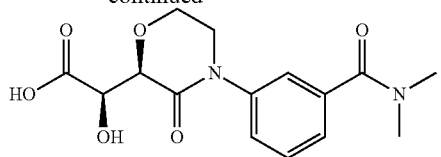

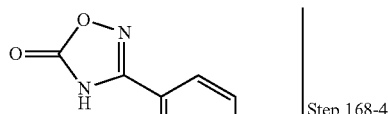

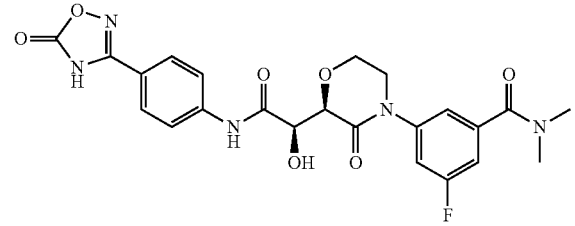

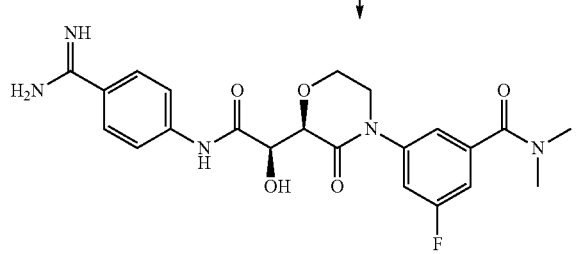

Step 168-2

According to Step 77-2 in the synthetic method for EXAMPLE 77, compound 168-1 (209 mg, 0.71 mmol) was used instead of compound 77-1 to obtain compound 168-2 (178 mg, 0.45 mmol).

Step 168-3

According to Step 77-3 in the synthetic method for EXAMPLE 77, compound 168-2 (178 mg, 0.45 mmol) was used instead of compound 77-2 to obtain compound 168-3 (0.45 mmol) which was used in the next step without further purification.

Step 168-4

According to Step 77-4 in the synthetic method for EXAMPLE 77, compound 168-3 (0.45 mmol) was used instead of compound 77-3 to obtain compound 168-4 (110 mg, 0.22 mmol).

Step 168-5

According to Step 77-5 in the synthetic method for EXAMPLE 77, compound 168-4 (110 mg, 0.22 mmol) was used instead of compound 77-4 to obtain compound EXAMPLE 168 (71 mg, 0.16 mmol) as a white amorphous solid.

Example 169
Synthesis of (2R)—N-(4-amidinophenyl)-2-hydroxy-2-[(2R)-3-oxo-4-(3-(dimethylaminocarbonyl)-2-methylphenyl)morpholin-2-yl]acetamide (EXAMPLE 169)
Synthesis of 3-iodo-2-methyl-N,N-dimethylbenzamide 169-1
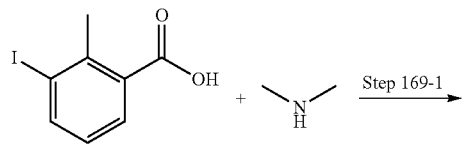
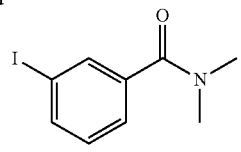
Step 169-1
According to Step 77-1 in the synthetic method for compound 77, 3-iodo-2-methylbenzoic acid and dimethylamine were used to obtain compound 169-1.
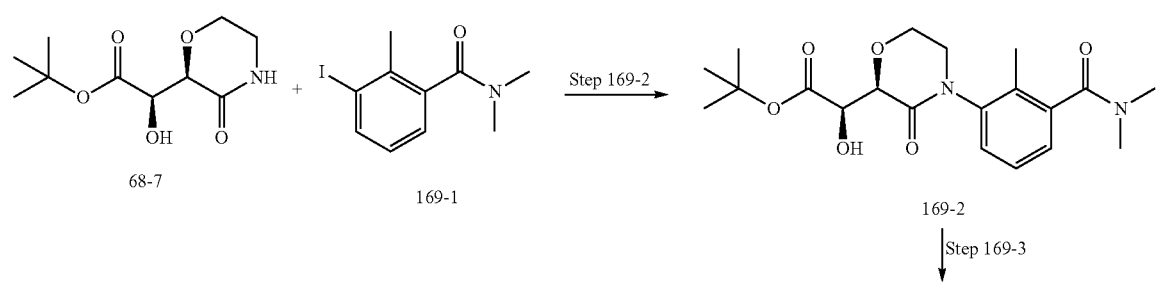
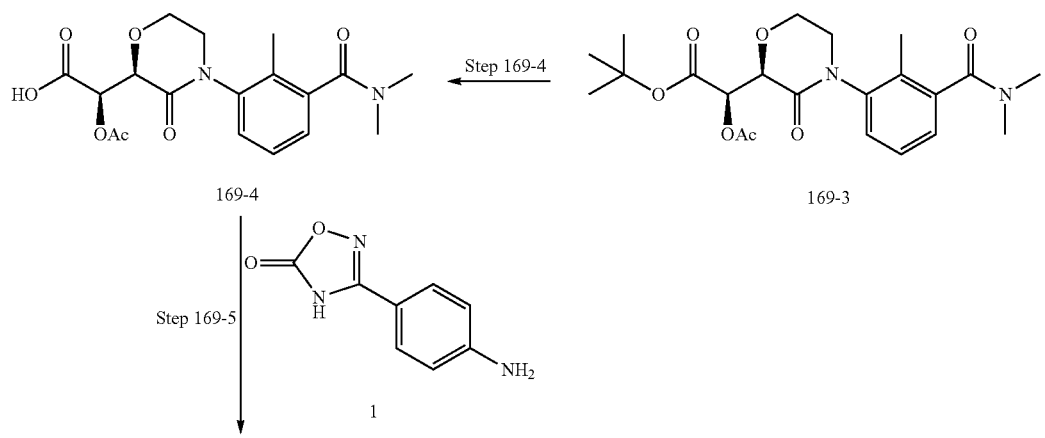
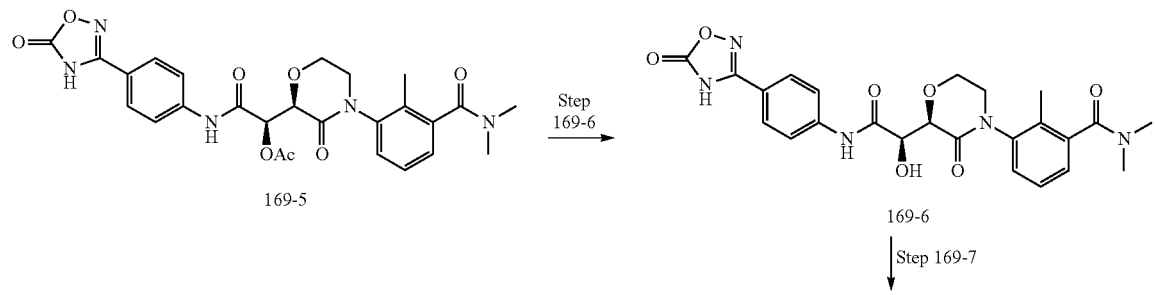

-continued

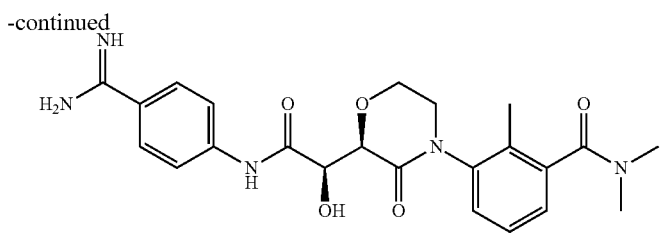

EXAMPLE 169

Step 169-2

According to Step 78-2 in the synthetic method for EXAMPLE 78, compound 169-1 (206 mg, 0.71 mmol) was used instead of compound 78-1 to obtain compound 169-2 (91 mg, 0.23 mmol).

Step 169-3

According to Step 78-3 in the synthetic method for EXAMPLE 78, compound 169-2 (91 mg, 0.23 mmol) was used instead of compound 78-2 to obtain compound 169-3 (0.23 mmol).

Step 169-4

According to Step 78-4 in the synthetic method for EXAMPLE 78, compound 169-3 (0.23 mmol) was used instead of compound 78-3 to obtain compound 169-4 (0.23 mmol) which was used in the next step without further purification.

Step 169-5

According to Step 78-5 in the synthetic method for EXAMPLE 78, compound 169-4 (0.23 mmol) was used instead of compound 78-4 to obtain compound 169-5 (80 mg, 0.15 mmol).

Step 169-6

According to Step 78-6 in the synthetic method for EXAMPLE 78, compound 169-5 (80 mg, 0.15 mmol) was used instead of compound 78-5 to obtain compound 169-6 (0.15 mmol) which was used in the next step without further purification.

Step 169-7

According to Step 78-7 in the synthetic method for EXAMPLE 78, compound 169-6 (0.15 mmol) was used instead of compound 78-6 to obtain EXAMPLE 169 (51 mg, 0.11 mmol) as a white amorphous solid.

Example 170

Synthesis of (2R)—N-(4-amidinophenyl)-2-hydroxy-2-[(2R)-3-oxo-4-(3-(piperidin-1-ylcarbonyl)phenyl)morpholin-2-yl]acetamide (EXAMPLE 170)

Synthesis of 1-[(3-iodophenyl)carbonyl]piperidine 170-1

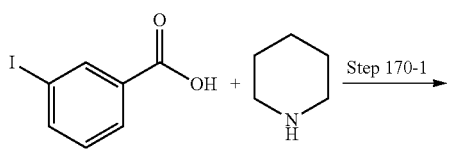

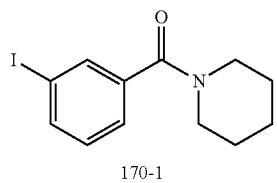

170-1

Step 170-1

According to Step 77-1 in the synthetic method for compound 77, 3-iodobenzoic acid and piperidine were used to obtain compound 170-1.

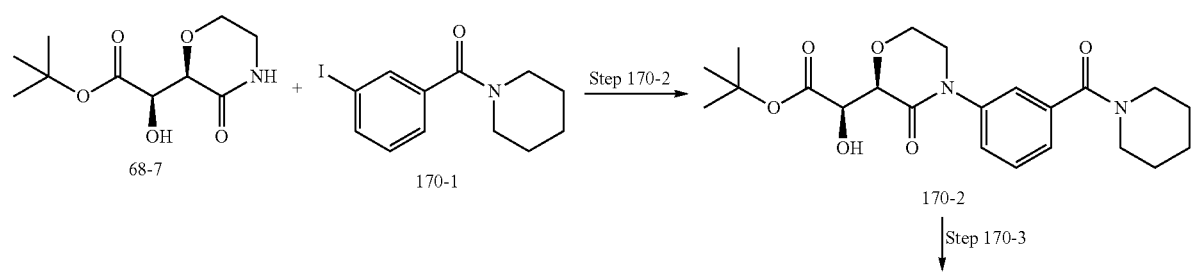

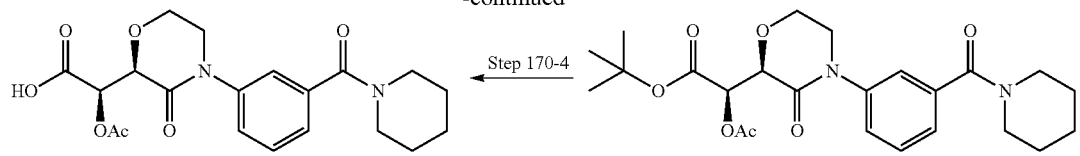

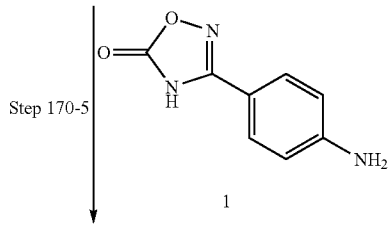

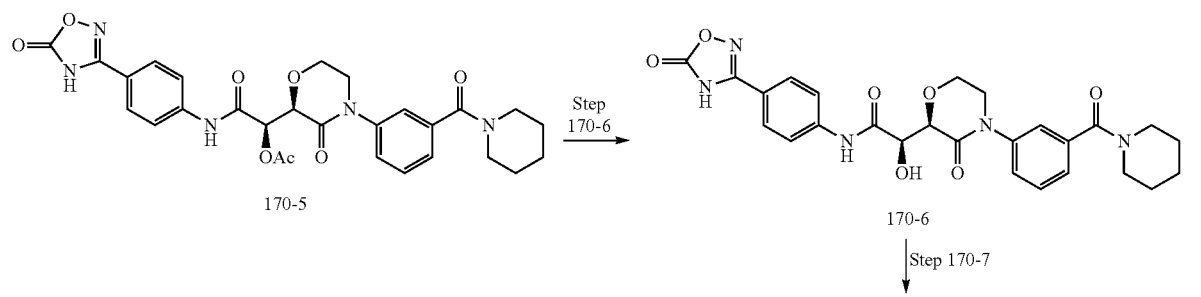

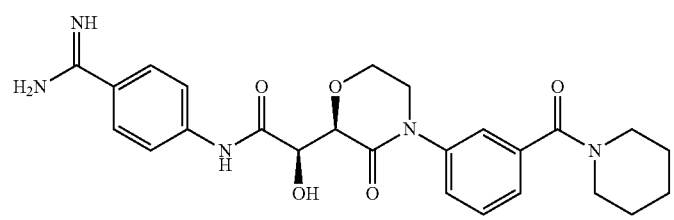

EXAMPLE 170

Step 170-2

According to Step 78-2 in the synthetic method for EXAMPLE 78, compound 170-1 (225 mg, 0.71 mmol) was used instead of compound 78-1 to obtain compound 170-2 (198 mg, 0.47 mmol).

Step 170-3

According to Step 78-3 in the synthetic method for EXAMPLE 78, compound 170-2 (198 mg, 0.47 mmol) was used instead of compound 78-2 to obtain compound 170-3 (0.47 mmol).

Step 170-4

According to Step 78-4 in the synthetic method for EXAMPLE 78, compound 170-3 (0.47 mmol) was used instead of compound 78-3 to obtain compound 170-4 (0.47 mmol) which was used in the next step without further purification.

Step 170-5

According to Step 78-5 in the synthetic method for EXAMPLE 78, compound 170-4 (0.47 mmol) was used instead of compound 78-4 to obtain compound 170-5 (249 mg, 0.44 mmol).

Step 170-6

According to Step 78-6 in the synthetic method for EXAMPLE 78, compound 170-5 (249 mg, 0.44 mmol) was used instead of compound 78-5 to obtain compound 170-6 (0.44 mmol) which was used in the next step without further purification.

Step 170-7

According to Step 78-7 in the synthetic method for EXAMPLE 78, compound 170-6 (0.44 mmol) was used instead of compound 78-6 to obtain EXAMPLE 170 (194 mg, 0.41 mmol) as a white amorphous solid.

Example 171
Synthesis of (2R)—N-(4-amidinophenyl)-2-hydroxy-2-[(2R)-3-oxo-4-(3-(azetidin-1-ylcarbonyl)phenyl)morpholin-2-yl]acetamide (EXAMPLE 171)
Synthesis of 1-[(3-iodophenyl)carbonyl]azetidine 171-1
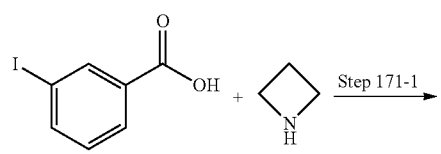
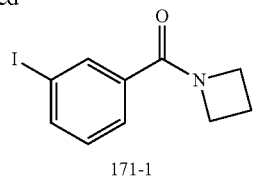
Step 171-1
According to Step 77-1 in the synthetic method for compound 77, 3-iodobenzoic acid and azetidine were used to obtain compound 171-1.
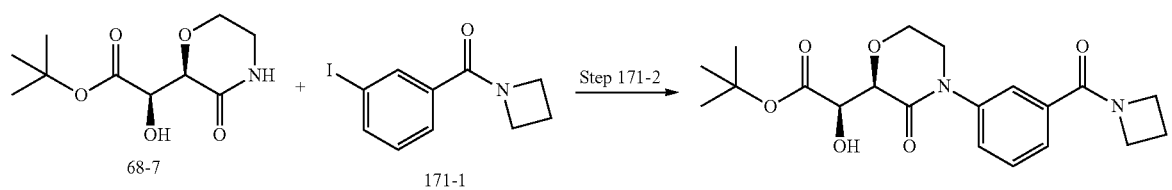
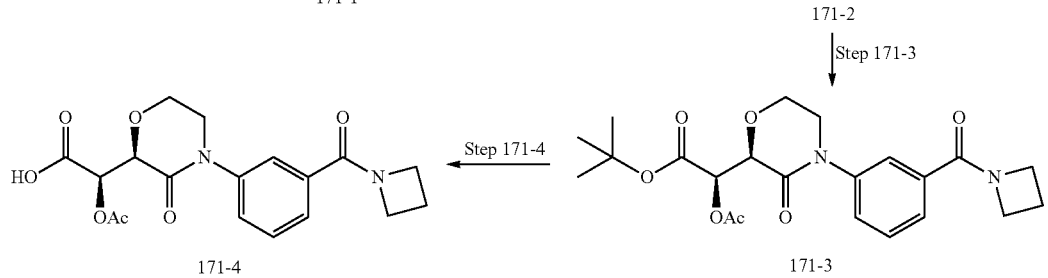
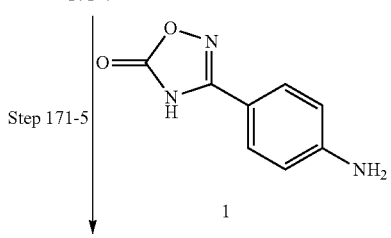
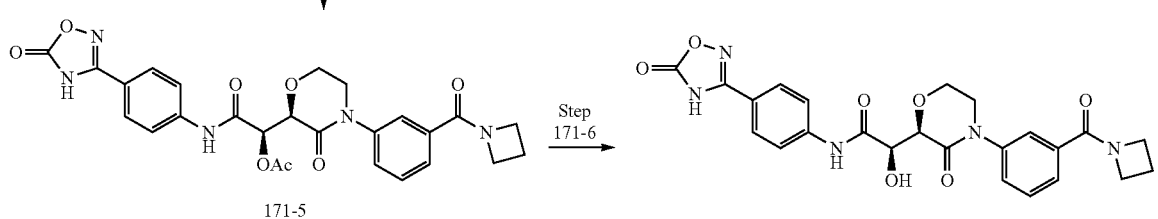
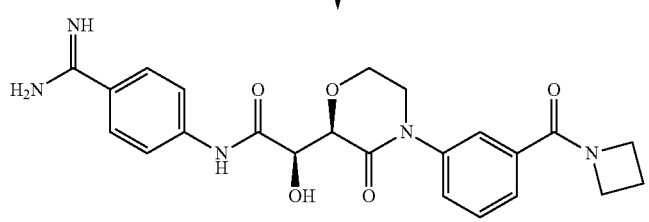
EXAMPLE 171

Step 171-2

According to Step 78-2 in the synthetic method for EXAMPLE 78, compound 171-1 (205 mg, 0.71 mmol) was used instead of compound 78-1 to obtain compound 171-2 (121 mg, 0.31 mmol).

Step 171-3

According to Step 78-3 in the synthetic method for EXAMPLE 78, compound 171-2 (121 mg, 0.31 mmol) was used instead of compound 78-2 to obtain compound 171-3 (111 mg, 0.26 mmol).

Step 171-4

According to Step 78-4 in the synthetic method for EXAMPLE 78, compound 171-3 (111 mg, 0.26 mmol) was used instead of compound 78-3 to obtain compound 171-4 (0.26 mmol) which was used in the next step without further purification.

Step 171-5

According to Step 78-5 in the synthetic method for EXAMPLE 78, compound 171-4 (0.26 mmol) was used instead of compound 78-4 to obtain compound 171-5 (112 mg, 0.21 mmol).

Step 171-6

According to Step 78-6 in the synthetic method for EXAMPLE 78, compound 171-5 (112 mg, 0.21 mmol) was used instead of compound 78-5 to obtain compound 171-6 (0.21 mmol) which was used in the next step without further purification.

Step 171-7

According to Step 78-7 in the synthetic method for EXAMPLE 78, compound 171-6 (0.21 mmol) was used instead of compound 78-6 to obtain EXAMPLE 171 (88 mg, 0.20 mmol) as a white amorphous solid.

Example 172

Synthesis of (2R)—N-(4-amidinophenyl)-2-hydroxy-2-[(2R)-3-oxo-4-(3-((2R,5R)-(−)-trans-dimethylpyrrolidin-1-ylcarbonyl)phenyl)morpholin-2-yl]acetamide (EXAMPLE 172)

Step 172-1

Synthesis of (2R,5R)-(−)-trans-dimethyl-1-[(3-iodophenyl)carbonyl]pyrrolidine 172-1

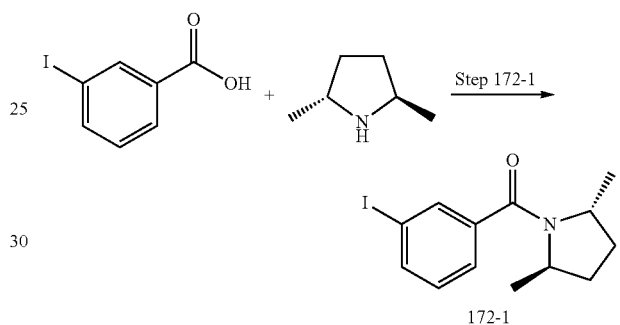

According to Step 77-1 in the synthetic method for compound 77, 3-iodobenzoic acid and (2R,5R)-(−)-trans-dimethylpyrrolidine were used to obtain compound 172-1.

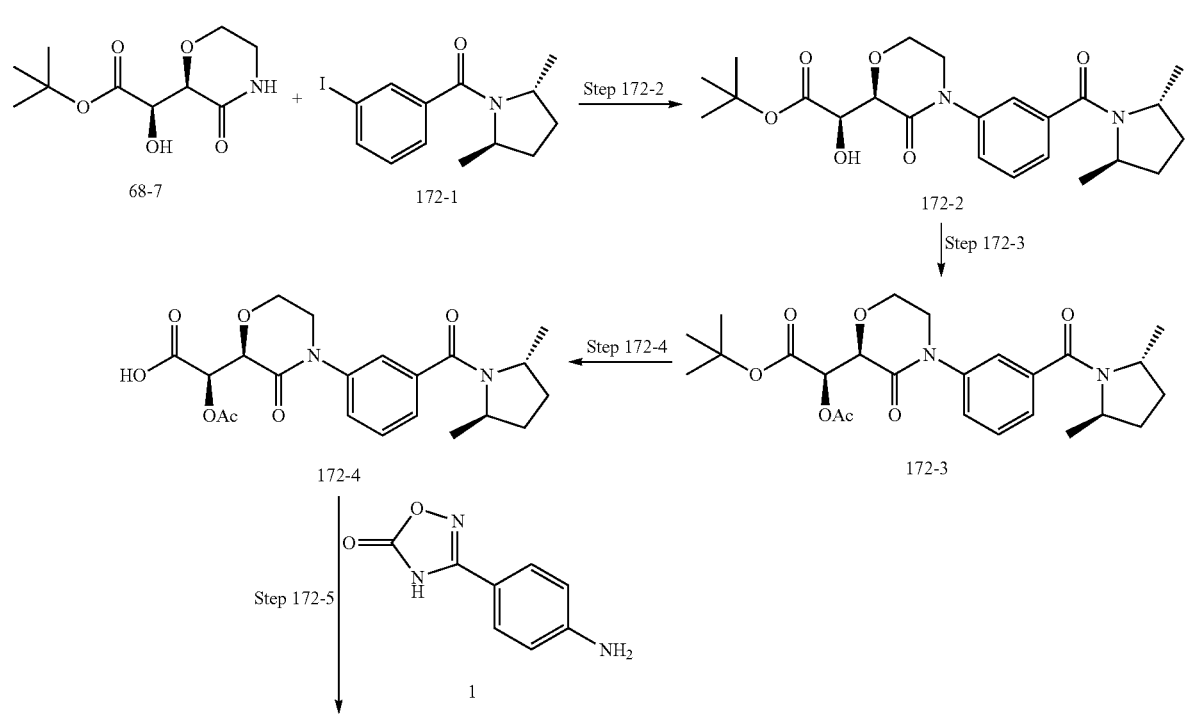

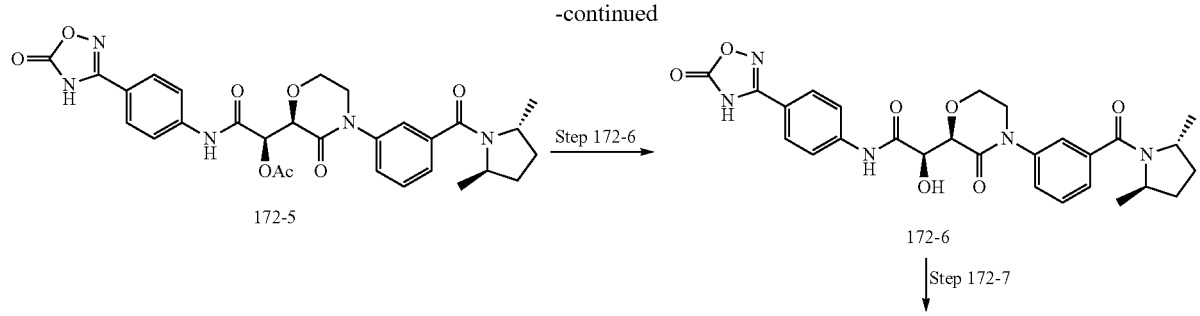

Step 172-2

According to Step 78-2 in the synthetic method for EXAMPLE 78, compound 172-1 (190 mg, 0.58 mmol) was used instead of compound 78-1 to obtain compound 172-2 (98 mg, 0.23 mmol).

Step 172-3

According to Step 78-3 in the synthetic method for EXAMPLE 78, compound 172-2 (98 mg, 0.23 mmol) was used instead of compound 78-2 to obtain compound 172-3 (85 mg, 0.18 mmol).

Step 172-4

According to Step 78-4 in the synthetic method for EXAMPLE 78, compound 172-3 (85 mg, 0.18 mmol) was used instead of compound 78-3 to obtain compound 172-4 (0.18 mmol) which was used in the next step without further purification.

Step 172-5

According to Step 78-5 in the synthetic method for EXAMPLE 78, compound 172-4 (0.18 mmol) was used instead of compound 78-4 to obtain compound 172-5 (103 mg, 0.18 mmol).

Step 172-6

According to Step 78-6 in the synthetic method for EXAMPLE 78, compound 172-5 (103 mg, 0.18 mmol) was used instead of compound 78-5 to obtain compound 172-6 (0.18 mmol) which was used in the next step without further purification.

Step 172-7

According to Step 78-7 in the synthetic method for EXAMPLE 78, compound 172-6 (0.18 mmol) was used instead of compound 78-6 to obtain EXAMPLE 172 (83 mg, 0.17 mmol) as a white amorphous solid.

Example 173

Synthesis of (2R)—N-(4-amidinophenyl)-2-hydroxy-2-[(2R)-3-oxo-4-(3-fluorophenyl)morpholin-2-yl]acetamide (EXAMPLE 173)

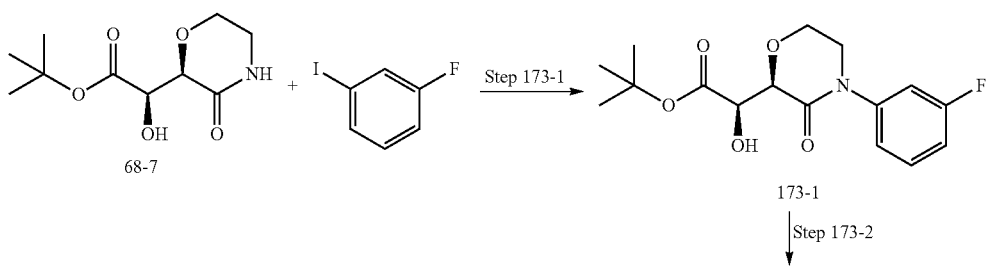

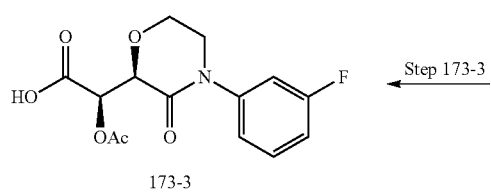

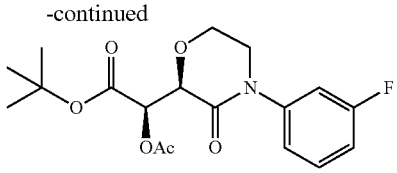

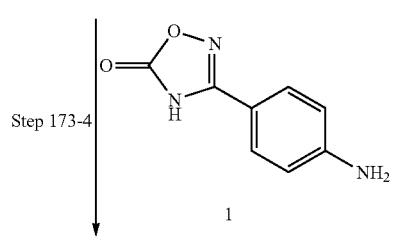

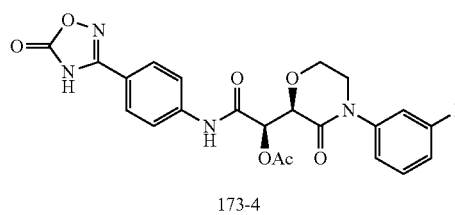

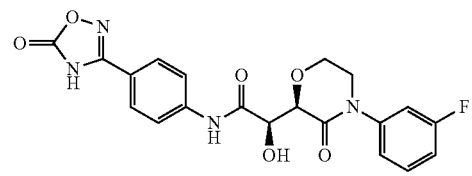

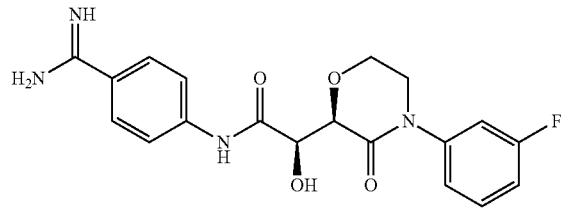

EXAMPLE 173

Step 173-1

According to Step 78-2 in the synthetic method for EXAMPLE 78, 3-fluoro-5-iodobenzene (79 mg, 0.36 mmol) was used instead of compound 78-1 to obtain compound 173-1 (87 mg, 0.27 mmol).

Step 173-2

According to Step 78-3 in the synthetic method for EXAMPLE 78, compound 173-1 (87 mg, 0.27 mmol) was used instead of compound 78-2 to obtain compound 173-2 (98 mg, 0.27 mmol).

Step 173-3

According to Step 78-4 in the synthetic method for EXAMPLE 78, compound 173-2 (98 mg, 0.27 mmol) was used instead of compound 78-3 to obtain compound 173-3 (0.27 mmol) which was used in the next step without further purification.

Step 173-4

According to Step 78-5 in the synthetic method for EXAMPLE 78, compound 173-3 (0.27 mmol) was used instead of compound 78-4 to obtain compound 173-4 (0.27 mmol).

Step 173-5

According to Step 78-6 in the synthetic method for EXAMPLE 78, compound 173-4 (0.27 mmol) was used instead of compound 78-5 to obtain compound 173-5 (0.27 mmol) which was used in the next step without further purification.

Step 173-6

According to Step 78-7 in the synthetic method for EXAMPLE 78, compound 173-5 (0.27 mmol) was used instead of compound 78-6 to obtain EXAMPLE 173 (81 mg, 0.21 mmol) as a white amorphous solid.

Example 174
Synthesis of (2R)—N-(4-amidinophenyl)-2-hydroxy-2-[(2R)-3-oxo-4-(3,4,5-trifluorophenyl)morpholin-2-yl]acetamide (EXAMPLE 174)
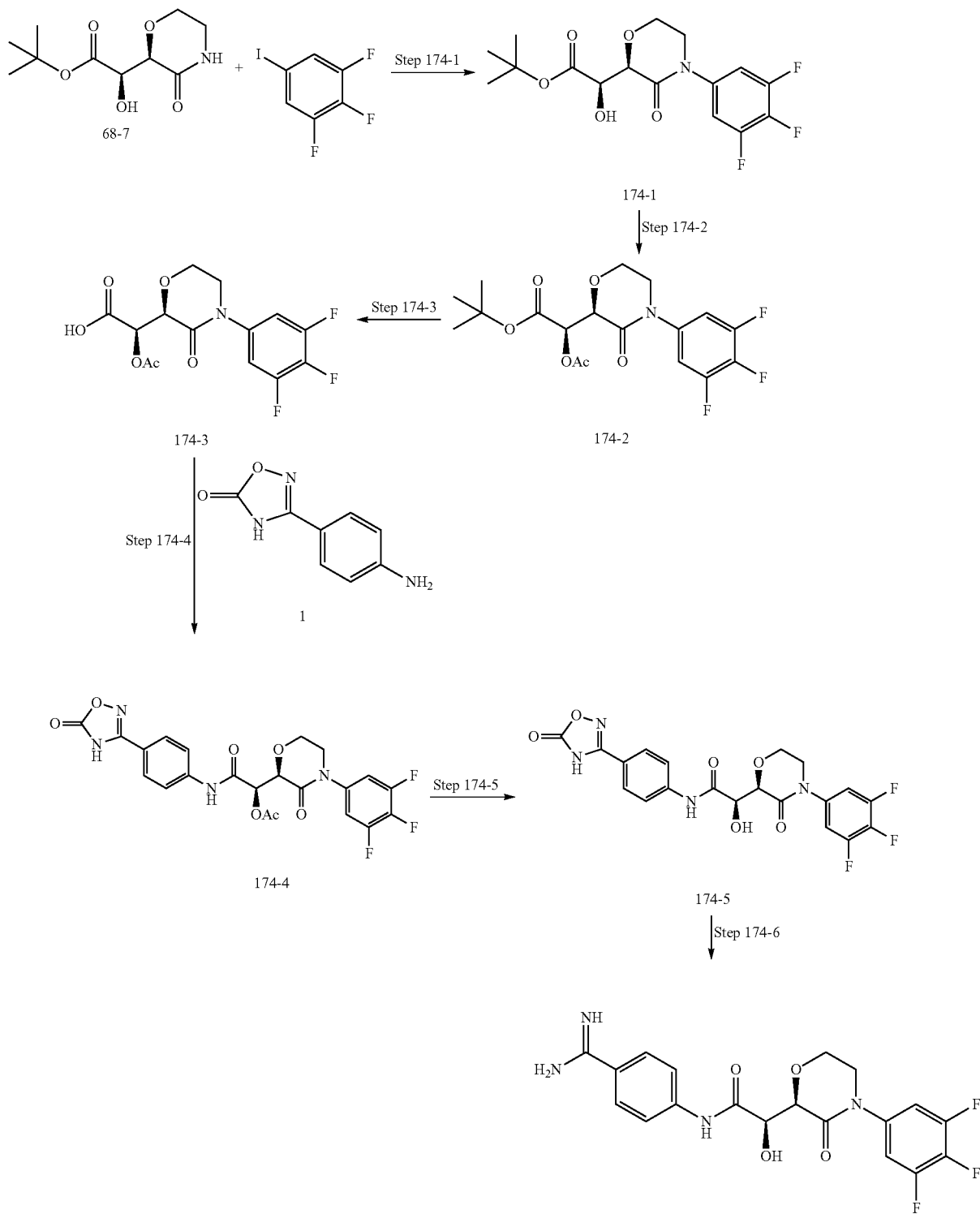

Step 174-1

According to Step 78-2 in the synthetic method for EXAMPLE 78, 3,4,5-trifluoro-5-iodobenzene (93 mg, 0.36 mmol) was used instead of compound 78-1 to obtain compound 174-1 (54 mg, 0.15 mmol).

Step 174-2

According to Step 78-3 in the synthetic method for EXAMPLE 78, compound 174-1 (117 mg, 0.32 mmol) was used instead of compound 78-2 to obtain compound 174-2 (121 mg, 0.30 mmol).

Step 174-3

According to Step 78-4 in the synthetic method for EXAMPLE 78, compound 174-2 (121 mg, 0.30 mmol) was used instead of compound 78-3 to obtain compound 174-3 (0.30 mmol) which was used in the next step without further purification.

Step 174-4

According to Step 78-5 in the synthetic method for EXAMPLE 78, compound 174-3 (0.30 mmol) was used instead of compound 78-4 to obtain compound 169-4 (151 mg, 0.30 mmol).

Step 174-5

According to Step 78-6 in the synthetic method for EXAMPLE 78, compound 174-4 (151 mg, 0.30 mmol) was used instead of compound 78-5 to obtain compound 174-5 (0.30 mmol) which was used in the next step without further purification.

Step 174-6

According to Step 78-7 in the synthetic method for EXAMPLE 78, compound 174-5 (0.30 mmol) was used instead of compound 78-6 to obtain EXAMPLE 174 (48 mg, 0.10 mmol) as a white amorphous solid.

Example 175

Synthesis of (2R)—N-(4-amidinophenyl)-2-hydroxy-2-[(2R)-3-oxo-4-(3,4-difluorophenyl)morpholin-2-yl]acetamide (EXAMPLE 175)

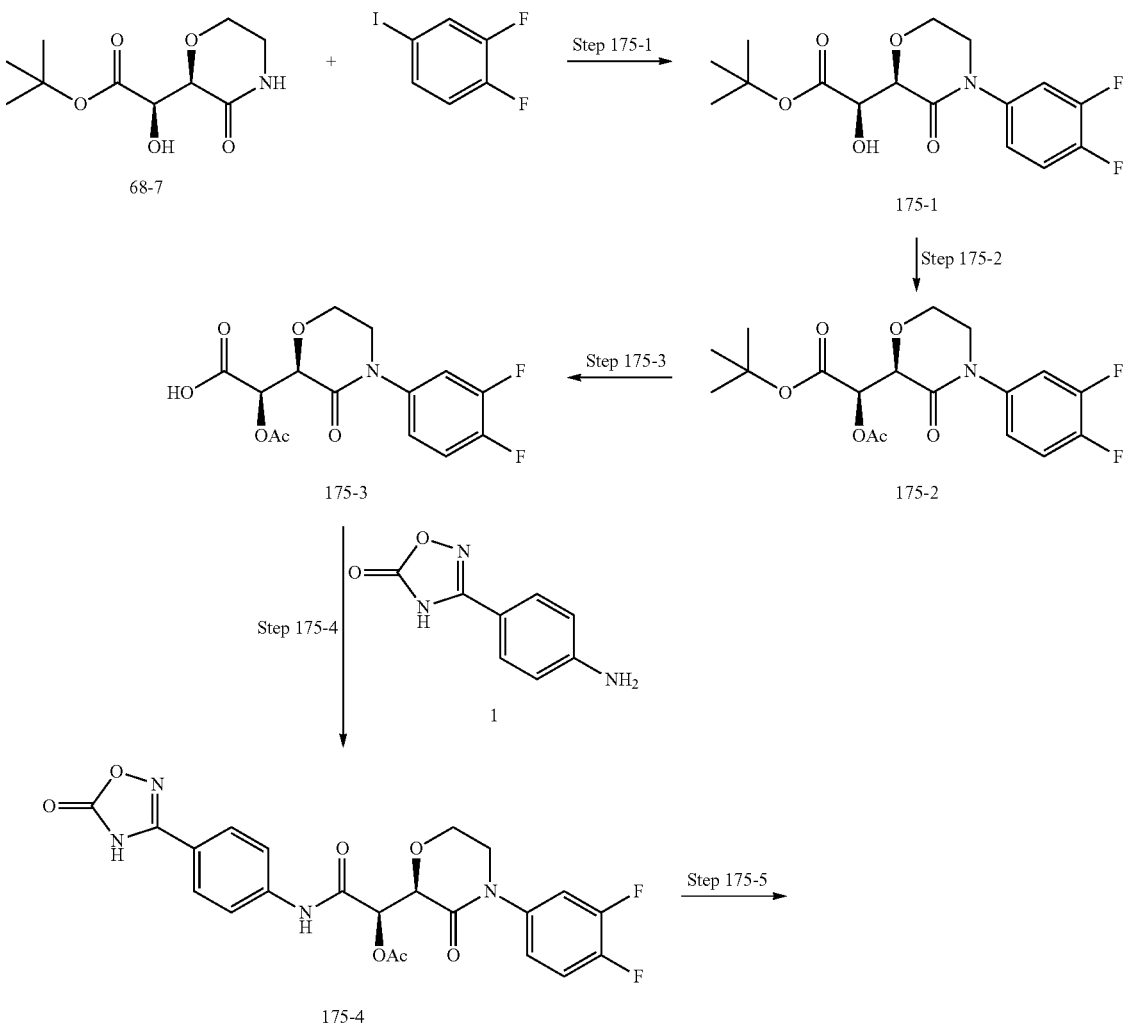

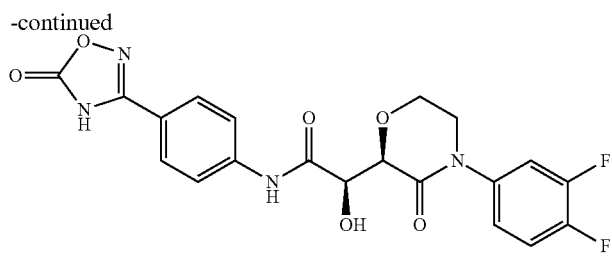

175-5

Step 175-6

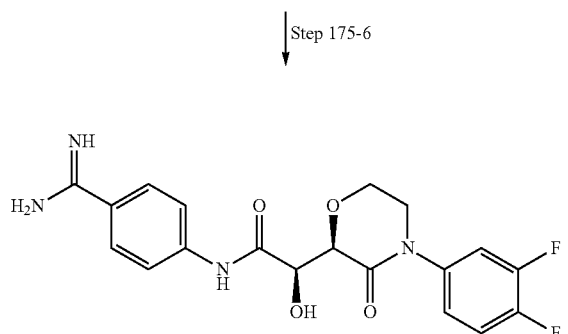

EXAMPLE 175

Step 175-1

According to Step 78-2 in the synthetic method for EXAMPLE 78, 3,4-difluoro-5-iodobenzene (86 mg, 0.36 mmol) was used instead of compound 78-1 to obtain compound 175-1 (54 mg, 0.13 mmol).

Step 175-2

According to Step 78-3 in the synthetic method for EXAMPLE 78, compound 175-1 (94 mg, 0.27 mmol) was used instead of compound 78-2 to obtain compound 175-2 (88 mg, 0.23 mmol).

Step 175-3

According to Step 78-4 in the synthetic method for EXAMPLE 78, compound 175-2 (88 mg, 0.23 mmol) was used instead of compound 78-3 to obtain compound 175-3 (0.23 mmol) which was used in the next step without further purification.

Step 175-4

According to Step 78-5 in the synthetic method for EXAMPLE 78, compound 175-3 (0.23 mmol) was used instead of compound 78-4 to obtain compound 175-4 (0.23 mmol).

Step 175-5

According to Step 78-6 in the synthetic method for EXAMPLE 78, compound 175-4 (0.23 mmol) was used instead of compound 78-5 to obtain compound 175-5 (0.23 mmol) which was used in the next step without further purification.

Step 175-6

According to Step 78-7 in the synthetic method for EXAMPLE 78, compound 175-5 (0.23 mmol) was used instead of compound 78-6 to obtain EXAMPLE 175 (99 mg, 0.23 mmol) as a white amorphous solid.

Example 176

Synthesis of (2R)—N-(4-amidinophenyl)-2-hydroxy-2-[(2R)-3-oxo-4-(2,4-difluoropyridin-3-yl)morpholin-2-yl]acetamide (EXAMPLE 176)

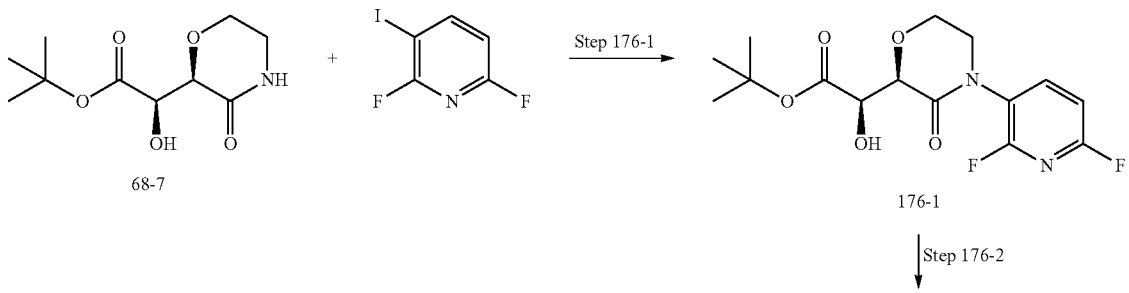

Step 176-2

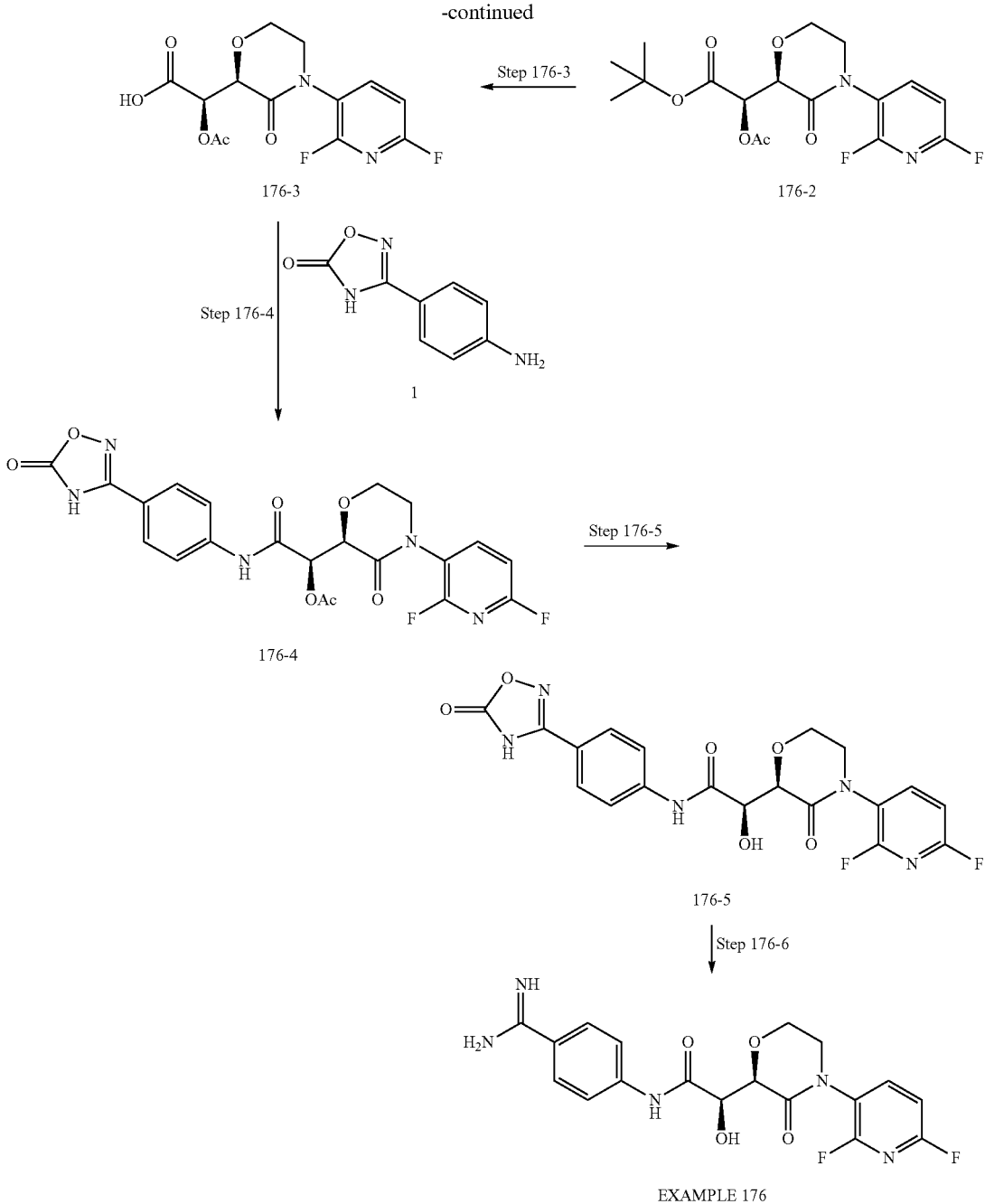

EXAMPLE 176

Step 176-1

According to Step 78-2 in the synthetic method for EXAMPLE 78, 2,6-difluoropyridine (174 mg, 0.72 mmol) was used instead of compound 78-1 to obtain compound 176-1 (42 mg, 0.12 mmol).

Step 176-2

According to Step 78-3 in the synthetic method for EXAMPLE 78, compound 176-1 (55 mg, 0.16 mmol) was used instead of compound 78-2 to obtain compound 176-2 (63 mg, 0.16 mmol).

Step 176-3

According to Step 78-4 in the synthetic method for EXAMPLE 78, compound 176-2 (63 mg, 0.16 mmol) was used instead of compound 78-3 to obtain compound 176-3 (0.16 mmol) which was used in the next step without further purification.

Step 176-4

According to Step 78-5 in the synthetic method for EXAMPLE 78, compound 176-3 (0.16 mmol) was used instead of compound 78-4 to obtain compound 176-4 (73 mg, 0.15 mmol).

Step 176-5

According to Step 78-6 in the synthetic method for EXAMPLE 78, compound 176-4 (73 mg, 0.15 mmol) was used instead of compound 78-5 to obtain compound 176-5 (0.15 mmol) which was used in the next step without further purification.

Step 176-6

According to Step 78-7 in the synthetic method for EXAMPLE 78, compound 176-5 (0.15 mmol) was used instead of compound 78-6 to obtain EXAMPLE 176 (13 mg, 0.032 mmol) as a white amorphous solid.

Example 177

Synthesis of (2R)—N-(4-amidinophenyl)-2-hydroxy-2-[(2R)-3-oxo-4-(4,5-difluoropyridin-3-yl)morpholin-2-yl]acetamide (EXAMPLE 177)

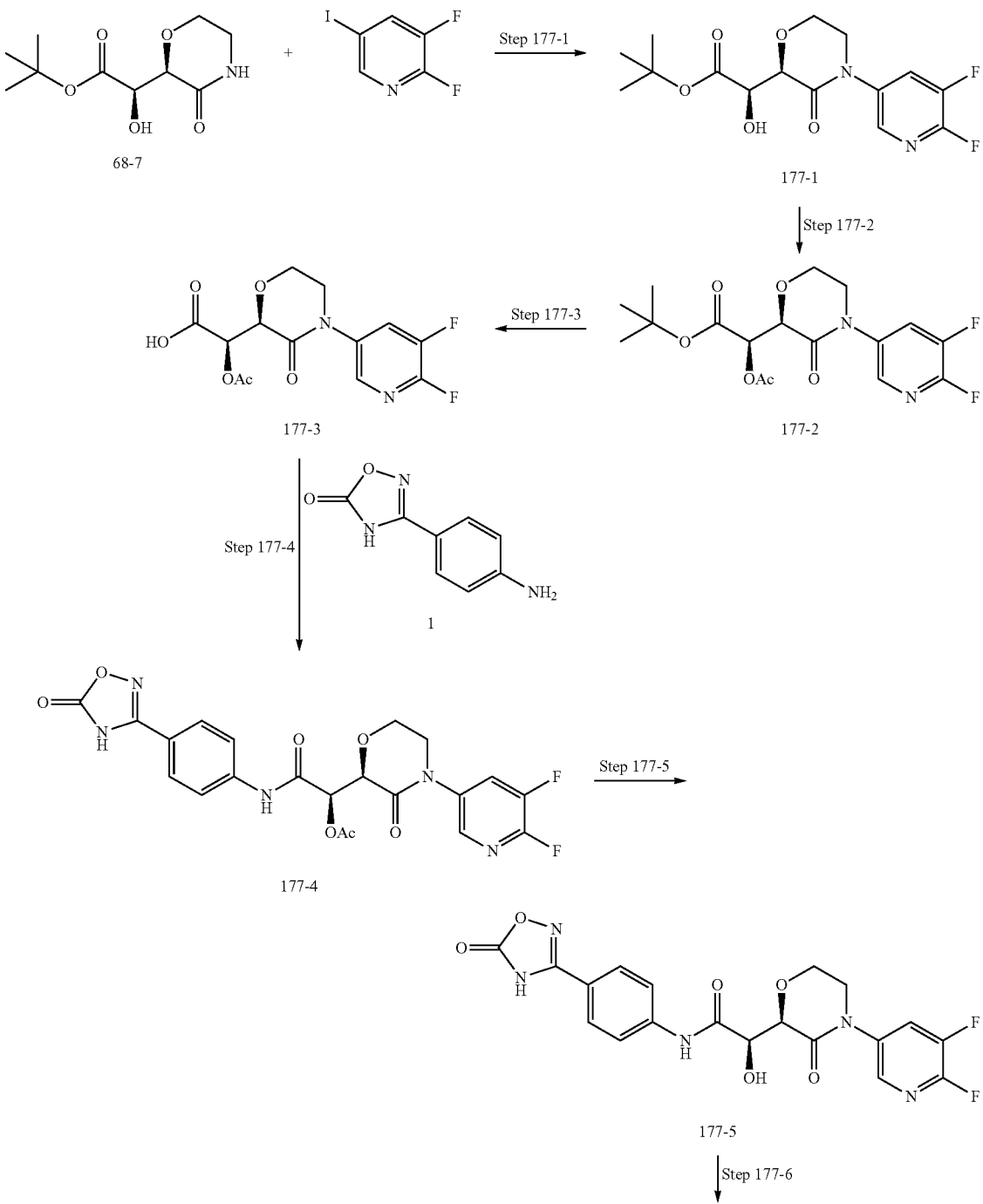

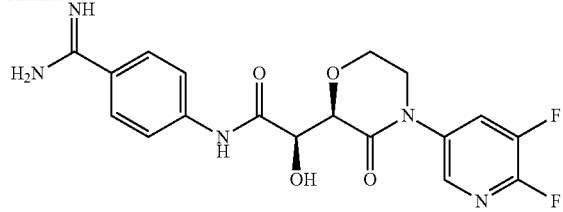

EXAMPLE 177

Step 177-1

According to Step 78-2 in the synthetic method for EXAMPLE 78, 2,3-difluoropyridine (174 mg, 0.72 mmol) was used instead of compound 78-1 to obtain compound 177-1 (106 mg, 0.31 mmol).

Step 177-2

According to Step 78-3 in the synthetic method for EXAMPLE 78, compound 177-1 (150 mg, 0.44 mmol) was used instead of compound 78-2 to obtain compound 177-2 (95 mg, 0.25 mmol).

Step 177-3

According to Step 78-4 in the synthetic method for EXAMPLE 78, compound 177-2 (95 mg, 0.25 mmol) was used instead of compound 78-3 to obtain compound 177-3 (0.25 mmol) which was used in the next step without further purification.

Step 177-4

According to Step 78-5 in the synthetic method for EXAMPLE 78, compound 177-3 (0.25 mmol) was used instead of compound 78-4 to obtain compound 177-4 (123 mg, 0.25 mmol).

Step 177-5

According to Step 78-6 in the synthetic method for EXAMPLE 78, compound 177-4 (123 mg, 0.25 mmol) was used instead of compound 78-5 to obtain compound 177-5 (0.25 mmol) which was used in the next step without further purification.

Step 177-6

According to Step 78-7 in the synthetic method for EXAMPLE 78, compound 177-5 (0.25 mmol) was used instead of compound 78-6 to obtain EXAMPLE 177 (65 mg, 0.15 mmol) as a white amorphous solid.

Example 178

Synthesis of (2R)—N-(4-amidinophenyl)-2-hydroxy-2-[(2R)-3-oxo-4-(4-carboxyphenyl)morpholin-2-yl]acetamide (EXAMPLE 178)

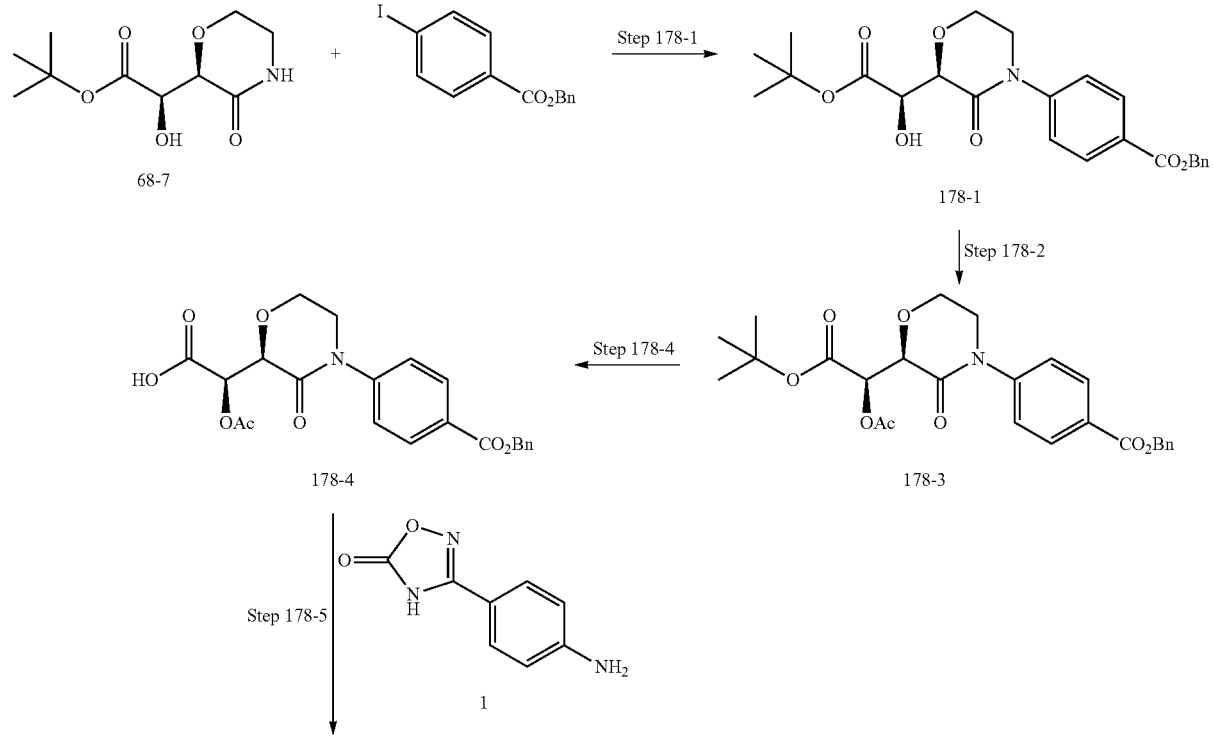

-continued

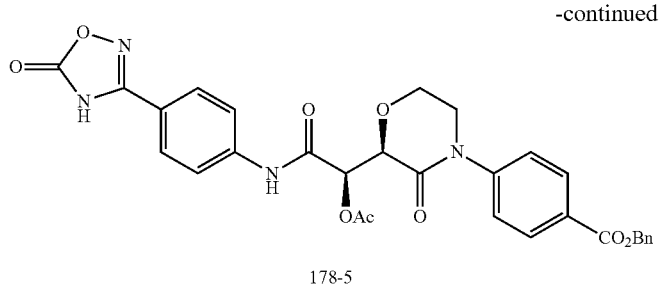
178-5

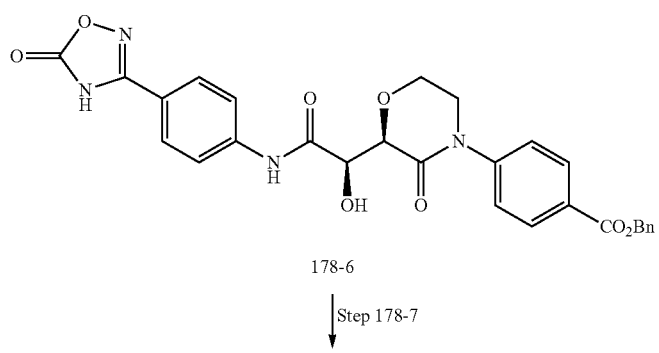
178-6

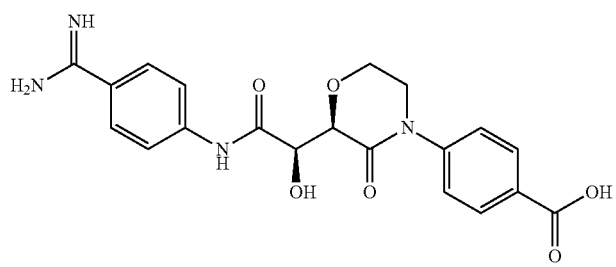
EXAMPLE 178

Step 178-1

According to Step 78-2 in the synthetic method for EXAMPLE 78, benzyl 4-iodobenzoate (122 mg, 0.36 mmol) was used instead of compound 78-1 to obtain compound 178-1 (110 mg, 0.25 mmol).

Step 178-2

According to Step 78-3 in the synthetic method for EXAMPLE 78, compound 178-1 (110 mg, 0.25 mmol) was used instead of compound 78-2 to obtain compound 178-2 (111 mg, 0.23 mmol).

Step 178-3

According to Step 78-4 in the synthetic method for EXAMPLE 78, compound 178-2 (111 mg, 0.23 mmol) was used instead of compound 78-3 to obtain compound 178-3 (0.23 mmol) which was used in the next step without further purification.

Step 178-4

According to Step 78-5 in the synthetic method for EXAMPLE 78, compound 178-3 (0.23 mmol) was used instead of compound 78-4 to obtain compound 169-4 (132 mg, 0.23 mmol).

Step 178-5

According to Step 78-6 in the synthetic method for EXAMPLE 78, compound 178-4 (132 mg, 0.23 mmol) was used instead of compound 78-5 to obtain compound 178-5 (0.23 mmol) which was used in the next step without further purification.

Step 178-6

According to Step 78-7 in the synthetic method for EXAMPLE 78, compound 178-5 (0.23 mmol) was used instead of compound 78-6 to obtain EXAMPLE 178 (61 mg, 0.15 mmol) as a white amorphous solid.

Example 179
Synthesis of (2R)—N-(4-amidinophenyl)-2-hydroxy-2-[(2R)-3-oxo-4-(3-(carboxymethyl)(methyl)carbamoylphenyl)morpholin-2-yl]acetamide (EXAMPLE 179)
Step 179-1
Synthesis of benzyl 2-(3-iodo-N-methylbenzamido)acetate 179-1
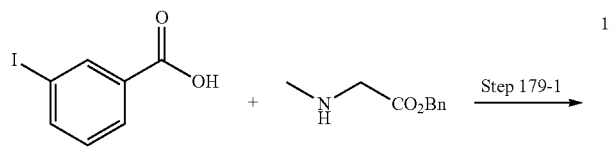
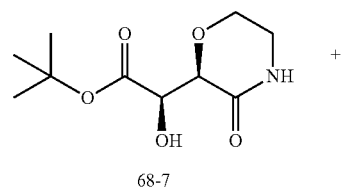
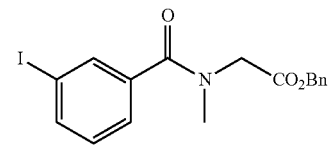
According to Step 77-1 in the synthetic method for compound 77, 3-iodobenzoic acid and sarcosine benzyl ester were used to obtain compound 179-1.
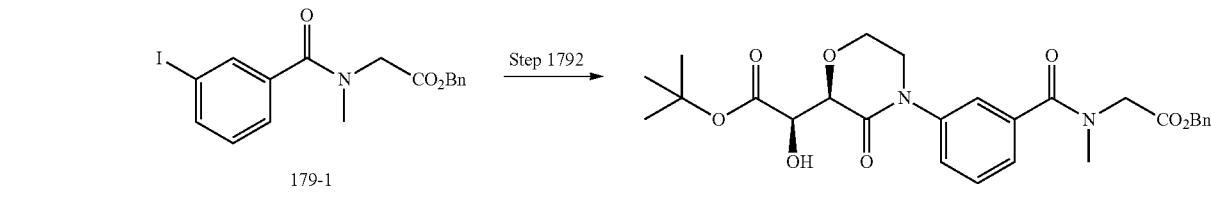
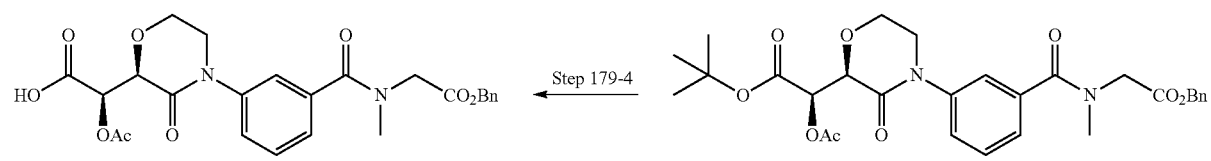
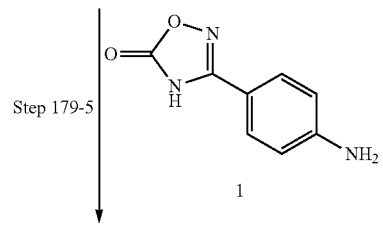

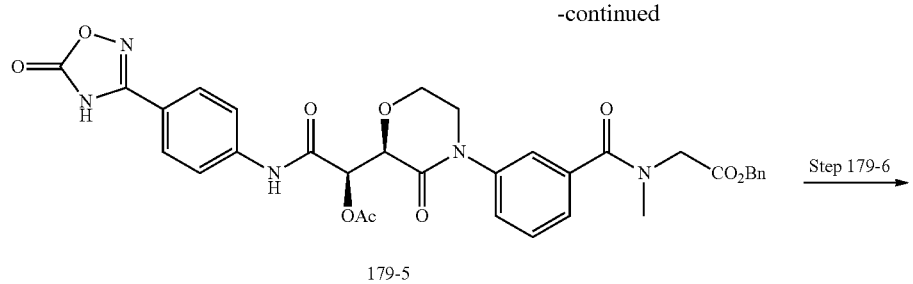

179-5

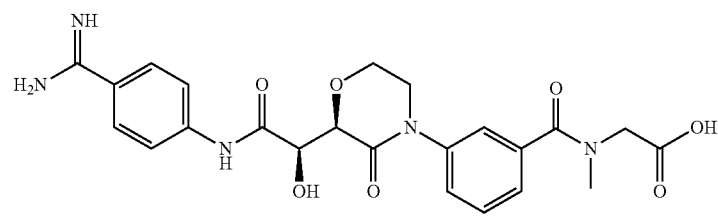

179-6

Step 179-7

[Structure of EXAMPLE 179]

EXAMPLE 179

Step 179-2

According to Step 78-3 in the synthetic method for EXAMPLE 78, compound 179-1 (189 mg, 0.46 mmol) was used instead of compound 78-2 to obtain compound 179-2 (150 mg, 0.29 mmol).

Step 179-3

According to Step 78-2 in the synthetic method for EXAMPLE 78, compound 179-2 (150 mg, 0.29 mmol) was used instead of compound 78-2 to obtain compound 179-3 (139 mg, 0.25 mmol).

Step 179-4

According to Step 78-4 in the synthetic method for EXAMPLE 78, compound 179-3 (139 mg, 0.25 mmol) was used instead of compound 78-3 to obtain compound 179-4 (0.25 mmol) which was used in the next step without further purification.

Step 179-5

According to Step 78-5 in the synthetic method for EXAMPLE 78, compound 179-4 (0.25 mmol) was used instead of compound 78-4 to obtain compound 179-5 (166 mg, 0.25 mmol).

Step 179-6

According to Step 78-6 in the synthetic method for EXAMPLE 78, compound 179-5 (252 mg, 0.38 mmol) was used instead of compound 78-5 to obtain compound 179-6 (145 mg, 0.24 mmol) which was used in the next step without further purification.

Step 179-7

According to Step 78-7 in the synthetic method for EXAMPLE 78, compound 179-6 (145 mg, 0.24 mmol) was used instead of compound 78-6 to obtain EXAMPLE 179 (54 mg, 0.11 mmol) as a white amorphous solid.

Example 180
Synthesis of (2R)—N-(4-amidinophenyl)-2-hydroxy-2-[(2R)-3-oxo-4-(3-carboxyphenyl)morpholin-2-yl]acetamide (EXAMPLE 180)
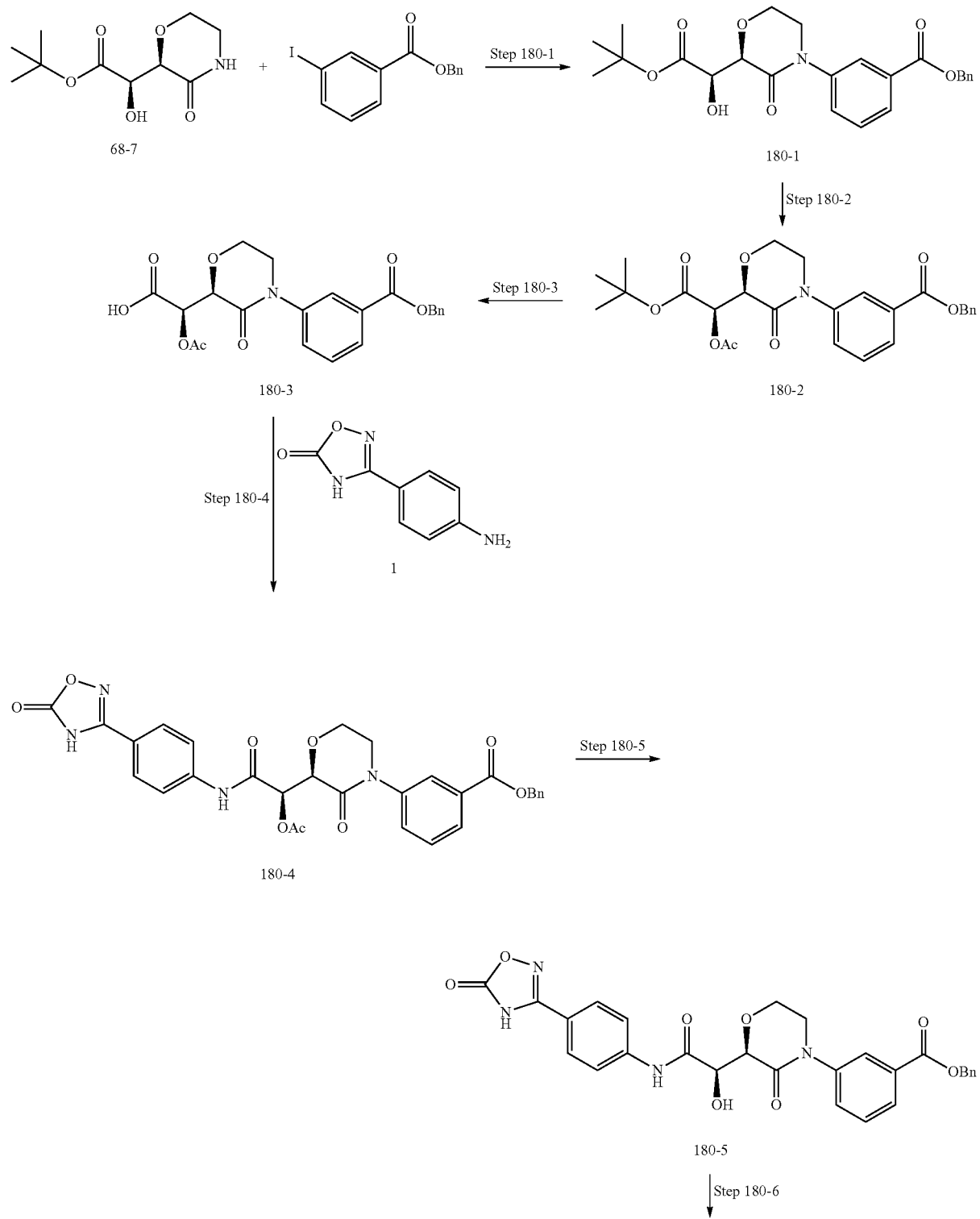

-continued

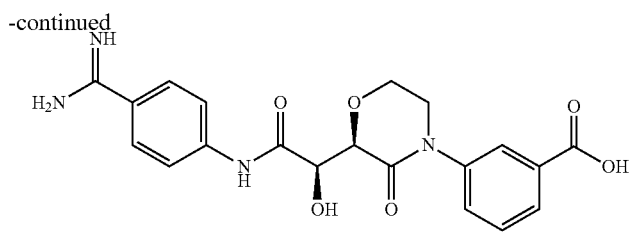

EXAMPLE 180

Step 180-1

According to Step 78-2 in the synthetic method for EXAMPLE 78, benzyl 3-iodobenzoate (122 mg, 0.36 mmol) was used instead of compound 78-1 to obtain compound 180-1 (127 mg, 0.29 mmol).

Step 180-2

According to Step 78-3 in the synthetic method for EXAMPLE 78, compound 180-1 (127 mg, 0.29 mmol) was used instead of compound 78-2 to obtain compound 180-2 (127 mg, 0.26 mmol).

Step 180-3

According to Step 78-4 in the synthetic method for EXAMPLE 78, compound 180-2 (127 mg, 0.26 mmol) was used instead of compound 78-3 to obtain compound 180-3 (0.26 mmol) which was used in the next step without further purification.

Step 180-4

According to Step 78-5 in the synthetic method for EXAMPLE 78, compound 180-3 (0.26 mmol) was used instead of compound 78-4 to obtain compound 180-4 (0.26 mmol) which was used in the next step without further purification.

Step 180-5

According to Step 78-6 in the synthetic method for EXAMPLE 78, compound 180-4 (0.26 mmol) was used instead of compound 78-5 to obtain compound 180-5 (130 mg, 0.24 mmol) which was used in the next step without further purification.

Step 180-6

According to Step 78-7 in the synthetic method for EXAMPLE 78, compound 180-5 (130 mg, 0.24 mmol) was used instead of compound 78-6 to obtain EXAMPLE 180 (64 mg, 0.16 mmol) as a white amorphous solid.

Example 181

Synthesis of (2R)—N-(4-amidinophenyl)-2-hydroxy-2-[(2R)-3-oxo-4-(4-methoxycarbonylphenyl)morpholin-2-yl]acetamide (EXAMPLE 181)

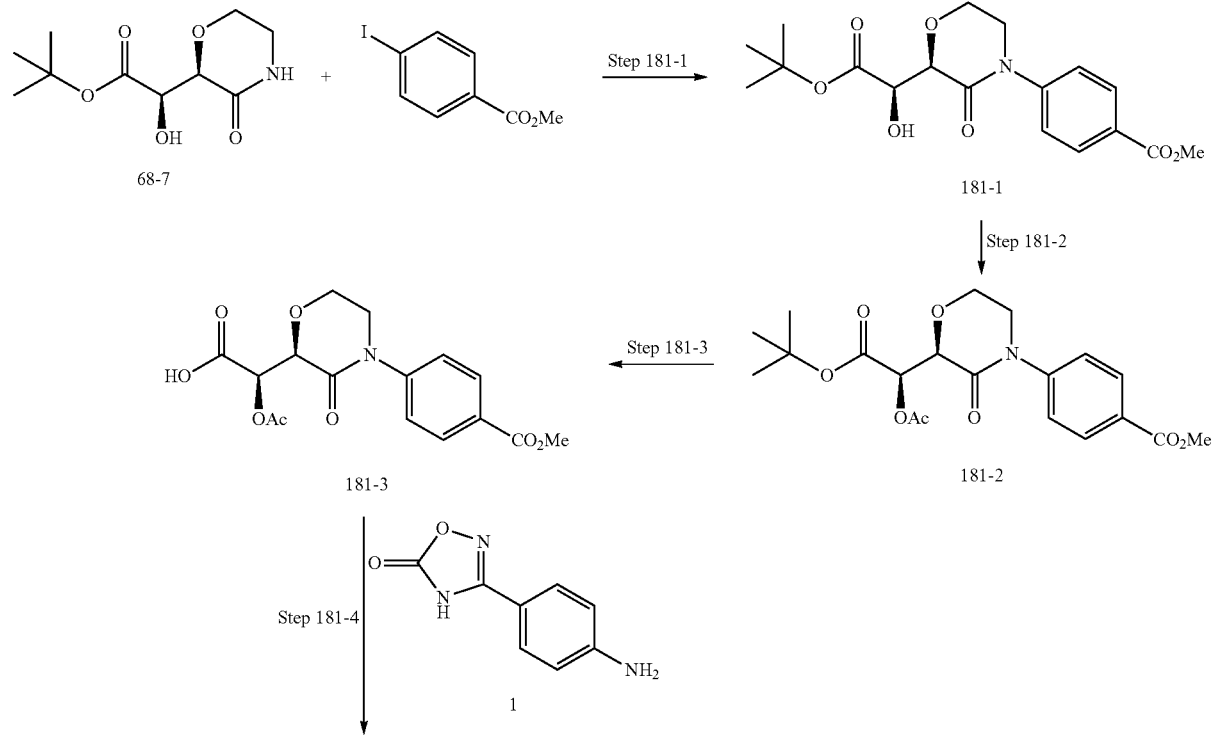

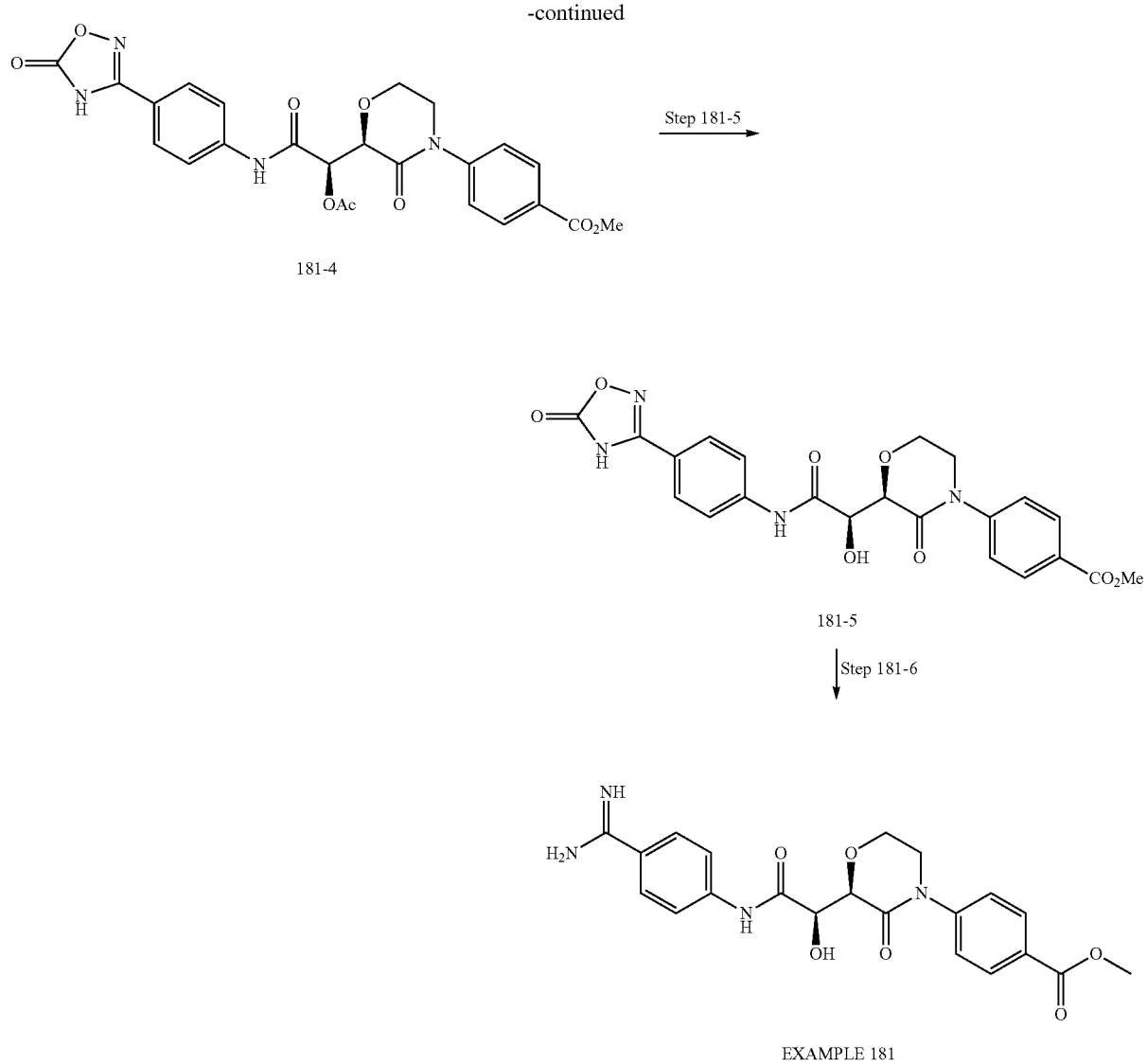

Step 181-1

According to Step 78-2 in the synthetic method for EXAMPLE 78, methyl 4-iodobenzoate (123 mg, 0.47 mmol) was used instead of compound 78-1 to obtain compound 181-1 (142 mg, 0.39 mmol).

Step 181-2

According to Step 78-3 in the synthetic method for EXAMPLE 78, compound 181-1 (142 mg, 0.39 mmol) was used instead of compound 78-2 to obtain compound 181-2 (145 mg, 0.37 mmol).

Step 181-3

According to Step 78-4 in the synthetic method for EXAMPLE 78, compound 181-2 (145 mg, 0.37 mmol) was used instead of compound 78-3 to obtain compound 181-3 (0.37 mmol) which was used in the next step without further purification.

Step 181-4

According to Step 78-5 in the synthetic method for EXAMPLE 78, compound 181-3 (0.37 mmol) was used instead of compound 78-4 to obtain compound 181-4 (0.37 mmol).

Step 181-5

According to Step 78-6 in the synthetic method for EXAMPLE 78, compound 181-4 (0.37 mmol) was used instead of compound 78-5 to obtain compound 181-5 (143 mg, 0.31 mmol) which was used in the next step without further purification.

Step 181-6

According to Step 78-7 in the synthetic method for EXAMPLE 78, compound 181-5 (143 mg, 0.31 mmol) was used instead of compound 78-6 to obtain EXAMPLE 181 (125 mg, 0.29 mmol) as a white amorphous solid.

Example 182
Synthesis of (2R)—N-(4-amidinophenyl)-2-hydroxy-2-[(2R)-3-oxo-4-(3-methoxycarbonylphenyl)morpholin-2-yl]acetamide (EXAMPLE 182)
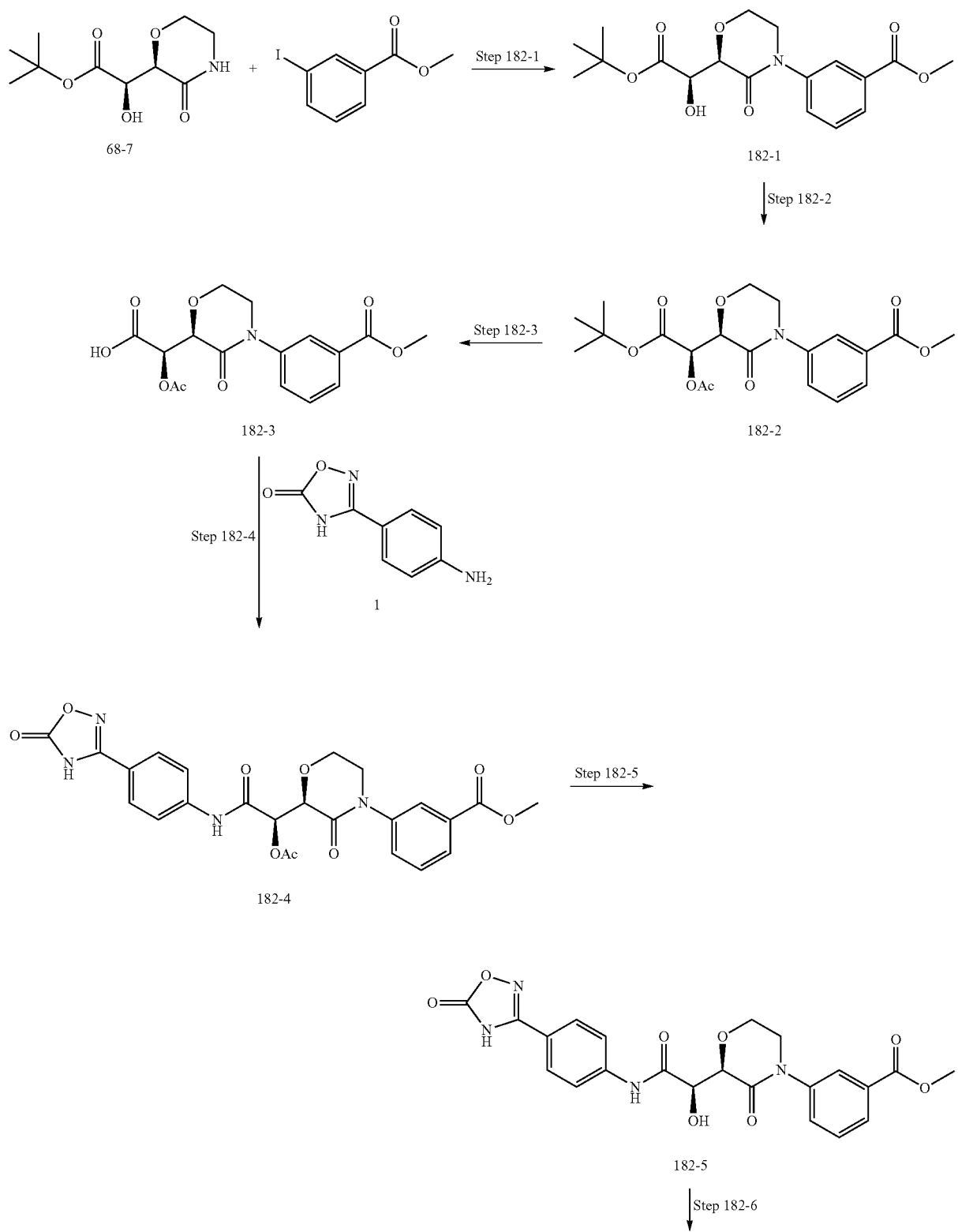

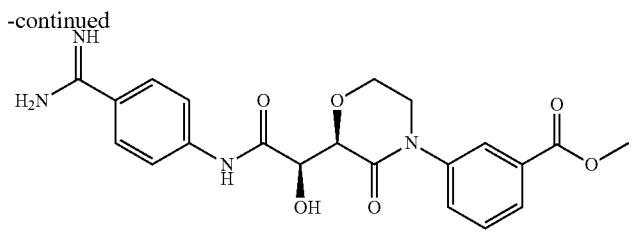

EXAMPLE 182

Step 182-1

According to Step 78-2 in the synthetic method for EXAMPLE 78, methyl 3-iodobenzoate (123 mg, 0.47 mmol) was used instead of compound 78-1 to obtain compound 182-1 (91 mg, 0.25 mmol).

Step 182-2

According to Step 78-3 in the synthetic method for EXAMPLE 78, compound 182-1 (91 mg, 0.25 mmol) was used instead of compound 78-2 to obtain compound 182-2 (90 mg, 0.22 mmol).

Step 182-3

According to Step 78-4 in the synthetic method for EXAMPLE 78, compound 182-2 (90 mg, 0.22 mmol) was used instead of compound 78-3 to obtain compound 182-3 (0.22 mmol) which was used in the next step without further purification.

Step 182-4

According to Step 78-5 in the synthetic method for EXAMPLE 78, compound 182-3 (0.22 mmol) was used instead of compound 78-4 to obtain compound 182-4 (106 mg, 0.21 mmol).

Step 182-5

According to Step 78-6 in the synthetic method for EXAMPLE 78, compound 182-4 (106 mg, 0.21 mmol) was used instead of compound 78-5 to obtain compound 182-5 (67 mg, 0.14 mmol) which was used in the next step without further purification.

Step 182-6

According to Step 78-7 in the synthetic method for EXAMPLE 78, compound 182-5 (67 mg, 0.14 mmol) was used instead of compound 78-6 to obtain EXAMPLE 182 (61 mg, 0.14 mmol) as a white amorphous solid.

Example 183

Synthesis of (2R)—N-(4-amidinophenyl)-2-hydroxy-2-[(2R)-3-oxo-4-(3-carboxy-4-fluorophenyl)morpholin-2-yl]acetamide (EXAMPLE 183)

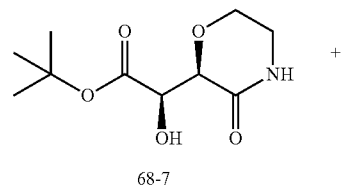

68-7

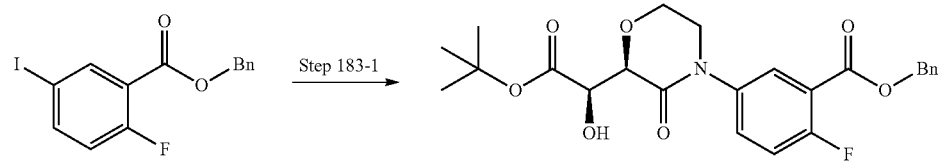

183-1

Step 183-2

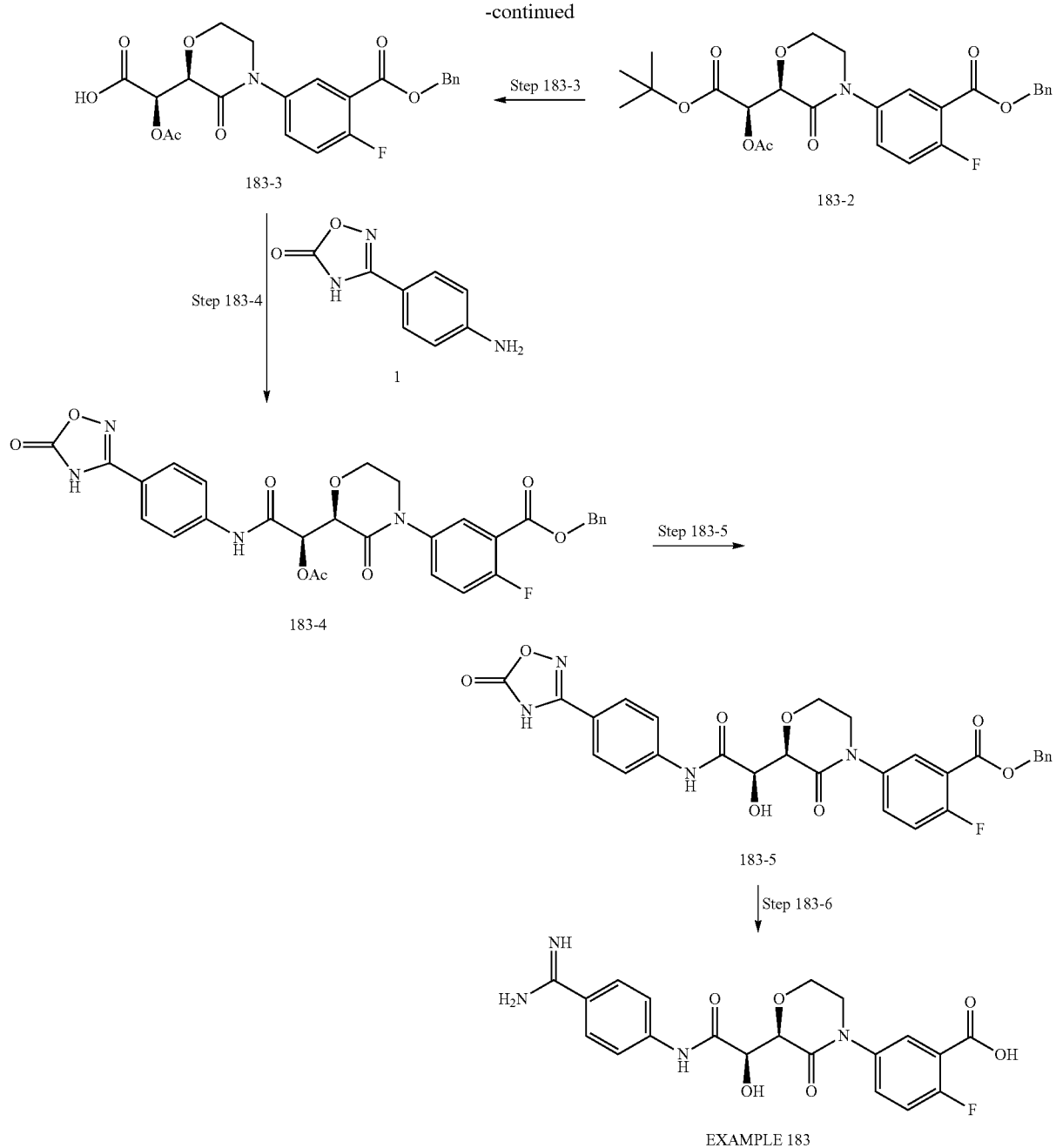

-continued

EXAMPLE 183

Step 183-1

According to Step 78-2 in the synthetic method for EXAMPLE 78, benzyl 2-fluoro-5-iodobenzoate (167 mg, 0.47 mmol) was used instead of compound 78-1 to obtain compound 183-1 (89 mg, 0.19 mmol).

Step 183-2

According to Step 78-3 in the synthetic method for EXAMPLE 78, compound 183-1 (89 mg, 0.19 mmol) was used instead of compound 78-2 to obtain compound 183-2 (91 mg, 0.18 mmol).

Step 183-3

According to Step 78-4 in the synthetic method for EXAMPLE 78, compound 183-2 (91 mg, 0.18 mmol) was used instead of compound 78-3 to obtain compound 183-3 (0.18 mmol) which was used in the next step without further purification.

Step 183-4

According to Step 78-5 in the synthetic method for EXAMPLE 78, compound 183-3 (0.18 mmol) was used instead of compound 78-4 to obtain compound 183-4 (80 mg, 0.13 mmol).

Step 183-5

According to Step 78-6 in the synthetic method for EXAMPLE 78, compound 183-4 (80 mg, 0.13 mmol) was used instead of compound 78-5 to obtain compound 183-5 (0.13 mmol) which was used in the next step without further purification.

Step 183-6

According to Step 78-7 in the synthetic method for EXAMPLE 78, compound 183-5 (0.13 mmol) was used instead of compound 78-6 to obtain EXAMPLE 183 (11 mg, 0.026 mmol) as a white amorphous solid.

Example 184

Synthesis of (2R)—N-(4-amidinophenyl)-2-hydroxy-2-[(2R)-3-oxo-4-(3-(methoxycarbonylmethyl)(methyl)carbamoylphenyl)morpholin-2-yl]acetamide (EXAMPLE 184)

Step 184-1

To a solution of compound 179-5 (184 mg, 0.28 mmol) in methanol (1.4 mL) and water (1.1 mL) was added triethylamine (280 mg, 2.8 mmol). The reaction mixture was stirred at room temperature for 16 hours. Solvent was evaporated under reduced pressure. The crude product was purified by RP-HPLC to afford compound 184-1 (45 mg, 0.083 mmol).

Step 184-2

According to Step 78-7 in the synthetic method for EXAMPLE 78, compound 184-1 (45 mg, 0.083 mmol) was used instead of compound 78-6 to obtain EXAMPLE 184 (35 mg, 0.07 mmol) as a white amorphous solid.

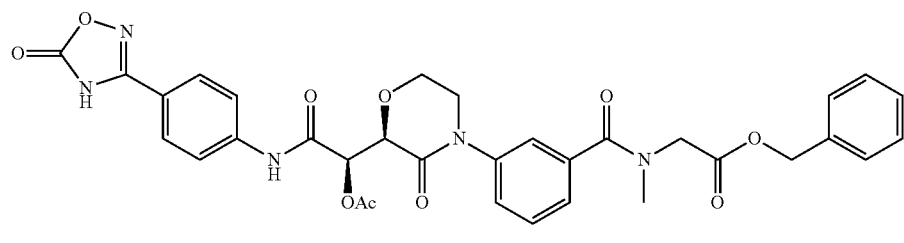

179-5

Step 184-1

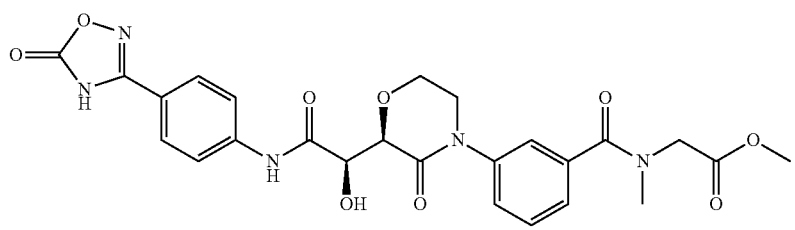

184-1

Step 184-2

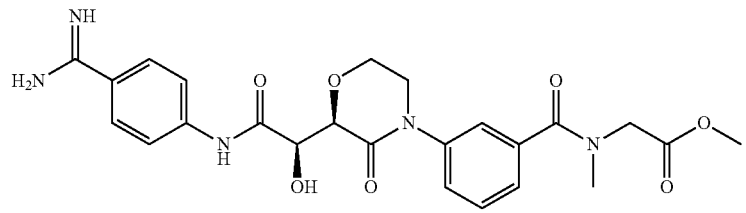

EXAMPLE 184

Example 185
Synthesis of (2R)—N-(4-amidinophenyl)-2-hydroxy-2-[(2R)-3-oxo-4-(3-carboxymethylphenyl)morpholin-2-yl]acetamide (EXAMPLE 185)
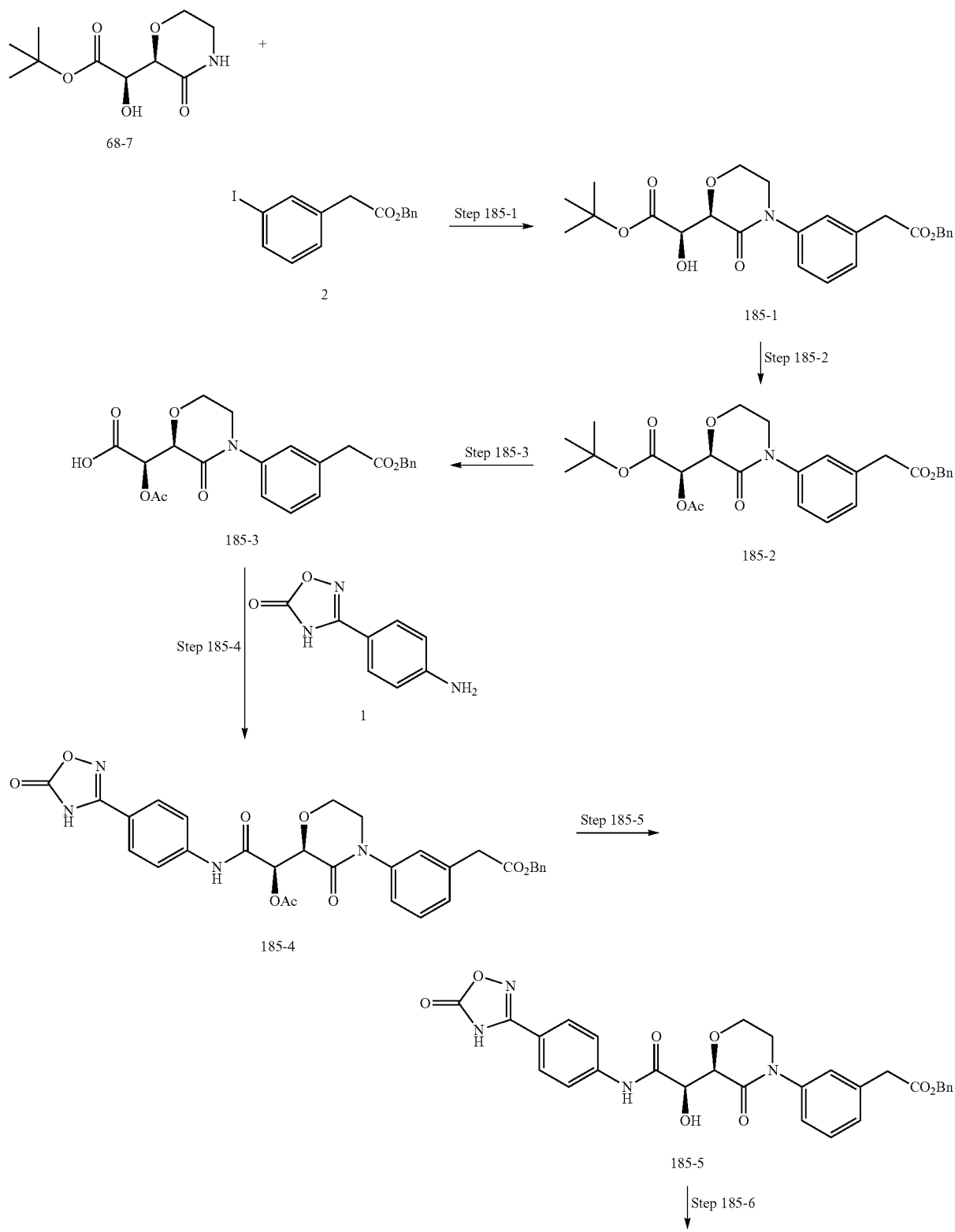

-continued

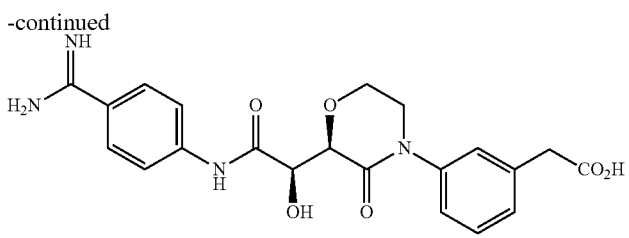

EXAMPLE 185

Step 185-1
According to Step 78-2 in the synthetic method for EXAMPLE 78, compound 2 (137 mg, 0.39 mmol) was used instead of compound 78-1 to obtain compound 185-1 (154 mg, 0.34 mmol).

Step 185-2
According to Step 78-3 in the synthetic method for EXAMPLE 78, compound 185-1 (154 mg, 0.34 mmol) was used instead of compound 78-2 to obtain compound 185-2 (77 mg, 0.31 mmol).

Step 185-3
According to Step 78-4 in the synthetic method for EXAMPLE 78, compound 185-2 (77 mg, 0.31 mmol) was used instead of compound 78-3 to obtain compound 185-3 (0.31 mmol) which was used in the next step without further purification.

Step 185-4
According to Step 78-5 in the synthetic method for EXAMPLE 78, compound 185-3 (0.31 mmol) was used instead of compound 78-4 to obtain compound 185-4 (0.31 mmol).

Step 185-5
According to Step 78-6 in the synthetic method for EXAMPLE 78, compound 185-4 (0.31 mmol) was used instead of compound 78-5 to obtain compound 185-5 (0.31 mmol) which was used in the next step without further purification.

Step 185-6
According to Step 78-7 in the synthetic method for EXAMPLE 78, compound 185-5 (0.31 mmol) was used instead of compound 78-6 to obtain EXAMPLE 185 (69 mg, 0.16 mmol) as a white amorphous solid.

Example 186

Synthesis of (2R)—N-(4-amidinophenyl)-2-hydroxy-2-[(2R)-3-oxo-4-(3-carboxy-5-fluorophenyl)morpholin-2-yl]acetamide (EXAMPLE 186)

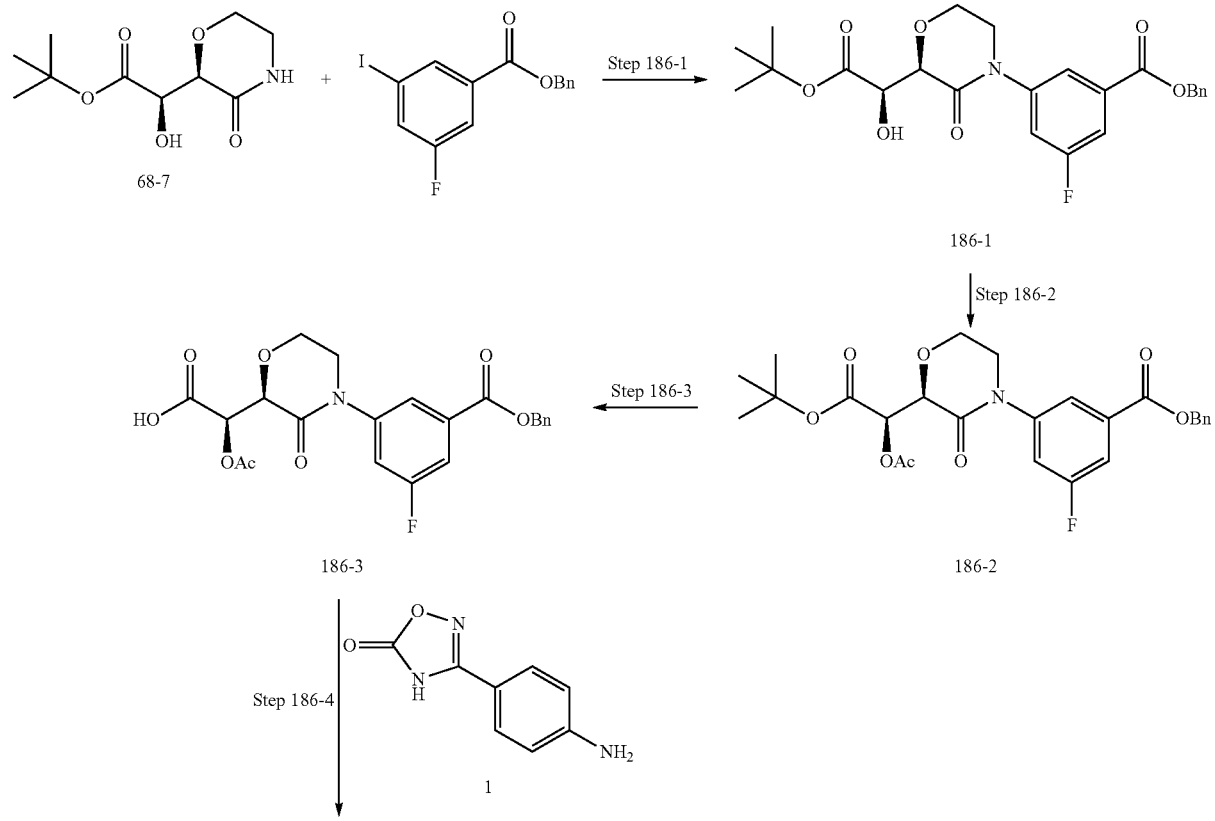

-continued

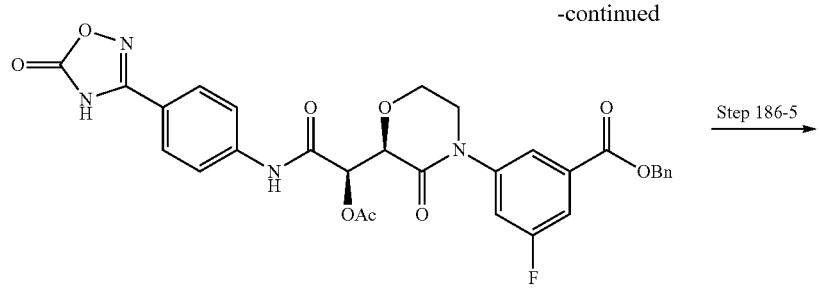

186-4

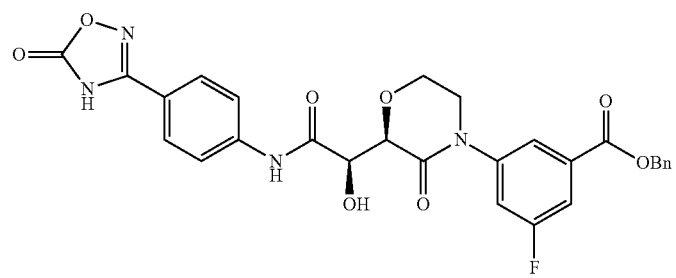

186-5

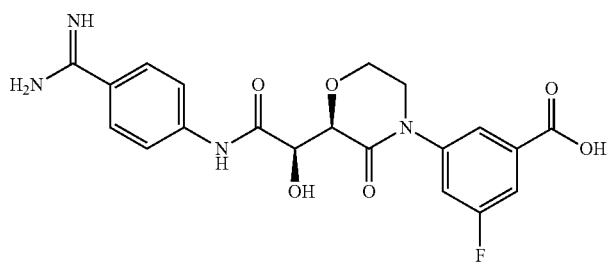

EXAMPLE 186

Step 186-1

According to Step 78-2 in the synthetic method for EXAMPLE 78, benzyl 3-fluoro-5-iodobenzoate (957 mg, 2.67 mmol) was used instead of compound 78-1 to obtain compound 186-1 (826 mg, 1.80 mmol).

Step 186-2

According to Step 78-3 in the synthetic method for EXAMPLE 78, compound 186-1 (826 mg, 1.80 mmol) was used instead of compound 78-1 to obtain compound 186-2 (840 mg, 1.68 mmol).

Step 186-3

According to Step 78-4 in the synthetic method for EXAMPLE 78, compound 186-2 (180 mg, 0.36 mmol) was used instead of compound 78-3 to obtain compound 186-3 (0.36 mmol) which was used in the next step without further purification.

Step 186-4

According to Step 78-5 in the synthetic method for EXAMPLE 78, compound 186-3 (0.36 mmol) was used instead of compound 78-4 to obtain compound 186-4 (208 mg, 0.34 mmol).

Step 186-5

According to Step 78-6 in the synthetic method for EXAMPLE 78, compound 186-4 (208 mg, 0.34 mmol) was used instead of compound 78-5 to obtain compound 186-5 (0.34 mmol) which was used in the next step without further purification.

Step 186-6

According to Step 78-7 in the synthetic method for EXAMPLE 78, compound 186-5 (0.34 mmol) was used instead of compound 78-6 to obtain EXAMPLE 186 (34 mg, 0.079 mmol) as a white amorphous solid.

Example 187

Synthesis of (2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide hydrochloride (EXAMPLE 187)

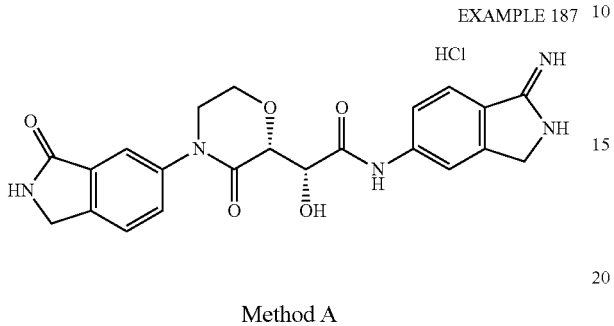

EXAMPLE 187

Method A

According to the synthetic method for EXAMPLE 142, EXAMPLE 187 can be prepared using corresponding carboxylic acid derived from 3-iodobenzoic acid instead of 3-iodoaniline.

Method B

According to the synthetic method for EXAMPLE 39, EXAMPLE 187 can be prepared using corresponding aniline derived from phthalimide instead of 4-(tert-butoxycarbonylamino)aniline.

Example 188

Synthesis of (2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide hydrochloride (EXAMPLE 188)

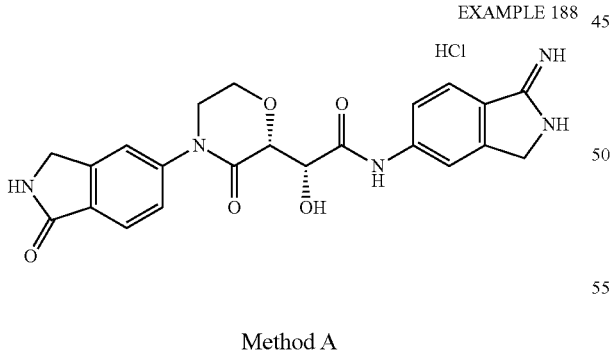

EXAMPLE 188

Method A

According to the synthetic method for EXAMPLE 142, EXAMPLE 188 can be prepared using corresponding carboxylic acid derived from 4-iodobenzoic acid instead of 3-iodoaniline.

Method B

According to the synthetic method for EXAMPLE 39, EXAMPLE 188 can be prepared using corresponding aniline derived from 2-methyl-4-nitro-benzoic acid instead of 4-(tert-butoxycarbonylamino)aniline.

Example 189

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide hydrochloride (EXAMPLE 189)

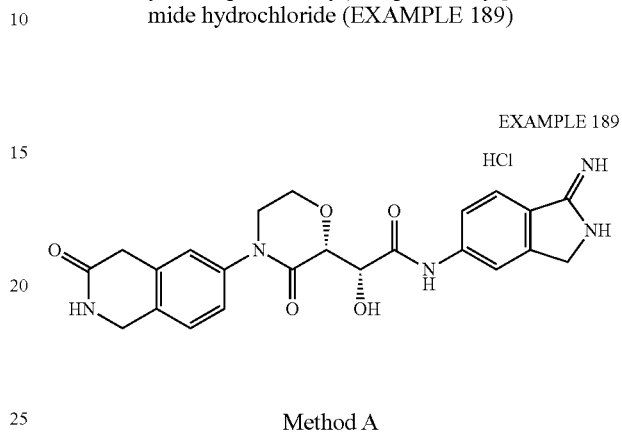

EXAMPLE 189

Method A

According to the synthetic method for EXAMPLE 142, EXAMPLE 189 can be prepared using corresponding carboxylic acid derived from 2-indanone instead of 3-iodoaniline.

Method B

According to the synthetic method for EXAMPLE 39, EXAMPLE 189 can be prepared using corresponding aniline derived from 2-indanone instead of 4-(tert-butoxycarbonylamino)aniline.

Example 190

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-7-yl)morpholin-2-yl]acetamide hydrochloride (EXAMPLE 190)

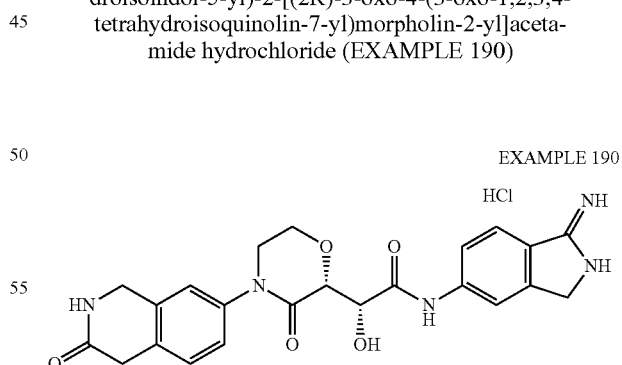

EXAMPLE 190

Method A

According to the synthetic method for EXAMPLE 142, EXAMPLE 190 can be prepared using corresponding carboxylic acid derived from 2-indanone instead of 3-iodoaniline.

Method B

According to the synthetic method for EXAMPLE 39, EXAMPLE 190 can be prepared using corresponding aniline derived from 2-indanone instead of 4-(tert-butoxycarbonylamino)aniline.

Example 191

Synthesis of (2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide hydrochloride (EXAMPLE 191)

EXAMPLE 191

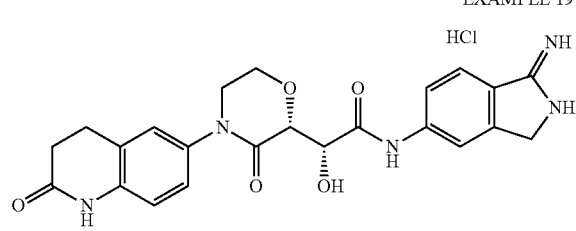

Method A

According to the synthetic method for EXAMPLE 142, EXAMPLE 208 can be prepared using corresponding carboxylic acid derived from 3,4-dihydro-2(1H)-quinolinone instead of 3-iodoaniline.

Method B

According to the synthetic method for EXAMPLE 39, EXAMPLE 191 can be prepared using corresponding aniline derived from 3,4-dihydro-2(1H)-quinolinone instead of 4-(tert-butoxycarbonylamino)aniline.

Example 192

Synthesis of (2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide hydrochloride (EXAMPLE 192)

EXAMPLE 192

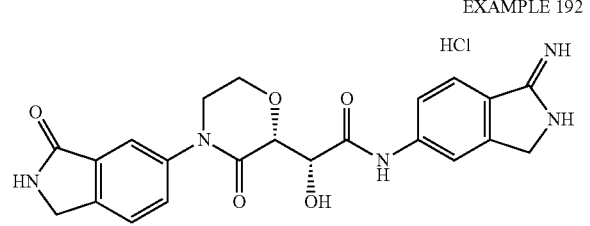 [SMILES: Cl ; N=C1NCc2cc(NC(=O)[C@H](O)[C@H]3OCCN(c4ccc5c(c4)C(=O)NC5)C3=O)ccc21]

Method A

According to the synthetic method for EXAMPLE 142, EXAMPLE 192 can be prepared using corresponding carboxylic acid derived from 3-iodobenzoic acid instead of 3-iodoaniline.

Method B

According to the synthetic method for EXAMPLE 39, EXAMPLE 192 can be prepared using corresponding aniline derived from phthalimide instead of 4-(tert-butoxycarbonylamino)aniline.

Example 193

Synthesis of (2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide hydrochloride (EXAMPLE 193)

EXAMPLE 193

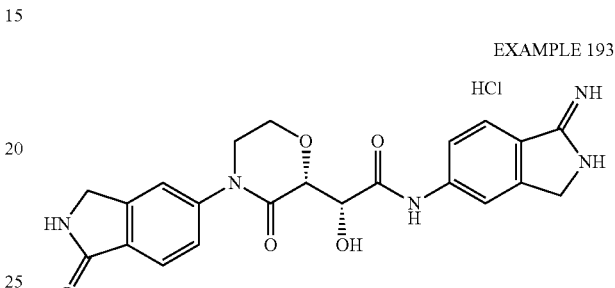

Method A

According to the synthetic method for EXAMPLE 142, EXAMPLE 193 can be prepared using corresponding carboxylic acid derived from 4-iodobenzoic acid instead of 3-iodoaniline.

Method B

According to the synthetic method for EXAMPLE 39, EXAMPLE 193 can be prepared using corresponding aniline derived from 2-methyl-4-nitro-benzoic acid instead of 4-(tert-butoxycarbonylamino)aniline.

Example 194

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide hydrochloride (EXAMPLE 194)

EXAMPLE 194

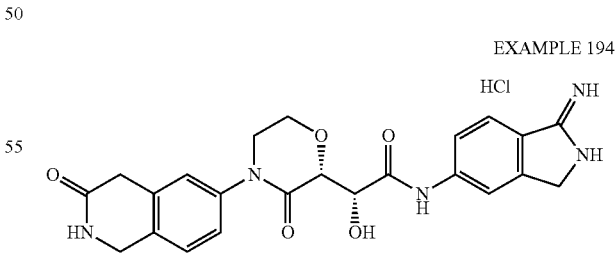

Method A

According to the synthetic method for EXAMPLE 142, EXAMPLE 194 can be prepared using corresponding carboxylic acid derived from 2-indanone instead of 3-iodoaniline.

Method B

According to the synthetic method for EXAMPLE 39, EXAMPLE 194 can be prepared using corresponding aniline derived from 2-indanone instead of 4-(tert-butoxycarbonylamino)aniline.

Example 195

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-7-yl)morpholin-2-yl]acetamide hydrochloride (EXAMPLE 195)

EXAMPLE 195

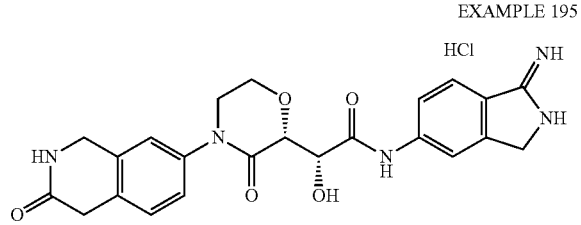 [SMILES: Cl ; N=C1NCc2cc(NC(=O)[C@H](O)[C@H]3OCCN(c4ccc5c(c4)CNC(=O)C5)C3=O)ccc21]

Method A

According to the synthetic method for EXAMPLE 142, EXAMPLE 195 can be prepared using corresponding carboxylic acid derived from 2-indanone instead of 3-iodoaniline.

Method B

According to the synthetic method for EXAMPLE 39, EXAMPLE 195 can be prepared using corresponding aniline derived from 2-indanone instead of 4-(tert-butoxycarbonylamino)aniline.

Example 196

Synthesis of (2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide hydrochloride (EXAMPLE 196)

EXAMPLE 196

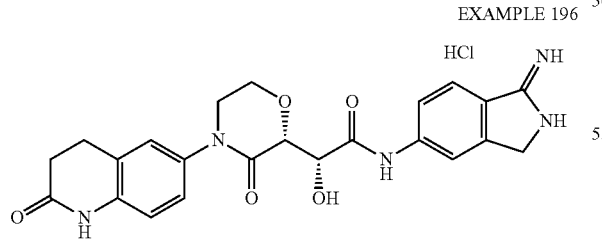

Method A

According to the synthetic method for EXAMPLE 142, EXAMPLE 196 can be prepared using corresponding carboxylic acid derived from 3,4-dihydro-2(1H)-quinolinone instead of 3-iodoaniline.

Method B

According to the synthetic method for EXAMPLE 39, EXAMPLE 196 can be prepared using corresponding aniline derived from 3,4-dihydro-2(1H)-quinolinone instead of 4-(tert-butoxycarbonylamino)aniline.

Example 197

Synthesis of (2R)-2-Hydroxy-N-(1-imino-2,3-dihydroisoindol-5-yl)-2-[(2R)-4-(2-methyl-3-oxo-1,2-dihydroisoindol-5-yl)-3-oxo-morpholin-2-yl]acetamide hydrochloride (EXAMPLE 197)

EXAMPLE 197

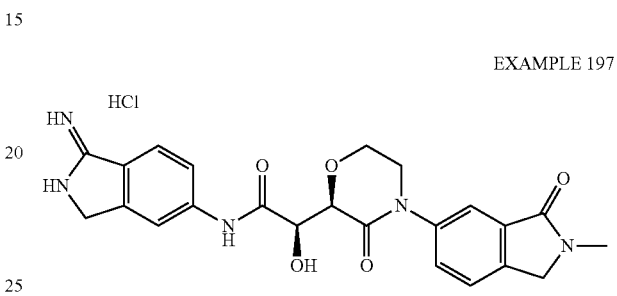

Method A

According to the synthetic method for EXAMPLE 142, EXAMPLE 197 can be prepared using corresponding carboxylic acid derived from 3-iodobenzoic acid instead of 3-iodoaniline.

Method B

According to the synthetic method for EXAMPLE 39, EXAMPLE 197 can be prepared using corresponding aniline derived from phthalimide instead of 4-(tert-butoxycarbonylamino)aniline.

Example 198

Synthesis of (2R)-2-Hydroxy-N-(1-imino-2,3-dihydroisoindol-5-yl)-2-[(2R)-3-oxo-4-(3-oxo-2-(2,2,2-trifluoroethyl)-1,2-dihydroisoindol-5-yl)morpholin-2-yl]acetamide hydrochloride (EXAMPLE 198)

EXAMPLE 198

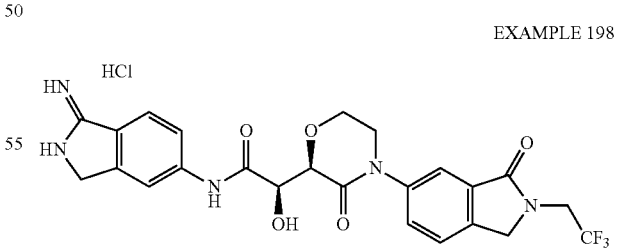

Method A

According to the synthetic method for EXAMPLE 142, EXAMPLE 198 can be prepared using corresponding carboxylic acid derived from 3-iodobenzoic acid instead of 3-iodoaniline.

Method B

According to the synthetic method for EXAMPLE 39, EXAMPLE 198 can be prepared using corresponding aniline derived from phthalimide instead of 4-(tert-butoxycarbonylamino)aniline.

Example 199

Synthesis of (2R)-2-Hydroxy-N-(1-imino-2,3-dihydroisoindol-5-yl)-2-[(2R)-3-oxo-4-(3-oxo-2-propyl-1,2-dihydroisoindol-5-yl)morpholin-2-yl]acetamide hydrochloride (EXAMPLE 199)

EXAMPLE 199

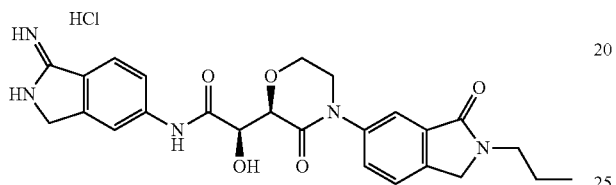

Method A

According to the synthetic method for EXAMPLE 142, EXAMPLE 199 can be prepared using corresponding carboxylic acid derived from 3-iodobenzoic acid instead of 3-iodoaniline.

Method B

According to the synthetic method for EXAMPLE 39, EXAMPLE 199 can be prepared using corresponding aniline derived from phthalimide instead of 4-(tert-butoxycarbonylamino)aniline.

Example 200

Synthesis of (2R)-2-Hydroxy-N-(1-imino-2,3-dihydroisoindol-5-yl)-2-[(2R)-4-(2-methyl-3-oxo-1,2-dihydroisoindol-6-yl)-3-oxo-morpholin-2-yl]acetamide hydrochloride (EXAMPLE 200)

EXAMPLE 200

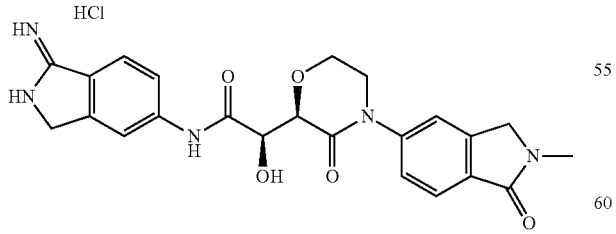

Method A

According to the synthetic method for EXAMPLE 142, EXAMPLE 200 can be prepared using corresponding carboxylic acid derived from 2,3-dihydro-5-iodo-1H-isoindole-1-one instead of 3-iodoaniline.

Method B

According to the synthetic method for EXAMPLE 39, EXAMPLE 200 can be prepared using corresponding aniline derived from methyl 2-methyl-4-nitrobenzoate instead of 4-(tert-butoxycarbonylamino)aniline.

Example 201

Synthesis of (2R)-2-[(2R)-4-(2-(Difluoromethoxy)phenyl)-3-oxo-morpholin-2-yl]-2-hydroxy-N-(1-imino-2,3-dihydroisoindol-5-yl)acetamide hydrochloride (EXAMPLE 201)

EXAMPLE 201

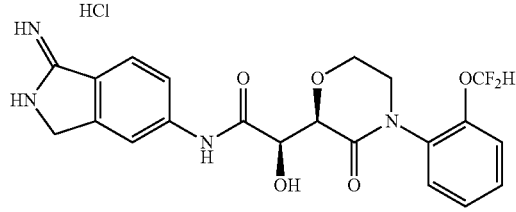

According to the synthetic method for EXAMPLE 142, EXAMPLE 201 can be prepared using corresponding carboxylic acid derived from 1-iodo-2-(difluoromethoxy)benzene instead of 3-iodoaniline.

Example 202

Synthesis of (2R)-2-[(2R)-4-(2-Fluorophenyl)-3-oxo-morpholin-2-yl]-2-hydroxy-N-(1-imino-2,3-dihydroisoindol-5-yl)acetamide hydrochloride (EXAMPLE 202)

EXAMPLE 202

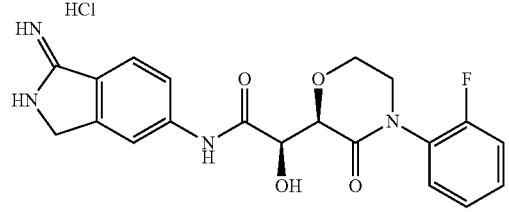

According to the synthetic method for EXAMPLE 142, EXAMPLE 202 can be prepared using corresponding carboxylic acid derived from 1-fluoro-2-iodobenzene instead of 3-iodoaniline.

Example 203

Synthesis of (2R)-2-[(2R)-4-(4-Fluorophenyl)-3-oxo-morpholin-2-yl]-2-hydroxy-N-(1-imino-2,3-dihydroisoindol-5-yl)acetamide hydrochloride (EXAMPLE 203)

EXAMPLE 203

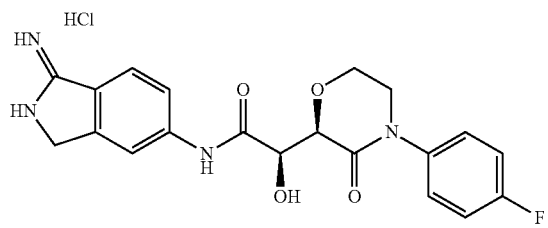

According to the synthetic method for EXAMPLE 142, EXAMPLE 203 can be prepared using corresponding carboxylic acid derived from 1-fluoro-4-iodobenzene instead of 3-iodoaniline.

Example 204

Synthesis of (2R)-2-[(2R)-4-(3-Fluorophenyl)-3-oxo-morpholin-2-yl]-2-hydroxy-N-(1-imino-2,3-dihydroisoindol-5-yl)acetamide hydrochloride (EXAMPLE 204)

EXAMPLE 204

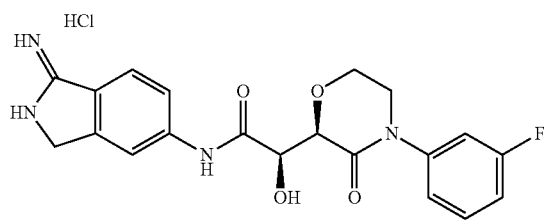

According to the synthetic method for EXAMPLE 142, EXAMPLE 204 can be prepared using corresponding carboxylic acid derived from 1-fluoro-3-iodobenzene instead of 3-iodoaniline.

Example 205

Synthesis of (2R)-2-[(2R)-4-(3,4-Difluorophenyl)-3-oxo-morpholin-2-yl]-2-hydroxy-N-(1-imino-2,3-dihydroisoindol-5-yl)acetamide hydrochloride (EXAMPLE 205)

EXAMPLE 205

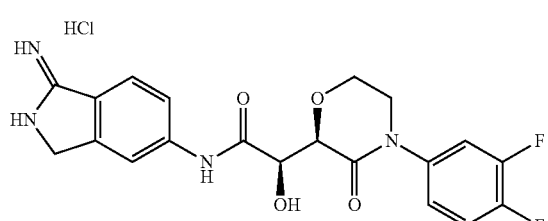

According to the synthetic method for EXAMPLE 142, EXAMPLE 205 can be prepared using corresponding carboxylic acid derived from 1,2-difluoro-4-iodobenzene instead of 3-iodoaniline.

Example 206

Synthesis of (2R)-2-[(2R)-4-(3,5-Difluorophenyl)-3-oxo-morpholin-2-yl]-2-hydroxy-N-(1-imino-2,3-dihydroisoindol-5-yl)acetamide hydrochloride (EXAMPLE 206)

EXAMPLE 206

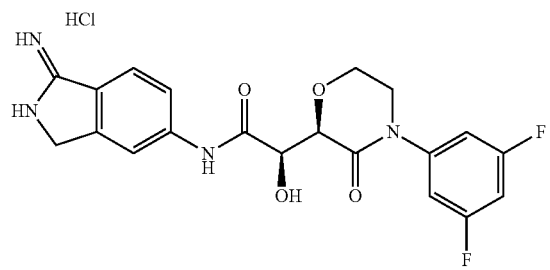

According to the synthetic method for EXAMPLE 142, EXAMPLE 206 can be prepared using corresponding carboxylic acid derived from 1,3-difluoro-5-iodobenzene instead of 3-iodoaniline.

Example 207

Synthesis of (2R)-2-Hydroxy-N-(1-imino-2,3-dihydroisoindol-5-yl)-2-[(2R)-3-oxo-4-(3,4,5-trifluoro phenyl)morpholin-2-yl]acetamide hydrochloride (EXAMPLE 207)

EXAMPLE 207

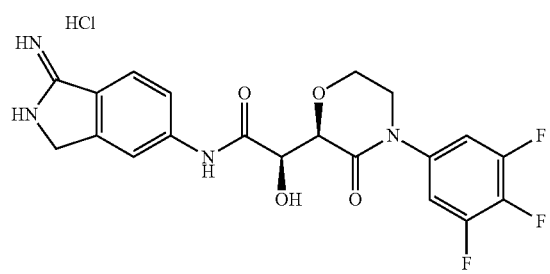

According to the synthetic method for EXAMPLE 142, EXAMPLE 207 can be prepared using corresponding carboxylic acid derived from 1,2,3-difluoro-5-iodobenzene instead of 3-iodoaniline.

Example 208

Synthesis of (2R)-2-Hydroxy-N-(1-imino-2,3-dihydroisoindol-5-yl)-2-[(2R)-3-oxo-4-(4-trifluoromethylphenyl)morpholin-2-yl]acetamide hydrochloride (EXAMPLE 208)

EXAMPLE 208

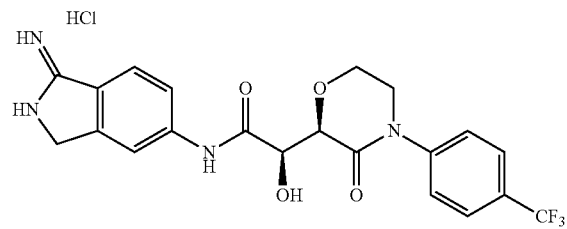

According to the synthetic method for EXAMPLE 142, EXAMPLE 208 can be prepared using corresponding carboxylic acid derived from 1-iodo-4-trifluoromethylbenzene instead of 3-iodoaniline.

Example 209

Synthesis of (2R)-2-Hydroxy-N-(1-imino-2,3-dihydroisoindol-5-yl)-2-[(2R)-3-oxo-4-(3-trifluoromethylphenyl)morpholin-2-yl]acetamide hydrochloride (EXAMPLE 209)

EXAMPLE 209

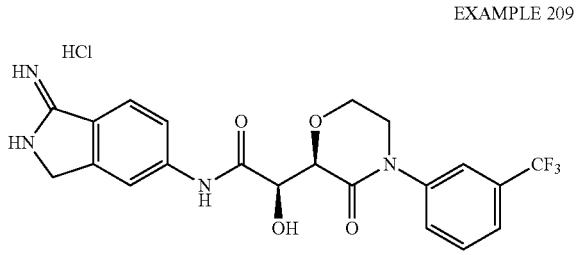 [SMILES: Cl ; N=C1NCc2cc(NC(=O)[C@H](O)[C@H]3OCCN(c4cccc(C(F)(F)F)c4)C3=O)ccc21]

According to the synthetic method for EXAMPLE 142, EXAMPLE 209 can be prepared using corresponding carboxylic acid derived from 1-iodo-3-trifluoromethylbenzene instead of 3-iodoaniline.

Example 210

Synthesis of (2R)-2-[(2R)-4-(4-Fluoro-3-(morpholin-4-ylcarbonyl)phenyl)-3-oxo-morpholin-2-yl]-2-hydroxy-N-(1-imino-2,3-dihydroisoindol-5-yl)acetamide hydrochloride (EXAMPLE 210)

EXAMPLE 210

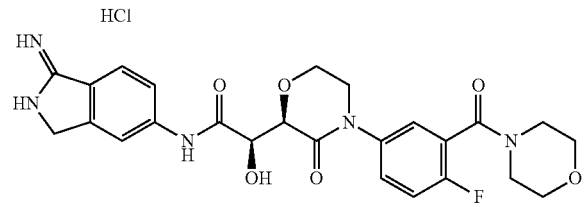

According to the synthetic method for EXAMPLE 142, EXAMPLE 210 can be prepared using corresponding carboxylic acid derived from 2-fluoro-5-iodobenzoic acid instead of 3-iodoaniline.

Example 211

Synthesis of (2R)-2-[(2R)-4-(3-(Dimethylaminocarbonyl)-4-fluorophenyl)-3-oxo-morpholin-2-yl]-2-hydroxy-N-(1-imino-2,3-dihydroisoindol-5-yl)acetamide hydrochloride (EXAMPLE 211)

EXAMPLE 211

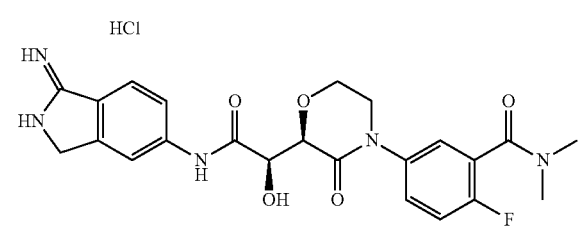

According to the synthetic method for EXAMPLE 142, EXAMPLE 211 can be prepared using corresponding carboxylic acid derived from 2-fluoro-5-iodobenzoic acid instead of 3-iodoaniline.

Example 212

Synthesis of (2R)-2-[(2R)-4-(4-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide hydrochloride (EXAMPLE 212)

EXAMPLE 212

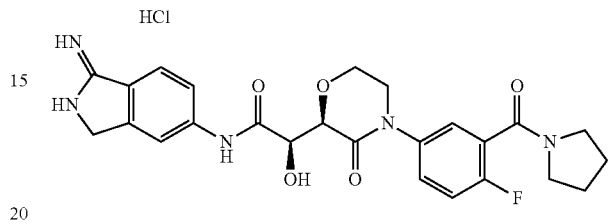

According to the synthetic method for EXAMPLE 142, EXAMPLE 212 can be prepared using corresponding carboxylic acid derived from 2-fluoro-5-iodobenzoic acid instead of 3-iodoaniline.

Example 213

Synthesis of (2R)-2-[(2R)-4-(3-(Dimethylaminocarbonyl)-5-fluorophenyl)-3-oxo-morpholin-2-yl]-2-hydroxy-N-(1-imino-2,3-dihydroisoindol-5-yl)acetamide hydrochloride (EXAMPLE 213

EXAMPLE 213

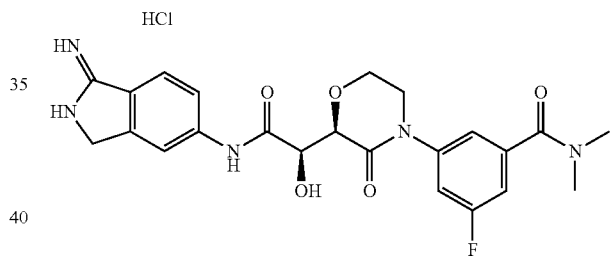

According to the synthetic method for EXAMPLE 142, EXAMPLE 213 can be prepared using corresponding carboxylic acid derived from 3-fluoro-5-iodobenzoic acid instead of 3-iodoaniline.

Example 214

Synthesis of (2R)-2-[(2R)-4-(5-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide hydrochloride (EXAMPLE 214)

EXAMPLE 214

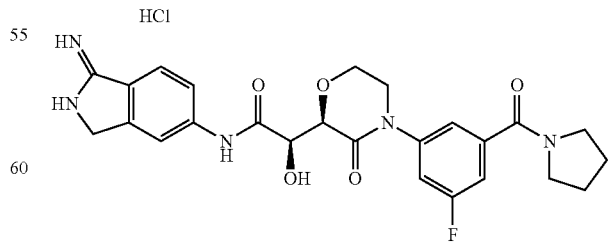

According to the synthetic method for EXAMPLE 142, EXAMPLE 214 can be prepared using corresponding carboxylic acid derived from 3-fluoro-5-iodobenzoic acid instead of 3-iodoaniline.

Example 215

Synthesis of (2R)-2-[(2R)-4-(5-Fluoro-3-(morpholin-4-ylcarbonyl)phenyl)-3-oxo-morpholin-2-yl]-2-hydroxy-N-(1-imino-2,3-dihydroisoindol-5-yl)acetamide hydrochloride (EXAMPLE 215)

EXAMPLE 215

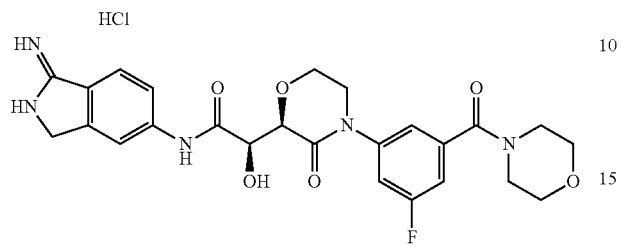

According to the synthetic method for EXAMPLE 142, EXAMPLE 215 can be prepared using corresponding carboxylic acid derived from 3-fluoro-5-iodobenzoic acid instead of 3-iodoaniline.

Example 216

Synthesis of (2R)-2-[(2R)-4-(3-Carboxyphenyl)-3-oxo-morpholin-2-yl]-2-hydroxy-N-(1-imino-2,3-dihydroisoindol-5-yl)acetamide hydrochloride (EXAMPLE 216)

EXAMPLE 216

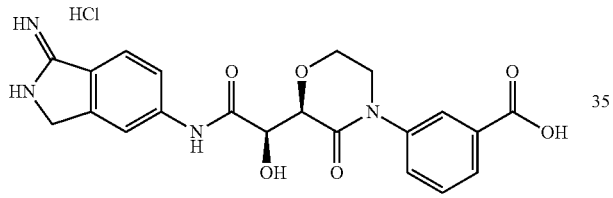

According to the synthetic method for EXAMPLE 142, EXAMPLE 216 can be prepared using corresponding carboxylic acid derived from 3-iodobenzoic acid instead of 3-iodoaniline.

Example 217

Synthesis of (2R)-2-[(2R)-4-(4-Chlorophenyl)-3-oxo-morpholin-2-yl]-2-hydroxy-N-(1-imino-2,3-dihydroisoindol-5-yl)acetamide hydrochloride (EXAMPLE 217)

EXAMPLE 217

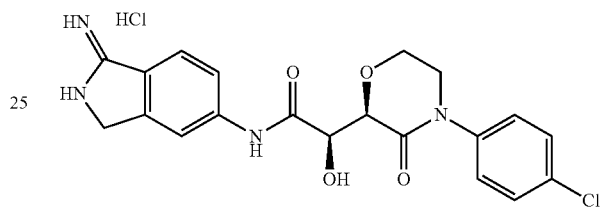

According to the synthetic method for EXAMPLE 142, EXAMPLE 217 can be prepared using corresponding carboxylic acid derived from 1-chloro-4-iodobenzene instead of 3-iodoaniline.

TABLE 3

| EXAMPLE | NMR (ppm) (No mark: 400 MHz, *: 300 MHz) |
| --- | --- |
| 1 | DMSO-$d_6$: 12.99 (1H, brs), 10.37 (1H, brs), 8.92 (2H, brs), 8.56-8.42 (2H, m), 8.06 (1H, d, J = 9 Hz), 7.62 (1H, d, J = 7 Hz), 7.28 (2H, d, J = 8 Hz), 7.23 (2H, d, J = 8 Hz), 7.16 (1H, d, J = 7 Hz), 6.57 (1H, brs), 4.76-4.63 (2H, m), 4.17-4.08 (1H, m), 3.98-3.89 (1H, m), 3.88-3.79 (1H, m), 3.77-3.41 (1H, m), 2.32 (3H, s) |
| 1-1 (LP) | CDCl$_3$: 7.23-7.18 (4H, m), 4.84 (1H, brs), 4.64 (1H, d, J = 2 Hz), 4.37-4.14 (3H, m), 4.00 (1H, ddd, J = 10, 10, 2 Hz), 3.95 (1H, ddd, J = 10, 10, 3 Hz), 3.60-3.52 (1H, m), 3.36 (1H, brs), 2.35 (3H, s), 1.33 (3H, t, J = 7 Hz) |
| 1-1 (MP) | CDCl$_3$: 7.23-7.16 (4H, m), 4.71 (2H, s), 4.37-4.20 (3H, m), 4.01 (1H, ddd, J = 11, 11, 2 Hz), 3.93 (1H, ddd, J = 11, 11, 4 Hz), 3.60-3.52 (1H, m), 3.38 (1H, brs), 2.34 (3H, s), 1.32 (3H, t, J = 7 Hz) |
| 1-2 | *CDCl$_3$: 7.22-7.12 (4H, m), 4.73-4.62 (2H, m), 4.21-4.10 (1H, m), 4.01-3.86 (2H, m), 3.50-3.38 (1H, m), 2.33 (3H, s) |
| 1-3 | *CDCl$_3$: 9.04 (1H, s), 8.52 (1H, d, J = 6 Hz), 7.96 (1H, d, J = 9 Hz), 7.70 (1H, d, J = 6 Hz), 7.60 (1H, dd, J = 9, 2 Hz), 7.21-7.15 (4H, m), 4.88 (1H, d, J = 2 Hz), 4.69 (1H, d, J = 2 Hz), 4.24-4.16 (1H, m), 4.12-3.96 (2H, m), 3.55-3.47 (1H, m), 2.16 (3H, s), 1.32 (18H, s) |
| 2 | DMSO-$d_6$: 10.19 (1H, s), 9.18 (2H, s), 8.77 (2H, brs), 8.03 (2H, d, J = 9 Hz), 7.79 (2H, d, J = 9 Hz), 7.27 (2H, d, J = 9 Hz), 7.22 (2H, d, J = 9 Hz), 6.49 (1H, brs), 4.66 (2H, s), 4.15-4.08 (1H, m), 3.97-3.88 (1H, m), 3.86-3.78 (1H, m), 3.64-3.57 (1H, m), 2.32 (3H, s) |
| 2-1 | *DMSO-$d_6$: 10.22 (1H, s), 8.01 (2H, d, J = 9 Hz), 7.78 (2H, d, J = 9 Hz), 7.27 (2H, d, J = 9 Hz), 7.24-7.18 (2H, m), 6.48 (1H, brs), 4.65 (2H, s), 4.15-4.07 (1H, m), 3.97-3.75 (2H, m), 3.63-3.55 (1H, m), 2.31 (3H, s) |

TABLE 3-continued

| EXAMPLE | NMR (ppm) (No mark: 400 MHz, *: 300 MHz) |
|---|---|
| 3 | DMSO-d$_6$: 11.01 (1H, s), 9.42 (1H, s), 7.98 (1H, d, J = 2 Hz), 7.36 (1H, dd, J = 9, 2 Hz), 7.32-7.26 (4H, m), 7.22 (2H, d, J = 8 Hz), 6.37 (1H, dd, J = 2, 2 Hz), 6.27 (1H, d, J = 7 Hz), 4.66 (1H, d, J = 2 Hz), 4.61 (1H, dd, J = 7, 2 Hz), 4.13 (1H, ddd, J = 11, 3, 3 Hz), 3.92 (1H, ddd, J = 11, 11, 3 Hz), 3.87-3.78 (1H, m), 3.60 (1H, ddd, J = 12, 3, 3 Hz), 2.32 (3H, s) |
| 7 | *DMSO-d$_6$: 10.21 (1H, s), 9.25 (2H, s), 8.94 (1H, s), 8.04 (2H, d, J = 9 Hz), 7.82 (2H, d, J = 9 Hz), 7.29 (2H, d, J = 9 Hz), 7.24 (2H, d, J = 9 Hz), 4.68 (2H, s), 4.18-4.08 (1H, m), 4.00-3.77 (2H, m), 3.67-3.57 (1H, m), 2.33 (3H, s) |
| 7-1 | *CDCl$_3$: 7.02 (2H, d, J = 8 Hz), 6.62 (2H, d, J = 8 Hz), 3.71 (2H, t, J = 6 Hz), 3.49 (2H, t, J = 6 Hz), 2.25 (3H, s) |
| 7-3 | *CDCl$_3$: 8.09 (1H, s), 7.63-7.59 (4H, m), 7.38 (2H, d, J = 9 Hz), 7.32-7.27 (2H, m), 5.59 (1H, d, J = 3 Hz), 5.42 (1H, d, J = 3 Hz), 3.99-3.84 (2H, m), 3.65-3.52 (2H, m), 2.41 (3H, s), 2.29 (3H, s), 2.05 (3H, s) |
| 7-5 | *DMSO-d$_6$: 10.22 (1H, brs), 8.01 (2H, d, J = 9 Hz), 7.78 (2H, d, J = 9 Hz), 7.27 (2H, d, J = 9 Hz), 7.22 (2H, d, J = 9 Hz), 6.47 (1H, brs), 4.65 (2H, s), 4.16-4.08 (1H, m), 3.97-3.75 (2H, m), 3.63-3.56 (1H, m), 2.31 (3H, s) |
| 8 | *DMSO-d$_6$ (100degC): 9.98 (1H, brs), 9.02 (4H, brs), 7.96 (2H, d, J = 8 Hz), 7.83 (2H, d, J = 8 Hz), 7.17-6.94 (3H, m), 6.09 (1H, brs), 4.67 (2H, s), 4.23-4.07 (1H, m), 4.01-3.86 (1H, m), 3.81-3.63 (1H, m), 3.49-3.33 (1H, m), 2.28 (3H, s), 2.17 (3H, s) |
| 9-5 | DMSO-d$_6$: 10.23 (1H, brs), 8.01 (2H, d, J = 9 Hz), 7.78 (2H, d, J = 9 Hz), 6.92 (1H, d, J = 8 Hz), 6.57 (1H, d, J = 2 Hz), 6.50-6.39 (1H, m), 6.41 (1H, dd, J = 8, 2 Hz), 4.96 (2H, s), 4.63 (1H, d, J = 2 Hz), 4.60 (1H, d, J = 2 Hz), 4.13-4.05 (1H, m), 3.93-3.84 (1H, m), 3.80-3.70 (1H, m), 3.52-3.45 (1H, m), 2.04 (3H, s) |
| 9-6 | DMSO-d$_6$: 10.21 (1H, s), 9.55 (1H, s), 8.01 (2H, d, J = 9 Hz), 7.78 (2H, d, J = 9 Hz), 7.43 (1H, d, J = 2 Hz), 7.27 (1H, d, J = 8 Hz), 7.16-7.12 (1H, m), 6.47 (1H, d, J = 8 Hz), 4.72-4.62 (4H, m), 4.16-4.08 (1H, m), 3.97-3.89 (1H, m), 3.85-3.75 (1H, m), 3.63-3.56 (1H, m), 2.19 (3H, s), 2.13 (3H, s) |
| 10 | *DMSO-d$_6$: 10.22 (1H, s), 9.04 (4H, brs), 8.05 (2H, d, J = 9 Hz), 7.92 (1H, dd, J = 3, 1 Hz), 7.82 (2H, d, J = 9 Hz), 7.79 (2H, d, J = 9 Hz), 7.67 (1H, dd, J = 5, 3 Hz), 7.59 (1H, dd, J = 5, 1 Hz), 7.47 (2H, d, J = 9 Hz), 6.52 (1H, brs), 4.74-4.68 (2H, m), 4.21-4.08 (1H, m), 4.03-3.84 (2H, m), 3.74-3.64 (1H, m) |
| 11 | *DMSO-d$_6$: 10.20 (1H, s), 9.21 (2H, s), 8.87 (2H, s), 8.03 (2H, d, J = 9 Hz), 7.80 (2H, d, J = 9 Hz), 7.44 (2H, d, J = 9 Hz), 7.31 (2H, d, J = 9 Hz), 6.47 (1H, brs), 4.67 (2H, s), 4.17-4.08 (1H, m), 3.98-3.77 (2H, m), 3.66-3.58 (1H, m), 1.30 (9H, s) |
| 12 | *DMSO-d$_6$: 10.20 (1H, s), 9.21 (2H, s), 8.86 (2H, s), 8.03 (2H, d, J = 9 Hz), 7.80 (2H, d, J = 9 Hz), 7.38-7.29 (4H, m), 4.67 (2H, s), 4.50 (2H, s), 4.17-4.08 (1H, m), 3.98-3.52 (3H, m) |
| 13 | DMSO-d$_6$: 10.50 (1H, s), 10.22 (1H, s), 9.26 (2H, s), 8.97 (2H, s), 8.04 (2H, d, J = 9 Hz), 7.83 (2H, d, J = 9 Hz), 7.25-7.10 (2H, m), 6.85 (1H, d, J = 8 Hz), 6.50 (1H, brs) 4.70-4.63 (2H, m), 4.16-4.08 (1H, m), 3.98-3.88 (1H, m), 3.84-3.75 (1H, m), 3.62-3.55 (1H, m), 3.53 (2H, s) |
| 14 | *DMSO-d$_6$: 10.18 (1H, s), 8.99 (4H, brs), 8.02 (2H, d, J = 9 Hz), 7.84-7.73 (4H, m), 7.25 (2H, d, J = 8 Hz), 6.50 (1H, brs), 4.73-4.61 (2H, m), 4.18-4.07 (1H, m), 3.99-3.78 (2H, m), 3.68-3.58 (1H, m) |
| 15 | DMSO-d$_6$: 10.17 (1H, s), 9.22 (2H, s), 8.93 (2H, s), 7.99 (2H, d, J = 9 Hz), 7.78 (2H, d, J = 9 Hz), 7.27-7.21 (4H, m), 6.44 (1H, d, J = 7 Hz), 4.65-4.58 (2H, m), 4.11-4.03 (1H, m), 3.93-3.84 (1H, m), 3.83-3.74 (1H, m), 3.62-3.54 (1H, m), 2.53-2.43 (1H, m), 1.82-1.63 (5H, m), 1.44-1.14 (5H, m) |
| 16 | DMSO-d$_6$: 10.18 (1H, s), 9.24 (2H, s), 8.99 (2H, s), 7.99 (2H, d, J = 9 Hz), 7.79 (2H, d, J = 9 Hz), 7.31-7.19 (4H, m), 6.45 (1H, d, J = 7 Hz), 4.67-4.59 (2H, m), 4.13-4.03 (1H, m), 3.94-3.84 (1H, m), 3.83-3.73 (1H, m), 3.62-3.54 (1H, m), 2.92-2.81 (1H, m), 1.17 (6H, d, J = 7 Hz) |
| 17 | *DMSO-d$_6$: 10.22 (1H, s), 9.24 (2H, s), 8.91 (2H, s), 8.04 (2H, d, J = 9 Hz), 7.82 (2H, d, J = 9 Hz), 7.31 (2H, d, J = 9 Hz), 7.27 (2H, d, J = 9 Hz), 6.52 (1H, brs), 4.68 (2H, s), 4.18-4.08 (1H, m), 4.01-3.78 (2H, m), 3.68-3.59 (1H, m), 2.63 (2H, q, J = 8 Hz), 1.20 (3H, t, J = 8 Hz) |
| 18 | DMSO-d$_6$: 11.21 (1H, s), 10.21 (1H, s), 9.19 (2H, s), 8.87-8.78 (2H, m), 8.04 (2H, d, J = 9 Hz), 7.80 (2H, d, J = 9 Hz), 7.55 (1H, d, J = 8 Hz), 7.40 (1H, t, J = 3 Hz), 7.39-7.35 (1H, m), 6.99-6.93 (1H, m), 6.53 (1H, d, J = 6 Hz), 6.47-6.43 (1H, m), 4.73-4.66 (2H, m), 4.17-4.09 (1H, m), 4.02-3.93 (1H, m), 3.91-3.82 (1H, m), 3.68-3.62 (1H, m) |
| 18-1 | DMSO-d$_6$: 11.34 (1H, brs), 10.33-10.18 (1H, m), 7.75 (2H, d, J = 9 Hz), 7.70 (2H, d, J = 9 Hz), 7.60 (1H, d, J = 8 Hz), 7.47-7.42 (1H, m), 7.41 (1H, s), 6.97 (1H, d, J = 8 Hz), 6.50-6.46 (1H, m), 5.61-5.42 (2H, m), 4.65 (1H, t, J = 5 Hz), 3.84-3.56 (2H, m), 3.49-3.42 (1H, m), 2.15 (3H, s), 1.88 (3H, s) |

TABLE 3-continued

| EXAMPLE | NMR (ppm)<br>(No mark: 400 MHz, *: 300 MHz) |
|---|---|
| 18-2 | DMSO-$d_6$: 11.46-11.30 (1H, m), 10.34-1018 (1H, m), 7.75 (2H, d, J = 9 Hz), 7.70 (2H, d, J = 9 Hz), 7.68-7.59 (1H, m), 7.50-7.39 (2H, m), 7.05-6.96 (1H, m), 6.52-6.47 (1H, m), 5.61-5.42 (2H, m), 4.30-4.19 (2H, m), 4.05-3.82 (2H, m), 3.15 (3H, s), 2.17 (3H, s), 1.93-1.86 (3H, m) |
| 18-3 | DMSO-$d_6$: 11.20 (1H, s), 10.24 (1H, s), 8.03 (2H, d, J = 9 Hz), 7.79 (2H, d, J = 9 Hz), 7.55 (1H, d, J = 8 Hz), 7.40 (1H, d, J = 3 Hz), 7.38-7.35 (1H, m), 6.95 (1H, dd, J = 8, 2 Hz), 6.52 (1H, brs), 6.44 (1H, d, J = 3 Hz), 4.72-4.65 (2H, m), 4.16-4.08 (1H, m), 4.01-3.93 (1H, m), 3.88-3.81 (1H, m), 3.66-3.61 (1H, m) |
| 19 | DMSO-$d_6$: 10.51 (1H, s), 10.23 (1H, s), 9.25 (2H, brs), 8.93 (2H, brs), 8.04 (2H, d, J = 9 Hz), 7.82 (2H, d, J = 9 Hz), 7.35 (1H, d, J = 8 Hz), 6.95 (1H, dd, J = 8 Hz, 2 Hz), 6.91 (1H, d, J = 2 Hz), 6.49 (1H, d, J = 6 Hz), 4.72-4.63 (2H, m), 4.17-4.08 (1H, m), 3.98-3.90 (1H, m), 3.89-3.79 (1H, m), 3.66-3.59 (1H, m), 1.28 (6H, s) |
| 20 | DMSO-$d_6$: 10.76 (1H, brs), 10.71 (1H, brs), 10.19 (1H, s), 9.19 (2H, brs), 8.82 (2H, brs), 8.02 (2H, d, J = 9 Hz), 7.82-7.76 (2H, m), 6.93 (1H, d, J = 8 Hz), 6.92 (1H, d, J = 2 Hz), 6.88 (1H, dd, J = 8, 2 Hz), 6.50 (1H, d, J = 6 Hz), 4.68-4.63 (2H, m), 4.14-4.06 (1H, m), 3.97-3.88 (1H, m), 3.83-3.75 (1H, m), 3.61-3.55 (1H, m) |
| 20-1 | *DMSO-$d_6$: 10.59 (1H, s), 10.55 (1H, s), 10.17 (1H, s), 7.45 (1H, brs), 7.01 (1H, dd, J = 8, 2 Hz), 6.86 (1H, d, J = 8 Hz), 4.22 (2H, s) |
| 20-2 | *DMSO-$d_6$: 10.26 (1H, s), 10.11 (1H, s), 6.66 (1H, d, J = 8 Hz), 6.29-6.20 (2H, m), 5.46 (1H, t, J = 6 Hz), 3.69 (2H, t, J = 6 Hz), 3.40-3.30 (2H, m) |
| 21 | *DMSO-$d_6$: 10.20 (1H, s), 9.22 (2H, s), 8.85 (2H, s), 8.04 (2H, d, J = 9 Hz), 7.80 (2H, d, J = 9 Hz), 7.21 (2H, d, J = 8 Hz), 7.18-7.08 (2H, m), 6.52 (1H, brs), 4.84 (1H, d, J = 15 Hz), 4.69 (1H, brs), 4.62 (1H, s), 4.34 (1H, d, J = 15 Hz), 4.05-3.94 (1H, m), 3.82-3.69 (1H, m), 3.55-3.08 (2H, m), 2.31 (3H, s) |
| 22 | DMSO-$d_6$: 10.21 (1H, s), 9.19 (2H, brs), 8.79 (2H, brs), 8.04 (2H, d, J = 9 Hz), 7.80 (2H, d, J = 9 Hz), 7.71 (2H, d, J = 9 Hz), 7.57 (1H, dd, J = 5, 1 Hz), 7.54 (1H, dd, J = 4, 1 Hz), 7.47 (2H, d, J = 9 Hz), 7.15 (1H, dd, J = 5, 4 Hz), 6.52 (1H, d, J = 7 Hz), 4.73-4.61 (2H, m), 4.18-4.11 (1H, m), 4.00-3.84 (2H, m), 3.72-3.64 (1H, m) |
| 22-1 | *DMSO-$d_6$: 10.23 (1H, s), 8.03 (2H, d, J = 9 Hz), 7.80 (2H, d, J = 9 Hz), 7.77-7.69 (2H, m), 7.58 (1H, d, J = 5 Hz), 7.55 (1H, d, J = 3 Hz), 7.48 (2H, d, J = 9 Hz), 7.19-7.14 (1H, m), 6.50 (1H, d, J = 6 Hz), 4.73-4.66 (2H, m), 4.20-4.11 (1H, m), 4.01-3.83 (2H, m), 3.72-3.64 (1H, m) |
| 23 | DMSO-$d_6$: 10.21 (1H, s), 8.99 (4H, brs), 8.03 (2H, d, J = 9 Hz), 7.80 (2H, d, J = 9 Hz), 7.73 (2H, d, J = 9 Hz), 7.69 (2H, dd, J = 8, 1 Hz), 7.54-7.43 (4H, m), 7.40-7.35 (1H, m), 6.54 (1H, brs), 4.71 (1H, d, J = 3 Hz), 4.70-4.67 (1H, m), 4.18-4.12 (1H, m), 4.01-3.86 (2H, m), 3.74-3.68 (1H, m) |
| 24 | DMSO-$d_6$: 10.21 (1H, s), 9.00 (4H, brs), 8.04 (2H, d, J = 9 Hz), 7.80 (2H, d, J = 9 Hz), 7.70 (2H, d, J = 9 Hz), 7.61 (2H, d, J = 8 Hz), 7.52-7.47 (4H, m), 6.52 (1H, brs), 4.72-4.67 (2H, m), 4.18-4.11 (1H, m), 4.01-3.85 (2H, m), 3.74-3.67 (1H, m), 1.32 (9H, s) |
| 25 | DMSO-$d_6$: 10.21 (1H, s), 9.29-9.17 (2H, m), 9.01-8.75 (2H, m), 8.08 (2H, s), 8.04 (2H, d, J = 9 Hz), 7.85-7.78 (2H, m), 7.65 (2H, d, J = 9 Hz), 7.38 (2H, d, J = 9 Hz), 6.54 (1H, brs), 4.68 (2H, s), 4.18-4.10 (1H, m), 4.00-3.82 (2H, m), 3.69-3.63 (1H, m) |
| 26A | DMSO-$d_6$: 10.20 (1H, s), 10.05 (1H, s), 9.20 (2H, brs), 8.79 (2H, s), 8.04 (2H, d, J = 9 Hz), 7.81 (2H, d, J = 9 Hz), 7.61 (2H, d, J = 9 Hz), 7.32 (2H, d, J = 9 Hz), 6.50 (1H, d, J = 7 Hz), 4.72-4.65 (2H, m), 4.16-4.08 (1H, m), 3.98-3.90 (1H, m), 3.88-3.79 (1H, m), 3.64-3.56 (1H, m), 2.06 (3H, s) |
| 26-5 | *DMSO-$d_6$: 8.02 (2H, d, J = 9 Hz), 7.79 (2H, d, J = 9 Hz), 6.98 (2H, d, J = 9 Hz), 6.56 (2H, d, J = 9 Hz), 5.16 (2H, s), 4.67-4.58 (2H, m), 4.13-4.04 (1H, m), 3.94-3.83 (1H, m), 3.79-3.68 (1H, m), 3.54-3.45 (1H, m) |
| 26-6 | *DMSO-$d_6$: 10.63 (1H, s), 10.04 (1H, s), 7.80 (4H, s), 7.61 (2H, d, J = 9 Hz), 7.32-7.22 (2H, m), 5.55 (1H, s), 4.89 (1H, s), 4.19-4.08 (1H, m), 4.05-3.92 (1H, m), 3.89-3.77 (1H, m), 3.71-3.59 (1H, m), 2.17 (3H, s), 2.05 (3H, s) |
| 26-9 | *CDCl$_3$: 7.51-7.34 (4H, m), 5.47 (1H, d, J = 3 Hz), 5.44 (1H, d, J = 3 Hz), 4.09-3.99 (1H, m), 3.89-3.78 (1H, m), 3.75-3.65 (1H, m), 3.63-3.53 (1H, m), 2.20 (3H, s), 2.12 (3H, s), 1.54 (9H, s) |
| 26-10 | *CDCl$_3$: 11.10 (1H, s), 8.52 (1H, s), 7.80 (2H, d, J = 9 Hz), 7.71 (2H, d, J = 9 Hz), 7.57-7.49 (2H, m), 7.44 (2H, d, J = 9 Hz), 6.74 (1H, s), 5.58 (1H, d, J = 3 Hz), 5.43 (1H, d, J = 3 Hz), 3.94 (2H, t, J = 7 Hz), 3.65-3.56 (1H, m), 2.26 (3H, s), 2.01 (3H, s), 1.54 (9H, s) |
| 27 | DMSO-$d_6$: 10.21 (1H, s), 9.21 (2H, s), 8.82 (2H, s), 8.67 (1H, s), 8.04 (2H, d, J = 9 Hz), 7.81 (2H, d, J = 9 Hz), 7.43 (2H, d, J = 9 Hz), 7.23 (2H, d, J = 9 Hz), 6.51 (1H, d, J = 6 Hz), 5.90 (2H, s), 4.70-4.65 (2H, m), 4.16-4.08 (1H, m), 3.98-3.89 (1H, m), 3.86-3.77 (1H, m), 3.63-3.55 (1H, m) |

TABLE 3-continued

| EXAMPLE | NMR (ppm)<br>(No mark: 400 MHz, *: 300 MHz) |
|---|---|
| 27-1 | *DMSO-d$_6$: 10.21 (1H, s), 8.63 (1H, s), 8.01 (2H, d, J = 9 Hz), 7.78 (2H, d, J = 9 Hz), 7.42 (2H, d, J = 9 Hz), 7.25-7.17 (2H, m), 6.46 (1H, brs), 5.88 (2H, s), 4.64 (2H, s), 4.17-4.05 (1H, m), 3.98-3.73 (2H, m), 3.63-3.50 (1H, m) |
| 28A | DMSO-d$_6$: 10.21 (1H, s), 9.86 (1H, s), 9.22 (2H, s), 8.83 (2H, s), 8.04 (2H, d, J = 9 Hz), 7.81 (2H, d, J = 9 Hz), 7.38 (2H, d, J = 9 Hz), 7.25 (2H, d, J = 9 Hz), 6.50 (1H, brs), 4.70-4.63 (2H, m), 4.17-4.10 (1H, m), 3.98-3.90 (1H, m), 3.89-3.80 (1H, m), 3.66-3.58 (1H, m), 3.03 (3H, s) |
| 28-1 | *DMSO-d$_6$: 10.22 (1H, s), 9.84 (1H, s), 8.02 (2H, d, J = 9 Hz), 7.79 (2H, d, J = 9 Hz), 7.37 (2H, d, J = 9 Hz), 7.24 (2H, d, J = 9 Hz), 6.46 (1H, d, J = 7 Hz), 4.70-4.63 (2H, m), 4.19-4.09 (1H, m), 3.98-3.78 (2H, m), 3.64-3.57 (1H, m), 3.02 (3H, s) |
| 29A | DMSO-d$_6$: 10.21 (1H, s), 9.22 (2H, s), 8.83 (2H, s), 8.05 (2H, d, J = 9 Hz), 7.81 (2H, d, J = 9 Hz), 7.71 (2H, d, J = 9 Hz), 7.41 (2H, d, J = 9 Hz), 6.52 (1H, d, J = 7 Hz), 4.72-4.66 (2H, m), 4.19-4.09 (1H, m), 4.00-3.81 (4H, m), 3.68-3.60 (1H, m), 2.61-2.46 (2H, m), 2.09 (2H, tt, J = 8, 8 Hz) |
| 29-1 | *DMSO-d$_6$: 10.22 (1H, s), 8.03 (2H, d, J = 9 Hz), 7.79 (2H, d, J = 9 Hz), 7.70 (2H, d, J = 9 Hz), 7.40 (2H, d, J = 9 Hz), 6.48 (1H, d, J = 8 Hz), 4.73-4.64 (2H, m), 4.19-4.09 (1H, m), 4.00-3.79 (4H, m), 3.68-3.59 (1H, m), 2.57-2.48 (2H, m), 2.08 (2H, tt, J = 8, 8 Hz) |
| 30A | DMSO-d$_6$: 10.22 (1H, s), 9.21 (2H, s), 8.81 (2H, s), 8.04 (2H, d, J = 9 Hz), 7.81 (2H, d, J = 9 Hz), 7.46 (4H, s), 6.52 (1H, d, J = 7 Hz), 4.72-4.67 (2H, m), 4.23 (2H, s), 4.19-4.11 (1H, m), 4.03-3.92 (3H, m), 3.92-3.83 (1H, m), 3.79-3.74 (2H, m), 3.72-3.66 (1H, m) |
| 31 | DMSO-d$_6$: 10.19 (1H, s), 9.34-8.62 (4H, m), 8.02 (2H, d, J = 9 Hz), 7.79 (2H, d, J = 9 Hz), 7.60 (2H, d, J = 9 Hz), 7.41 (2H, d, J = 9 Hz), 6.51 (1H, brs), 4.67 (2H, s), 4.44 (2H, t, J = 8 Hz), 4.16-4.03 (3H, m), 3.98-3.89 (1H, m), 3.88-3.79 (1H, m), 3.66-3.59 (1H, m) |
| 32 | DMSO-d$_6$: 10.21 (1H, s), 9.92 (1H, s), 9.20 (2H, s), 8.79 (2H, s), 8.04 (2H, d, J = 9 Hz), 7.81 (2H, d, J = 9 Hz), 7.70 (2H, d, J = 9 Hz), 7.45-7.30 (7H, m), 6.51 (1H, d, J = 7 Hz), 4.70-4.66 (2H, m), 4.63 (2H, s), 4.17-4.09 (3H, m), 3.98-3.90 (1H, m), 3.89-3.80 (1H, m), 3.66-3.59 (1H, m) |
| 33 | DMSO-d$_6$: 10.20 (1H, s), 9.78 (1H, s), 9.21 (2H, s), 8.84 (2H, s), 8.03 (2H, d, J = 9 Hz), 7.80 (2H, d, J = 9 Hz), 7.74 (2H, d, J = 9 Hz), 7.32 (2H, d, J = 9 Hz), 6.50 (1H, d, J = 7 Hz), 5.74-5.69 (1H, m), 4.70-4.65 (2H, m), 4.18-4.05 (1H, m), 4.00 (2H, d, J = 6 Hz), 3.97-3.89 (1H, m), 3.88-3.79 (1H, m), 3.64-3.58 (1H, m) |
| 34 | *DMSO-d$_6$: 10.43 (1H, s), 10.18 (1H, s), 9.21 (2H, s), 8.86 (2H, s), 8.03 (2H, d, J = 9 Hz), 7.80 (2H, d, J = 9 Hz), 7.31 (1H, d, J = 2 Hz), 7.15 (1H, dd, J = 8, 2 Hz), 6.87 (1H, d, J = 8 Hz), 6.49 (1H, d, J = 7 Hz), 4.72-4.61 (2H, m), 4.17-4.05 (1H, m), 3.98-3.75 (2H, m), 3.64-3.54 (1H, m), 1.26 (3H, s), 1.26 (3H, s) |
| 35 | *DMSO-d$_6$: 11.22 (1H, brs), 10.16 (1H, brs), 7.98 (2H, d, J = 9 Hz), 7.77 (2H, d, J = 9 Hz), 7.48 (1H, d, J = 2 Hz), 7.44-7.37 (2H, m), 7.04 (1H, dd, J = 8, 2 Hz), 6.44 (1H, d, J = 3 Hz), 4.70-4.63 (2H, m), 4.17-4.07 (1H, m), 4.02-3.78 (2H, m), 3.67-3.58 (1H, m), 1.72 (3H, s) |
| 36 | DMSO-d$_6$: 11.80 (1H, s), 10.21 (1H, s), 9.24 (2H, s), 8.94 (2H, s), 8.03 (2H, d, J = 9 Hz), 7.81 (2H, d, J = 9 Hz), 7.40-7.35 (1H, m), 7.21-7.05 (2H, m), 6.52 (1H, brs), 4.67 (2H, s), 4.17-4.08 (1H, m), 3.98-3.77 (2H, m), 3.70-3.56 (1H, m) |
| 37 | DMSO-d$_6$: 10.22 (1H, s), 9.23 (2H, s), 8.90 (2H, s), 8.66 (1H, s), 8.04 (2H, d, J = 9 Hz), 7.81 (2H, d, J = 9 Hz), 7.73-7.69 (1H, m), 7.66-7.59 (2H, m), 6.55 (1H, d, J = 6 Hz), 4.74-4.66 (2H, m), 4.39 (2H, s), 4.18-4.11 (1H, m), 4.02-3.85 (2H, m), 3.75-3.68 (1H, m) |
| 38 | *DMSO-d$_6$: 12.97 (1H, brs), 10.39 (1H, s), 10.09 (1H, s), 8.95 (2H, brs), 8.56-8.49 (2H, m), 8.07 (1H, dd, J = 9, 2 Hz), 7.68-7.58 (3H, m), 7.33 (2H, d, J = 9 Hz), 7.17 (1H, d, J = 7 Hz), 4.72 (1H, d, J = 2 Hz), 4.70 (1H, d, J = 2 Hz), 4.19-4.09 (1H, m), 4.00-3.79 (2H, m), 3.66-3.58 (1H, m), 2.07 (3H, s) |
| 38-3 | *DMSO-d$_6$: 10.38 (1H, s), 10.17 (1H, s), 8.37-8.30 (2H, m), 7.88-7.67 (5H, m), 7.35 (2H, d, J = 8 Hz), 5.57 (1H, d, J = 3 Hz), 5.49 (1H, d, J = 3 Hz), 3.97-3.77 (2H, m), 3.67-3.58 (2H, m), 2.19 (3H, s), 2.08 (3H, s), 1.95 (3H, s), 1.29 (18H, s) |
| 39 | DMSO-d$_6$: 10.25 (2H, s), 10.13 (1H, s), 9.75 (1H, s), 9.21 (1H, s), 8.32 (1H, s), 8.22 (1H, d, J = 9 Hz), 7.94-7.90 (1H, m), 7.61 (2H, d, J = 9 Hz), 7.29 (2H, d, J = 9 Hz), 6.49 (1H, brs), 4.77 (2H, s), 4.68-4.64 (2H, m), 4.15-4.07 (1H, m), 3.96-3.77 (2H, m), 3.62-3.54 (1H, m), 2.04 (3H, s) |
| 39-1 | *CDCl$_3$: 8.25-8.18 (2H, m), 7.86 (1H, d, J = 8 Hz), 5.12 (2H, s), 1.51 (18H, s) |
| 39-2 | *DMSO-d$_6$: 7.36 (1H, d, J = 8 Hz), 6.51-6.45 (1H, m), 6.39-6.36 (1H, m), 6.23 (2H, s), 4.70 (2H, s), 1.39 (18H, s) |
| 40 | DMSO-d$_6$: 10.20 (1H, s), 10.01 (1H, s), 9.24 (2H, s), 8.94 (2H, s), 8.03 (2H, d, J = 9 Hz), 7.81 (2H, d, J = 9 Hz), 7.63 (2H, d, J = 9 Hz), 7.30 (2H, d, J = 9 Hz), 6.53-6.46 (1H, m), 4.66 (2H, s), 4.15-4.08 (1H, m), 3.97-3.78 (2H, m), 3.63-3.56 (1H, m), 2.33 (2H, q, J = 8 Hz), 1.08 (3H, t, J = 8 Hz) |

TABLE 3-continued

| EXAMPLE | NMR (ppm) (No mark: 400 MHz, *: 300 MHz) |
|---|---|
| 41 | *DMSO-$d_6$: 10.20 (1H, s), 9.95 (1H, s), 9.23 (2H, s), 8.91 (2H, s), 8.03 (2H, d, J = 9 Hz), 7.81 (2H, d, J = 9 Hz), 7.64 (2H, d, J = 9 Hz), 7.31 (2H, d, J = 9 Hz), 6.49 (1H, d, J = 8 Hz), 4.70-4.64 (2H, m), 4.16-4.08 (1H, m), 3.98-3.77 (2H, m), 3.64-3.55 (1H, m), 2.21 (2H, d, J = 7 Hz), 1.12-1.00 (1H, m), 0.52-0.44 (2H, m), 0.23-0.17 (2H, m) |
| 42 | *DMSO-$d_6$: 10.18 (1H, s), 9.90 (1H, s), 9.20 (2H, brs), 8.81 (2H, brs), 8.03 (2H, d, J = 9 Hz), 7.80 (2H, d, J = 9 Hz), 7.63 (2H, d, J = 9 Hz), 7.29 (2H, d, J = 9 Hz), 6.48 (1H, d, J = 8 Hz), 4.69-4.64 (2H, m), 4.16-4.07 (1H, m), 3.97-3.76 (2H, m), 3.63-3.55 (1H, m), 2.38-2.25 (1H, m), 1.85-1.60 (5H, m), 1.49-1.13 (5H, m) |
| 43 | *DMSO-$d_6$: 10.22 (1H, s), 9.28 (2H, s), 9.02 (2H, s), 8.02 (2H, d, J = 9 Hz), 7.83 (2H, d, J = 9 Hz), 7.43 (2H, d, J = 9 Hz), 7.28 (2H, d, J = 9 Hz), 4.72-4.65 (2H, m), 4.18-4.09 (1H, m), 3.99-3.80 (2H, m), 3.68-3.59 (1H, m) |
| 44 | *DMSO-$d_6$ (100degC): 9.91 (1H, s), 8.97 (3H, brs), 7.95 (2H, d, J = 9 Hz), 7.84 (2H, d, J = 9 Hz), 7.14 (1H, dd, J = 8, 8 Hz), 6.82 (1H, s), 6.75-6.66 (2H, m), 4.70 (1H, d, J = 2 Hz), 4.66 (1H, d, J = 2 Hz), 4.20-4.12 (1H, m), 3.97-3.88 (1H, m), 3.87-3.78 (1H, m), 3.75-3.31 (1H, m) |
| 45 | *DMSO-$d_6$ (100degC): 9.90 (1H, s), 9.72 (1H, s), 8.91 (3H, brs), 7.94 (2H, d, J = 9 Hz), 7.82 (2H, d, J = 9 Hz), 7.66 (1H, dd, J = 2, 2 Hz), 7.44-7.39 (1H, m), 7.29 (1H, dd, J = 8, 8 Hz), 7.07-7.02 (1H, m), 5.98 (1H, brs), 4.71-4.66 (2H, m), 4.20-4.12 (1H, m), 3.98-3.80 (2H, m), 3.63-3.55 (1H, m), 2.04 (3H, s) |
| 46 | *DMSO-$d_6$ (100degC): 9.89 (1H, s), 8.93 (3H, brs), 7.94 (2H, d, J = 9 Hz), 7.82 (2H, d, J = 9 Hz), 7.72 (1H, dd, J = 2, 2 Hz), 7.52-7.47 (1H, m), 7.37 (1H, dd, J = 8, 8 Hz), 7.18-7.13 (1H, m), 4.71-4.67 (2H, m), 4.21-4.13 (1H, m), 3.99-3.79 (4H, m), 3.67-3.60 (1H, m), 2.52-2.45 (2H, m), 2.09 (2H, tt, J = 7, 7 Hz) |
| 47 | *DMSO-$d_6$ (100degC): 9.89 (1H, s), 8.88 (2H, brs), 8.46 (1H, s), 7.94 (2H, d, J = 9 Hz), 7.82 (2H, d, J = 9 Hz), 7.52-7.48 (1H, m), 7.26-7.21 (2H, m), 6.94-6.89 (1H, m), 5.98 (1H, brs), 5.60 (2H, brs), 4.72-4.65 (2H, m), 4.20-4.11 (1H, m), 3.98-3.79 (2H, m), 3.62-3.54 (1H, m) |
| 48 | *DMSO-$d_6$: 10.20 (1H, s), 9.20 (2H, s), 8.81 (2H, s), 8.03 (2H, d, J = 9 Hz), 7.80 (2H, d, J = 9 Hz), 7.68 (1H, s), 7.46-7.41 (2H, m), 7.18-7.12 (1H, m), 6.51 (1H, d, J = 7 Hz), 4.71-4.65 (2H, m), 4.46 (2H, t, J = 8 Hz), 4.18-3.81 (5H, m), 3.67-3.59 (1H, m) |
| 49 | *DMSO-$d_6$: 10.20 (1H, s), 9.91 (1H, s), 9.21 (2H, s), 8.84 (2H, s), 8.03 (2H, d, J = 9 Hz), 7.80 (2H, d, J = 9 Hz), 7.39 (1H, dd, J = 8, 8 Hz), 7.30-7.27 (1H, m), 7.16-7.08 (2H, m), 6.48 (1H, d, J = 6 Hz), 4.72-4.63 (2H, m), 4.16-4.08 (1H, m), 4.00-3.82 (2H, m), 3.64-3.55 (1H, m), 3.03 (3H, s) |
| 50 | *DMSO-$d_6$: 10.20 (1H, s), 9.77 (1H, s), 9.20 (2H, s), 8.83 (2H, s), 8.03 (2H, d, J = 9 Hz), 7.84-7.77 (3H, m), 7.59-7.54 (1H, m), 7.35 (1H, dd, J = 8, 8 Hz), 7.12-7.07 (1H, m), 6.48 (1H, d, J = 7 Hz), 5.69 (1H, t, J = 6 Hz), 4.71-4.64 (2H, m), 4.17-4.09 (1H, m), 4.02-3.80 (4H, m), 3.63-3.55 (1H, m) |
| 51 | *DMSO-$d_6$: 10.21 (1H, s), 9.33-9.19 (2H, m), 9.06-8.86 (2H, m), 8.03 (2H, d, J = 9 Hz), 7.82 (2H, d, J = 9 Hz), 7.52-7.43 (2H, m), 7.37-7.28 (2H, m), 6.60-6.44 (1H, m), 4.72-4.64 (2H, m), 4.22 (2H, s), 4.19-4.10 (1H, m), 4.02-3.82 (4H, m), 3.78-3.63 (3H, m) |
| 52 | *DMSO-$d_6$: 12.87 (1H, brs), 10.40 (1H, s), 8.89 (2H, brs), 8.54-8.48 (2H, m), 8.06 (1H, dd, J = 9, 2 Hz), 7.63 (1H, d, J = 7 Hz), 7.45 (2H, d, J = 9 Hz), 7.33 (2H, d, J = 9 Hz), 7.18 (1H, d, J = 7 Hz), 6.55 (1H, d, J = 7 Hz), 4.76-4.69 (2H, m), 4.19-4.10 (1H, m), 4.01-3.80 (2H, m), 3.69-3.60 (1H, m), 1.31 (9H, s) |
| 52-1 | *CDCl$_3$: 7.50 (2H, d, J = 9 Hz), 7.37 (2H, d, J = 9 Hz), 5.49 (1H, d, J = 3 Hz), 5.24 (1H, d, J = 3 Hz), 4.20-3.98 (1H, m), 3.88-3.66 (2H, m), 3.63-3.46 (1H, m), 2.20 (3H, s), 2.11 (3H, s), 1.34 (9H, s), 1.26 (9H, s) |
| 52-4 | *DMSO-$d_6$: 12.73 (1H, brs), 7.41 (2H, d, J = 9 Hz), 7.27 (2H, d, J = 9 Hz), 5.41 (1H, brs), 4.55 (1H, d, J = 2 Hz), 4.52 (1H, d, J = 2 Hz), 4.16-4.08 (1H, m), 3.96-3.77 (2H, m), 3.64-3.55 (1H, m), 1.29 (9H, s) |
| 53 | DMSO-$d_6$: 10.25 (1H, s), 10.17 (1H, brs), 9.56 (1H, brs), 9.12 (1H, brs), 8.33-8.31 (1H, m), 8.14 (1H, d, J = 9 Hz), 7.93 (1H, dd, J = 9, 2 Hz), 7.43 (2H, d, J = 9 Hz), 7.30 (2H, d, J = 9 Hz), 6.48 (1H, d, J = 7 Hz), 4.78 (2H, s), 4.69-4.65 (2H, m), 4.14-4.08 (1H, m), 3.95-3.78 (2H, m), 3.65-3.58 (1H, m), 1.29 (9H, s) |
| 54 | *DMSO-$d_6$: 12.90 (1H, brs), 10.39 (1H, s), 8.91 (2H, brs), 8.54-8.47 (2H, m), 8.05 (1H, dd, J = 9, 2 Hz), 7.82 (2H, d, J = 9 Hz), 7.70 (2H, d, J = 9 Hz), 7.62 (1H, d, J = 7 Hz), 7.16 (1H, d, J = 7 Hz), 6.59 (1H, brs), 4.79-4.70 (2H, m), 4.21-4.13 (1H, m), 4.03-3.88 (2H, m), 3.78-3.70 (1H, m) |
| 54-3 | *CDCl$_3$: 7.79 (2H, d, J = 9 Hz), 7.71-7.64 (2H, m), 5.43 (1H, d, J = 2 Hz), 5.20 (1H, d, J = 2 Hz), 4.07-3.98 (1H, m), 3.96-3.85 (1H, m), 3.79-3.58 (2H, m), 2.20 (3H, s), 2.11 (3H, s), 1.28 (9H, s) |

TABLE 3-continued

| EXAMPLE | NMR (ppm) (No mark: 400 MHz, *: 300 MHz) |
|---|---|
| 55 | *DMSO-d$_6$: 12.93 (1H, brs), 10.38 (1H, s), 8.90 (2H, brs), 8.54-8.47 (2H, m), 8.05 (1H, dd, J = 9, 2 Hz), 7.65-7.53 (3H, m), 7.45 (2H, d, J = 8 Hz), 7.16 (1H, d, J = 7 Hz), 6.56 (1H, d, J = 7 Hz), 4.76-4.68 (2H, m), 4.20-4.11 (1H, m), 4.02-3.84 (2H, m), 3.72-3.63 (1H, m) |
| 56 | *DMSO-d$_6$: 10.21 (1H, s), 9.25 (2H, s), 8.96 (2H, s), 8.03 (2H, d, J = 9 Hz), 7.82 (2H, d, J = 9 Hz), 7.56 (2H, d, J = 9 Hz), 7.45 (2H, d, J = 9 Hz), 6.50 (1H, d, J = 7 Hz), 4.74-4.63 (2H, m), 4.20-4.09 (1H, m), 4.01-3.83 (2H, m), 3.72-3.63 (1H, m) |
| 57 | DMSO-d$_6$: 10.29-10.21 (2H, m), 9.68 (1H, brs), 9.18 (1H, brs), 8.33-8.32 (1H, m), 8.19 (1H, d, J = 9 Hz), 7.93 (1H, dd, J = 9, 2 Hz), 7.56 (2H, d, J = 9 Hz), 7.48-7.42 (2H, m), 6.51 (1H, d, J = 7 Hz), 4.78 (2H, s), 4.73-4.66 (2H, m), 4.18-4.11 (1H, m), 3.99-3.85 (2H, m), 3.71-3.65 (1H, m) |
| 58 | *DMSO-d$_6$: 12.88 (1H, brs), 10.37 (1H, s), 8.86 (2H, brs), 8.53-8.46 (2H, m), 8.05 (1H, dd, J = 9, 2 Hz), 7.67-7.60 (3H, m), 7.40 (2H, d, J = 9 Hz), 7.16 (1H, d, J = 7 Hz), 6.56 (1H, d, J = 8 Hz), 4.74-4.68 (2H, m), 4.18-4.10 (1H, m), 4.00-3.82 (2H, m), 3.69-3.61 (1H, m) |
| 59 | DMSO-d$_6$: 12.82 (1H, brs), 10.36 (1H, s), 8.82 (2H, brs), 8.52-8.46 (2H, m), 8.04 (1H, dd, J = 9, 2 Hz), 7.61 (1H, d, J = 7 Hz), 7.46-7.41 (2H, m), 7.27 (2H, dd, J = 9, 9 Hz), 7.15 (1H, d, J = 7 Hz), 6.56 (1H, d, J = 7 Hz), 4.73-4.68 (2H, m), 4.16-4.09 (1H, m), 3.98-3.80 (2H, m), 3.66-3.59 (1H, m) |
| 59-2 | *CDCl$_3$: 6.92 (2H, dd, J = 9, 9 Hz), 6.63-6.56 (2H, m), 3.95 (1H, brs), 3.72 (2H, t, J = 6 Hz), 3.47 (2H, t, J = 6 Hz) |
| 60 | DMSO-d$_6$: 12.78 (1H, brs), 10.36 (1H, s), 8.81 (2H, brs), 8.51-8.45 (2H, m), 8.04 (1H, dd, J = 9, 2 Hz), 7.61 (1H, d, J = 7 Hz), 7.50 (2H, d, J = 9 Hz), 7.45 (2H, d, J = 9 Hz), 7.15 (1H, d, J = 7 Hz), 6.56 (1H, d, J = 7 Hz), 4.73-4.68 (2H, m), 4.16-4.10 (1H, m), 3.98-3.82 (2H, m), 3.68-3.61 (1H, m) |
| 60-2 | *CDCl$_3$: 7.15 (2H, d, J = 9 Hz), 6.57 (2H, d, J = 9 Hz), 4.06 (1H, brs), 3.71 (2H, t, J = 6 Hz), 3.53-3.45 (2H, m) |
| 61 | *DMSO-d$_6$: 12.94 (1H, brs), 10.39 (1H, s), 8.93 (2H, brs), 8.57-8.48 (2H, m), 8.07 (1H, dd, J = 9, 2 Hz), 7.63 (1H, d, J = 7 Hz), 7.28 (2H, d, J = 9 Hz), 7.17 (1H, d, J = 7 Hz), 6.96 (2H, d, J = 9 Hz), 6.55 (1H, brs), 4.75-4.58 (3H, m), 4.18-4.09 (1H, m), 3.99-3.77 (2H, m), 3.65-3.56 (1H, m), 1.29 (6H, d, J = 6 Hz) |
| 61-2 | *CDCl$_3$: 6.84-6.76 (2H, m), 6.65-6.57 (2H, m), 4.45-4.32 (1H, m), 3.76-3.68 (2H, m), 3.50-3.42 (2H, m), 1.34-1.28 (6H, m) |
| 62 | DMSO-d$_6$: 12.94 (1H, brs), 10.38 (1H, s), 8.92 (2H, brs), 8.54-8.48 (2H, m), 8.05 (1H, dd, J = 9, 2 Hz), 7.62 (1H, d, J = 7 Hz), 7.28 (2H, d, J = 9 Hz), 7.23 (2H, d, J = 9 Hz), 7.16 (1H, d, J = 7 Hz), 6.56 (1H, brs), 4.73-4.67 (2H, m), 4.16-4.09 (1H, m), 3.98-3.90 (1H, m), 3.87-3.78 (1H, m), 3.64-3.58 (1H, m), 2.32 (3H, s) |
| 63 | *DMSO-d$_6$(100degC): 10.11 (1H, s), 8.73 (2H, brs), 8.50 (1H, d, J = 9 Hz), 8.35 (1H, d, J = 2 Hz), 8.03 (1H, dd, J = 9, 2 Hz), 7.58 (1H, d, J = 7 Hz), 7.27-7.19 (1H, m), 7.14-6.99 (3H, m), 4.74-4.68 (2H, m), 4.22-4.12 (1H, m), 4.01-3.91 (1H, m), 3.81-3.69 (1H, m), 3.49-3.40 (1H, m), 2.23 (3H, s) |
| 64 | *DMSO-d$_6$(100degC): 9.92 (1H, s), 8.89 (4H, brs), 7.95 (2H, d, J = 9 Hz), 7.85-7.79 (2H, m), 7.26-7.18 (1H, m), 7.14-6.99 (2H, m), 4.68 (2H, s), 4.21-4.11 (1H, m), 4.00-3.90 (1H, m), 3.80-3.67 (1H, m), 3.48-3.39 (1H, m), 2.22 (3H, s) |
| 65 | DMSO-d$_6$: 9.41 (4H, brs), 7.98 (1H, d, J = 9 Hz), 7.71 (1H, s), 7.69-7.64 (1H, m), 7.44 (2H, d, J = 9 Hz), 7.32 (2H, d, J = 9 Hz), 4.72-4.65 (2H, m), 4.18-4.12 (1H, m), 4.00-3.82 (2H, m), 3.66-3.60 (1H, m), 2.31 (3H, s), 1.30 (9H, s) |
| 66 | *DMSO-d$_6$: 8.54-8.47 (1H, m), 8.04-8.00 (1H, m), 7.82 (1H, d, J = 9 Hz), 7.43 (2H, d, J = 9 Hz), 7.32 (2H, d, J = 9 Hz), 4.76-4.66 (2H, m), 4.17-4.08 (1H, m), 4.00-3.82 (2H, m), 3.65-3.56 (1H, m), 1.73 (3H, s), 1.30 (9H, s) |
| 66-2 | *DMSO-d$_6$: 9.73 (1H, s), 9.55 (1H, s), 8.35 (1H, d, J = 9 Hz), 7.81 (1H, d, J = 2 Hz), 7.68 (1H, dd, J = 9, 2 Hz), 7.43 (2H, d, J = 9 Hz), 7.31 (2H, d, J = 9 Hz), 6.95 (1H, d, J = 5 Hz), 5.89 (2H, s), 4.73-4.65 (2H, m), 4.17-4.10 (1H, m), 3.99-3.82 (2H, m), 3.63-3.56 (1H, m), 1.30 (9H, s) |
| 67 | *DMSO-d$_6$: 8.27 (1H, dd, J = 8, 8 Hz), 7.84-7.63 (2H, m), 7.43 (2H, d, J = 9 Hz), 7.31 (2H, d, J = 9 Hz), 4.72 (1H, s), 4.68 (1H, s), 4.18-4.08 (1H, m), 4.00-3.80 (2H, m), 3.66-3.56 (1H, m), 1.73 (3H, s), 1.29 (9H, s) |
| 68 | $^1$H NMR (DMSO-d$_6$, 400 MHz): δ 10.2 (s, 1H), 9.22 (s, 2H), 8.89 (s, 2H), 8.03 (d, J = 8.5 Hz, 2H), 7.81 (d, J = 8.5 Hz, 2H), 7.72 (s, 1H), 7.66-7.60 (m, 2H), 6.52 (d, J = 6.8 Hz, 1H), 4.71-4.68 (m, 2H), 4.48 (s, 2H), 4.18-4.13 (m, 1H), 4.01-3.85 (m, 2H), 3.75-3.70 (m, 1H), 3.49 (t, J = 7.2 Hz, 2H), 1.63 (sextet, J = 7.2 Hz, 2H), 0.87 (t, J = 7.2 Hz, 3H)<br>13C NMR (CDCl$_3$, 400 MHz): δ 171.0, 166.4, 166.2, 164.3, 143.0, 141.3, 139.4, 132.8, 128.7, 128.0, 123.5, 121.8, 119.6, 118.8, 78.6, 72.6, 62.2, 49.2, 48.8, 42.9, 20.7, 10.8; |

TABLE 3-continued

| EXAMPLE | NMR (ppm) (No mark: 400 MHz, *: 300 MHz) |
|---|---|
| 68-8 | $^1$H NMR (CDCl$_3$, 300 MHz): δ 8.19 (d, J = 1.7 Hz, 1H), 7.83 (dd, J = 8.0 Hz, 1.7 Hz 1H), 7.20 (d, J = 8.0 Hz, 1H), 4.32 (s, 2H), 3.57 (t, J = 7.3 Hz, 2H), 1.69 (sextet, J = 7.3 Hz, 2H), 0.96 (t, J = 7.3 Hz, 3H). 13C NMR (CDCl$_3$, 400 MHz): δ 166.8, 141.4, 139.8, 135.3, 132.8, 124.5, 93.1, 49.7, 44.1, 21.7, 11.3; |
| 68-9 | CDCl$_3$, 300 MHz: δ 7.73 (d, J = 1.8 Hz, 1H), 7.64 (dd, J = 8.1 Hz, 1.8 Hz, 1H), 7.47 (d, J = 8.1 Hz, 1H), 4.73 (br, s, 1H), 4.65 (d, J = 2.1 Hz, 1H), 4.37 (s, 2H), 4.28-4.20 (m, 1H), 4.06-3.94 (m, 2H), 3.70-3.56 (m, 3H), 3.25 (br, s, 1H), 1.69 (sextet, J = 7.5 Hz, 2H), 1.52 (s, 9H), 0.96 (t, J = 7.5 Hz, 3H); |
| 68-10 | CDCl$_3$, 300 MHz: δ 7.70 (d, J = 2.1 Hz, 1H), 7.57 (dd, J = 8.1 Hz, 2.1 Hz, 1H), 7.47 (d, J = 8.1 Hz, 1H), 5.65 (d, J = 2.4 Hz, 1H), 4.88 (d, J = 2.4 Hz, 1H), 4.38 (s, 2H), 4.32-4.26 (m, 1H), 4.14-3.98 (m, 2H), 3.70-3.56 (m, 3H), 2.17 (s, 3H), 1.70 (sextet, J = 7.5 Hz, 2H), 1.50 (s, 9H), 0.96 (t, J = 7.5 Hz, 3H); |
| 68-11 | DMSO-d6, 300 MHz: δ 7.64-7.62 (m, 2H), 7.55 (dd, J = 8.1 Hz, 2.1 Hz, 1H), 5.43 (d, J = 2.4 Hz, 1H), 4.86 (d, J = 2.4 Hz, 1H), 4.48 (s, 2H), 4.19-3.90 (m, 3H), 3.75-3.68 (m, 1H), 3.48 (t, J = 7.2 Hz, 2H), 2.17 (s, 3H), 1.62 (sextet, J = 7.2 Hz, 2H), 0.96 (t, J = 7.2 Hz, 3H); |
| 68-13 | DMSO-d6, 400 MHz: δ 12.8 (s, 1H), 10.5 (s, 1H), 7.82-7.78 (m, 4H), 7.67-7.64 (m, 2H), 7.58 (dd, J = 8.1 Hz, 2.1 Hz, 1H), 5.59 (d, J = 2.4 Hz, 1H), 4.95 (d, J = 2.4 Hz, 1H), 4.48 (s, 2H), 4.20-4.14 (m, 1H), 4.07-4.00 (m, 1H), 3.98-3.90 (m, 1H), 3.78-3.72 (m, 1H), 3.49 (t, J = 7.2 Hz, 2H), 2.17 (s, 3H), 1.62 (sextet, J = 7.2 Hz, 2H), 0.87 (t, J = 7.2 Hz, 3H); |
| 68-14 | DMSO-d6, 400 MHz: δ 12.8 (br, s, 1H), 10.0 (s, 1H), 8.00-7.98 (m, 2H), 7.78-7.71 (m, 3H), 7.66-7.50 (m, 2H), 6.46 (d, J = 6.8 Hz, 1H), 4.71-4.67 (m, 2H), 4.48 (s, 2H), 4.18-4.13 (m, 1H), 4.00-3.85 (m, 2H), 3.74-3.70 (m, 1H), 3.49 (t, J = 7.2 Hz, 2H), 1.62 (sextet, J = 7.2 Hz, 2H), 0.87 (t, J = 7.2 Hz, 3H) |
| 69 | CD$_3$OD, 400 MHz: δ 9.94 (s, 1H), 9.18 (br, s, 1H), 8.64 (br, s, 1H), 7.96 (d, J = 8.8 Hz, 2H), 7.85-7.80 (m, 3H), 7.72-7.67 (m, 2H), 4.68 (s, 2H), 4.35 (q, J = 9.6 Hz, 2H), 4.27-4.20 (m, 1H), 4.10-4.02 (m, 2H), 3.75-3.69 (m, 1H); E |
| 69-1 | DMSO-d6, 300 MHz: δ 8.60 (br, s, 1H), 7.95-7.91 (m, 2H), 7.42 (d, J = 7.8 Hz, 1H), 4.32 (s, 2H). 13C NMR (CDCl3, 400 MHz) δ 168.2, 143.5, 139.5, 134.9, 130.6, 125.9, 93.2, 44.7; |
| 69-2 | $^1$H NMR (CDCl$_3$, 400 MHz): δ 8.23 (d, J = 1.6 Hz, 1H), 7.90 (dd, J = 8.0 Hz, 1.6 Hz, 1H), 7.24 (d, J = 8.0 Hz, 1H), 4.50 (s, 2H), 4.20 (q, J = 9.2 Hz, 2H) 13C NMR (CDCl$_3$, 400 MHz): δ 167.2, 140.9, 140.5, 133.4, 133.1, 124.6, 124.1 (q, J = 280.3 Hz), 93.3, 50.5, 44.1 (q, J = 34.8 Hz). |
| 69-3 | CDCl$_3$, 400 MHz: δ 7.80 (d, J = 2.0 Hz, 1H), 7.71 (dd, J = 8.4 Hz, 2.0 Hz, 1H), 7.51 (d, J = 8.4 Hz, 1H), 4.73 (dd, J = 6.8 Hz, 2.0 Hz, 1H), 4.65 (d, J = 2.0 Hz, 1H), 4.55 (s, 2H), 4.29-4.19 (m, 3H), 4.05-3.96 (m, 2H), 3.70-3.63 (m, 1H), 3.26 (d, J = 7.2 Hz, 1H), 1.52 (s, 9H). |
| 69-4 | CDCl$_3$, 300 MHz: δ 7.76 (d, J = 2.1 Hz, 1H), 7.65 (dd, J = 8.1 Hz, 2.1 Hz, 1H), 7.52 (d, J = 8.4 Hz, 1H), 5.65 (d, J = 2.4 Hz, 1H), 4.89 (d, J = 2.4 Hz, 1H), 4.56 (s, 2H), 4.33-3.99 (m, 5H), 3.70-3.64 (m, 1H), 2.17 (s, 3H), 1.51 (s, 9H). |
| 69-5 | CDCl$_3$, 300 MHz: δ 7.79 (d, J = 2.1 Hz, 1H), 7.65 (dd, J = 8.1 Hz, 2.1 Hz, 1H), 7.53 (d, J = 8.1 Hz, 1H), 5.80 (d, J = 2.4 Hz, 1H), 4.93 (d, J = 2.4 Hz, 1H), 4.58 (s, 2H), 4.34-4.02 (m, 5H), 3.71-3.65 (m, 1H), 2.19 (s, 3H). |
| 69-6 | CD$_3$OD, 300 MHz: δ 10.2 (br, s, 1H), 7.84-7.64 (m, 8H), 5.70 (d, J = 2.7 Hz, 1H), 4.92 (s, 1H), 4.68 (s, 2H), 4.40-4.02 (m, 5H), 3.80-3.71 (m, 1H), 2.23 (s, 3H). |
| 69-7 | DMSO-d$_6$, 300 MHz: δ 10.0 (br, s, 1H), 7.98 (d, J = 9.0 Hz, 2H), 7.82-7.70 (m, 6H), 6.46 (d, J = 6.8 Hz, 1H), 4.73-4.63 (m, 4H), 4.41 (q, J = 9.6 Hz, 2H), 4.20-4.13 (m, 1H), 4.03-3.85 (m, 2H), 3.77-3.68 (m, 1H); |
| 70 | DMSO-d6: 10.2 (1H, s), 9.28 (2H, s), 9.01 (2H, s), 8.04 (2H, d, J = 7.9 Hz), 7.83 (2H, d, J = 7.5 Hz), 7.73 (1H, s), 7.66-7.63 (2H, m), 6.57 (1H, s), 4.71 (2H, s), 4.50 (2H, s), 4.17-4.14 (1H, m), 3.99-3.95 (1H, m), 3.93-3.90 (1H, m), 3.74-3.71 (1H, m), 3.09 (2H, s), 2.08 (2H, s) |
| 71 | DMSO-d6: 9.93 (1H, s), 8.22 (2H, brs), 7.83 (2H, d, J = 8.2 Hz), 7.73 (1H, s), 7.65-7.62 (2H, m), 7.41 (2H, d, J = 8.5 Hz), 6.47 (1H, d, J = 6.7 Hz), 4.70 (1H, s), 4.66-4.64 (2H, m), 4.48 (2H, s), 4.16-4.13 (1H, m), 3.98 (1H, s), 3.95-3.91 (1H, m), 3.90-3.88 (2H, m), 3.73-3.71 (1H, m), 3.52-3.45 (2H, m) |
| 72 | DMSO-d6: 9.74 (1H, s), 9.31-9.24 (2H, m), 7.72 (2H, s), 7.67-7.59 (3H, m), 7.17 (1H, d, J = 8.5 Hz), 4.69 (1H, s), 4.64 (1H, s), 4.48 (2H, s), 4.28 (2H, s), 4.15 (1H, m), 3.99-3.87 (2H, m), 3.73-3.71 (3H, m), 3.52-3.42 (3H, m), 3.42 (1H, d, J = 5.3 Hz), 3.10 (3H, s) |

TABLE 3-continued

| EXAMPLE | NMR (ppm) (No mark: 400 MHz, *: 300 MHz) |
|---|---|
| 73 | DMSO-d6: 10.4 (1H, s), 9.26 (2H, s), 8.95 (2H, s), 8.22 (2H, s), 8.04 (2H, d, J = 11.6 Hz), 7.83 (2H, d, J = 7.9 Hz), 6.58 (1H, d, J = 6.6 Hz), 4.78 (1H, s), 4.71 (1H, d, J = 5.1 Hz), 4.20-4.18 (1H, m), 3.99 (2H, m), 3.87-3.85 (1H, m) |
| 74 | MeOH-$d_4$: 8.15 (2H, s), 8.11 (1H, s), 7.93 (2H, d, J = 11.1 Hz), 7.79-7.75 (2H, m), 7.72-7.67 (2H, m), 4.64 (2H, s), 4.47 (2H, d, J = 10.9 Hz), 4.49-4.45 (1H, m), 4.35-4.32 (1H, m), 4.30-4.27 (3H, m), 3.82-3.79 (1H, m), 3.73 (1H, d, J = 6.2 Hz) |
| 75 | MeOH-$d_4$: 8.62 (1H, brs), 7.96 (2H, d, J = 10.9 Hz), 7.82 (2H, d, J = 8.9 Hz), 7.29 (2H, d, J = 8.6 Hz), 6.92 (3H, d, J = 8.9 Hz), 4.91 (1H, s), 4.85 (1H, s), 4.73 (1H, d, J = 14.4 Hz), 4.52 (1H, d, J = 14.4 Hz), 4.10-4.02 (1H, m), 3.83-3.78 (1H, m), 3.81 (3H, s), 3.54-3.49 (1H, m), 3.22-3.18 (1H, m) |
| 76 | MeOH-$d_4$: 8.37 (1H, s) 8.35-8.34 (1H, d, J = 2.1 Hz), 7.99-7.97 (1H, dd, J = 2.16 Hz), 7.50-7.48 (1H, d, J = 7.06 Hz), 7.27-7.25 (2H, d, J = 8.74 Hz), 7.13-7.11 (1H, d, J = 7.06 Hz), 6.89-6.88 (2H, d, J = 8.74 Hz), 4.91 (1H, s), 4.85 (1H, s), 4.75 (1H, d, J = 14.4 Hz), 4.52 (1H, d, J = 14.4 Hz), 4.08-4.02 (1H, m), 3.80-3.78 (1H, m), 3.79 (3H, s), 3.53-3.43 (1H, m), 3.22-3.18 (1H, m) |
| 93 | MeOH-$d_4$: 7.97 (1H, d, J = 1.2 Hz), 7.75 (2H, d, J = 8.4 Hz), 7.69 (1H, d, J = 8.4 Hz), 7.64 (2H, d, J = 8.4 Hz), 7.41 (1 H, dd, J = 8.4, 1.5 Hz), 4.84 (2H, m), 4.26-4.22 (1H, m), 4.08-4.04 (2H, m), 3.72-3.69 (1H, m) |
| 94 | MeOH-$d_4$: 7.91 (1H, m), 7.75 (2H, d, J = 8.5 Hz), 7.65-7.62 (3H, m), 7.05 (1H, dd, J = 8.7, 1.8 Hz), 4.84-4.82 (2H, m), 4.26-4.22 (1H, m), 4.08-4.04 (2H, m), 3.72-3.69 (1H, m) |
| 95 | MeOH-$d_4$: 7.96 (1H, d, J = 13.5 Hz), 7.65 (2H, d, J = 8.5 Hz), 7.66-7.63 (4H, m), 4.83 (2H, m), 4.25-4.22 (1H, m), 4.06-4.04 (2H, m), 3.73-3.70 (1H, m) |
| 96 | MeOH-$d_4$: 3.70-3.73 (m, 1H), 4.04-4.07 (m, 2H), 4.22-4.25 (m, 1H), 4.83-4.84 (m, 2H), 7.64 (d, 2H, J = 8 Hz), 7.75 (d, 2H, J = 8 Hz), 7.81 (d, 2H, J = 7 Hz), 7.96 (d, 2H, J = 7 Hz). |
| 97 | MeOH-$d_4$: 3.69-3.72 (m, 1H), 4.02-4.08 (m, 2H), 4.22-4.25 (m, 1H), 4.83-4.84 (m, 2H), 7.62-7.69 (m, 3H), 7.79-7.83 (m, 3H), 7.96 (d, 2H, J = 7 Hz), 8.45 (br s, 1H) |
| 98 | Formate salt in MeOH-$d_4$: 8.46 (1H, s), 8.37 (1H, d, J = 1.18 Hz), 8.17 (1H, d, J = 8.8 Hz), 7.82 (1H, dd, J = 9.2, 1.8 Hz), 7.75 (2H, d, J = 8.80 Hz), 7.64 (2H, d, J = 8.4 Hz), 4.87-4.85 (2H, m), 4.27-4.22 (1H, m), 4.10-4.00 (2H, m), 3.74-3.70 (1H, m) |
| 99 | HCl salt in DMSO-$d_6$: 9.79 (s, 1H), 8.25 (s, 2H), 7.79 (d, 7.66 Hz, 4H), 7.67 (d, 8.32 Hz, 2H), 7.39 (d, 8.40 Hz, 2H), 6.40 (d, 6.14 Hz, 1H), 4.70 (s, 1H), 4.61 (m, 1H), 4.17-4.08 (m, 1H), 3.99-3.85 (m, 4H), 3.73-3.67 (m, 1H) |
| 100 | HCl salt in DMSO-$d_6$: 9.32 (s, 1H), 9.15 (s, 1H), 8.85 (s, 1H), 8.65 (s, 1H), 8.61-8.47 (m, 2H), 8.01 (d, 8.92 Hz, 1H), 7.83 (d, 8.90 Hz, 1H), 7.62-7.56 (m, 2H), 7.46-7.38 (m, 3H), 7.31 (s, 1H), 7.19 (s, 1H), 6.65 (d, 8.78 Hz, 1H), 4.67 (dd, 12.34 Hz, 1.88 Hz, 2H), 4.19-3.55 (m, 4H). |
| 101 | DMSO-$d_6$: 9.94 (s, 1H), 7.85-7.86 (m, 3H), 7.68 (d, 8.38 Hz, 1H), 7.55-7.18 (m, 4H), 4.71 (d, 1.96 Hz, 1H), 4.63 (d, 1.89 Hz, 1H), 4.17-4.12 (m, 1H), 3.98-3.86 (m, 2H), 3.74-3.67 (m, 1H) |
| 102 | DMSO-d6: 10.19 (1H, s), 9.25 (2H, s), 8.95 (2H, s), 8.02 (2H, d, J = 9 Hz), 7.81 (2H, d, J = 9 Hz), 7.32 (1H, dd, J = 8, 8 Hz), 7.23 (1H, s), 7.21 (1H, d, J = 8 Hz), 7.16-7.11 (1H, m), 4.66 (2H, s), 4.15-4.08 (1H, m), 3.97-3.78 (2H, m), 3.65-3.58 (3H, m), 2.73 (2H, t, J = 7 Hz) |
| 103 | DMSO-d6: 10.25 (1H, s), 9.27 (2H, s), 8.99 (2H, s), 8.39 (1H, d, J = 9 Hz), 8.30 (1H, dd, J = 9, 3 Hz), 8.04 (2H, d, J = 9 Hz), 7.83 (2H, d, J = 9 Hz), 6.54 (1H, brs), 4.83 (1H, d, J = 2 Hz), 4.73 (1H, brs), 4.25-4.11 (2H, m), 4.00-3.92 (2H, m) |
| 104 | DMSO-d6 (100degC): 9.93 (1H, s), 8.97 (4H, brs), 7.96 (2H, d, J = 9 Hz), 7.85 (2H, d, J = 9 Hz), 7.50 (1H, s), 7.48-7.43 (2H, m), 7.37-7.31 (1H, m), 6.08 (1H, brs), 4.72 (2H, s), 4.47 (2H, s), 4.23-4.16 (1H, m), 4.02-3.87 (2H, m), 3.71-3.64 (1H, m), 2.91 (3H, s) |
| 105 | *DMSO-d6: 10.21 (1H, s), 9.23 (2H, s), 8.89 (2H, s), 8.10 (1H, d, J = 8 Hz), 8.04 (2H, d, J = 9 Hz), 7.85-7.65 (4H, m), 7.57-7.39 (5H, m), 6.53 (1H, d, J = 7 Hz), 4.77-4.66 (2H, m), 4.22-4.11 (1H, m), 4.03-3.90 (2H, m), 3.78-3.67 (1H, m), 2.86 (3H, s) |
| 106 | CD3OD: 9.87 (1H, s), 9.10 (1H, s), 8.57 (1H, s), 7.87 (2H, d, J = 9 Hz), 7.72 (2H, d, J = 9 Hz), 7.65-7.44 (2H, m), 7.38-7.05 (6H, m), 4.92-4.67 (2H, m), 4.19-4.10 (1H, m), 4.01-3.92 (2H, m), 3.67-3.60 (1H, m), 3.49 (2H, t, J = 7 Hz), 2.74 (2H, t, J = 7 Hz) |
| 107 | DMSO-d6: 10.23 (1H, s), 9.29 (2H, s), 9.03 (2H, s), 8.82 (1H, s), 8.54 (1H, s), 8.14-8.02 (4H, m), 7.84 (2H, d, J = 9 Hz), 7.65-7.51 (2H, m), 7.45-7.38 (2H, m), 7.27-7.13 (1H, m), 6.69-6.62 (1H, m), 4.71 (2H, s), 4.26-3.25 (4H, m) |
| 108 | DMSO-d6: 12.77 (1H, s), 10.05 (1H, s), 8.80 (2H, brs), 8.46-8.40 (2H, m), 8.00 (1H, dd, J = 9, 2 Hz), 7.58 (1H, d, J = 7 Hz), 7.18-7.06 (5H, m), 6.39 (1H, d, J = 6 Hz), 4.36-4.29 (1H, m), 3.66-3.57 (1H, m), 3.53-3.45 (1H, m), 3.16-3.08 (1H, m), 2.26 (3H, s), 2.10-1.86 (4H, m) |

TABLE 3-continued

| EXAMPLE | NMR (ppm) (No mark: 400 MHz, *: 300 MHz) |
|---|---|
| 108-3 | *CDCl3: 9.09 (1H, s), 8.41-8.35 (2H, m), 7.90 (1H, d, J = 9 Hz), 7.59 (1H, d, J = 6 Hz), 7.53 (1H, dd, J = 9, 2 Hz), 7.24-7.19 (2H, m), 7.08 (2H, d, J = 9 Hz), 5.32 (1H, brs), 4.63-4.54 (1H, m), 3.71-3.63 (2H, m), 3.15-3.06 (1H, m), 2.39-2.23 (4H, m), 2.19-1.84 (3H, m), 1.30 (18H, s) |
| 109 | DMSO-d6: 12.63 (1H, brs), 10.61-10.37 (1H, m), 8.76 (2H, brs), 8.52-8.26 (2H, m), 8.03-7.90 (1H, m), 7.66-7.57 (1H, m), 7.29-7.14 (5H, m), 6.85-6.30 (1H, m), 5.27-4.79 (2H, m), 4.56-3.89 (2H, m), 3.76-3.19 (2H, m), 2.35-2.29 (3H, m), 2.05-1.98 (3H, m) |
| 110 | DMSO-d6: 12.72 (1H, brs), 10.55-10.45 (1H, m), 8.81 (2H, brs), 8.52-8.27 (2H, m), 8.11-7.88 (2H, m), 7.65-7.58 (1H, m), 7.28-7.14 (5H, m), 6.98-6.38 (1H, m), 5.07-4.76 (2H, m), 4.35-3.84 (2H, m), 3.80-3.21 (2H, m), 2.35-2.29 (3H, m) |
| 110-1 | DMSO-d6: 8.22-7.94 (1H, m), 7.23-7.16 (4H, m), 6.35-5.85 (1H, m), 5.07-4.54 (2H, m), 4.36-3.47 (6H, m), 2.35-2.27 (3H, m), 1.29-1.12 (3H, m) |
| 111 | *DMSO-d6: 12.76-11.88 (1H, m), 10.53-9.88 (1H, m), 8.49-6.88 (16H, m), 6.57-6.45 (1H, m), 5.63-5.43 (1H, m), 5.01-2.19 (8H, m) |
| 112 | *CD3OD: 7.95 (2H, d, J = 9 Hz), 7.79 (2H, d, J = 9 Hz), 7.24 (2H, d, J = 9 Hz), 7.20-7.15 (2H, m), 5.06-4.78 (1H, m), 4.22-4.18 (1H, m), 4.11-3.95 (2H, m), 3.58-3.22 (1H, m), 2.94-2.82 (1H, m), 2.35 (3H, s), 1.89-1.87 (3H, m) |
| 113 | *CD3OD: 7.99-7.71 (4H, m), 7.32-7.12 (4H, m), 5.11-4.56 (2H, m), 4.21-3.93 (2H, m), 3.86-3.62 (2H, m), 2.42-2.29 (3H, m) |
| 113-1 | *DMSO-d6: 12.87 (1H, brs), 10.18-10.01 (1H, m), 7.99-7.87 (2H, m), 7.79-7.69 (2H, m), 7.28-7.00 (5H, m), 4.97-4.83 (1H, m), 4.67-4.55 (1H, m), 4.16-3.58 (4H, m), 2.35-2.27 (3H, m) |
| 114 | DMSO-d6: 10.34 (1H, s), 9.29 (2H, brs), 9.06 (2H, brs), 7.96 (2H, d, J = 8 Hz), 7.83 (2H, d, J = 8 Hz), 7.20 (2H, d, J = 8 Hz), 7.14-7.07 (2H, m), 6.22 (1H, brs), 4.69-4.62 (1H, s), 4.51-4.44 (1H, s), 4.19-3.99 (2H, m), 3.88-3.69 (2H, m), 2.31 (3H, s), 2.04-1.89 (2H, m) |
| 115 | *DMSO-d6 (100degC): 10.00-9.83 (1H, m), 8.96 (4H, brs), 7.93-7.74 (4H, m), 7.32-7.15 (4H, m), 4.17-3.39 (4H, m), 3.22-2.69 (4H, m), 2.37-2.29 (3H, m) |
| 115-1 | *CDCl3: 7.38-7.26 (5H, m), 4.45 (1H, dd, J = 9, 4 Hz), 4.06-3.95 (1H, m), 3.90-3.46 (5H, m), 2.84-2.74 (1H, m), 2.72-2.61 (1H, m), 2.42-2.22 (2H, m) |
| 115-2 | *DMSO-d6: 7.66-7.56 (1H, m), 7.50-7.43 (5H, m), 4.44-4.28 (2H, m), 4.24-3.76 (6H, m), 3.53-3.15 (2H, m), 3.11-2.81 (2H, m), 1.21-1.13 (3H, m) |
| 116 | *DMSO-d6: 10.35-10.06 (1H, m), 9.23 (2H, s), 8.95 (2H, s), 7.97-7.75 (4H, m), 7.63 (2H, d, J = 8 Hz), 7.48 (2H, d, J = 8 Hz), 6.29-6.02 (1H, m), 4.25-3.70 (3H, m), 3.64-3.22 (3H, m), 2.43 (3H, s), 2.38-2.14 (2H, m) |
| 117 | DMSO-d6: 12.63 (1H, brs), 10.28 (1H, s), 8.78 (1H, brs), 8.51-8.38 (2H, m), 8.05-7.95 (1H, m), 7.64-7.52 (1H, m), 7.20-7.12 (1H, m), 7.08-6.97 (2H, m), 6.89-6.77 (2H, m), 6.20 (1H, brs), 4.27 (1H, brs), 4.01-3.85 (2H, m), 3.64-3.16 (3H, m), 2.80-2.28 (2H, m), 2.21 (3H, s) |
| 118 | CD3OD-d4: 9.21 (1H, s), 8.70 (1H, s), 7.98 (2H, d, J = 8.5 Hz), 7.84 (2H, d, J = 8.5 Hz), 7.57 (1H, t, J = 8.1 Hz), 7.45 (2H, m), 7.28 (1H, d, J = 8.3 Hz), 4.86 (1H, s), 4.85 (1H, s), 4.25 (1H, m), 4.06 (2H, m), 3.71 (1H, m). |
| 119 | DMSO-d6: 10.2 (1H, s), 9.31 (2H, s), 9.08 (2H, s), 8.04 (2H, d, J = 8.5 Hz), 7.85 (2H, d, J = 8.5 Hz), 7.72 (1H, d, J = 8.1 Hz), 7.66 (1H, s), 7.53 (1H, d, J = 8.1 Hz), 6.65 (1H, s), 4.74 (1H, s), 4.69 (1H, s), 4.49 (2H, s), 4.16 (1H, d, J = 11.0 Hz), 3.99-3.90 (2H, m), 3.72 (1H, d, J = 11.0 Hz), 3.09 (3H, s). |
| 120 | DMSO-d6: 9.83 (1H, s), 8.26 (2H, s), 7.83 (2H, d, J = 8.3 Hz), 7.72 (1H, d, J = 8.2 Hz), 7.66 (1H, s), 7.53 (1H, d, J = 9.3 Hz), 7.42 (2H, d, J = 8.3 Hz), 6.43 (1H, d, J = 6.3 Hz), 4.72 (1H, s), 4.65 (1H, m), 4.49 (2H, s), 4.16 (1H, d, J = 10.2 Hz), 3.99-3.90 (4H, m), 3.71 (1H, d, J = 10.2 Hz), 3.09 (3H, s). |
| 121 | Cd3OD-d4: 7.75-7.73 (2H, d, J = 8.6 Hz), 7.51-7.35 (6H, m), 4.80 (2H, s), 4.28 (2H, s), 4.12-4.09 (1H, m), 4.08-4.02 (8H, m), 3.79 (2H, m), 3.65-3.61 (1H, m). |
| 122 | CD3OD-d4: 8.42 (1H, s), 8.36 (2H, d, J = 9.9 Hz), 8.01 (2H, dd, J = 7.8, 13.9 Hz), 7.56-7.51 (3H, m), 7.40 (2H, dd, J = 7.8, 13.9 Hz), 4.86 (1H, s), 4.31 (2H, s), 4.28 (1H, m), 4.09-4.03 (4H, m), 3.83 (2H, m), 3.31 (1H, m). |
| 123 | Cd3OD-d4: 8.15 (1H, s), 7.97 (1H, s), 7.83-7.81 (1H, dd, J = 8.6, 10.7 Hz), 7.64 (2H, m), 7.36 (2H, t, J = 1.1 Hz), 4.81 (2H, s), 4.29 (2H, s), 4.28-4.27 (1H, m), 4.04-4.01 (3H, m), 3.81-3.80 (2H, m). |
| 124 | Cd3OD-d4: 9.2 (1H, s), 8.8 (1H, s), 7.73 (2H, s), 7.72-7.34 (5H, m), 4.81 (2H, s), 4.28 (2H, s), 4.28 (1H, d, J = 3.1 Hz), 4.04-4.01 (3H, m), 3.81-3.6 (4H, m), 2.44 (3H, s). |

TABLE 3-continued

| EXAMPLE | NMR (ppm)<br>(No mark: 400 MHz, *: 300 MHz) |
|---|---|
| 125 | Cd3OD-d4: 7.62 (1H, s), 7.54-7.47 (3H, m), 7.36 (2H, t, J = 1.0 Hz), 7.18 (1H, d, J = 8.5 Hz), 4.79 (2H, s), 4.32 (2H, s), 4.28 (2H, s), 4.31 (1H, s), 4.28 (1H, s), 4.05-4.04 (3H, m), 3.81 (2H, t, J = 5.2 Hz), 3.70 (1H, d, J = 6.0 Hz), 3.48 (2H, t, J = 6.5 Hz), 3.3 (2H, s), 3.11 (2H, t, J = 6.4 Hz). |
| 126 | DMSO-d6: 10.2 (1H, s), 9.23 (2H, s), 8.88 (2H, s), 8.04 (2H, d, J = 8.4 Hz), 7.81 (2H, d, J = 8.4 Hz), 7.34 (1H, t, J = 7.8 Hz), 7.03 (2H, m), 6.85 (1H, d, 8.2 Hz), 6.52 (1H, s), 4.74-4.66 (4H, m), 4.13 (1H, m), 3.93 (1H, m), 3.85 (1H, m), 3.65 (1H, d, J = 12.6 Hz). |
| 127 | CD3OD-d4: 8.60 (1H, s), 7.70 (2H, d, J = 8.5 Hz), 7.46 (2H, d, J = 8.5 Hz), 7.40 (1H, m), 7.03 (2H, m), 6.93 (1H, d, J = 8.5 Hz), 4.83 (1H, s), 4.81 (1H, s), 4.75 (2H, s), 4.30-4.20 (3H, m), 4.11 (2H, s), 4.09-3.98 (2H, m), 3.65 (1H, m), 1.31 (3H, t, J = 7.4 Hz). |
| 128 | Cd3OD-d4: 8.22 (2H, d, J = 5.5 Hz), 7.77-7.60 (3H, m), 4.58 (2H, s), 4.2-4.1 (1H, m), 3.95-3.94 (1H, m), 3.90-3.85 (1H, m), 3.74-3.71 (1H, m), 3.09 (2H, s), 2.80 (3H, t), 1.1 (2H, m). |
| 129 | Cd3OD-d4: 7.66 (1H, d, J = 1.8 Hz), 7.53-7.46 (2H, m), 7.38-7.33 (2H, m), 7.22 (1H, d, J = 8.6 Hz), 7.15 (1H, d, J = 2.0 Hz), 6.1 (1H, s), 4.80 (2H, d, J = 2 Hz), 4.28 (1H, s), 4.24 (1H, d, J = 5.9 Hz), 4.04-4.01 (4H, m), 3.80 (1H, t, J = 3.7 Hz), 3.78-3.68 (1H, m), 2.39 (3H, s). |
| 130 | Cd3OD-d4: 8.1 (1H, m), 7.52-7.22 (8H, m), 4.69 (1H, d, J = 1.9 Hz), 4.63 (1H, d, J = 1.8 Hz), 4.27 (2H, s), 4.11-4.08 (1H, m), 4.04-3.96 (4H, m), 3.80 (3H, t, J = 4.4 Hz), 3.62-3.60 (1H, m), 3.50-3.40 (2H, m), 3.27 (2H, s), 2.81 (2H, t, J = 7.3 Hz). |
| 131 | (CD3OD) 3.46-3.49 (m, 1H), 3.84-3.88 (m, 1H), 3.86 (s, 3H), 3.97-4.03 (m, 1H), 4.18-4.21 (m, 1H), 4.79-4.82 (m, 2H), 7.00 (t, 1H, J = 8 Hz), 7.12 (d, 1H, J = 8 Hz), 7.24 (d, 1H, J = 8 Hz), 7.36 (t, 1H, J = 8 Hz), 7.81 (d, 2H, J = 7 Hz), 7.94 (d, 2H, J = 7 Hz) |
| 132 | (CD3OD) 7.96 (d, J = 8.8 Hz, 2H), 7.81 (d, J = 8.8 Hz, 2H), 7.38-7.46 (m, 2H), 7.22-7.31 (m, 2H), 4.84 (d, J = 3.7 Hz, 2H), 4.21-4.28 (m, 1H), 3.95-4.10 (m, 2H), 3.53-3.63 (m, 1H) |
| 133 | (CD3OD) 7.92 (d, J = 8.8 Hz, 2H), 7.77 (d, J = 8.8 Hz, 2H), 7.35-7.45 (m, 2H), 7.30 (t, J = 7.7 Hz, 2H), 6.74 (t, J = 74.3 Hz, 1H), 4.77 (s, 2H), 4.20 (d, J = 10.6 Hz, 1H), 3.88-4.04 (m, 2H), 3.49 (d, J = 9.9 Hz, 1H) |
| 134 | (DMSO-d6) 3.68-3.71 (m, 1H), 3.80-3.82 (m, 2H), 4.02-4.06 (m, 4H), 4.18-4.22 (m, 1H), 4.29 (s, 2H), 4.82 (d, 1H, J = 2 Hz), 4.87 (d, 1H, J = 2 Hz), 7.33-7.54 (m, 4H), 8.16 (d, 1H, J = 9 Hz), 8.28 (br s, 1H), 8.51 (dd, 1H, J = 9, 2 Hz), 9.12 (d, 1H, J = 3 Hz). |
| 135 | (DMSO-d6) 9.20 (br. s., 2H), 8.84-9.05 (m, 2H), 8.03 (d, J = 8.8 Hz, 2H), 7.80 (d, J = 8.8 Hz, 2H), 7.43 (t, J = 8.1 Hz, 1H), 7.24 (s, 1H), 7.09-7.19 (m, 2H), 6.53 (d, J = 6.1 Hz, 1H), 4.69 (s, 1H), 4.65 (br. s, 1H), 4.13 (d, J = 11.6 Hz, 1H), 3.91-4.02 (m, 1H), 3.81-3.91 (m, 1H), 3.75 (t, J = 6.5 Hz, 2H), 3.62 (d, J = 11.7 Hz, 1H), 3.54 (t, J = 7.4 Hz, 2H), 2.42 (quin, J = 6.9 Hz, 2H) |
| 136 | (CD3OD) 7.95 (d, J = 8.6 Hz, 2H), 7.81 (d, J = 8.6 Hz, 2H), 7.26 (dd, J = 8.5, 6.1 Hz, 1H), 6.92 (dd, J = 10.7, 2.5 Hz, 1H), 6.74 (td, J = 8.3, 2.6 Hz, 1H), 4.81 (d, J = 6.8 Hz, 2H), 4.13-4.26 (m, 1H), 3.86-4.06 (m, 2H), 3.88 (s, 3H), 3.46 (d, J = 11.9 Hz, 1H) |
| 137 | (CD3OD) 7.95 (d, J = 8.8 Hz, 2H), 7.79 (d, J = 8.6 Hz, 2H), 7.32 (t, J = 7.0 Hz, 1H), 7.22 (d, J = 7.7 Hz, 1H), 7.11 (d, J = 8.4 Hz, 1H), 6.96 (t, J = 7.3 Hz, 1H), 4.80 (d, J = 1.5 Hz, 1H), 4.77 (s, 1H), 4.65 (dt, J = 12.0, 6.0 Hz, 1H), 4.20 (d, J = 11.4 Hz, 1H), 3.89-4.02 (m, 2H), 3.47 (d, J = 9.5 Hz, 1H), 1.33 (dd, J = 5.9, 2.4 Hz, 6H) |
| 138 | (CD3OD) 7.97 (d, J = 8.8 Hz, 2H), 7.82 (d, J = 8.8 Hz, 2H), 7.27-7.44 (m, 2H), 7.05-7.15 (m, 2H), 4.83 (s, 2H), 4.59-4.65 (m, 2H), 4.15-4.28 (m, 1H), 3.90-4.12 (m, 2H), 3.55 (d, J = 11.7 Hz, 1H) |
| 139 | MeOH-d4: 7.96 (1H, d, J = 13.5 Hz), 7.66 (2H, m), 7.52 (1H, t, J = 8 Hz), 7.47 (1H, m), 7.36 (2H, m), 4.81 (2H, d, J = 11 Hz), 4.29 (2H, br s) 4.23-4.21 (1H, m), 4.06-4.01 (4H, m), 3.81 (2H, m), 3.70-3.68 (1H, m) |
| 140 | MeOH-d4: 7.71 (2H, d, J = 8.5 Hz), 7.52 (1H, t, J = 8 Hz), 7.47 (1H, m), 7.36 (2H, m), 4.80 (2H, d, J = 12 Hz), 4.29 (2H, br s) –4.23-4.20 (1H, m), 4.06-4.01 (4H, m), 3.82-3.80 (2H, m), 3.70-3.68 (1H, m) |
| 141 | MeOH-d4: 7.99-7.95 (3H, m), 7.67-7.63 (3H, m), 7.56 (1H, t, J = 7.5 Hz), ), 4.83 (2H, m), 4.24-4.22 (1H, m), 4.05-4.05 (2H, m), 3.70-3.68 (1H, m) |
| 142 | HCl salt in CD3OD: 8.25 (d, J = 1.1 Hz, 1H), 8.04 (d, J = 8.1 Hz, 1H), 7.90 (dd, J = 2.0, 8.6 Hz, 1H), 7.50 (t, J = 7.9 Hz, 1H), 7.4 (t, J = 1.8 Hz, 1H), 7.39-7.33 (m, 2H), 4.87-4.84 (m, 4H), 4.29 (s, 2H), 4.23-4.21 (m, 1H), 4.06-4.01 (m, 4H), 3.82-3.80 (m, 2H), 3.70 (dd, J = 2.5, 9.1 Hz, 1H) |
| 143 | HCl salt in DMSO-d6: 10.43 (s, 2H), 9.91 (s, 1H), 9.38 (s, 1H), 8.48 (s, 1H), 8.38 (d, J = 7.7 Hz, 1H), 8.12 (s, 1H), 8.08 (d, J = 8.5 Hz, 1H), 7.97 (d, J = 8.1 Hz, 1H), 7.92 (d, J = 7.7 Hz, 1H), 7.81 (t, J = 8.1 Hz, 1H), 4.94 (s, 2H), 4.89 (s, 1H), 4.85 (s, 1H), 4.32-4.28 (m, 1H), 4.13-4.04 (m, 2H), 3.93-3.89 (m, 1H), |

TABLE 3-continued

| EXAMPLE | NMR (ppm) (No mark: 400 MHz, *: 300 MHz) |
|---|---|
| 144 | HCl salt in CD3OD: 8.2 (s, 1H), 8.06 (d, J = 8.4 Hz, 1H), 7.89-7.86 (m, 1H), 7.63 (d, J = 8.4 Hz, 2H), 7.54 (d, J = 8.1 Hz, 2H), 4.85-4.81 (m, 4H), 4.27-4.21 (m, 1H), 3.63 (t, J = 6.8 Hz, 2H), 3.52 (t, J = 6.4 Hz, 2H), 2.05-1.90 (m, 2H) |
| 145 | HCl salt in DMSO-d6: 10.24 (s, 1H), 10.21 (s, 1H), 9.65 (s, 1H), 9.15 (s, 1H), 8.31 (s, 1H), 8.16 (d, J = 8.8 Hz, 1H), 7.92 (dd, J = 1.8, 8.8 Hz, 1H), 7.48-7.46 (m, 3H), 7.31-7.28 (m, 1H), 4.76 (s, 2H), 4.67 (dd, J = 2.2, 5.1 Hz, 2H), 4.14-4.10 (m, 1H), 3.95-3.84 (m, 2H), 3.69-3.65 (m, 1H), 2.97 (s, 3H), 2.91 (s, 3H) |
| 146 | HCl salt in CD3OD: 8.25 (s, 1H), 8.05 (d, J = 8.5 Hz, 1H), 7.91-7.87 (m, 1H), 7.78-7.56 (m, 1H), 7.61-7.48 (m, 4H), 4.85-4.81 (m, 4H), 4.26-4.19 (m, 1H), 4.07-4.0 (m, 2H), 3.73-3.65 (m, 1H), 3.63-3.57 (m, 2H), 3.50 (t, J = 6.6 Hz, 2H), 2.03-2.18 (m, 4H) |
| 147 | HCl salt in DMSO-d6: 10.25 (s, 1H), 10.28 (s, 1H), 9.58 (s, 1H), 9.12 (s, 1H), 8.31 (s, 1H), 8.13 (d, J = 8.8 Hz, 1H), 7.94 (dd, J = 1.8, 8.8 Hz, 1H), 7.49-7.44 (m, 4H), 6.50 (d, J = 7.0 Hz, 1H), 4.77 (s, 2H), 4.70-4.66 (m, 2H), 4.14-4.11 (m, 1H), 3.96-3.85 (m, 2H), 3.68-3.65 (m, 1H), 2.97 (s, 3H), 2.92 (s, 3H) |
| 148 | HCl salt in DMSO-d6: 9.20-9.29 (m, 2H), 8.98-9.07 (m, 2H), 8.19 (s, 1H), 7.89-8.04 (m, 3H), 7.53-7.68 (m, 2H), 4.56-4.74 (m, 2H), 4.06-4.19 (m, 1H), 3.85-4.02 (m, 2H), 3.60-3.81 (m, 1H). |
| 149 | HCl salt in DMSO-d6: 9.86 (s, 1H), 9.52 (br. s., 1H), 7.94 (s, 1H), 7.66 (d, J = 8.8 Hz, 1H), 7.42-7.52 (m, 2H), 7.28-7.37 (m, 3H), 4.56 (d, J = 14.3 Hz, 2H), 4.47 (d, J = 15.8 Hz, 4H), 4.22 (s, 2H), 4.09-4.18 (m, 1H), 3.83-4.02 (m, 4H), 3.71-3.78 (m, 2H), 3.67 (d, J = 10.6 Hz, 2H). |
| 150 | HCl salt in CD3OD: 7.98-7.95 (2H, m), 7.92-7.89 (2H, m), 7.82-7.79 (2H, m), 7.65 (1H, d, J = 8.8 Hz), 4.84 (s, 2H); 4.25-4.21 (1H, m), 4.10-4.00 (2H, m), 3.75-3.68 (1H, m) |
| 151 | Formate salt in CD3OD: 8.00 (1H, br s), 7.47 (3H, app d, J = 7.7 Hz), 7.31 (3H, app d, J = 7.3 Hz), 7.16 (2H, br s),, 4.35-4.33 (m, 2H), 3.76-3.70 (1H, m), 3.59-3.52 (2H, m), 3.25-3.20 (1H, m) |

TABLE 4

| EXAMPLE | LC/MS m/z [M + 1]+ | RT min | Method/ Solvent |
|---|---|---|---|
| 1 | 407 | 2.65 | B |
| 1-1 (LP) | 294 | 3.05 | A |
| 1-1 (MP) | 294 | 3.03 | A |
| 1-2 | 266 | 4.08 | A |
| 1-3 | 607 | 4.47 | A |
| 2 | 383 | 2.33 | B |
| 2-1 | 366 | 3.50 | A |
| 3 | 380 | 3.47 | B |
| 4 | 394 | 3.67 | B |
| 5 | 370 | 2.45 | B |
| 6 | 396 | 2.52 | B |
| 7 | 383 | 2.30 | B |
| 7-1 | 170 | 4.50 | A |
| 7-2 | 335 | 2.82 | B |
| 7-3 | 486 | 4.68 | A |
| 7-4 | 402 | 3.92 | A |
| 7-5 | 366 | 3.50 | A |
| 8 | 397 | 2.48 | B |
| 8-1 | 184 | 4.92 | A |
| 8-2 | 500 | 4.82 | A |
| 8-3 | 416 | 4.12 | A |
| 8-4 | 380 | 3.73 | A |
| 9 | 456 | 1.30 | B |
| 9-1 | 215 | 4.52 | A |
| 9-2 | 531 | 4.55 | A |
| 9-3 | 447 | 3.92 | A |
| 9-4 | 411 | 3.75 | A |
| 9-5 | 381 | 2.95 | A |
| 9-6 | 481 | 3.08 | A |
| 10 | 451 | 2.27 | A |
| 10-1 | 238 | 5.03 | A |
| 10-2 | 554 | 5.02 | A |
| 10-3 | 470 | 4.35 | A |
| 10-4 | 434 | 4.05 | A |
| 11 | 425 | 3.07 | B |
| 11-1 | 212 | 5.40 | A |
| 11-2 | 528 | 5.33 | A |
| 11-3 | 444 | 4.63 | A |
| 11-4 | 408 | 4.30 | A |
| 12 | 399 | 0.93 | B |
| 12-1 | 186 | 2.58 | A |
| 12-2 | 502 | 3.68 | A |
| 12-3 | 418 | 2.97 | A |
| 12-4 | 382 | 2.78 | A |
| 13 | 424 | 0.85 | B |
| 13-1 | 211 | 3.18 | C |
| 13-2 | 527 | 3.40 | A |
| 13-3 | 443 | 2.82 | A |
| 13-4 | 407 | 2.72 | A |
| 14 | 495 | 1.13 | A |
| 14-1 | 282 | 4.98 | A |
| 14-2 | 598 | 4.95 | A |
| 14-3 | 514 | 4.32 | A |
| 14-4 | 478 | 4.07 | A |
| 15 | 449 [M − 1]− | 2.57 | A |
| 15-1 | 238 | 6.52 | C |
| 15-2 | 554 | 6.45 | C |
| 15-3 | 434 | 4.75 | A |
| 16 | 409 [M − 1]− | 1.97 | A |
| 16-1 | 198 | 5.97 | C |
| 16-2 | 514 | 6.05 | C |
| 16-3 | 394 | 4.10 | A |
| 17 | 397 | 1.02 | A |
| 17-1 | 184 | 4.83 | A |
| 17-2 | 500 | 4.87 | A |
| 17-3 | 416 | 4.20 | A |
| 17-4 | 380 | 3.83 | A |
| 18 | 408 | 2.33 | B |

TABLE 4-continued

| EXAMPLE | LC/MS m/z [M + 1]+ | RT min | Method/Solvent |
|---|---|---|---|
| 18-1 | 493 | 3.60 | A |
| 18-2 | 571 | 4.08 | A |
| 18-3 | 391 | 3.35 | A |
| 19 | 452 | 2.22 | B |
| 19-1 | 239 | 4.87 | C |
| 19-2 | 555 | 3.95 | A |
| 19-3 | 471 | 3.33 | A |
| 19-4 | 435 | 3.55 | A |
| 20 | 425 | 0.80 | B |
| 20-1 | 226 | 2.85 | C |
| 20-2 | 212 | 2.87 | C |
| 20-3 | 528 | 3.32 | A |
| 20-4 | 444 | 2.68 | A |
| 20-5 | 408 | 2.67 | A |
| 21 | 397 | 2.60 | B |
| 21-1 | 500 | 4.77 | A |
| 21-2 | 416 | 4.23 | A |
| 21-3 | 380 | 3.87 | A |
| 22 | 451 | 3.25 | C |
| 22-1 | 434 | 4.20 | A |
| 23 | 445 | 3.38 | C |
| 23-1 | 428 | 4.20 | A |
| 24 | 501 | 4.20 | C |
| 24-1 | 484 | 5.13 | A |
| 25 | 435 | 3.27 | D |
| 25-1 | 418 | 3.05 | A |
| 26A | 426 | 3.02 | D |
| 26-1 | 271 | 5.22 | C |
| 26-2 | 587 | 4.95 | A |
| 26-3 | 503 | 4.25 | A |
| 26-4 | 467 | 3.90 | A |
| 26-5 | 367 | 2.57 | A |
| 26-6 | 451 | 3.15 | A |
| 26B | 426 | 3.02 | D |
| 26-7 | 285 | 4.85 | C |
| 26-8 | 271 | 5.25 | C |
| 26-9 | 487 | 5.48 | D |
| 26-10 | 646 | 6.52 | C |
| 26-11 | 562 | 5.95 | C |
| 26-12 | 526 | 5.47 | C |
| 26-13 | 426 | 3.75 | C |
| 26-14 | 468 | 4.20 | C |
| 27 | 427 | 2.80 | D |
| 27-1 | 410 | 3.78 | C |
| 28A | 462 | 2.97 | D |
| 28-1 | 445 | 3.02 | A |
| 28B | 462 | 2.98 | D |
| 28-2 | 504 | 4.13 | C |
| 29A | 452 | 3.20 | D |
| 29-1 | 435 | 3.03 | A |
| 29B | 452 | 3.23 | C |
| 29-2 | 494 | 4.35 | C |
| 30A | 468 | 2.90 | D |
| 30-1 | 451 | 2.82 | A |
| 30B | 468 | 2.80 | D |
| 30-2 | 510 | 3.93 | C |
| 31 | 454 | 3.05 | D |
| 31-1 | 437 | 3.05 | A |
| 32 | 532 | 3.98 | D |
| 32-1 | 515 | 3.85 | A |
| 33 | 442 | 2.81 | D |
| 34 | 452 | 2.47 | C |
| 34-1 | 239 | 4.17 | C |
| 34-2 | 455 | 4.43 | D |
| 34-3 | 614 | 5.72 | C |
| 34-4 | 530 | 4.87 | C |
| 34-5 | 494 | 4.47 | C |
| 35 | 408 | 2.35 | C |
| 35-1 | 209 | 3.52 | C |
| 35-2 | 195 | 1.32 | C |
| 35-3 | 411 | 4.60 | D |
| 35-4 | 570 | 6.10 | C |
| 35-5 | 486 | 5.03 | C |
| 35-6 | 450 | 4.58 | C |
| 36 | 426 | 1.05 | C |
| 36-1 | 213 | 3.83 | C |
| 36-2 | 429 | 4.10 | D |
| 36-3 | 588 | 5.22 | C |
| 36-4 | 504 | 4.50 | C |
| 36-5 | 468 | 4.23 | C |
| 37 | 424 | 0.73 | C |
| 37-1 | 211 | 3.87 | C |
| 37-2 | 427 | 3.68 | D |
| 37-3 | 586 | 4.88 | C |
| 37-4 | 502 | 4.23 | C |
| 37-5 | 466 | 3.87 | C |
| 38 | 450 | 2.70 | C |
| 38-1 | 213 | 3.58 | C |
| 38-2 | 429 | 4.12 | D |
| 38-3 | 770 | 5.62 | C |
| 38-4 | 686 | 5.23 | C |
| 38-5 | 650 | 5.00 | C |
| 39 | 438 | 3.00 | D |
| 39-1 | 400 [M + Na]+ | 5.93 | C |
| 39-2 | 370 [M + Na]+ | 5.43 | C |
| 39-3 | 780 [M + Na]+ | 5.78 | C |
| 39-4 | 696 [M + Na]+ | 5.68 | C |
| 39-5 | 660 [M + Na]+ | 5.48 | C |
| 39-6 | 438 | 1.75 | C |
| 40 | 440 | 2.13 | C |
| 40-1 | 482 | 4.35 | C |
| 41 | 466 | 2.67 | C |
| 41-1 | 508 | 4.78 | C |
| 42 | 494 | 3.05 | C |
| 42-1 | 536 | 5.47 | C |
| 43 | 384 | 0.25 | C |
| 44 | 384 | 1.02 | D |
| 44-1 | 307 [M + Na]+ | 4.97 | C |
| 44-2 | 271 | 5.45 | C |
| 44-3 | 509 [M + Na]+ | 5.50 | D |
| 44-4 | 646 | 5.65 | D |
| 44-5 | 562 | 6.12 | C |
| 44-6 | 526 | 5.82 | C |
| 44-7 | 426 | 3.83 | C |
| 45 | 426 | 2.90 | D |
| 45-1 | 468 | 4.22 | C |
| 46 | 452 | 3.05 | D |
| 46-1 | 494 | 4.33 | C |
| 47 | 427 | 2.70 | D |
| 47-1 | 469 | 3.95 | C |
| 48 | 454 | 2.97 | D |
| 48-1 | 496 | 4.18 | C |
| 49 | 462 | 2.82 | D |
| 49-1 | 504 | 4.22 | C |
| 50 | 442 | 2.70 | D |
| 50-1 | 574 | 5.35 | C |
| 51 | 468 | 2.72 | D |
| 51-1 | 510 | 4.07 | C |
| 52 | 449 | 3.57 | C |
| 52-1 | 506 [M + Na]+ | 6.15 | C |
| 52-2 | 422 [M + Na]+ | 5.93 | C |
| 52-3 | 364 | 5.68 | C |
| 52-4 | 308 | 4.97 | D |
| 52-5 | 649 | 5.88 | C |
| 53 | 437 | 3.37 | C |
| 53-1 | 659 [M + Na]+ | 6.15 | C |
| 53-2 | 437 | 3.38 | C |
| 54 | 461 | 3.20 | C |
| 54-1 | 238 | 5.22 | C |
| 54-2 | 224 | 5.73 | C |
| 54-3 | 518 [M + Na]+ | 5.82 | C |
| 54-4 | 434 [M + Na]+ | 5.53 | C |
| 54-5 | 398 [M + Na]+ | 5.15 | C |
| 54-6 | 342 [M + Na]+ | 4.17 | D |
| 54-7 | 661 | 5.62 | C |
| 55 | 477 | 3.32 | C |
| 55-1 | 254 | 5.22 | C |
| 55-2 | 240 | 5.82 | C |
| 55-3 | 534 [M + Na]+ | 5.90 | C |
| 55-4 | 450 [M + Na]+ | 5.65 | C |

TABLE 4-continued

| EXAMPLE | m/z [M + 1]+ | RT min | Method/ Solvent |
|---|---|---|---|
| 55-5 | 414 [M + Na]+ | 5.25 | C |
| 55-6 | 336 | 4.37 | D |
| 55-7 | 677 | 5.68 | C |
| 56 | 453 | 2.82 | C |
| 56-1 | 495 | 5.03 | D |
| 57 | 465 | 3.12 | C |
| 57-1 | 687 [M + Na]+ | 6.12 | C |
| 57-2 | 465 | 3.08 | C |
| 58 | 471 | 3.03 | C |
| 58-1 | 248 | 5.00 | C |
| 58-2 | 234 | 5.70 | C |
| 58-3 | 528 [M + Na]+ | 5.83 | C |
| 58-4 | 422 | 5.53 | C |
| 58-5 | 408 [M + Na]+ | 5.15 | C |
| 58-6 | 330 | 4.05 | D |
| 58-7 | 671 | 5.67 | C |
| 59 | 411 | 2.57 | C |
| 59-1 | 188 | 4.07 | C |
| 59-3 | 468 [M + Na]+ | 5.47 | C |
| 59-4 | 384 [M + Na]+ | 5.15 | C |
| 59-5 | 348 [M + Na]+ | 4.55 | C |
| 59-6 | 270 | 2.92 | D |
| 59-7 | 611 | 5.32 | C |
| 60 | 427 | 2.85 | C |
| 60-1 | 204 | 4.82 | C |
| 60-3 | 484 [M + Na]+ | 5.73 | C |
| 60-4 | 400 [M + Na]+ | 5.47 | C |
| 60-5 | 364 [M + Na]+ | 5.07 | C |
| 60-6 | 286 | 3.72 | D |
| 60-7 | 627 | 5.52 | C |
| 61 | 451 | 3.17 | C |
| 61-1 | 228 | 4.77 | C |
| 61-3 | 508 [M + Na]+ | 5.99 | C |
| 61-4 | 424 [M + Na]+ | 5.60 | C |
| 61-5 | 388 [M + Na]+ | 5.22 | C |
| 61-6 | 310 | 4.15 | D |
| 61-7 | 651 | 5.60 | C |
| 62 | 407 | 2.82 | C |
| 62-1 | 464 [M + Na]+ | 5.73 | C |
| 62-2 | 380 [M + Na]+ | 5.43 | C |
| 62-3 | 344 [M + Na]+ | 4.87 | C |
| 62-4 | 266 | 3.65 | D |
| 62-5 | 607 | 5.58 | C |
| 63 | 425 | 2.93 | C |
| 63-1 | 202 | 4.17 | C |
| 63-2 | 188 | 5.62 | C |
| 63-3 | 482 [M + Na]+ | 5.78 | C |
| 63-4 | 398 [M + Na]+ | 5.47 | C |
| 63-5 | 362 [M + Na]+ | 4.88 | C |
| 63-6 | 284 | 3.53 | D |
| 63-7 | 625 | 5.53 | C |
| 64 | 401 | 3.53 | D |
| 64-1 | 443 | 5.02 | C |
| 65 | 439 | 3.25 | C |
| 65-1 | 422 | 5.48 | C |
| 66 | 459 | 3.57 | C |
| 66-1 | 442 | 5.73 | C |
| 66-2 | 475 | 4.98 | C |
| 67 | 443 | 3.35 | C |
| 67-1 | 426 | 5.55 | C |
| 67-2 | 459 | 4.63 | C |
| 68 | 466 | — | — |
| 68-8 | 302 | — | — |
| 68-9 | 405 | — | — |
| 68-10 | 447 | — | — |
| 68-11 | 391 | — | — |
| 68-13 | 550 | — | — |
| 68-14 | 508 | — | — |
| 69 | 506 | — | — |
| 69-1 | 260 | — | — |
| 69-2 | 342 | — | — |
| 69-3 | 389 | — | — |
| 69-5 | 431 | — | — |
| 69-6 | 590 | — | — |
| 69-7 | 548 | — | — |
| 70 | 438 | 1.92 | E |
| 70-1 | 274 | 3.36 | E |
| 70-2 | 321 | 3.08 | E |
| 70-3 | 419 | 3.23 | E |
| 70-4 | 363 | 1.18 | F |
| 70-5 | 522 | 3 | E |
| 70-6 | 480 | 1.59 | E |
| 71 | 425 | 0.97 | E |
| 71-1 | 567 | 2.17 | E |
| 71-2 | 525 | 1.61 | F |
| 72 | 451 | 0.97 | E |
| 72-1 | 593 | 4.2 | E |
| 72-2 | 551 | 2.29 | E |
| 73 | 505 | 2 | E |
| 73-1 | 444 | 5.38 | E |
| 73-2 | 486 | 3.17 | E |
| 73-3 | 430 | 2.46 | E |
| 73-4 | 589 | 5.11 | E |
| 73-5 | 547 | 1.81 | F |
| 74 | 518 | 2.31 | E |
| 74-1 | 560 | 4.57 | E |
| 75 | 413 | 2.7 | E |
| 75-1 | 296 | 2.96 | E |
| 75-2 | 396 | 3.52 | E |
| 76 | 437 | 2.4 | E |
| 76-1 | 637 | 5.62 | E |
| 77 | 516.3 | — | — |
| 78 | 447.2 | — | — |
| 79 | 466.2 | — | — |
| 80 | 516.3 | — | — |
| 81 | 514.3 | — | — |
| 82 | 466.3 | — | — |
| 83 | 405.2 | — | — |
| 84 | 559.3 | — | — |
| 85 | 530.3 | — | — |
| 86 | 502.3 | — | — |
| 87 | 445.2 | — | — |
| 88 | 482.3 | — | — |
| 89 | 528.3 | — | — |
| 90 | 482.3 | — | — |
| 91 | 387.2 | — | — |
| 92 | 518.3 | — | — |
| 93-1 | 398 (M + Na) | 2.05 | G |
| 93-2 | 440 (M + Na) | 2.12 | H |
| 93-3 | 362 | 1.77 | G |
| 93-4 | 480 | 2.11 | G |
| 93 | 451 | 1.74 | G |
| 94 | 450 | 1.61 | G |
| 95 | 455 | 1.57 | G |
| 96 | 437.2 | | |
| 97 | 437.2 | | |
| 98-1 | 192.2 | 1.47 | J |
| 98-2 | 191.2 | 0.89 | I |
| 98-3 | 291.2 | 4.33 | K |
| 98-4 | 261.1 | 1.47 | I |
| 98 | 462.2 | 1.62 | I |
| 99-2 | 484 (M + Na)+ | 2.03 | I |
| 99 | 424.2 | 2.95 | K |
| 100 | 398 | 0.6 | K |
| 101 | 438.2 | 3.45 | K |
| 102 | 413 | 3.02 | D |
| 102-1 | 442 | 5.70 | C |
| 102-2 | 386 | 4.97 | D |
| 102-3 | 545 | 5.37 | D |
| 103 | 438 | 4.00 | D |
| 103-1 | 399 [M + Na]+ | 5.43 | C |
| 103-2 | 321 | 4.42 | D |
| 103-3 | 480 | 5.08 | D |
| 104 | 461 | 2.72 | D |
| 104-1 | 400 | 4.05 | C |
| 104-2 | 344 | 1.93 | D |
| 104-3 | 503 | 3.97 | D |
| 105 | 523 | 2.80 | C |
| 105-1 | 456 [M + Na]+ | 5.20 | C |
| 105-2 | 484 [M + Na]+ | 4.88 | C |

TABLE 4-continued

| EXAMPLE | LC/MS m/z [M + 1]+ | RT min | Method/ Solvent |
|---|---|---|---|
| 105-3 | 406 | 3.88 | D |
| 105-4 | 565 | 5.03 | C |
| 106 | 489 | 3.07 | C |
| 106-1 | 378 | 4.20 | D |
| 106-2 | 537 | 5.63 | C |
| 106-3 | 531 | 5.47 | C |
| 107 | 435 | 3.25 | D |
| 107-1 | 456 [M + Na]+ | 5.15 | C |
| 107-2 | 474 | 5.40 | C |
| 107-3 | 318 | 3.30 | D |
| 107-4 | 477 | 4.43 | D |
| 108 | 405 | 2.15 | A |
| 108-1 | 292 | 3.42 | A |
| 108-2 | 264 | 2.90 | A |
| 108-3 | 605 | 4.78 | A |
| 109 | 448 | 2.48 | B |
| 109-1 | 427 | 4.27 | A |
| 109-2 | 293 | 0.73 1.40 | A |
| 109-3 | 357 [M + Na]+ | 2.78 | A |
| 109-4 | 329 [M + Na]+ | 2.88 3.25 | A |
| 109-5 | 648 | 4.25 | A |
| 110 | 434 | 2.47 | B |
| 110-1 | 321 | 2.78 | A |
| 110-2 | 315 [M + Na]+ | 3.08 3.47 | A |
| 110-3 | 634 | 4.23 | A |
| 111 | 510 | 2.37 | A |
| 111-1 | 397 | 4.83 | D |
| 111-2 | 369 | 4.32 | A |
| 111-3 | 710 | 4.72 | A |
| 112 | 399 | 2.88 | C |
| 112-1 | 310 | 4.55 4.65 | C |
| 112-2 | 282 | 4.03 4.17 | D |
| 112-3 | 441 | 4.90 5.03 | D |
| 113 | 431 | 3.20 3.35 | D |
| 113-1 | 473 | 4.73 | C |
| 114 | 397 | 3.80 | D |
| 114-1 | 422 [M + Na]+ | 5.35 | D |
| 114-2 | 559 | 5.72 | D |
| 114-3 | 475 | 5.25 | D |
| 114-4 | 439 | 4.88 | D |
| 115 | 397 | 3.45 | D |
| 115-1 | 233 | 0.70 0.97 | C |
| 115-2 | 280 | 2.40 2.67 | D |
| 115-3 | 190 | 0.28 | D |
| 115-4 | 308 | 4.33 | C |
| 115-5 | 280 | 3.65 | D |
| 115-6 | 439 | 5.07 | C |
| 116 | 433 | 3.73 | D |
| 116-1 | 344 | 4.55 | C |
| 116-2 | 316 | 4.02 | D |
| 116-3 | 475 | 5.3 | C |
| 117 | 393 | 2.13 | A |
| 117-1 | 280 | 3.98 | A |
| 117-2 | 252 | 2 | B |
| 117-3 | 593 | 5.17 | A |
| 118 | 453 | 2.46 | A |
| 118-1 | 392 | 4.86 | A |
| 118-2 | 434 | 1.95 | B |
| 118-3 | 378 | 1.64 | B |
| 118-4 | 537 | 1.76 | B |
| 118-5 | 495 | 1.68 | B |
| 119 | 438 | 1.51 | A |
| 119-1 | 274 | 1.65 | B |
| 119-2 | 377 | 1.53 | B |
| 119-3 | 419 | 1.65 | B |
| 119-4 | 363 | 1.17 | B |
| 119-5 | 522 | 1.66 | B |
| 119-6 | 480 | 1.6 | B |
| 120 | 408 | 1.8 | A |
| 120-1 | 567 | 3.26 | A |
| 120-2 | 425 | 1.61 | B |
| 121 | 455 | 1.66 | A |
| 121-1 | 264 | 3.33 | A |
| 121-2 | 304 | 3.97 | A |
| 121-3 | 407 | 1.5 | B |
| 121-4 | 449 | 1.65 | B |
| 121-5 | 393 | 1.13 | B |
| 121-6 | 597 | 3.4 | A |
| 121-7 | 555 | 3.17 | A |
| 122 | 492 | 1.28 | B |
| 122-1 | 734 | 1.79 | B |
| 122-2 | 692 | 1.72 | B |
| 123 | 544 | 1.85 | A |
| 123-1 | 186 | 0.98 | B |
| 123-2 | 212 | 1.15 | B |
| 123-3 | 586 | 3.36 | A |
| 123-4 | 544 | 2.65 | A |
| 124 | 482 | 1.59 | A |
| 124-1 | 196 | 1.48 | A |
| 124-2 | 222 | 1.51 | B |
| 124-3 | 192 | 0.62 | B |
| 124-4 | 566 | 1.48 | B |
| 124-5 | 544 | 1.41 | B |
| 125 | 481 | 1.56 | A |
| 125-1 | 623 | 3.63 | A |
| 125-2 | 581 | 1.72 | B |
| 126 | 443 | 1.85 | A |
| 126-1 | 410 | 1.69 | B |
| 126-2 | 452 | 1.82 | B |
| 126-3 | 396 | 1.53 | B |
| 126-4 | 555 | 1.63 | B |
| 126-5 | 513 | 1.56 | B |
| 127 | 458 | 1.37 | B |
| 127-1 | 600 | 1.8 | B |
| 127-2 | 558 | 1.76 | B |
| 128 | 468 | 1.16 | A |
| 128-1 | 274 | 3.36 | A |
| 128-2 | 321 | 3.08 | A |
| 128-3 | 419 | 3.23 | A |
| 128-4 | 363 | 1.18 | B |
| 128-5 | 491 | 1.82 | B |
| 128-6 | 449 | 1.58 | B |
| 129 | 479 | 2.71 | A |
| 129-1 | 521 | 2.97 | A |
| 130 | 488 | 3.06 | A |
| 130-1 | 530 | 3.3 | A |
| 131 | 399.2 | — | — |
| 132 | 387.2 | — | — |
| 133 | 435.2 | — | — |
| 134 | 469.2 | — | — |
| 135 | 488.2 | — | — |
| 136 | 417.2 | — | — |
| 137 | 427.2 | — | — |
| 138 | 442.2 | — | — |
| 139-2 | 196 | 1.02 | A |
| 139-3 | 570 | 1.542 | A |
| 140-2 | 214 | 1.125 | A |
| 140-3 | 605 | 1.965 | A |
| 139 | 486 | 1.2 | A |
| 140 | 504 | 1.183 | A |
| 141 | 431 | 1.198 | A |
| 142-2 | 744.2 (MNa+) | — | — |
| 142-3 | 702.2 (MNa+) | — | — |
| 142 | 480.3 | — | — |
| 143 | 406.2 | — | — |
| 144-1 | 778.6 (MNa+) | — | — |
| 144-2 | 688.6 (MNa+) | — | — |
| 144-3 | 742 (MNa+) | — | — |
| 144 | 478.2 | — | — |
| 145 | 451.8 | — | — |
| 146 | 478.2 | — | — |

TABLE 4-continued

| EXAMPLE | LC/MS m/z [M + 1]+ | RT min | Method/ Solvent |
|---|---|---|---|
| 147 | 452.2 | — | — |
| 148-1 | 479 | — | — |
| 148 | 437.2 | — | — |
| 149 | 467.3 | — | — |
| 152 | 530.3 | — | — |
| 153 | 440.2 | — | — |
| 154 | 476.3 | — | — |
| 155 | 440.2 | — | — |
| 156 | 500.3 | — | — |
| 157 | 446.2 | — | — |
| 158 | 446.2 | — | — |
| 159 | 458.3 | — | — |
| 160 | 402.2 | — | — |
| 161 | 402.2 | — | — |
| 162 | 484.3 | — | — |
| 163 | 454.2 | — | — |
| 164 | 496.3 | — | — |
| 165 | 480.3 | — | — |
| 166 | 484.3 | — | — |
| 167 | 500.3 | — | — |
| 168 | 458.3 | — | — |
| 169 | 454.2 | — | — |
| 170 | 480.3 | — | — |
| 171 | 452.2 | — | — |
| 172 | 494.3 | — | — |
| 173 | 387.2 | — | — |
| 174 | 423.2 | — | — |
| 175 | 405.2 | — | — |
| 176 | 406.2 | — | — |
| 177 | 406.2 | — | — |
| 178 | 413.2 | — | — |
| 179 | 484.3 | — | — |
| 180 | 413.2 | — | — |
| 181 | 427.2 | — | — |
| 182 | 427.2 | — | — |
| 183 | 431.2 | — | — |
| 184 | 498.3 | — | — |
| 185 | 427.2 | — | — |
| 186 | 431.2 | — | — |

Examples aa1-aa38

Example aa1

Synthesis of (2R)-2-[(2R)-4-(4-tert-butylphenyl)-3-oxomorpholin-2-yl]-2-hydroxy-N-[4-(N-methylcarbamimidoyl)phenyl]acetamide hydrochloride (EXAMPLE aa1)

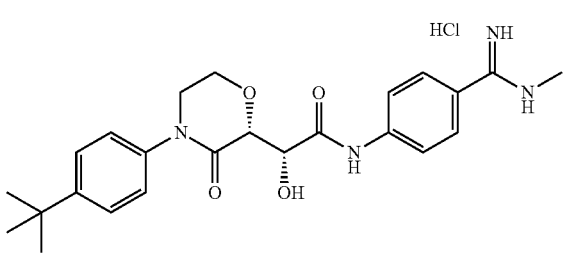

EXAMPLE aa1

Step 1-1

Synthesis of 4-tert-butyl-N-(2-chloroethyl)aniline (compound aa1-1)

To a solution of 4-tert-butylaniline (5.00 g) in MeOH (100 mL) was added 40% chroloacetaldehyde solution in water (8.24 mL) and AcOH (3.84 mL) at 0° C. The mixture was stirred for 15 minutes at the same temperature, sodium acetoxyborohydride (NaBH(OAc)$_3$; 14.2 g) was added into the reaction mixture at one portion and the mixture was stirred for 15 minutes.

The reaction mixture was diluted with water and was extracted with EtOAc. The extract was washed with water, sat.NaHCO$_3$ and brine. The organic layer was dried with anhyd. Na$_2$SO$_4$. It was filtrated to remove insoluble matters and it was concentrated in vacuo. The residue was purified by silica gel flush chromatography (NH-type, eluent:Hexane) to obtain aa1-1 (4.8 g) as pale yellow oil.

Step 1-2

Synthesis of (2R,3R)-2,3-diacetyloxy-4-(4-cyanoanilino)-4-oxobutanoic acid (compound aa1-2)

To a solution of (+)-Diacetyl-L-tartaric anhydride (9.15 g) in dry DMF (100 mL), was added 4-aminobenzonitrile (5 g) under ice cooling and the reaction mixture was stirred at room temperature overnight to obtain compound aa1-2. The solution of compound aa1-2 was used in the next step without any treatment.

Step 1-3

Synthesis of [(2R,3R)-3-acetyloxy-1-[4-tert-butyl-N-(2-chloroethyl)-anilino]-4-(4-cyanoanilino)-1,4-dioxobutan-2-yl]acetate (compound aa1-3)

The above DMF solution of aa1-2 (25.4 mL) was diluted with CH$_2$Cl$_2$ (25.4 mL). The internal temperature of the mixture was kept below −70° C. over all additions with dry ice bath.

Oxalyl chloride (1.0 mL) in CH$_2$Cl$_2$ (3 mL) was added dropwise into the reaction mixture. After stirring for 1 hour, pyridine (3.67 mL) was added dropwise thereto and stirred for 15 min. Then compound aa1-1 (2.28 g) in CH$_2$Cl$_2$ (13.7 mL) was added dropwise into the reaction mixture. The mixture was stirred below −70° C. for 12 hours.

The reaction mixture was quenched with water and was extracted with EtOAc. The extract was washed with water, 1N HCl, sat.NaHCO$_3$ and brine. The organic layer was dried with anhyd. Na$_2$SO$_4$. It was filtrated and was concentrated in vacuo. The residue was purified by silica gel flush chromatography (eluent:Hexane:EtOAc=90:10~25:75) to obtain 1-3 (1.19 g) as a white amorphous solid.

Step 1-4

Synthesis of (2R,3R)—N-(4-tert-butylphenyl)-N-(2-chloroethyl)-N'-(4-cyanophenyl)-2,3-dihydroxybutanediamide (compound aa1-4)

To a solution of aa1-3 (0.3 g) in MeOH (6 mL), was added 8N NH$_3$/MeOH (0.36 mL) at 0° C. and the mixture was stirred for 10 minutes in the same temperature. The mixture was concentrated and was dried in vacuo to obtain crude aa1-4. The crude aa1-4 was used in the next step without further purification.

Step 1-5

Synthesis of (2R)-2-[(2R)-4-(4-tert-butylphenyl)-3-oxomorpholin-2-yl]-N-(4-cyanophenyl)-2-hydroxyacetamide (compound aa1-5)

The crude aa1-4 was dissolved in t-BuOH (4.5 mL)-DMSO (3 mL), and t-BuOK (191 mg) was added portionwise into the reaction mixture at 0° C. The mixture was stirred for 5 minutes in the same temperature.
To the reaction mixture was added 1N HCl and $Et_2O$ to obtain precipitate. Then the precipitate was collected by filtration, was rinsed with water, was washed with $Et_2O$ and was dried in vacuo to obtain aa1-5 (115 mg) as a white amorphous solid.

Step 1-6

Synthesis of (2R)-2-[(2R)-4-(4-tert-butylphenyl)-3-oxomorpholin-2-yl]-2-hydroxy-N-[4-(N-methylcarbamimidoyl)phenyl]acetamide hydrochloride (EXAMPLE aa1)

A mixture of compound aa1-5 (0.15 g) in $CH_2Cl_2$-MeOH (10-50 mL) was bubbled with HCl gas at 0° C. for 1 h. Then the mixture was left at room temperature overnight. The mixture was concentrated in vacuo. Then the resulting mixture was solved in MeOH (10 mL) and 2M $MeNH_2$ in THF (0.74 mL) were added into the mixture at 0° C. The solution was stirred at room temperature overnight. The solvent was removed and the resulting residue was purified by preparative LC/MS to obtain EXAMPLE aa1 (15 mg) as a beige amorphous solid.

Example aa2

Synthesis of (2R)-2-hydroxy-N-(1-imino-2,3-dihydroisoindol-5-yl)-2-[(2R)-3-oxo-4-(1-oxo-2,3-dihydroisoindol-5-yl)morpholin-2-yl]acetamide hydrochloride (EXAMPLE aa2)

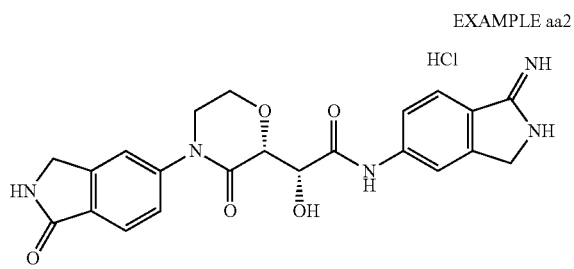 [SMILES: Cl ; N=C1NCc2cc(NC(=O)[C@H](O)[C@H]3OCCN(c4ccc5c(c4)CNC5=O)C3=O)ccc21]

EXAMPLE aa2

Step 2-1

Synthesis of 2-[tert-butyl(diphenyl)silyl]-5-iodo-3H-isoindol-1-one (compound aa2-1)

To a suspension of 5-iodo-2,3-dihydroisoindol-1-one (3 g) in DMF (60 mL), were added N,N-dimethylaminopyridine (DMAP: 14 mg), $Et_3N$ (4.84 mL) and tert-butyl-diphenylsilyl chloride (9.0 mL). The mixture was stirred at 50° C. for 2 h. After cooling, saturated $NaHCO_3$ aq. was added into the reaction mixture. Then it was extracted with EtOAc. The organic layer was washed with water and brine, then was dried over anhydrous $Na_2SO_4$. The solvent was removed under reduced pressure. The trituration with $Et_2O$ followed by filtration gave compound aa2-1 (2.78 g) as a yellow amorphous solid.

Step 2-2

Synthesis of tert-butyl (2R)-2-[(2R)-4-[2-[tert-butyl(diphenyl)silyl]-1-oxo-3H-isoindol-5-yl]-3-oxomorpholin-2-yl]-2-hydroxyacetate (compound aa2-2)

The mixture of (R)-tert-butyl (2-hydroxy-2-(R)-3-oxomorpholin-2-yl)acetate (1.2 g) and compound 2-1 (2.71 g) were solved in degassed DMSO (17 mL). Then crushed $K_3PO_4$ (2.2 g) and CuI (0.2 g) were added into the mixture. Then trans-N,N-dimethyl cyclohexanediamine (0.49 mL) was immediately added into the mixture. The mixture was stirred at room temperature for 3 h, then CuI (0.1 g) and trans-N,N-dimethyl cyclohexanediamine (0.29 mL) were added to complete the reaction. The reaction mixture was stirred at room temperature for more 2 h. Then, 1N HCl was added to the mixture and it was extracted with EtOAc. The organic solvent was washed with water and brine. It was dried over anhydrous $Na_2SO_4$ and the solvent was removed under reduced pressure. The resulting residue was purified by silica gel flash column chromatography (Hexane/EtOAc=100/0-50/50) to obtain compound aa2-2 (1.40 g) as a pale yellow amorphous solid.

Step 2-3

Synthesis of tert-butyl (2R)-2-acetyloxy-2-[(2R)-4-[2-[tert-butyl(diphenyl)silyl]-1-oxo-3H-isoindol-5-yl]-3-oxomorpholin-2-yl]acetate (compound aa2-3)

To the solution of compound aa2-2 (0.1 g) and DMAP (2.0 mg) in $CH_2Cl_2$ (1.7 mL), were added pyridine (27 uL) and $Ac_2O$ (31 uL) at 0° C. The mixture was stirred at 0° C. for 75 min. Then the mixture was diluted with EtOAc, the organic layer was washed with 5% $CuSO_4$ aq., water and brine. It was dried over anhydrous $Na_2SO_4$. The solvent was removed under reduced pressure to obtain compound aa2-3 (101 mg) as a white amorphous solid. It was used to the next step without further purification.

Step 2-4

Synthesis of (2R)-2-acetyloxy-2-[(2R)-3-oxo-4-(1-oxo-2,3-dihydroisoindol-5-yl)morpholin-2-yl]acetic acid (compound aa2-4)

To a solution of compound aa2-3 (91 mg) in $CH_2Cl_2$ (0.6 mL), was added trifluoroacetic acid (TFA: 2.4 mL) at 0° C. The reaction mixture was stirred at room temperature for 2 h. The solvent was removed in vacuo. The resulting residue was co-evaporated with $CH_2Cl_2$, several times. Then trituration with $Et_2O$ gave compound aa2-4 (46 mg) as a white amorphous solid.

Step 2-5

Synthesis of [(1R)-2-[3-[[bis[(2-methylpropan-2-yl)oxycarbonyl]amino]-methyl]-4-cyanoanilino]-2-oxo-1-[(2R)-3-oxo-4-(1-oxo-2,3-dihydroisoindol-5-yl)morpholin-2-yl]ethyl]acetate (compound aa2-5)

To the suspension of compound aa2-4 (40 mg), N-[(5-amino-2-cyanophenyl)methyl]-N-[(2-methylpropan-2-yl)oxycarbonyl]carbamate (39.9 mg) and DMAP (1.4 mg) in CH$_2$Cl$_2$ (1.1 mL), were added WSC—HCl (28.6 mg) at 0° C. The reaction mixture was stirred at 0° C. for 4 h. The mixture was diluted with EtOAc and the organic layer was washed with 1N HCl and brine. It was dried over anhydrous Na$_2$SO$_4$ and the solvent was removed under reduced pressure. The resulting residue was purified by silica gel flash column chromatography (EtOAc/MeOH=100/0-90/10) to obtain compound aa2-5 (26 mg) as a colorless amorphous solid.

Step 2-6

Synthesis of tert-butyl N—[[2-cyano-5-[[(2R)-2-hydroxy-2-[(2R)-3-oxo-4-(1-oxo-2,3-dihydroisoindol-5-yl)morpholin-2-yl]acetyl]amino]phenyl]methyl]-N-[(2-methylpropan-2-yl)oxycarbonyl]carbamate (compound aa2-6)

A solution of compound aa2-5 (25.9 mg) in 8N NH$_3$-MeOH (1 mL) was stirred at room temperature for 2 h. Then the solvent was removed in vacuo. Acetonitrile was added to the resulting residue and the mixture was concentrated in vacuo to obtain compound aa2-6 (23 mg) as a white amorphous solid.

Step 2-7

Synthesis of (2R)—N-[3-(aminomethyl)-4-cyanophenyl]-2-hydroxy-2-[(2R)-3-oxo-4-(1-oxo-2,3-dihydroisoindol-5-yl)morpholin-2-yl]acetamide hydrochloride (compound aa2-7)

Compound aa2-6 (23 mg) was suspended in 4N HCl-dioxane (2 mL). The reaction mixture was stirred at room temperature for 2 h and evaporated. The residue was co-evaporated with toluene (2 times) to obtain compound aa2-7 (17 mg) as a colorless amorphous solid.

Step 2-8

Synthesis of (2R)-2-hydroxy-N-(1-imino-2,3-dihydroisoindol-5-yl)-2-[(2R)-3-oxo-4-(1-oxo-2,3-dihydroisoindol-5-yl)morpholin-2-yl]acetamide hydrochloride (EXAMPLE aa2)

A solution of compound aa2-7 (15 mg) in EtOH (3 mL) was refluxed for 7 h 30 m. After cooling, the mixture was concentrated in vacuo and trituration with Et$_2$O followed by filtration gave EXAMPLE aa2 (14.8 mg) as a colorless amorphous solid.

Example aa3

Synthesis of (2R)-2-hydroxy-N-(1-imino-2,3-dihydroisoindol-5-yl)-2-[(2R)-3-oxo-4-(2-oxo-1H-quinolin-6-yl)morpholin-2-yl]acetamide hydrochloride (EXAMPLE aa3)

EXAMPLE aa3

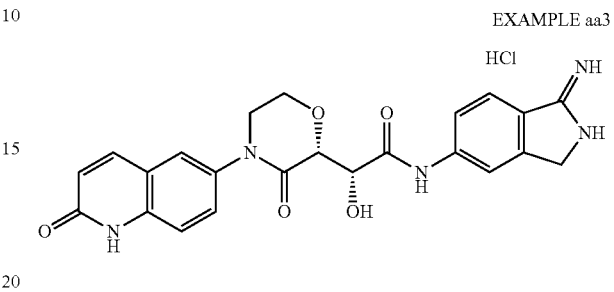

Step 3-1

Synthesis of tert-butyl (2R)-2-hydroxy-2-[(2R)-3-oxo-4-(2-oxo-1H-quinolin-6-yl)morpholin-2-yl]acetate (compound aa3-1)

According to the Step 2-2 in synthetic method for EXAMPLE aa2, 6-iodo-1H-quinolin-2-one (2.00 g) was used instead of aa2-1 to obtain compound aa3-1 (1.13 g) as a colorless amorphous solid.

Step 3-2

Synthesis of tert-butyl (2R)-2-acetyloxy-2-[(2R)-3-oxo-4-(2-oxo-1H-quinolin-6-yl)morpholin-2-yl]acetate (compound aa3-2)

According to the Step 2-3 in synthetic method for EXAMPLE aa2, compound aa3-1 (1.00 g) was used instead of aa2-2 to obtain compound aa3-2 (0.85 g) as a colorless amorphous solid.

Step 3-3

Synthesis of (2R)-2-acetyloxy-2-[(2R)-3-oxo-4-(2-oxo-1H-quinolin-6-yl)morpholin-2-yl]acetic acid (compound aa3-3)

According to the Step 2-4 in synthetic method for EXAMPLE aa2, compound aa3-2 (0.80 g) was used instead of aa2-3 to obtain compound aa3-3 (0.56 g) as a pale brown amorphous solid.

Step 3-4

Synthesis of [(1R)-2-[3-[[bis[(2-methylpropan-2-yl)oxycarbonyl]-amino]methyl]-4-cyanoanilino]-2-oxo-1-[(2R)-3-oxo-4-(2-oxo-1H-quinolin-6-yl)morpholin-2-yl]ethyl]acetate (compound aa3-4)

According to the Step 2-5 in synthetic method for EXAMPLE aa2, compound aa3-3 (0.10 g) was used instead of aa2-4 to obtain compound aa3-4 (47 mg) as a colorless amorphous solid.

Step 3-5

Synthesis of tert-butyl N—[[2-cyano-5-[[(2R)-2-hydroxy-2-[(2R)-3-oxo-4-(2-oxo-1H-quinolin-6-yl)morpholin-2-yl]acetyl]amino]phenyl]methyl]-N-[(2-methylpropan-2-yl)oxycarbonyl]carbamate (compound aa3-5)

According to the Step 2-6 in synthetic method for EXAMPLE aa2, compound aa3-4 (45 mg) was used instead of aa2-5 to obtain compound aa3-5 (35 mg) as a colorless amorphous solid.

Step 3-6

Synthesis of methyl (2R)-2-hydroxy-2-[(2R)-4-(4-iodophenyl)-3-oxomorpholin-2-yl]acetate hydrochloride (compound aa3-6)

According to the Step 2-7 in synthetic method for EXAMPLE aa2, compound aa3-5 (35 mg) was used instead of aa2-6 to obtain compound aa3-6 (25 mg) as a colorless amorphous solid.

Step 3-7

Synthesis of (2R)-2-hydroxy-N-(1-imino-2,3-dihydroisoindol-5-yl)-2-[(2R)-3-oxo-4-(2-oxo-1H-quinolin-6-yl)morpholin-2-yl]acetamide hydrochloride (EXAMPLE aa3)

According to the Step 2-8 in synthetic method for EXAMPLE aa2, compound aa3-6 (25 mg) was used instead of aa2-7 to obtain EXAMPLE aa3 (20 mg) as a pale brown amorphous solid.

Example aa4

Synthesis of (2R)-2-[(2R)-4-[7-(difluoromethoxy)-2-oxo-1H-quinolin-6-yl]-3-oxomorpholin-2-yl]-2-hydroxy-N-(1-imino-2,3-dihydroisoindol-5-yl)acetamide hydrochloride (EXAMPLE aa4)

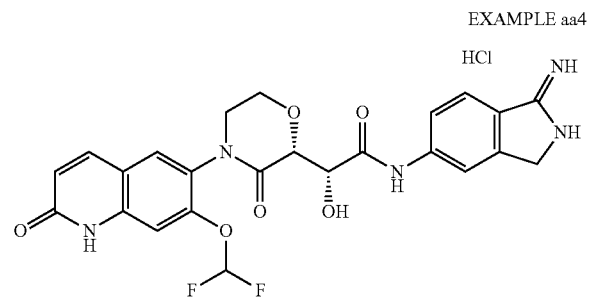 [SMILES: Cl ; N=C1NCc2cc(NC(=O)[C@H](O)[C@H]3OCCN(c4cc5ccc(=O)[nH]c5cc4OC(F)F)C3=O)ccc21]

EXAMPLE aa4

Step 4-1

Synthesis of 2-(difluoromethoxy)-1-iodo-4-nitrobenzene (compound aa4-1)

A mixture of 2-iodo-5-nitrophenol (8.98 g), $K_2CO_3$ (18.7 g) and 2-chloro-2,2-difluoro-acetic acid sodium salt (5.17 g) in DMF-$H_2O$ (60-6 mL) was stirred at 110° C. for 3.5 h and at room temperature for 12 h. The mixture was diluted with EtOAc and washed with 1H HCl, saturated $NaHCO_3$ aq., water and brine, and dried over anhydrous $Na_2SO_4$. The solvent was removed under reduced pressure. The resulting residue was purified by silica gel column chromatography (Hexane/EtOAc=9/1) to obtain compound aa4-1 (9.17 g) as a brown amorphous solid.

Step 4-2

Synthesis of 3-(difluoromethoxy)-4-iodoaniline (compound aa4-2)

A mixture of compound aa4-1 (8 g) and $Na_2S_2O_4$ in THF-EtOH—$H_2O$ (150-75-225 mL) was stirred at 0° C. for 1 h and at room temperature for 6 h. The mixture was extracted with EtOAc and the organic layer was washed with $H_2O$, brine. It was dried over anhydrous $Na_2SO_4$. The solvent was removed under reduced pressure to obtain compound aa4-2 (2.36 g) as brown oil. It was used to the next step without further purification.

Step 4-3

Synthesis of (E)-N-[3-(difluoromethoxy)-4-iodophenyl]-3-ethoxyprop-2-enamide (compound aa4-3)

To a solution of compound aa4-2 (2.35 g) and pyridine (1.33 mL) in $CH_2Cl_2$ (60 mL), was added dropwise 3-ethoxy-2-propenoyl chloride (1.33 g) at 0° C. The reaction mixture was stirred at 0° C. for 5 min and at room temperature for 20 min. The mixture was concentrated in vacuo, and the resulting residue was solved in EtOAt and the organic layer was washed with 1N HCl, saturated $NaHCO_3$ aq., water and brine, and dried over anhydrous $Na_2SO_4$. The solvent was removed under reduced pressure to obtain compound aa4-3 (3.2 g) as brown oil. It was used to the next step without further purification.

Step 4-4

Synthesis of 7-(difluoromethoxy)-6-iodo-1H-quinolin-2-one (compound aa4-4)

To compound aa4-3 (3.15 g), conc. $H_2SO_4$ was added dropwise at 0° C. The mixture was stirred at 0° C. for 10 min then it was poured into crashed ice. The mixture was diluted with water and it was extracted with EtOAc. The organic layer was washed with saturated $NaHCO_3$ aq., water and brine, and dried over anhydrous $Na_2SO_4$. The solvent was removed under reduced pressure to obtain compound aa4-4 (2.06 g) as a pale brown amorphous solid. It was used to the next step without further purification.

Step 4-5

Synthesis of tert-butyl (2R)-2-[(2R)-4-[7-(difluoromethoxy)-2-oxo-1H-quinolin-6-yl]-3-oxomorpholin-2-yl]-2-hydroxyacetate (compound aa4-5)

According to the Step 2-2 in synthetic method for EXAMPLE aa2, compound aa4-4 (1.91 g) was used instead of aa2-1 to obtain compound aa4-5 (0.6 g) as a brown amorphous solid.

Step 4-6

Synthesis of tert-butyl (2R)-2-acetyloxy-2-[(2R)-4-[7-(difluoromethoxy)-2-oxo-1H-quinolin-6-yl]-3-oxomorpholin-2-yl]acetate (compound aa4-6)

According to the Step 2-3 in synthetic method for EXAMPLE aa2, compound aa4-5 (0.59 g) was used instead of aa2-2 to obtain compound aa4-6 (0.58 g) as a brown amorphous solid.

Step 4-7

Synthesis of (2R)-2-acetyloxy-2-[(2R)-4-[7-(difluoromethoxy)-2-oxo-1H-quinolin-6-yl]-3-oxomorpholin-2-yl]acetic acid (compound aa4-7)

According to the Step 2-4 in synthetic method for EXAMPLE aa2, compound aa4-6 (0.57 g) was used instead of aa2-3 to obtain compound aa4-7 (0.53 g) as a brown amorphous solid.

Step 4-8

Synthesis of [(1R)-2-[3-[[bis[(2-methylpropan-2-yl)oxycarbonyl]amino]-methyl]-4-cyanoanilino]-1-[(2R)-4-[7-(difluoromethoxy)-2-oxo-1H-quinolin-6-yl]-3-oxomorpholin-2-yl]-2-oxoethyl]acetate (compound aa4-8)

According to the Step 2-5 in synthetic method for EXAMPLE aa2, compound aa4-7 (0.35 g) was used instead of aa2-4 to obtain compound aa4-8 (97 mg) as a pale yellow amorphous solid.

Step 4-9

Synthesis of tert-butyl N—[[2-cyano-5-[[(2R)-2-[(2R)-4-[7-(difluoromethoxy)-2-oxo-1H-quinolin-6-yl]-3-oxomorpholin-2-yl]-2-hydroxyacetyl]amino]phenyl]methyl]-N-[(2-methylpropan-2-yl)oxycarbonyl]carbamate (compound aa4-9)

According to the Step 2-6 in synthetic method for EXAMPLE aa2, compound aa4-8 (96 mg) was used instead of aa2-5 to obtain compound aa4-9 (88 mg) as a white amorphous solid.

Step 4-10

Synthesis of (2R)—N-[3-(aminomethyl)-4-cyanophenyl]-2-[(2R)-4-[7-(difluoromethoxy)-2-oxo-1H-quinolin-6-yl]-3-oxomorpholin-2-yl]-2-hydroxyacetamide hydrochloride (compound aa4-10)

According to the Step 2-7 in synthetic method for EXAMPLE aa2, compound aa4-9 (82 mg) was used instead of aa2-6 to obtain compound aa4-10 (59 mg) as a white amorphous solid.

Step 4-11

Synthesis of (2R)-2-[(2R)-4-[7-(difluoromethoxy)-2-oxo-1H-quinolin-6-yl]-3-oxomorpholin-2-yl]-2-hydroxy-N-(1-imino-2,3-dihydroisoindol-5-yl)acetamide hydrochloride (EXAMPLE aa4)

According to the Step 2-8 in synthetic method for EXAMPLE aa2, compound aa4-10 (57 mg) was used instead of aa2-7 to obtain EXAMPLE aa4 (39 mg) as a white amorphous solid.

Example aa5

Synthesis of (2R)—N-(4-carbamimidoylphenyl)-2-hydroxy-2-[(2R)-3-oxo-4-(2-oxo-1H-quinolin-6-yl)morpholin-2-yl]acetamide hydrochloride (EXAMPLE aa5)

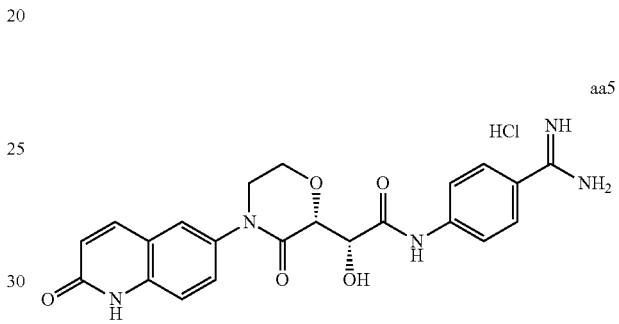

aa5

Step 5-1

Synthesis of [(1R)-2-oxo-2-[4-(5-oxo-2H-1,2,4-oxadiazol-3-yl)anilino]-1-[(2R)-3-oxo-4-(2-oxo-1H-quinolin-6-yl)morpholin-2-yl]ethyl]acetate (compound aa5-1)

To a solution of compound aa3-3 (100 mg) in DMF (2.5 mL), was added oxalyl chloride (48 uL) at 0° C. The reaction mixture was stirred at 0° C. for 0.5 h, then $CH_2Cl_2$ (2.5 mL) and pyridine (95.5 uL) were added into the reaction mixture at 0° C. The mixture was stirred at 0° C. for 0.5 h, then 3-(4-aminophenyl)-1,2,4-oxadiazol-5(2H)-one (60.2 mg) was added into the mixture at 0° C. The mixture was stirred at room temperature for 3 days. Then water and 1N HCl were added into the reaction mixture and the mixture was extracted with EtOAc. The organic layer was washed with water and brine, and was dried over anhydrous $Na_2SO_4$. The solvent was removed under reduced pressure to obtain compound aa5-1 (77 mg) as a beige amorphous solid. It was used to the next step without further purification.

Step 5-2

Synthesis of (2R)-2-hydroxy-N-[4-(5-oxo-2H-1,2,4-oxadiazol-3-yl)phenyl]-2-[(2R)-3-oxo-4-(2-oxo-1H-quinolin-6-yl)morpholin-2-yl]acetamide ammonium salt (compound aa5-2)

According to the Step 2-6 in synthetic method for EXAMPLE aa2, compound aa5-1 (75 mg) was used instead of aa2-5 to obtain compound aa5-2 (44 mg) as a beige amorphous solid.

Step 5-3

Synthesis of (2R)—N-(4-carbamimidoylphenyl)-2-hydroxy-2-[(2R)-3-oxo-4-(2-oxo-1H-quinolin-6-yl)morpholin-2-yl]acetamide hydrochloride (EXAMPLE aa5)

To the solution of compound aa5-2 (40 mg) in 1N HCl-dioxane/MeOH-MeOH (=0.34-40 mL), was added 10% palladium charcoal (Pd/C: 40 mg). The reaction mixture was stirred under hydrogen gas atmosphere for 1 h. MeOH (20 mL) was added into the reaction mixture and the mixture was stirred for more 1.5 h to complete the reaction. Then Pd/C was removed by filtration with Celite® pad and rinsed with MeOH. The filtrate was concentrated in vacuo and trituration with MeOH/Et$_2$O followed by filtration gave EXAMPLE aa5 (30 mg) as a beige amorphous solid.

Example aa6

Synthesis of (2R)—N-(4-carbamimidoyl-3-fluorophenyl)-2-hydroxy-2-[(2R)-3-oxo-4-(2-oxo-1H-quinolin-6-yl)morpholin-2-yl]acetamide hydrochloride (EXAMPLE aa6)

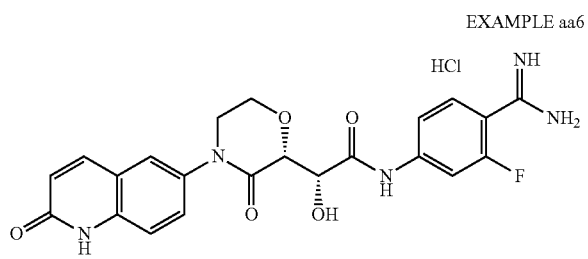 [SMILES: N=C(N)c1ccc(NC(=O)[C@H](O)[C@H]2OCCN(c3ccc4[nH]c(=O)ccc4c3)C2=O)cc1F ; Cl]

EXAMPLE aa6

Step 6-1

Synthesis of [(1R)-2-[3-fluoro-4-(5-oxo-2H-1,2,4-oxadiazol-3-yl)anilino]-2-oxo-1-[(2R)-3-oxo-4-(2-oxo-1H-quinolin-6-yl)morpholin-2-yl]ethyl]acetate (compound aa6-1)

According to the Step 5-1 in synthetic method for EXAMPLE aa5, 3-fluoro-4-(5-oxo-2H-1,2,4-oxadiazol-3-yl)aniline (55 mg) was used instead of 4-(5-oxo-2H-1,2,4-oxadiazol-3-yl)aniline to obtain compound aa6-1 (31 mg) as a colorless amorphous solid.

Step 6-2

Synthesis of (2R)—N-[3-fluoro-4-(5-oxo-2H-1,2,4-oxadiazol-3-yl)phenyl]-2-hydroxy-2-[(2R)-3-oxo-4-(2-oxo-1H-quinolin-6-yl)morpholin-2-yl]acetamide ammonium salt (compound aa6-2)

According to the Step 2-6 in synthetic method for EXAMPLE aa2, compound aa6-1 (30 mg) was used instead of aa2-5 to obtain compound aa6-2 (28 mg) as a beige amorphous solid.

Step 6-3

Synthesis of (2R)—N-(4-carbamimidoyl-3-fluorophenyl)-2-hydroxy-2-[(2R)-3-oxo-4-(2-oxo-1H-quinolin-6-yl)morpholin-2-yl]acetamide hydrochloride (EXAMPLE aa6)

According to the Step 5-3 in synthetic method for EXAMPLE aa5, compound aa6-2 (22 mg) was used instead of aa5-2 to obtain EXAMPLE aa6 (19 mg) as a beige amorphous solid.

Example aa7

Synthesis of (2R)-2-hydroxy-N-(1-imino-2,3-dihydroisoindol-5-yl)-2-[(2R)-3-oxo-4-(2-oxo-1H-quinolin-7-yl)morpholin-2-yl]acetamide hydrochloride (EXAMPLE aa7)

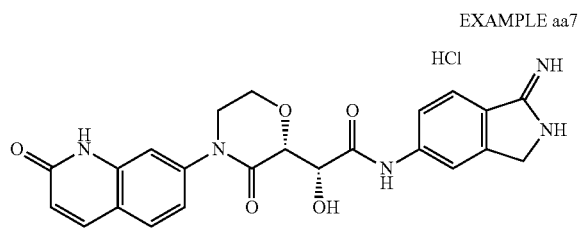 [SMILES: Cl ; N=C1NCc2cc(NC(=O)[C@H](O)[C@H]3OCCN(c4ccc5ccc(=O)[nH]c5c4)C3=O)ccc21]

EXAMPLE aa7

Step 7-1

Synthesis of 7-iodo-1H-quinolin-2-one (compound aa7-1)

According to the Step 4-4 in synthetic method for EXAMPLE aa4, (E)-N-(3-iodophenyl)-3-ethoxyprop-2-enamide (13.00 g) was used instead of aa4-3 to obtain compound aa7-1 (11.2 g) as a colorless powder.

Step 7-2

Synthesis of tert-butyl (2R)-2-hydroxy-2-[(2R)-3-oxo-4-(2-oxo-1H-quinolin-7-yl)morpholin-2-yl]acetate (compound aa7-2)

According to the Step 2-2 in synthetic method for EXAMPLE aa2, compound aa7-1 (4.00 g) was used instead of aa2-1 to obtain compound aa7-2 (1.76 g) as a yellow amorphous solid.

Step 7-3

Synthesis of tert-butyl (2R)-2-acetyloxy-2-[(2R)-3-oxo-4-(2-oxo-1H-quinolin-7-yl)morpholin-2-yl]acetate (compound aa7-3)

According to the Step 2-3 in synthetic method for EXAMPLE aa2, compound aa7-2 (0.83 g) was used instead of aa2-2 to obtain compound aa7-3 (0.64 g) as a yellow amorphous solid.

Step 7-4

Synthesis of (2R)-2-acetyloxy-2-[(2R)-3-oxo-4-(2-oxo-1H-quinolin-7-yl)morpholin-2-yl]acetic acid (compound aa7-4)

According to the Step 2-4 in synthetic method for EXAMPLE aa2, compound aa7-3 (0.63 g) was used instead of aa2-3 to obtain compound aa7-4 (0.50 g) as a pale yellow amorphous solid.

Step 7-5

Synthesis of N-[[2-cyano-5-[[[(2R)-2-hydroxy-2-[(2R)-3-oxo-4-(2-oxo-1H-quinolin-7-yl)morpholin-2-yl]acetyl]amino]phenyl]methyl]-N-[(2-methylpropan-2-yl)oxycarbonyl]carbamate (compound aa7-5)

According to the Step 2-5 and 2-6 in synthetic method for EXAMPLE aa2, compound aa7-4 (1.0 g) was used instead of aa2-4 to obtain compound aa7-5 (0.39 g) as a pale yellow amorphous solid.

Step 7-6

Synthesis of (2R)—N-[3-(aminomethyl)-4-cyanophenyl]-2-hydroxy-2-[(2R)-3-oxo-4-(2-oxo-1H-quinolin-7-yl)morpholin-2-yl]acetamide hydrochloride (compound aa7-6)

According to the Step 2-7 in synthetic method for EXAMPLE aa2, compound aa7-5 (0.38 g) was used instead of aa2-6 to obtain compound aa7-6 (0.27 g) as a yellow amorphous solid.

Step 7-7

Synthesis of (2R)-2-hydroxy-N-(1-imino-2,3-dihydroisoindol-5-yl)-2-[(2R)-3-oxo-4-(2-oxo-1H-quinolin-7-yl)morpholin-2-yl]acetamide hydrochloride (EXAMPLE aa7)

According to the Step 2-8 in synthetic method for EXAMPLE aa2, compound aa7-6 (0.27 g) was used instead of aa2-7 to obtain EXAMPLE aa7 (0.27 g) as a yellow amorphous solid.

Example aa8

Synthesis of (2R)-2-hydroxy-N-(1-imino-2,3-dihydroisoindol-5-yl)-2-[(2R)-4-(1-methyl-2-oxoquinolin-7-yl)-3-oxomorpholin-2-yl]acetamide hydrochloride (EXAMPLE aa8)

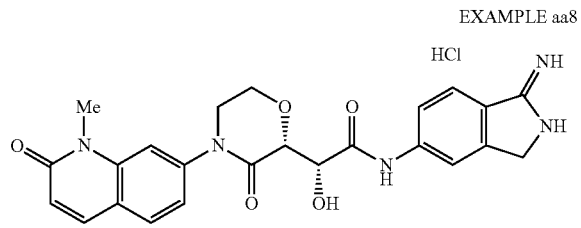 [SMILES: Cl ; Cn1c(=O)ccc2ccc(N3CCO[C@H]([C@@H](O)C(=O)Nc4ccc5c(c4)CNC5=N)C3=O)cc21]

EXAMPLE aa8

Step 8-1

Synthesis of 7-iodo-1-methylquinolin-2-one (compound aa8-1)

To a solution of compound aa7-1 (1 g) in DMF (18 mL), was added 60% NaH (0.22 g) at 0° C. and the mixture was stirred at 0° C. for 15 min. Then MeI (0.46 mL) was added into the reaction mixture at 0° C. and the mixture was stirred at room temperature for 3 h. After the reaction, water and 1N HCl were added into the reaction mixture at 0° C. The mixture was extracted with EtOAc and the organic layer was washed with saturated $NaHCO_3$ aq. and brine, and dried over anhydrous $Na_2SO_4$. The solvent was removed under reduced pressure to obtain the crude product. Trituration with hexane followed by filtration gave compound aa8-1 (0.73 g) as a yellow amorphous solid.

Step 8-2

Synthesis of tert-butyl (2R)-2-hydroxy-2-[(2R)-4-(1-methyl-2-oxoquinolin-7-yl)-3-oxomorpholin-2-yl]acetate (compound aa8-2)

According to the Step 2-2 in synthetic method for EXAMPLE aa2, compound aa8-1 (0.71 g) was used instead of aa2-1 to obtain compound aa8-2 (0.43 g) as a yellow amorphous solid.

Step 8-3

Synthesis of tert-butyl (2R)-2-acetyloxy-2-[(2R)-4-(1-methyl-2-oxoquinolin-7-yl)-3-oxomorpholin-2-yl]acetate (compound aa8-3)

According to the Step 2-3 in synthetic method for EXAMPLE aa2, compound aa8-2 (0.45 g) was used instead of aa2-2 to obtain compound aa8-3 (0.46 g) as a yellow amorphous solid.

Step 8-4

Synthesis of (2R)-2-acetyloxy-2-[(2R)-4-(1-methyl-2-oxoquinolin-7-yl)-3-oxomorpholin-2-yl]acetic acid (compound aa8-4)

According to the Step 2-4 in synthetic method for EXAMPLE aa2, compound aa8-3 (0.45 g) was used instead of aa2-3 to obtain compound aa8-4 (0.48 g) as a pale brown amorphous solid.

Step 8-5

Synthesis of [(1R)-2-[3-[[bis[(2-methylpropan-2-yl)oxycarbonyl]amino]methyl]-4-cyanoanilino]-1-[(2R)-4-(1-methyl-2-oxoquinolin-7-yl)-3-oxomorpholin-2-yl]-2-oxoethyl]acetate (compound aa8-5)

According to the Step 2-5 in synthetic method for EXAMPLE aa2, compound aa8-4 (0.47 g) was used instead of aa2-4 to obtain compound aa8-5 (0.52 g) as a yellow amorphous.

Step 8-6

Synthesis of tert-butyl N-[[2-cyano-5-[[(2R)-2-hydroxy-2-[(2R)-4-(1-methyl-2-oxoquinolin-7-yl)-3-oxomorpholin-2-yl]acetyl]amino]phenyl]methyl]-N-[(2-methylpropan-2-yl)oxycarbonyl]carbamate (compound aa8-6)

According to the Step 2-6 in synthetic method for EXAMPLE aa2, compound aa8-5 (0.51 g) was used instead of aa2-5 to obtain compound aa8-6 (0.47 g) as a yellow amorphous solid.

Step 8-7

Synthesis of (2R)—N-[3-(aminomethyl)-4-cyanophenyl]-2-hydroxy-2-[(2R)-4-(1-methyl-2-oxoquinolin-7-yl)-3-oxomorpholin-2-yl]acetamide hydrochloride (compound aa8-7)

According to the Step 2-7 in synthetic method for EXAMPLE aa2, compound aa8-6 (0.46 g) was used instead of aa2-6 to obtain compound aa8-7 (0.35 g) as a pale yellow amorphous solid.

Step 8-8

Synthesis of (2R)-2-hydroxy-N-(1-imino-2,3-dihydroisoindol-5-yl)-2-[(2R)-4-(1-methyl-2-oxoquinolin-7-yl)-3-oxomorpholin-2-yl]acetamide hydrochloride (EXAMPLE aa8)

According to the Step 2-8 in synthetic method for EXAMPLE aa2, compound aa8-7 (0.34 g) was used instead of aa2-7 to obtain EXAMPLE aa8 (0.33 g) as a pale yellow amorphous solid.

Example aa9

Synthesis of (2R)-2-[(2R)-4-[1-(cyclopropylmethyl)-2-oxoquinolin-7-yl]-3-oxomorpholin-2-yl]-2-hydroxy-N-(1-imino-2,3-dihydroisoindol-5-yl)acetamide hydrochloride (EXAMPLE aa9)

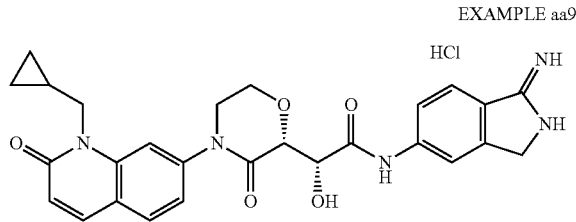 [SMILES: N=C1NCc2cc(NC(=O)[C@H](O)[C@H]3OCCN(c4ccc5ccc(=O)n(CC6CC6)c5c4)C3=O)ccc21 ; Cl]

EXAMPLE aa9

Step 9-1

Synthesis of 1-(cyclopropylmethyl)-7-iodoquinolin-2-one (compound aa9-1)

According to the Step 8-1 in synthetic method for EXAMPLE aa8, (bromomethyl)cyclopropane (1.00 g) was used instead of iodomethane to obtain compound aa9-1 (0.48 g) as a colorless amorphous solid.

Step 9-2

Synthesis of tert-butyl (2R)-2-[(2R)-4-[1-(cyclopropylmethyl)-2-oxoquinolin-7-yl]-3-oxomorpholin-2-yl]-2-hydroxyacetate (compound aa9-2)

According to the Step 2-2 in synthetic method for EXAMPLE aa2, compound aa9-1 (0.47 g) was used instead of aa2-1 to obtain compound aa9-2 (0.34 g) as a colorless amorphous solid.

Step 9-3

Synthesis of tert-butyl (2R)-2-acetyloxy-2-[(2R)-4-[1-(cyclopropylmethyl)-2-oxoquinolin-7-yl]-3-oxomorpholin-2-yl]acetate (compound aa9-3)

According to the Step 2-3 in synthetic method for EXAMPLE aa2, compound aa9-2 (0.34 g) was used instead of aa2-2 to obtain compound aa9-3 (0.37 g) as a colorless amorphous solid.

Step 9-4

Synthesis of (2R)-2-acetyloxy-2-[(2R)-4-[1-(cyclopropylmethyl)-2-oxoquinolin-7-yl]-3-oxomorpholin-2-yl]acetic acid (compound aa9-4)

According to the Step 2-4 in synthetic method for EXAMPLE aa2, compound aa9-3 (0.36 g) was used instead of aa2-3 to obtain compound aa9-4 (0.32 g) as a colorless amorphous solid.

Step 9-5

Synthesis of [(1R)-2-[3-[[bis[(2-methylpropan-2-yl)oxycarbonyl]amino]-methyl]-4-cyanoanilino]-1-[(2R)-4-[1-(cyclopropylmethyl)-2-oxoquinolin-7-yl]-3-oxo morpholin-2-yl]-2-oxoethyl]acetate (compound aa9-5)

According to the Step 2-5 in synthetic method for EXAMPLE aa2, compound aa9-4 (0.32 g) was used instead of aa2-4 to obtain compound aa9-5 (0.42 g) as a colorless amorphous solid.

Step 9-6

Synthesis of tert-butyl N-[[2-cyano-5-[[(2R)-2-[(2R)-4-[1-(cyclopropylmethyl)-2-oxoquinolin-7-yl]-3-oxomorpholin-2-yl]-2-hydroxyacetyl]amino]phenyl]methyl]-N-[(2-methylpropan-2-yl)oxycarbonyl]carbamate (compound aa9-6)

According to the Step 2-6 in synthetic method for EXAMPLE aa2, compound aa9-5 (0.41 g) was used instead of aa2-5 to obtain compound aa9-6 (0.38 g) as a colorless amorphous solid.

Step 9-7

Synthesis of (2R)—N-[3-(aminomethyl)-4-cyanophenyl]-2-[(2R)-4-[1-(cyclopropylmethyl)-2-oxoquinolin-7-yl]-3-oxomorpholin-2-yl]-2-hydroxyacetamide hydrochloride (compound aa9-7)

According to the Step 2-7 in synthetic method for EXAMPLE aa2, compound aa9-6 (0.39 g) was used instead of aa2-6 to obtain compound aa9-7 (0.30 g) as a colorless amorphous solid.

Step 9-8

Synthesis of (2R)-2-[(2R)-4-[1-(cyclopropylmethyl)-2-oxoquinolin-7-yl]-3-oxomorpholin-2-yl]-2-hydroxy-N-(1-imino-2,3-dihydroisoindol-5-yl)acetamide hydrochloride (EXAMPLE aa9)

According to the Step 2-8 in synthetic method for EXAMPLE aa2, compound aa9-7 (0.30 g) was used instead of aa2-7 to obtain EXAMPLE aa9 (0.24 g) as a yellow amorphous solid.

Example aa10

Synthesis of methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetate hydrochloride (EXAMPLE aa10)

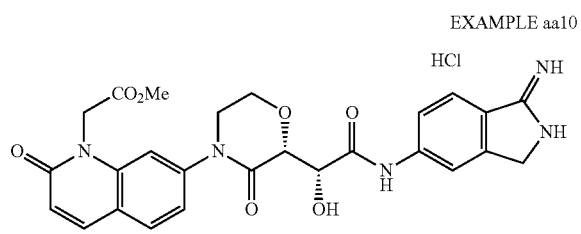 [SMILES: Cl ; COC(=O)Cn1c(=O)ccc2ccc(N3CCO[C@H]([C@@H](O)C(=O)Nc4ccc5c(c4)CNC5=N)C3=O)cc21]

EXAMPLE aa10

Step 10-1

Synthesis of methyl 2-(7-iodo-2-oxoquinolin-1-yl)acetate (compound aa10-1)

According to the Step 8-1 in synthetic method for EXAMPLE aa8, methyl bromoacetate (1.75 ml) was used instead of iodomethane to obtain compound aa10-1 (1.76 g) as a pale yellow amorphous solid.

Step 10-2

Synthesis of tert-butyl (2R)-2-hydroxy-2-[(2R)-4-[1-(2-methoxy-2-oxoethyl)-2-oxoquinolin-7-yl]-3-oxomorpholin-2-yl]acetate (compound aa10-2)

According to the Step 2-2 in synthetic method for EXAMPLE aa2, compound aa10-1 (1.69 g) was used instead of aa2-1 to obtain compound aa10-2 (1.52 g) as a yellow amorphous solid.

Step 10-3

Synthesis of tert-butyl (2R)-2-acetyloxy-2-[(2R)-4-[1-(2-methoxy-2-oxoethyl)-2-oxoquinolin-7-yl]-3-oxomorpholin-2-yl]acetate (compound aa10-3)

According to the Step 2-3 in synthetic method for EXAMPLE aa2, compound aa10-2 (1.50 g) was used instead of aa2-2 to obtain compound aa10-3 (1.77 g) as a pale yellow amorphous.

Step 10-4

Synthesis of (2R)-2-acetyloxy-2-[(2R)-4-[1-(2-methoxy-2-oxoethyl)-2-oxoquinolin-7-yl]-3-oxomorpholin-2-yl]acetic acid (compound aa10-4)

According to the Step 2-4 in synthetic method for EXAMPLE aa2, compound aa10-3 (1.63 g) was used instead of aa2-3 to obtain compound aa10-4 (1.69 g) as a pale yellow amorphous.

Step 10-5

Synthesis of methyl 2-[7-[(2R)-2-[(1R)-1-acetyloxy-2-[3-[[bis[(2-methylpropan-2-yl)oxycarbonyl]amino]methyl]-4-cyanoanilino]-2-oxoethyl]-3-oxomorpholin-4-yl]-2-oxoquinolin-1-yl]acetate (compound aa10-5)

According to the Step 2-5 in synthetic method for EXAMPLE aa2, compound aa10-4 (1.00 g) was used instead of aa2-4 to obtain compound aa10-5 (1.13 g) as a pale yellow amorphous.

Step 10-6

Synthesis of methyl 2-[7-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-2-oxoquinolin-1-yl]acetate (compound aa10-6)

To a solution of compound aa10-5 (0.4 g) in MeOH (5.3 mL), was added 28% NaOMe in MeOH (0.13 mL) at 0° C. The reaction mixture was stirred at 0° C. for 15 min. Then water was added into the mixture and it was extracted with EtOAc. The organic layer was washed with brine, dried over anhydrous $Na_2SO_4$. The solvent was removed under reduced pressure to obtain compound aa10-6 (0.34 g) as a pale yellow amorphous solid. It was used to the next step without further purification.

Step 10-7

Synthesis of methyl 2-[7-[(2R)-2-[(1R)-2-[3-(aminomethyl)-4-cyanoanilino]-1-hydroxy-2-oxoethyl]-3-oxomorpholin-4-yl]-2-oxoquinolin-1-yl]acetate hydrochloride (compound aa10-7)

According to the Step 2-7 in synthetic method for EXAMPLE aa2, compound aa10-6 (0.32 g) was used instead of aa2-6 to obtain compound aa10-7 (0.22 g) as a pale yellow amorphous solid.

Step 10-8

Synthesis of methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetate hydrochloride (EXAMPLE aa10)

According to the Step 2-8 in synthetic method for EXAMPLE aa2, compound aa10-7 (0.21 g) was used instead of aa2-7 to obtain EXAMPLE aa10 (0.20 g) as a pale yellow amorphous solid.

Example aa11

Synthesis of 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetic acid hydrochloride (EXAMPLE aa11)

EXAMPLE aa11

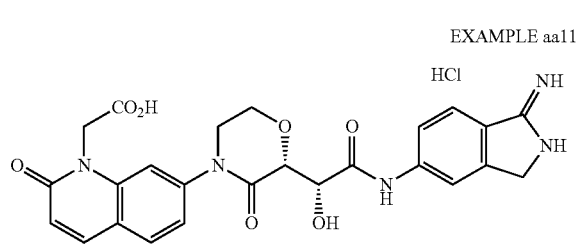 [SMILES: Cl ; N=C1NCc2cc(NC(=O)[C@H](O)[C@H]3OCCN(c4ccc5ccc(=O)n(CC(=O)O)c5c4)C3=O)ccc21]

Step 11-1

Synthesis of 2-[7-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-2-oxoquinolin-1-yl]acetic acid (compound aa11-1)

To a solution of compound aa10-5 (0.4 g) in MeOH (5 mL), was added 1N NaOH (5 mL) at 0° C. The reaction mixture was stirred at room temperature for 35 min. Then water and 1N HCl were added into the mixture and it was extracted with EtOAc. The organic layer was washed with brine, dried over anhydrous $Na_2SO_4$. The solvent was removed under reduced pressure. The resulting residue was purified by silica gel column chromatography ($CH_2Cl_2$/MeOH=95/5) to obtain compound aa11-1 (0.18 g) as a white amorphous solid.

Step 11-2

Synthesis of 2-[7-[(2R)-2-[(1R)-2-[3-(aminomethyl)-4-cyanoanilino]-1-hydroxy-2-oxoethyl]-3-oxomorpholin-4-yl]-2-oxoquinolin-1-yl]acetic acid hydrochloride (compound aa11-2)

According to the Step 2-7 in synthetic method for EXAMPLE aa2, compound aa11-1 (0.18 g) was used instead of aa2-6 to obtain compound aa11-2 (0.13 g) as a white amorphous solid.

Step 11-3

Synthesis of 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetic acid hydrochloride (EXAMPLE aa11)

According to the Step 2-8 in synthetic method for EXAMPLE aa2, compound aa11-2 (0.13 g) was used instead of aa2-7 to obtain EXAMPLE aa11 (0.11 g) as a white amorphous solid.

Example aa12

Synthesis of (2R)-2-hydroxy-N-(1-imino-2,3-dihydroisoindol-5-yl)-2-[(2R)-4-(8-methyl-2-oxo-1H-quinolin-7-yl)-3-oxomorpholin-2-yl]acetamide hydrochloride (EXAMPLE aa12)

EXAMPLE aa12

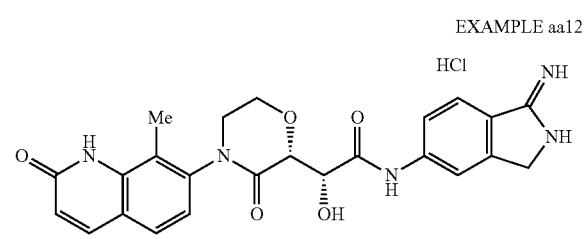 [SMILES: Cl ; Cc1c(N2CCO[C@H]([C@@H](O)C(=O)Nc3ccc4c(c3)CNC4=N)C2=O)ccc2ccc(=O)[nH]c12]

Step 12-1

Synthesis of (E)-3-ethoxy-N-(3-iodo-2-methylphenyl)prop-2-enamide (compound aa12-1)

According to the Step 4-3 in synthetic method for EXAMPLE aa4, 3-Iodo-2-methylaniline (0.50 g) was used instead of aa4-2 to obtain compound aa12-1 (0.68 g) as a brown amorphous solid.

Step 12-2

Synthesis of 7-iodo-8-methyl-1H-quinolin-2-one (compound aa12-2)

According to the Step 4-4 in synthetic method for EXAMPLE aa4, compound aa12-1 (0.68 g) was used instead of aa4-3 to obtain compound aa12-2 (0.47 g) as a pale yellow amorphous solid.

Step 12-3

Synthesis of tert-butyl (2R)-2-hydroxy-2-[(2R)-4-(8-methyl-2-oxo-1H-quinolin-7-yl)-3-oxomorpholin-2-yl]acetate (compound aa12-3)

According to the Step 2-2 in synthetic method for EXAMPLE aa2, compound aa12-2 (0.20 g) was used instead of aa2-1 to obtain compound aa12-3 (89 mg) as a pale yellow amorphous solid.

Step 12-4

Synthesis of tert-butyl (2R)-2-acetyloxy-2-[(2R)-4-(8-methyl-2-oxo-1H-quinolin-7-yl)-3-oxomorpholin-2-yl]acetate (compound aa12-4)

According to the Step 2-3 in synthetic method for EXAMPLE aa2, compound aa12-3 (1.11 g) was used instead of aa2-2 to obtain compound aa12-4 (1.23 g) as a yellow amorphous solid.

Step 12-5

Synthesis of (2R)-2-acetyloxy-2-[(2R)-4-(8-methyl-2-oxo-1H-quinolin-7-yl)-3-oxomorpholin-2-yl]acetic acid (compound aa12-5)

According to the Step 2-4 in synthetic method for EXAMPLE aa2, compound aa12-4 (1.22 g) was used instead of aa2-3 to obtain compound aa12-5 (1.39 g) as a colorless amorphous solid.

Step 12-6

Synthesis of [(1R)-2-[3-[[bis[(2-methylpropan-2-yl)oxycarbonyl]-amino]methyl]-4-cyanoanilino]-1-[(2R)-4-(8-methyl-2-oxo-1H-quinolin-7-yl)-3-oxomorpholin-2-yl]-2-oxoethyl]acetate (compound aa12-6)

According to the Step 2-5 in synthetic method for EXAMPLE aa2, compound aa12-5 (1.38 g) was used instead of aa2-4 to obtain compound aa12-6 (0.89 g) as a pale yellow amorphous solid.

Step 12-7

Synthesis of tert-butyl N-[[2-cyano-5-[[(2R)-2-hydroxy-2-[(2R)-4-(8-methyl-2-oxo-1H-quinolin-7-yl)-3-oxomorpholin-2-yl]acetyl]amino]phenyl]methyl]-N-[(2-methylpropan-2-yl)oxycarbonyl]carbamate (compound aa12-7)

According to the Step 2-6 in synthetic method for EXAMPLE aa2, compound aa12-6 (0.88 g) was used instead of aa2-5 to obtain compound aa12-7 (0.80 g) as a pale yellow amorphous solid.

Step 12-8

Synthesis of (2R)—N-[3-(aminomethyl)-4-cyanophenyl]-2-hydroxy-2-[(2R)-4-(8-methyl-2-oxo-1H-quinolin-7-yl)-3-oxomorpholin-2-yl]acetamide hydrochloride (compound aa12-8)

According to the Step 2-7 in synthetic method for EXAMPLE aa2, compound aa12-7 (0.78 g) was used instead of aa2-6 to obtain compound aa12-8 (0.57 g) as a pale yellow amorphous solid.

Step 12-9

Synthesis of (2R)-2-hydroxy-N-(1-imino-2,3-dihydroisoindol-5-yl)-2-[(2R)-4-(8-methyl-2-oxo-1H-quinolin-7-yl)-3-oxomorpholin-2-yl]acetamide hydrochloride (EXAMPLE aa12)

According to the Step 2-8 in synthetic method for EXAMPLE aa2, compound aa12-8 (0.56 g) was used instead of aa2-7 to obtain EXAMPLE aa12 (0.55 g) as a pale yellow amorphous solid.

Example aa13

Synthesis of (2R)-2-hydroxy-N-(1-imino-2,3-dihydroisoindol-5-yl)-2-[(2R)-4-(2-methoxyquinolin-7-yl)-3-oxomorpholin-2-yl]acetamide hydrochloride (EXAMPLE aa13)

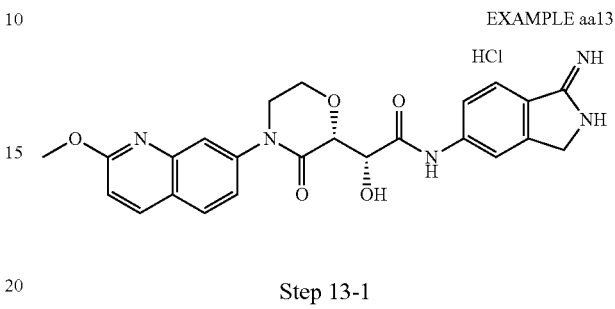

EXAMPLE aa13

Step 13-1

Synthesis of 7-iodo-2-methoxyquinoline (compound aa13-1)

To a solution of compound aa7-1 (1.00 g) in $CH_2Cl_2$ (100 mL), was added trimethyloxonium tetrafluoroborate (1.09 g) at 0° C. The reaction mixture was stirred at room temperature for 4 days. The mixture was concentrated in vacuo, then water was added to the resulting residue. The mixture was extracted with EtOAc and the organic layer was washed with brine and was dried over anhydrous $Na_2SO_4$. The solvent was removed under reduced pressure to obtain compound aa13-1 (0.95 g) as a colorless amorphous solid. It was used to the next step without further purification.

Step 13-2

Synthesis of tert-butyl (2R)-2-hydroxy-2-[(2R)-4-(2-methoxyquinolin-7-yl)-3-oxomorpholin-2-yl]acetate (compound aa13-2)

According to the Step 2-2 in synthetic method for EXAMPLE aa2, compound aa13-1 (0.93 g) was used instead of aa2-1 to obtain compound aa13-2 (0.28 g) as a colorless amorphous solid.

Step 13-3

Synthesis of tert-butyl (2R)-2-acetyloxy-2-[(2R)-4-(2-methoxyquinolin-7-yl)-3-oxomorpholin-2-yl]acetate (compound aa13-3)

According to the Step 2-3 in synthetic method for EXAMPLE aa2, compound aa13-2 (0.28 g) was used instead of aa2-2 to obtain compound aa13-3 (0.32 g) as a colorless amorphous solid.

Step 13-4

Synthesis of (2R)-2-acetyloxy-2-[(2R)-4-(2-methoxyquinolin-7-yl)-3-oxomorpholin-2-yl]acetic acid (compound aa13-4)

According to the Step 2-4 in synthetic method for EXAMPLE aa2, compound aa13-3 (0.31 g) was used instead of aa2-3 to obtain compound aa13-4 (0.27 g) as a colorless amorphous solid.

Step 13-5

Synthesis of [(1R)-2-[3-[[bis[(2-methylpropan-2-yl)oxycarbonyl]-amino]methyl]-4-cyanoanilino]-1-[(2R)-4-(2-methoxyquinolin-7-yl)-3-oxomorpholin-2-yl]-2-oxoethyl]acetate (compound aa13-5)

According to the Step 2-5 in synthetic method for EXAMPLE aa2, compound aa13-4 (0.27 g) was used instead of aa2-4 to obtain compound aa13-5 (0.33 g) as a colorless amorphous solid.

Step 13-6

Synthesis of tert-butyl N-[[2-cyano-5-[[(2R)-2-hydroxy-2-[(2R)-4-(2-methoxyquinolin-7-yl)-3-oxomorpholin-2-yl]acetyl]amino]phenyl]methyl]-N-[(2-m ethylpropan-2-yl)oxycarbonyl]carbamate (compound aa13-6)

According to the Step 2-6 in synthetic method for EXAMPLE aa2, compound aa13-5 (0.32 g) was used instead of aa2-5 to obtain compound aa13-6 (0.28 g) as a colorless amorphous solid.

Step 13-7

Synthesis of (2R)—N-[3-(aminomethyl)-4-cyanophenyl]-2-hydroxy-2-[(2R)-4-(2-methoxyquinolin-7-yl)-3-oxomorpholin-2-yl]acetamide hydrochloride (compound aa13-7)

According to the Step 2-7 in synthetic method for EXAMPLE aa2, compound aa13-6 (0.30 g) was used instead of aa2-6 to obtain compound aa13-7 (0.23 g) as a colorless amorphous solid.

Step 13-8

Synthesis of (2R)-2-hydroxy-N-(1-imino-2,3-dihydroisoindol-5-yl)-2-[(2R)-4-(2-methoxyquinolin-7-yl)-3-oxomorpholin-2-yl]acetamide hydrochloride (EXAMPLE aa13)

According to the Step 2-8 in synthetic method for EXAMPLE aa2, compound aa13-7 (0.22 g) was used instead of aa2-7 to obtain EXAMPLE aa13 (45 mg) as a yellow amorphous solid.

Example aa14

Synthesis of (2R)-2-hydroxy-N-(1-imino-2,3-dihydroisoindol-5-yl)-2-[(2R)-3-oxo-4-quinolin-7-ylmorpholin-2-yl]acetamide dihydrochloride (EXAMPLE aa14)

EXAMPLE aa14

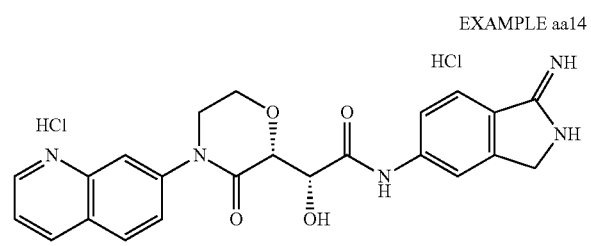 [SMILES: Cl ; N=C1NCc2cc(NC(=O)[C@H](O)[C@H]3OCCN(c4ccc5cccnc5c4)C3=O)ccc21 ; Cl]

Step 14-1

Synthesis of tert-butyl (2R)-2-hydroxy-2-[(2R)-3-oxo-4-quinolin-7-ylmorpholin-2-yl]acetate (compound aa14-1)

According to the Step 2-2 in synthetic method for EXAMPLE aa2, 7-Iodoquinoline (2.76 g) was used instead of aa2-1 to obtain compound aa14-1 (2.50 g) as a colorless amorphous solid.

Step 14-2

Synthesis of tert-butyl (2R)-2-acetyloxy-2-[(2R)-3-oxo-4-quinolin-7-ylmorpholin-2-yl]acetate (compound aa14-2)

According to the Step 2-3 in synthetic method for EXAMPLE aa2, compound aa14-1 (1.25 g) was used instead of aa2-2 to obtain compound aa14-2 (1.32 g) as a colorless amorphous solid.

Step 14-3

Synthesis of (2R)-2-acetyloxy-2-[(2R)-3-oxo-4-quinolin-7-ylmorpholin-2-yl]acetic acid trifluoroacetic acid salt (compound aa14-3)

According to the Step 2-4 in synthetic method for EXAMPLE aa2, compound aa14-2 (1.3 g) was used instead of aa2-3 to obtain compound aa14-3 (1.4 g) as a colorless amorphous solid.

Step 14-4

Synthesis of [(1R)-2-[3-[[bis[(2-methylpropan-2-yl)oxycarbonyl]amino]methyl]-4-cyanoanilino]-2-oxo-1-[(2R)-3-oxo-4-quinolin-7-ylmorpholin-2-yl]ethyl]acetate (compound aa14-4)

According to the Step 2-5 in synthetic method for EXAMPLE aa2, compound aa14-3 (0.5 g) was used instead of aa2-4 to obtain compound aa14-4 (0.64 g) as a colorless amorphous solid.

Step 14-5

Synthesis of tert-butyl N-[[2-cyano-5-[[(2R)-2-hydroxy-2-[(2R)-3-oxo-4-quinolin-7-ylmorpholin-2-yl]acetyl]amino]phenyl]methyl]-N-[(2-methylpropan-2-yl)oxycarbonyl]carbamate (compound aa14-5)

According to the Step 2-6 in synthetic method for EXAMPLE aa2, compound aa14-4 (0.63 g) was used instead of aa2-5 to obtain compound aa14-5 (0.59 g) as a colorless amorphous solid.

Step 14-6

Synthesis of (2R)—N-[3-(aminomethyl)-4-cyanophenyl]-2-hydroxy-2-[(2R)-3-oxo-4-quinolin-7-ylmorpholin-2-yl]acetamide dihydrochloride (compound aa14-6)

According to the Step 2-7 in synthetic method for EXAMPLE aa2, compound aa14-5 (0.58 g) was used instead of aa2-6 to obtain compound aa14-6 (0.46 g) as a colorless amorphous solid.

Step 14-7

Synthesis of (2R)-2-hydroxy-N-(1-imino-2,3-dihydroisoindol-5-yl)-2-[(2R)-3-oxo-4-quinolin-7-ylmorpholin-2-yl]acetamide dihydrochloride (EXAMPLE aa14)

According to the Step 2-8 in synthetic method for EXAMPLE aa2, compound aa14-6 (0.45 g) was used instead of aa2-7 to obtain EXAMPLE aa14 (0.31 g) as a yellow amorphous solid.

Example aa15

Synthesis of (2R)—N-(3-amino-1,2-benzisoxazol-6-yl)-2-hydroxy-2-[(2R)-3-oxo-4-quinolin-7-ylmorpholin-2-yl]acetamide hydrochloride (EXAMPLE aa15)

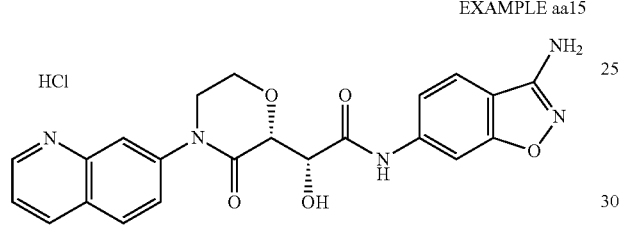

EXAMPLE aa15

Step 15-1

Synthesis of [(1R)-2-[[3-(1,3-dioxoisoindol-2-yl)-1,2-benzisoxazol-6-yl]amino]-2-oxo-1-[(2R)-3-oxo-4-quinolin-7-ylmorpholin-2-yl]ethyl]acetate (compound aa15-1)

According to the Step 2-5 in synthetic method for EXAMPLE aa2, compound aa14-3 (0.5 g) and 6-amino-3-(1,3-dioxoisoindol-2-yl)-1,2-benzisoxazole (0.61 g) were used instead of aa2-4 and tert-butyl N-(2-cyano-5-aminophenyl)methyl-N-[(2-methylpropan-2-yl)oxycarbonyl]carbamate to obtain compound 15-1 (0.42 g) as a colorless amorphous solid.

Step 15-2

Synthesis of (2R)—N-(3-amino-1,2-benzisoxazol-6-yl)-2-hydroxy-2-[(2R)-3-oxo-4-quinolin-7-ylmorpholin-2-yl]acetamide hydrochloride (EXAMPLE aa15)

To a solution of compound aa15-1 (400 mg) in $CH_2Cl_2$-MeOH (14-14 mL), was added $NH_2NH_2$—$H_2O$ (0.32 mL) at 0° C. The reaction mixture was stirred at room temperature for 3 h. The precipitate was appeared. The precipitate was collected by filtration and the filtrate was concentrated in vacuo. The resulting residue was suspended in $CH_2Cl_2$-MeOH, then the precipitate was collected by filtration and combined the first crops. Then the precipitate was solved in 10% HCl-MeOH then the solvent was removed in vacuo to obtain EXAMPLE aa15 (240 mg) as a pale yellow amorphous solid.

Example aa16

Synthesis of (2R)-2-hydroxy-N-(1-imino-2,3-dihydroisoindol-5-yl)-2-[(2R)-3-oxo-4-(2-oxo-1H-quinolin-5-yl)morpholin-2-yl]acetamide hydrochloride (EXAMPLE aa16)

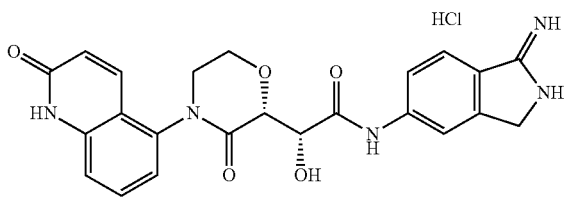

EXAMPLE aa16

Step 16-1

Synthesis of 5-iodo-1H-quinolin-2-one (compound aa16-1)

To the mixture of 5-aminoquinolin-2(1H)-one (0.1 g) in AcOH—$H_2O$ (0.73-0.3 mL), was added dropwise conc. $H_2SO_4$ (66 uL) at 0° C. Then a solution of $NaNO_2$ (86 mg) in water (0.38 mL) was added dropwise into the reaction mixture at 0° C. The mixture was stirred at 0° C. for 30 min, then a solution of KI (0.31 g) in water (0.25 mL) was added dropwise at 0° C. The reaction mixture was stirred at room temperature for 4 h. Water was added to the reaction mixture and it was extracted with EtOAc. The organic layer was washed with water, saturated $NaHCO_3$ aq. and brine, dried over anhydrous $Na_2SO_4$. The solvent was removed under reduced pressure. Trituration with $Et_2O$ followed by filtration gave a16-1 (0.14 g) as a brown amorphous solid. It was used to the next step without further purification.

Step 16-2

Synthesis of tert-butyl (2R)-2-hydroxy-2-[(2R)-3-oxo-4-(2-oxo-1H-quinolin-5-yl)morpholin-2-yl]acetate (compound aa16-2)

According to the Step 2-2 in synthetic method for EXAMPLE aa2, compound aa16-1 (1.20 g) was used instead of aa2-1 to obtain compound aa16-2 (0.48 g) as an orange amorphous solid.

Step 16-3

Synthesis of tert-butyl (2R)-2-acetyloxy-2-[(2R)-3-oxo-4-(2-oxo-1H-quinolin-5-yl)morpholin-2-yl]acetate (compound aa16-3)

According to the Step 2-3 in synthetic method for EXAMPLE aa2, compound aa16-2 (0.47 g) was used instead of aa2-2 to obtain compound aa16-3 (0.55 g) as a brown amorphous solid.

Step 16-4

Synthesis of (2R)-2-acetyloxy-2-[(2R)-3-oxo-4-(2-oxo-1H-quinolin-5-yl)morpholin-2-yl]acetic acid (compound aa16-4)

According to the Step 2-4 in synthetic method for EXAMPLE aa2, compound aa16-3 (0.51 g) was used instead of aa2-3 to obtain compound aa16-4 (0.38 g) as an orange amorphous solid.

Step 16-5

Synthesis of [(1R)-2-[3-[[bis[(2-methylpropan-2-yl)oxycarbonyl]-amino]methyl]-4-cyanoanilino]-2-oxo-1-[(2R)-3-oxo-4-(2-oxo-1H-quinolin-5-yl)morpholin-2-yl]ethyl]acetate (compound aa16-5)

According to the Step 2-5 in synthetic method for EXAMPLE aa2, compound aa16-4 (0.37 g) was used instead of aa2-4 to obtain compound aa16-5 (0.19 g) as an orange amorphous solid.

Step 16-6

Synthesis of tert-butyl N-[[2-cyano-5-[[(2R)-2-hydroxy-2-[(2R)-3-oxo-4-(2-oxo-1H-quinolin-5-yl)morpholin-2-yl]acetyl]amino]phenyl]methyl]-N-[(2-methyl propan-2-yl)oxycarbonyl]carbamate (compound aa16-6)

According to the Step 2-6 in synthetic method for EXAMPLE aa2, compound aa16-5 (0.18 g) was used instead of aa2-5 to obtain compound aa16-6 (0.16 g) as an orange amorphous solid.

Step 16-7

Synthesis of (2R)—N-[3-(aminomethyl)-4-cyanophenyl]-2-hydroxy-2-[(2R)-3-oxo-4-(2-oxo-1H-quinolin-5-yl)morpholin-2-yl]acetamide hydrochloride (compound aa16-7)

According to the Step 2-7 in synthetic method for EXAMPLE aa2, compound aa16-6 (0.15 g) was used instead of aa2-6 to obtain compound aa16-7 (0.13 g) as a pale yellow amorphous solid.

Step 16-8

Synthesis of (2R)-2-hydroxy-N-(1-imino-2,3-dihydroisoindol-5-yl)-2-[(2R)-3-oxo-4-(2-oxo-1H-quinolin-5-yl)morpholin-2-yl]acetamide hydrochloride (EXAMPLE aa16)

According to the Step 2-8 in synthetic method for EXAMPLE aa2, compound aa16-7 (0.12 g) was used instead of aa2-7 to obtain EXAMPLE aa16 (0.10 g) as a pale yellow amorphous solid.

Example aa17

Synthesis of (2R)-2-hydroxy-N-(1-imino-2,3-dihydroisoindol-5-yl)-2-[(2R)-3-oxo-4-(1-oxo-3,4-dihydro-2H-isoquinolin-6-yl)morpholin-2-yl]acetamide hydrochloride (EXAMPLE aa17)

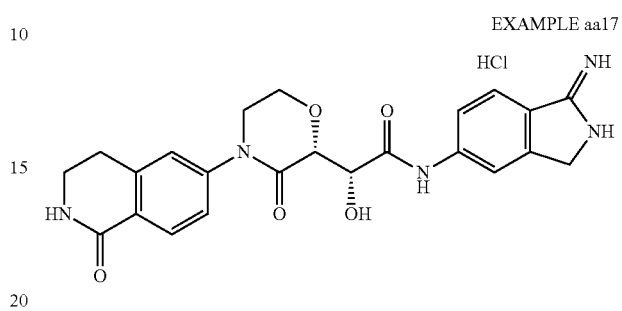

EXAMPLE aa17

Step 17-1

Synthesis of tert-butyl (2R)-2-hydroxy-2-[(2R)-3-oxo-4-(1-oxo-3,4-dihydro-2H-isoquinolin-6-yl)morpholin-2-yl]acetate (compound aa17-1)

According to the Step 2-2 in synthetic method for EXAMPLE aa2, 6-bromo-3,4-dihydroisoquinolin-1(2H)-one (500 mg) was used instead of aa2-1 to obtain compound aa17-1 (288 mg) as a yellow amorphous solid (contained diastereomer).

Step 17-2

Synthesis of tert-butyl (2R)-2-acetyloxy-2-[(2R)-3-oxo-4-(1-oxo-3,4-dihydro-2H-isoquinolin-6-yl)morpholin-2-yl]acetate (compound aa17-2)

According to the Step 2-3 in synthetic method for EXAMPLE aa2, compound aa17-1 (231 mg) was used instead of aa2-2 to obtain compound aa17-2 (313 g) as a white amorphous solid (contained diastereomer).

Step 17-3

Synthesis of (2R)-2-acetyloxy-2-[(2R)-3-oxo-4-(1-oxo-3,4-dihydro-2H-isoquinolin-6-yl)morpholin-2-yl]acetic acid (compound aa17-3)

According to the Step 2-4 in synthetic method for EXAMPLE aa2, compound aa17-2 (270 mg) was used instead of aa2-3 to obtain compound aa17-3 (254 mg) as a white amorphous solid (contained diastereomer).

Step 17-4

Synthesis of [(1R)-2-[3-[[bis[(2-methylpropan-2-yl)oxycarbonyl]-amino]methyl]-4-cyanoanilino]-2-oxo-1-[(2R)-3-oxo-4-(1-oxo-3,4-dihydro-2H-isoquinolin-6-yl)morpholin-2-yl]ethyl]acetate (compound aa17-4)

According to the Step 2-5 in synthetic method for EXAMPLE aa2, compound aa17-3 (250 mg) was used instead of aa2-4 to obtain compound aa17-4 (120 mg) as a white amorphous solid.

Step 17-5

Synthesis of tert-butyl N-[[2-cyano-5-[[(2R)-2-hydroxy-2-[(2R)-3-oxo-4-(1-oxo-3,4-dihydro-2H-isoquinolin-6-yl)morpholin-2-yl]acetyl]amino]phenyl]methyl]-N-[(2-methylpropan-2-yl)oxycarbonyl]carbamate (compound aa17-5)

According to the Step 2-6 in synthetic method for EXAMPLE aa2, compound aa17-4 (98 mg) was used instead of aa2-5 to obtain compound aa17-5 (83 mg) as a white amorphous solid.

Step 17-6

Synthesis of (2R)—N-[3-(aminomethyl)-4-cyanophenyl]-2-hydroxy-2-[(2R)-3-oxo-4-(1-oxo-3,4-dihydro-2H-isoquinolin-6-yl)morpholin-2-yl]acetamide hydrochloride (compound aa17-6)

According to the Step 2-7 in synthetic method for EXAMPLE aa2, compound aa17-5 (79 mg) was used instead of aa2-6 to obtain compound aa17-6 (75 mg) as a white amorphous solid.

Step 17-7

Synthesis of (2R)-2-hydroxy-N-(1-imino-2,3-dihydroisoindol-5-yl)-2-[(2R)-3-oxo-4-(1-oxo-3,4-dihydro-2H-isoquinolin-6-yl)morpholin-2-yl]acetamide hydrochloride (EXAMPLE aa17)

According to the Step 2-8 in synthetic method for EXAMPLE aa2, compound aa17-6 (55 mg) was used instead of aa2-7 to obtain EXAMPLE aa17 (47 mg) as a white amorphous solid.

Example aa18

Synthesis of (2R)-2-hydroxy-N-(1-imino-2,3-dihydroisoindol-5-yl)-2-[(2R)-3-oxo-4-(2-oxo-3,4-dihydro-1H-quinolin-7-yl)morpholin-2-yl]acetamide hydrochloride (EXAMPLE aa18)

EXAMPLE aa18

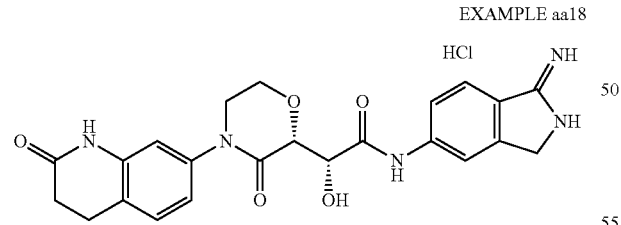

Step 18-1

Synthesis of tert-butyl (2R)-2-hydroxy-2-[(2R)-3-oxo-4-(2-oxo-3,4-dihydro-1H-quinolin-7-yl)morpholin-2-yl]acetate (compound aa18-1)

According to the Step 2-2 in synthetic method for EXAMPLE aa2, 3,4-dihydro-7-iodo-2(1H)-quinolinone (3.40 g) was used instead of aa2-1 to obtain compound aa18-1 (0.59 g) as a brown amorphous solid.

Step 18-2

Synthesis of tert-butyl (2R)-2-acetyloxy-2-[(2R)-3-oxo-4-(2-oxo-3,4-dihydro-1H-quinolin-7-yl)morpholin-2-yl]acetate (compound aa18-2)

According to the Step 2-3 in synthetic method for EXAMPLE aa2, compound aa18-1 (0.57 g) was used instead of aa2-2 to obtain compound aa18-2 (0.59 g) as a white amorphous solid.

Step 18-3

Synthesis of (2R)-2-acetyloxy-2-[(2R)-3-oxo-4-(2-oxo-3,4-dihydro-1H-quinolin-7-yl)morpholin-2-yl]acetic acid (compound aa18-3)

According to the Step 2-4 in synthetic method for EXAMPLE aa2, compound aa18-2 (0.28 g) was used instead of aa2-3 to obtain compound aa18-3 (0.21 g) as a white amorphous solid.

Step 18-4

Synthesis of [(1R)-2-[3-[[bis[(2-methylpropan-2-yl)oxycarbonyl]-amino]methyl]-4-cyanoanilino]-2-oxo-1-[(2R)-3-oxo-4-(2-oxo-3,4-dihydro-1H-quinolin-7-yl)morpholin-2-yl]ethyl]acetate (compound aa18-4)

According to the Step 2-5 in synthetic method for EXAMPLE aa2, compound aa18-3 (75 mg) was used instead of aa2-4 to obtain compound aa18-4 (62 mg) as a white amorphous solid.

Step 18-5

Synthesis of tert-butyl N-[[2-cyano-5-[[(2R)-2-hydroxy-2-[(2R)-3-oxo-4-(2-oxo-3,4-dihydro-1H-quinolin-7-yl)morpholin-2-yl]acetyl]amino]phenyl]methyl]-N-[(2-methylpropan-2-yl)oxycarbonyl]carbamate (compound aa18-5)

According to the Step 2-6 in synthetic method for EXAMPLE aa2, compound aa18-4 (52 mg) was used instead of aa2-5 to obtain compound aa18-5 (47 mg) as a white amorphous solid.

Step 18-6

Synthesis of (2R)—N-[3-(aminomethyl)-4-cyanophenyl]-2-hydroxy-2-[(2R)-3-oxo-4-(2-oxo-3,4-dihydro-1H-quinolin-7-yl)morpholin-2-yl]acetamide hydrochloride (compound aa18-6)

According to the Step 2-7 in synthetic method for EXAMPLE aa2, compound aa18-5 (44 mg) was used instead of aa2-6 to obtain compound aa18-6 (33 mg) as a white amorphous solid.

Step 18-7

Synthesis of (2R)-2-hydroxy-N-(1-imino-2,3-dihydroisoindol-5-yl)-2-[(2R)-3-oxo-4-(2-oxo-3,4-dihydro-1H-quinolin-7-yl)morpholin-2-yl]acetamide hydrochloride (EXAMPLE aa18)

According to the Step 2-8 in synthetic method for EXAMPLE aa2, compound aa18-6 (31 g) was used instead of aa2-7 to obtain EXAMPLE aa18 (26 g) as a white amorphous solid.

Example aa19

Synthesis of (2R)-2-hydroxy-N-(1-imino-2,3-dihydroisoindol-5-yl)-2-[(2R)-4-(1-methyl-2-oxo-3,4-dihydroquinolin-7-yl)-3-oxomorpholin-2-yl]acetamide hydrochloride (EXAMPLE aa19)

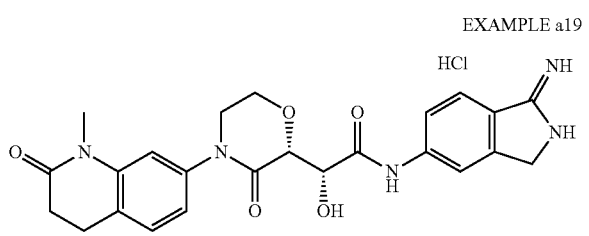 [SMILES: Cl ; CN1C(=O)CCc2ccc(N3CCO[C@H]([C@@H](O)C(=O)Nc4ccc5c(c4)CNC5=N)C3=O)cc21]

EXAMPLE a19

Step 19-1

Synthesis of 7-iodo-1-methyl-3,4-dihydroquinolin-2-one (compound aa19-1)

According to the Step 8-1 in synthetic method for EXAMPLE aa8, 3,4-dihydro-7-iodo-2(1H)-quinolinone (1.50 g) was used instead of aa7-1 to obtain compound aa19-1 (1.23 g) as a pale yellow amorphous solid.

Step 19-2

Synthesis of tert-butyl (2R)-2-hydroxy-2-[(2R)-4-(1-methyl-2-oxo-3,4-dihydroquinolin-7-yl)-3-oxomorpholin-2-yl]acetate (compound aa19-2)

According to the Step 2-2 in synthetic method for EXAMPLE aa2, compound aa19-1 (1.22 g) was used instead of aa2-1 to obtain compound aa19-2 (0.95 g) as a pale yellow amorphous solid.

Step 19-3

Synthesis of tert-butyl (2R)-2-acetyloxy-2-[(2R)-4-(1-methyl-2-oxo-3,4-dihydroquinolin-7-yl)-3-oxomorpholin-2-yl]acetate (compound aa19-3)

According to the Step 2-3 in synthetic method for EXAMPLE aa2, compound aa19-2 (0.60 g) was used instead of aa2-2 to obtain compound aa19-3 (0.68 g) as a pale yellow amorphous solid.

Step 19-4

Synthesis of (2R)-2-acetyloxy-2-[(2R)-4-(1-methyl-2-oxo-3,4-dihydroquinolin-7-yl)-3-oxomorpholin-2-yl]acetic acid (compound aa19-4)

According to the Step 2-4 in synthetic method for EXAMPLE aa2, compound aa19-3 (0.65 g) was used instead of aa2-3 to obtain compound aa19-4 (0.74 g) as a pale brown amorphous solid.

Step 19-5

Synthesis of [(1R)-2-[3-[[bis[(2-methylpropan-2-yl)oxycarbonyl]-amino]methyl]-4-cyanoanilino]-1-[(2R)-4-(1-methyl-2-oxo-3,4-dihydroquinolin-7-yl)-3-oxomorpholin-2-yl]-2-oxoethyl]acetate (compound aa19-5)

According to the Step 2-5 in synthetic method for EXAMPLE aa2, compound aa19-4 (0.56 g) was used instead of aa2-4 to obtain compound aa19-5 (0.78 g) as a white amorphous solid.

Step 19-6

Synthesis of tert-butyl N-[[2-cyano-5-[[(2R)-2-hydroxy-2-[(2R)-4-(1-methyl-2-oxo-3,4-dihydroquinolin-7-yl)-3-oxomorpholin-2-yl]acetyl]amino]phenyl]methyl]-N-[(2-methylpropan-2-yl)oxycarbonyl]carbamate (compound aa19-6)

According to the Step 2-6 in synthetic method for EXAMPLE aa2, compound aa19-5 (0.75 g) was used instead of aa2-5 to obtain compound aa19-6 (0.69 g) as a white amorphous solid.

Step 19-7

Synthesis of (2R)—N-[3-(aminomethyl)-4-cyanophenyl]-2-hydroxy-2-[(2R)-4-(1-methyl-2-oxo-3,4-dihydroquinolin-7-yl)-3-oxomorpholin-2-yl]acetamide hydrochloride (compound aa19-7)

According to the Step 2-7 in synthetic method for EXAMPLE aa2, compound aa19-6 (0.67 g) was used instead of aa2-6 to obtain compound aa19-7 (0.50 g) as a white amorphous solid.

Step 19-8

Synthesis of (2R)-2-hydroxy-N-(1-imino-2,3-dihydroisoindol-5-yl)-2-[(2R)-4-(1-methyl-2-oxo-3,4-dihydroquinolin-7-yl)-3-oxomorpholin-2-yl]acetamide hydrochloride (EXAMPLE aa19)

According to the Step 2-8 in synthetic method for EXAMPLE aa2, compound aa19-7 (0.49 g) was used instead of aa2-7 to obtain EXAMPLE aa19 (0.35 g) as a white amorphous solid.

Example aa20

Synthesis of (2R)-2-[(2R)-4-[1-(cyclopropylmethyl)-2-oxo-3,4-dihydroquinolin-7-yl]-3-oxomorpholin-2-yl]-2-hydroxy-N-(1-imino-2,3-dihydroisoindol-5-yl)acetamide hydrochloride (EXAMPLE aa20)

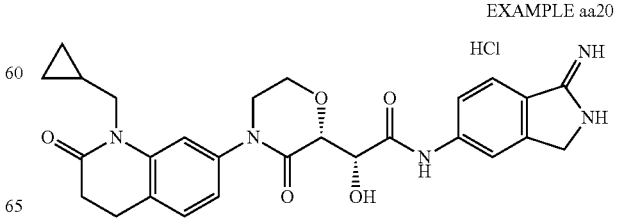

EXAMPLE aa20

Step 20-1

Synthesis of 1-(cyclopropylmethyl)-7-iodo-3,4-dihydroquinolin-2-one (compound aa20-1)

According to the Step 8-1 in synthetic method for EXAMPLE aa8, 3,4-dihydro-7-iodo-2(1H)-quinolinone (1.50 g) and cyclopropylmethyl bromide (0.80 mL) were used instead of a7-1 and MeI to obtain compound aa20-1 (1.23 g) as a pale red amorphous solid.

Step 20-2

Synthesis of tert-butyl (2R)-2-[(2R)-4-[1-(cyclopropylmethyl)-2-oxo-3,4-dihydroquinolin-7-yl]-3-oxomorpholin-2-yl]-2-hydroxyacetate (compound aa20-2)

According to the Step 2-2 in synthetic method for EXAMPLE aa2, compound aa20-1 (1.22 g) was used instead of aa2-1 to obtain compound aa20-2 (1.16 g) as a pale brown amorphous solid.

Step 20-3

Synthesis of tert-butyl (2R)-2-acetyloxy-2-[(2R)-4-[1-(cyclopropylmethyl)-2-oxo-3,4-dihydroquinolin-7-yl]-3-oxomorpholin-2-yl]acetate (compound aa20-3)

According to the Step 2-3 in synthetic method for EXAMPLE aa2, compound aa20-2 (0.60 g) was used instead of aa2-2 to obtain compound aa20-3 (0.65 g) as a pale yellow amorphous solid.

Step 20-4

Synthesis of (2R)-2-acetyloxy-2-[(2R)-4-[1-(cyclopropylmethyl)-2-oxo-3,4-dihydroquinolin-7-yl]-3-oxomorpholin-2-yl]acetic acid (compound aa20-4)

According to the Step 2-4 in synthetic method for EXAMPLE aa2, compound aa20-3 (0.64 g) was used instead of aa2-3 to obtain compound aa20-4 (0.70 g) as a pale brown amorphous solid.

Step 20-5

Synthesis of [(1R)-2-[3-[[bis[(2-methylpropan-2-yl)oxycarbonyl]amino]methyl]-4-cyanoanilino]-1-[(2R)-4-[1-(cyclopropylmethyl)-2-oxo-3,4-dihydroquinolin-7-yl]-3-oxomorpholin-2-yl]-2-oxoethyl]acetate (compound aa20-5)

According to the Step 2-5 in synthetic method for EXAMPLE aa2, compound aa20-4 (0.55 g) was used instead of aa2-4 to obtain compound aa20-5 (0.67 g) as a white amorphous solid.

Step 20-6

Synthesis of tert-butyl N-[[2-cyano-5-[[(2R)-2-[(2R)-4-[1-(cyclopropylmethyl)-2-oxo-3,4-dihydroquinolin-7-yl]-3-oxomorpholin-2-yl]-2-hydroxy acetyl]amino]phenyl]methyl]-N-[(2-methylpropan-2-yl)oxycarbonyl]carbamate (compound aa20-6)

According to the Step 2-6 in synthetic method for EXAMPLE aa2, compound aa20-5 (0.66 g) was used instead of aa2-5 to obtain compound aa20-6 (0.62 g) as a white amorphous solid.

Step 20-7

Synthesis of (2R)—N-[3-(aminomethyl)-4-cyanophenyl]-2-[(2R)-4-[1-(cyclopropylmethyl)-2-oxo-3,4-dihydroquinolin-7-yl]-3-oxomorpholin-2-yl]-2-hydr oxyacetamide hydrochloride (compound aa20-7)

According to the Step 2-7 in synthetic method for EXAMPLE aa2, compound aa20-6 (0.61 g) was used instead of aa2-6 to obtain compound aa20-7 (0.47 g) as a white amorphous solid.

Step 20-8

Synthesis of (2R)-2-[(2R)-4-[1-(cyclopropylmethyl)-2-oxo-3,4-dihydroquinolin-7-yl]-3-oxomorpholin-2-yl]-2-hydroxy-N-(1-imino-2,3-dihydroisoindol-5-yl)acetamide hydrochloride (EXAMPLE aa20)

According to the Step 2-8 in synthetic method for EXAMPLE aa2, compound aa20-7 (0.46 g) was used instead of aa2-7 to obtain EXAMPLE aa20 (0.43 g) as a white amorphous solid.

Example aa21

Synthesis of methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetate hydrochloride (EXAMPLE a21)

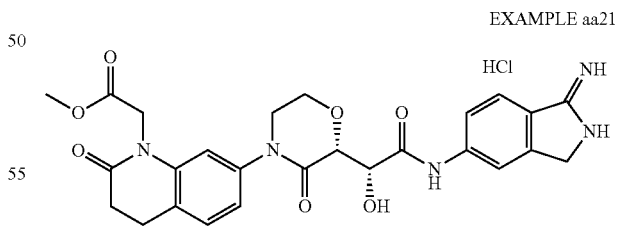

EXAMPLE aa21

Step 21-1

Synthesis of methyl 2-(7-iodo-2-oxo-3,4-dihydroquinolin-1-yl)acetate (compound aa21-1)

According to the Step 8-1 in synthetic method for EXAMPLE aa8, 3,4-dihydro-7-iodo-2(1H)-quinolinone (2.12 g) and bromoacetic acid methyl ester (1.10 mL) were used instead of aa7-1 and MeI to obtain compound aa21-1 (2.24 g) as a white amorphous solid.

Step 21-2

Synthesis of tert-butyl (2R)-2-hydroxy-2-[(2R)-4-[1-(2-methoxy-2-oxoethyl)-2-oxo-3,4-dihydroquinolin-7-yl]-3-oxomorpholin-2-yl]acetate (compound aa21-2)

According to the Step 2-2 in synthetic method for EXAMPLE aa2, compound aa21-1 (2.23 g) was used instead of aa2-1 to obtain compound aa21-2 (2.27 g) as a pale brown amorphous solid.

Step 21-3

Synthesis of tert-butyl (2R)-2-acetyloxy-2-[(2R)-4-[1-(2-methoxy-2-oxoethyl)-2-oxo-3,4-dihydroquinolin-7-yl]-3-oxomorpholin-2-yl]acetate (compound aa21-3)

According to the Step 2-3 in synthetic method for EXAMPLE aa2, compound aa21-2 (2.27 g) was used instead of aa2-2 to obtain compound aa21-3 (2.17 g) as a pale yellow amorphous solid.

Step 21-4

Synthesis of (2R)-2-acetyloxy-2-[(2R)-4-[1-(2-methoxy-2-oxoethyl)-2-oxo-3,4-dihydroquinolin-7-yl]-3-oxomorpholin-2-yl]acetic acid (compound aa21-4)

According to the Step 2-4 in synthetic method for EXAMPLE aa2, compound aa21-3 (2.15 g) was used instead of aa2-3 to obtain compound aa21-4 (2.11 g) as a white amorphous.

Step 21-5

Synthesis of methyl 2-[7-[(2R)-2-[(1R)-1-acetyloxy-2-[3-[[bis[(2-methylpropan-2-yl)oxycarbonyl]amino]methyl]-4-cyanoanilino]-2-oxoethyl]-3-oxomorpholin-4-yl]-2-oxo-3,4-dihydroquinolin-1-yl]acetate (compound aa21-5)

According to the Step 2-5 in synthetic method for EXAMPLE aa2, compound aa21-4 (1.90 g) was used instead of aa2-4 to obtain compound aa21-5 (2.44 g) as a white amorphous solid.

Step 21-6

Synthesis of methyl 2-[7-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-2-oxo-3,4-dihydroquinolin-1-yl]acetate (compound a21-6)

According to the Step 10-6 in synthetic method for EXAMPLE aa10, compound aa21-5 (0.54 g) was used instead of aa10-5 to obtain compound aa21-6 (0.50 g) as a white amorphous solid.

Step 21-7

Synthesis of methyl 2-[7-[(2R)-2-[(1R)-2-[3-(aminomethyl)-4-cyanoanilino]-1-hydroxy-2-oxoethyl]-3-oxomorpholin-4-yl]-2-oxo-3,4-dihydroquinolin-1-yl]acetate hydrochloride (compound aa21-7)

According to the Step 2-7 in synthetic method for EXAMPLE aa2, compound aa21-6 (0.40 g) was used instead of aa2-6 to obtain compound aa21-7 (0.29 g) as a white amorphous solid.

Step 21-8

Synthesis of methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetate hydrochloride (EXAMPLE aa21)

According to the Step 2-8 in synthetic method for EXAMPLE aa2, compound aa21-7 (0.28 g) was used instead of aa2-7 to obtain EXAMPLE aa21 (0.12 g) as a white amorphous solid.

Example aa22

Synthesis of 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetic acid hydrochloride (EXAMPLE aa22)

EXAMPLE aa22

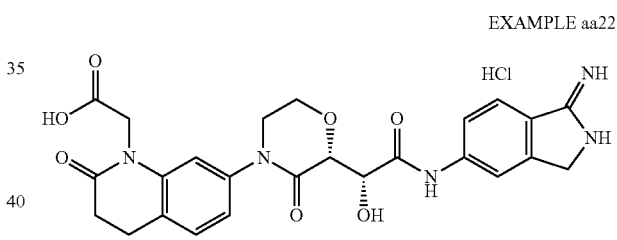

Step 22-1

Synthesis of 2-[7-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-2-oxo-3,4-dihydroquinolin-1-yl]acetic acid (compound aa22-1)

According to the Step 11-1 in synthetic method for EXAMPLE aa11, compound aa21-5 (1.20 g) was used instead of aa10-5 to obtain compound aa22-1 (0.99 g) as a pale yellow amorphous solid.

Step 22-2

Synthesis of 2-[7-[(2R)-2-[(1R)-2-[3-(aminomethyl)-4-cyanoanilino]-1-hydroxy-2-oxoethyl]-3-oxomorpholin-4-yl]-2-oxo-3,4-dihydroquinolin-1-yl]acetic acid hydrochloride (compound aa22-2)

According to the Step 2-7 in synthetic method for EXAMPLE aa2, compound aa22-1 (0.40 g) was used instead of aa2-6 to obtain compound aa22-2 (0.30 g) as a white amorphous solid.

Step 22-3

Synthesis of 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetic acid hydrochloride (EXAMPLE aa22)

According to the Step 2-8 in synthetic method for EXAMPLE aa2, compound aa22-2 (0.29 g) was used instead of aa2-7 to obtain EXAMPLE aa22 (0.19 g) as a white amorphous solid.

Example aa23

Synthesis of (2R)—N-(4-carbamimidoyl-3-fluorophenyl)-2-hydroxy-2-[(2R)-3-oxo-4-(2-oxo-3,4-dihydro-1H-quinolin-7-yl)morpholin-2-yl]acetamide hydrochloride (EXAMPLE aa23)

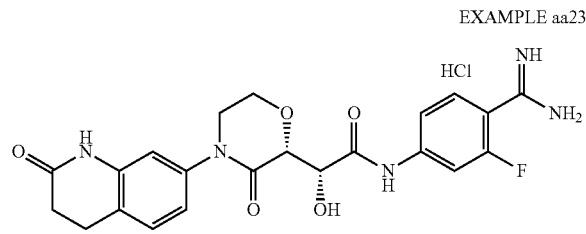 [SMILES: N=C(N)c1ccc(NC(=O)[C@H](O)[C@H]2OCCN(c3ccc4c(c3)NC(=O)CC4)C2=O)cc1F ; Cl]

EXAMPLE aa23

Step 23-1

Synthesis of [(1R)-2-[3-fluoro-4-(5-oxo-2H-1,2,4-oxadiazol-3-yl)anilino]-2-oxo-1-[(2R)-3-oxo-4-(2-oxo-1H-quinolin-7-yl)morpholin-2-yl]ethyl]acetate (compound aa23-1)

According to the Step 5-1 in synthetic method for EXAMPLE aa5, aa7-4 (0.20 g) was used instead of aa3-3 to obtain compound aa23-1 (0.12 g) as a beige amorphous solid.

Step 23-2

Synthesis of (2R)—N-[3-fluoro-4-(5-oxo-2H-1,2,4-oxadiazol-3-yl)phenyl]-2-hydroxy-2-[(2R)-3-oxo-4-(2-oxo-1H-quinolin-7-yl)morpholin-2-yl]acetamide ammonium salt (compound aa23-2)

According to the Step 2-6 in synthetic method for EXAMPLE aa2, compound aa23-1 (0.18 g) was used instead of aa2-5 to obtain compound aa23-2 (0.12 g) as a beige amorphous solid.

Step 23-3

Synthesis of (2R)—N-(4-carbamimidoyl-3-fluorophenyl)-2-hydroxy-2-[(2R)-3-oxo-4-(2-oxo-3,4-dihydro-1H-quinolin-7-yl)morpholin-2-yl]acetamide hydrochloride (EXAMPLE aa23)

According to the Step 5-3 in synthetic method for EXAMPLE aa5, compound aa23-2 (0.12 g) was used instead of aa5-2 to obtain EXAMPLE aa23 (88 mg) as a beige amorphous solid.

Example aa24

Synthesis of (2R)—N-(3-amino-1,2-benzoxazol-6-yl)-2-hydroxy-2-[(2R)-3-oxo-4-(2-oxo-3,4-dihydro-1H-quinolin-7-yl)morpholin-2-yl]acetamide (EXAMPLE aa24)

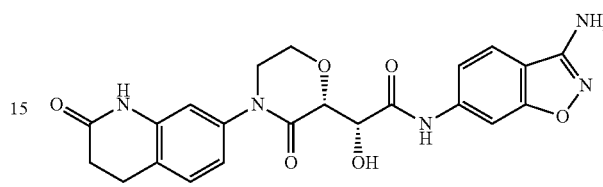

EXAMPLE aa24

Step 24-1

Synthesis of [(1R)-2-[[3-(1,3-dioxoisoindol-2-yl)-1,2-benzisoxazol-6-yl]-amino]-2-oxo-1-[(2R)-3-oxo-4-(2-oxo-3,4-dihydro-1H-quinolin-7-yl)morpholin-2-yl]ethyl]acetate (compound aa24-1)

According to the Step 2-5 in synthetic method for EXAMPLE aa2, compound aa18-3 (0.50 g) and 6-amino-3-(1,3-dioxoisoindol-2-yl)-1,2-benzisoxazole (0.50 g) were used instead of aa2-4 and tert-butyl N-(2-cyano-5-aminophenyl)methyl-N-[(2-methylpropan-2-yl)oxycarbonyl]carbamate to obtain compound aa24-1 (0.40 g) as a pale yellow amorphous solid.

Step 24-2

Synthesis of (2R)—N-(3-amino-1,2-benzisoxazol-6-yl)-2-hydroxy-2-[(2R)-3-oxo-4-(2-oxo-3,4-dihydro-1H-quinolin-7-yl)morpholin-2-yl]acetamide (EXAMPLE aa24)

According to the Step 15-2 in synthetic method for EXAMPLE aa15, compound aa24-1 (0.35 g) was used instead of aa15-1 to obtain EXAMPLE aa24 (0.27 g) as a colorless amorphous solid.

Example aa25

Synthesis of (2R)—N-(1-aminoisoquinolin-6-yl)-2-hydroxy-2-[(2R)-3-oxo-4-(2-oxo-3,4-dihydro-1H-quinolin-7-yl)morpholin-2-yl]acetamide hydrochloride (EXAMPLE aa25)

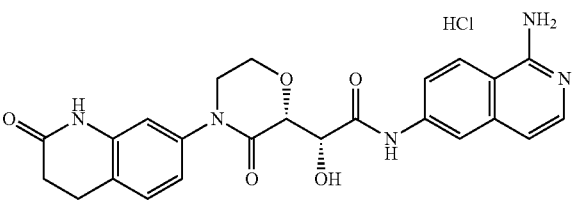

EXAMPLE aa25

Step 25-1

Synthesis of [(1R)-2-[[1-[bis[(2-methylpropan-2-yl)oxycarbonyl]-amino]isoquinolin-6-yl]amino]-2-oxo-1-[(2R)-3-oxo-4-(2-oxo-3,4-dihydro-1H-quinolin-7-yl)morpholin-2-yl]ethyl]acetate (compound aa25-1)

According to the Step 2-5 in synthetic method for EXAMPLE aa2, compound aa18-3 (0.50 g), 6-amino-1-bis(tert-butoxycarbonyl)aminoisoquinoline (0.5 g), (1-cyano-2-ethoxy-2-oxoethylidenaminooxy)dimethylamino-morpholino-carbenium hexafluorophosphate (COMU: 1.18 g) and diisopropylethylamine (0.96 mL) were used instead of 2-4, N-[(5-Amino-2-cyanophenyl)methyl]-N-[(2-methylpropan-2-yl)oxycarbonyl]carbamate, WSC—HCl, and DMAP to obtain compound aa25-1 (0.49 g) as a brown amorphous solid.

Step 25-2

Synthesis of tert-butyl N-[6-[[(2R)-2-hydroxy-2-[(2R)-3-oxo-4-(2-oxo-3,4-dihydro-1H-quinolin-7-yl)morpholin-2-yl]acetyl]amino]isoquinolin-1-yl]-N-[(2-methyl propan-2-yl)oxycarbonyl]carbamate (compound aa25-2)

According to the Step 2-6 in synthetic method for EXAMPLE aa2, compound aa25-1 (0.47 g) was used instead of aa2-5 to obtain compound aa25-2 (0.43 g) as a pale yellow amorphous solid.

Step 25-3

Synthesis of (2R)—N-(1-aminoisoquinolin-6-yl)-2-hydroxy-2-[(2R)-3-oxo-4-(2-oxo-3,4-dihydro-1H-quinolin-7-yl)morpholin-2-yl]acetamide hydrochloride (EXAMPLE aa25)

According to the Step 2-7 in synthetic method for EXAMPLE aa2, compound aa25-2 (0.41 g) was used instead of aa2-6 to obtain EXAMPLE aa25 (0.25 g) as a pale brown amorphous solid.

Example aa26

Synthesis of (2R)—N-(4-aminoquinazolin-7-yl)-2-hydroxy-2-[(2R)-3-oxo-4-(2-oxo-3,4-dihydro-1H-quinolin-7-yl)morpholin-2-yl]acetamide (EXAMPLE aa26)

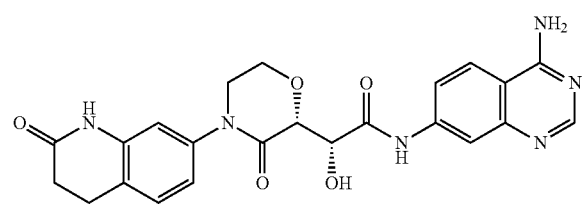

EXAMPLE aa26

Step 26-1

Synthesis of [(1R)-2-[[4-[(2-methylpropan-2-yl)oxycarbonylamino]-quinazolin-7-yl]amino]-2-oxo-1-[(2R)-3-oxo-4-(2-oxo-3,4-dihydro-1H-quinolin-7-yl)morpholin-2-yl]ethyl]acetate (compound aa26-1)

According to the Step 2-5 in synthetic method for EXAMPLE aa2, compound aa18-3 (0.50 g), 7-amino-4-(tert-butoxycarbonyl)aminoquinazoline (0.36 g), O-(7-azabenzotriazol-1-yl)-N,N,N',N'-tetramethyluronium hexafluorophosphate (HATU: 1.05 g) and diisopropylethylamine (0.96 mL) were used instead of 2-4, N-[(5-amino-2-cyanophenyl)methyl]-N-[(2-methylpropan-2-yl)oxycarbonyl]carbamate, WSC—HCl, and DMAP to obtain compound aa26-1 (0.21 g) as a pale yellow amorphous solid.

Step 26-2

Synthesis of tert-butyl N-[7-[[(2R)-2-hydroxy-2-[(2R)-3-oxo-4-(2-oxo-3,4-dihydro-1H-quinolin-7-yl)morpholin-2-yl]acetyl]amino]quinazolin-4-yl]carbamate (compound aa26-2)

According to the Step 2-6 in synthetic method for EXAMPLE aa2, compound aa26-1 (0.21 g) was used instead of aa2-5 to obtain compound aa26-2 (0.19 g) as a white amorphous solid.

Step 26-3

Synthesis of (2R)—N-(4-aminoquinazolin-7-yl)-2-hydroxy-2-[(2R)-3-oxo-4-(2-oxo-3,4-dihydro-1H-quinolin-7-yl)morpholin-2-yl]acetamide (EXAMPLE aa26)

According to the Step 2-7 in synthetic method for EXAMPLE aa2, compound aa26-2 (0.18 g) was used instead of aa2-6 to obtain EXAMPLE aa26 (20 mg) as a pale brown amorphous solid.

Example aa27

Synthesis of (2R)-2-hydroxy-N-(1-imino-2,3-dihydroisoindol-5-yl)-2-[(2R)-3-oxo-4-(2-oxo-3,4-dihydro-1H-quinolin-5-yl)morpholin-2-yl]acetamide hydrochloride (EXAMPLE aa27)

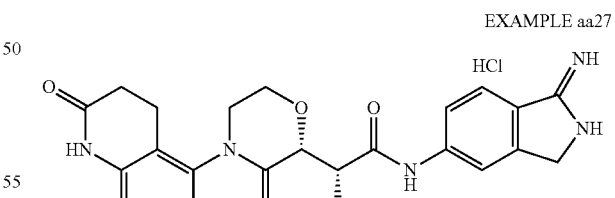

EXAMPLE aa27

Step 27-1

Synthesis of tert-butyl (2R)-2-hydroxy-2-[3-oxo-4-(2-oxo-3,4-dihydro-1H-quinolin-5-yl)morpholin-2-yl]acetate (compound aa27-1)

According to the Step 2-2 in synthetic method for EXAMPLE aa2, 5-bromo-3,4-dihydroquinolin-2(1H)-one (2.0 g) was used instead of aa2-1 to obtain compound aa27-1 (0.34 g) as a white amorphous solid (contained diastereomer).

Step 27-2

Synthesis of tert-butyl (2R)-2-acetyloxy-2-[3-oxo-4-(2-oxo-3,4-dihydro-1H-quinolin-5-yl)morpholin-2-yl]acetate (compound aa27-2)

According to the Step 2-3 in synthetic method for EXAMPLE aa2, compound aa27-1 (0.30 g) was used instead of aa2-2 to obtain compound aa27-2 (0.32 g) as a white amorphous solid (contained diastereomer).

Step 27-3

Synthesis of (2R)-2-acetyloxy-2-[3-oxo-4-(2-oxo-3,4-dihydro-1H-quinolin-5-yl)morpholin-2-yl]acetic acid (compound aa27-3)

According to the Step 2-4 in synthetic method for EXAMPLE aa2, compound aa27-2 (0.30 g) was used instead of aa2-3 to obtain compound aa27-3 (0.24 g) as a white amorphous solid (contained diastereomer).

Step 27-4

Synthesis of tert-butyl N-[[2-cyano-5-[[(2R)-2-hydroxy-2-[(2R)-3-oxo-4-(2-oxo-3,4-dihydro-1H-quinolin-5-yl)morpholin-2-yl]acetyl]amino]phenyl]methyl]-N-[(2-methylpropan-2-yl)oxycarbonyl]carbamate (compound aa27-4)

According to the Step 2-5 and 2-6 in synthetic method for EXAMPLE aa2, compound aa27-3 (0.24 g) was used instead of aa2-4 to obtain compound aa27-4 (38 mg) as a white amorphous solid.

Step 27-5

Synthesis of (2R)—N-[3-(aminomethyl)-4-cyanophenyl]-2-hydroxy-2-[(2R)-3-oxo-4-(2-oxo-3,4-dihydro-1H-quinolin-5-yl)morpholin-2-yl]acetamide hydrochloride (compound aa27-5)

According to the Step 2-7 in synthetic method for EXAMPLE aa2, compound aa27-4 (36 mg) was used instead of aa2-6 to obtain compound aa27-5 (33 mg) as a white amorphous solid.

Step 27-6

Synthesis of (2R)-2-hydroxy-N-(1-imino-2,3-dihydroisoindol-5-yl)-2-[(2R)-3-oxo-4-(2-oxo-3,4-dihydro-1H-quinolin-5-yl)morpholin-2-yl]acetamide hydrochloride (EXAMPLE aa27)

According to the Step 2-8 in synthetic method for EXAMPLE aa2, compound aa27-5 (30 mg) was used instead of aa2-7 to obtain EXAMPLE aa27 (22 mg) as a white amorphous solid.

Example aa28

Synthesis of (2R)-2-hydroxy-2-[(2R)-4-[2-(3-hydroxy-3-methylbutoxy)phenyl]-3-oxomorpholin-2-yl]-N-(1-imino-2,3-dihydroisoindol-5-yl)acetamide hydrochloride (EXAMPLE aa28)

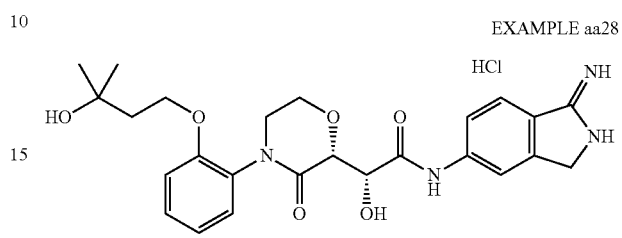

EXAMPLE aa28

Step 28-1

Synthesis of 4-(2-iodophenoxy)-2-methylbutan-2-ol (compound aa28-1)

A mixture of 2-iodophenol (6 g), 3-hydroxy-3-methylbutyl tosylate (7.4 g) and $Cs_2CO_3$ (13.3 g) in DMF (120 mL) was stirred at 0° C. for 2 h and at room temperature for 10 h. The mixture was diluted with EtOAc and washed with 1N HCl, saturated $NaHCO_3$ aq., $H_2O$, and brine, and dried over anhydrous $Na_2SO_4$. The solvent was removed under reduced pressure. The resulting residue was purified by silica gel column chromatography (Hexane/EtOAc=7/3) to obtain compound aa28-1 (8.02 g) as pale yellow oil.

Step 28-2

Synthesis of tert-butyl (2R)-2-hydroxy-2-[(2R)-4-[2-(3-hydroxy-3-methylbutoxy)phenyl]-3-oxomorpholin-2-yl]acetate (compound aa28-2)

According to the Step 2-2 in synthetic method for EXAMPLE aa2, compound aa28-1 (2.20 g) was used instead of aa2-1 to obtain compound aa28-2 (1.69 g) as a pale brown amorphous solid.

Step 28-3

Synthesis of tert-butyl (2R)-2-acetyloxy-2-[(2R)-4-[2-(3-hydroxy-3-methylbutoxy)phenyl]-3-oxomorpholin-2-yl]acetate (compound aa28-3)

According to the Step 2-3 in synthetic method for EXAMPLE aa2, compound aa28-2 (1.60 g) was used instead of aa2-2 to obtain compound aa28-3 (1.72 g) as a white amorphous solid.

Step 28-4

Synthesis of (2R)-2-acetyloxy-2-[(2R)-4-[2-(3-hydroxy-3-methylbutoxy)phenyl]-3-oxomorpholin-2-yl]acetic acid (compound aa28-4)

According to the Step 2-4 in synthetic method for EXAMPLE aa2, compound aa28-3 (0.85 g) was used instead of aa2-3 to obtain compound aa28-4 (0.85 g) as a white amorphous solid.

Step 28-5

Synthesis of [(1R)-2-[3-[[bis[(2-methylpropan-2-yl)oxycarbonyl]-amino]methyl]-4-cyanoanilino]-1-[(2R)-4-[2-(3-hydroxy-3-methylbutoxy)phenyl]-3-oxomorpholin-2-yl]-2-oxoethyl]acetate (compound aa28-5)

According to the Step 2-5 in synthetic method for EXAMPLE aa2, compound aa28-4 (0.40 g) was used instead of aa2-4 to obtain compound aa28-5 (0.33 g) as a white amorphous solid.

Step 28-6

Synthesis of tert-butyl N-[[2-cyano-5-[[(2R)-2-hydroxy-2-[(2R)-4-[2-(3-hydroxy-3-methylbutoxy)phenyl]-3-oxomorpholin-2-yl]acetyl]amino]phenyl]methyl]-N-[(2-methylpropan-2-yl)oxycarbonyl]carbamate (compound aa28-6)

According to the Step 2-6 in synthetic method for EXAMPLE aa2, compound aa28-5 (0.30 g) was used instead of aa2-5 to obtain compound aa28-6 (87 mg) as a white amorphous solid.

Step 28-7

Synthesis of (2R)—N-[3-(aminomethyl)-4-cyanophenyl]-2-hydroxy-2-[(2R)-4-[2-(3-hydroxy-3-methylbutoxy)phenyl]-3-oxomorpholin-2-yl]acetamide hydrochloride (compound aa28-7)

According to the Step 2-7 in synthetic method for EXAMPLE aa2, compound aa28-6 (83 mg) was used instead of aa2-6 to obtain compound aa28-7 (63 mg) as a white amorphous solid.

Step 28-8

Synthesis of (2R)-2-hydroxy-2-[(2R)-4-[2-(3-hydroxy-3-methylbutoxy)phenyl]-3-oxomorpholin-2-yl]-N-(1-imino-2,3-dihydroisoindol-5-yl)acetamide hydrochloride (EXAMPLE aa28)

According to the Step 2-8 in synthetic method for EXAMPLE aa2, compound aa28-7 (61 mg) was used instead of aa2-7 to obtain EXAMPLE aa28 (24 mg) as a white amorphous solid.

Example aa29

Synthesis of (2R)-2-hydroxy-N-(1-imino-2,3-dihydroisoindol-5-yl)-2-[(2R)-4-[2-(3-methoxy-3-methylbutoxy)phenyl]-3-oxomorpholin-2-yl]acetamide hydrochloride (EXAMPLE aa29)

EXAMPLE aa29

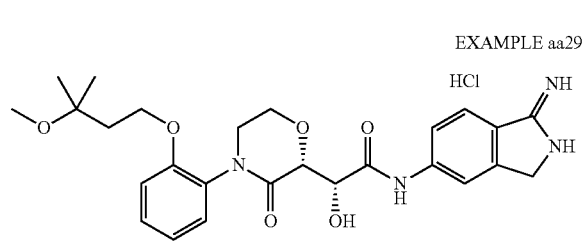 [SMILES: COC(C)(C)CCOc1ccccc1N1CCO[C@H]([C@@H](O)C(=O)Nc2ccc3c(c2)CNC3=N)C1=O ; Cl]

Step 29-1

Synthesis of 1-iodo-2-(3-methoxy-3-methylbutoxy)benzene (compound aa29-1)

According to the Step 28-1 in synthetic method for EXAMPLE aa28, 3-methoxy-3-methylbutyl p-toluenesulfonate (6.50 g) was used instead of 3-hydroxy-3-methylbutyl p-toluenesulfonate to obtain compound aa29-1 (5.77 g) as colorless oil.

Step 29-2

Synthesis of tert-butyl (2R)-2-hydroxy-2-[(2R)-4-[2-(3-methoxy-3-methylbutoxy)phenyl]-3-oxomorpholin-2-yl]acetate (compound aa29-2)

According to the Step 2-2 in synthetic method for EXAMPLE aa2, compound aa29-1 (4.00 g) was used instead of aa2-1 to obtain compound aa29-2 (2.43 g) as pale yellow oil.

Step 29-3

Synthesis of tert-butyl (2R)-2-acetyloxy-2-[(2R)-4-[2-(3-methoxy-3-methylbutoxy)phenyl]-3-oxomorpholin-2-yl]acetate (compound aa29-3)

According to the Step 2-3 in synthetic method for EXAMPLE aa2, compound aa29-2 (2.42 g) was used instead of aa2-2 to obtain compound aa29-3 (2.61 g) as a white amorphous solid.

Step 29-4

Synthesis of (2R)-2-acetyloxy-2-[(2R)-4-[2-(3-methoxy-3-methylbutoxy)phenyl]-3-oxomorpholin-2-yl]acetic acid (compound aa29-4)

According to the Step 2-4 in synthetic method for EXAMPLE aa2, compound aa29-3 (2.50 g) was used instead of aa2-3 to obtain compound aa29-4 (2.78 g) as pale brown oil.

Step 29-5

Synthesis of [(1R)-2-[3-[[bis[(2-methylpropan-2-yl)oxycarbonyl]amino]methyl]-4-cyanoanilino]-1-[(2R)-4-[2-(3-methoxy-3-methylbutoxy)phenyl]-3-oxomorpholin-2-yl]-2-oxoethyl]acetate (compound aa29-5)

According to the Step 2-5 in synthetic method for EXAMPLE aa2, compound aa29-4 (1.00 g) was used instead of aa2-4 to obtain compound aa29-5 (0.96 g) as a white amorphous solid.

Step 29-6

Synthesis of tert-butyl N-[[2-cyano-5-[[(2R)-2-hydroxy-2-[(2R)-4-[2-(3-methoxy-3-methylbutoxy)phenyl]-3-oxomorpholin-2-yl]acetyl]amino]phenyl]methyl]-N-[(2-methylpropan-2-yl)oxycarbonyl]carbamate (compound aa29-6)

According to the Step 2-6 in synthetic method for EXAMPLE aa2, compound aa29-5 (0.70 g) was used instead of aa2-5 to obtain compound aa29-6 (0.64 g) as a white amorphous solid.

Step 29-7

Synthesis of (2R)—N-[3-(aminomethyl)-4-cyanophenyl]-2-hydroxy-2-[(2R)-4-[2-(3-methoxy-3-methylbutoxy)phenyl]-3-oxomorpholin-2-yl]acetamide hydrochloride (compound aa29-7)

According to the Step 2-7 in synthetic method for EXAMPLE aa2, compound aa29-6 (0.62 g) was used instead of aa2-6 to obtain compound aa29-7 (0.45 g) as a cream amorphous solid.

Step 29-8

Synthesis of (2R)-2-hydroxy-N-(1-imino-2,3-dihydroisoindol-5-yl)-2-[(2R)-4-[2-(3-methoxy-3-methylbutoxy)phenyl]-3-oxomorpholin-2-yl]acetamide hydrochloride (EXAMPLE aa29)

According to the Step 2-8 in synthetic method for EXAMPLE aa2, compound aa29-7 (0.25 g) was used instead of aa2-7 to obtain EXAMPLE aa29 (0.21 g) as a white amorphous solid.

Example aa30

Synthesis of (2R)-2-hydroxy-N-(1-imino-2,3-dihydroisoindol-5-yl)-2-[(2R)-3-oxo-4-[2-(2-oxopiperidin-1-yl)phenyl]morpholin-2-yl]acetamide hydrochloride (EXAMPLE aa30)

EXAMPLE aa30

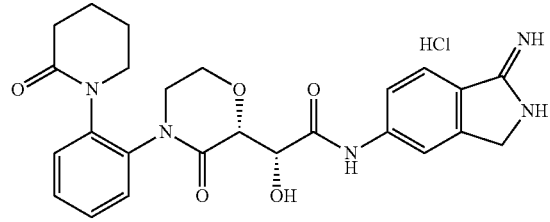

Step 30-1

Synthesis of tert-butyl (2R)-2-hydroxy-2-[(2R)-3-oxo-4-[2-(2-oxopiperidin-1-yl)phenyl]morpholin-2-yl]acetate (compound aa30-1)

According to the Step 2-2 in synthetic method for EXAMPLE aa2, 1-(2-iodophenyl)-2-piperidinone (2.73 g) was used instead of aa2-1 to obtain compound aa30-1 (0.85 g) as a brown amorphous solid.

Step 30-2

Synthesis of tert-butyl (2R)-2-acetyloxy-2-[(2R)-3-oxo-4-[2-(2-oxopiperidin-1-yl)phenyl]morpholin-2-yl]acetate (compound aa30-2)

According to the Step 2-3 in synthetic method for EXAMPLE aa2, compound aa30-1 (0.85 g) was used instead of aa2-2 to obtain compound aa30-2 (0.80 g) as a pale yellow amorphous solid.

Step 30-3

Synthesis of (2R)-2-acetyloxy-2-[(2R)-3-oxo-4-[2-(2-oxopiperidin-1-yl)phenyl]morpholin-2-yl]acetic acid (compound aa30-3)

According to the Step 2-4 in synthetic method for EXAMPLE aa2, compound aa30-2 (0.79 g) was used instead of aa2-3 to obtain compound aa30-3 (0.58 g) as a colorless amorphous solid.

Step 30-4

Synthesis of [(1R)-2-[3-[[bis[(2-methylpropan-2-yl)oxycarbonyl]-amino]methyl]-4-cyanoanilino]-2-oxo-1-[(2R)-3-oxo-4-[2-(2-oxopiperidin-1-yl)phenyl]morpholin-2-yl]ethyl]acetate (compound aa30-4)

According to the Step 2-5 in synthetic method for EXAMPLE aa2, compound aa30-3 (0.30 g) was used instead of aa2-4 to obtain compound aa30-4 (0.16 g) as a pale yellow amorphous solid.

Step 30-5

Synthesis of tert-butyl N-[[2-cyano-5-[[(2R)-2-hydroxy-2-[(2R)-3-oxo-4-[2-(2-oxopiperidin-1-yl)phenyl]morpholin-2-yl]acetyl]amino]phenyl]methyl]-N-[(2-methylpropan-2-yl)oxycarbonyl]carbamate (compound aa30-5)

According to the Step 2-6 in synthetic method for EXAMPLE aa2, compound aa30-4 (0.15 g) was used instead of aa2-5 to obtain compound aa30-5 (0.14 g) as pale yellow oil.

Step 30-6

Synthesis of (2R)—N-[3-(aminomethyl)-4-cyanophenyl]-2-hydroxy-2-[(2R)-3-oxo-4-[2-(2-oxopiperidin-1-yl)phenyl]morpholin-2-yl]acetamide hydrochloride (compound aa30-6)

According to the Step 2-7 in synthetic method for EXAMPLE aa2, compound aa30-5 (0.14 g) was used instead of aa2-6 to obtain compound aa30-6 (78 mg) as a colorless amorphous solid.

Step 30-7

Synthesis of (2R)-2-hydroxy-N-(1-imino-2,3-dihydroisoindol-5-yl)-2-[(2R)-3-oxo-4-[2-(2-oxopiperidin-1-yl)phenyl]morpholin-2-yl]acetamide hydrochloride (EXAMPLE aa30)

According to the Step 2-8 in synthetic method for EXAMPLE aa2, compound aa30-6 (78 mg) was used instead of aa2-7 to obtain EXAMPLE aa30 (72 mg) as a colorless amorphous solid.

Example aa31

Synthesis of (2R)-2-[(2R)-4-[2-(difluoromethoxy)-5-fluorophenyl]-3-oxomorpholin-2-yl]-2-hydroxy-N-(1-imino-2,3-dihydroisoindol-5-yl)acetamide hydrochloride (EXAMPLE aa31)

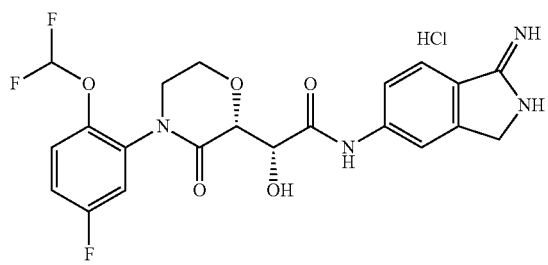

EXAMPLE aa31

Step 31-1

Synthesis of 2-bromo-1-(difluoromethoxy)-4-fluorobenzene (compound aa31-1)

According to the Step 4-1 in synthetic method for EXAMPLE aa4, 2-bromo-4-fluorophenol (5.0 g) was used instead of 2-iodo-5-nitrophenol to obtain compound aa31-1 (5.25 g) as a red amorphous solid.

Step 31-2

Synthesis of tert-butyl (2R)-2-[(2R)-4-[2-(difluoromethoxy)-5-fluorophenyl]-3-oxomorpholin-2-yl]-2-hydroxyacetate (compound aa31-2)

According to the Step 2-2 in synthetic method for EXAMPLE aa2, compound aa31-1 (2.08 g) was used instead of aa2-1 to obtain compound aa31-2 (0.75 g) as pale yellow oil.

Step 31-3

Synthesis of tert-butyl (2R)-2-acetyloxy-2-[(2R)-4-[2-(difluoromethoxy)-5-fluorophenyl]-3-oxomorpholin-2-yl]acetate (compound aa31-3)

According to the Step 2-3 in synthetic method for EXAMPLE aa2, compound aa31-2 (0.74 g) was used instead of aa2-2 to obtain compound aa31-3 (0.82 g) as pale yellow oil.

Step 31-4

Synthesis of (2R)-2-acetyloxy-2-[(2R)-4-[2-(difluoromethoxy)-5-fluorophenyl]-3-oxomorpholin-2-yl]acetic acid (compound aa31-4)

According to the Step 2-4 in synthetic method for EXAMPLE aa2, compound aa31-3 (0.80 g) was used instead of aa2-3 to obtain compound aa31-4 (0.56 g) as a colorless amorphous solid.

Step 31-5

Synthesis of [(1R)-2-[3-[[bis[(2-methylpropan-2-yl)oxycarbonyl]-amino]methyl]-4-cyanoanilino]-1-[(2R)-4-[2-(difluoromethoxy)-5-fluorophenyl]-3-oxomorpholin-2-yl]-2-oxoethyl]acetate (compound aa31-5)

According to the Step 2-5 in synthetic method for EXAMPLE aa2, compound aa31-4 (0.20 g) was used instead of aa2-4 to obtain compound aa31-5 (0.19 g) as a colorless amorphous solid.

Step 31-6

Synthesis of tert-butyl N-[[2-cyano-5-[[(2R)-2-[(2R)-4-[2-(difluoromethoxy)-5-fluorophenyl]-3-oxomorpholin-2-yl]-2-hydroxyacetyl]amino]phenyl]methyl]-N-[(2-methylpropan-2-yl)oxycarbonyl]carbamate (compound aa31-6)

According to the Step 2-6 in synthetic method for EXAMPLE aa2, compound aa31-5 (0.18 g) was used instead of aa2-5 to obtain compound aa31-6 (0.11 g) as colorless oil.

Step 31-7

Synthesis of (2R)—N-[3-(aminomethyl)-4-cyanophenyl]-2-[(2R)-4-[2-(difluoromethoxy)-5-fluorophenyl]-3-oxomorpholin-2-yl]-2-hydroxyacetamide hydrochloride (compound aa31-7)

According to the Step 2-7 in synthetic method for EXAMPLE a2, compound aa31-6 (95 mg) was used instead of aa2-6 to obtain compound aa31-7 (70 mg) as a pale yellow amorphous solid.

Step 31-8

Synthesis of (2R)-2-[(2R)-4-[2-(difluoromethoxy)-5-fluorophenyl]-3-oxomorpholin-2-yl]-2-hydroxy-N-(1-imino-2,3-dihydroisoindol-5-yl)acetamide hydrochloride (EXAMPLE aa31)

According to the Step 2-8 in synthetic method for EXAMPLE aa2, compound aa31-7 (70 mg) was used instead of aa2-7 to obtain EXAMPLE aa31 (57 mg) as a pale yellow amorphous solid.

Example aa32

Synthesis of methyl 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoate hydrochloride (EXAMPLE aa32)

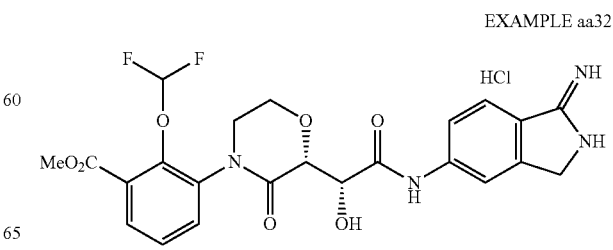

EXAMPLE aa32

Step 32-1

Synthesis of methyl 2-(difluoromethoxy)-3-nitrobenzoate (compound aa32-1)

According to the Step 4-1 in synthetic method for EXAMPLE aa4, 2-hydroxy-3-nitrobenzoic acid methyl ester (18.3 g) was used instead of 2-iodo-5-nitrophenol to obtain compound aa32-1 (3.70 g) as a colorless amorphous solid.

Step 32-2

Synthesis of methyl 3-amino-2-(difluoromethoxy)benzoate (compound aa32-2)

According to the Step 5-3 in synthetic method for EXAMPLE aa5, compound aa32-1 (3.75 g) was used instead of aa5-2 to obtain compound aa32-2 (3.17 g) as colorless amorphous solid.

Step 32-3

Synthesis of methyl 2-(difluoromethoxy)-3-iodobenzoate (compound aa32-3)

According to the Step 16-1 in synthetic method for EXAMPLE aa16, compound aa32-2 (2.87 g) was used instead of 5-Aminoquinolin-2(1H)-one to obtain compound aa32-3 (3.99 g) as a yellow amorphous solid.

Step 32-4

Synthesis of methyl 2-(difluoromethoxy)-3-[(2R)-2-[(1R)-1-hydroxy-2-[(2-methylpropan-2-yl)oxy]-2-oxoethyl]-3-oxomorpholin-4-yl]benzoate (compound aa32-4)

According to the Step 2-2 in synthetic method for EXAMPLE aa2, compound aa32-3 (3.98 g) was used instead of aa2-1 to obtain compound aa32-4 (1.21 g) as a yellow amorphous solid.

Step 32-5

Synthesis of methyl 3-[(2R)-2-[(1R)-1-acetyloxy-2-[(2-methylpropan-2-yl)oxy]-2-oxoethyl]-3-oxomorpholin-4-yl]-2-(difluoromethoxy)benzoate (compound aa32-5)

According to the Step 2-3 in synthetic method for EXAMPLE aa2, compound aa32-4 (1.20 g) was used instead of aa2-2 to obtain compound aa32-5 (1.32 g) as a yellow amorphous solid.

Step 32-6

Synthesis of (2R)-2-acetyloxy-2-[(2R)-4-[2-(difluoromethoxy)-3-methoxycarbonylphenyl]-3-oxomorpholin-2-yl]acetic acid (compound aa32-6)

According to the Step 2-4 in synthetic method for EXAMPLE aa2, compound aa32-5 (1.32 g) was used instead of aa2-3 to obtain compound aa32-6 (1.16 g) as a pink amorphous solid.

Step 32-7

Synthesis of methyl 3-[(2R)-2-[(1R)-1-acetyloxy-2-[3-[[bis[(2-methylpropan-2-yl)oxycarbonyl]amino]methyl]-4-cyanoanilino]-2-oxoethyl]-3-oxomorpholin-4-yl]-2-(difluoromethoxy)benzoate (compound aa32-7)

According to the Step 2-5 in synthetic method for EXAMPLE aa2, compound aa32-6 (0.93 g) was used instead of aa2-4 to obtain compound aa32-7 (0.60 g) as a colorless amorphous solid.

Step 32-8

Synthesis of methyl 3-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-2-(difluoromethoxy)benzoate (compound aa32-8)

According to the Step 10-6 in synthetic method for EXAMPLE aa10, compound aa32-7 (0.12 g) was used instead of aa10-5 to obtain compound aa32-8 (0.11 g) as a colorless amorphous solid.

Step 32-9

Synthesis of methyl 3-[(2R)-2-[(1R)-2-[3-(aminomethyl)-4-cyanoanilino]-1-hydroxy-2-oxoethyl]-3-oxomorpholin-4-yl]-2-(difluoromethoxy)benzoate hydrochloride (compound aa32-9)

According to the Step 2-7 in synthetic method for EXAMPLE aa2, compound aa32-8 (0.10 g) was used instead of aa2-6 to obtain compound aa32-9 (70 mg) as a yellow amorphous solid.

Step 32-10

Synthesis of methyl 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoate hydrochloride (EXAMPLE aa32)

According to the Step 2-8 in synthetic method for EXAMPLE aa2, compound aa32-9 (70 mg) was used instead of aa2-7 to obtain EXAMPLE aa32 (57 mg) as a yellow amorphous solid.

Example aa33

Synthesis of 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoic acid hydrochloride (EXAMPLE aa33)

EXAMPLE aa33

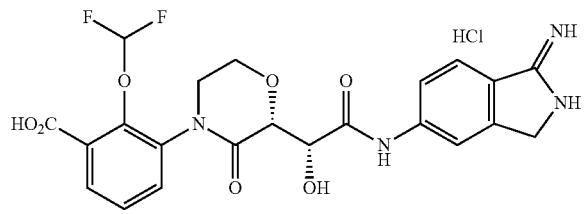

Step 33-1

Synthesis of 3-[(2R)-2-[(1R)-2-[3-[[bis[(2-methyl-propan-2-yl)oxycarbonyl]amino]methyl]-4-cyanoa-nilino]-1-hydroxy-2-oxoethyl]-3-oxomorpholin-4-yl]-2-(difluoromethoxy)benzoic acid (compound aa33-1)

According to the Step 11-1 in synthetic method for EXAMPLE aa11, compound aa32-7 (0.30 g) was used instead of aa10-5 to obtain compound aa33-1 (0.26 g) as a colorless amorphous solid.

Step 33-2

Synthesis of 3-[(2R)-2-[(1R)-2-[3-(aminomethyl)-4-cyanoanilino]-1-hydroxy-2-oxoethyl]-3-oxomorpholin-4-yl]-2-(difluoromethoxy)benzoic acid hydrochloride (compound aa33-2)

According to the Step 2-7 in synthetic method for EXAMPLE aa2, compound aa33-1 (0.10 g) was used instead of aa2-6 to obtain compound aa33-2 (76 mg) as a colorless amorphous solid.

Step 33-3

Synthesis of 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoic acid hydrochloride (EXAMPLE aa33)

According to the Step 2-8 in synthetic method for EXAMPLE aa2, compound aa33-2 (76 mg) was used instead of aa2-7 to obtain EXAMPLE aa33 (60 mg) as a colorless amorphous solid.

Example aa34

Synthesis of 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]-N,N-di methylbenzamide hydrochloride (EXAMPLE aa34)

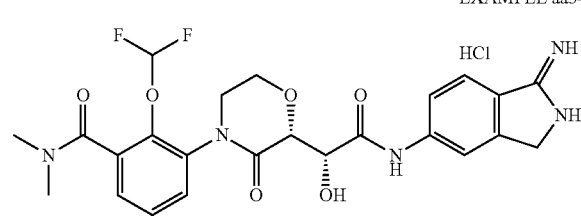

EXAMPLE aa34

Step 34-1

Synthesis of tert-butyl N-[[2-cyano-5-[[(2R)-2-[(2R)-4-[2-(difluoromethoxy)-3-(dimethylcarbam-oyl)phenyl]-3-oxomorpholin-2-yl]-2-hydroxyacetyl]amino]phenyl]methyl]-N-[(2-methylpropan-2-yl)oxycarbonyl]carbamate (compound aa34-1)

According to the Step 2-5 in synthetic method for EXAMPLE aa2, compound aa33-1 (0.12 g), dimethylamine (2M in THF, 174 μl), and HOBt (3 mg) were used instead of 2-4, tert-butyl N-(5-amino-2-cyanophenyl)methyl-N-[(2-methylpropan-2-yl)oxycarbonyl]carbamate, and DMAP to obtain compound aa34-1 (24 mg) as a colorless amorphous solid.

Step 34-2

Synthesis of 3-[(2R)-2-[(1R)-2-[3-(aminomethyl)-4-cyanoanilino]-1-hydroxy-2-oxoethyl]-3-oxomorpho-lin-4-yl]-2-(difluoromethoxy)-N,N-dimethylbenza-mide hydrochloride (compound aa34-2)

According to the Step 2-7 in synthetic method for EXAMPLE aa2, compound aa34-1 (24 mg) was used instead of aa2-6 to obtain compound aa34-2 (18 mg) as a colorless amorphous solid.

Step 34-3

Synthesis of 2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]-N,N-di methylbenzamide hydrochloride (EXAMPLE aa34)

According to the Step 2-8 in synthetic method for EXAMPLE aa2, compound aa34-2 (18 mg) was used instead of aa2-7 to obtain EXAMPLE aa34 (15 mg) as a colorless amorphous solid.

Example aa35

Synthesis of 2-(difluoromethoxy)-3-[2-[(1-hydroxy-2-[(1-imino-2,3-dihydroisoindol-5-yl)amino]-2-oxo-ethyl]-3-oxomorpholin-4-yl]benzamide hydrochloride (EXAMPLE aa35)

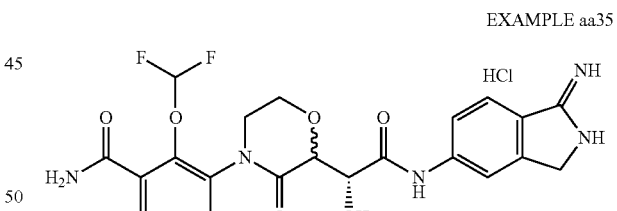

EXAMPLE aa35

Step 35-1

Synthesis of tert-butyl N—[[5-[[2-[4-[3-carbamoyl-2-(difluoromethoxy)phenyl]-3-oxomorpholin-2-yl]-2-hydroxyacetyl]amino]-2-cyanophenyl]methyl]-N-[(2-methylpropan-2-yl)oxycarbonyl]carbamate (compound aa35-1)

According to the Step 2-6 in synthetic method for EXAMPLE aa2, compound aa32-7 (0.12 g) was used instead of aa2-5 to obtain compound aa35-1 (40 mg) as a colorless amorphous solid (diastereomer mixture).

Step 35-2

Synthesis of 3-[2-[2-[3-(aminomethyl)-4-cyanoanilino]-1-hydroxy-2-oxoethyl]-3-oxomorpholin-4-yl]-2-(difluoromethoxy)benzamide hydrochloride (compound aa35-2)

According to the Step 2-7 in synthetic method for EXAMPLE aa2, compound aa35-1 (39 mg) was used instead of aa2-6 to obtain compound aa35-2 (30 mg) as a colorless amorphous solid (diastereomer mixture).

Step 35-3

Synthesis of 2-(difluoromethoxy)-3-[2-[(1R)-1-hydroxy-2-[(1-imino-2,3-dihydroisoindol-5-yl)amino]-2-oxoethyl]-3-oxomorpholin-4-yl]benzamide hydrochloride (EXAMPLE aa35)

According to the Step 2-8 in synthetic method for EXAMPLE aa2, compound aa35-2 (54 mg) was used instead of aa2-7 to obtain EXAMPLE aa35 (49 mg) as a pale yellow amorphous solid (diastereomer mixture).

Example aa36

Synthesis of methyl 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoate hydrochloride (EXAMPLE aa36)

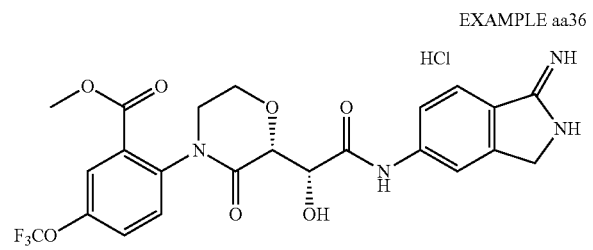 [SMILES: COC(=O)c1cc(OC(F)(F)F)ccc1N1CCO[C@H]([C@@H](O)C(=O)Nc2ccc3c(c2)CNC3=N)C1=O ; Cl]

EXAMPLE aa36

Step 36-1

Synthesis of methyl 2-iodo-5-(trifluoromethoxy)benzoate (compound aa36-1)

According to the Step 16-1 in synthetic method for EXAMPLE aa16, methyl 2-amino-5-trifluoromethoxybenzoate (4.0 g) was used instead of 5-Aminoquinolin-2(1H)-one to obtain compound aa36-1 (4.73 g) as pale yellow oil.

Step 36-2

Synthesis of methyl 2-[(2R)-2-[(1R)-1-hydroxy-2-[(2-methylpropan-2-yl)oxy]-2-oxoethyl]-3-oxomorpholin-4-yl]-5-(trifluoromethoxy)benzoate (compound aa36-2)

According to the Step 2-2 in synthetic method for EXAMPLE aa2, compound aa36-1 (2.35 g) was used instead of aa2-1 to obtain compound aa36-2 (0.74 g) as a white amorphous solid.

Step 36-3

Synthesis of methyl 2-[(2R)-2-[(1R)-1-acetyloxy-2-[(2-methylpropan-2-yl)oxy]-2-oxoethyl]-3-oxomorpholin-4-yl]-5-(trifluoromethoxy)benzoate (compound aa36-3)

According to the Step 2-3 in synthetic method for EXAMPLE aa2, compound aa36-2 (0.74 g) was used instead of aa2-2 to obtain compound aa36-3 (0.86 g) as colorless oil.

Step 36-4

Synthesis of (2R)-2-acetyloxy-2-[(2R)-4-[2-methoxycarbonyl-4-(trifluoromethoxy)phenyl]-3-oxomorpholin-2-yl]acetic acid (compound a36-4)

According to the Step 2-4 in synthetic method for EXAMPLE aa2, compound aa36-3 (0.86 g) was used instead of aa2-3 to obtain compound aa36-4 (0.74 g) as a white amorphous solid.

Step 36-5

Synthesis of methyl 2-[(2R)-2-[(1R)-1-acetyloxy-2-[3-[[bis[(2-methylpropan-2-yl)oxycarbonyl]amino]methyl]-4-cyanoanilino]-2-oxoethyl]-3-oxomorpholin-4-yl]-5-(trifluoromethoxy)benzoate (compound aa36-5)

According to the Step 2-5 in synthetic method for EXAMPLE aa2, compound aa36-4 (0.35 g) was used instead of aa2-4 to obtain compound aa36-5 (0.43 g) as a white amorphous solid.

Step 36-6

Synthesis of methyl 2-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-5-(trifluoromethoxy)benzoate (compound aa36-6)

According to the Step 2-6 in synthetic method for EXAMPLE aa2, compound aa36-5 (70 mg) was used instead of aa2-5 to obtain compound aa36-6 (63 mg) as a white amorphous solid.

Step 36-7

Synthesis of methyl 2-[(2R)-2-[(1R)-2-[3-(aminomethyl)-4-cyanoanilino]-1-hydroxy-2-oxoethyl]-3-oxomorpholin-4-yl]-5-(trifluoromethoxy)benzoate hydrochloride (compound aa36-7)

According to the Step 2-7 in synthetic method for EXAMPLE aa2, compound aa36-6 (59 mg) was used instead of aa2-6 to obtain compound aa36-7 (45 mg) as a white solid.

Step 36-8

Synthesis of methyl 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoate hydrochloride (EXAMPLE aa36)

According to the Step 2-8 in synthetic method for EXAMPLE aa2, compound aa36-7 (43 mg) was used instead of aa2-7 to obtain EXAMPLE aa36 (32 mg) as a white amorphous solid.

Example aa37

Synthesis of 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoic acid hydrochloride (EXAMPLE aa37)

Example aa38

Synthesis of 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzamide hydrochloride (EXAMPLE aa38)

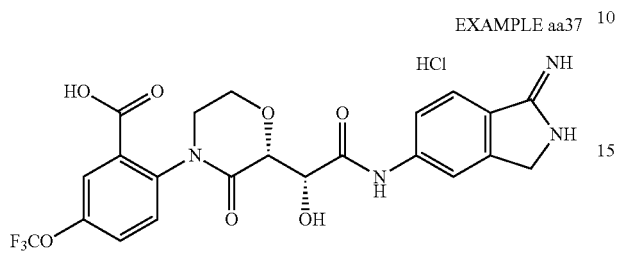

EXAMPLE aa37

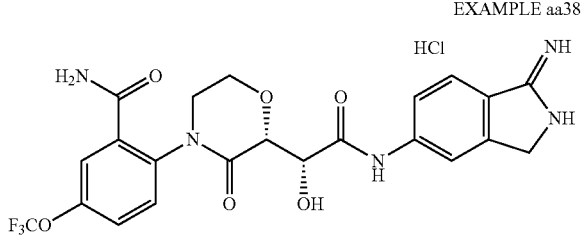 [SMILES: N=C1NCc2cc(NC(=O)[C@H](O)[C@H]3OCCN(c4ccc(OC(F)(F)F)cc4C(N)=O)C3=O)ccc21 ; Cl]

EXAMPLE aa38

Step 37-1

Synthesis of 2-[(2R)-2-[(1R)-2-[3-[[bis[(2-methylpropan-2-yl)oxycarbonyl]amino]methyl]-4-cyanoanilino]-1-hydroxy-2-oxoethyl]-3-oxomorpholin-4-yl]-5-(trifluoromethoxy)benzoic acid (compound aa37-1)

According to the Step 11-1 in synthetic method for EXAMPLE aa11, compound aa36-5 (0.35 g) was used instead of aa10-5 to obtain compound aa37-1 (0.33 g) as a white amorphous solid.

Step 37-2

Synthesis of 2-[(2R)-2-[(1R)-2-[3-(aminomethyl)-4-cyanoanilino]-1-hydroxy-2-oxoethyl]-3-oxomorpholin-4-yl]-5-(trifluoromethoxy)benzoic acid hydrochloride (compound aa37-2)

According to the Step 2-7 in synthetic method for EXAMPLE aa2, compound aa37-1 (33 mg) was used instead of aa2-6 to obtain compound aa37-2 (26 mg) as a white amorphous solid.

Step 37-3

Synthesis of 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoic acid hydrochloride (EXAMPLE aa37)

According to the Step 2-8 in synthetic method for EXAMPLE aa2, compound aa37-2 (24 mg) was used instead of aa2-7 to obtain EXAMPLE aa37 (16 mg) as a white amorphous solid.

Step 38-1

Synthesis of tert-butyl N—[[5-[[(2R)-2-[(2R)-4-[2-carbamoyl-4-(trifluoromethoxy)phenyl]-3-oxomorpholin-2-yl]-2-hydroxyacetyl]amino]-2-cyanophenyl]methyl]-N-[(2-methylpropan-2-yl)oxycarbonyl]carbamate (compound aa38-1)

According to the Step 2-5 in synthetic method for EXAMPLE aa2, compound aa37-1 (88 mg), NH₄Cl (33 mg), HOBt (30 mg), and diisopropylethylamine (0.11 ml) were used instead of compound aa37-1, tert-butyl N-(5-amino-2-cyanophenyl)methyl-N-[(2-methylpropan-2-yl)oxycarbonyl]carbamate, and DMAP to obtain compound aa38-1 (9.8 mg) as a white amorphous solid.

Step 38-2

Synthesis of 2-[(2R)-2-[(1R)-2-[3-(aminomethyl)-4-cyanoanilino]-1-hydroxy-2-oxoethyl]-3-oxomorpholin-4-yl]-5-(trifluoromethoxy)benzamide hydrochloride (compound aa38-2)

According to the Step 2-7 in synthetic method for EXAMPLE aa2, compound aa38-1 (9 mg) was used instead of aa2-6 to obtain compound aa38-2 (9 mg) as a white amorphous solid.

Step 38-3

Synthesis of 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzamide hydrochloride (EXAMPLE aa38)

According to the Step 2-8 in synthetic method for EXAMPLE aa2, compound aa38-2 (8 mg) was used instead of aa2-7 to obtain EXAMPLE aa38 (5 mg) as a white amorphous solid.

TABLE 1

| EXAMPLE | NMR (ppm) (No mark: 400 MHz,*: 300 MHz) |
|---|---|
| aa1 | *DMSO-d₆: 10.19 (1H, s), 8.80-7.68 (3H, m), 8.03 (2H, d, J = 9 Hz), 7.74 (2H, d, 9 Hz), 7.49-7.40 (2H, m), 7.35-7.25 (2H, m), 6.49 (1H, d, J = 8 Hz), 4.72-4.62 (2H, m), 4.18-4.08 (1H, m), 4.01-3.77 (2H, m), 3.71-3.56 (1H, m), 3.00 (3H, s), 1.31 (9H, s) |

TABLE 1-continued

| EXAMPLE | NMR (ppm) (No mark: 400 MHz,*: 300 MHz) |
|---|---|
| aa2 | DMSO-d$_6$: 10.25 (1H, s), 9.50-8.90 (3H, m), 8.62 (1H, s), 8.32 (1H, s), 8.10 (1H, d, J = 9 Hz), 7.94 (1H, d, J = 9 Hz), 7.72 (1H, d, J = 8 Hz), 7.63 (1H, s), 7.52 (1H, d, J = 8 Hz), 6.52 (1H, d, J = 7 Hz), 4.78 (2H, s), 4.72 (1H, d, J = 2 Hz), 4.72-4.66 (1H, m), 4.40 (2H, s), 4.24-4.07 (1H, m), 4.06-3.83 (2H, m), 3.78-3.64 (1H, m) |
| aa3 | *DMSO-d$_6$: 11.86 (1H, s), 10.26 (1H, s), 10.19 (1H, s), 9.59 (1H, s), 9.13 (1H, s), 8.36-8.32 (1H, m), 8.15 (1H, d, J = 9 Hz), 7.99-7.87 (2H, m), 7.70 (1H, d, 2 Hz), 7.55 (1H, dd, J = 9, 2 Hz), 7.34 (1H, d, J = 9 Hz), 6.64-6.41 (2H, m), 4.80 (2H, s), 4.71 (2H, s), 4.23-4.12 (1H, m), 4.03-3.93 (2H, m), 3.73-3.61 (1H, m) |
| aa4 | *DMSO-d$_6$: 11.93 (1H, s), 10.30 (1H, s), 10.22 (1H, s), 9.63 (1H, s), 9.16 (1H, s), 8.34 (1H, s), 8.18 (1H, d, J = 9 Hz), 8.00-7.88 (2H, m), 7.75 (1H, s), 7.22 (1H, s), 7.19 (1H, t, J = 73 Hz), 6.59-6.37 (2H, m), 4.80 (2H, s), 4.73-4.64 (2H, m), 4.26-4.14 (1H, m), 4.00-3.77 (2H, m), 3.56-3.45 (1H, m) |
| aa4-1 | *CDCl$_3$: 8.12-8.05 (1H, m), 8.04-7.98 (1H, m), 7.89-7.81 (1H, m), 6.66 (1H, t, J = 72 Hz) |
| aa5 | *DMSO-d$_6$: 11.85 (1H, brs), 10.20 (1H, s), 9.30-8.82 (4H, m), 8.03 (2H, d, J = 8 Hz), 7.90 (1H, d, J = 9 Hz), 7.80 (2H, d, J = 8 Hz), 7.68 (1H, s), 7.57-7.49 (1H, m), 7.32 (1H, d, J = 9 Hz), 6.59-6.42 (2H, m), 4.73-4.62 (2H, m), 4.22-4.08 (1H, m), 4.02-3.82 (2H, m), 3.70-3.58 (1H, m) |
| aa6 | *DMSO-d$_6$: 11.87 (1H, d, J = 1 Hz), 10.38 (1H, s), 9.33 (2H, s), 9.08 (2H, s), 7.99 (1H, dd, J = 13, 2 Hz), 7.91 (1H, d, J = 10 Hz), 7.84 (1H, dd, J = 9, 2 Hz), 7.73-7.62 (2H, m), 7.55 (1H, dd, J = 9, 2 Hz), 7.38-7.30 (1H, m), 6.61-6.51 (2H, m), 4.75-4.63 (2H, m), 4.23-4.10 (1H, m), 4.04-3.83 (2H, m), 3.72-3.62 (1H, m) |
| aa7 | DMSO-d$_6$ (100degC): 11.44 (1H, s), 10.00 (2H, s), 9.16 (2H, brs), 8.21 (1H, s), 8.16 (1H, d, J = 9 Hz), 7.90 (1H, d, J = 9 Hz), 7.83 (1H, d, J = 10 Hz), 7.64 (1H, d, J = 9 Hz), 7.39 (1H, s), 7.25-7.18 (1H, m), 6.44 (1H, d, J = 10 Hz), 4.79-4.69 (4H, m), 4.22-4.13 (1H, m), 4.01-3.87 (2H, m), 3.70-3.62 (1H, m) |
| aa8 | DMSO-d$_6$: 10.27 (1H, s), 10.21 (1H, s), 9.61 (1H, s), 9.14 (1H, s), 8.33 (1H, s), 8.16 (1H, d, J = 9 Hz), 7.95 (1H, d, J = 9 Hz), 7.92 (1H, d, J = 10 Hz), 7.77 (1H, d, J = 8 Hz), 7.58 (1H, s), 7.34 (1H, d, J = 8 Hz), 6.62 (1H, d, J = 10 Hz), 6.57 (1H, d, J = 7 Hz), 4.79 (2H, s), 4.77-4.68 (2H, m), 4.25-4.10 (1H, m), 4.07-3.90 (2H, m), 3.88-3.74 (1H, m), 3.61 (3H, s) |
| aa9 | *DMSO-d$_6$: 10.30-10.21 (2H, m), 9.69 (1H, s), 9.19 (1H, s), 8.33 (1H, s), 8.24-8.16 (1H, m), 7.98-7.88 (2H, m), 7.81-7.72 (2H, m), 7.31 (1H, dd, J = 8, 2 Hz), 6.65-6.36 (2H, m), 4.82-4.71 (4H, m), 4.25-4.12 (3H, m), 4.05-3.93 (2H, m), 3.83-3.75 (1H, m), 1.34-1.22 (1H, m), 0.55-0.40 (4H, m) |
| aa10 | DMSO-d$_6$: 10.26 (1H, s), 10.21 (1H, s), 9.63 (1H, s), 9.15 (1H, s), 8.32 (1H, s), 8.17 (1H, d, J = 9 Hz), 8.02-7.97 (1H, m), 7.94 (1H, d, J = 9 Hz), 7.80 (1H, d, J = 8 Hz), 7.56 (1H, d, J = 1 Hz), 7.35 (1H, dd, J = 8, 1 Hz), 6.65 (1H, d, J = 9 Hz), 6.54 (1H, d, J = 7 Hz), 5.17-4.99 (2H, m), 4.79 (2H, s), 4.76-4.68 (2H, m), 4.25-4.10 (1H, m), 4.04-3.86 (2H, m), 3.85-3.73 (1H, m), 3.71 (3.H, s) |
| aa11 | DMSO-d$_6$: 13.08 (1H, s), 10.25 (1H, s), 10.20 (1H, s), 9.57 (1H, s), 9.13 (1H, s), 8.33 (1H, s), 8.14 (1H, d, J = 9 Hz), 8.02-7.90 (2H, m), 7.79 (1H, d, J = 9 Hz), 7.53 (1H, d, J = 1 Hz), 7.38-7.28 (1H, m), 6.64 (1H, d, J = 9 Hz), 6.56 (1H, d, J = 6 Hz), 5.04-4.89 (2H, m), 4.79 (2H, s), 4.73 (1H, d, J = 2 Hz), 4.73-4.68 (1H, m), 4.23-4.09 (1H, m), 4.03-3.85 (2H, m), 3.83-3.71 (1H, m) |
| aa12 | DMSO-d$_6$ (100degC): 10.53 (1H, brs), 10.20-9.79 (2H, m), 9.59-8.73 (2H, m), 8.22 (1H, s), 8.18 (1H, d, J = 9 Hz), 7.90 (1H, d, J = 9 Hz), 7.85 (1H, d, J = 10 Hz), 7.54 (1H, d, J = 8 Hz), 7.15-6.91 (1H, m), 6.50 (1H, d, J = 10 Hz), 6.42-5.52 (1H, m), 4.83-4.57 (4H, m), 4.33-3.26 (4H, m), 2.40-2.15 (3H, m) |
| aa13 | *DMSO-d$_6$: 9.95 (1H, s), 8.24 (1H, d, J = 9 Hz), 8.12 (1H, s), 7.92 (1H, d, J = 9 Hz), 7.85-7.75 (3H, m), 7.58-7.52 (1H, m), 7.06-7.00 (1H, m), 4.77-4.68 (2H, m), 4.50 (2H, s), 4.24-4.14 (1H, m), 4.04-3.93 (5H, m), 3.88-3.78 (1H, m) |
| aa14 | *DMSO-d$_6$: 10.32 (1H, s), 10.28 (1H, s), 9.76 (1H, s), 9.23 (1H, s), 9.16 (1H, d, J = 4 Hz), 8.88 (1H, d, J = 8 Hz), 8.41-8.19 (4H, m), 8.03-7.82 (3H, m), 4.86-4.71 (4H, m), 4.27-4.17 (1H, m), 4.13-3.98 (2H, m), 3.92-3.83 (1H, m) |
| aa15 | *DMSO-d$_6$: 10.06 (1H, s), 9.28-9.18 (1H, m), 9.03 (1H, d, J = 8 Hz), 8.43 (1H, s), 8.35 (1H, d, J = 9 Hz), 8.12-8.01 (2H, m), 7.97 (1H, dd, J = 8, 5 Hz), 7.72 (1H, d, J = 9 Hz), 7.58 (1H, dd, J = 9, 1 Hz), 4.84 (1H, d, J = 2 Hz), 4.71 (1H, d, J = 2 Hz), 4.33-4.17 (1H, m), 4.17-3.95 (2H, m), 3.94-3.73 (1H, m) |
| aa16 | *DMSO-d$_6$ (100degC): 11.53 (1H, brs), 10.16-9.82 (2H, m), 9.43-8.86 (2H, m), 8.23 (1H, s), 8.18 (1H, d, J = 8 Hz), 7.99-7.69 (2H, m), 7.59-7.47 (1H, m), 7.34 (1H, d, J = 8 Hz), 7.12 (1H, s), 6.48 (1H, d, J = 9 Hz), 4.93-4.61 (4H, m), 4.38-3.34 (4H, m) |

TABLE 1-continued

| EXAMPLE | NMR (ppm)<br>(No mark: 400 MHz,*: 300 MHz) |
|---|---|
| aa17 | *DMSO-d$_6$: 10.26 (1H, s), 8.33 (1H, s), 8.16 (1H, d, J = 9 Hz), 8.00-7.84 (3H, m), 7.44-7.38 (2H, m), 6.51 (1H, d, J = 7 Hz), 4.83-4.66 (4H, m), 4.21-4.08 (1H, m), 3.99-3.83 (2H, m), 3.74-3.63 (1H, m), 3.43-3.35 (2H, m), 2.97-2.87 (2H, m) |
| aa18 | *DMSO-d$_6$: 10.35-10.12 (3H, m), 9.66 (1H, brs), 9.18 (1H, brs), 8.33 (1H, s), 8.19 (1H, d, J = 8 Hz), 8.00-7.88 (1H, m), 7.22 (1H, d, J = 7 Hz), 6.98-6.83 (2H, m), 6.45 (1H, d, J = 6 Hz), 4.79 (2H, s), 4.72-4.62 (2H, m), 4.19-4.05 (1H, m), 4.01-3.75 (2H, m), 3.63-3.49 (1H, m), 2.95-2.82 (2H, m), 2.51-2.40 (2H, m) |
| aa19 | DMSO-d$_6$: 10.40-8.99 (4H, m), 8.32 (1H, s), 8.22-8.12 (1H, m), 7.94 (1H, d, J = 7 Hz), 7.31-7.22 (1H, m), 7.11 (1H, s), 7.01 (1H, d, J = 6 Hz), 6.54 (1H, brs), 4.79 (2H, s), 4.69 (2H, s), 4.19-4.08 (1H, m), 4.00-3.89 (1H, m), 3.88-3.78 (1H, m), 3.71-3.61 (1H, m), 3.24 (3H, s), 2.92-2.82 (2H, m), 2.61-2.53 (2H, m) |
| aa20 | *DMSO-d$_6$: 10.32-10.06 (2H, m), 9.64 (1H, brs), 9.17 (1H, brs), 8.33-8.32 (1H, m), 8.17 (1H, d, J = 9 Hz), 7.94 (1H, dd, J = 9, 2 Hz), 7.35-7.22 (2H, m), 6.99 (1H, dd, J = 8, 2 Hz), 6.55-6.45 (1H, m), 4.78 (2H, s), 4.72-4.66 (2H, m), 4.20-4.08 (1H, m), 4.00-3.72 (4H, m), 3.70-3.60 (1H, m), 2.93-2.80 (2H, m), 2.64-2.53 (2H, m), 1.18-1.04 (1H, m), 0.50-0.28 (4H, m) |
| aa21 | *DMSO-d$_6$: 10.34-9.93 (2H, m), 9.45 (2H, brs), 8.32 (1H, s), 8.18 (1H, d, J = 9 Hz), 7.94 (1H, d, J = 9 Hz), 7.29 (1H, d, J = 8 Hz), 7.09-6.97 (2H, m), 6.49 (1H, d, J = 7 Hz), 4.78 (2H, s), 4.69-4.58 (4H, m), 4.20-4.07 (1H, m), 3.99-3.76 (2H, m), 3.74-3.58 (4H, m), 2.98-2.83 (2H, m), 2.66-2.56 (2H, m) |
| aa22 | DMSO-d$_6$: 12.92 (1H, brs), 10.25 (2H, brs), 9.62 (1H, brs), 9.18 (1H, brs), 8.32 (1H, s), 8.16 (1H, d, J = 8 Hz), 7.98-7.88 (1H, m), 7.28 (1H, d, J = 7 Hz), 7.06-6.94 (2H, m), 6.53 (1H, d, J = 6 Hz), 4.78 (2H, s), 4.67 (2H, s), 4.61-4.45 (2H, m), 4.18-4.06 (1H, m), 3.99-3.88 (1H, m), 3.86-3.75 (1H, m), 3.69-3.59 (1H, m), 2.96-2.82 (2H, m), 2.65-2.55 (2H, m) |
| aa23 | *DMSO-d$_6$: 10.37 (1H, s), 10.18 (1H, s), 9.33 (2H, s), 9.15 (2H, s), 7.96 (1H, dd, J = 13, 2 Hz), 7.81 (1H, dd, J = 9, 2 Hz), 7.68-7.60 (1H, m), 7.36 (1H, s), 7.25-7.14 (2H, m), 7.02 (1H, s), 6.94-6.83 (2H, m), 6.49 (1H, d, J = 7 Hz), 4.71-4.58 (2H, m), 4.17-3.72 (3H, m), 3.59-3.46 (1H, m), 2.93-2.80 (2H, m), 2.49-2.39 (2H, m) |
| aa24 | DMSO-d$_6$: 10.18 (1H, s), 10.01 (1H, s), 8.03 (1H, d, J = 1 Hz), 7.70 (1H, d, J = 9 Hz), 7.57 (1H, dd, J = 9, 1 Hz), 7.21 (1H, d, J = 8 Hz), 6.91 (1H, dd, J = 8, 2 Hz), 6.88 (1H, d, J = 2 Hz), 4.67 (1H, d, J = 2 Hz), 4.64 (1H, d, J = 2 Hz), 4.17-4.07 (1H, m), 3.99-3.88 (1H, m), 3.88-3.74 (1H, m), 3.60-3.47 (1H, m), 2.87 (2H, t, J = 7 Hz), 2.49-2.42 (2H, m) |
| aa25 | *DMSO-d$_6$: 13.02 (1H, brs), 10.39 (1H, s), 10.19 (1H, s), 8.93 (2H, brs), 8.59-8.41 (2H, m), 8.04 (1H, d, J = 10 Hz), 7.63 (1H, d, J = 7 Hz), 7.29-7.08 (2H, m), 6.99-6.81 (2H, m), 6.50 (1H, d, J = 7 Hz), 4.69 (2H, s), 4.20-4.05 (1H, m), 4.01-3.74 (2H, m), 3.62-3.50 (1H, m), 2.95-2.80 (2H, m), 2.50-2.38 (2H, m) |
| aa26 | DMSO-d$_6$: 10.18 (1H, s), 10.07 (1H, s), 8.32 (1H, s), 8.23 (1H, s), 8.12 (1H, d, J = 9 Hz), 7.80 (1H, d, J = 8 Hz), 7.64 (2H, brs), 7.22 (1H, d, J = 8 Hz), 6.97-6.84 (2H, m), 6.39 (1H, d, J = 4 Hz), 4.75-4.60 (2H, m), 4.19-4.06 (1H, m), 4.01-3.89 (1H, m), 3.87-3.76 (1H, m), 3.62-3.50 (1H, m), 2.94-2.81 (2H, m), 2.49-2.40 (2H, m) |
| aa27 | DMSO-d$_6$: 10.34-10.07 (3H, m), 9.59 (1H, brs), 9.13 (1H, brs), 8.33 (1H, s), 8.14 (1H, d, J = 9 Hz), 8.00-7.83 (1H, m), 7.27-7.18 (1H, m), 6.98-6.78 (2H, m), 6.64-6.46 (1H, m), 4.83-4.60 (4H, m), 4.18-3.39 (4H, m), 2.88-2.62 (2H, m), 2.49-2.27 (2H, m) |
| aa28 | *DMSO-d$_6$: 10.28 (1H, s), 10.21 (1H, brs), 9.62 (1H, brs), 9.15 (1H, brs), 8.34 (1H, s), 8.17 (1H, d, J = 9 Hz), 7.96 (1H, d, J = 9 Hz), 7.39-7.29 (1H, m), 7.25-7.10 (2H, m), 7.05-6.93 (1H, m), 6.48 (1H, d, J = 7 Hz), 4.80 (2H, s), 4.71-4.60 (2H, m), 4.40 (1H, s), 4.25-4.05 (3H, m), 3.95-3.82 (1H, m), 3.80-3.65 (1H, m), 3.50-3.39 (1H, m), 1.91-1.81 (2H, m), 1.18 (6H, s) |
| aa29 | *DMSO-d$_6$: 10.37-10.12 (2H, m), 9.69 (1H, brs), 9.19 (1H, brs), 8.33 (1H, s), 8.20 (1H, d, J = 9 Hz), 7.94 (1H, d, J = 9 Hz), 7.38-7.26 (1H, m), 7.23-7.09 (2H, m), 7.03-6.92 (1H, m), 6.54-6.39 (1H, m), 4.78 (2H, s), 4.70-4.57 (2H, m), 4.20-3.99 (3H, m), 3.94-3.80 (1H, m), 3.79-3.64 (1H, m), 3.50-3.30 (1H, m), 3.11 (3H, s), 1.98-1.87 (2H, m), 1.17 (6H, s) |
| aa30 | *DMSO-d$_6$ (100degC): 10.10-9.83 (2H, m), 9.39-8.92 (2H, m), 8.19 (1H, s), 8.17 (1H, d, J = 9 Hz), 7.89 (1H, d, J = 9 Hz), 7.45-7.22 (5H, m), 4.76 (2H, s), 4.69 (1H, d, J = 2 Hz), 4.66 (1H, d, J = 2 Hz), 4.15-4.07 (1H, m), 3.90-3.69 (2H, m), 3.68-3.42 (3H, m), 2.52-2.33 (2H, m), 1.99-1.68 (4H, m) |
| aa31 | DMSO-d$_6$: 10.27 (1H, s), 9.61-9.02 (3H, m), 8.34-8.32 (1H, m), 8.14 (1H, d, J = 9 Hz), 7.94 (1H, dd, J = 9, 2 Hz), 7.44-7.29 (3H, m), 7.05 (1H, t, J = 74 Hz), 6.47 (1H, d, J = 6 Hz), 4.78 (2H, s), 4.73-4.62 (2H, m), 4.22-4.12 (1H, m), 3.99-3.75 (2H, m), 3.55-3.47 (1H, m) |

TABLE 1-continued

| EXAMPLE | NMR (ppm) (No mark: 400 MHz,*: 300 MHz) |
|---|---|
| aa31-1 | *CDCl₃: 7.36 (1H, dd, J = 8, 3 Hz), 7.27-7.18 (1H, m), 7.08-6.99 (1H, m), 6.48 (1H, t, J = 73 Hz) |
| aa32 | *DMSO-d₆ (100degC): 9.99 (1H, s), 9.27 (3H, brs), 8.20 (1H, s), 8.16 (1H, d, J = 8 Hz), 7.92-7.86 (1H, m), 7.81 (1H, dd, J = 8, 2 Hz), 7.63 (1H, dd, J = 8, 2 Hz), 7.49 (1H, t, J = 8 Hz), 6.80 (1H, t, J = 74 Hz), 6.03 (1H, s), 4.76 (2H, s), 4.70 (2H, s), 4.25-4.16 (1H, m), 3.97-3.79 (2H, m), 3.86 (3H, s), 3.58-3.48 (1H, m) |
| aa33 | $$ DMSO-d₆ (100degC): 9.99 (1H, s), 9.35 (3H, brs), 8.23-8.13 (2H, m), 7.89 (1H, dd, J = 8, 2 Hz), 7.79 (1H, dd, J = 8, 2 Hz), 7.56 (1H, dd, J = 8, 2 Hz), 7.44 (1H, t, J = 8 Hz), 6.82 (1H, t, J = 75 Hz), 6.02 (1H, s), 4.76 (2H, s), 4.73-4.67 (2H, m), 4.25-4.16 (1H, m), 3.98-3.79 (2H, m), 3.58-3.49 (1H, m) |
| aa34 | *DMSO-d₆: 10.27 (1H, s), 9.36 (3H, brs), 8.33 (1H, s), 8.14 (1H, d, J = 9 Hz), 7.97-7.91 (1H, m), 7.54-7.36 (3H, m), 7.03-6.44 (2H, m), 4.78 (2H, s), 4.72-4.64 (2H, m), 4.24-4.12 (1H, m), 3.98-3.80 (2H, m), 3.60-3.48 (1H, m), 2.99 (3H, s), 2.80 (3H, s) |
| aa35 | *DMSO-d₆: 10.33-9.99 (2H, m), 9.70-9.60 (1H, m), 9.20-9.10 (1H, m), 8.36-8.26 (1H, m), 8.21-8.13 (1H, m), 7.99-7.77 (2H, m), 7.71-7.62 (1H, m), 7.57-7.40 (3H, m), 7.10-6.39 (2H, m), 4.79 (2H, s), 4.67-4.59 (2H, m), 4.24-4.12 (1H, m), 4.01-3.36 (3H, m) |
| aa36 | DMSO-d₆: 10.27 (1H, s), 8.32 (1H, s), 8.14 (1H, d, J = 9 Hz), 7.94 (1H, dd, J = 9, 2 Hz), 7.83-7.73 (2H, m), 7.57 (1H, d, J = 9 Hz), 6.42 (1H, d, J = 7 Hz), 4.83-4.59 (4H, m), 4.24-4.13 (1H, m), 4.01-3.89 (2H, m), 3.85 (3H, s), 3.59-3.47 (1H, m) |
| aa37 | DMSO-d₆: 10.29-10.22 (2H, m), 9.64 (1H, m), 9.18 (1H, s), 8.32 (1H, s), 8.17 (1H, d, J = 9 Hz), 7.93 (1H, dd, J = 9, 1 Hz), 7.82-7.67 (2H, m), 7.49 (1H, d, J = 9 Hz), 6.48 (1H, brs), 4.78 (2H, s), 4.68-4.55 (2H, m), 4.23-4.14 (1H, m), 3.98-3.83 (2H, m), 3.55-3.46 (1H, m) |
| aa38 | *DMSO-d₆: 10.25 (1H, s), 8.32 (1H, s), 8.20-8.06 (1H, m), 7.98-7.88 (2H, m), 7.65-7.40 (4H, m), 6.38-6.26 (1H, m), 4.78 (2H, s), 4.68-4.62 (1H, m), 4.61-4.56 (1H, m), 4.21-4.07 (1H, m), 3.96-3.81 (2H, m), 3.62-3.48 (1H, m) |

TABLE 2

| EXAMPLE | LC/MS m/z [M + 1]⁺ | RT min | solvent system |
|---|---|---|---|
| aa1 | 439 | 4.30 | B |
| aa1-1 | 212 | 5.40 | C |
| aa1-2 | 335 | 2.82 | D |
| aa1-3 | 528 | 5.33 | C |
| aa1-4 | 444 | 4.63 | C |
| aa1-5 | 408 | 4.30 | C |
| aa2 | 436 | 2.85 | B |
| aa2-1 | 498 | 6.87 | A |
| aa2-2 | 601 | 6.33 | A |
| aa2-3 | 643 | 6.37 | A |
| aa2-4 | 349 | 2.52 | B |
| aa2-5 | 700 [M + Na]⁺ | 5.40 | A |
| aa2-6 | 658 [M + Na]⁺ | 5.42 | A |
| aa2-7 | 436 | 0.27 | A |
| aa3 | 448 | 3.12 | B |
| aa3-1 | 375 | 4.13 | A |
| aa3-2 | 417 | 4.37 | B |
| aa3-3 | 361 | 2.90 | B |
| aa3-4 | 712 [M + Na]⁺ | 5.47 | B |
| aa3-5 | 670 [M + Na]⁺ | 5.42 | B |
| aa3-6 | 448 | 3.03 | B |
| aa4 | 514 | 3.40 | B |
| aa4-2 | 286 | 4.97 | A |
| aa4-3 | 384 | 5.67 | A |
| aa4-4 | 338 | 5.10 | A |
| aa4-5 | 441 | 4.57 | A |
| aa4-6 | 483 | 4.83 | A |
| aa4-7 | 427 | 3.48 | B |
| aa4-8 | 778 [M + Na]⁺ | 5.60 | A |
| aa4-9 | 736 [M + Na]⁺ | 5.58 | A |
| aa4-10 | 514 | 3.37 | B |
| aa5 | 436 | 2.95 | B |
| aa5-1 | 520 | 4.18 | B |
| aa5-2 | 478 | 4.05 | B |
| aa6 | 454 | 3.00 | B |
| aa6-1 | 538 | 4.17 | B |
| aa6-2 | 496 | 3.98 | B |
| aa7 | 448 | 3.08 | B |
| aa7-1 | 272 | 4.70 | A |
| aa7-2 | 375 | 4.20 | A |
| aa7-3 | 417 | 4.50 | A |
| aa7-4 | 361 | 3.27 | B |
| aa7-5 | 648 | 5.48 | A |
| aa7-6 | 448 | 3.12 | B |
| aa8 | 462 | 3.27 | B |
| aa8-1 | 286 | 4.92 | A |
| aa8-2 | 389 | 4.35 | A |
| aa8-3 | 431 | 4.58 | A |
| aa8-4 | 375 | 3.37 | B |
| aa8-5 | 726 [M + Na]⁺ | 5.52 | A |
| aa8-6 | 684 [M + Na]⁺ | 5.48 | A |
| aa8-7 | 462 | 3.12 | B |
| aa9 | 502 | 3.70 | B |
| aa9-1 | 326 | 5.58 | A |
| aa9-2 | 429 | 4.87 | A |
| aa9-3 | 471 | 5.05 | A |
| aa9-4 | 415 | 3.97 | B |
| aa9-5 | 744 | 5.75 | A |
| aa9-6 | 702 | 5.73 | A |
| aa9-7 | 502 | 2.87 | A |
| aa10 | 520 | 3.30 | B |
| aa10-1 | 344 | 4.70 | A |
| aa10-2 | 447 | 4.30 | A |
| aa10-3 | 489 | 4.58 | A |
| aa10-4 | 433 | 3.33 | B |

TABLE 2-continued

| EXAMPLE | LC/MS m/z [M + 1]+ | RT min | solvent system |
|---|---|---|---|
| aa10-5 | 784 [M + Na]+ | 5.53 | A |
| aa10-6 | 742 [M + Na]+ | 5.55 | A |
| aa10-7 | 520 | 3.18 | B |
| aa11 | 506 | 3.17 | B |
| aa11-1 | 728 [M + Na]+ | 5.50 | B |
| aa11-2 | 506 | 3.15 | B |
| aa12 | 462 | 3.27 | B |
| aa12-1 | 332 | 5.22 | A |
| aa12-2 | 286 | 5.07 | A |
| aa12-3 | 389 | 4.15 | A |
| aa12-4 | 431 | 4.45 | A |
| aa12-5 | 375 | 3.09 | B |
| aa12-6 | 704 | 5.50 | A |
| aa12-7 | 662 | 5.47 | A |
| aa12-8 | 462 | 3.10 | B |
| aa13 | 462 | 3.78 | B |
| aa13-1 | 286 | 6.15 | A |
| aa13-2 | 389 | 5.05 | A |
| aa13-3 | 431 | 5.23 | A |
| aa13-4 | 375 | 4.20 | B |
| aa13-5 | 704 | 5.90 | A |
| aa13-6 | 662 | 5.87 | A |
| aa13-7 | 462 | 2.92 | A |
| aa14 | 432 | 2.72 | B |
| aa14-1 | 359 | 4.27 | A |
| aa14-2 | 401 | 3.92 | B |
| aa14-3 | 345 | 2.02 | B |
| aa14-4 | 674 | 5.28 | B |
| aa14-5 | 632 | 5.62 | A |
| aa14-6 | 432 | 2.72 | B |
| aa15 | 434 | 2.97 | B |
| aa15-1 | 606 | 4.43 | B |
| aa16 | 448 | 3.07 | B |
| aa16-1 | 272 | 4.82 | A |
| aa16-2 | 375 | 4.08 | A |
| aa16-3 | 417 | 4.28 | A |
| aa16-4 | 361 | 2.77 | B |
| aa16-5 | 690 | 5.42 | A |
| aa16-6 | 648 | 5.42 | A |
| aa16-7 | 448 | 3.03 | B |
| aa17 | 450 | 2.97 | B |
| aa17-1 | 377 | 4.10 | A |
| aa17-2 | 419 | 4.35 | A |
| aa17-3 | 363 | 3.03 | B |
| aa17-4 | 714 [M + Na]+ | 5.43 | A |
| aa17-5 | 650 | 5.40 | A |
| aa17-6 | 450 | 3.05 | B |
| aa18 | 450 | 2.47 | A |
| aa18-1 | 399 [M + Na]+ | 4.27 | A |
| aa18-2 | 419 | 4.52 | A |
| aa18-3 | 363 | 3.27 | B |
| aa18-4 | 692 | 5.52 | A |
| aa18-5 | 650 | 5.52 | A |
| aa18-6 | 450 | 3.15 | B |
| aa19 | 464 | 2.57 | A |
| aa19-1 | 288 | 5.27 | A |
| aa19-2 | 391 | 4.37 | A |
| aa19-3 | 433 | 4.60 | A |
| aa19-4 | 377 | 3.35 | B |
| aa19-5 | 728 [M + Na]+ | 5.57 | A |
| aa19-6 | 686 [M + Na]+ | 5.55 | A |
| aa19-7 | 464 | 2.53 | A |
| aa20 | 504 | 2.88 | A |
| aa20-1 | 328 | 5.87 | A |
| aa20-2 | 453 [M + Na]+ | 4.93 | A |
| aa20-3 | 473 | 5.13 | A |
| aa20-4 | 417 | 4.07 | B |
| aa20-5 | 768 [M + Na]+ | 5.78 | A |
| aa20-6 | 726 [M + Na]+ | 5.82 | A |
| aa20-7 | 504 | 2.87 | A |
| aa21 | 522 | 3.37 | B |
| aa21-1 | 346 | 4.97 | A |
| aa21-2 | 449 | 4.38 | A |
| aa21-3 | 491 | 4.62 | A |
| aa21-4 | 435 | 3.40 | B |
| aa21-5 | 786 [M + Na]+ | 5.62 | A |
| aa21-6 | 744 [M + Na]+ | 5.57 | A |
| aa21-7 | 522 | 2.57 | A |
| aa22 | 508 | 3.23 | B |
| aa22-1 | 730 [M + Na]+ | 5.50 | B |
| aa22-2 | 508 | 3.12 | B |
| aa23 | 456 | 3.15 | B |
| aa23-1 | 538 | 4.25 | B |
| aa23-2 | 496 | 4.12 | B |
| aa24 | 452 | 3.68 | A |
| aa24-1 | 624 | 4.53 | A |
| aa25 | 462 | 3.45 | B |
| aa25-1 | 704 | 5.17 | A |
| aa25-2 | 662 | 5.05 | A |
| aa26 | 463 | 3.27 | B |
| aa26-1 | 605 | 4.77 | A |
| aa26-2 | 563 | 4.63 | A |
| aa27 | 450 | 2.87 | B |
| aa27-1 | 377 | 4.03 | A |
| aa27-2 | 419 | 4.28 | A |
| aa27-3 | 363 | 2.90 | B |
| aa27-4 | 672 [M + Na]+ | 5.80 | A |
| aa27-5 | 450 | 2.80 | A |
| aa28 | 483 | 3.73 | B |
| aa28-1 | 329 [M + Na]+ | 5.65 | A |
| aa28-2 | 410 | 4.92 | A |
| aa28-3 | 474 [M + Na]+ | 5.07 | A |
| aa28-4 | 396 | 3.98 | B |
| aa28-5 | 747 [M + Na]+ | 5.80 | A |
| aa28-6 | 705 | 5.80 | A |
| aa28-7 | 483 | 2.87 | A |
| aa29 | 497 | 3.97 | B |
| aa29-1 | 343 [M + Na]+ | 6.22 | A |
| aa29-2 | 424 | 5.32 | A |
| aa29-3 | 466 | 5.35 | A |
| aa29-4 | 432 [M + Na]+ | 4.47 | B |
| aa29-5 | 761 [M + Na]+ | 6.05 | A |
| aa29-6 | 719 | 5.97 | A |
| aa29-7 | 497 | 3.12 | A |
| aa30 | 478 | 3.15 | B |
| aa30-1 | 405 | 4.38 | A |
| aa30-2 | 447 | 4.65 | A |
| aa30-3 | 391 | 3.23 | B |
| aa30-4 | 742 [M + Na]+ | 5.63 | A |
| aa30-5 | 700 [M + Na]+ | 5.57 | A |
| aa30-6 | 478 | 0.37 | B |
| aa31 | 465 | 3.62 | B |
| aa31-2 | 414 [M + Na]+ | 4.95 | A |
| aa31-3 | 456 [M + Na]+ | 5.18 | A |
| aa31-4 | 378 | 4.15 | B |
| aa31-5 | 729 [M + Na]+ | 5.83 | A |
| aa31-6 | 687 [M + Na]+ | 5.82 | A |
| aa31-7 | 465 | 3.58 | B |
| aa32 | 505 | 3.58 | B |
| aa32-1 | 270 [M + Na]+ | 4.58 | B |

TABLE 2-continued

| EXAMPLE | LC/MS m/z [M + 1]+ | RT min | solvent system |
|---|---|---|---|
| aa32-2 | 240 [M + Na]+ | 4.03 | A |
| aa32-3 | 351 [M + Na]+ | 5.25 | A |
| aa32-4 | 432 | 4.97 | A |
| aa32-5 | 474 | 5.12 | A |
| aa32-6 | 418 | 4.02 | B |
| aa32-7 | 769 [M + Na]+ | 5.88 | B |
| aa32-8 | 727 [M + Na]+ | 5.85 | B |
| aa32-9 | 505 | 3.72 | B |
| aa33 | 491 | 3.22 | B |
| aa33-1 | 713 [M + Na]+ | 5.70 | B |
| aa33-2 | 491 | 3.37 | B |
| aa34 | 518 | 3.23 | B |
| aa34-1 | 740 [M + Na]+ | 5.65 | A |
| aa34-2 | 518 | 3.20 | B |
| aa35 | 490 | 2.90 | B |
| aa35-1 | 712 [M + Na]+ | 5.45 | A |
| aa35-2 | 490 | 2.82 | B |
| aa36 | 523 | 4.18 | B |
| aa36-1 | 346 | 5.93 | A |
| aa36-2 | 450 | 5.43 | A |
| aa36-3 | 492 | 5.55 | A |
| aa36-4 | 436 | 4.85 | B |
| aa36-5 | 787 [M + Na]+ | 6.10 | A |
| aa36-6 | 745 [M + Na]+ | 5.97 | A |
| aa36-7 | 523 | 4.15 | B |
| aa37 | 509 | 4.00 | B |
| aa37-1 | 731 [M + Na]+ | 5.93 | B |
| aa37-2 | 509 | 4.02 | B |
| aa38 | 508 | 3.62 | B |
| aa38-1 | 730 [M + Na]+ | 5.73 | A |
| aa38-2 | 508 | 3.58 | B |

Example ap1

Synthesis of (2R)—N-(3-amino-1,2-benzisoxazol-6-yl)-2-hydroxy-2-[(2R)-3-oxo-4-(2-oxo-1H-quinolin-6-yl)morpholin-2-yl]acetamide (EXAMPLE ap1)

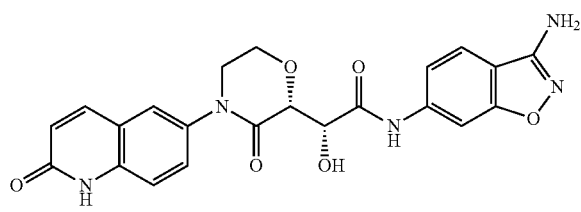 [SMILES: Nc1noc2cc(NC(=O)[C@H](O)[C@H]3OCCN(c4ccc5[nH]c(=O)ccc5c4)C3=O)ccc12]

Example ap1

According to the Step 15-1 in the synthetic method for Example aa15, (2R)-2-acetyloxy-2-[(2R)-3-oxo-4-(2-oxo-1H-quinolin-6-yl)morpholin-2-yl]acetic acid (compound aa3-3) and 6-amino-3-(1,3-dioxoisoindol-2-yl)-1,2-benzisoxazole can be used to obtain [(1R)-2-[[3-(1,3-dioxoisoindol-2-yl)-1,2-benzisoxazol-6-yl]amino]-2-oxo-1-[(2R)-3-oxo-4-(2-oxo-1H-quinolin-6-yl)morpholin-2-yl]ethyl] acetate (compound ap1-1), then further treatment can be achieved according to the Step 15-2 to obtain the title compound ap1.

Example ap2

Synthesis of (2R)—N-(3-amino-1,2-benzisoxazol-6-yl)-2-hydroxy-2-[(2R)-3-oxo-4-(2-oxo-1H-quinolin-7-yl)morpholin-2-yl]acetamide (EXAMPLE ap2)

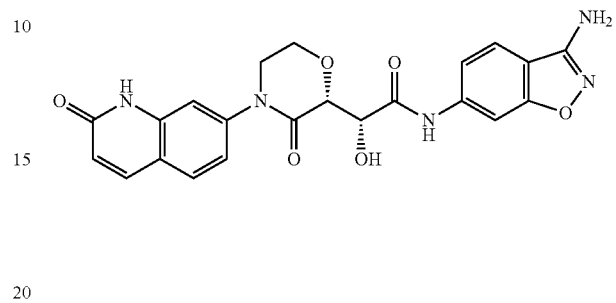

Example ap2

According to the Step 15-1 in the synthetic method for Example aa15, (2R)-2-acetyloxy-2-[(2R)-3-oxo-4-(2-oxo-1H-quinolin-7-yl)morpholin-2-yl]acetic acid (compound aa7-4) and 6-amino-3-(1,3-dioxoisoindol-2-yl)-1,2-benzisoxazole can be used to obtain [(1R)-2-[[3-(1,3-dioxoisoindol-2-yl)-1,2-benzisoxazol-6-yl]amino]-2-oxo-1-[(2R)-3-oxo-4-(2-oxo-1H-quinolin-7-yl)morpholin-2-yl]ethyl] acetate (compound ap2-1), then further treatment can be achieved according to the Step 15-2 to obtain the title compound ap2.

Example ap3

Synthesis of (2R)—N-(3-amino-1,2-benzisoxazol-6-yl)-2-hydroxy-2-[(2R)-3-oxo-4-(2-oxo-1H-quinolin-5-yl)morpholin-2-yl]acetamide (EXAMPLE ap3)

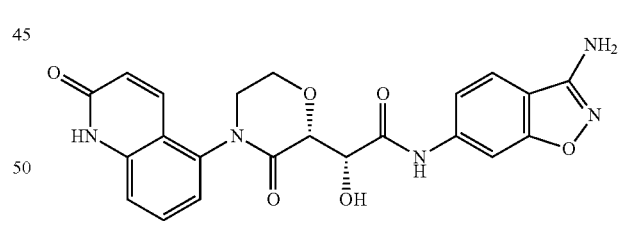

Example ap3

According to the Step 15-1 in the synthetic method for Example aa15, (2R)-2-acetyloxy-2-[(2R)-3-oxo-4-(2-oxo-1H-quinolin-5-yl)morpholin-2-yl]acetic acid (compound aa16-4) and 6-amino-3-(1,3-dioxoisoindol-2-yl)-1,2-benzisoxazole can be used to obtain [(1R)-2-[[3-(1,3-dioxoisoindol-2-yl)-1,2-benzisoxazol-6-yl]amino]-2-oxo-1-[(2R)-3-oxo-4-(2-oxo-1H-quinolin-5-yl)morpholin-2-yl]ethyl] acetate (compound ap3-1), then further treatment can be achieved according to the Step 15-2 to obtain the title compound ap3.

EXAMPLES aa39-aa94
| Structure | EXAMPLE | M + H |
|---|---|---|
| 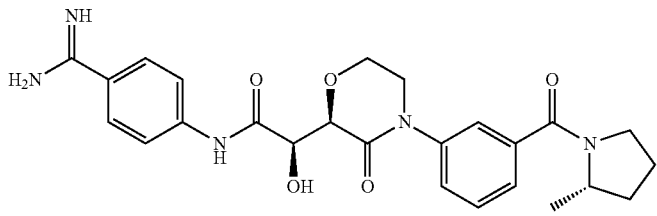 [SMILES: C[C@H]1CCCN1C(=O)c1cccc(N2CCO[C@H]([C@@H](O)C(=O)Nc3ccc(C(=N)N)cc3)C2=O)c1] | aa39 | 480.3 |
| 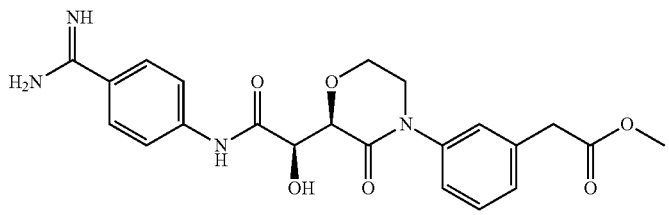 [SMILES: COC(=O)Cc1cccc(N2CCO[C@H]([C@@H](O)C(=O)Nc3ccc(C(=N)N)cc3)C2=O)c1] | aa40 | 441.2 |
| 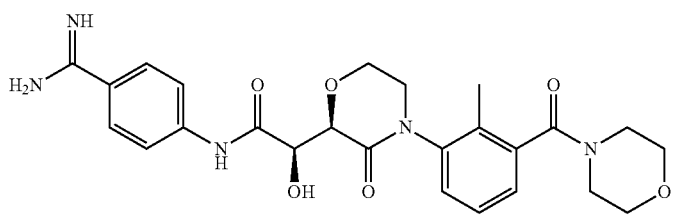 [SMILES: Cc1c(C(=O)N2CCOCC2)cccc1N1CCO[C@H]([C@@H](O)C(=O)Nc2ccc(C(=N)N)cc2)C1=O] | aa41 | 496.3 |
| 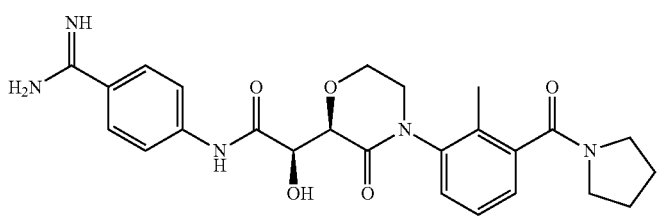 [SMILES: Cc1c(C(=O)N2CCCC2)cccc1N1CCO[C@H]([C@@H](O)C(=O)Nc2ccc(C(=N)N)cc2)C1=O] | aa42 | 480.3 |
| 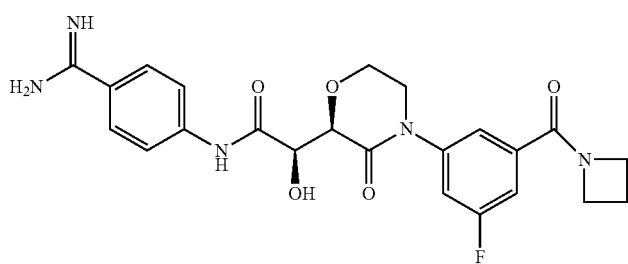 [SMILES: N=C(N)c1ccc(NC(=O)[C@H](O)[C@H]2OCCN(c3cc(F)cc(C(=O)N4CCC4)c3)C2=O)cc1] | aa43 | 470.3 |
| 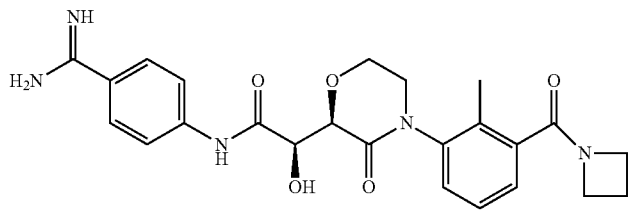 [SMILES: Cc1c(C(=O)N2CCC2)cccc1N1CCO[C@H]([C@@H](O)C(=O)Nc2ccc(C(=N)N)cc2)C1=O] | aa44 | 466.3 |
| 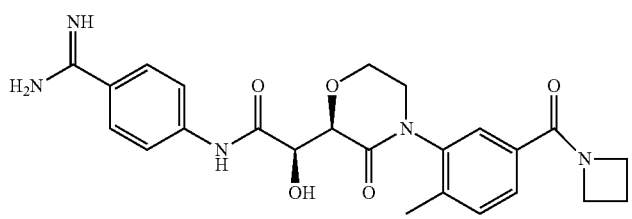 [SMILES: Cc1ccc(C(=O)N2CCC2)cc1N1CCO[C@H]([C@@H](O)C(=O)Nc2ccc(C(=N)N)cc2)C1=O] | aa45 | 466.3 |

-continued
| Structure | EXAMPLE | M + H |
|---|---|---|
| 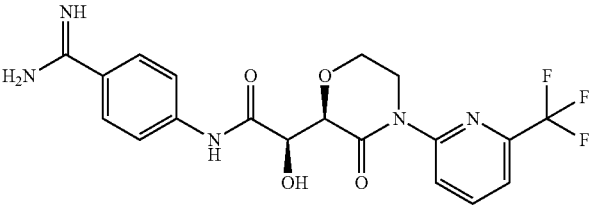 [SMILES: N=C(N)c1ccc(NC(=O)[C@H](O)[C@H]2OCCN(c3cccc(C(F)(F)F)n3)C2=O)cc1] | aa46 | 438.2 |
| 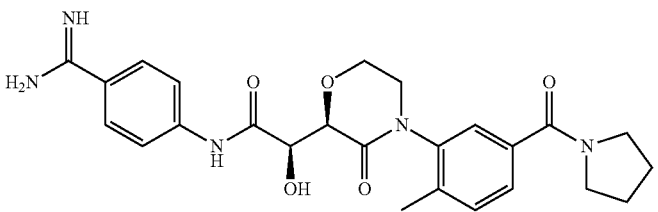 [SMILES: Cc1ccc(C(=O)N2CCCC2)cc1N1CCO[C@H]([C@@H](O)C(=O)Nc2ccc(C(=N)N)cc2)C1=O] | aa47 | 480.3 |
| 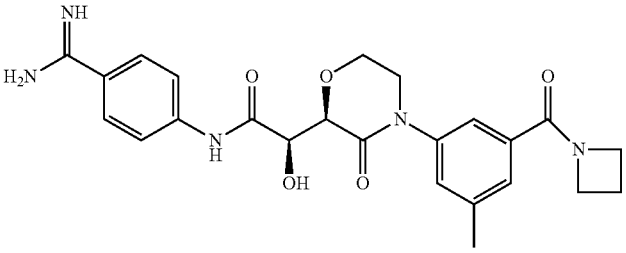 [SMILES: Cc1cc(C(=O)N2CCC2)cc(N2CCO[C@H]([C@@H](O)C(=O)Nc3ccc(C(=N)N)cc3)C2=O)c1] | aa48 | 466.3 |
| 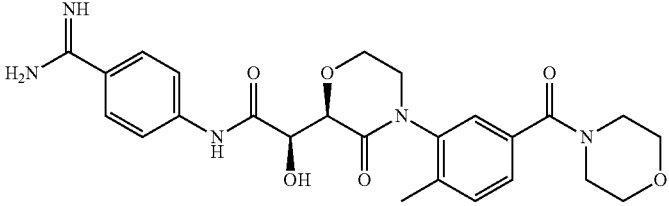 [SMILES: Cc1ccc(C(=O)N2CCOCC2)cc1N1CCO[C@H]([C@@H](O)C(=O)Nc2ccc(C(=N)N)cc2)C1=O] | aa49 | 496.3 |
| 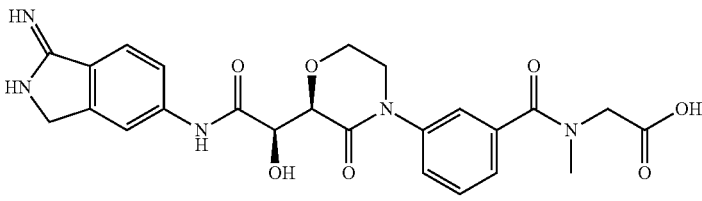 [SMILES: CN(CC(=O)O)C(=O)c1cccc(N2CCO[C@H]([C@@H](O)C(=O)Nc3ccc4c(c3)CNC4=N)C2=O)c1] | aa50 | 496.2 |
| 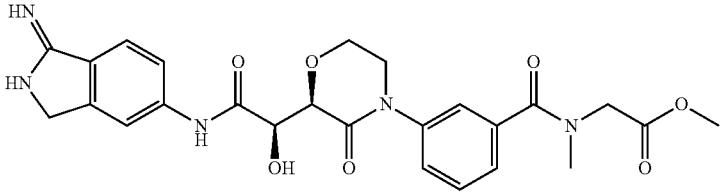 [SMILES: COC(=O)CN(C)C(=O)c1cccc(N2CCO[C@H]([C@@H](O)C(=O)Nc3ccc4c(c3)CNC4=N)C2=O)c1] | aa51 | 510.2 |
| 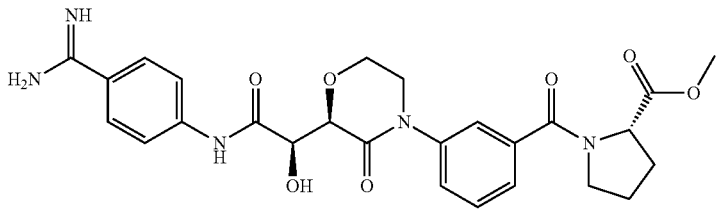 [SMILES: COC(=O)[C@@H]1CCCN1C(=O)c1cccc(N2CCO[C@H]([C@@H](O)C(=O)Nc3ccc(C(=N)N)cc3)C2=O)c1] | aa52 | 524.2 |

EXAMPLES aa39-aa94
| Structure | EXAMPLE | M + H |
|---|---|---|
| 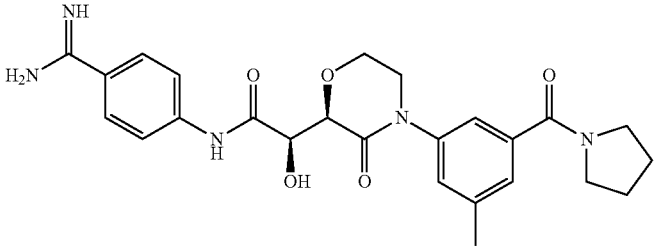 [SMILES: Cc1cc(C(=O)N2CCCC2)cc(N2CCO[C@H]([C@@H](O)C(=O)Nc3ccc(C(=N)N)cc3)C2=O)c1] | aa53 | 480.3 |
| 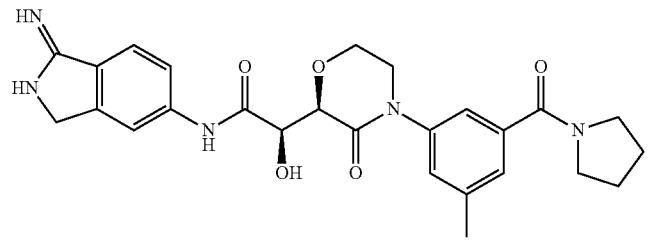 [SMILES: Cc1cc(C(=O)N2CCCC2)cc(N2CCO[C@H]([C@@H](O)C(=O)Nc3ccc4c(c3)CNC4=N)C2=O)c1] | aa54 | 492.2 |
| 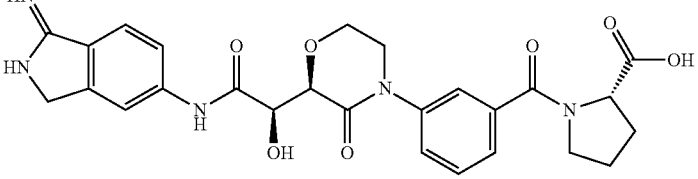 | aa55 | 522.6 |
| 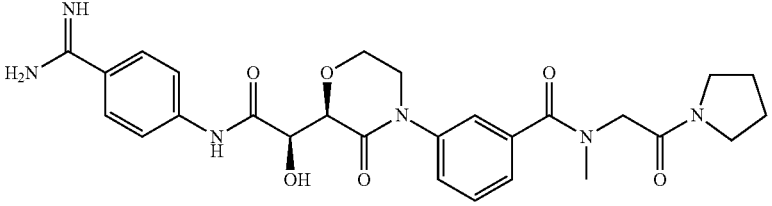 [SMILES: CN(CC(=O)N1CCCC1)C(=O)c1cccc(N2CCO[C@H]([C@@H](O)C(=O)Nc3ccc(C(=N)N)cc3)C2=O)c1] | aa56 | 537.3 |
| 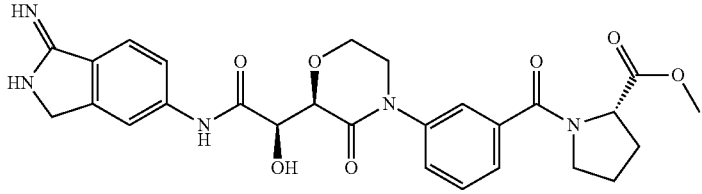 [SMILES: COC(=O)[C@@H]1CCCN1C(=O)c1cccc(N2CCO[C@H]([C@@H](O)C(=O)Nc3ccc4c(c3)CNC4=N)C2=O)c1] | aa57 | 536.6 |
| 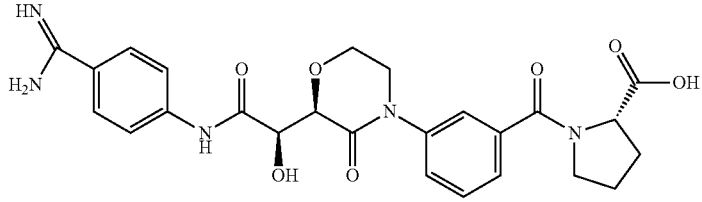 [SMILES: N=C(N)c1ccc(NC(=O)[C@H](O)[C@H]2OCCN(c3cccc(C(=O)N4CCC[C@H]4C(=O)O)c3)C2=O)cc1] | aa58 | 510.7 |
| 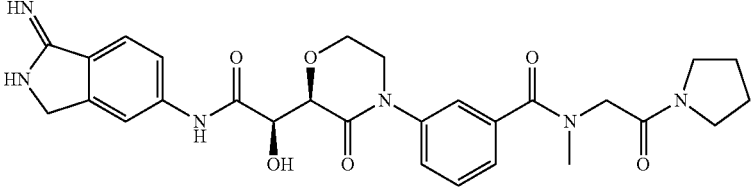 [SMILES: CN(CC(=O)N1CCCC1)C(=O)c1cccc(N2CCO[C@H]([C@@H](O)C(=O)Nc3ccc4c(c3)CNC4=N)C2=O)c1] | aa59 | 549.3 |

-continued
EXAMPLES aa39-aa94
| Structure | EXAMPLE | M + H |
|---|---|---|
| 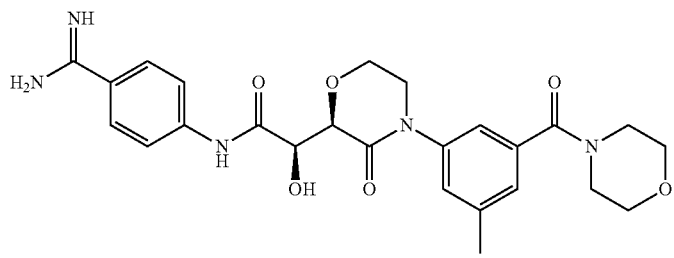 [SMILES: Cc1cc(C(=O)N2CCOCC2)cc(N2CCO[C@H]([C@@H](O)C(=O)Nc3ccc(C(=N)N)cc3)C2=O)c1] | aa60 | 496.3 |
| 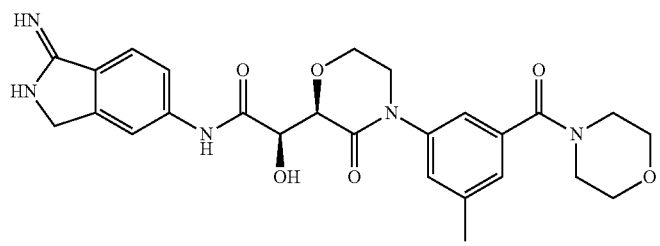 [SMILES: Cc1cc(C(=O)N2CCOCC2)cc(N2CCO[C@H]([C@@H](O)C(=O)Nc3ccc4c(c3)CNC4=N)C2=O)c1] | aa61 | 508.3 |
| 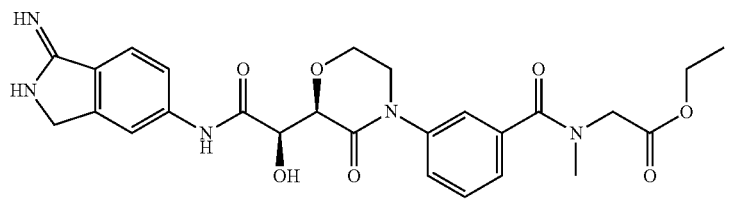 [SMILES: CCOC(=O)CN(C)C(=O)c1cccc(N2CCO[C@H]([C@@H](O)C(=O)Nc3ccc4c(c3)CNC4=N)C2=O)c1] | aa62 | 524.2 |
| 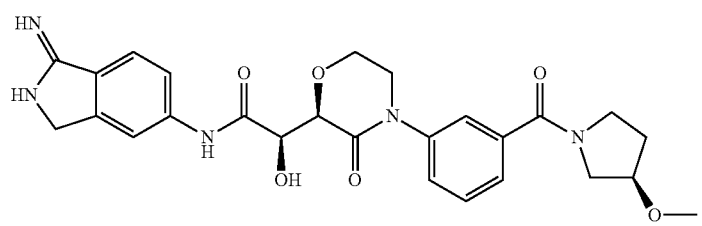 [SMILES: CO[C@@H]1CCN(C(=O)c2cccc(N3CCO[C@H]([C@@H](O)C(=O)Nc4ccc5c(c4)CNC5=N)C3=O)c2)C1] | aa63 | 508.3 |
| 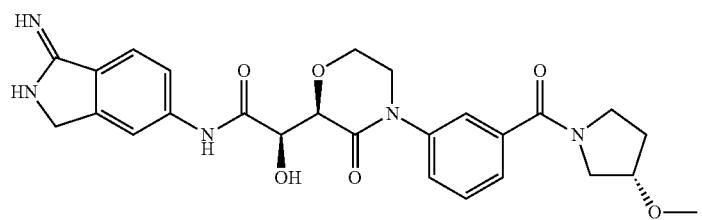 [SMILES: CO[C@H]1CCN(C(=O)c2cccc(N3CCO[C@H]([C@@H](O)C(=O)Nc4ccc5c(c4)CNC5=N)C3=O)c2)C1] | aa64 | 508.3 |
| 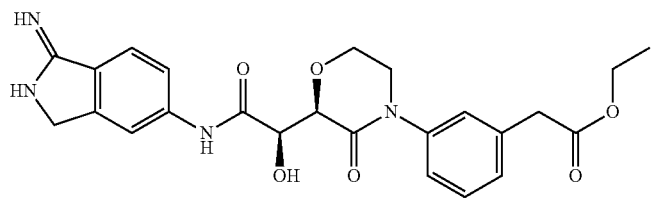 [SMILES: CCOC(=O)Cc1cccc(N2CCO[C@H]([C@@H](O)C(=O)Nc3ccc4c(c3)CNC4=N)C2=O)c1] | aa65 | 467.2 |

EXAMPLES aa39-aa94

| Structure | EXAMPLE | M + H |
|---|---|---|
| 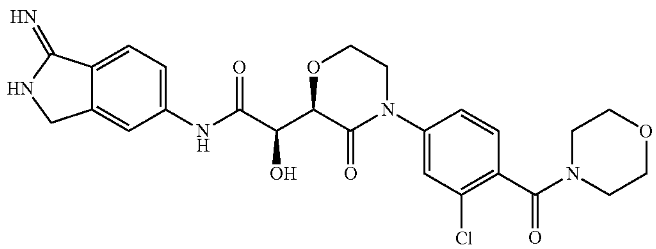 [SMILES: N=C1NCc2cc(NC(=O)[C@H](O)[C@H]3OCCN(c4ccc(C(=O)N5CCOCC5)c(Cl)c4)C3=O)ccc21] | aa66 | 528.3 |
| 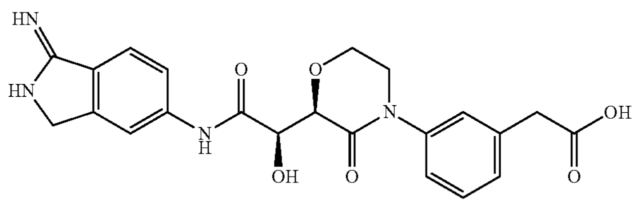 [SMILES: N=C1NCc2cc(NC(=O)[C@H](O)[C@H]3OCCN(c4cccc(CC(=O)O)c4)C3=O)ccc21] | aa67 | 439.2 |
| 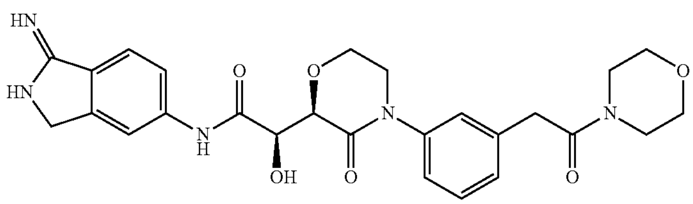 [SMILES: N=C1NCc2cc(NC(=O)[C@H](O)[C@H]3OCCN(c4cccc(CC(=O)N5CCOCC5)c4)C3=O)ccc21] | aa68 | 508.3 |
| 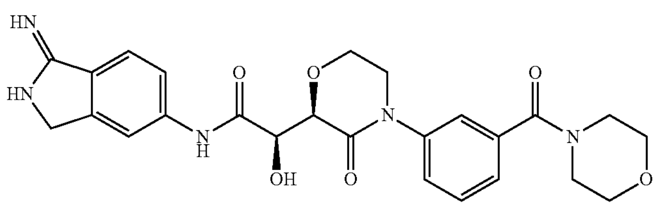 [SMILES: N=C1NCc2cc(NC(=O)[C@H](O)[C@H]3OCCN(c4cccc(C(=O)N5CCOCC5)c4)C3=O)ccc21] | aa69 | 494.3 |
| 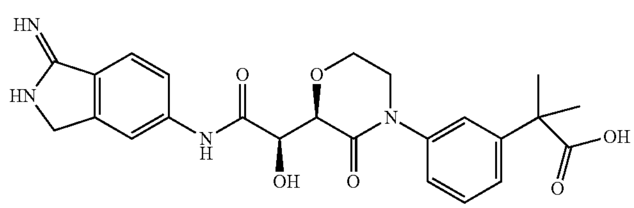 [SMILES: CC(C)(C(=O)O)c1cccc(N2CCO[C@H]([C@@H](O)C(=O)Nc3ccc4c(c3)CNC4=N)C2=O)c1] | aa70 | 467.2 |
| 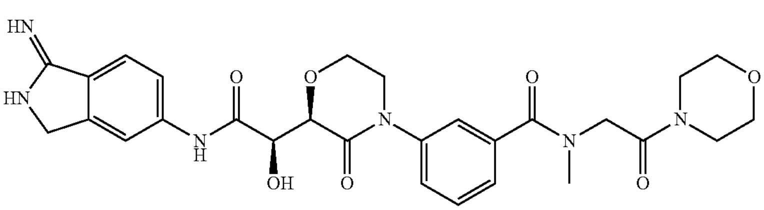 [SMILES: CN(CC(=O)N1CCOCC1)C(=O)c1cccc(N2CCO[C@H]([C@@H](O)C(=O)Nc3ccc4c(c3)CNC4=N)C2=O)c1] | aa71 | 565.3 |
| 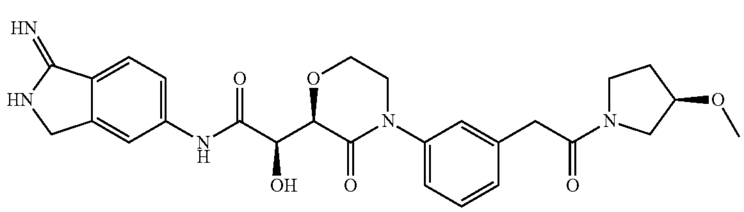 [SMILES: CO[C@@H]1CCN(C(=O)Cc2cccc(N3CCO[C@H]([C@@H](O)C(=O)Nc4ccc5c(c4)CNC5=N)C3=O)c2)C1] | aa72 | 522.3 |

-continued
EXAMPLES aa39-aa94
| Structure | EXAMPLE | M + H |
|---|---|---|
| 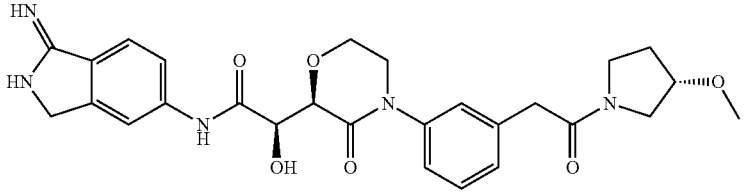 [SMILES: CO[C@H]1CCN(C(=O)Cc2cccc(N3CCO[C@H]([C@@H](O)C(=O)Nc4ccc5c(c4)CNC5=N)C3=O)c2)C1] | aa73 | 522.3 |
| 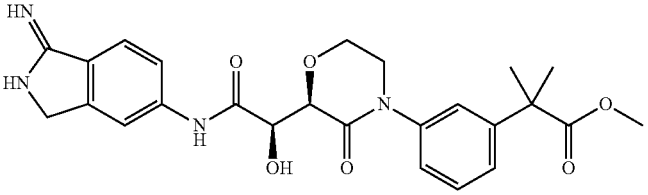 [SMILES: COC(=O)C(C)(C)c1cccc(N2CCO[C@H]([C@@H](O)C(=O)Nc3ccc4c(c3)CNC4=N)C2=O)c1] | aa74 | 481.2 |
| 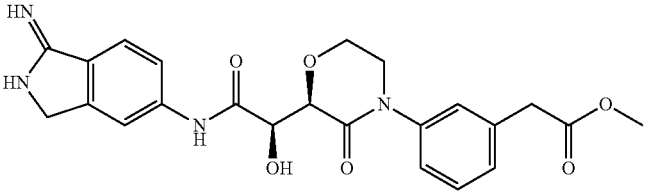 [SMILES: COC(=O)Cc1cccc(N2CCO[C@H]([C@@H](O)C(=O)Nc3ccc4c(c3)CNC4=N)C2=O)c1] | aa75 | 453.2 |
| 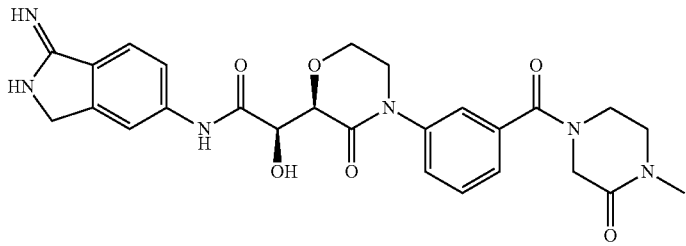 [SMILES: CN1CCN(C(=O)c2cccc(N3CCO[C@H]([C@@H](O)C(=O)Nc4ccc5c(c4)CNC5=N)C3=O)c2)CC1=O] | aa76 | 521.3 |
| 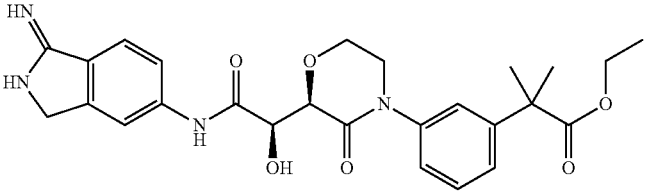 [SMILES: CCOC(=O)C(C)(C)c1cccc(N2CCO[C@H]([C@@H](O)C(=O)Nc3ccc4c(c3)CNC4=N)C2=O)c1] | aa77 | 495.2 |
| 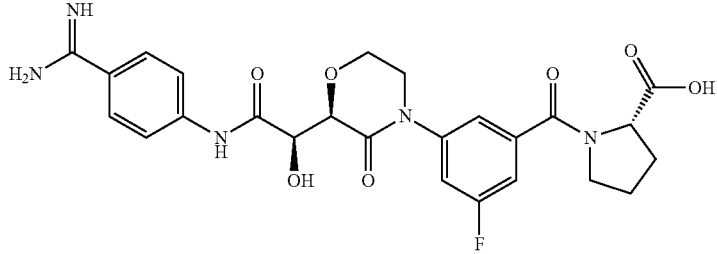 | aa78 | 528.2 |
| 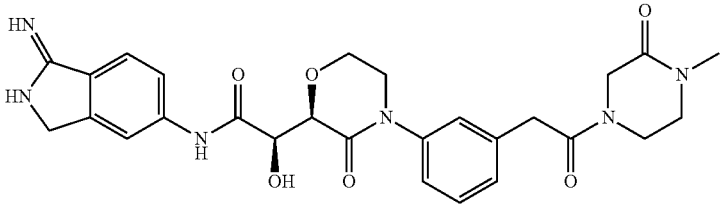 [SMILES: CN1CCN(C(=O)Cc2cccc(N3CCO[C@H]([C@@H](O)C(=O)Nc4ccc5c(c4)CNC5=N)C3=O)c2)CC1=O] | aa79 | 535.3 |

EXAMPLES aa39-aa94

| Structure | EXAMPLE | M + H |
|---|---|---|
| 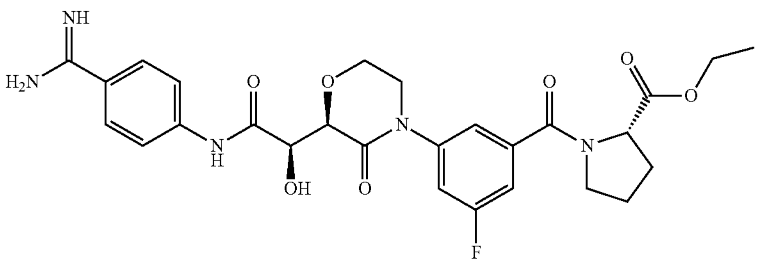 [SMILES: CCOC(=O)[C@@H]1CCCN1C(=O)c1cc(F)cc(N2CCO[C@H]([C@@H](O)C(=O)Nc3ccc(C(=N)N)cc3)C2=O)c1] | aa80 | 556.2 |
| 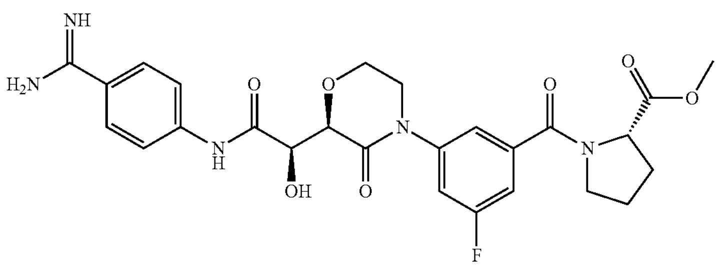 [SMILES: COC(=O)[C@@H]1CCCN1C(=O)c1cc(F)cc(N2CCO[C@H]([C@@H](O)C(=O)Nc3ccc(C(=N)N)cc3)C2=O)c1] | aa81 | 542.2 |
| 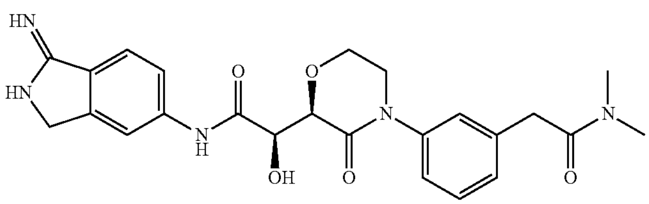 [SMILES: CN(C)C(=O)Cc1cccc(N2CCO[C@H]([C@@H](O)C(=O)Nc3ccc4c(c3)CNC4=N)C2=O)c1] | aa82 | 466.3 |
| 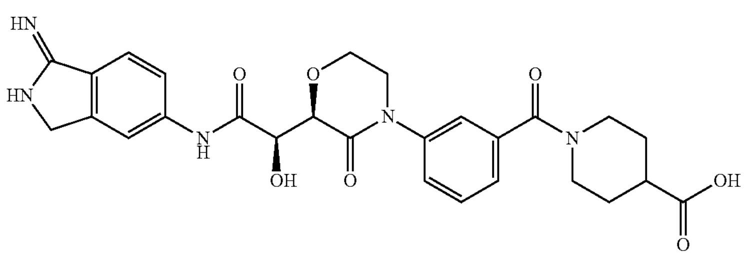 [SMILES: N=C1NCc2cc(NC(=O)[C@H](O)[C@H]3OCCN(c4cccc(C(=O)N5CCC(C(=O)O)CC5)c4)C3=O)ccc21] | aa83 | 536.2 |
| 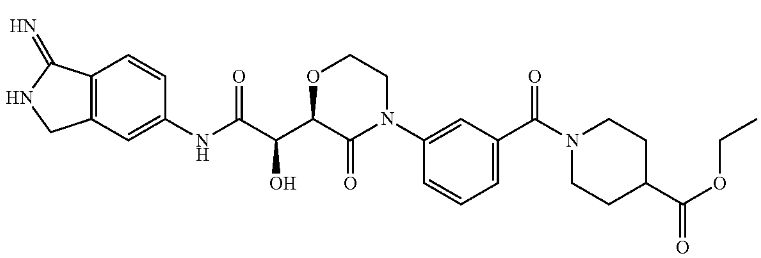 [SMILES: CCOC(=O)C1CCN(C(=O)c2cccc(N3CCO[C@H]([C@@H](O)C(=O)Nc4ccc5c(c4)CNC5=N)C3=O)c2)CC1] | aa84 | 564.2 |
| 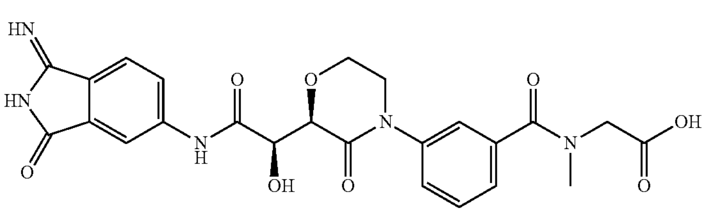 [SMILES: CN(CC(=O)O)C(=O)c1cccc(N2CCO[C@H]([C@@H](O)C(=O)Nc3ccc4c(c3)C(=O)NC4=N)C2=O)c1] | aa85 | 510.2 |

-continued
EXAMPLES aa39-aa94
| Structure | EXAMPLE | M + H |
|---|---|---|
| 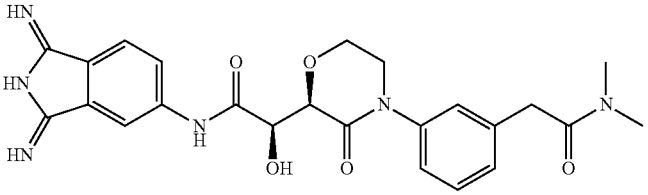 [SMILES: CN(C)C(=O)Cc1cccc(N2CCO[C@H]([C@@H](O)C(=O)Nc3ccc4c(c3)C(=N)NC4=N)C2=O)c1] | aa86 | 479.3 |
| 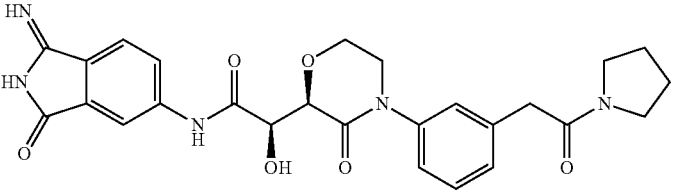 [SMILES: N=C1NC(=O)c2cc(NC(=O)[C@H](O)[C@H]3OCCN(c4cccc(CC(=O)N5CCCC5)c4)C3=O)ccc21] | aa87 | 506.3 |
| 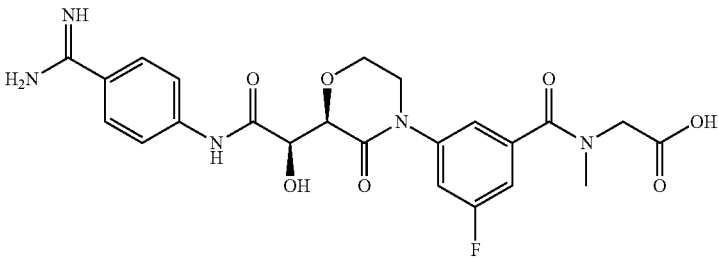 [SMILES: CN(CC(=O)O)C(=O)c1cc(F)cc(N2CCO[C@H]([C@@H](O)C(=O)Nc3ccc(C(=N)N)cc3)C2=O)c1] | aa88 | 502.2 |
| 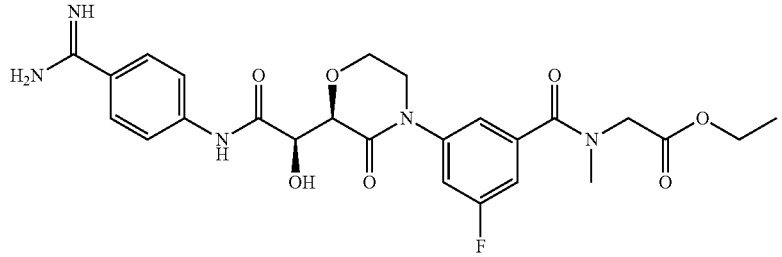 [SMILES: CCOC(=O)CN(C)C(=O)c1cc(F)cc(N2CCO[C@H]([C@@H](O)C(=O)Nc3ccc(C(=N)N)cc3)C2=O)c1] | aa89 | 530.2 |
| 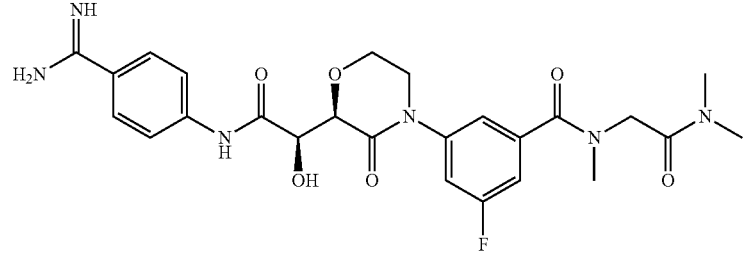 [SMILES: CN(C)C(=O)CN(C)C(=O)c1cc(F)cc(N2CCO[C@H]([C@@H](O)C(=O)Nc3ccc(C(=N)N)cc3)C2=O)c1] | aa90 | 529.3 |
| 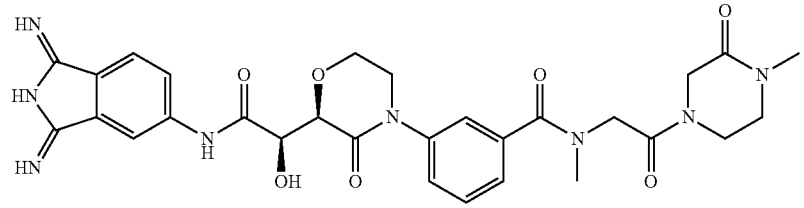 [SMILES: CN1CCN(C(=O)CN(C)C(=O)c2cccc(N3CCO[C@H]([C@@H](O)C(=O)Nc4ccc5c(c4)C(=N)NC5=N)C3=O)c2)CC1=O] | aa91 | 605.3 |

EXAMPLES aa39-aa94
| Structure | EXAMPLE | M + H |
|---|---|---|
| 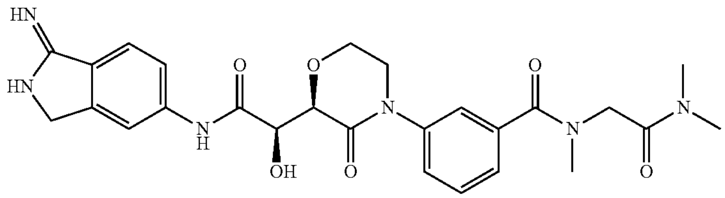 [SMILES: CN(C)C(=O)CN(C)C(=O)c1cccc(N2CCO[C@H]([C@@H](O)C(=O)Nc3ccc4c(c3)CNC4=N)C2=O)c1] | aa92 | 523.3 |
| 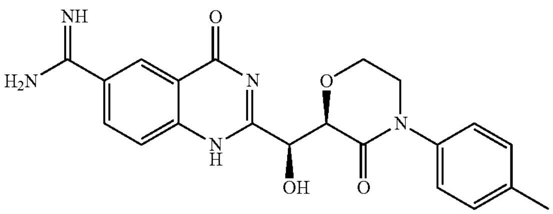 [SMILES: Cc1ccc(N2CCO[C@H]([C@@H](O)c3nc(=O)c4cc(C(=N)N)ccc4[nH]3)C2=O)cc1] | aa93 | 408.2 |
| 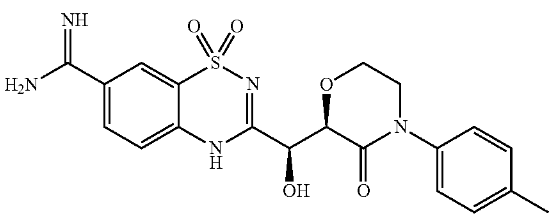 [SMILES: Cc1ccc(N2CCO[C@H]([C@@H](O)C3=NS(=O)(=O)c4cc(C(=N)N)ccc4N3)C2=O)cc1] | aa94 | 444.2 |
Example aa39
Preparation of (R)—N-(4-carbamimidoylphenyl)-2-hydroxy-2-((R)-4-(3-((S)-2-methylpyrrolidine-1-carbonyl)phenyl)-3-oxomorpholin-2-yl)acetamide
EXAMPLE aa39
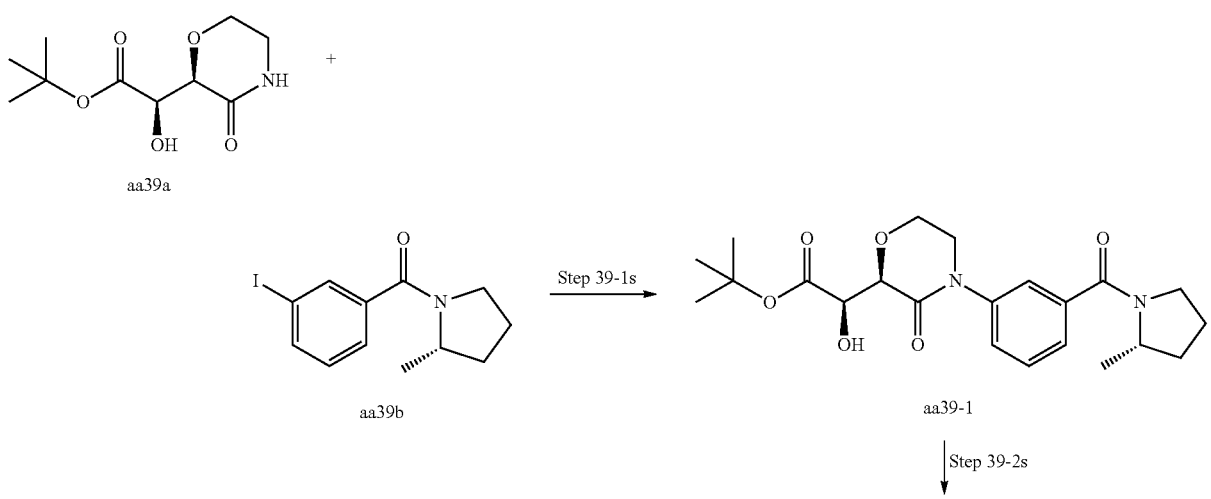

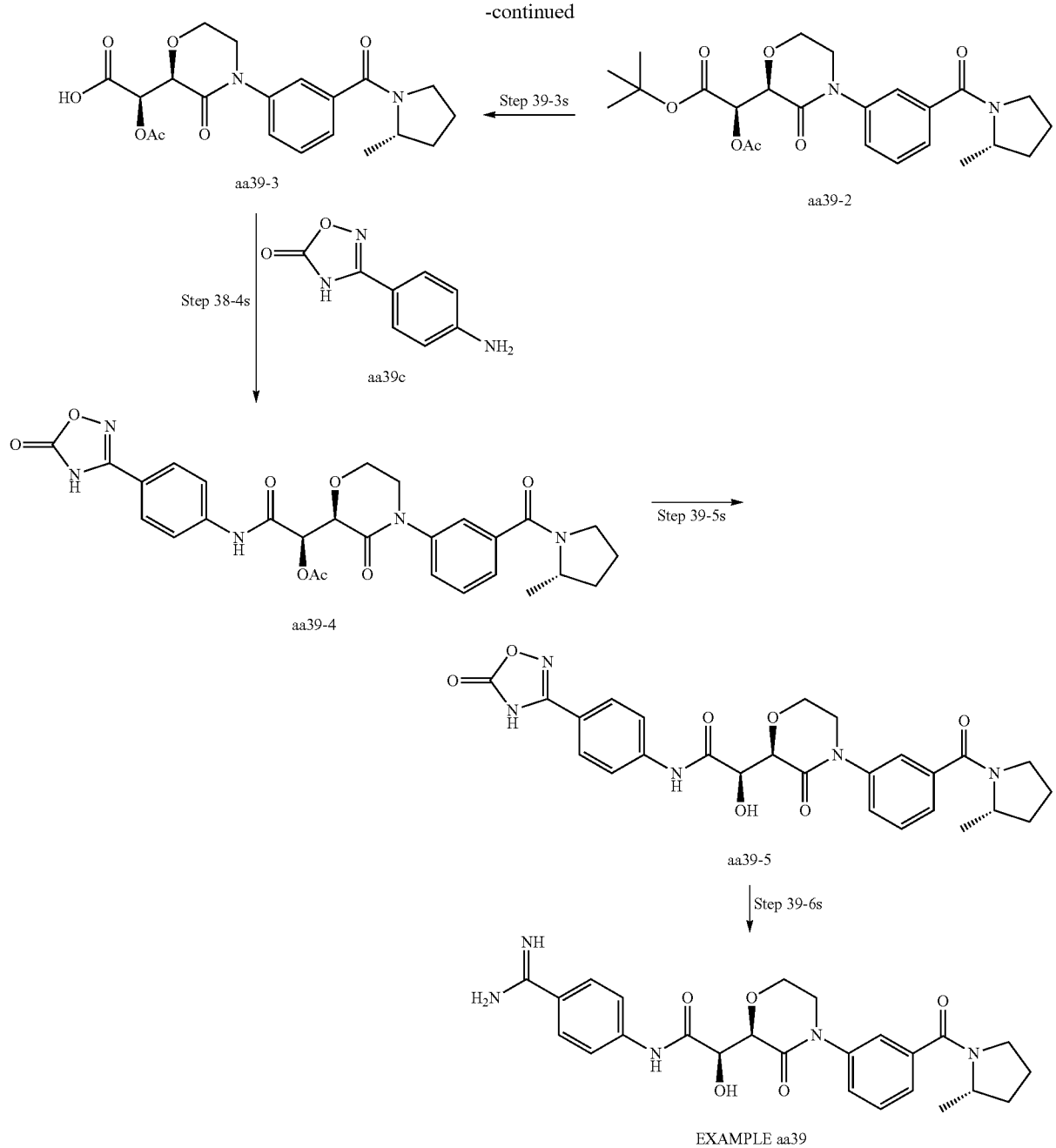

Step 39-1s

To a solution of aa39a (150 mg, 0.65 mmol) in anhydrous DMSO (8 mL) under a nitrogen atmosphere was added aa39b (225 mg, 0.71 mmol), potassium phosphate (275 mg, 1.30 mmol), copper (I) iodide (12 mg, 0.063 mmol) and trans-N,N'-dimethylcyclohexane-1,2-diamine (18 mg, 0.13 mmol). The reaction mixture was heated at 80° C. for 2 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired aa39-1 (170 mg, 0.41 mmol).

Step 39-2s

To a solution of aa39-1 (170 mg, 0.41 mmol) in anhydrous dichloromethane (6 mL) under a nitrogen atmosphere was added acetic anhydride (84 mg, 0.82 mmol), DMAP (5.0 mg, 0.041 mmol) and triethylamine (124 mg, 1.23 mmol). The reaction mixture was stirred at room temperature for 1 hour. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired aa39-2 (179 mg, 0.39 mmol).

Step 39-2s

To aa39-2 (179 mg, 0.39 mmol) was added a 50% solution of trifluoroacetic acid in dichloromethane (8 mL). The reaction mixture was stirred at room temperature for 16 hours. The organic solvent was evaporated under reduced pressure to afford the desired aa39-3 (0.39 mmol) which was used in the next step without further purification.

Step 39-4s

To a solution of aa39-3 (0.39 mmol) in acetonitrile (8 mL) was added aa39c (114 mg, 0.64 mmol), EDCI (107 mg, 0.56 mmol) and DMAP (5 mg, 0.041 mmol). The reaction mixture was stirred at room temperature for 2 hour. The organic solvent was evaporated under reduced pressure. The crude product was purified by flash column chromatography to afford the desired aa39-4 (208 mg, 0.37 mmol).

Step 39-5s

To aa39-4 (208 mg, 0.37 mmol) was added a solution of 7 N ammonia in methanol (8 mL). The reaction mixture was stirred at room temperature for 40 minutes. The organic solvent was evaporated under reduced pressure to afford the desired aa39-5 (0.37 mmol) which was used in the next step without further purification.

Step 39-6s

To a solution of aa39-5 (0.37 mmol) in a 50% solution of 1 N hydrochloric acid in methanol (5 mL) was added palladium-charcoal (10%, 200 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE aa39 (171 mg, 0.36 mmol) as a white amorphous solid.

Example aa40

Preparation of methyl 2-(3-((R)-2-((R)-2-(4-carbamimidoylphenylamino)-1-hydroxy-2-oxoethyl)-3-oxomorpholino)phenyl)acetate EXAMPLE aa40

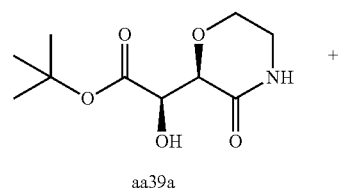

aa39a

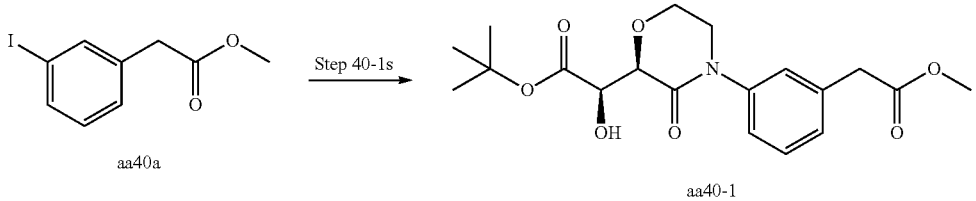

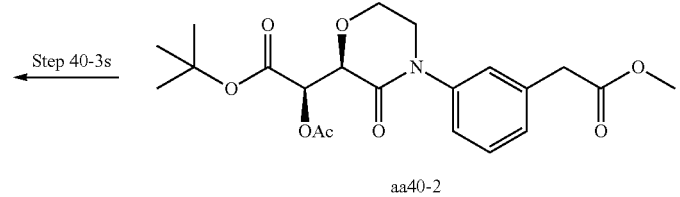

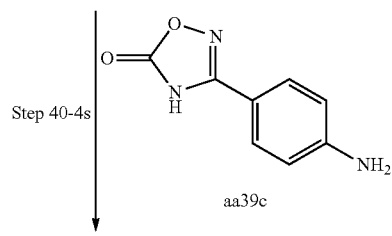

-continued

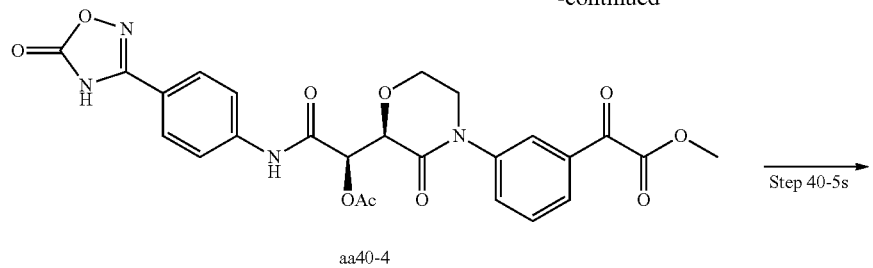

aa40-4

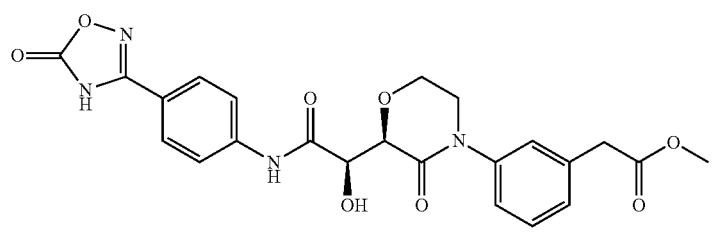

aa40-5

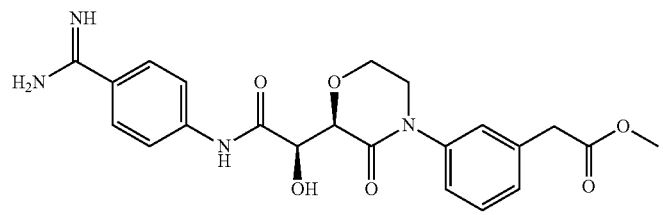

EXAMPLE aa40

Step 40-1s

According to Step 39-1s in the synthetic method for EXAMPLE aa39, compound aa40a (420 mg, 1.52 mmol) was used instead of compound aa39b to obtain compound aa40-1 (468 mg, 1.23 mmol).

Step 40-2s

According to Step 39-2s in the synthetic method for EXAMPLE aa39, compound aa40-1 (468 mg, 1.23 mmol) was used instead of compound aa39-1 to obtain compound aa40-2 (484 mg, 1.15 mmol).

Step 40-3s

According to Step 39-3s in the synthetic method for EXAMPLE aa39, compound aa40-2 (332 mg, 0.79 mmol) was used instead of compound aa39-2 to obtain compound aa40-3 (0.79 mmol) which was used in the next step without further purification.

Step 40-4s

According to Step 39-4s in the synthetic method for EXAMPLE aa39, compound aa40-3 (0.79 mmol) was used instead of compound aa39-3 to obtain compound aa40-4 (381 mg, 0.73 mmol).

Step 40-5s

According to Step 39-5s in the synthetic method for EXAMPLE aa39, compound aa40-4 (190 mg, 0.36 mmol) was used instead of compound aa39-4 to obtain compound aa40-5 (93 mg, 0.19 mmol) which was used in the next step without further purification.

Step 40-6s

According to Step 39-6s in the synthetic method for EXAMPLE aa39, compound aa40-5 (93 mg, 0.19 mmol) was used instead of compound aa39-5 to obtain EXAMPLE aa40 (65 mg, 0.15 mmol) as a white amorphous solid.

Example aa41
Preparation of (R)—N-(4-carbamimidoylphenyl)-2-hydroxy-2-((R)-4-(2-methyl-3-(morpholine-4-carbonyl)phenyl)-3-oxomorpholin-2-yl)acetamide EXAMPLE aa41
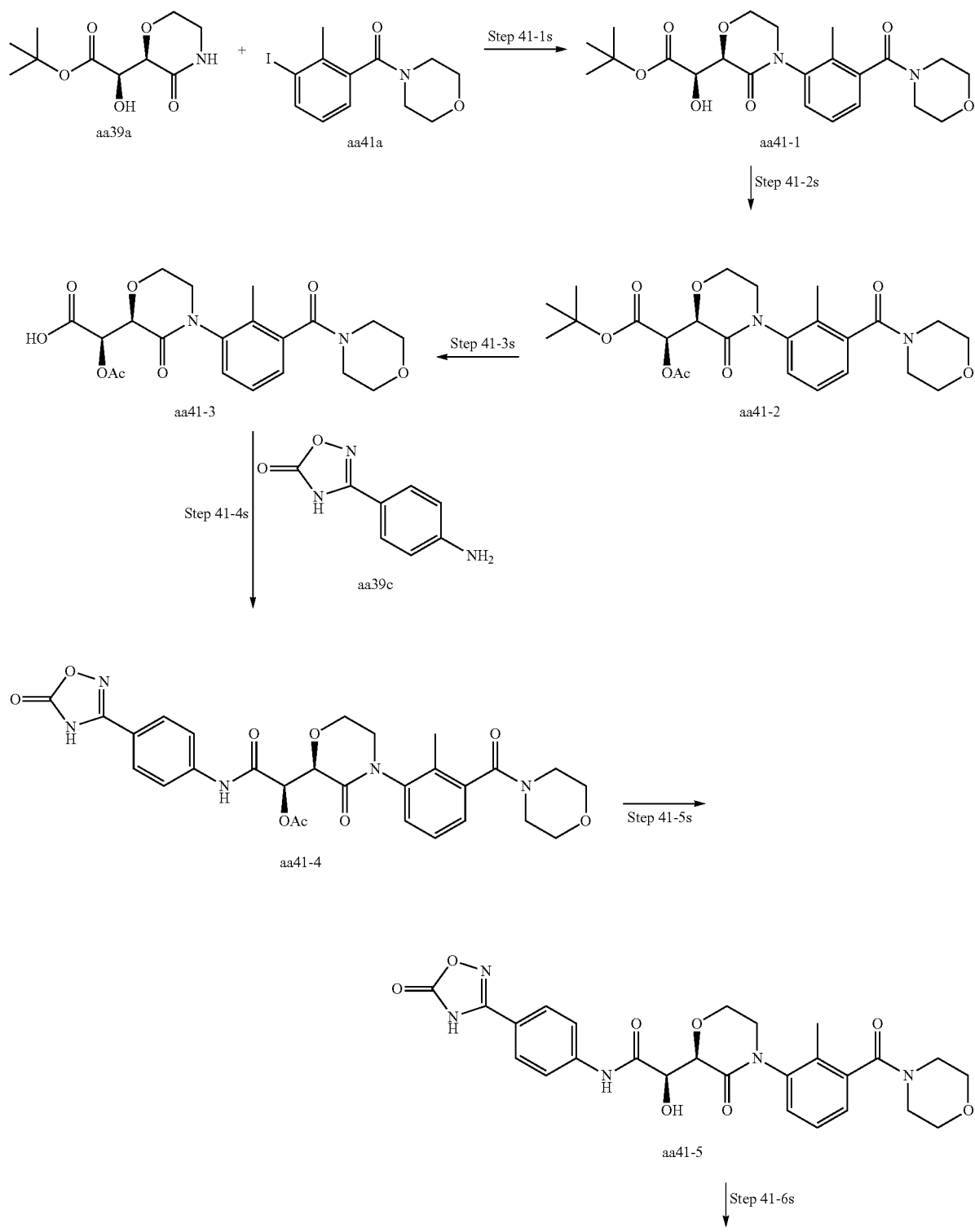

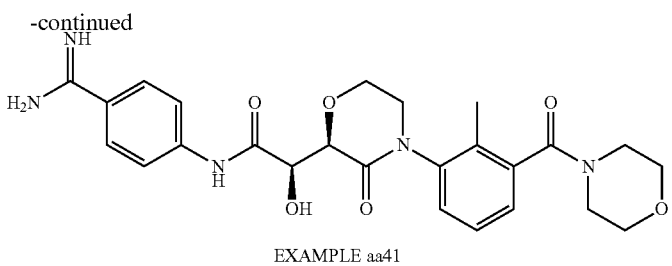

EXAMPLE aa41

Step 41-1s

According to Step 39-1s in the synthetic method for EXAMPLE aa39, compound aa41a (236 mg, 0.71 mmol) was used instead of compound aa39b to obtain compound aa41-1 (81 mg, 0.19 mmol).

Step 41-2s

According to Step 39-2s in the synthetic method for EXAMPLE aa39, compound aa41-1 (81 mg, 0.19 mmol) was used instead of compound aa39-1 to obtain compound aa40-2 (82 mg, 0.17 mmol).

Step 41-3s

According to Step 39-3s in the synthetic method for EXAMPLE aa39, compound aa41-2 (82 mg, 0.17 mmol) was used instead of compound aa39-2 to obtain compound aa41-3 (0.17 mmol) which was used in the next step without further purification.

Step 41-4s

According to Step 39-4s in the synthetic method for EXAMPLE aa39, compound aa41-3 (0.17 mmol) was used instead of compound aa39-3 to obtain compound aa41-4 (50 mg, 0.086 mmol).

Step 41-5s

According to Step 39-5s in the synthetic method for EXAMPLE aa39, compound aa41-4 (50 mg, 0.086 mmol) was used instead of compound aa39-4 to obtain compound aa41-5 (0.086 mmol) which was used in the next step without further purification.

Step 41-6s

According to Step 39-6s in the synthetic method for EXAMPLE aa39, compound aa41-5 (0.086 mmol) was used instead of compound aa39-5 to obtain EXAMPLE aa41 (21 mg, 0.042 mmol) as a white amorphous solid.

Example aa42

Preparation of (R)—N-(4-carbamimidoylphenyl)-2-hydroxy-2-((R)-4-(2-methyl-3-(pyrrolidine-1-carbonyl)phenyl)-3-oxomorpholin-2-yl)acetamide EXAMPLE aa42

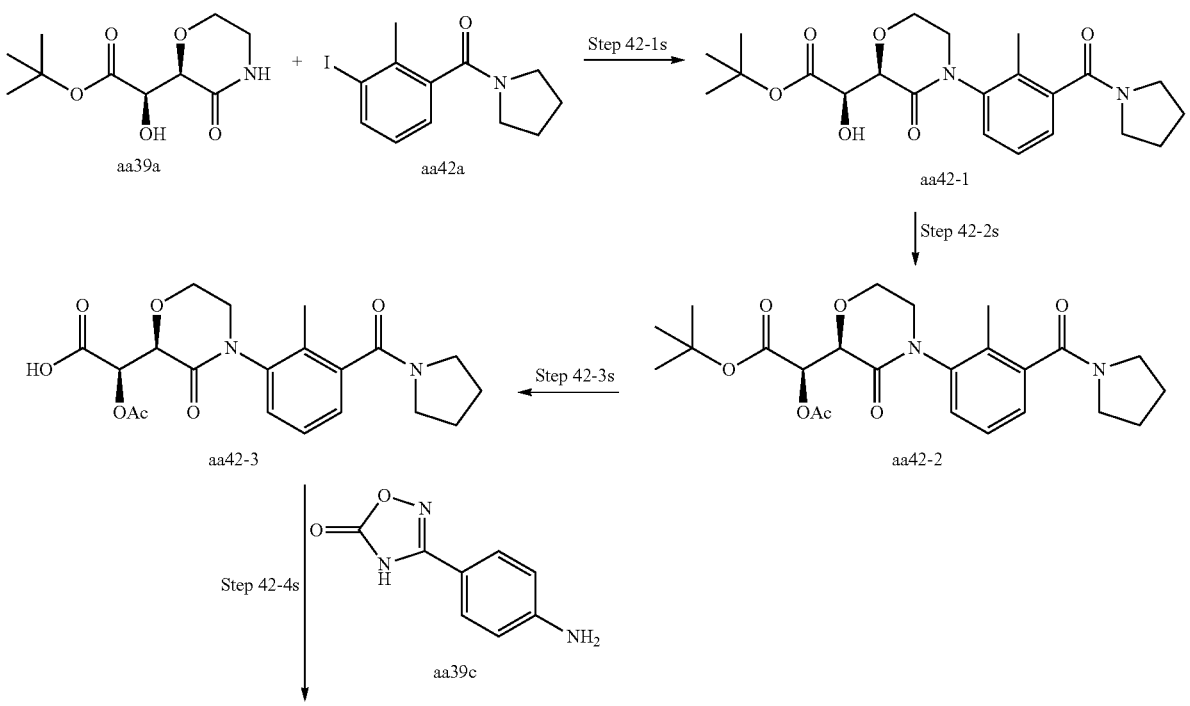

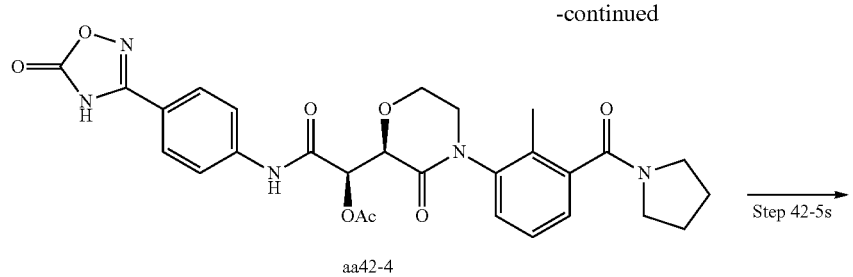

aa42-4

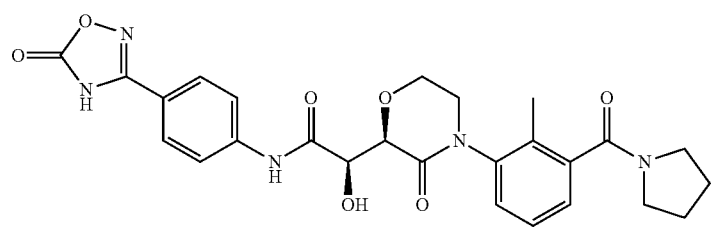

aa42-5

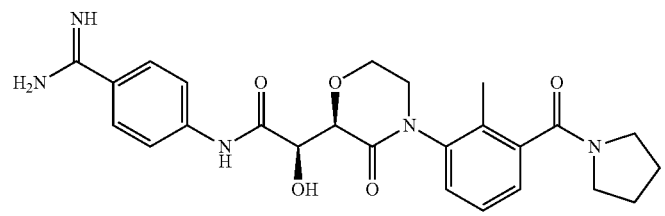

EXAMPLE aa42

Step 42-1s

According to Step 39-1s in the synthetic method for EXAMPLE aa39, compound aa42a (225 mg, 0.71 mmol) was used instead of compound aa39b to obtain compound aa42-1 (92 mg, 0.22 mmol).

Step 42-2s

According to Step 39-2s in the synthetic method for EXAMPLE aa39, compound aa42-1 (92 mg, 0.22 mmol) was used instead of compound aa39-1 to obtain compound aa42-2 (88 mg, 0.19 mmol).

Step 42-3s

According to Step 39-3s in the synthetic method for EXAMPLE aa39, compound aa42-2 (88 mg, 0.19 mmol) was used instead of compound aa39-2 to obtain compound aa42-3 (0.19 mmol) which was used in the next step without further purification.

Step 42-4s

According to Step 39-4s in the synthetic method for EXAMPLE aa39, compound aa42-3 (0.19 mmol) was used instead of compound aa39-3 to obtain compound aa42-4 (70 mg, 0.12 mmol).

Step 42-5s

According to Step 39-5s in the synthetic method for EXAMPLE aa39, compound aa42-4 (70 mg, 0.12 mmol) was used instead of compound aa39-4 to obtain compound aa42-5 (0.12 mmol) which was used in the next step without further purification.

Step 42-6s

According to Step 39-6s in the synthetic method for EXAMPLE aa39, compound aa42-5 (0.12 mmol) was used instead of compound aa39-5 to obtain EXAMPLE aa42 (28 mg, 0.058 mmol) as a white amorphous solid.

Example aa43
Preparation of (R)-2-((R)-4-(3-(azetidine-1-carbonyl)-5-fluorophenyl)-3-oxomorpholin-2-yl)-N-(4-carbamimidoylphenyl)-2-hydroxyacetamide
EXAMPLE aa43
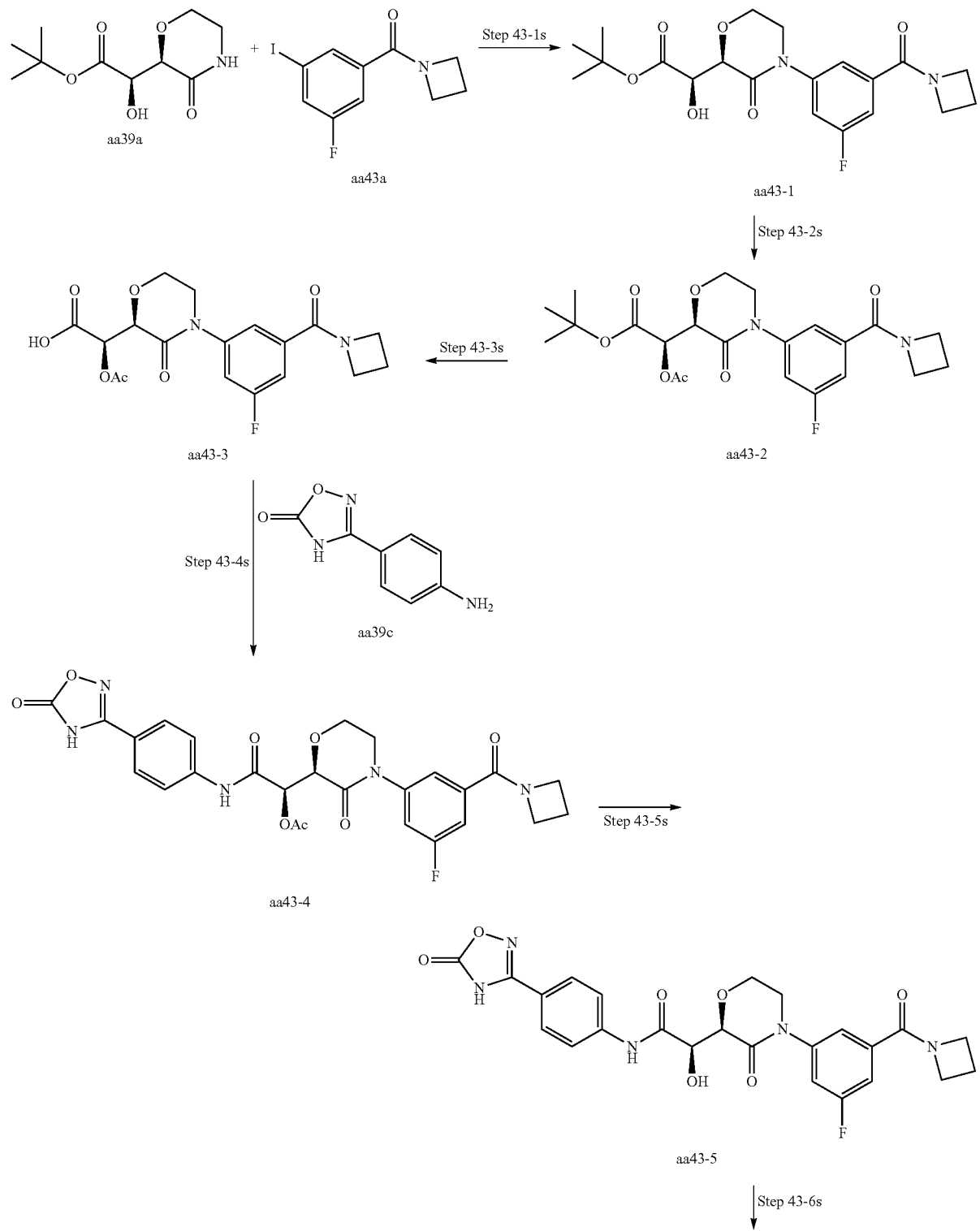

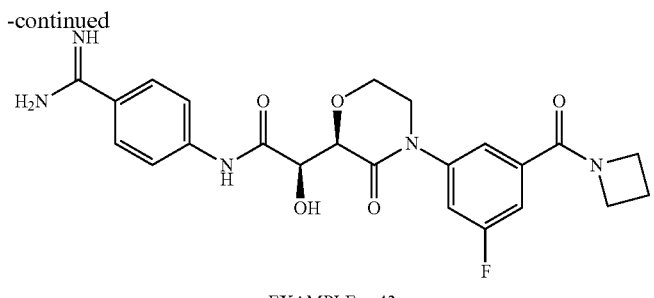

EXAMPLE aa43

Step 43-1s

According to Step 39-1s in the synthetic method for EXAMPLE aa39, compound aa42a (290 mg, 0.95 mmol) was used instead of compound aa39b to obtain compound aa43-1 (243 mg, 0.60 mmol).

Step 43-2s

According to Step 39-2s in the synthetic method for EXAMPLE aa39, compound aa43-1 (243 mg, 0.60 mmol) was used instead of compound aa39-1 to obtain compound aa43-2 (0.60 mmol).

Step 43-3s

According to Step 39-3s in the synthetic method for EXAMPLE aa39, compound aa43-2 (0.60 mmol) was used instead of compound aa39-2 to obtain compound aa43-3 (0.60 mmol) which was used in the next step without further purification.

Step 43-4s

According to Step 39-4s in the synthetic method for EXAMPLE aa39, compound aa43-3 (0.60 mmol) was used instead of compound aa39-3 to obtain compound aa43-4 (316 mg, 0.57 mmol).

Step 43-5s

According to Step 39-5s in the synthetic method for EXAMPLE aa39, compound aa43-4 (316 mg, 0.57 mmol) was used instead of compound aa39-4 to obtain compound aa43-5 (0.57 mmol) which was used in the next step without further purification.

Step 43-6s

According to Step 39-6s in the synthetic method for EXAMPLE aa39, compound aa43-5 (0.57 mmol) was used instead of compound aa39-5 to obtain EXAMPLE aa43 (237 mg, 0.51 mmol) as a white amorphous solid.

Example aa44

Preparation of (R)-2-((R)-4-(3-(azetidine-1-carbonyl)-2-methylphenyl)-3-oxomorpholin-2-yl)-N-(4-carbamimidoylphenyl)-2-hydroxyacetamide EXAMPLE aa44

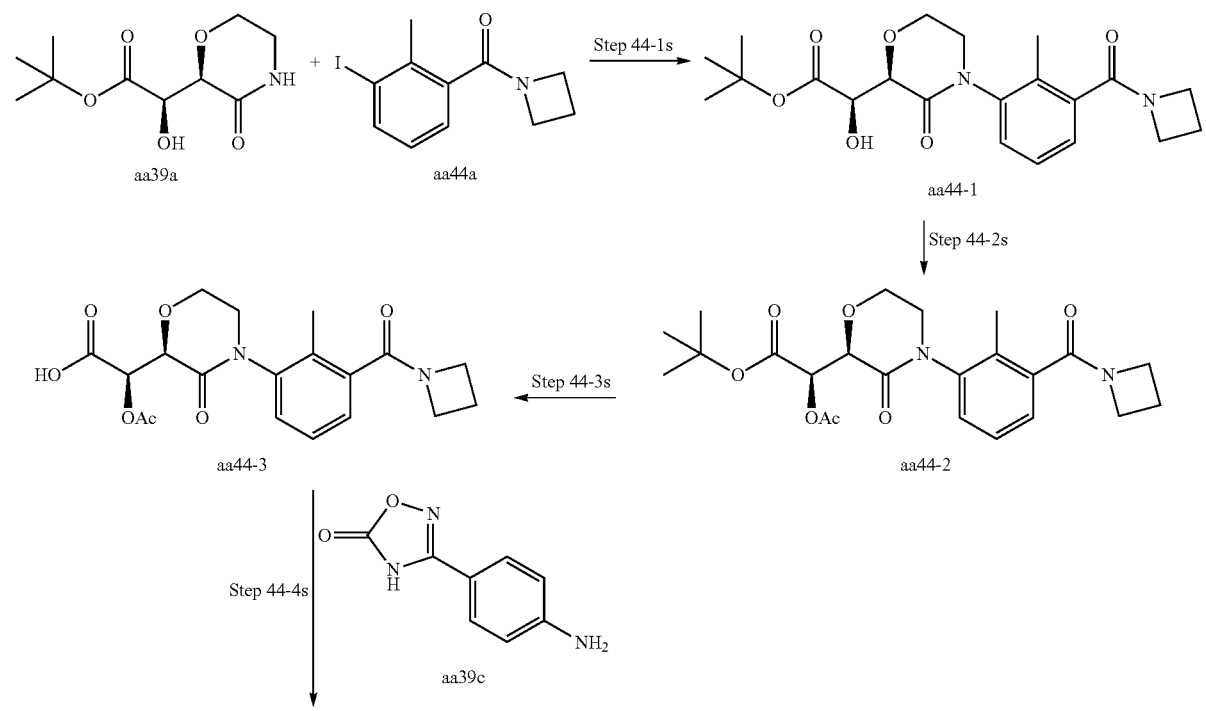

-continued

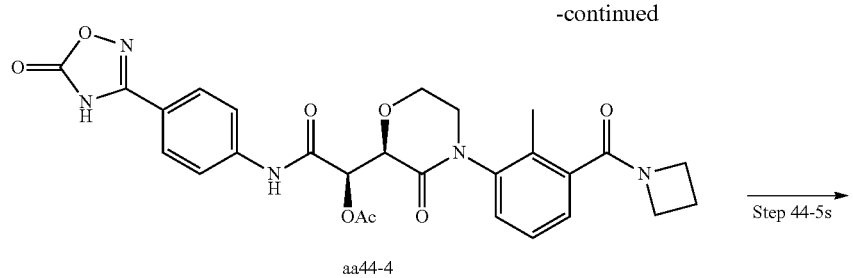

aa44-4

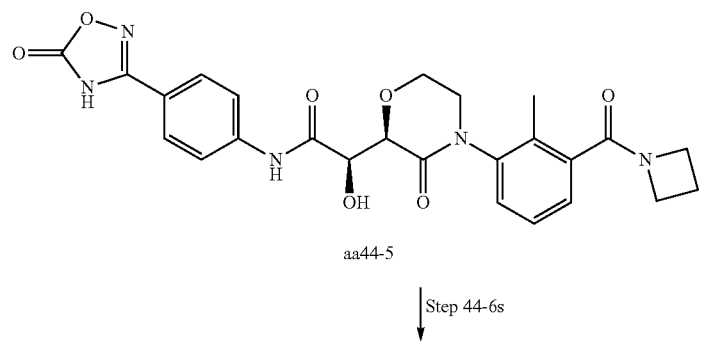

aa44-5

[structure]

EXAMPLE aa44

Step 44-1s

According to Step 39-1s in the synthetic method for EXAMPLE aa39, compound aa44a (300 mg, 1.00 mmol) was used instead of compound aa39b to obtain compound aa44-1 (129 mg, 0.32 mmol).

Step 44-2s

According to Step 39-2s in the synthetic method for EXAMPLE aa39, compound aa44-1 (129 mg, 0.32 mmol) was used instead of compound aa39-1 to obtain compound aa44-2 (144 mg, 0.32 mmol).

Step 44-3s

According to Step 39-3s in the synthetic method for EXAMPLE aa39, compound aa44-2 (144 mg, 0.32 mmol) was used instead of compound aa39-2 to obtain compound aa44-3 (0.32 mmol) which was used in the next step without further purification.

Step 44-4s

According to Step 39-4s in the synthetic method for EXAMPLE aa39, compound aa44-3 (0.32 mmol) was used instead of compound aa39-3 to obtain compound aa44-4 (48 mg, 0.087 mmol).

Step 44-5s

According to Step 39-5s in the synthetic method for EXAMPLE aa39, compound aa44-4 (48 mg, 0.087 mmol) was used instead of compound aa39-4 to obtain compound aa44-5 (0.087 mmol) which was used in the next step without further purification.

Step 44-6s

According to Step 39-6s in the synthetic method for EXAMPLE aa39, compound aa44-5 (0.087 mmol) was used instead of compound aa39-5 to obtain EXAMPLE aa44 (33 mg, 0.071 mmol) as a white amorphous solid.

Example aa45
Preparation of (R)-2-((R)-4-(5-(azetidine-1-carbonyl)-2-methylphenyl)-3-oxomorpholin-2-yl)-N-(4-carbamimidoylphenyl)-2-hydroxyacetamide
EXAMPLE aa45
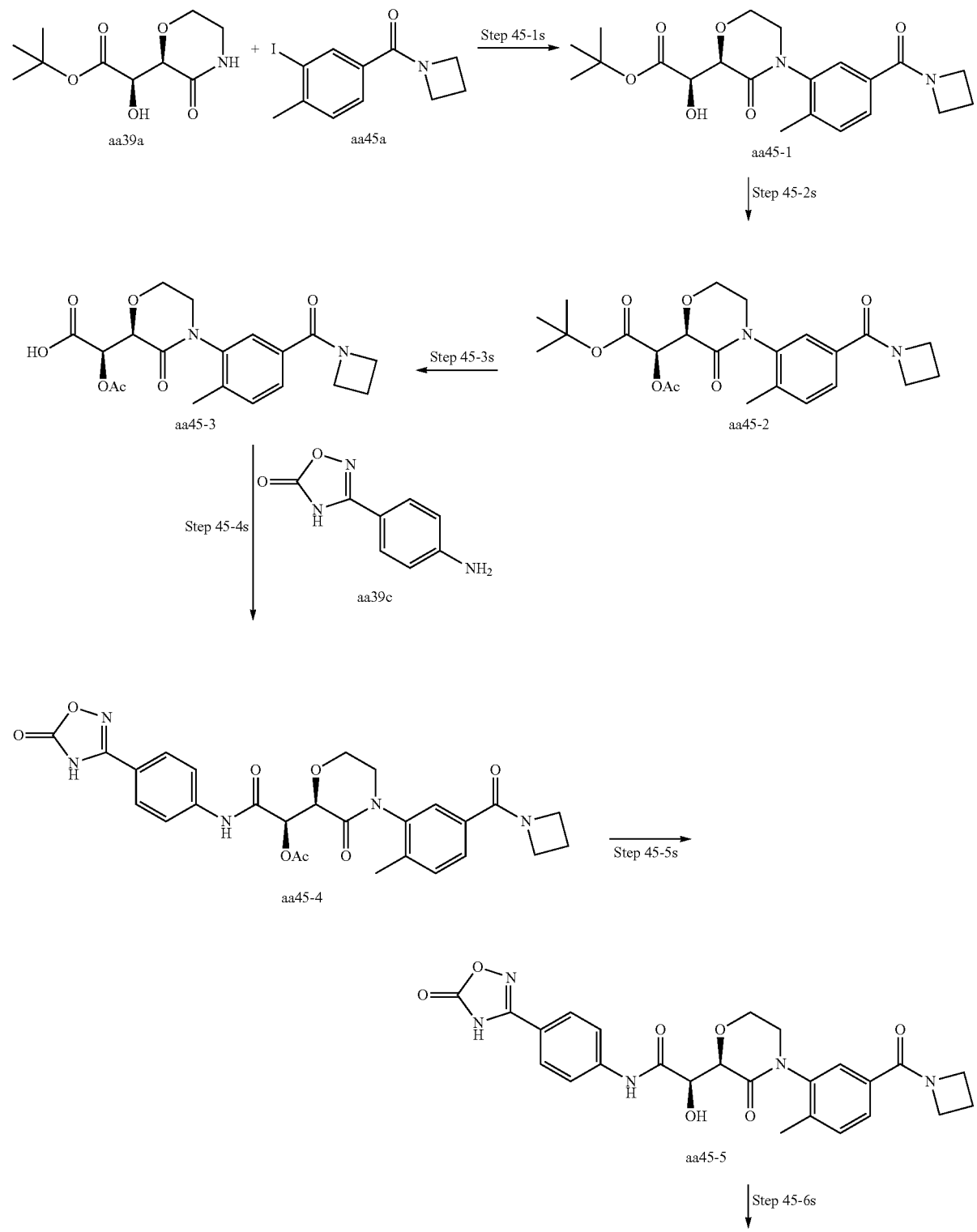

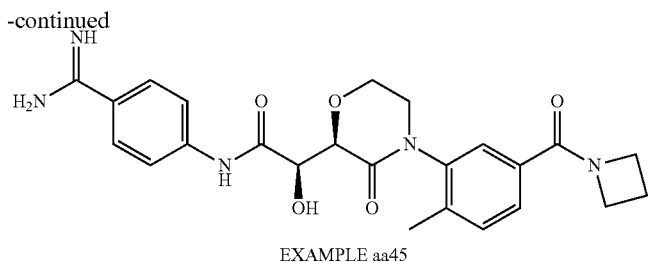

EXAMPLE aa45

Step 45-1s

According to Step 39-1s in the synthetic method for EXAMPLE aa39, compound aa45a (282 mg, 0.94 mmol) was used instead of compound aa39b to obtain compound aa45-1 (186 mg, 0.46 mmol).

Step 45-2s

According to Step 39-2s in the synthetic method for EXAMPLE aa39, compound aa45-1 (186 mg, 0.46 mmol) was used instead of compound aa39-1 to obtain compound aa45-2 (96 mg, 0.22 mmol).

Step 45-3s

According to Step 39-3s in the synthetic method for EXAMPLE aa39, compound aa45-2 (96 mg, 0.22 mmol) was used instead of compound aa39-2 to obtain compound aa45-3 (0.22 mmol) which was used in the next step without further purification.

Step 45-4s

According to Step 39-4s in the synthetic method for EXAMPLE aa39, compound aa45-3 (0.22 mmol) was used instead of compound aa39-3 to obtain compound aa45-4 (117 mg, 0.21 mmol).

Step 45-5s

According to Step 39-5s in the synthetic method for EXAMPLE aa39, compound aa45-4 (117 mg, 0.21 mmol) was used instead of compound aa39-4 to obtain compound aa45-5 (0.21 mmol) which was used in the next step without further purification.

Step 45-6s

According to Step 39-6s in the synthetic method for EXAMPLE aa39, compound aa45-5 (0.21 mmol) was used instead of compound aa39-5 to obtain EXAMPLE aa45 (48 mg, 0.10 mmol) as a white amorphous solid.

Example aa46

Preparation of (R)—N-(4-carbamimidoylphenyl)-2-hydroxy-2-((R)-3-oxo-4-(6-(trifluoromethyl)pyridin-2-yl)morpholin-2-yl)acetamide EXAMPLE aa46

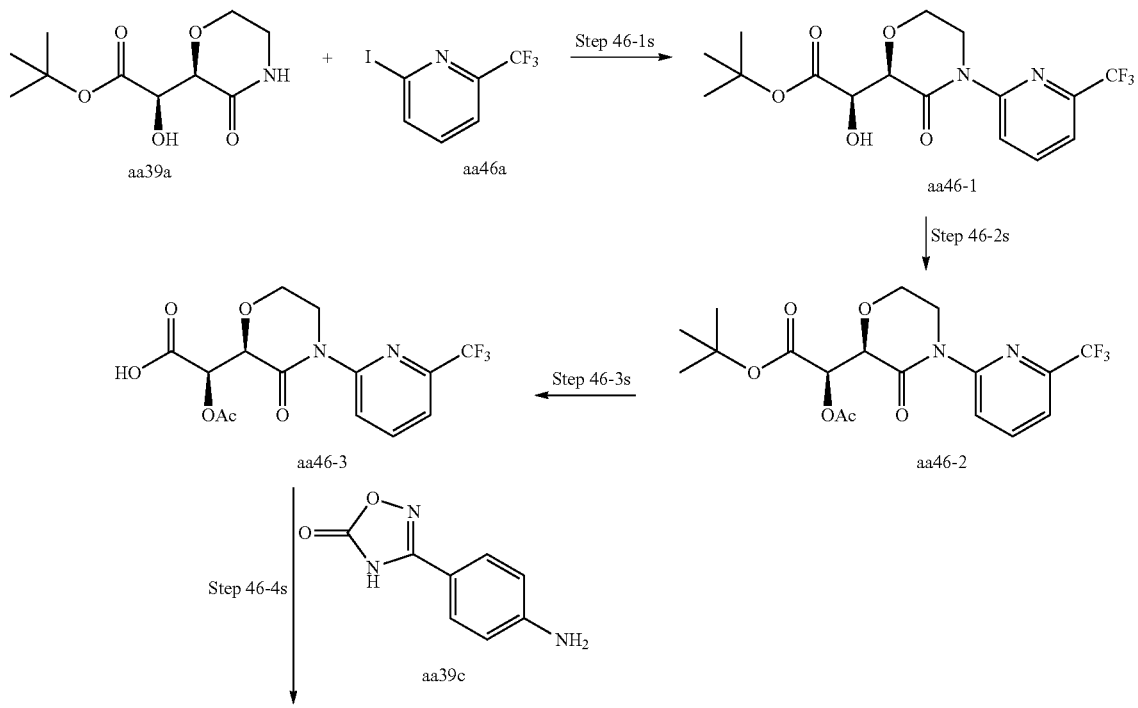

-continued

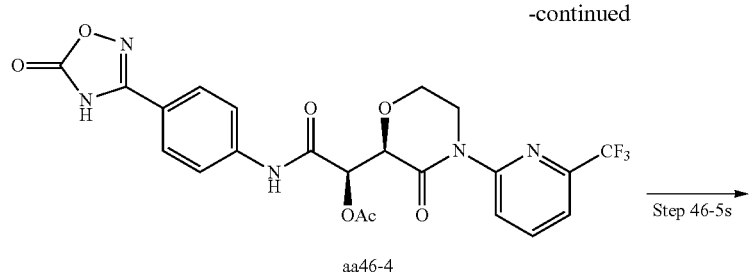

aa46-4

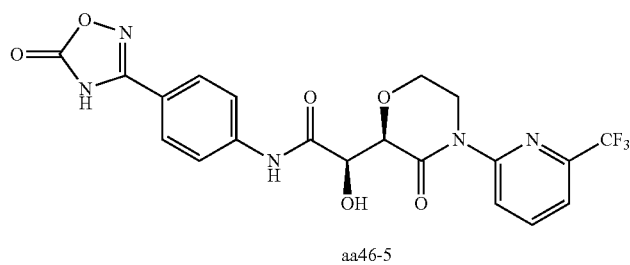

aa46-5

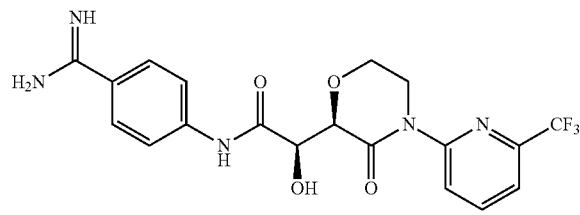

EXAMPLE aa46

Step 46-1s

According to Step 39-1s in the synthetic method for EXAMPLE aa39, compound aa46a (500 mg, 1.83 mmol) was used instead of compound aa39b to obtain compound aa46-1 (380 mg, 1.01 mmol).

Step 46-2s

According to Step 39-2s in the synthetic method for EXAMPLE aa39, compound aa46-1 (380 mg, 1.01 mmol) was used instead of compound aa39-1 to obtain compound aa46-2 (1.01 mmol).

Step 46-3s

According to Step 39-3s in the synthetic method for EXAMPLE aa39, compound aa46-2 (222 mg, 0.53 mmol) was used instead of compound aa39-2 to obtain compound aa46-3 (0.53 mmol) which was used in the next step without further purification.

Step 46-4s

According to Step 39-4s in the synthetic method for EXAMPLE aa39, compound aa46-3 (0.53 mmol) was used instead of compound aa39-3 to obtain compound aa46-4 (155 mg, 0.30 mmol).

Step 46-5s

According to Step 39-5s in the synthetic method for EXAMPLE aa39, compound aa46-4 (155 mg, 0.30 mmol) was used instead of compound aa39-4 to obtain compound aa46-5 (0.30 mmol) which was used in the next step without further purification.

Step 46-6s

According to Step 39-6s in the synthetic method for EXAMPLE aa39, compound aa46-5 (0.30 mmol) was used instead of compound aa39-5 to obtain EXAMPLE aa46 (59 mg, 0.14 mmol) as a white amorphous solid.

Example aa47
Preparation of (R)—N-(4-carbamimidoylphenyl)-2-hydroxy-2-((R)-4-(2-methyl-5-(pyrrolidine-1-carbonyl)phenyl)-3-oxomorpholin-2-yl)acetamide
EXAMPLE aa47
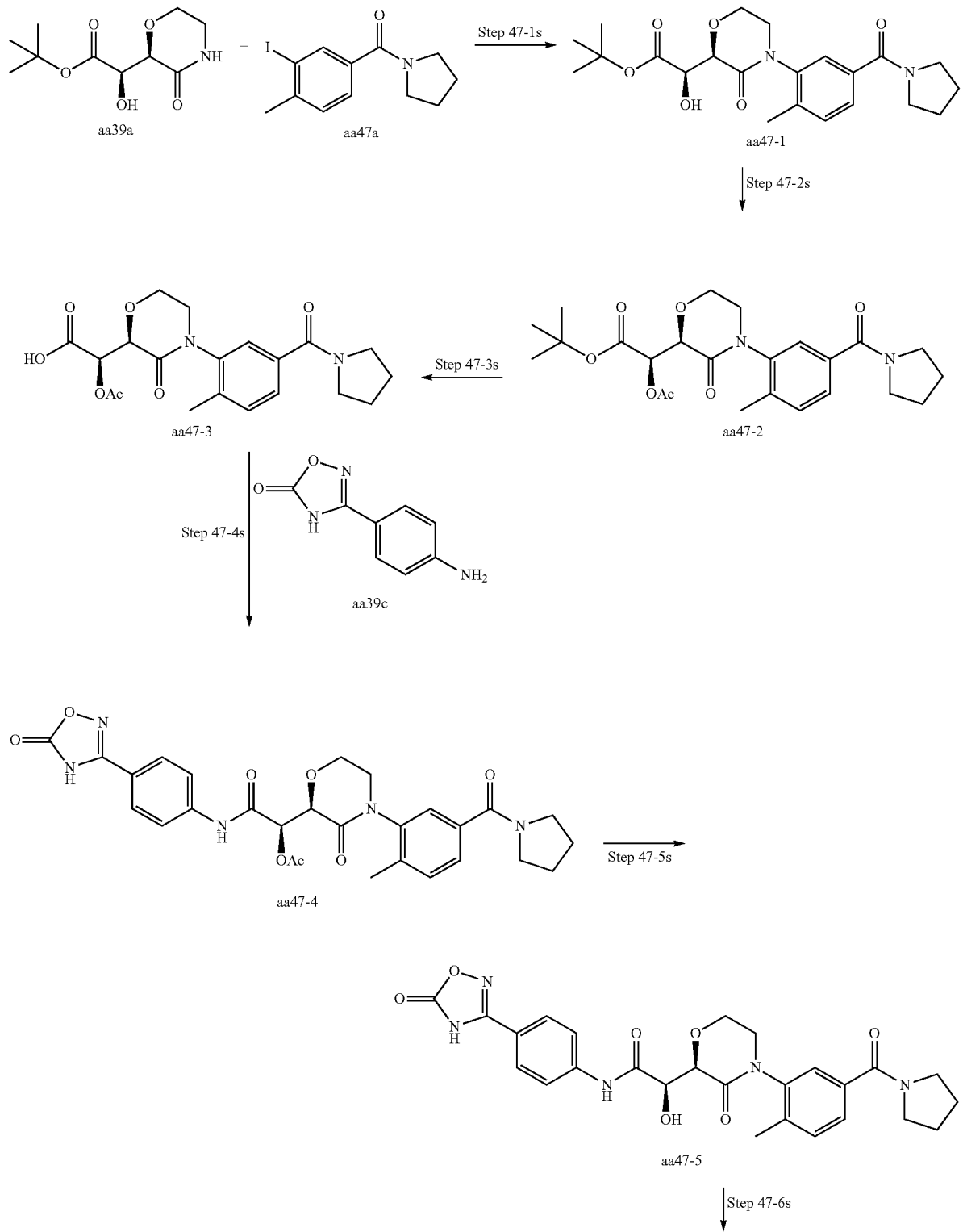

-continued

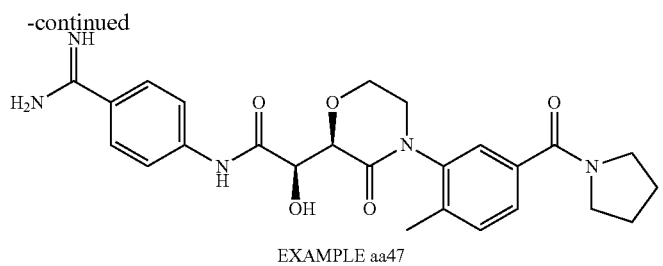

EXAMPLE aa47

Step 47-1s

According to Step 39-1s in the synthetic method for EXAMPLE aa39, compound aa47a (300 mg, 0.95 mmol) was used instead of compound aa39b to obtain compound aa47-1 (338 mg, 0.81 mmol).

Step 47-2s

According to Step 39-2s in the synthetic method for EXAMPLE aa39, compound aa47-1 (338 mg, 0.81 mmol) was used instead of compound aa39-1 to obtain compound aa47-2 (146 mg, 0.32 mmol).

Step 47-3s

According to Step 39-3s in the synthetic method for EXAMPLE aa39, compound aa47-2 (146 mg, 0.32 mmol) was used instead of compound aa39-2 to obtain compound aa47-3 (0.32 mmol) which was used in the next step without further purification.

Step 47-4s

According to Step 39-4s in the synthetic method for EXAMPLE aa39, compound aa47-3 (0.32 mmol) was used instead of compound aa39-3 to obtain compound aa47-4 (163 mg, 0.29 mmol).

Step 47-5s

According to Step 39-5s in the synthetic method for EXAMPLE aa39, compound aa47-4 (163 mg, 0.29 mmol) was used instead of compound aa39-4 to obtain compound aa47-5 (0.29 mmol) which was used in the next step without further purification.

Step 47-6s

According to Step 39-6s in the synthetic method for EXAMPLE aa39, compound aa47-5 (0.29 mmol) was used instead of compound aa39-5 to obtain EXAMPLE aa47 (115 mg, 0.24 mmol) as a white amorphous solid.

Example aa48

Preparation of (R)-2-((R)-4-(3-(azetidine-1-carbonyl)-5-methylphenyl)-3-oxomorpholin-2-yl)-N-(4-carbamimidoylphenyl)-2-hydroxyacetamide
EXAMPLE aa48

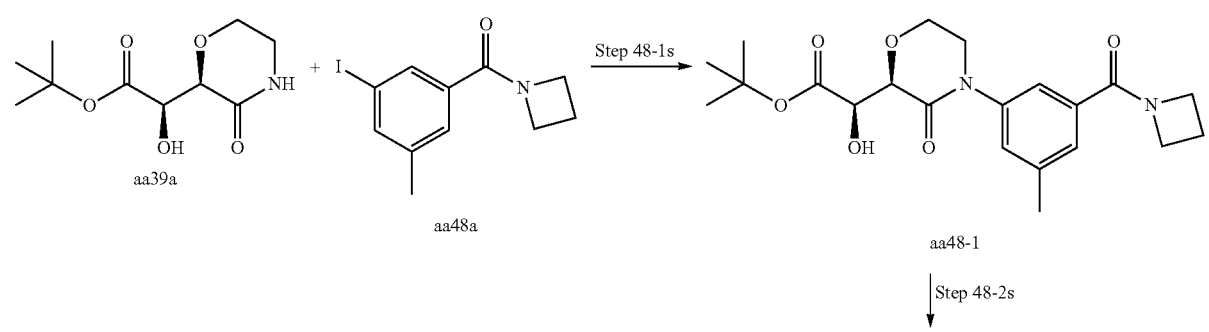

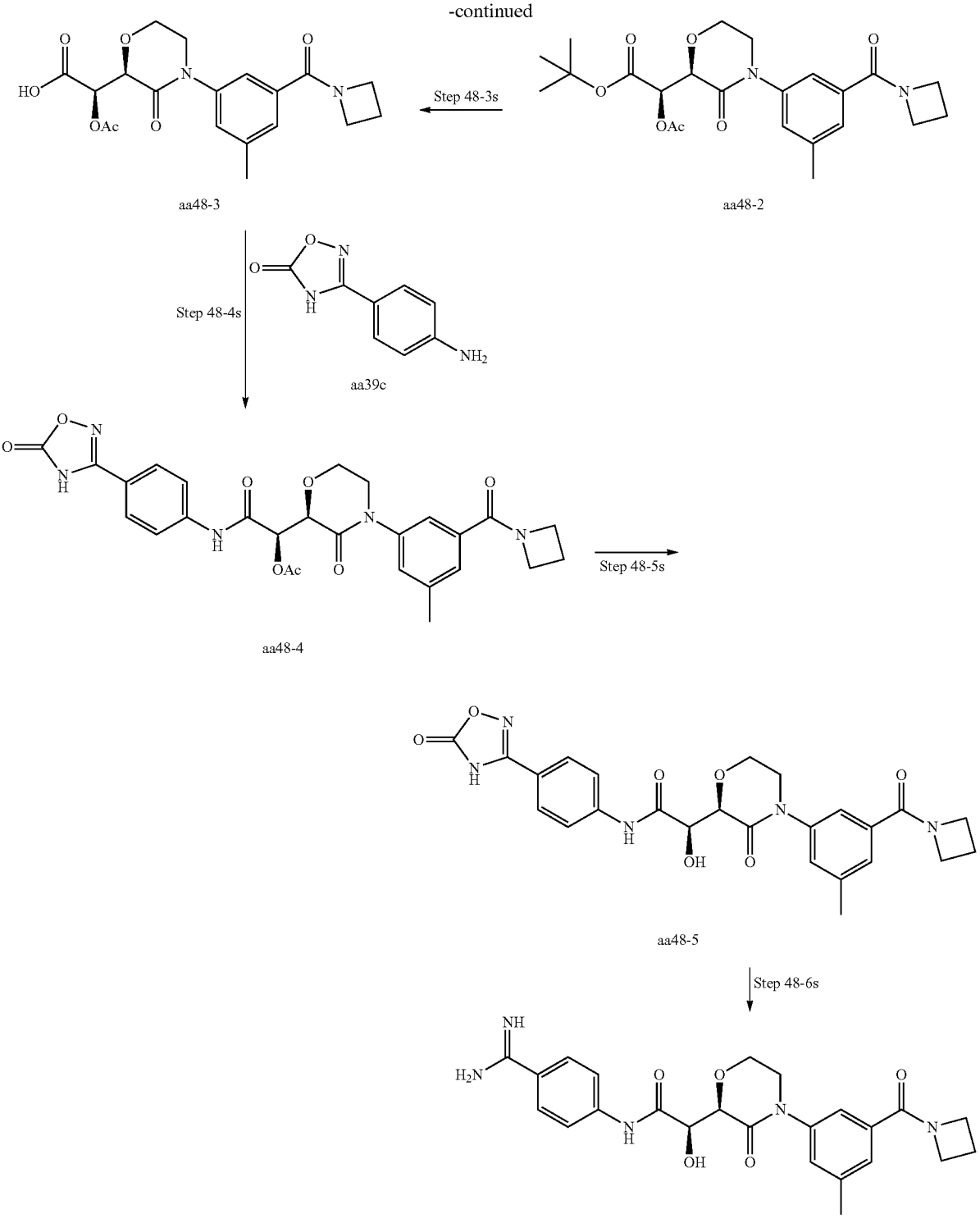
Step 48-1s
According to Step 39-1s in the synthetic method for EXAMPLE aa39, compound aa48a (205 mg, 0.68 mmol) was used instead of compound aa39b to obtain compound aa48-1 (222 mg, 0.55 mmol).
Step 48-2s
According to Step 39-2s in the synthetic method for EXAMPLE aa39, compound aa48-1 (222 mg, 0.55 mmol) was used instead of compound aa39-1 to obtain compound aa48-2 (219 mg, 0.49 mmol).

Step 48-3s

According to Step 39-3s in the synthetic method for EXAMPLE aa39, compound aa48-2 (219 mg, 0.49 mmol) was used instead of compound aa39-2 to obtain compound aa48-3 (0.49 mmol) which was used in the next step without further purification.

Step 48-4s

According to Step 39-4s in the synthetic method for EXAMPLE aa39, compound aa48-3 (0.49 mmol) was used instead of compound aa39-3 to obtain compound aa48-4 (182 mg, 0.33 mmol).

Step 48-5s

According to Step 39-5s in the synthetic method for EXAMPLE aa39, compound aa48-4 (182 mg, 0.33 mmol) was used instead of compound aa39-4 to obtain compound aa48-5 (0.33 mmol) which was used in the next step without further purification.

Step 48-6s

According to Step 39-6s in the synthetic method for EXAMPLE aa39, compound aa48-5 (0.33 mmol) was used instead of compound aa39-5 to obtain EXAMPLE aa48 (118 mg, 0.25 mmol) as a white amorphous solid.

Example aa49

Preparation of (R)—N-(4-carbamimidoylphenyl)-2-hydroxy-2-((R)-4-(2-methyl-5-(morpholine-4-carbonyl)phenyl)-3-oxomorpholin-2-yl)acetamide EXAMPLE aa49

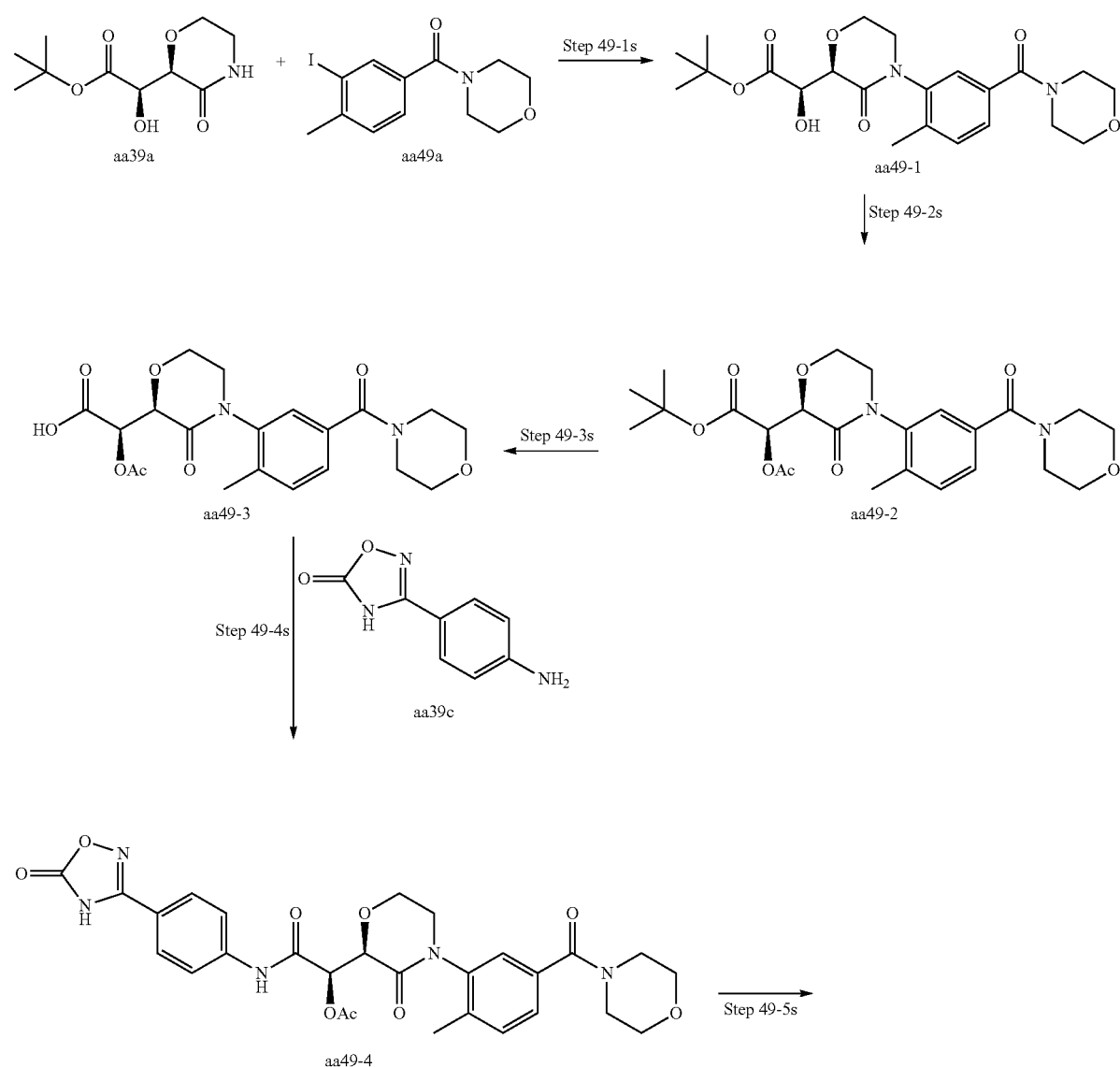

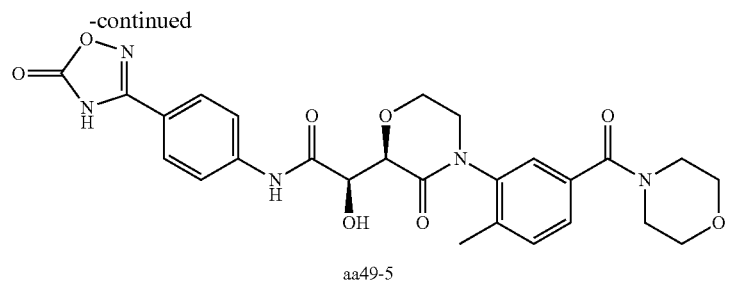

aa49-5

↓ Step 49-6s

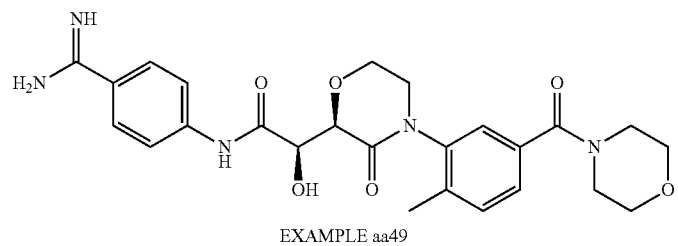

EXAMPLE aa49

Step 49-1s

According to Step 39-1s in the synthetic method for EXAMPLE aa39, compound aa49a (315 mg, 0.95 mmol) was used instead of compound aa39b to obtain compound aa49-1 (177 mg, 0.41 mmol).

Step 49-2s

According to Step 39-2s in the synthetic method for EXAMPLE aa39, compound aa49-1 (177 mg, 0.41 mmol) was used instead of compound aa39-1 to obtain compound aa49-2 (160 mg, 0.34 mmol).

Step 49-3s

According to Step 39-3s in the synthetic method for EXAMPLE aa39, compound aa49-2 (160 mg, 0.34 mmol) was used instead of compound aa39-2 to obtain compound aa49-3 (0.34 mmol) which was used in the next step without further purification.

Step 49-4s

According to Step 39-4s in the synthetic method for EXAMPLE aa39, compound aa49-3 (0.34 mmol) was used instead of compound aa39-3 to obtain compound aa49-4 (90 mg, 0.16 mmol).

Step 49-5s

According to Step 39-5s in the synthetic method for EXAMPLE aa39, compound aa49-4 (90 mg, 0.16 mmol) was used instead of compound aa39-4 to obtain compound aa49-5 (0.16 mmol) which was used in the next step without further purification.

Step 49-6s

According to Step 39-6s in the synthetic method for EXAMPLE aa39, compound aa49-5 (0.16 mmol) was used instead of compound aa39-5 to obtain EXAMPLE aa49 (60 mg, 0.12 mmol) as a white amorphous solid.

Example aa53

Preparation of (R)—N-(4-carbamimidoylphenyl)-2-hydroxy-2-((R)-4-(3-methyl-5-(pyrrolidine-1-carbonyl)phenyl)-3-oxomorpholin-2-yl)acetamide
EXAMPLE aa53

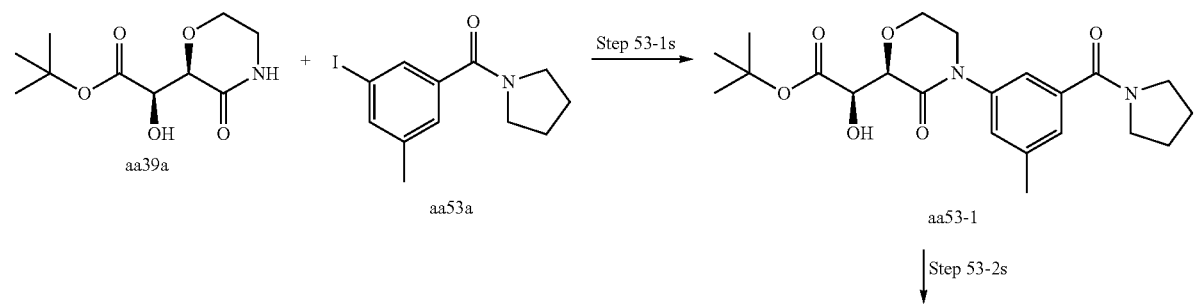

↓ Step 53-2s

671 672
-continued
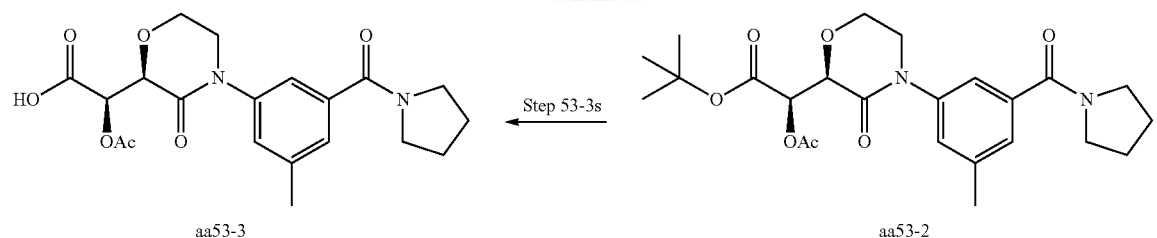
aa53-3     aa53-2
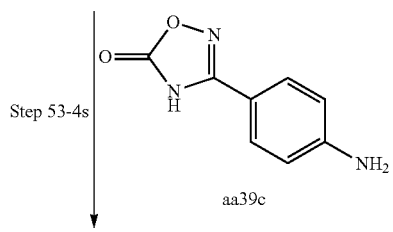
aa39c
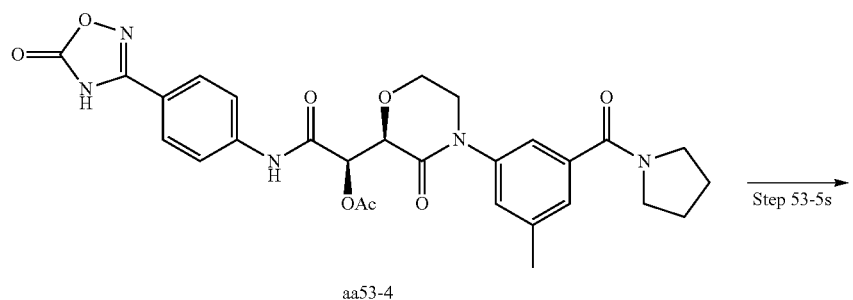
aa53-4
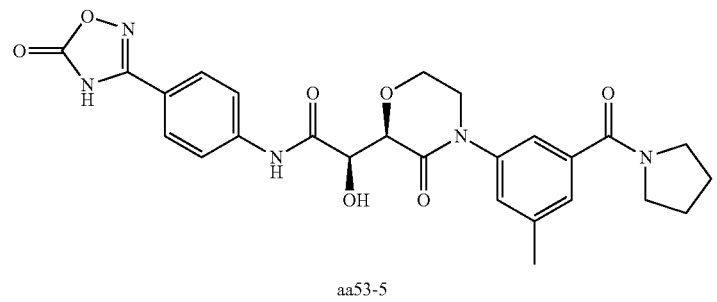
aa53-5
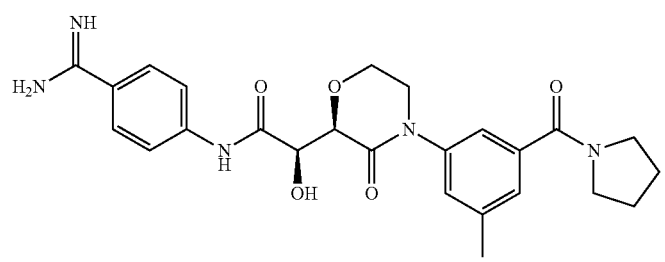
EXAMPLE aa53

Step 53-1s

According to Step 39-1s in the synthetic method for EXAMPLE aa39, compound aa53a (225 mg, 0.71 mmol) was used instead of compound aa39b to obtain compound aa53-1 (222 mg, 0.53 mmol).

Step 53-2s

According to Step 39-2s in the synthetic method for EXAMPLE aa39, compound aa53-1 (222 mg, 0.53 mmol) was used instead of compound aa39-1 to obtain compound aa53-2 (207 mg, 0.45 mmol).

Step 53-3s

According to Step 39-3s in the synthetic method for EXAMPLE aa39, compound aa53-2 (207 mg, 0.45 mmol) was used instead of compound aa39-2 to obtain compound aa53-3 (0.45 mmol) which was used in the next step without further purification.

Step 53-4s

According to Step 39-4s in the synthetic method for EXAMPLE aa39, compound aa53-3 (106 mg, 0.26 mmol) was used instead of compound aa39-3 to obtain compound aa53-4 (147 mg, 0.26 mmol).

Step 53-5s

According to Step 39-5s in the synthetic method for EXAMPLE aa39, compound aa53-4 (147 mg, 0.26 mmol) was used instead of compound aa39-4 to obtain compound aa53-5 (0.26 mmol) which was used in the next step without further purification.

Step 53-6s

According to Step 39-6s in the synthetic method for EXAMPLE aa39, compound aa53-5 (0.26 mmol) was used instead of compound aa39-5 to obtain EXAMPLE aa53 (83 mg, 0.17 mmol) as a white amorphous solid.

Example aa54

Preparation of (R)-2-hydroxy-N-(1-iminoisoindolin-5-yl)-2-((R)-4-(3-methyl-5-(pyrrolidine-1-carbonyl)phenyl)-3-oxomorpholin-2-yl)acetamide EXAMPLE aa54

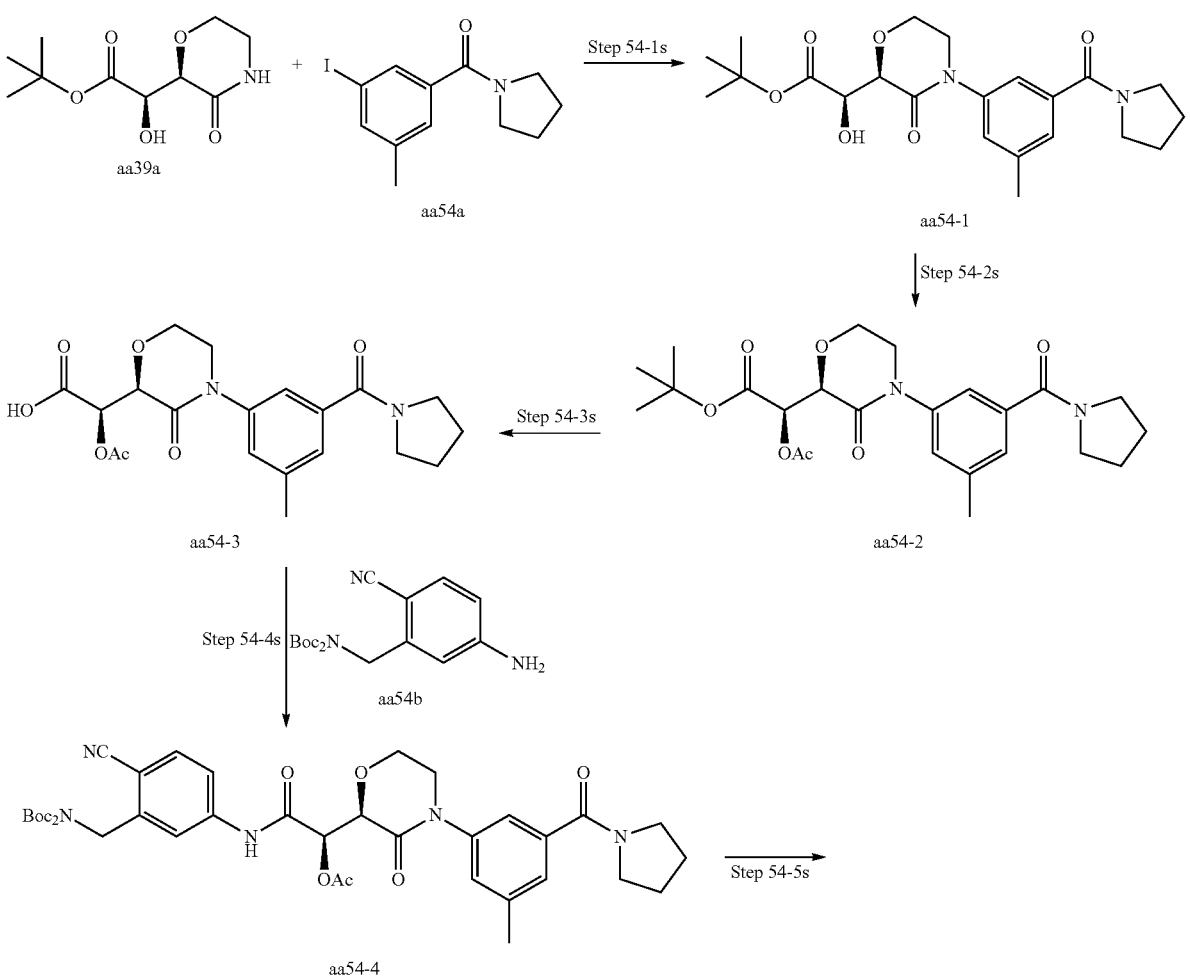

-continued

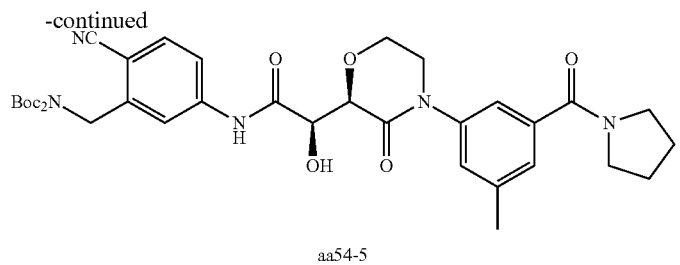

aa54-5

Step 54-6s

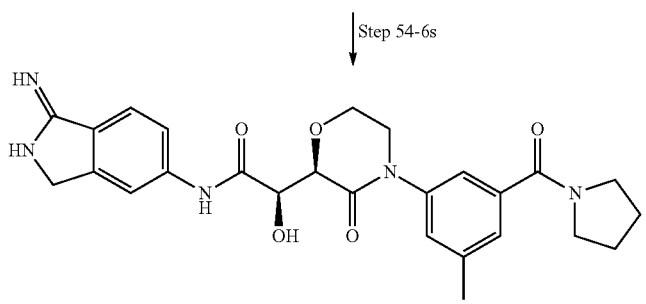

EXAMPLE aa54

Step 54-1s

According to Step 39-1s in the synthetic method for EXAMPLE aa39, compound aa54a (225 mg, 0.71 mmol) was used instead of compound aa39b to obtain compound aa54-1 (222 mg, 0.53 mmol).

Step 54-2s

According to Step 39-2s in the synthetic method for EXAMPLE aa39, compound aa54-1 (222 mg, 0.53 mmol) was used instead of compound aa39-1 to obtain compound aa54-2 (207 mg, 0.45 mmol).

Step 54-3s

According to Step 39-3s in the synthetic method for EXAMPLE aa39, compound aa54-2 (207 mg, 0.45 mmol) was used instead of compound aa39-2 to obtain compound aa54-3 (0.45 mmol) which was used in the next step without further purification.

Step 54-4s

According to Step 39-4s in the synthetic method for EXAMPLE aa39, compound aa53-3 (109 mg, 0.27 mmol) was used instead of compound aa39-3 and compound aa54b (140 mg, 0.40 mmol) was instead of compound aa39c to obtain compound aa54-4 (116 mg, 0.16 mmol).

Step 54-5s

According to Step 39-5s in the synthetic method for EXAMPLE aa39, compound aa54-4 (116 mg, 0.16 mmol) was used instead of compound aa39-4 to obtain compound aa54-5 (0.16 mmol) which was used in the next step without further purification.

Step 54-6s

To a solution of compound aa54-5 (0.16 mmol) was added a 4 N solution of hydrogen chloride in dioxane (10 mL). The reaction mixture was stirred at room temperature for 2 hours. The organic solvent was evaporated under reduced pressure. Anhydrous ethanol (12 mL) was added and the reaction mixture was heated under reflux for 16 hours. The organic solvent was evaporated under reduced pressure. The crude product was purified by RP-HPLC to afford the desired EXAMPLE aa54 (55 mg, 0.11 mmol) as a white amorphous solid.

Example aa50

Preparation of 2-(3-((R)-2-((R)-1-hydroxy-2-(1-iminoisoindolin-5-ylamino)-2-oxoethyl)-3-oxomorpholino)-N-methylbenzamido)acetic acid
EXAMPLE aa50

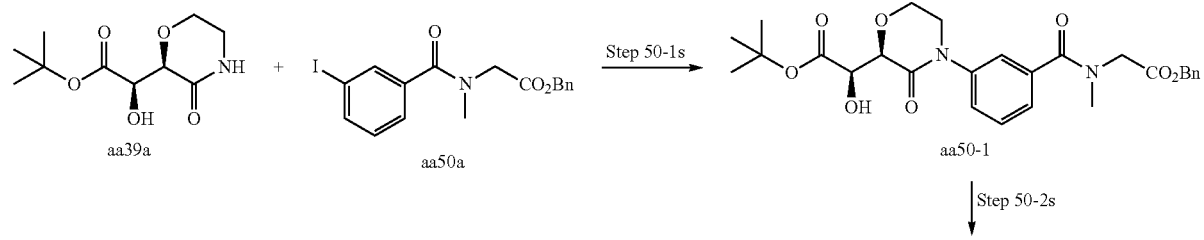

Step 50-2s

-continued

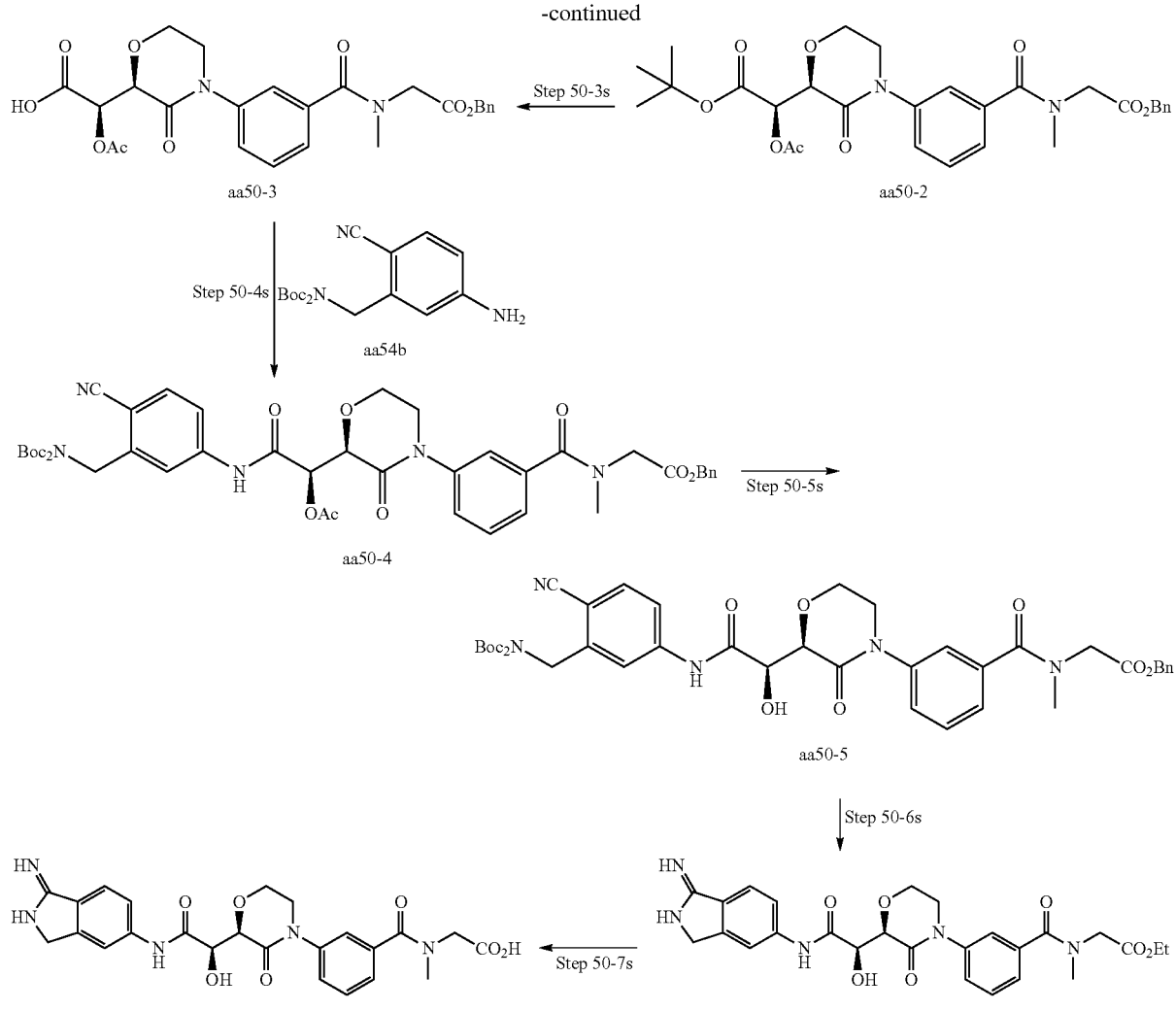

Step 50-1s

According to Step 39-1s in the synthetic method for EXAMPLE aa39, compound aa50a (1.24 g, 3.03 mmol) was used instead of compound aa39b to obtain compound aa50-1 (1.16 g, 2.27 mmol).

Step 50-2s

According to Step 39-2s in the synthetic method for EXAMPLE aa39, compound aa50-1 (1.16 g, 2.27 mmol) was used instead of compound aa39-1 to obtain compound aa50-2 (1.16 g, 2.09 mmol).

Step 50-3S

According to Step 39-3s in the synthetic method for EXAMPLE aa39, compound aa50-2 (250 mg, 0.50 mmol) was used instead of compound aa39-2 to obtain compound aa50-3 (0.50 mmol) which was used in the next step without further purification.

Step 50-4s

According to Step 54-4s in the synthetic method for EXAMPLE aa54, compound aa50-3 (0.50 mmol) was used instead of compound aa54-3 to obtain compound aa50-4 (255 mg, 0.31 mmol).

Step 50-5s

According to Step 39-5s in the synthetic method for EXAMPLE aa39, compound aa50-4 (255 mg, 0.31 mmol) was used instead of compound aa39-4 to obtain compound aa40-5 (0.31 mmol) which was used in the next step without further purification.

Step 50-6s

According to Step 54-6s in the synthetic method for EXAMPLE aa54, compound aa50-5 (0.31 mmol) was used instead of compound aa54-5 to obtain compound aa50-6 (0.31 mmol) which was used in the next step without further purification.

Step 50-7s

To a solution of compound aa50-6 (0.31 mmol) in methanol (2 mL) and water (2 mL) was added triethylamine (0.43 mL). The reaction mixture was stirred at room temperature for 16 hours. The organic solvent was evaporated under reduced pressure. The crude product was purified by RP-HPLC to afford the desired EXAMPLE aa50 (153 mg, 0.31 mmol) as a white amorphous solid.

Example aa51

Preparation of methyl 2-(3-((R)-2-((R)-1-hydroxy-2-(1-iminoisoindolin-5-ylamino)-2-oxoethyl)-3-oxo-morpholino)-N-methylbenzamido)acetate EXAMPLE aa51

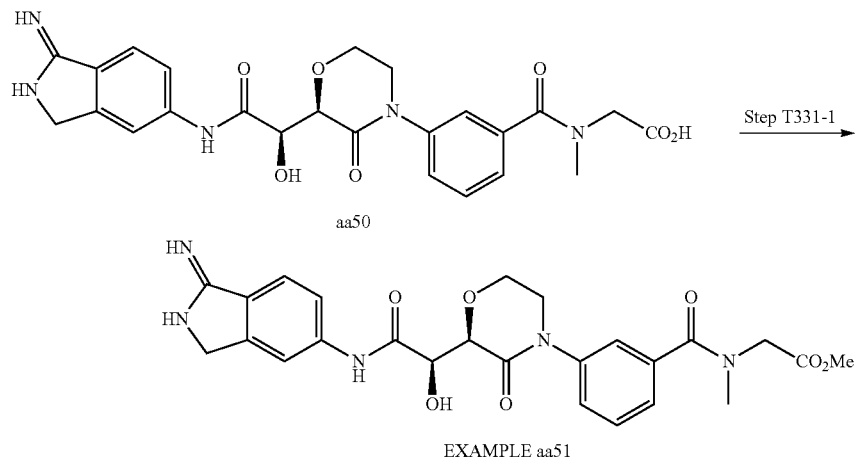

Step 51-1s

To a solution of compound aa50 (90 mg, 0.18 mmol) in methanol (4 mL) was added 1 N hydrochloric acid (1 mL). The reaction mixture was stirred at room temperature for 3 days. The organic solvent was evaporated under reduced pressure. The crude product was purified by RP-HPLC to afford the desired EXAMPLE aa51 (48 mg, 0.094 mmol) as a white amorphous solid.

Example aa58

Preparation of (S)-1-(3-((R)-2-((R)-2-(4-carbamimidoylphenylamino)-1-hydroxy-2-oxoethyl)-3-oxomorpholino)benzoyl)pyrrolidine-2-carboxylic acid EXAMPLE aa58

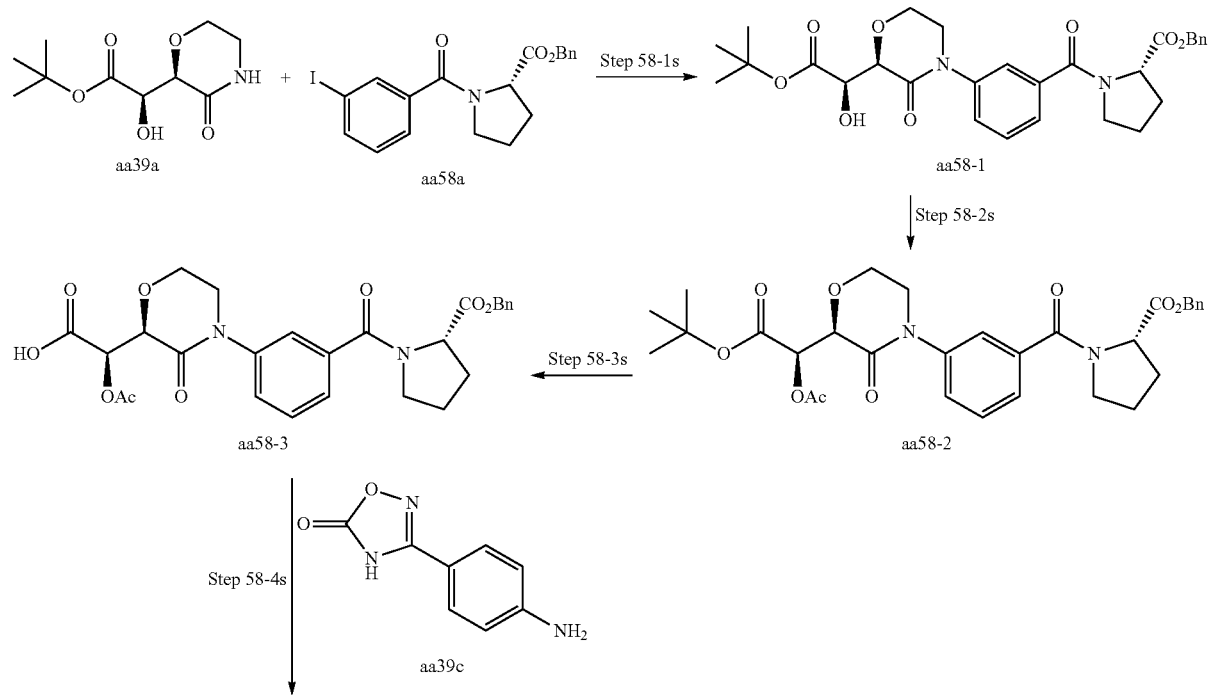

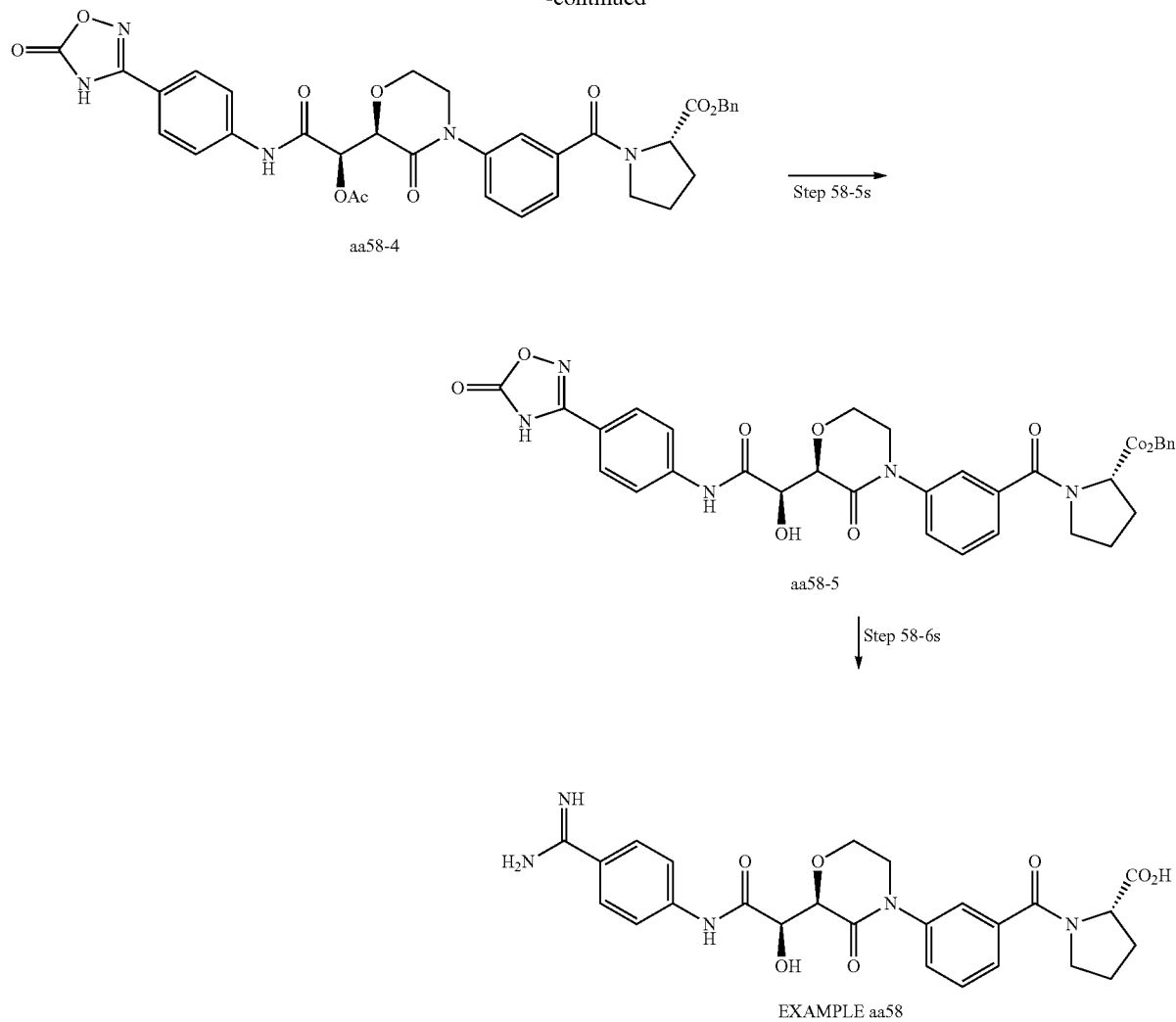

Step 58-1s

According to Step 39-1s in the synthetic method for EXAMPLE aa39, compound aa58a (616 mg, 1.42 mmol) was used instead of compound aa39B to obtain compound aa58-1 (710 mg, 1.32 mmol).

Step 58-2s

According to Step 39-2s in the synthetic method for EXAMPLE aa39, compound aa58-1 (710 mg, 1.32 mmol) was used instead of compound aa39-1 to obtain compound aa58-2 (707 mg, 1.22 mmol).

Step 58-3s

According to Step 39-3s in the synthetic method for EXAMPLE aa39, compound aa58-2 (0.66 mmol) was used instead of compound aa39-2 to obtain compound aa58-3 (0.66 mmol) which was used in the next step without further purification.

Step 58-4s

According to Step 39-4s in the synthetic method for EXAMPLE aa39, compound aa58-3 (0.66 mmol) was used instead of compound aa39-3 to obtain compound aa58-4 (445 mg, 0.65 mmol).

Step 58-5s

According to Step 39-5s in the synthetic method for EXAMPLE aa39, compound aa58-4 (445 mg, 0.65 mmol) was used instead of compound aa39-4 to obtain compound aa58-5 (0.65 mmol) which was used in the next step without further purification.

Step 58-6s

According to Step 39-6s in the synthetic method for EXAMPLE aa39, compound aa58-5 (0.65 mmol) was used instead of compound aa39-5 to obtain EXAMPLE aa58 (42 mg, 0.083 mmol) as a white amorphous solid.

Example aa52

Preparation of (S)-methyl 1-(3-((R)-2-((R)-2-(4-carbamimidoylphenylamino)-1-hydroxy-2-oxoethyl)-3-oxomorpholino)benzoyl)pyrrolidine-2-carboxylate EXAMPLE aa52

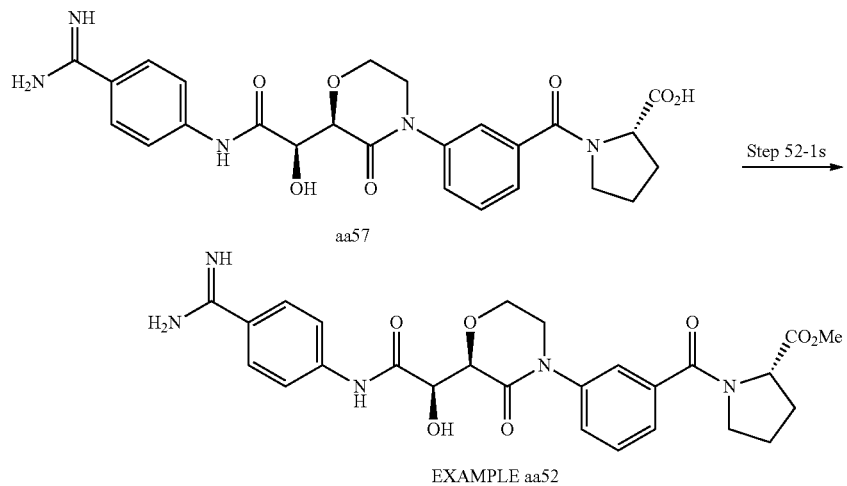

Step 52-1s

According to Step 51-1s in the synthetic method for EXAMPLE aa51, compound aa58 (24 mg, 0.047 mmol) was used instead of compound aa50 to obtain EXAMPLE aa52 (24 mg, 0.046 mmol) as a white amorphous solid.

Example aa56

Preparation of 3-((R)-2-((R)-2-(4-carbamimidoylphenylamino)-1-hydroxy-2-oxoethyl)-3-oxomorpholino)-N-methyl-N-(2-oxo-2-(pyrrolidin-1-yl)ethyl)benzamide EXAMPLE aa56

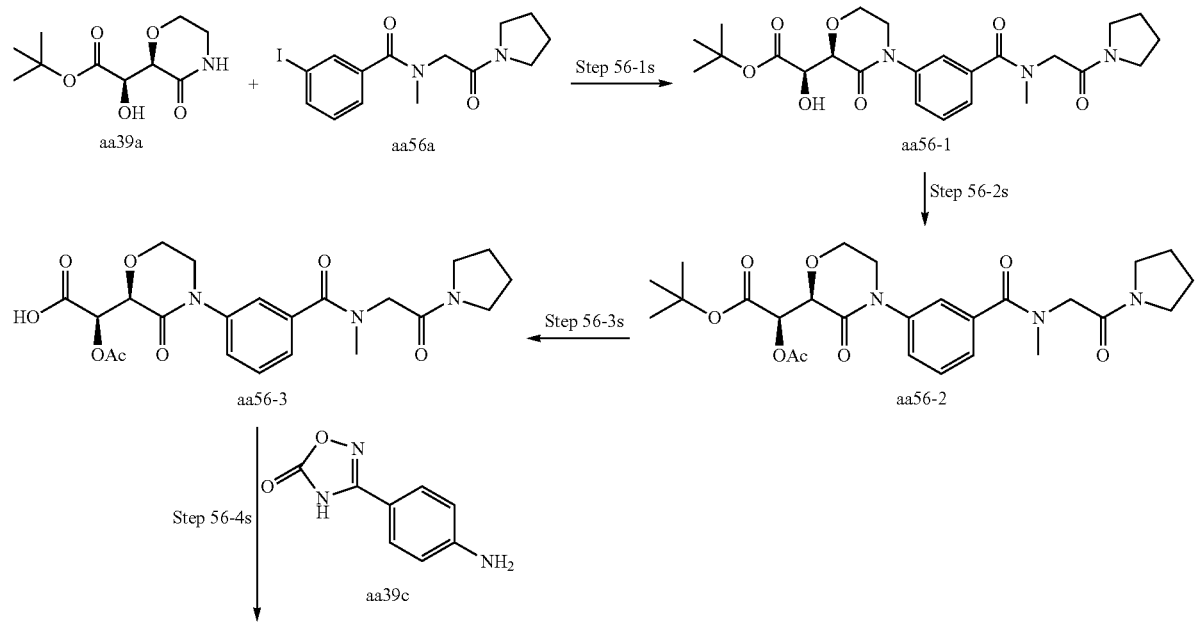

-continued

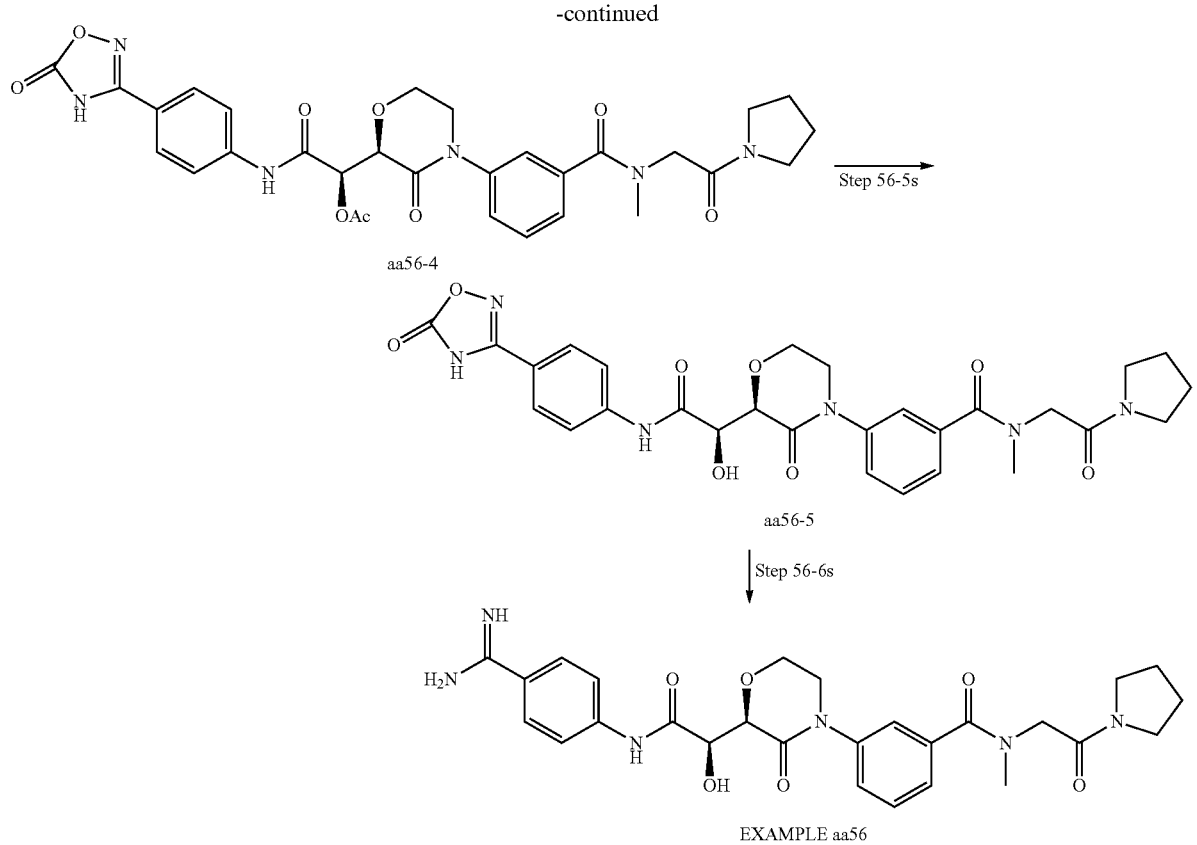

Step 56-1s
According to Step 39-1s in the synthetic method for EXAMPLE aa39, compound aa56 (886 mg, 2.38 mmol) was used instead of compound aa39b to obtain compound aa56-1 (669 mg, 1.41 mmol).

Step 56-2s
According to Step 39-2s in the synthetic method for EXAMPLE aa39, compound aa56-1 (669 mg, 1.41 mmol) was used instead of compound aa39-1 to obtain compound aa56-2 (477 mg, 0.92 mmol).

Step 56-3s
According to Step 39-3s in the synthetic method for EXAMPLE aa39, compound aa56-2 (477 mg, 0.92 mmol) was used instead of compound aa39-2 to obtain compound aa40-3 (0.92 mmol) which was used in the next step without further purification.

Step 56-4s
According to Step 39-4s in the synthetic method for EXAMPLE aa39, compound aa40-3 (235 mg, 0.51 mmol) was used instead of compound aa39-3 to obtain compound aa56-4 (244 mg, 0.39 mmol).

Step 56-5s
According to Step 39-5s in the synthetic method for EXAMPLE aa39, compound aa56-4 (244 mg, 0.39 mmol) was used instead of compound aa39-4 to obtain compound aa56-5 (0.39 mmol) which was used in the next step without further purification.

Step 56-6s
According to Step 39-6s in the synthetic method for EXAMPLE aa39, compound aa56-5 (0.39 mmol) was used instead of compound aa39-5 to obtain EXAMPLE aa56 (160 mg, 0.30 mmol) as a white amorphous solid.

Example aa59

Preparation of 3-((R)-2-((R)-1-hydroxy-2-(1-iminoisoindolin-5-ylamino)-2-oxoethyl)-3-oxomorpholino)-N-methyl-N-(2-oxo-2-(pyrrolidin-1-yl)ethyl)benzamide EXAMPLE aa59

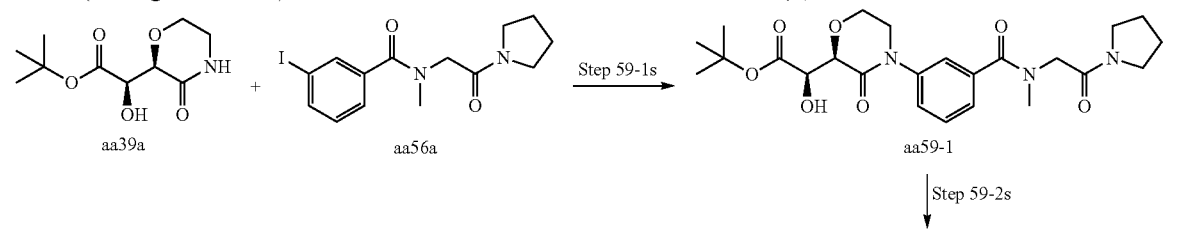

-continued

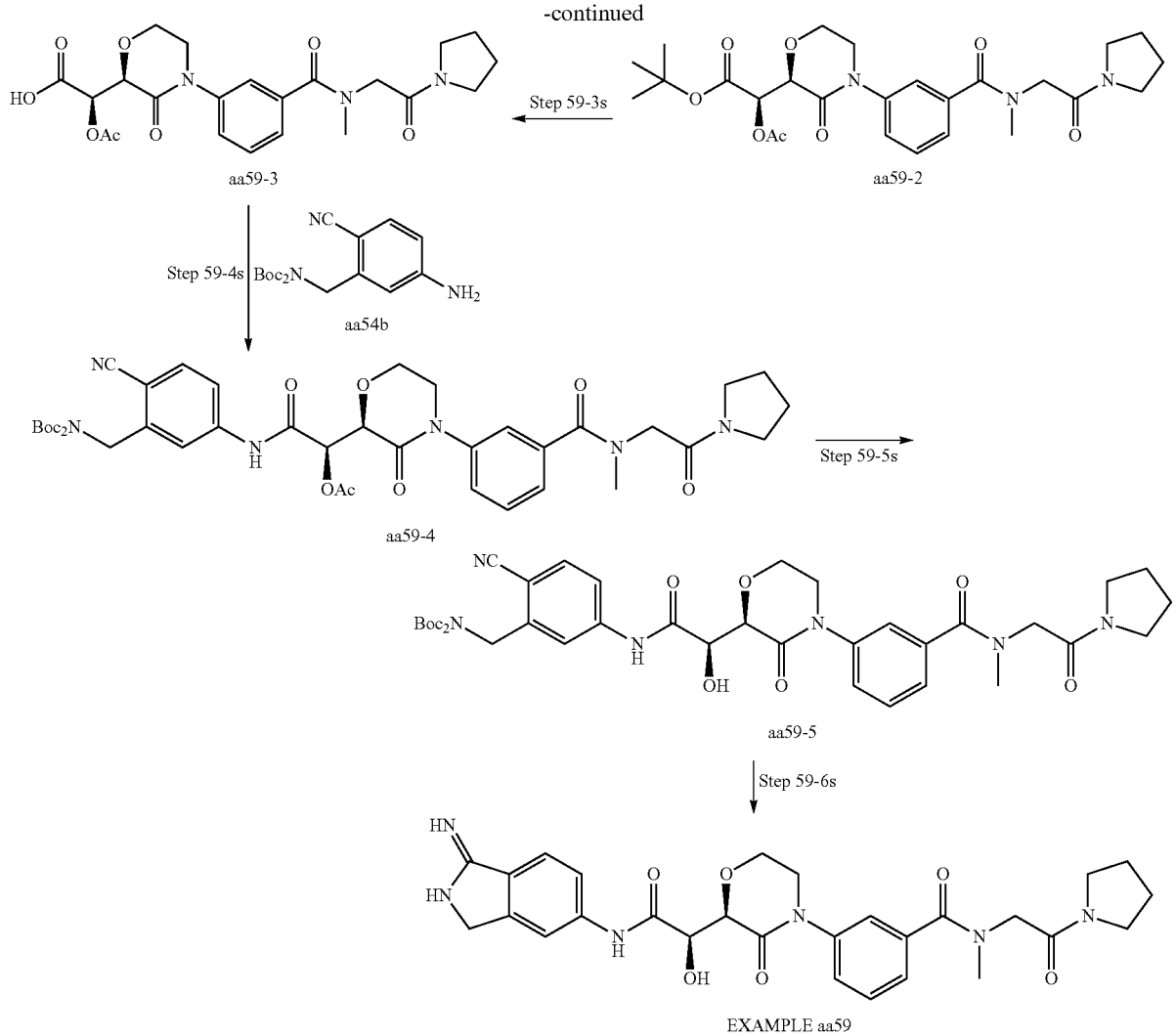

Step 59-1s

According to Step 39-1s in the synthetic method for EXAMPLE aa39, compound aa56a (886 mg, 2.38 mmol) was used instead of compound aa39b to obtain compound aa59-1 (669 mg, 1.41 mmol).

Step 59-2s

According to Step 39-2s in the synthetic method for EXAMPLE aa39, compound aa59-1 (669 mg, 1.41 mmol) was used instead of compound aa39-1 to obtain compound aa59-2 (477 mg, 0.92 mmol).

Step 59-3s

According to Step 39-3s in the synthetic method for EXAMPLE aa39, compound aa59-2 (477 mg, 0.92 mmol) was used instead of compound aa39-2 to obtain compound aa59-3 (0.92 mmol) which was used in the next step without further purification.

Step 59-4s

According to Step 54-4s in the synthetic method for EXAMPLE aa54, compound aa54b (235 mg, 0.51 mmol) was used instead of compound aa54-3 to obtain compound aa59-4 (224 mg, 0.28 mmol).

Step 59-5s

According to Step 39-5s in the synthetic method for EXAMPLE aa39, compound aa59-4 (224 mg, 0.28 mmol) was used instead of compound aa39-4 to obtain compound aa59-5 (0.28 mmol) which was used in the next step without further purification.

Step 59-6s

According to Step 54-6s in the synthetic method for EXAMPLE aa54, compound aa59-5 (0.28 mmol) was used instead of compound aa54-5 to obtain EXAMPLE aa59 (57 mg, 0.10 mmol) as a white amorphous solid.

Example aa60
Preparation of (R)—N-(4-carbamimidoylphenyl)-2-hydroxy-2-((R)-4-(3-methyl-5-(morpholine-4-carbonyl)phenyl)-3-oxomorpholin-2-yl)acetamide
EXAMPLE aa60
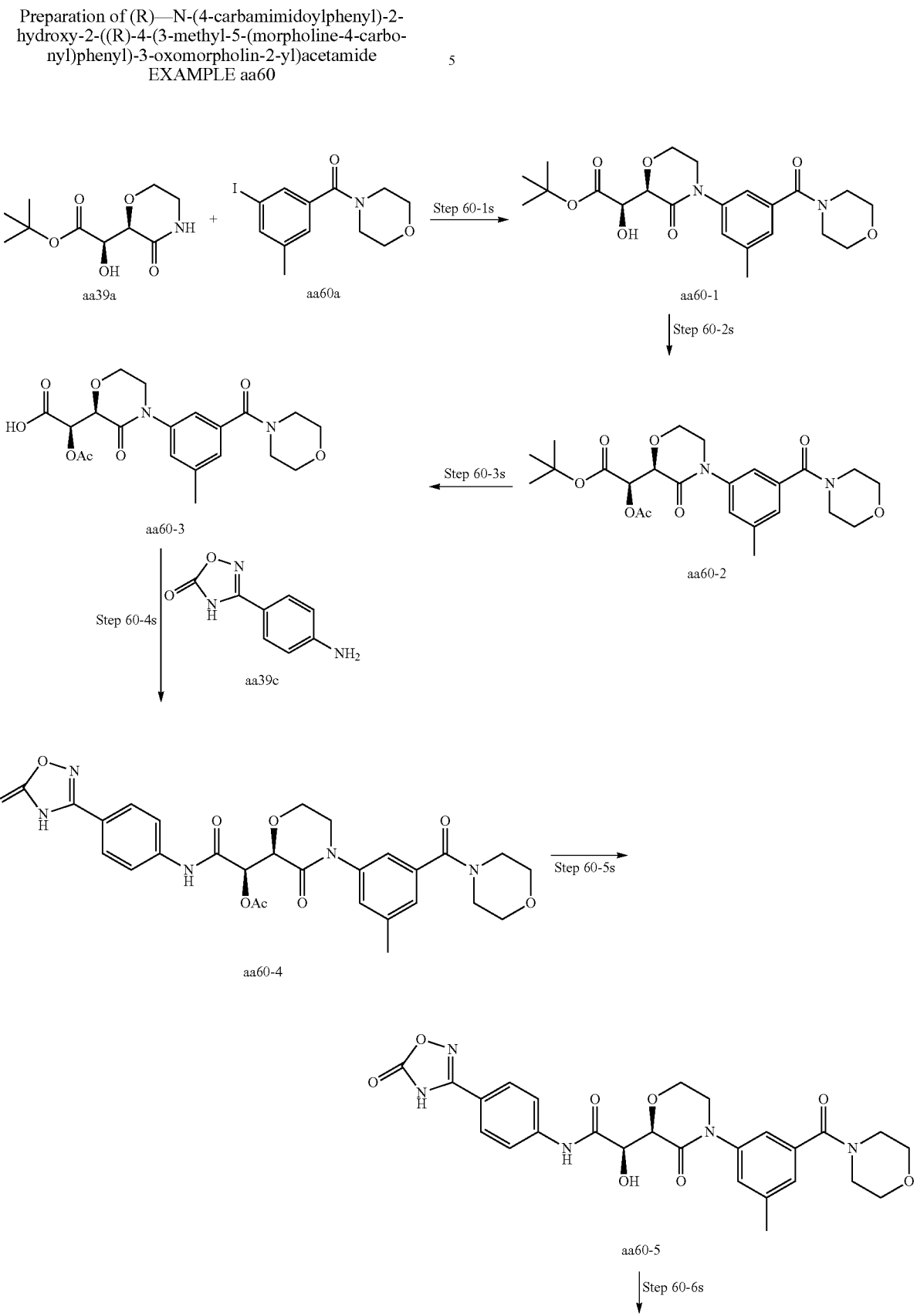

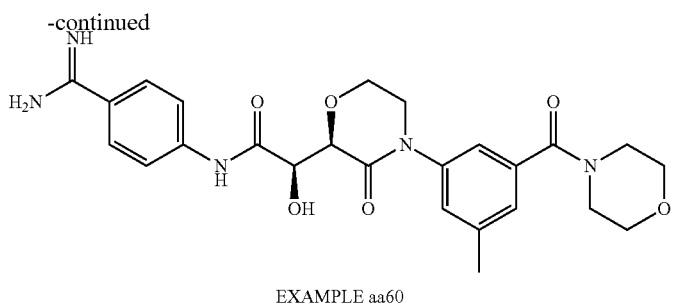

EXAMPLE aa60

Step 60-1s

According to Step 39-1s in the synthetic method for EXAMPLE aa39, compound aa60a (315 mg, 0.95 mmol) was used instead of compound aa39b to obtain compound aa60-1 (218 mg, 0.50 mmol).

Step 60-2s

According to Step 39-2s in the synthetic method for EXAMPLE aa39, compound aa60-1 (218 mg, 0.50 mmol) was used instead of compound aa39-1 to obtain compound aa60-2 (226 mg, 0.47 mmol).

Step 60-3s

According to Step 39-3s in the synthetic method for EXAMPLE aa39, compound aa60-2 (226 mg, 0.47 mmol) was used instead of compound aa39-2 to obtain compound aa60-3 (0.47 mmol) which was used in the next step without further purification.

Step 60-4s

According to Step 39-4s in the synthetic method for EXAMPLE aa39, compound aa60-3 (100 mg, 0.24 mmol) was used instead of compound aa39-3 to obtain compound aa60-4 (87 mg, 0.15 mmol).

Step 60-5s

According to Step 39-5s in the synthetic method for EXAMPLE aa39, compound aa60-4 (87 mg, 0.15 mmol) was used instead of compound aa39-4 to obtain compound aa60-5 (0.15 mmol) which was used in the next step without further purification.

Step 60-6s

According to Step 39-6s in the synthetic method for EXAMPLE aa39, compound aa60-5 (0.15 mmol) was used instead of compound aa39-5 to obtain EXAMPLE aa60 (71 mg, 0.14 mmol) as a white amorphous solid.

Example aa61

Preparation of (R)-2-hydroxy-N-(1-iminoisoindolin-5-yl)-2-((R)-4-(3-methyl-5-(morpholine-4-carbonyl)phenyl)-3-oxomorpholin-2-yl)acetamide EXAMPLE aa61

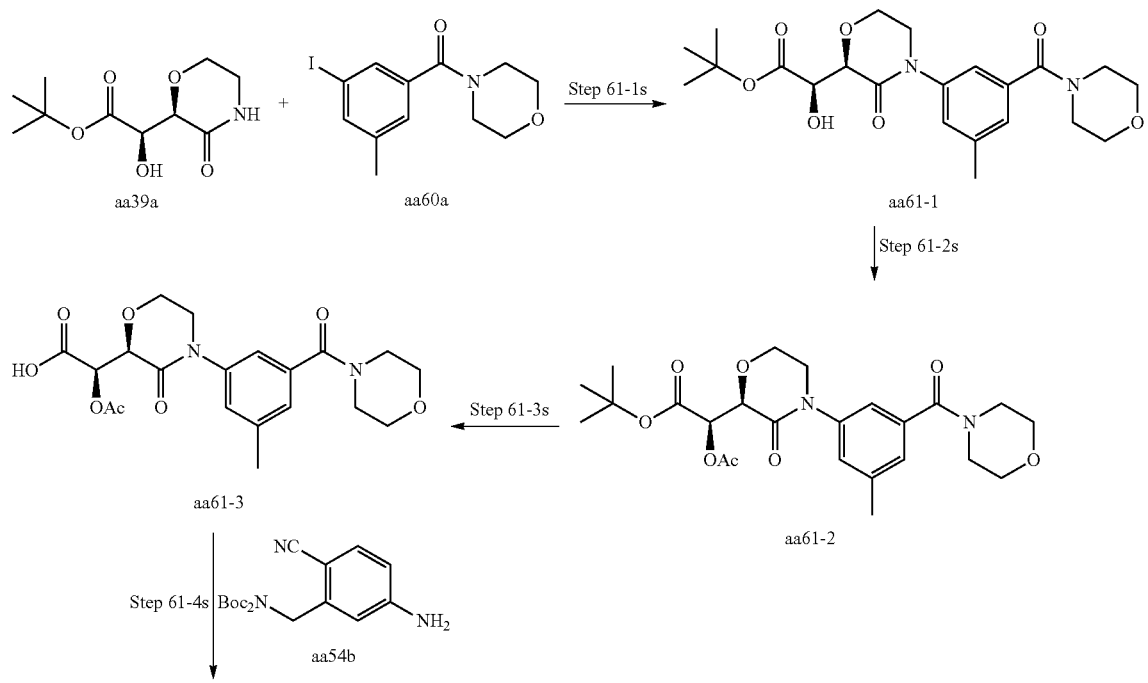

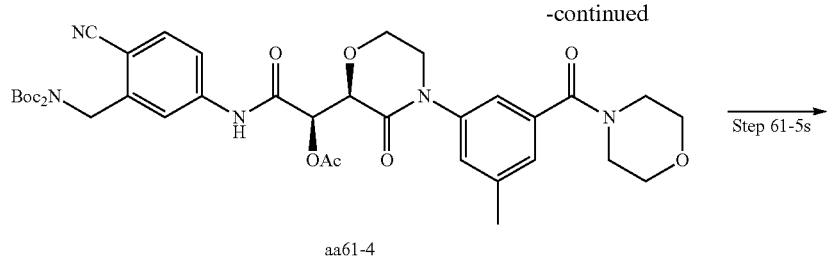

aa61-4

-continued

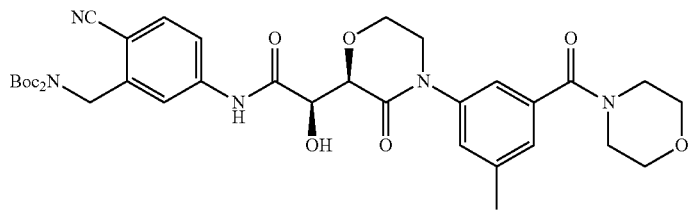

aa61-5

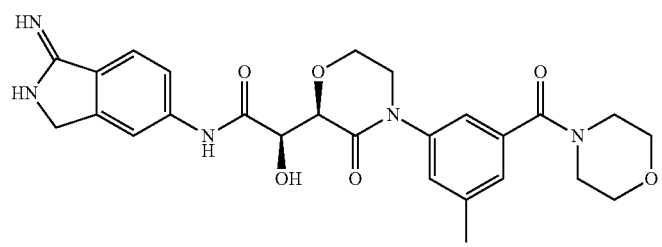

EXAMPLE aa61

Step 61-1s

According to Step 39-1s in the synthetic method for EXAMPLE aa39, compound aa60a (315 mg, 0.95 mmol) was used instead of compound aa39b to obtain compound aa61-1 (218 mg, 0.50 mmol).

Step 61-2s

According to Step 39-2s in the synthetic method for EXAMPLE aa39, compound aa61-1 (218 mg, 0.50 mmol) was used instead of compound aa39-1 to obtain compound aa61-2 (226 mg, 0.47 mmol).

Step 61-3s

According to Step 39-3s in the synthetic method for EXAMPLE aa39, compound aa61-2 (226 mg, 0.47 mmol) was used instead of compound aa39-2 to obtain compound aa61-3 (0.47 mmol) which was used in the next step without further purification.

Step 61-4s

According to Step 54-4s in the synthetic method for EXAMPLE aa54, compound aa61-3 (124 mg, 0.30 mmol) was used instead of compound aa54-3 to obtain compound aa61-4 (118 mg, 0.16 mmol).

Step 61-5s

According to Step 39-5s in the synthetic method for EXAMPLE aa39, compound aa61-4 (118 mg, 0.16 mmol) was used instead of compound aa39-4 to obtain compound aa61-5 (0.16 mmol) which was used in the next step without further purification.

Step 61-6s

According to Step 54-6s in the synthetic method for EXAMPLE aa54, compound aa61-5 (0.16 mmol) was used instead of compound aa54-5 to obtain EXAMPLE aa61 (71 mg, 0.14 mmol) as a white amorphous solid.

Example aa63

Preparation of (R)-2-hydroxy-N-(1-iminoisoindolin-5-yl)-2-((R)-4-(3-((R)-3-methoxypyrrolidine-1-carbonyl)phenyl)-3-oxomorpholin-2-yl)acetamide
EXAMPLE aa63

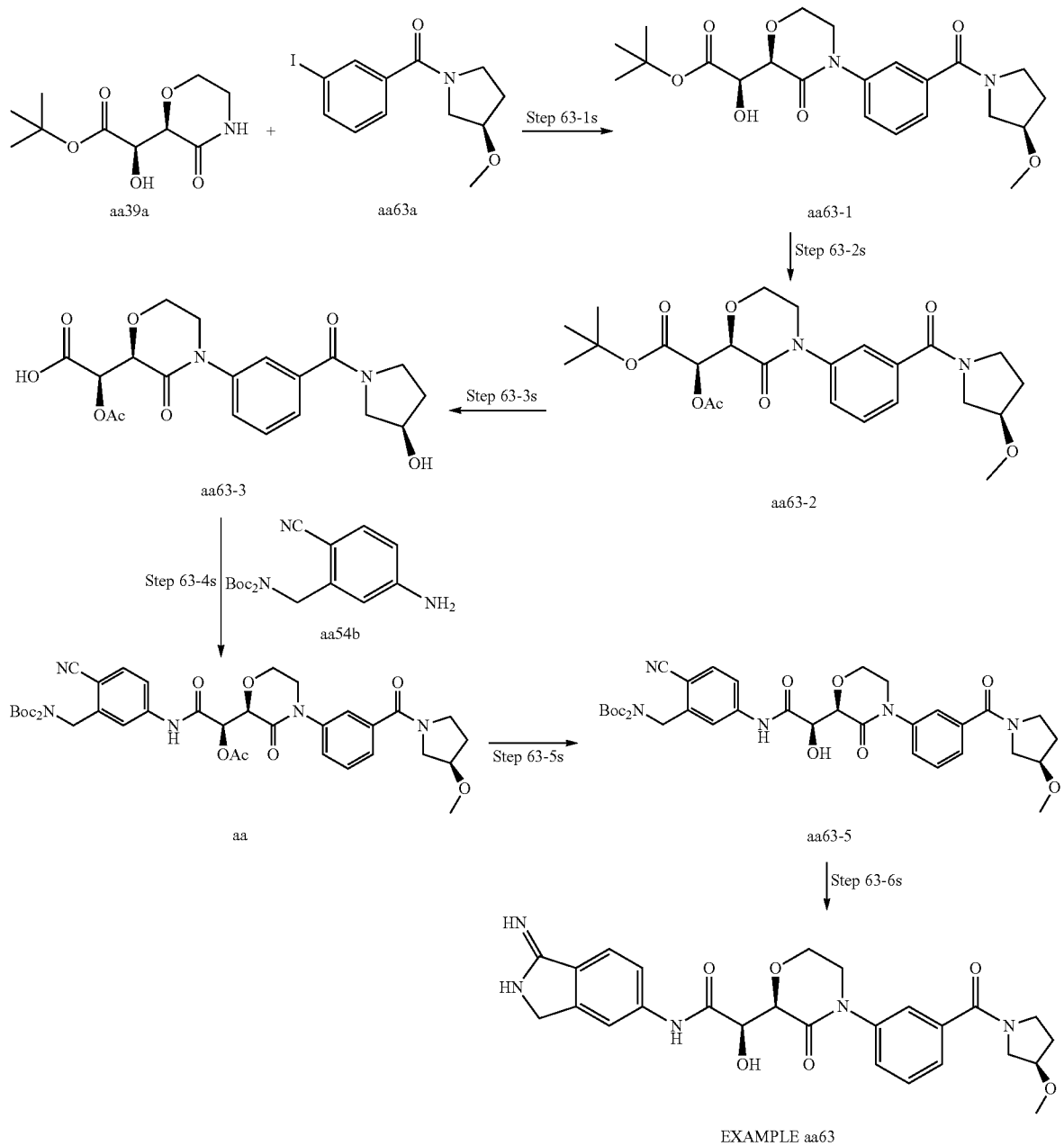

Step 63-1s

According to Step 39-1s in the synthetic method for EXAMPLE aa39, compound aa63a (158 mg, 0.48 mmol) was used instead of compound aa39b to obtain compound aa63-1 (124 mg, 0.29 mmol).

Step 63-2s

According to Step 39-2s in the synthetic method for EXAMPLE aa39, compound aa63-1 (124 mg, 0.29 mmol) was used instead of compound aa39-1 to obtain compound aa63-2 (132 mg, 0.28 mmol).

Step 63-3s

According to Step 39-3 in the synthetic method for EXAMPLE aa39, compound aa63-2 (132 mg, 0.28 mmol) was used instead of compound aa39-2 to obtain compound aa63-3 (0.28 mmol) which was used in the next step without further purification.

Step 63-4s

According to Step 54-4s in the synthetic method for EXAMPLE aa54, compound aa63-3 (0.28 mmol) was used instead of compound aa54-3 to obtain compound aa63-4 (88 mg, 0.12 mmol).

Step 63-5s

According to Step 39-5s in the synthetic method for EXAMPLE aa39, compound aa63-4 (88 mg, 0.12 mmol) was used instead of compound aa39-4 to obtain compound 63-5 (0.12 mmol) which was used in the next step without further purification.

Step 63-6s

According to Step 54-6s in the synthetic method for EXAMPLE aa54, compound aa63-5 (0.12 mmol) was used instead of compound aa54-5 to obtain EXAMPLE aa63 (26 mg, 0.051 mmol) as a white amorphous solid.

Example aa64

Preparation of (R)-2-hydroxy-N-(1-iminoisoindolin-5-yl)-2-((R)-4-(3-((S)-3-methoxypyrrolidine-1-carbonyl)phenyl)-3-oxomorpholin-2-yl)acetamide EXAMPLE aa64

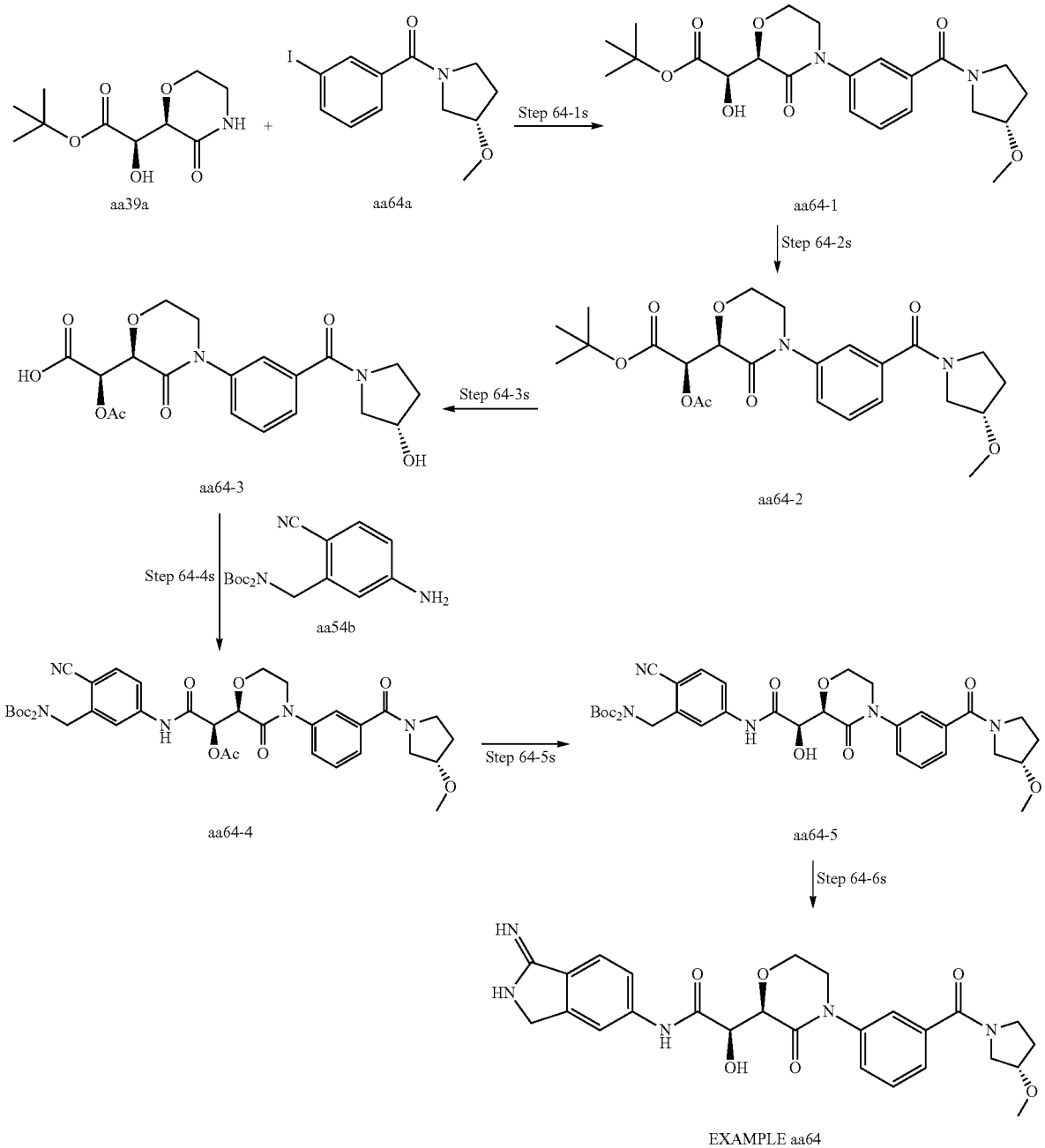

EXAMPLE aa64

Step 64-1s

According to Step 39-1s in the synthetic method for EXAMPLE aa39, compound aa64a (158 mg, 0.48 mmol) was used instead of compound aa39b to obtain compound aa64-1 (125 mg, 0.29 mmol).

Step 64-2s

According to Step 39-2s in the synthetic method for EXAMPLE aa39, compound aa64-1 (125 mg, 0.29 mmol) was used instead of compound aa39-1 to obtain compound aa64-2 (136 mg, 0.29 mmol).

Step 64-3s

According to Step 39-3s in the synthetic method for EXAMPLE aa39, compound aa64-2 (136 mg, 0.29 mmol) was used instead of compound aa39-2 to obtain compound aa64-3 (0.29 mmol) which was used in the next step without further purification.

Step 64-4s

According to Step 54-4s in the synthetic method for EXAMPLE aa54, compound aa64-3 (0.29 mmol) was used instead of compound aa54-3 to obtain compound aa64-4 (109 mg, 0.15 mmol).

Step 64-5s

According to Step 39-5s in the synthetic method for EXAMPLE aa39, compound aa64-4 (109 mg, 0.15 mmol) was used instead of compound aa39-4 to obtain compound aa64-5 (0.15 mmol) which was used in the next step without further purification.

Step 64-6s

According to Step 54-6s in the synthetic method for EXAMPLE aa54, compound aa64-5 (0.15 mmol) was used instead of compound aa54-5 to obtain EXAMPLE aa64 (70 mg, 0.14 mmol) as a white amorphous solid.

Example aa66

Preparation of (R)-2-((R)-4-(3-chloro-4-(morpholine-4-carbonyl)phenyl)-3-oxomorpholin-2-yl)-2-hydroxy-N-(1-iminoisoindolin-5-yl)acetamide EXAMPLE aa66

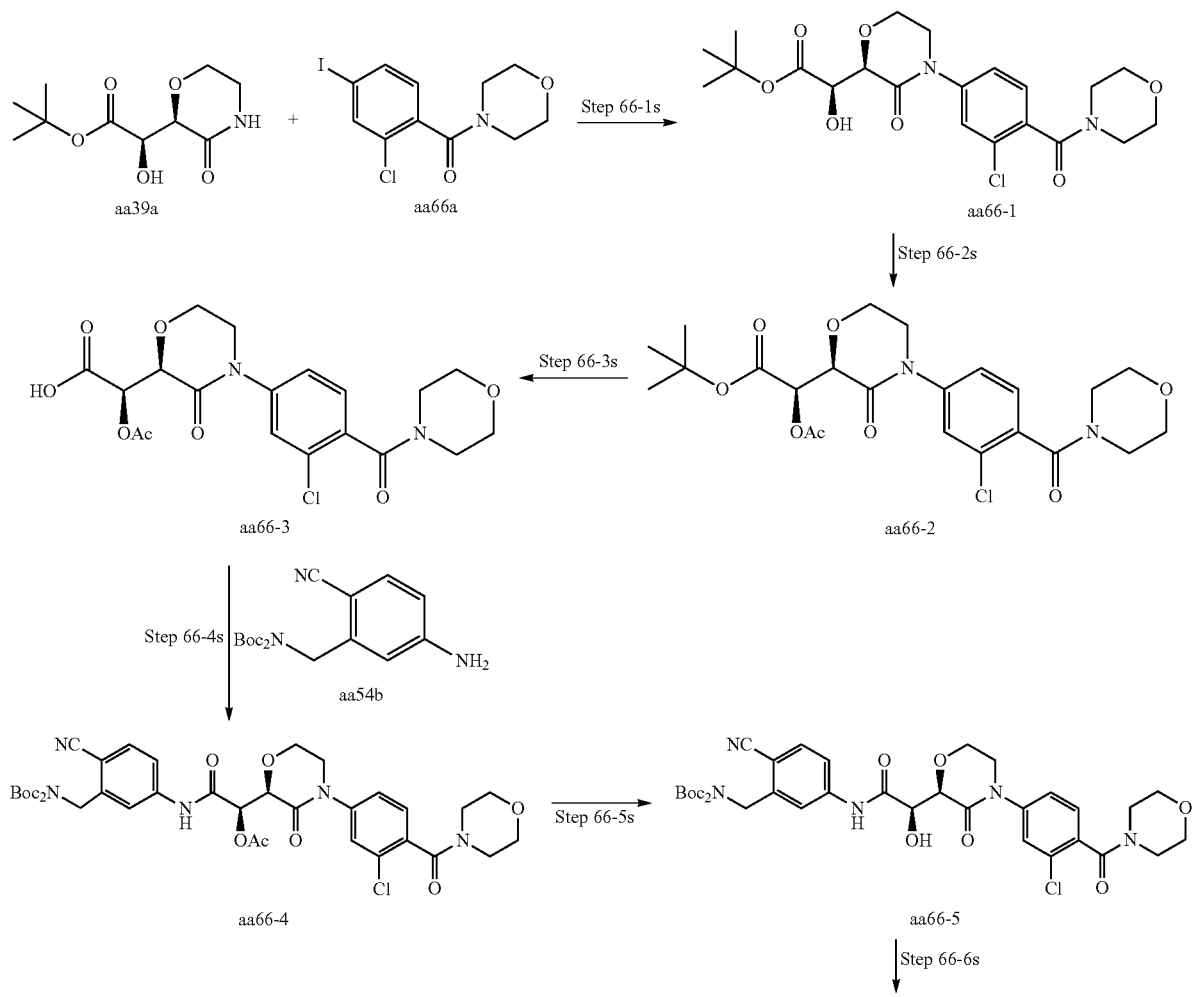

-continued

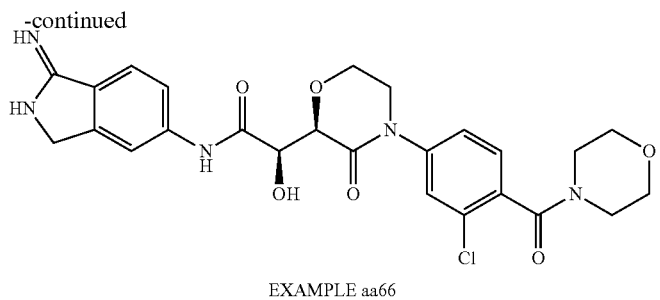

EXAMPLE aa66

Step 66-1s

According to Step 39-1s in the synthetic method for EXAMPLE aa39, compound aa66a (334 mg, 0.95 mmol) was used instead of compound aa39B to obtain compound aa66-1 (276 mg, 0.61 mmol).

Step 66-2s

According to Step 39-2s in the synthetic method for EXAMPLE aa39, compound aa66-1 (276 mg, 0.61 mmol) was used instead of compound aa39-1 to obtain compound aa66-2 (0.61 mmol).

Step 66-3s

According to Step 39-3s in the synthetic method for EXAMPLE aa39, compound aa66-2 (0.61 mmol) was used instead of compound aa39-2 to obtain compound aa66-3 (0.61 mmol) which was used in the next step without further purification.

Step 66-4s

According to Step 54-4s in the synthetic method for EXAMPLE aa54, compound aa66-3 (213 mg, 0.48 mmol) was used instead of compound aa54-3 to obtain compound aa66-4 (310 mg, 0.40 mmol).

Step 66-5s

According to Step 39-5s in the synthetic method for EXAMPLE aa39, compound aa66-4 (310 mg, 0.40 mmol) was used instead of compound aa39-4 to obtain compound aa66-5 (0.40 mmol) which was used in the next step without further purification.

Step 66-6s

According to Step 54-6s in the synthetic method for EXAMPLE aa54, compound aa66-5 (0.40 mmol) was used instead of compound aa54-5 to obtain EXAMPLE aa66 (208 mg, 0.39 mmol) as a white amorphous solid.

Example aa68

Preparation of (R)-2-hydroxy-N-(1-iminoisoindolin-5-yl)-2-((R)-4-(3-(2-morpholino-2-oxoethyl)phenyl)-3-oxomorpholin-2-yl)acetamide EXAMPLE aa68

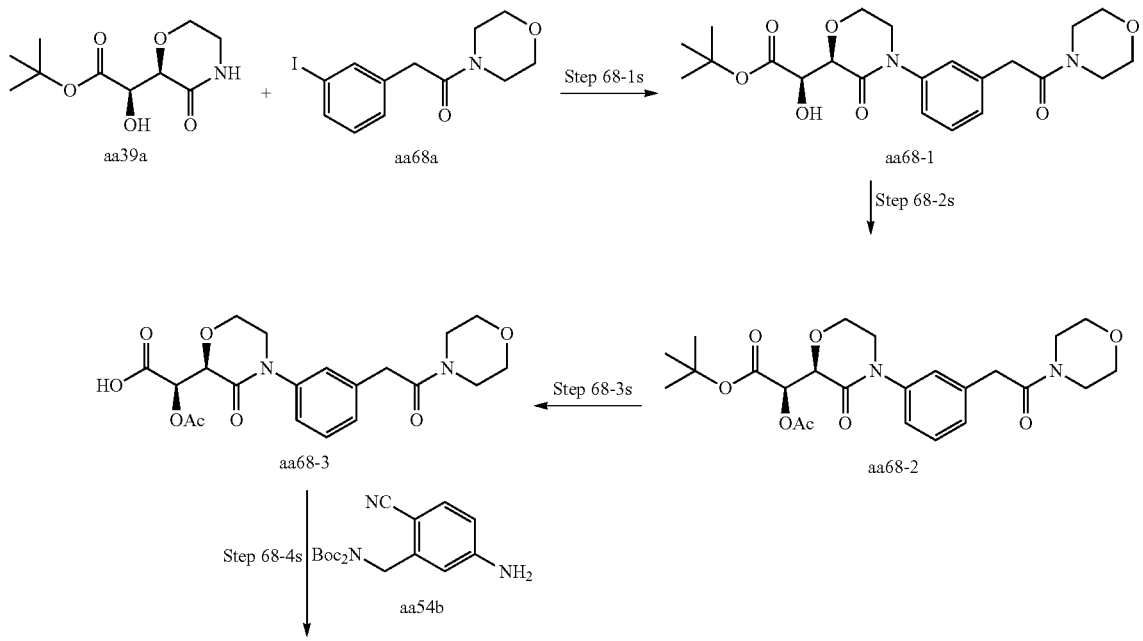

-continued

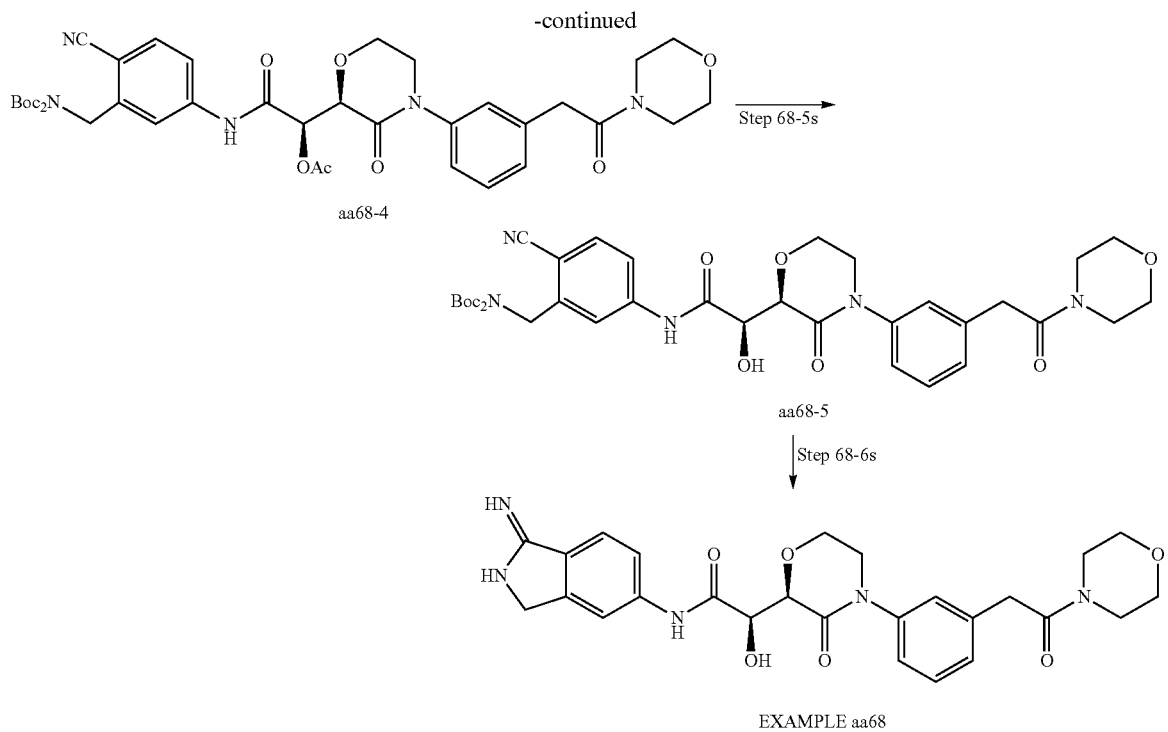

Step 68-1s

According to Step 39-1s in the synthetic method for EXAMPLE aa39, compound aa68a (923 mg, 2.38 mmol) was used instead of compound aa39b to obtain compound aa68-1 (701 mg, 1.43 mmol).

Step 68-2s

According to Step 39-2s in the synthetic method for EXAMPLE aa39, compound aa68-1 (485 mg, 0.99 mmol) was used instead of compound aa39-1 to obtain compound aa68-2 (477 mg, 0.89 mmol).

Step 68-3s

According to Step 39-3s in the synthetic method for EXAMPLE aa39, compound aa68-2 (477 mg, 0.89 mmol) was used instead of compound aa39-2 to obtain compound aa68-3 (0.89 mmol) which was used in the next step without further purification.

Step 68-4s

According to Step 54-4s in the synthetic method for EXAMPLE aa54, compound aa68-3 (0.89 mmol) was used instead of compound aa54-3 to obtain compound aa68-4 (536 mg, 0.67 mmol).

Step 68-5s

According to Step 39-5s in the synthetic method for EXAMPLE aa39, compound aa68-4 (536 mg, 0.67 mmol) was used instead of compound aa39-4 to obtain compound aa68-5 (0.67 mmol) which was used in the next step without further purification.

Step 68-6s

According to Step 54-6s in the synthetic method for EXAMPLE aa54, compound aa68-5 (0.67 mmol) was used instead of compound aa54-5 to obtain EXAMPLE aa68 (291 mg, 0.36 mmol) as a white amorphous solid.

Example aa55

Preparation of (S)-1-(3-((R)-2-((R)-1-hydroxy-2-(1-iminoisoindolin-5-ylamino)-2-oxoethyl)-3-oxomorpholino)benzoyl)pyrrolidine-2-carboxylic acid
EXAMPLE aa55

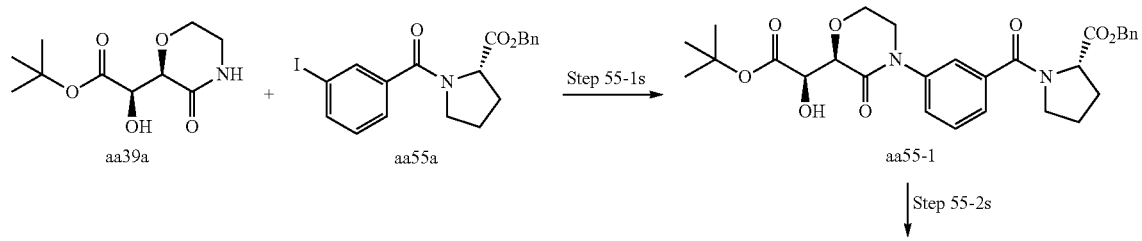

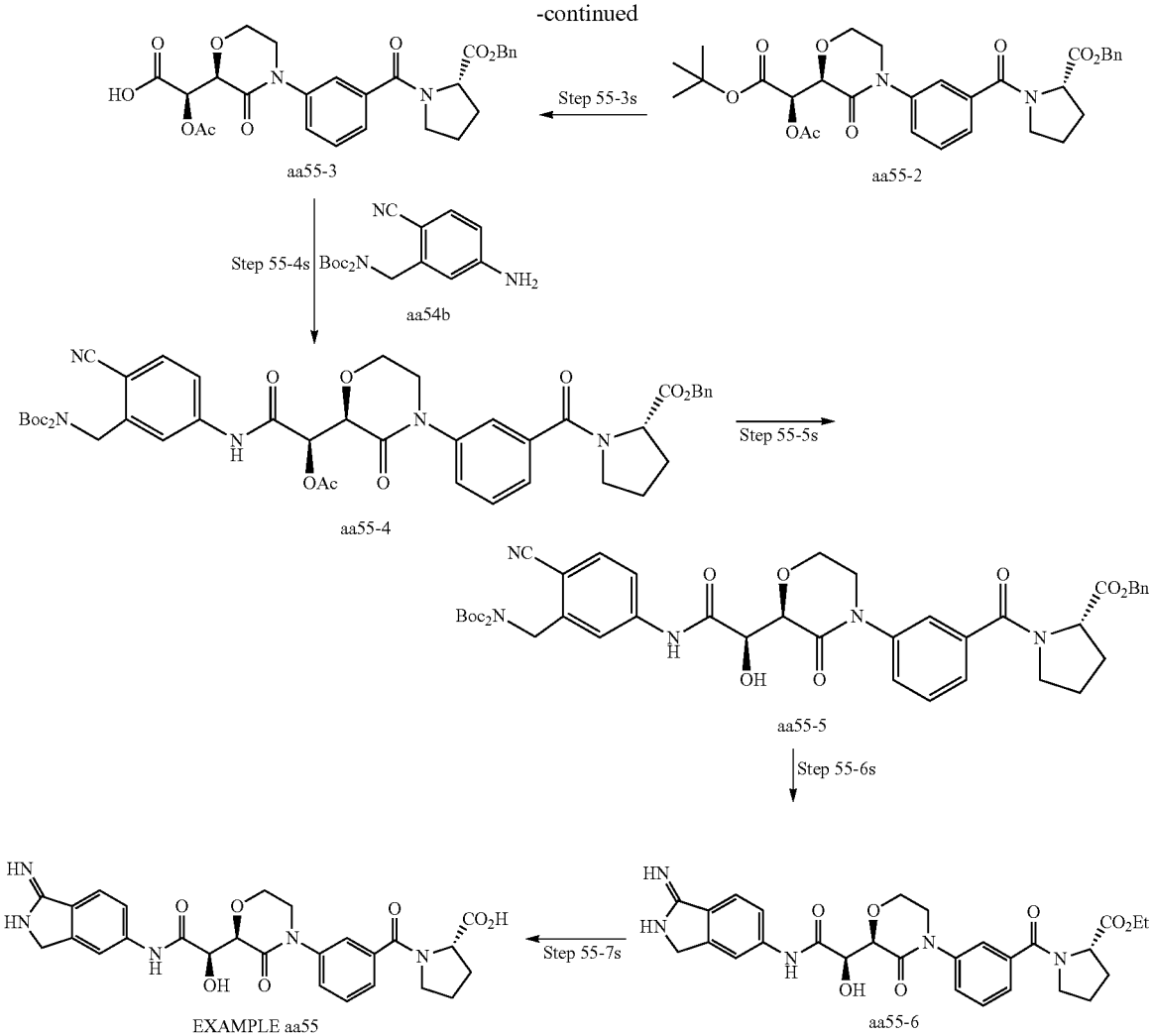

Step 55-1s

According to Step 39-1s in the synthetic method for EXAMPLE aa39, compound aa55a (616 mg, 1.42 mmol) was used instead of compound aa39b to obtain compound aa55-1 (710 mg, 1.32 mmol).

Step 55-2s

According to Step 39-2s in the synthetic method for EXAMPLE aa39, compound aa55-1 (710 mg, 1.32 mmol) was used instead of compound aa39-1 to obtain compound aa55-2 (707 mg, 1.22 mmol).

Step 55-3s

According to Step 39-3s in the synthetic method for EXAMPLE aa39, compound aa55-2 (707 mg, 1.22 mmol) was used instead of compound aa39-2 to obtain compound aa55-3 (1.22 mmol) which was used in the next step without further purification.

Step 55-4s

According to Step 54-4 in the synthetic method for EXAMPLE aa54, compound aa55-3 (1.22 mmol) was used instead of compound aa54-3 to obtain compound aa55-4 (409 mg, 0.48 mmol).

Step 55-5s

According to Step 39-5s in the synthetic method for EXAMPLE aa39, compound aa55-4 (409 mg, 0.48 mmol) was used instead of compound aa39-4 to obtain compound aa55-5 (0.48 mmol) which was used in the next step without further purification.

Step 55-6s

According to Step 54-6s in the synthetic method for EXAMPLE aa54, compound aa55-5 (0.48 mmol) was used instead of compound aa54-5 to obtain compound aa55-6 (0.48 mmol) which was used in the next step without further purification.

Step 55-7s

According to Step 50-7s in the synthetic method for EXAMPLE aa50, compound aa55-6 (0.48 mmol) was used instead of compound aa50-6 to obtain EXAMPLE aa55 (80 mg, 0.15 mmol) as a white amorphous solid.

Example aa57

Preparation of (S)-methyl 1-(3-((R)-2-((R)-1-hydroxy-2-(1-iminoisoindolin-5-ylamino)-2-oxoethyl)-3-oxomorpholino)benzoyl)pyrrolidine-2-carboxylate EXAMPLE aa57

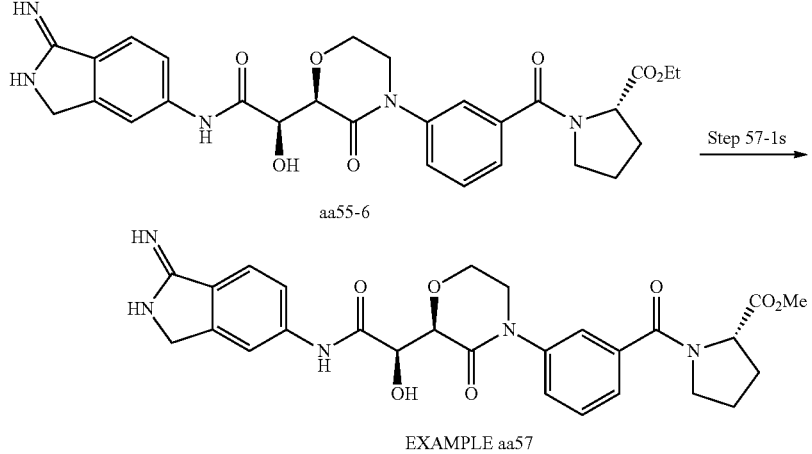

Step 57-1s

According to Step 50-7s in the synthetic method for EXAMPLE aa50, compound aa55-6 (0.48 mmol) was used instead of compound aa50-6 to obtain EXAMPLE aa57 (31 mg, 0.058 mmol) as a white amorphous solid.

Example aa65

Preparation of ethyl 2-(3-((R)-2-((R)-1-hydroxy-2-(1-iminoisoindolin-5-ylamino)-2-oxoethyl)-3-oxomorpholino)phenyl)acetate EXAMPLE aa65

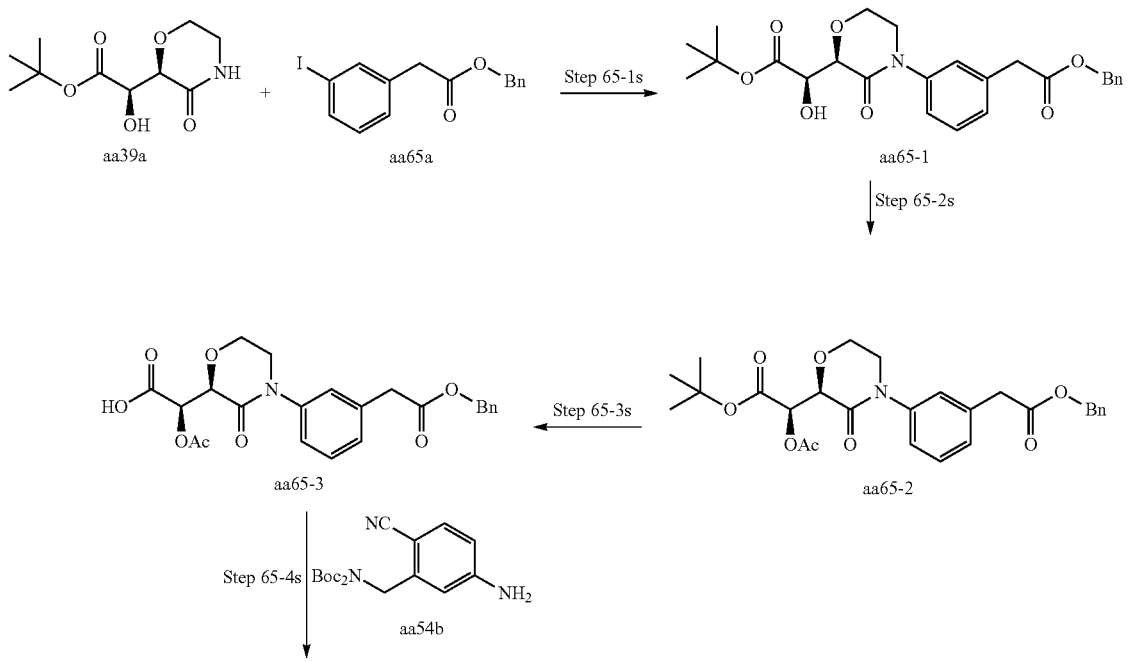

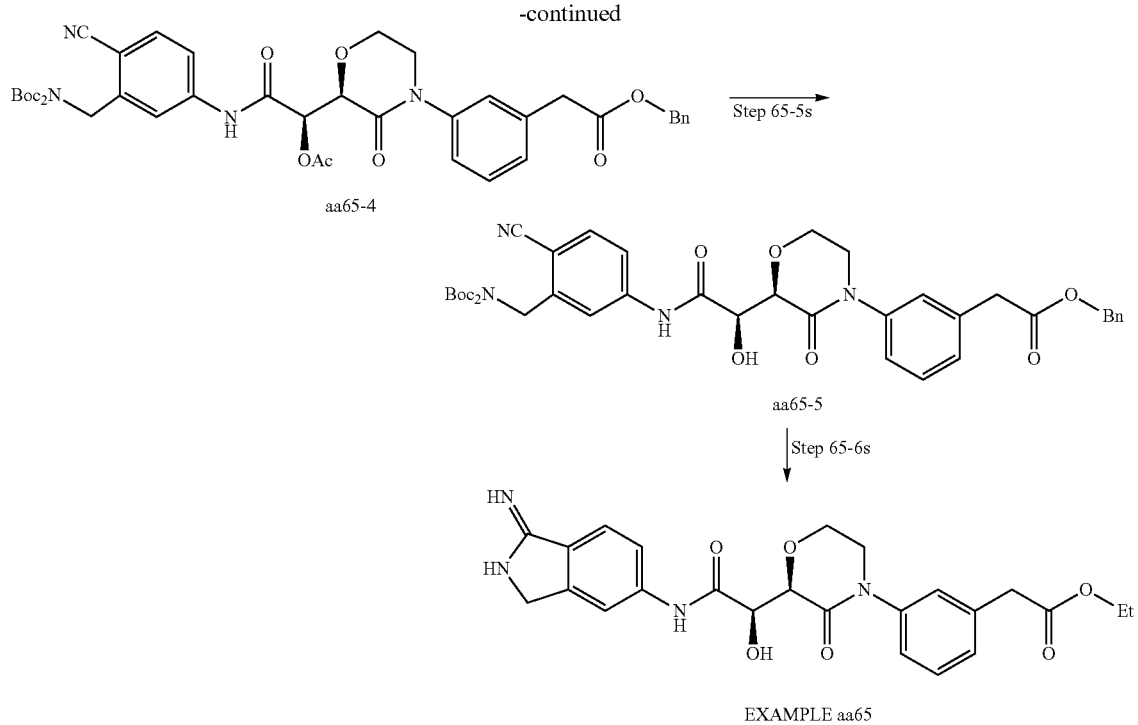

EXAMPLE aa65

Step 65-1s

According to Step 39-1s in the synthetic method for EXAMPLE aa39, compound aa65a (636 mg, 1.81 mmol) was used instead of compound aa39b to obtain compound aa65-1 (694 mg, 1.53 mmol).

Step 65-2s

According to Step 39-2s in the synthetic method for EXAMPLE aa39, compound aa65-1 (694 mg, 1.53 mmol) was used instead of compound aa39-1 to obtain compound aa65-2 (723 mg, 1.45 mmol).

Step 65-3s

According to Step 39-3s in the synthetic method for EXAMPLE aa39, compound aa65-2 (723 mg, 1.45 mmol) was used instead of compound aa39-2 to obtain compound aa65-3 (1.45 mmol) which was used in the next step without further purification.

Step 65-4s

According to Step 54-4s in the synthetic method for EXAMPLE aa54, compound aa65-3 (1.45 mmol) was used instead of compound aa54-3 to obtain compound aa65-4 (715 mg, 0.93 mmol).

Step 65-5s

According to Step 39-5s in the synthetic method for EXAMPLE aa39, compound aa65-4 (715 mg, 0.93 mmol) was used instead of compound aa39-4 to obtain compound aa65-5 (0.93 mmol) which was used in the next step without further purification.

Step 65-6s

According to Step 54-6s in the synthetic method for EXAMPLE aa54, compound aa65-5 (0.93 mmol) was used instead of compound aa54-5 to obtain EXAMPLE aa65 (261 mg, 0.56 mmol) as a white amorphous solid.

Example aa67

Preparation of 2-(3-((R)-2-((R)-1-hydroxy-2-(1-iminoisoindolin-5-ylamino)-2-oxoethyl)-3-oxomorpholino)phenyl)acetic acid EXAMPLE aa67

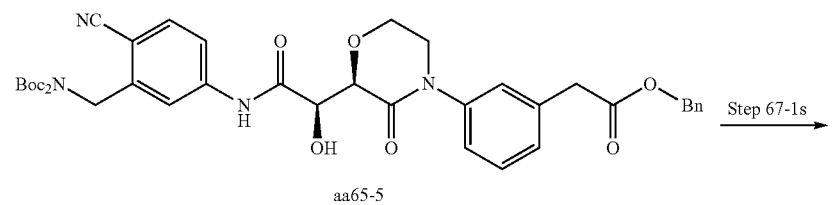

aa65-5

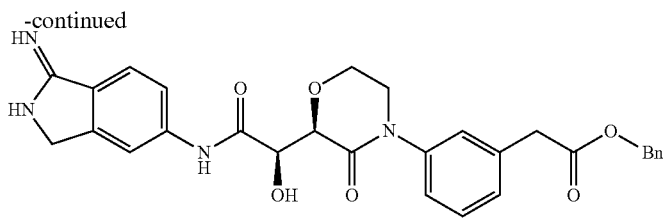

aa67-1

↓ Step 67-2s

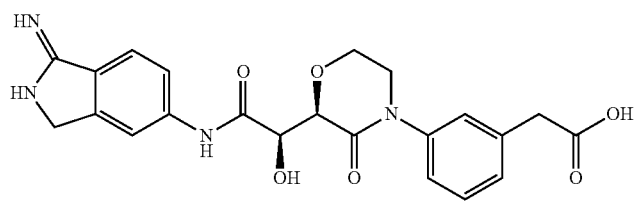

EXAMPLE aa67

Step 67-1s

According to Step 54-6s in the synthetic method for EXAMPLE aa54, compound aa65-5 (715 mg, 0.93 mmol) was used instead of compound aa54-5 to obtain aa67-1 (64 mg, 0.12 mmol).

Step 67-2s

According to Step 39-6s in the synthetic method for EXAMPLE aa39, compound aa67-1 (64 mg, 0.12 mmol) was used instead of compound aa39-5 to obtain EXAMPLE aa67 (30 mg, 0.068 mmol) as a white amorphous solid.

Example aa62

Preparation of ethyl 2-(3-((R)-2-((R)-1-hydroxy-2-(1-iminoisoindolin-5-ylamino)-2-oxoethyl)-3-oxo-morpholino)-N-methylbenzamido)acetate EXAMPLE aa62

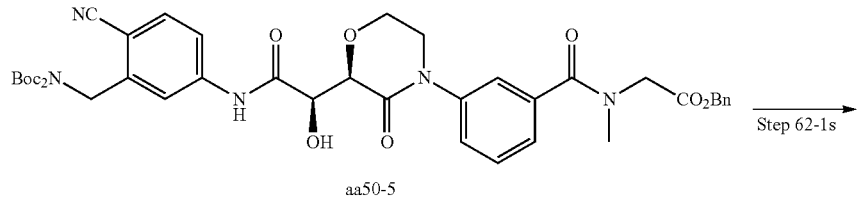

aa50-5

Step 62-1s →

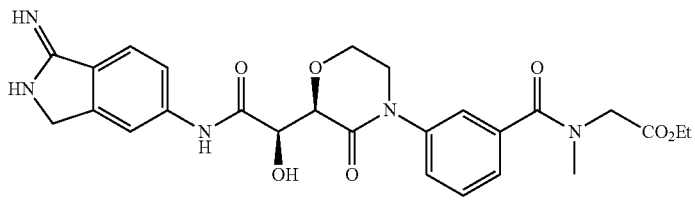

EXAMPLE aa62

Step 62-1

According to Step 54-6s in the synthetic method for EXAMPLE aa54, compound aa50-5 (276 mg, 0.35 mmol) was used instead of compound aa54-5 to obtain EXAMPLE aa62 (65 mg, 0.12 mmol) as a white amorphous solid.

Example aa70
Preparation of benzyl 2-(3-((R)-2-((R)-1-hydroxy-2-(1-iminoisoindolin-5-ylamino)-2-oxoethyl)-3-oxo-morpholino)phenyl)-2-methylpropanoate EXAMPLE aa70
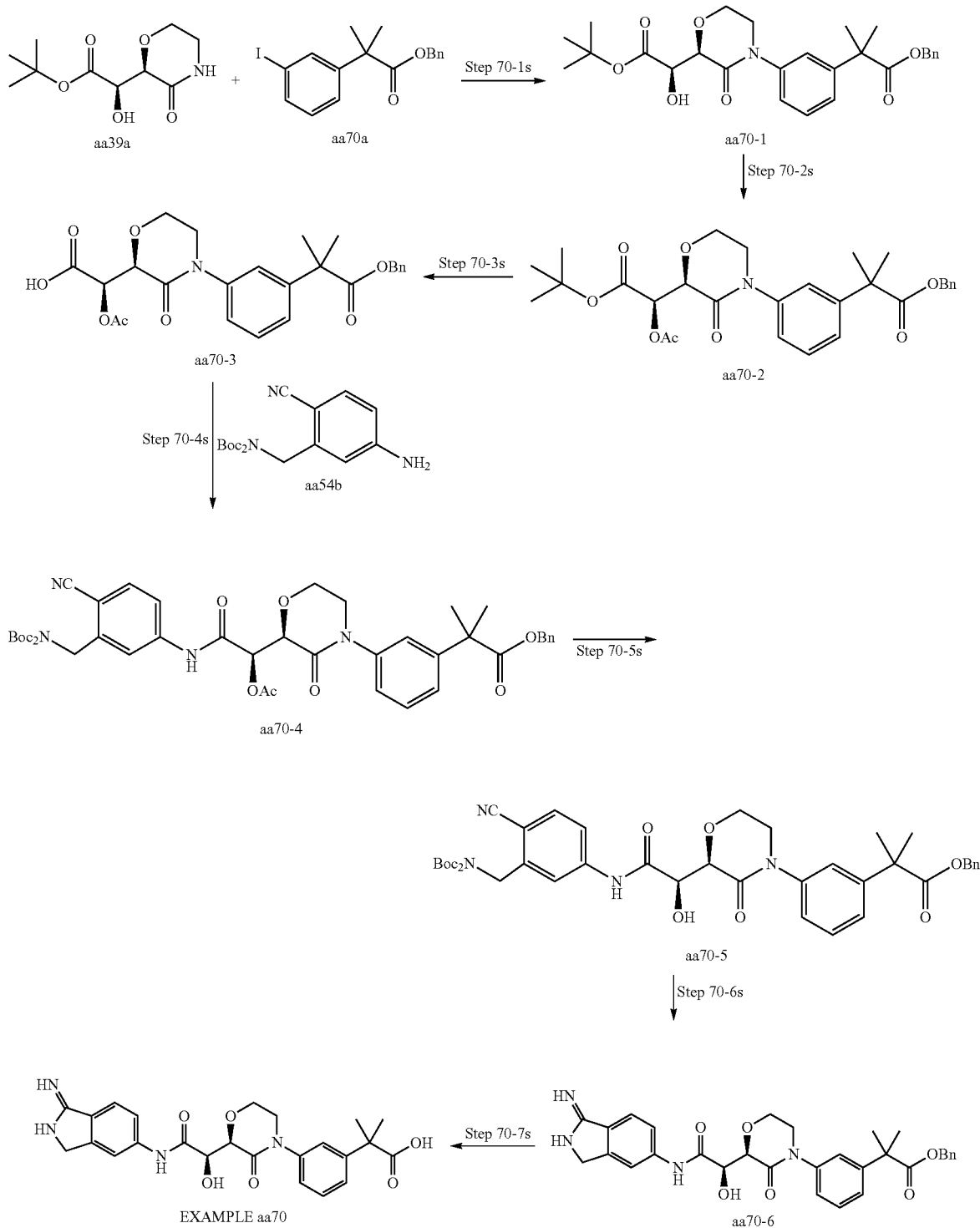

Step 70-1s

According to Step 39-1s in the synthetic method for EXAMPLE aa39, compound aa70a (559 mg, 1.47 mmol) was used instead of compound aa39b to obtain compound aa70-1 (524 mg, 1.08 mmol).

Step 70-2s

According to Step 39-2s in the synthetic method for EXAMPLE aa39, compound aa70-1 (524 mg, 1.08 mmol) was used instead of compound aa39-1 to obtain compound aa70-2 (558 mg, 1.06 mmol).

Step 70-3s

According to Step 39-3s in the synthetic method for EXAMPLE aa39, compound aa70-2 (558 mg, 1.06 mmol) was used instead of compound aa39-2 to obtain compound aa70-3 (1.06 mmol) which was used in the next step without further purification.

Step 70-4s

According to Step 54-4s in the synthetic method for EXAMPLE aa54, compound aa70-3 (1.06 mmol) was used instead of compound aa54-3 to obtain compound aa70-4 (415 mg, 0.54 mmol).

Step 70-5s

According to Step 39-5s in the synthetic method for EXAMPLE aa39, compound aa70-4 (415 mg, 0.54 mmol) was used instead of compound aa39-4 to obtain compound aa70-5 (0.54 mmol) which was used in the next step without further purification.

Step 70-6s

According to Step 54-6s in the synthetic method for EXAMPLE aa54, compound aa70-5 (0.54 mmol) was used instead of compound aa54-5 to obtain aa70-6 (0.54 mmol).

Step 70-7s

According to Step 39-6s in the synthetic method for EXAMPLE aa39, compound aa70-6 (0.54 mmol) was used instead of compound aa39-5 to obtain EXAMPLE aa70 (83 mg, 0.18 mmol) as a white amorphous solid.

Example aa69

Preparation of (R)-2-hydroxy-N-(1-iminoisoindolin-5-yl)-2-((R)-4-(3-(morpholine-4-carbonyl)phenyl)-3-oxomorpholin-2-yl)acetamide EXAMPLE aa69

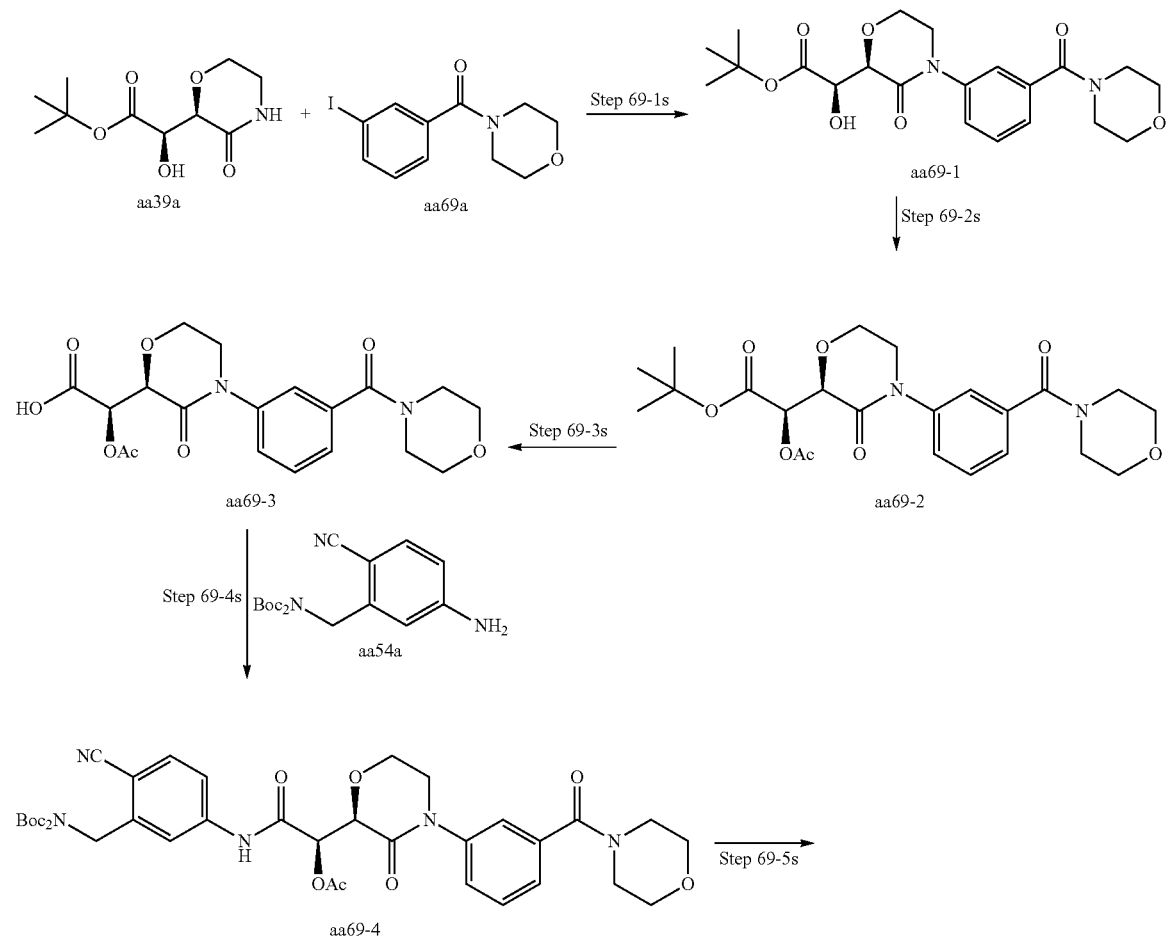

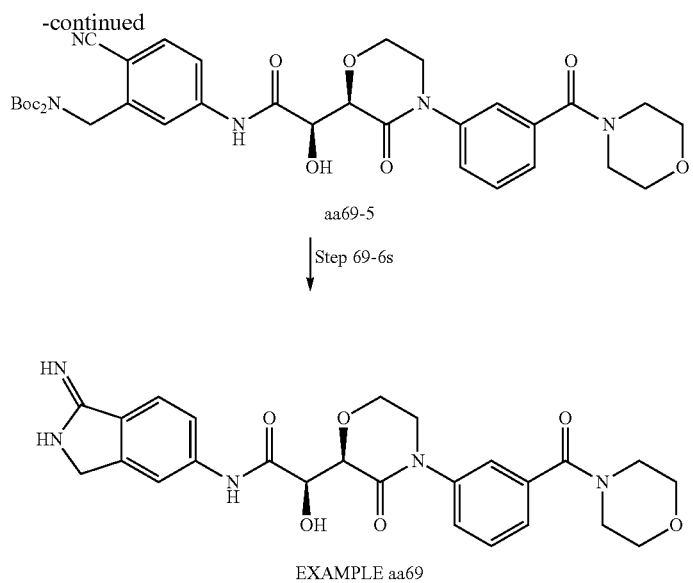

aa69-5

Step 69-6s

EXAMPLE aa69

Step 69-1s

According to Step 39-1s in the synthetic method for EXAMPLE aa39, compound aa69a (296 mg, 0.93 mmol) was used instead of compound aa39b to obtain compound aa69-1 (345 mg, 0.82 mmol).

Step 69-2s

According to Step 39-2s in the synthetic method for EXAMPLE aa39, compound aa69-1 (345 mg, 0.82 mmol) was used instead of compound aa39-1 to obtain compound aa69-2 (372 mg, 0.81 mmol).

Step 69-3s

According to Step 39-3s in the synthetic method for EXAMPLE aa39, compound aa69-2 (372 mg, 0.81 mmol) was used instead of compound aa39-2 to obtain compound aa69-3 (0.81 mmol) which was used in the next step without further purification.

Step 69-4s

According to Step 54-4s in the synthetic method for EXAMPLE aa54, compound aa69-3 (0.81 mmol) was used instead of compound aa54-3 to obtain compound aa69-4 (523 mg, 0.71 mmol).

Step 69-5s

According to Step 39-5s in the synthetic method for EXAMPLE aa39, compound aa69-4 (523 mg, 0.71 mmol) was used instead of compound aa39-4 to obtain compound aa69-5 (0.71 mmol) which was used in the next step without further purification.

Step 69-6s

According to Step 54-6s in the synthetic method for EXAMPLE aa54, compound aa69-5 (0.71 mmol) was used instead of compound aa54-5 to obtain EXAMPLE aa69 (274 mg, 0.56 mmol) as a white amorphous solid.

Example aa71

Preparation of 3-((R)-2-((R)-1-hydroxy-2-(1-iminoisoindolin-5-ylamino)-2-oxoethyl)-3-oxomorpholino)-N-methyl-N-(2-morpholino-2-oxoethyl)benzamide EXAMPLE aa71

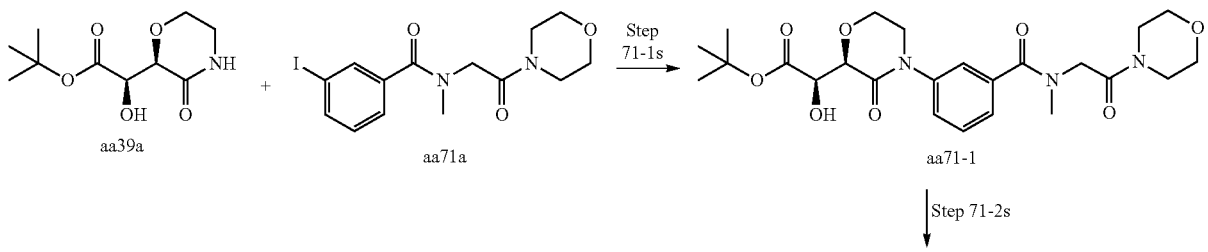

Step 71-2s

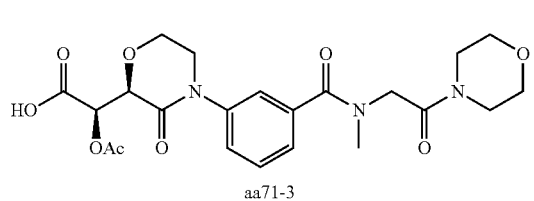
aa71-3

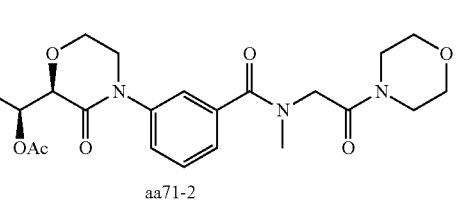
aa71-2

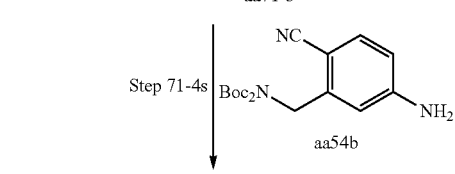
aa54b

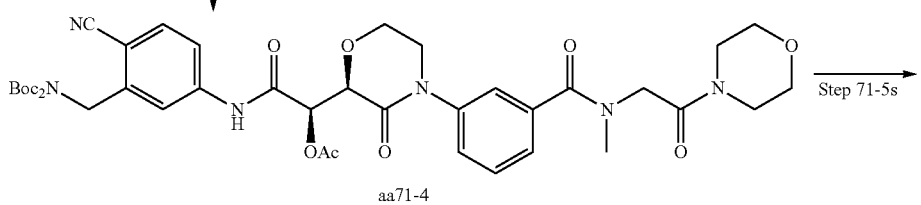
aa71-4

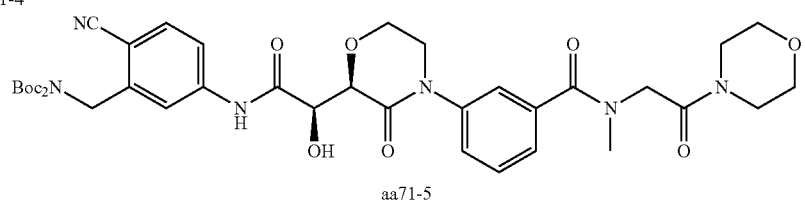
aa71-5

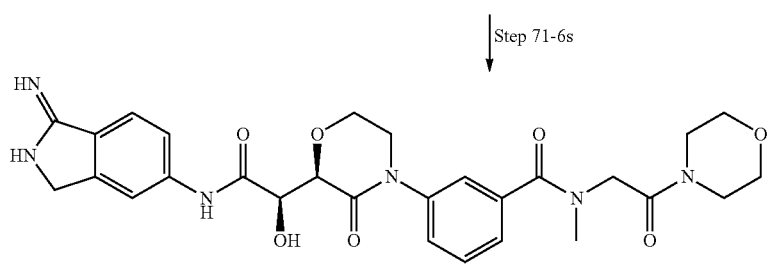
EXAMPLE aa71

Step 71-1s

According to Step 39-1s in the synthetic method for EXAMPLE aa39, compound aa71a (923 mg, 2.38 mmol) was used instead of compound aa39b to obtain compound aa71-1 (701 mg, 1.43 mmol).

Step 71-2s

According to Step 39-2s in the synthetic method for EXAMPLE aa39, compound aa71-1 (485 mg, 0.99 mmol) was used instead of compound aa39-1 to obtain compound aa71-2 (477 mg, 0.89 mmol).

Step 71-3s

According to Step 39-3s in the synthetic method for EXAMPLE aa39, compound aa71-2 (477 mg, 0.89 mmol) was used instead of compound aa39-2 to obtain compound aa71-3 (0.89 mmol) which was used in the next step without further purification.

Step 71-4s

According to Step 54-4s in the synthetic method for EXAMPLE aa54, compound aa71-3 (345 mg, 0.85 mmol) was used instead of compound aa54-3 to obtain compound aa71-4 (523 mg, 0.71 mmol).

Step 71-5s

According to Step 39-5s in the synthetic method for EXAMPLE aa39, compound aa71-4 (523 mg, 0.71 mmol) was used instead of compound aa39-4 to obtain compound aa71-5 (0.71 mmol) which was used in the next step without further purification.

Step 71-6s

According to Step 54-6s in the synthetic method for EXAMPLE aa54, compound aa71-5 (0.71 mmol) was used instead of compound aa54-5 to obtain EXAMPLE aa71 (274 mg, 0.56 mmol) as a white amorphous solid.

Example aa72

Preparation of (R)-2-hydroxy-N-(1-iminoisoindolin-5-yl)-2-((R)-4-(3-(2-((R)-3-methoxypyrrolidin-1-yl)-2-oxoethyl)phenyl)-3-oxomorpholin-2-yl)acetamide
EXAMPLE aa72

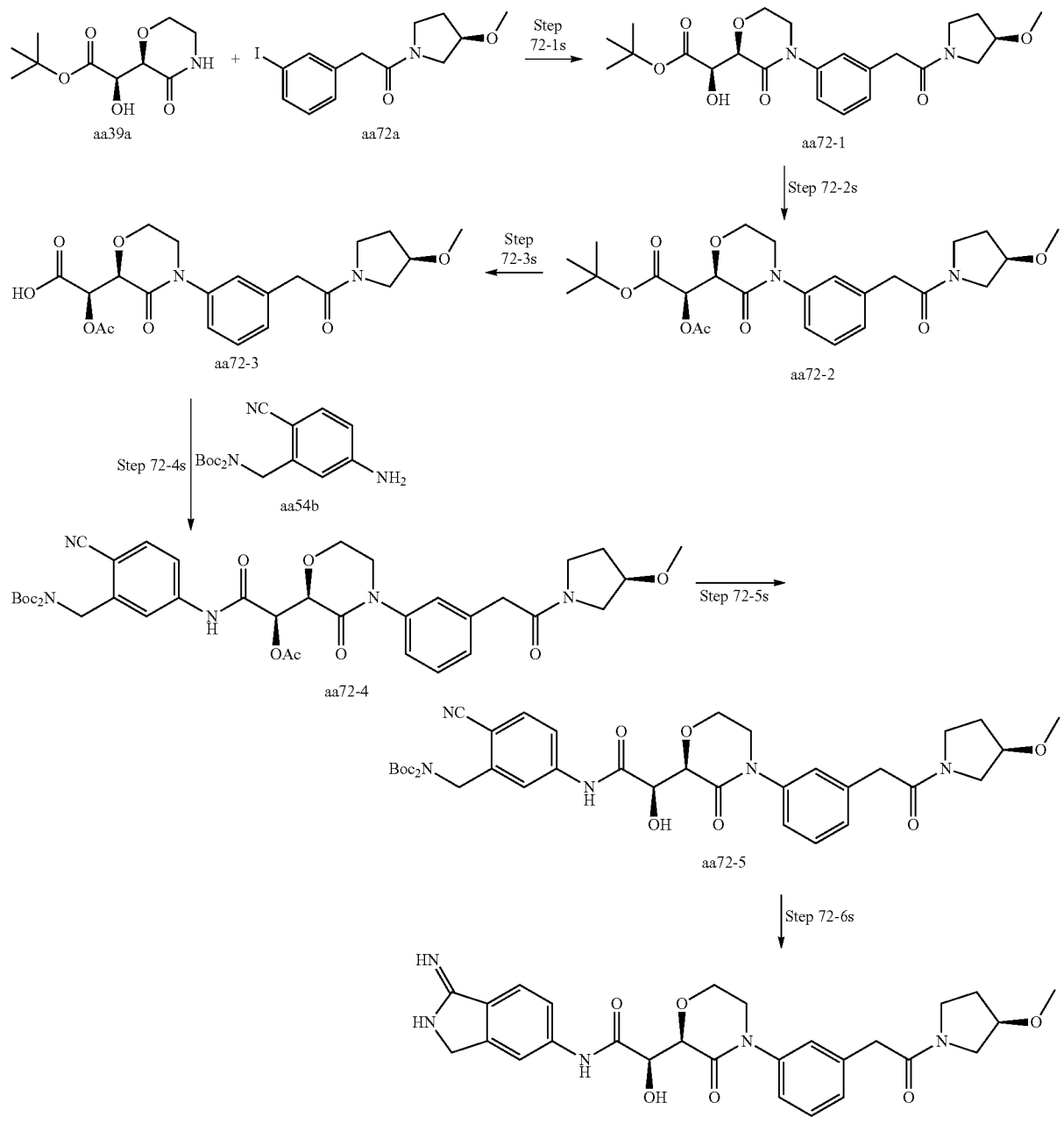

Step 72-1s

According to Step 39-1s in the synthetic method for EXAMPLE aa39, compound aa72a (356 mg, 1.03 mmol) was used instead of compound aa39b to obtain compound aa72-1 (358 mg, 0.80 mmol).

Step 72-2s

According to Step 39-2s in the synthetic method for EXAMPLE aa39, compound aa72-1 (358 mg, 0.80 mmol) was used instead of compound aa39-1 to obtain compound aa72-2 (391 mg, 0.80 mmol).

Step 72-3s

According to Step 39-3s in the synthetic method for EXAMPLE aa39, compound aa72-2 (391 mg, 0.80 mmol) was used instead of compound aa39-2 to obtain compound aa72-3 (0.80 mmol) which was used in the next step without further purification.

Step 72-4s

According to Step 54-4s in the synthetic method for EXAMPLE aa54, compound aa72-3 (0.80 mmol) was used instead of compound aa54-3 to obtain compound aa72-4 (534 mg, 0.70 mmol).

Step 72-5s

According to Step 39-5s in the synthetic method for EXAMPLE aa39, compound aa72-4 (534 mg, 0.70 mmol) was used instead of compound aa39-4 to obtain compound aa72-5 (0.70 mmol) which was used in the next step without further purification.

Step 72-6s

According to Step 54-6s in the synthetic method for EXAMPLE aa54, compound aa72-5 (0.70 mmol) was used instead of compound aa54-5 to obtain EXAMPLE aa72 (283 mg, 0.56 mmol) as a white amorphous solid.

Example aa73

Preparation of (R)-2-hydroxy-N-(1-iminoisoindolin-5-yl)-2-((R)-4-(3-(2-((S)-3-methoxypyrrolidin-1-yl)-2-oxoethyl)phenyl)-3-oxomorpholin-2-yl)acetamide EXAMPLE aa73

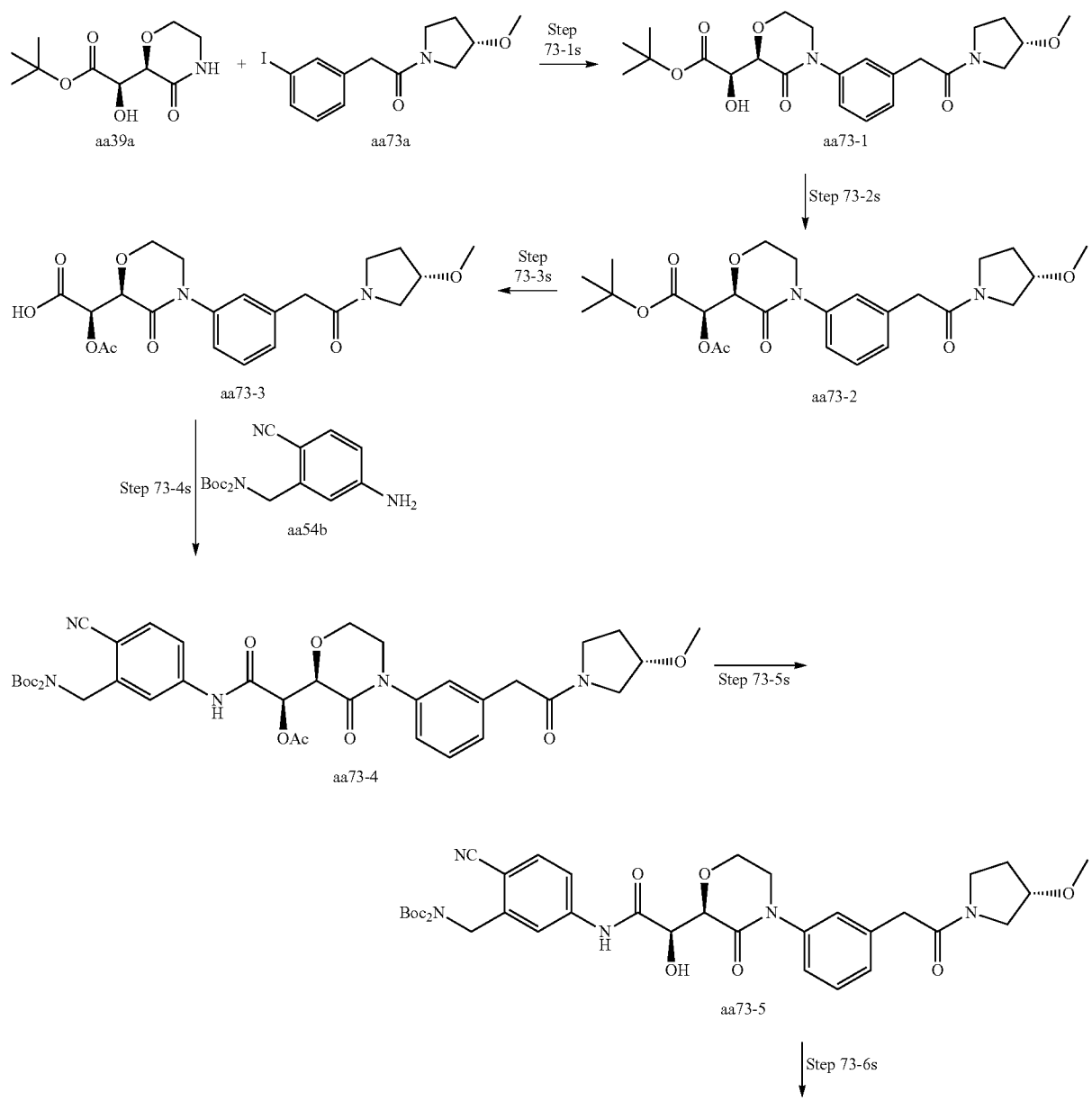

-continued

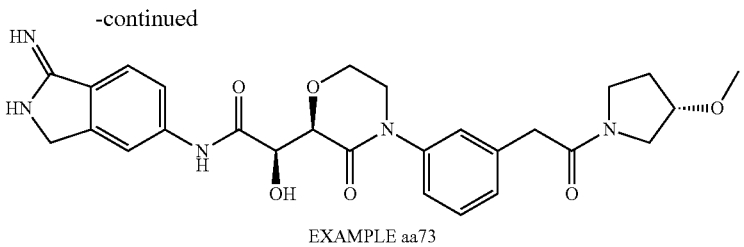

EXAMPLE aa73

Step 73-1s

According to Step 39-1s in the synthetic method for EXAMPLE aa39, compound aa73a (724 mg, 2.10 mmol) was used instead of compound aa39b to obtain compound aa73-1 (331 mg, 0.74 mmol).

Step 73-2s

According to Step 39-2s in the synthetic method for EXAMPLE aa39, compound aa73-1 (331 mg, 0.74 mmol) was used instead of compound aa39-1 to obtain compound aa73-2 (359 mg, 0.73 mmol).

Step 73-3s

According to Step 39-3s in the synthetic method for EXAMPLE aa39, compound aa73-2 (359 mg, 0.73 mmol) was used instead of compound aa39-2 to obtain compound aa73-3 (0.73 mmol) which was used in the next step without further purification.

Step 73-4s

According to Step 54-4s in the synthetic method for EXAMPLE aa54, compound aa73-3 (0.73 mmol) was used instead of compound aa54-3 to obtain compound aa73-4 (395 mg, 0.52 mmol).

Step 73-5s

According to Step 39-5s in the synthetic method for EXAMPLE aa39, compound aa73-4 (395 mg, 0.52 mmol) was used instead of compound aa39-4 to obtain compound aa73-5 (0.52 mmol) which was used in the next step without further purification.

Step 73-6s

According to Step 54-6s in the synthetic method for EXAMPLE aa54, compound aa73-5 (0.52 mmol) was used instead of compound aa54-5 to obtain EXAMPLE aa73 (222 mg, 0.43 mmol) as a white amorphous solid.

Example aa74

Preparation of methyl 2-(3-((R)-2-((R)-1-hydroxy-2-(1-iminoisoindolin-5-ylamino)-2-oxoethyl)-3-oxo-morpholino)phenyl)-2-methylpropanoate EXAMPLE aa74

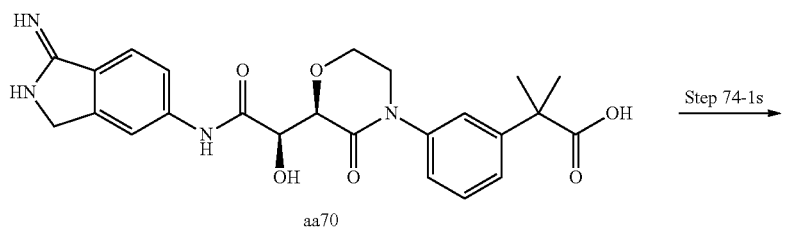

Step 74-1s

To a solution of compound aa70 (44 mg, 0.094 mmol) in methanol (4 mL) was concentrated sulfuric acid (0.08 mL). The reaction mixture was heated at 80° C. for 16 hours. Triethylamine (0.5 mL) was added. The organic solvent was evaporated under reduced pressure. The crude product was purified RP-HPLC to afford the desired EXAMPLE aa74 (20 mg, 0.042 mmol) as a white amorphous solid.

Example aa75

Preparation of methyl 2-(3-((R)-2-((R)-1-hydroxy-2-(1-iminoisoindolin-5-ylamino)-2-oxoethyl)-3-oxomorpholino)phenyl)acetate EXAMPLE aa75

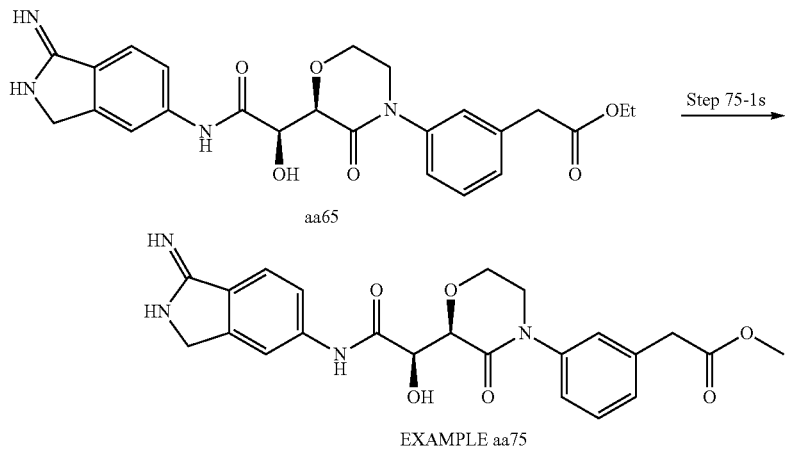

Step 75-1s

To a solution of compound aa65 (237 mg, 0.51 mmol) in methanol (5 mL) and water (5 mL) was added triethylamine (0.5 mL). The reaction mixture was stirred at room temperature for 3 days. The organic solvent was evaporated under reduced pressure. The residue was dissolved in methanol (5 mL) and concentrated sulfuric acid (0.1 mL) was added. The reaction mixture was heated at 80° C. for 16 hours. Triethylamine (1 mL) was added. The organic solvent was evaporated under reduced pressure. The crude product was purified RP-HPLC to afford the desired EXAMPLE aa75 (20 mg, 0.042 mmol) as a white amorphous solid.

Example aa76

Preparation of (R)-2-hydroxy-N-(1-iminoisoindolin-5-yl)-2-((R)-4-(3-(4-methyl-3-oxopiperazine-1-carbonyl)phenyl)-3-oxomorpholin-2-yl)acetamide EXAMPLE aa76

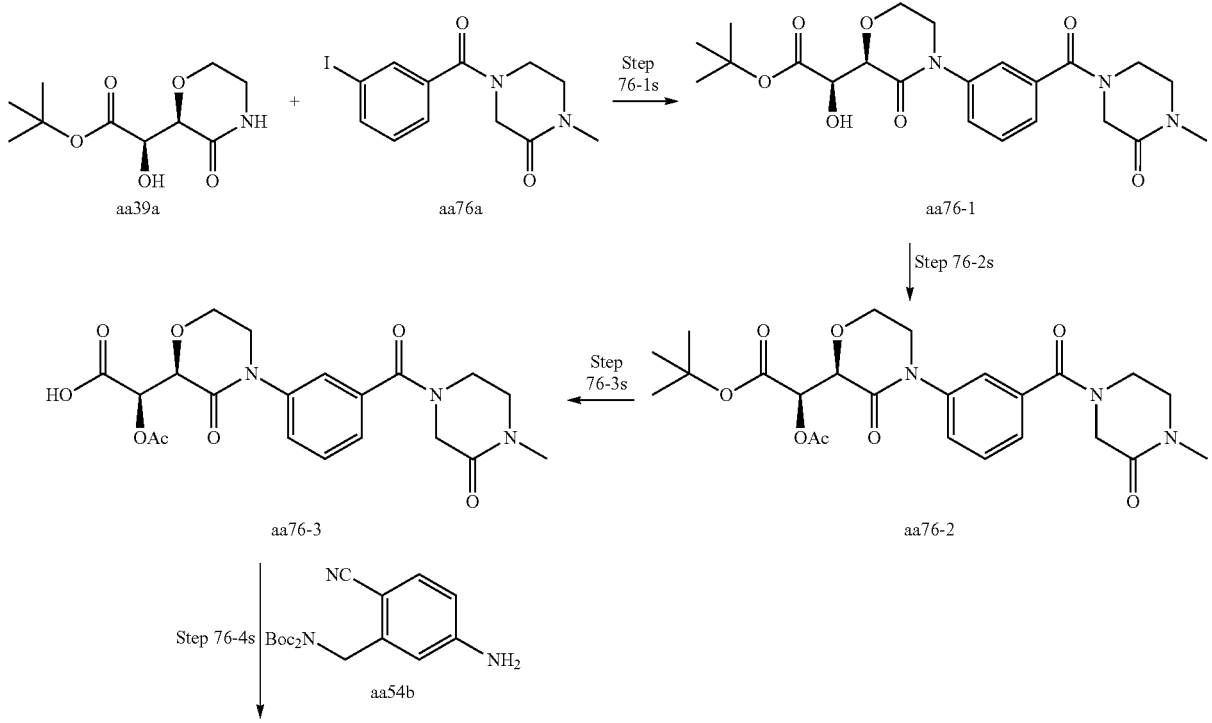

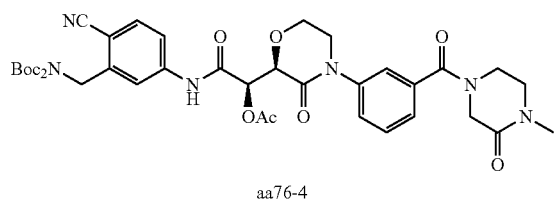

aa76-4

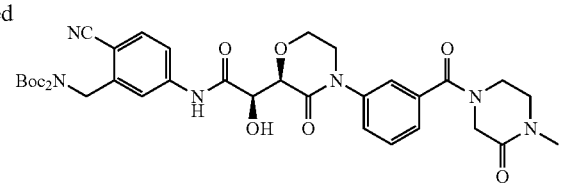

aa76-5

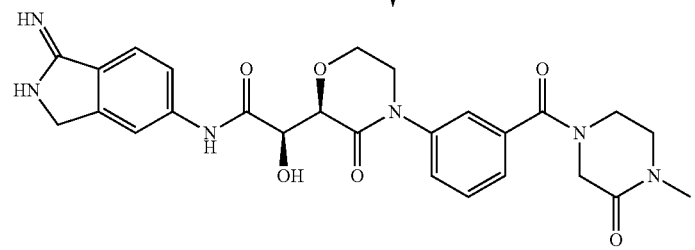

EXAMPLE aa76

Step 76-1s

According to Step 39-1s in the synthetic method for EXAMPLE aa39, compound aa76a (328 mg, 0.95 mmol) was used instead of compound aa39b to obtain compound aa76-1 (347 mg, 0.71 mmol).

Step 76-2s

According to Step 39-2s in the synthetic method for EXAMPLE aa39, compound aa76-1 (347 mg, 0.71 mmol) was used instead of compound aa39-1 to obtain compound aa76-2 (265 mg, 0.54 mmol).

Step 76-3s

According to Step 39-3s in the synthetic method for EXAMPLE aa39, compound aa76-2 (265 mg, 0.54 mmol) was used instead of compound aa39-2 to obtain compound aa76-3 (0.54 mmol) which was used in the next step without further purification.

Step 76-4s

According to Step 54-4s in the synthetic method for EXAMPLE aa54, compound aa76-3 (0.54 mmol) was used instead of compound aa54-3 to obtain compound aa76-4 (282 mg, 0.37 mmol).

Step 76-5s

According to Step 39-5s in the synthetic method for EXAMPLE aa39, compound aa76-4 (282 mg, 0.37 mmol) was used instead of compound aa39-4 to obtain compound aa76-5 (0.37 mmol) which was used in the next step without further purification.

Step 76-6s

According to Step 54-6s in the synthetic method for EXAMPLE aa54, compound aa76-5 (0.37 mmol) was used instead of compound aa54-5 to obtain EXAMPLE aa76 (135 mg, 0.26 mmol) as a white amorphous solid.

Example aa77

Preparation of ethyl 2-(3-((R)-2-((R)-1-hydroxy-2-(1-iminoisoindolin-5-ylamino)-2-oxoethyl)-3-oxo-morpholino)phenyl)-2-methylpropanoate
EXAMPLE aa77

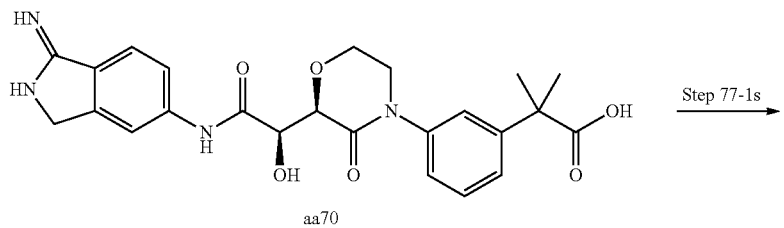

aa70

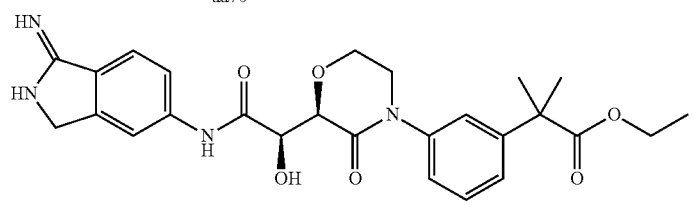

EXAMPLE aa77

731

Step 77-1s

To a solution of compound aa70 (55 mg, 0.12 mmol) in absolute ethanol (4 mL) was added concentrated sulfuric acid (0.05 mL). The reaction mixture was heated at 80° C. for 16 hours. Triethylamine (0.5 mL) was added. The organic solvent was evaporated under reduced pressure. The crude product was purified RP-HPLC to afford the desired EXAMPLE aa77 (24 mg, 0.049 mmol) as a white amorphous solid.

732

Example aa78

Preparation of (S)-1-(3-((R)-2-((R)-2-(4-carbamimidoylphenylamino)-1-hydroxy-2-oxoethyl)-3-oxomorpholino)-5-fluorobenzoyl)pyrrolidine-2-carboxylic acid EXAMPLE aa78

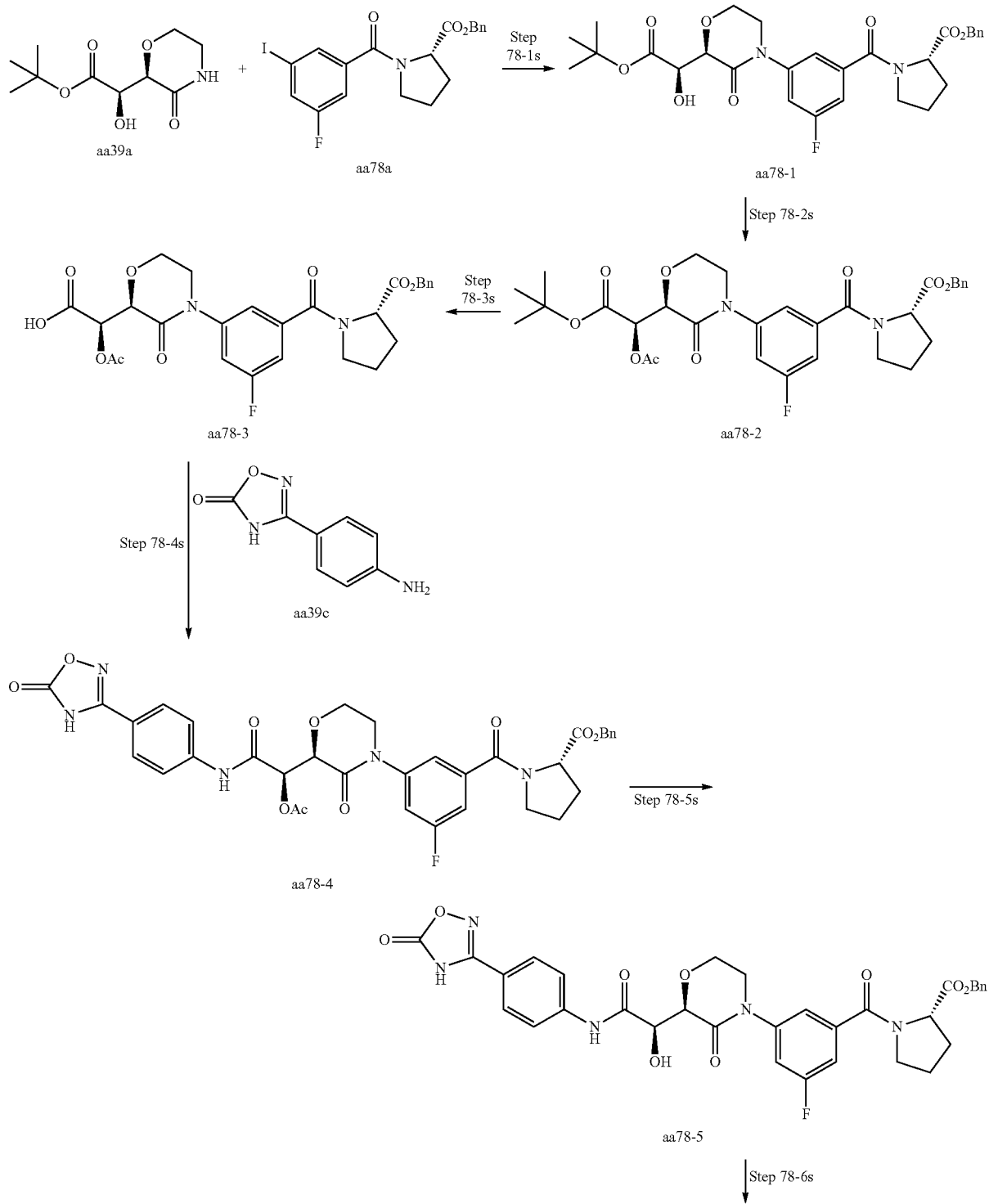

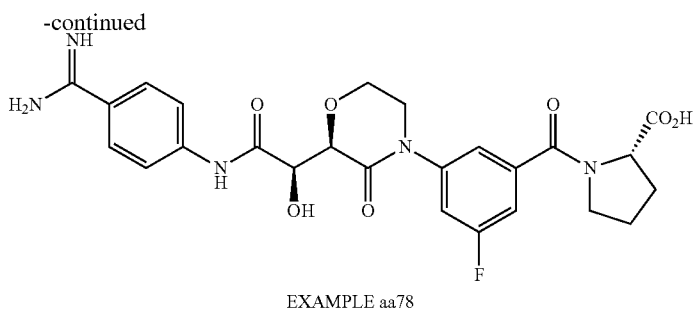

EXAMPLE aa78

Step 78-1s

According to Step 39-1s in the synthetic method for EXAMPLE aa39, compound aa78a (1.59 g, 3.51 mmol) was used instead of compound aa39b to obtain compound aa78-1 (895 mg, 1.61 mmol).

Step 78-2s

According to Step 39-2s in the synthetic method for EXAMPLE aa39, compound aa78-1 (895 mg, 1.61 mmol) was used instead of compound aa39-1 to obtain compound aa78-2 (854 mg, 1.43 mmol).

Step 78-3s

According to Step 39-3s in the synthetic method for EXAMPLE aa39, compound aa78-2 (854 mg, 1.43 mmol) was used instead of compound aa39-2 to obtain compound aa78-3 (1.43 mmol) which was used in the next step without further purification.

Step 78-4s

According to Step 39-4s in the synthetic method for EXAMPLE aa39, compound aa78-3 (1.43 mmol) was used instead of compound aa39-3 to obtain compound aa78-4 (968 mg, 1.38 mmol).

Step 78-5s

According to Step 39-5s in the synthetic method for EXAMPLE aa39, compound aa78-4 (968 mg, 1.38 mmol) was used instead of compound aa39-4 to obtain compound aa78-5 (1.38 mmol) which was used in the next step without further purification.

Step 78-6s

According to Step 39-6s in the synthetic method for EXAMPLE aa39, compound aa78-5 (1.38 mmol) was used instead of compound aa39-5 to obtain EXAMPLE aa78 (542 mg, 1.03 mmol) as a white amorphous solid.

Example aa79

Preparation of (R)-2-hydroxy-N-(1-iminoisoindolin-5-yl)-2-((R)-4-(3-(2-(4-methyl-3-oxopiperazin-1-yl)-2-oxoethyl)phenyl)-3-oxomorpholin-2-yl)acetamide EXAMPLE aa79

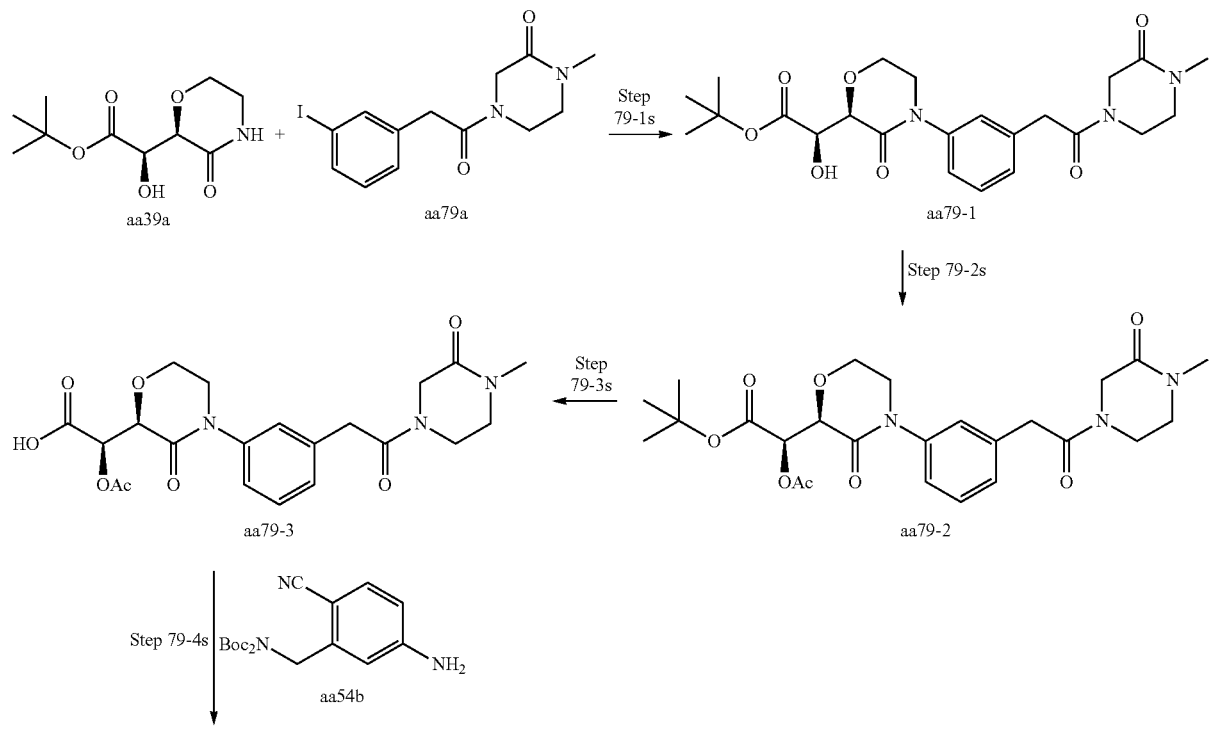

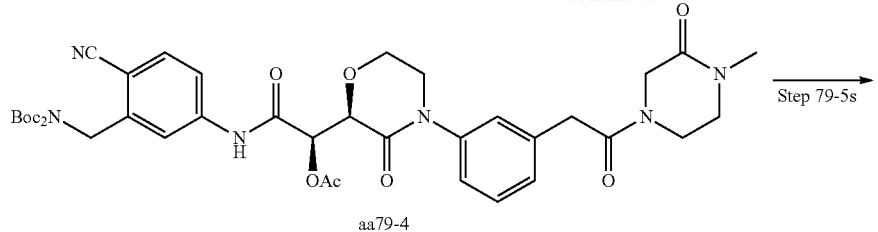

aa79-4

-continued

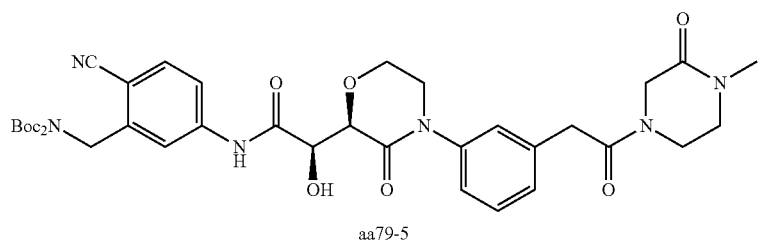

aa79-5

Step 79-6s

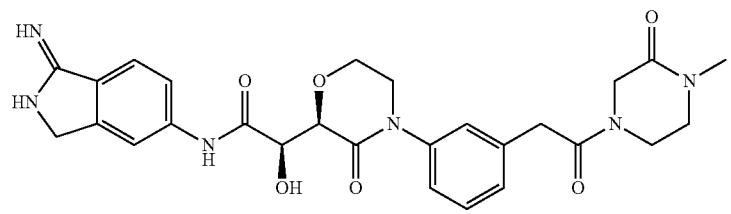

EXAMPLE aa79

Step 79-1s

According to Step 39-1s in the synthetic method for EXAMPLE aa39, compound aa79a (341 mg, 0.95 mmol) was used instead of compound aa39b to obtain compound aa79-1 (214 mg, 0.46 mmol).

Step 79-2s

According to Step 39-2s in the synthetic method for EXAMPLE aa39, compound aa79-1 (214 mg, 0.46 mmol) was used instead of compound aa39-1 to obtain compound aa79-2 (207 mg, 0.41 mmol).

Step 79-3s

According to Step 39-3s in the synthetic method for EXAMPLE aa39, compound aa79-2 (207 mg, 0.41 mmol) was used instead of compound aa39-2 to obtain compound aa79-3 (0.41 mmol) which was used in the next step without further purification.

Step 79-4s

According to Step 54-4s in the synthetic method for EXAMPLE aa54, compound aa79-3 (0.41 mmol) was used instead of compound aa54-3 to obtain compound aa79-4 (277 mg, 0.36 mmol).

Step 79-5s

According to Step 39-5s in the synthetic method for EXAMPLE aa39, compound aa79-4 (277 mg, 0.36 mmol) was used instead of compound aa39-4 to obtain compound aa79-5 (0.36 mmol) which was used in the next step without further purification.

Step 79-6s

According to Step 54-6s in the synthetic method for EXAMPLE aa54, compound aa79-5 (0.36 mmol) was used instead of compound aa54-5 to obtain EXAMPLE aa79 (147 mg, 0.28 mmol) as a white amorphous solid.

Example aa80

Preparation of (S)-ethyl 1-(3-((R)-2-((R)-2-(4-carbamimidoylphenylamino)-1-hydroxy-2-oxoethyl)-3-oxomorpholino)-5-fluorobenzoyl)pyrrolidine-2-carboxylate EXAMPLE aa80

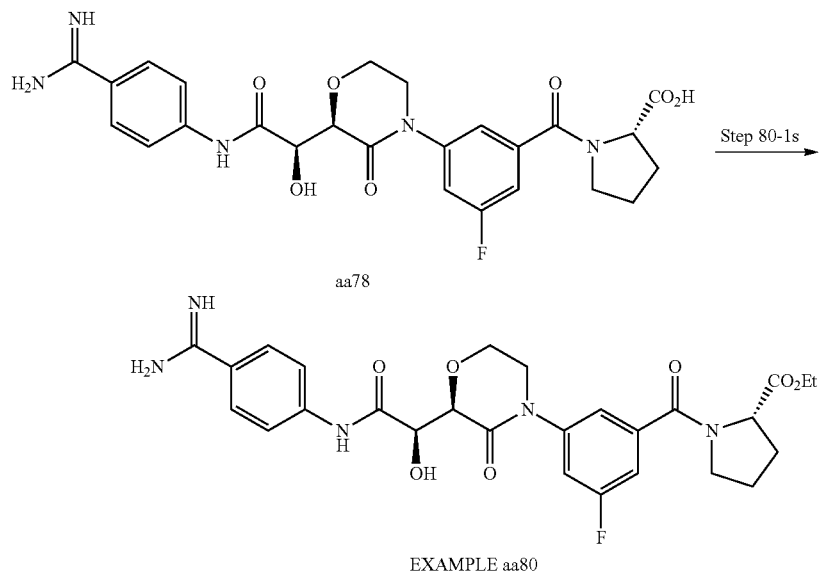

According to Step 77-1s in the synthetic method for EXAMPLE aa77, compound aa78 (60 mg, 0.11 mmol) was used instead of compound aa70 to obtain EXAMPLE aa80 (29 mg, 0.049 mmol) as a white amorphous solid.

Example aa81

Preparation of (S)-methyl 1-(3-((R)-2-((R)-2-(4-carbamimidoylphenylamino)-1-hydroxy-2-oxoethyl)-3-oxomorpholino)-5-fluorobenzoyl)pyrrolidine-2-carboxylate EXAMPLE aa81

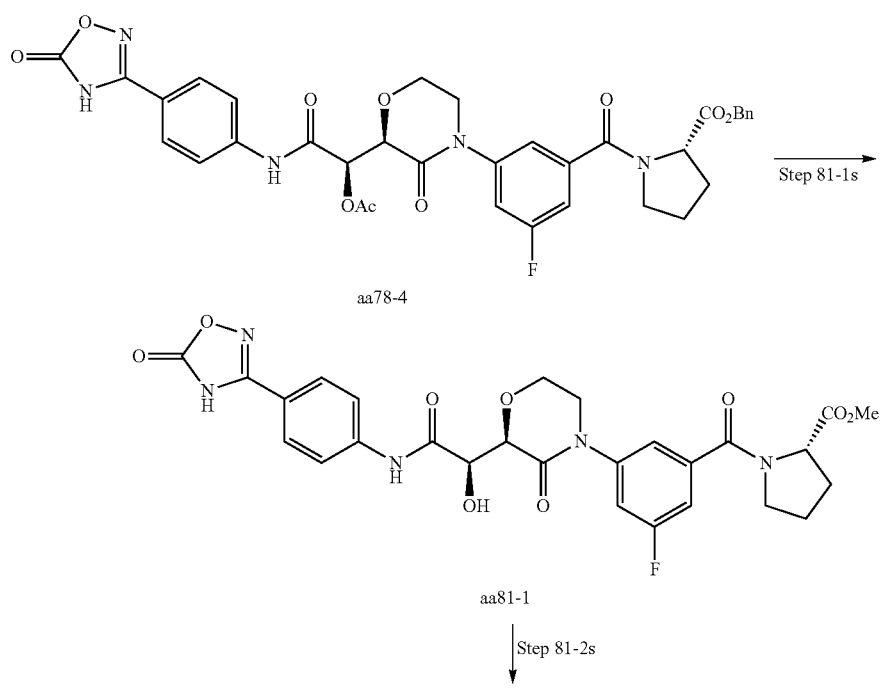

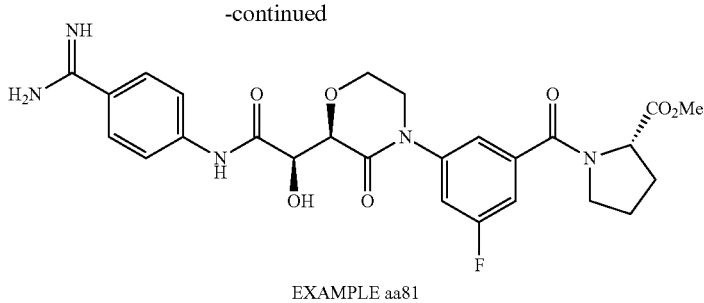

EXAMPLE aa81

Step 81-1s

According to Step 39-5s in the synthetic method for EXAMPLE aa39, compound aa78-4 (968 mg, 1.38 mmol) was used instead of compound aa39-4 to obtain compound aa81-1 which was used in the next step without further purification.

Step 81-2s

According to Step 39-6s in the synthetic method for EXAMPLE aa39, compound aa81-1 was used instead of compound aa39-5 to obtain EXAMPLE aa81 (50 mg, 0.092 mmol) as a white amorphous solid.

Example aa82

Preparation of (R)-2-((R)-4-(3-(2-(dimethylamino)-2-oxoethyl)phenyl)-3-oxomorpholin-2-yl)-2-hydroxy-N-(1-iminoisoindolin-5-yl)acetamide EXAMPLE aa82

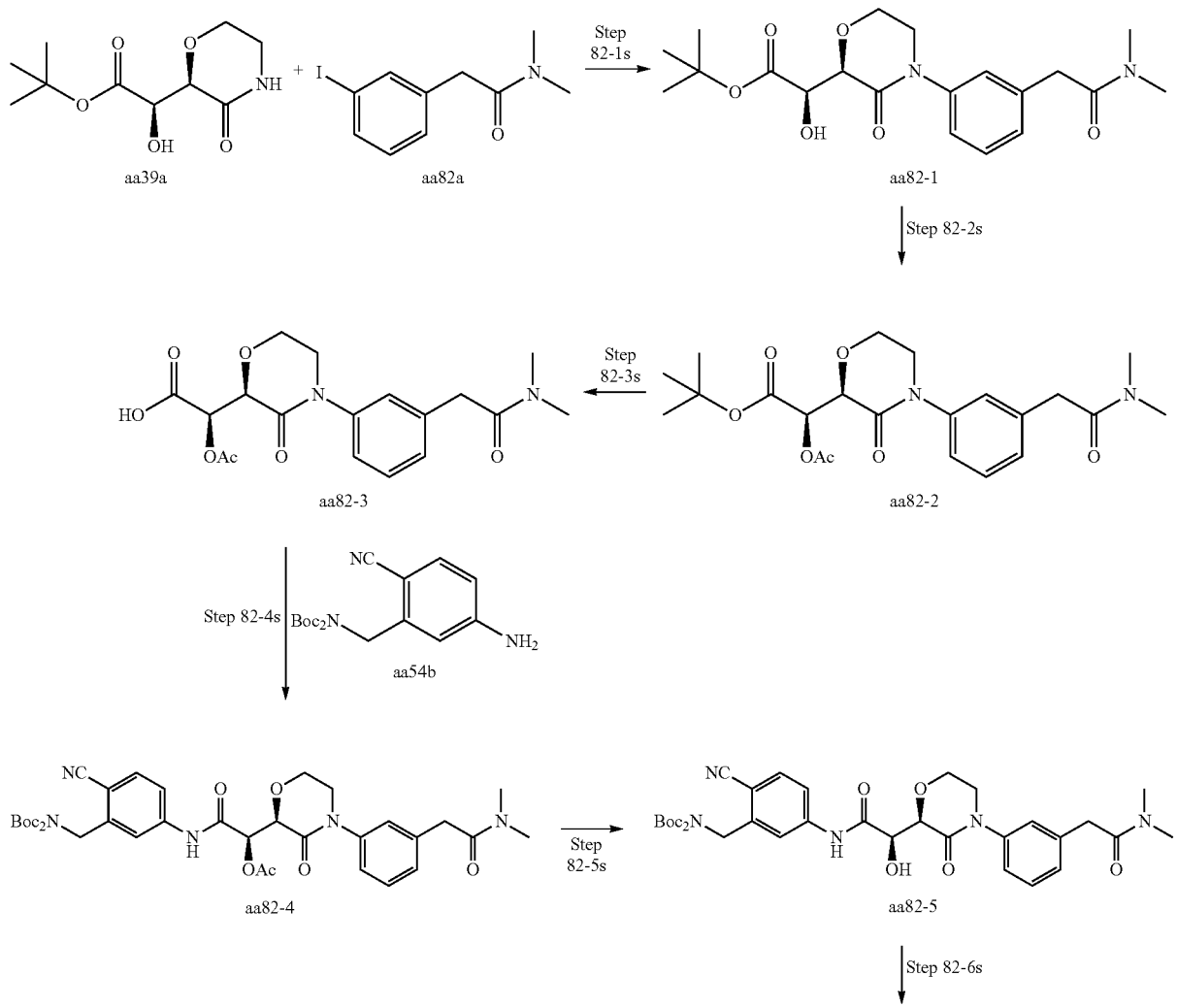

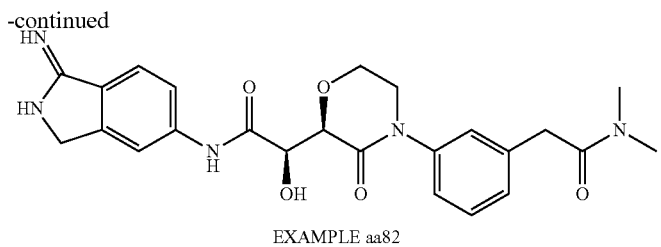

EXAMPLE aa82

Step 82-1s

According to Step 39-1s in the synthetic method for EXAMPLE aa39, compound aa82a (275 mg, 0.95 mmol) was used instead of compound aa39b to obtain compound aa82-1 (304 mg, 0.78 mmol).

Step 82-2s

According to Step 39-2s in the synthetic method for EXAMPLE aa39, compound aa82-1 (304 mg, 0.78 mmol) was used instead of compound aa39-1 to obtain compound aa82-2 (302 mg, 0.70 mmol).

Step 82-3s

According to Step 39-3s in the synthetic method for EXAMPLE aa39, compound aa82-2 (302 mg, 0.70 mmol) was used instead of compound aa39-2 to obtain compound aa82-3 (0.70 mmol) which was used in the next step without further purification.

Step 82-4s

According to Step 54-4s in the synthetic method for EXAMPLE aa54, compound aa82-3 (104 mg, 0.28 mmol) was used instead of compound aa54-3 to obtain compound aa82-4 (143 mg, 0.20 mmol).

Step 82-5s

According to Step 39-5s in the synthetic method for EXAMPLE aa39, compound aa82-4 (143 mg, 0.20 mmol) was used instead of compound aa39-4 to obtain compound aa82-5 (0.20 mmol) which was used in the next step without further purification.

Step 82-6s

According to Step 54-6s in the synthetic method for EXAMPLE aa54, compound aa82-5 (0.20 mmol) was used instead of compound aa54-5 to obtain EXAMPLE aa82 (61 mg, 0.13 mmol) as a white amorphous solid.

Example aa83

Preparation of 1-(3-((R)-2-((R)-1-hydroxy-2-(1-iminoisoindolin-5-ylamino)-2-oxoethyl)-3-oxomorpholino)benzoyl)piperidine-4-carboxylic acid
EXAMPLE aa83

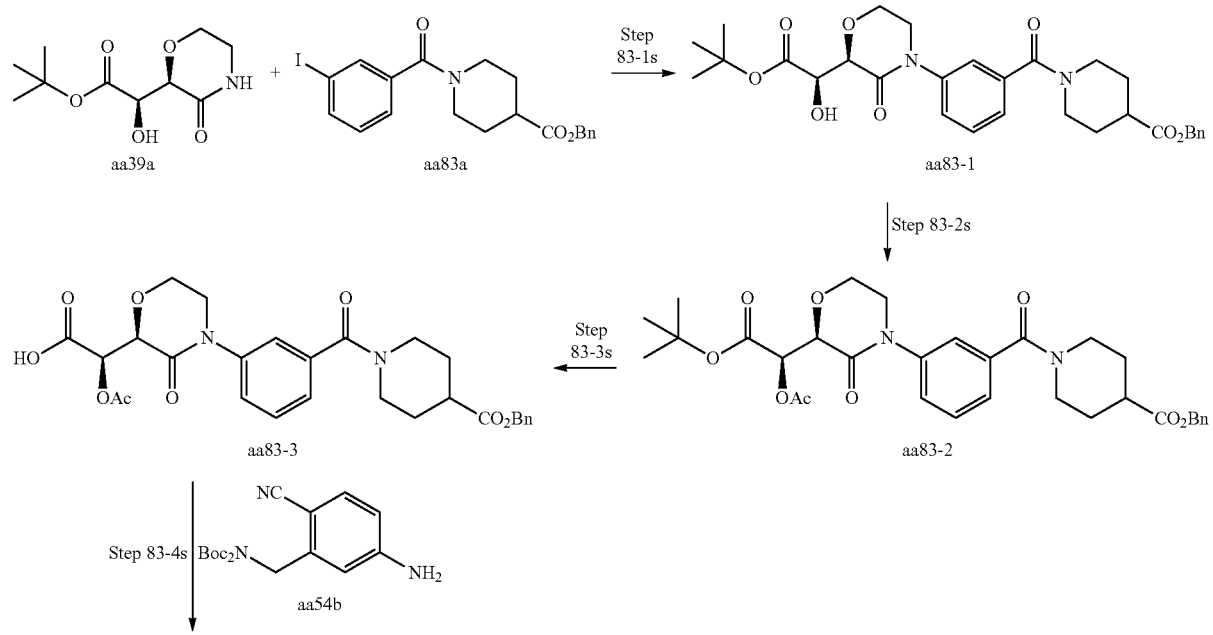

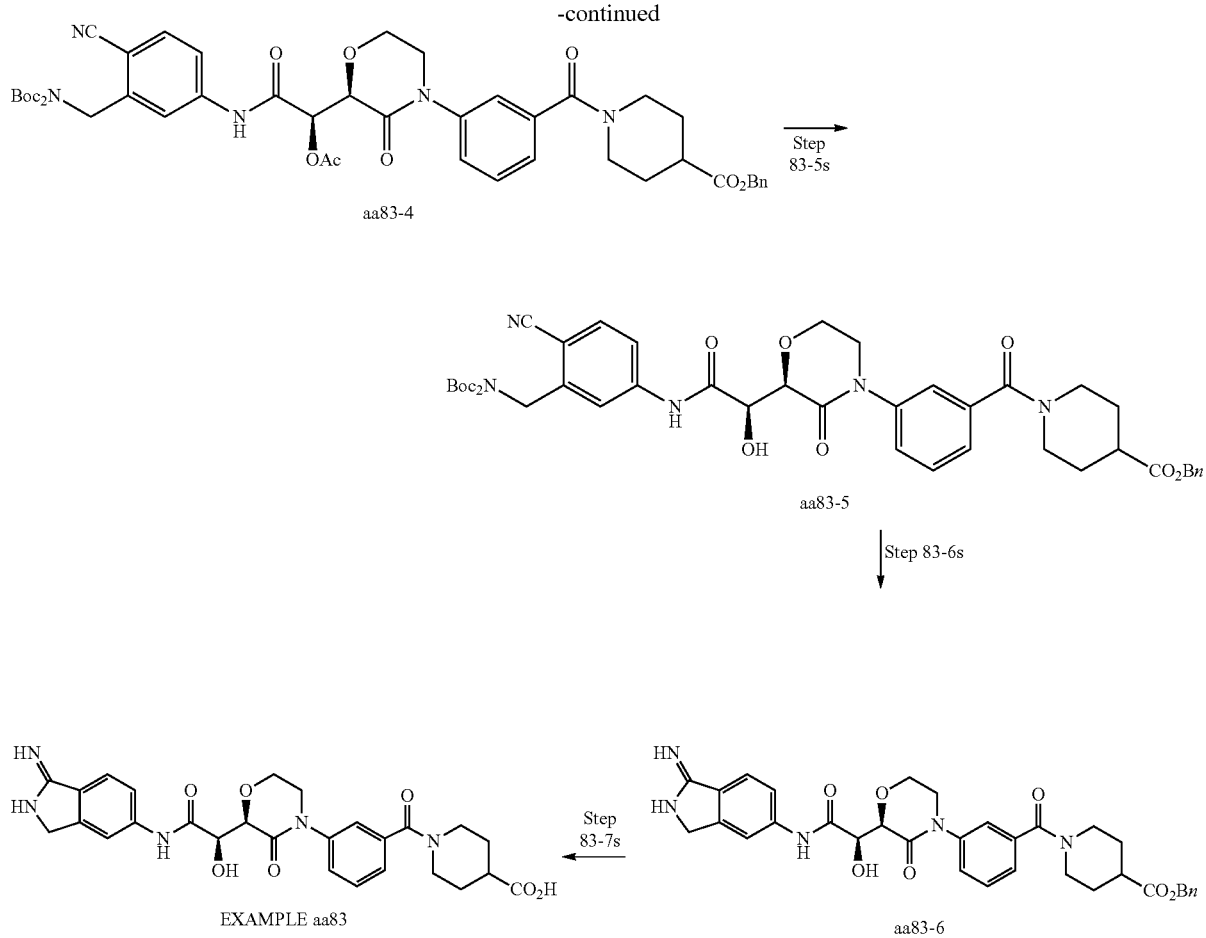

Step 83-1s

According to Step 39-1s in the synthetic method for EXAMPLE aa39, compound aa83a (616 mg, 1.37 mmol) was used instead of compound aa39b to obtain compound aa83-1 (592 mg, 1.07 mmol).

Step 83-2s

According to Step 39-2s in the synthetic method for EXAMPLE aa39, compound aa83-1 (592 mg, 1.07 mmol) was used instead of compound aa39-1 to obtain compound aa83-2 (608 mg, 1.02 mmol).

Step 83-3s

According to Step 39-3s in the synthetic method for EXAMPLE aa39, compound aa83-2 (608 mg, 1.02 mmol) was used instead of compound aa39-2 to obtain compound aa83-3 (1.02 mmol) which was used in the next step without further purification.

Step 83-4s

According to Step 54-4s in the synthetic method for EXAMPLE aa54, compound aa83-3 (1.02 mmol) was used instead of compound aa54-3 to obtain compound aa83-4 (612 mg, 0.71 mmol).

Step 83-5s

According to Step 39-5s in the synthetic method for EXAMPLE aa39, compound aa83-4 (612 mg, 0.71 mmol) was used instead of compound aa39-4 to obtain compound aa83-5 (0.71 mmol) which was used in the next step without further purification.

Step 83-6s

According to Step 54-6s in the synthetic method for EXAMPLE aa54, compound aa83-5 (0.71 mmol) was used instead of compound aa54-5 to obtain compound aa83-6 (0.71 mmol) which was used in the next step without further purification.

Step 83-7s

According to Step 39-6s in the synthetic method for EXAMPLE aa39, compound aa83-6 (0.71 mmol) was used instead of compound aa39-5 to obtain EXAMPLE aa83 (124 mg, 0.23 mmol) as a white amorphous solid.

Example aa84

Preparation of ethyl 1-(3-((R)-2-((R)-1-hydroxy-2-(1-iminoisoindolin-5-ylamino)-2-oxoethyl)-3-oxomorpholino)benzoyl)piperidine-4-carboxylate EXAMPLE aa84

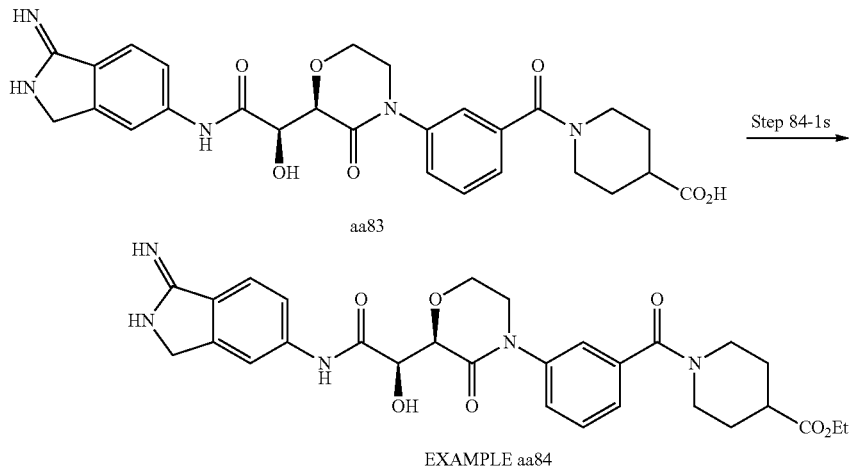

Step 84-1s

According to Step 77-1s in the synthetic method for EXAMPLE aa77, compound aa83 (90 mg, 0.17 mmol) was used instead of compound aa70 to obtain EXAMPLE aa84 (92 mg, 0.16 mmol) as a white amorphous solid.

Example aa85

Preparation of 2-(3-((R)-2-((R)-1-acetoxy-2-(1-imino-3-oxoisoindolin-5-ylamino)-2-oxoethyl)-3-oxo morpholino)-N-methylbenzamido)acetic acid EXAMPLE aa85

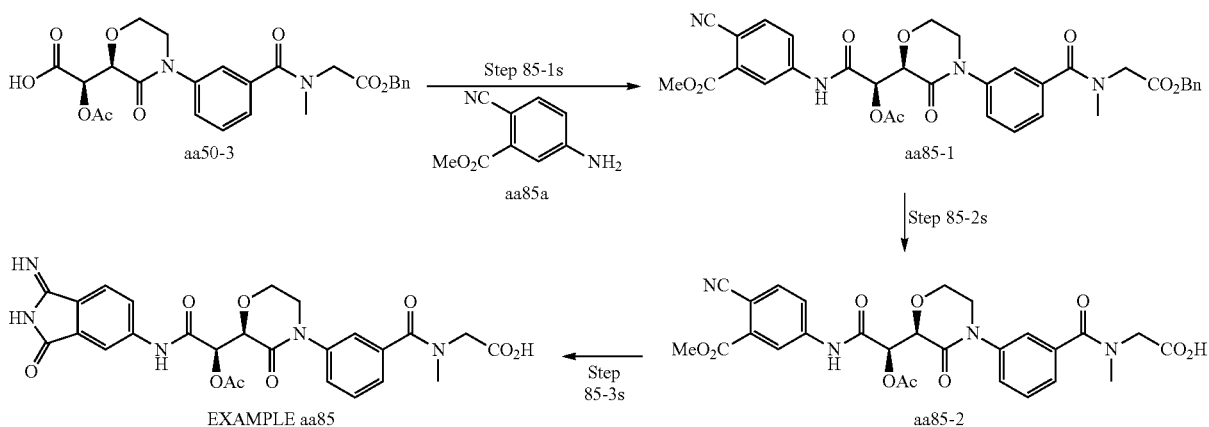

Step 85-1s

According to Step 39-4s in the synthetic method for EXAMPLE aa39, compound aa50-3 (250 mg, 0.50 mmol) was used instead of compound aa39-3 and compound aa85a (105 mg, 0.60 mmol) was used instead of compound aa39c to obtain compound aa85-1 (254 mg, 0.39 mmol).

Step 85-2s

To a solution of aa85-1 (254 mg, 0.39 mmol) in methanol (8 mL) was added palladium-charcoal (10%, 26 mg). The reaction mixture was stirred at room temperature under a hydrogen atmosphere for 16 hours. The reaction mixture was filtered. The filtrate was evaporated under reduced pressure to obtain compound aa85-2 (0.39 mmol) which was used in the next step without further purification.

Step 85-3s

To compound aa85-2 (0.39 mmol) was added a 7 N solution of ammonia in methanol (2 mL). The reaction mixture was stirred at room temperature for 5 days. The organic solvent was evaporated under reduced pressure. The crude product was purified by high pH RP-HPLC to afford the desired EXAMPLE aa85 (4 mg, 0.0073 mmol) as a white amorphous solid.

Example aa86

Preparation of (R)—N-(1,3-diiminoisoindolin-5-yl)-2-((R)-4-(3-(2-(dimethylamino)-2-oxoethyl)phenyl)-3-oxomorpholin-2-yl)-2-hydroxyacetamide EXAMPLE a86

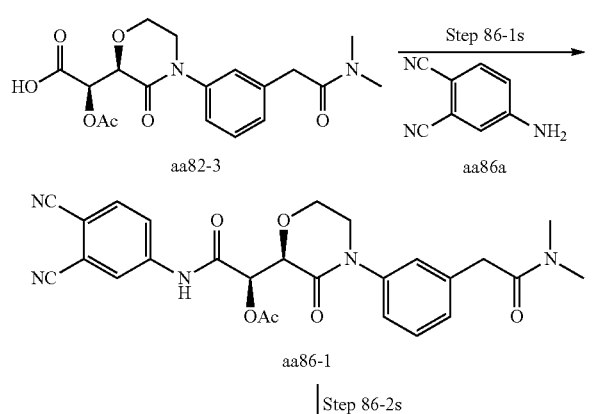

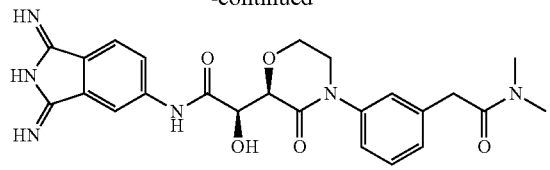

EXAMPLE aa86

Step 86-1s

According to Step 39-4s in the synthetic method for EXAMPLE aa39, compound aa82-3 (175 mg, 0.46 mmol) was used instead of compound aa39-3 and compound aa86a (100 mg, 0.70 mmol) was used instead of compound aa39c to obtain compound aa86-1 (81 mg, 0.16 mmol).

Step 86-2s

To compound aa86-1 (81 mg, 0.16 mmol) was added a 7 N solution of ammonia in methanol (10 mL). The reaction mixture was stirred at room temperature for 4 days. The organic solvent was evaporated under reduced pressure. The crude product was purified by high pH RP-HPLC to afford the desired EXAMPLE aa86 (45 mg, 0.094 mmol) as a white amorphous solid.

Example aa87

Preparation of (R)-2-(1-imino-3-oxoisoindolin-5-ylamino)-1-((R)-4-(3-(methyl(2-oxo-2-(pyrrolidin-1-yl)ethyl)carbamoyl)phenyl)-3-oxomorpholin-2-yl)-2-oxoethyl acetate EXAMPLE aa87

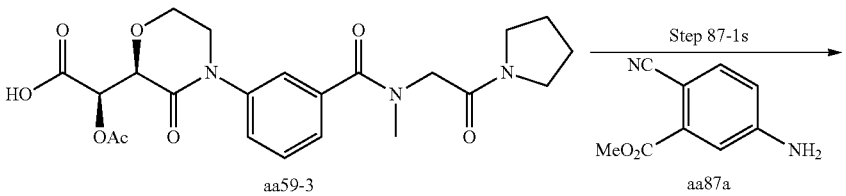

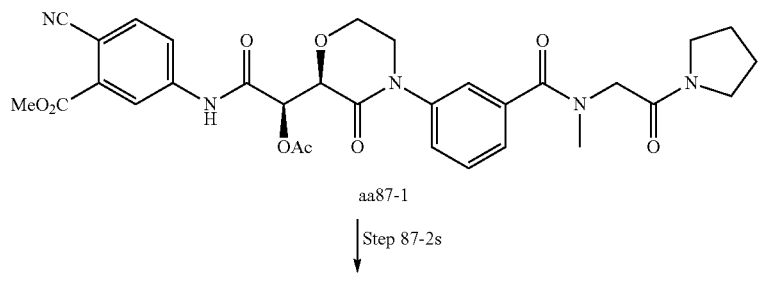

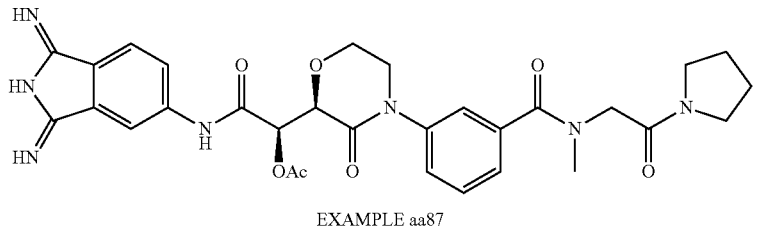

EXAMPLE aa87

Step 87-1s

According to Step 39-4s in the synthetic method for EXAMPLE aa39, compound aa59-3 (179 mg, 0.44 mmol) was used instead of compound aa39-3 and compound aa87a (117 mg, 0.66 mmol) was used instead of compound aa39c to obtain compound aa87-1 (163 mg, 0.29 mmol).

Step 87-2s

To compound aa87-1 (163 mg, 0.29 mmol) was added a 7 N solution of ammonia in methanol (20 mL). The reaction mixture was stirred at room temperature for 3 days. The organic solvent was evaporated under reduced pressure to afford the desired EXAMPLE aa87 (144 mg, 0.29 mmol) as a white amorphous solid.

Example aa88

Preparation of 2-(3-((R)-2-((R)-2-(4-carbamimidoylphenylamino)-1-hydroxy-2-oxoethyl)-3-oxomorpholino)-5-fluoro-N-methylbenzamido)acetic acid EXAMPLE aa88

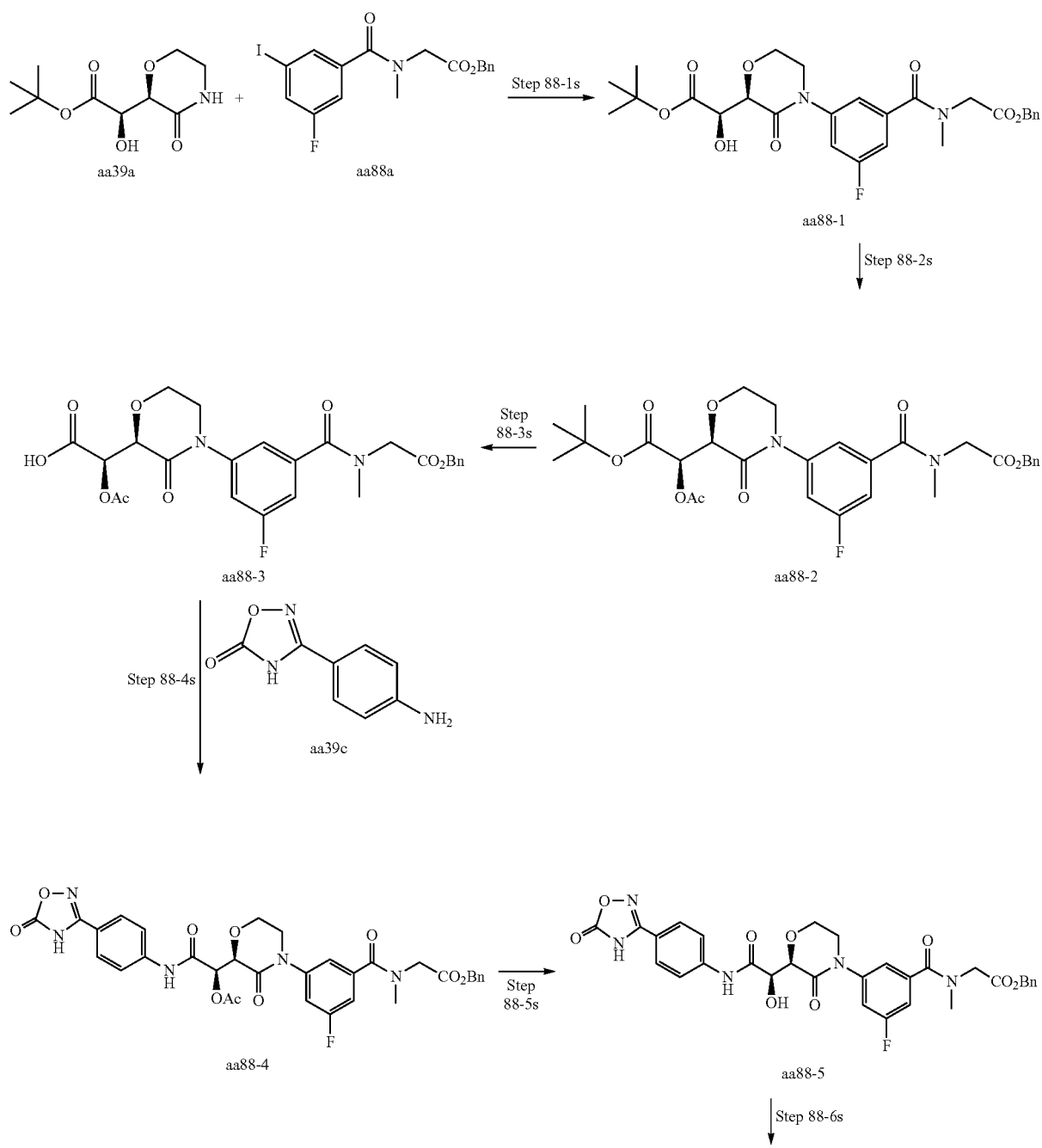

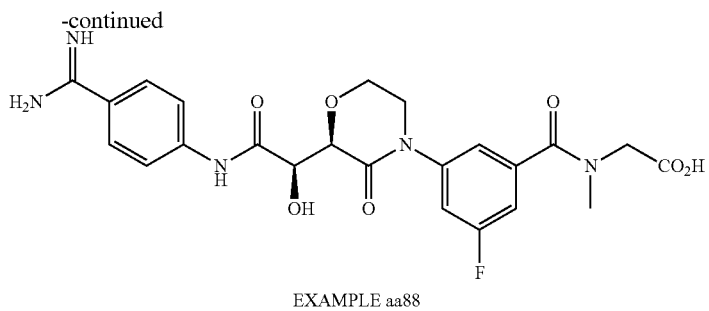

EXAMPLE aa88

Step 88-1s

According to Step 39-1s in the synthetic method for EXAMPLE aa39, compound aa88a (760 mg, 1.78 mmol) was used instead of compound aa39b to obtain compound aa88-1 (618 mg, 1.17 mmol).

Step 88-2s

According to Step 39-2s in the synthetic method for EXAMPLE aa39, compound aa88-1 (618 mg, 1.17 mmol) was used instead of compound aa39-1 to obtain compound aa88-2 (550 mg, 0.99 mmol).

Step 88-3s

According to Step 39-3s in the synthetic method for EXAMPLE aa39, compound aa88-2 (550 mg, 0.99 mmol) was used instead of compound aa39-2 to obtain compound aa88-3 (0.99 mmol) which was used in the next step without further purification.

Step 88-4s

According to Step 39-4s in the synthetic method for EXAMPLE aa39, compound aa88-3 (0.99 mmol) was used instead of compound aa39-3 to obtain compound aa88-4 (649 mg, 0.96 mmol).

Step 88-5s

According to Step 39-5s in the synthetic method for EXAMPLE aa39, compound aa88-4 (649 mg, 0.96 mmol) was used instead of compound aa39-4 to obtain compound aa88-5 (0.96 mmol) which was used in the next step without further purification.

Step 88-6s

According to Step 39-6s in the synthetic method for EXAMPLE aa39, compound aa88-5 (0.96 mmol) was used instead of compound aa39-5 to obtain EXAMPLE aa88 (156 mg, 0.31 mmol) as a white amorphous solid.

Example aa89

Preparation of ethyl 2-(3-((R)-2-((R)-2-(4-carbamimidoylphenylamino)-1-hydroxy-2-oxoethyl)-3-oxomorpholino)-5-fluoro-N-methylbenzamido)acetate EXAMPLE aa89

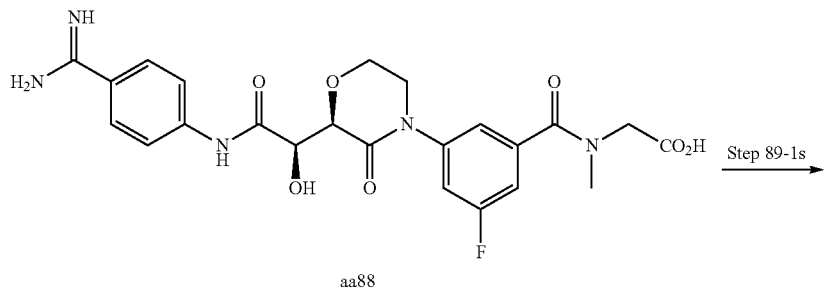

aa88

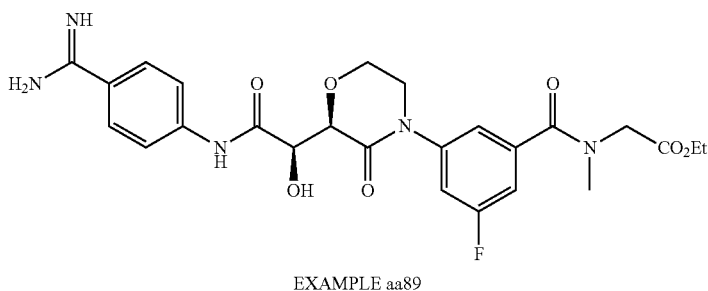

EXAMPLE aa89

Step 89-1s

According to Step 77-1s in the synthetic method for EXAMPLE aa77, compound aa88 (150 mg, 0.30 mmol) was used instead of compound aa70 to obtain EXAMPLE aa89 (136 mg, 0.28 mmol) as a white amorphous solid.

Example aa90

Preparation of 3-((R)-2-((R)-2-(4-carbamimidoylphenylamino)-1-hydroxy-2-oxoethyl)-3-oxomorpholino)-N-(2-(dimethylamino)-2-oxoethyl)-5-fluoro-N-methylbenzamide EXAMPLE aa90

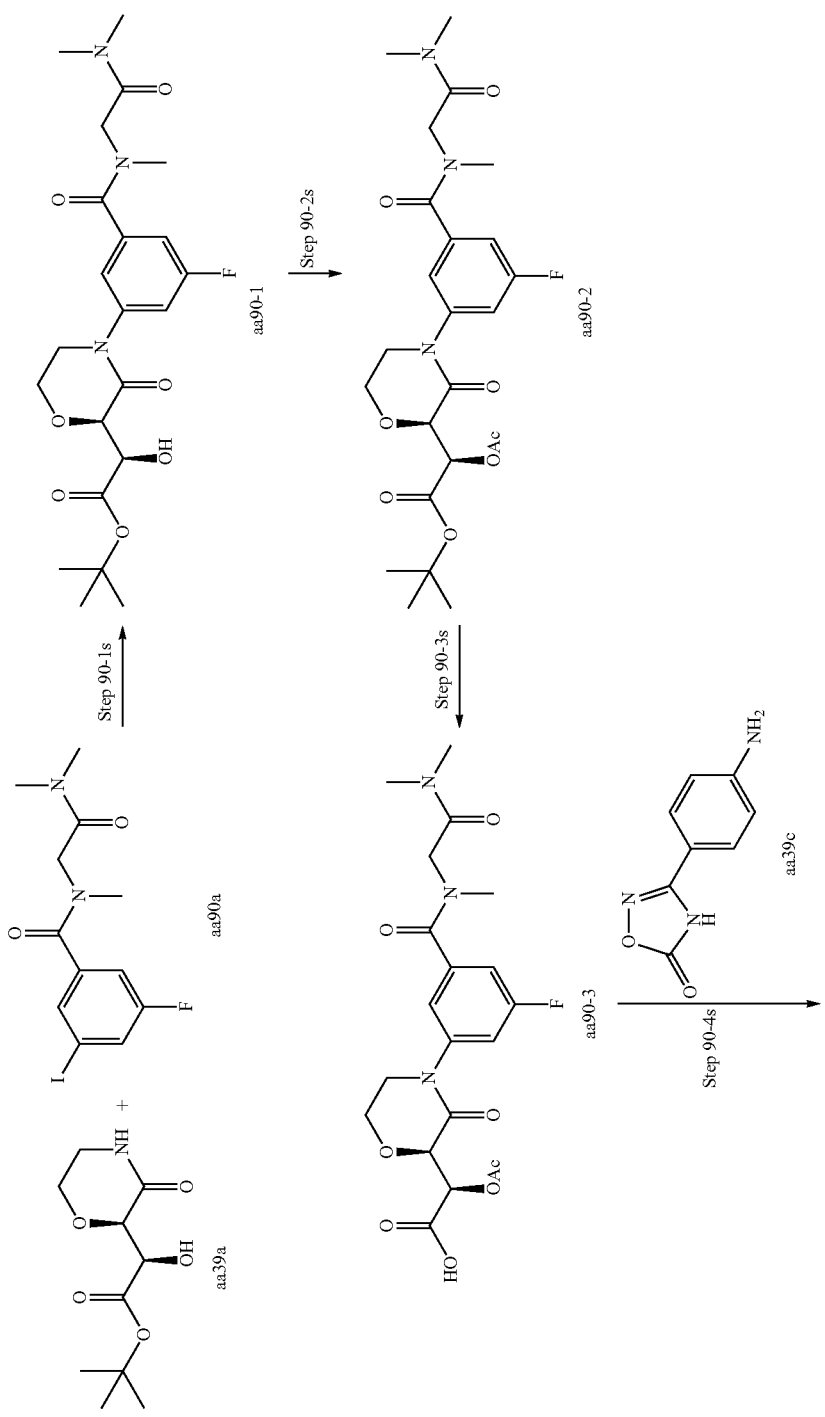

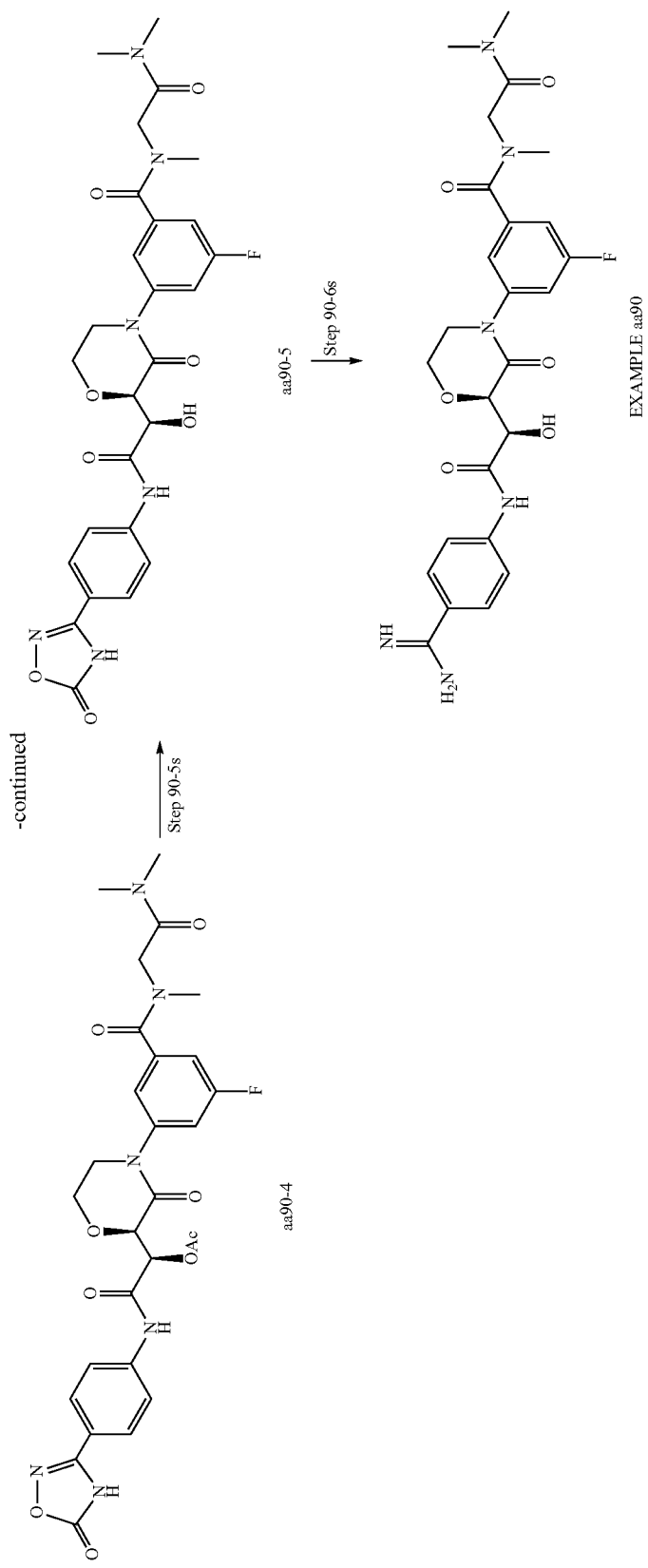

Step 90-1s

According to Step 39-1s in the synthetic method for EXAMPLE aa39, compound aa90a (293 mg, 0.80 mmol) was used instead of compound aa39b to obtain compound aa90-1 (347 mg, 0.74 mmol).

Step 90-2s

According to Step 39-2s in the synthetic method for EXAMPLE aa39, compound aa90-1 (347 mg, 0.74 mmol) was used instead of compound aa39-1 to obtain compound aa90-2 (282 mg, 0.55 mmol).

Step 90-3s

According to Step 39-3s in the synthetic method for EXAMPLE aa39, compound aa90-2 (282 mg, 0.55 mmol) was used instead of compound aa39-2 to obtain compound aa90-3 (0.55 mmol) which was used in the next step without further purification.

Step 90-4s

According to Step 39-4s in the synthetic method for EXAMPLE aa39, compound aa90-3 (0.55 mmol) was used instead of compound aa39-3 to obtain compound aa90-4 (219 mg, 0.36 mmol).

Step 90-5s

According to Step 39-5s in the synthetic method for EXAMPLE aa39, compound aa90-4 (219 mg, 0.36 mmol) was used instead of compound aa39-4 to obtain compound aa90-5 (0.36 mmol) which was used in the next step without further purification.

Step 90-6s

According to Step 39-6s in the synthetic method for EXAMPLE aa39, compound aa90-5 (0.36 mmol) was used instead of compound aa39-5 to obtain EXAMPLE aa90 (156 mg, 0.30 mmol) as a white amorphous solid.

Example aa91

Preparation of (R)—N-(1,3-diiminoisoindolin-5-yl)-2-hydroxy-2-((R)-4-(3-(2-(4-methyl-3-oxopiperazin-1-yl)-2-oxoethyl)phenyl)-3-oxomorpholin-2-yl)acetamide EXAMPLE aa91

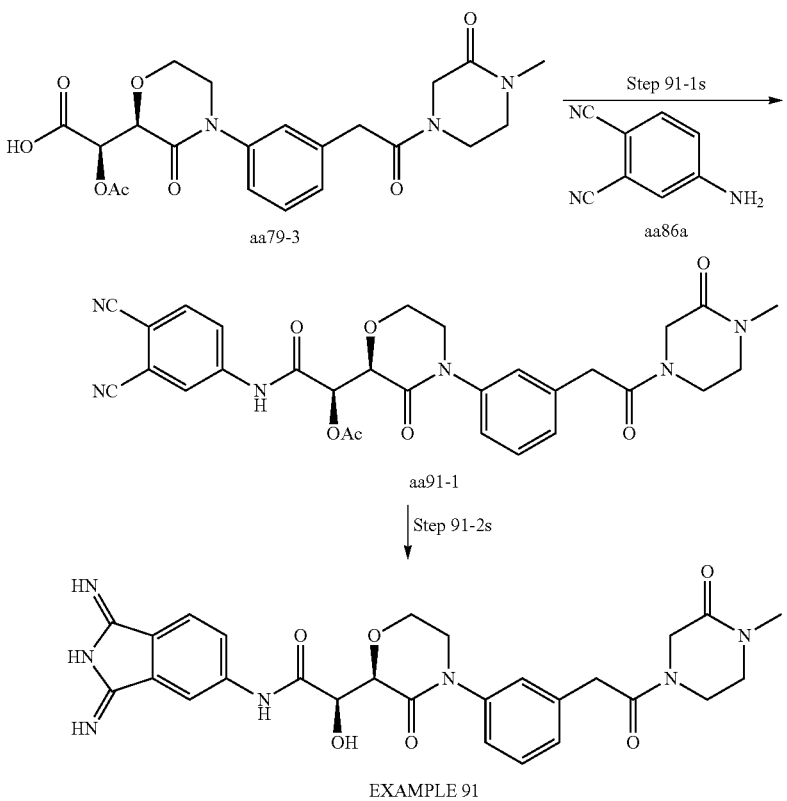

Step 91-1s

According to Step 86-1s in the synthetic method for EXAMPLE aa86, compound aa79-3 (176 mg, 0.35 mmol) was used instead of compound aa82-3 to obtain compound aa91-1 (50 mg, 0.079 mmol).

Step 91-2s

According to Step 86-2s in the synthetic method for EXAMPLE aa86, compound aa91-1 (50 mg, 0.079 mmol) was used instead of compound aa86-1 to obtain EXAMPLE aa91 (29 mg, 0.048 mmol).

Example aa92

Preparation of N-(2-(dimethylamino)-2-oxoethyl)-3-((R)-2-((R)-1-hydroxy-2-(1-iminoisoindolin-5-ylamino)-2-oxoethyl)-3-oxomorpholino)-N-methyl-benzamide EXAMPLE aa92

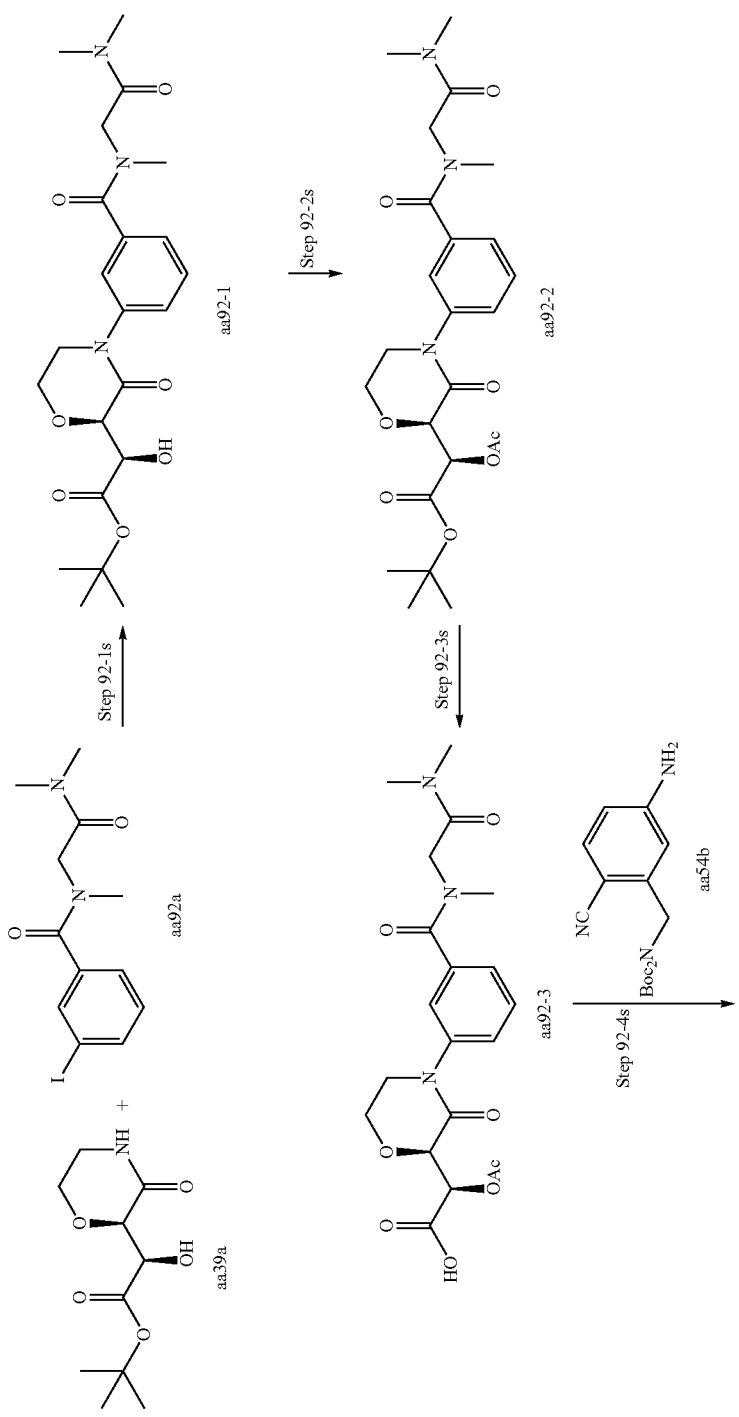

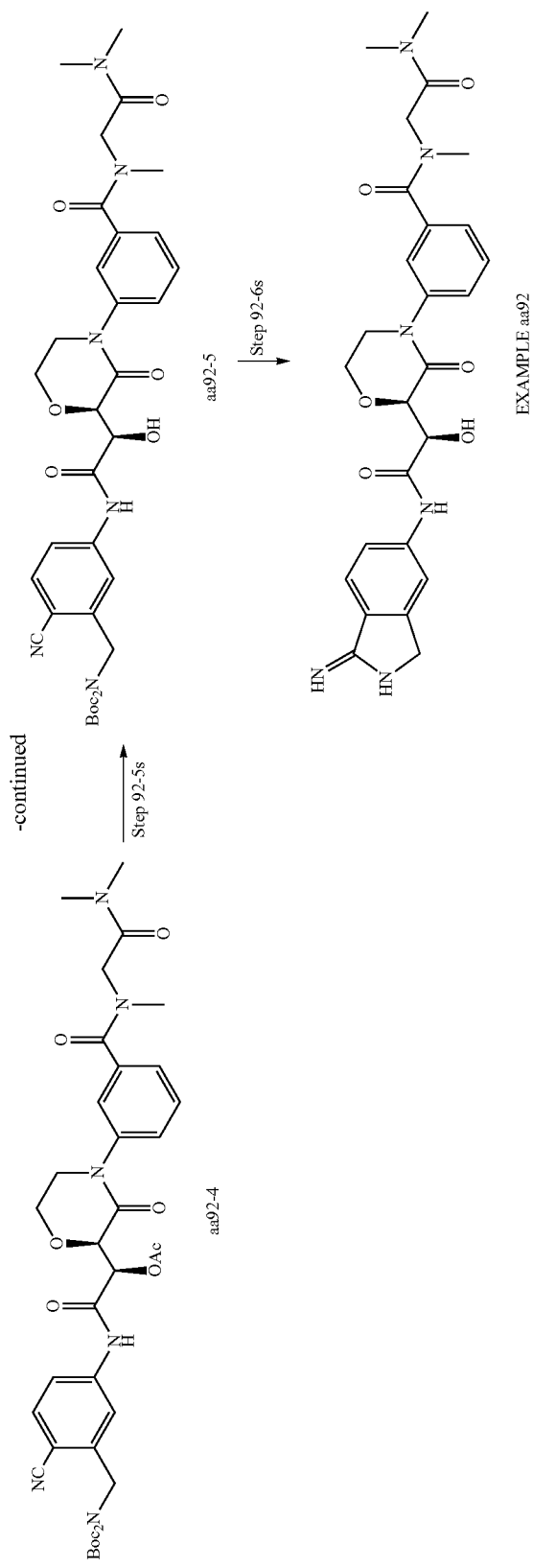

Step 92-1s

According to Step 39-1s in the synthetic method for EXAMPLE aa39, compound aa92a (330 mg, 0.95 mmol) was used instead of compound aa39b to obtain compound aa92-1 (223 mg, 0.45 mmol).

Step 92-2s

According to Step 39-2s in the synthetic method for EXAMPLE aa39, compound aa92-1 (223 mg, 0.45 mmol) was used instead of compound aa39-1 to obtain compound aa92-2 (234 mg, 0.48 mmol).

Step 92-3s

According to Step 39-3s in the synthetic method for EXAMPLE aa39, compound aa92-2 (210 mg, 0.48 mmol) was used instead of compound aa39-2 to obtain compound aa92-3 (0.48 mmol) which was used in the next step without further purification.

Step 92-4s

According to Step 54-4s in the synthetic method for EXAMPLE aa54, compound aa92-3 (0.48 mmol) was used instead of compound aa54-3 to obtain compound aa92-4 (292 mg, 0.38 mmol).

Step 92-5s

According to Step 39-5s in the synthetic method for EXAMPLE aa39, compound aa92-4 (292 mg, 0.38 mmol) was used instead of compound aa39-4 to obtain compound aa92-5 (0.38 mmol) which was used in the next step without further purification.

Step 92-6s

According to Step 54-6s in the synthetic method for EXAMPLE aa54, compound aa92-5 (0.38 mmol) was used instead of compound aa54-5 to obtain EXAMPLE aa92 (160 mg, 0.0.31 mmol) as a white amorphous solid.

Example aa93

Preparation of 2-((S)-hydroxy((R)-3-oxo-4-p-tolyl-morpholin-2-yl)methyl)-4-oxo-1,4-dihydroquinazoline-6-carboximidamide EXAMPLE aa93

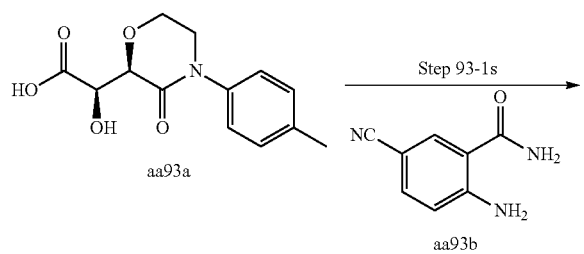

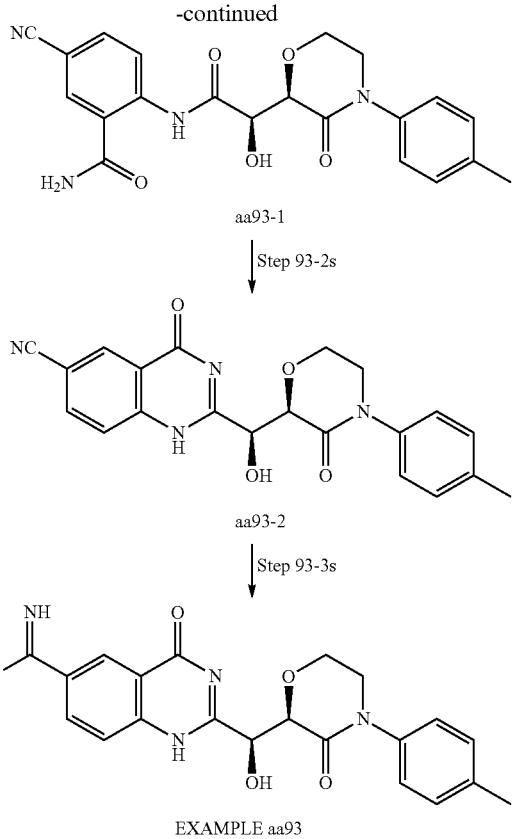

Step 93-1s

To a solution of imidazole (258 mg, 3.79 mmol) in anhydrous DCM (4 mL) cooled at −10° C. was added thionyl chloride (113 mg, 0.95 mmol). The reaction mixture was stirred at room temperature for 10 minutes and was added to a solution of compound 93b (304 mg, 1.89 mmol) in anhydrous DCM (3 mL) cooled at −40° C. The reaction mixture was stirred at room temperature for 30 minutes. The reaction mixture was filtered. The filtrate was added to a solution of compound aa93a (100 mg, 0.38 mmol) and 1,2,4-triazole (39 mg, 0.57 mmol) in anhydrous DCM (3 mL) cooled at 0° C. The reaction mixture was stirred at room temperature for 16 hours. Ethyl acetate (100 mL) was added and the organic layer was washed with 2 N hydrochloric acid, saturated sodium bicarbonate solution and brine. The organic layer was dried over anhydrous sodium sulfate. The organic solvent was evaporated under reduced pressure. The crude product was purified by flash column chromatography to afford the desired aa93-1 (15 mg, 0.037 mmol).

Step 93-2s

To a solution of aa93-1 (5 mg, 0.012 mmol) in 1,4-dioxane was added a 1 N sodium hydroxide solution (0.1 mL). The reaction mixture was stirred at room temperature for 2 hours. Ethyl acetate (50 mL) was added and the organic layer was washed with 1 N hydrochloric acid, water and brine. The organic solvent was evaporated under reduced pressure to afford the desired aa93-2 (0.012 mmol). The crude product was used in the next step without further purification.

Step 93-3s

Acetyl chloride (3 mL) was added to absolute ethanol (1 mL) cooled at 0° C. to generate a hydrogen chloride solution. To the hydrogen chloride solution was added a solution of aa93-2 (0.012 mmol) in absolute ethanol (2 mL). The reaction mixture was stirred at room temperature for 2 days. The organic solvent was evaporated under reduced pressure. To the residue was added a 7 N solution of ammonia in methanol (5 mL). The reaction mixture was stirred at room temperature for 16 hours. The organic solvent was evaporated under reduced pressure. The crude product was purified by RP-HPLC to afford the desired EXAMPLE aa93 (1 mg, 0.0023 mmol).

Example aa94

Preparation of 1,1-dioxo-3-((S)-hydroxy((R)-3-oxo-4-p-tolylmorpholin-2-yl)methyl)-4H-benzo[e][1,2,4]thiadiazine-7-carboximidamide EXAMPLE aa94

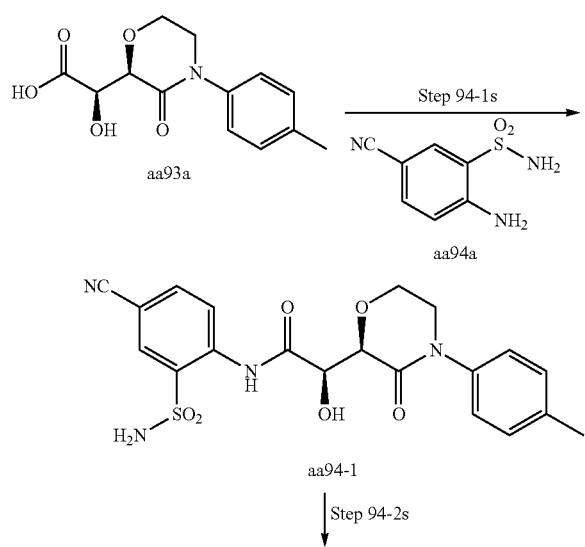

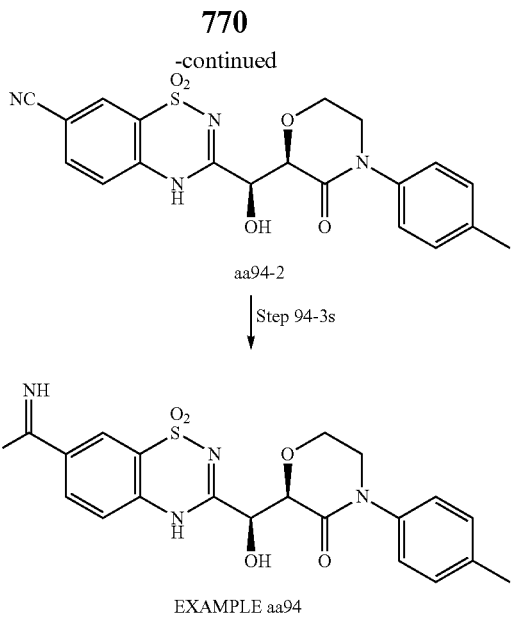

Step 94-1s

According to Step 93-1s in the synthetic method for EXAMPLE aa93, compound aa94a (606 mg, 3.08 mmol) was used instead of compound aa93b to obtain compound aa94-1 (86 mg, 0.19 mmol).

Step 94-2s

To compound aa94-1 (86 mg, 0.19 mmol) was added saturated ammonium hydroxide solution (8 mL). The reaction mixture was heated under reflux for 2 days. The solvent was evaporated under reduced pressure. The crude product was purified by RP-HPLC to afford the desired compound aa94-2 (8.5 mg, 0.020 mmol).

Step 94-3s

According to Step 93-3s in the synthetic method for EXAMPLE aa93, compound aa94-2 (8.5 mg, 0.020 mmol) was used instead of compound aa93-2 to obtain EXAMPLE aa94 (7.2 mg, 0.016 mmol).

Examples aa95-aa116

Example aa95

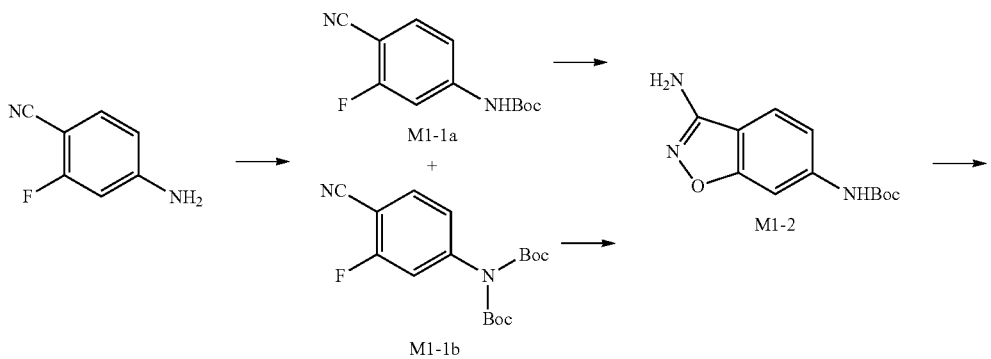

-continued
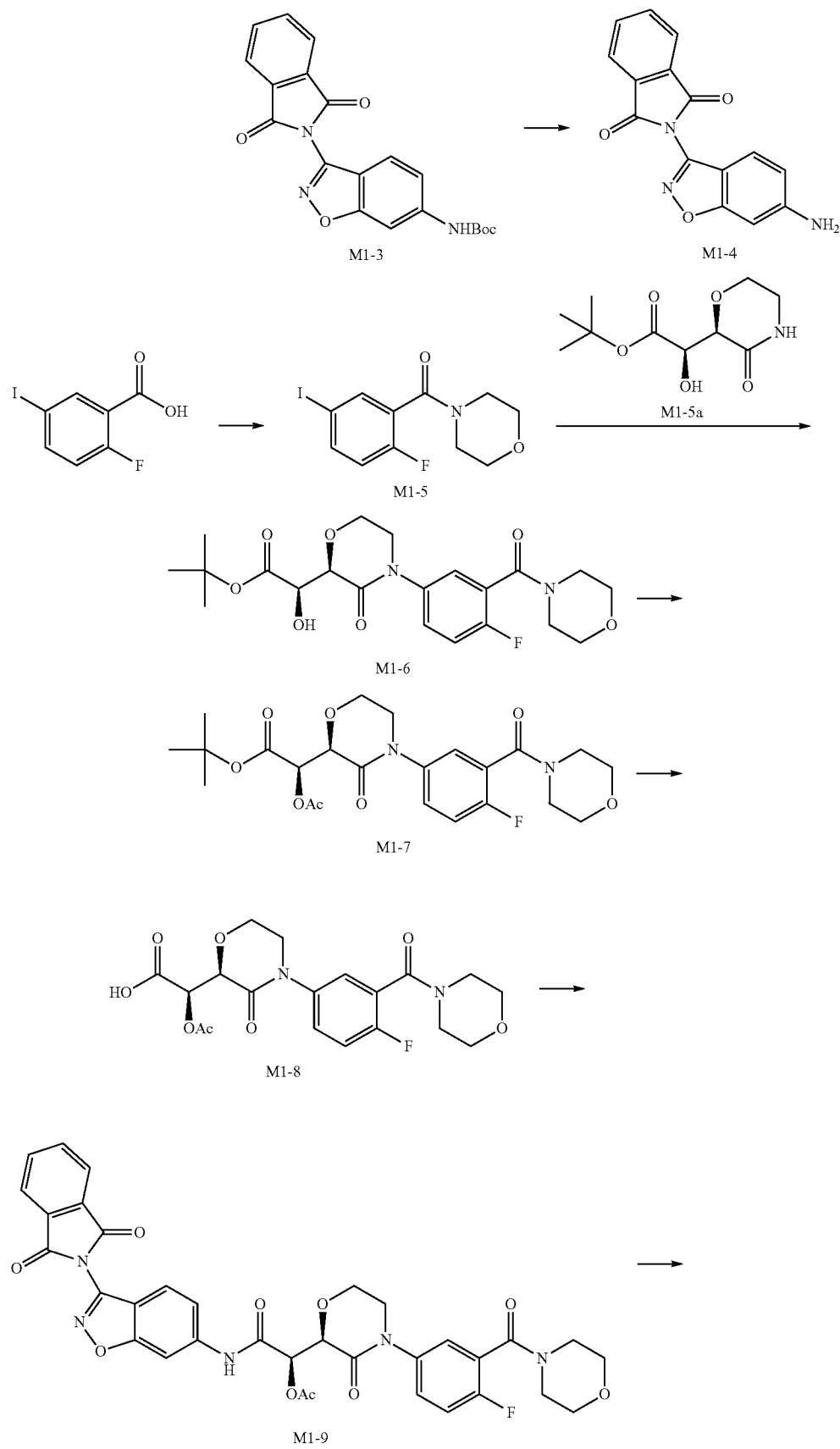

-continued

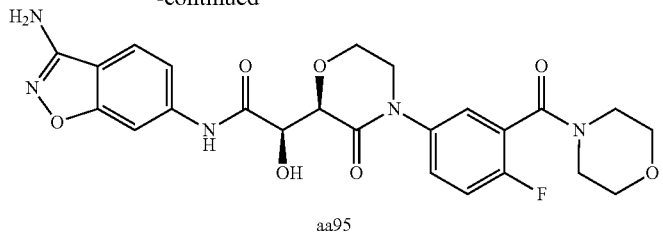

aa95

Synthesis of tert-butyl 4-cyano-3-fluorophenylcarbamate (compound M1-1a) and (compound M1-1b)

4-amino-2-fluorobenzonitrile (10 g, 0.0735 mol) was dissolved in THF (50 ml), NaH (2.94 g of a 60% dispersion, 1 eq) was added. After 30 minutes the resulting mixture was added to a mixture of Boc$_2$O (16 g, 1 eq) and DMAP (0.897 g, 10%) in THF (100 ml). This mixture was stirred for 2 hours and was diluted with EtOAc. The mixture was washed with NH$_4$Cl$_{(sat)}$, dried (MgSO$_4$) and concentrated. The residue was purified by silica gel chromatography (0-60% EtOAc in hexane) to give, in order of elution, 7.7 g (31%) of M-1-1b and 4.4 g (25%) of M1-1a.

Synthesis of tert-butyl 3-aminobenzo[d]isoxazol-6-ylcarbamate (compound M1-2)

Compound M1-1a or M1-1b (0.0229 mol) was dissolved in 10:1 DMF/H$_2$O (114 ml). Acetohydroxamic acid (10.3 g, 6 eq) and K$_2$CO$_3$ (38 g, 12 eq) were added and the mixture heated at 55° C. overnight. After cooling to room temperature the mixture was diluted with EtOAc, washed with NH$_4$Cl$_{(sat)}$ and dried (MgSO$_4$). The residue was purified by silica gel chromatography (0-70% EtOAc in hexane) to give 5 g (87%) of M1-2.

Synthesis of tert-butyl 3-(1,3-dioxoisoindolin-2-yl)benzo[d]isoxazol-6-ylcarbamate (compound M1-3)

Compound M1-2 (5.3 g, 0.0213 mol) was dissolved in CH$_2$Cl$_2$ (106 ml) and cooled to 0° C. o-phthaloyl dichloride (3.7 ml, 1.2 eq) was added followed by Et$_3$N (7.18 ml, 2.4 eq). The mixture was stirred overnight. The mixture was diluted with EtOAc, washed with NH$_4$Cl$_{(sat)}$ and dried (MgSO$_4$). The residue was purified by silica gel chromatography (0-100% EtOAc in hexane) to give 5.6 g of M1-3.

Synthesis of 2-(6-aminobenzo[d]isoxazol-3-yl)isoindoline-1,3-dione (compound M1-4)

Compound M1-3 (1.37 g, 0.00363 mol) was dissolved in 1,4-dioxane (18 ml), 4N HCl in 1,4-dioxane (18 ml) was added and the mixture stirred overnight. The mixture was concentrated and the residue suspended in EtOAc. NaHCO$_3$ $_{(sat)}$ was added and stirred until a clear organic layer persisted. The organic layer was dried (MgSO$_4$), and concentrated to give 1 g of M1-4 (98%).

Synthesis of (2-fluoro-5-iodophenyl)(morpholino)methanone (compound M1-5)

2-Fluoro-5-iodobenzoic acid (2 g, 0.0088 mol) was dissolved in MeCN (44 ml) and the mixture cooled to 0° C. Morpholine (0.929 ml, 1.2 eq) followed by EDCI.HCl (2.03 g, 1.2 eq) and DMAP (108 mg, 0.1 eq) were added and the mixture stirred overnight. The mixture was diluted with EtOAc, washed with NH$_4$Cl(sat), dried (MgSO$_4$), and concentrated. The resulting residue was then purified by silica gel chromatography (0-30% EtOAc in hexane) gave 2 g of M1-5. LCMS MH$^+$=336.

Synthesis of (R)-tert-butyl 2-((R)-4-(4-fluoro-3-(morpholine-4-carbonyl)phenyl)-3-oxomorpholin-2-yl)-2-hydroxy acetate (compound M1-6)

Compound M1-5a (1.37 g, 0.0059 mol) and compound M1-1 (1.99 g, 1 eq) were dissolved in 1,4-dioxane (60 ml), to this mixture were added CuI (339 mg, 0.2 eq), Cs$_2$CO$_3$ (3.87 g, 2 eq), and trans-N,N-dimethylcyclohexane-1,2-diamine (0.281 ml, 0.3 eq). The resulting solution was degassed and heated at 90° C. for 6.5 hours. The mixture was cooled to rt, NH$_4$Cl(sat) was added and the mixture extracted with EtOAc. The extracts were washed with NH$_4$Cl(sat), dried (MgSO$_4$), and concentrated. The resulting residue was then purified by silica gel chromatography (0-100% EtOAc in hexane) gave 1.6 g of M1-6.

Synthesis of (R)-tert-butyl 2-acetoxy-2-((R)-4-(4-fluoro-3-(morpholine-4-carbonyl)phenyl)-3-oxomorpholin-2-yl)acetate (compound M1-7)

M1-6 (1.6 g, 0.00365 mol) was dissolved in CH$_2$Cl$_2$ (18.25 ml) and cooled to 0° C., Ac$_2$O (0.69 ml, 2 eq), pyridine (0.59 ml, 2 eq), and DMAP (45 mg, 0.1 eq) was added. The mixture was stirred for 1 hours, diluted with EtOAc, washed with CuSO$_4$ solution, water, dried, and concentrated to give 1.75 g of M1-7.

Synthesis of (R)-2-acetoxy-2-((R)-4-(4-fluoro-3-(morpholine-4-carbonyl)phenyl)-3-oxomorpholin-2-yl)acetic acid (compound M1-8)

M1-7 (1.75 g, 0.00364 mol) was dissolved in 1:1 CH$_2$Cl$_2$/TFA (40 ml) and stirred for 30 minutes. The mixture was concentrated to give 1.6 g of M1-8.

Synthesis of (R)-2-(3-(1,3-dioxoisoindolin-2-yl)benzo[d]isoxazol-6-ylamino)-1-((R)-4-(4-fluoro-3-(morpholine-4-carbonyl)phenyl)-3-oxomorpholin-2-yl)-2-oxoethyl acetate (compound M1-9)

Compound M1-8 (1 g, 0.00235 mol) and compound M1-4 (724 mg, 1.1 eq) were dissolved in MeCN (4.71 ml, 0.5M) and the mixture cooled to 0° C. EDCI.HCl (0.542 g, 1.1 eq) and DMAP (29 mg, 10%) were added and the mixture stirred overnight. The mixture was diluted with EtOAc, washed with NH$_4$Cl$_{(sat)}$, dried (MgSO$_4$), and concentrated. The residue was purified by silica gel chromatography (0-5% MeOH in CH$_2$Cl$_2$) to give 1 g (63%) of M1-9.

Synthesis of (R)—N-(3-aminobenzo[d]isoxazol-6-yl)-2-((R)-4-(4-fluoro-3-(morpholine-4-carbonyl)phenyl)-3-oxomorpholin-2-yl)-2-hydroxyacetamide (example aa95)

Compound M1-9 (1 g, 0.00146 mol) was dissolved in a 1:1 mixture of CH$_2$Cl$_2$/MeOH (58 ml), NH$_2$NH$_2$ (0.458 ml, 10 eq) was added and the mixture stirred for 2 hours. The mixture was concentrated. The residue was purified by silica gel chromatography (0-5% MeOH in CH$_2$Cl$_2$) to give 0.5 g (67%) of Example aa95.

Example aa96

Synthesis of 2-chloro-5-iodobenzaldehyde (compound M2-1)

M2-1 was synthesized using the procedure described in WO 2008/077009, page 39, example 27, steps (a) to (b).

Synthesis of 4-(2-chloro-5-iodobenzyl)morpholine (compound M2-2)

M2-1 (0.875 g, 0.0033 mol) was dissolved in DCE (8.2 ml), morpholine (0.373 ml, 1.3 eq) and AcOH (0.94 ml, 5 eq) were added and the mixture stirred for 30 minutes. Na(OAc)$_3$BH (1.392 g, 2 eq) was added and the mixture stirred overnight. The mixture was diluted with EtOAc and washed with

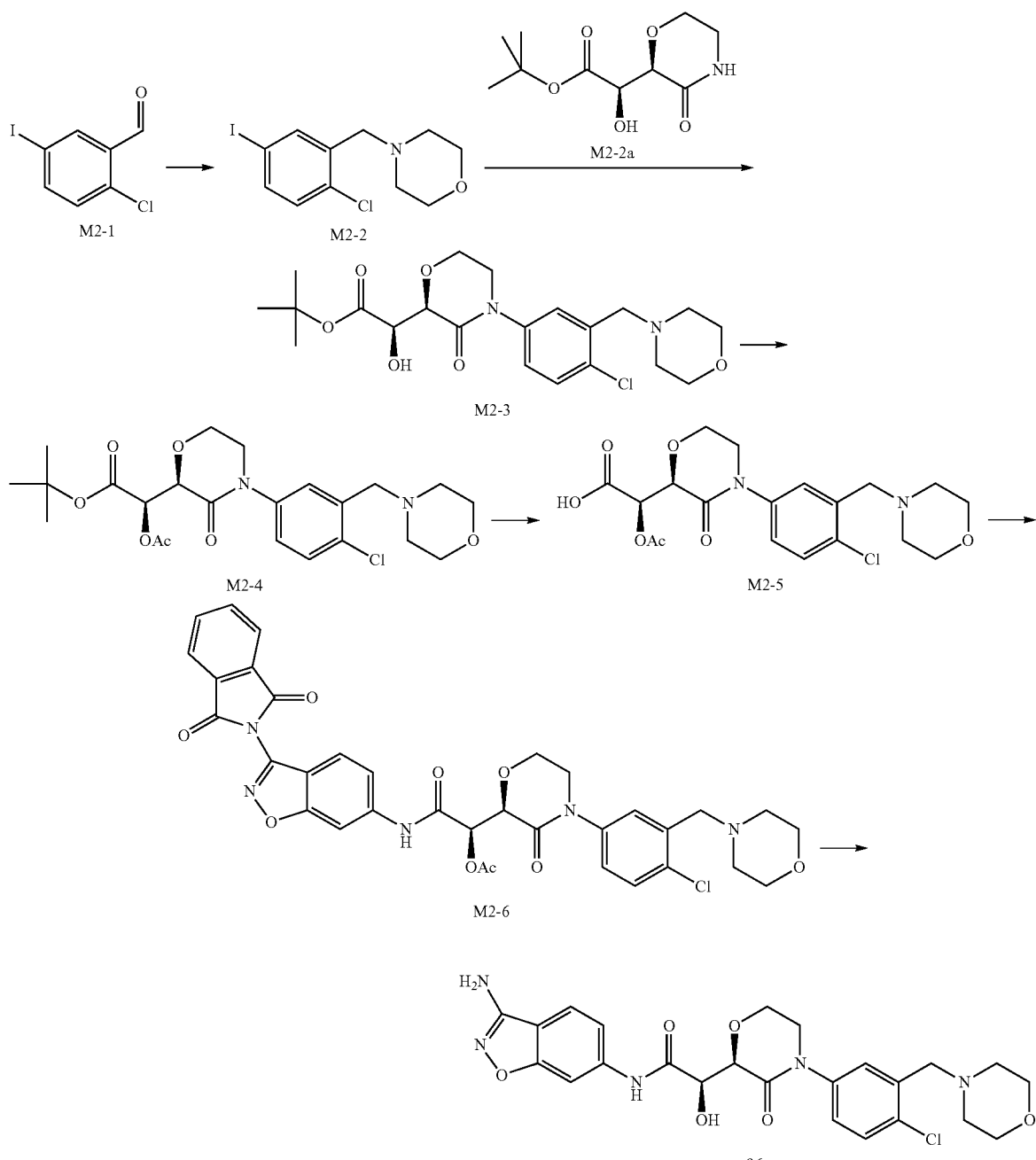

NaHCO$_{3(sat)}$, dried (MgSO4), and concentrated. The residue was dissolved in ether and acidified with 1M HCl in ether. The resulting precipitate was collected, suspended in EtOAc, and neutralized with NaHCO$_{3(sat)}$. The organic layer was dried (MgSO4) and concentrated to give 305 mg of M2-2.

Synthesis of (R)-tert-butyl 2-((R)-4-(4-chloro-3-(morpholinomethyl)phenyl)-3-oxomorpholin-2-yl)-2-hydroxyacetate (compound M2-3)

Compound M2-2a (0.23 g, 0.001 mol) and compound M2-2 (0.305 g, 1 eq) were dissolved in DMSO (10 ml), to this mixture were added CuI (57 mg, 0.2 eq), K$_3$PO$_4$ (422 mg, 2 eq), and trans-N,N-dimethylcyclohexane-1,2-diamine (0.047 ml, 0.3 eq). The resulting solution was degassed and heated at 90° C. for 1.5 hours. The mixture was cooled to rt, NH$_4$Cl(sat) was added and the mixture extracted with EtOAc. The extracts were washed with NH$_4$Cl(sat), dried (MgSO$_4$), and concentrated. The resulting residue was then purified by silica gel chromatography (0-100% EtOAc in hexane) gave 266 mg of M2-3.

Synthesis of (R)-tert-butyl 2-acetoxy-2-((R)-4-(4-chloro-3-(morpholinomethyl)phenyl)-3-oxomorpholin-2-yl)acetate (compound M2-4)

Compound M2-4 was synthesized using a procedure similar to the synthesis of compound M1-7.

Synthesis of (R)-2-acetoxy-2-((R)-4-(4-chloro-3-(morpholinomethyl)phenyl)-3-oxomorpholin-2-yl) acetic acid (compound M2-5)

M2-4 (230 mg, 0.000476) was treated with 4M HCl in dioxane for 16 hours. The mixture was then concentrated to give M2-5 as a hydrochloride salt.

Synthesis of (R)-1-((R)-4-(4-chloro-3-(morpholinomethyl)phenyl)-3-oxomorpholin-2-yl)-2-(3-(1,3-dioxoisoindolin-2-yl)benzo[d]isoxazol-6-ylamino)-2-oxoethyl acetate (compound M2-6)

M2-5.HCl (100 mg, 0.000216) and M1-4 (66 mg, 1.1 eq) were dissolved in MeCN and cooled to 0° C. DMAP (3 mg, 0.1 eq), pyridine (0.017 ml, 1 eq), and EDCI.HCl (50 mg, 1.2 eq) were added and the mixture stirred for 2 hours. The mixture was diluted with EtOAc, washed with NH$_4$Cl$_{(sat)}$, dried (MgSO$_4$), and concentrated. The residue was purified by silica gel chromatography (0-5% MeOH in CH$_2$Cl$_2$) to give 40 mg of M2-6.

Synthesis of (R)—N-(3-aminobenzo[d]isoxazol-6-yl)-2-((R)-4-(4-chloro-3-(morpholinomethyl)phenyl)-3-oxomorpholin-2-yl)-2-hydroxyacetamide (Example aa96)

Example aa96 was synthesized using a procedure similar to the synthesis of compound aa95. Additionally an ether solution of aa96 was converted to the hydrochloride salt by treatment with 1M HCl in ether and isolated by filtration.

Example aa97

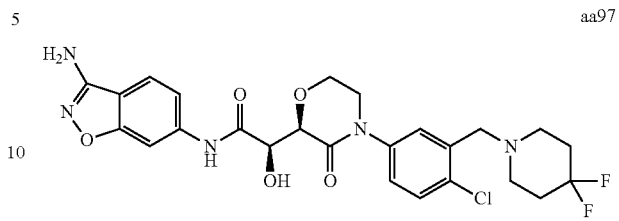

aa97

(R)—N-(3-aminobenzo[d]isoxazol-6-yl)-2-((R)-4-(4-chloro-3-((4,4-difluoropiperidin-1-yl)methyl)phenyl)-3-oxomorpholin-2-yl)-2-hydroxyacetamide (Example aa97) was synthesized in a similar manner to example aa96 using previously described procedures.

Example aa98

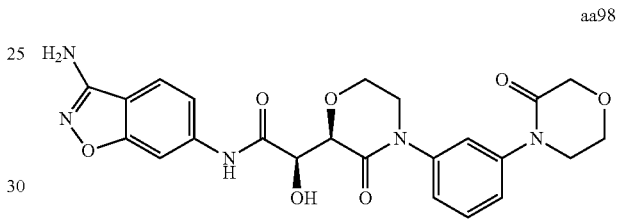

aa98

(R)—N-(3-aminobenzo[d]isoxazol-6-yl)-2-hydroxy-2-((R)-3-oxo-4-(3-(3-oxomorpholino)phenyl)morpholin-2-yl) acetamide (Example aa98) was synthesized in a similar manner to example aa95 using previously described procedures.

Example aa99

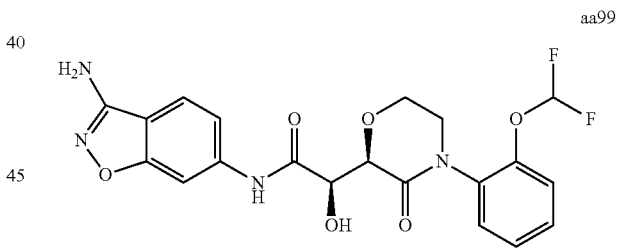

aa99

(R)—N-(3-aminobenzo[d]isoxazol-6-yl)-2-((R)-4-(2-(difluoromethoxy)phenyl)-3-oxomorpholin-2-yl)-2-hydroxyacetamide (Example aa99) was synthesized in a similar manner to example aa95 using previously described procedures.

Example aa100

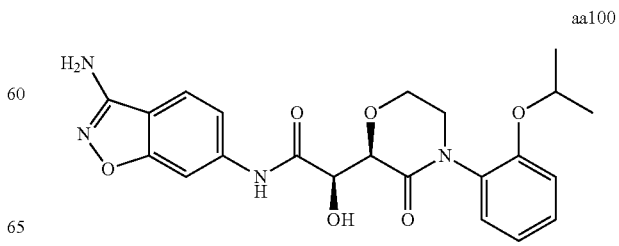

aa100

(R)—N-(3-aminobenzo[d]isoxazol-6-yl)-2-hydroxy-2-((R)-4-(2-isopropoxyphenyl)-3-oxomorpholin-2-yl)acetamide (Example aa100) was synthesized in a similar manner to example aa95 using previously described procedures.

Example aa101

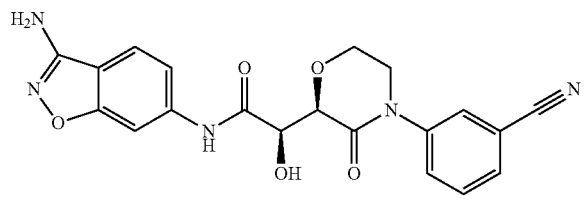

aa101

(R)—N-(3-aminobenzo[d]isoxazol-6-yl)-2-((R)-4-(3-cyanophenyl)-3-oxomorpholin-2-yl)-2-hydroxyacetamide (Example aa101) was synthesized in a similar manner to example aa95 using previously described procedures.

Example aa102

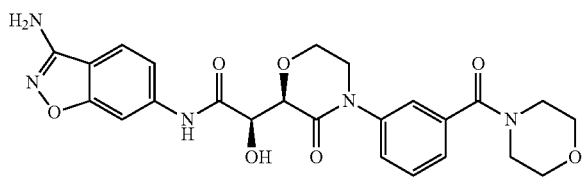

(R)—N-(3-aminobenzo[d]isoxazol-6-yl)-2-hydroxy-2-((R)-4-(3-(morpholine-4-carbonyl)phenyl)-3-oxomorpholin-2-yl)acetamide (Example aa102) was synthesized in a similar manner to example aa95 using previously described procedures.

Example aa103 aa103

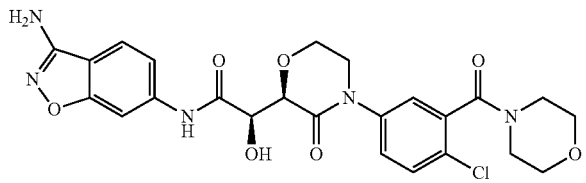

(R)—N-(3-aminobenzo[d]isoxazol-6-yl)-2-((R)-4-(4-chloro-3-(morpholine-4-carbonyl)phenyl)-3-oxomorpholin-2-yl)-2-hydroxyacetamide (Example aa103) was synthesized in a similar manner to example aa95 using previously described procedures.

Example aa104 aa104

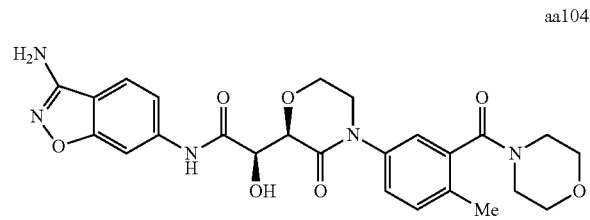 [SMILES: Cc1ccc(N2CCO[C@H]([C@@H](O)C(=O)Nc3ccc4c(N)noc4c3)C2=O)cc1C(=O)N1CCOCC1]

(R)—N-(3-aminobenzo[d]isoxazol-6-yl)-2-hydroxy-2-((R)-4-(4-methyl-3-(morpholine-4-carbonyl)phenyl)-3-oxomorpholin-2-yl)acetamide (Example aa104) was synthesized in a similar manner to example aa95 using previously described procedures.

Example aa105 aa105

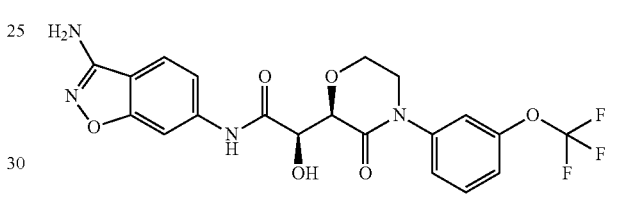

(R)—N-(3-aminobenzo[d]isoxazol-6-yl)-2-hydroxy-2-((R)-3-oxo-4-(3-(trifluoromethoxy)phenyl)morpholin-2-yl)acetamide (Example aa105) was synthesized in a similar manner to example aa95 using previously described procedures.

Example aa106 aa106

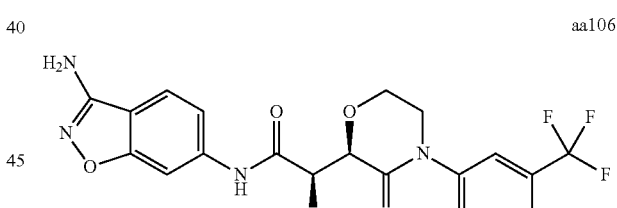

(R)—N-(3-aminobenzo[d]isoxazol-6-yl)-2-hydroxy-2-((R)-3-oxo-4-(3-(trifluoromethyl)phenyl)morpholin-2-yl)acetamide (Example aa106) was synthesized in a similar manner to example aa95 using previously described procedures.

Example aa107 aa107

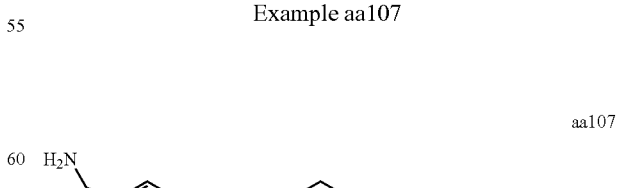

(R)—N-(3-aminobenzo[d]isoxazol-6-yl)-2-((R)-4-(4-chloro-3-(1,2,3,4-tetrahydroisoquinoline-2-carbonyl)phenyl)-3-oxomorpholin-2-yl)-2-hydroxyacetamide (Example aa107) was synthesized in a similar manner to example aa95 using previously described procedures.

Example aa108

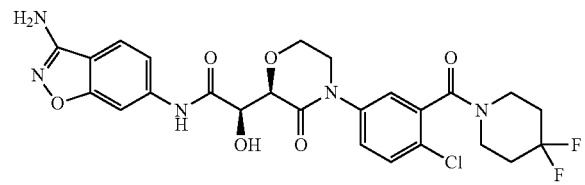

aa108

(R)—N-(3-aminobenzo[d]isoxazol-6-yl)-2-((R)-4-(4-chloro-3-(4,4-difluoropiperidine-1-carbonyl)phenyl)-3-oxomorpholin-2-yl)-2-hydroxyacetamide (Example aa108) was synthesized in a similar manner to example a95 using previously described procedures.

Example aa109

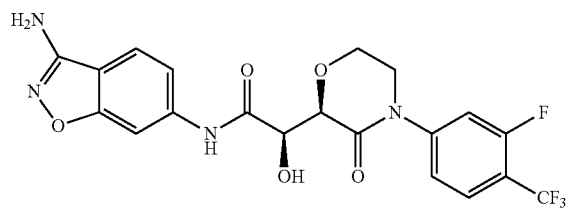

aa109

(R)—N-(3-aminobenzo[d]isoxazol-6-yl)-2-((R)-4-(3-fluoro-4-(trifluoromethyl)phenyl)-3-oxomorpholin-2-yl)-2-hydroxyacetamide (Example aa109) was synthesized in a similar manner to example a95 using previously described procedures.

Example aa110

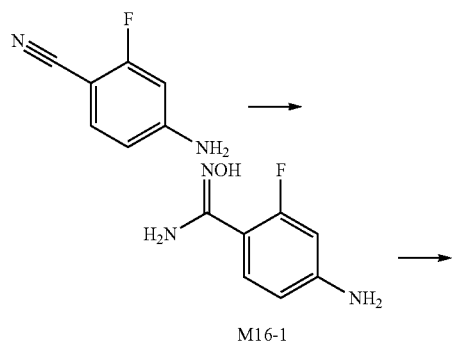

M16-1

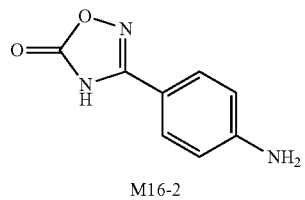

M16-2

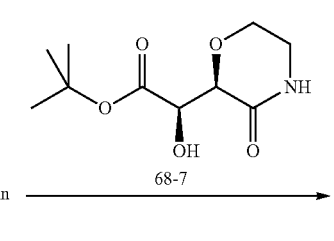

M16-3

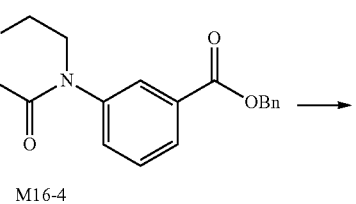

M16-4

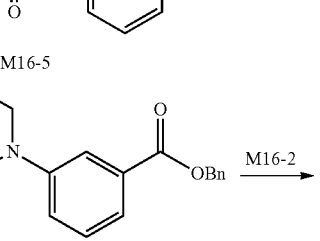

M16-5

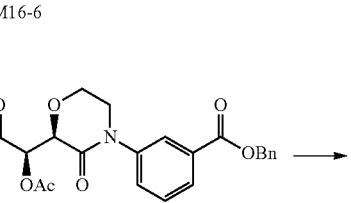

M16-6

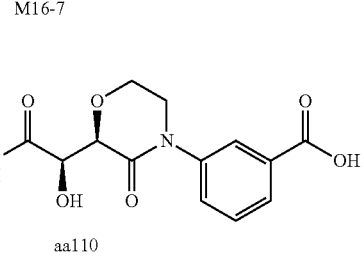

aa110

Synthesis of 4-amino-2-fluoro-N'-hydroxybenzimidamide (compound M16-1)

4-cyano-3-fluoroaniline (10 g, 0.073 mol) dissolved in EtOH (36 ml). Water (7.3 ml) was added followed by Na$_2$CO$_3$ (5.06 g, 0.65 eq) and the temperature of the mixture raised to 60° C. NH$_2$OH.HCl (5.6 g, 1.1 eq) in water (7.3 ml) was added slowly, and the mixture heated at 60° C. overnight. The mixture was cooled to rt, the solid was collected by filtration, washed with, water (7 ml), EtOH (7 ml), ether (20 ml), and dried to give 7.5 g of M16-1.

Synthesis of 3-(4-aminophenyl)-1,2,4-oxadiazol-5 (4H)-one (compound M16-2)

M16-1 (7.5 g, 0.044 mol) was suspended in EtOH (26 ml), diethyl carbonate (5.34 ml, 1 eq) was added and the mixture warmed to 65° C. NaOEt (16.5 g of a 21% wt solution in EtOH, 1.15 eq) added slowly and the temperature of the mixture raised to 70° C. for 2 hours. The mixture was cooled to rt, concentrated and dissolved in water (25 ml) at 70° C., HCl(c) added to bring the PH to 2, the mixture was cooled to 0° C. The solid was collected by filtration and washed with water (20 ml), EtOH (7 ml), and ether (20 ml) to give 6.4 g of M16-2.

Synthesis of 1-(3-iodophenyl)-2-phenylethanone (compound M16-3)

m-Iodobenzoic acid (1 g, 0.004 mol) was dissolved in MeCN (20 ml), Cs$_2$CO$_3$ (2.63 g, 2 eq) and benzyl bromide (0.528 ml, 1.1 eq) added. The mixture was heated at reflux overnight. The mixture was concentrated, taken up in EtOAc, washed with water, dried (MgSO$_4$), and concentrated. The residue was purified by silica gel chromatography (0-60% EtOAc in hexane) to give 1.6 g of M16-3.

Synthesis of benzyl 3-((R)-2-((R)-1-acetoxy-2-(3-fluoro-4-(5-oxo-4,5-dihydro-1,2,4-oxadiazol-3-yl)phenyl amino)-2-oxoethyl)-3-oxomorpholino)benzoate (compound M16-7)

Compound M16-3 was converted to compound M16-7 using previously described procedures.

Synthesis of 3-((R)-2-((R)-2-(4-carbamimidoyl-3-fluorophenylamino)-1-hydroxy-2-oxoethyl)-3-oxo morpholino)benzoic acid (Example aa110)

Compound M16-7 (200 mg, 0.00033 mol) was dissolved in MeOH (5.5 ml), 7N NH$_3$ (0.284 ml, 6 eq) was added, and the mixture stirred for 1 hour. The mixture was concentrated, taken up in MeOH (5 ml). 1M HCl (0.662 ml, 2 eq) was added followed by 10% Pd(C) (100 mg). The mixture was put under H$_2$ (1 atm) for 1 hour. The solids were removed by filtration, the mixture was concentrated. The residue was triturated with ether/MeOH, and solid collected to give 143 mg of Example aa110.

Example aa111

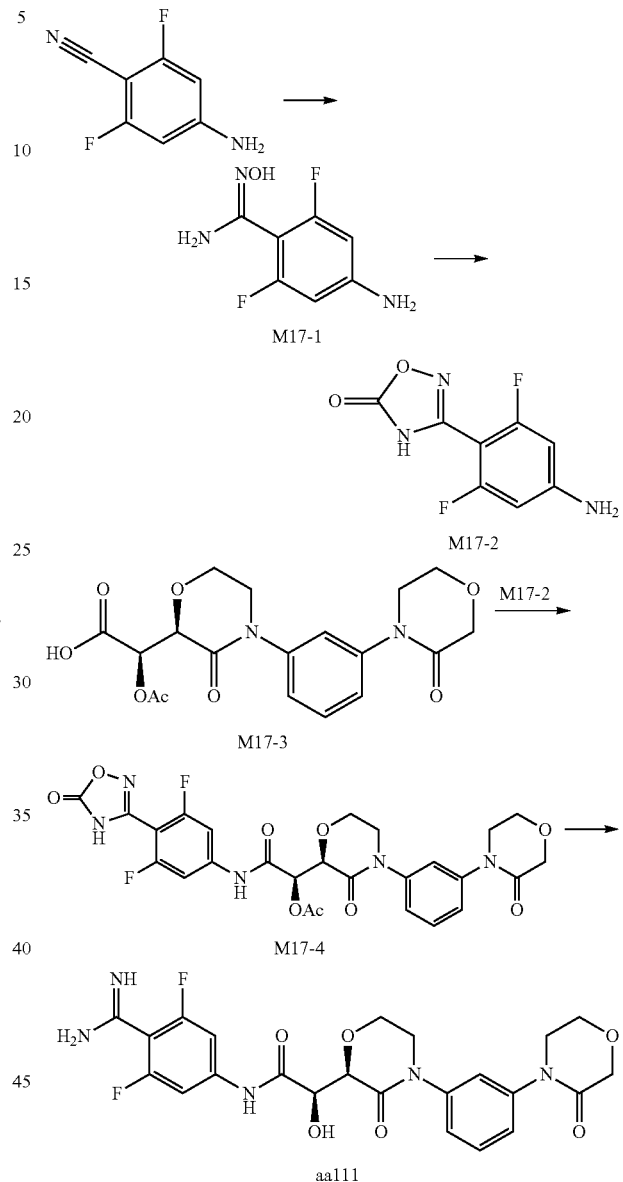

(R)—N-(4-carbamimidoyl-3,5-difluorophenyl)-2-hydroxy-2-((R)-3-oxo-4-(3-(3-oxomorpholino)phenyl)morpholin-2-yl)acetamide (Example aa111) was synthesized in a similar manner to previously described examples.

Example aa112

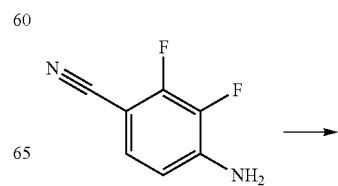

785

-continued

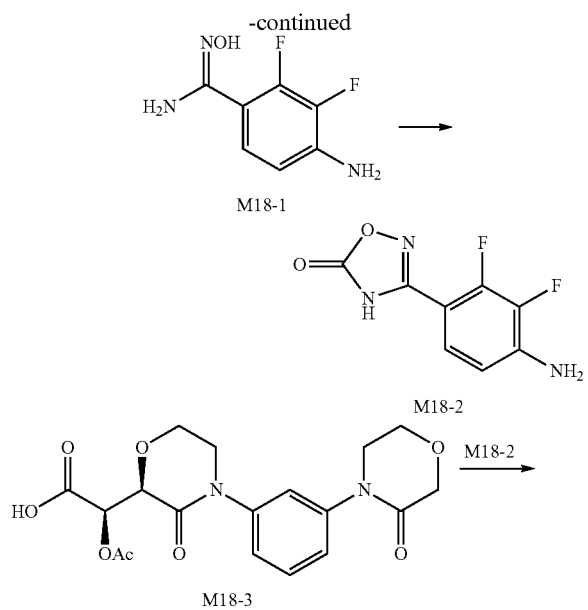

M18-1

M18-2

M18-3

M18-4 aa112

(R)—N-(4-carbamimidoyl-2,3-difluorophenyl)-2-hydroxy-2-((R)-3-oxo-4-(3-(3-oxomorpholino)phenyl)morpholin-2-yl)acetamide (Example aa112) was synthesized in a similar manner to previously described examples.

Example aa113

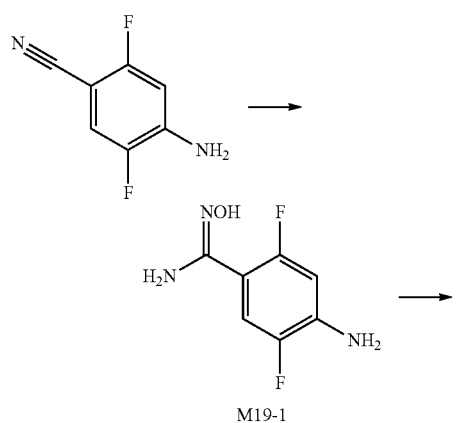

M19-1

786

-continued

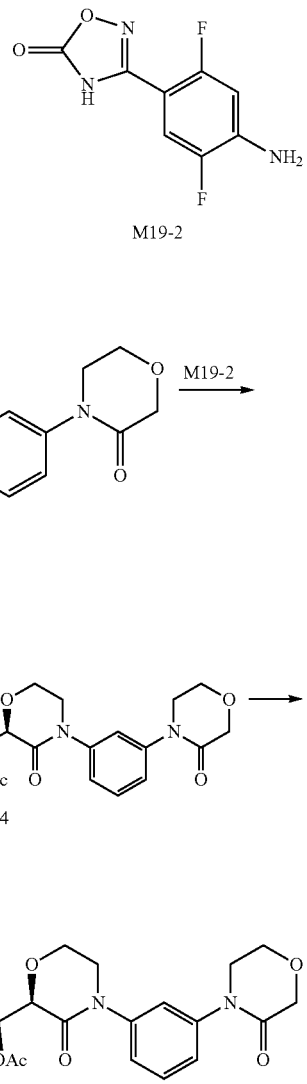

M19-2

M19-3

M19-4 aa113

(R)—N-(4-carbamimidoyl-2,5-difluorophenyl)-2-hydroxy-2-((R)-3-oxo-4-(3-(3-oxomorpholino)phenyl)morpholin-2-yl)acetamide (Example aa113) was synthesized in a similar manner to previously described examples.

Example aa114

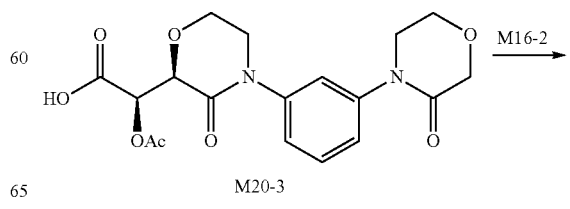

M20-3

787
-continued
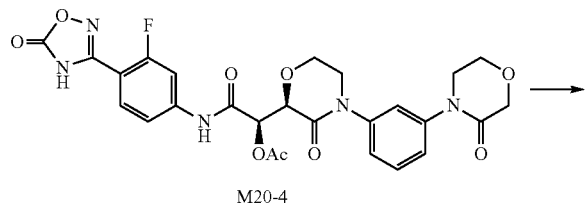
M20-4
788
-continued
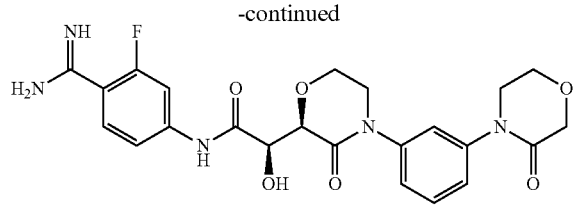
aa114
(R)—N-(4-carbamimidoyl-3-fluorophenyl)-2-hydroxy-2-((R)-3-oxo-4-(3-(3-oxomorpholino)phenyl)morpholin-2-yl)acetamide (Example aa114) as synthesized in a similar manner to previously described examples.
Examples aa115 and aa116
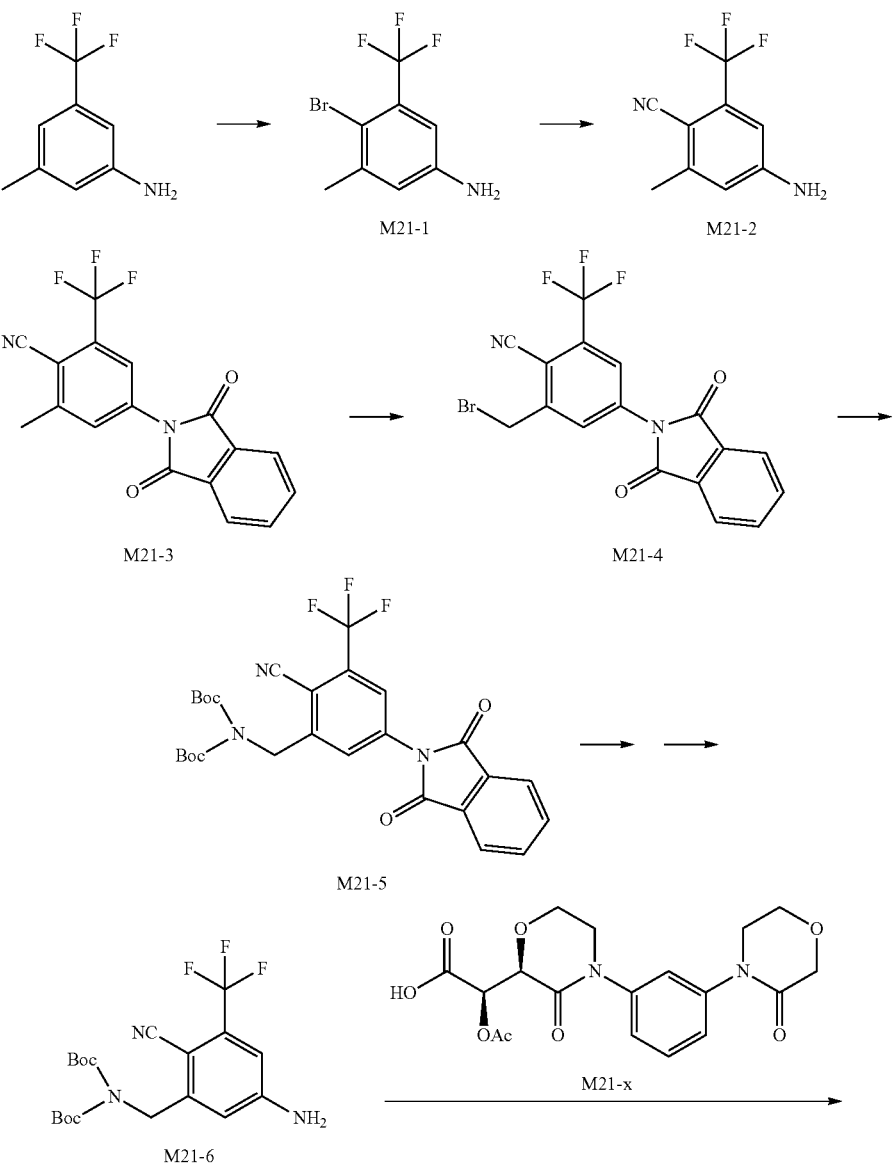

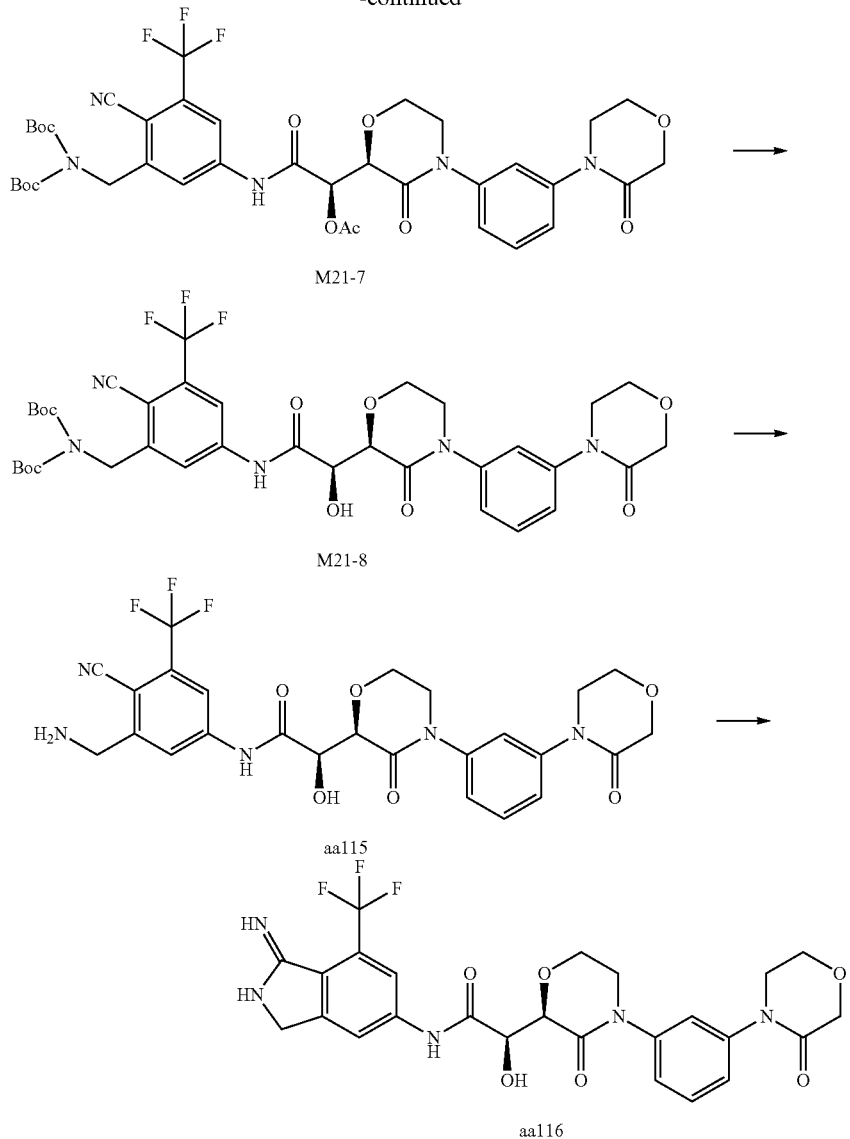

Synthesis of 4-bromo-3-methyl-5-(trifluoromethyl)aniline (Compound M21-1)

3-methyl-5-(trifluoromethyl)aniline (4.84 g, 0.011 mol) was dissolved in CH$_2$Cl$_2$ and cooled to 0° C. NBS (4.92 g, 1 eq) was added and the mixture stirred overnight. The reaction mixture was loaded onto silica gel and eluted with 0-20% EtOAc in hexane to give 2.3 g of M21-1.

Synthesis of 4-amino-2-methyl-6-(trifluoromethyl)benzonitrile (Compound M21-2)

M21-1 (2.3 g, 0.009053 mol) was dissolved in NMP (45 ml). Pd(Ph$_3$P)$_4$ (0.937 mg, 0.1 eq), Zn(CN)$_2$ (1.27 g, 1.2 eq), and Zn powder (0.592 g, 1 eq) were added. The mixture was degassed and heated at 110° C. overnight. After cooling to rt the mixture was diluted with EtOAc and washed with saturated aqueous NaHCO$_3$ solution. The extracts were dried (MgSO4) and concentrated. The residue was purified by silica gel chromatography (0-30% EtOAc in hexane) to give 1.5 g of M21-2

Synthesis of 4-(1,3-dioxoisoindolin-2-yl)-2-methyl-6-(trifluoromethyl)benzonitrile (Compound M21-3)

M21-2 (1.5 g, 0.00614 mol), was dissolved in AcOH (30 ml), phthalic anhydride (1 g, 1.1 eq) was added and the mixture heated at 130° C. for 2 hours. The mixture was cooled to rt and concentrated. The residue was purified by silica gel chromatography (0-30% EtOAc in hexane) to give 2.0 g of M21-3.

Synthesis of 2-(bromomethyl)-4-(1,3-dioxoisoindolin-2-yl)-6-(trifluoromethyl)benzonitrile (Compound M21-4)

M21-3 (2.6 g, 0.0078 mol) was dissolved in CCl$_4$ (39 ml), AIBN (0.259 g, 0.2 eq) and NBS (1.822 g, 1.3 eq) was added and the mixture heated at reflux while being irradiated with a 250 W lamp for 2 days. The mixture was concentrated and the residue was purified by silica gel chromatography (0-30% EtOAc in hexane) to give 2.15 g of M21-4.

Synthesis of Compound M21-5

M21-4 (2.15 g, 0.00525 mol) was dissolved in DMF (52 ml), $K_2CO_3$ (1.45 g, 2 eq) and $(Boc)_2NH$ (2.28 g, 2 eq) was added and the mixture stirred overnight. The mixture was diluted with EtOAc and washed with $NH_4Cl_{(sat)}$. The organic layers were dried ($MgSO_4$) concentrated and the residue was purified by silica gel chromatography (0-30% EtOAc in hexane) to give 1.4 g of M21-5.

Synthesis of Compound M21-6

M21-5 (1.4 g, 0.00257) was dissolved in 1:1 MeOH/$CH_2Cl_2$ (25 ml) and cooled to 0° C. Hydrazine (1.6 ml, 20 eq) was added, after 15 minutes the mixture was allowed to warm to rt and then stirred for an additional 1.5 hours. The resulting suspension was filtered and the filtrate purified by silica gel chromatography (0-40% EtOAc in hexane) to give 0.583 g of M21-6.

Synthesis of Compound M20-7

M21-6 (0.538 g, 0.0013 mol) and M21-x (disclosed previously in this filing) (0.661 g, 1.3 eq) were dissolved in MeCN (2.6 ml) and cooled to 0° C. EDCI.HCl (0.372 g, 1.5 eq) and DMAP (16 mg, 0.1 eq) were added and the mixture stirred overnight. The mixture was diluted with EtOAc, washed with $NH_4Cl_{(sat)}$, the extracts were dried ($MgSO_4$), and concentrated. The residue was purified by silica gel chromatography (0-100% EtOAc in hexane) to give 167 mg of M21-7.

Synthesis of Compound M21-8

M21-7 (167 mg, 0.00021 mol) was treated with 7N $NH_3$ in MeOH for 1 hour. The mixture was concentrated and the residue was purified by silica gel chromatography (0-5% MeOH in $CH_2Cl_2$) to give 60 mg of M21-8.

Example aa115

Compound M21-8 (60 mg) was treated with 4M HCl in dioxane for 1 hour. The mixture was concentrated to give 60 mg of (R)—N-(3-(aminomethyl)-4-cyano-5-(trifluoromethyl)phenyl)-2-hydroxy-2-((R)-3-oxo-4-(3-(3-oxomorpholino)phenyl)morpholin-2-yl)acetamide (Example aa115).

Example aa116

Example aa115 (5 mg) was dissolved in EtOH and heated at 90° C. for 2 hours. After cooling to rt the mixture was concentrated to give 4 mg of (R)-2-hydroxy-N-(1-imino-7-(trifluoromethyl)isoindolin-5-yl)-2-((R)-3-oxo-4-(3-(3-oxomorpholino)phenyl)morpholin-2-yl)acetamide (example aa116).

| | LC/MS | | |
|---|---|---|---|
| EXAMPLE | m/z *[M + 1]+ | RT min | Solvent system |
| aa95 | 514 | 1.29 | A |
| aa96 | 516 | 1.27 | B |
| aa97 | 550 | 1.55 | A |
| aa98 | 482 | 1.26 | A |
| aa99 | 448 | 1.44 | A |
| aa100 | 441 | 1.54 | A |
| aa101 | 430 [MNa]+ | 1.70 | B |
| aa102 | 496 | 1.30 | A |
| aa103 | 530 | 1.34 | A |
| aa104 | 510 | 1.32 | A |
| aa105 | 467 | 1.80 | A |
| aa106 | 451 | 1.86 | B |
| aa107 | 576 | 1.84 | A |
| aa108 | 564 | 0.81 | B |
| aa109 | 469 | 1.81 | A |
| aa110 | 431 | 1.19 | A |
| aa111 | 504 | 1.18 | A |
| aa112 | 504 | 1.18 | A |
| aa113 | 504 | 1.48 | B |
| aa114 | 486 | 1.23 | A |
| aa115 | 548 | 1.34 | A |
| aa116 | 548 | 1.29 | A |

*except when noted.
Solvent A: Column: Agilent SBC (3.0 × 50 mm, 1.8u); Flow: 1.0 ml/min; solvent A: H2O-0.1% TFA: Solvent B: ACN-0.1% TFA; Gradient Table: 0.1 min. 5% B, 2.3 min: 99% B, 2.90 min: 99% B, 3.0 min: 5% B stop time 3.50 min.
Solvent B: Column: Agilent SBC (3.0 × 50 mm, 1.8u); Flow: 1.0 ml/min; solvent A: H2O-0.1% TFA: Solvent B: ACN-0.1% TFA; Gradient Table: 0 min. 10% B, 1.5 min: 95% B, 2.76 min: 10% B, stop time 3.60 min, Post Time 0.70 min.

| EXAMPLE | NMR ppm 400 MHz |
|---|---|
| aa95 | DMSO-$d_6$ 9.98 (1H, s), 8.01 (1H, m), 7.68 (1H, d, J = 8.8 Hz), 7.58-7.55 (1H, m), 7.54-7.48 (2H, m), 7.37 (1H, t, J = 9.1 Hz), 6.43 (1H, J = 6.6 Hz), 6.31 (2H, s), 4.68-4.66 (1H, m), 4.65-4.63 (1H, m), 4.14-4.10 (1H, m), 3.95-3.83 (2H, m), 3.66-3.61 (5H, m), 3.54-3.52 (2H, m), 3.26-3.23 (2H, m). |
| aa96 | DMSO-$d_6$ 10.00 (1H, s), 8.02 (1H, m), 7.97 (1H, s), 7.69 (1H, d, J = 8.5 Hz), 7.63 (2H, m), 7.56-7.54 (1H, m), 4.72 (1H, m), 4.64 (1H, m), 4.48 (1H, br s), 4.20-4.13 (1H, m), 3.98-3.69 (11H, m), 3.33-3.21 (4H, m). |
| aa97 | DMSO-$d_6$ 10.00 (1H, s), 8.02 (1H, m), 7.96-7.90 (1H, m), 7.69 (1H, d, = 8.5 Hz), 7.64-7.61 (1H, m), 7.56-7.54 (1H, m), 4.72 (1H, m), 4.65 (1H, m), 4.58-4.51 (1H, m), 4.18-4.14 (1H, m), 3.97-3.70 (9H, m), 3.55-3.24 (4H, m), 2.40-2.30 (3H, m). |
| aa98 | DMSO-$d_6$ 9.98 (1H, s), 8.02 (1H, m), 7.68 (1H, d, J = 8.5 Hz), 7.56 (1H, dd, J = 7.8, 1.5 Hz), 7.48-7.46 (1H, m), 7.43 (1H, d, J = 7.8 Hz), 7.33-7.29 (2H, m), 6.43 (1H, d, J = 6.5 Hz), 6.32 (2H, s), 4.67-4.63 (2H, m), 4.2 (2H, s), 4.15-4.10 (1H, m), 3.98-3.95 (2H, m), 3.93-3.82 (2H, m), 3.75-3.71 (2H, m), 3.70-3.62 (1H, m). |

-continued

| EXAMPLE | NMR ppm 400 MHz |
|---|---|
| aa99 | DMSO-d$_6$ 10.01 (1H, s), 8.02 (1H, m), 7.68 (1H, d, J = 8.05), 7.58 (1H, m), 7.45-7.38 (2H, m), 7.35-7.27 (2H, m), 7.37 (1H, d, J = 7.01 Hz), 6.31 (2H, m), 4.66 (1H, m), 4.63-4.61 (1H, m), 4.18-4.13 (1H, m), 3.92-3.76 (2H, m), 3.45-3.41 (1H, m). |
| aa100 | DMSO-d$_6$ 9.99 (1H, s), 8.02 (1H, m), 7.68 (1H, d, J = 8.4 Hz), 7.59-7.56 (1H, m), 7.30-7.26 (1H, m), 7.18-7.15 (1H, m), 7.13-7.11 (1H, m), 7.96-7.92 (1H, m), 6.36-6.30 (3H, m), 4.63-4.56 (3H, m), 4.16-4.10 (1H, m), 3.89-3.33 (1H, m), 3.79-3.67 (1H, m), 3.40-3.35 (1H, m), 1.25 (3H, s), 1.24 (3H, s). |
| aa101 | DMSO-d$_6$ 9.98 (1H, s), 8.02 (1H, m), 7.95 (1H, m), 7.81-7.79 (1H, m), 7.75-7.73 (1H, m), 7.69-7.61 (2H, m), 7.58-7.55 (1H, m), 6.44 (1H, d, J = 7.0 Hz), 6.32 (2H, m), 4.71 (1H, m), 4.66-4.64 (1H, m), 4.17-4.12 (1H, m) 3.96-3.87 (2H, m), 3.74-3.68 (1H, m). |
| aa102 | DMSO-d$_6$ 9.99 (1H, s), 8.07-8.02 (2H, m), 7.87-7.85 (1H, m), 7.68 (1H, d, J = 8.9 Hz), 7.57 (1H, d, J = 8.76 Hz), 7.48 (2H, m), 7.32-7.26 (1H, m), 7.46-7.41 (1H, m), 6.32 (2H, s), 4.69 (1H, s), 4.66-4.60 (1H, m), 4.15-4.09 (1H, m), 3.96-3.85 (2H, m), 3.69-3.5 (8H, m). |
| aa103 | DMSO-d$_6$ 9.97 (1H, s), 8.01 (1H, m), 7.68 (1H, d, J = 8.5 Hz), 7.58-7.50 (4H, m), 6.43 (1H, dd, J = 9.0, 6.5 Hz), 6.31 (2H, s), 4.68 (1H, m), 4.64 (1H, d, J = 7.0 Hz), 4.15-4.06 (2H, m), 3.95-3.84 (2H, m), 3.70-3.53 (6H, m), 3.16-3.14 (2H, m). |
| aa104 | DMSO-d$_6$ 9.99 (1H, s), 8.04 (1H, m), 7.71 (1H, d, J = 8.5 Hz), 7.60-7.58 (1H, m), 7.38-7.29 (3H, m), 6.44-6.42 (1H, s), 6.33 (2H, s), 4.70-4.65 (2H, m), 4.16-4.11 (1H, m), 3.98-3.83 (2H, m), 3.70-3.62 (4H, m), 3.56-3.48 (2H, m), 3.20-3.14 (2H, m), 2.24 (3H, s). |
| aa105 | DMSO-d$_6$ 9.98 (1H, s), 8.01 (1H, m), 7.68 (1H, d, J = 8.66 Hz), 7.58-7.53 (3H, m), 7.47 (1H, d, J = 6.2 Hz), 7.28 (1H, d, J = 8 Hz), 6.44 (1H, d, J = 6.88 Hz), 6.32 (2H, s), 4.70 (1H, m), 4.66-4.63 (1H, m), 4.15-4.10 (1H, m), 3.97-3.86 (2H, m), 3.73-3.65 (1H, m), |
| aa106 | DMSO-d$_6$ 9.98 (1H, s), 8.02 (1H, m), 7.84 (1H, m), 7.44-7.62 (4H, m), 7.56 (1H, dd, J = 8.5, 1.5 Hz), 6.46 (1H, d, J = 6.8 Hz), 6.32 (2H, m), 4.71 (1H, m), 4.66-4.64 (1H, m), 4.16-4.12 (1H, m), 3.97-3.87 (2H, m), 3.75-3.69 (1H, m). |
| aa107 | DMSO-d$_6$ 9.97 (1H, s), 8.0 (1H, m), 7.67 (1H, d, J = 8.4 Hz), 7.61 (1H, d, J = 9.2 Hz), 7.58-7.53 (3H, m), 7.27-7.10 (4H, m), 6.46-6.42 (1H, m), 6.31 (2H, s), 4.70-4.62 (2H, m), 4.37 (1H, m), 4.14-4.10 (1H, m), 3.95-3.83 (3H, m), 3.72-3.65 (1H, m), 3.44-3.41 (1H, m), 3.29 (1H, m), 2.90-2.86 (1H, m), 2.82-2.79 (1H, m). |
| aa108 | DMSO-d$_6$ 9.97 (1H, s), 8.01 (1H, m), 7.68 (1H, d, J = 8.44 Hz), 7.60-7.51 (4H, m), 6.43 (1H, t, J = 5.5 Hz), 6.32 (2H, s), 4.70 (1H, s), 4.64 (1H, d, J = 6.7 Hz), 4.16-4.10 (1H, m), 3.96-3.81 (3H, m), 3.29-3.24 (2H, m), 2.15-2.89 (5H, m). |
| aa109 | DMSO-d$_6$ 9.98 (1H, s), 8.01 (1H, m), 7.84 (1H, t, J = 8.5 Hz), 7.75-7.71 (1H, m), 7.68 (1H, d, J = 8.8 Hz), 7.56 (2H, d, J = 8.3 Hz), 6.44 (1H, d, J = 6.88 Hz), 6.32 (2H, s), 4.74 (1H, m), 4.66-4.64 (1H, m), 4.17-4.14 (1H, m), 3.93 (2H, q, J = 9.5 Hz), 3.76-3.73 (1H, m). |
| aa110 | CD$_3$OD 10.01 (1H, s), 8.05 (1H, m), 7.99-7.95 (2H, m), 7.67-7.62 (3H, m), 7.56 (1H, t, J = 7.5 Hz), 4.83-4.81 (2H, m,), 4.25-4.21 (1H, m), 3.70-3.66 (1H, m), 3.34 (2H, m). |
| aa111 | CD$_3$OD 7.71 (2H, d, J = 10.64), 7.54-7.45 (2H, m), 7.38-7.33 (2H, m), 4.82-4.78 (2H, m), 4.28 (2H, m), 4.24-4.18 (1H, m), 4.07-3.97 (4H, m), 3.82-3.78 (2H, m), 3.73-3.68 (1H, m). |
| aa112 | CD$_3$OD 8.31-8.27 (1H, m), 7.54-7.46 (3H, m), 7.38-7.33 (2H, m), 4.81 (2H, m), 4.31-4.27 (2H, m), 4.23-4.20 (1H, m), 4.07-4.00 (4H, m), 3.83-3.79 (2H, m), 3.70-3.67 (1H, m). |
| aa113 | CD$_3$OD 8.46-8.41 (1H, m), 7.66-7.62 (1H, m), 7.52 (1H, t, J = 8.05 Hz), 7.47 (1H, m), 7.38-7.34 (2H, m), 4.81 (2H, m), 4.28 (2H, m), 4.20 (1H, dd, J = 2.5, 8.4 Hz), 4.07-4.02 (4H, m), 3.82-3.78 (2H, m), 3.67-3.62 (1H, m). |
| aa114 | CD$_3$OD 7.96 (1H, d, J = 13.9 Hz), 7.66-7.65 (2H, m), 7.52 (1H, t, J = 8.06 Hz), 7.47 (1H, m), 7.38 (2H, m), 4.82-4.80 (2H, m), 4.28 (2H, m), 4.25-4.18 (1H, m), 4.06-4.00 (4H, m), 3.82-3.79 (2H, m), 3.72-3.66 (1H, m). |
| aa115 | DMSO-d$_6$ 10.66 (1H, s), 8.69 (1H, s), 8.44 (2H, s), 8.39 (1H, m), 7.42 (1H, m), 7.44 (1H, d, J = 8.1 Hz), 7.24-7.12 (1H, m), 7.33-7.29 (2H, m), 6.64 (1H, d, J = 6.7 Hz), 4.71-4.67 (2H, m), 4.24 (1H, s), 4.19 (2H, s), 4.13-4.09 (1H, m), 3.97 (1H, t, J = 5 Hz), 3.91-3.82 (2H, m), 3.74-3.6 (3H, m), 3.54 (2H, s). |
| aa116 | DMSO-d$_6$ 10.60 (1H, s), 8.64 (1H, s), 8.48 (1H, s), 7.48-7.43 (2H, m0, 7.32-7.29 (2H, m), 6.59 (1H, d, J = 6.5 Hz), 4.83 (1H, s), 4.72-4.67 (2H, m), 4.19 (1H, s), 4.13-4.10 (1H, m), 3.97 (1H, t, J = 4.7 Hz), 3.95-3.82 (2H, m), 3.74-3.64 (3H, m). |

Examples aa117-aa135

Example aa117

(R)-2-Hydroxy-N-(1-iminoisoindolin-5-yl)-2-((R)-3-oxo-4-(3-(trifluoromethoxy)phenyl)morpholin-2-yl)acetamide EXAMPLE aa117

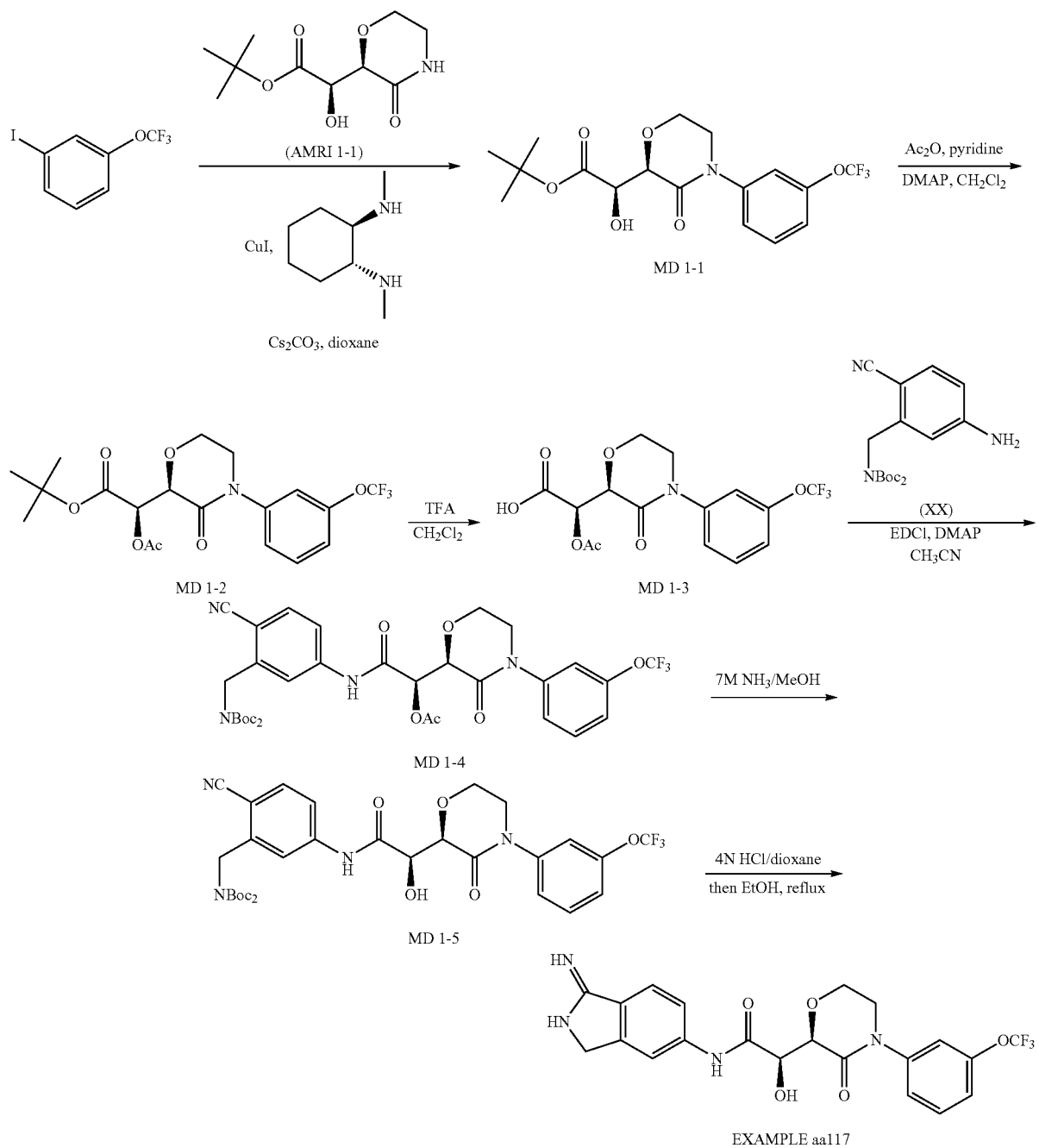

Step MD 1-1

(R)-tert-Butyl 2-hydroxy-2-((R)-3-oxo-4-(3-(trifluoromethoxy)phenyl)morpholin-2-yl)acetate MD 1-1

To a round bottom flask charged with a stir bar was added morpholinone (0.15 g) AMRI 1-1 and 3-trifluoromethoxy-iodobenzene (0.12 mL) in dioxane (4 mL) at rt was added $Cs_2CO_3$ (0.42 g), and CuI (37 mg) under $N_2$. trans-N,N'-Dimethylcyclohexane-1,2-diamine (31 L) was added dropwise and the mixture was affixed with a condenser. The mixture was degassed under vacuum (~20 mm), filled with $N_2$, and heated to 90° C. The mixture stirred for 3 h at 90° C., cooled to rt, and was diluted with conc $NH_4OH$ and water, EtOAc. The mixture was extracted with EtOAc three times and the organic layers were combined. The organic layer was washed with brine, dried ($Na_2SO_4$), filtered, and concentrated under reduced pressure to afford a yellow oil. The crude product was purified by flash chromatography using a 95% $CH_2Cl_2$/5% MeOH mixture to afford MD1-1 (0.21 g) as a white solid.

Step MD 1-2

(R)-tert-butyl 2-acetoxy-2-((R)-3-oxo-4-(3-(trifluoromethoxy)phenyl)morpholin-2-yl)acetate MD 1-2

To a solution of MD 1-1 (0.21 g) in $CH_2Cl_2$ (2.5 ml) at 0° C. was added pyridine (63 µL), $Ac_2O$ (74 µA), and DMAP (5 mg). The mixture was stirred for 1 hour at 0° C., warmed to rt, and stirred for an additional 12 h. The mixture was diluted with EtOAc and the organic layer was washed sequentially with sat. aq. $CuSO_4$ solution, water, and brine. The organic layer was dried ($Na_2SO_4$), filtered, and concentrated under reduced pressure to afford MD 1-2 (0.22 g) as a light yellow semisolid. This material was used without further purification.

Step MD 1-3

(R)-2-acetoxy-2-((R)-3-oxo-4-(3-(trifluoromethoxy)phenyl)morpholin-2-yl)acetic acid MD 1-3

To a solution of MD 1-2 (0.22 g) in $CH_2Cl_2$ (2 mL) at 0° C. was added TFA (0.6 mL) dropwise. The mixture was stirred for 1 h at 0° C. and at rt for 30 min whereupon an additional portion of TFA (0.4 mL) was added. After an additional 1 h at rt, the mixture was diluted with $CH_2Cl_2$ and concentrated to dryness under reduced pressure. The crude mixture was redissolved in a 10:1 mixture of toluene/$CH_2Cl_2$ and concentrated and this protocol was repeated 5 times with to afford MD1-3 (0.18 g) as a light yellow solid. This material was used without further purification.

Step MD 1-4

(R)-2-(3-((Bis(tert-butoxycarbonyl)amino)methyl)-4-cyanophenylamino)-2-oxo-1-((R)-3-oxo-4-(3-(trifluoromethoxy)phenyl)morpholin-2-yl)ethyl acetate MD 1-4

To a solution of MD 1-3 (0.41 g) in $CH_2Cl_2$ (5 mL) at 0° C. was added 3-bis(tert-butoxycarbonylaminomethyl)-4-cyanophenylamine XX (0.42 g) followed by EDCI (0.27 g) and DMAP (13 mg). The reaction mixture was warmed to rt and stirred for 12 h. The mixture was diluted with EtOAc (15 mL) and the organic layer was washed with 1N HCl (2×3 mL) and brine (1×2 mL). The organic layer was dried ($Na_2SO_4$), filtered, and concentrated under reduced pressure. The crude product was purified by flash chromatography (ISCO, 20 g) using a gradient of 100% $CH_2Cl_2$ to 90:10 $CH_2Cl_2$/MeOH to afford MD 1-4 (0.35 g) as a white solid.

Step MD 1-5

(R)-2-(3-((Bis(tert-butoxycarbonyl)amino)methyl)-4-cyanophenylamino)-2-oxo-1-((R)-3-oxo-4-(3-(trifluoromethoxy)phenyl)morpholin-2-yl)ethyl MD 1-5

To a solution of the MD 1-4 (0.35 g) in MeOH (0.5 mL) at rt was added 7M $NH_3$/MeOH (2.5 mL) dropwise. The mixture was stirred for 45 min at rt and the mixture was concentrated under reduced pressure and placed under high vacuum. The crude product was purified by flash chromatography (ISCO, 12 g) using a gradient of 100% $CH_2Cl_2$ to 90:10 $CH_2Cl_2$/MeOH to afford MD 1-5 (0.26 g) as a white solid.

Step MD 1-6

(R)-2-Hydroxy-N-(1-iminoisoindolin-5-yl)-2-((R)-3-oxo-4-(3-(trifluoromethoxy)phenyl)morpholin-2-yl)acetamide EXAMPLE aa117

To a flask containing MD 1-5 (0.26 g) and a stir bar was added 4N HCl in dioxane (4 mL) at rt. The mixture was stirred for 1.5 h and was concentrated to ~2 mL. Toluene (8 mL) was added and the mixture was concentrated under reduced pressure. The crude material was treated with toluene (2×8 mL) and concentrated under reduced pressure. The crude product was taken up in EtOH (8 mL) and was heated at reflux for 12 h. The mixture was cooled to rt, concentrated under reduced pressure, and placed under high vacuum. The crude residue was treated with MeOH followed by dilution with $Et_2O$ and the resultant solid was collected by filtration and dried under vacuum to afford Example aa117 (106 mg) hydrochloride as a white solid.

Example aa118

(R)-2-Hydroxy-N-(1-iminoisoindolin-5-yl)-2-((R)-4-(2-methyl-1-oxoisoindolin-5-yl)-3-oxomorpholin-2-yl)acetamide EXAMPLE aa118

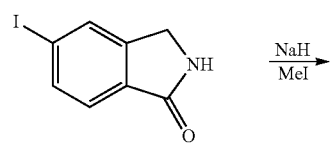
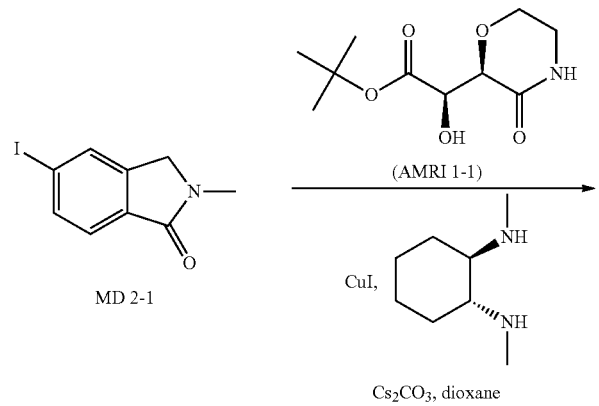

MD 2-1

-continued

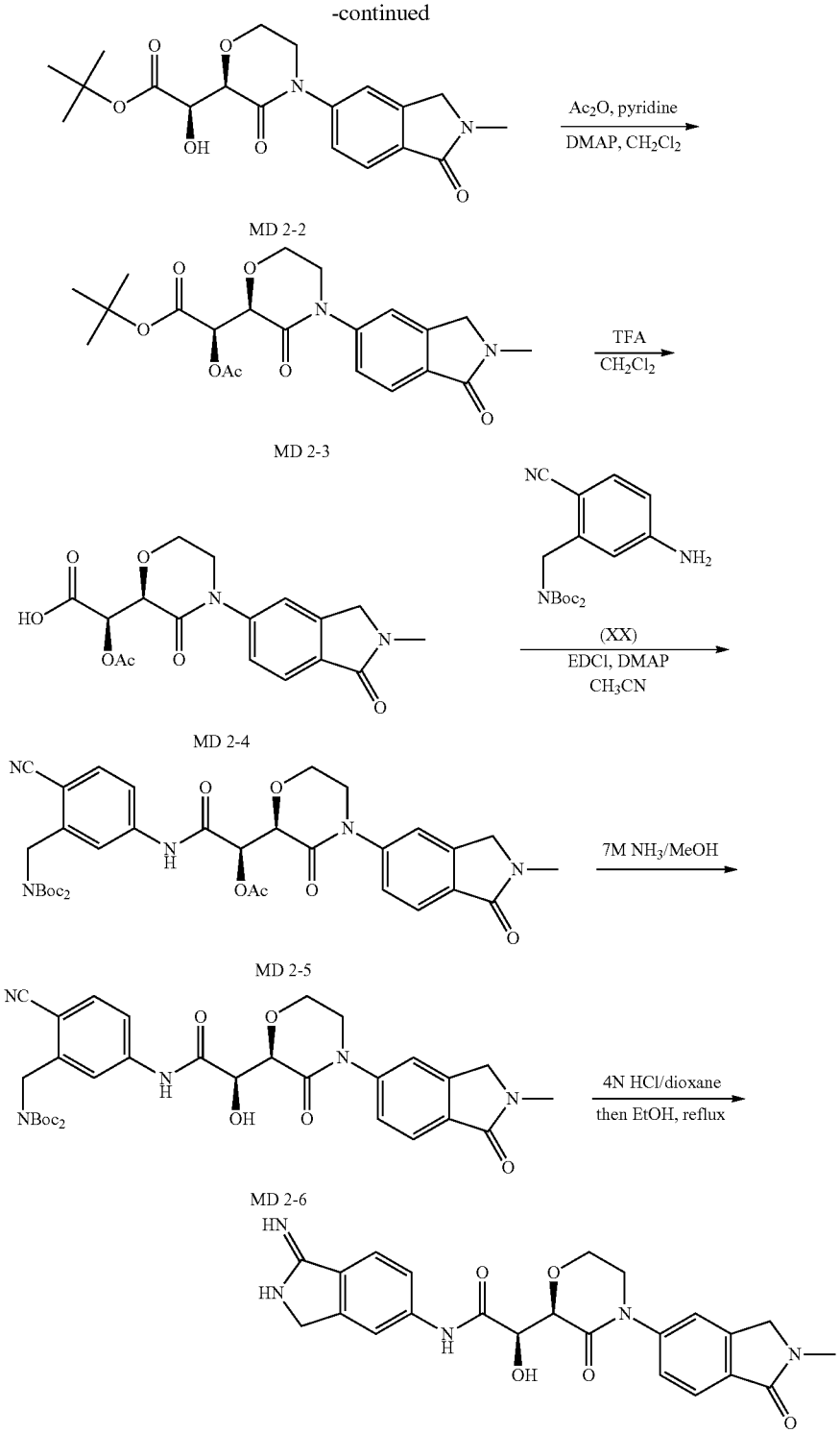

MD 2-2

MD 2-3

MD 2-4

(XX)

MD 2-5

MD 2-6

EXAMPLE aa118

Step MD 2-1

5-Iodo-2-methylisoindolin-1-one MD 2-1

To a mixture of 2,3-dihydro-5-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. NH$_4$Cl (~3 mL) and was diluted with EtOAc (10 mL). The layers were separated and the aqueous layer was extracted with EtOAc. The organic layers were combined and washed sequentially with water and brine. The organic layer was dried (Na$_2$SO$_4$),

Step MD 2-2

(R)-tert-Butyl 2-hydroxy-2-((R)-4-(2-methyl-1-ox-oisoindolin-5-yl)-3-oxomorpholin-2-yl)acetate MD 2-2

According to the Step MD 1-1 in the synthetic method for EXAMPLE aa117, compound MD 2-1 (0.20 g) was used instead of MD 1-1 to obtain MD 2-2 (0.29 g) as an off-white solid.

Step MD 2-3

(R)-tert-butyl 2-acetoxy-2-((R)-4-(2-methyl-1-ox-oisoindolin-5-yl)-3-oxomorpholin-2-yl)acetate MD 2-3

According to the Step MD 1-2 in the synthetic method for EXAMPLE aa117, compound MD 2-2 (0.29 g) was used instead of MD 1-1 to obtain MD 2-3 (0.31 g) as an off-white solid which was used without further purification.

Step MD 2-4

(R)-2-Acetoxy-2-((R)-4-(2-methyl-1-oxoisoindolin-5-yl)-3-oxomorpholin-2-yl)acetic acid MD 2-4

According to the Step MD 1-3 in the synthetic method for EXAMPLE aa117, compound MD 2-3 (0.31 g) was used instead of MD 1-2 to obtain MD 2-4 (0.27 g) as a white solid which was used without further purification.

Step MD 2-5

(R)-2-(3-((Bis(tert-butoxycarbonyl)amino)methyl)-4-cyanophenylamino)-1-((R)-4-(2-methyl-1-ox-oisoindolin-5-yl)-3-oxomorpholin-2-yl)-2-oxoethyl acetate MD 2-5

According to the Step MD 1-4 in the synthetic method for EXAMPLE aa117, compound MD 2-4 (0.11 g) was used instead of MD 1-3 to obtain MD 2-5 (0.14 g) as an off-white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 2-6

(R)-2-(3-((Bis(tert-butoxycarbonyl)amino)methyl)-4-cyanophenylamino)-1-((R)-4-(2-methyl-1-ox-oisoindolin-5-yl)-3-oxomorpholin-2-yl)-2-oxoethyl MD 2-6

According to the Step MD 1-5 in the synthetic method for EXAMPLE aa117, compound MD 2-5 (0.14 g) was used instead of MD 1-4 to obtain MD 2-6 (0.13 mg) as a off-white solid which was used without further purification.

Step MD 2-7

(R)-2-Hydroxy-N-(1-iminoisoindolin-5-yl)-2-((R)-4-(2-methyl-1-oxoisoindolin-5-yl)-3-oxomorpholin-2-yl)acetamide EXAMPLE aa118

According to the Step MD 1-6 in the synthetic method for EXAMPLE aa117, compound MD 2-5 (0.13 g) was used instead of MD 1-5 to obtain EXAMPLE aa118 (25 mg) as a pale white solid as the hydrochloride salt after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$ and treatment with HCl.

Example aa119

(R)-2-Hydroxy-N-(1-iminoisoindolin-5-yl)-2-((R)-4-(2-methyl-3-oxoisoindolin-5-yl)-3-oxomorpholin-2-yl)acetamide hydrochloride EXAMPLE aa119

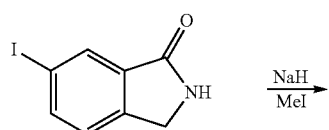 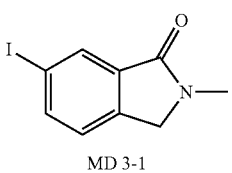 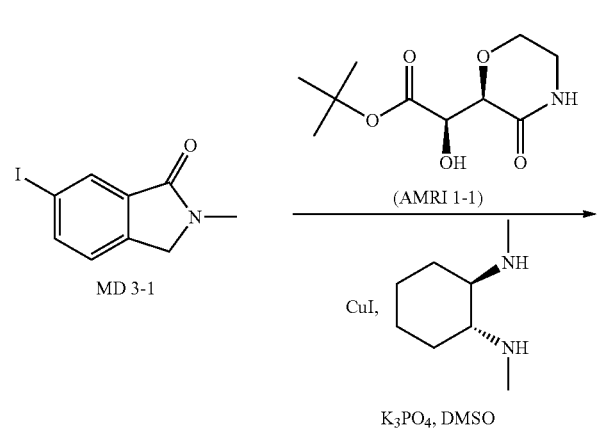

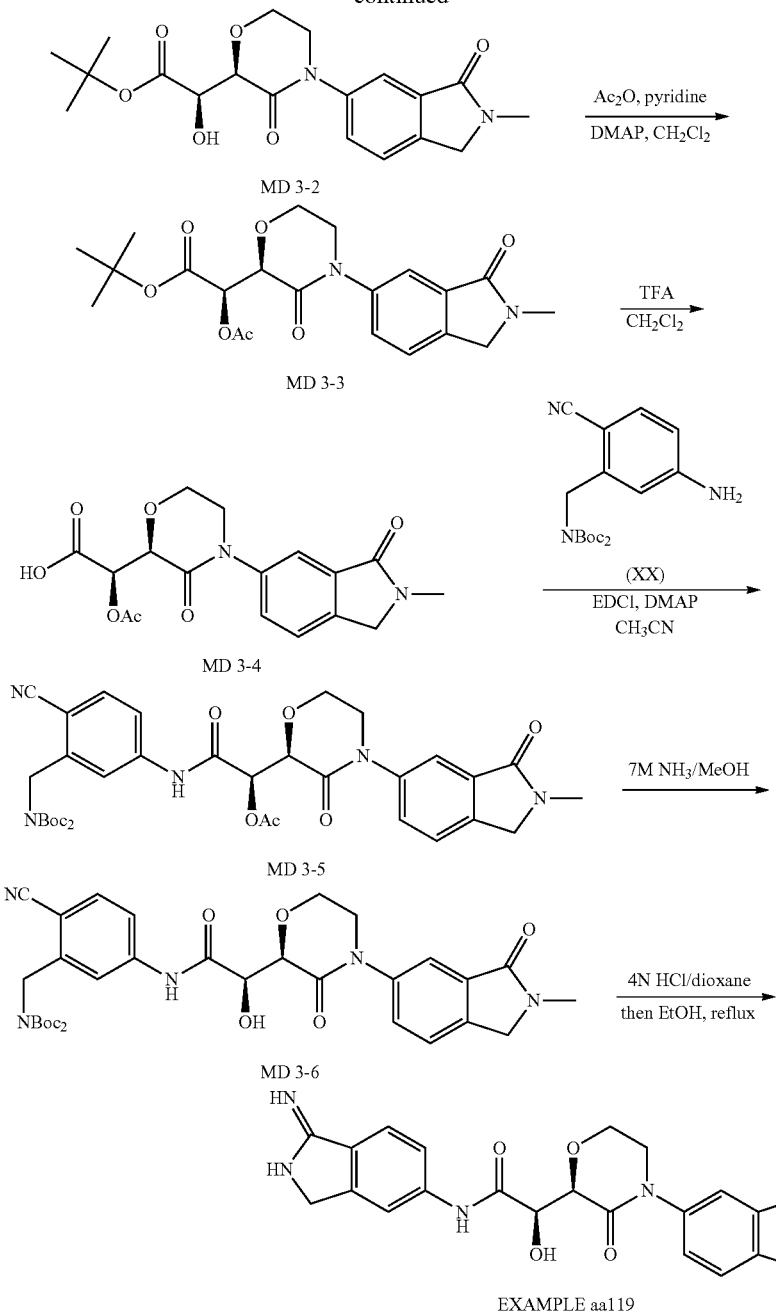

EXAMPLE aa119

Step MD 3-1

6-Iodo-2-methylisoindolin-1-one MD 3-1

To a mixture of 2,3-dihydro-6-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. NH$_4$Cl (~3 mL) and was diluted with EtOAc (10 mL). The layers were separated and the aqueous layer was extracted with EtOAc. The organic layers were combined and washed sequentially with water and brine. The organic layer was dried (Na$_2$SO$_4$), filtered, and concentrated under reduced pressure. The crude material was purified The crude product was purified by flash chromatography (ISCO, 120 g) using a gradient of 100% hexanes to 80:20 hexanes/EtOAc to afford MD 3-1 (0.84 g) as a yellow solid.

Step MD 3-2

(R)-tert-Butyl 2-hydroxy-2-((R)-4-(2-methyl-3-oxoisoindolin-5-yl)-3-oxomorpholin-2-yl)acetate MD 3-2

To a round bottom flask charged with a stir bar was added AMRI 1-1 (0.28 g) and MD 11-1 (0.40 g) in DMSO (8 mL) at rt was added K₃PO₄ (0.51 g), and CuI (23 mg) under N₂. trans-N,N'-Dimethylcyclohexane-1,2-diamine (37 μL) was added dropwise and the mixture was affixed with a condenser. The mixture was degassed under vacuum (~20 mm), filled with N₂, and heated to 80° C. The mixture stirred for 2.5 h at 80° C., cooled to rt, and was diluted with EtOAc. The mixture was then sequentially washed with conc NH₄OH, water, and brine. The organic layer was dried (Na₂SO₄), filtered, and concentrated under reduced pressure to afford a yellow oil. The crude product was purified by flash chromatography using a gradient of 100% CH₂Cl₂ to 60% CH₂Cl₂/40% MeOH to afford MD3-2 (0.23 g) as a yellow solid.

Step MD 3-3

(R)-tert-Butyl 2-acetoxy-2-((R)-4-(2-methyl-3-ox-oisoindolin-5-yl)-3-oxomorpholin-2-yl)acetate MD 3-3

According to the Step MD 1-2 in the synthetic method for EXAMPLE aa117, compound MD 3-2 (80 mg) was used instead of MD 1-1 to obtain MD 3-3 (85 mg) as an off-white solid which was used without further purification.

Step MD 3-4

(R)-2-Acetoxy-2-((R)-4-(2-methyl-3-oxoisoindolin-5-yl)-3-oxomorpholin-2-yl)acetic acid MD 3-4

According to the Step MD 1-3 in the synthetic method for EXAMPLE aa117, compound MD 3-3 (85 mg) was used instead of MD 1-2 to obtain MD 3-4 (65 mg) as a light yellow semisolid solid which was used without further purification.

Step MD 3-5

(R)-2-(3-((Bis(tert-butoxycarbonyl)amino)methyl)-4-cyanophenylamino)-1-((R)-4-(2-m ethyl-3-ox-oisoindolin-5-yl)-3-oxomorpholin-2-yl)-2-oxoethyl acetate MD 3-5

According to the Step MD 1-4 in the synthetic method for EXAMPLE aa117, compound MD 3-4 (0.25 g) was used instead of MD 1-3 to in the presence of aniline XX (0.29 g) obtain MD 3-5 (0.23 g) as a pale yellow solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 3-6

(R)-2-(3-((Bis(tert-butoxycarbonyl)amino)methyl)-4-cyanophenylamino)-1-((R)-4-(2-m ethyl-3-ox-oisoindolin-5-yl)-3-oxomorpholin-2-yl)-2-oxoethyl MD 3-6

According to the Step MD 1-5 in the synthetic method for EXAMPLE aa117, compound MD 3-5 (0.23 g) was used instead of MD 1-4 to obtain MD 3-6 (0.16 g) as a white solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 3-7

(R)—N-(4-Carbamimidoyl-2-ethylphenyl)-2-hydroxy-2-((R)-4-(2-methyl-3-oxoisoindolin-5-yl)-3-oxomorpholin-2-yl)acetamide hydrochloride EXAMPLE aa119

According to the Step MD 1-6 in the synthetic method for EXAMPLE aa117, compound MD 3-6 (0.16 g) was used instead of MD 1-5 to obtain EXAMPLE aa119 (0.11 g) as a white solid as the hydrochloride salt after HCl treatment.

Example aa120

Ethyl 2-(3-((R)-2-((R)-1-hydroxy-2-(1-iminoisoindolin-5-ylamino)-2-oxoethyl)-3-oxomorpholino)phenoxy)acetate EXAMPLE aa120

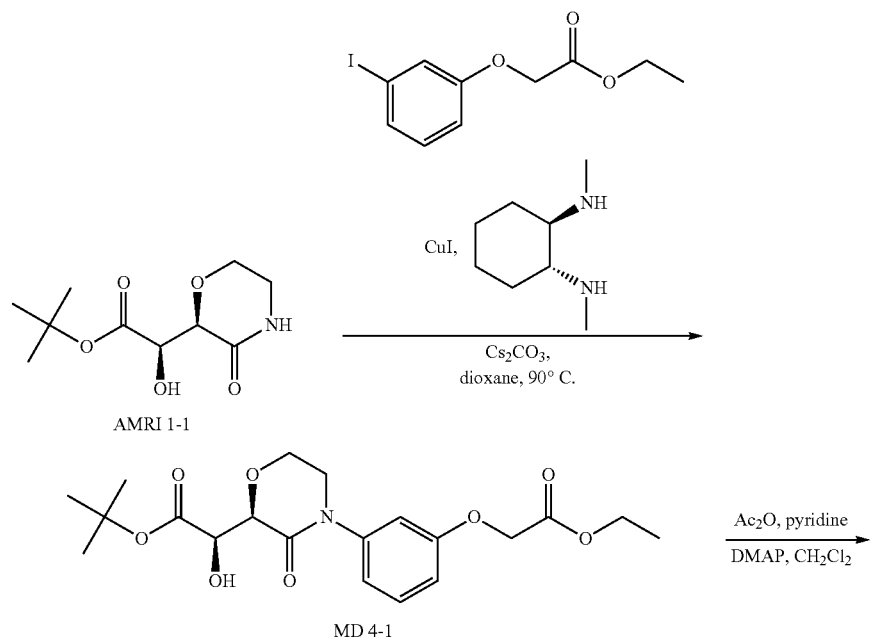

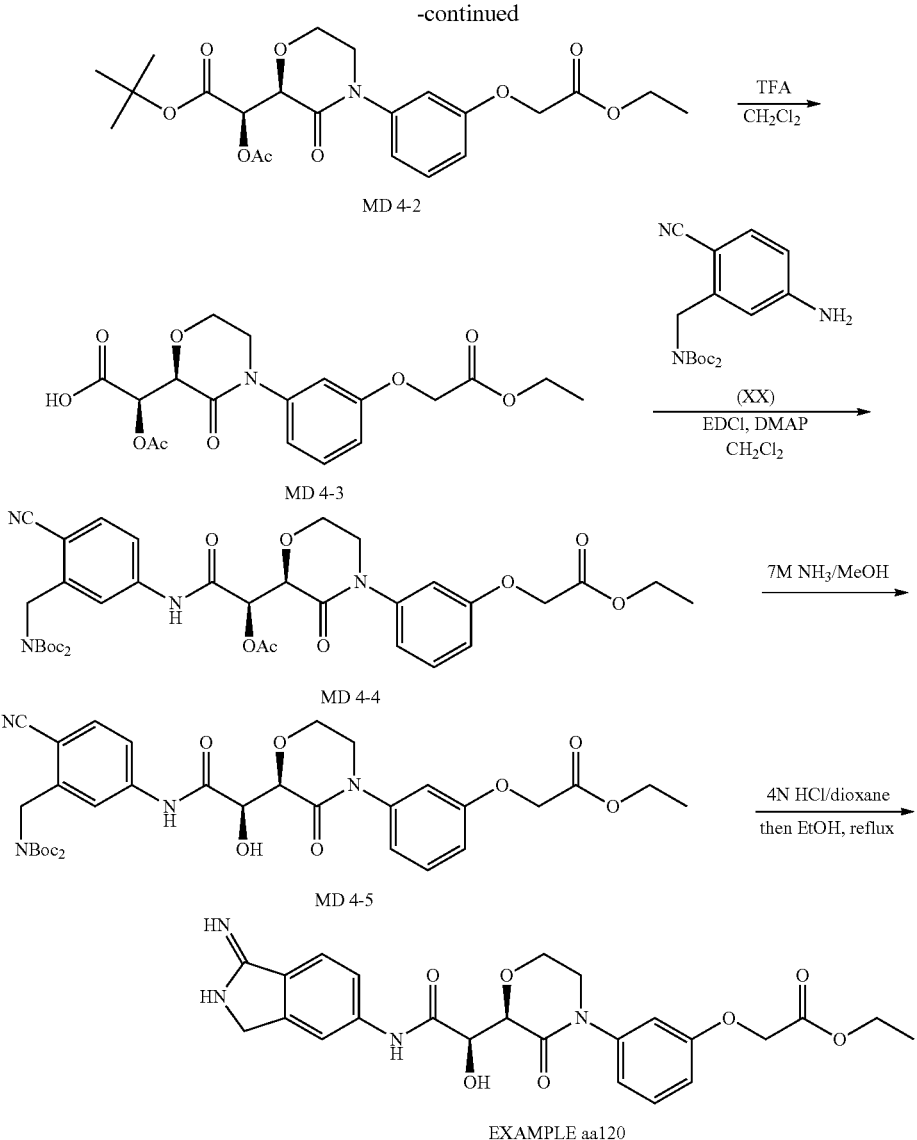

Step MD 4-1

(R)-tert-Butyl 2-((R)-4-(3-(2-ethoxy-2-oxoethoxy) phenyl)-3-oxomorpholin-2-yl)-2-hydroxyacetate MD 4-1

According to the Step MD 1-1 in the synthetic method for EXAMPLE aa117, AMRI 1-1 (0.35 g) was treated with ethyl 2-(3-iodophenoxy)acetate (0.56 g) from Eur J. Org. Chem. 2008, 337 to obtain MD 4-1 (0.54 g) as an yellow solid after flash chromatography with 40:1 $CH_2Cl_2$/MeOH as eluent.

Step MD 4-2

(R)-tert-Butyl 2-acetoxy-2-((R)-4-(3-(2-ethoxy-2-oxoethoxy)phenyl)-3-oxomorpholin-2-yl)acetate MD 4-2

According to the Step MD 1-2 in the synthetic method for EXAMPLE aa117, compound MD 4-1 (0.54 g) was used instead of MD 1-1 to obtain MD 4-2 (0.56 g) as a yellow oil which was used without further purification.

Step MD 4-3

(R)-2-Acetoxy-2-((R)-4-(3-(2-ethoxy-2-oxo ethoxy) phenyl)-3-oxomorpholin-2-yl)acetic acid MD 4-3

According to the Step MD 1-3 in the synthetic method for EXAMPLE aa117, compound MD 9-2 (0.55 g) was used instead of MD 1-2 to obtain MD 4-3 (0.45 g) as a yellow solid which was used without further purification.

Step MD 4-4

Ethyl 2-(3-((R)-2-((R)-1-acetoxy-2-(3-((bis(tert-butoxycarbonyl)amino)methyl)-4-cyanophenylamino)-2-oxoethyl)-3-oxomorpholino)phenoxy) acetate MD 4-4

According to the Step MD 1-4 in the synthetic method for EXAMPLE aa117, compound MD 4-3 (0.38 g) was used instead of MD 1-3 to obtain MD 3-4 (0.26 g) after flash chromatography using a gradient of 100% hexanes to 100% EtOAc.

Step MD 4-5

Ethyl 2-(3-((R)-2-((R)-1-hydroxyl-2-(3-((bis(tert-butoxycarbonyl)amino)methyl)-4-cyanophenylamino)-2-oxoethyl)-3-oxo morpholino)phenoxy)acetate MD 4-5

According to the Step MD 1-5 in the synthetic method for EXAMPLE aa117 except using 2M NH$_3$ in EtOH, compound MD 4-4 (0.26 g) was used instead of MD 1-4 to obtain MD 5-5 (0.21 g) as an off-white solid after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H.

Step MD 4-6

Ethyl 2-(3-((R)-2-((R)-1-hydroxy-2-(1-iminoisoindolin-5-ylamino)-2-oxoethyl)-3-oxomorpholino)phenoxy)acetate EXAMPLE aa120

According to the Step MD 1-6 in the synthetic method for EXAMPLE aa117 except substituting EtOH for MeOH as solvent, compound MD 4-5 (0.20 g) was used instead of MD 1-5 to obtain EXAMPLE aa120 (81 mg) as the hydrochloride salt after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H and subsequent treatment with HCl.

Example aa121

(R)-2-Hydroxy-N-(1-iminoisoindolin-5-yl)-2-((R)-4-(4-methoxybenzyl)-3-oxomorpholin-2-yl)acetamide EXAMPLE aa121

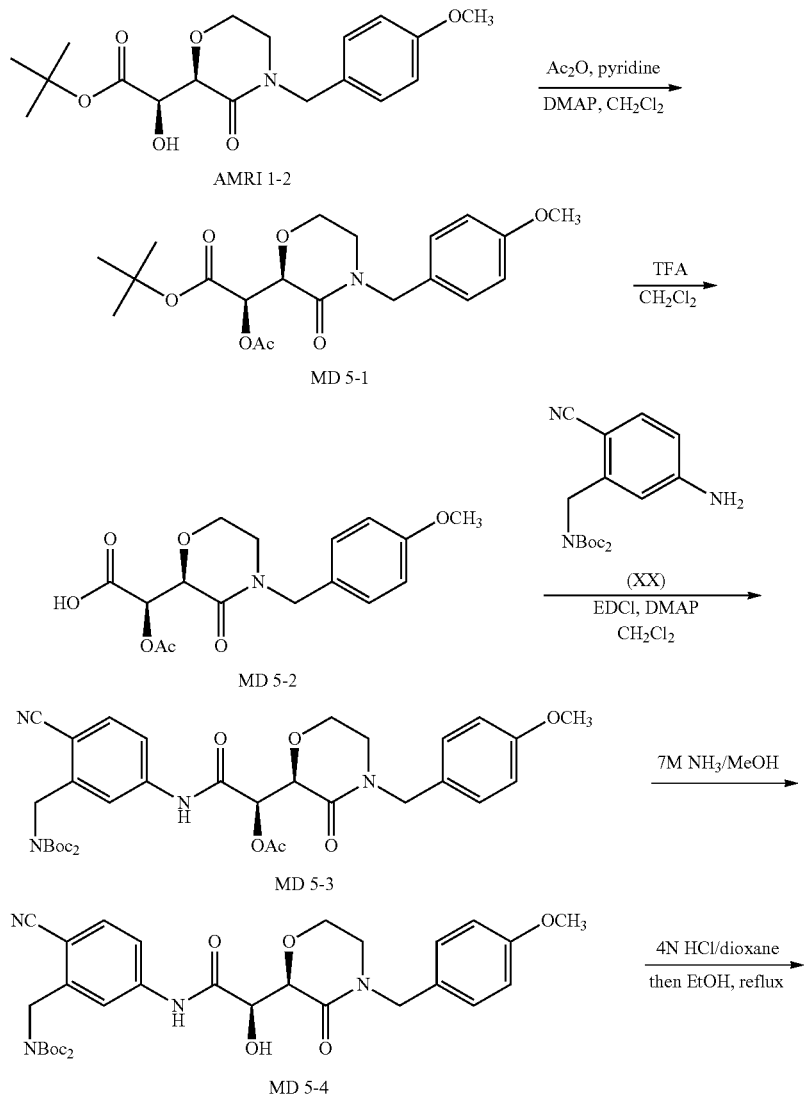

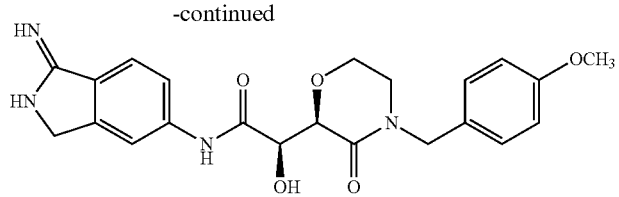

EXAMPLE aa121

Step MD 5-1

(R)-tert-Butyl 2-acetoxy-2-((R)-4-(4-methoxybenzyl)-3-oxomorpholin-2-yl)acetate MD 5-1

According to the Step MD 1-2 in the synthetic method for EXAMPLE aa117, compound AMRI 2-1 (0.35 g) was used instead of MD 1-1 to obtain MD 5-1 (0.37 g) as a yellow oil which was used without further purification.

Step MD 5-2

(R)-2-Acetoxy-2-((R)-4-(4-methoxybenzyl)-3-oxomorpholin-2-yl)acetic acid MD 5-2

According to the Step MD 1-3 in the synthetic method for EXAMPLE aa117, compound MD 5-1 (0.37 g) was used instead of MD 1-2 to obtain MD 5-2 (0.32 g) as a yellow solid which was used without further purification.

Step MD 5-3

(R)-2-(3-((bis(tert-Butoxycarbonyl)amino)methyl)-4-cyanophenylamino)-1-((R)-4-(4-methoxybenzyl)-3-oxomorpholin-2-yl)-2-oxoethyl acetate MD 5-3

According to the Step MD 1-4 in the synthetic method for EXAMPLE aa117, compound MD 5-2 (0.25 g) was used instead of MD 1-3 to obtain MD 5-3 (0.24 g) of a white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 5-4

(R)-2-(3-((bis(tert-Butoxycarbonyl)amino)methyl)-4-cyanophenylamino)-1-((R)-4-(4-methoxybenzyl)-3-oxomorpholin-2-yl)-2-hydroxyacetamide MD 5-4

According to the Step MD 1-5 in the synthetic method for EXAMPLE aa117, compound MD 5-3 (0.24 g) was used instead of MD 1-4 to obtain MD 5-4 (0.23 g) as an off-white solid which was used without further purification.

Step MD 5-5

(R)-2-Hydroxy-N-(1-iminoisoindolin-5-yl)-2-((R)-4-(4-methoxybenzyl)-3-oxomorpholin-2-yl)acetamide EXAMPLE aa121

According to the Step MD 1-6 in the synthetic method for EXAMPLE aa117, compound MD 5-4 (0.23 g) was used instead of MD 1-5 to obtain EXAMPLE aa121 (0.15 g) as a pale yellow solid as the hydrochloride salt.

Example aa122

This Example is intentionally left blank.

Example aa123

(R)-2-((R)-4-(3-(Benzyloxy)phenyl)-3-oxomorpholin-2-yl)-2-hydroxy-N-(1-iminoisoindolin-5-yl)acetamide EXAMPLE aa123

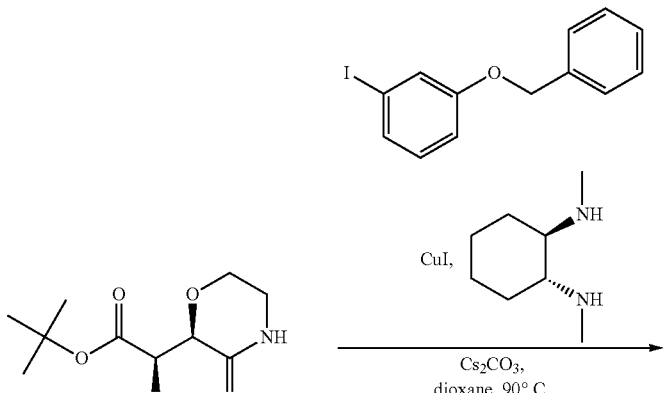

AMRI 1-1

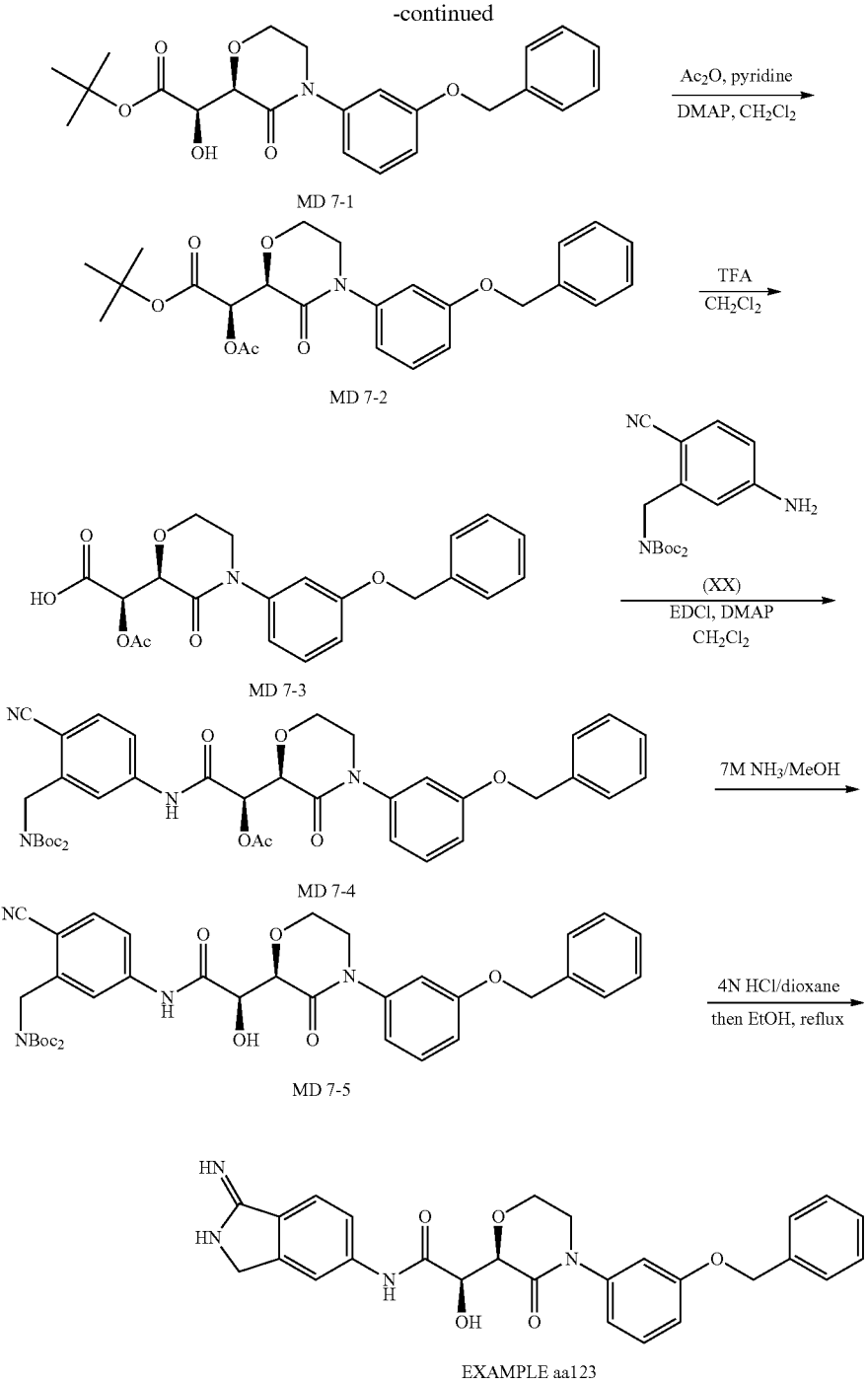

Step MD 7-1

(R)-tert-Butyl 2-((R)-4-(3-(benzyloxy)phenyl)-3-oxomorpholin-2-yl)-2-hydroxyacetate MD 7-1

According to the Step MD 1-1 in the synthetic method for EXAMPLE aa117, AMRI 1-1 (0.50 g) was treated with 1-benzyloxy-3-iodobenzene (0.81 g) to obtain MD 7-1 (0.71 g) as a clear oil after flash chromatography with 50:1 CH$_2$Cl$_2$/MeOH as eluent.

Step MD 7-2

(R)-tert-Butyl 2-acetoxy-2-((R)-4-(3-(benzyloxy)phenyl)-3-oxomorpholin-2-yl)acetate MD 7-2

According to the Step MD 1-2 in the synthetic method for EXAMPLE aa117, compound MD 7-1 (0.71 g) was used instead of MD 1-1 to obtain MD 7-2 (0.78 g) as a yellow oil which was used without further purification.

Step MD 7-3

(R)-2-Acetoxy-2-((R)-4-(3-(benzyloxy)phenyl)-3-oxomorpholin-2-yl)acetic acid MD 7-3

According to the Step MD 1-3 in the synthetic method for EXAMPLE aa117, compound MD 7-2 (0.78 g) was used instead of MD 1-2 to obtain MD 7-3 (0.68 g) as a yellow solid which was used without further purification.

Step MD 7-4

(R)-1-((R)-4-(3-(Benzyloxy)phenyl)-3-oxomorpholin-2-yl)-2-(3-((bis(tert-butoxycarbonyl)amino)methyl)-4-cyanophenylamino)-2-oxoethyl acetate MD 7-4

According to the Step MD 1-4 in the synthetic method for EXAMPLE aa117, compound MD 7-3 (0.68 g) was used instead of MD 1-3 to obtain MD 7-4 (0.20 g) of an off-white solid after flash chromatography with a gradient of 100% hexanes to 50:50 hexanes/EtOAc.

Step MD 7-5

R)-1-((R)-4-(3-(Benzyloxy)phenyl)-3-oxomorpholin-2-yl)-2-(3-((bis(tert-butoxycarbonyl)amino)methyl)-4-cyanophenylamino)-2-hydroxyacetamide MD 7-5

According to the Step MD 1-5 in the synthetic method for EXAMPLE aa117, compound MD 7-4 (0.20 g) was used instead of MD 1-4 to obtain MD 7-5 (0.16 g) as an off-white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 7-6

(R)-2-((R)-4-(3-(Benzyloxy)phenyl)-3-oxomorpholin-2-yl)-2-hydroxy-N-(1-iminoisoindolin-5-yl)acetamide EXAMPLE aa123

According to the Step MD 1-6 in the synthetic method for EXAMPLE aa117, compound MD 7-5 (0.16 g) was used instead of MD 1-5 to obtain EXAMPLE aa123 (86 mg) as the hydrochloride salt.

Example aa124

(R)-2-((R)-4-(2-(Cyclopropylmethyl)-3-oxoisoindolin-5-yl)-3-oxomorpholin-2-yl)-2-hydroxy-N-(1-iminoisoindolin-5-yl)acetamide EXAMPLE aa124

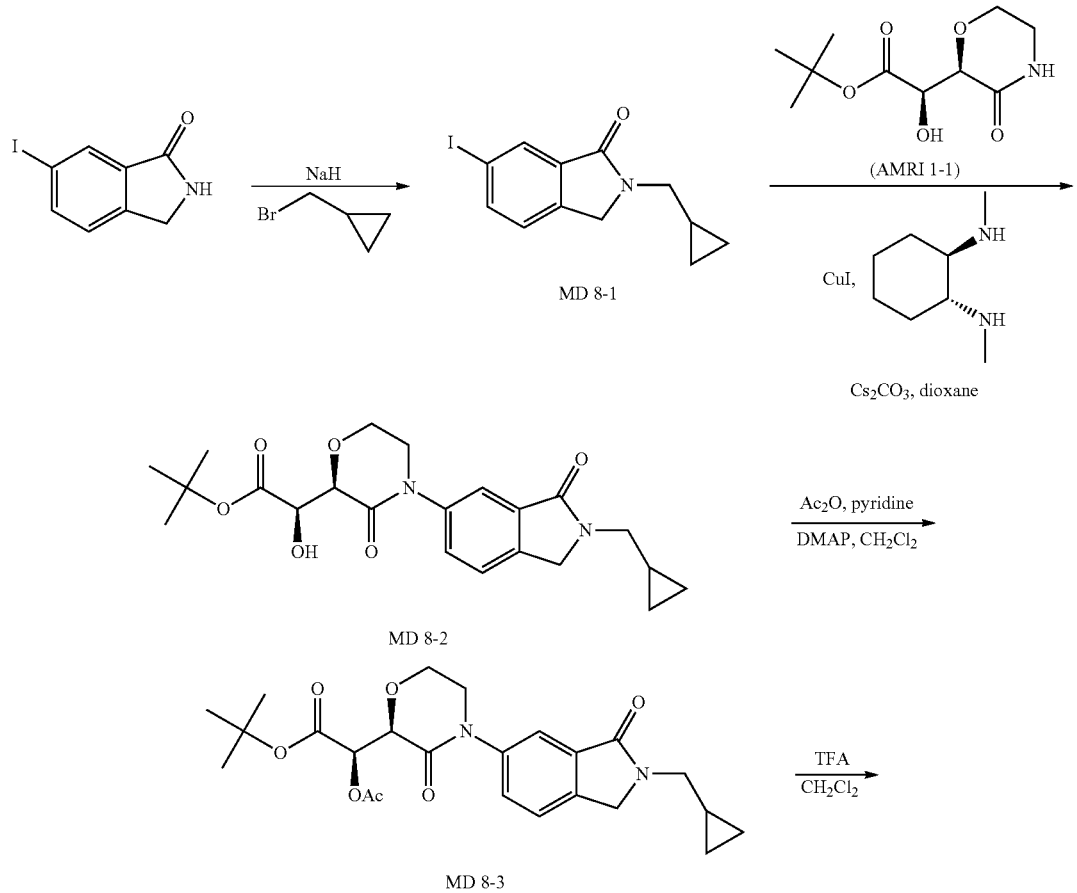

-continued

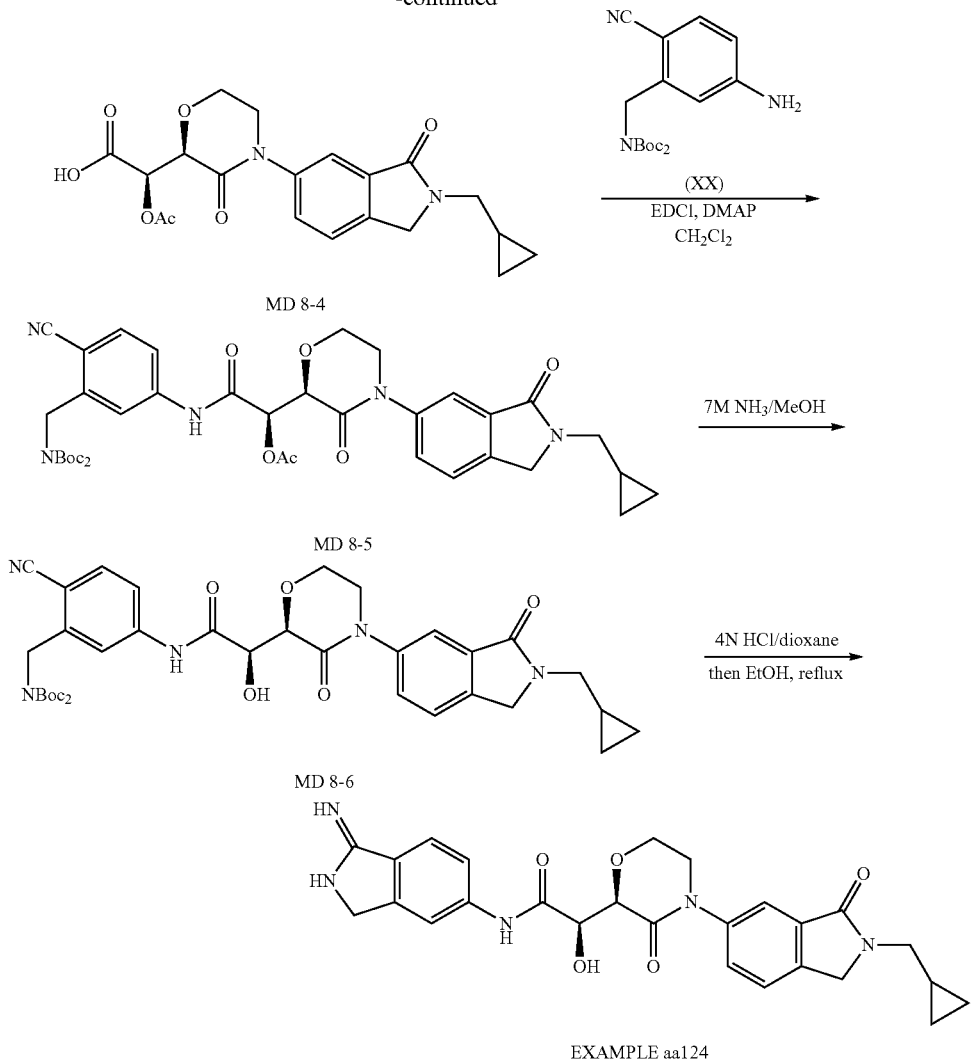

EXAMPLE aa124

Step MD 8-1

2-(Cyclopropylmethyl)-6-iodoisoindolin-1-one MD 8-1

According to the Step MD 3-1 in the synthetic method for EXAMPLE 3, 2,3-dihydro-6-iodo-1H-isoindol-1-one (0.50 g) was treated with cyclopropyl bromide (0.20 mL) to afford MD 8-1 (0.22 g) of a yellow solid after purification by flash chromatography (ISCO, 120 g) using a gradient of 100% hexanes to 40:60 hexanes/EtOAc.

Step MD 8-2

(R)-tert-Butyl 2-((R)-4-(2-(cyclopropylmethyl)-3-oxoisoindolin-5-yl)-3-oxomorpholin-2-yl)-2-hydroxyacetate MD 8-2

According to the Step MD 1-1 in the synthetic method for EXAMPLE aa117, AMRI 1-1 (0.14 g) was treated with MD 8-1 (0.22 g) to obtain MD 8-2 (0.22 g) as a white solid after flash chromatography with 50:1 CH$_2$Cl$_2$/MeOH as eluent.

Step MD 8-3

(R)-tert-Butyl 2-acetoxy-2-((R)-4-(2-(cyclopropylmethyl)-3-oxoisoindolin-5-yl)-3-oxomorpholin-2-yl)acetate MD 8-3

According to the Step MD 1-2 in the synthetic method for EXAMPLE aa117, compound MD 8-2 (0.22 g) was used instead of MD 1-1 to obtain MD 8-3 (0.24 g) as an off-white solid which was used without further purification.

Step MD 8-4

(R)-2-Acetoxy-2-((R)-4-(2-(cyclopropylmethyl)-3-oxoisoindolin-5-yl)-3-oxomorpholin-2-yl)acetic acid MD 8-4

According to the Step MD 1-3 in the synthetic method for EXAMPLE aa117, compound MD 8-3 (0.24 g) was used instead of MD 1-2 to obtain MD 8-4 (0.22 g) as a light yellow semisolid solid which was used without further purification.

Step MD 8-5

(R)-2-(3-((bis(tert-Butoxycarbonyl)amino)methyl)-4-cyanophenylamino)-1-((R)-4-(2-(cyclopropylmethyl)-3-oxoisoindolin-5-yl)-3-oxomorpholin-2-yl)-2-oxoethyl acetate MD 8-5

According to the Step MD 1-4 in the synthetic method for EXAMPLE aa117, compound MD 8-4 (0.22 g) was used instead of MD 1-3 to in the presence of aniline XX (0.22 g) obtain MD 8-5 (0.25 g) as a pale yellow solid after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H.

Step MD 8-6

(R)-2-(3-((bis(tert-Butoxycarbonyl)amino)methyl)-4-cyanophenylamino)-1-((R)-4-(2-(cyclopropylmethyl)-3-oxoisoindolin-5-yl)-3-oxomorpholin-2-yl)-2-hydroxyacetamide MD 8-6

According to the Step MD 1-5 in the synthetic method for EXAMPLE aa117, compound MD 8-5 (0.25 g) was used instead of MD 1-4 to obtain MD 8-6 (0.18 g) as a white solid after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H.

Step MD 8-7

(R)-2-((R)-4-(2-(Cyclopropylmethyl)-3-oxoisoindolin-5-yl)-3-oxomorpholin-2-yl)-2-hydroxy-N-(1-iminoisoindolin-5-yl)acetamide EXAMPLE aa124

According to the Step MD 1-6 in the synthetic method for EXAMPLE aa117, compound MD 8-6 (0.18 g) was used instead of MD 1-5 to obtain EXAMPLE aa124 (78 mg) as a white solid as the hydrochloride salt after HCl treatment.

Example aa125

(R)—N-(4-(Aminomethyl)-3-fluorophenyl)-2-hydroxy-2-((R)-3-oxo-4-(3-(3-oxomorpholino)phenyl)morpholin-2-yl)acetamide EXAMPLE aa125

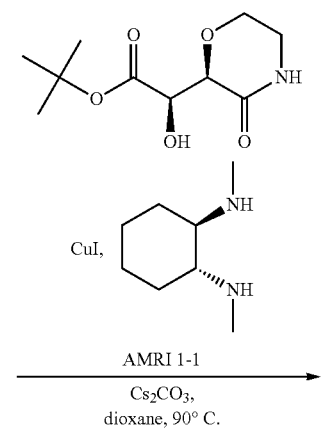

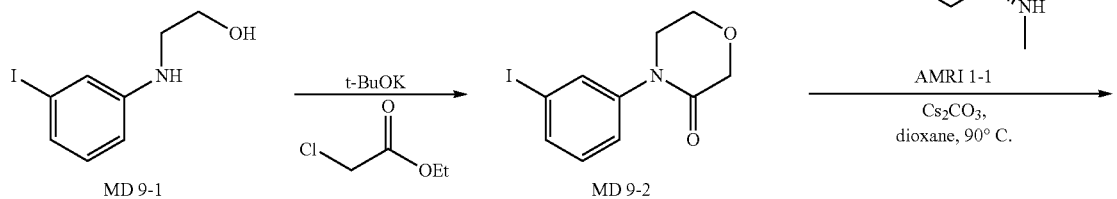

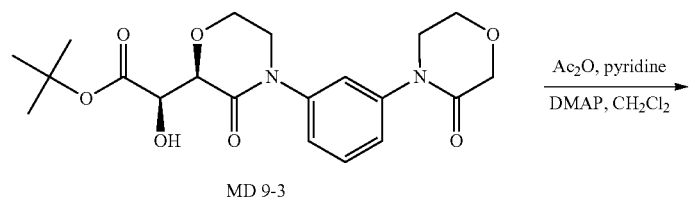

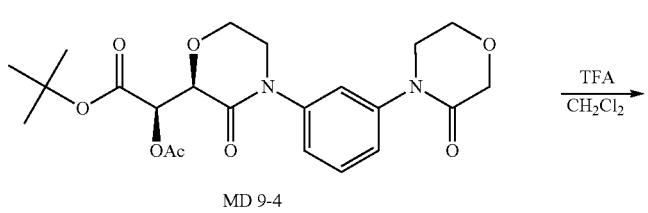

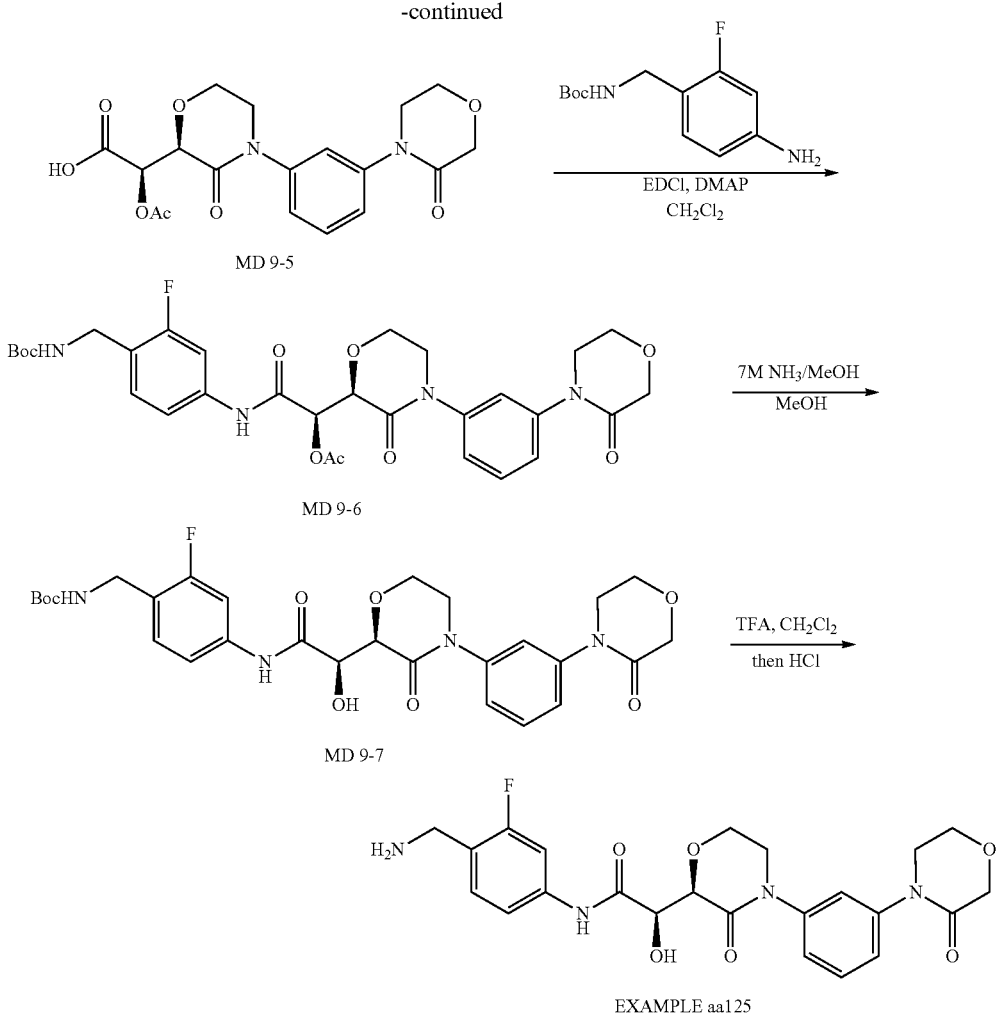

Step MD 9-2

4-(3-Iodophenyl)morpholin-3-one MD 9-2

To a solution of t-BuOK (1.3 g) in THF (15 mL) at rt was added 2-(3-iodophenylamino)ethanol MD 9-1 (3.0 g) prepared from US 2004/0167188 followed by ethyl chloroacetate (1.1 mL). The resulting mixture was stirred for 12 h at rt whereupon an additional portion of t-BuOK (0.6 g) and ethyl chloroacetate (0.5 mL) was added. The mixture was heated to 55° C., stirred for 12 h, and was cooled to rt. The mixture was treated with sat. aq $NaHCO_3$ and water and was extracted with EtOAc. The organic layers were combined, dried ($Na_2SO_4$), filtered, and concentrated under reduced pressure. The crude material was purified by flash chromatography using a gradient of 100% hexanes to 20% hexanes/80% EtOAc to afford MD 9-2 (1.5 g) of the title compound as a light yellow solid.

Step MD 9-3

(R)-tert-butyl 2-hydroxy-2-((R)-3-oxo-4-(3-(3-oxo-morpholino)phenyl)morpholin-2-yl)acetate MD 9-3

According to the Step MD 1-1 in the synthetic method for EXAMPLE aa117, compound MD 9-2 (0.72 g) was used in the presence of AMRI 1-1 (0.50 g) to obtain MD 9-3 (0.65 g) as yellow crystalline solid after flash chromatography using a 20:1 mixture of $CH_2Cl_2$/MeOH.

Step MD 9-4

(R)-tert-butyl 2-acetoxy-2-((R)-3-oxo-4-(3-(3-oxo-morpholino)phenyl)morpholin-2-yl)acetate MD 9-4

According to the Step MD 1-2 in the synthetic method for EXAMPLE aa117, compound MD 9-3 (0.65 g) was used instead of MD 1-1 to obtain MD 9-4 (0.72 g) as an off-white solid which was used without further purification.

Step MD 9-5

(R)-2-acetoxy-2-((R)-3-oxo-4-(3-(3-oxomorpholino) phenyl)morpholin-2-yl)acetic acid MD 9-5

According to the Step MD 1-3 in the synthetic method for EXAMPLE aa117, compound MD 9-4 (0.72 g) was used instead of MD 1-2 to obtain MD 9-5 (0.60 g) as a light yellow solid which was used without further purification.

Step MD 9-6

(R)-2-(4-((tert-Butoxycarbonylamino)methyl)-3-fluorophenylamino)-2-oxo-1-((R)-3-oxo-4-(3-(3-oxomorpholino)phenyl)morpholin-2-yl)ethyl acetate MD 9-6

According to the Step MD 1-4 in the synthetic method for EXAMPLE aa117, MD 4-5 (70 mg) was treated with tert-butyl-4-amino-2-fluorobenzylcarbamate (65 mg) to afford MD 9-6 (0.10 g) as a pale yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 9-7 tert-Butyl 2-fluoro-4-((R)-2-hydroxy-2-((R)-3-oxo-4-(3-(3-oxomorpholino)phenyl)morpholin-2-yl)acetamido)benzylcarbamate MD 9-7

According to the Step MD 1-5 in the synthetic method for EXAMPLE aa117, MD 9-6 (0.10 g) was used instead of compound MD 1-4 to obtain MD 9-7 (90 mg) as a white solid. Crude MD 9-7 was used without further purification in the next step.

Step MD 9-8

(R)—N-(4-(Aminomethyl)-3-fluorophenyl)-2-hydroxy-2-((R)-3-oxo-4-(3-(3-oxomorpholino)phenyl)morpholin-2-yl)acetamide EXAMPLE aa125

To a solution of MD 9-7 (90 mg) in $CH_2Cl_2$ (5 mL) at 0° C. was added TFA (1.5 mL) dropwise. The mixture was stirred for 3 h at 0° C. and concentrated to dryness and this protocol was repeated 5 times. The crude mixture was taken up in MeOH and treated with 1M HCl in $Et_2O$ to afford after filtration EXAMPLE aa125 (45 mg) as a pale yellow solid.

Example aa126

(R)—N-(4-Guanidinophenyl)-2-hydroxy-2-((R)-3-oxo-4-(3-(3-oxomorpholino)phenyl)morpholin-2-yl)acetamide EXAMPLE aa126

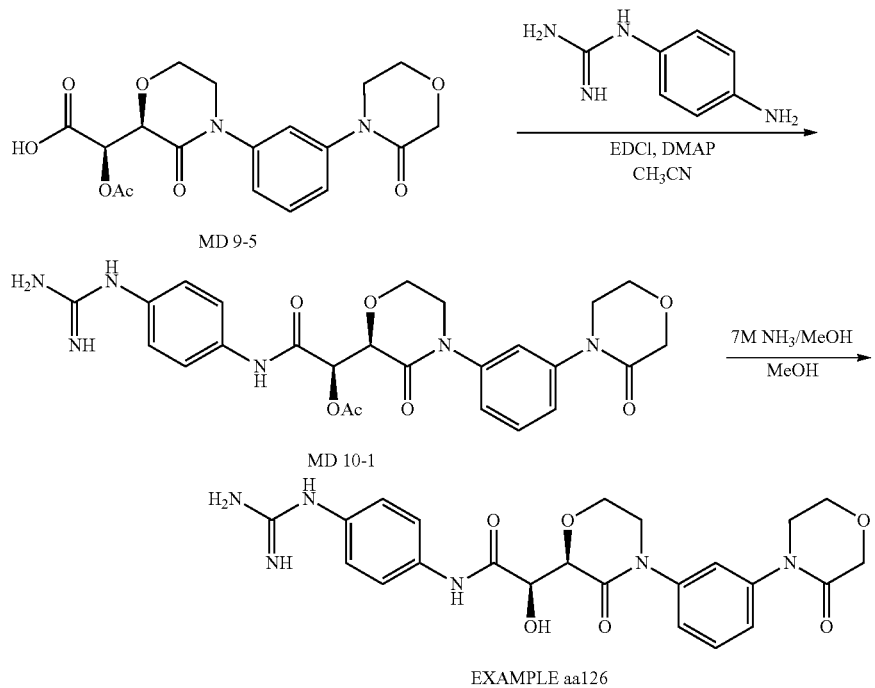

Step MD 10-1

(R)-2-(4-Guanidinophenylamino)-2-oxo-1-((R)-3-oxo-4-(3-(3-oxomorpholino)phenyl)morpholin-2-yl)ethyl acetate MD 10-1

According to the Step MD 1-4 in the synthetic method for EXAMPLE aa117, MD 9-5 (70 mg) was treated with N-(4-aminophenyl)guanidine (41 mg) to afford MD 10-1 (65 mg) as a pale yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 10-2

(R)—N-(4-Guanidinophenyl)-2-hydroxy-2-((R)-3-oxo-4-(3-(3-oxomorpholino)phenyl)morpholin-2-yl)acetamide EXAMPLE aa126

According to the Step MD 1-5 in the synthetic method for EXAMPLE aa117, MD 10-1 (60 mg) was used instead of compound MD 1-4 to obtain EXAMPLE aa126 (35 mg) as a yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Example aa127
(R)—N-(4-(Aminomethyl)phenyl)-2-((R)-4-(4-fluoro-3-(morpholine-4-carbonyl)phenyl)-3-oxomorpholin-2-yl)-2-hydroxyacetamide EXAMPLE aa127
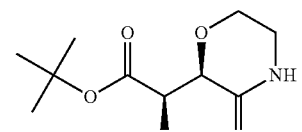
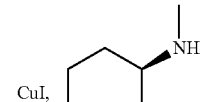
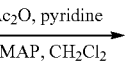
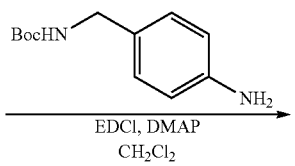
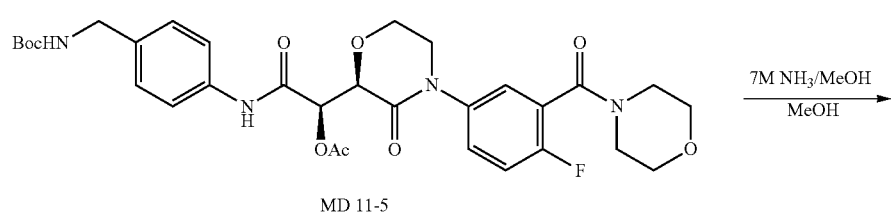

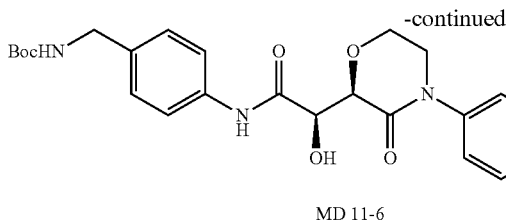

MD 11-6

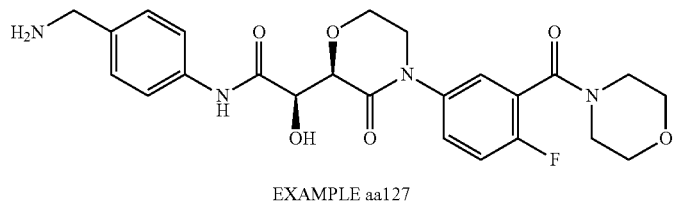

EXAMPLE aa127

Step MD 11-1

(2-Fluoro-5-iodophenyl)(morpholino)methanone MD 11-1

To a solution of 3-iodo-6-fluorobenzoic acid (5.0 g) in DMF (50 mL) at rt was added morpholine (1.8 mL), HATU (8.6 g), and DIPEA (9.8 mL). The mixture was stirred for 12 h at rt whereupon the mixture was diluted with EtOAc. The organic layers were washed with 1N NaOH, 1M HCl, water, and brine. The organic layer was dried ($Na_2SO_4$), filtered, and concentrated under reduced pressure. The crude material was purified by flash chromatography using a gradient of 100% $CH_2Cl_2$ to 97.5% $CH_2Cl_2$/2.5% MeOH to afford MD 11-1 (5.2 g) of the title compound as a brown solid.

Step MD 11-2

(R)-tert-Butyl 2-((R)-4-(4-fluoro-3-(morpholine-4-carbonyl)phenyl)-3-oxomorpholin-2-yl)-2-hydroxy acetate MD 11-2

According to the Step MD 1-1 in the synthetic method for EXAMPLE aa117, compound MD 11-1 (0.87 g) was used in the presence of AMRI 1-1 (0.50 g) to obtain MD 11-2 (0.64 g) as yellow semisolid after flash chromatography using a 50:1 mixture of $CH_2Cl_2$/MeOH.

Step MD 11-3

(R)-tert-Butyl 2-acetoxy-2-((R)-4-(4-fluoro-3-(morpholine-4-carbonyl)phenyl)-3-oxomorpholin-2-yl) acetate MD 11-3

According to the Step MD 1-2 in the synthetic method for EXAMPLE aa117, compound MD 11-2 (0.64 g) was used instead of MD 1-1 to obtain MD 11-3 (0.71 g) as an light yellow oil which was used without further purification.

Step MD 11-4

(R)-2-Acetoxy-2-((R)-4-(4-fluoro-3-(morpholine-4-carbonyl)phenyl)-3-oxomorpholin-2-yl)acetic acid MD 11-4

According to the Step MD 1-3 in the synthetic method for EXAMPLE aa117, MD 11-3 (0.71 g) was used instead of MD 1-2 to obtain MD 11-4 (0.60 g) as a light yellow solid which was used without further purification.

Step MD 11-5

(R)-2-(4-((tert-Butoxycarbonylamino)methyl)phenylamino)-1-((R)-4-(4-fluoro-3-(morpholine-4-carbonyl)phenyl)-3-oxomorpholin-2-yl)-2-oxoethyl acetate MD 11-5

According to the Step MD 1-4 in the synthetic method for EXAMPLE aa117, MD 11-4 (0.62 g) was treated with tert-butyl-4-aminobenzylcarbamate (0.48 g) to afford MD 11-5 (0.71 g) as a pale yellow solid after flash chromatography using a 50:1 mixture of $CH_2Cl_2$/MeOH.

Step MD 11-6 tert-Butyl 4-((R)-2-((R)-4-(4-fluoro-3-(morpholine-4-carbonyl)phenyl)-3-oxomorpholin-2-yl)-2-hydroxyacetamido)benzylcarbamate MD 11-6

According to the Step MD 1-5 in the synthetic method for EXAMPLE aa117, MD 11-5 (0.71 g) was used instead of compound MD 1-4 to obtain MD 11-6 (0.66 g) as a white solid. Crude MD 9-7 was used without further purification in the next step.

Step MD 11-7

(R)—N-(4-(Aminomethyl)phenyl)-2-((R)-4-(4-fluoro-3-(morpholine-4-carbonyl)phenyl)-3-oxomorpholin-2-yl)-2-hydroxyacetamide EXAMPLE aa127

According to the Step MD 9-8 in the synthetic method for EXAMPLE aa125, MD 11-6 (0.66 g) was used instead of compound MD 9-7 to obtain EXAMPLE aa127 (0.21 g) as a pale yellow hydrochloride salt upon treatment with HCl.

Example aa128

(R)-2-(4-Carbamoylphenylamino)-1-((R)-4-(4-fluoro-3-(morpholine-4-carbonyl)phenyl)-3-oxomorpholin-2-yl)-2-oxoethyl acetate EXAMPLE aa128

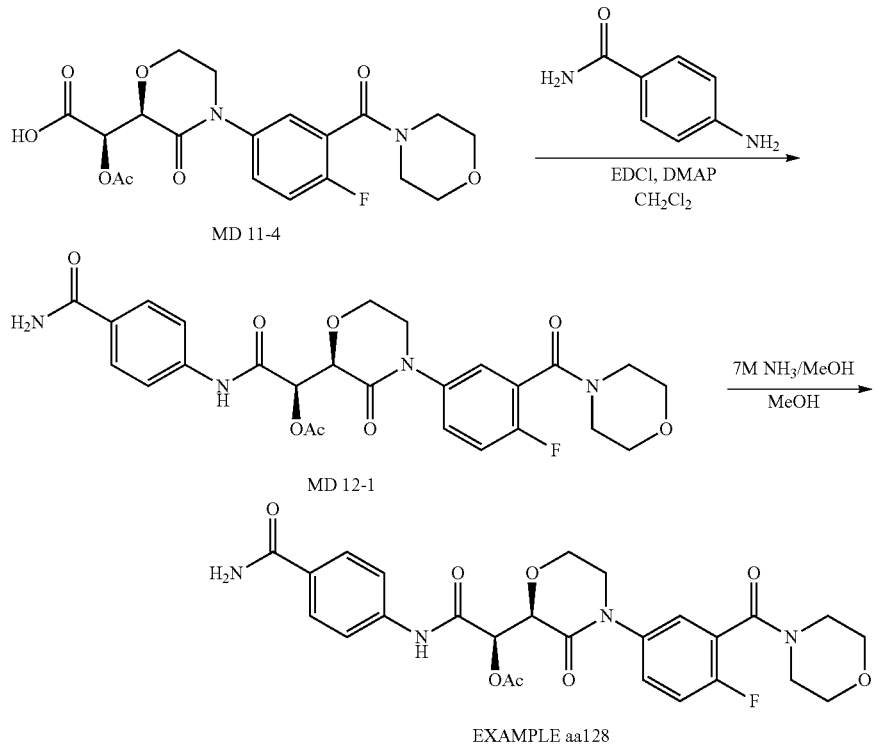

Step MD 12-1

(R)-2-(4-carbamoylphenylamino)-1-((R)-4-(4-fluoro-3-(morpholine-4-carbonyl)phenyl)-3-oxomorpholin-2-yl)-2-oxoethyl acetate MD 12-1

According to the Step MD 1-4 in the synthetic method for EXAMPLE aa117, MD 11-4 (0.10 g) was treated with 4-aminobenzamide (49 mg) to afford MD 12-1 (60 mg) as a yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step 12-2

(R)-2-(4-Carbamoylphenylamino)-1-((R)-4-(4-fluoro-3-(morpholine-4-carbonyl)phenyl)-3-oxomorpholin-2-yl)-2-oxoethyl acetate EXAMPLE aa128

According to the Step MD 1-5 in the synthetic method for EXAMPLE aa117, MD 12-1 (60 mg) was used instead of compound MD 1-4 to obtain EXAMPLE aa128 (31 mg) as a pale white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Example aa129

(R)-2-((R)-4-(4-Fluoro-3-(morpholine-4-carbonyl)phenyl)-3-oxomorpholin-2-yl)-2-hydroxy-N-(1,2,3,4-tetrahydroisoquinolin-6-yl)acetamide EXAMPLE aa129

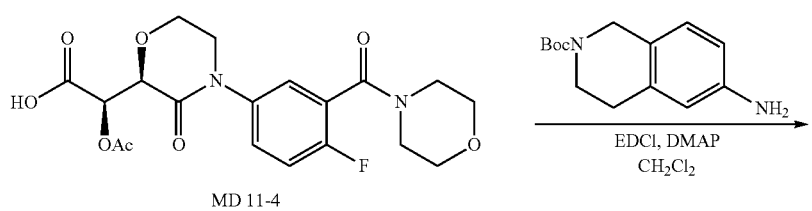

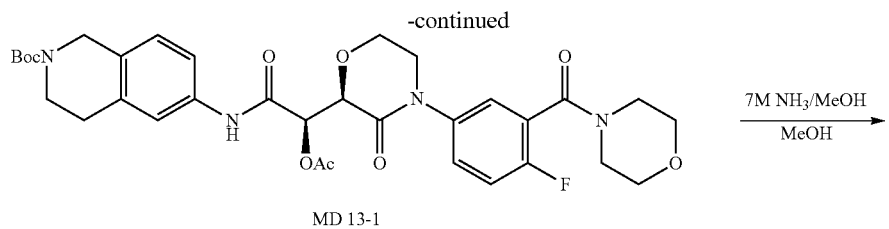

MD 13-1

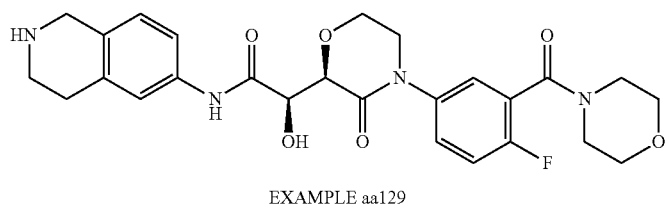

MD 13-2

[Structure of EXAMPLE aa129]

EXAMPLE aa129

Step MD 13-1 tert-Butyl 6-((R)-2-acetoxy-2-((R)-4-(4-fluoro-3-(morpholine-4-carbonyl)phenyl)-3-oxomorpholin-2-yl)acetamido)-3,4-dihydroisoquinoline-2(1H)-carboxylate MD 13-1

According to the Step MD 1-4 in the synthetic method for EXAMPLE aa117, MD 11-4 (0.10 g) was treated with tert-butyl 6-amino-3,4-dihydroisoquinoline-2(1H)-carboxylate (89 mg) to afford MD 13-1 (0.10 g) as a yellow solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 13-2 tert-Butyl 6-((R)-2-((R)-4-(4-fluoro-3-(morpholine-4-carbonyl)phenyl)-3-oxomorpholin-2-yl)-2-hydroxyacetamido)-3,4-dihydroisoquinoline-2(1H)-carboxylate MD 13-2

According to the Step MD 1-5 in the synthetic method for EXAMPLE aa117, MD 13-1 (0.10 g) was used instead of compound MD 1-4 to obtain MD 13-2 (94 mg) as a pale yellow solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 13-3

(R)-2-((R)-4-(4-Fluoro-3-(morpholine-4-carbonyl)phenyl)-3-oxomorpholin-2-yl)-2-hydroxy-N-(1,2,3,4-tetrahydroisoquinolin-6-yl)acetamide EXAMPLE aa129

According to the Step MD 9-8 in the synthetic method for EXAMPLE aa125, MD 13-2 (94 mg) was used instead of compound MD 9-7 to obtain EXAMPLE aa129 (90 mg) as a pale yellow solid after treatment with HCl.

Example aa130

(R)—N-(4-(Aminomethyl)-3-fluorophenyl)-2-((R)-4-(4-fluoro-3-(morpholine-4-carbonyl)phenyl)-3-oxomorpholin-2-yl)-2-hydroxyacetamide EXAMPLE aa130

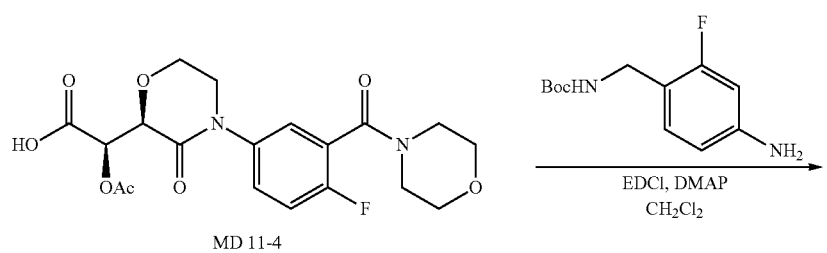

MD 11-4

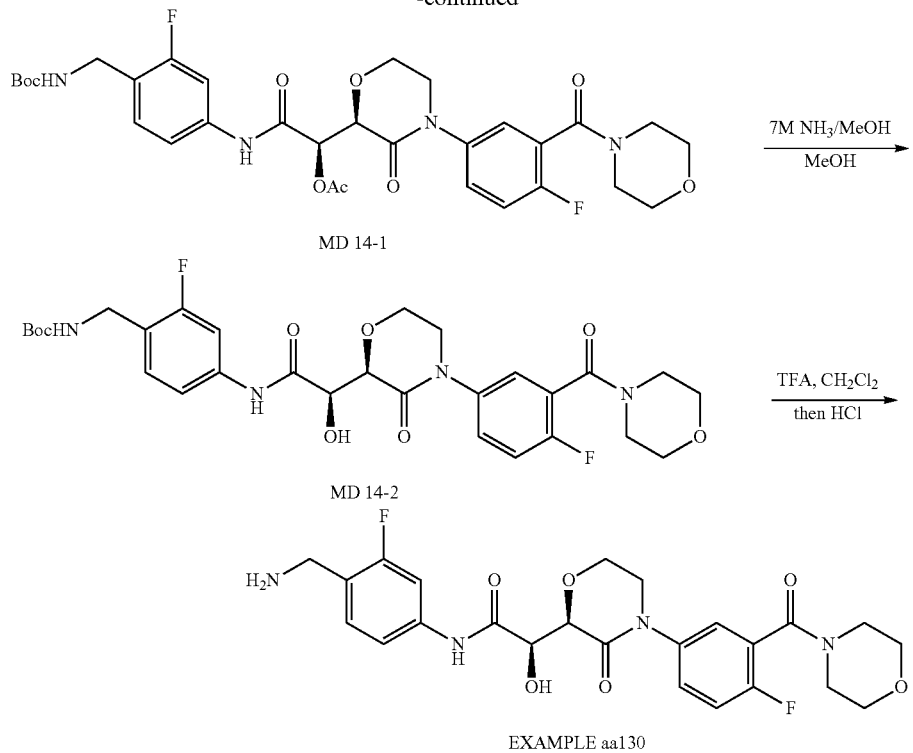

MD 14-1

MD 14-2

EXAMPLE aa130

Step MD 14-1

(R)-2-(4-((tert-Butoxycarbonylamino)methyl)-3-fluorophenylamino)-1-((R)-4-(4-fluoro-3-(morpholine-4-carbonyl)phenyl)-3-oxomorpholin-2-yl)-2-oxoethyl acetate MD 14-1

According to the Step MD 1-4 in the synthetic method for EXAMPLE aa117, MD 11-4 (0.10 g) was treated with tert-butyl-4-amino-2-fluorobenzylcarbamate (86 mg) to afford MD 14-1 (0.13 g) as an off-white solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 14-2 tert-Butyl 2-fluoro-4-((R)-2-((R)-4-(4-fluoro-3-(morpholine-4-carbonyl)phenyl)-3-oxomorpholin-2-yl)-2-hydroxyacetamido)benzylcarbamate MD 14-2

According to the Step MD 1-5 in the synthetic method for EXAMPLE aa117, MD 14-1 (0.13 g) was used instead of compound MD 1-4 to obtain MD 14-2 (90 mg) as a pale yellow solid after reverse phase HPLC purification using a C18 column and a gradient of 89.95:9.95:0.1 H₂O:MeCN:HCO₂H to 9.95:89.95:0.1 H₂O:MeCN:HCO₂H.

Step MD 14-3

(R)—N-(4-(Aminomethyl)-3-fluorophenyl)-2-((R)-4-(4-fluoro-3-(morpholine-4-carbonyl)phenyl)-3-oxomorpholin-2-yl)-2-hydroxyacetamide EXAMPLE aa130

According to the Step MD 9-8 in the synthetic method for EXAMPLE aa125, MD 14-2 (90 mg) was used instead of compound MD 9-7 to obtain EXAMPLE aa130 (95 mg) as a pale yellow solid after treatment with HCl.

Example aa131

(R)—N-(4-((R)-1-Aminoethyl)phenyl)-2-((R)-4-(4-fluoro-3-(morpholine-4-carbonyl)phenyl)-3-oxomorpholin-2-yl)-2-hydroxyacetamide EXAMPLE aa131

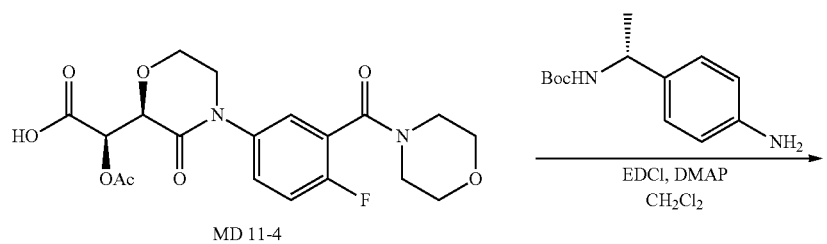

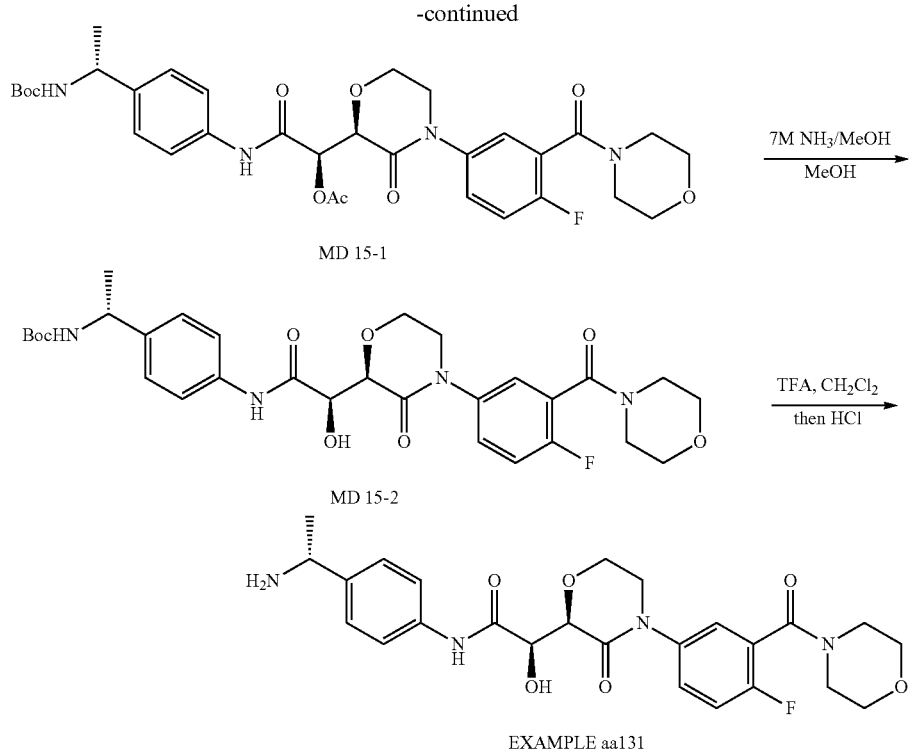

MD 15-1

MD 15-2

EXAMPLE aa131

Step MD 15-1

(R)-2-(4-((R)-1-(tert-Butoxycarbonylamino)ethyl) phenylamino)-1-((R)-4-(4-fluoro-3-(morpholine-4-carbonyl)phenyl)-3-oxomorpholin-2-yl)-2-oxoethyl acetate MD 15-1

According to the Step MD 1-4 in the synthetic method for EXAMPLE aa117, MD 11-4 (0.10 g) was treated with (R)-[1-(4-amino-phenyl)-ethyl]-carbamic acid tert-butyl ester (85 mg) to afford MD 15-1 (0.12 g) as an off-white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 15-2 tert-Butyl (R)-1-(4-((R)-2-((R)-4-(4-fluoro-3-(morpholine-4-carbonyl)phenyl)-3-oxomorpholin-2-yl)-2-hydroxyacetamido)phenyl)ethylcarbamate MD 15-2

According to the Step MD 1-5 in the synthetic method for EXAMPLE aa117, MD 15-1 (0.12 g) was used instead of compound MD 1-4 to obtain MD 15-2 (80 mg) as a pale yellow solid after reverse phase HPLC purification using a C18 column and a gradient of 89.95:9.95:0.1 $H_2O$:MeCN: $HCO_2H$ to 9.95:89.95:0.1 $H_2O$:MeCN:$HCO_2H$.

Step MD 15-3

(R)—N-(4-((R)-1-Aminoethyl)phenyl)-2-((R)-4-(4-fluoro-3-(morpholine-4-carbonyl)phenyl)-3-oxomorpholin-2-yl)-2-hydroxyacetamide EXAMPLE aa131

According to the Step MD 9-8 in the synthetic method for EXAMPLE aa125, MD 15-3 (90 mg) was used instead of compound MD 9-7 to obtain EXAMPLE aa131 (80 mg) as a pale yellow solid after treatment with HCl.

Example aa132

(R)—N-(1-Aminoisoquinolin-6-yl)-2-((R)-4-(4-fluoro-3-(morpholine-4-carbonyl)phenyl)-3-oxomorpholin-2-yl)-2-hydroxyacetamide EXAMPLE aa132

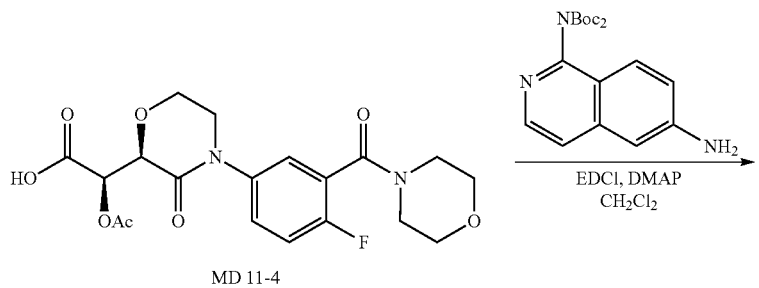

MD 11-4

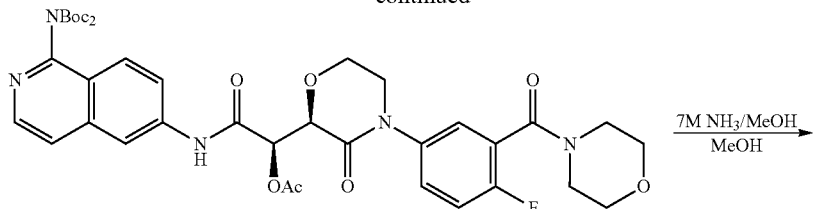

MD 16-1

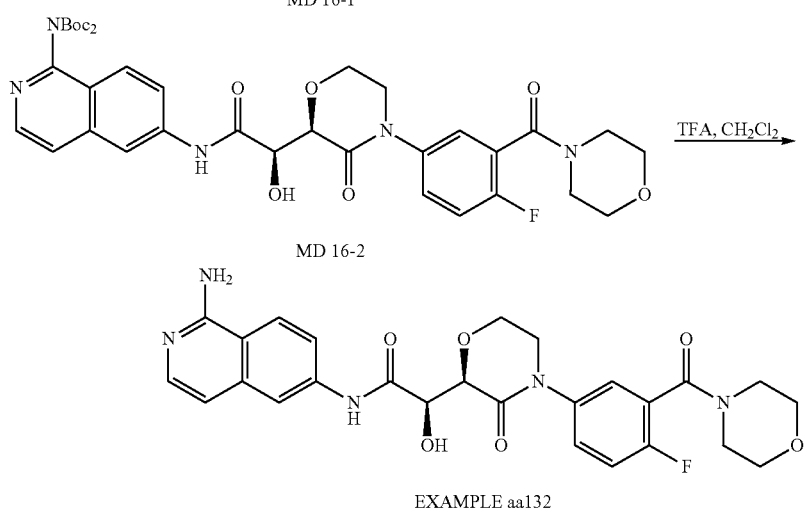

MD 16-2

EXAMPLE aa132

Step MD 16-1

(R)-2-(1-(bis(tert-Butoxycarbonyl)amino)isoquinolin-6-ylamino)-1-((R)-4-(4-fluoro-3-(morpholine-4-carbonyl)phenyl)-3-oxomorpholin-2-yl)-2-oxoethyl acetate MD 16-1

According to the Step MD 1-4 in the synthetic method for EXAMPLE aa117, MD 11-4 (0.23 g) was treated with di-tert-butyl(6-aminoisoquinolin-1-yl)imidocarbonate (0.25 g) from WO 2006/062972 to afford MD 16-1 (0.29 g) as an yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 16-2

(R)-2-(1-(bis(tert-Butoxycarbonyl)amino)isoquinolin-6-ylamino)-1-((R)-4-(4-fluoro-3-(morpholine-4-carbonyl)phenyl)-3-oxomorpholin-2-yl)-2-hydroxyacetamide MD 16-2

According to the Step MD 1-5 in the synthetic method for EXAMPLE aa117, MD 16-1 (0.29 g) was used instead of compound MD 1-4 to obtain MD 16-2 (0.27 g) as maize solid which was used without further purification.

Step MD 16-3

(R)—N-(1-Aminoisoquinolin-6-yl)-2-((R)-4-(4-fluoro-3-(morpholine-4-carbonyl)phenyl)-3-oxomorpholin-2-yl)-2-hydroxyacetamide EXAMPLE aa132

According to the Step MD 9-8 in the synthetic method for EXAMPLE aa125, MD 16-3 (0.27 g) was used instead of compound MD 9-7 to obtain EXAMPLE aa132 (0.11 g) as a pale yellow solid after reverse phase HPLC purification using a C18 column and a gradient of 89.95:9.95:0.1 $H_2O$:MeCN:TFA to 9.95:89.95:0.1 $H_2O$:MeCN:TFA to afford the trifluoroacetate salt.

Example aa133

(R)—N—((R)-1-amino-2,3-dihydro-1H-inden-5-yl)-2-((R)-4-(4-fluoro-3-(morpholine-4-carbonyl)phenyl)-3-oxomorpholin-2-yl)-2-hydroxyacetamide EXAMPLE aa133

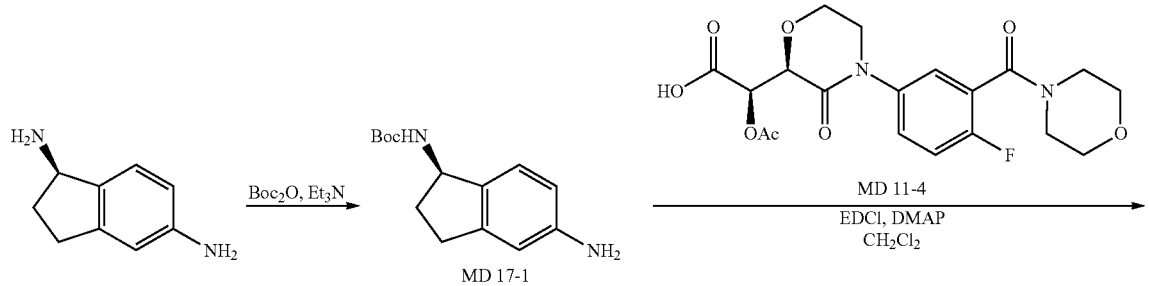

-continued

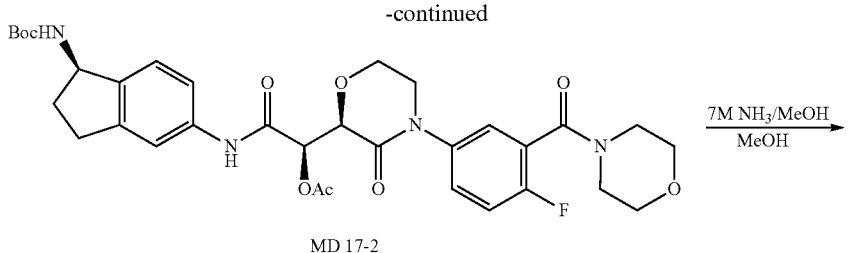

MD 17-2

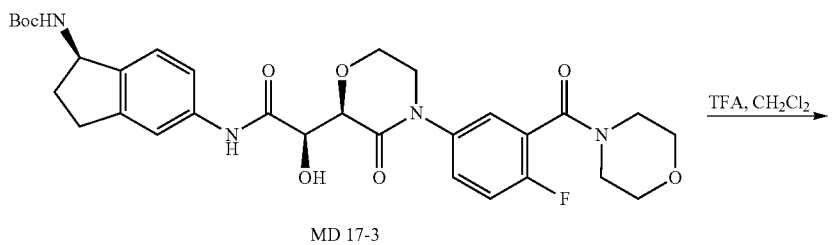

MD 17-3

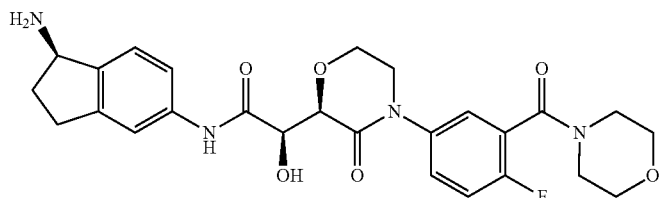

EXAMPLE aa133

Step MD 17-1

(R)-tert-Butyl 5-amino-2,3-dihydro-1H-inden-1-ylcarbamate MD 17-1

To a solution of (1R)-indane-1,5-amine hydrochloride (0.60 g) in $CH_2Cl_2$ (16 mL) at 0° C. was added $Et_3N$ (1.4 mL) followed by $Boc_2O$ (0.85 g). The mixture was allowed to warm to rt and was stirred for 12 h. The mixture was diluted with $CH_2Cl_2$ (5 mL) and sat. aq. $NaHCO_3$ (3 mL) and the layers were separated. The aqueous layer was extracted with $CH_2Cl_2$ (2×5 mL) and the organic layers were combined. The organic layer was dried ($Na_2SO_4$), filtered and concentrated under reduced pressure. The crude material was purified by flash chromatography using a gradient of 100% hexanes to 20% hexanes/80% EtOAc to afford MD 17-1 (0.26 g) as a yellow/orange semisolid.

Step MD 17-2

(R)-2-((R)-1-(tert-Butoxycarbonylamino)-2,3-dihydro-1H-inden-5-ylamino)-1-((R)-4-(4-fluoro-3-(morpholine-4-carbonyl)phenyl)-3-oxomorpholin-2-yl)-2-oxoethyl acetate MD 17-2

According to the Step MD 1-4 in the synthetic method for EXAMPLE aa117, MD 17-1 (0.11 g) was treated with MD 11-4 (0.15 g) to afford MD 17-2 (0.21 g) as a white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 17-3 tert-Butyl (R)-5-((R)-2-((R)-4-(4-fluoro-3-(morpholine-4-carbonyl)phenyl)-3-oxomorpholin-2-yl)-2-hydroxyacetamido)-2,3-dihydro-1H-inden-1-ylcarbamate MD 17-3

According to the Step MD 1-5 in the synthetic method for EXAMPLE aa117, MD 17-2 (0.21 g) was used instead of compound MD 1-4 to obtain MD 17-2 (0.14 g) as a white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 17-4

(R)—N—((R)-1-amino-2,3-dihydro-1H-inden-5-yl)-2-((R)-4-(4-fluoro-3-(morpholine-4-carbonyl)phenyl)-3-oxomorpholin-2-yl)-2-hydroxyacetamide EXAMPLE aa133

According to the Step MD 9-8 in the synthetic method for EXAMPLE aa125, MD 17-3 (0.14 g) was used instead of compound MD 9-7 to obtain EXAMPLE aa133 (38 mg) as a clear glass after reverse phase HPLC purification using a C18 column and a gradient of 89.95:9.95:0.1 $H_2O$:MeCN:TFA to 9.95:89.95:0.1 $H_2O$:MeCN:TFA to afford the trifluoroacetate salt.

Example aa134

(R)—N—((S)-1-Amino-2,3-dihydro-1H-inden-5-yl)-2-((R)-4-(4-fluoro-3-(morpholine-4-carbonyl)phenyl)-3-oxomorpholin-2-yl)-2-hydroxyacetamide
EXAMPLE aa134

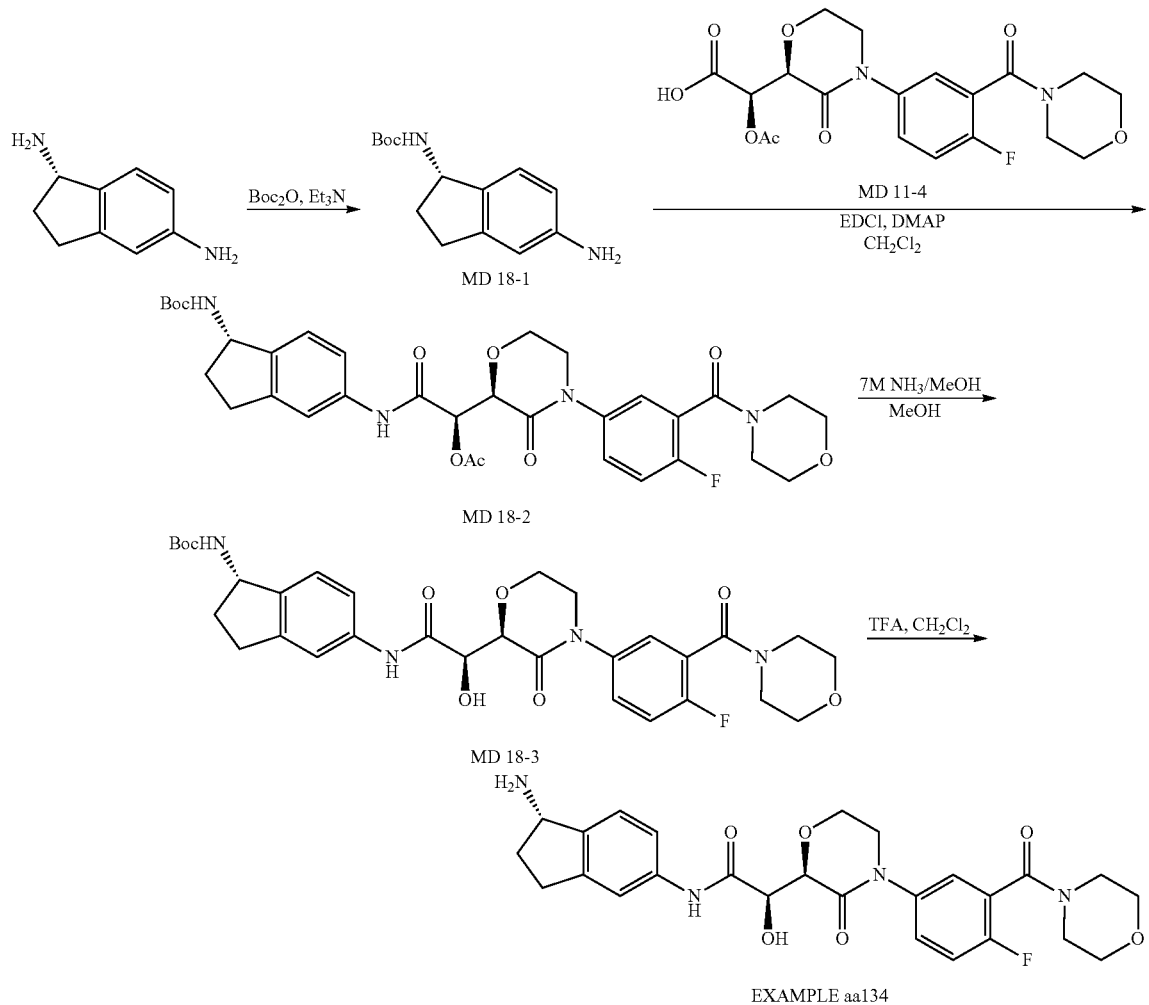

Step MD 18-1

(S)-tert-Butyl 5-amino-2,3-dihydro-1H-inden-1-yl-carbamate MD 18-1

According to the Step MD 17-1 in the synthetic method for EXAMPLE aa133, (1S)-indane-1,5-amine hydrochloride (0.72 g) was used to produce MD 18-1 (0.40 g) as a yellow semisolid.

Step MD 18-2

(R)-2-((S)-1-(tert-Butoxycarbonylamino)-2,3-dihydro-1H-inden-5-ylamino)-1-((R)-4-(4-fluoro-3-(morpholine-4-carbonyl)phenyl)-3-oxomorpholin-2-yl)-2-oxoethyl acetate MD 18-2

According to the Step MD 1-4 in the synthetic method for EXAMPLE aa117, MD 18-1 (0.11 g) was treated with MD 11-4 (0.15 g) to afford MD 17-2 (0.24 g) as a white solid after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H.

Step MD 18-3 tert-Butyl (S)-5-((R)-2-((R)-4-(4-fluoro-3-(morpholine-4-carbonyl)phenyl)-3-oxomorpholin-2-yl)-2-hydroxyacetamido)-2,3-dihydro-1H-inden-1-ylcarbamate MD 18-3

According to the Step MD 1-5 in the synthetic method for EXAMPLE aa117, MD 18-2 (0.24 g) was used instead of compound MD 1-4 to obtain MD 18-3 (0.18 g) as a white solid after reverse phase HPLC purification using a C18 column and a gradient of 89.95:9.95:0.1 H$_2$O:MeCN:HCO$_2$H to 9.95:89.95:0.1 H$_2$O:MeCN:HCO$_2$H.

Step MD 18-4

(R)—N—((S)-1-Amino-2,3-dihydro-1H-inden-5-yl)-2-((R)-4-(4-fluoro-3-(morpholine-4-carbonyl)phenyl)-3-oxomorpholin-2-yl)-2-hydroxyacetamide EXAMPLE aa134

According to the Step MD 9-8 in the synthetic method for EXAMPLE aa125, MD 18-3 (0.14 g) was used instead of compound MD 9-7 to obtain EXAMPLE aa134 (56 mg) as a clear glass after reverse phase HPLC purification using a C18 column and a gradient of 89.95:9.95:0.1 $H_2O$:MeCN:TFA to 9.95:89.95:0.1 $H_2O$:MeCN:TFA to afford the trifluoroacetate salt.

Example aa135

(R)—N-(2-Aminoquinolin-6-yl)-2-((R)-4-(4-fluoro-3-(morpholine-4-carbonyl)phenyl)-3-oxomorpholin-2-yl)-2-hydroxyacetamide EXAMPLE aa135

Step MD 19-1

2-bis(tert-Butoxycarbonylamine)-6-nitroquinoline MD 19-1

To a solution of 6-nitroquinoline-2-amine (1.0 g) in THF (30 mL) was added $Boc_2O$ (2.9 g) and DMAP (32 mg). The mixture was heated at reflux for 12 h whereupon an additional portion of $Boc_2O$ (0.7 g) and DMAP (60 mg) were added. The mixture was stirred at reflux for an additional 12 h whereupon the mixture was cooled and concentrated under reduced pressure. The resultant solid was dissolved in $CH_2Cl_2$ (50 mL) and was washed with sat. aq. $NH_4Cl$ (1×15 mL) and sat. aq. $NaHCO_3$ (1×15 mL). The organic layer was dried ($Na_2SO_4$), filtered, and concentrated under reduced pressure. The crude material was purified by flash chromatography using a gradient of 100% hexanes to 50% hexanes/50% EtOAc to afford MD 19-1 (2.1 g) as a white solid.

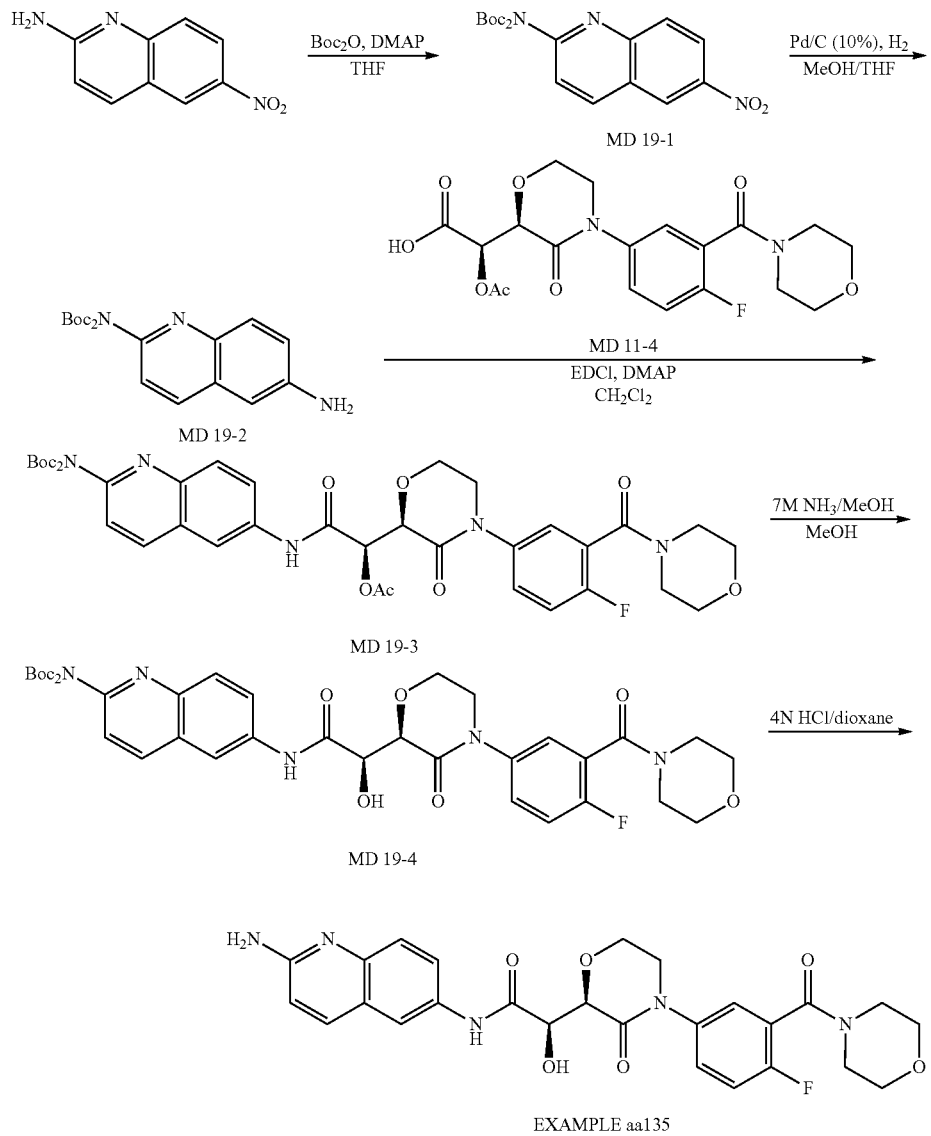

Step MD 19-2

2-(bis(tert-Butoxycarbonyl)amino)quinolin-6-ylamine MD 19-2

To a heterogenous mixture of MD 19-1 (2.0 g) in MeOH/THF (12 mL/12 mL) was added 10% Pd/C (100 mg). The mixture was stirred under a $H_2$ balloon for 12 h whereupon the mixture was purged to $N_2$. The mixture was filtered thru a pad of Celite and the pad was generously washed with MeOH (5×10 mL). The filtrate was concentrated under reduced pressure and placed under high vacuum to afford MD 19-2 (1.7 g) as a light yellow solid.

Step MD 19-3

(R)-2-(2-(bis(tert-Butoxycarbonyl)amino)quinolin-6-ylamino)-1-((R)-4-(4-fluoro-3-(morpholine-4-carbonyl)phenyl)-3-oxomorpholin-2-yl)-2-oxoethyl acetate MD 19-3

According to the Step MD 1-4 in the synthetic method for EXAMPLE aa117, MD 11-4 (0.15 g) was treated with MD 19-2 (0.17 g) to afford MD 19-3 (0.13 g) as an yellow solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 19-4

(R)-2-(2-(bis(tert-Butoxycarbonyl)amino)quinolin-6-ylamino)-1-((R)-4-(4-fluoro-3-(morpholine-4-carbonyl)phenyl)-3-oxomorpholin-2-yl)-2-hydroxyacetamide MD 19-4

According to the Step MD 1-5 in the synthetic method for EXAMPLE aa117, MD 19-3 (0.13 g) was used instead of compound MD 1-4 to obtain MD 19-4 (0.10 g) as white solid after reverse phase HPLC purification using a C18 column and a gradient of 89.95:9.95:0.1 $H_2O$:MeCN:$HCO_2H$ to 9.95:89.95:0.1 $H_2O$:MeCN:$HCO_2H$.

Step MD 19-5

(R)—N-(2-Aminoquinolin-6-yl)-2-((R)-4-(4-fluoro-3-(morpholine-4-carbonyl)phenyl)-3-oxomorpholin-2-yl)-2-hydroxyacetamide EXAMPLE aa135

According to the Step MD 9-8 in the synthetic method for EXAMPLE aa125, MD 19-4 (0.10 g) was used instead of compound MD 9-7 using 4N HCl in dioxane obtain EXAMPLE aa135 (85 mg) as a yellow solid after treatment with HCl.

| EXAMPLE | LCMS m/z $[M + 1]^+$ | RT min | Method |
|---|---|---|---|
| aa117 | 465 | 2.48 | A |
| MD 1-1 | 392 | 4.86 | A |
| MD 1-2 | 434 | 1.95 | B |
| MD 1-3 | 378 | 1.64 | B |
| MD 1-4 | 729 (Na) | 1.99 | B |
| MD 1-5 | 687 | 1.94 | B |
| aa118 | 450 | 1.73 | A |
| MD 2-1 | 274 | 1.65 | B |
| MD 2-2 | 377 | 1.53 | B |
| MD 2-3 | 419 | 1.65 | B |
| MD 2-4 | 363 | 1.17 | B |
| MD 2-5 | 714 (Na) | 1.93 | B |
| MD 2-6 | 672 (Na) | 1.79 | B |
| aa119 | 450 | 1.70 | A |
| MD 3-1 | 274 | 3.36 | A |
| MD 3-2 | 321 | 3.08 | A |
| MD 3-3 | 419 | 3.23 | A |
| MD 3-4 | 363 | 1.18 | B |
| MD 3-5 | 714 (Na) | 1.81 | B |
| MD 3-6 | 672 (Na) | 1.77 | B |
| aa120 | 483 | 2.17 | A |
| MD 4-1 | 410 | 1.69 | B |
| MD 4-2 | 452 | 1.82 | B |
| MD 4-3 | 396 | 1.53 | B |
| MD 4-4 | 747 (Na) | 1.92 | B |
| MD 4-5 | 705 (Na) | 1.88 | B |
| aa121 | 425 | 2.12 | A |
| MD 5-1 | 416 (Na) | 1.71 | B |
| MD 5-2 | 338 | 1.35 | B |
| MD 5-3 | 481 (Na) | 1.68 | B |
| MD 5-4 | 647 (Na) | 1.87 | B |
| aa122 | 305 | 1.19 | A |
| MD 6-1 | 296 (Na) | 1.28 | B |
| MD 6-2 | 218 | — | B |
| MD 6-3 | 569 (Na) | 1.71 | B |
| MD 6-4 | 527 (Na) | 1.67 | B |
| aa123 | 487 | 3.28 | A |
| MD 7-1 | 414 | 4.25 | A |
| MD 7-2 | 478 (Na) | 1.85 | B |
| MD 7-3 | 400 | 1.61 | B |
| MD 7-4 | 729 | 2.41 | B |
| MD 7-5 | 709 (Na) | 2.38 | B |
| aa124 | 490 | 2.18 | A |
| MD 8-1 | 314 | 1.84 | B |
| MD 8-2 | 417 | 1.93 | B |
| MD 8-3 | 459 | 1.92 | B |
| MD 8-4 | 403 | 1.39 | B |
| MD 8-5 | 754 (Na) | 1.89 | B |
| MD 8-6 | 712 (Na) | 1.96 | B |
| aa125 | 473 | 1.71 | A |
| MD 9-1 | 264 | 3.33 | A |
| MD 9-2 | 304 | 3.97 | A |
| MD 9-3 | 407 | 1.50 | B |
| MD 9-4 | 449 | 1.65 | B |
| MD 9-5 | 393 | 1.13 | B |
| MD 9-6 | 615 | 3.55 | A |
| MD 9-7 | 595 (Na) | 1.61 | A |
| aa126 | 483 | 1.61 | A |
| MD 10-1 | 525 | 1.82 | A |
| aa127 | 487 | 1.86 | A |
| MD 11-1 | 336 | 1.48 | B |
| MD 11-2 | 439 | 2.81 | A |
| MD 11-3 | 481 | 1.91 | B |
| MD 11-4 | 425 | 1.55 | B |
| MD 11-5 | 629 | 3.98 | A |
| MD 11-6 | 587 | 3.72 | A |
| aa128 | 501 | 2.08 | A |
| MD 12-1 | 543 | 1.30 | B |
| aa129 | 513 | 1.68 | A |
| MD 13-1 | 655 | 1.79 | B |
| MD 13-2 | 613 | 3.51 | A |
| aa130 | 505 | 1.76 | A |
| MD 14-1 | 665 (Na) | 1.72 | B |
| MD 14-2 | 505 (-Boc) | 1.65 | B |
| aa131 | 501 | 1.78 | A |

-continued

| EXAMPLE | LCMS m/z [M + 1]⁺ | RT min | Method |
|---|---|---|---|
| MD 15-1 | 543 (-Boc) | 1.72 | B |
| MD 15-2 | 501 (-Boc) | 1.65 | B |
| aa132 | 524 | 1.95 | A |
| MD 16-1 | 788 (Na) | 2.22 | B |
| MD 16-2 | 724 | 1.01 | B |
| aa133 | 535 (Na) | 1.33 | B |
| MD 17-1 | 249 | 2.42 | A |
| MD 17-2 | 677 (Na) | 1.94 | B |
| MD 17-3 | 635 (Na) | 1.97 | B |
| aa134 | 535 (Na) | 1.34 | B |
| MD 18-1 | 249 | 2.38 | A |
| MD 18-2 | 677 (Na) | 2.48 | B |
| MD 18-3 | 635 (Na) | 1.97 | B |
| aa135 | 524 | 1.79 | A |
| MD 19-1 | — | — | — |
| MD 19-2 | 360 | 1.01 | B |
| MD 19-3 | 766 | 2.16 | B |
| MD 19-3 | 724 | 2.04 | B |

Method A:
Electro Spray Ionization Liquid Chromatography-Mass Spectrometry (ESI-LC/MS)
Column: Phenomenex Gemini C18, 50 × 4.6 mm, 5 micron
Mobile Phase: A: 0.05% Trifluoroacetic acid in water
B: 0.05% Trifluoroacetic acid in acetonitrile
Gradient: 90% A and 10% B to 5% A and 95% B over 5 minutes
Flow rate: 1.0 ml/min
UV detection: 254 nM
Spectrometer: PE SCIEX API-150EX, single quadrupole mass spectrometer
Method B:
Column: Zorbax SB-C-18; 1.8 micron
Mobile Phase: A: 0.1% Trifluoroacetic acid in water
B: 0.1% Trifluoroacetic acid in acetonitrile
Gradient: 0 min = 10% B
1.3 min = 55% B
2.7 min = 95% B
2.8 min = 10% B
Flow rate: 1.0 ml/min
UV detection: 254 nM
Spectrometer: Agilent 6140 Quadrapole LC-MS, single quadrupole mass spectrometer

| EXAMPLE | NMR (ppm)(400 MHz unless otherwise indicated) |
|---|---|
| aa117 | DMSO-d6: 10.3 (1H, s), 10.2 (1H, s), 9.68 (1H, s), 9.18 (1H, s), 8.33 (1H, s), 8.20 (1H, d, J = 8.3 Hz), 7.95 (1H, d, J = 8.2 Hz), 7.60-7.56 (2H, m), 7.49 (1H, d, J = 8.3 Hz), 7.31 (1H, d, J = 8.2 Hz), 6.52 (1H, d, J = 7.0 Hz), 4.79 (2H, s), 4.73 (1H, s), 4.70 (m, 1H), 4.14 (1H, m), 3.98-3.90 (2H, m), 3.72 (1H, m). |
| aa118 | Cd3od-d4: 8.25 (1H, s), 8.00 (1H, d, J = 8.4 Hz), 7.90-7.88 (1H, d, J = 1.8 Hz), 7.80-7.70 (1H, d, J = 1.8 Hz), 4.85 (2H, s), 4.83 (2H, s), 4.53 (2H, s), 4.25 (1H, m), 4.07 (2H, m), 3.71 (1H, m), 3.20 (3H, s).2H |
| aa119 | Cd3od-d4: 8.26 (1H, s), 8.05 (1H, d, J = 8.4 Hz), 7.90-7.88 (1H, d, J = 1.8 Hz), 7.70 (1H, s), 7.64 (2H, s), 4.85 (2H, s), 4.83 (2H, s), 4.53 (2H, s), 4.22 (1H, m), 4.06-4.03 (2H, m), 3.67 (1H, m), 3.21 (3H, s). |
| aa120 | DMSO-d6: 10.3 (1H, s), 9.80 (1H, br s), 8.43 (1H, s), 8.28 (1H, s), 8.05 (1H, d, J = 8.5 Hz), 7.95 (1H, d, J = 8.5 Hz), 7.34 (1H, t, J = 8.2 Hz), 7.05-7.01 (2H, m), 6.86 (1H, dd, J = 1.3, 8.2 Hz), 4.80 (2H, s), 4.74 (1H, s), 4.68 (1H, s), 4.19 (2H, q, J = 6.8 Hz), 4.13 (1H, m), 3.95-3.91 (m, 1H), 3.87-3.82 (1H, m), 3.69-3.60 (1H, m), 3.40 (1H, br s), 1.23 (3H, t, J = 6.8 Hz). |
| aa121 | Cd3od-d4: 8.21 (1H, s), 8.05 (1H, d, J = 8.4 Hz), 7.90 (1H, d, J = 8.1 Hz), 7.25-7.15 (2H, d, J = 8.5 Hz) 6.80-6.71 (2H, d, J = 8.5 Hz), 4.50 (2H, s), 4.22 (1H, s) 3.82-3.40 (6H, m), 3.20 (3H, s). |
| aa122 | Cd3od-d4: 8.21 (1H, s), 8.00 (1H, d, J = 8.6 Hz), 7.81 (1H, s), 4.60 (2H, d, J = 1.7 Hz), 4.10 (2H, m), 3.85 (2H, m). |
| aa123 | Cd3od-d4: 8.21 (1H, s), 8.00 (1H, d, J = 8.6 Hz), 7.82 (1H, d, J = 1.8 Hz), 7.40-7.21 (6H, m), 7.10-7.05 (3H, m), 5.40 (2H, s), 4.80 (2H, s), 4.20 (1H, m), 4.05-3.95 (2H, m), 3.60 (1H, m), 3.35 (2H, s). |
| aa124 | Cd3od-d4: 8.25 (1H, s), 8.05 (1H, d, J = 8.6 Hz), 7.90-7.81 (1H, d, J = 1.9 Hz), 7.72 (1H, s), 7.60 (3H, m), 4.60 (2H, s), 4.22 (1H, m) 4.19-3.90 (2H, m), 3.65 (2H, m), 3.45 (2H, m), 1.10 (1H, t, J = 6.9 Hz), 0.55 (2H, d, J = 1.4 Hz), 0.45 (2H, d, J =1.42 Hz). |
| aa125 | Cd3od-d4: 7.84-7.15 (7H, m), 4.79 (2H, s), 4.20-3.91 (7H, m), 3.81-3.62 (5H, m), 3.31 (2H, s). |
| aa126 | Cd3od-d4: 7.71-7.68 (2H, m), 7.53-7.45 (2H, m), 7.36-7.24 (4H, m), 5.62 (1H, s), 4.27 (3H, m), 4.11-4.08 (4H, m), 3.80 (4H, m) |
| aa127 | Cd3od-d4: 9.7 (1H, s), 7.75-7.73 (2H, d, J = 1.5 Hz), 7.58-7.41 (4H, m), 7.35-7.25 (1H, t, J = 9.2 Hz), 4.80 (2H, s), 4.28-3.93 (4H, m), 3.85-3.31 (8H, m). |
| aa128 | Cd3od-d4: 7.90-7.77 (4H, m), 7.62-7.53 (2H, m), 7.41-7.33 (1H, m), 4.80 (2H, s), 4.28-4.23 (1H, m), 4.19-4.02 (2H, m), 3.85-3.31 (7H, m). |
| aa129 | Cd3od-d4: 7.68-7.42 (5H, m), 7.30-7.20 (2H, m), 4.80 (2H, s), 4.35 (1H, s), 4.26 (2H, m), 4.10-4.05 (2H, m) 3.80-3.12 (5H, m). |
| aa130 | Cd3od-d4: 7.85-7.19 (7H, m), 4.79 (2H, s), 4.21-3.90 (7H, m), 3.81-3.62 (5H, m), 3.31 (2H, s). |
| aa131 | Cd3od-d4: 7.74 (2H, m), 7.48-7.43 (2H, m), 7.42 (2H, d, J = 8.4 Hz), 7.28 (1H, t, J = 8.8 Hz), 4.77 (2H, s), 4.42 (1H, m), 4.21-4.19 (2H, m), 3.99 (2H, m), 3.76-3.73 (4H, m), 3.64-3.61 (4H, m), 3.39 (2H, m), 1.61 (3H, d, J = 7.0 Hz). |

-continued
| EXAMPLE | NMR (ppm)(400 MHz unless otherwise indicated) |
|---|---|
| aa132 | Cd3OD-d4: 8.45 (1H, s), 8.32 (2H, s), 7.96 (1H, d, J = 9.2 Hz), 7.59-7.49 (3H, m), 7.334-7.30 (1H, m), 7.08 (1H, d, J = 6.7 Hz), 4.88 (2H, s), 4.28-4.25 (1H, m), 4.10-4.02 (2H, m), 3.79-3.72 (4H, m), 3.69-3.65 (3H, m), 3.42 (2H, m). |
| aa133 | Cd3OD-d4: 8.30 (1H, br s), 7.72 (1H, s), 7.60-7.48 (4H, m), 7.33 (1H, t, J = 9.1 Hz), 4.82 (2H, m), 4.80-4.74 (2H, m), 4.24 (1H, m), 4.08-4.00 (2H, m), 3.79-3.73 (4H, m), 3.70-3.63 (3H, m), 3.43 (2H, s), 3.23-3.17 (1H, m), 3.05-3.00 (1H, m), 2.68-2.60 (1H, m), 2.17-2.06 (1H, m). |
| aa134 | Cd3OD-d4: 8.31 (1H, br s), 7.73 (1H, s), 7.59-7.48 (4H, m), 7.33 (1H, t, J = 8.9 Hz), 4.81 (2H, s), 4.77 (2H, m), 4.24-4.21 (1H, m), 4.08-4.00 (2H, m), 3.80-3.77 (4H, m), 3.70-3.64 (3H, m), 3.37 (2H, s), 3.23-3.17 (1H, m), 3.05-2.98 (1H, m), 2.68-2.60 (1H, m), 2.18-2.11 (1H, m). |
| aa135 | DMSO-d6: 10.1 (1H, s), 9.00 (1H, br s), 8.46 (1H, d, J = 1.6 Hz), 8.37 (1H, d, J = 9.4 Hz), 8.07 (1H, d, J = 1.6, 8.8 Hz), 7.68 (1H, d, J = 8.8 Hz), 7.58-7.52 (2H, m), 7.40 (1H, t, J = 8.8 Hz), 7.08 (1H, d, J = 9.4 Hz), 4.71 (1H, s), 4.68 (1H, s), 4.15 (1H, d, J = 11.6 Hz), 3.97-3.91 (2H, m), 3.87-3.30 (9H, m). |
Examples aa136-aa153
Example aa136
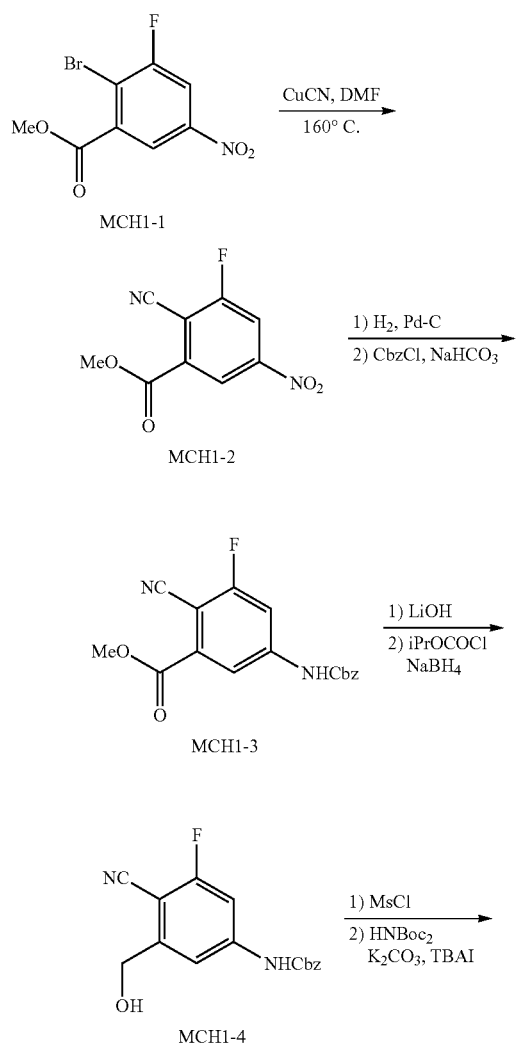
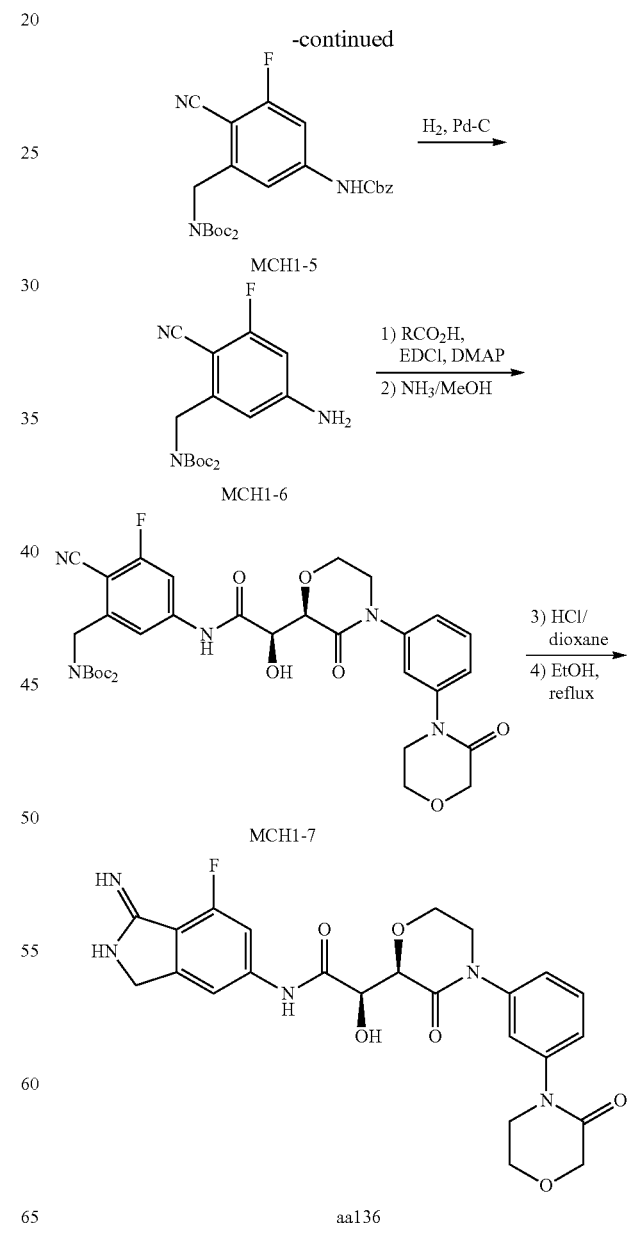

Step 1

Synthesis of

Methyl 2-cyano-3-fluoro-5-nitrobenzoate (compound MCH1-2)

A mixture of MCH1-1 (3.9 g, 14.03 mmol (prepared according to the procedure described in WO 2006/021457 A2)), CuCN (6.3 g, 70.34 mmol, 5 eq.) in 40 mL DMF was degassed under vacuum, filled with argon atmosphere and heated in an oil bath at ~160° C. (bath temp.) for 20 min. It was removed from the bath, cooled to rt then diluted with ethyl acetate while being stirred vigorously. The mixture was filtered through a pad of CELITE, rinsed with ethyl acetate and the filtrate was washed with water and brine. It was dried over MgSO$_4$, filtered and evaporated to dryness to give 3.02 g of MCH1-2 as solid.

Step 2

Synthesis of Methyl 5-(benzyloxycarbonylamino)-2-cyano-3-fluorobenzoate (compound MCH1-3)

A suspension of 3 (500 mg) and 10% Pd/C (50 mg) in 10 mL of 1:1 THF-EtOH was under overnight under a hydrogen balloon. It was filtered through a CELITE pad and evaporated to dryness to give 435 mg of aniline.

To a solution of the above aniline (430 mg, 2.22 mmol) and NaHCO3 (930 mg, 11.07 mmol, 5 eq.) in 10 mL THF at rt was added benzylchloroformate (0.95 mL, 0.66 mmol, 3 eq.). The mixture was stirred overnight at rt, diluted with water and extracted 3× with ethyl acetate. The combined organic layer was washed with brine, dried over MgSO$_4$, filtered and concentrated to a small volume to give a suspension. The suspension was diluted with ether and the solid was filtered, washed with ether and dried to give 485 mg MCH1-3.

Step 3

Synthesis of Benzyl 3-((di-tert-butoxycarbonyl)aminomethyl)-4-cyano-5-fluorophenylcarbamate (compound MCH1-5)

To a solution of MCH1-3 (650 mg, 1.98 mmol), LiOH.H$_2$O (330 mg, 5.96 mmol, 3 eq.) in 10 mL THF and 2 mL water was stirred at rt for 45 min. and diluted with water. The solution was acidified with 1N HCl to ~pH 1 and extracted 3× with ethyl acetate. The combined organic layer was washed with brine, dried over MgSO$_4$, filtered and evaporated to dryness to give 620 g of the acid.

To a solution of the above acid (620 mg, 1.97 mmol) and triethyl amine (0.55 mL, 3.95 mmol, 2 eq.) in 10 mL THF at ~–20° C. was added a 1M solution of isopropylchlroformate in toluene (2.4 mL, 2.4 mmol, 1.2 eq.). The mixture was stirred for about 10 min and filtered through a fritted funnel and the precipitate rinsed with 10 mL THF. The filtrate was cooled to ~–20° C. and a solution of sodium borohydride (375 mmol, 9.91 mmol, 5 eq.) in 2 mL water was added. After being stirred for 10 min. at –20° C., the reaction mixture was diluted with water and extracted 3× with ethyl acetate. The combined organic layers was washed aq. NH$_4$Cl solution followed by brine, dried over MgSO$_4$, filtered and evaporated to dryness to provide the crude alcohol.

The above alcohol was dissolved in 10 mL of dichloromethane and cooled to 0° C. To this was added triethyl amine (0.55 mL, 3.95 mmol, 2 eq) followed by methane sulfonylchloride (0.185 mL, 2.39 mmol, 1.2 eq.). The mixture was stirred for 1 hr, diluted with ethyl acetate, washed with 1N HCl, 2× with aq. NaHCO$_3$ and brine. It was dried over MgSO$_4$, filtered and concentrated to provide the crude mesylate which was used for the subsequent step.

A solution of the above mesylate, di-tert-butyl iminodicarboxylate (560 mg, 2.58 mmol, 1.3 eq.), K$_2$CO$_3$ (540 mg, 3.97 mmol), and tetrabutylammonium iodide (973 mg, 0.198 mmol, 0.1 eq) in 10 mL DMF was stirred overnight at rt. The mixture was diluted with water, extracted 3× with ethyl acetate. The combined organic layer was washed with brine, dried over MgSO$_4$, filtered, concentrated and purified by chromatography eluting with 0% to 20% ethyl acetate in hexane to provide 49 mg of MCH1-5.

Step 4

Synthesis of 4-Amino-2-((di-tert-butoxycarbonyl)aminomethyl)-6-fluorobenzonitrile (compound MCH1-6)

A suspension of 5 (180 mg), 10% Pd—C (30 mg) in 2 mL THF and 2 mL ethanol was stirred under a hydrogen balloon for 6 hr, filtered through a CELITE pad, concentrated and purified by chromatography eluting with 100% hexane to 1:1:3 ethyl acetate/dichloromethane/hexane to provide 50 mg of MCH1-6.

Step 5

Synthesis of N-(7-fluoro-2,3-dihydro-1-imino-1H-isoindol-5-yl)-alpha(R)-hydroxy-3-oxo-4-[3-(3-oxo-4-morpholinyl)phenyl]-2(R)-morpholineacetamide (Example aa136)

Compound MCH1-6 was converted to example aa136 using a procedure similar to the preparation of Example 57.

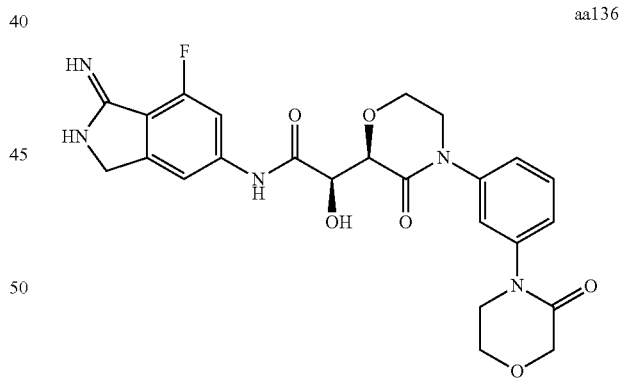

aa136

Example aa137

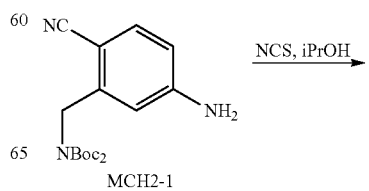

MCH2-1

853

-continued

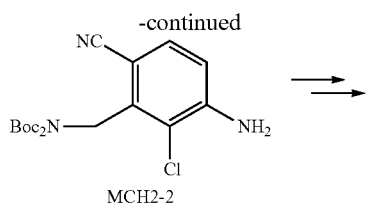

MCH2-2

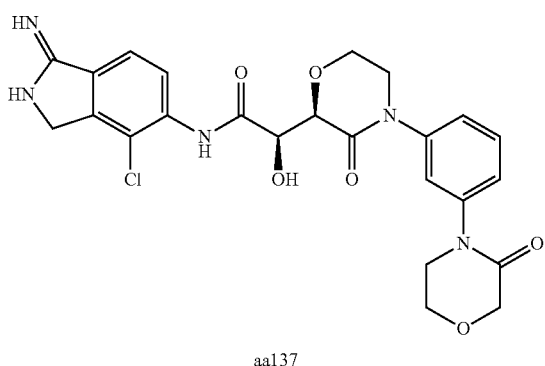

aa137

854

Step 1

Synthesis of 4-Amino-2-((di-tert-butoxycarbonyl)aminomethyl)-3-chlorobenzonitrile (compound MCH 2-2)

To a solution of MCH2-1 (950 mg, 2.73 mmol) in 10 ml isopropanol at 60° C. was added N-chlorosuccinimide (400 mg, 2.99 mmol, 1.1 eq). The mixture was heated at reflux for 1.5 hr, left overnight at rt, concentrated and diluted with ethyl acetate. The solution was washed 2× with water, brine, dried over $MgSO_4$, filtered, concentrated and purified by flash chromatography using 40% ethyl acetate in hexanes to provide 288 mg of MCH2-2.

Step 2

Synthesis of N-(4-chloro-2,3-dihydro-1-imino-1H-isoindol-5-yl)-alpha(R)-hydroxy-3-oxo-4-[3-(3-oxo-4-morpholinyl)phenyl]-2(R)-morpholineacetamide (Example aa137)

Compound MCH2-2 was converted to example aa137 using procedure similar to the preparation of Example 57.

The following analogs were prepared using analogous procedure:

| Example | Structure | Name |
|---|---|---|
| aa138 | 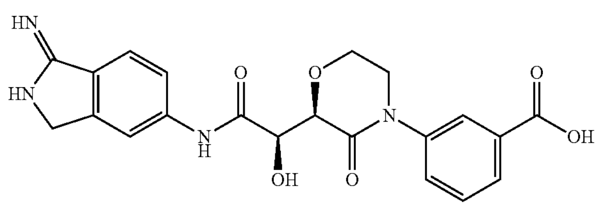 [SMILES: N=C1NCc2cc(NC(=O)[C@H](O)[C@H]3OCCN(c4cccc(C(=O)O)c4)C3=O)ccc21] | 3-[2(R)-[2-[(2,3-Dihydro-1-imino-1h-isoindol-5-yl)amino]-1(R)-hydroxy-2-oxoethyl]-3-oxo-4-morpholinyl] benzoic acid |
| aa139 | 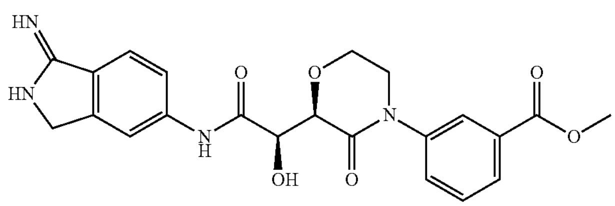 [SMILES: COC(=O)c1cccc(N2CCO[C@H]([C@@H](O)C(=O)Nc3ccc4c(c3)CNC4=N)C2=O)c1] | Methyl 3-[2(R)-[2-[(2,3-dihydro-1-imino-1H-isoindol-5-yl)amino]-1(R)-hydroxy-2-oxoethyl]-3-oxo-4-morpholinyl] benzoate |
| aa140 | 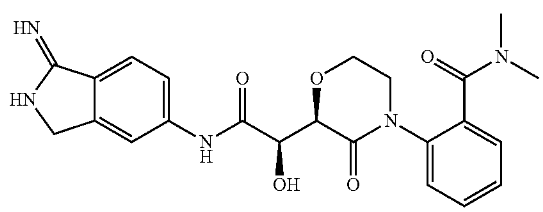 [SMILES: CN(C)C(=O)c1ccccc1N1CCO[C@H]([C@@H](O)C(=O)Nc2ccc3c(c2)CNC3=N)C1=O] | N-(2,3-Dihydro-1-imino-1h-isoindol-5-yl)-4-[2-[(dimethylamino)carbonyl]phenyl]-alpha(R)-hydroxy-3-oxo-2(R)-morpholincacetamide |
| aa141 | 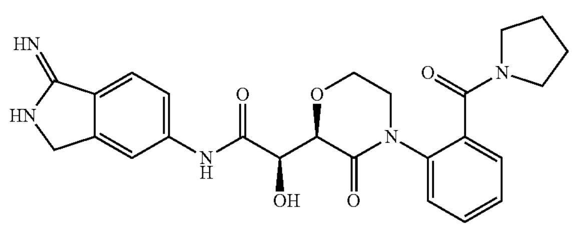 [SMILES: N=C1NCc2cc(NC(=O)[C@H](O)[C@H]3OCCN(c4ccccc4C(=O)N4CCCC4)C3=O)ccc21] | N-(2,3-Dihydro-1-imino-1H-isoindol-5-yl)-alpha(R)-hydroxy-3-oxo-4-[2-(1-pyrrolidinylcarbonyl)phenyl]-2(R)-morpholine acetamide |

| Example | Structure | Name |
|---|---|---|
| aa142 | 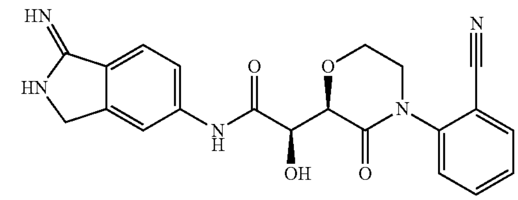 [SMILES: N#Cc1ccccc1N1CCO[C@H]([C@@H](O)C(=O)Nc2ccc3c(c2)CNC3=N)C1=O] | 4-(2-Cyanophenyl)-N-(2,3-dihydro-1-imino-1h-isoindol-5-yl)-alpha(R)-hydroxy-3-oxo-2(R)-morpholine acetamide |
| aa143 | 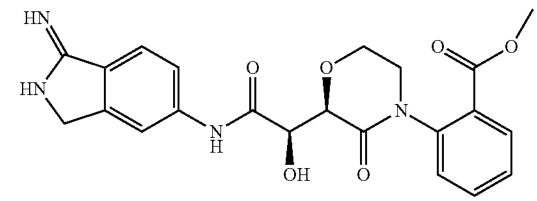 [SMILES: COC(=O)c1ccccc1N1CCO[C@H]([C@@H](O)C(=O)Nc2ccc3c(c2)CNC3=N)C1=O] | Methyl 2-[2(R)-[2-[(2,3-dihydro-1-imino-1h-isoindol-5-yl)amino]-1(R)-hydroxy-2-oxoethyl]-3-oxo-4-morpholinyl] benzoate |
| aa144 | 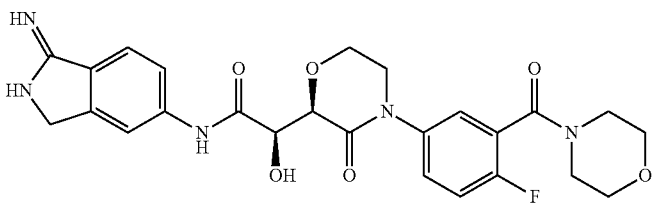 [SMILES: N=C1NCc2cc(NC(=O)[C@H](O)[C@H]3OCCN(c4ccc(F)c(C(=O)N5CCOCC5)c4)C3=O)ccc21] | N-(2,3-Dihydro-1-imino-1h-isoindol-5-yl)-4-[4-fluoro-3-(4-morpholinylcarbonyl)phenyl]-alpha(R)-hydroxy-3-oxo-2(R)-morpholineacetamide |
| aa145 | 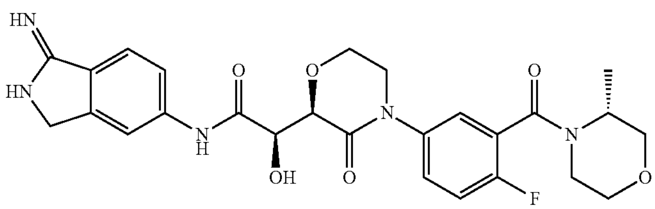 [SMILES: C[C@@H]1COCCN1C(=O)c1cc(N2CCO[C@H]([C@@H](O)C(=O)Nc3ccc4c(c3)CNC4=N)C2=O)ccc1F] | N-(2,3-Dihydro-1-imino-1h-isoindol-5-yl)-4-[4-fluoro-3-[(3(R)-methyl-4-morpholinyl)carbonyl]phenyl]-alpha(R)-hydroxy-3-oxo-2(R)-morpholine acetamide |
| aa146 | 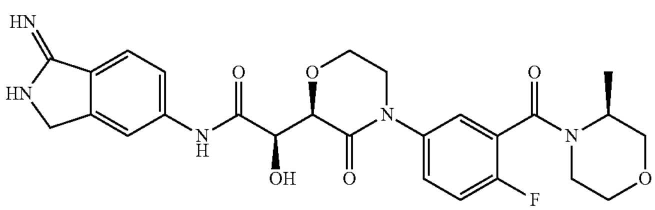 [SMILES: C[C@H]1COCCN1C(=O)c1cc(N2CCO[C@H]([C@@H](O)C(=O)Nc3ccc4c(c3)CNC4=N)C2=O)ccc1F] | N-(2,3-Dihydro-1-imino-1h-isoindol-5-yl)-4-[4-fluoro-3-[(3(S)-methyl-4-morpholinyl)carbonyl]phenyl]-alpha(R)-hydroxy-3-oxo-2(R)-morpholine acetamide |

Example aa147

N-[4-(Aminoiminomethyl)phenyl]-4-(2-cyanophenyl)-alpha(R)-hydroxy-3-oxo-2(R)-morpholineacetamide (Example aa147)

Example aa147 was prepared using procedures similar to the preparation of Example 73.

Example aa148

N-(4-Amino-7-quinazolinyl)-4-[4-fluoro-3-(4-morpholinylcarbonyl)phenyl]-alpha(R)-hydroxy-3-oxo-2(R)-morpholineacetamide (Example aa148)

Example aa148 was prepared using procedures similar to the preparation of example 98.

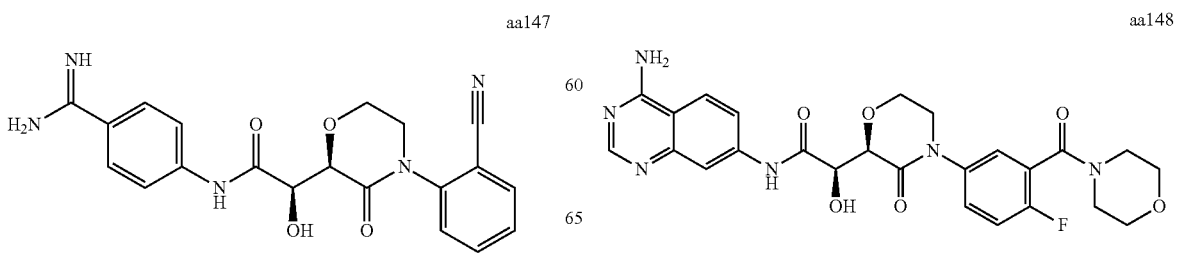

Example aa149

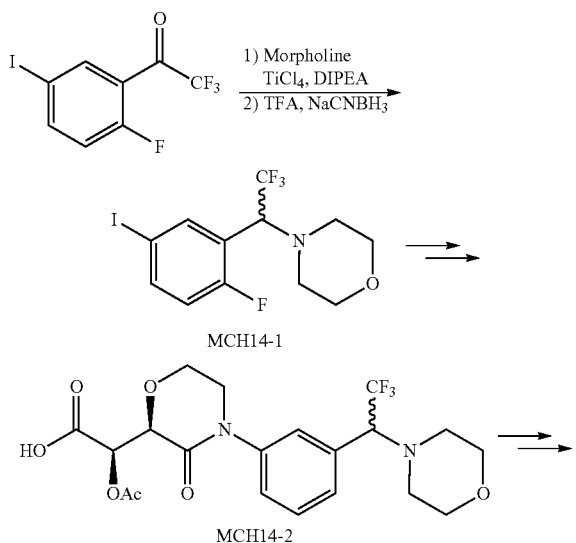

Step 1

Synthesis of 4-(2,2,2-trifluoro-1-(2-fluoro-5-iodophenyl)ethyl)morpholine (compound MCH14-1)

To a solution of commercially available 2,2,2-trifluoro-1-(2-fluoro-5-iodophenyl)ethanone (2 g, 6.29 mmol) in 20 mL dichloromethane at rt was added N,N-diisopropylethylamine (3.3 mL, 18.95 mmol, 3 eq.) followed by 1M solution of TiCl$_4$ in dichloromethane (6.3 mL, 6.3 mmol, 1 eq.). The mixture was stirred at rt for 3 days, added 10 mL of methanol followed by NaCNBH$_3$ (3.2 g) and trifluoroacetic acid (4.7 mL). The mixture was stirred overnight at rt, poured into aq. NaHCO$_3$ and extracted 3× with dichloromethane. The combined organic layer was washed with brine, dried over MgSO$_4$, filtered, concentrated and purified by chromatography eluting with 0% to 20% ethyl acetate in hexane to provide 1.16 g of MCH14-1.

Step 2

Synthesis of N-(3-Amino-1,2-benzisoxazol-6-yl)-4-[4-fluoro-3-[2,2,2-trifluoro-1-(4-morpholinyl)ethyl]phenyl]-alpha(R)-hydroxy-3-oxo-2(R)-morpholineacetamide (example aa149)

Compound MCH14-1 was converted to example aa149 using experimental procedure similar to the one described for the preparation of aa95

The following examples were prepared using analogous procedure:

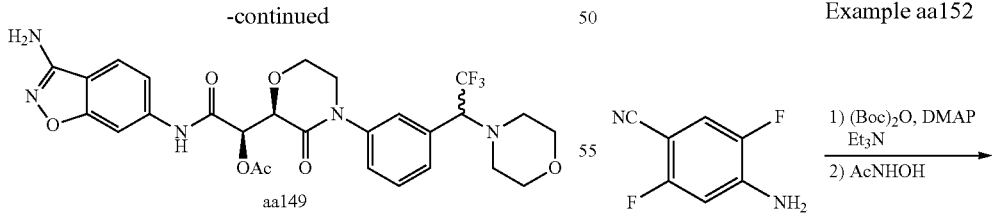

| EXAMPLE | Structure | Name |
|---|---|---|
| aa150 | 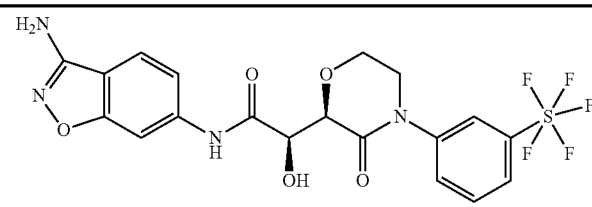 | [3-[2(R)-[2-[(3-Amino-1,2-benzisoxazol-6-yl)amino]-1(R)-hydroxy-2-oxoethyl]-3-oxo-4-morpholinyl]phenyl] pentafluorosulfur |
| aa151 | 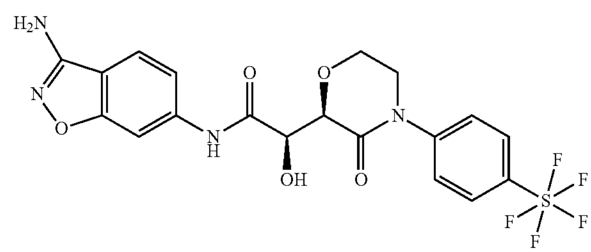 [SMILES: Nc1noc2cc(NC(=O)[C@H](O)[C@H]3OCCN(c4ccc(S(F)(F)(F)(F)F)cc4)C3=O)ccc12] | [4-[2(R)-[2-[(3-Amino-1,2-benzisoxazol-6-yl)amino]-1(R)-hydroxy-2-oxoethyl]-3-oxo-4-morpholinyl]phenyl] pentafluorosulfur |

-continued aa149

Example aa152

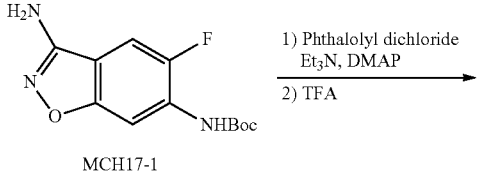

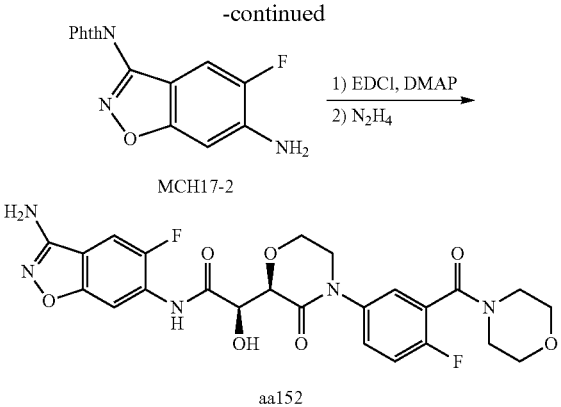

Step 1

Synthesis of tert-Butyl 3-amino-5-fluorobenzo[d]isoxazol-6-ylcarbamate (compound MCH17-1)

To a solution of 4-amino-2,5-difluorobenzonitrile (10 g, 64.88 mmol) di-tert-butyldicarbonate (43 g, 197 mmol, 3 eq.) in dichloromethane at rt was added DMAP (1.6 g, 13.10 mmol, 0.2 eq.) and triethyl amine (28 mL, 200 mmol, 3 eq.). The mixture was stirred overnight at rt and poured into 1N HCl. The organic layer separated and the aqueous phase extracted twice with dichloromethane. The combined organic layer was washed with brined, dried over MgSO4, filtered and evaporated to dryness to obtain 22.6 g of the protected aniline.

To a solution of the above aniline (12.6 g, 36 mmol) acetohydroxamic acid (16 g, 213 mmol, 6 eq.) and $K_2CO_3$ (58 g, 0.426 mmol, 12 eq.) in 150 mL of 9:1 DMF-water was heated overnight in an oil bath kept ~60° C. It was poured into water, extracted 3× with ethyl acetate, the combined organic layer was washed with brine, dried over $MgSO_4$, filtered, concentrated and purified by chromatography eluting with 0% to 50% ethyl acetate in hexane to provide 5.76 g of MCH17-1 contaminated with an unknown byproduct.

Step 2

Synthesis of 2-(6-Amino-5-fluorobenzo[d]isoxazol-3-yl)isoindoline-1,3-dione (compound MCH17-2)

To a solution of MCH17-1 (520 mg), triethyl amine (0.82 mL) and DMAP (24 mg) in 10 mL dichloromethane at 0° C. was added phthaloyl chloride (0.36 mL). The mixture was stirred overnight at rt, diluted with ethyl acetate and washed with 1N HCl, aq. $NaHCO_3$ and brine. It was dried over anhydrous $MgSO_4$, filtered, concentrated and purified by chromatography eluting with 0% to 50% ethyl acetate in hexane to provide 338 mg of phthalimide protected intermediate which was stirred with 5 mL of trifluoroacetic acid at rt for 40 min. The reaction mixture was evaporated to dryness, the residue was suspended in aq. $NaHCO_3$ and extracted 3× with ethyl acetate. The combined organic layer was washed with brine, dried over $MgSO_4$, filtered and evaporated to dryness to obtain 220 mg MCH 17-2.

Step 3

Preparation of N-(3-Amino-5-fluoro-1,2-benzisoxazol-6-yl)-4-[4-fluoro-3-(4-morpholinylcarbonyl)phenyl]-alpha(R)-hydroxy-3-oxo-2(R)-morpholineacetamide (example aa152)

Compound MCH17-2 was converted to aa152 using a procedure similar to the preparation of aa149

Example aa153

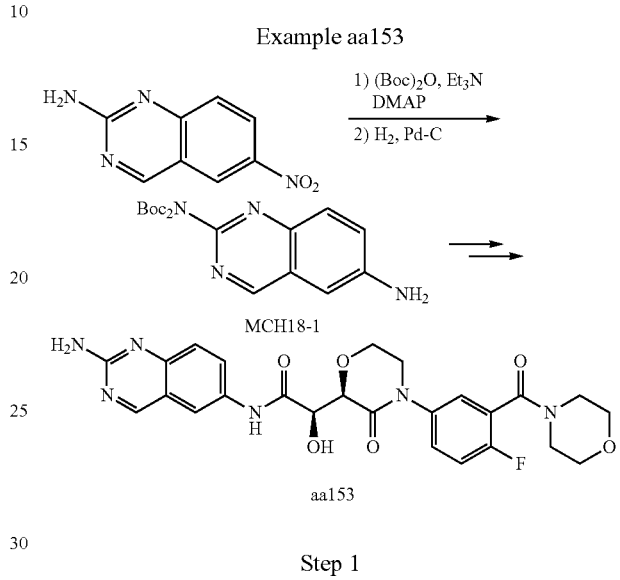

Step 1

Preparation of (compound MCH18-1)

To 1.7 g of 6-nitroquinazolin-2-amine (prepared according the procedure described in WO 2006/039718) in 45 mL of dry dichloromethane at room temperature was added 6.2 mL of triethylamine, 5.85 g of di-tert-butyldicarbonate, and 110 mg of DMAP and the mixture was stirred under nitrogen overnight. The reaction mixture was washed with water, aq. sodium bicarbonate and brine then dried with magnesium sulfate, filtered and evaporated to dryness. Purification by flash chromatography yielded 3.04 g of the protected aniline.

To 0.5 g of the above product in 20 mL of methanol was added 50 mg of 10% palladium on carbon and the mixture was shaken under 40 psi of hydrogen for 45 minutes. The mixture was filtered and evaporated to dryness. Recrystallization from ethyl acetate/hexanes yielded 220 mg of MCH18-1.

Step 2

Synthesis of N-(2-Amino-6-quinazolinyl)-4-[4-fluoro-3-(4-morpholinylcarbonyl)phenyl]-alpha(R)-hydroxy-3-oxo-2(R)-morpholineacetamide (example aa153)

Compound MCH18-1 was converted to aa153 using a procedure similar to the preparation of Example 98.
Analytical Data:
Mass Spectra:

| EXAMPLE | LCMS m/e |
|---|---|
| MCH1-3 | 351.2 (MH+) |
| aa136 | 498.3 (MH+) |
| MCH2-2 | 282.2 (MH-Boc+) |

-continued

| EXAMPLE | LCMS m/e |
|---|---|
| aa137 | 514.0 (MH$^+$) |
| aa138 | 425.2 (MH$^+$) |
| aa39 | 438.8 (MH$^+$) |
| MCH1-5 | 522.2 (MNa$^+$) |
| MCH1-6 | 388.2 (MNa$^+$) |
| aa140 | 452.2 (MH$^+$) |
| aa141 | 478.3 (MH$^+$) |
| aa142 | 406.2 (MH$^+$) |
| aa143 | 439.2 (MH$^+$) |
| aa144 | 512.3 (MH$^+$) |
| aa145 | 526.3 (MH$^+$) |
| aa146 | 526.3 (MH$^+$) |

-continued

| EXAMPLE | LCMS m/e |
|---|---|
| aa147 | 394.2 (MH$^+$) |
| aa148 | 525.2 (MH$^+$) |
| MCH14-1 | MS: 390 (MH$^+$) |
| aa149 | 568.0 (MH$^+$) |
| aa150 | 509.0 (MH$^+$) |
| aa151 | 509.0 (MH$^+$) |
| MCH17-1 | 268.2 (MH$^+$) |
| MCH17-2 | 298.2 (MH$^+$) |
| aa152 | 532.2 (MH$^+$) |
| aa153 | 525.3 (MH$^+$) |

| EXAMPLE | NMR (400 MHz, ppm) |
|---|---|
| aa136 | HCl salt in CD$_3$OD: 7.6 (s, 1H), 7.87 (d, J = 12.1 Hz, 1H), 7.54-7.47 (m, 2H), 7.38-7.34 (m, 2H), 4.84-4.80, m, 4H), 4.28 (s, 2H), 4.24-4.20 (m, 1H), 4.06-4.01 (m, 4H), 3.82-3.80 (m, 2H), 3.73-3.67 (m, 1H) |
| aa137 | HCl salt in CD$_3$OD: 8.77 (dd, J = 8.6, 3.3 Hz, 1H), 8.07 (d, J = 8.6 Hz, 1H), 7.45-7.55 (m, 2H), 7.33-7.41 (m, 2H), 4.87 (br. s., 4H), 4.29 (s, 2H), 4.14-4.25 (m, 1H), 4.01-4.08 (m, 4H), 3.79-3.84 (m, 1H), 3.65 (s, 4H) |
| aa138 | HCl salt in DMSO-d$_6$: 10.25 (s, 1H), 10.19 (s, 1H), 9.6, (s, 1H), 9.13 (s, 1H), 8.31 (s, 1H), 8.16 (d, J = 8.5 Hz, 1H), 7.97 (s, 1H), 7.94 (d, J = 10.3 Hz, 1H), 7.84 (d, J = 7.7 Hz, 1H), 7.64 (d, J = 6.6 Hz, 1H), 7.55 (t, J = 7.5 Hz, 2H), 6.53 (br, 1H), 4.77 (s, 2H), 4.70-4.67 (m, 2H), 4.14-4.11 (m, 1H), 3.98-3.84 (m, 2H), 3.70-3.67 (m, 2H). |
| aa139 | HCl salt in CD$_3$OD: 8.26 (d, J = 1.1 Hz, 1H), 8.06-8.04 (m, 1H), 7.99-7.96 (m, 1H), 7.88 (dd, J = 8.5, 1.8 Hz, 1H), 7.68-7.65 (m, 1H), 7.57 (t, J = 7.7 Hz, 2H), 4.85-4.83 (m, 2H), 4.81 (s, 2H), 4.26-4.20 (m, 1H), 4.08-4.00 (m, 2H), 3.92 (s, 3H), 3.73-3.68 (m, 1H) |
| aa140 | HCl salt in CD$_3$OD: 8.25 (s, 1H), 8.05 (d, J = 8.4 Hz, 1H), 7.88 (d, J = 8.6 Hz, 1H), 7.55 (dd, J = 7.6, 1.4 Hz, 1H), 7.37-7.50 (m, 3H), 4.71-4.84 (m, 4H), 4.17 (d, J = 11.2 Hz, 1H), 3.91-4.08 (m, 2H), 3.58 (d, J = 11.7 Hz, 1H), 3.09 (s, 3H), 2.95 (s, 3H) |
| aa141 | HCl salt in CD$_3$OD: 8.25 (s, 1H), 8.05 (d, J = 8.6 Hz, 1H), 7.87 (d, J = 8.6 Hz, 1H), 7.53-7.60 (m, 1H), 7.39-7.50 (m, 3H), 4.70-4.83 (m, 4H), 4.17 (d, J = 11.2 Hz, 1H), 3.91-4.11 (m, 2H), 3.37-3.66 (m, 5H), 1.80-2.03 (m, 4H) |
| aa142 | HCl salt in CD$_3$OD: 8.98-9.48 (m, 1H), 8.41 (dd, J = 7.9, 1.1 Hz, 1H), 8.26 (s, 1H), 7.95-8.15 (m, 3H), 7.90 (dd, J = 8.6, 1.5 Hz, 1H), 7.83 (t, J = 7.6 Hz, 1H), 5.51 (d, J = 2.0 Hz, 1H), 5.05 (d, J = 2.4 Hz, 1H), 4.79-4.84 (m, 2H), 4.53-4.62 (m, 1H), 4.41-4.51 (m, 2H), 4.13-4.24 (m, 1H) |
| aa143 | HCl salt in CD$_3$OD: 8.26 (s, 1H), 7.99-8.08 (m, 2H), 7.88 (dd, J = 8.6, 1.7 Hz, 1H), 7.66-7.73 (m, 1H), 7.48-7.54 (m, 1H), 7.40 (d, J = 7.9 Hz, 1H), 4.74-4.83 (m, 4H), 4.20-4.28 (m, 1H), 4.02-4.02 (m, 0H), 3.99-4.15 (m, 2H), 3.90 (s, 3H), 3.52-3.59 (m, 1H) |
| aa144 | HCl salt in CD$_3$OD: 8.25 (s, 1H), 8.05 (d, J = 8.6 Hz, 1H), 7.88 (d, J = 8.6 Hz, 1H), 7.46-7.58 (m, 2H), 7.30 (t, J = 8.9 Hz, 1H), 4.79-4.84 (m, 4H), 4.16-4.26 (m, 1H), 3.95-4.08 (m, 2H), 3.76 (d, J = 5.9 Hz, 4H), 3.60-3.70 (m, 3H), 3.41 (br. s., 2H) |
| aa145 | HCl salt in DMSO-d$_6$: 9.77 (s, 1H), 9.22 (s, 1H), 8.31 (s, 1H), 8.23 (d, J = 8.6 Hz, 1H), 7.91 (dd, J = 8.7, 1.2 Hz, 1H), 7.30-7.58 (m, 3H), 4.76 (s, 2H), 4.68 (br. s., 2H), 4.05-4.21 (m, 1H), 3.80-3.99 (m, 2H), 3.61-3.78 (m, 3H), 3.27-3.55 (m, 4H), 3.02-3.19 (m, 1H), 1.14-1.30 (m, 3H) |
| aa146 | HCl salt in DMSO-d$_6$: 9.78 (br. s., 1H), 9.23 (s, 1H), 8.31 (s, 1H), 8.23 (d, J = 8.4 Hz, 1H), 7.85-7.96 (m, 1H), 7.13-7.58 (m, 3H), 4.76 (s, 2H), 4.67 (d, J = 5.7 Hz, 2H), 4.06-4.20 (m, 1H), 3.79-3.98 (m, 2H), 3.60-3.78 (m, 3H), 3.23-3.59 (m, 4H), 3.09 (t, J = 12.6 Hz, 1H), 1.05-1.29 (m, 3H) |
| aa147 | HCl salt in CD$_3$OD: 9.19 (br. s, 2H), 8.68 (br. s., 2H), 7.92-8.00 (m, 2H), 7.75-7.90 (m, 4H), 7.53-7.62 (m, 2H), 4.75-4.87 (m, J = 11.6, 1.9 Hz, 1H), 4.25-4.33 (m, 1H), 3.97-4.14 (m, 3H), 3.56-3.68 (m, 1H) |
| aa148 | HCl salt in DMSO-d$_6$: 10.56 (s, 1H), 9.66 (s, 1H), 9.61 (s, 1H), 8.76 (s, 1H), 8.56 (d, J = 1.8 Hz, 1H), 8.35 (dd, J = 9.2, 1.8 Hz, 1H), 7.56-7.49 (m, 2H), 7.56-7.49 (m, 2H), 7.38 (t, J = 8.9 Hz, 2H), 4.75 (s, 2H), 4.15-4.11 (m, 1H), 4.00-3.83 (m, 2H), 3.78-3.43 (m), 3.25 (br, 2H). |
| aa149 | CDCl$_3$: 8.96 (s, 1H), 8.0 (s, 1H), 7.47 (d, J = 6.3 Hz, 1H), 7.40 (d, J = 8.4 Hz, 1H), 7.36-7.32 (m, 1H), 7.26-7.23 (m, 1H), 7.16 (m, J = 8.9 Hz, 2H), 4.95-4.90 (m, 1H), 4.72 (d, J = 7.4 Hz, 1H), 4.53 (s, 2H), 4.50-4.42 (m, 1H), 4.25 (d, J = 9.5 Hz, 1H), 4.14-4.02 (m, 2H), 3.7-3.62 (m, 4H), 3.55 (d, J = 10.3 Hz, 1H), 2.66-2.51 (m, 4H) |

| EXAMPLE | NMR (400 MHz, ppm) |
|---|---|
| aa150 | DMSOd$_6$: 9.98 (s, 1H), 8.04-8.02 (m, 2H), 7.82-7.80 (m, 1H), 7.72-7.66 (m, 3H), 7.57 (dd, J = 8.8, 1.5 Hz, 1H), 4.73 (d, J = 1.8 Hz, 1H), 4.65 (d, J = 1.8 Hz, 1H), 4.16-4.10 (m, 1H), 3.99-3.90 (m, 2H), 3.78-3.70 (m, 1H). |
| aa151 | DMSOd$_6$: 9.98 (s, 1H), 8.01 (s, 1H), 7.96 (d, J = 9.2 Hz, 2H), 7.71-7.18 (m, 3H), 7.57 (d, J = 7.7 Hz, 1H), 4.73 (d, J = 1.8 Hz, 1H), 4.65 (d, J = 1.8 Hz, 1H), 4.17-4.11 (m, 1H), 3.98-3.89 (m, 2H), 3.74 (m, 1H). |
| aa152 | CD$_3$OD: 8.39 (d, J = 8.4 Hz, 1H), 7.57 (d, J = 7.7 Hz, 1H), 7.56-7.52 (m, 1H), 7.50 (dd, J = 5.9, 2.6 Hz, 1H), 7.30 (t, J = 8.9 Hz, 1H), 4.86 (d, J = 1.8 Hz, 1H), 4.83 (d, J = 1.81 Hz, 1H), 4.24-4.18 (m, 1H), 4.07-3.99 (m, 2H), 3.78-3.75 (m, 4H), 3.65-3.63 (m, 2H), 3.41-3.40 (m, 2H). |
| aa153 | DMSOd$_6$: 10.26 (s, 1H), 9.54 (s, 1H), 8.67 (br. s., 1H), 8.23 (d, J = 8.4 Hz, 1H), 7.68 (d, J = 8.8 Hz, 1H), 7.51 (d, J = 15.4 Hz, 2H), 7.37 (t, J = 8.8 Hz, 1H), 4.68 (d, J = 8.1 Hz, 2H), 4.13 (d, J = 10.6 Hz, 1H), 3.80-3.97 (m, 2H), 3.35-3.75 (m, 7H), 3.25 (br. s., 2H) |

Examples aa154-aa159

Example aa154

(R)-2-((R)-4-(5-fluoro-2-isopropoxyphenyl)-3-oxo-morpholin-2-yl)-2-hydroxy-N-(1-iminoisoindolin-5-yl)acetamide

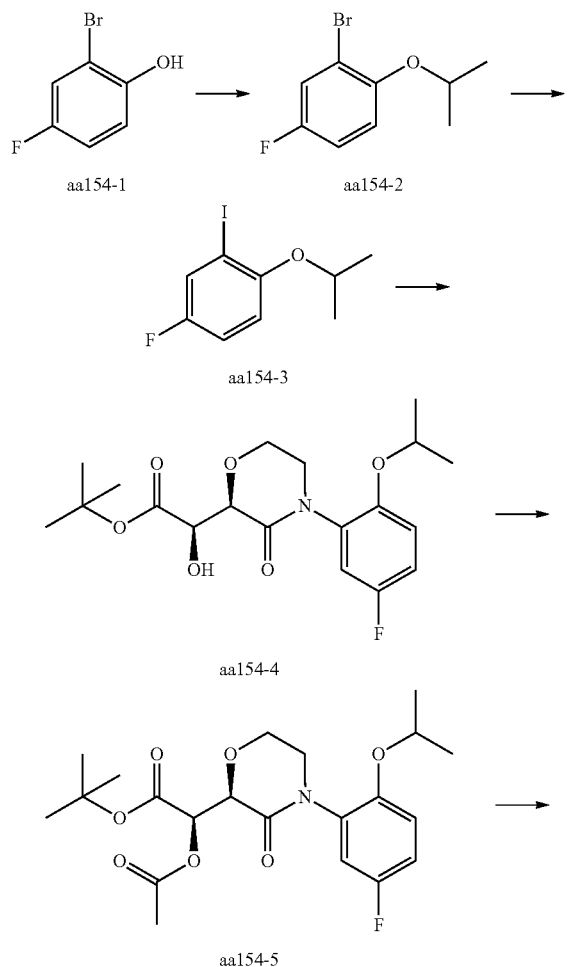

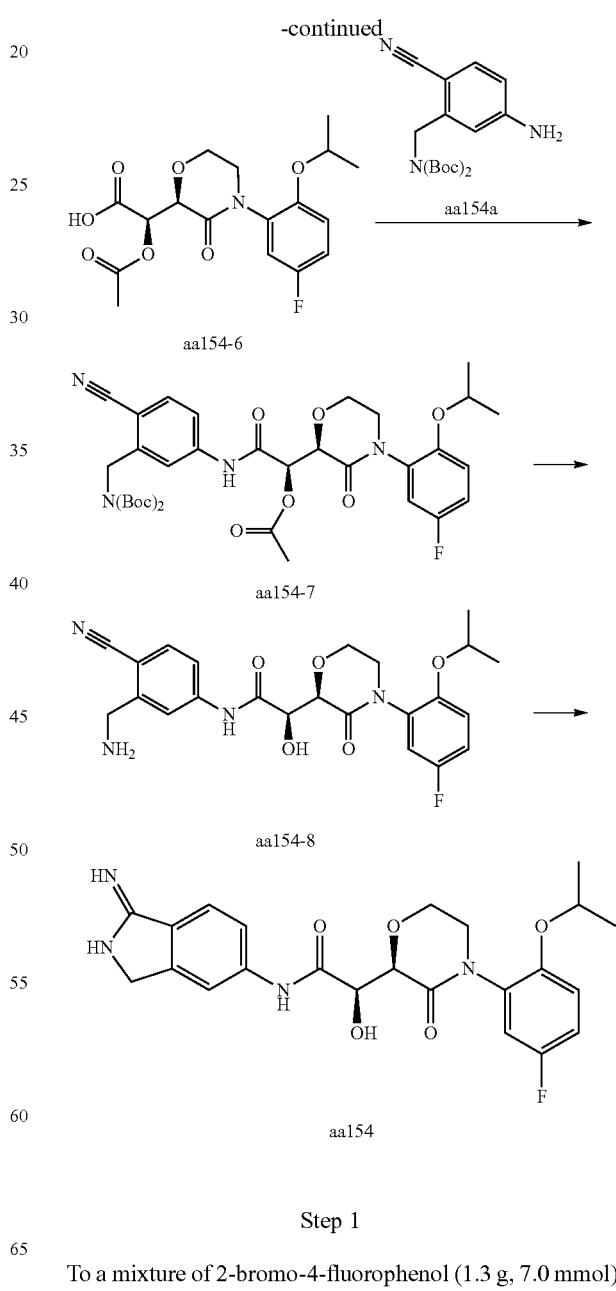

Step 1

To a mixture of 2-bromo-4-fluorophenol (1.3 g, 7.0 mmol) and potassium carbonate (2.0 g, 14 mmol) in DMF (15 mL), 2-iodopropane (1.8 g, 10.5 mmol) was added. The mixture was heated to 55° C. and stirred for 16 h. The reaction mixture was cooled to room temperature and diluted with diethyl ether. The organics were washed with saturated aqueous ammonium chloride, water, and dried with Na$_2$SO$_4$. The organics were evaporated to dryness to give Compound aa154-2 (1.4 g, 86%) which was used without further purification in the next step.

Step 2

To a nitrogen purged vessel, a solution of compound aa154-2 (1.4 g, 6.0 mmol) in 1,4-dioxane (6 mL), sodium iodide (1.8 g, 12.0 mmol), copper iodide (0.057 g, 0.3 mmol), and trans-N,N'-dimethylcyclohexane-1,2-diamine (0.085 g, 0.6 mmol) were added. The vessel was sealed and heated to 110° C. for 16 h. The reaction mixture was cooled to room temperature, washed with saturated aqueous ammonium chloride, and extracted with ethyl acetate. The organics were dried with Na$_2$SO$_4$ and evaporated to dryness to give Compound aa154-3 (1.4 g, 83%) which was used without further purification in the next step.

Step 3

To a nitrogen purged vessel, a solution of compound aa154-3 (1.4 g, 5.0 mmol) in DMSO (40 mL), (R)-tert-butyl 2-hydroxy-2-((R)-3-oxomorpholin-2-yl)acetate (0.96 g, 4.1 mmol), potassium phosphate (1.75 g, 8.2 mmol), copper iodide (0.157 g, 0.82 mmol), and trans-N,N'-dimethylcyclohexane-1,2-diamine (0.116 g, 0.82 mmol) were added. The vessel was sealed and heated to 85° C. for 3 h. The reaction mixture was cooled to room temperature, washed with saturated aqueous ammonium chloride, and extracted with ethyl acetate. The organics were dried with Na$_2$SO$_4$ and evaporated to dryness. The crude material was purified by silica gel chromatography (ethyl acetate/Hexanes 0 to 45%) to give Compound aa154-4 (1.2 g, 76%).

Step 4

To a solution of compound aa154-4 (1.2 g, 3.1 mmol) in DCM (30 mL) that was chilled to 0° C. was added DMAP (0.038 g, 0.31 mmol), pyridine (0.49 g, 6.2 mmol), and acetic anhydride (0.64 g, 6.2 mmol). The reaction was stirred at 0° C. for 3 h. The reaction was diluted with ethyl acetate, washed with aqueous Cu$_2$SO$_4$ and H$_2$O (×3). The organics were dried with Na$_2$SO$_4$ and evaporated to dryness. The crude material was purified by silica gel chromatography (ethyl acetate/Hexanes 0 to 45%) to give Compound aa154-5 (0.9 g, 68%).

Step 5

Compound aa154-5 was dissolved in DCM (20 mL), TFA (10 mL) and H$_2$O (0.1 mL). The reaction was stirred at room temperature for 2 h. The reaction was evaporated to dryness. The residue was dissolved in 50 mL of toluene and evaporated to dryness (×3). The residue was dissolved in 50 mL of hexanes and evaporated to dryness (×2) to give Compound aa154-6 (0.8 g, 100%) which was used without further purification in the next step.

Step 6

According to the step 70-5 in the synthetic method for EXAMPLE 70, compound aa154-6 (0.6 g, 1.6 mmol) was used instead of compound 70-4 to couple to compound aa154a (0.55 g, 1.6 mmol) instead of compound 68-12 to obtain compound aa154-7 (0.16 g, 14%) after chromatography purification on silica gel eluting with DCM/Ethyl Acetate (90/10).

Step 7

According to the step 70-6 in the synthetic method for EXAMPLE 70, compound aa154-7 (0.16 g, 0.23 mmol) was used instead of compound 70-5. The crude reaction mixture was evaporated to dryness and dissolved in 4N HCl in dioxane (3 mL). The reaction was stirred at ambient temperature for two h. The reaction mixture was evaporated to dryness to give compound aa154-8 (0.1 g, 95%) which was used without further purification in the next step.

Step 8

Compound aa154-8 was dissolved in ethanol (5 mL) and heated to 85° C. for 16 h. The reaction was cooled to ambient temperature, evaporated to dryness, and purified by HPLC. The resulting fraction was purified by silica gel chromatography and eluted with DCM/(7N NH$_3$ in MeOH) (90/10) to obtain compound aa154 ((R)-2-((R)-4-(5-fluoro-2-isopropoxyphenyl)-3-oxomorpholin-2-yl)-2-hydroxy-N-(1-iminoisoindolin-5-yl)acetamide) (0.002 g, 2%).

Example aa155

(R)-2-hydroxy-N-(1-iminoisoindolin-5-yl)-2-((R)-3-oxo-4-(2-(trifluoromethyl)phenyl)morpholin-2-yl)acetamide

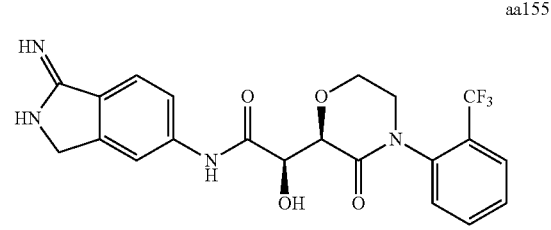 [SMILES: N=C1NCc2cc(NC(=O)[C@H](O)[C@H]3OCCN(c4ccccc4C(F)(F)F)C3=O)ccc21]

aa155

Compound was obtained using the synthetic method for EXAMPLE aa154 beginning from Step 3 using 1-iodo-2-(trifluoromethyl)benzene instead of compound aa154-3.

Example aa156

(R)-2-((R)-4-(2-(difluoromethoxy)phenyl)-3-oxomorpholin-2-yl)-2-hydroxy-N-(1-iminoisoindolin-5-yl)acetamide

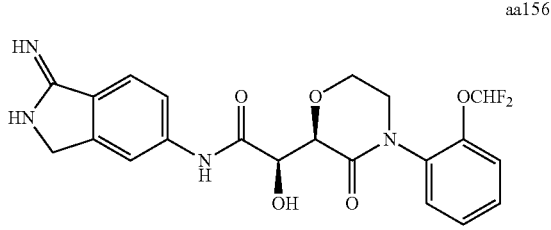 [SMILES: N=C1NCc2cc(NC(=O)[C@H](O)[C@H]3OCCN(c4ccccc4OC(F)F)C3=O)ccc21]

aa156

Compound was obtained using the synthetic method for EXAMPLE aa154 beginning from Step 3 using 1-(difluoromethoxy)-2-iodobenzene instead of compound aa154-3.

Example aa157

(R)-2-hydroxy-N-(1-iminoisoindolin-5-yl)-2-((R)-4-(2-isopropoxyphenyl)-3-oxomorpholin-2-yl)acetamide

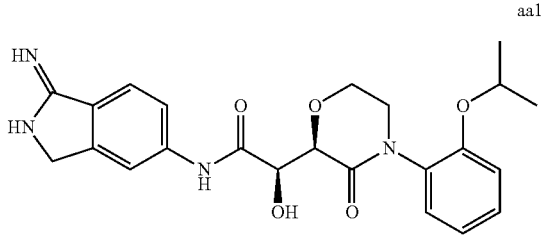

aa157

Compound was obtained using the synthetic method for EXAMPLE aa154 using with 2-iodophenol instead of 2-bromo-4-fluorophenol in Step 1. Step 2 was skipped.

Example aa158

(R)-2-((R)-4-(5-chloro-2-isopropoxyphenyl)-3-oxomorpholin-2-yl)-2-hydroxy-N-(1-iminoisoindolin-5-yl)acetamide

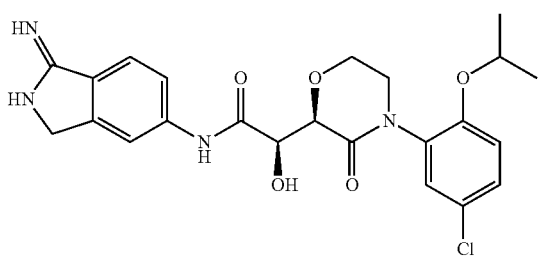

aa158

Compound was obtained using the synthetic method for EXAMPLE aa154 using 2-bromo-4-chlorophenol instead of 2-bromo-4-fluorophenol in Step 1.

Example aa159

(R)-2-hydroxy-N-(1-iminoisoindolin-5-yl)-2-((R)-3-oxo-4-(2-(trifluoromethoxy)phenyl)morpholin-2-yl)acetamide

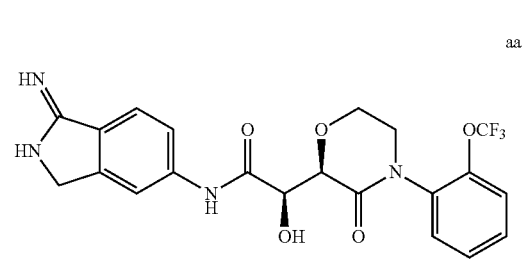

aa159

Compound was obtained using the synthetic method for EXAMPLE aa154 beginning from Step 3 using 1-iodo-2-(trifluoromethoxy)benzene instead of compound aa154-3.

| EXAMPLE | LCMS (MH$^+$) |
| --- | --- |
| aa155 | 449.2 |
| aa156 | 447.2 |
| aa154 | 457.2 |
| aa157 | 439.2 |
| aa158 | 473.2 |
| aa159 | 465.2 |

| EXAMPLE | $^1$H NMR (400 MHz) |
| --- | --- |
| aa155 | (CD$_3$OD) δ 10.04 (s, 1H), 8.24 (s, 1H), 8.04 (d, J = 8.6 Hz, 1H), 7.70-7.94 (m, 3H), 7.62 (t, J = 6.8 Hz, 1H), 7.43-7.55 (m, 1H), 7.00-7.27 (m, 1H), 4.77-4.84 (m, 4H), 4.32 (dt, J = 11.7, 3.8 Hz, 1H), 4.15-4.26 (m, 1H), 3.87-4.11 (m, 2H), 3.59 (d, J = 12.1 Hz, 1H), 3.42-3.52 (m, 1H). |
| aa156 | (CD$_3$OD) δ 8.25 (s, 1H), 8.05 (d, J = 8.6 Hz, 1H), 7.88 (dd, J = 8.6, 1.7 Hz, 1H), 7.39-7.52 (m, 2H), 7.34 (t, J = 8.3 Hz, 2H), 6.79 (t, J = 73.5 Hz, 1H), 4.73-4.85 (m, 3H), 4.18-4.29 (m, 1H), 3.98 (quin, J = 10.8 Hz, 2H), 3.45-3.60 (m, 1H). |
| aa154 | (CD$_3$OD) δ 9.42 (br. s., 1H), 8.99 (br. s., 1H), 8.26 (s, 1H), 8.05 (d, J = 8.4 Hz, 1H), 7.88 (d, J = 8.6 Hz, 1H), 6.95-7.23 (m, 3H), 4.73-4.85 (m, 3H), 4.49-4.67 (m, 1H), 4.21 (d, J = 11.6 Hz, 1H), 4.10-3.80 (m, 2H), 3.40-3.62 (m, 2H), 1.33 (t, J = 5.0 Hz, 4H), 1.17 (t, J = 7.0 Hz, 2H). |
| aa157 | (CD$_3$OD) δ 9.88-10.08 (m, 1H), 9.34-9.52 (m, 1H), 8.99 (br. s, 1H), 8.26 (s, 2H), 8.05 (d, J = 8.4 Hz, 2H), 7.88 (dd, J = 8.6, 1.3 Hz, 2H), 7.33 (t, J = 8.1 Hz, 1H), 7.24 (dd, J = 7.7, 1.3 Hz, 2H), 7.12 (d, J = 8.1 Hz, 3H), 6.98 (t, J = 7.5 Hz, 1H), 4.76-4.85 (m, 3H), 4.67 (quin, J = 6.1 Hz, 1H), 4.22 (d, J = 11.4 Hz, 1H), 3.92-4.08 (m, 2H), 1.34 (dd, J = 5.9, 2.2 Hz, 6H). |

| EXAMPLE | $^1$H NMR (400 MHz) |
|---|---|
| aa158 | (CD$_3$OD) δ 10.02 (s, 1H), 9.42 (br. s., 1H), 8.99 (br. s., 1H), 8.25 (s, 1H), 8.04 (d, J = 8.6 Hz, 1H), 7.88 (d, J = 8.4 Hz, 1H), 7.21-7.46 (m, 2H), 7.12 (d, J = 8.8 Hz, 1H), 4.76-4.84 (m, 3H), 4.57-4.72 (m, 1H), 4.15-4.27 (m, 1H), 3.93-4.06 (m, 1H), 3.43-3.56 (m, 1H), 1.34 (dd, J = 6.0, 2.5 Hz, 6H). |
| aa159 | (CD$_3$OD) δ 8.25 (s, 1H), 8.05 (d, J = 8.6 Hz, 1H), 7.89 (dd, J = 8.6, 1.7 Hz, 1H), 7.38-7.57 (m, 4H), 4.77-4.84 (m, 3H), 4.18-4.31 (m, 1H), 3.90-4.10 (m, 2H), 3.57 (d, J = 8.6 Hz, 1H). |

Examples aa160-aa163

Example aa160

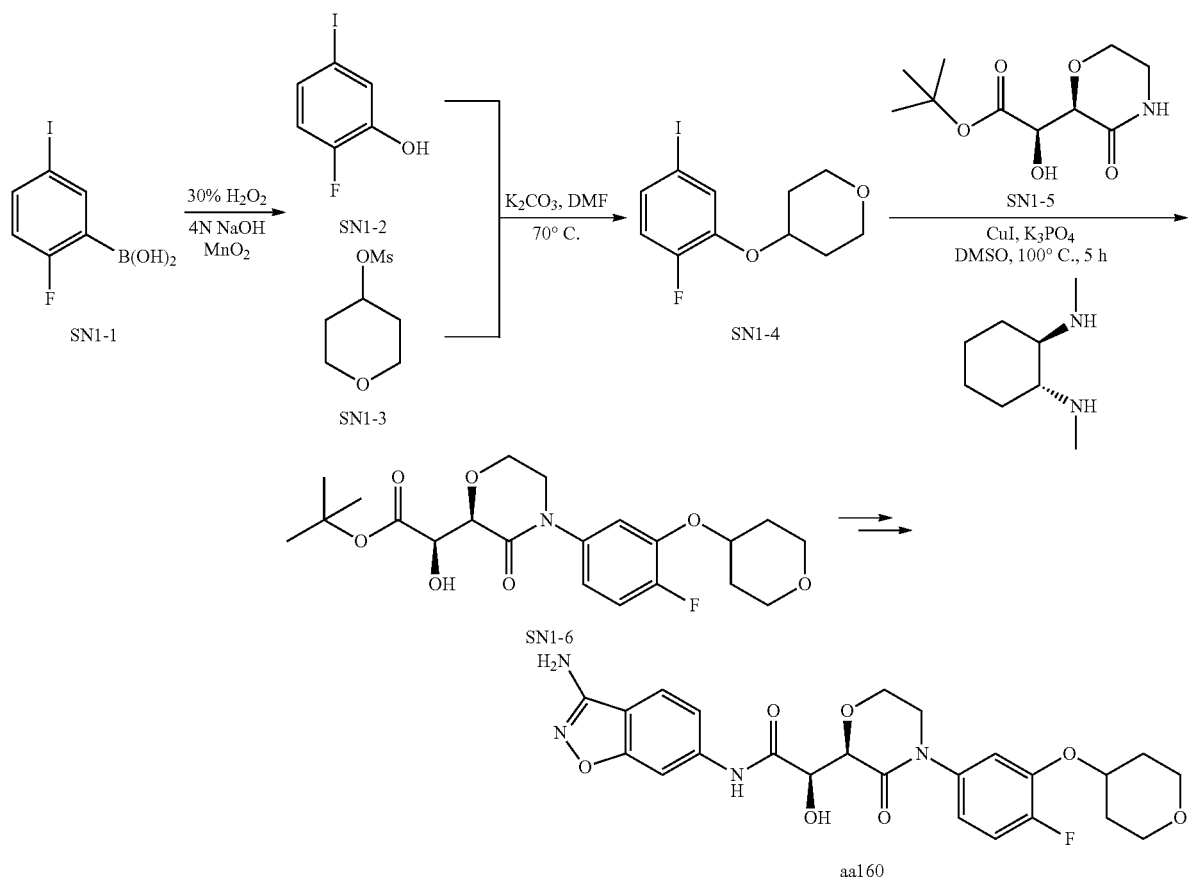

aa160

Step 1-2

Synthesis of SN1-2

To a cooled solution of 2-fluoro-5-iodophenylboronic acid (5.0 g, 18.81 mmol) in THF (200 mL) at 0° C. was added an aqueous solution of 30% H$_2$O$_2$ (1.73 mL, 18.0 mmol) dropwise and stirred for 10 min. This was followed by the addition of an aqueous solution of 4N NaOH (0.3 mL, 1.2 mmol). The reaction was then warmed to rt and stirred overnight. MnO$_2$ (40.0 mg) was then added to the reaction mixture and stirred for 90 min. The reaction mixture was then filtered and concentrated and partitioned between diethyl ether (150 mL) and water (150 mL). Separated the organics and washed further with brine and dried. The product was purified by eluting with silica-gel from 100:0 to 70:30 hexanes to ethyl acetate to give the product SN1-2 (3.4 g, 76%).

Step 1-4

Synthesis of SN1-4

To a sealed tube was added SN1-2 (218 mg, 0.92 mmol), commercially available tetrahydro-2H-pyran-4-yl methanesulfonate (0.2 g, 1.1 mmol), potassium carbonate (0.384 g, 2.78 mmol) in DMF (4.0 mL) and heated at 70° C. overnight. The reaction mixture was then cooled and extracted with ethyl acetate. The organics were washed multiple times with water and brine and this was followed by washing with 1M NaOH. The organic fractions were concentrated and purified over column chromatography using 25% acetone/hexanes to give product SN1-4 (120 mg, 41%). The yield of this reaction was greatly improved by heating at 100° C. for a similar substrate.

Step 1-6

Synthesis of SN1-6

A mixture of aryl iodide SN1-4 (0.120 g, 0.37 mmol), previously described SN1-5 (0.064 g, 0.28 mmol), CuI (11 mg, 0.056 mmol), $K_3PO_4$ (119 mg, 0.56 mmol) and trans-N,N'-dimethylcyclohexane-1,2-diamine (9 μL, 0.056 mmol) were stirred in DMSO (4.0 mL). The degassed reaction mixture was then heated at 100° C. for 5.0 h. The reaction was then cooled, quenched with water, extracted with EtOAc and washed with brine. The organic fractions were concentrated and purified with 50-60% EtOAc/hexanes to give the product SN1-6 (0.084 mg, 71%).

Synthesis of aa160

N-(3-Amino-1,2-benzisoxazol-6-yl)-4-[4-fluoro-3-[(tetrahydro-2H-pyran-4-yl)oxy]phenyl]-alpha(R)-hydroxy-3-oxo-2(R)-morpholineacetamide The iodide SN1-6 was converted to aa160 using experimental procedure described for the preparation of aa95.

Example aa161

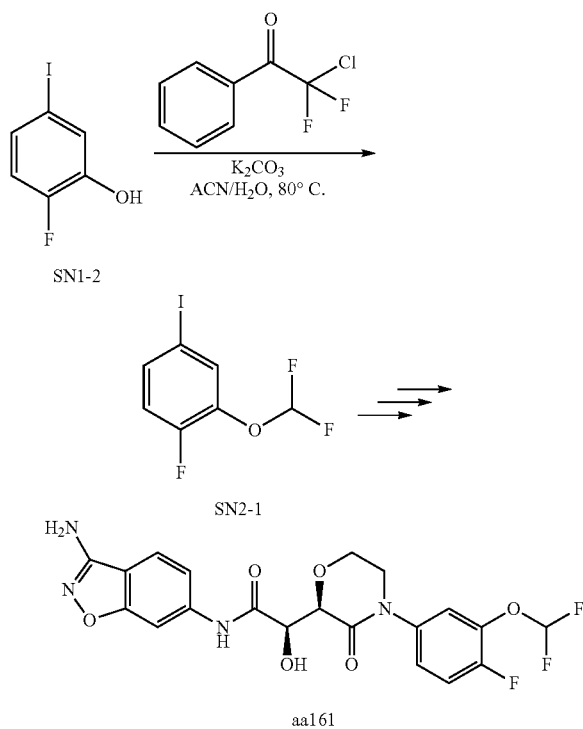

Step 2-1

Synthesis of 2-1

A mixture of aryl iodide SN1-2 (1.0 g, 4.2 mmol), potassium carbonate (21.0 g, 151.9 mmol), 2-chloro-2,2-difluoro-1-phenylethanone (3.9 g, 20.5 mmol) were stirred in acetonitrile/water (1:1, 50 mL) and heated in a sealed tube at 85° C. for 5.0 h. The reaction mixture was cooled and the organics were extracted thrice with ether. The ether fractions were washed with 1M NaOH and concentrated. The product was purified by column chromatography with 10-20% EtOAc/hexanes to give the product SN2-1 (0.5 g, 42%).

Synthesis of aa161

N-(3-Amino-1,2-benzisoxazol-6-yl)-4-[3-(difluoromethoxy)-4-fluorophenyl]-alpha(R)-hydroxy-3-oxo-2(R)-morpholineacetamide The iodide SN2-1 was converted to aa161 using experimental procedure similar to the preparation of aa95.

Example aa162

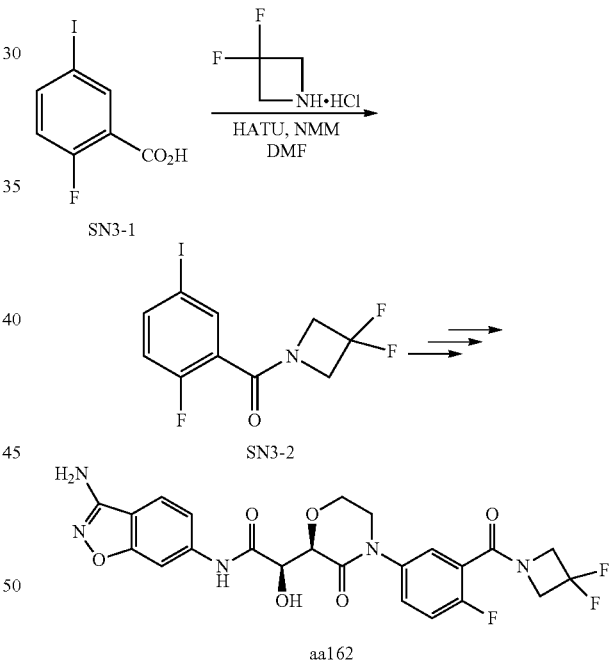

Step 3-2

Synthesis of SN3-2

To commercially available SN3-1 (0.5 g, 1.88 mmol) was added 3,3-difluoroazetidine hydrochloride (0.244 g, 1.88 mmol), HATU (1.17 g, 3.1 mmol), NMM (1.2 mL, 11 mmol) in DMF (4.0 mL) and stirred at 0° C. The reaction was quenched with $NH_4Cl$ and extracted with ethyl acetate. The organics were washed with brine, concentrated and purified by column chromatography using 40% EtOAc/Hexanes to give the product SN3-2 (0.45 g, 70%).

Synthesis of aa162

N-(3-Amino-1,2-benzisoxazol-6-yl)-4-[3-[(3,3-difluoro-1-azetidinyl)carbonyl]-4-fluoro phenyl]-alpha(R)-hydroxy-3-oxo-2(R)-morpholineacetamide The iodide SN3-2 was converted to aa162 using experimental procedure described for the preparation of aa95.

Example aa163

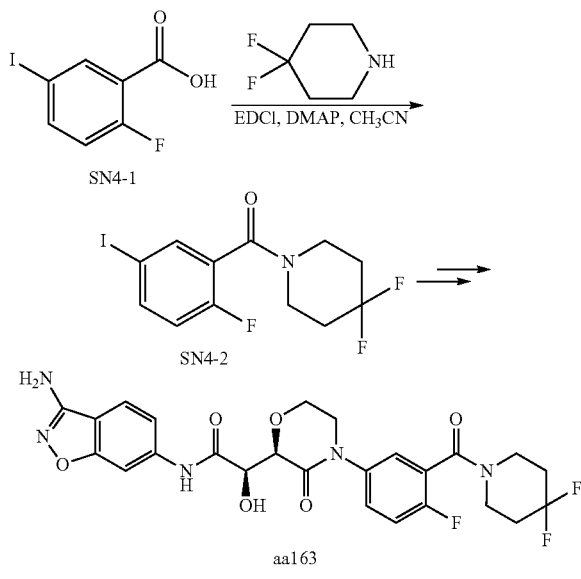

Step 4-2

Synthesis of SN4-2

2-fluoro-5-iodobenzoic acid (1.1 g, 4.14 mmol) was dissolved in CH₃CN (20 mL) and cooled to 0° C. 4,4-Difluoropiperidine (0.6 g, 4.96 mmol) was added to the mixture followed by EDCI (0.95 g, 4.96 mmol) and DMAP (0.05 g, 0.41 mmol) and the resulting mixture was stirred overnight at room temperature. Reaction mixture was diluted with ethyl acetate and washed with saturated NH₄Cl, water and brine respectively. Organic layer was dried over anhydrous MgSO₄, filtered, concentrated, purified by silica gel column chromatography using (0-70) % ethyl acetate-hexanes as mobile phase and the product SN1-1 (1.15 g, 75.65%) was obtained.

Synthesis of aa163

N-(3-Amino-1,2-benzisoxazol-6-yl)-4-[3-[(4,4-difluoro-1-piperidinyl)carbonyl]-4-fluorophenyl]-alpha(R)-hydroxy-3-oxo-2(R)-morpholineacetamide The iodide SN4-2 was converted to aa163 using experimental procedure similar to the preparation of aa95.
Analytical Data:
Mass Spectra:

| EXAMPLE | LCMS m/e |
|---------|----------|
| aa160 | 501 (M + H)⁺ |
| aa161 | 467 (M + H)⁺ |
| aa162 | 520 (M + H)⁺ |
| aa163 | 548 (M + H)⁺ |

| EXAMPLE | NMR (400 MHz, ppm) |
|---------|---------------------|
| aa160 | CDCl₃: 9.06 (s, 1H), 7.97 (s, 1H), 7.38 (d, 1H, J = 8.4 Hz), 7.22 (d, 1H, J = 8.4 Hz), 7.10-7.05 (m, 1H), 7.00-6.98 (m, 1H), 6.86-6.82 (m, 1H), 5.09 (br s, 1H), 4.94 (br d, 1H, J = 5.5 Hz), 4.89 (br s, 1H), 4.62 (s, 2H), 4.40-4.36 (m, 1H), 4.22-4.19 (m, 1H), 3.52-3.42 (m, 5H), 1.98-1.87 (m, 2H), 1.80-1.70 (m, 4H). |
| aa161 | DMSO-d₆: 9.97 (s, 1H), 8.01 (d, 1H, J = 1.1 Hz), 7.68 (d, 1H, J = 8.4 Hz), 7.56 (dd, 1H, J = 8.4, 1.5 Hz), 7.51-7.43 (m, 2H), 7.36-7.32 (m, 1H), 7.25 (s, 1H), 6.43 (d, 1H, J = 6.97 Hz), 6.32 (s, 2H), 4.68 (d, 1H, J = 1.8 Hz), 4.63 (dd, 1H, J = 6.6, 1.8 Hz), 4.14-4.10 (m, 1H, J = 1.0 Hz), 3.95-3.82 (m, 2H), 3.66-3.62 (m, 1H). |
| aa162 | CDCl₃: 8.86 (s, 1H), 8.01 (d, 1H, J = 1.5 Hz), 7.65-7.63 (m, 1H); 7.51-7.47 (m, 1H), 7.45 (d, 1H, J = 8.4 Hz), 7.30 (dd, 1H, J = 8.8, 1.5 Hz), 7.18 (t, 1H, J = 9.2 Hz), 4.94-4.90 (m, 2H), 4.53-4.44 (m, 4H), 4.38 (s, 2H), 4.26-4.22 (s, 1H), 4.14-4.02 (m, 2H), 3.97-3.95 (m, 1H), 3.59-3.56 (m, 1H). |
| aa163 | DMSO-d₆: 9.99 (s, 1H); 8.02 (s, 1H), 7.69 (d, 1H, J = 8.8 Hz); 7.57-7.54 (m, 3H); 7.40 (t, 1H, J = 9.4 Hz); 6.43 (d, 1H, J = 6.9 Hz); 6.31 (s, 2H); 4.69 (d, 1H, J = 1.8 Hz); 4.66 (dd, 1H, J = 1.8, 6.6 Hz); 4.14 (dd, 1H, J = 2.2, 8.8 Hz); 3.94 ppm (m, 4H); 3.66 (dd, 1H, J = 2.2, 9.2 Hz); 3.37 (t, 2H, J = 5.5 Hz); 2.12-1.90 (m, 4H). |

Example aa164-aa165

Example aa164

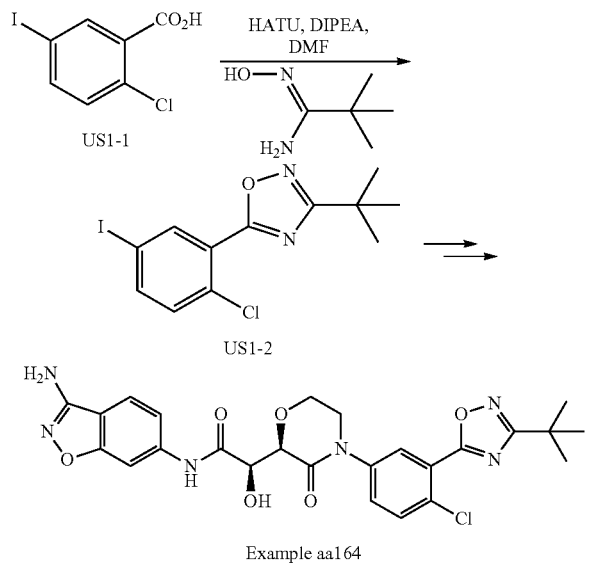

Example aa164

Synthesis of intermediate US1-2 (3-tert-butyl-5-(2-chloro-5-iodophenyl)-1,2,4-oxadiazole)

To a solution of 2-chloro-5-iodobenzoic acid (1.0 g, 3.54 mmol) in 40 mL DMF was added diisopropylethyl amine (1.23 mL, 7.08 mmol) followed by HATU (2.02 g, 5.31 mmol). After stirring the reaction at room temperature for 10 min, N-hydroxy-2,2-dimethylpropanimidamide (0.82 g, 7.08 mmol) was added. The resulting reaction mixture was stirred at room temperature for 1 h and then at 110° C. for 16 h. After cooling to room temperature the reaction was quenched with water and extracted with ethyl acetate. The combined organic fractions were washed with brine, dried ($Na_2SO_4$), concentrated, and purified by flash chromatography (2-5% EtOAc in hexanes) to yield 660 mg of intermediate US1-2.

Synthesis of Example aa164

N-(3-amino-1,2-benzisoxazol-6-yl)-4-[4-chloro-3-[3-(1,1-dimethylethyl)-1,2,4-oxadiazol-5-yl]phenyl]-alpha(R)-hydroxy-3-oxo-2(R)-morpholineacetamide Intermediate US1-2 was converted to Example aa164 using previously described procedures.

Example aa165

N-(3-amino-1,2-benzisoxazol-6-yl)-4-[2-fluoro-5-(trifluoromethyl)phenyl]-alpha(R)-hydroxy-3-oxo-2(R)-morpholineacetamide

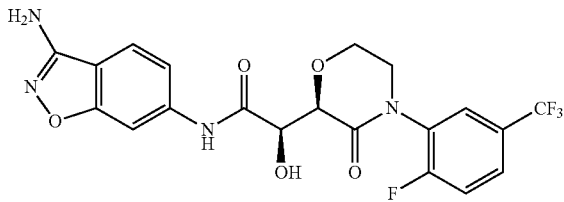

Example aa165

Example aa165 was prepared starting from 1-fluoro-2-iodo-4-(trifluoromethyl)benzene using previously described procedures.

Analytical Data:
Mass Spectra:

| EXAMPLE | LCMS (M + H)+ |
|---|---|
| aa164 | 541.3, 543.3 |
| aa165 | 469.2 |

$^1$H-NMR Data:

| EXAMPLE | NMR (400 MHz, ppm) |
|---|---|
| aa164 | CDCl$_3$: 8.91 (1H, brs), 8.03 (2H, d, J = 12.9 Hz), 7.59-7.42 (3H, m), 7.28-7.26 (m, 1H), 4.97-4.94 (2H, m), 4.42 (2H, brs), 4.37-4.25 (2H, m), 4.19-4.05 (2H, m), 3.33 (1H, d, J = 11 Hz), 1.43 (9H, s) |
| aa165 | DMSO: 10.0 (1H, s), 8.02 (1H, s), 7.93 (1H, dd, J = 2.2, 7.0 Hz), 7.84-7.80 (1H, m), 7.68 (1H, d, J = 8.8 Hz), 7.62-7.56 (2H, m), 6.45 (1H, d, J = 7.0 Hz), 6.32 (2H, brs), 4.72 (1H, d, J = 1.8 Hz), 4.62 (1H, dd, J = 1.8, 7.0 Hz), 4.17-4.13 (1H, m), 4.0-3.94 (1H, m), 3.91-3.84 (1H, m), 3.61 (1H, d, J = 11.7 Hz) |

Utility

The invention also relates to medicaments which contain an efficacious amount of at least one compound of the Formula (I) and/or of a pharmaceutically acceptable salt of the compound of the Formula (I) and/or an optionally stereoisomeric form of the compound of the Formula (I), together with a pharmaceutically suitable and pharmaceutically acceptable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the Formula (I) can be employed in patients who are suffering from disorders of well-being or diseases which accompany thromboses, embolisms, hypercoagulability or fibrotic changes.

These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the Formula (I) can be employed in all interventions which lead to contact of the blood with foreign surfaces, as in dialysis patients and patients with indwelling catheters. Compounds of the Formula (I) can also be employed in order to reduce the risk of thrombosis after surgical interventions such as in knee and hip joint operations.

Compounds of the Formula (I) are suitable for the treatment of patients with disseminated intravascular coagulation, sepsis and other intravascular events which accompany inflammation. Furthermore, compounds of the Formula (I) are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the Formula (I) are suitable for the retardation or prevention of such processes.

Further indications for the use of the compounds of the Formula (I) are fibrotic changes of the lungs such as chronic obstructive pulmonary disease, adult respiratory distress syndrome (ARDS) and of the eye, such as fibrin deposits after eye operations. Compounds of the Formula (I) are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the Formula (I) according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to Formula (I), daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the Formula (I) can be administered both as a monotherapy and in combination or together with all antithrombotics (anticoagulants and platelet aggregation inhibitors), thrombolytics (plasminogen activators of any type), other profibrinolytically active substances, hypotensives, blood sugar regulators, lipid-lowering agents and antiarrhythmics.

The inhibitory effectiveness of compounds of the present invention to the coagulation factors XIa, VIIa, IXa, Xa, plasma kallikrein or thrombin, can be determined using a relevant purified serine protease, respectively, and an appropriate synthetic substrate.

Pharmacological Examples

Determination of Inhibitory Activity Against Factor IXa

Inhibitory activity against factor IXa was tested using the substrate SPECTROFLUOR FIXa (american diagnostica inc.; 500 West Avenue, Stamford, Conn. 06902 USA; Pr. No. 299F) and human factor IXa (american diagnostica inc.; Pr. No. 449b). Test substances dissolved in buffer A (50 mM $\alpha,\alpha,\alpha$-tris(hydroxymethyl)methylamine (Tris), 100 mM NaCl, 5 mM $CaCl_2$, 15% (v/v) ethylene glycol, pH 8.0) were mixed with factor IXa (2.0 µg/ml final concentration). The enzyme reaction was started by addition of SPECTROFLUOR FIXa (100 µM final concentration). After incubation for 60 minutes at room temperature, the reaction was stopped by the addition of 20% (v/v) acetic acid solution, and then measured the fluorescence value (Excitation Wavelength: 355 nm, Emission Wavelength; 460 nm) in a microtiter plate reader (ARVO 1420 Multilabel Counter; PerkinElmer).

The $IC_{50}$ was calculated from a dilution series of the test substance with the aid of the software, Symix Assay Explorer (Symyx Technologies, Inc.). Tables 5a and 5b show the results.

TABLE 5a

| Compound from Example | Factor IXa enzyme assay $IC_{50}$ [micro M] | Compound from Example | Factor IXa enzyme assay $IC_{50}$ [micro M] |
|---|---|---|---|
| 1 | 0.04 | 2 | 0.03 |
| 15 | 0.02 | 21 | 0.13 |
| 50 | 0.02 | 62 | 0.02 |
| 67 | 0.06 | 105 | 0.01 |
| 109 | 0.06 | 114 | 0.03 |

TABLE 5b

| Example | Factor IXa enzyme assay $IC_{50}$ [nM] |
|---|---|
| a1 | 32 |
| a3 | 12 |
| a6 | 9.3 |
| a11 | 9.6 |
| a21 | 9 |
| aa142 | 66 |
| aa144 | 13 |
| aa150 | 83 |
| aa151 | 380 |
| aa152 | 1200 |

In one embodiment, the compounds of the present invention were selective factor IXa inhibitors, i.e., selective for factor IXa over other coagulation factors, such as factor Xa.

Determination of Inhibitory Activity Against Factor Xa

This measuring was performed as well as Factor IXa method excluding the following conditions. As substrate and enzyme, SPECTROFLUOR FXa (american diagnostica inc.; Pr. No. 222F, 100 µM final concentration) and human factor Xa (american diagnostica inc.; Pr. No. 526, 44 ng/ml final concentration) were used respectively. Test substances dissolved in buffer B (20 mM Tris, 200 mM NaCl, 2.5 mM $CaCl_2$, pH 8.0).

Selectivity Calculation

Selectivity for Factor IXa activity over Factor Xa activity can be determined by the following calculation: (IC50 Factor Xa)/(IC50 Factor IXa). Similar calculations can be made for selectivity of compounds for Factor IXa compared to other coagulation factors.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

A number of references have been cited, the entire disclosures of which have been incorporated herein in their entirety.

The compounds of the present invention may also be useful as inhibitors of additional serine protease, notably human thrombin, human plasma kallikrein and human plasmin. Because of their inhibitory action, these compounds are indicated for use in the prevention or treatment of physiological reactions, as it were "Conditions" including thromboembolic disorder (arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis), blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents anti-platelet or platelet inhibitory agents, anti-inflammatory agents, thrombin inhibitors, thrombolytic or fibrinolytic agents, thrombin receptor (PAR-1) antagonist, a factor VIIa inhibitor, factor VIIIa inhibitor, a factor IXa inhibitor different from the compound of claim 1, a factor Xa inhibitor, a factor XIa inhibitor, TAFI, and fibrinogen inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANO), aprotinin, synthetic pentasaccharide, direct acting thrombin inhibitors including hirudin and argatroban, as well as other factor VIIa inhibitor, VIIIa inhibitor, IXa inhibitor, Xa inhibitor, XIa inhibitor, thrombin inhibitor, fibrinogen inhibitors, TAFI, and known in the art. Factor IXa inhibitors different from the compounds of Formula (I) include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulants. *Arterioscler Thromb Vasc Biol.* 2007; 27: 722-727.).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-111 (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptiders include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and WO 01/96330 and Ser. No. 10/271,715.

Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); K+ cannel openers such as IAch inhibitors, and IKur inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamterene, amiloride, spironolactone); rennin inhibitors; angiotensin-converting enzyme (ACE) inhibitors (e.g., captopril, Lisinopril, fosinopril, enalapril, ceranopril, cilazopril, delapril, pentopril, quinapril, ramipril, Lisinopril); angiotensin-II-receptor antagonists (e.g., irbestatin, Losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual CCE/NEP inhibitors, e.g., omapatrilat, gemopatrilat, nitrates); and β-blockers (e.g., propranolol, nadolol, or carvedilol).

Examples of suitable cardiac glycosides for use in combination with compounds of the present invention include digitalis and ouabain.

Examples of suitable mineralocorticoid receptor antagonists for use in combination with the compounds of the present invention include spironolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atrbastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagons-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; piroxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitor (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporine A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

What is claimed is:

1. A compound of the Formula:

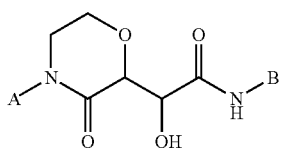

or a pharmaceutically acceptable salt thereof, wherein A is

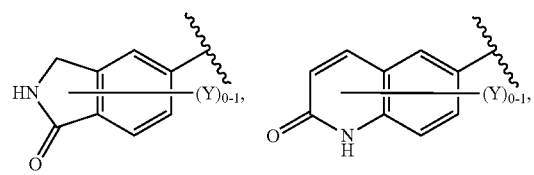

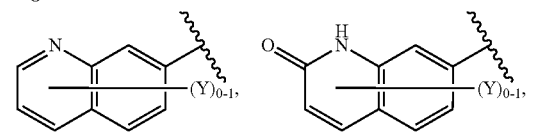

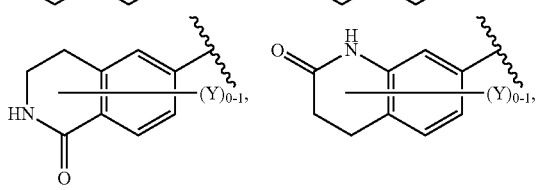

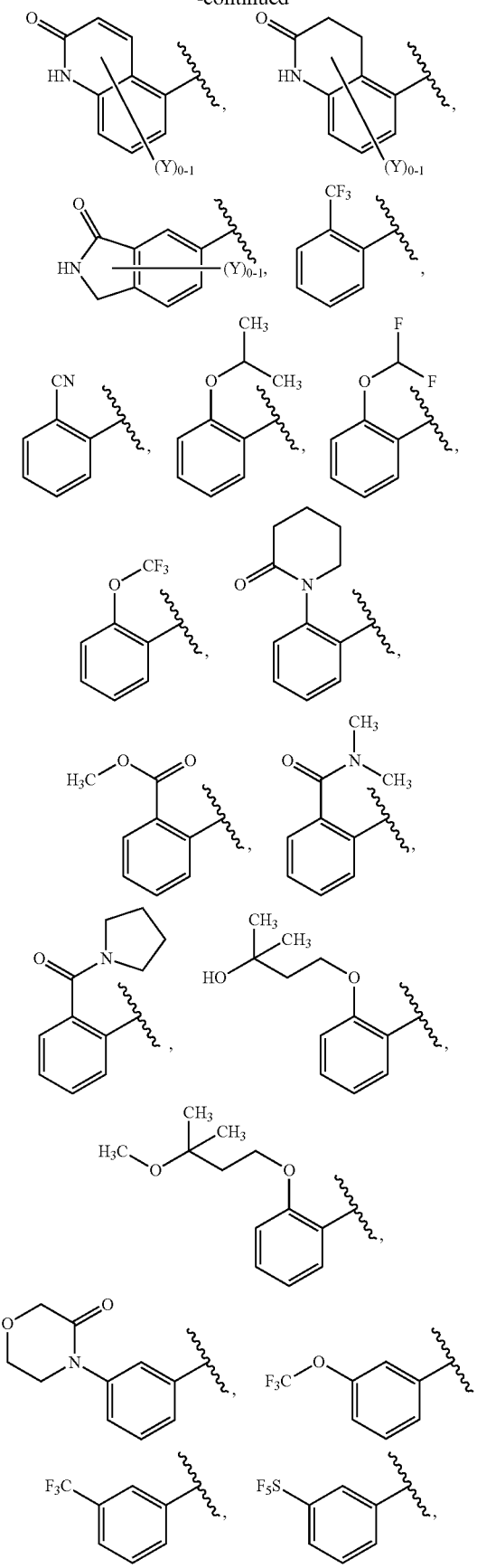

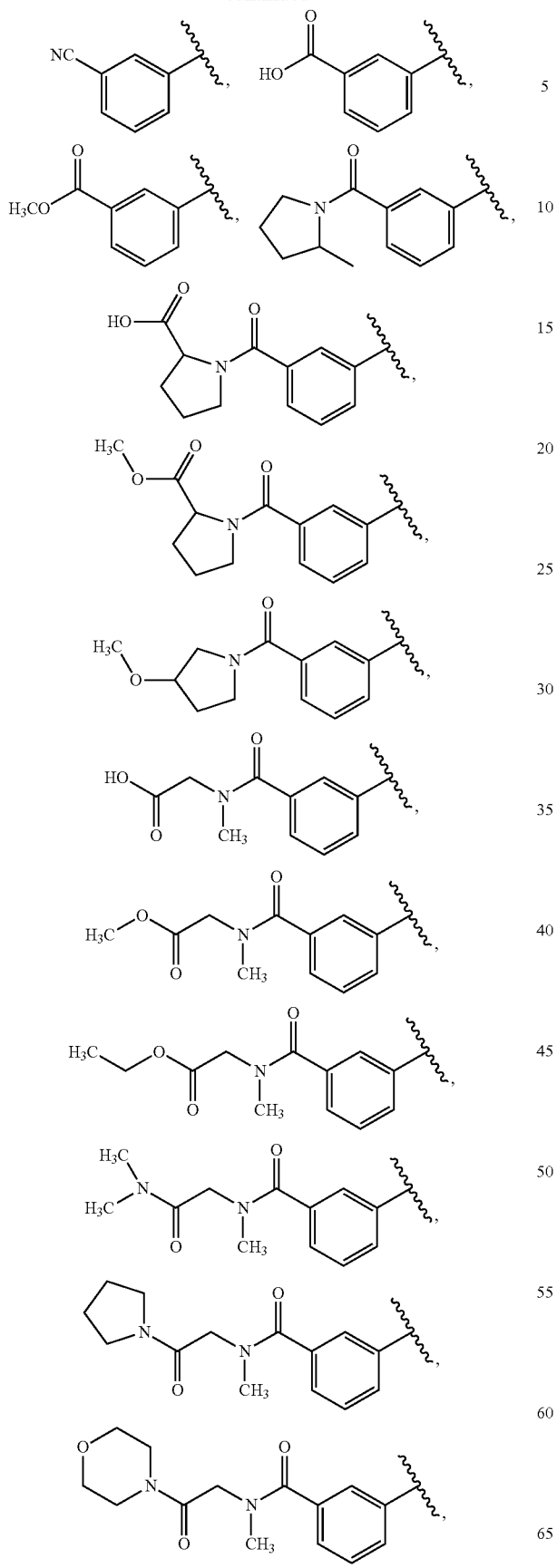
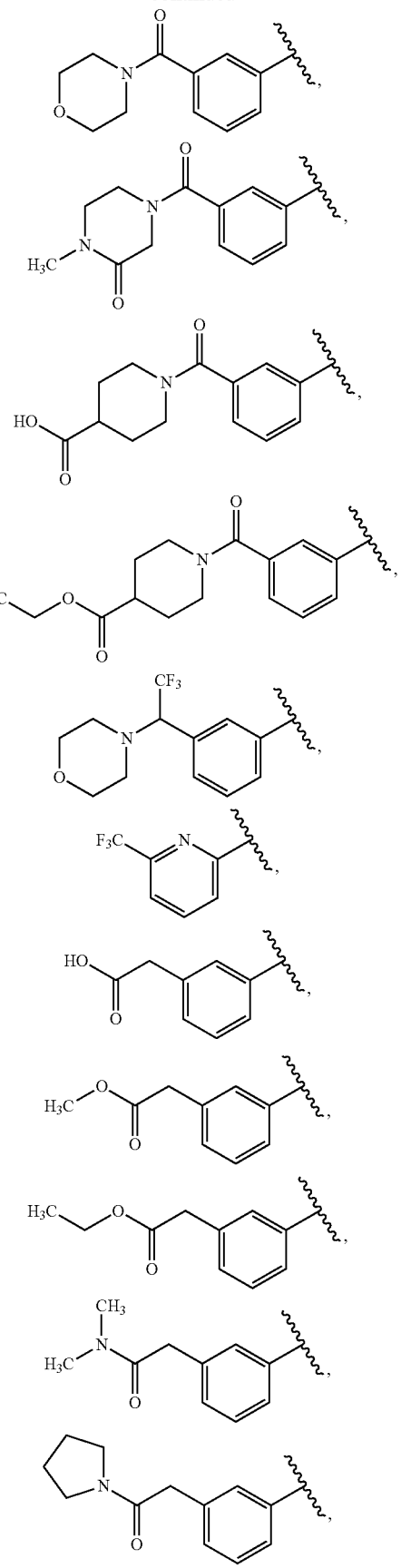

887
-continued
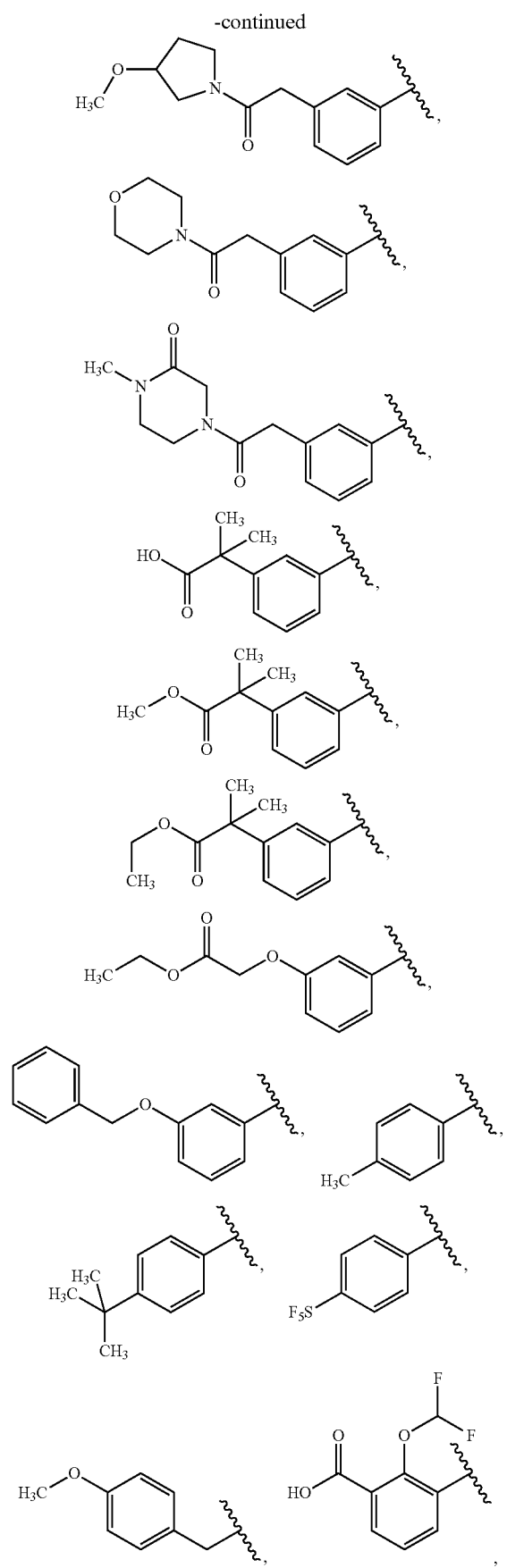
888
-continued
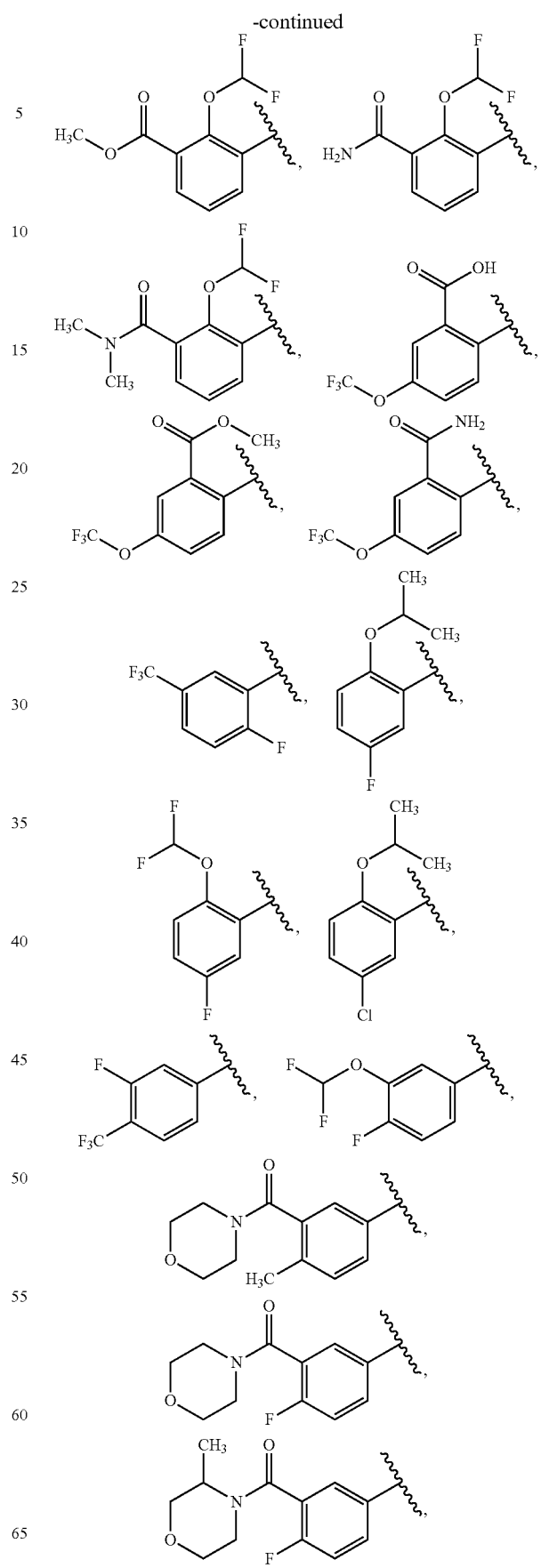

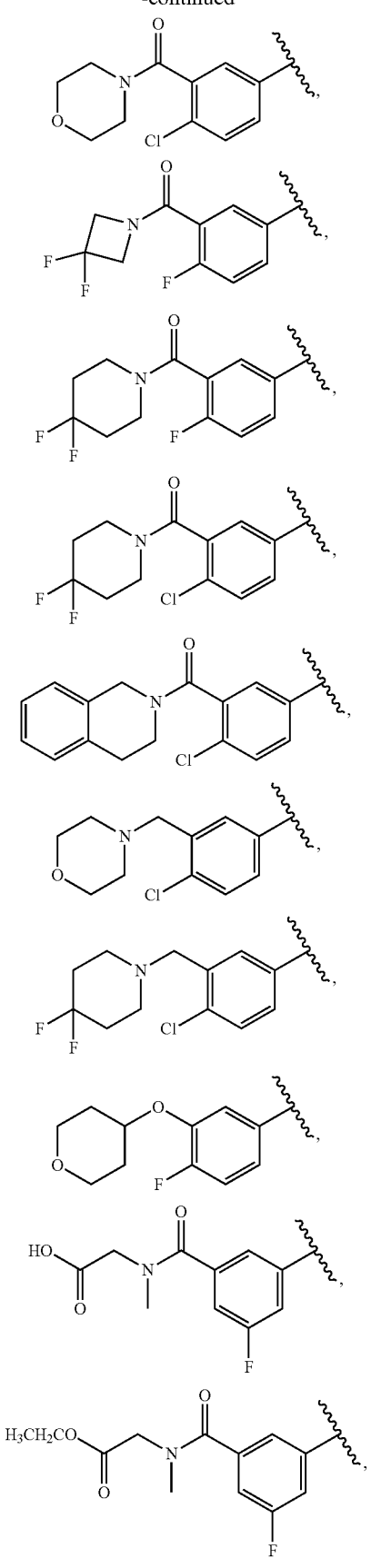
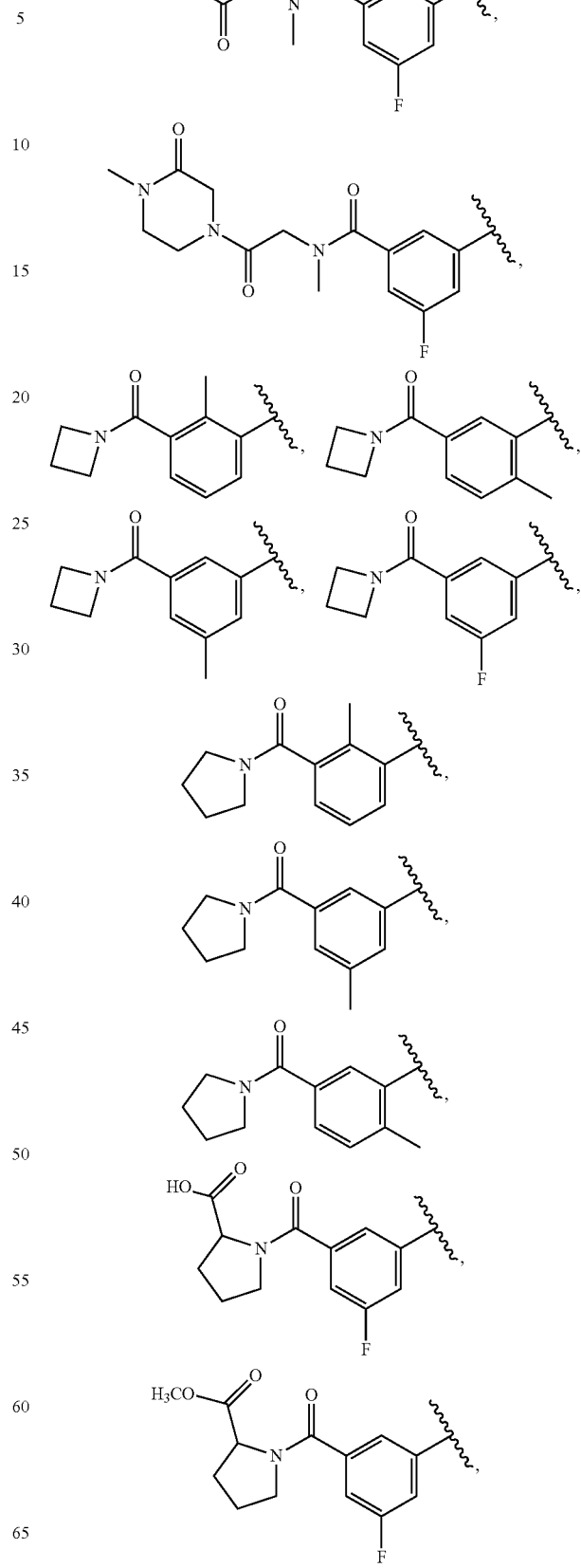

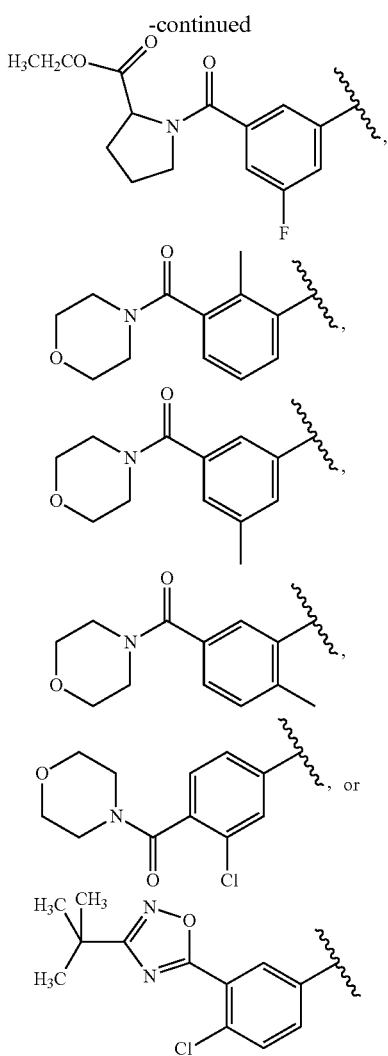
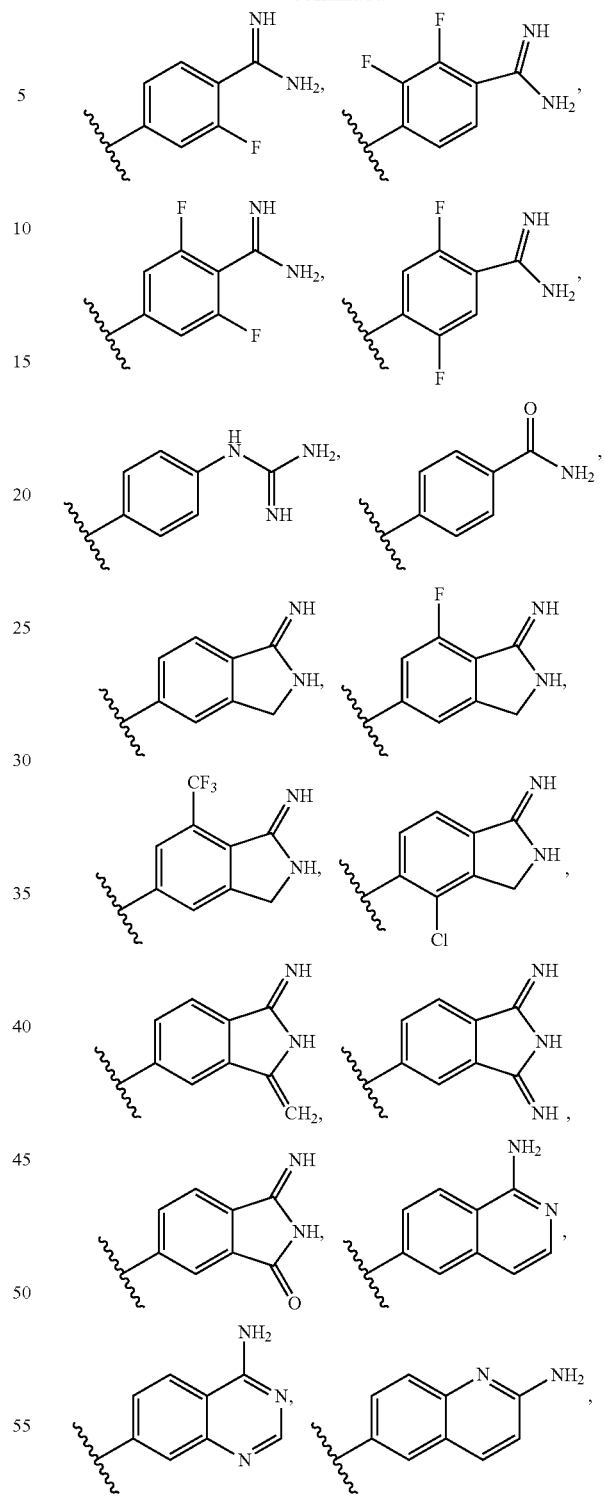
Y, attached to a carbon or nitrogen ring atom, is
1) halogen,
2) —(C$_1$-C$_6$)-alkyl,
3) —(C$_1$-C$_3$)-haloalkyl,
4) —(C$_3$-C$_8$)-cycloalkyl,
5) —OH,
6) —O—(C$_1$-C$_6$)-alkyl,
7) —O—(C$_1$-C$_3$)-haloalkyl,
8) =O (oxo),
wherein said —(C$_1$-C$_6$)-alkyl part of 2) and 6) of said Y is unsubstituted or substituted independently with the substituents selected from the group consisting of —(C$_3$-C$_8$)-cycloalkyl, —C(O)OH, and —C(O)—(C$_1$-C$_6$)-alkyl,
B is
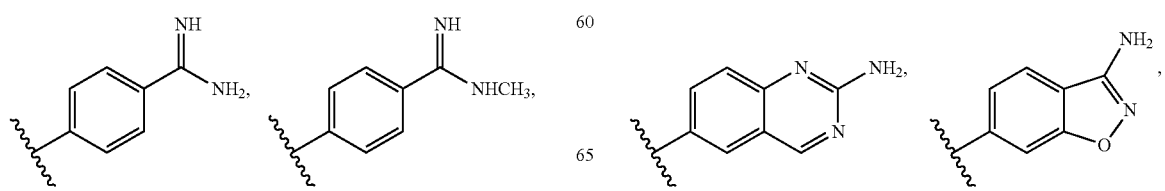

-continued
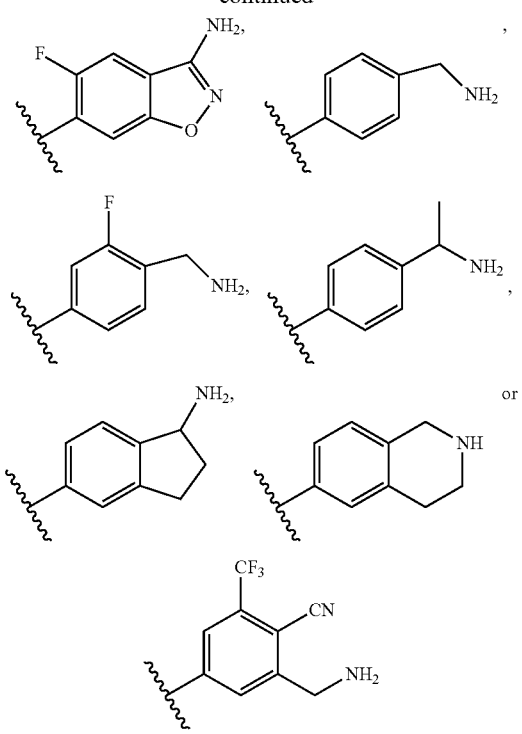
provided that when A is
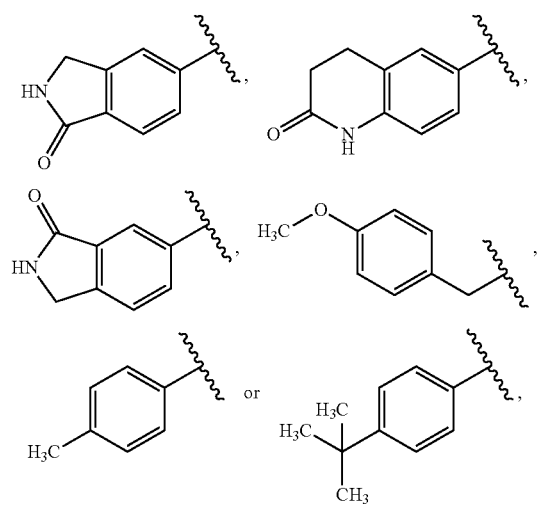
B is not
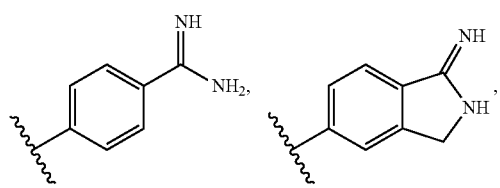
-continued
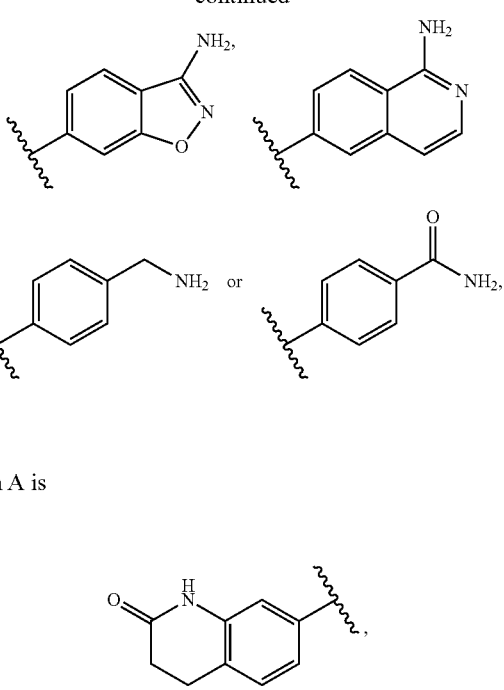
and
when A is
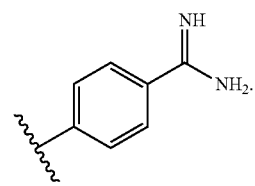
B is not
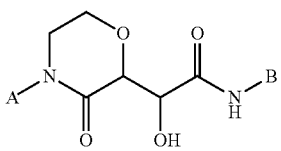
2. The compound of claim 1 of the Formula:
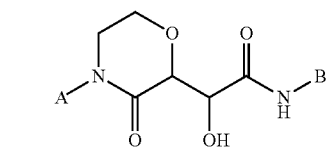
or a pharmaceutically acceptable salt thereof, wherein A is
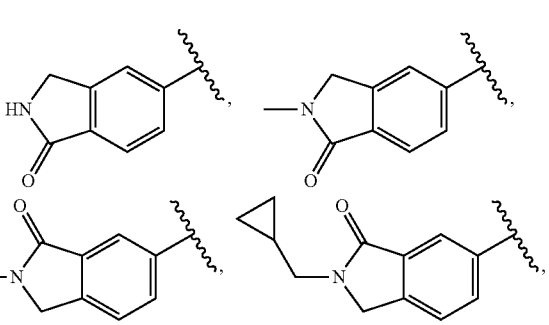

895
-continued
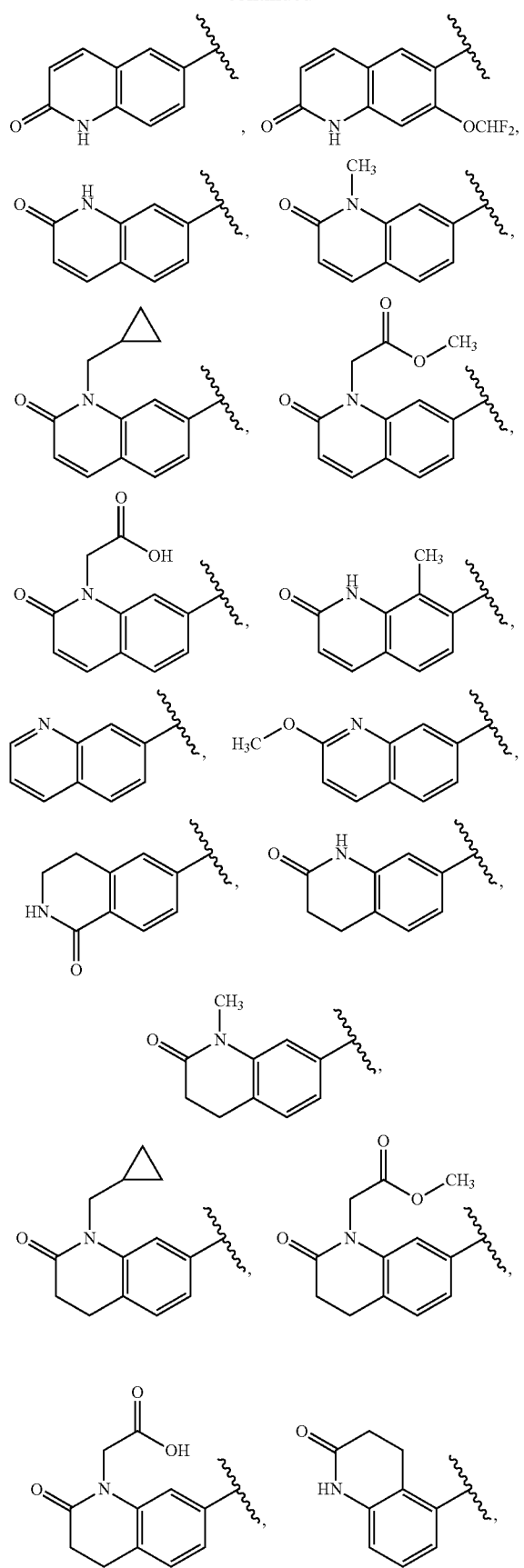
896
-continued
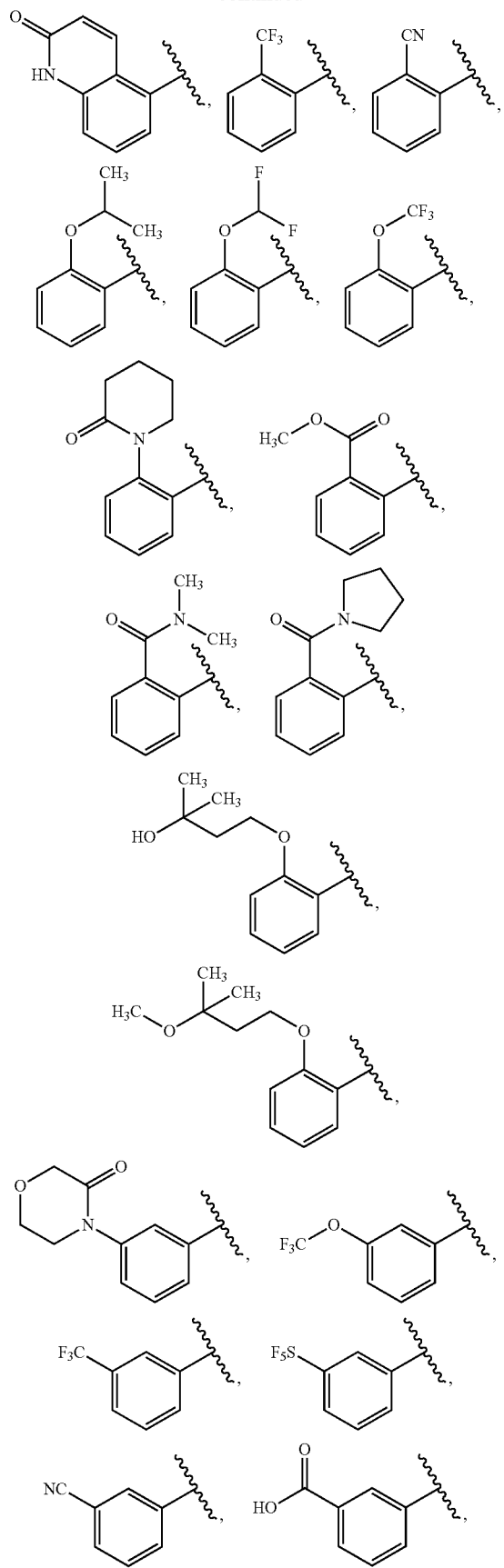

897
-continued
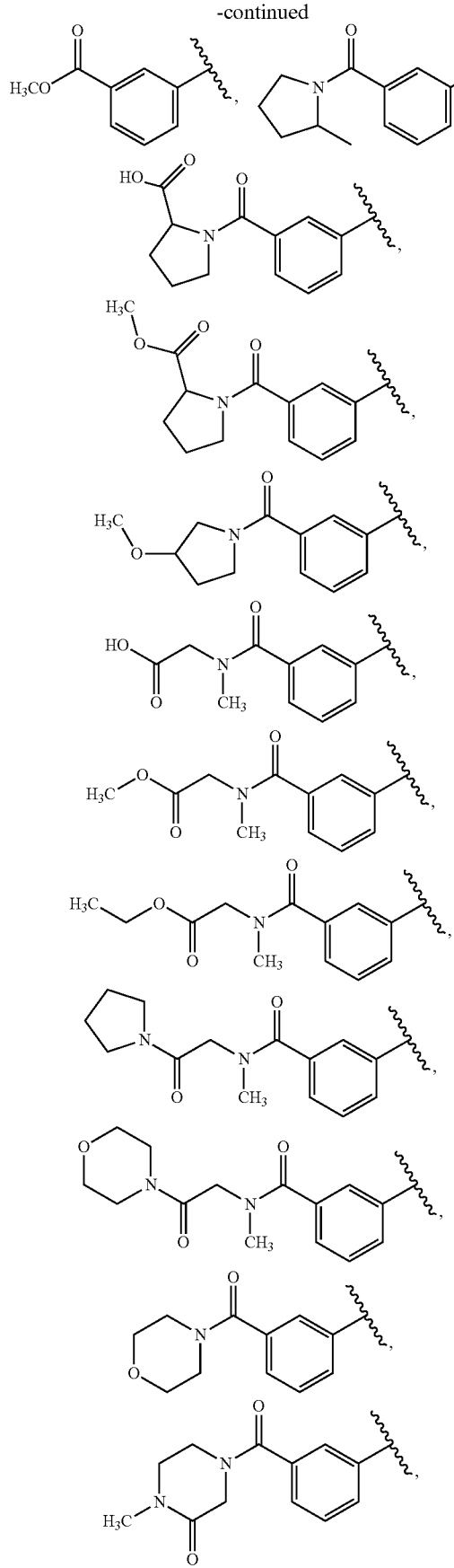
898
-continued
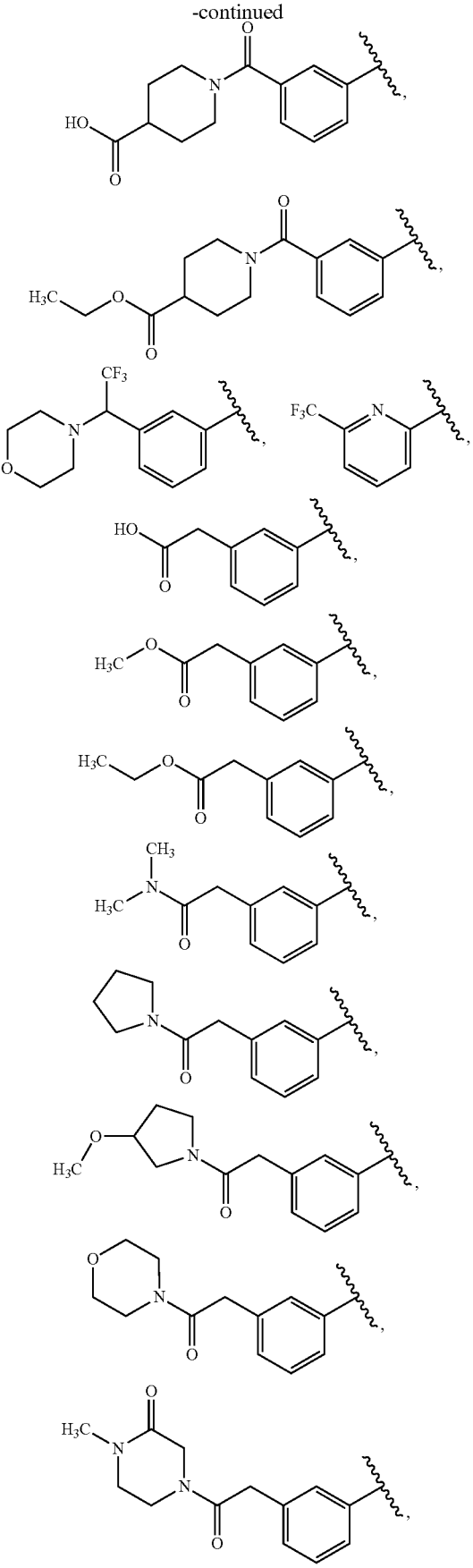

899
-continued
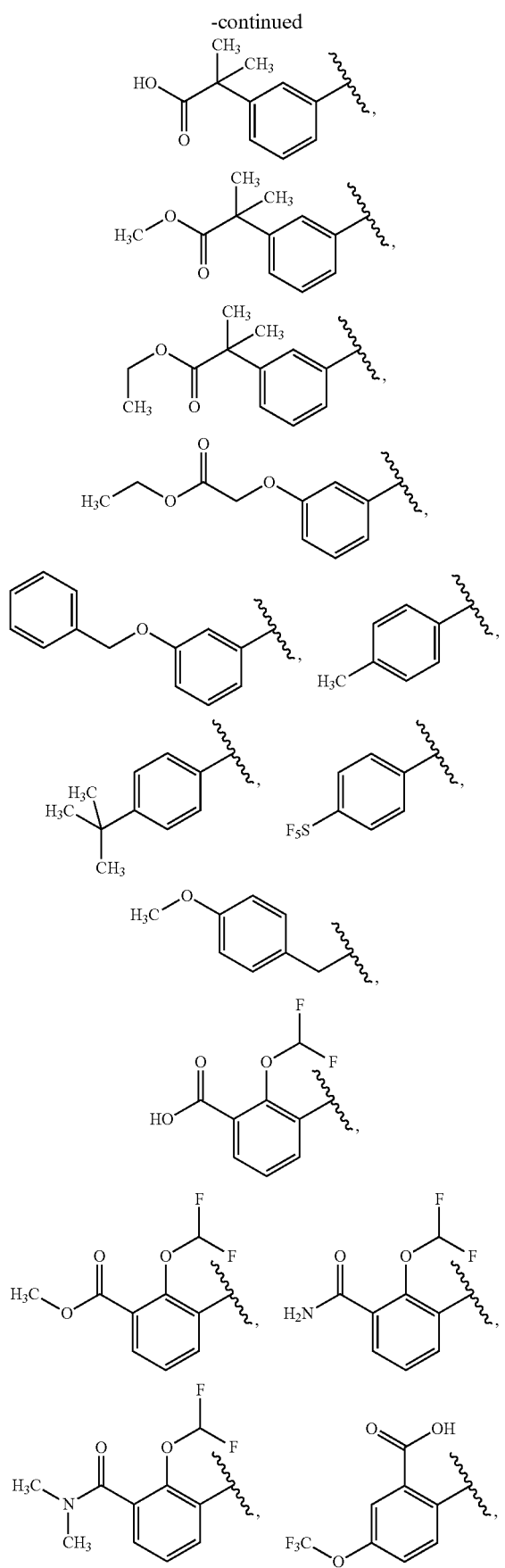
900
-continued
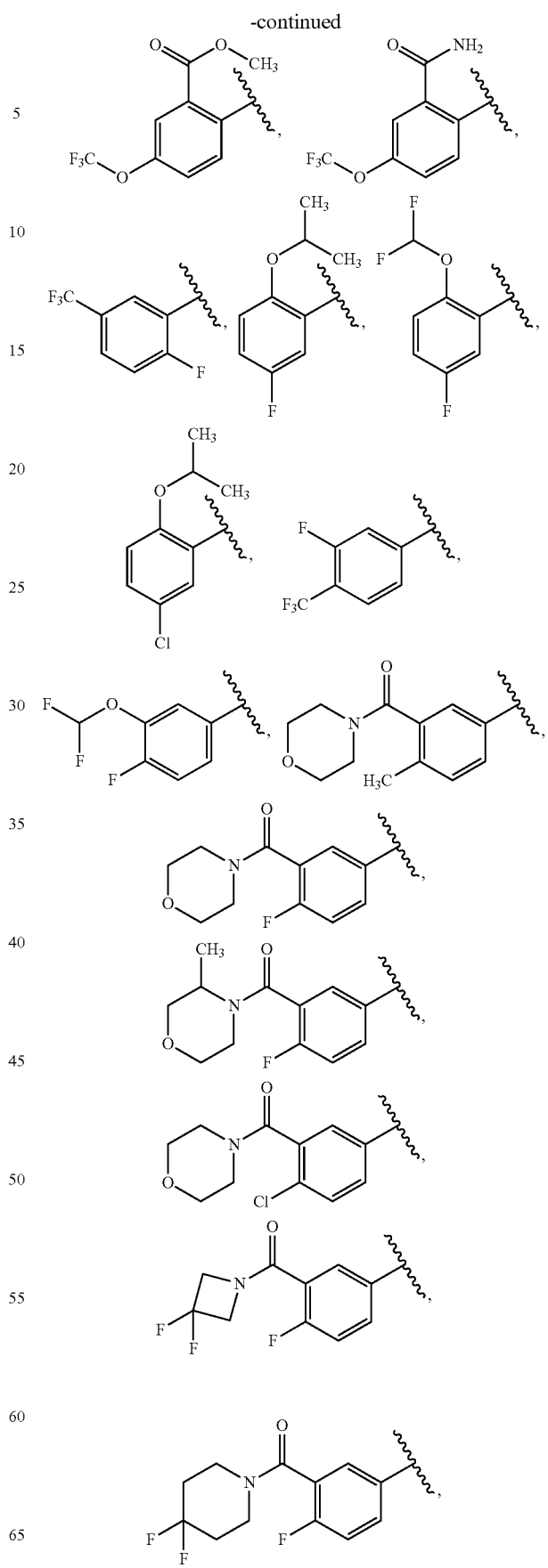

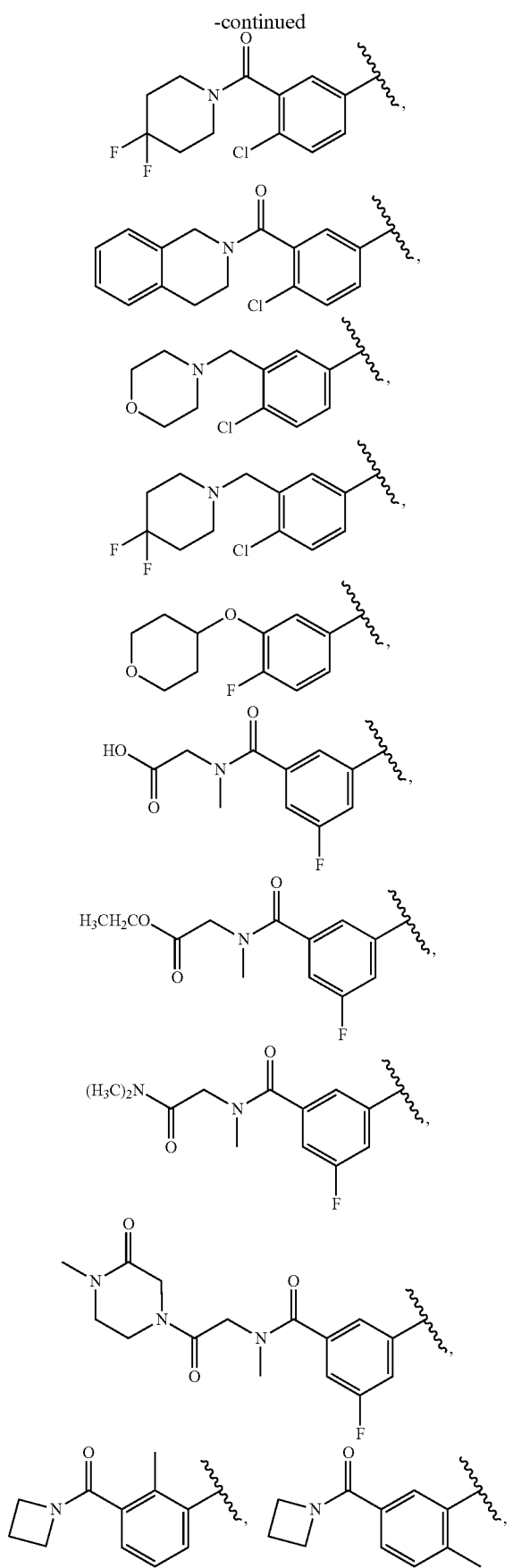
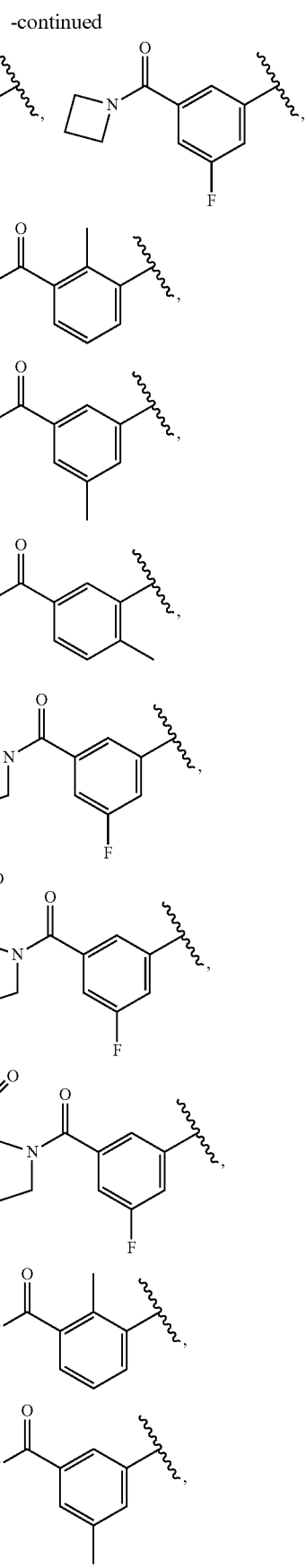

903
-continued
904
-continued
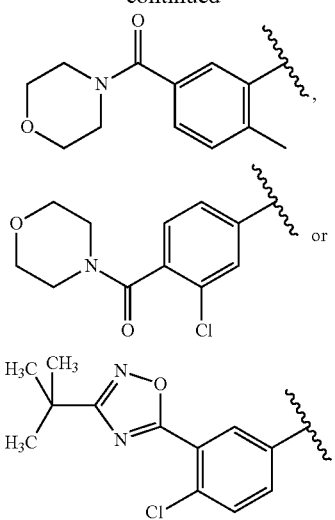
B is
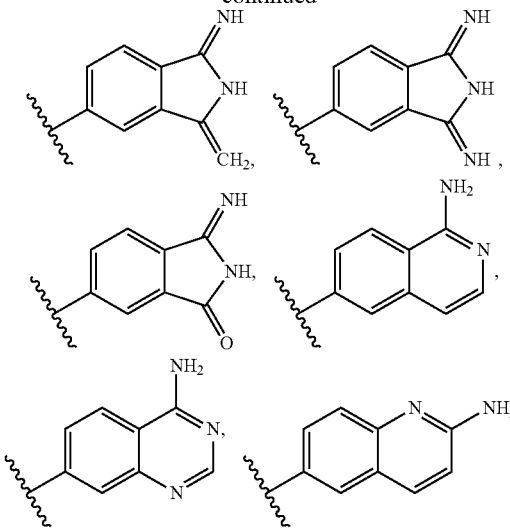
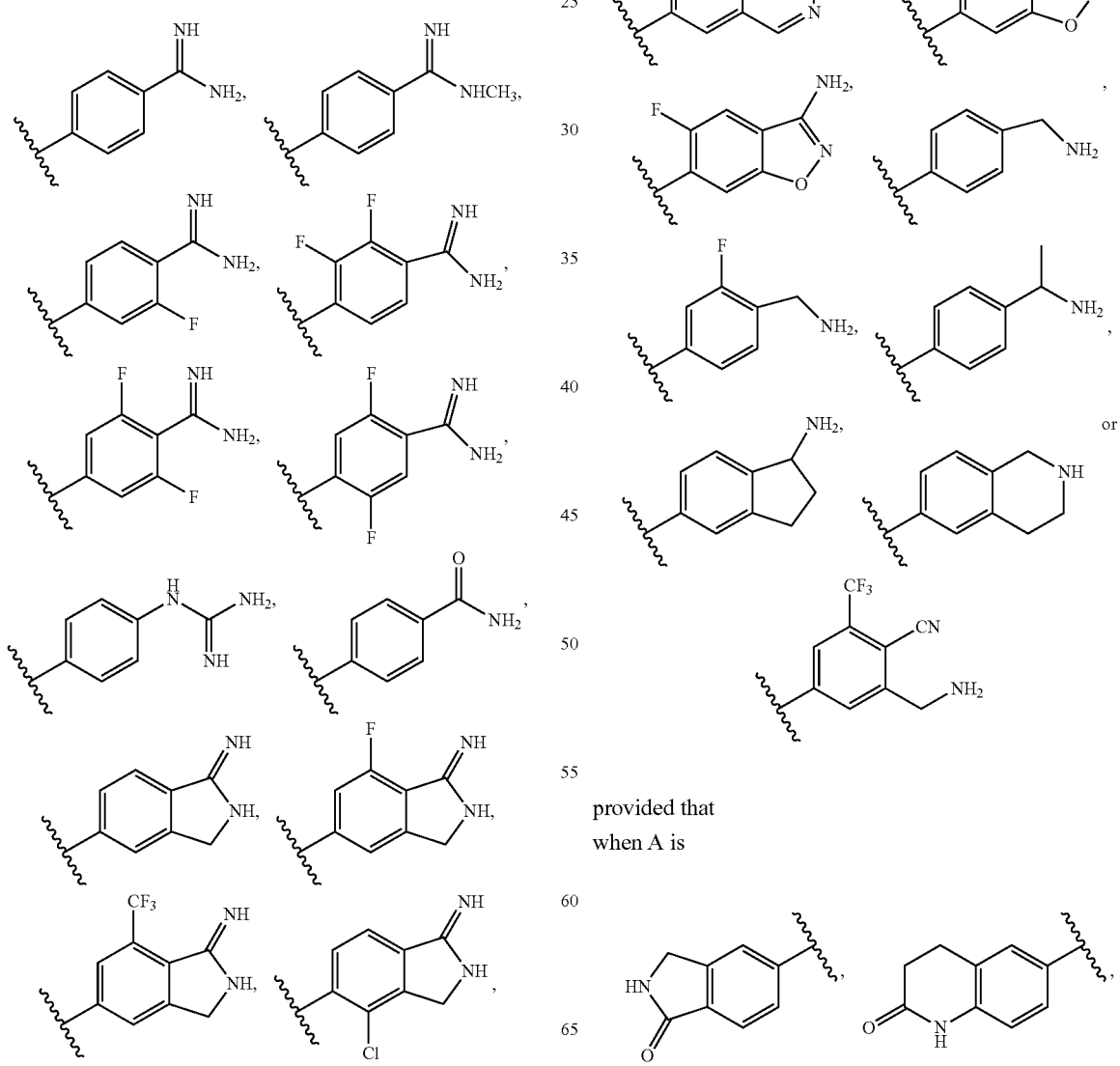
provided that when A is

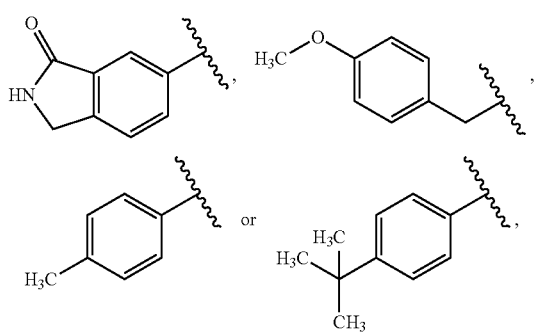

B is not

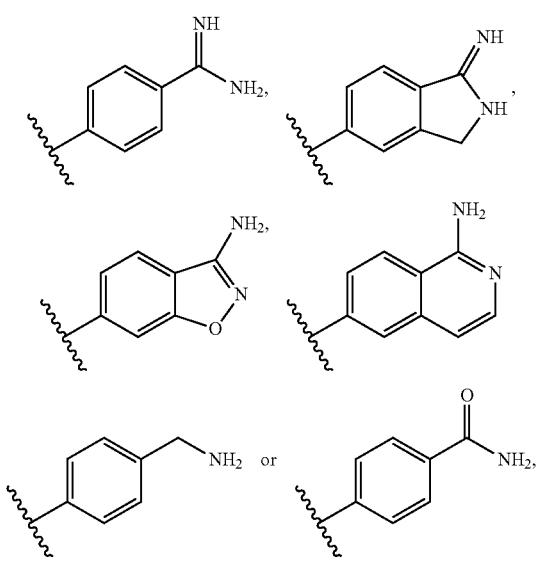

and
when A is

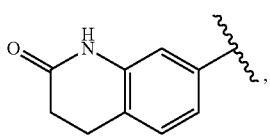 [SMILES: *c1ccc2c(c1)NC(=O)CC2]

B is not

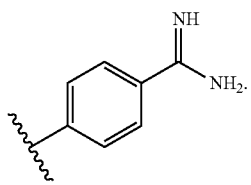 [SMILES: *c1ccc(C(=N)N)cc1]

3. The compound of claim 1, or a pharmaceutically acceptable salt thereof, wherein the absolute configuration of the Formula is

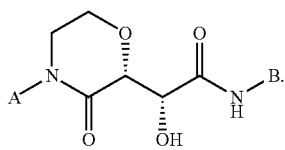

4. A compound of claim 1, which is
2-(3-((R)-2-((R)-2-(4-carbamimidoylphenylamino)-1-hydroxy-2-oxoethyl)-3-oxomorpholino)phenyl)acetate,
(R)—N-(4-carbamimidoylphenyl)-2-hydroxy-2-((R)-4-(3-methyl-5-(pyrrolidine-1-carbonyl)phenyl)-3-oxomorpholin-2-yl)acetamide,
(R)-2-hydroxy-N-(1-iminoisoindolin-5-yl)-2-((R)-4-(3-methyl-5-(pyrrolidine-1-carbonyl)phenyl)-3-oxomorpholin-2-yl)acetamide,
2-(3-((R)-2-((R)-1-hydroxy-2-(1-iminoisoindolin-5-ylamino)-2-oxoethyl)-3-oxomorpholino)-N-methylbenzamido)acetic acid,
2-(3-((R)-2-((R)-1-hydroxy-2-(1-iminoisoindolin-5-ylamino)-2-oxoethyl)-3-oxomorpholino)-N-methylbenzamido)acetate,
(S)-1-(3-((R)-2-((R)-2-(4-carbamimidoylphenylamino)-1-hydroxy-2-oxoethyl)-3-oxomorpholino)benzoyl)pyrrolidine-2-carboxylic acid,
1-(3-((R)-2-((R)-2-(4-carbamimidoylphenylamino)-1-hydroxy-2-oxoethyl)-3-oxomorpholino)benzoyl)pyrrolidine-2-carboxylate,
3-((R)-2-((R)-2-(4-carbamimidoylphenylamino)-1-hydroxy-2-oxoethyl)-3-oxomorpholino)-N-methyl-N-(2-oxo-2-(pyrrolidin-1-yl)ethyl)benzamide,
3-((R)-2-((R)-1-hydroxy-2-(1-iminoisoindolin-5-ylamino)-2-oxoethyl)-3-oxomorpholino)-N-methyl-N-(2-oxo-2-(pyrrolidin-1-yl)ethyl)benzamide,
(R)—N-(4-carbamimidoylphenyl)-2-hydroxy-2-((R)-4-(3-methyl-5-(morpholine-4-carbonyl)phenyl)-3-oxomorpholin-2-yl)acetamide,
(R)-2-hydroxy-N-(1-iminoisoindolin-5-yl)-2-((R)-4-(3-methyl-5-(morpholine-4-carbonyl)phenyl)-3-oxomorpholin-2-yl)acetamide,
(R)-2-hydroxy-N-(1-iminoisoindolin-5-yl)-2-((R)-4-(3-((R)-3-methoxypyrrolidine-1-carbonyl)phenyl)-3-oxomorpholin-2-yl)acetamide,
(R)-2-hydroxy-N-(1-iminoisoindolin-5-yl)-2-((R)-4-(3-((S)-3-methoxypyrrolidine-1-carbonyl)phenyl)-3-oxomorpholin-2-yl)acetamide,
(R)-2-((R)-4-(3-chloro-4-(morpholine-4-carbonyl)phenyl)-3-oxomorpholin-2-yl)-2-hydroxy-N-(1-iminoisoindolin-5-yl)acetamide,
(R)-2-hydroxy-N-(1-iminoisoindolin-5-yl)-2-((R)-4-(3-(2-morpholino-2-oxoethyl)phenyl)-3-oxomorpholin-2-yl)acetamide,
(S)-1-(3-((R)-2-((R)-1-hydroxy-2-(1-iminoisoindolin-5-ylamino)-2-oxoethyl)-3-oxomorpholino)benzoyl)pyrrolidine-2-carboxylic acid,
1-(3-((R)-2-((R)-1-hydroxy-2-(1-iminoisoindolin-5-ylamino)-2-oxoethyl)-3-oxomorpholino)benzoyl)pyrrolidine-2-carboxylate,
2-(3-((R)-2-((R)-1-hydroxy-2-(1-iminoisoindolin-5-ylamino)-2-oxoethyl)-3-oxomorpholino)phenyl)acetate,
2-(3-((R)-2-((R)-1-hydroxy-2-(1-iminoisoindolin-5-ylamino)-2-oxoethyl)-3-oxomorpholino)phenyl)acetic acid, 2-(3-((R)-2-((R)-1-hydroxy-2-(1-iminoisoindolin-5-ylamino)-2-oxoethyl)-3-oxomorpholino)-N-methylbenzamido)acetate,
2-(3-((R)-2-((R)-1-hydroxy-2-(1-iminoisoindolin-5-ylamino)-2-oxoethyl)-3-oxomorpholino)phenyl)-2-methylpropanoate,
(R)-2-hydroxy-N-(1-iminoisoindolin-5-yl)-2-((R)-4-(3-(morpholine-4-carbonyl)phenyl)-3-oxomorpholin-2-yl)acetamide,
3-((R)-2-((R)-1-hydroxy-2-(1-iminoisoindolin-5-ylamino)-2-oxoethyl)-3-oxomorpholino)-N-methyl-N-(2-morpholino-2-oxoethyl)benzamide,
(R)-2-hydroxy-N-(1-iminoisoindolin-5-yl)-2-((R)-4-(3-(2-((R)-3-methoxypyrrolidin-1-yl)-2-oxoethyl)phenyl)-3-oxomorpholin-2-yl)acetamide,
(R)-2-hydroxy-N-(1-iminoisoindolin-5-yl)-2-((R)-4-(3-(2-((S)-3-methoxypyrrolidin-1-yl)-2-oxoethyl)phenyl)-3-oxomorpholin-2-yl)acetamide,
2-(3-((R)-2-((R)-1-hydroxy-2-(1-iminoisoindolin-5-ylamino)-2-oxoethyl)-3-oxomorpholino)phenyl)-2-methylpropanoate,
2-(3-((R)-2-((R)-1-hydroxy-2-(1-iminoisoindolin-5-ylamino)-2-oxoethyl)-3-oxomorpholino)phenyl)acetate,
(R)-2-hydroxy-N-(1-iminoisoindolin-5-yl)-2-((R)-4-(3-(4-methyl-3-oxopiperazine-1-carbonyl)phenyl)-3-oxomorpholin-2-yl)acetamide,
2-(3-((R)-2-((R)-1-hydroxy-2-(1-iminoisoindolin-5-ylamino)-2-oxoethyl)-3-oxomorpholino)phenyl)-2-methylpropanoate,
(R)-2-hydroxy-N-(1-iminoisoindolin-5-yl)-2-((R)-4-(3-(2-(4-methyl-3-oxopiperazin-1-yl)-2-oxoethyl)phenyl)-3-oxomorpholin-2-yl)acetamide,
(R)-2-((R)-4-(3-(2-(dimethylamino)-2-oxoethyl)phenyl)-3-oxomorpholin-2-yl)-2-hydroxy-N-(1-iminoisoindolin-5-yl)acetamide,
1-(3-((R)-2-((R)-1-hydroxy-2-(1-iminoisoindolin-5-ylamino)-2-oxoethyl)-3-oxomorpholino)benzoyl)piperidine-4-carboxylic acid,
1-(3-((R)-2-((R)-1-hydroxy-2-(1-iminoisoindolin-5-ylamino)-2-oxoethyl)-3-oxomorpholino)benzoyl)piperidine-4-carboxylate,
2-(3-((R)-2-((R)-1-acetoxy-2-(1-imino-3-oxoisoindolin-5-ylamino)-2-oxoethyl)-3-oxomorpholino)-N-methylbenzamido)acetic acid,
(R)—N-(1,3-diiminoisoindolin-5-yl)-2-((R)-4-(3-(2-(dimethylamino)-2-oxoethyl)phenyl)-3-oxomorpholin-2-yl)-2-hydroxyacetamide,
(R)-2-(1-imino-3-oxoisoindolin-5-ylamino)-1-((R)-4-(3-(methyl(2-oxo-2-(pyrrolidin-1-yl)ethyl)carbamoyl)phenyl)-3-oxomorpholin-2-yl)-2-oxoethyl acetate,
(R)—N-(3-aminobenzo[d]isoxazol-6-yl)-2-((R)-4-(4-fluoro-3-(morpholine-4-carbonyl)phenyl)-3-oxomorpholin-2-yl)-2-hydroxyacetamide,
(R)—N-(3-aminobenzo[d]isoxazol-6-yl)-2-((R)-4-(4-chloro-3-((4,4-difluoropiperidin-1-yl)methyl)phenyl)-3-oxomorpholin-2-yl)-2-hydroxyacetamide),
(R)—N-(3-aminobenzo[d]isoxazol-6-yl)-2-hydroxy-2-((R)-3-oxo-4-(3-(3-oxomorpholino)phenyl)morpholin-2-yl)acetamide,
(R)—N-(3-aminobenzo[d]isoxazol-6-yl)-2-((R)-4-(2-(difluoromethoxy)phenyl)-3-oxomorpholin-2-yl)-2-hydroxyacetamide,
(R)—N-(3-aminobenzo[d]isoxazol-6-yl)-2-hydroxy-2-((R)-4-(2-isopropoxyphenyl)-3-oxomorpholin-2-yl)acetamide,
(R)—N-(3-aminobenzo[d]isoxazol-6-yl)-2-((R)-4-(3-cyanophenyl)-3-oxomorpholin-2-yl)-2-hydroxyacetamide,
(R)—N-(3-aminobenzo[d]isoxazol-6-yl)-2-((R)-4-(4-chloro-3-(morpholine-4-carbonyl)phenyl)-3-oxomorpholin-2-yl)-2-hydroxyacetamide,
(R)—N-(3-aminobenzo[d]isoxazol-6-yl)-2-hydroxy-2-((R)-4-(4-methyl-3-(morpholine-4-carbonyl)phenyl)-3-oxomorpholin-2-yl)acetamide,
(R)—N-(3-aminobenzo[d]isoxazol-6-yl)-2-hydroxy-2-((R)-3-oxo-4-(3-(trifluoromethoxy)phenyl)morpholin-2-yl)acetamide,
(R)—N-(3-aminobenzo[d]isoxazol-6-yl)-2-hydroxy-2-((R)-3-oxo-4-(3-(trifluoromethyl)phenyl)morpholin-2-yl)acetamide,
(R)—N-(3-aminobenzo[d]isoxazol-6-yl)-2-((R)-4-(4-chloro-3-(1,2,3,4-tetrahydroisoquinoline-2-carbonyl)phenyl)-3-oxomorpholin-2-yl)-2-hydroxyacetamide,
(R)—N-(3-aminobenzo[d]isoxazol-6-yl)-2-((R)-4-(4-chloro-3-(4,4-difluoropiperidine-1-carbonyl)phenyl)-3-oxomorpholin-2-yl)-2-hydroxyacetamide,
(R)—N-(3-aminobenzo[d]isoxazol-6-yl)-2-((R)-4-(3-fluoro-4-(trifluoromethyl)phenyl)-3-oxomorpholin-2-yl)-2-hydroxyacetamide,
(R)—N-(4-carbamimidoyl-3-fluorophenyl)-2-hydroxy-2-((R)-3-oxo-4-(3-(3-oxomorpholino)phenyl)morpholin-2-yl)acetamide,
(R)-2-hydroxy-N-(1-imino-7-(trifluoromethyl)isoindolin-5-yl)-2-((R)-3-oxo-4-(3-(3-oxomorpholino)phenyl)morpholin-2-yl)acetamide,
(R)-2-Hydroxy-N-(1-iminoisoindolin-5-yl)-2-((R)-3-oxo-4-(3-(trifluoromethoxy)phenyl)morpholin-2-yl)acetamide,
Ethyl 2-(3-((R)-2-((R)-1-hydroxy-2-(1-iminoisoindolin-5-ylamino)-2-oxoethyl)-3-oxomorpholino)phenoxy)acetate,
(R)-2-Hydroxy-N-(1-iminoisoindolin-5-yl)-2-((R)-4-(4-methoxybenzyl)-3-oxomorpholin-2-yl)acetamide,
(R)-2-((R)-4-(3-(Benzyloxy)phenyl)-3-oxomorpholin-2-yl)-2-hydroxy-N-(1-iminoisoindolin-5-yl)acetamide,
(R)—N-(1-Aminoisoquinolin-6-yl)-2-((R)-4-(4-fluoro-3-(morpholine-4-carbonyl)phenyl)-3-oxomorpholin-2-yl)-2-hydroxyacetamide,
N-(2,3-Dihydro-1-imino-1h-isoindol-5-yl)-4-[2-[(dimethylamino)carbonyl]phenyl]-alpha(R)-hydroxy-3-oxo-2(R)-morpholineacetamide,
N-(2,3-Dihydro-1-imino-1H-isoindol-5-yl)-alpha(R)-hydroxy-3-oxo-4-[2-(1-pyrrolidinylcarbonyl)phenyl]-2(R)-morpholineacetamide,
4-(2-Cyanophenyl)-N-(2,3-dihydro-1-imino-1h-isoindol-5-yl)-alpha(R)-hydroxy-3-oxo-2(R)-morpholineacetamide,
N-(2,3-Dihydro-1-imino-1h-isoindol-5-yl)-4-[4-fluoro-3-(4-morpholinylcarbonyl)phenyl]-alpha(R)-hydroxy-3-oxo-2(R)-morpholineacetamide,
N-(2,3-Dihydro-1-imino-1h-isoindol-5-yl)-4-[4-fluoro-3-[(3 R)-methyl-4-morpholinyl)carbonyl]phenyl]-alpha(R)-hydroxy-3-oxo-2(R)-morpholineacetamide,
N-(2,3-Dihydro-1-imino-1h-isoindol-5-yl)-4-[4-fluoro-3-[(3 S)-methyl-4-morpholinyl)carbonyl]phenyl]-alpha(R)-hydroxy-3-oxo-2(R)-morpholineacetamide,
N-[4-(Aminoiminomethyl)phenyl]-4-(2-cyanophenyl)-alpha(R)-hydroxy-3-oxo-2(R)-morpholineacetamide,
N-(4-Amino-7-quinazolinyl)-4-[4-fluoro-3-(4-morpholinylcarbonyl)phenyl]-alpha(R)-hydroxy-3-oxo-2(R)-morpholineacetamide,

[3-[2(R)-[2-[(3-Amino-1,2-benzisoxazol-6-yl)amino]-1(R)-hydroxy-2-oxoethyl]-3-oxo-4-morpholinyl]phenyl]pentafluorosulfur,

[4-[2(R)-[2-[(3-Amino-1,2-benzisoxazol-6-yl)amino]-1(R)-hydroxy-2-oxoethyl]-3-oxo-4-morpholinyl]phenyl]pentafluorosulfur, N-(3-Amino-5-fluoro-1,2-benzisoxazol-6-yl)-4-[4-fluoro-3-(4-morpholinylcarbonyl)phenyl]-alpha(R)-hydroxy-3-oxo-2(R)-morpholineacetamide, N-(2-Amino-6-quinazolinyl)-4-[4-fluoro-3-(4-morpholinylcarbonyl)phenyl]-alpha(R)-hydroxy-3-oxo-2(R)-morpholineacetamide, (R)-2-((R)-4-(5-fluoro-2-isopropoxyphenyl)-3-oxomorpholin-2-yl)-2-hydroxy-N-(1-iminoisoindolin-5-yl)acetamide, (R)-2-hydroxy-N-(1-iminoisoindolin-5-yl)-2-((R)-3-oxo-4-(2-(trifluoromethyl)phenyl)morpholin-2-yl)acetamide, (R)-2-((R)-4-(2-(difluoromethoxy)phenyl)-3-oxomorpholin-2-yl)-2-hydroxy-N-(1-iminoisoindolin-5-yl)acetamide, (R)-2-hydroxy-N-(1-iminoisoindolin-5-yl)-2-((R)-4-(2-isopropoxyphenyl)-3-oxomorpholin-2-yl)acetamide, (R)-2-hydroxy-N-(1-iminoisoindolin-5-yl)-2-((R)-3-oxo-4-(2-(trifluoromethoxy)phenyl)morpholin-2-yl)acetamide, N-(3-Amino-1,2-benzisoxazol-6-yl)-4-[4-fluoro-3-[(tetrahydro-2H-pyran-4-yl)oxy]phenyl]-alpha(R)-hydroxy-3-oxo-2(R)-morpholineacetamide, N-(3-Amino-1,2-benzisoxazol-6-yl)-4-[3-[(3,3-difluoro-1-azetidinyl)carbonyl]-4-fluorophenyl]-alpha(R)-hydroxy-3-oxo-2(R)-morpholineacetamide, N-(3-Amino-1,2-benzisoxazol-6-yl)-4-[3-[(4,4-difluoro-1-piperidinyl)carbonyl]-4-fluorophenyl]-alpha(R)-hydroxy-3-oxo-2(R)-morpholineacetamide, N-(3-amino-1,2-benzisoxazol-6-yl)-4-[4-chloro-3-[3-(1,1-dimethylethyl)-1,2,4-oxadiazol-5-yl]phenyl]-alpha(R)-hydroxy-3-oxo-2(R)-morpholineacetamide, N-(3-amino-1,2-benzisoxazol-6-yl)-4-[2-fluoro-5-(trifluoromethyl)phenyl]-alpha(R)-hydroxy-3-oxo-2(R)-morpholineacetamide, or a pharmaceutically acceptable salt thereof.

5. A pharmaceutical composition comprising at least one compound of claim 1, or a pharmaceutically acceptable salt, solvate, or ester thereof and at least one pharmaceutically acceptable carrier.

6. A pharmaceutical composition comprising:
a therapeutically effective amount of at least one compound of claim 1 or a pharmaceutically acceptable salt thereof, and at least one pharmaceutically acceptable carrier, and an effective amount of at least one agent selected from the group consisting of: (a) anticoagulants, (b) anti-thrombin agents, (c) anti-platelet agents, (d) fibrinolytics, (e) hypolipidemic agents, (f) antihypertensive agents, and (g) anti-ischemic agents.

7. A pharmaceutical composition comprising:
a therapeutically effective amount of at least one compound of claim 1 or a pharmaceutically acceptable salt thereof, and at least one pharmaceutically acceptable carrier, and an effective amount of at least one agent selected from the group consisting of (a-1) warfarin, (a-2) heparin, (a-3) aprotinin, (a-4) synthetic pentasaccharide, (a-5) direct acting thrombin inhibitors including hirudin and argatroban, (a-6) a factor VIIa inhibitor, (a-7) a factor VIIIa inhibitor, (a-8) a factor IXa inhbitor different from the compounds of Formula (I), (a-9) a factor Xa inhibitor, (a-10) a factor XIa inhibitor, (a-11) a thrombin inhibitor, (a-12) a TAFI, (a-13) a fibrinogen inhibitor, (b-1) a boroarginine derivative, (b-2) a boropeptide, (b-3) heparin, (b-4) hirudin, (b-5) argatroban, (c-1) a NSAID, (c-2) a IIb/IIIa antagonist, (c-3) a thromboxane-A2-receptor antagonist, (c-4) a thromboxane-A2-synthetase inhibitor, (c-5) a PDE-III inhibitor, (c-6) a PDE V inhibitor, (c-7) a ADP receptor antagonist, (c-8) an antagonist of the purinergic receptor P2Y1, (c-9) an antagonist of the purinergic receptor P2Y12, (d-1) tissue plasminogen activator (TPA, natural or recombinant) and modified forms thereof, (d-2) anistreplase, (d-3) urokinase, (d-4) streptokinase, (d-5) tenecteplase (TNK), (d-6) lanoteplase (nPA), (d-7) a factor VIIa inhibitor, (d-8) a PAI-I inhibitor, (d-9) an alpha-2-antiplasmin inhibitor, (d-10) an anisoylated plasminogen streptokinase activator complex, (e-1) a HMG-CoA reductase inhibitor, (e-2) a squalene synthetase inhibitor, (e-3) a fibrate, (e-4) a bile acid sequestrant, (e-5) an ACAT inhibitor, (e-6) a MTP inhibitor, (e-7) a lipooxygenase inhibitor, (e-8) a cholesterol absorption inhibitor, (e-9) a cholesterol ester transfer protein inhibitor, (f-1) an alpha adrenergic blocker, (f-2) a beta adrenergic blocker, (f-3) a calcium channel blocker, (f-4) a diuretics, (f-5) a rennin inhibitor, (f-6) an angiotensin-converting enzyme inhibitor, (f-7) an angiotensin-II-receptor antagonist, (f-8) an ET receptor antagonist, (f-9) a Dual ET/All antagonist, (f-10) a neutral endopeptidase inhibitors, (f-11) a vasopepsidase inhibitor, (g-1) a Class I agent, (g-2) a Class II agent, (g-3) a Class III agent, a (g-4) Class IV agent, (g-5) a K+ cannel opener, (g-6) an IKur inhibitor and (g-7) a cardiac glycoside.

8. A compound of claim 1, which is
(2R)-2-[(2R)-4-(4-tert-butylphenyl)-3-oxomorpholin-2-yl]-2-hydroxy-N-[4-(N-methylcarbamimidoyl)phenyl]acetamide, (2R)-2-hydroxy-N-(1-imino-2,3-dihydroisoindol-5-yl)-2-[(2R)-3-oxo-4-(1-oxo-2,3-dihydroisoindol-5-yl)morpholin-2-yl]acetamide, (2R)-2-hydroxy-N-(1-imino-2,3-dihydroisoindol-5-yl)-2-[(2R)-3-oxo-4-(2-oxo-1H-quinolin-6-yl)morpholin-2-yl]acetamide, (2R)-2-[(2R)-4-[7-(difluoromethoxy)-2-oxo-1H-quinolin-6-yl]-3-oxomorpholin-2-yl]-2-hydroxy-N-(1-imino-2,3-dihydroisoindol-5-yl)acetamide, (2R)—N-(4-carbamimidoylphenyl)-2-hydroxy-2-[(2R)-3-oxo-4-(2-oxo-1H-quinolin-6-yl)morpholin-2-yl]acetamide, (2R)—N-(4-carbamimidoyl-3-fluorophenyl)-2-hydroxy-2-[(2R)-3-oxo-4-(2-oxo-1H-quinolin-6-yl)morpholin-2-yl]acetamide, (2R)-2-hydroxy-N-(1-imino-2,3-dihydroisoindol-5-yl)-2-[(2R)-3-oxo-4-(2-oxo-1H-quinolin-7-yl)morpholin-2-yl]acetamide, (2R)-2-hydroxy-N-(1-imino-2,3-dihydroisoindol-5-yl)-2-[(2R)-4-(1-methyl-2-oxoquinolin-7-yl)-3-oxomorpholin-2-yl]acetamide, (2R)-2-[(2R)-4-[1-(cyclopropylmethyl)-2-oxoquinolin-7-yl]-3-oxomorpholin-2-yl]-2-hydroxy-N-(1-imino-2,3-dihydroisoindol-5-yl)acetamide, 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetate, 2-[7-[(2R)-2-[(1R)-1-hydroxy-2-[(1-imino-2,3-dihydroisoindol-5-yl)amino]-2-oxoethyl]-3-oxomorpholin-4-yl]-2-oxoquinolin-1-yl]acetic acid, (2R)-2-hydroxy-N-(1-imino-2,3-dihydroisoindol-5-yl)-2-[(2R)-4-(8-methyl-2-oxo-1H-quinolin-7-yl)-3-oxomorpholin-2-yl]acetamide,
(2R)-2-hydroxy-N-(1-imino-2,3-dihydroisoindol-5-yl)-2-[(2R)-4-(2-methoxyquinolin-7-yl)-3-oxomorpholin-2-yl]acetamide,
(2R)-2-hydroxy-N-(1-imino-2,3-dihydroisoindol-5-yl)-2-[(2R)-3-oxo-4-quinolin-7-ylmorpholin-2-yl]acetamide,
(2R)—N-(3-amino-1,2-benzisoxazol-6-yl)-2-hydroxy-2-[(2R)-3-oxo-4-quinolin-7-ylmorpholin-2-yl]acetamide,
(2R)-2-hydroxy-N-(1-imino-2,3-dihydroisoindol-5-yl)-2-[(2R)-3-oxo-4-(2-oxo-1H-quinolin-5-yl)morpholin-2-yl]acetamide,
(2R)-2-hydroxy-N-(1-imino-2,3-dihydroisoindol-5-yl)-2-[(2R)-3-oxo-4-(1-oxo-3,4-dihydro-2H-isoquinolin-6-yl)morpholin-2-yl]acetamide,
(2R)-2-hydroxy-N-(1-imino-2,3-dihydroisoindol-5-yl)-2-[(2R)-3-oxo-4-(2-oxo-3,4-dihydro-1H-quinolin-7-yl)morpholin-2-yl]acetamide,
(2R)-2-hydroxy-N-(1-imino-2,3-dihydroisoindol-5-yl)-2-[(2R)-4-(1-methyl-2-oxo-3,4-dihydroquinolin-7-yl)-3-oxomorpholin-2-yl]acetamide,
(2R)-2-[(2R)-4-[1-(cyclopropylmethyl)-2-oxo-3,4-dihydroquinolin-7-yl]-3-oxomorpholin-2-yl]-2-hydroxy-N-(1-imino-2,3-dihydroisoindol-5-yl)acetamide,
methyl 2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetate,
2-[7-[(2R)-2-[(1R)-1-hydroxy-2-[(1-imino-2,3-dihydroisoindol-5-yl)amino]-2-oxoethyl]-3-oxomorpholin-4-yl]-2-oxo-3,4-dihydroquinolin-1-yl]acetic acid,
(2R)—N-(4-carbamimidoyl-3-fluorophenyl)-2-hydroxy-2-[(2R)-3-oxo-4-(2-oxo-3,4-dihydro-1H-quinolin-7-yl)morpholin-2-yl]acetamide,
(2R)—N-(3-amino-1,2-benzoxazol-6-yl)-2-hydroxy-2-[(2R)-3-oxo-4-(2-oxo-3,4-dihydro-1H-quinolin-7-yl)morpholin-2-yl]acetamide,
(2R)—N-(1-aminoisoquinolin-6-yl)-2-hydroxy-2-[(2R)-3-oxo-4-(2-oxo-3,4-dihydro-1H-quinolin-7-yl)morpholin-2-yl]acetamide,
(2R)—N-(4-aminoquinazolin-7-yl)-2-hydroxy-2-[(2R)-3-oxo-4-(2-oxo-3,4-dihydro-1H-quinolin-7-yl)morpholin-2-yl]acetamide,
(2R)-2-hydroxy-N-(1-imino-2,3-dihydroisoindol-5-yl)-2-[(2R)-3-oxo-4-(2-oxo-3,4-dihydro-1H-quinolin-5-yl)morpholin-2-yl]acetamide,
(2R)-2-hydroxy-2-[(2R)-4-[2-(3-hydroxy-3-methylbutoxy)phenyl]-3-oxomorpholin-2-yl]-N-(1-imino-2,3-dihydroisoindol-5-yl)acetamide,
(2R)-2-hydroxy-N-(1-imino-2,3-dihydroisoindol-5-yl)-2-[(2R)-4-[2-(3-methoxy-3-methylbutoxy)phenyl]-3-oxomorpholin-2-yl]acetamide,
(2R)-2-hydroxy-N-(1-imino-2,3-dihydroisoindol-5-yl)-2-[(2R)-3-oxo-4-[2-(2-oxopiperidin-1-yl)phenyl]morpholin-2-yl]acetamide,
(2R)-2-[(2R)-4-[2-(difluoromethoxy)-5-fluorophenyl]-3-oxomorpholin-2-yl]-2-hydroxy-N-(1-imino-2,3-dihydroisoindol-5-yl)acetamide,
methyl 2-(difluoromethoxy)-3-[(2R)-2-[(1R)-1-hydroxy-2-[(1-imino-2,3-dihydro-isoindol-5-yl)amino]-2-oxoethyl]-3-oxomorpholin-4-yl]benzoate,
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]benzoic acid,
2-(difluoromethoxy)-3-[(2R)-2-[(1R)-1-hydroxy-2-[(1-imino-2,3-dihydroisoindol-5-yl)amino]-2-oxoethyl]-3-oxomorpholin-4-yl]-N,N-dimethylbenzamide,
2-(difluoromethoxy)-3-[2-[(1-hydroxy-2-[(1-imino-2,3-dihydroisoindol-5-yl)amino]-2-oxoethyl]-3-oxomorpholin-4-yl]benzamide,
methyl 2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoate,
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzoic acid,
2-[(2R)-2-[(1R)-1-hydroxy-2-[(1-imino-2,3-dihydroisoindol-5-yl)amino]-2-oxoethyl]-3-oxomorpholin-4-yl]-5-(trifluoromethoxy)benzamide,
(2R)—N-(3-amino-1,2-benzisoxazol-6-yl)-2-hydroxy-2-[(2R)-3-oxo-4-(2-oxo-1H-quinolin-6-yl)morpholin-2-yl]acetamide,
(2R)—N-(3-amino-1,2-benzisoxazol-6-yl)-2-hydroxy-2-[(2R)-3-oxo-4-(2-oxo-1H-quinolin-7-yl)morpholin-2-yl]acetamide, or
(2R)—N-(3-amino-1,2-benzisoxazol-6-yl)-2-hydroxy-2-[(2R)-3-oxo-4-(2-oxo-1H-quinolin-5-yl)morpholin-2-yl]acetamide,
or a pharmaceutically acceptable salt thereof.

9. A compound of claim 1, which is
(R)—N-(4-carbamimidoylphenyl)-2-hydroxy-2-((R)-4-(3-((S)-2-methylpyrrolidine-1-carbonyl)phenyl)-3-oxomorpholin-2-yl)acetamide,
(R)—N-(4-carbamimidoylphenyl)-2-hydroxy-2-((R)-4-(2-methyl-3-(morpholine-4-carbonyl)phenyl)-3-oxomorpholin-2-yl)acetamide,
(R)—N-(4-carbamimidoylphenyl)-2-hydroxy-2-((R)-4-(2-methyl-3-(pyrrolidine-1-carbonyl)phenyl)-3-oxomorpholin-2-yl)acetamide,
(R)-2-((R)-4-(3-(azetidine-1-carbonyl)-5-fluorophenyl)-3-oxomorpholin-2-yl)-N-(4-carbamimidoylphenyl)-2-hydroxyacetamide,
(R)-2-((R)-4-(3-(azetidine-1-carbonyl)-2-methylphenyl)-3-oxomorpholin-2-yl)-N-(4-carbamimidoylphenyl)-2-hydroxyacetamide,
(R)-2-((R)-4-(5-(azetidine-1-carbonyl)-2-methylphenyl)-3-oxomorpholin-2-yl)-N-(4-carbamimidoylphenyl)-2-hydroxyacetamide,
(R)—N-(4-carbamimidoylphenyl)-2-hydroxy-2-((R)-3-oxo-4-(6-(trifluoromethyl)pyridin-2-yl)morpholin-2-yl)acetamide,
(R)—N-(4-carbamimidoylphenyl)-2-hydroxy-2-((R)-4-(2-methyl-5-(pyrrolidine-1-carbonyl)phenyl)-3-oxomorpholin-2-yl)acetamide,
(R)-2-((R)-4-(3-(azetidine-1-carbonyl)-5-methylphenyl)-3-oxomorpholin-2-yl)-N-(4-carbamimidoylphenyl)-2-hydroxyacetamide,
(R)—N-(4-carbamimidoylphenyl)-2-hydroxy-2-((R)-4-(2-methyl-5-(morpholine-4-carbonyl)phenyl)-3-oxomorpholin-2-yl)acetamide,
(S)-1-(3-((R)-2-((R)-2-(4-carbamimidoylphenylamino)-1-hydroxy-2-oxoethyl)-3-oxomorpholino)-5-fluorobenzoyl)pyrrolidine-2-carboxylic acid,
1-(3-((R)-2-((R)-2-(4-carbamimidoylphenylamino)-1-hydroxy-2-oxoethyl)-3-oxomorpholino)-5-fluorobenzoyl)pyrrolidine-2-carboxylate,
1-(3-((R)-2-((R)-2-(4-carbamimidoylphenylamino)-1-hydroxy-2-oxoethyl)-3-oxomorpholino)-5-fluorobenzoyl)pyrrolidine-2-carboxylate, 2-(3-((R)-2-((R)-2-(4-carbamimidoylphenylamino)-1-hydroxy-2-oxoethyl)-3-oxomorpholino)-5-fluoro-N-methylbenzamido)acetic acid,
2-(3-((R)-2-((R)-2-(4-carbamimidoylphenylamino)-1-hydroxy-2-oxoethyl)-3-oxomorpholino)-5-fluoro-N-methylbenzamido)acetate,
3-((R)-2-((R)-2-(4-carbamimidoylphenylamino)-1-hydroxy-2-oxoethyl)-3-oxomorpholino)-N-(2-(dimethylamino)-2-oxoethyl)-5-fluoro-N-methylbenzamide,
(R)—N-(1,3-diiminoisoindolin-5-yl)-2-hydroxy-2-((R)-4-(3-(2-(4-methyl-3-oxopiperazin-1-yl)-2-oxoethyl)phenyl)-3-oxomorpholin-2-yl)acetamide,
N-(2-(dimethylamino)-2-oxoethyl)-3-((R)-2-((R)-1-hydroxy-2-(1-iminoisoindolin-5-ylamino)-2-oxoethyl)-3-oxomorpholino)-N-methylbenzamide,
2-((S)-hydroxy((R)-3-oxo-4-p-tolylmorpholin-2-yl)methyl)-4-oxo-1,4-dihydroquinazoline-6-carboximidamide,
1,1-dioxo-3-((S)-hydroxy((R)-3-oxo-4-p-tol(Example ylmorpholin-2-yl)methyl)-4H-benzo[e][1,2,4]thiadiazine-7-carboximidamide,
(R)—N-(3-aminobenzo[d]isoxazol-6-yl)-2-((R)-4-(4-chloro-3-(morpholinomethyl)phenyl)-3-oxomorpholin-2-yl)-2-hydroxyacetamide,
(R)—N-(3-aminobenzo[d]isoxazol-6-yl)-2-hydroxy-2-((R)-4-(3-(morpholine-4-carbonyl)phenyl)-3-oxomorpholin-2-yl)acetamide,
3-((R)-2-((R)-2-(4-carbamimidoyl-3-fluorophenylamino)-1-hydroxy-2-oxoethyl)-3-oxomorpholino)benzoic acid,
(R)—N-(4-carbamimidoyl-3,5-difluorophenyl)-2-hydroxy-2-((R)-3-oxo-4-(3-(3-oxomorpholino)phenyl)morpholin-2-yl)acetamide,
(R)—N-(4-carbamimidoyl-2,3-difluorophenyl)-2-hydroxy-2-((R)-3-oxo-4-(3-(3-oxomorpholino)phenyl)morpholin-2-yl)acetamide,
(R)—N-(4-carbamimidoyl-2,5-difluorophenyl)-2-hydroxy-2-((R)-3-oxo-4-(3-(3-oxomorpholino)phenyl)morpholin-2-yl)acetamide,
(R)—N-(3-(aminomethyl)-4-cyano-5-(trifluoromethyl)phenyl)-2-hydroxy-2-((R)-3-oxo-4-(3-(3-oxomorpholino)phenyl)morpholin-2-yl)acetamide,
(R)-2-Hydroxy-N-(1-iminoisoindolin-5-yl)-2-((R)-4-(2-methyl-1-oxoisoindolin-5-yl)-3-oxomorpholin-2-yl)acetamide,
(R)-2-Hydroxy-N-(1-iminoisoindolin-5-yl)-2-((R)-4-(2-methyl-3-oxoisoindolin-5-yl)-3-oxomorpholin-2-yl)acetamide hydrochloride,
(R)-2-((R)-4-(2-(Cyclopropylmethyl)-3-oxoisoindolin-5-yl)-3-oxomorpholin-2-yl)-2-hydroxy-N-(1-iminoisoindolin-5-yl)acetamide,
(R)—N-(4-(Aminomethyl)-3-fluorophenyl)-2-hydroxy-2-((R)-3-oxo-4-(3-(3-oxomorpholino)phenyl)morpholin-2-yl)acetamide,
(R)—N-(4-Guanidinophenyl)-2-hydroxy-2-((R)-3-oxo-4-(3-(3-oxomorpholino)phenyl)morpholin-2-yl)acetamide,
(R)—N-(4-(Aminomethyl)phenyl)-2-((R)-4-(4-fluoro-3-(morpholine-4-carbonyl)phenyl)-3-oxomorpholin-2-yl)-2-hydroxyacetamide,
(R)-2-(4-Carbamoylphenylamino)-1-((R)-4-(4-fluoro-3-(morpholine-4-carbonyl)phenyl)-3-oxomorpholin-2-yl)-2-oxoethyl acetate,
(R)-2-((R)-4-(4-Fluoro-3-(morpholine-4-carbonyl)phenyl)-3-oxomorpholin-2-yl)-2-hydroxy-N-(1,2,3,4-tetrahydroisoquinolin-6-yl)acetamide,
(R)—N-(4-(Aminomethyl)-3-fluorophenyl)-2-((R)-4-(4-fluoro-3-(morpholine-4-carbonyl)phenyl)-3-oxomorpholin-2-yl)-2-hydroxyacetamide,
(R)—N-(4-((R)-1-Aminoethyl)phenyl)-2-((R)-4-(4-fluoro-3-(morpholine-4-carbonyl)phenyl)-3-oxomorpholin-2-yl)-2-hydroxyacetamide,
(R)—N—((R)-1-amino-2,3-dihydro-1H-inden-5-yl)-2-((R)-4-(4-fluoro-3-(morpholine-4-carbonyl)phenyl)-3-oxomorpholin-2-yl)-2-hydroxyacetamide,
(R)—N—((S)-1-Amino-2,3-dihydro-1H-inden-5-yl)-2-((R)-4-(4-fluoro-3-(morpholine-4-carbonyl)phenyl)-3-oxomorpholin-2-yl)-2-hydroxyacetamide,
(R)—N-(2-Aminoquinolin-6-yl)-2-((R)-4-(4-fluoro-3-(morpholine-4-carbonyl)phenyl)-3-oxomorpholin-2-yl)-2-hydroxyacetamide,
N-(7-fluoro-2,3-dihydro-1-imino-1H-isoindol-5-yl)-alpha(R)-hydroxy-3-oxo-4-[3-(3-oxo-4-morpholinyl)phenyl]-2(R)-morpholineacetamide,
N-(4-chloro-2,3-dihydro-1-imino-1H-isoindol-5-yl)-alpha(R)-hydroxy-3-oxo-4-[3-(3-oxo-4-morpholinyl)phenyl]-2(R)-morpholineacetamide,
3-[2(R)-[2-[(2,3-Dihydro-1-imino-1h-isoindol-5-yl)amino]-1(R)-hydroxy-2-oxoethyl]-3-oxo-4-morpholinyl]benzoic acid,
Methyl 3-[2(R)-[2-[(2,3-dihydro-1-imino-1H-isoindol-5-yl)amino]-1(R)— hydroxy-2-oxoethyl]-3-oxo-4-morpholinyl]benzoate,
Methyl 2-[2(R)-[2-[(2,3-dihydro-1-imino-1h-isoindol-5-yl)amino]-1(R)-hydroxy-2-oxoethyl]-3-oxo-4-morpholinyl]benzoate,
N-(3-Amino-1,2-benzisoxazol-6-yl)-4-[4-fluoro-3-[2,2,2-trifluoro-1-(4-morpholinyl)ethyl]phenyl]-alpha(R)-hydroxy-3-oxo-2(R)-morpholineacetamide,
(R)-2-((R)-4-(5-chloro-2-isopropoxyphenyl)-3-oxomorpholin-2-yl)-2-hydroxy-N-(1-iminoisoindolin-5-yl)acetamide,
N-(3-Amino-1,2-benzisoxazol-6-yl)-4-[3-(difluoromethoxy)-4-fluorophenyl]-alpha(R)-hydroxy-3-oxo-2(R)-morpholineacetamide,
or a pharmaceutically acceptable salt thereof.

\* \* \* \* \*